US010689396B2

(12) United States Patent
Arora et al.

(10) Patent No.: US 10,689,396 B2
(45) Date of Patent: Jun. 23, 2020

(54) INHIBITORS OF BRUTON'S TYROSINE KINASE AND METHODS OF THEIR USE

(71) Applicant: JANSSEN PHARMACEUTICA NV, Beerse (BE)

(72) Inventors: Nidhi Arora, San Diego, CA (US); Genesis M. Bacani, San Diego, CA (US); Joseph Kent Barbay, Flourtown, PA (US); Scott D. Bembenek, San Diego, CA (US); Min Cai, Shanghai (CN); Wei Chen, Shanghai (CN); Charlotte Pooley Deckhut, San Diego, CA (US); James P. Edwards, Ambler, PA (US); Brahmananda Ghosh, Spring House, PA (US); Baoyu Hao, Shanghai (CN); Kevin D. Kreutter, Arlington, MA (US); Gang Li, Shanghai (CN); Mark S. Tichenor, San Diego, CA (US); Jennifer D. Venable, Solana Beach, CA (US); Jianmei Wei, San Diego, CA (US); John J. M. Wiener, San Diego, CA (US); Yao Wu, Shanghai (CN); Yaoping Zhu, Shanghai (CN); Feihuang Zhang, Shanghai (CN); Zheng Zhang, Shanghai (CN); Kun Xiao, Shanghai (CN)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/374,945

(22) Filed: Dec. 9, 2016

(65) Prior Publication Data

US 2017/0283431 A1 Oct. 5, 2017

Related U.S. Application Data

(60) Provisional application No. 62/265,780, filed on Dec. 10, 2015.

(51) Int. Cl.
*C07D 495/16* (2006.01)
*C07D 519/00* (2006.01)

(52) U.S. Cl.
CPC ......... *C07D 495/16* (2013.01); *C07D 519/00* (2013.01)

(58) Field of Classification Search
CPC ............................ C07D 495/16; C07D 519/00
See application file for complete search history.

(56) References Cited

U.S. PATENT DOCUMENTS

| 5,300,478 A | 4/1994 | Michaely et al. |
| 7,579,356 B2 | 8/2009 | Battista et al. |
| 2006/0058341 A1 | 3/2006 | Connolly et al. |
| 2008/0076921 A1 | 3/2008 | Honigberg et al. |
| 2014/0249105 A1 | 9/2014 | Diverchim |
| 2017/0283430 A1 | 10/2017 | Arora et al. |

FOREIGN PATENT DOCUMENTS

| EP | 0061588 A1 | 10/1982 |
| EP | 0602306 A1 | 6/1994 |
| WO | 2006031929 A2 | 3/2006 |
| WO | WO 2006/118749 | * 9/2006 ........... C07D 495/14 |
| WO | 2006118749 A1 | 11/2006 |
| WO | 2007019191 A2 | 2/2007 |
| WO | 2007092879 A2 | 8/2007 |
| WO | 2010056875 A1 | 5/2010 |
| WO | 2011133609 A3 | 3/2014 |
| WO | 2014139970 A1 | 9/2014 |
| WO | WO 2017/100662 A1 | 6/2017 |
| WO | WO 2017/100668 A1 | 6/2017 |
| WO | WO 2018/103058 A1 | 6/2018 |
| WO | WO 2018/103060 A1 | 6/2018 |

OTHER PUBLICATIONS

West, Anthony R., Solid State Chemistry and Its Applications, Wiley, New York, 1988, 358.*
Corneth et al., "BTK Signaling in B Cell Differentiation and Autoimmunity", Current Topics in Microbiology and Immunology, 2016, pp. 67-105, vol. 393.
Di Paolo, et al., "Specific BTK Inhibition Suppresses B-Cell and Myeloid Cell-Mediated Arthritis", Natre Chemical Biology, vol. 7: pp. 41-50 (Jan. 2011).
Evan, et al., "Inhibition of BTK with CC-292 Provides Early Pharmacodynamic Assessment of Activity in Mice and Humans", The Journal of Pharmacology and Experimental Therapeutics, vol. 346: pp. 219-228 (Aug. 2013).
Hendriks, et al., "Targeting Bruton's Tyrosine Kinase in B Cell Malignancies", Nature Reviews Cancer, vol. 14: pp. 219-232 (Apr. 2014).
Honigberg, et al., "The Bruton Tyrosine Kinase Inhibitor PCI-32765 Blocks B-Cell Activation and is Efficacious in Models of Automimmune Disease and B-cell Malignancy", PNAS, vol. 107 (29): pp. 13075-13080 (Jul. 20, 2010).
Kenny, et al., "Bruton's Tyrosine Kinase Mediates the Syngergistic Signalling between TLR9 and the B Cell Receptor by Regulating Calcium and Calmodulin", PLOS One, vol. 8 (8) e74103: pp. 1-14, (Aug. 2013).

(Continued)

*Primary Examiner* — Erich A Leeser

(57) ABSTRACT

The present disclosure is directed to compounds of formula I' and methods of their use and preparation, as well as compositions comprising compounds of formula I'.

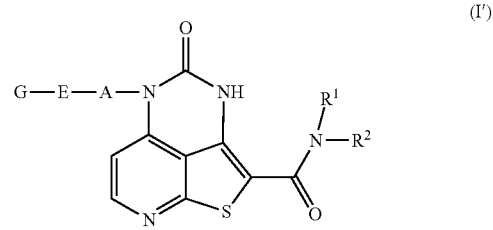

(I')

23 Claims, No Drawings

(56) References Cited

OTHER PUBLICATIONS

Liu, et al., "Antiarthritis Effect of a Novel Bruton's Trosine Kinase (BTK) Inhibitor in Rat Collagen-Induced Arthritis and Mechanism-Based Pharmacokinetic/Pharmacodynamic Modeling: Relationships Between Inhibition of BTK Phosphorylation and Efficacy", The Journal of Pharmacolocy and Experimental Therapeutics, vol. 338 (1): pp. 154-163 (2011).

Svensson, et al., "B cell-deficient mice do not develop type II collagen-induced arthritis (CIA)", Clin Exp Immunol, vol. 111: pp. 521-526 (1998).

International Search Report and Written Opinion Corresponding to International Patent Application No. PCT/US2016/065964, dated Mar. 1, 2017.

Selby, T. P., "Synthesis of a Novel Thiadiazacyclazine", Journal of Organic Chemistry, vol. 53 (10): pp. 2386-2388 (1988).

Jan, et al, "Discovery of Selective Irreverisible Inhibitors for Bruton's Tyrosine Kinase", Chem Med Chem, vol. 2; v. 58-61 (2007).

Kametani, Tetsuji and Sato, Minoru, "Syntheses of heterocyclic compounds. LXXVI. Synthesis of 4-methylpyridine derivatives" Yakugaku Kenkyu (1962) 34, 117-24 English language translation of Abstract only).

Magidson, O. Yu and Menshikov, G. P., "Iodization of α-aminopyridine" Trudy Nauchnoao Khimiko-Farmatsevticheskoao Institute (1926) (No. 16), 23-31 (English language translation of Abstract only).

Kong, W. et al., Increased Expression of Bruton Tyrosine Kinase in Patients with Lupus Nephritis and Its Clinic Significance, 2015 ACR/ARNP Annual Meeting, Sep. 29, 2015, Abstract No. 1848.

Whang, J., et al., Bruton's tyrosine kinase inhibitors for the treatment of rheumatoid arthritis, Drug Discovery Today, vol. 19/No. 8, Aug. 2014, pg. 1200-1201.

Woyach, J., et al., Bruton's tyrosine kinase (BTK) function is important to the development and expansion of chronic lymphocytic leukemia (CLL), Blood, vol. 123/No. 8, Feb. 2014, p. 1207-1213. < https://rarediseases.ordrare-diseases/pemphigush, accessed Jun. 4, 2019.

U.S. Appl. No. 16/413,453, filed May 15, 2019, Nidhi Arora et al.

Rocca, P. et al., "First Metalation of Aryl Iodides: Directed Ortho-Lithiation of Iodopyridines, Halogen-Dance, and Application to Synthesis", J. Org. Chem. 58 (1993) pp. 7832-7838.

International Search Report with Written Opinion Corresponding to PCT/US2016/065954, dated Feb. 9, 2017.

International Search Report with Written Opinion Corresponding to PCT/CN2016/109134, dated Aug. 2, 2017.

International Search Report with Written Opinion Corresponding to PCT/CN2016/109143, dated Sep. 14, 2017.

* cited by examiner

INHIBITORS OF BRUTON'S TYROSINE KINASE AND METHODS OF THEIR USE

CROSS REFERENCE TO RELATED APPLICATION

This application claims the benefit of U.S. Provisional Application No. 62/265,780, filed on Dec. 10, 2015, which is incorporated herein by reference in its entirety.

TECHNICAL FIELD

The present disclosure is directed to small molecule tyrosine kinase inhibitors.

BACKGROUND

Rheumatoid arthritis ("RA") is a chronic, autoimmune, inflammatory disorder that affects the lining of the joints, causing painful swelling that can result in bone erosion and joint deformation. RA presents a significant societal impact—it has a relatively high prevalence (about 1% of the United States population suffers from RA), produces irreversible joint damage, and has a widespread occurrence of co-morbidities. While many patients benefit from currently marketed biologic and small molecule medicines, most patients still suffered from the chronic pain and inflammation of the disease.

Cancer, in particular mantle cell lymphoma, chronic lymphocytic leukemia, macroglobulinemia, and multiple myeloma, continues to afflict patients. Alternative, effective treatments of cancer are still needed.

Human Bruton's tyrosine kinase ("Btk") is a ~76 kDa protein belonging to the Tec family of non-receptor tyrosine kinases. Tec kinases form the second largest family of cytoplasmic tyrosine kinases in mammalian cells, which consists of four other members in addition to BTK: the eponymous kinase TEC, ITK, TXK/RLK and BMX. Tec kinases are evolutionarily conserved throughout vertebrates. They are related to, but structurally distinct from, the larger Src and Syk kinase families. Tec family proteins are abundantly expressed in hematopoietic tissues and play important roles in the growth and differentiation of blood and endothelial cells in mammals.

Based upon Btk expression from IHC studies described in the art, Btk inhibition has the potential to modulate biology associated with B cells, macrophages, mast cells, osteoclasts, and platelet microparticles. Cometh, O. B., et al. Curr. Top. Microbiol. Immunol. *BTK Signaling in B Cell Differentiation and Autoimmunity.* 2015 Sep. 5. The role of B cells in RA is supported by the therapeutic benefit exhibited in the clinic upon B cell depletion with Rituximab™. Since autoreactive antibodies play such a critical role in synovial inflammation, therapeutic modulation of the B cell compartment is an attractive mechanism to treat early RA and potentially modulate disease at the earliest stages. B cell depletion in murine models such as collagen-induced arthritis (CIA) prevents arthritis development. Svensson, et al. (1998) B cell-deficient mice do not develop type II collagen-induced arthritis (CIA). *Clin Exp Immunol* 111, 521-526.

Use of Btk inhibitors in preclinical models support the role of Btk in B cell biology associated with RA. Btk inhibitors block antigen receptor-induced signaling at the earliest stages and subsequent B cell proliferation. In addition, critical aspects of antigen presentation function, such as antigen internalization and upregulation of co-stimulation molecules such as CD80 and CD86 and MHC-IIs can be blocked with Btk inhibitors (Kenny, E. F., et al. (2013) *PLoS One* 8, e74103). Btk inhibitors exhibit efficacy in a variety of rodent arthritis models, whether dosed prophylactically or fully therapeutically (Di Paolo, J. A., et al. *Nat Chem Biol* (2011) 7, 41-50; Liu, L., et al. (2011) *J Pharmacol Exp Ther* 338, 154-163; Honigberg, L. A., et al. (2010) *Proc Natl Acad Sci USA* 107, 13075-13080; Evans, E. K., et al. (2013) *J Pharmacol Exp Ther* 346, 219-228). In addition to ameliorating disease symptoms, Btk inhibition decreases autoantibody production and isotype switching, as well as epitope spreading from bovine collagen to rodent collagen. In addition, Btk inhibition shows significant reductions in inflammation scores as assessed by inflamed paw histopathology. Together, these data provide a rationale for testing Btk inhibitors in inflammatory autoimmune disorders where B cells play a major role. In addition, Btk is a clinically validated target for the treatment of hematological malignancies, with the irreversible covalent inhibitor (ICI) ibrutinib approved for treatment of B cell malignancies such as mantle cell lymphoma, chronic lymphocytic leukemia (CLL) and Waldenström's macroglobulinemia (Hendriks, R. W., et al. (2014) *Nat Rev Cancer* 14, 219-232).

In view of Btk's role in a variety of immunological and oncological pathways, inhibitors of Btk are needed.

SUMMARY

The present disclosure is directed to compounds of formula I:

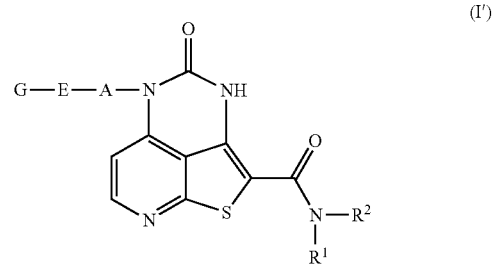

(I')

wherein
$R^1$ is H or $C_{1-6}$alkyl;
$R^2$ is —$C_{0-6}$alk-piperidinyl; —$C_{0-6}$alk-pyrrolidinyl; —$C_{0-6}$alk-oxazepanyl; —$C_{0-6}$alk-azetidinyl; —$C_{0-6}$alk-aziridinyl; —$C_{0-6}$alk-azepanyl; —$C_{0-6}$alk-quinuclidinyl; —$C_{0-6}$alk-imidazolidinyl; —$C_{0-6}$alk-piperazinyl; —$C_{0-6}$alkmorpholinyl; —$C_{0-6}$alk-tetrahydropyranyl; or —$C_{0-6}$alk-tetrahydrofuranyl wherein the $R^2$ is optionally substituted with 1, 2, or 3 substituents independently selected from the group consisting of
—$NR^8$—C(O)—C($R^3$)=C$R^4$($R^5$); —C(O)—C($R^3$)=C$R^4$($R^5$); oxo; halogen; —CN; —OH; —$NR^6R^7$; —$C_{1-6}$alkyl; —$C_{1-6}$alk-OH; —$OC_{1-6}$alkyl; —$C_{3-6}$cycloalkyl; —$C_{1-6}$haloalkyl; —$C_{1-6}$alkaryl; —$SO_2$—$C_{1-6}$alkyl; —$SO_2$—$C_{2-6}$alkenyl; —C(O)H; —C(O)—$C_{1-6}$alkyl; —C(O)—$C_{3-6}$cycloalkyl; —C(O)—$C_{1-6}$haloalkyl; —C(O)—$C_{2-6}$alkynyl; —C(O)—$C_{6-10}$aryl; —C(O)-heteroaryl; —C(O)—$C_{1-6}$alk-CN; —C(O)—$C_{1-6}$alk-OH; —C(O)—$C_{1-6}$alk-$SO_2$—$C_{1-6}$alkyl; —C(O)—O—$C_{1-6}$alkyl; —C(O)—$C_{1-6}$alk-$NR^6R^7$; —C(O)—$C_{1-6}$alk-O—$C_{1-6}$alkyl wherein the —$C_{1-6}$alk- is optionally substituted with —OH, —$OC_{1-6}$alkyl, or —$NR^6R^7$; and —C(O)—$C_{0-6}$alk-heterocycloalkyl wherein the -alk- is optionally substituted with oxo and the heterocycloalkyl is optionally substituted with —$C_{1-6}$alkyl; wherein $R^3$ is H; —CN; halogen; —$C_{1-6}$haloalkyl; or —$C_{1-6}$alkyl;

$R^4$ and $R^5$ are each independently H; halogen; —$C_{1-6}$alkyl; —$OC_{1-6}$alkyl; —$C_{0-6}$alk-$C_{3-6}$cycloalkyl optionally substituted with $C_{1-6}$alkyl; —$C_{0-6}$alk-heterocycloalkyl optionally substituted with —C(O)$C_{1-6}$ alkyl or —$C_{1-6}$alkyl; —$C_{1-6}$alk-OH; —$C_{0-6}$alk-$NR^6R^7$; —$C_{1-6}$alk-O—$C_{1-6}$alkyl; —$C_{1-6}$alk-NH—$C_{0-6}$alk-O—$C_{1-6}$alkyl; —$C_{1-6}$alk-NHSO$_2$—$C_{1-6}$alkyl; —$C_{1-6}$alk-SO$_2$—$C_{1-6}$alkyl; —NHC(O)—$C_{1-6}$alkyl; or -linker-PEG-Biotin; and $R^6$ and $R^7$ are each independently H; —$C_{1-6}$alkyl; —$C_{3-6}$cycloalkyl; C(O)H, or —CN; and $R^8$ is H or $C_{1-6}$alkyl;

A is a bond, pyridyl; phenyl; napthalenyl; pyrimidinyl; pyrazinyl; pyridazinyl; benzo[d][1,3]dioxolyl optionally substituted with halogen; benzothiophenyl; or pyrazolyl; optionally substituted with 1, 2, or 3 substituents independently selected from the group consisting of —$C_{1-6}$alkyl; halogen; —SF$_5$; —$OC_{1-6}$alkyl; —C(O)—$C_{1-6}$alkyl; and —$C_{1-6}$haloalkyl;

E is —O—; a bond; —C(O)—NH—; —CH$_2$—; or —CH$_2$—O—;

G is H; —$C_{3-6}$cycloalkyl; -phenyl; -thiophenyl; —$C_{1-6}$alkyl; -pyrimidinyl; -pyridyl; -pyridazinyl; -benzofuranyl; —$C_{1-6}$ haloalkyl; -heterocycloalkyl that contains an oxygen heteroatom; -phenyl-CH$_2$—O-phenyl; —$C_{1-6}$alk-O—$C_{1-6}$alkyl; —$NR^6R^7$; —SO$_2C_{1-6}$alkyl; or —OH; wherein the phenyl; thiophenyl; pyrimidinyl; pyridyl; pyridazinyl; or benzofuranyl is optionally substituted with 1, 2, or 3 substituents independently selected from the group consisting of halogen; —$C_{1-6}$alkyl; —$C_{1-6}$haloalkyl; —$OC_{1-6}$haloalkyl; —$C_{3-6}$cycloalkyl; —$OC_{1-6}$alkyl; —CN; —OH; —$C_{1-6}$alk-O—$C_{1-6}$alkyl; —C(O)—$NR^6R^7$; and —C(O)—$C_{1-6}$alkyl;

or a stereoisomer or isotopic variant thereof, or a pharmaceutically acceptable salt thereof.

Compositions comprising compounds of formula I are also described. Methods of using compounds of formula I are also within the scope of the disclosure.

DETAILED DESCRIPTION OF ILLUSTRATIVE EMBODIMENTS

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect. Conversely, various features of the disclosed compositions and methods that are, for brevity, described in the context of a single aspect, may also be provided separately or in any subcombination.

The term "alkyl," when used alone or as part of a substituent group, refers to a straight- or branched-chain alkyl group having from 1 to 12 carbon atoms ("$C_{1-12}$"), preferably 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples.

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The term "$C_{1-6}$alk" refers to an aliphatic linker having 1, 2, 3, 4, 5, or 6 carbon atoms and includes, for example, —CH$_2$—, —CH(CH$_3$)—, —CH(CH$_3$)—CH$_2$—, and —C(CH$_3$)$_2$—. The term "—$C_0$alk-" refers to a bond. In some aspects, the $C_{1-6}$alk can be substituted with an oxo group or an —OH group.

The term "alkenyl," when used alone or as part of a substituent group, refers to straight and branched carbon chains having from 2 to 12 carbon atoms ("$C_{2-12}$"), preferably 2 to 6 carbon atoms ("$C_{2-6}$"), wherein the carbon chain contains at least one, preferably one to two, more preferably one double bond. For example, alkenyl moieties include, but are not limited to allyl, 1-propen-3-yl, 1-buten-4-yl, propa-1,2-dien-3-yl, and the like.

The term "alkynyl," when used alone or as part of a substituent group, refers to straight and branched carbon chains having from 2 to 12 carbon atoms ("$C_{2-12}$"), preferably 2 to 6 carbon atoms ("$C_{2-6}$"), wherein the carbon chain contains at least one, preferably one to two, more preferably one triple bond. For example, alkynyl moieties include, but are not limited to vinyl, 1-propyn-3-yl, 2-butyn-4-yl, and the like.

The term "aryl" refers to carbocylic aromatic groups having from 6 to 10 carbon atoms ("$C_{6-10}$") such as phenyl, naphthyl, and the like.

The term "cycloalkyl" refers to monocyclic, non-aromatic hydrocarbon groups having from 3 to 10 carbon atoms ("$C_{3-10}$"), preferably from 3 to 6 carbon atoms ("$C_{3-6}$"). Examples of cycloalkyl groups include, for example, cyclopropyl ($C_3$), cyclobutyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like.

The term "heterocycloalkyl" refers to any five to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahyofuranyl, tetrahydropyranyl, piperazinyl, hexahydro-5H-[1,4]dioxino[2,3-c]pyrrolyl, benzo[d][1,3]dioxolyl, and the like.

The term "heteroaryl" refers to a mono- or bicyclic aromoatic ring structure including carbon atoms as well as up to four heteroatoms selected from nitrogen, oxygen, and sulfur. Heteroaryl rings can include a total of 5, 6, 9, or 10 ring atoms ("$C_{5-10}$"). Examples of heteroaryl groups include but are not limited to, pyrrolyl, furyl, thiophenyl (thienyl), oxazolyl, imidazolyl, purazolyl, isoxazolyl, isothiazolyl, triazolyl, thiadiazolyl, pyrazolyl, pyridyl, pyridazinyl, pyrimidinyl, pyrazinyl, pyranyl, furazanyl, indolizinyl, indolyl, isoindolinyl, indazolyl, benzofuranyl, benzothiophenyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The term "halogen" represents chlorine, fluorine, bromine, or iodine. The term "halo" represents chloro, fluoro, bromo, or iodo.

The term "haloalkyl" refers to an alkyl moiety wherein one or more of the hydrogen atoms has been replaced with one or more halogen atoms. One exemplary substitutent is fluoro. Preferred haloalkyl groups of the disclosure include trihalogenated alkyl groups such as trifluoromethyl groups.

The term "oxo" refers to a =O moiety, wherein two hydrogens from the same carbon atom have be replaced with a carbonyl. For example, an oxo-substituted pyrrolidinyl moiety could be a pyrrolidin-2-one moiety or a pyrrolidin-3-one moiety.

The term "benzofuranyl" represents the following moiety:

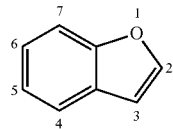

The benzofuranyl moiety can be attached through any one of the 2-, 3-, 4-, 5-, 6-, or 7-carbon atoms.

The term "benzo[d][1,3]dioxolyl" represents the following moiety:

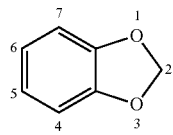

The benzo[d][1,3]dioxolyl moiety can be attached through any one of the 2-, 4-, 5-, 6-, or 7-carbon atoms. In those aspects wherein the "benzo[d][1,3]dioxolyl moiety is substituted with halogen," the following moieties are preferred:

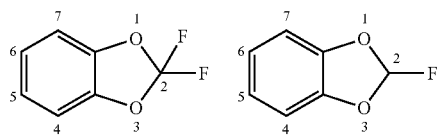

The term "benzothiophenyl" represents the following moiety:

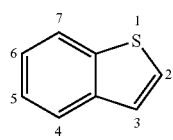

The benzothiophenyl moiety can be attached through any one of the 2-, 3-, 4-, 5-, 6-, or 7-carbon atoms.

The term "phenyl" represents the following moiety:

The phenyl moiety can be attached through any of the carbon atoms.

The term "napthalenyl" (i.e., naphthyl) represents the following moiety:

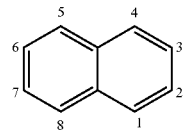

The naphthalenyl moiety can be attached through any one of the 1-, 2-, 3-, 4-, 5-, 6-, 7-, or 8-position carbon atoms.

The term "pyridyl" represents the following moiety:

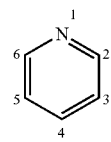

The pyridyl moiety can b attached through any one of the 2-, 3-, 4-, 5-, or 6-position carbon atoms.

The term "pyrimidinyl" represents the following moiety:

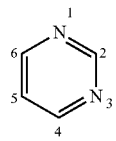

The pyrimidinyl moiety can be attached through any one of the 2-, 4-, 5-, or 6-position carbon atoms.

The term "pyrazinyl" represents the following moiety:

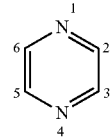

The pyrazinyl moiety can be attached through any one of the 2-, 3-, 5-, or 6-position carbon atoms.

The term "pyridazinyl" represents the following moiety:

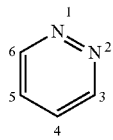

The pyridazinyl moiety can be attached through any one of the 3-, 4-, 5-, or 6-position carbon atoms.

The term "pyrazolyl" represents the following moiety:

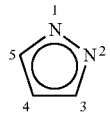

The pyrazolyl moiety can be attached through any one of the 1-, 2-, 3-, 4-, or 5-position carbon atoms.

The term "thiophenyl" represents the following moiety:

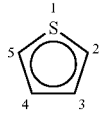

The thiophenyl moiety can be attached through any one of the 2-, 3-, 4-, or 5-position carbon atoms.

The term "linker-PEG-Biotin" refers to a moiety comprising linker-PEG-CH$_2$—NH-biotinyl. Compounds of the disclosure that include a linker-PEG-Biotin moiety can be used according to any of the methods described herein. Alternatively, compounds of the disclosure that include a linker-PEG-Biotin moiety can be used as diagnostic probes according to methods known in the art. Preferred linkers are known in the art, with the linker —CH$_2$—NHC(O)—(CH$_2$)$_3$—C(O)—NH—CH$_2$— being particularly preferred. Preferred PEG moieties include at least two or three repeating —CH$_2$—CH$_2$—O— moieties. A preferred linker-PEG-Biotin moiety is

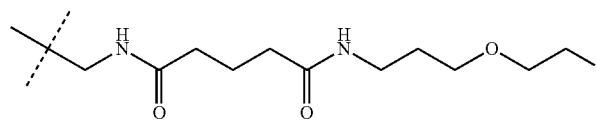

The term "piperidinyl" represents the following moiety:

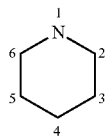

Within the disclosure, when R$^2$ is a C$_0$alk-piperidinyl moiety, it can be attached to the compound of formula I through any one of the 2-, 3-, 4-, 5-, or 6-position atoms. In other aspects, when R$^2$ is a C$_0$alk-piperidinyl moiety, it can be attached to the compound of formula I through any ring atom. Within the disclosure, when R$^2$ is a C$_{1-6}$alk-piperidinyl moiety, it can be attached to the compound of formula I through any one of the 1-, 2-, 3-, 4-, 5-, or 6-position atoms. When the piperidinyl moiety is a substituent, it can be attached through any one of the 1-, 2-, 3-, 4-, 5-, or 6-position atoms.

The term "pyrrolidinyl" represents the following moiety:

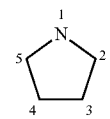

Within the disclosure, when R$^2$ is a C$_0$alk-pyrrolidinyl moiety, it can be attached to the compound of formula I through any one of the 2-, 3-, 4-, or 5-position atoms. In other aspects, when R$^2$ is a C$_0$alk-pyrrolidinyl moiety, it can be attached to the compound of formula I through any ring atom. Within the disclosure, when R$^2$ is a C$_{1-6}$alk-pyrrolidinyl moiety, it can be attached to the compound of formula I through any one of the 1-, 2-, 3-, 4-, or 5-position atoms. When the pyrrolidinyl moiety is a substituent, it can be attached through any one of the 1-, 2-, 3-, 4-, or 5-position atoms.

The term "oxazepanyl" refers to a 7-membered heterocycloalkyl moiety having one ring nitrogen atom and one ring oxygen atom. Examples include 1,3-oxazepanyl and 1,4-oxazepanyl moieties

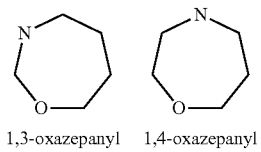

1,3-oxazepanyl    1,4-oxazepanyl

Within the disclosure, when R$^2$ is a C$_0$alk-oxazepanyl moiety, it can be attached to the compound of formula I through any one of the ring carbon atoms. In other aspects, when R$^2$ is a C$_0$alk-oxazepanyl moiety, it can be attached to the compound of formula I through any ring nitrogen or carbon atom. Within the disclosure, when R$^2$ is a C$_{1-6}$alk-oxazepanyl moiety, it can be attached to the compound of formula I through any one of the ring carbon atoms or nitrogen ring atom. When the oxazepanyl moiety is a substituent, it can be attached through any ring carbon atom or through the nitrogen atom.

The term "aziridinyl" represents a 3-membered heterocycloalkyl moiety having one ring nitrogen. Within the disclosure, when R$^2$ is a C$_0$alk-aziridinyl moiety, it can be attached to the compound of formula I through any one of the ring carbon atoms. In other aspects, when R$^2$ is a $C_{1-6}$alk-aziridinyl moiety, it can be attached to the compound of formula I through any one of the ring carbon atoms or the nitrogen ring atom. When the aziridinyl moiety is a substituent, it can be attached through any carbon atom or through the nitrogen atom.

The term "azetidinyl" represents a 4-membered heterocycloalkyl moiety having one ring nitrogen. Within the disclosure, when $R^2$ is an $C_0$alk-azetidinyl moiety, it can be attached to the compound of formula I through any one of the ring carbon atoms. In other aspects, when $R^2$ is a $C_{1-6}$alk-azetidinyl moiety, it can be attached to the compound of formula I through any one of the ring carbon atoms or the nitrogen ring atom. Within the disclosure, when $R^2$ is an $C_{1-6}$alk-azetidinyl moiety, it can be attached to the compound of formula I through any one of the ring carbon atoms or the nitrogen ring atom. When the azetidinyl moiety is a substituent, it can be attached through any carbon atom or through the nitrogen atom.

The term "azepanyl" represents a 7-membered heterocycloalkyl moiety having one ring nitrogen. Within the disclosure, when $R^2$ is an $C_0$alk-azepanyl moiety, it can be attached to the compound of formula I through any one of the ring carbon atoms. In other aspects, when $R^2$ is a $C_{1-6}$alk-azepanyl moiety, it can be attached to the compound of formula I through any one of the ring carbon atoms or the nitrogen ring atom. Within the disclosure, when $R^2$ is an $C_{1-6}$alk-azepanyl moiety, it can be attached to the compound of formula I through any one of the ring carbon atoms or nitrogen ring atom. When the azepanyl moiety is a substitutent, it can be attached through any carbon atom or through the nitrogen atom.

The term "quinuclidinyl" represents the following moiety:

Within the disclosure, when $R^2$ is a quinuclidinyl moiety, or when the quinuclidinyl moiety is a substituent, it can be attached to the compound of formula I through any one of the ring carbon atoms.

The term "imidazolidinyl" represents the following moiety:

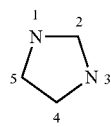

Within the disclosure, when $R^2$ is an $C_0$alk-imidazolidinyl moiety, it can be attached to the compound of formula I through any one of the ring carbon atoms. In other aspects, when $R^2$ is a $C_{1-6}$alk- imidazolidinyl moiety, it can be attached to the compound of formula I through any one of the ring carbon atoms or the nitrogen ring atom. Within the disclosure, when $R^2$ is an $C_{1-6}$alk-imidazolidinyl moiety, it can be attached to the compound of formula I through any one of the ring carbon atoms or any nitrogen ring atom. When the imidazolidinyl moiety is a substituent, it can be attached through any one of the 1-, 2-, 3-, 4-, or 5-position atoms.

The term "piperazinyl" represents the following moiety:

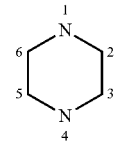

Within the disclosure, when $R^2$ is a $C_0$alk-piperazinyl moiety, it can be attached to the compound of formula I through any one of the ring carbon atoms. In other aspects, when $R^2$ is a $C_{1-6}$alk-piperazinyl moiety, it can be attached to the compound of formula I through any one of the ring carbon atoms or the nitrogen ring atom. Within the disclosure, when $R^2$ is a $C_{1-6}$alk-piperazinyl moiety, it can be attached to the compound of formula I through any one of the ring carbon atoms or nitrogen ring atoms. When the piperazinyl moiety is a substituent, it can be attached through any one of the 1-, 2-, 3-, 4-, 5-, or 6-position atoms.

The term "morpholinyl" represents the following moiety:

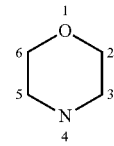

Within the disclosure, when $R^2$ is a $C_0$alk-morpholinyl moiety, it can be attached to the compound of formula I through any one of the ring carbon atoms. In other aspects, when $R^2$ is a $C_{1-6}$alk-morpholinyl moiety, it can be attached to the compound of formula I through any one of the ring carbon atoms or the nitrogen ring atom. Within the disclosure, when $R^2$ is a $C_{1-6}$alk-morpholinyl moiety, it can be attached to the compound of formula I through any one of the ring carbon atoms or nitrogen ring atom. When the morpholinyl moiety is a substituent, it can be attached through any one of the 2-, 3-, 4-, 5-, or 6-position atoms.

The term "tetrahydropyranyl" represents a 6-membered heterocycloalkyl moiety having one ring oxygen. The tetrahydropyranyl moiety can be attached through any carbon atom on the ring.

The term "tetrahydrofuranyl" represents a 5-membered heterocycloalkyl moiety having one ring oxygen. The tetrahydrofuranyl moiety can be attached through any carbon atom on the ring.

As used herein, the term "compound(s) of formula I" includes those compounds of "formula I," as well as compounds of any of the formula I subgenera.

Within the scope of the disclosure, solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3) (November 2005) Hydrates are formed when the solvent is water, or alcoholates are formed when the solvent is alcohol. In some embodiments solvates of the described compounds, or pharmaceutically acceptable salts thereof, are conveniently prepared or formed during the processes described herein. In some embodiments, solvates of the compounds described herein are anhydrous. In some embodiments, the compounds described herein or pharmaceutically acceptable salts thereof, exist in unsolvated form. In some embodiments, the compounds described herein, or pharmaceutically acceptable salts thereof; exist in unsolvated form and are anhydrous.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the disclosure may include the preparation of isotopic variants with radioisotopes, in the instance for example, where the resulting compounds may be used for drug and/or substrate tissue distribution studies. Radiolabeled compounds of the disclosure can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the disclosure, radioactive or not, are intended to be encompassed within the scope of the disclosure.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers.

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Atropisomers" refer to stereoisomers that arise because of hindered rotation around a single bond.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

The present disclosure is directed to compounds of formula I:

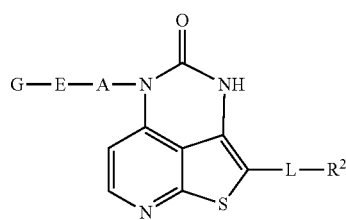

(I)

wherein L is —C(O)NR$^1$—, —C$_{1-6}$alk-NR$^1$—, a bond, or —NR$^1$—C(O)—. In preferred embodiments, L is —C(O)NR$^1$—, corresponding to compounds of formula I':

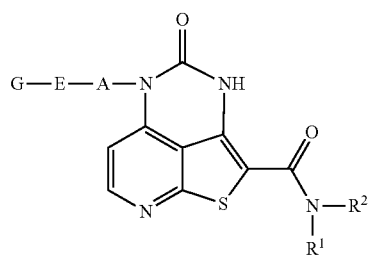

(I')

In other aspects, L is —C$_{1-6}$alk-NR$^1$—, corresponding to compounds of formula I":

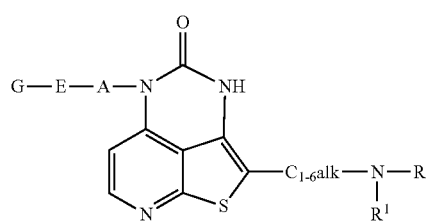

(I")

In other aspects, L is a bond, corresponding to compounds of formula I''':

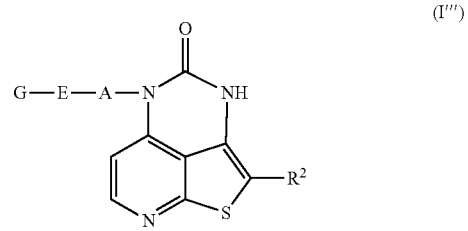

(I''')

In other aspects, L is —NR—C(O)—, corresponding to compounds of formula I'''':

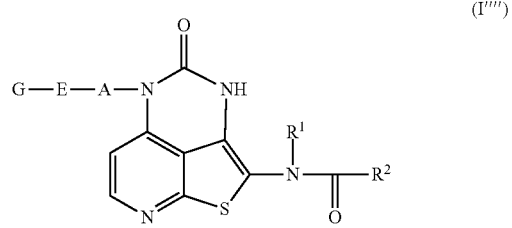

(I'''')

A preferred embodiment of the disclosure is a compound of Formula (I) having the Formula (I'):

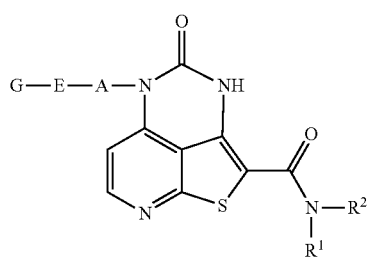

(I')

wherein

R$^1$ is H or C$_{1-6}$alkyl;

R$^2$ is —C$_{0-6}$alk-piperidinyl; —C$_{0-6}$alk-pyrrolidinyl; —C$_{0-6}$alk-oxazepanyl; —C$_{0-6}$alk-azetidinyl; —C$_{0-6}$alk-aziridinyl; —C$_{0-6}$alk-azepanyl; —C$_{0-6}$alk-quinuclidinyl; —C$_{0-6}$alk-imidazolidinyl; —C$_{0-6}$alk-piperazinyl; —C$_{0-6}$alkmorpholinyl; —C$_{0-6}$alk-tetrahydropyranyl; or —C$_{0-6}$alk-tetrahydrofuranyl wherein the $R^2$ is optionally substituted with 1, 2, or 3 substituents independently selected from the group consisting of —NR—C(O)—C($R^3$)═C$R^4$($R^5$); —C(O)—C($R^3$)═C$R^4$($R^5$); oxo; halogen; —CN; —OH; —N$R^6R^7$; —$C_{1-6}$alkyl; —$C_{1-6}$alk-OH; —O$C_{1-6}$alkyl; —$C_{3-6}$cycloalkyl; —$C_{1-6}$haloalkyl; —$C_{1-6}$alkaryl; —SO$_2$—$C_{1-6}$alkyl; —SO$_2$—$C_{2-6}$alkenyl; —C(O)H; —C(O)—$C_{1-6}$alkyl; —C(O)—$C_{3-6}$cycloalkyl; —C(O)—$C_{1-6}$haloalkyl; —C(O)—$C_{2-6}$alkynyl; —C(O)—$C_{6-10}$aryl; —C(O)-heteroaryl; —C(O)—$C_{1-6}$alk-CN; —C(O)—$C_{1-6}$alk-OH; —C(O)—$C_{1-6}$alk-SO$_2$—$C_{1-6}$alkyl; —C(O)—O—$C_{1-6}$alkyl; —C(O)—$C_{1-6}$alk-N$R^6R^7$; —C(O)—$C_{1-6}$alk-O—$C_{1-6}$alkyl wherein the —$C_{1-6}$alk- is optionally substituted with —OH, —O$C_{1-6}$alkyl, or —N$R^6R^7$; and —C(O)—$C_{0-6}$alk-heterocycloalkyl wherein the -alk- is optionally substituted with oxo and the heterocycloalkyl is optionally substituted with —$C_{1-6}$alkyl; wherein $R^3$ is H; —CN; halogen; —$C_{1-6}$haloalkyl; or —$C_{1-6}$alkyl;

$R^4$ and $R^5$ are each independently H; halogen; —$C_{1-6}$alkyl; —O$C_{1-6}$alkyl; —$C_{0-6}$alk-$C_{3-6}$cycloalkyl optionally substituted with $C_{1-6}$alkyl; —$C_{0-6}$alk-heterocycloalkyl optionally substituted with —C(O)$C_{1-6}$alkyl or —$C_{1-6}$alkyl; —$C_{1-6}$alk-OH; —$C_{0-6}$alk-N$R^6R^7$; —$C_{1-6}$alk-O—$C_{1-6}$alkyl; —$C_{1-6}$alk-NH—$C_{0-6}$alk-O—$C_{1-6}$alkyl; —$C_{1-6}$alk-NHSO$_2$—$C_{1-6}$alkyl; —$C_{1-6}$alk-SO$_2$—$C_{1-6}$alkyl; —NHC(O)—$C_{1-6}$alkyl; or -linker-PEG-Biotin; and $R^6$ and $R^7$ are each independently H; —$C_{1-6}$alkyl; —$C_{3-6}$cycloalkyl; C(O)H, or —CN; and $R^8$ is H or $C_{1-6}$alkyl;

A is a bond, pyridyl; phenyl; napthalenyl; pyrimidinyl; pyrazinyl; pyridazinyl; benzo[d][1,3]dioxolyl optionally substituted with halogen; benzothiophenyl; or pyrazolyl; optionally substituted with 1, 2, or 3 substituents independently selected from the group consisting of —$C_{1-6}$alkyl; halogen; —SF$_5$; —O$C_{1-6}$alkyl; —C(O)—$C_{1-6}$alkyl; and —$C_{1-6}$haloalkyl;

E is —O—; a bond; —C(O)—NH—; —CH$_2$—; or —CH$_2$—O—; and

G is H; —$C_{3-6}$cycloalkyl; -phenyl; -thiophenyl; —$C_{1-6}$alkyl; -pyrimidinyl; -pyridyl; -pyridazinyl; -benzofuranyl; —$C_{1-6}$haloalkyl; -heterocycloalkyl that contains an oxygen heteroatom; -phenyl-CH$_2$—O-phenyl; —$C_{1-6}$alk-O—$C_{1-6}$alkyl; —N$R^6R^7$; —SO$_2C_{1-6}$alkyl; or —OH; wherein the phenyl; thiophenyl; pyrimidinyl; pyridyl; pyridazinyl; or benzofuranyl is optionally substituted with 1, 2, or 3 substituents independently selected from the group consisting of halogen; —$C_{1-6}$alkyl; —$C_{1-6}$haloalkyl; —O$C_{1-6}$haloalkyl; —$C_{3-6}$cycloalkyl; —O$C_{1-6}$alkyl; —CN; —OH; —$C_{1-6}$alk-O—$C_{1-6}$alkyl; —C(O)—N$R^6R^7$; and —C(O)—$C_{1-6}$alkyl.

Stereoisomers and isotopic variants of Formula I' are also within the scope of the disclosure. Pharmaceutically acceptable salts of Formula I' are also within the scope of the disclosure.

The present disclosure is preferably directed to compounds of Formula (I')

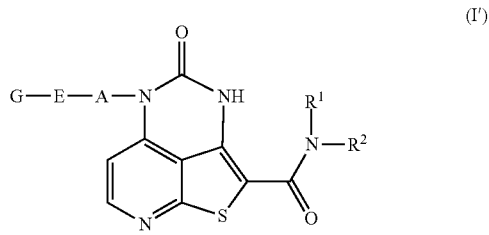

(I')

wherein $R^1$ is H or $C_{1-6}$alkyl;

$R^2$ is selected from the group consisting of: $C_{0-2}$alk-piperidinyl; $C_{0-2}$alk-pyrrolidinyl; oxazepanyl; azetidinyl; azepanyl; quinuclidinyl; $C_2$alk-imidazolidinyl; $C_2$alk-piperazinyl; $C_2$alk-morpholinyl; tetrahydropyranyl; and $C_{0-1}$alk-tetrahydrofuranyl; wherein the $R^2$ is optionally substituted with 1, 2, or 3 substituents each independently selected from the group consisting of:

(C═O)—C($R^3$)═C$R^4$($R^5$); oxo; halogen; OH; NH$_2$; CN; $C_{1-6}$alkyl; $C_{1-6}$alk-OH; O$C_{1-6}$alkyl; $C_{1-6}$haloalkyl; $C_{3-6}$cycloalkyl; SO$_2C_{1-6}$alkyl; SO$_2$—$C_{2-6}$alkenyl; $C_{1-2}$alk-aryl; (C═O)H; (C═O)$C_{1-6}$alkyl; (C═O)$C_{1-6}$haloalkyl; (C═O)—$C_{2-6}$alkenyl; (C═O)—$C_{2-6}$alkynyl; (C═O)$C_{3-6}$cycloalkyl; (C═O)-phenyl; (C═O)-imidazolyl; (C═O)—$C_{1-6}$alkCN; (C═O)—$C_{1-6}$alk-OH; (C═O)—$C_{1-6}$alk-SO$_2C_{1-6}$alkyl; (C═O)—$C_{1-6}$alk-N$R^6R^7$; (C═O)—$C_{1-6}$alk-O—$C_{1-6}$alkyl wherein the —$C_{1-6}$alk- is optionally substituted with OH, O$C_{1-6}$alkyl, or N$R^6R^7$; (C═O)$C_{0-1}$alk-heterocycloalkyl wherein the -alk- is optionally substituted with oxo and the heterocycloalkyl is optionally substituted with $C_{1-6}$alkyl; and NH(C═O)—C($R^3$)═C$R^4$($R^5$);

wherein $R^3$ is selected from the group consisting of: H, CN, halogen, $C_{1-6}$haloalkyl, and $C_{1-6}$alkyl;

$R^4$ and $R^5$ are each independently selected from the group consisting of: H; halogen; $C_{1-6}$alkyl; CH$_2$OH; $C_{1-6}$alk-O$C_{1-6}$alkyl; O$C_{1-6}$alkyl; $C_{1-4}$alk-N$R^6R^7$; $C_{3-6}$cycloalkyl substituted with NH$_2$ or CH$_3$; oxetanyl substituted with CH$_3$; 1-acetylpyrrolidin-2-yl; CH$_2$-pyrrolidinyl; CH$_2$-piperidinyl; C(CH$_3$)$_2$-piperidinyl; CH$_2$-morpholinyl; C(CH$_3$)$_2$-morpholinyl; CH$_2$-(4aR,7aS)-tetrahydro-2H-[1,4]dioxino[2,3-c] pyrrol-6(3H)-yl; C(CH$_3$)$_2$NH(CH$_2$CH$_2$OCH$_3$); CH$_2$SO$_2$CH$_3$; CH$_2$NHSO$_2$CH$_3$; NH(C═O)$C_{1-6}$alkyl; and linker-PEG-Biotin; and $R^6$ and $R^7$ are each independently selected from the group consisting of: H, $C_{1-6}$alkyl, cyclopropyl, (C═O)H, and CN;

A is selected from the group consisting of: a bond, phenyl; naphthalenyl, pyridyl; pyrimidinyl; pyrazinyl; pyridazinyl; benzothiophenyl; and pyrazolyl; wherein the A is optionally substituted with 1, 2, or 3 substituents each independently selected from the group consisting of: $C_{1-6}$alkyl, halogen, O$C_{1-6}$alkyl, (C═O)$C_{1-6}$alkyl, and $C_{1-6}$haloalkyl;

E is selected from the group consisting of: —O—, a bond, (C═O)—NH, CH$_2$, and CH$_2$—O; and G is selected from the group consisting of: H, $C_{1-6}$alkyl; $C_{1-6}$haloalkyl; $C_{1-6}$alk-O$C_{1-6}$alkyl; N$R^6R^7$; SO$_2C_{1-6}$alkyl; OH; $C_{3-6}$cycloalkyl; phenyl; thiophenyl; pyrimidinyl; pyridyl; pyridazinyl; benzofuranyl; heterocycloalkyl that contains an oxygen heteroatom; phenyl-CH$_2$—O-phenyl; wherein the phenyl, thiophenyl, pyrimidinyl, pyridyl, pyridazinyl, or benzofuranyl is optionally substituted with 1, 2, or 3 substituents each independently selected from the group consisting of: halogen, C$_{1-6}$alkyl, C$_{1-6}$haloalkyl, OC$_{1-6}$haloalkyl, OC$_{1-6}$alkyl, OC$_{1-6}$alkyl-OC$_{1-6}$alkyl, C$_{3-6}$cycloalkyl, CN, OH, NH$_2$, N(CH$_3$)$_2$, C$_{1-6}$alk-OC$_{1-6}$alkyl, SO$_2$C$_{1-6}$alkyl, (C=O)—NR$^6$R$^7$, SF$_5$, and (C=O)C$_{1-6}$alkyl.

Stereoisomers and isotopic variants, pharmaceutically acceptable salts, N-oxides, and solvates of Formula I' are also within the scope of the disclosure.

An additional embodiment of the disclosure is directed to compounds of Formula (II'), as well as the stereoisomers, isotopic variants, and pharmaceutically acceptable salt thereof:

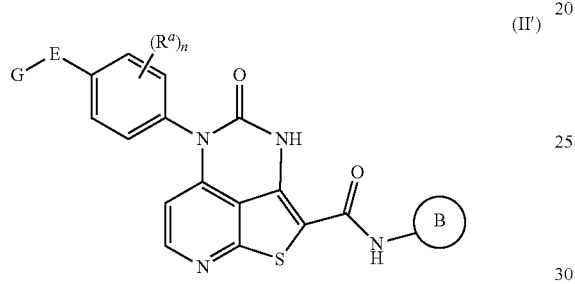

(II')

wherein
R$^a$ is independently selected from the group consisting of: H, Cl, F, CH$_3$, and CF$_3$; n is 0-2;
E is O;
G is selected from the group consisting of: C$_{3-6}$cycloalkyl; oxetanyl; tetrahydrofuranyl; tetrahydropyranyl; benzofuran-7-yloxy; pyridyl; pyridyl substituted with CH$_3$; phenyl; phenyl substituted with one or two members independently selected from the group consisting of: halogen, C$_{1-6}$alkyl, C$_{1-6}$haloalkyl, OH, OC$_{1-6}$alkyl, OC$_{1-6}$haloalkyl, CH$_2$OCH$_3$, (C=O)NH$_2$, and C$_{3-6}$cycloalkyl; and

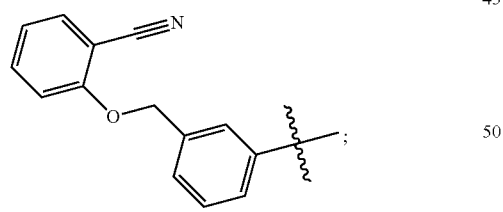

Ring B is selected from the group consisting of:
(a)

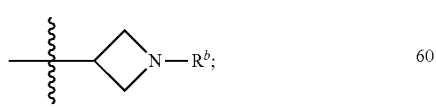

where R$^b$ is selected from the group consisting of: H; C$_{1-6}$alkyl, C$_{3-6}$cycloalkyl, (C=O)CH=CH$_2$, (C=O)CH$_2$CH$_2$OCH$_3$, (C=O)CH$_2$CH$_2$SO$_2$CH$_3$, and

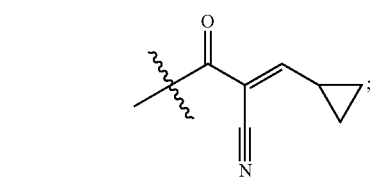

(b)

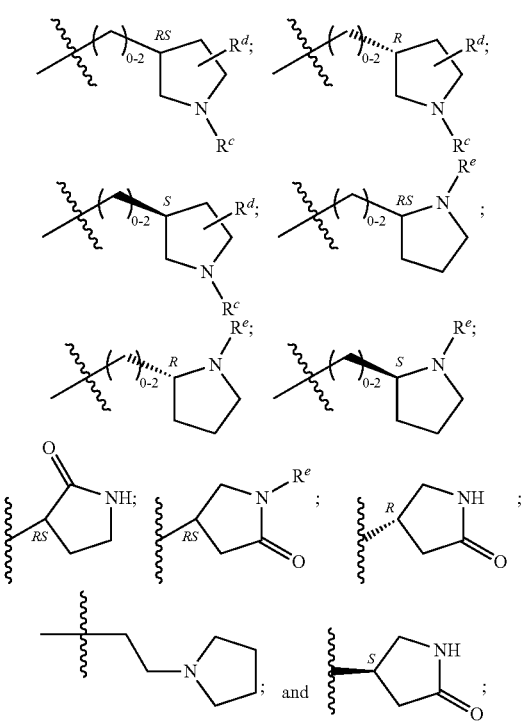

where R$^c$ is selected from the group consisting of: H, C$_{1-6}$alkyl, CN, (C=O)C$_{1-3}$alkyl, (C=O)CH=CH$_2$, C$_{3-6}$cycloalkyl, (C=O)CH$_2$NH$_2$, (C=O)CH$_2$NH(CH$_3$), (C=O)CH$_2$N(CH$_3$)$_2$, (C=O)CH$_2$CN, CH$_2$-phenyl, (C=O)CH$_2$Cl, (C=O)CH=CHCH$_2$NH$_2$, (C=O)CH$_2$CH$_2$OCH$_3$, (C=O)CH=CHCH$_2$NH(CH$_3$), (C=O)CH=CHCH$_2$N(CH$_3$)$_2$, (C=O)CH=CHCH$_2$OH, (C=O)-phenyl, SO$_2$CH=CH$_2$, (C=O)CH$_2$CH$_2$SO$_2$CH$_3$,

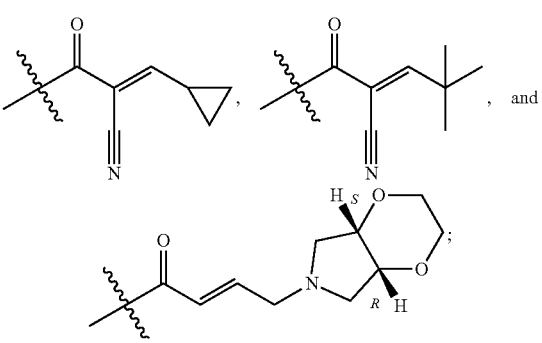

R$^d$ is selected from the group consisting of: H, F, OH, and OCH$_3$;
R$^e$ is H or C$_{1-6}$alkyl;

(c)

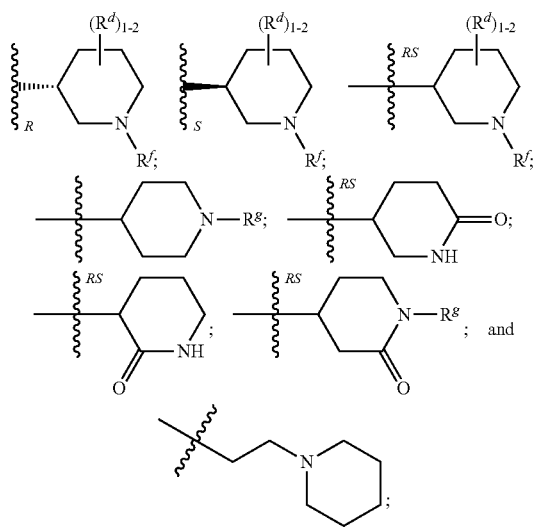

where
- $R^d$ is selected from the group consisting of: H, F, OH, and $OCH_3$;
- $R^f$ is selected from the group consisting of: (C=O)—C($R^3$)=C$R^4$($R^5$); H; $C_{1-6}$alkyl; CN; (C=O)$C_{1-3}$alkyl; (C=O)$C_{1-3}$haloalkyl; (C=O)$C_{2-6}$alkenyl; (C=O)$C_{2-6}$alkynyl; (C=O)(CH$_2$)$_{1-2}$OH; (C=O)(CH$_2$)$_{1-2}$OCH$_3$; (C=O)H; (C=O)(CH$_2$)$_{0-1}$CN; (C=O)CH$_2$NH$_2$; (C=O)(CH$_2$)$_{1-2}$NH(CH$_3$); (C=O)(CH$_2$)$_{1-2}$N(CH$_3$)$_2$; (C=O)CH(CH$_3$)NH(CH$_3$); (C=O)(CH$_2$)$_{1-2}$SO$_2$CH$_3$; (C=O)CH$_2$CH(CH$_3$)(OCH$_3$); (C=O)CH(CH$_3$)CH$_2$(OH); (C=O)CH(CH$_3$)CH$_2$(OCH$_3$); (C=O)C(CH$_3$)$_2$CH$_2$(OCH$_3$); (C=O)CH$_2$C(CH$_3$)$_2$(OCH$_3$); (C=O)CH(NH$_2$)CH$_2$(OCH$_3$); (C=O)CH(OCH$_3$)CH$_2$(OCH$_3$); (C=O)CH(OH)CH$_2$(OCH$_3$);

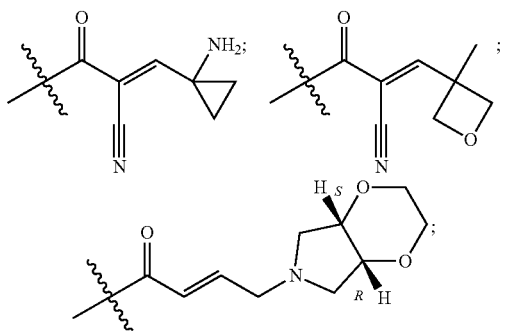

$C_{3-6}$cycloalkyl; (C=O)(CH$_2$)$_{0-1}$azetidinyl; (C=O)oxetanyl; (C=O)tetrahydrofuranyl; (C=O)tetrahydropyranyl; (C=O)(CH$_2$)$_{0-1}$pyrrolidinyl, wherein said pyrrolidinyl is optionally substituted with CH$_3$; (C=O)(CH$_2$)$_{0-1}$piperidinyl; (C=O)(CH$_2$)$_{0-1}$morpholinyl; SO$_2$—C$_{2-6}$alkenyl; SO$_2$C$_{1-6}$ alkyl; and linker-PEG-Biotin;

- $R^3$ is selected from the group consisting of H, CN, halogen, $C_{1-6}$haloalkyl, and $C_{1-6}$alkyl;
- $R^4$ and $R^5$ are each independently selected from the group consisting of: H; halogen; $C_{1-6}$alkyl; CH$_2$OH; $C_{1-6}$alk-O$C_{1-6}$alkyl; O$C_{1-6}$alkyl; $C_{1-4}$alk-NR$^6$R$^7$; $C_{3-6}$cycloalkyl substituted with NH$_2$ or CH$_3$; oxetanyl substituted with CH$_3$; 1-acetylpyrrolidin-2-yl; CH$_2$-pyrrolidinyl; CH$_2$-piperidinyl; C(CH$_3$)$_2$-piperidinyl; CH$_2$-morpholinyl; C(CH$_3$)$_2$-morpholinyl; CH$_2$-(4aR,7aS)-tetrahydro-2H-[1,4]dioxino[2,3-c]pyrrol-6(3H)-yl; C(CH$_3$)$_2$NH(CH$_2$CH$_2$OCH$_3$); CH$_2$SO$_2$CH$_3$; CH$_2$NHSO$_2$CH$_3$; NH(C=O)$C_{1-6}$ alkyl; and linker-PEG-Biotin; and
- $R^6$ and $R^7$ are each independently selected from the group consisting of: H, $C_{1-6}$alkyl, $C_{3-6}$cycloalkyl, and CN;
- $R^g$ is selected from the group consisting of H, $C_{1-6}$alkyl, and CN; and (d)

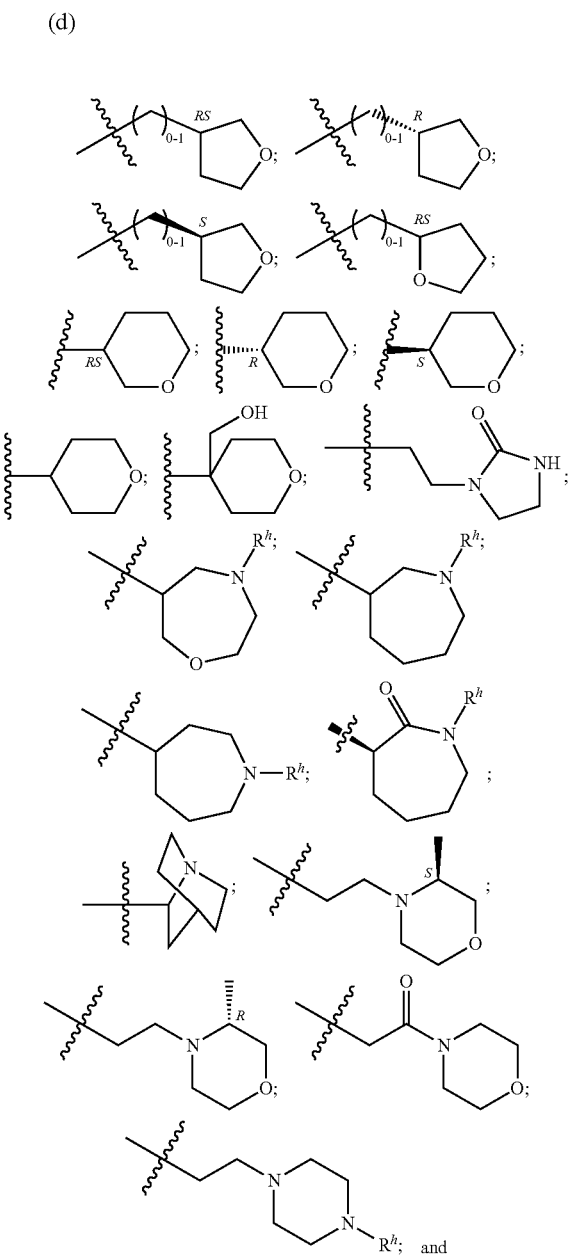

-continued

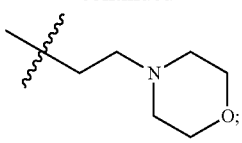

and where $R^h$ is selected from the group consisting of H, CN, $CH_3$, and $CH_2$phenyl.

An additional embodiment of the disclosure is directed to compounds of Formula (III'), as well as the stereoisomers, isotopic variants, and pharmaceutically acceptable salt thereof:

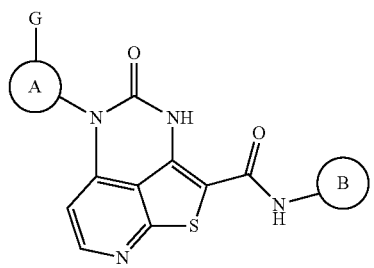

(III')

wherein
G-A is selected from the group consisting of:

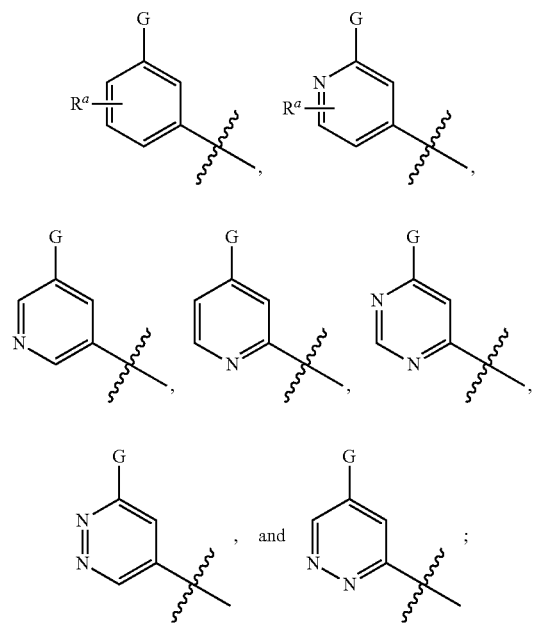

where G is phenyl; or phenyl substituted with one or two members independently selected from the group consisting of: halogen, $C_{1-6}$alkyl, $C_{1-6}$haloalkyl, $C_{3-6}$cycloalkyl, pyridyl, oxetan-3-yl, and tetrahydro-2H-pyran-4-yl;

$R^a$ is H or $CH_3$;

Ring B is selected from the group consisting of:

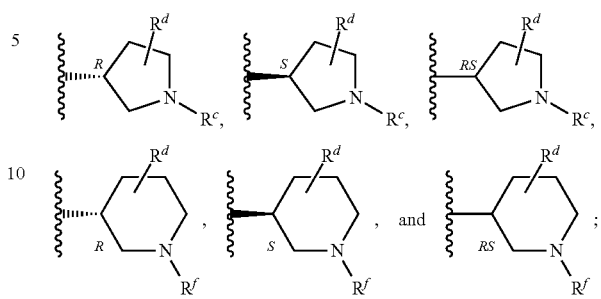

where $R^c$ and $R^f$ are independently selected from the group consisting of: H, $C_{1-6}$alkyl, $(C=O)CH=CH_2$, $(C=O)CH_2NH(CH_3)$, $(C=O)CH=CHCH_2N(CH_3)_2$, and

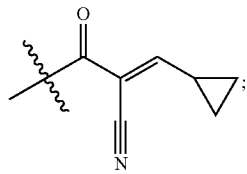 [SMILES: *C(=O)/C(C#N)=C/C1CC1]

and $R^d$ is selected from the group consisting of: H, OH and $OCH_3$.

An additional embodiment of the disclosure is directed to compounds of Formula (IV'), as well as the stereoisomers, isotopic variants, and pharmaceutically acceptable salt thereof:

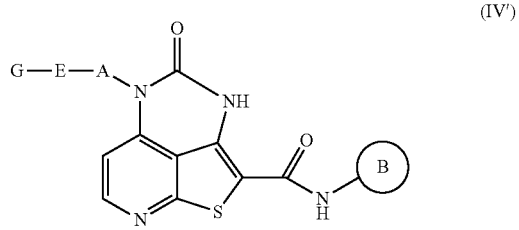

(IV')

wherein
G-E-A is selected from the group consisting of:

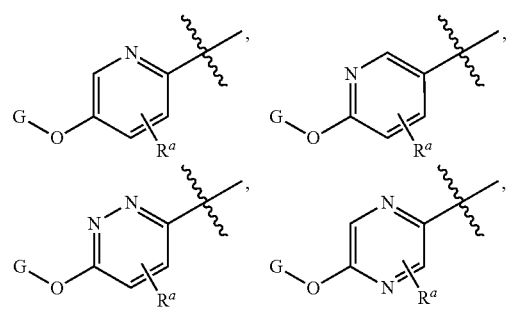

-continued

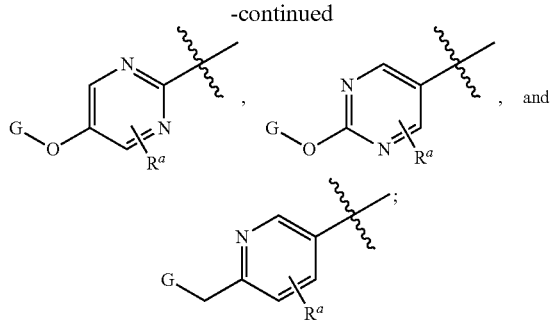

where G is selected from the group consisting of: $C_{1-6}$alkyl, $C_{3-6}$cycloalkyl, tetrahydro-2H-pyran-4-yl, pyridazin-3-yl, phenyl, and phenyl substituted with F;
$R^a$ is H or $CH_3$;
Ring B is selected from the group consisting of:

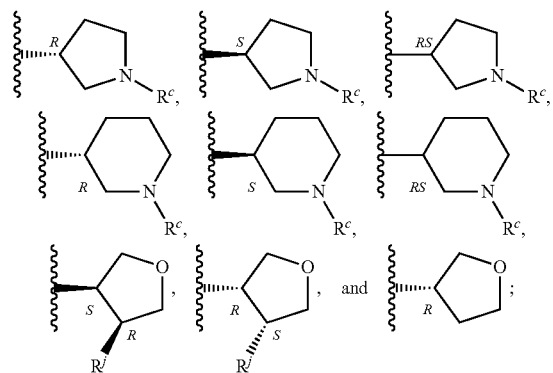

$R^c$ is selected from the group consisting of: H, $C_{1-6}$alkyl, $(C=O)C_{1-3}$alkyl, $(C=O)CH=CH_2$, $(C=O)C_{1-6}$haloalkyl,

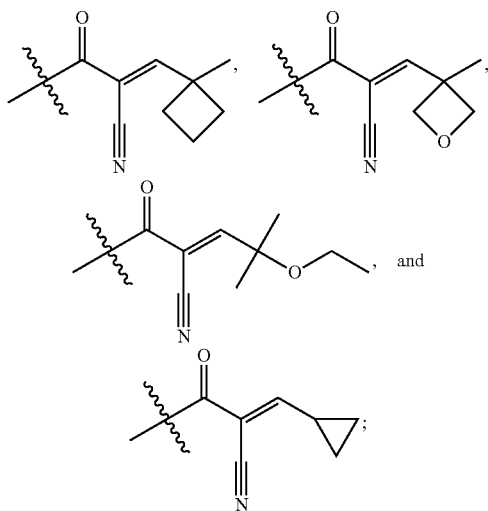

and
$R^j$ is selected from the group consisting of: H, $NH_2$, and $NH(C=O)CH=CH_2$.

An additional embodiment of the disclosure is directed to compounds of Formula (V'), as well as the stereoisomers, isotopic variants, and pharmaceutically acceptable salt thereof:

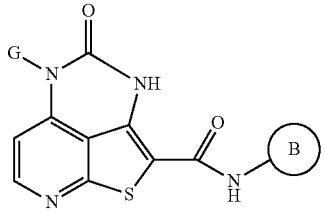

(V')

wherein
G is selected from the group consisting of: $C_{1-6}$alkyl; $C_{1-6}$haloalkyl; phenyl; phenyl substituted with one or two members independently selected from the group consisting of: halogen, $C_{1-6}$alkyl, $C_{1-6}$haloalkyl, $OC_{1-6}$alkyl, $OC_{1-6}$haloalkyl, $(C=O)$—$C_{1-6}$alkyl, $SF_5$, OH, $NH_2$, $N(CH_3)_2$, $OCH_2CH_2OCH(CH_3)_2$, and $SO_2C_{1-6}$alkyl; benzo[d][1,3]dioxolyl optionally substituted with Cl; 2-methylpyridin-3-yl; 2-isopropylpyridin-4-yl; benzothiophenyl; napthalenyl; and 2,2-difluorobenzo[d][1,3]dioxol-5-yl;
Ring B is selected from the group consisting of:

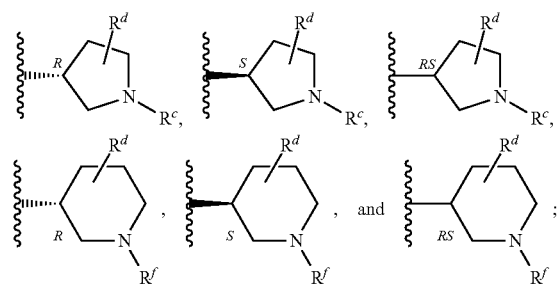

where $R^e$ and $R^f$ are independently selected from the group consisting of: H, $C_{1-6}$alkyl, $(C=O)C_{1-3}$alkyl, $(C=O)CH=CH_2$, $(C=O)CH_2NHCH_3$,

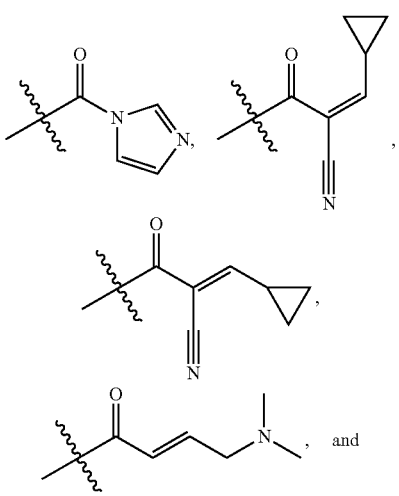

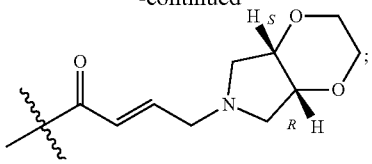

and $R^d$ is H or OH.

According to the disclosure, $R^1$ is H or $C_{1-6}$alkyl. In some aspects, $R^1$ is $C_{1-6}$alkyl, for example, methyl, ethyl, n-propyl, isopropyl, n-butyl, s-butyl, or t-butyl. In preferred aspects, $R^1$ is H.

According to the disclosure $R^2$ is a $C_{0-6}$ alk-heterocycloalkyl moiety that is unsubstituted or substituted with 1, 2, or 3 substituents. In those embodiments wherein $R^2$ is —$C_0$ alk-heterocycloalkyl, the heterocycloalkyl is directly attached to the compound of formula I through a bond. In those aspects wherein $R^2$ is a —$C_{1-6}$ alk-heterocycloalkyl moiety, the heterocycloalkyl moiety is attached to the compound of formula I through an aliphatic linker having 1, 2, 3, 4, 5, or 6 carbon atoms, wherein the $C_{1-6}$ alk includes, for example, —$CH_2$—, —$CH(CH_3)$—, —$CH(CH_3)$—$CH_2$—, and —$C(CH_3)_2$—. In some embodiments, the $C_{1-6}$ alk linker is substituted by oxo, e.g, —$CH_2$—$C(O)$—. In preferred aspects, $R^2$ is —$C_{0-1}$ alk-heterocycloalkyl, for example —$C_0$alk-heterocycloalkyl (i.e., -heterocycloalkyl) or —$C_1$ alk-heterocycloalkyl (i.e., —$CH_2$-heterocycloalkyl).

In preferred aspects, the $R^2$ heterocycloalkyl moiety is a 3-, 4-, 5-, or 6-membered heterocycloalkyl, preferably a 5- or 6-membered heterocycloalkyl, with a 6-membered heterocycloalkyl being most preferred. According to the disclosure, the heterocycloalkyl moiety can include one nitrogen atom, two nitrogen atoms, one nitrogen atom and one oxygen atom, or one oxygen atom. Preferred one nitrogen-containing heterocycloalkyl groups for $R^2$ are piperidinyl; pyrrolidinyl; azetidinyl; azepanyl; aziridinyl; and quinuclidinyl, with piperidinyl and pyrrolidinyl being preferred and piperidinyl being more preferred. Preferred two nitrogen-containing heterocycloalkyl groups for $R^2$ are imidazolidinyl and piperazinyl. Preferred one nitrogen, one oxygen containing heterocycloalkyl groups for $R^2$ are oxazepanyl, with 1,4-oxazepanyl being preferred; and morpholinyl. Preferred one oxygen-containing heterocycloalkyl groups for $R^2$ are tetrahydropyranyl and tetrahydrofuranyl.

In some aspects of the disclosure, $R^2$ is —$C_{0-6}$alk-piperidinyl, preferably —$C_0$ alk-piperidinyl or —$C_1$ alk-piperidinyl, optionally substituted with 1, 2, or 3 substituents as recited herein. In more preferred aspects, $R^2$ is —$C_{0-6}$alk-piperidinyl, preferably —$C_0$ alk-piperidinyl or —$C_1$ alk-piperidinyl, substituted with 1 or 2 substituents as recited herein. The substituents can be attached through any position on the piperidinyl ring. In preferred aspects, at least one substituent is attached through the piperidinyl nitrogen atom.

In some aspects of the disclosure, $R^2$ is —$C_{0-6}$alk-pyrrolidinyl, preferably —$C_0$ alk-pyrrolidinyl or —$C_1$ alk-pyrrolidinyl, optionally substituted with 1, 2, or 3 substituents as recited herein. In more preferred aspects, $R^2$ is —$C_{0-6}$alk-pyrrolidinyl, preferably —$C_0$ alk-pyrrolidinyl or —$C_1$ alk-pyrrolidinyl, substituted with 1 or 2 substituents as recited herein. The substituents can be attached through any position on the pyrrolidinyl ring. In preferred aspects, at least one substituent is attached through the pyrrolidinyl nitrogen atom.

In some aspects of the disclosure, $R^2$ is —$C_{0-6}$alk-oxazepanyl, preferably —$C_0$ alk-oxazepanyl or —$C_1$ alk-oxazepanyl, optionally substituted with 1, 2, or 3 substituents as recited herein. In more preferred aspects, $R^2$ is —$C_{0-6}$alk- oxazepanyl, preferably —$C_0$ alk-oxazepanyl or —$C_1$ alk-oxazepanyl, substituted with 1 or 2 substituents as recited herein. The substituents can be attached through any position on the oxazepanyl ring. In some aspects, at least one substituent is attached through the oxazepanyl nitrogen atom.

In some aspects of the disclosure, $R^2$ is —$C_{0-6}$alk-azetidinyl, preferably —$C_0$ alk-azetidinyl or —$C_1$ alk-azetidinyl, optionally substituted with 1, 2, or 3 substituents as recited herein. In more preferred aspects, $R^2$ is —$C_{0-6}$alk-azetidinyl, preferably —$C_0$ alk-azetidinyl or —$C_1$ alk-azetidinyl, substituted with 1 or 2 substituents as recited herein. The substituents can be attached through any position on the azetidinyl ring. In some aspects, at least one substituent is attached through the azetidinyl nitrogen atom.

In some aspects of the disclosure, $R^2$ is —$C_{0-6}$alk-azepanyl, preferably —$C_0$ alk-azepanyl or —$C_1$ alk-azepanyl, optionally substituted with 1, 2, or 3 substituents as recited herein. In more preferred aspects, $R^2$ is —$C_{0-6}$alk-azepanyl, preferably —$C_0$ alk-azepanyl or —$C_1$ alk-azepanyl, substituted with 1 or 2 substituents as recited herein. The substituents can be attached through any position on the azepanyl ring. In some aspects, at least one substituent is attached through the azepanyl nitrogen atom.

In some aspects of the disclosure, $R^2$ is —$C_{0-6}$alk-aziridinyl, preferably —$C_0$ alk-aziridinyl or —$C_1$ alk-aziridinyl, optionally substituted with 1, 2, or 3 substituents as recited herein. In more preferred aspects, $R^2$ is —$C_{0-6}$alk-aziridinyl, preferably —$C_0$ alk-aziridinyl or —$C_1$ alk-aziridinyl, substituted with 1 or 2 substituents as recited herein. The substituents can be attached through any position on the aziridinyl ring. In some aspects, at least one substituent is attached through the azepanyl nitrogen atom.

In some aspects of the disclosure, $R^2$ is —$C_{0-6}$alk-quinuclidinyl, preferably —$C_0$ alk-quinuclidinyl or —$C_1$ alk-quinuclidinyl, optionally substituted with 1, 2, or 3 substituents as recited herein. In more preferred aspects, $R^2$ is —$C_{0-6}$alk-quinuclidinyl, preferably —$C_0$ alk-quinuclidinyl or —$C_1$ alk-quinuclidinyl, substituted with 1 or 2 substituents as recited herein. The substituents can be attached through any position on the quinuclidinyl ring.

In some aspects of the disclosure, $R^2$ is —$C_{0-6}$alk-imidazolidinyl, preferably —$C_0$ alk-imidazolidinyl or —$C_1$ alk-imidazolidinyl, optionally substituted with 1, 2, or 3 substituents as recited herein. In more preferred aspects, $R^2$ is —$C_{0-6}$alk-imidazolidinyl, preferably —$C_0$ alk-imidazolidinyl or —$C_1$ alk-imidazolidinyl, substituted with 1 or 2 substituents as recited herein. The substituents can be attached through any position on the imidazolidinyl ring. In some aspects, at least one substituent is attached through one of the imidazolidinyl nitrogen atoms.

In some aspects of the disclosure, $R^2$ is —$C_{0-6}$alk-piperazinyl, preferably —$C_0$ alk-piperazinyl or —$C_1$ alk-piperazinyl, optionally substituted with 1, 2, or 3 substituents as recited herein. In more preferred aspects, $R^2$ is —$C_{0-6}$alk-piperazinyl, preferably —$C_0$ alk-piperazinyl or —$C_1$ alk-piperazinyl, substituted with 1 or 2 substituents as recited herein. The substituents can be attached through any position on the piperazinyl ring. In some aspects, at least one substituent is attached through one of the piperazinyl nitrogen atoms.

In some aspects of the disclosure, $R^2$ is —$C_{0-6}$alk-morpholinyl, preferably —$C_0$ alk-morpholinyl or —$C_1$ alkmorpholinyl, optionally substituted with 1, 2, or 3 substituents as recited herein. In more preferred aspects, $R^2$ is $—C_{0-6}$alk-morpholinyl, preferably $—C_0$ alk-morpholinyl or $—C_1$ alk-morpholinyl, substituted with 1 or 2 substituents as recited herein. The substituents can be attached through any position on the morpholinyl ring. In some aspects, at least one substituent is attached the morpholinyl nitrogen atom.

In some aspects of the disclosure, $R^2$ is $—C_{0-6}$alk-tetrahydropyranyl, preferably $—C_0$ alk-tetrahydropyranyl or $—C_1$ alk-tetrahydropyranyl, optionally substituted with 1, 2, or 3 substituents as recited herein. In more preferred aspects, $R^2$ is $—C_{0-6}$alk-tetrahydropyranyl, preferably $—C_0$ alk-tetrahydropyranyl or $—C_1$ alk-tetrahydropyranyl, substituted with 1 or 2 substituents as recited herein. The substituents can be attached through any carbon atom on the tetrahydropyranyl ring.

In some aspects of the disclosure, $R^2$ is $—C_{0-6}$alk-tetrahydrofuranyl, preferably $—C_0$ alk-tetrahydrofuranyl or $—C_1$ alk-tetrahydrofuranyl, optionally substituted with 1, 2, or 3 substituents as recited herein. In more preferred aspects, $R^2$ is $—C_{0-6}$alk-tetrahydrofuranyl, preferably $—C_0$ alk-tetrahydrofuranyl or $—C_1$ alk-tetrahydrofuranyl, substituted with 1 or 2 substituents as recited herein. The substituents can be attached through any carbon atom on the tetrahydrofuranyl ring.

In preferred aspects of the disclosure, $R^2$ is piperidinyl, $CH_2CH_2$-piperidinyl, pyrrolidinyl, $CH_2$-pyrrolidinyl, or $CH_2CH_2$-pyrrolidinyl. In other preferred aspects, $R^2$ is azetidinyl; azepanyl; quinuclidinyl; $CH_2CH_2$-imidazolidinyl; or $CH_2CH_2$-piperazinyl. In some aspects, $R^2$ is oxazepanyl or $CH_2CH_2$-morpholinyl, $CH_2(C=O)$-morpholinyl. In other aspects, $R^2$ is tetrahydropyranyl or tetrahydrofuranyl, or $CH_2$-tetrahydrofuranyl.

In some aspects, the $R^2$ moiety can be defined as "Ring B." In some aspects, particularly those wherein the compound is of Formula (II'), Ring B is

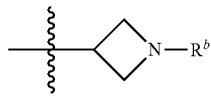

wherein $R^b$ is selected from the group consisting of: H; $C_{1-6}$alkyl, $C_{3-6}$cycloalkyl, $(C=O)CH=CH_2$, $(C=O)CH_2CH_2OCH_3$, $(C=O)CH_2CH_2SO_2CH_3$, and

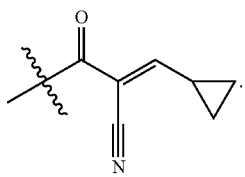 [SMILES: *C(=O)/C(C#N)=C/C1CC1]

In other aspects, Ring B is selected from the group consisting of:

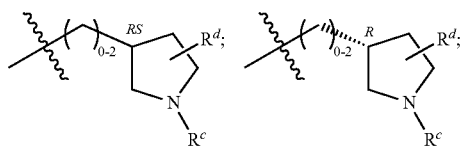

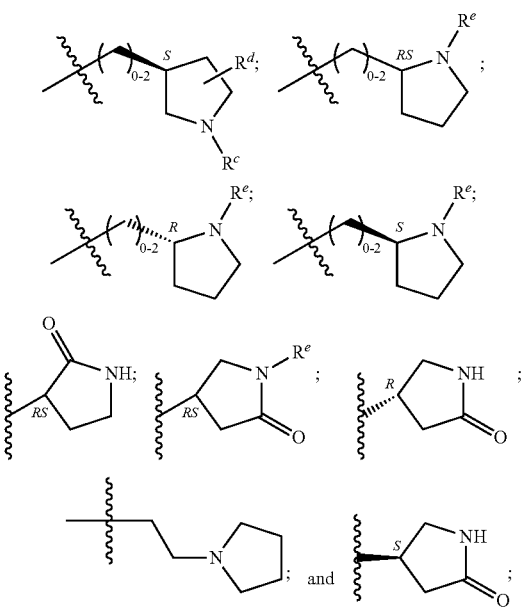

wherein $R^c$ is selected from the group consisting of: H, $C_{1-6}$alkyl, CN, $(C=O)C_{1-3}$alkyl, $(C=O)CH=CH_2$, $C_{3-6}$cycloalkyl, $(C=O)CH_2NH_2$, $(C=O)CH_2NH(CH_3)$, $(C=O)CH_2N(CH_3)_2$, $(C=O)CH_2CN$, $CH_2$-phenyl, $(C=O)CH_2Cl$, $(C=O)CH=CHCH_2NH_2$, $(C=O)CH_2CH_2OCH_3$, $(C=O)CH=CHCH_2NH(CH_3)$, $(C=O)CH=CHCH_2N(CH_3)_2$, $(C=O)CH=CHCH_2OH$, $(C=O)$-phenyl, $SO_2CH=CH_2$, $(C=O)CH_2CH_2SO_2CH_3$,

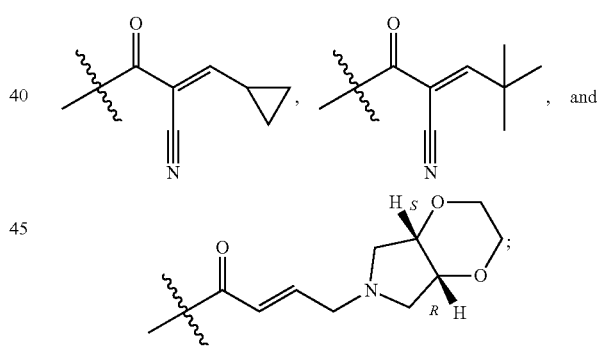

$R^d$ is selected from the group consisting of: H, F, OH, and $OCH_3$; and $R^e$ is H or $C_{1-6}$alkyl. In other aspects, Ring B is selected from the group consisting of

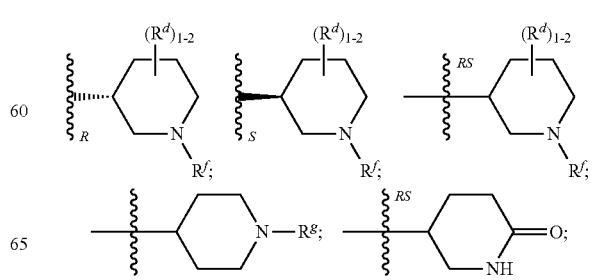

-continued

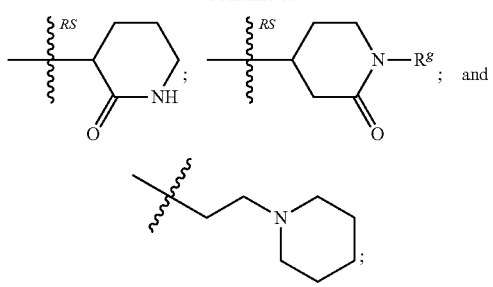

wherein $R^d$ is selected from the group consisting of: H, F, OH, and OCH$_3$; $R^f$ is selected from the group consisting of: (C=O)—C(R$^3$)=CR$^4$(R$^5$); H; C$_{1-6}$alkyl; CN; (C=O)C$_{1-3}$alkyl; (C=O)C$_{1-3}$haloalkyl; (C=O)C$_{2-6}$alkenyl; (C=O)C$_{2-6}$alkynyl; (C=O)(CH$_2$)$_{1-2}$OH; (C=O)(CH$_2$)$_{1-2}$OCH$_3$; (C=O)H; (C=O)(CH$_2$)$_{0-1}$CN; (C=O)CH$_2$NH$_2$; (C=O)(CH$_2$)$_{1-2}$NH(CH$_3$); (C=O)(CH$_2$)$_{1-2}$N(CH$_3$)$_2$; (C=O)CH(CH$_3$)NH(CH$_3$); (C=O)(CH$_2$)$_{1-2}$SO$_2$CH$_3$; (C=O)CH$_2$CH(CH$_3$)(OCH$_3$); (C=O)CH(CH$_3$)CH$_2$(OH); (C=O)CH(CH$_3$)CH$_2$(OCH$_3$); (C=O)C(CH$_3$)$_2$CH$_2$(OCH$_3$); (C=O)CH$_2$C(CH$_3$)$_2$(OCH$_3$); (C=O)CH(NH$_2$)CH$_2$(OCH$_3$); (C=O)CH(OCH$_3$)CH$_2$(OCH$_3$); (C=O)CH(OH)CH$_2$(OCH$_3$);

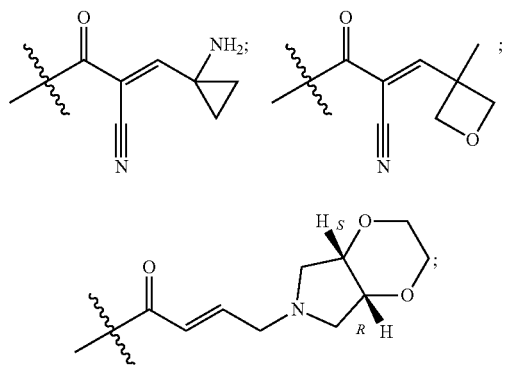

C$_{3-6}$cycloalkyl; (C=O)(CH$_2$)$_{0-1}$azetidinyl; (C=O)oxetanyl; (C=O)tetrahydrofuranyl; (C=O)tetrahydropyranyl; (C=O)(CH$_2$)$_{0-1}$pyrrolidinyl, wherein said pyrrolidinyl is optionally substituted with CH$_3$; (C=O)(CH$_2$)$_{0-1}$piperidinyl; (C=O)(CH$_2$)$_{0-1}$morpholinyl; SO$_2$—C$_{2-6}$alkenyl; SO$_2$C$_{1-6}$alkyl; and linker-PEG-Biotin; wherein R$^3$ is selected from the group consisting of: H, CN, halogen, C$_{1-6}$haloalkyl, and C$_{1-6}$alkyl; R$^4$ and R$^5$ are each independently selected from the group consisting of: H; halogen; C$_{1-6}$alkyl; CH$_2$OH; C$_{1-6}$alk-OC$_{1-6}$alkyl; OC$_{1-6}$alkyl; C$_{1-4}$alk-NR$^6$R$^7$; C$_{3-6}$cycloalkyl substituted with NH$_2$ or CH$_3$; oxetanyl substituted with CH$_3$; 1-acetylpyrrolidin-2-yl; CH$_2$-pyrrolidinyl; CH$_2$-piperidinyl; C(CH$_3$)$_2$-piperidinyl; CH$_2$-morpholinyl; C(CH$_3$)$_2$-morpholinyl; CH$_2$-(4aR,7aS)-tetrahydro-2H-[1,4]dioxino[2,3-c]pyrrol-6(3H)-yl; C(CH$_3$)$_2$NH(CH$_2$CH$_2$OCH$_3$); CH$_2$SO$_2$CH$_3$; CH$_2$NHSO$_2$CH$_3$; NH(C=O)C$_{1-6}$alkyl; and linker-PEG-Biotin; and R$^6$ and R$^7$ are each independently selected from the group consisting of: H, C$_{1-6}$alkyl, C$_{3-6}$cycloalkyl, and CN; and R$^g$ is selected from the group consisting of: H, C$_{1-6}$alkyl, and CN. In other aspects, Ring B is selected from the group consisting of

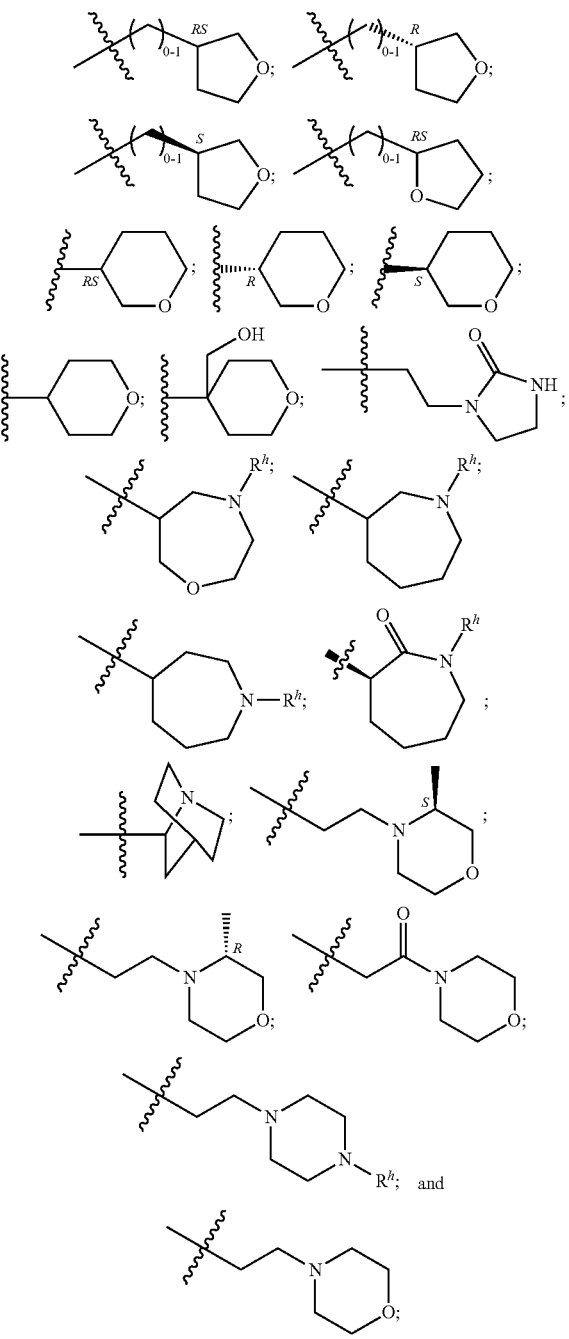

wherein R$^h$ is selected from the group consisting of: H, CN, CH$_3$, and CH$_2$phenyl. In preferred aspects, Ring B is selected from the group consisting of

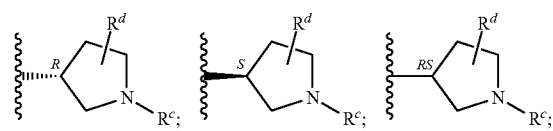

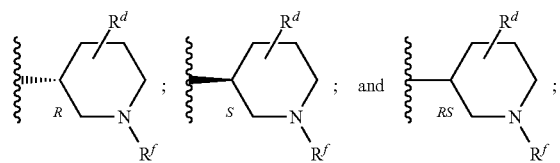

and $R^c$ and $R^f$ are (C=O)CH=CH$_2$; and $R^d$ is H.

In some aspects, the $R^2$ moiety can be defined as "Ring B." In some aspects, particularly those wherein the compound is of Formula (III'), Ring B is selected from the group consisting of

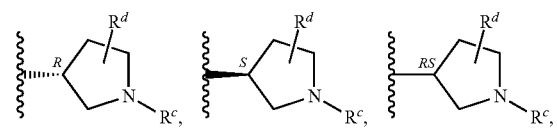

wherein $R^c$ and $R^f$ are independently selected from the group consisting of: H, $C_{1-6}$alkyl, (C=O)CH=CH$_2$, (C=O)CH$_2$NH(CH$_3$), (C=O)CH=CHCH$_2$N(CH$_3$)$_2$, and

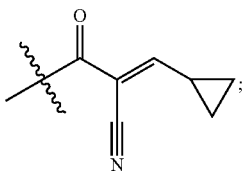 [SMILES: *C(=O)/C(C#N)=C/C1CC1]

and $R^d$ is selected from the group consisting of: H, OH and OCH$_3$. In preferred aspects, Ring B is selected from the group consisting of

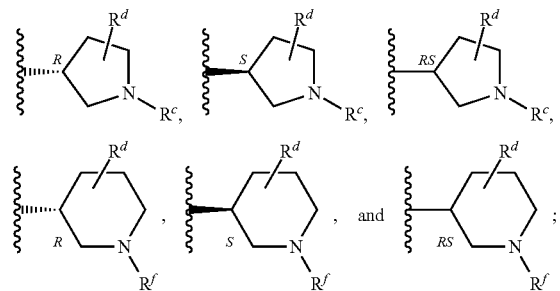

and $R^c$ and $R^f$ are (C=O)CH=CH$_2$; and $R^d$ is H.

In some aspects, the $R^2$ moiety can be defined as "Ring B." In some aspects, particularly those wherein the compound is of Formula (IV'), Ring B is selected from the group consisting of

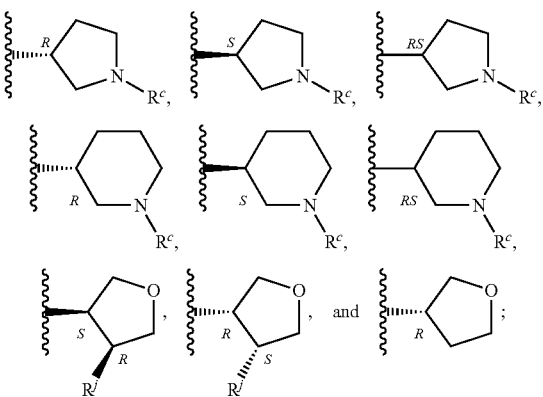

wherein $R^c$ is selected from the group consisting of: H, $C_{1-6}$alkyl, (C=O)$C_{1-3}$alkyl, (C=O)CH=CH$_2$, (C=O)$C_{1-6}$haloalkyl,

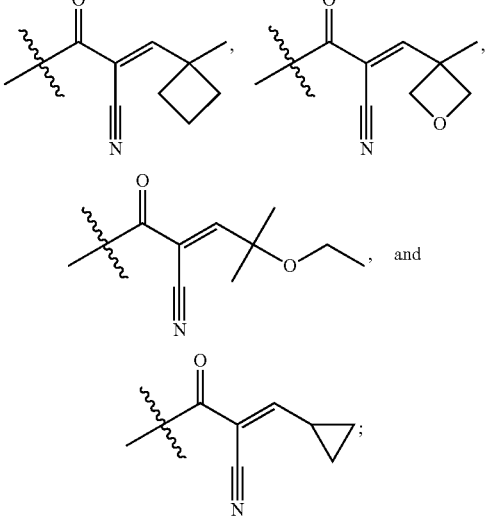

and $R^j$ is selected from the group consisting of: H, NH$_2$, and NH(C=O)CH=CH$_2$. In preferred aspects, Ring B is selected from the group consisting of

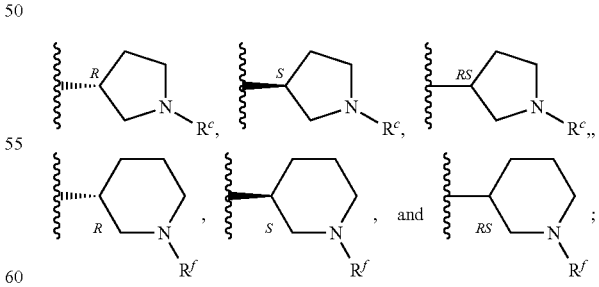

and $R^c$ and $R^f$ are (C=O)CH=CH$_2$.

In some aspects, the $R^2$ moiety can be defined as "Ring B." In some aspects, particularly those wherein the compound is of Formula (V'), Ring B is selected from the group consisting of

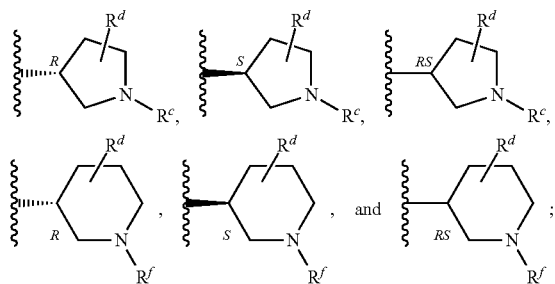

where $R^c$ and $R^f$ are independently selected from the group consisting of: H, $C_{1-6}$alkyl, (C=O)$C_{1-3}$alkyl, (C=O)CH=CH$_2$, (C=O)CH$_2$NHCH$_3$,

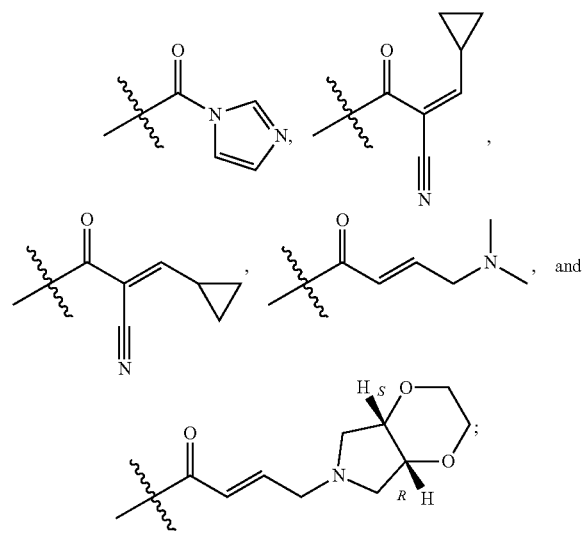

and $R^d$ is H or OH.

According to the disclosure, in some embodiments, the $R^2$ heterocycloalkyl is unsubstituted. In preferred aspects, the $R^2$ heterocycloalkyl is substituted with 1, 2, or 3 substituents. In preferred aspects, the $R^2$ heterocycloalkyl is substituted with 1 or 2 substituents, more preferably 1 substituent. In those aspects wherein the $R^2$ heterocycloalkyl is substituted, the substituents may be independently selected from the group consisting of —NR—C(O)—C($R^3$)=C$R^4$($R^5$); —C(O)—C($R^3$)=C$R^4$($R^5$); oxo; halogen; —CN; —OH; —N$R^6R^7$; —C$_{1-6}$alkyl; —C$_{1-6}$alk-OH; —O$C_{1-6}$alkyl; —C$_{3-6}$cycloalkyl; —C$_{1-6}$haloalkyl; —C$_{1-6}$alkaryl; —SO$_2$C$_{1-6}$alkyl; —SO$_2$C$_{2-6}$alkenyl; —C(O)H; —C(O)—C$_{1-6}$alkyl; —C(O)—C$_{3-6}$cycloalkyl; —C(O)—C$_{1-6}$haloalkyl; —C(O)—C$_{2-6}$alkynyl; —C(O)—C$_{6-10}$aryl; —C(O)-heteroaryl; —C(O)—C$_{1-6}$alk-CN; —C(O)—C$_{1-6}$alk-OH; —C(O)—C$_{1-6}$alk-SO$_2$—C$_{1-6}$alkyl; —C(O)—O—C$_{1-6}$alkyl; —C(O)—C$_{1-6}$alk-N$R^6R^7$; —C(O)—C$_{1-6}$alk-O—C$_{1-6}$alkyl wherein the -alk- is optionally substituted with —OH, —O$C_{1-6}$alkyl, or —N$R^6R^7$; and —C(O)—C$_{0-6}$alk-heterocycloalkyl wherein the -alk- is optionally substituted with oxo and the heterocycloalkyl is optionally substituted with —C$_{1-6}$alkyl; and wherein $R^3$, $R^4$, $R^5$, $R^6$, $R^7$, and $R^8$ are as defined herein. In those aspects wherein the $R^2$ heterocycloalkyl is substituted, the substituents are preferably independently selected from the group consisting of —N$R^8$—C(O)—C($R^3$)=C$R^4$($R^5$); —C(O)—C($R^3$)=C$R^4$($R^5$); oxo; halogen; —CN; —OH; —N$R^6R^7$; —C$_{1-6}$alk-OH; —O$C_{1-6}$alkyl; —C$_{3-6}$cycloalkyl; —C$_{1-6}$haloalkyl; —C$_{1-6}$alkaryl; —SO$_2$C$_{1-6}$alkyl; —SO$_2$C$_{2-6}$alkenyl; —C(O)H; —C(O)—C$_{1-6}$alkyl; —C(O)—C$_{3-6}$cycloalkyl; —C(O)—C$_{1-6}$haloalkyl; —C(O)—C$_{2-6}$alkynyl; —C(O)—C$_{6-10}$aryl; —C(O)-heteroaryl; —C(O)—C$_{1-6}$alk-CN; —C(O)—C$_{1-6}$alk-OH; —C(O)—C$_{1-6}$alk-SO$_2$—C$_{1-6}$alkyl; —C(O)—O—C$_{1-6}$alkyl; —C(O)—C$_{1-6}$alk-N$R^6R^7$; —C(O)—C$_{1-6}$alk-O—C$_{1-6}$alkyl wherein the -alk- is optionally substituted with —OH, —O$C_{1-6}$alkyl, or —N$R^6R^7$; and —C(O)—C$_{0-6}$alk-heterocycloalkyl wherein the -alk- is optionally substituted with oxo and the heterocycloalkyl is optionally substituted with —C$_{1-6}$alkyl; and wherein $R^3$, $R^4$, $R^5$, $R^6$, $R^7$, and $R^8$ are as defined herein.

In some aspects, the $R^2$ heterocycloalkyl is substituted with an oxo moiety, for example one oxo moiety. In those aspects wherein the $R^2$ heterocycloalkyl is substituted with an oxo moiety, the heterocycloalkyl ring may optionally be substituted with one or two additional substituents as defined herein for the $R^2$ substituents.

In some aspects, the $R^2$ heterocycloalkyl is substituted with a halogen, for example a fluorine or chlorine. In some aspects, the $R^2$ heterocycloalkyl is substituted with one or two halogens, preferably one halogen. In those aspects wherein the $R^2$ heterocycloalkyl is substituted with a halogen, the heterocycloalkyl ring may optionally be substituted with one or two additional substituents as defined herein for the $R^2$ substituents.

In some aspects, the $R^2$ heterocycloalkyl is substituted with —CN. In some aspects, the $R^2$ heterocycloalkyl is substituted with one or two —CN, preferably one —CN. In those aspects wherein the $R^2$ heterocycloalkyl is substituted with —CN, the heterocycloalkyl ring may optionally be substituted with one or two additional substituents as defined herein for the $R^2$ substituents.

In some aspects, the $R^2$ heterocycloalkyl is substituted with —OH. In some aspects, the $R^2$ heterocycloalkyl is substituted with one or two —OH, preferably one —OH. In those aspects wherein the $R^2$ heterocycloalkyl is substituted with —OH, the heterocycloalkyl ring may optionally be substituted with one or two additional substituents as defined herein for the $R^2$ substituents.

In some aspects, the $R^2$ heterocycloalkyl is substituted with —N$R^6R^7$ wherein $R^6$ and $R^7$ are each independently H; —C$_{1-6}$alkyl, —C$_{3-6}$cycloalkyl; —C(O)H; or —CN. In preferred aspects, $R^6$ and $R^7$ are each independently H or —C$_{1-6}$alkyl. In those aspects wherein the $R^2$ heterocycloalkyl is substituted with —N$R^6R^7$, the heterocycloalkyl ring may optionally be substituted with one or two additional substituents as defined herein for the $R^2$ substituents.

In some aspects, the $R^2$ heterocycloalkyl is substituted with —C$_{1-6}$ alkyl, for example, —C$_{1-5}$alkyl, —C$_{1-4}$alkyl, —C$_{1-3}$alkyl, —C$_{1-2}$alkyl, or —C$_1$alkyl. In some aspects, the $R^2$ heterocycloalkyl is substituted with one or two —C$_{1-6}$alkyl, preferably one —C$_{1-6}$alkyl. In those aspects wherein the $R^2$ heterocycloalkyl is substituted with —C$_{1-6}$alkyl, the heterocycloalkyl ring may optionally be substituted with one or two additional substituents as defined herein for the $R^2$ substituents.

In some aspects, the $R^2$ heterocycloalkyl is substituted with —C$_{1-6}$alk-OH, for example, —C$_{1-5}$alk-OH, —C$_{1-4}$alk-OH, —C$_{1-3}$alk-OH, —C$_{1-2}$alk-OH, or —C$_1$alk-OH, wherein the —OH moiety can be attached to any carbon of the —C$_{1-6}$alk group, preferably the ω carbon. In some aspects, the $R^2$ heterocycloalkyl is substituted with one or two —C$_{1-6}$alk-OH, preferably one —C$_{1-6}$alk-OH. In those aspects wherein the $R^2$ heterocycloalkyl is substituted with —C$_{1-6}$alk-OH, the heterocycloalkyl ring may optionally be substituted with one or two additional substituents as defined herein for the $R^2$ substituents.

In some aspects, the $R^2$ heterocycloalkyl is substituted with —$OC_{1-6}$alkyl, for example, —O—$C_{1-5}$alkyl, —O—$C_{1-4}$ alkyl, —O—$C_{1-3}$alkyl, —O—$C_{1-2}$alkyl, or —O—$C_1$alkyl. In some aspects, the $R^2$ heterocycloalkyl is substituted with one or two —$OC_{1-6}$alkyl, preferably one —$OC_{1-6}$alkyl. In those aspects wherein the $R^2$ heterocycloalkyl is substituted with —$OC_{1-6}$alkyl, the heterocycloalkyl ring may optionally be substituted with one or two additional substituents as defined herein for the $R^2$ substituents.

In some aspects, the $R^2$ heterocycloalkyl is substituted with —$C_{3-6}$cycloalkyl, for example, cyclopropyl, cyclobutyl, cyclopentyl, or cyclohexyl. In some aspects, the $R^2$ heterocycloalkyl is substituted with one or two —$C_{3-6}$cycloalkyl, preferably one —$C_{3-6}$cycloalkyl. In those aspects wherein the $R^2$ heterocycloalkyl is substituted with —$C_{3-6}$cycloalkyl, the heterocycloalkyl ring may optionally be substituted with one or two additional substituents as defined herein for the $R^2$ substituents.

In some aspects, the $R^2$ heterocycloalkyl is substituted with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, —$CH_2CH_2F$, and the like. In some aspects, the $R^2$ heterocycloalkyl is substituted with one or two —$C_{1-6}$haloalkyl, preferably one —$C_{1-6}$haloalkyl. In those aspects wherein the $R^2$ heterocycloalkyl is substituted with —$C_{1-6}$haloalkyl, the heterocycloalkyl ring may optionally be substituted with one or two additional substituents as defined herein for the $R^2$ substituents.

In some aspects, the $R^2$ heterocycloalkyl is substituted with —$C_{1-6}$alkaryl, for example, benzyl (i.e., —$CH_2$-phenyl). In some aspects, the $R^2$ heterocycloalkyl is substituted with one or two —$C_{1-6}$alkaryl, preferably one —$C_{1-6}$alkaryl. In those aspects wherein the $R^2$ heterocycloalkyl is substituted with —$C_{1-6}$alkaryl, the heterocycloalkyl ring may optionally be substituted with one or two additional substituents as defined herein for the $R^2$ substituents.

In some aspects, the $R^2$ heterocycloalkyl is substituted with —$SO_2C_{1-6}$alkyl, for example, —$SO_2$—$C_{1-5}$alkyl, —$SO_2$—$C_{1-4}$alkyl, —$SO_2$—$C_{1-3}$alkyl, —$SO_2$—$C_{1-2}$alkyl, or —$SO_2$—$C_1$alkyl. In some aspects, the $R^2$ heterocycloalkyl is substituted with one or two —$SO_2C_{1-6}$alkyl, preferably one —$SO_2C_{1-6}$alkyl. In those aspects wherein the $R^2$ heterocycloalkyl is substituted with —$SO_2C_{1-6}$alkyl, the heterocycloalkyl ring may optionally be substituted with one or two additional substituents as defined herein for the $R^2$ substituents.

In some aspects, the $R^2$ heterocycloalkyl is substituted with —$SO_2C_{2-6}$alkenyl, for example, —$SO_2C_{2-5}$alkenyl, —$SO_2C_{2-4}$alkenyl, —$SO_2C_{2-3}$alkenyl, or —$SO_2C_2$alkenyl. In some aspects, the $R^2$ heterocycloalkyl is substituted with one or two —$SO_2C_{2-6}$alkenyl, preferably one —$SO_2C_{2-6}$alkenyl. In those aspects wherein the $R^2$ heterocycloalkyl is substituted with —$SO_2C_{2-6}$alkenyl, the heterocycloalkyl ring may optionally be substituted with one or two additional substituents as defined herein for the $R^2$ substituents.

In some aspects, the $R^2$ heterocycloalkyl is substituted with —C(O)H. In some aspects, the $R^2$ heterocycloalkyl is substituted with one or two —C(O)H, preferably one —C(O)H. In those aspects wherein the $R^2$ heterocycloalkyl is substituted with —C(O)H, the heterocycloalkyl ring may optionally be substituted with one or two additional substituents as defined herein for the $R^2$ substituents.

In some aspects, the $R^2$ heterocycloalkyl is substituted with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)— $C_1$alkyl. In some aspects, the $R^2$ heterocycloalkyl is substituted with one or two —C(O)—$C_{1-6}$alkyl, preferably one —C(O)—$C_{1-6}$alkyl. In those aspects wherein the $R^2$ heterocycloalkyl is substituted with —C(O)—$C_{1-6}$alkyl, the heterocycloalkyl ring may optionally be substituted with one or two additional substituents as defined herein for the $R^2$ substituents.

In some aspects, the $R^2$ heterocycloalkyl is substituted with —C(O)—$C_{3-6}$cycloalkyl, for example, —C(O)-cyclopropyl, —C(O)-cyclobutyl, —C(O)-cyclopentyl, or —C(O)-cyclohexyl. In some aspects, the $R^2$ heterocycloalkyl is substituted with one or two —C(O)—$C_{3-6}$cycloalkyl, preferably one —C(O)—$C_{3-6}$cycloalkyl. In those aspects wherein the $R^2$ heterocycloalkyl is substituted with —C(O)—$C_{3-6}$cycloalkyl, the heterocycloalkyl ring may optionally be substituted with one or two additional substituents as defined herein for the $R^2$ substituents.

In some aspects, the $R^2$ heterocycloalkyl is substituted with —C(O)—$C_{1-6}$haloalkyl, for example, —C(O)—$C_{1-6}$haloalkyl, —C(O)—$C_{1-4}$haloalkyl, —C(O)—$C_{1-3}$haloalkyl, —C(O)—$C_{1-2}$haloalkyl, or —C(O)—$C_1$haloalkyl, including —C(O)—$CF_3$, —C(O)—$CH_2CH_2F$, and the like. In some aspects, the $R^2$ heterocycloalkyl is substituted with one or two —C(O)—$C_{1-6}$haloalkyl, preferably one —C(O)—$C_{1-6}$haloalkyl. In those aspects wherein the $R^2$ heterocycloalkyl is substituted with —C(O)—$C_{1-6}$haloalkyl, the heterocycloalkyl ring may optionally be substituted with one or two additional substituents as defined herein for the $R^2$ substituents.

In some aspects, the $R^2$ heterocycloalkyl is substituted with —C(O)—$C_{2-6}$alkynyl, for example, —C(O)—$C_{2-5}$alkynyl, —C(O)—$C_{2-4}$alkynyl, —C(O)—$C_{2-3}$alkynyl, or —C(O)—$C_2$alkynyl. In some aspects, the $R^2$ heterocycloalkyl is substituted with one or two —C(O)—$C_{2-6}$alkynyl, preferably one —C(O)—$C_{2-6}$alkynyl. In those aspects wherein the $R^2$ heterocycloalkyl is substituted with —C(O)—$C_{2-6}$alkynyl, the heterocycloalkyl ring may optionally be substituted with one or two additional substituents as defined herein for the $R^2$ substituents.

In some aspects, the $R^2$ heterocycloalkyl is substituted with —C(O)—$C_{6-10}$aryl, for example, —C(O)-phenyl or —C(O)-napthalenyl. In some aspects, the $R^2$ heterocycloalkyl is substituted with one or two —C(O)—$C_{6-10}$aryl, preferably one —C(O)—$C_{6-10}$aryl. In those aspects wherein the $R^2$ heterocycloalkyl is substituted with —C(O)—$C_{6-10}$aryl, the heterocycloalkyl ring may optionally be substituted with one or two additional substituents as defined herein for the $R^2$ substituents.

In some aspects, the $R^2$ heterocycloalkyl is substituted with —C(O)-heteroaryl, for example, —C(O)-pyrrolyl, —C(O)-thienyl, —C(O)-oxazolyl, —C(O)-pyrazolyl, —C(O)-pyridyl, —C(O)-pyrimidinyl, and the like. In some aspects, the $R^2$ heterocycloalkyl is substituted with one or two —C(O)-heteroaryl, preferably one —C(O)-heteroaryl. In those aspects wherein the $R^2$ heterocycloalkyl is substituted with —C(O)-heteroaryl, the heterocycloalkyl ring may optionally be substituted with one or two additional substituents as defined herein for the $R^2$ substituents.

In some aspects, the $R^2$ heterocycloalkyl is substituted with —C(O)—$C_{1-6}$alk-CN, for example, —C(O)—$C_{1-5}$alk-CN, —C(O)—$C_{1-4}$alk-CN, —C(O)—$C_{1-3}$alk-CN, —C(O)—$C_{1-2}$alk-CN, or —C(O)—$C_1$alk-CN. In some aspects, the $R^2$ heterocycloalkyl is substituted with one or two —C(O)—$C_{1-6}$alk-CN, preferably one —C(O)—$C_{1-6}$alk-CN. In those aspects wherein the $R^2$ heterocycloalkyl is substituted with —C(O)—$C_{1-6}$alk-CN, the heterocycloalkyl ring may optionally be substituted with one or two additional substituents as defined herein for the $R^2$ substituents.

In some aspects, the $R^2$ heterocycloalkyl is substituted with —C(O)—$C_{1-6}$alk-OH, for example, —C(O)—$C_{1-5}$alk-OH, —C(O)—$C_{1-4}$alk-OH, —C(O)—$C_{1-3}$alk-OH, —C(O)—$C_{1-2}$alk-OH, or —C(O)—$C_1$alk-OH. In some aspects, the $R^2$ heterocycloalkyl is substituted with one or two —C(O)—$C_{1-6}$alk-OH, preferably one —C(O)—$C_{1-6}$alk-OH. The —OH moiety can be attached to any carbon of the —$C_{1-6}$alk group, preferably the ω carbon. In those aspects wherein the $R^2$ heterocycloalkyl is substituted with —C(O)—$C_{1-6}$alk-OH, the heterocycloalkyl ring may optionally be substituted with one or two additional substituents as defined herein for the $R^2$ substituents.

In some aspects, the $R^2$ heterocycloalkyl is substituted with —C(O)—$C_{1-6}$alk-$SO_2$—$C_{1-6}$alkyl, for example, —C(O)—$C_{1-5}$alk-$SO_2$—$C_{1-5}$alkyl, —C(O)—$C_{1-4}$alk-$SO_2$—$C_{1-4}$alkyl, —C(O)—$C_{1-3}$alk-$SO_2$—$C_{1-3}$alkyl, —C(O)—$C_{1-2}$alk-$SO_2$—$C_{1-2}$alkyl, or —C(O)—$C_1$alk-$SO_2$—$C_1$alkyl. In some aspects, the $R^2$ heterocycloalkyl is substituted with one or two —C(O)—$C_{1-6}$alk-$SO_2$—$C_{1-6}$alkyl, preferably one —C(O)—$C_{1-6}$alk-$SO_2$—$C_{1-6}$alkyl. In those aspects wherein the $R^2$ heterocycloalkyl is substituted with —C(O)—$C_{1-6}$alk-$SO_2$—$C_{1-6}$alkyl, the heterocycloalkyl ring may optionally be substituted with one or two additional substituents as defined herein for the $R^2$ substituents.

In some aspects, the $R^2$ heterocycloalkyl is substituted with —C(O)—O—$C_{1-6}$alkyl, for example, —C(O)—O—$C_{1-5}$alkyl, —C(O)—O—$C_{1-4}$alkyl, —C(O)—O—$C_{1-3}$alkyl, —C(O)—O—$C_{1-2}$alkyl, or —C(O)—O—$C_1$alkyl. In some aspects, the $R^2$ heterocycloalkyl is substituted with one or two —C(O)—O—$C_{1-6}$alkyl, preferably one —C(O)—O—$C_{1-6}$alkyl. In those aspects wherein the $R^2$ heterocycloalkyl is substituted with —C(O)—O—$C_{1-6}$alkyl, the heterocycloalkyl ring may optionally be substituted with one or two additional substituents as defined herein for the $R^2$ substituents.

In some aspects, the $R^2$ heterocycloalkyl is substituted with —C(O)—$C_{1-6}$alk-$NR^6R^7$, for example, —C(O)—$C_{1-5}$alk-$NR^6R^{7'}$—C(O)—$C_{1-4}$alk-$NR^6R^{7'}$—C(O)—$C_{1-3}$alk-$NR^6R^{7'}$ —C(O)—$C_{1-2}$alk-$NR^6R^7$, or —C(O)—$C_1$alk-$NR^6R^7$, wherein $R^6$ and $R^7$ are each independently H; —$C_{1-6}$alkyl, for example, —$C_{1-5}$alkyl, —$C_{1-4}$alkyl, —$C_{1-3}$alkyl, —$C_{1-2}$alkyl, or —$C_1$alkyl; —$C_{3-6}$cycloalkyl, for example, cyclopropyl, cyclobutyl, cyclopentyl, or cyclohexyl; —C(O)H, or —CN. In preferred aspects, $R^6$ and $R^7$ are each independently H, —$C_{1-6}$alkyl; or —$C_{3-6}$cycloalkyl, with H and —$C_{1-6}$alkyl being preferred, and H and —$C_{1-2}$alkyl being more preferred. In some aspects, the $R^2$ heterocycloalkyl is substituted with one or two —C(O)—$C_{1-6}$alk-$NR^6R^7$, preferably one —C(O)—$C_{1-6}$alk-$NR^6R^7$. In those aspects wherein the $R^2$ heterocycloalkyl is substituted with —C(O)—$C_{1-6}$alk-$NR^6R^7$, the heterocycloalkyl ring may optionally be substituted with one or two additional substituents as defined herein for the $R^2$ substituents.

In some aspects, the $R^2$ heterocycloalkyl is substituted with —C(O)—$C_{1-6}$alk-O—$C_{1-6}$alkyl, for example, —C(O)—$C_{1-5}$alk-O—$C_{1-5}$alkyl, —C(O)—$C_{1-4}$alk-O—$C_{1-4}$alkyl, —C(O)—$C_{1-3}$alk-O—$C_{1-3}$alkyl, —C(O)—$C_{1-2}$alk-O—$C_{1-2}$alkyl, or —C(O)—$C_1$alk-O—$C_1$alkyl. In certain aspects wherein the $R^2$ heterocycloalkyl is substituted with —C(O)—$C_{1-6}$alk-O—$C_{1-6}$alkyl, the —$C_{1-6}$alk- is optionally substituted with —OH; —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl; or —$NR^6R^7$ (wherein $R^6$ and $R^7$ are each independently H; —$C_{1-6}$alkyl, for example, —$C_{1-5}$alkyl, —$C_{1-4}$alkyl, —$C_{1-3}$alkyl, —$C_{1-2}$alkyl, or —$C_1$alkyl; —$C_{3-6}$cycloalkyl; —C(O)H; or —CN). In preferred aspects, $R^6$ and $R^7$ are each independently H, —$C_{1-6}$alkyl; or —$C_{3-6}$cycloalkyl, with H and —$C_{1-6}$alkyl being preferred, and H and —$C_{1-2}$alkyl being more preferred. In some aspects, the —$C_{1-6}$alk- of the —C(O)—$C_{1-6}$alk-O—$C_{1-6}$alkyl moiety is substituted with —OH. In other aspects, the —$C_{1-6}$alk- is substituted with —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl. In some aspects, the $R^2$ heterocycloalkyl is substituted with one or two —C(O)—$C_{1-6}$alk-O—$C_{1-6}$alkyl, preferably one —C(O)—$C_{1-6}$alk-O—$C_{1-6}$alkyl. In those aspects wherein the $R^2$ heterocycloalkyl is substituted with —C(O)—$C_{1-6}$alk-O—$C_{1-6}$alkyl, the heterocycloalkyl ring may optionally be substituted with one or two additional substituents as defined herein for the $R^2$ substituents.

In some aspects, the $R^2$ heterocycloalkyl is substituted with —C(O)—$C_{0-6}$alk-heterocycloalkyl, for example, —C(O)—$C_{0-5}$alk-heterocycloalkyl, —C(O)—$C_{0-4}$alk-heterocycloalkyl, —C(O)—$C_{0-3}$alk-heterocycloalkyl, —C(O)—$C_{0-2}$alk-heterocycloalkyl, —C(O)—$C_{0-1}$alk-heterocycloalkyl, —C(O)—$C_1$alk-heterocycloalkyl, or —C(O)—$C_0$alk-heterocycloalkyl. Preferred substituent heterocycloalkyl groups include tetrahydrofuranyl, piperidinyl, pyrrolidinyl, and the like. In certain aspects wherein the $R^2$ heterocycloalkyl is substituted with —C(O)—$C_{1-6}$alk-heterocycloalkyl, the —$C_{1-6}$alk- is optionally substituted with oxo. In certain aspects wherein the $R^2$ heterocycloalkyl is substituted with —C(O)—$C_{0-6}$alk-heterocycloalkyl, the substituent heterocycloalkyl moiety can be unsubstituted or substituted with —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. In those aspects wherein the $R^2$ heterocycloalkyl is substituted with —C(O)—$C_{0-6}$alk-heterocycloalkyl, the $R^2$ heterocycloalkyl ring may optionally be substituted with one or two additional substituents as defined herein for the $R^2$ substituents.

In some aspects, the $R^2$ heterocycloalkyl is substituted with —$NR^8$—C(O)—C($R^3$)=C$R^4$($R^5$), wherein $R^3$, $R^4$, and $R^5$ are as described herein and $R^8$ is H or $C_{1-6}$alkyl, for example, —$C_{1-5}$alkyl, —$C_{1-4}$alkyl, —$C_{1-3}$alkyl, —$C_{1-2}$alkyl, or —$C_1$alkyl. In preferred aspects, $R^8$ is H. In these aspects, $R^3$ is H; —CN; halogen; —$C_{1-6}$haloalkyl; or —$C_{1-6}$alkyl. In some embodiments, $R^3$ is H. In other aspects, $R^3$ is —CN. In still other aspects, $R^3$ is halogen, for example F or Cl. In yet other aspects, $R^3$ is —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, —$CH_2CH_2F$, and the like. In further aspects, $R^3$ is —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. In those aspects wherein the $R^2$ heterocycloalkyl is substituted with —$NR^8$—C(O)—C($R^3$)=$CR^4$($R^5$), the heterocycloalkyl ring may optionally be substituted with one or two additional substituents as defined herein for the $R^2$ substituents.

In preferred aspects of the disclosure, the $R^2$ heterocycloalkyl is substituted with —C(O)—C($R^3$)=$CR^4$($R^5$). In these embodiments, $R^3$ is H; —CN; halogen; —$C_{1-6}$haloalkyl; or —$C_{1-6}$alkyl. In some embodiments, $R^3$ is H. In other aspects, $R^3$ is —CN. In still other aspects, $R^3$ is halogen, for example F or Cl. In yet other aspects, $R^3$ is —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, —$CH_2CH_2F$, and the like. In further aspects, $R^3$ is —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. In those aspects wherein the $R^2$ heterocycloalkyl is substituted with —C(O)—C(R$^3$)=CR$^4$(R$^5$), the heterocycloalkyl ring may optionally be substituted with one or two additional substituents as defined herein for the R$^2$ substituents.

In preferred aspects, the R$^2$ heterocycloalkyl is substituted with —C(O)—C(R$^3$)=CR$^4$(R$^5$); —C(O)—C$_{1-6}$alk-NR$^6$R$^7$; —C(O)—C$_{1-6}$alkyl; or —NR$^6$R$^7$. In more preferred aspects, the R$^2$ heterocycloalkyl is substituted with —C(O)—C(R$^3$)=CR$^4$(R$^5$). In other preferred aspects, the R$^2$ heterocycloalkyl is substituted with —C(O)—C$_{1-6}$alk-NR$^6$R$^7$; —C(O)—C$_{1-6}$alkyl; or —NR$^6$R$^7$; wherein R$^6$ and R$^7$ are each independently H or C$_{1-6}$alkyl.

In other aspects, the R$^2$ is substituted with halogen; CN; OH; C$_{1-6}$alkyl; C$_{1-6}$haloalkyl; C$_{1-6}$alk-OH; OC$_{1-6}$alkyl; C$_{3-6}$cycloalkyl; NH$_2$; or C$_{1-2}$alkaryl. In yet other aspects, the R$^2$ is substituted with C(=O)H; (C=O)C$_{1-6}$alkyl; (C=O) C$_{3-6}$cycloalkyl; (C=O)C$_{1-6}$haloalkyl; (C=O)-alkynyl; (C=O)-phenyl; (C=O)—C$_{1-6}$alkCN; (C=O)—C$_{1-6}$alk-OH; (C=O)—C$_{1-6}$alk-NR$^6$R$^7$; or (C=O)—C$_{1-6}$alk-O—C$_{1-6}$ alkyl wherein the —C$_{1-6}$alk- is optionally substituted with OH, OC$_{1-6}$alkyl, or NR$^6$R$^7$. In some aspects, the R$^2$ is substituted with (C=O)C$_{0-1}$alk-heterocycloalkyl wherein the heterocycloalkyl is optionally substituted with C$_{1-6}$alkyl. In other aspects, the R$^2$ is substituted with SO$_2$alkyl, (C=O)—C$_{1-6}$alk-SO$_2$C$_{1-6}$alkyl, or SO$_2$—C$_{2-6}$alkenyl.

In those embodiments employing R$^4$ and R$^5$, that is, those aspects wherein the R$^2$ heterocycloalkyl is substituted with —C(O)—C(R$^3$)=CR$^4$(R$^5$) or —NR$^8$—C(O)—C(R$^3$)=CR$^4$(R$^5$), R$^4$ and R$^5$ are each independently H; halogen; —C$_{1-6}$alkyl; —OC$_{1-6}$alkyl; —C$_{0-6}$alk-C$_{3-6}$cycloalkyl optionally substituted with —C$_{1-6}$alkyl; —C$_{1-6}$alk-OH; —C$_{0-6}$alk-NR$^6$R$^7$; —C$_{1-6}$alk-O—C$_{1-6}$alkyl; —C$_{1-6}$alk-NH—C$_{0-6}$alk-O—C$_{1-6}$alkyl; —C$_{0-6}$alk-heterocycloalkyl optionally substituted with —C(O)C$_{1-6}$alkyl or —C$_{1-6}$alkyl; —C$_{1-6}$alk-NHSO$_2$—C$_{1-6}$alkyl; —C$_{1-6}$alk-SO$_2$—C$_{1-6}$alkyl; —NHC(O)—C$_{1-6}$alkyl; or linker-PEG-Biotin.

Within the scope of the disclosure, the double bond present in either —C(O)—C(R$^3$)=CR$^4$(R$^5$) or —NR$^8$—C(O)—C(R$^3$)=CR$^4$(R$^5$) may be of the Z or E configuration.

In some aspects, neither R$^4$ nor R$^5$ is H.

In most preferred aspects, each of R$^4$ and R$^5$ is H.

In some aspects, one of R$^4$ and R$^5$ is H. In certain of these aspects, the other of R$^4$ and R$^5$ is halogen, for example F or Cl.

In some aspects, one of R$^4$ and R$^5$ is H. In certain of these aspects, the other of R$^4$ and R$^5$ is —C$_{1-6}$alkyl, for example, —C$_{1-5}$alkyl, —C$_{1-4}$alkyl, —C$_{1-3}$alkyl, —C$_{1-2}$alkyl, or —C$_1$alkyl.

In some aspects, one of R$^4$ and R$^5$ is H. In certain of these aspects, the other of R$^4$ and R$^5$ is —OC$_{1-6}$alkyl, for example, —OC$_{1-5}$alkyl, —OC$_{1-4}$alkyl, —OC$_{1-3}$alkyl, —OC$_{1-2}$alkyl, or —OC$_1$alkyl.

In some aspects, one of R$^4$ and R$^5$ is H. In certain of these aspects, the other of R$^4$ and R$^5$ is —C$_{0-6}$alk-C$_{3-6}$cycloalkyl, for example, —C$_{0-5}$alk-C$_{3-5}$cycloalkyl, —C$_{0-4}$alk-C$_{3-4}$cycloalkyl, —C$_{0-3}$alk-C$_3$cycloalkyl, —C$_{0-2}$alk-C$_{3-6}$cycloalkyl, —C$_{0-1}$alk-C$_{3-6}$cycloalkyl, —C$_0$alk-C$_{3-6}$cycloalkyl or —C$_1$alk-C$_{3-6}$cycloalkyl. In these aspects, the cycloalkyl moiety can be unsubstituted or can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The substitution can be a spiro-substitution or a non-spiro-substitution.

In some aspects, one of R$^4$ and R$^5$ is H. In certain of these aspects, the other of R$^4$ and R$^5$ is —C$_{0-6}$alk-heterocycloalkyl, for example, —C$_{1-6}$alk-heterocycloalkyl, —C$_{0-4}$alk-heterocycloalkyl, —C$_{0-3}$alk-heterocycloalkyl, —C$_{0-2}$alk-heterocycloalkyl, —C$_{0-1}$alk-heterocycloalkyl, —C$_1$alk-heterocycloalkyl, or —C$_0$alk-heterocycloalkyl. In these aspects, the substituent heterocycloalkyl is preferably an oxygen-containing heterocycloalkyl, for example, tetrahydropyranyl, tetrahydrofuranyl, or oxetanyl. In other aspects, the heterocycloalkyl is a nitrogen-containing heterocycloalkyl, for example, pyrrolidinyl, aziridinyl, or piperidinyl. In certain of these aspects, the substituent heterocycloalkyl can be substituted with —C(O)C$_{1-6}$alkyl, for example, —C(O)C$_{1-5}$alkyl, —C(O)C$_{1-4}$alkyl, —C(O)C$_{1-3}$alkyl, —C(O)C$_{1-2}$alkyl, or —C(O)C$_1$alkyl. In other aspects, the substituent heterocycloalkyl can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl.

In some aspects, one of R$^4$ and R$^5$ is H. In certain of these aspects, the other of R$^4$ and R$^5$ is —C$_{1-6}$alk-OH, for example, —C$_{1-5}$alk-OH, —C$_{1-4}$alk-OH, —C$_{1-3}$alk-OH, —C$_{1-2}$alk-OH, or —C$_1$alk-OH. The —OH moiety can be attached to any carbon of the —C$_{1-6}$alk group, preferably the ω carbon.

In some aspects, one of R$^4$ and R$^5$ is H. In certain of these aspects, the other of R$^4$ and R$^5$ is —C$_{0-6}$alk-NR$^6$R$^7$, for example, —C$_{0-5}$alk-NR$^6$R$^7$, —C$_{0-4}$alk-NR$^6$R$^7$, —C$_{0-3}$alk-NR$^6$R$^7$, —C$_{0-2}$alk-NR$^6$R$^7$, —C$_{0-1}$alk-NR$^6$R$^7$, C$_1$alk-NR$^6$R$^7$, or —C$_0$alk-NR$^6$R$^7$, wherein R$^6$ and R$^7$ are each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; —C$_{3-6}$cycloalkyl, for example, cyclopropyl, cyclobutyl, cyclopentyl, or cyclohexyl; —C(O)H; or —CN. In preferred aspects, R$^6$ and R$^7$ are each independently H; —C$_{1-6}$alkyl; or —C$_{3-6}$cycloalkyl, more preferably, R$^6$ and R$^7$ are each independently H or —C$_{1-6}$alkyl.

In some aspects, one of R$^4$ and R$^5$ is H. In certain of these aspects, the other of R$^4$ and R$^5$ is —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl.

In some aspects, one of R$^4$ and R$^5$ is H. In certain of these aspects, the other of R$^4$ and R$^5$ is —C$_{1-6}$alk-NH—C$_{0-6}$alk-O—C$_{1-6}$alkyl, for example, —C$_{1-5}$alk-NH—C$_{0-6}$alk-O—C$_{1-5}$alkyl, —C$_{1-4}$alk-NH—C$_{0-6}$alk-O—C$_{1-4}$alkyl, —C$_{1-3}$alk-NH—C$_{0-6}$alk-O—C$_{1-3}$alkyl, —C$_{1-2}$alk-NH—C$_{0-6}$alk-O—C$_{1-2}$alkyl, —C$_1$alk-NH—C$_{0-6}$alk-O—C$_1$alkyl, —C$_{1-5}$alk-NH—C$_{0-6}$alk-O—C$_{1-5}$alkyl, —C$_{1-4}$alk-NH—C$_{1-5}$alk-O—C$_{1-4}$alkyl, —C$_{1-3}$alk-NH—C$_{1-4}$alk-O—C$_{1-3}$alkyl, —C$_{1-2}$alk-NH—C$_{1-3}$alk-O—C$_{1-2}$alkyl, —C$_1$alk-NH—C$_{1-2}$alk-O—C$_{1-6}$alkyl, or —C$_{1-6}$alk-NH—C$_0$alk-O—C$_{1-6}$alkyl.

In some aspects, one of R$^4$ and R$^5$ is H. In certain of these aspects, the other of R$^4$ and R$^5$ is —C$_{1-6}$alk-NHSO$_2$—C$_{1-6}$alkyl, for example, —C$_{1-5}$alk-NHSO$_2$—C$_{1-5}$alkyl —C$_{1-4}$alk-NHSO$_2$—C$_{1-4}$alkyl, —C$_{1-3}$alk-NHSO$_2$—C$_{1-3}$alkyl, —C$_{1-2}$alk-NHSO$_2$—C$_{1-2}$alkyl, or —C$_1$alk-NHSO$_2$—C$_1$alkyl.

In some aspects, one of R$^4$ and R$^5$ is H. In certain of these aspects, the other of R$^4$ and R$^5$ is —C$_{1-6}$alk-SO$_2$—C$_{1-6}$alkyl, for example, —C$_{1-5}$alk-SO$_2$—C$_{1-5}$alkyl, —C$_{1-4}$alk-SO$_2$—C$_{1-4}$alkyl, —C$_{1-3}$alk-SO$_2$—C$_{1-3}$alkyl, —C$_{1-2}$alk-SO$_2$—C$_{1-2}$alkyl, or —C$_1$alk-SO$_2$—C$_1$alkyl.

In some aspects, one of R$^4$ and R$^5$ is H. In certain of these aspects, the other of R$^4$ and R$^5$ is —NHC(O)—C$_{1-6}$alkyl, for example, —NHC(O)—C$_{1-5}$alkyl, —NHC(O)—C$_{1-4}$alkyl, —NHC(O)—C$_{1-3}$alkyl, —NHC(O)—C$_{1-2}$alkyl, or —NHC(O)—C$_1$alkyl.

In some aspects, one of R$^4$ and R$^5$ is H. In certain of these aspects, the other of R$^4$ and R$^5$ is linker-PEG-Biotin, preferably

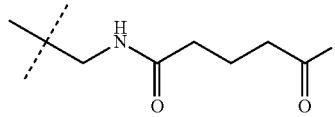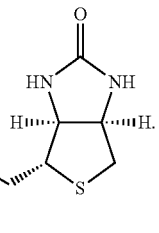

In preferred aspects, one of $R^4$ and $R^5$ is H and the other of $R^4$ and $R^5$ is $C_{1-6}$alkyl (e.g., methyl, t-butyl); cycloalkyl (e.g., cyclopropyl); —$C_{1-6}$alk-$NR^6R^7$ (e.g., —$CH_2$—$NH_2$, —$CH_2$—$NHCH_3$, —$CH_2$—$N(CH_3)_2$, —$C(CH_3)_2$—$NH_2$, —$C(CH_3)_2$—$NHCH_3$, —$C(CH_3)_2$—$N(CH_3)_2$; —$C_{1-6}$alk-O—$C_{1-6}$alkyl (e.g., —$C(CH_3)_2$—$OCH_3$, —$C(CH_3)_2$—$OCH_2CH_3$); —$C_{0-6}$alk-heterocycloalkyl substituted with —$C_{1-6}$alkyl (e.g., —C($CH_3$)-oxetanyl).

A preferred subgenus of formula I is:

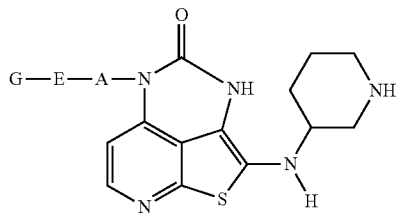

(I-A)

wherein the piperidinyl ring is substituted at the ring nitrogen with any 1 or 2 of the $R^2$ substituents defined herein.

Additional embodiments of the disclosure include compounds of Formula (I) having the subgenera of Formula (I-B-1) and Formula (I-B-2):

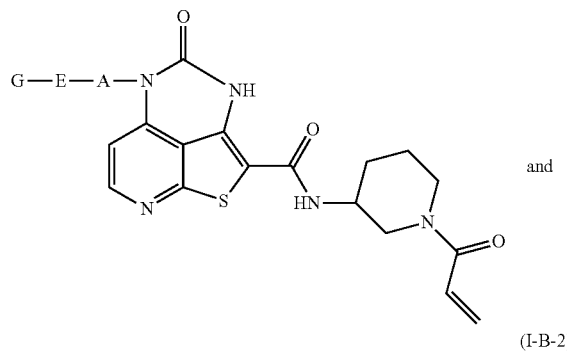

(I-B-1)

and

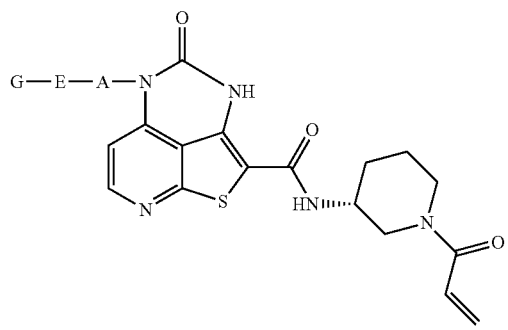

(I-B-2)

Within the scope of the disclosure, A can be a bond. Also within the scope of the disclosure, A can be pyridyl; phenyl; napthalenyl; pyrimidinyl; pyrazinyl; pyridazinyl; benzo[d][1,3]dioxolyl optionally substituted with halogen, preferably F; benzothiophenyl; or pyrazolyl. Also within the scope of the disclosure, A can be pyridyl; phenyl; napthalenyl; pyrimidinyl; pyrazinyl; pyridazinyl; benzothiophenyl; or pyrazolyl. Also according to the disclosure, any of the A moieties (excluding a bond) can be unsubstituted or substituted with 1, 2, or 3 substituents, preferably 1 or 2 substituents, more preferably 1 substituent, independently selected from the group consisting of —$C_{1-6}$alkyl, for example, —$C_{1-5}$alkyl, —$C_{1-4}$alkyl, —$C_{1-3}$alkyl, —$C_{1-2}$alkyl, or —$C_1$alkyl; halogen, for example F or Cl; —$SF_5$; —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl; —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl; and —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, —$CH_2CH_2F$, and the like.

In some aspects, A is pyridyl. The pyridyl can be attached to any of the compounds of formula I (or its subgenera) through any ring carbon atom, but preferably it attached through the 2- or 3-position carbon. Preferably, the pyridyl is substituted with one or two substituents, preferably one substituent. The pyridyl substituent can be attached to any ring carbon atom of the pyridyl ring. In those embodiments wherein the pyridyl is attached to the compound of formula I through the 3-position carbon, the substituent is preferably attached to the pyridyl at the 2- or 4-position. The pyridyl can be substituted at any available ring carbon atom with —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. The pyridyl can be substituted at any available ring carbon atom with halogen, for example F or Cl. The pyridyl can be substituted at any available ring carbon atom with —$SF_5$. The pyridyl can be substituted at any available ring carbon atom with —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl. The pyridyl can be substituted at any available ring carbon atom with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl. The pyridyl can be substituted at any available ring carbon atom with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, $CH_2CH_2F$, and the like. Preferred substituents wherein A is pyridyl include —$C_{1-6}$alkyl, with —$C_1$alkyl being most preferred, and with one —$C_1$alkyl substituent being more preferred. Other preferred substituents include halogen, in particular F and Cl.

In some aspects, A is phenyl. Preferably, the phenyl is substituted with one or two substituents, preferably one substituent. The phenyl can be substituted at any available ring carbon atom with —$C_{1-6}$alkyl, for example, —$C_{1-5}$ alkyl, —$C_{1-4}$alkyl, —$C_{1-3}$alkyl, —$C_{1-2}$alkyl, or —$C_1$alkyl. The phenyl can be substituted at any available ring carbon atom with halogen, for example F or Cl. The phenyl can be substituted at any available ring carbon atom with —$SF_5$. The phenyl can be substituted at any available ring carbon atom with —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl. The phenyl can be substituted at any available ring carbon atom with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl. The phenyl can be substituted at any available ring carbon atom with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, $CH_2CH_2F$, and the like. The phenyl's substituent can be attached to any ring carbon atom of the phenyl ring, preferably ortho to the phenyl moiety's point of attachment to the compound of formula I. Preferred substituents wherein A is phenyl include —$C_{1-6}$alkyl, with —$C_1$alkyl being most preferred. Other preferred substituents include halogen, in particular F and Cl.

In some aspects, A is napthalenyl. Preferably, the napthalenyl is substituted with one or two substituents, preferably one substituent. The napthalenyl can be substituted at any available ring carbon atom with —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. The napthalenyl can be substituted at any available ring carbon atom with halogen, for example F or Cl. The napthalenyl can be substituted at any available ring carbon atom with —$SF_5$. The napthalenyl can be substituted at any available ring carbon atom with —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl. The napthalenyl can be substituted at any available ring carbon atom with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl. The napthalenyl can be substituted at any available ring carbon atom with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, $CH_2CH_2F$, and the like. The napthalenyl can be attached through any of its carbon atoms to the compound of formula I. The napthalenyl substituent can be attached to any ring carbon atom of the napthalenyl ring, preferably ortho to the napthalenyl moiety's point of attachment to the compound of formula I. Preferred substituents wherein A is napthalenyl include —$C_{1-6}$alkyl, with —$C_1$alkyl being most preferred. Other preferred substituents include halogen, in particular F and Cl.

In some aspects, A is pyrimidinyl. The pyrimidinyl can be attached to any of the compounds of formula I (or its subgenera) through any ring carbon atom through any ring carbon atom. Preferably, the pyrimidinyl is substituted with one or two substituents, preferably one substituent. The pyrimidinyl can be substituted at any available ring carbon atom with —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. The pyrimidinyl can be substituted at any available ring carbon atom with halogen, for example F or Cl. The pyrimidinyl can be substituted at any available ring carbon atom with —$SF_5$. The pyrimidinyl can be substituted at any available ring carbon atom with —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl. The pyrimidinyl can be substituted at any available ring carbon atom with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl. The pyrimidinyl can be substituted at any available ring carbon atom with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, $CH_2CH_2F$, and the like. Preferred substituents wherein A is pyrimidinyl include —$C_{1-6}$alkyl, with —$C_1$alkyl being most preferred. Other preferred substituents include halogen, in particular F and Cl.

In some aspects, A is pyrazinyl. The pyrazinyl can be attached to any of the compounds of formula I (or its subgenera) through any ring carbon atom. Preferably, the pyrazinyl is substituted with one or two substituents, preferably one substituent. The pyrazinyl can be substituted at any available ring carbon atom with —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. The pyrazinyl can be substituted at any available ring carbon atom with halogen, for example F or Cl. The pyrazinyl can be substituted at any available ring carbon atom with —$SF_5$. The pyrazinyl can be substituted at any available ring carbon atom with —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl. The pyrazinyl can be substituted at any available ring carbon atom with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl. The pyrazinyl can be substituted at any available ring carbon atom with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, $CH_2CH_2F$, and the like. Preferred substituents wherein A is pyrazinyl include —$C_{1-6}$alkyl, with —$C_1$alkyl being most preferred. Other preferred substituents include halogen, in particular F and Cl.

In some aspects, A is pyridazinyl. The pyridazinyl can be attached to any of the compounds of formula I (or its subgenera) through any ring carbon atom. Preferably, the pyridazinyl is substituted with one or two substituents, preferably one substituent. The pyridazinyl can be substituted at any available ring carbon atom with —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. The pyridazinyl can be substituted at any available ring carbon atom with halogen, for example F or Cl. The pyridazinyl can be substituted at any available ring carbon atom with —$SF_5$. The pyridazinyl can be substituted at any available ring carbon atom with —$OC_{1-6}$alkyl, for example, —$OC_{1-5}$alkyl, —$OC_{1-4}$alkyl, —$OC_{1-3}$alkyl, —$OC_{1-2}$alkyl, or —$OC_1$alkyl. The pyridazinyl can be substituted at any available ring carbon atom with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl. The pyridazinyl can be substituted at any available ring carbon atom with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl, including —$CF_3$, $CH_2CH_2F$, and the like. Preferred substituents wherein A is pyridazinyl include —$C_{1-6}$alkyl, with —$C_1$alkyl being most preferred. Other preferred substituents include halogen, in particular F and Cl.

In some aspects, A is benzo[d][1,3]dioxolyl. The benzo[d][1,3]dioxolyl can be attached to any of the compounds of formula I (or its subgenera) through any ring carbon atom. The benzo[d][1,3]dioxolyl can be unsubstituted or can be substituted with one or two halogen, preferably F. Preferably, the benzo[d][1,3]dioxolyl is substituted with one or two other substituents. The benzo[d][1,3]dioxolyl can be substituted at any available ring carbon atom with —$C_{1-6}$alkyl, for example, —$C_{1-5}$alkyl, —$C_{1-4}$alkyl, —$C_{1-3}$alkyl, —C$_{1-2}$alkyl, or —C$_1$alkyl. The benzo[d][1,3]dioxolyl can be substituted at any available ring carbon atom with halogen, for example F or Cl. The benzo[d][1,3]dioxolyl can be substituted at any available ring carbon atom with —SF$_5$. The benzo[d][1,3]dioxolyl can be substituted at any available ring carbon atom with —OC$_{1-6}$alkyl, for example, —OC$_{1-5}$alkyl, —OC$_{1-4}$alkyl, —OC$_{1-3}$alkyl, —OC$_{1-2}$alkyl, or —OC$_1$alkyl. The benzo[d][1,3]dioxolyl can be substituted at any available ring carbon atom with —C(O)—C$_{1-6}$alkyl, for example, —C(O)—C$_{1-5}$alkyl, —C(O)—C$_{1-4}$alkyl, —C(O)—C$_{1-3}$alkyl, —C(O)—C$_{1-2}$alkyl, or —C(O)—C$_1$alkyl. The benzo[d][1,3]dioxolyl can be substituted at any available ring carbon atom with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl, including —CF$_3$, CH$_2$CH$_2$F, and the like.

In some aspects, A is benzothiophenyl. The benzothiophenyl can be attached to any of the compounds of formula I (or its subgenera) through any ring carbon atom. Preferably, the benzothiophenyl is substituted with one or two substituents, preferably one substituent. The benzothiophenyl can be substituted at any available ring carbon atom with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The benzothiophenyl can be substituted at any available ring carbon atom with halogen, for example F or Cl. The benzothiophenyl can be substituted at any available ring carbon atom with —SF$_5$. The benzothiophenyl can be substituted at any available ring carbon atom with —OC$_{1-6}$alkyl, for example, —OC$_{1-5}$alkyl, —OC$_{1-4}$alkyl, —OC$_{1-3}$alkyl, —OC$_{1-2}$alkyl, or —OC$_1$alkyl. The benzothiophenyl can be substituted at any available ring carbon atom with —C(O)—C$_{1-6}$alkyl, for example, —C(O)—C$_{1-5}$alkyl, —C(O)—C$_{1-4}$alkyl, —C(O)—C$_{1-3}$alkyl, —C(O)—C$_{1-2}$alkyl, or —C(O)—C$_1$alkyl. The benzothiophenyl can be substituted at any available ring carbon atom with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl, including —CF$_3$, CH$_2$CH$_2$F, and the like.

In some aspects, A is pyrazolyl. The pyrazolyl can be attached to any of the compounds of formula I (or its subgenera) through any ring carbon atom. Preferably, the pyrazolyl is substituted with one or two substituents, preferably one substituent. The pyrazolyl can be substituted at any available ring carbon atom with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The pyrazolyl can be substituted at any available ring carbon atom with halogen, for example F or Cl. The pyrazolyl can be substituted at any available ring carbon atom with —SF$_5$. The pyrazolyl can be substituted at any available ring carbon atom with —OC$_{1-6}$alkyl, for example, —OC$_{1-5}$alkyl, —OC$_{1-4}$alkyl, —OC$_{1-3}$alkyl, —OC$_{1-2}$alkyl, or —OC$_1$alkyl. The pyrazolyl can be substituted at any available ring carbon atom with —C(O)—C$_{1-6}$alkyl, for example, —C(O)—C$_{1-5}$alkyl, —C(O)—C$_{1-4}$alkyl, —C(O)—C$_{1-3}$alkyl, —C(O)—C$_{1-2}$alkyl, or —C(O)—C$_1$alkyl. The pyrazolyl can be substituted at any available ring carbon atom with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C haloalkyl, including —CF$_3$, CH$_2$CH$_2$F, and the like.

In preferred aspects, A is an unsubstituted or substituted phenyl, pyridyl, pyrimidyl, or pyrazinyl moiety, with pyridinyl being particularly preferred. In those aspects wherein the phenyl, pyridyl, pyrimidyl, or pyrazinyl moiety is substituted, the preferred substituents include —C$_{1-6}$alkyl (e.g., methyl) and halogen (e.g., F or Cl), with methyl being particularly preferred.

Additional embodiments of the disclosure are compounds of Formula (I) having the subgenera of Formula (I-D):

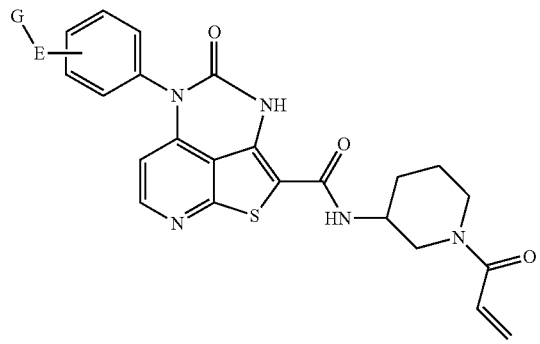

(I-D)

wherein the phenyl moiety can be unsubstituted or substituted with 1 or 2 substituents at any available carbon atom.

Additional embodiments of the disclosure are compounds of Formula (I) having the subgenera of Formula (I-E):

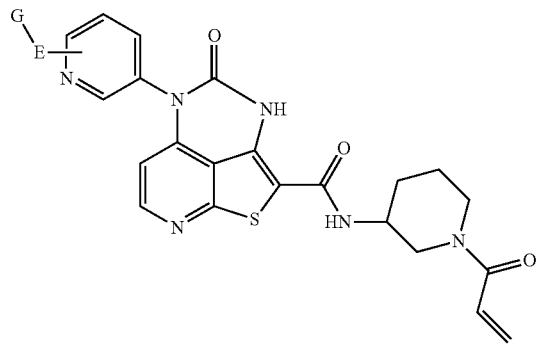

(I-E)

wherein the pyridyl moiety can be unsubstituted or substituted with 1 or 2 substituents at any available carbon atom.

Additional embodiments of the disclosure are compounds of Formula (I) having the subgenera of Formula (I-F):

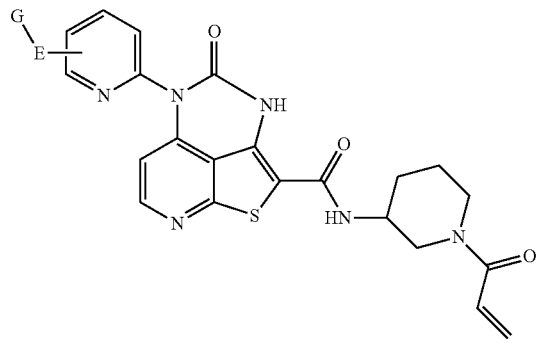

(I-F)

wherein the pyridyl moiety can be unsubstituted or substituted with 1 or 2 substituents at any available carbon atom.

According to the disclosure, E is —O—; a bond; —C(O)—NH—; —CH₂—; or —CH₂—O—. The E moiety can be attached through any available carbon atom on the A moiety. The E moiety can also be attached through any available carbon atom on the G moiety.

In preferred aspects, E is —O—. In other preferred aspects, E is a bond.

In some aspects of the disclosure, E is —C(O)—NH—, wherein the A-E-G moiety is A-C(O)—NH-G.

In other aspects of the disclosure, E is —CH₂—.

In yet other aspects of the disclosure, E is —CH₂—O—, wherein the A-E-G moiety is A-CH₂—O-G.

Additional embodiments of the disclosure are compounds of Formula (I) having the subgenera of Formula (I-G-1):

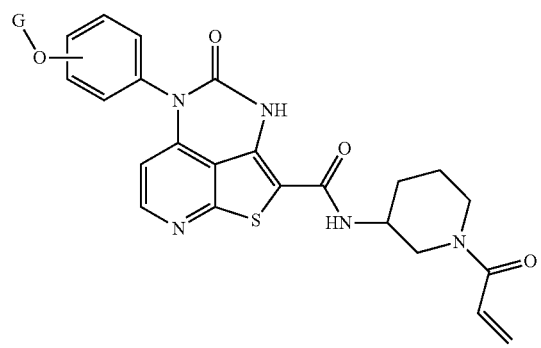

(I-G-1)

wherein the phenyl moiety can be unsubstituted or substituted with 1 or 2 substituents at any available carbon atom.

Additional embodiments of the disclosure are compounds of Formula (I) having the subgenera of Formula (I-G-2):

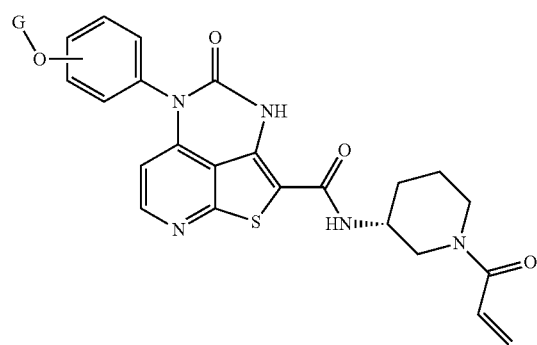

(I-G-2)

wherein the phenyl moiety can be unsubstituted or substituted with 1 or 2 substituents at any available carbon atom.

Additional embodiments of the disclosure are compounds of Formula (I) having the subgenera of Formula (I-H-1):

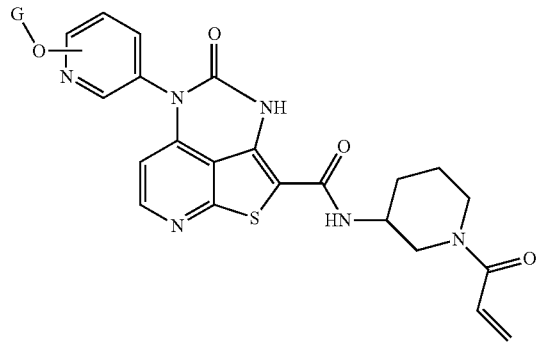

(I-H-1)

wherein the pyridyl moiety can be unsubstituted or substituted with 1 or 2 substituents at any available carbon atom.

Additional embodiments of the disclosure are compounds of Formula (I) having the subgenera of Formula (I-H-2):

I-H-2

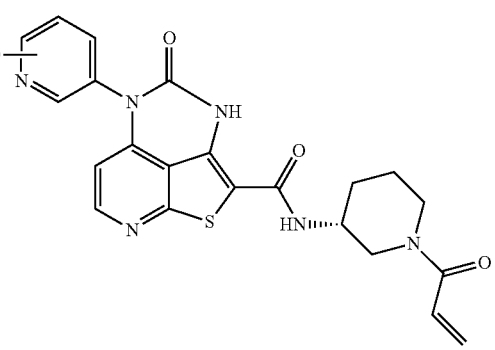

(I-H-2)

wherein the pyridyl moiety can be unsubstituted or substituted with 1 or 2 substituents at any available carbon atom.

Additional embodiments of the disclosure are compounds of Formula (I) having the subgenera of Formula (I-J-1):

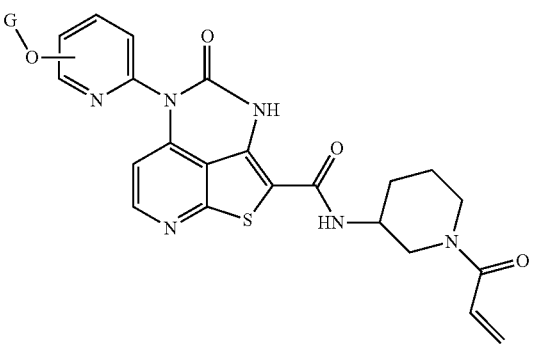

(I-J-1)

wherein the pyridyl moiety can be unsubstituted or substituted with 1 or 2 substituents at any available carbon atom.

Additional embodiments of the disclosure are compounds of Formula (I) having the subgenera of Formula (I-J-2):

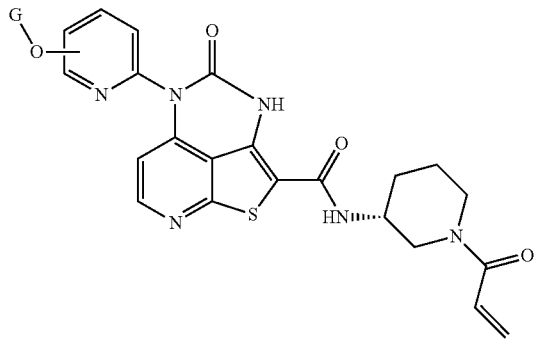

(I-J-2)

wherein the pyridyl moiety can be unsubstituted or substituted with 1 or 2 substituents at any available carbon atom.

Other preferred subgenera of formula I are:

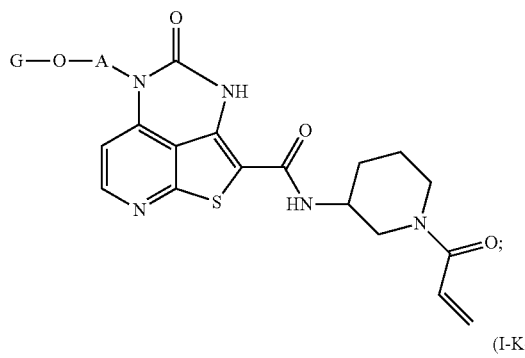

(I-K-1)

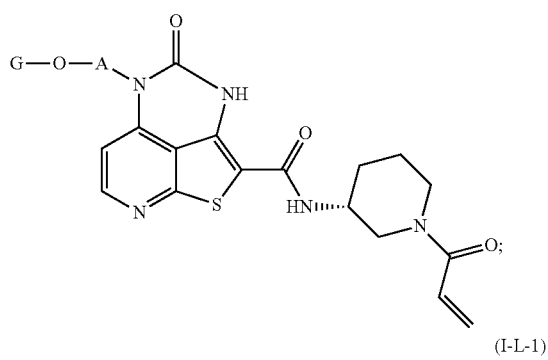

(I-K-2)

(I-L-1)

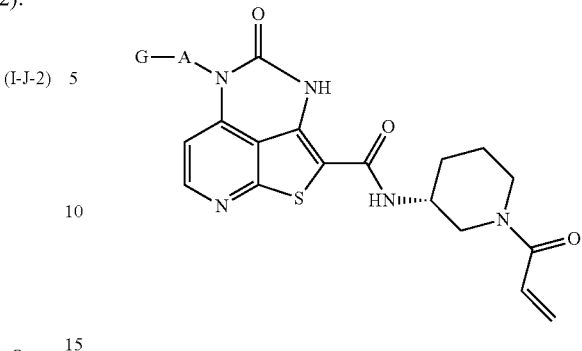

(I-L-2)

; and

-continued

According to the disclosure, G is H; —$C_{3-6}$cycloalkyl; -phenyl; -thiophenyl; —$C_{1-6}$alkyl; -pyrimidinyl; -pyridyl; -pyridazinyl; -benzofuranyl; —$C_{1-6}$haloalkyl; -heterocycloalkyl that contains an oxygen heteroatom; -phenyl-$CH_2$—O-phenyl; —$C_{1-6}$alk-O—$C_{1-6}$alkyl; —$NR^6R^7$; —$SO_2C_{1-6}$alkyl; or —OH; wherein the phenyl; pyridyl; pyridazinyl; pyrimidinyl; benzofuranyl; or thiophenyl is optionally substituted with 1, 2, or 3 substituents independently selected from the group consisting of halogen; —$C_{1-6}$ alkyl; —$C_{1-6}$haloalkyl; —$OC_{1-6}$haloalkyl; —$C_{3-6}$cycloalkyl; —$OC_{1-6}$alkyl; —CN; —OH; —$C_{1-6}$alk-O—$C_{1-6}$ alkyl; —C(O)—$NR^6R^7$; and —C(O)—$C_{1-6}$alkyl.

In some aspects, G is H.

In other aspects, G is —$C_{3-6}$cycloalkyl, for example, cyclopropyl, cyclobutyl, cyclopentyl, or cyclohexyl.

In some aspects, G is —$C_{1-6}$alkyl, for example, —$C_{1-5}$ alkyl, —$C_{1-4}$lkyl, —$C_{1-3}$alkyl, —$C_{1-2}$alkyl, or —$C_1$alkyl.

In some aspects, G is —$C_{1-6}$haloalkyl, for example, —$C_{1-5}$haloalkyl, —$C_{1-4}$haloalkyl, —$C_{1-3}$haloalkyl, —$C_{1-2}$ haloalkyl, or —$C_1$haloalkyl, including —$CF_3$, —$CH_2CH_2F$, and the like.

In other aspects, G is a -heterocycloalkyl that contains an oxygen heteroatom, for example, tetrahydropyranyl, tetrahydrofuranyl, or oxetanyl.

In preferred aspects, G is -phenyl-$CH_2$—O-phenyl. In these aspects, the -phenyl-$CH_2$—O-phenyl can be unsubstituted or substituted with 1, 2, or 3 substituents, preferably 1 or 2 substituents, more preferably 1 substituent, independently selected from the group consisting of halogen; —$C_{1-6}$ alkyl; —$C_{1-6}$haloalkyl; —$OC_{1-6}$haloalkyl; —$C_{3-6}$cycloalkyl; —$OC_{1-6}$alkyl; —CN; —OH; —$C_{1-6}$alk-O—$C_{1-6}$ alkyl; —C(O)—$NR^6R^7$ (wherein $R^6$ and $R^7$ are as previously described herein); and —C(O)—$C_{1-6}$alkyl. The one or both of the phenyl rings of the -phenyl-$CH_2$—O-phenyl moiety can be substituted with halogen, for example F or Cl. The one or both of the phenyl rings of the -phenyl-$CH_2$—O-phenyl moiety can be substituted with —$C_{1-6}$alkyl, for example, —$C_{1-5}$alkyl, —$C_{1-4}$alkyl, —$C_{1-3}$alkyl, —$C_{1-2}$ alkyl, or —$C_1$alkyl. The one or both of the phenyl rings of the -phenyl-$CH_2$—O-phenyl moiety can be substituted with —$C_{1-6}$haloalkyl, for example, —$C_{1-5}$haloalkyl, —$C_{1-4}$haloalkyl, —$C_{1-3}$haloalkyl, —$C_{1-2}$haloalkyl, or —$C_1$haloalkyl. The one or both of the phenyl rings of the -phenyl-$CH_2$—O-phenyl moiety can be substituted with —$OC_{1-6}$haloalkyl, for example, —$OC_{1-5}$haloalkyl, —$OC_{1-4}$ haloalkyl, —$OC_{1-3}$haloalkyl, —$OC_{1-2}$haloalkyl, or —$OC_1$haloalkyl. The one or both of the phenyl rings of the -phenyl-$CH_2$—O-phenyl moiety can be substituted with —$C_{3-6}$cycloalkyl, for example, cyclopropyl, cyclobutyl, cyclopentyl, or cyclohexyl. The one or both of the phenyl rings of the -phenyl-$CH_2$—O-phenyl moiety can be substituted with —OC$_{1-6}$alkyl, for example, —OC$_{1-5}$-alkyl, —OC$_{1-4}$alkyl, —OC$_{1-3}$alkyl, —OC$_{1-2}$alkyl, or —OC$_1$alkyl. The one or both of the phenyl rings of the -phenyl-CH$_2$—O-phenyl moiety can be substituted with —CN. The one or both of the phenyl rings of the -phenyl-CH$_2$—O-phenyl moiety can be substituted with —OH. The one or both of the phenyl rings of the -phenyl-CH$_2$—O-phenyl moiety can be substituted with —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl. The one or both of the phenyl rings of the -phenyl-CH$_2$—O-phenyl moiety can be substituted with —C(O)—NR$^6$R$^7$, wherein R$^6$ and R$^7$ are preferably each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The one or both of the phenyl rings of the -phenyl-CH$_2$—O-phenyl moiety can be substituted with —C(O)—C$_{1-6}$alkyl, for example, —C(O)—C$_{1-65}$alkyl, —C(O)—C$_{1-4}$alkyl, —C(O)—C$_{1-3}$alkyl, —C(O)—C$_{1-2}$alkyl, or —C(O)—C$_1$alkyl.

In some aspects, G is —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl.

In other aspects, G is —NR$^6$R$^7$, wherein R$^6$ and R$^7$ are each independently H; —C$_{1-6}$alkyl; —C$_{3-6}$cycloalkyl; —C(O)H, or —CN. In these aspects, R$^6$ and R$^7$ are preferably each independently H; —C$_{1-6}$alkyl, for example, —C$_{1-5}$ alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —C$_{1-6}$alkyl, for example, —C$_{1-5}$alkyl, —C$_{1-4}$alkyl, —C$_{1-3}$alkyl, —C$_{1-2}$alkyl, or —C$_1$alkyl.

In some aspects, G is —SO$_2$C$_{1-6}$alkyl, for example, —SO$_2$C$_{1-5}$alkyl, —SO$_2$C$_{1-4}$alkyl, —SO$_2$C$_{1-3}$alkyl, —SO$_2$C$_{1-2}$alkyl, or —SO$_2$C$_1$alkyl.

In some aspects, G is —OH.

In preferred aspects, G is phenyl. In these aspects, the phenyl can be unsubstituted or substituted with 1, 2, or 3 substituents, preferably 1 or 2 substituents, more preferably 1 substituent, independently selected from the group consisting of halogen; —C$_{1-6}$alkyl; —C$_{1-6}$haloalkyl; —OC$_{1-6}$haloalkyl; —C$_{3-6}$cycloalkyl; —OC$_{1-6}$alkyl; —CN; —OH; —C$_{1-6}$alk-O—C$_{1-6}$alkyl; —C(O)—NR$^6$R$^7$ (wherein R$^6$ and R$^7$ are as previously described herein); and —C(O)—C$_{1-6}$alkyl. The phenyl can be substituted with halogen, for example F or Cl. The phenyl can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The phenyl can be substituted with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl. The phenyl can be substituted with —OC$_{1-6}$haloalkyl, for example, —OC$_{1-5}$haloalkyl, —OC$_{1-4}$haloalkyl, —OC$_{1-3}$haloalkyl, —OC$_{1-2}$haloalkyl, or —OC$_1$haloalkyl. The phenyl can be substituted with —C$_{3-6}$cycloalkyl, for example, cyclopropyl, cyclobutyl, cyclopentyl, or cyclohexyl. The phenyl can be substituted with —OC$_{1-6}$alkyl, for example, —OC$_{1-5}$alkyl, —OC$_{1-4}$alkyl, —OC$_{1-3}$alkyl, —OC$_{1-2}$alkyl, or —OC$_1$alkyl. The phenyl can be substituted with —CN. The phenyl can be substituted with —OH. The phenyl can be substituted with —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl. The phenyl can be substituted with —C(O)—NR$^6$R$^7$, wherein R$^6$ and R$^7$ are preferably each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The phenyl can be substituted with —C(O)—C$_{1-6}$alkyl, for example, —C(O)—C$_{1-65}$alkyl, —C(O)—C$_{1-4}$alkyl, —C(O)—C$_{1-3}$alkyl, —C(O)—C$_{1-2}$alkyl, or —C(O)—C$_1$alkyl.

In some aspects, G is pyridyl. In these aspects, the pyridyl can be unsubstituted or substituted with 1, 2, or 3 substituents, preferably 1 or 2 substituents, more preferably 1 substituent, independently selected from the group consisting of halogen; —C$_{1-6}$alkyl; —C$_{1-6}$haloalkyl; —OC$_{1-6}$haloalkyl; —C$_{3-6}$cycloalkyl; —OC$_{1-6}$alkyl; —CN; —OH; —C$_{1-6}$alk-O—C$_{1-6}$alkyl; —C(O)—NR$^6$R$^7$ (wherein R$^6$ and R$^7$ are as previously described herein); and —C(O)—C$_{1-6}$alkyl. The pyridyl can be substituted with halogen, for example F or Cl. The pyridyl can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The pyridyl can be substituted with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl. The pyridyl can be substituted with —OC$_{1-6}$haloalkyl, for example, —OC$_{1-5}$haloalkyl, —OC$_{1-4}$haloalkyl, —OC$_{1-3}$haloalkyl, —OC$_{1-2}$haloalkyl, or —OC$_1$haloalkyl. The pyridyl can be substituted with —C$_{3-6}$cycloalkyl, for example, cyclopropyl, cyclobutyl, cyclopentyl, or cyclohexyl. The pyridyl can be substituted with —OC$_{1-6}$alkyl, for example, —OC$_{1-5}$alkyl, —OC$_{1-4}$alkyl, —OC$_{1-3}$alkyl, —OC$_{1-2}$alkyl, or —OC$_1$alkyl. The pyridyl can be substituted with —CN. The pyridyl can be substituted with —OH. The pyridyl can be substituted with —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl. The pyridyl can be substituted with —C(O)—NR$^6$R$^7$, wherein R$^6$ and R$^7$ are preferably each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The pyridyl can be substituted with —C(O)—C$_{1-6}$alkyl, for example, —C(O)—C$_{1-65}$alkyl, —C(O)—C$_{1-4}$alkyl, —C(O)—C$_{1-3}$alkyl, —C(O)—C$_{1-2}$alkyl, or —C(O)—C$_1$alkyl.

In some aspects, G is pyridazinyl. In these aspects, the pyridazinyl can be unsubstituted or substituted with 1, 2, or 3 substituents, preferably 1 or 2 substituents, more preferably 1 substituent, independently selected from the group consisting of halogen; —C$_{1-6}$alkyl; —C$_{1-6}$haloalkyl; —OC$_{1-6}$haloalkyl; —C$_{3-6}$cycloalkyl; —OC$_{1-6}$alkyl; —CN; —OH; —C$_{1-6}$alk-O—C$_{1-6}$alkyl; —C(O)—NR$^6$R$^7$ (wherein R$^6$ and R$^7$ are as previously described herein); and —C(O)—C$_{1-6}$alkyl. The pyridazinyl can be substituted with halogen, for example F or Cl. The pyridazinyl can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The pyridazinyl can be substituted with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl. The pyridazinyl can be substituted with —OC$_{1-6}$haloalkyl, for example, —OC$_{1-5}$haloalkyl, —OC$_{1-4}$ haloalkyl, —OC$_{1-3}$haloalkyl, —OC$_{1-2}$haloalkyl, or —OC$_1$haloalkyl. The pyridazinyl can be substituted with —C$_{3-6}$cycloalkyl, for example, cyclopropyl, cyclobutyl, cyclopentyl, or cyclohexyl. The pyridazinyl can be substituted with —OC$_{1-6}$alkyl, for example, —OC$_{1-5}$-alkyl, —OC$_{1-4}$alkyl, —OC$_{1-3}$alkyl, —OC$_{1-2}$alkyl, or —OC$_1$alkyl. The pyridazinyl can be substituted with —CN. The pyridazinyl can be substituted with —OH. The pyridazinyl can be substituted with —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl. The pyridazinyl can be substituted with —C(O)—NR$^6$R$^7$, wherein R$^6$ and R$^7$ are preferably each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The pyridazinyl can be substituted with —C(O)—C$_{1-6}$alkyl, for example, —C(O)—C$_{1-65}$alkyl, —C(O)—C$_{1-4}$alkyl, —C(O)—C$_{1-3}$alkyl, —C(O)—C$_{1-2}$alkyl, or —C(O)—C$_1$alkyl.

In some aspects, G is pyrimidinyl. In these aspects, the pyrimidinyl can be unsubstituted or substituted with 1, 2, or 3 substituents, preferably 1 or 2 substituents, more preferably 1 substituent, independently selected from the group consisting of halogen; —C$_{1-6}$alkyl; —C$_{1-6}$haloalkyl; —OC$_{1-6}$haloalkyl; —C$_{3-6}$cycloalkyl; —OC$_{1-6}$alkyl; —CN; —OH; —C$_{1-6}$alk-O—C$_{1-6}$alkyl; —C(O)—NR$^6$R$^7$ (wherein R$^6$ and R$^7$ are as previously described herein); and —C(O)—C$_{1-6}$alkyl. The pyrimidinyl can be substituted with halogen, for example F or Cl. The pyrimidinyl can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The pyrimidinyl can be substituted with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl. The pyrimidinyl can be substituted with —OC$_{1-6}$haloalkyl, for example, —OC$_{1-5}$haloalkyl, —OC$_{1-4}$haloalkyl, —OC$_{1-3}$haloalkyl, —OC$_{1-2}$haloalkyl, or —OC$_1$haloalkyl. The pyrimidinyl can be substituted with —C$_{3-6}$cycloalkyl, for example, cyclopropyl, cyclobutyl, cyclopentyl, or cyclohexyl. The pyrimidinyl can be substituted with —OC$_{1-6}$alkyl, for example, —OC$_{1-5}$-alkyl, —OC$_{1-4}$alkyl, —OC$_{1-3}$alkyl, —OC$_{1-2}$alkyl, or —OC$_1$alkyl. The pyrimidinyl can be substituted with —CN. The pyrimidinyl can be substituted with —OH. The pyrimidinyl can be substituted with —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl. The pyrimidinyl can be substituted with —C(O)—NR$^6$R$^7$, wherein R$^6$ and R$^7$ are preferably each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The pyrimidinyl can be substituted with —C(O)—C$_{1-6}$alkyl, for example, —C(O)—C$_{1-65}$alkyl, —C(O)—C$_{1-4}$alkyl, —C(O)—C$_{1-3}$alkyl, —C(O)—C$_{1-2}$alkyl, or —C(O)—C$_1$alkyl.

In some aspects, G is benzofuranyl. In these aspects, the benzofuranyl can be unsubstituted or substituted with 1, 2, or 3 substituents, preferably 1 or 2 substituents, more preferably 1 substituent, independently selected from the group consisting of halogen; —C$_{1-6}$alkyl; —C$_{1-6}$haloalkyl; —OC$_{1-6}$haloalkyl; —C$_{3-6}$cycloalkyl; —OC$_{1-6}$alkyl; —CN; —OH; —C$_{1-6}$alk-O—C$_{1-6}$alkyl; —C(O)—NR$^6$R$^7$ (wherein R$^6$ and R$^7$ are as previously described herein); and —C(O)—C$_{1-6}$alkyl. The benzofuranyl can be substituted with halogen, for example F or Cl. The benzofuranyl can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The benzofuranyl can be substituted with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl. The benzofuranyl can be substituted with —OC$_{1-6}$haloalkyl, for example, —OC$_{1-5}$haloalkyl, —OC$_{1-4}$haloalkyl, —OC$_{1-3}$haloalkyl, —OC$_{1-2}$haloalkyl, or —OC$_1$haloalkyl. The benzofuranyl can be substituted with —C$_{3-6}$cycloalkyl, for example, cyclopropyl, cyclobutyl, cyclopentyl, or cyclohexyl. The benzofuranyl can be substituted with —OC$_{1-6}$alkyl, for example, —OC$_{1-5}$-alkyl, —OC$_{1-4}$alkyl, —OC$_{1-3}$alkyl, —OC$_{1-2}$alkyl, or —OC$_1$alkyl. The benzofuranyl can be substituted with —CN. The benzofuranyl can be substituted with —OH. The benzofuranyl can be substituted with —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl. The benzofuranyl can be substituted with —C(O)—NR$^6$R$^7$, wherein R$^6$ and R$^7$ are preferably each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The benzofuranyl can be substituted with —C(O)—C$_{1-6}$alkyl, for example, —C(O)—C$_{1-65}$alkyl, —C(O)—C$_{1-4}$alkyl, —C(O)—C$_{1-3}$alkyl, —C(O)—C$_{1-2}$alkyl, or —C(O)—C$_1$alkyl.

In some aspects, G is thiophenyl. In these aspects, the thiophenyl can be unsubstituted or substituted with 1, 2, or 3 substituents, preferably 1 or 2 substituents, more preferably 1 substituent, independently selected from the group consisting of halogen; —C$_{1-6}$alkyl; —C$_{1-6}$haloalkyl; —OC$_{1-6}$haloalkyl; —C$_{3-6}$cycloalkyl; —OC$_{1-6}$alkyl; —CN; —OH; —C$_{1-6}$alk-O—C$_{1-6}$alkyl; —C(O)—NR$^6$R$^7$ (wherein R$^6$ and R$^7$ are as previously described herein); and —C(O)—C$_{1-6}$alkyl. The thiophenyl can be substituted with halogen, for example F or Cl. The thiophenyl can be substituted with —C$_{1-6}$alkyl, for example, —C$_{1-5}$alkyl, —C$_{1-4}$alkyl, —C$_{1-3}$alkyl, —C$_{1-2}$alkyl, or —C$_1$alkyl. The thiophenyl can be substituted with —C$_{1-6}$haloalkyl, for example, —C$_{1-5}$haloalkyl, —C$_{1-4}$haloalkyl, —C$_{1-3}$haloalkyl, —C$_{1-2}$haloalkyl, or —C$_1$haloalkyl. The thiophenyl can be substituted with —OC$_{1-6}$haloalkyl, for example, —OC$_{1-5}$haloalkyl, —OC$_{1-4}$haloalkyl, —OC$_{1-3}$haloalkyl, —OC$_{1-2}$haloalkyl, or —OC$_1$haloalkyl. The thiophenyl can be substituted with —C$_{3-6}$cycloalkyl, for example, cyclopropyl, cyclobutyl, cyclopentyl, or cyclohexyl. The thiophenyl can be substituted with —OC$_{1-6}$alkyl, for example, —OC$_{1-5}$alkyl, —OC$_{1-4}$alkyl, —OC$_{1-3}$alkyl, —OC$_{1-2}$alkyl, or —OC$_1$alkyl. The thiophenyl can be substituted with —CN. The thiophenyl can be substituted with —OH. The thiophenyl can be substituted with —C$_{1-6}$alk-O—C$_{1-6}$alkyl, for example, —C$_{1-5}$alk-O—C$_{1-5}$alkyl, —C$_{1-4}$alk-O—C$_{1-4}$alkyl, —C$_{1-3}$alk-O—C$_{1-3}$alkyl, —C$_{1-2}$alk-O—C$_{1-2}$alkyl, or —C$_1$alk-O—C$_1$alkyl. The thiophenyl can be substituted with —C(O)—NR$^6$R$^7$, wherein R$^6$ and R$^7$ are preferably each independently H; —C$_{1-6}$alkyl, for example, —C$_{1-5}$alkyl, —C$_{1-4}$alkyl, —C$_{1-3}$alkyl, —C$_{1-2}$alkyl, or —C$_1$alkyl; or —C$_{3-6}$cycloalkyl, for example, cyclopropyl, cyclobutyl, cyclopentyl, or cyclohexyl. More preferably, R$^6$ and R$^7$ are each independently H or —$C_{1-6}$alkyl, for example, —$C_{1-5}$alkyl, —$C_{1-4}$alkyl, —$C_{1-3}$alkyl, —$C_{1-2}$alkyl, or —$C_1$alkyl. The thiophenyl can be substituted with —C(O)—$C_{1-6}$alkyl, for example, —C(O)—$C_{1-5}$alkyl, —C(O)—$C_{1-4}$alkyl, —C(O)—$C_{1-3}$alkyl, —C(O)—$C_{1-2}$alkyl, or —C(O)—$C_1$alkyl.

In preferred aspects, G is unsubstituted or substituted phenyl, pyridyl, pyridizinyl, or pyrazinyl. In those aspects wherein G is substituted phenyl, pyridyl, pyridizinyl, or pyrazinyl, preferred substituents include $C_{1-6}$alkyl (e.g., methyl). In other preferred aspects, G is $C_{1-6}$alkyl (e.g., -isopropyl).

In preferred aspects, G is unsubstituted or substituted phenyl, pyridyl, pyridizinyl, or pyrazinyl and E is —$CH_2$— or O. In those aspects wherein G is substituted phenyl, pyridyl, pyridizinyl, or pyrazinyl and E is —$CH_2$— or O, preferred substituents include $C_{1-6}$alkyl (e.g., methyl). In other preferred aspects, G is $C_{1-6}$alkyl (e.g., -isopropyl) and E is —$CH_2$— or O.

In preferred embodiments, particularly those wherein the compounds are of Formula II', G is selected from the group consisting of $C_{3-6}$cycloalkyl; oxetanyl; tetrahydrofuranyl; tetrahydropyranyl; benzofuran-7-yloxy; pyridyl; pyridyl substituted with $CH_3$; phenyl; phenyl substituted with one or two members independently selected from the group consisting of: halogen, $C_{1-6}$alkyl, $C_{1-6}$haloalkyl, OH, $OC_{1-6}$alkyl, $OC_{1-6}$haloalkyl, $CH_2OCH_3$, (C=O)$NH_2$, and $C_{3-6}$cycloalkyl; and

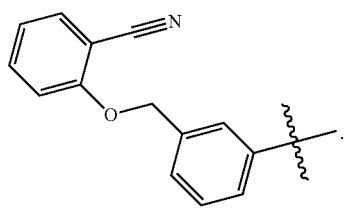 [SMILES: *c1cccc(COc2ccccc2C#N)c1]

In more preferred aspects, G is phenyl or phenyl substituted with $C_{1-6}$alkyl.

In preferred embodiments, particularly those wherein the compounds are of Formula III', G-A is selected from the group consisting of

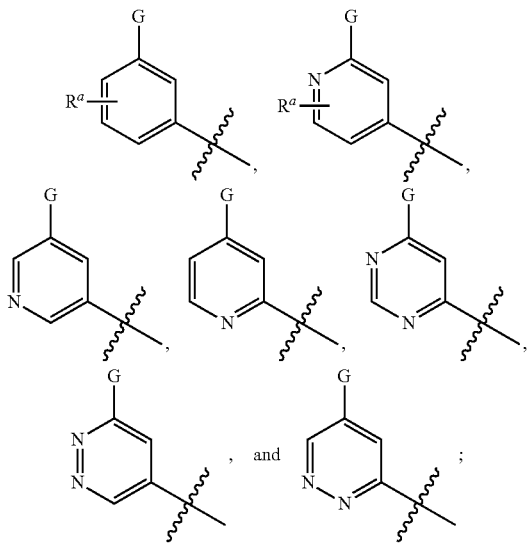

wherein G is phenyl; or phenyl substituted with one or two members independently selected from the group consisting of: halogen, $C_{1-6}$alkyl, $C_{1-6}$haloalkyl, $C_{3-6}$cycloalkyl, pyridyl, oxetan-3-yl, and tetrahydro-2H-pyran-4-yl; and $R^a$ is H or $CH_3$. In more preferred aspects, G-A is

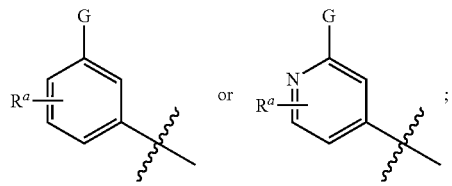

wherein G is phenyl, or phenyl substituted with $C_{1-6}$alkyl.

In preferred embodiments, particularly those wherein the compounds are of Formula IV', G-E-A is selected from the group consisting of:

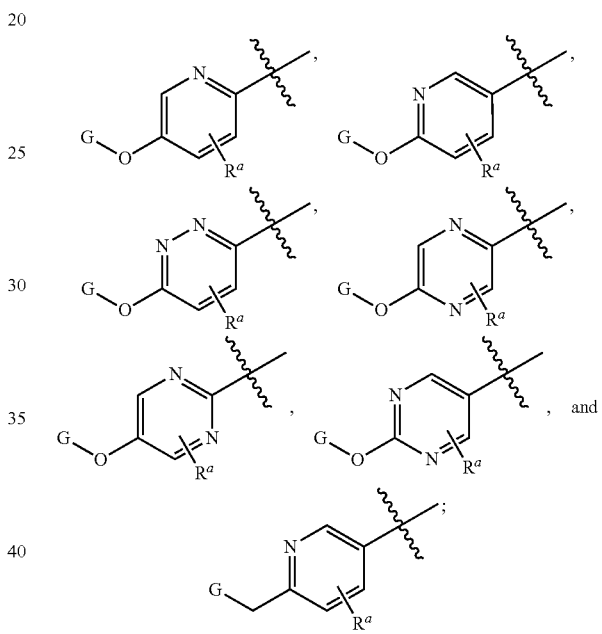

where G is selected from the group consisting of: $C_{1-6}$alkyl, $C_{3-6}$cycloalkyl, tetrahydro-2H-pyran-4-yl, pyridazin-3-yl, phenyl, and phenyl substituted with F; and $R^a$ is H or $CH_3$. In more preferred aspects, G-E-A is

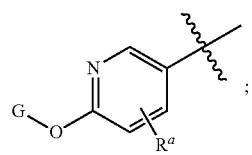

$R^a$ is $CH_3$; and G is phenyl.

In preferred embodiments, particularly those wherein the compounds are of Formula V', G is selected from the group consisting of: $C_{1-6}$alkyl; $C_{1-6}$haloalkyl; phenyl; phenyl substituted with one or two members independently selected from the group consisting of: halogen, $C_{1-6}$alkyl, $C_{1-6}$haloalkyl, $OC_{1-6}$alkyl, $OC_{1-6}$haloalkyl, (C=O)—$C_{1-6}$alkyl, $SF_5$, OH, $NH_2$, $N(CH_3)_2$, $OCH_2CH_2OCH(CH_3)_2$, and $SO_2C_{1-6}$alkyl; benzo[d][1,3]dioxolyl optionally substituted with Cl; 2-methylpyridin-3-yl; 2-isopropylpyridin-4-yl; benzothiophenyl; napthalenyl; and 2,2-difluorobenzo[d][1,3]dioxol-5-yl.

Preferred subgenera of formula I include:
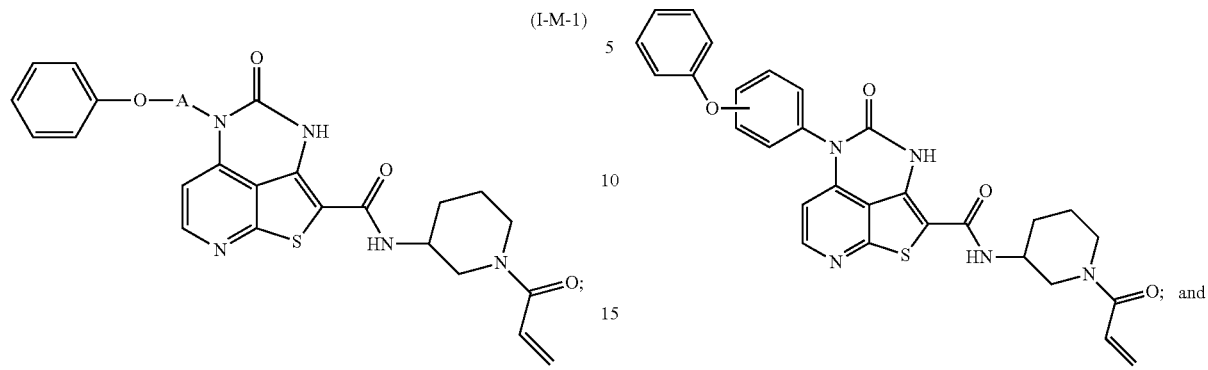
(I-M-1)
(I-M-2)
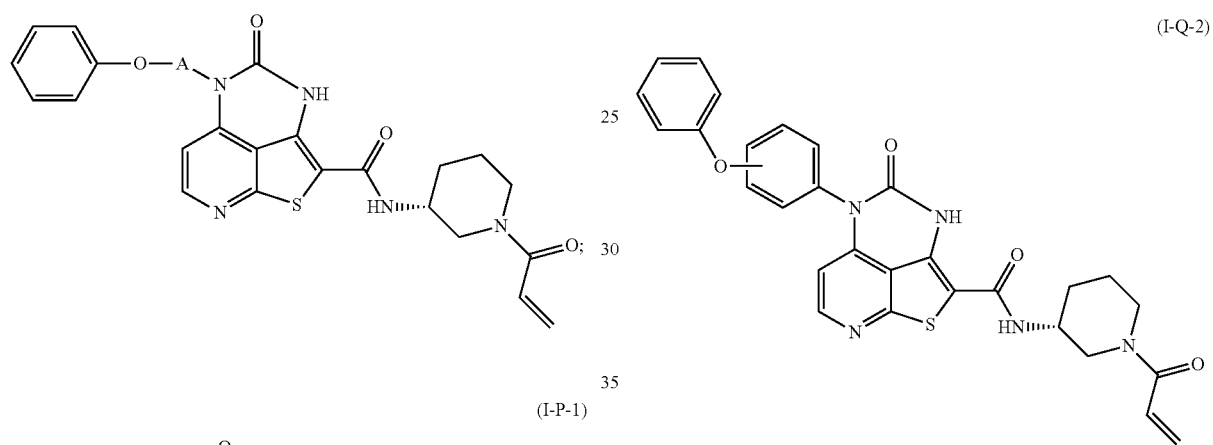
(I-P-1)
(I-P-2)
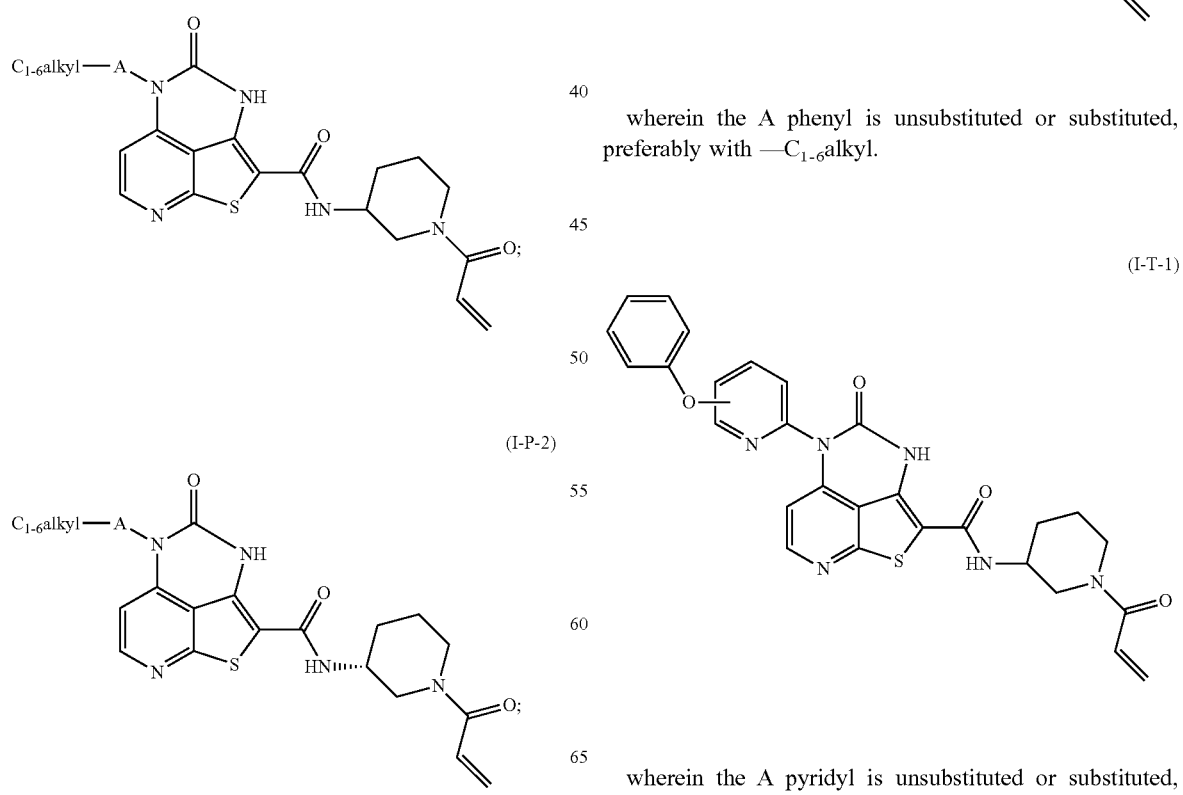
(I-Q-1)
(I-Q-2)
wherein the A phenyl is unsubstituted or substituted, preferably with —$C_{1-6}$alkyl.
(I-T-1)
wherein the A pyridyl is unsubstituted or substituted, preferably with —$C_{1-6}$alkyl.

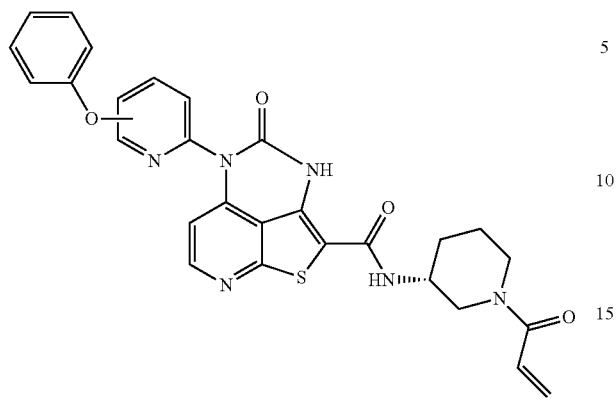
(I-T-2)

wherein the A pyridyl is unsubstituted or substituted, preferably with —$C_{1-6}$alkyl.

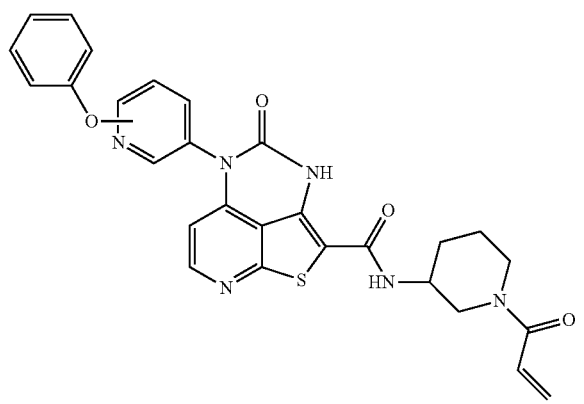
(I-U-1)

wherein the A pyridyl is unsubstituted or substituted, preferably with —$C_{1-6}$alkyl.

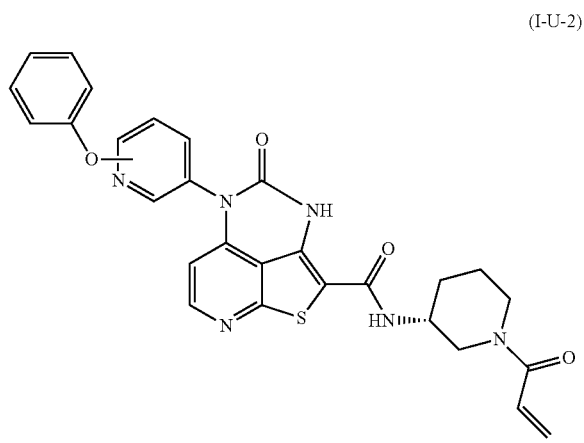
(I-U-2)

wherein the A pyridyl is unsubstituted or substituted, preferably with —$C_{1-6}$alkyl.

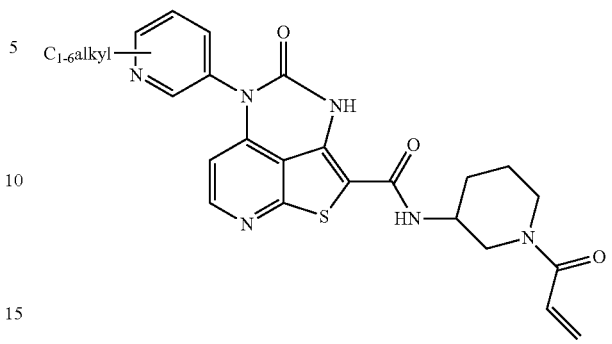
(I-V-1)

wherein the A pyridyl is unsubstituted or substituted, preferably with —$C_{1-6}$alkyl.

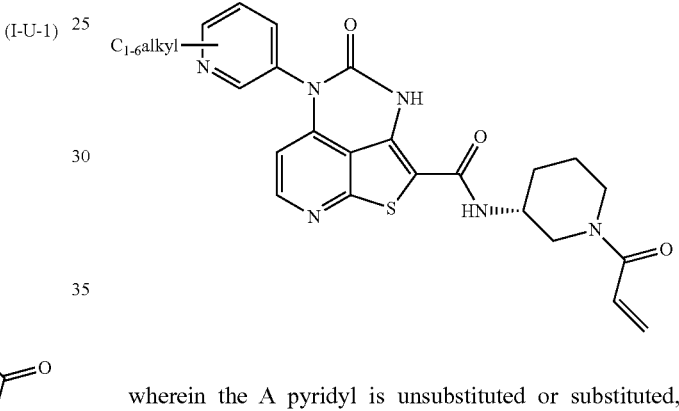
(I-V-2)

wherein the A pyridyl is unsubstituted or substituted, preferably with —$C_{1-6}$alkyl.

In those embodiments of the disclosure wherein the compounds are of Formula (II'), preferably $R^a$ is H or $CH_3$; n is 1; E is O; G is phenyl or phenyl substituted with $C_{1-6}$alkyl; Ring B is

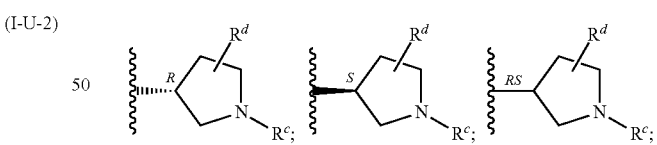

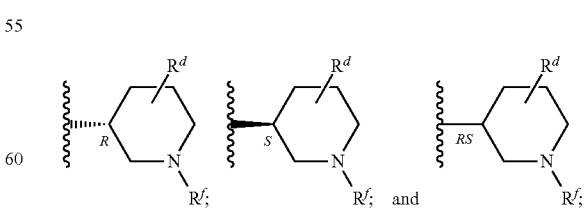

and $R^c$ and $R^f$ are (C=O)CH=$CH_2$; and $R^d$ is H.

In those embodiments of the disclosure wherein the compounds are of Formula (III'), preferably G-A is

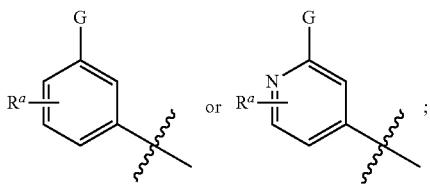

G is phenyl, or phenyl substituted with $C_{1-6}$alkyl;
Ring B is:

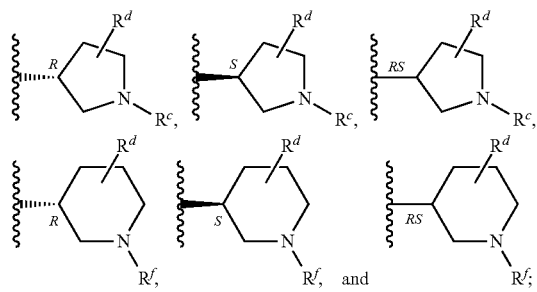

and $R^c$ and $R^f$ are (C=O)CH=CH$_2$; and $R^d$ is H.

In those embodiments of the disclosure wherein the compounds are of Formula (IV'), preferably G-E-A is

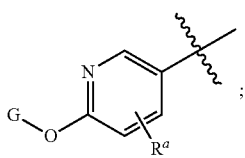

$R^a$ is CH$_3$; G is phenyl;
Ring B is

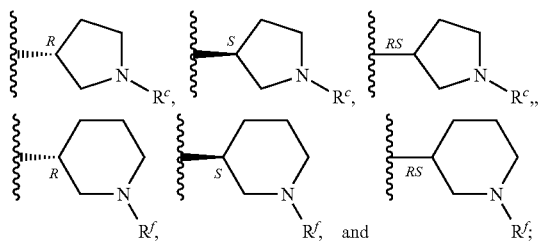

and $R^c$ and $R^f$ are (C=O)CH=CH$_2$.

A further embodiment of the present disclosure is a compound selected from the group consisting of:

N-((3R,5R)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3-fluoro-2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5R)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(3-fluoro-2-methyl-4-phenoxyphenyl)-4-oxo-4,5-dihydro-3H-1-thia-3,5,8-triazaacenaphthylene-2-carboxamide;

N-((3R,5R)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2-fluoro-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(2-chloro-4-phenoxyphenyl)-4-oxo-4,5-dihydro-3H-1-thia-3,5,8-triazaacenaphthylene-2-carboxamide;

N-((3R,5S)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2-chloro-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-(benzofuran-7-yloxy)-2-methylphenyl)-4-oxo-4,5-dihydro-3H-1-thia-3,5,8-triazaacenaphthylene-2-carboxamide;

(R)—N-(1-Acryloylpyrrolidin-3-yl)-5-(4-(2,6-difluorophenoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-5-(4-(2-ethylphenoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(2-fluoro-6-methyl-4-phenoxyphenyl)-4-oxo-4,5-dihydro-3H-1-thia-3,5,8-triazaacenaphthylene-2-carboxamide;

(R,E)-N-(1-(2-cyano-3-(3-methyloxetan-3-yl)acryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(4-(benzofuran-7-yloxy)-2-methylphenyl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide;

(R)-5-(4-(3-((2-Cyanophenoxy)methyl)phenoxy)-2-methylphenyl)-N-(1-methylpiperidin-3-yl)-4-oxo-4,5-dihydro-3H-1-thia-3,5,8-triazaacenaphthylene-2-carboxamide;

(S,E)-N-(1-(4-Hydroxybut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Chloroacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(4-Aminobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

N-((3S,4R)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,EZ)—N-(1-(2-Cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(4-Hydroxybut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;

N-(4-Cyano-1,4-oxazepan-6-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-(cyclohexyloxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-isopropoxy-2-methylphenyl)-4-oxo-4,5-dihydro-3H-1-thia-3,5,8-triazaacenaphthylene-2-carboxamide;

N-((3S,4R)-1-Acryloyl-4-methoxypyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Cyanopiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide;

N-((3S,4R)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide;

(R)—N-(1-Acryloylpyrrolidin-3-yl)-5-(4-(cyclohexyloxy)-2-methylphenyl)-4-oxo-4,5-dihydro-3H-1-thia-3,5,8-triazaacenaphthylene-2-carboxamide;

(R,E)-N-(1-(2-Cyano-4-methoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-13C-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(But-2-ynoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-methyl-4-morpholinopent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(S)—N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(4-fluoro-6-methyl-4-phenoxyphenyl)-4-oxo-4,5-dihydro-3H-1-thia-3,5,8-triazaacenaphthylene-2-carboxamide;

(R)-5-(*S)-(2-methyl-4-phenoxyphenyl)-4-oxo-N-(1-propioloylpiperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-4-oxo-5-(4-phenoxyphenyl)-4,5-dihydro-3H-1-thia-3,5,8-triazaacenaphthylene-2-carboxamide;

(R)—N-(1-(2-Fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Fluoroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-cyclopropoxy-2-methylphenyl)-4-oxo-4,5-dihydro-3H-1-thia-3,5,8-triazaacenaphthylene-2-carboxamide;

(R)-5-(4-(2,6-Difluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(5-chlorobenzo[d][1,3]dioxol-4-yl)-4-oxo-4,5-dihydro-3H-1-thia-3,5,8-triazaacenaphthylene-2-carboxamide;

N-((3S,4S)-1-Acryloyl-4-methoxypyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(But-2-ynoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-(2-(Dimethylamino)acetyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)-5-(4-(2-Fluorophenoxy)-2-methylphenyl)-N-(1-methylpiperidin-3-yl)-4-oxo-4,5-dihydro-3H-1-thia-3,5,8-triazaacenaphthylene-2-carboxamide;

N-((3S,4R)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-propylpiperidin-3-yl)-4,5-dihydro-3H-1-thia-3,5,8-triazaacenaphthylene-2-carboxamide;

(S)-5-(3-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)—N-(1-Acryloylpiperidin-3-yl)-5-(4-ethyl-2-methylphenyl)-4-oxo-4,5-dihydro-3H-1-thia-3,5,8-triazaacenaphthylene-2-carboxamide;

(R,E)-N-(1-(2-Cyano-4-methyl-4-(tetrahydro-2H-pyran-4-yl)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-(2,6-difluorophenoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(4-ethoxy-2-methylphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(S)-5-(*S)-(2-Methyl-4-phenoxyphenyl)-4,5-dihydro-3H-1-thia-3,5,8-triazaacenaphthylene-2-carboxamide;

(R)—N-(1-Acryloylpiperidin-3-yl)-5-(2,6-difluoro-4-phenoxyphenyl)-4-oxo-4,5-dihydro-3H-1-thia-3,5,8-triazaacenaphthylene-2-carboxamide;

(R)-5-(4-(Benzofuran-7-yloxy)-2-methylphenyl)-N-(1-methylpiperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)—N-(1-(3-Methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-Ethylpiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(3-Hydroxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-(2-ethylphenoxy)-2-methylphenyl)-4-oxo-4,5-dihydro-3H-1-thia-3,5,8-triazaacenaphthylene-2-carboxamide;

(R)—N-(1-Acryloylpyrrolidin-3-yl)-5-(2,3-dimethyl-4-phenoxyphenyl)-4-oxo-4,5-dihydro-3H-1-thia-3,5,8-triazaacenaphthylene-2-carboxamide;

(R)—N-(1-(2-(Dimethylamino)acetyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-fluoro-4-phenoxyphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(tetrahydrofuran-3-yl)-4,5-dihydro-3H-1-thia-3,5,8-triazaacenaphthylene-2-carboxamide;

(R)—N-(1-Acryloylpyrrolidin-3-yl)-5-(2,6-dimethyl-4-phenoxyphenyl)-4-oxo-4,5-dihydro-3H-1-thia-3,5,8-triazaacenaphthylene-2-carboxamide;

(S)—N-(1-acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2-methyl-4-(pentafluorothio)phenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide;

(R)-Tetrahydro-2H-pyran-3-yl 5-(2-methyl-4-phenoxyphenyl)-4-oxo-4,5-dihydro-3H-1-thia-3,5,8-triazaacenaphthylene-2-carboxylate;

(R)—N-(1-Acryloylpiperidin-3-yl)-5-(2,4-dimethylphenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide;

(S)-5-(*S)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)-5-(3-Fluoro-2-methyl-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide;

(S)-5-(2-Methyl-4-phenoxyphenyl)-4-oxo-N-(tetrahydrofuran-3-yl)-4,5-dihydro-3H-1-thia-3,5,8-triazaacenaphthylene-2-carboxamide;

(R)-5-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;

N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Isopropylpyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4R)-4-Fluoro-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Methoxyacetyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

N-(1-Cyanoazepan-3-yl)-5-(2-methyl-4-phenoxyphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide;

(R)—N-(1-(3-Hydroxypropanoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Isopropylpiperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-isopropoxy-2-methylphenyl)-4-oxo-4,5-dihydro-3H-1-thia-3,5,8-triazaacenaphthylene-2-carboxamide;

N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide;

(R,E)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-(3-(methylamino)propanoyl)piperidin-3-yl)-4-oxo-4,5-dihydro-3H-1-thia-3,5,8-triazaacenaphthylene-2-carboxamide;

(R)-5-(2-Fluoro-4-phenoxyphenyl)-4-oxo-N-(piperidin-3-yl)-4,5-dihydro-3H-1-thia-3,5,8-triazaacenaphthylene-2-carboxamide;

(R)-5-(2-Methyl-4-phenoxyphenyl)-4-oxo-N-(tetrahydrofuran-3-yl)-4,5-dihydro-3H-1-thia-3,5,8-triazaacenaphthylene-2-carboxamide;

N-(1-Acryloylazetidin-3-yl)-5-(2-methyl-4-phenoxyphenyl)-4-oxo-4,5-dihydro-3H-1-thia-3,5,8-triazaacenaphthylene-2-carboxamide;

(R)—N-(1-13C-Acryloylpiperidin-3-yl)-5-(4-methoxy-2-methylphenyl)-4-oxo-4,5-dihydro-3H-1-thia-3,5,8-triazaacenaphthylene-2-carboxamide;

N—((R)-1-((R)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-methyl-4-morpholinopent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(2-hydroxyacetyl)piperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(2-methoxyacetyl)piperidin-3-yl)-4-oxo-4,5-dihydro-3H-1-thia-3,5,8-triazaacenaphthylene-2-carboxamide;

(R,Z)—N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide;

(R)—N-(1-Isopropylpyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(4-ethyl-2-methylphenyl)-4-oxo-4,5-dihydro-3H-1-thia-3,5,8-triazaacenaphthylene-2-carboxamide;

N—((R)-1-((S)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(6-phenoxypyridazin-3-yl)-4,5-dihydro-3H-1-thia-3,5,8-triazaacenaphthylene-2-carboxamide;

N—((R)-1-((S)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-(tetrahydro-2H-pyran-4-yl)-4,5-dihydro-3H-1-thia-3,5,8-triazaacenaphthylene-2-carboxamide;

(R)—N-(1-(2-Hydroxyacetyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N—((R)-1-((S)-1-methylpyrrolidine-3-carbonyl)piperidin-3-yl)-4-oxo-4,5-dihydro-3H-1-thia-3,5,8-triazaacenaphthylene-2-carboxamide;

(R)—N-(1-Acryloylpyrrolidin-3-yl)-5-(4-isopropoxy-2-methylphenyl)-4-oxo-4,5-dihydro-3H-1-thia-3,5,8-triazaacenaphthylene-2-carboxamide;

(R)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(3-hydroxypropanoyl)piperidin-3-yl)-4-oxo-4,5-dihydro-3H-1-thia-3,5,8-triazaacenaphthylene-2-carboxamide;

N-(4-Methyl-1,4-oxazepan-6-yl)-5-(2-methyl-4-phenoxyphenyl)-4-oxo-4,5-dihydro-3H-1-thia-3,5,8-triazaacenaphthylene-2-carboxamide;

(R)—N-(1-(3-(Dimethylamino)propanoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((S)-pyrrolidine-3-carbonyl)piperidin-3-yl)-4,5-dihydro-3H-1-thia-3,5,8-triazaacenaphthylene-2-carboxamide;

N-((3S,4R)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Chloro-4-phenoxyphenyl)-N-(1-methylpiperidin-3-yl)-4-oxo-4,5-dihydro-3H-1-thia-3,5,8-triazaacenaphthylene-2-carboxamide;

(R,Z)— N-(1-(2-Cyano-4-(dimethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Fluoro-4-phenoxyphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-N-(1-(oxetane-3-carbonyl)piperidin-3-yl)-4-oxo-4,5-dihydro-3H-1-thia-3,5,8-triazaacenaphthylene-2-carboxamide;

(R)—N-(1-Acryloylpyrrolidin-3-yl)-N-methyl-5-(2-methyl-4-phenoxyphenyl)-4-oxo-4,5-dihydro-3H-1-thia-3,5,8-triazaacenaphthylene-2-carboxamide;

N-((3R,5R)-5-Fluoropiperidin-3-yl)-5-(2-methyl-4-phenoxyphenyl)-4-oxo-4,5-dihydro-3H-1-thia-3,5,8-triazaacenaphthylene-2-carboxamide;

N-((3S,4S)-4-Hydroxy-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Cyano-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Ethylpyrrolidin-3-yl)-5-(2-methyl-4-phenoxyphenyl)-4-oxo-4,5-dihydro-3H-1-thia-3,5,8-triazaacenaphthylene-2-carboxamide;

N—((R)-1-((S)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

N—((R)-1-((R)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-(2-(trifluoromethyl)acryloyl)piperidin-3-yl)-4,5-dihydro-3H-1-thia-3,5,8-triazaacenaphthylene-2-carboxamide;

5-(2-Methyl-4-phenoxyphenyl)-N—((R)-1-((R)-1-methylpyrrolidine-3-carbonyl)piperidin-3-yl)-4-oxo-4,5-dihydro-3H-1-thia-3,5,8-triazaacenaphthylene-2-carboxamide;

(R)-5-(2-Methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide;

(R)-5-(2-Methyl-4-(o-tolyloxy)phenyl)-N-(1-methylpiperidin-3-yl)-4-oxo-4,5-dihydro-3H-1-thia-3,5,8-triazaacenaphthylene-2-carboxamide;

(R)—N-(1-Cyclopropylpyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-methyl-4-(piperidin-1-yl)pent-2-enoyl)piperidin-3-yl)-5-(2-methyl-4-phenoxy phenyl)-4-oxo-4,5-dihydro-3H-1-thia-3,5,8-triazaacenaphthylene-2-carboxamide;

(R)—N-(1-(2-Aminoacetyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-(cyclopropylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((6S)-6-methylpiperidin-3-yl)-4-oxo-4,5-dihydro-3H-1-thia-3,5,8-triazaacenaphthylene-2-carboxamide;

N-((3S,4R)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide;

N-((3R)-1-(3-Methoxybutanoyl)piperidin-3-yl)-5-(2-methyl-4-phenoxyphenyl)-4-oxo-4,5-dihydro-3H-1-thia-3,5,8-triazaacenaphthylene-2-carboxamide;

N—((R)-1-((S)-3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(2-Ethoxyphenoxy)-2-methylphenyl)-N-(1-methylpiperidin-3-yl)-4-oxo-4,5-dihydro-3H-1-thia-3,5,8-triazaacenaphthylene-2-carboxamide;

N-((3R)-1-(3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(pyrrolidin-3-yl)-4,5-dihydro-3H-1-thia-3,5,8-triazaacenaphthylene-2-carboxamide;

N-((3R,5R)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-propioloylpiperidin-3-yl)-4,5-dihydro-3H-1-thia-3,5,8-triazaacenaphthylene-2-carboxamide;

5-(2-Methyl-4-phenoxyphenyl)-N-(1-methyl-6-oxopiperidin-3-yl)-4-oxo-4,5-dihydro-3H-1-thia-3,5,8-triazaacenaphthylene-2-carboxamide;

(R)—N-(1-(3-Aminopropanoyl)piperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide;

N-(1,3-Dimethylpiperidin-4-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-(2-oxopiperidin-4-yl)-4,5-dihydro-3H-1-thia-3,5,8-triazaacenaphthylene-2-carboxamide;

N-((3R,5S)-5-fluoropiperidin-3-yl)-5-(2-methyl-4-phenoxyphenyl)-4-oxo-4,5-dihydro-3H-1-thia-3,5,8-triazaacenaphthylene-2-carboxamide;

N-((3R,5R)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(4-(2-Ethylphenoxy)-2-methylphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-4-oxo-N-(quinuclidin-2-yl)-4,5-dihydro-3H-1-thia-3,5,8-triazaacenaphthylene-2-carboxamide;

5-(2-Methyl-4-phenoxyphenyl)-N-(3-methylpiperidin-4-yl)-4-oxo-4,5-dihydro-3H-1-thia-3,5,8-triazaacenaphthylene-2-carboxamide;

5-(2-Methyl-4-phenoxyphenyl)-N-((6R)-6-methylpiperidin-3-yl)-4-oxo-4,5-dihydro-3H-1-thia-3,5,8-triazaacenaphthylene-2-carboxamide;

(R)—N-(5,5-Difluoropiperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2,6-difluoro-4-phenoxyphenyl)-4-oxo-4,5-dihydro-3H-1-thia-3,5,8-triazaacenaphthylene-2-carboxamide;

13C—(R,Z)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

13C—(R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-(cyclohexyloxy)-2-methylphenyl)-4-oxo-4,5-dihydro-3H-1-thia-3,5,8-triazaacenaphthylene-2-carboxamide;

N-((3R,5R)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Methyl-4-phenyoxyphenyl)-N-(1-methylpiperidin-3-yl)-4-oxo-4,5-dihydro-3H-1-thia-3,5,8-triazaacenaphthylene-2-carboxamide;

(R)—N-(1-(2-Cyanoacetyl)piperidin-3-yl)-4-oxo-5-(4-phenoxyphenyl)-4,5-dihydro-3H-1-thia-3,5,8-triazaacenaphthylene-2-carboxamide;

(R)—N-(1-Methylpiperidin-3-yl)-4-oxo-5-(4-phenoxyphenyl)-4,5-dihydro-3H-1-thia-3,5,8-triazaacenaphthylene-2-carboxamide;

(R)-5-(*S)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-cyclopropoxy-2-methylphenyl)-4-oxo-4,5-dihydro-3H-1-thia-3,5,8-triazaacenaphthylene-2-carboxamide;

N-((3S,4S)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(1-methylazepan-4-yl)-4-oxo-4,5-dihydro-3H-1-thia-3,5,8-triazaacenaphthylene-2-carboxamide;

(R)—N-(1-(3-Methoxy-2,2-dimethylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

N-(1-Cyanoazepan-4-yl)-5-(2-methyl-4-phenoxyphenyl)-4-oxo-4,5-dihydro-3H-1-thia-3,5,8-triazaacenaphthylene-2-carboxamide;

N—((R)-1-((R)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((R)-pyrrolidine-3-carbonyl)piperidin-3-yl)-4,5-dihydro-3H-1-thia-3,5,8-triazaacenaphthylene-2-carboxamide;

N-(4-(Hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-ethoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(2-fluorophenyl)-4-oxo-4,5-dihydro-3H-1-thia-3,5,8-triazaacenaphthylene-2-carboxamide;

(R,Z)—N-(1-(4-Amino-2-cyano-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(3-(1-Aminocyclopropyl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((R)-tetrahydrofuran-3-carbonyl)piperidin-3-yl)-4,5-dihydro-3H-1-thia-3,5,8-triazaacenaphthylene-2-carboxamide;

(R,E)-N-(1-(3-Cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

N-((3S,4R)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(2-Cyclopropylphenoxy)-2-methylphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

N-(1,2-Dimethylpiperidin-4-yl)-5-(2-methyl-4-phenoxyphenyl)-4-oxo-4,5-dihydro-3H-1-thia-3,5,8-triazaacenaphthylene-2-carboxamide;

(R)—N-(1-Methacryloylpiperidin-3-yl)-5-(2-methyl-4-phenoxyphenyl)-4-oxo-4,5-dihydro-3H-1-thia-3,5,8-triazaacenaphthylene-2-carboxamide;

N-(1-(Cyclopropanecarbonyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(1-methylazepan-3-yl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((S)-tetrahydrofuran-3-carbonyl)piperidin-3-yl)-4,5-dihydro-3H-1-thia-3,5,8-triazaacenaphthylene-2-carboxamide;

N-((3S,4R)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(5-chlorobenzo[d][1,3]dioxol-4-yl)-4-oxo-4,5-dihydro-3H-1-thia-3,5,8-triazaacenaphthylene-2-carboxamide;

(R)-5-(2-Methyl-4-(m-tolyloxy)phenyl)-N-(1-methylpiperidin-3-yl)-4-oxo-4,5-dihydro-3H-1-thia-3,5,8-triazaacenaphthylene-2-carboxamide;

N-((3S,4R)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-(ethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Cyclopropylpiperidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(3-Fluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(2-Fluoro-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide;

(R)—N-(1-Acryloylpiperidin-3-yl)-4-oxo-5-(o-tolyl)-4,5-dihydro-3H-1-thia-3,5,8-triazaacenaphthylene-2-carboxamide;

5-(2-Methyl-4-phenoxyphenyl)-4-oxo-N-(2-(2-oxoimidazolidin-1-yl)ethyl)-4,5-dihydro-3H-1-thia-3,5,8-triazaacenaphthylene-2-carboxamide;

N-((3S,4S)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-(tetrahydro-2H-pyran-4-carbonyl)piperidin-3-yl)-4,5-dihydro-3H-1-thia-3,5,8-triazaacenaphthylene-2-carboxamide;

(R)-5-(4-(2-Hydroxyphenoxy)-2-methylphenyl)-N-(1-methylpiperidin-3-yl)-4-oxo-4,5-dihydro-3H-1-thia-3,5,8-triazaacenaphthylene-2-carboxamide;

(R,E)-N-(1-(3-Ethoxyacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Fluoro-6-methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(4-(2-Isopropylphenoxy)-2-methylphenyl)-N-(1-methylpiperidin-3-yl)-4-oxo-4,5-dihydro-3H-1-thia-3,5,8-triazaacenaphthylene-2-carboxamide;

N-((3R,5R)-5-Methoxypiperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-(3-methylbut-2-enoyl)piperidin-3-yl)-4-oxo-4,5-dihydro-3H-1-thia-3,5,8-triazaacenaphthylene-2-carboxamide;

(R)-5-(4-(3-(Methoxymethyl)phenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-(2-(trifluoromethoxy)phenoxy)phenyl)-N-(1-methylpiperidin-3-yl)-4-oxo-4,5-dihydro-3H-1-thia-3,5,8-triazaacenaphthylene-2-carboxamide;

(R,Z)—N-(1-(3-Cyclopropyl-2-fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)azetidin-3-yl)-5-(2-methyl-4-phenoxyphenyl)-4-oxo-4,5-dihydro-3H-1-thia-3,5,8-triazaacenaphthylene-2-carboxamide;

N-(1-Cyclopropylazetidin-3-yl)-5-(2-methyl-4-phenoxyphenyl)-4-oxo-4,5-dihydro-3H-1-thia-3,5,8-triazaacenaphthylene-2-carboxamide;

(R,EZ)—N-(1-(2-Cyano-3-methoxyacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-5-(*S)-(5-Chlorobenzo[d][1,3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R,EZ)—N-(1-(2-Cyano-4-((2-methoxy ethyl)amino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2,6-Difluoro-4-phenoxyphenyl)-4-oxo-N-(piperidin-3-yl)-4,5-dihydro-3H-1-thia-3,5,8-triazaacenaphthylene-2-carboxamide;

N-((3S,4S)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide;

N1-((E)-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)-N5-(15-oxo- 19-((3aS,4R,6aR)-2-oxohexahydro-1H-thieno[3,4-d]imidazol-4-yl)-4,7,10-trioxa-14-azanonadecyl)glutaramide;

(R,E)-N-(1-(2-Cyano-4-methyl-4-(methylamino)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-5-(5-Chlorobenzo[d][1,3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide;

5-(2-Methyl-4-phenoxyphenyl)-N-(1-(3-(methylsulfonyl)propanoyl)azetidin-3-yl)-4-oxo-4,5-dihydro-3H-1-thia-3,5,8-triazaacenaphthylene-2-carboxamide;

N-((3S,4R)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-(2-(trifluoromethyl)phenoxy)phenyl)-N-(1-methylpiperidin-3-yl)-4-oxo-4,5-dihydro-3H-1-thia-3,5,8-triazaacenaphthylene-2-carboxamide;

N-((3S,4S)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

N-((3S,4S)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

N-((3S,4S)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide;

N-(1-(3-Methoxypropanoyl)azetidin-3-yl)-5-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-N-(1-(4-methylpent-2-enoyl)piperidin-3-yl)-4-oxo-4,5-dihydro-3H-1-thia-3,5,8-triazaacenaphthylene-2-carboxamide;

5-(2-Methyl-4-phenoxyphenyl)-N-(1-methylazetidin-3-yl)-4-oxo-4,5-dihydro-3H-1-thia-3,5,8-triazaacenaphthylene-2-carboxamide;

(S)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(4-(Cyclohexyloxy)-2-methylphenyl)-N-(1-methylpiperidin-3-yl)-4-oxo-4,5-dihydro-3H-1-thia-3,5,8-triazaacenaphthylene-2-carboxamide;

N-(1-Ethylazetidin-3-yl)-5-(2-methyl-4-phenoxyphenyl)-4-oxo-4,5-dihydro-3H-1-thia-3,5,8-triazaacenaphthylene-2-carboxamide;

N-(Azetidin-3-yl)-5-(2-methyl-4-phenoxyphenyl)-4-oxo-4,5-dihydro-3H-1-thia-3,5,8-triazaacenaphthylene-2-carboxamide;

(R)-5-(*R)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;

(R)—N-(1-Acryloylpiperidin-3-yl)-5-(4-methoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-fluorophenyl)-4-oxo-4,5-dihydro-3H-1-thia-3,5,8-triazaacenaphthylene-2-carboxamide;

(R)—N-(1-Acryloylpiperidin-3-yl)-5-(4-chlorophenyl)-4-oxo-4,5-dihydro-3H-1-thia-3,5,8triazaacenaphthylene-2-carboxamide;

(R)—N-(1-Acryloylpiperidin-3-yl)-4-oxo-5-phenyl-4,5-dihydro-3H-1-thia-3,5,8-triazaacenaphthylene-2-carboxamide;

5-(2-Methyl-4-phenoxyphenyl)-N-(2-methylpiperidin-4-yl)-4-oxo-4,5-dihydro-3H-1-thia-3,5,8-triazaacenaphthylene-2-carboxamide;

N-((3R,5R)-5-Methoxy-1-methylpiperidin-3-yl)-4-oxo-5-(4-phenoxyphenyl)-4,5-dihydro-3H-1-thia-3,5,8-triazaacenaphthylene-2-carboxamide;

(R)—N-(1-(2-chloro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,Z)—N-(1-(2-Fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

N-(1-Methyl-5-oxopyrrolidin-3-yl)-4-oxo-5-(4-phenoxyphenyl)-4,5-dihydro-3H-1-thia-3,5,8-triazaacenaphthylene-2-carboxamide;

(R)—N-(1-(2-Fluoro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(2-methyl-4-(pentafluorothio)phenyl)-4-oxo-4,5-dihydro-3H-1-thia-3,5,8-triazaacenaphthylene-2-carboxamide;

(S)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide;

N-((3R,5S)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide;

(S)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

N-((3R,5S)-5-Methoxypiperidin-3-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide;

(R)—N-(1-Acryloylpyrrolidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-4-oxo-5-(p-tolyl)-4,5-dihydro-3H-1-thia-3,5,8-triazaacenaphthylene-2-carboxamide;

(R)—N-(5,5-Difluoro-1-methylpiperidin-3-yl)-5-(2-methyl-4-phenoxyphenyl)-4-oxo-4,5-dihydro-3H-1-thia-3,5,8-triazaacenaphthylene-2-carboxamide;

N-(1-Isopropylazetidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(4,4-Dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(2-morpholinoethyl)-4-oxo-4,5-dihydro-3H-1-thia-3,5,8-triazaacenaphthylene-2-carboxamide;

(R)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide;

(R,Z)—N-(1-(2-Chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(4-phenoxy-2-(trifluoromethyl)phenyl)-4,5-dihydro-3H-1-thia-3,5,8-triazaacenaphthylene-2-carboxamide;

(R)—N-(1-Acryloylpiperidin-3-yl)-4-oxo-5-(m-tolyl)-4,5-dihydro-3H-1-thia-3,5,8-triazaacenaphthylene-2-carboxamide;

(R)-5-(4-Chloro-3-(trifluoromethyl)phenyl)-4-oxo-N-(piperidin-3-yl)-4,5-dihydro-3H-1-thia-3,5,8-triazaacenaphthylene-2-carboxamide;

(R)-5-(2,3-Dimethyl-4-phenoxyphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-N-((1-methylpyrrolidin-3-yl)methyl)-4-oxo-4,5-dihydro-3H-1-thia-3,5,8-triazaacenaphthylene-2-carboxamide;

(R)-5-(4-(2-Isopropoxyphenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(4-Cyclobutoxy-2-methylphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide;

(R)-5-(4-(3,5-Difluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-(2-Dimethylamino)acetyl)piperidin-3-yl) 5-(*R)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(3-(trifluoromethyl)phenyl)-4,5-dihydro-3H-1-thia-3,5,8-triazaacenaphthylene-2-carboxamide;

(S)—N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(2-Methyl-4-(p-tolyloxy)phenyl)-N-(1-methylpiperidin-3-yl)-4-oxo-4,5-dihydro-3H-1-thia-3,5,8-triazaacenaphthylene-2-carboxamide;

(S)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide;

(R,E)-5 (*R)(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide;

(R)-5-(2-Methyl-4-(pyridin-3-yloxy)phenyl)-N-(1-methylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(3-chlorophenyl)-4-oxo-4,5-dihydro-3H-1-thia-3,5,8-triazaacenaphthylene-2-carboxamide;

(R)-5-(4-(4-Fluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide;

(R)-5-(4-(Cyclopentyloxy)-2-methylphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-N-(2-(1-methylpyrrolidin-2-yl)ethyl)-4-oxo-4,5-dihydro-3H-1-thia-3,5,8-triazaacenaphthylene-2-carboxamide;

(R)—N-(1-Acryloylpyrrolidin-3-yl)-5-(4-methoxy-2-methylphenyl)-4-oxo-4,5-dihydro-3H-1-thia-3,5,8-triazaacenaphthylene-2-carboxamide;

(R)-5-(*R)-(2-Methyl-4-phenyoxyphenyl)-4-oxo-N-(piperidin-3-yl)-4,5-dihydro-3H-1-thia-3,5,8-triazaacenaphthylene-2-carboxamide;

(R)—N-(1-Acryloylpyrrolidin-3-yl)-5-(2-fluorophenyl)-4-oxo-4,5-dihydro-3H-1-thia-3,5,8-triazaacenaphthylene-2-carboxamide;

(R)-5-(4-(2,4-Difluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(5-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide;

(R)—N-(1-Acryloylpyrrolidin-3-yl)-5-(2,4-dimethylphenyl)-4-oxo-4,5-dihydro-3H-1-thia-3,5,8-triazaacenaphthylene-2-carboxamide;

(R)-5-(5-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)-5-(2-Methyl-4-(pyridin-2-yloxy)phenyl)-N-(1-methylpiperidin-3-yl)-4-oxo-4,5-dihydro-3H-1-thia-3,5,8-triazaacenaphthylene-2-carboxamide;

(R)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(S)-5-(5-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(S)—N-(1-Benzyl-2-oxoazepan-3-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(piperidin-2-ylmethyl)-4,5-dihydro-3H-1-thia-3,5,8-triazaacenaphthylene-2-carboxamide;

(R)—N-(1-Acryloylpyrrolidin-3-yl)-4-oxo-5-(6-phenoxypyridazin-3-yl)-4,5-dihydro-3H-1-thia-3,5,8-triazaacenaphthylene-2-carboxamide;

N-((3R,5S)-5-Methoxy-1-methylpiperidin-3-yl)-5-(2-methyl-4-phenoxyphenyl)-4-oxo-4,5-dihydro-3H-1-thia-3,5,8-triazaacenaphthylene-2-carboxamide;

(R,EZ)—N-(1-(3-Cyclopropyl-2-(trifluoromethyl)acryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-4-oxo-5-(o-tolyl)-4,5-dihydro-3H-1-thia-3,5,8-triazaacenaphthylene-2-carboxamide;

5-(2-Methyl-4-phenoxyphenyl)-N-(2-morpholino-2-oxoethyl)-4-oxo-4,5-dihydro-3H-1-thia-3,5,8-triazaacenaphthylene-2-carboxamide;

(R)—N-(1-Methylpiperidin-3-yl)-4-oxo-4,5-dihydro-3H-1-thia-3,5,8-triazaacenaphthylene-2-carboxamide;

(R)-5-(2,6-Dimethyl-4-phenoxyphenyl)-N-(1-methylpiperidin-3-yl)-4-oxo-4,5-dihydro-3H-1-thia-3,5,8-triazaacenaphthylene-2-carboxamide;

(R)—N-(1-(3-Hydroxypropanoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(*S)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide;

(R)—N-(1-Ethylpiperidin-3-yl)-5-(4-(2-isopropylphenoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(*R)-(5-chlorobenzo[d][1,3]dioxol-4-yl)-4-oxo-4,5-dihydro-3H-1-thia-3,5,8-triazaacenaphthylene-2-carboxamide;

(R)-5-(4-Cyclopropoxy-2-methylphenyl)-N-(1-methylpiperidin-3-yl)-4-oxo-4,5-dihydro-3H-1-thia-3,5,8-triazaacenaphthylene-2-carboxamide;

(S)-5-(*R)-(2-Methy-4-phenoxyphenyl)-4-oxo-N-(tetrahydrofuran-3-yl)-4,5-dihydro-3H-1-thia-3,5,8-triazaacenaphthylene-2-carboxamide;

(R)—N-(1-Acryloylpyrrolidin-3-yl)-4-oxo-5-(4-phenoxy-2-(trifluoromethyl)phenyl)-4,5-dihydro-3H-1-thia-3,5,8-triazaacenaphthylene-2-carboxamide;

(R)-5-(*R)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide;

(R)-5-(4-(2-Carbamoylphenoxy)-2-methylphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-2-(piperazin-1-yl)-3H-1-thia-3,5,8-triazaacenaphthylen-4(5H)-one;

(R)-6-Methyl-4-oxo-5-(4-phenoxyphenyl)-N-(piperidin-3-yl)-4,5-dihydro-3H-1-thia-3,5,8-triazaacenaphthylene-2-carboxamide;

(R)—N-(1-Cyanopiperidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(3,5-Dichlorophenyl)-4-oxo-N-(piperidin-3-yl)-4,5-dihydro-3H-1-thia-3,5,8-triazaacenaphthylene-2-carboxamide;

(R)—N-Methyl-5-(2-methyl-4-phenoxyphenyl)-4-oxo-N-(pyrrolidin-3-yl)-4,5-dihydro-3H-1-thia-3,5,8-triazaacenaphthylene-2-carboxamide;

(R)-5-(4-Isopropoxy-2-methylphenyl)-N-(1-methylpiperidin-3-yl)-4-oxo-4,5-dihydro-3H-1-thia-3,5,8-triazaacenaphthylene-2-carboxamide;

(R)-5-(4-Ethoxy-2-methylphenyl)-N-(1-methylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(4-(tert-butyl)phenyl)-4-oxo-4,5-dihydro-3H-1-thia-3,5,8-triazaacenaphthylene-2-carboxamide;

(R)-5-(*S)-(2-Methyl-4-((tetrahydro-2H-pyran-4-yl)oxy)phenyl)-N-(1-methylpiperidin-3-yl)-4-oxo-4,5-dihydro-3H-1-thia-3,5,8-triazaacenaphthylene-2-carboxamide;

(R)-5-(3-Chlorophenyl)-4-oxo-N-(piperidin-3-yl)-4,5-dihydro-3H-1-thia-3,5,8-triazaacenaphthylene-2-carboxamide;

(R)—N-(1-Acryloylpyrrolidin-3-yl)-4-oxo-5-phenyl-4,5-dihydro-3H-1-thia-3,5,8-triazaacenaphthylene-2-carboxamide;

(R)—N-Methyl-5-(2-methyl-4-phenoxyphenyl)-N-(1-methylpyrrolidin-3-yl)-4-oxo-4,5-dihydro-3H-1-thia-3,5,8-triazaacenaphthylene-2-carboxamide;

(S)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(4-Methoxy-2-methylphenyl)-N-(1-methylpiperidin-3-yl)-4-oxo-4,5-dihydro-3H-1-thia-3,5,8-triazaacenaphthylene-2-carboxamide;

(R)-4-Oxo-N-(piperidin-3-yl)-5-(4-(trifluoromethyl)phenyl)-4,5-dihydro-3H-1-thia-3,5,8-triazaacenaphthylene-2-carboxamide;

(R)-5-(4-Methoxyphenyl)-4-oxo-N-(piperidin-3-yl)-4,5-dihydro-3H-1-thia-3,5,8-triazaacenaphthylene-2-carboxamide;

(R)-5-(*R)-(2-Methyl-4-((tetrahydro-2H-pyran-4-yl)oxy)phenyl)-N-(1-methylpiperidin-3-yl)-4-oxo-4,5-dihydro-3H-1-thia-3,5,8-triazaacenaphthylene-2-carboxamide;

(R)-5-([1,1'-Biphenyl]-4-yl)-4-oxo-N-(piperidin-3-yl)-4,5-dihydro-3H-1-thia-3,5,8-triazaacenaphthylene-2-carboxamide;

(R)-5-(*R)-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

(R)-5-(3,4-Dichlorophenyl)-4-oxo-N-(piperidin-3-yl)-4,5-dihydro-3H-1-thia-3,5,8-triazaacenaphthylene-2-carboxamide;

(R)-4-Oxo-N-(piperidin-3-yl)-5-(3-(trifluoromethyl)phenyl)-4,5-dihydro-3H-1-thia-3,5,8-triazaacenaphthylene-2-carboxamide;

(R)-4-Oxo-5-phenyl-N-(piperidin-3-yl)-4,5-dihydro-3H-1-thia-3,5,8-triazaacenaphthylene-2-carboxamide;

(R)—N-(1-Methylpiperidin-3-yl)-4-oxo-5-(4-phenoxy-2-(trifluoromethyl)phenyl)-4,5-dihydro-3H-1-thia-3,5,8-triazaacenaphthylene-2-carboxamide;

(R)-5-(4-Methyl-6-phenoxypyridazin-3-yl)-N-(1-methylpiperidin-3-yl)-4-oxo-4,5-dihydro-3H-1-thia-3,5,8-triazaacenaphthylene-2-carboxamide;

(R)—N-(1-Acryloylpyrrolidin-3-yl)-5-(4-methyl-6-phenoxypyridazin-3-yl)-4-oxo-4,5-dihydro-3H-1-thia-3,5,8-triazaacenaphthylene-2-carboxamide;

(R)—N-(1-Methylpiperidin-3-yl)-4-oxo-5-(o-tolyl)-4,5-dihydro-3H-1-thia-3,5,8-triazaacenaphthylene-2-carboxamide;

(R)-5-(*R)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide;

(R)-5-(2-Methyl-4-(pyridin-4-yloxy)phenyl)-N-(1-methylpiperidin-3-yl)-4-oxo-4,5-dihydro-3H-1-thia-3,5,8-triazaacenaphthylene-2-carboxamide;

(R)—N-(1-Acryloylpiperidin-3-yl)-4-oxo-5-(4-(trifluoromethyl)phenyl)-4,5-dihydro-3H-1-thia-3,5,8-triazaacenaphthylene-2-carboxamide;

(R)-5-(3-(Dimethylamino)phenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-isopropyl-4-oxo-4,5-dihydro-3H-1-thia-3,5,8-triazaacenaphthylene-2-carboxamide;

(R)—N-(1-Acryloylpiperidin-3-yl)-5-(2-methylpyridin-3-yl)-4-oxo-4,5-dihydro-3H-1-thia-3,5,8-triazaacenaphthylene-2-carboxamide;

(R)-5-(2-Methylpyridin-3-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(3,4-dichlorophenyl)-4-oxo-4,5-dihydro-3H-1-thia-3,5,8-triazaacenaphthylene-2-carboxamide;

(R)-5-Isopropyl-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(4-chloro-3-(trifluoromethyl)phenyl)-4-oxo-4,5-dihydro-3H-1-thia-3,5,8-triazaacenaphthylene-2-carboxamide;

(R)—N-(1-(3-Methoxy-3-methylbutanoyl)piperidin-3-yl)-5-(2-methyl-4-phenoxyphenyl)-4-oxo-4,5-dihydro-3H-1-thia-3,5,8-triazaacenaphthylene-2-carboxamide;

(R,Z)—N-(1-(3-Acetamidoacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R)—N-(1-(2-Chloroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(4-Aminobut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,E)-N-(1-(4-(Dimethylamino)but-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;
(R)-5-(2-Methyl-4-phenoxyphenyl)-4-oxo-N-(1-(vinylsulfonyl)pyrrolidin-3-yl)-4,5-dihydro-3H-1-thia-3,5,8-triazaacenaphthylene-2-carboxamide;
(R)-5-(2-Methyl-4-phenoxyphenyl)-N-(1-trideuteriomethylpiperidin-3-yl)-4-oxo-4,5-dihydro-3H-1-thia-3,5,8-triazaacenaphthylene-2-carboxamide;
(R,E)-N-(1-(4-(Dimethylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide;
(R)-5-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide;
(R,E)-N-(1-(4-(Dimethylamino)but-2-enoyl)piperidin-3-yl)-4-oxo-5-(4-phenoxyphenyl)-4,5-dihydro-3H-1-thia-3,5,8-triazaacenaphthylene-2-carboxamide;
(R,E)-5-(2-Methyl-4-phenoxyphenyl)-N-(1-(4-(methylsulfonyl)but-2-enoyl)piperidin-3-yl)-4-oxo-4,5-dihydro-3H-1-thia-3,5,8-triazaacenaphthylene-2-carboxamide;
(R)—N-(1-Acryloylpiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;
(R)—N-(1-Acryloylpyrrolidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;
(R,E)-5-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide;
(R,E)-N-(1-(2-Cyano-3-cyclopropylacryloyl)piperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;
(R)—N-(1-Cyanopiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;
(R)-5-(2-Methyl-4-(2,3,4,5,6-pentadeuteriophenoxy)phenyl)-N-(1-(trideuteriomethyl)piperidin-3-yl)-4-oxo-4,5-dihydro-3H-1-thia-3,5,8-triazaacenaphthylene-2-carboxamide;
(R)-5-(2-Methyl-4-(2,3,4,5,6-pentadeuteriophenoxy)phenyl)-N-(1-methylpiperidin-3-yl)-4-oxo-4,5-dihydro-3H-1-thia-3,5,8-triazaacenaphthylene-2-carboxamide;
(R,E)-N-(1-(4-Aminobut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;
(R,E)-5-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide;
(R)—N-(1-(2-(Dimethylamino)acetyl)pyrrolidin-3-yl)-5-(2-methyl-4-phenoxyphenyl)-4-oxo-4,5-dihydro-3H-1-thia-3,5,8-triazaacenaphthylene-2-carboxamide;
(R,E)-N-(1-(2-Cyanobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;
N—((R)-1-((S)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide;
(R,E)-N-(1-(2-Cyano-3-(3-methyloxetan-3-yl)acryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide;
(R,Z)—N-(1-(2-Fluoro-4-(methylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide;
(R)-5-(2-Methyl-4-phenoxyphenyl)-4-oxo-N-(1-(2-(pyrrolidin-1-yl)acetyl)piperidin-3-yl)-4,5-dihydro-3H-1-thia-3,5,8-triazaacenaphthylene-2-carboxamide;
(R)-2-(((1-Acryloylpiperidin-3-yl)amino)methyl)-5-(2-methyl-4-phenoxyphenyl)-3H-1-thia-3,5,8-triazaacenaphthylen-4(5H)-one;
(R)-5-(2-Methyl-4-phenoxyphenyl)-N-(1-(2-(methylamino)acetyl)pyrrolidin-3-yl)-4-oxo-4,5-dihydro-3H-1-thia-3,5,8-triazaacenaphthylene-2-carboxamide;
(R)—N-(1-(2-Aminoacetyl)pyrrolidin-3-yl)-5-(2-methyl-4-phenoxyphenyl)-4-oxo-4,5-dihydro-3H-1-thia-3,5,8-triazaacenaphthylene-2-carboxamide;
(R)-5-(2-Methyl-4-phenoxyphenyl)-4-oxo-N-(1-(2-(piperidin-1-yl)acetyl)piperidin-3-yl)-4,5-dihydro-3H-1-thia-3,5,8-triazaacenaphthylene-2-carboxamide;
(R)-5-(2-Methyl-4-phenoxyphenyl)-N-(1-(2-morpholinoacetyl)piperidin-3-yl)-4-oxo-4,5-dihydro-3H-1-thia-3,5,8-triazaacenaphthylene-2-carboxamide;
(R)—N-(1-(2-Chloroacetyl)pyrrolidin-3-yl)-5-(2-methyl-4-phenoxyphenyl)-4-oxo-4,5-dihydro-3H-1-thia-3,5,8-triazaacenaphthylene-2-carboxamide;
(R)—N-(1-(2-Chloroacetyl)piperidin-3-yl)-5-(2-methyl-4-phenoxyphenyl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(thiophen-2-yl)phenyl)-4,5-dihydro-3H-1-thia-3,5,8-triazaacenaphthylene-2-carboxamide;
(R,E)-N-(1-(2-Cyano-4,4-dimethylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;
(R,E)-N-(1-(2-Cyano-3-cyclopropylacryloyl)piperidin-3-yl)-5-(4-isopropoxyphenyl)-4-oxo-4,5-dihydro-3H-1-thia-3,5,8-triazaacenaphthylene-2-carboxamide;
(R)—N-(1-Acryloylpiperidin-3-yl)-5-(4-isopropoxyphenyl)-4-oxo-4,5-dihydro-3H-1-thia-3,5,8-triazaacenaphthylene-2-carboxamide;
(R,E)-N-(1-(3-Cyclopropyl-2-methylacryloyl)piperidin-3-yl)-5-(2-methyl-4-phenoxyphenyl)-4-oxo-4,5-dihydro-3H-1-thia-3,5,8-triazaacenaphthylene-2-carboxamide;
(R,EZ)—N-(1-(2-Chloro-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;
(R,E)-5-(2-Methyl-4-phenoxyphenyl)-N-(1-(4-morpholinobut-2-enoyl)piperidin-3-yl)-4-oxo-4,5-dihydro-3H-1-thia-3,5,8-triazaacenaphthylene-2-carboxamide;
(R)—N-(1-Acryloylpiperidin-3-yl)-5-(benzo[b]thiophen-5-yl)-4-oxo-4,5-dihydro-3H-1-thia-3,5,8-triazaacenaphthylene-2-carboxamide;
(R)-5-(4-Isopropoxyphenyl)-4-oxo-N-(piperidin-3-yl)-4,5-dihydro-3H-1-thia-3,5,8-triazaacenaphthylene-2-carboxamide;
(R)-5-(4-Isopropoxyphenyl)-4-oxo-N-(1-propionylpiperidin-3-yl)-4,5-dihydro-3H-1-thia-3,5,8-triazaacenaphthylene-2-carboxamide;
(R)-4-Oxo-N-(piperidin-3-yl)-5-(4-(thiophen-2-yl)phenyl)-4,5-dihydro-3H-1-thia-3,5,8-triazaacenaphthylene-2-carboxamide;
(R)—N-(1-Acryloylpiperidin-3-yl)-4-oxo-5-(4-phenoxybenzyl)-4,5-dihydro-3H-1-thia-3,5,8-triazaacenaphthylene-2-carboxamide;

(R)—N-(1-Methylpyrrolidin-3-yl)-4-oxo-5-(4-phenoxybenzyl)-4,5-dihydro-3H-1-thia-3,5,8-triazaacenaphthylene-2-carboxamide;

(R)-5-(Benzo[b]thiophen-5-yl)-4-oxo-N-(piperidin-3-yl)-4,5-dihydro-3H-1-thia-3,5,8-triazaacenaphthylene-2-carboxamide;

(R)—N-(1-Methylpiperidin-3-yl)-4-oxo-5-(4-phenoxybenzyl)-4,5-dihydro-3H-1-thia-3,5,8-triazaacenaphthylene-2-carboxamide;

(R)-4-Oxo-5-(4-phenoxybenzyl)-N-(piperidin-3-yl)-4,5-dihydro-3H-1-thia-3,5,8-triazaacenaphthylene-2-carboxamide;

(R)-5-(2-Methyl-4-(trifluoromethoxy)phenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(2-methyl-4-(trifluoromethoxy)phenyl)-4-oxo-4,5-dihydro-3H-1-thia-3,5,8-triazaacenaphthylene-2-carboxamide;

(R)-4-Oxo-N-(piperidin-3-yl)-5-(4-(trifluoromethoxy)phenyl)-4,5-dihydro-3H-1-thia-3,5,8-triazaacenaphthylene-2-carboxamide;

(R)—N-(1-Acryloylpiperidin-3-yl)-4-oxo-5-(4-(trifluoromethoxy)phenyl)-4,5-dihydro-3H-1-thia-3,5,8-triazaacenaphthylene-2-carboxamide;

(R)—N-(1-Acryloylpiperidin-3-yl)-5-(*S)-(4-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(*R)-(4-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(naphthalen-2-yl)-4-oxo-4,5-dihydro-3H-1-thia-3,5,8-triazaacenaphthylene-2-carboxamide;

(R)—N-(1-Acryloylpiperidin-3-yl)-5-(1-benzyl-1H-pyrazol-3-yl)-4-oxo-4,5-dihydro-3H-1-thia-3,5,8-triazaacenaphthylene-2-carboxamide;

(R)-5-([1,1'-Biphenyl]-3-yl)-N-(1-acryloylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(4-benzylphenyl)-4-oxo-4,5-dihydro-3H-1-thia-3,5,8-triazaacenaphthylene-2-carboxamide;

(R)-5-([1,1'-Biphenyl]-4-yl)-N-(1-acryloylpiperidin-3-yl)-4-oxo-4,5-dihydro-3H-1-thia-3,5,8-triazaacenaphthylene-2-carboxamide;

(R)—N-(1-(2-(Dimethylamino)acetyl)piperidin-3-yl)-4-oxo-5-(4-phenoxyphenyl)-4,5-dihydro-3H-1-thia-3,5,8-triazaacenaphthylene-2-carboxamide;

(R)—N-(1-(2-(Dimethylamino)acetyl)pyrrolidin-3-yl)-4-oxo-5-(4-phenoxyphenyl)-4,5-dihydro-3H-1-thia-3,5,8-triazaacenaphthylene-2-carboxamide;

(R)-5-([1,1'-Biphenyl]-3-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(benzo[b]thiophen-2-yl)-4-oxo-4,5-dihydro-3H-1-thia-3,5,8-triazaacenaphthylene-2-carboxamide;

(R)-5-(Benzo[b]thiophen-2-yl)-4-oxo-N-(piperidin-3-yl)-4,5-dihydro-3H-1-thia-3,5,8-triazaacenaphthylene-2-carboxamide;

(R)-5-(Naphthalen-2-yl)-4-oxo-N-(piperidin-3-yl)-4,5-dihydro-3H-1-thia-3,5,8-triazaacenaphthylene-2-carboxamide;

(R)-5-(4-Benzylphenyl)-4-oxo-N-(piperidin-3-yl)-4,5-dihydro-3H-1-thia-3,5,8-triazaacenaphthylene-2-carboxamide;

(R)-5-(1-Benzyl-1H-pyrazol-3-yl)-4-oxo-N-(piperidin-3-yl)-4,5-dihydro-3H-1-thia-3,5,8-triazaacenaphthylene-2-carboxamide;

5-(*S)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide;

5-(*R)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide;

5-(*S)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide;

5-(*R)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide;

N-(4-(Hydroxymethyl)tetrahydro-2H-pyran-4-yl)-5-(*S)-(2-methyl-4-phenoxyphenyl)-4-oxo-4,5-dihydro-3H-1-thia-3,5,8-triazaacenaphthylene-2-carboxamide;

N-(4-(Hydroxymethyl)tetrahydro-2H-pyran-4-yl)-5-(*R)-(2-methyl-4-phenoxyphenyl)-4-oxo-4,5-dihydro-3H-1-thia-3,5,8-triazaacenaphthylene-2-carboxamide;

(R)—N-(1-(2-Chloro-3-methylbut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-(2-Chloro-3-methylbut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,E)-N-(1-(4-(Dimethylamino)but-2-enoyl)pyrrolidin-3-yl)-4-oxo-5-(4-phenoxyphenyl)-4,5-dihydro-3H-1-thia-3,5,8-triazaacenaphthylene-2-carboxamide;

(R)—N-(1-Acryloylpyrrolidin-3-yl)-N-methyl-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-N-methyl-5-(*R)-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-5-(4-isopropyl-2-methylphenyl)-4-oxo-4,5-dihydro-3H-1-thia-3,5,8-triazaacenaphthylene-2-carboxamide;

(R)—N-(1-Acryloylpyrrolidin-3-yl)-5-(4-isopropyl-2-methylphenyl)-4-oxo-4,5-dihydro-3H-1-thia-3,5,8-triazaacenaphthylene-2-carboxamide;

(R)-5-(4-Isopropyl-2-methylphenyl)-4-oxo-N-(piperidin-3-yl)-4,5-dihydro-3H-1-thia-3,5,8-triazaacenaphthylene-2-carboxamide;

(R)-5-(4-Isopropyl-2-methylphenyl)-N-(1-methylpiperidin-3-yl)-4-oxo-4,5-dihydro-3H-1-thia-3,5,8-triazaacenaphthylene-2-carboxamide;

(R,*Z)—N-(1-(2-Cyano-4-methoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*Z)—N-(1-(2-Cyano-4-methoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-methoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-methoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

N-((1-Acryloylpyrrolidin-3-yl)methyl)-4-oxo-5-(4-phenoxyphenyl)-4,5-dihydro-3H-1-thia-3,5,8-triazaacenaphthylene-2-carboxamide;

4-Oxo-5-(4-phenoxyphenyl)-N-(pyrrolidin-3-ylmethyl)-4,5-dihydro-3H-1-thia-3,5,8-triazaacenaphthylene-2-carboxamide;

(R)—N-(1-(1H-Imidazole-1-carbonyl)piperidin-3-yl)-5-(2,2-difluorobenzo[d][1,3]dioxol-5-yl)-4-oxo-4,5-dihydro-3H-1-thia-3,5,8-triazaacenaphthylene-2-carboxamide;

(R)—N-(1-Acryloylpiperidin-3-yl)-5-(4-methoxy-3-(trifluoromethyl)phenyl)-4-oxo-4,5-dihydro-3H-1-thia-3,5,8-triazaacenaphthylene-2-carboxamide;

(R)—N-(1-Acryloylpiperidin-3-yl)-5-(4-cyclobutoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-cyclobutoxyphenyl)-4-oxo-4,5-dihydro-3H-1-thia-3,5,8-triazaacenaphthylene-2-carboxamide;

4-Oxo-N-(2-oxopiperidin-3-yl)-5-(4-phenoxyphenyl)-4,5-dihydro-3H-1-thia-3,5,8-triazaacenaphthylene-2-carboxamide;

(R)-5-(4-Methoxy-3-(trifluoromethyl)phenyl)-4-oxo-N-(piperidin-3-yl)-4,5-dihydro-3H-1-thia-3,5,8-triazaacenaphthylene-2-carboxamide;

(R)-5-(3-Chloro-4-methylphenyl)-4-oxo-N-(piperidin-3-yl)-4,5-dihydro-3H-1-thia-3,5,8-triazaacenaphthylene-2-carboxamide;

(R)-5-(4-Methyl-3-(trifluoromethyl)phenyl)-4-oxo-N-(piperidin-3-yl)-4,5-dihydro-3H-1-thia-3,5,8-triazaacenaphthylene-2-carboxamide;

4-Oxo-5-(4-phenoxyphenyl)-N-((tetrahydrofuran-2-yl)methyl)-4,5-dihydro-3H-1-thia-3,5,8-triazaacenaphthylene-2-carboxamide;

N-((3S,4S)-1-Acryloyl-4-hydroxypyrrolidin-3-yl)-4-oxo-5-(4-phenoxyphenyl)-4,5-dihydro-3H-1-thia-3,5,8-triazaacenaphthylene-2-carboxamide;

N-((3S,4S)-4-Hydroxypyrrolidin-3-yl)-4-oxo-5-(4-phenoxyphenyl)-4,5-dihydro-3H-1-thia-3,5,8-triazaacenaphthylene-2-carboxamide;

(R)-5-(3-Benzylphenyl)-4-oxo-N-(piperidin-3-yl)-4,5-dihydro-3H-1-thia-3,5,8-triazaacenaphthylene-2-carboxamide;

(R)-4-Oxo-5-(3-phenoxyphenyl)-N-(piperidin-3-yl)-4,5-dihydro-3H-1-thia-3,5,8-triazaacenaphthylene-2-carboxamide;

N-((3R,5S)-5-Methoxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-5-Methoxypiperidin-3 yl)-5-(*R)-(2-methyl-4-phenoxyphenyl)-4-oxo-4,5-dihydro-3H-1-thia-3,5,8-triazaacenaphthylene-2-carboxamide;

(*S)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

(*S)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

(*R)-5 (*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

(*R)-5 (*R)-(2-Methy-4-phenoxyphenyl)-4-oxo-N-(5-oxopyrrolidin-3-yl)-4,5-dihydro-3H-1-thia-3,5,8-triazaacenaphthylene-2-carboxamide;

(R,*E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*Z)—N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,*Z)—N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*Z)—N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*Z)—N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

N-((3R,5R)-1-Acryloyl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5R)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-fluoropiperidin-3-yl)-5-(*S)-(2-methyl-4-phenoxyphenyl)-4-oxo-4,5-dihydro-3H-1-thia-3,5,8-triazaacenaphthylene-2-carboxamide;

N-(4-Cyano-1,4-oxazepan-6-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(4-(Dimethylamino)but-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4R)-1-Acryloyl-4-hydroxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-methoxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide;

(R)—N-(1-(2-Methoxyacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

N-(1-Acryloylazetidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3-methyl-5-phenoxypyridin-2-yl)-4-oxo-4,5-dihydro-3H-1-thia-3,5,8-triazaacenaphthylene-2-carboxamide;

(R)—N-(1-Acryloylpiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

N-((3R,5R)-1-Acryloyl-5-fluoropiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3'-fluoro-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide;

(R,E)-N-(1-(4-(Dimethylamino)but-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(4-Hydroxybut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2'-methyl-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-(trifluoromethoxy)phenyl)-4-oxo-4,5-dihydro-3H-1-thia-3,5,8-triazaacenaphthylene-2-carboxamide;

(R)—N-(1-Acryloylpiperidin-3-yl)-4-oxo-5-(6-phenoxypyridin-3-yl)-4,5-dihydro-3H-1-thia-3,5,8-triazaacenaphthylene-2-carboxamide;

(R)—N-(1-Acryloylpiperidin-3-yl)-5-(3'-chloro-[1,1'-biphenyl]-3-yl)-4-oxo-4,5-dihydro-3H-1-thia-3,5,8-triazaacenaphthylene-2-carboxamide;

N-((3S,4R)-1-Acryloyl-4-methoxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2'-chloro-[1,1'-biphenyl]-3-yl)-4-oxo-4,5-dihydro-3H-1-thia-3,5,8-triazaacenaphthylene-2-carboxamide;

(R,E)-N-(1-(4-Aminobut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(2-phenylpyridin-4-yl)-4,5-dihydro-3H-1-thia-3,5,8-triazaacenaphthylene-2-carboxamide;

(R)—N-(1-Acryloylpiperidin-3-yl)-4-oxo-5-(5-phenoxypyridin-2-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2',4'-difluoro-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(3-benzylphenyl)-4-oxo-4,5-dihydro-3H-1-thia-3,5,8-triazaacenaphthylene-2-carboxamide;

(R)—N-(1-Acryloylpiperidin-3-yl)-5-(3'-methyl-[1,1'-biphenyl]-3-yl)-4-oxo-4,5-dihydro-3H-1-thia-3,5,8-triazaacenaphthylene-2-carboxamide;

(S)—N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3-cyclohexylphenyl)-4-oxo-4,5-dihydro-3H-1-thia-3,5,8-triazaacenaphthylene-2-carboxamide;

(R,E)-N-(1-(4-Aminobut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4'-methyl-[1,1'-biphenyl]-3-yl)-4-oxo-4,5-dihydro-3H-1-thia-3,5,8-triazaacenaphthylene-2-carboxamide;

(R,E)-N-(1-(4-Hydroxybut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-hydroxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N—((R)-1-((S)-2-(methylamino)propanoyl)piperidin-3-yl)-4-oxo-4,5-dihydro-3H-1-thia-3,5,8-triazaacenaphthylene-2-carboxamide;

(R)—N-(1-Acryloylpiperidin-3-yl)-5-(2,2-difluorobenzo[d][1,3]dioxol-5-yl)-4-oxo-4,5-dihydro-3H-1-thia-3,5,8-triazaacenaphthylene-2-carboxamide;

(R)—N-(1-Acryloylpiperidin-3-yl)-4-oxo-5-(4-phenylpyridin-2-yl)-4,5-dihydro-3H-1-thia-3,5,8-triazaacenaphthylene-2-carboxamide;

(R)—N-(1-Acryloylpiperidin-3-yl)-4-oxo-5-(3-phenoxyphenyl)-4,5-dihydro-3H-1-thia-3,5,8-triazaacenaphthylene-2-carboxamide;

(R)—N-(1-Acryloylpiperidin-3-yl)-4-oxo-5-(5-phenoxypyrazin-2-yl)-4,5-dihydro-3H-1-thia-3,5,8-triazaacenaphthylene-2-carboxamide;

(R)—N-(1-Acryloylpiperidin-3-yl)-5-(3-isopropylphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide;

(R)-5-([1,1'-Biphenyl]-3-yl)-N-(1-acryloylpyrrolidin-3-yl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide;

(R)—N-(1-Acryloylpiperidin-3-yl)-4-oxo-5-(3-propylphenyl)-4,5-dihydro-3H-1-thia-3,5,8-triazaacenaphthylene-2-carboxamide;

(R)—N-(1-Acryloylpiperidin-3-yl)-5-(3-cyclobutylphenyl)-4-oxo-4,5-dihydro-3H-1-thia-3,5,8-triazaacenaphthylene-2-carboxamide;

(R)-5-(*S)-(2-Methyl-4-phenoxyphenyl)-N-(1-trideuteriomethylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(3-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(5-phenylpyridin-3-yl)-4,5-dihydro-3H-1-thia-3,5,8-triazaacenaphthylene-2-carboxamide;

(R)—N-(1-Acryloylpiperidin-3-yl)-5-(3-(pyridin-3-yl)phenyl)-4,5-dihydro-3H-1-thia-3,5,8-triazaacenaphthylene-2-carboxamide;

(R)—N-(1-(Ethylsulfonyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(3-(pyridin-2-yl)phenyl)-4,5-dihydro-3H-1-thia-3,5,8-triazaacenaphthylene-2-carboxamide;

(R,E)-5-(3-Chloro-4-phenoxyphenyl)-N-(1-(4-(dimethylamino)but-2-enoyl)piperidin-3-yl)-4-oxo-4,5-dihydro-3H-1-thia-3,5,8-triazaacenaphthylene-2-carboxamide;

(R)—N-(1-Isopropylpiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-fluoropyrrolidin-3-yl)-4-oxo-5-(4-phenoxyphenyl)-4,5-dihydro-3H-1-thia-3,5,8-triazaacenaphthylene-2-carboxamide;

(S)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide;

(R)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide;

(R)—N-(1-(2-(Methylamino)acetyl)piperidin-3-yl)-4-oxo-5-(4-phenoxyphenyl)-4,5-dihydro-3H-1-thia-3,5,8-triazaacenaphthylene-2-carboxamide;

N—((R)-1-((S)-3-Hydroxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-methoxypyrrolidin-3-yl)-4-oxo-5-(4-phenoxyphenyl)-4,5-dihydro-3H-1-thia-3,5,8-triazaacenaphthylene-2-carboxamide;

(R,Z)—N-(1-(4-Amino-2-fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,Z)—N-(1-(4-Amino-2-chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-([1,1'-Biphenyl]-3-yl)-N-(1-(2-(methylamino)acetyl)piperidin-3-yl)-4-oxo-4,5-dihydro-3H-1-thia-3,5,8-triazaacenaphthylene-2-carboxamide;

(R)-5-([1,1'-Biphenyl]-3-yl)-N-(1-methylpiperidin-3-yl)-4-oxo-4,5-dihydro-3H-1-thia-3,5,8-triazaacenaphthylene-2-carboxamide;

(R)-5-(3'-Methyl-[1,1'-biphenyl]-3-yl)-4-oxo-N-(piperidin-3-yl)-4,5-dihydro-3H-1-thia-3,5,8-triazaacenaphthylene-2-carboxamide;

(R)-5-(2'-Methyl-[1,1'-biphenyl]-3-yl)-4-oxo-N-(piperidin-3-yl)-4,5-dihydro-3H-1-thia-3,5,8-triazaacenaphthylene-2-carboxamide;

5-(*S)-(2-Methyl-4-phenoxyphenyl)-4-oxo-N—((R)-1-((E)-4-((4aR,7aS)-tetrahydro-2H-[1,4]dioxino[2,3-c]pyrrol-6(3H)-yl)but-2-enoyl)pyrrolidin-3-yl)-4,5-dihydro-3H-1-thia-3,5,8-triazaacenaphthylene-2-carboxamide;

(R)—N-(1-Acryloylpiperidin-3-yl)-4-oxo-5-(2-phenoxypyrimidin-5-yl)-4,5-dihydro-3H-1-thia-3,5,8-triazaacenaphthylene-2-carboxamide;

N-((3R,5R)-1-Acryloyl-5-hydroxypiperidin-3-yl)-5-(4-isopropoxy-2-methylphenyl)-4-oxo-4,5-dihydro-3H-1-thia-3,5,8-triazaacenaphthylene-2-carboxamide;

(R)—N-(1-Acryloylpyrrolidin-3-yl)-5-(3-chloro-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-4-oxo-5-(2-phenylpyridin-4-yl)-4,5-dihydro-3H-1-thia-3,5,8-triazaacenaphthylene-2-carboxamide;

(R)—N-(1-Acryloylpiperidin-3-yl)-5-(3-(cyclohexyloxy)phenyl)-4-oxo-4,5-dihydro-3H-1-thia-3,5,8-triazaacenaphthylene-2-carboxamide;

(R)—N-(1-Acryloylpiperidin-3-yl)-5-(3-(cyclopentyloxy)phenyl)-4-oxo-4,5-dihydro-3H-1-thia-3,5,8-triazaacenaphthylene-2-carboxamide;

(R,E)-N-(1-(4-(Dimethylamino)but-2-enoyl)pyrrolidin-3-yl)-5-(4-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(2'-(trifluoromethyl)-[1,1'-biphenyl]-3-yl)-4,5-dihydro-3H-1-thia-3,5,8-triazaacenaphthylene-2-carboxamide;

N—((R)-1-((R)-3-Hydroxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3-isopropoxyphenyl)-4-oxo-4,5-dihydro-3H-1-thia-3,5,8-triazaacenaphthylene-2-carboxamide;

(R)-5-(3-Acetylphenyl)-N-(1-acryloylpiperidin-3-yl)-4-oxo-4,5-dihydro-3H-1-thia-3,5,8-triazaacenaphthylene-2-carboxamide;

(R)—N-(1-Acryloylpyrrolidin-3-yl)-4-oxo-5-(2-phenylpyridin-4-yl)-4,5-dihydro-3H-1-thia-3,5,8-triazaacenaphthylene-2-carboxamide;

(R)—N-(1-Acryloylpiperidin-3-yl)-4-oxo-5-(3-(trifluoromethoxy)phenyl)-4,5-dihydro-3H-1-thia-3,5,8-triazaacenaphthylene-2-carboxamide;

(R)—N-(1-Acryloylpiperidin-3-yl)-5-(3-cyclopropylphenyl)-4-oxo-4,5-dihydro-3H-1-thia-3,5,8-triazaacenaphthylene-2-carboxamide;

(R,E)-5-([1,1'-Biphenyl]-3-yl)-N-(1-(4-(dimethylamino)but-2-enoyl)pyrrolidin-3-yl)-4-oxo-4,5-dihydro-3H-1-thia-3,5,8-triazaacenaphthylene-2-carboxamide;

N—((R)-1-((R)-3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(3-Chloro-4-phenoxyphenyl)-N-(1-(2-(dimethylamino)acetyl)piperidin-3-yl)-4-oxo-4,5-dihydro-3H-1-thia-3,5,8-triazaacenaphthylene-2-carboxamide;

(R,E)-5-([1,1'-Biphenyl]-3-yl)-N-(1-(4-(dimethylamino)but-2-enoyl)piperidin-3-yl)-4-oxo-4,5-dihydro-3H-1-thia-3,5,8-triazaacenaphthylene-2-carboxamide;

N-(cis)-1-Acryloyl-3-hydroxypiperidin-4-yl)-4-oxo-5-(4-phenoxyphenyl)-4,5-dihydro-3H-1-thia-3,5,8-triazaacenaphthylene-2-carboxamide;

(R)-5-(3-Chloro-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;

(R)—N-(1-(2-Methoxyacetyl)piperidin-3-yl)-4-oxo-5-(4-phenoxyphenyl)-4,5-dihydro-3H-1-thia-3,5,8-triazaacenaphthylene-2-carboxamide;

(R)-5-(3-Chloro-4-phenoxyphenyl)-4-oxo-N-(pyrrolidin-3-yl)-4,5-dihydro-3H-1-thia-3,5,8-triazaacenaphthylene-2-carboxamide;

4-Oxo-N-(6-oxopiperidin-3-yl)-5-(4-phenoxyphenyl)-4,5-dihydro-3H-1-thia-3,5,8-triazaacenaphthylene-2-carboxamide;

N-((3S,4S)-4-Fluoropyrrolidin-3-yl)-4-oxo-5-(4-phenoxyphenyl)-4,5-dihydro-3H-1-thia-3,5,8-triazaacenaphthylene-2-carboxamide;

(R)-5-(4'-Methyl-[1,1'-biphenyl]-3-yl)-4-oxo-N-(piperidin-3-yl)-4,5-dihydro-3H-1-thia-3,5,8-triazaacenaphthylene-2-carboxamide;

(R)-5-(3-Chloro-4-phenoxyphenyl)-4-oxo-N-(piperidin-3-yl)-4,5-dihydro-3H-1-thia-3,5,8-triazaacenaphthylene-2-carboxamide;

(R)—N-(1-Acetylpiperidin-3-yl)-5-(3-chloro-4-phenoxyphenyl)-4-oxo-4,5-dihydro-3H-1-thia-3,5,8-triazaacenaphthylene-2-carboxamide;

(R)-5-(3-Methyl-4-phenoxyphenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(3-chloro-4-methylphenyl)-4-oxo-4,5-dihydro-3H-1-thia-3,5,8-triazaacenaphthylene-2-carboxamide;

(R)-4-Oxo-5-(2-phenylpyridin-4-yl)-N-(piperidin-3-yl)-4,5-dihydro-3H-1-thia-3,5,8-triazaacenaphthylene-2-carboxamide;

N-((3R,5R)-5-Hydroxypiperidin-3-yl)-4-oxo-5-(4-phenoxyphenyl)-4,5-dihydro-3H-1-thia-3,5,8-triazaacenaphthylene-2-carboxamide;

(R)-5-([1,1'-Biphenyl]-3-yl)-N-(1-methylpyrrolidin-3-yl)-4-oxo-4,5-dihydro-3H-1-thia-3,5,8-triazaacenaphthylene-2-carboxamide;

N-((3S,4S)-4-Methoxypyrrolidin-3-yl)-4-oxo-5-(4-phenoxyphenyl)-4,5-dihydro-3H-1-thia-3,5,8-triazaacenaphthylene-2-carboxamide;

N-((3R,5R)-1-Acryloyl-5-hydroxypiperidin-3-yl)-4-oxo-5-(4-phenoxyphenyl)-4,5-dihydro-3H-1-thia-3,5,8-triazaacenaphthylene-2-carboxamide;

(R,E)-N-(1-(4-Hydroxybut-2-enoyl)piperidin-3-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-5-(2-cyclobutylpyridin-4-yl)-4-oxo-4,5-dihydro-3H-1-thia-3,5,8-triazaacenaphthylene-2-carboxamide;

(R)—N-(1-Cyanopiperidin-3-yl)-4-oxo-5-(4-phenoxyphenyl)-4,5-dihydro-3H-1-thia-3,5,8-triazaacenaphthylene-2-carboxamide;

(R)—N-(1-(3-Methoxypropanoyl)piperidin-3-yl)-4-oxo-5-(4-phenoxyphenyl)-4,5-dihydro-3H-1-thia-3,5,8-triazaacenaphthylene-2-carboxamide;

N-(1-Cyanopiperidin-4-yl)-4-oxo-5-(4-phenoxyphenyl)-4,5-dihydro-3H-1-thia-3,5,8-triazaacenaphthylene-2-carboxamide;

(R)-5-(3-Methyl-5-phenoxypyridin-2-yl)-4-oxo-N-(piperidin-3-yl)-4,5-dihydro-3H-1-thia-3,5,8-triazaacenaphthylene-2-carboxamide;

(E)-N-(1-(4-Hydroxybut-2-enoyl)piperidin-4-yl)-4-oxo-5-(4-phenoxyphenyl)-4,5-dihydro-3H-1-thia-3,5,8-triazaacenaphthylene-2-carboxamide;

N-(1-(3-Methoxypropanoyl)piperidin-4-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-3-amino-4-((3-cyclobutoxyphenyl)amino)thieno[2,3-b]pyridine-2-carboxamide;

(R)-5-([1,1'-Biphenyl]-3-yl)-4-oxo-N-(pyrrolidin-3-yl)-4,5-dihydro-3H-1-thia-3,5,8-triazaacenaphthylene-2-carboxamide;

2-((1-Acryloylpiperidin-3-yl)amino)-5-(2-methyl-4-phenoxyphenyl)-3H-1-thia-3,5,8-triazaacenaphthylen-4(5H)-one;

(R)-5-([1,1'-Biphenyl]-3-yl)-N-(1-(2-(methylamino)acetyl)pyrrolidin-3-yl)-4-oxo-4,5-dihydro-3H-1-thia-3,5,8-triazaacenaphthylene-2-carboxamide;

(R)-4-Oxo-5-(2-phenylpyridin-4-yl)-N-(pyrrolidin-3-yl)-4,5-dihydro-3H-1-thia-3,5,8-triazaacenaphthylene-2-carboxamide;

(R)-5-(3-Cyclobutylphenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-4-oxo-5-(6-phenylpyridin-2-yl)-4,5-dihydro-3H-1-thia-3,5,8-triazaacenaphthylene-2-carboxamide;

(R)-5-(4-Cyclobutoxy-2-methylphenyl)-4-oxo-N-(piperidin-3-yl)-4,5-dihydro-3H-1-thia-3,5,8-triazaacenaphthylene-2-carboxamide;

2-((1-Acryloylpiperidin-4-yl)amino)-5-(2-methyl-4-phenoxyphenyl)-3H-1-thia-3,5,8-triazaacenaphthylen-4(5H)-one;

(R)—N-(1-Acryloylpiperidin-3-yl)-5-(4-methyl-3-(trifluoromethyl)phenyl)-4-oxo-4,5-dihydro-3H-1-thia-3,5,8-triazaacenaphthylene-2-carboxamide;

5-(4-Isopropoxy-2-methylphenyl)-4-oxo-N—((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide;

(R)—N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide;

(R)-4-Oxo-5-(4-phenylpyridin-2-yl)-N-(piperidin-3-yl)-4,5-dihydro-3H-1-thia-3,5,8-triazaacenaphthylene-2-carboxamide;

(3R,5R)-tert-Butyl 3-hydroxy-5-(4-oxo-5-(4-phenoxyphenyl)-4,5-dihydro-3H-1-thia-3,5,8-triazaacenaphthylene-2-carboxamido)piperidine-1-carboxylate;

(R)—N-(1-Acryloylpiperidin-3-yl)-5-(4-(oxetan-3-yloxy)phenyl)-4-oxo-4,5-dihydro-3H-1-thia-3,5,8-triazaacenaphthylene-2-carboxamide;

(R)-5-(3-(Cyclopentyloxy)phenyl)-4-oxo-N-(piperidin-3-yl)-4,5-dihydro-3H-1-thia-3,5,8-triazaacenaphthylene-2-carboxamide;

N-((3S,4R)-1-Acryloyl-4-hydroxypyrrolidin-3-yl)-5-(4-isopropoxy-2-methylphenyl)-4-oxo-4,5-dihydro-3H-1-thia-3,5,8-triazaacenaphthylene-2-carboxamide;

N-(trans-3-Hydroxypiperidin-4-yl)-4-oxo-5-(4-phenoxyphenyl)-4,5-dihydro-3H-1-thia-3,5,8-triazaacenaphthylene-2-carboxamide;

(R)-5-(3-(Cyclohexyloxy)phenyl)-4-oxo-N-(piperidin-3-yl)-4,5-dihydro-3H-1-thia-3,5,8-triazaacenaphthylene-2-carboxamide;

trans-tert-Butyl 3-hydroxy-4-(4-oxo-5-(4-phenoxyphenyl)-4,5-dihydro-3H-1-thia-3,5,8-triazaacenaphthylene-2-carboxamido)piperidine-1-carboxylate;

(R)-4-Oxo-5-(5-phenylpyridin-3-yl)-N-(piperidin-3-yl)-4,5-dihydro-3H-1-thia-3,5,8-triazaacenaphthylene-2-carboxamide;

(R)—N-(1-Acryloylpiperidin-3-yl)-5-(2-methoxypyrimidin-5-yl)-4-oxo-4,5-dihydro-3H-1-thia-3,5,8-triazaacenaphthylene-2-carboxamide;

(R)-4-Oxo-N-(piperidin-3-yl)-5-(3-(trifluoromethoxy)phenyl)-4,5-dihydro-3H-1-thia-3,5,8-triazaacenaphthylene-2-carboxamide;

(R)-5-(3-Cyclobutoxyphenyl)-4-oxo-N-(piperidin-3-yl)-4,5-dihydro-3H-1-thia-3,5,8-triazaacenaphthylene-2-carboxamide;

(R)-4-Oxo-N-(piperidin-3-yl)-5-(3-(pyridin-2-yl)phenyl)-4,5-dihydro-3H-1-thia-3,5,8-triazaacenaphthylene-2-carboxamide;

(R)-4-Oxo-5-(6-phenylpyridin-2-yl)-N-(piperidin-3-yl)-4,5-dihydro-3H-1-thia-3,5,8-triazaacenaphthylene-2-carboxamide;

(R)—N-(1-Acryloylpiperidin-3-yl)-5 (*R)-(2-methyl-4-(trifluoromethoxy)phenyl)-4-oxo-4,5-dihydro-3H-1-thia-3,5,8-triazaacenaphthylene-2-carboxamide;

(3S,4S)-tert-Butyl 3-fluoro-4-(4-oxo-5-(4-phenoxyphenyl)-4,5-dihydro-3H-1-thia-3,5,8-triazaacenaphthylene-2-carboxamido)pyrrolidine-1-carboxylate;

(R)-5-(4-Cyclobutoxyphenyl)-4-oxo-N-(piperidin-3-yl)-4,5-dihydro-3H-1-thia-3,5,8-triazaacenaphthylene-2-carboxamide;

tert-Butyl 4-(4-oxo-5-(4-phenoxyphenyl)-4,5-dihydro-3H-1-thia-3,5,8-triazaacenaphthylene-2-carboxamido)piperidine-1-carboxylate;

(R)-tert-Butyl 3-(4-oxo-5-(4-phenoxyphenyl)-4,5-dihydro-3H-1-thia-3,5,8-triazaacenaphthylene-2-carboxamido)piperidine-1-carboxylate;

(R)-5-(3-Cyclohexylphenyl)-4-oxo-N-(piperidin-3-yl)-4,5-dihydro-3H-1-thia-3,5,8-triazaacenaphthylene-2-carboxamide;

(R)-5-(3-Isopropylphenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-4-oxo-5-(3-(pyridin-4-yl)phenyl)-4,5-dihydro-3H-1-thia-3,5,8-triazaacenaphthylene-2-carboxamide;

(R)—N-(1-Acryloylpiperidin-3-yl)-5-(3-(oxetan-3-yl)phenyl)-4-oxo-4,5-dihydro-3H-1-thia-3,5,8-triazaacenaphthylene-2-carboxamide;

(R)—N-(1-Acryloylpiperidin-3-yl)-5-(4-isopropoxy-3-methylphenyl)-4-oxo-4,5-dihydro-3H-1-thia-3,5,8-triazaacenaphthylene-2-carboxamide;

(R)-5-(2-Cyclobutylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-4-oxo-5-(6-phenoxypyridin-2-yl)-4,5-dihydro-3H-1-thia-3,5,8-triazaacenaphthylene-2-carboxamide;

(R)-5-(2,2-Difluorobenzo[d][1,3]dioxol-5-yl)-4-oxo-N-(piperidin-3-yl)-4,5-dihydro-3H-1-thia-3,5,8-triazaacenaphthylene-2-carboxamide;

(R)-5-(3-Isopropoxyphenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(3-(tert-butyl)phenyl)-4-oxo-4,5-dihydro-3H-1-thia-3,5,8-triazaacenaphthylene-2-carboxamide;

(3S,4S)-tert-Butyl 3-methoxy-4-(4-oxo-5-(4-phenoxyphenyl)-4,5-dihydro-3H-1-thia-3,5,8-triazaacenaphthylene-2-carboxamido)pyrrolidine-1-carboxylate;

(R)—N-(1-Acryloylpiperidin-3-yl)-5-(5-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-(tert-butylsulfonyl)phenyl)-4-oxo-4,5-dihydro-3H-1-thia-3,5,8-triazaacenaphthylene-2-carboxamide;

(R)-5-(4-Hydroxyphenyl)-4-oxo-N-(piperidin-3-yl)-4,5-dihydro-3H-1-thia-3,5,8-triazaacenaphthylene-2-carboxamide;

(R)-5-(3-Acetylphenyl)-4-oxo-N-(piperidin-3-yl)-4,5-dihydro-3H-1-thia-3,5,8-triazaacenaphthylene-2-carboxamide;

(R)-5-(5-Isopropoxy-2-methylphenyl)-4-oxo-N-(piperidin-3-yl)-4,5-dihydro-3H-1-thia-3,5,8-triazaacenaphthylene-2-carboxamide;

(R)-4-Oxo-5-(6-phenoxypyridin-2-yl)-N-(piperidin-3-yl)-4,5-dihydro-3H-1-thia-3,5,8-triazaacenaphthylene-2-carboxamide;

(R)-5-(3-(tert-Butyl)phenyl)-4-oxo-N-(piperidin-3-yl)-4,5-dihydro-3H-1-thia-3,5,8-triazaacenaphthylene-2-carboxamide;

(R)-4-Oxo-N-(piperidin-3-yl)-5-(3-(pyridin-4-yl)phenyl)-4,5-dihydro-3H-1-thia-3,5,8-triazaacenaphthylene-2-carboxamide;

(R)-tert-Butyl 3-(5-(3-(tert-butyl)phenyl)-4-oxo-4,5-dihydro-3H-1-thia-3,5,8-triazaacenaphthylene-2-carboxamido)piperidine-1-carboxylate;

(R)-tert-Butyl 3-(5-(3-acetylphenyl)-4-oxo-4,5-dihydro-3H-1-thia-3,5,8-triazaacenaphthylene-2-carboxamido)piperidine-1-carboxylate;

(R)-5-(4-(tert-Butylsulfonyl)phenyl)-4-oxo-N-(piperidin-3-yl)-4,5-dihydro-3H-1-thia-3,5,8-triazaacenaphthylene-2-carboxamide;

(R)-tert-Butyl 3-(5-(4-(tert-butylsulfonyl)phenyl)-4-oxo-4,5-dihydro-3H-1-thia-3,5,8-triazaacenaphthylene-2-carboxamido)piperidine-1-carboxylate;

(R)-tert-Butyl 3-(5-(4-(tert-butoxy)phenyl)-4-oxo-4,5-dihydro-3H-1-thia-3,5,8-triazaacenaphthylene-2-carboxamido)piperidine-1-carboxylate;

(R)-tert-Butyl 3-(5-(2,2-difluorobenzo[d][1,3]dioxol-5-yl)-4-oxo-4,5-dihydro-3H-1-thia-3,5,8-triazaacenaphthylene-2-carboxamido)piperidine-1-carboxylate;

(R)-tert-Butyl 3-(5-(6-cyclobutoxypyridin-3-yl)-4-oxo-4,5-dihydro-3H-1-thia-3,5,8-triazaacenaphthylene-2-carboxamido)piperidine-1-carboxylate;

N-((3R,4R)-1-Acryloyl-4-hydroxypiperidin-3-yl)-4-oxo-5-(4-phenoxyphenyl)-4,5-dihydro-3H-1-thia-3,5,8-triazaacenaphthylene-2-carboxamide;

(R)-5-(3-Methyl-5-phenoxypyrazin-2-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(3-methyl-5-phenoxypyrazin-2-yl)-4-oxo-4,5-dihydro-3H-1-thia-3,5,8-triazaacenaphthylene-2-carboxamide;

N-((3R,4R)-4-Hydroxypiperidin-3-yl)-4-oxo-5-(4-phenoxyphenyl)-4,5-dihydro-3H-1-thia-3,5,8-triazaacenaphthylene-2-carboxamide;

N-(cis-3-Hydroxypiperidin-4-yl)-4-oxo-5-(4-phenoxyphenyl)-4,5-dihydro-3H-1-thia-3,5,8-triazaacenaphthylene-2-carboxamide;

4-Oxo-N-(2-oxopyrrolidin-3-yl)-5-(4-phenoxyphenyl)-4,5-dihydro-3H-1-thia-3,5,8-triazaacenaphthylene-2-carboxamide;

(R)—N-(1-Acryloylpiperidin-3-yl)-5-(R)-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(*S)-(4-methyl-2-phenoxypyrimidin-5-yl)-4-oxo-4,5-dihydro-3H-1-thia-3,5,8-triazaacenaphthylene-2-carboxamide;

(R)—N-(1-Acryloylpiperidin-3-yl)-4-oxo-5-(5-phenoxypyrimidin-2-yl)-4,5-dihydro-3H-1-thia-3,5,8-triazaacenaphthylene-2-carboxamide;

(R)—N-(1-Acryloylpyrrolidin-3 yl)-5-(*R)-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(4-methyl-6-phenoxypyridin-3-yl)-4-oxo-4,5-dihydro-3H-1-thia-3,5,8-triazaacenaphthylene-2-carboxamide;

N-(cis-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(6-isobutyl-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(6-isobutyl-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(6-cyclobutoxy-4-methylpyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

N-((3R,5S)-1-Acryloyl-5-hydroxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(3-methyl-2-phenylpyridin-4-yl)-4-oxo-4,5-dihydro-3H-1-thia-3,5,8-triazaacenaphthylene-2-carboxamide;

(R)—N-(1-Acryloylpiperidin-3-yl)-5-(2-cyclohexylpyridin-4-yl)-4-oxo-4,5-dihydro-3H-1-thia-3,5,8-triazaacenaphthylene-2-carboxamide;

(R)—N-(1-Acryloylpiperidin-3-yl)-4-oxo-5-(6-phenylpyridazin-4-yl)-4,5-dihydro-3H-1-thia-3,5,8-triazaacenaphthylene-2-carboxamide;

N-((3R,5S)-1-Acryloyl-5-methoxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

(R)—N-(1-Acryloylpyrrolidin-3-yl)-4-oxo-5-(6-phenoxypyridin-3-yl)-4,5-dihydro-3H-1-thia-3,5,8-triazaacenaphthylene-2-carboxamide;

N—((R)-1-((*E)-3-((S)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(*S)-(6-cyclobutoxy-2-methylpyridin-3-yl)-4-oxo-4,5-dihydro-3H-1-thia-3,5,8-triazaacenaphthylene-2-carboxamide;

N—((R)-1-((E)-3-((R)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-4-oxo-N—((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide;

(R)—N-(1-Acryloylpiperidin-3-yl)-4-oxo-5-(6-phenylpyrimidin-4-yl)-4,5-dihydro-3H-1-thia-3,5,8-triazaacenaphthylene-2-carboxamide;

(R)—N-(1-Acryloylpiperidin-3-yl)-5-(3-chloro-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(6-cyclobutoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(4-methyl-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(3-isobutylphenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*R)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(2-cyclopentylpyridin-4-yl)-4-oxo-4,5-dihydro-3H-1-thia-3,5,8-triazaacenaphthylene-2-carboxamide;

(R)—N-(1-Acryloylpiperidin-3-yl)-5-(4-(cyclopentyloxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-methoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(5-methyl-2-phenylpyridin-4-yl)-4-oxo-4,5-dihydro-3H-1-thia-3,5,8-triazaacenaphthylene-2-carboxamide;

(R)—N-(1-Acryloylpiperidin-3-yl)-5-(4-(2-isopropoxyethoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(2-isopropylpyridin-4-yl)-4-oxo-4,5-dihydro-3H-1-thia-3,5,8-triazaacenaphthylene-2-carboxamide;

(R)—N-(1-Acryloylpyrrolidin-3-yl)-4-oxo-5-(5-phenoxypyridin-2-yl)-4,5-dihydro-3H-1-thia-3,5,8-triazaacenaphthylene-2-carboxamide;

(R)—N-(1-Acryloylpyrrolidin-3-yl)-4-oxo-5-(5-phenoxypyrazin-2-yl)-4,5-dihydro-3H-1-thia-3,5,8-triazaacenaphthylene-2-carboxamide;

(R)—N-(1-Acryloylpiperidin-3-yl)-5-(*R)-(6-cyclobutoxy-4-methylpyridin-3-yl)-4-oxo-4,5-dihydro-3H-1-thia-3,5,8-triazaacenaphthylene-2-carboxamide;

(R)-5-([2,3'-Bipyridin]-4-yl)-N-(1-acryloylpiperidin-3-yl)-4-oxo-4,5-dihydro-3H-1-thia-3,5,8-triazaacenaphthylene-2-carboxamide;

(R)-5-(*S)-(4-Methyl-6-phenoxypyridin-3-yl)-4-oxo-N-(pyrrolidin-3-yl)-4,5-dihydro-3H-1-thia-3,5,8-triazaacenaphthylene-2-carboxamide;

(R,E)-5-(3-Chloro-4-phenoxyphenyl)-N-(1-(4-(dimethylamino)but-2-enoyl)pyrrolidin-3-yl)-4-oxo-4,5-dihydro-3H-1-thia-3,5,8-triazaacenaphthylene-2-carboxamide;

(R)—N-(1-Acryloylpiperidin-3-yl)-5-(6-cyclobutoxy-2-methylpyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(3-isopropylphenyl)-4-oxo-4,5-dihydro-3H-1-thia-3,5,8-triazaacenaphthylene-2-carboxamide;

(R)-5-(2',3'-Difluoro-[1,1'-biphenyl]-3-yl)-4-oxo-N-(piperidin-3-yl)-4,5-dihydro-3H-1-thia-3,5,8-triazaacenaphthylene-2-carboxamide;

N-((1RS,2RS)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-4-oxo-5-(3-(tetrahydro-2H-pyran-4-yl)phenyl)-4,5-dihydro-3H-1-thia-3,5,8-triazaacenaphthylene-2-carboxamide;

(R)-5-([2,2'-Bipyridin]-4-yl)-N-(1-acryloylpiperidin-3-yl)-4-oxo-4,5-dihydro-3H-1-thia-3,5,8-triazaacenaphthylene-2-carboxamide;

(R)-5-(2',3'-Difluoro-[1,1'-biphenyl]-3-yl)-N-(1-methylpiperidin-3-yl)-4-oxo-4,5-dihydro-3H-1-thia-3,5,8-triazaacenaphthylene-2-carboxamide;

(R)-5-(2-Methyl-6-phenoxypyridin-3-yl)-4-oxo-N-(piperidin-3-yl)-4,5-dihydro-3H-1-thia-3,5,8-triazaacenaphthylene-2-carboxamide;

N-(trans-1-Acryloyl-3-hydroxypiperidin-4-yl)-4-oxo-5-(4-phenoxyphenyl)-4,5-dihydro-3H-1-thia-3,5,8-triazaacenaphthylene-2-carboxamide;

(R)-5-(*S)-(2-Methyl-6-phenoxypyridin-3-yl)-4-oxo-N-(piperidin-3-yl)-4,5-dihydro-3H-1-thia-3,5,8-triazaacenaphthylene-2-carboxamide;

(R)—N-(1-(Methylglycyl)piperidin-3-yl)-4-oxo-5-(2-phenylpyridin-4-yl)-4,5-dihydro-3H-1-thia-3,5,8-triazaacenaphthylene-2-carboxamide;

(R)-5-(*S)-(4-Methyl-2-phenoxypyrimidin-5-yl)-4-oxo-N-(pyrrolidin-3-yl)-4,5-dihydro-3H-1-thia-3,5,8-triazaacenaphthylene-2-carboxamide;

(R)—N-(1-Acryloylpyrrolidin-3-yl)-5-(*S)-(2-methyl-6-phenoxypyridin-3-yl)-4-oxo-4,5-dihydro-3H-1-thia-3,5,8-triazaacenaphthylene-2-carboxamide;

(R)-5-(*S)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide;

N-((3S,4R)-1-Acryloyl-4-hydroxypyrrolidin-3-yl)-4-oxo-5-(2-phenylpyridin-4-yl)-4,5-dihydro-3H-1-thia-3,5,8-triazaacenaphthylene-2-carboxamide;

(R)-4-Oxo-5-(5-phenoxypyrimidin-2-yl)-N-(piperidin-3-yl)-4,5-dihydro-3H-1-thia-3,5,8-triazaacenaphthylene-2-carboxamide;

(R)-5-(2-Cyclopentylpyridin-4-yl)-4-oxo-N-(piperidin-3-yl)-4,5-dihydro-3H-1-thia-3,5,8-triazaacenaphthylene-2-carboxamide;

(R)-5-(3-Isobutylphenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(*R)-(6-isobutyl-4-methylpyridin-3-yl)-4-oxo-4,5-dihydro-3H-1-thia-3,5,8-triazaacenaphthylene-2-carboxamide;

(R)-4-Oxo-5-(6-phenylpyrimidin-4-yl)-N-(piperidin-3-yl)-4,5-dihydro-3H-1-thia-3,5,8-triazaacenaphthylene-2-carboxamide;

(R)—N-(1-Acryloylpyrrolidin-3-yl)-5-(*R)-(4-methyl-2-phenoxypyrimidin-5-yl)-4-oxo-4,5-dihydro-3H-1-thia-3,5,8-triazaacenaphthylene-2-carboxamide;

(R)-5-(4-Methyl-[1,1'-biphenyl]-3-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(*S)-(6-cyclobutoxy-4-methylpyridin-3-yl)-4-oxo-4,5-dihydro-3H-1-thia-3,5,8-triazaacenaphthylene-2-carboxamide;

(R)-5-(2-Isopropylpyridin-4-yl)-4-oxo-N-(piperidin-3-yl)-4,5-dihydro-3H-1-thia-3,5,8-triazaacenaphthylene-2-carboxamide;

(R)-5-(*R)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide;

(R)-5-(5-Methyl-2-phenylpyridin-4-yl)-4-oxo-N-(piperidin-3-yl)-4,5-dihydro-3H-1-thia-3,5,8-triazaacenaphthylene-2-carboxamide;

(R)-5-(4-(2-Isopropoxyethoxy)-2-methylphenyl)-4-oxo-N-(piperidin-3-yl)-4,5-dihydro-3H-1-thia-3,5,8-triazaacenaphthylene-2-carboxamide;

(R)-5-(2-Cyclohexylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(6-isopropoxy-2-methylpyridin-3-yl)-4-oxo-4,5-dihydro-3H-1-thia-3,5,8-triazaacenaphthylene-2-carboxamide;

(R)-5-(3-Methyl-2-phenylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(2-methyl-6-phenylpyridin-4-yl)-4-oxo-4,5-dihydro-3H-1-thia-3,5,8-triazaacenaphthylene-2-carboxamide;

(R)-5-(2-Methyl-6-phenylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(*R)-(6-cyclobutoxy-2-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(3-methyl-2-phenylpyridin-4-yl)-4-oxo-4,5-dihydro-3H-1-thia-3,5,8-triazaacenaphthylene-2-carboxamide;

(R)-4-Oxo-N-(piperidin-3-yl)-5-(3-(tetrahydro-2H-pyran-4-yl)phenyl)-4,5-dihydro-3H-1-thia-3,5,8-triazaacenaphthylene-2-carboxamide;

(R)-tert-Butyl 3-(4-oxo-5-(3-(tetrahydro-2H-pyran-4-yl)phenyl)-4,5-dihydro-3H-1-thia-3,5,8-triazaacenaphthylene-2-carboxamido)piperidine-1-carboxylate;

(R)-4-Oxo-5-(6-phenylpyridazin-4-yl)-N-(piperidin-3-yl)-4,5-dihydro-3H-1-thia-3,5,8-triazaacenaphthylene-2-carboxamide;

(R)-4-Oxo-5-(6-phenoxypyridin-3-yl)-N-(pyrrolidin-3-yl)-4,5-dihydro-3H-1-thia-3,5,8-triazaacenaphthylene-2-carboxamide;

(R)—N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)-tert-Butyl 3-(5-(2-methyl-6-phenoxypyridin-3-yl)-4-oxo-4,5-dihydro-3H-1-thia-3,5,8-triazaacenaphthylene-2-carboxamido)piperidine-1-carboxylate;

(R)-5-(6-Cyclobutoxypyridin-3-yl)-4-oxo-N-(piperidin-3-yl)-4,5-dihydro-3H-1-thia-3,5,8-triazaacenaphthylene-2-carboxamide;

N-((3*S,4*R)-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(4-methyl-2-phenoxypyrimidin-5-yl)-4-oxo-4,5-dihydro-3H-1-thia-3,5,8-triazaacenaphthylene-2-carboxamide;

(R)—N-(1-Acryloylpyrrolidin-3-yl)-5-(*S)-(6-isobutyl-4-methylpyridin-3-yl)-4-oxo-4,5-dihydro-3H-1-thia-3,5,8-triazaacenaphthylene-2-carboxamide;

(R)—N-(1-Acryloylpyrrolidin-3-yl)-4-oxo-5-(2-phenoxypyrimidin-5-yl)-4,5-dihydro-3H-1-thia-3,5,8-triazaacenaphthylene-2-carboxamide;

(R)—N-(1-Acryloylpyrrolidin-3-yl)-4-oxo-5-(5-phenoxypyrimidin-2-yl)-4,5-dihydro-3H-1-thia-3,5,8-triazaacenaphthylene-2-carboxamide;

(R)—N-(1-Acryloylpiperidin-3-yl)-5-(4-isobutylphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(5-phenylpyridazin-3-yl)-4,5-dihydro-3H-1-thia-3,5,8-triazaacenaphthylene-2-carboxamide;

N-((*3R,*4S)-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(6-isopropoxy-2-methylpyridin-3-yl)-4-oxo-4,5-dihydro-3H-1-thia-3,5,8-triazaacenaphthylene-2-carboxamide;

(R)-5-(4-Isobutylphenyl)-4-oxo-N-(piperidin-3-yl)-4,5-dihydro-3H-1-thia-3,5,8-triazaacenaphthylene-2-carboxamide;

(R)-4-Oxo-5-(5-phenylpyridazin-3-yl)-N-(piperidin-3-yl)-4,5-dihydro-3H-1-thia-3,5,8-triazaacenaphthylene-2-carboxamide;
(R)—N-(1-Acryloylpyrrolidin-3-yl)-5-(*R)-(6-isobutyl-4-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(*R)-(6-isopropoxy-2-methylpyridin-3-yl)-4-oxo-4,5-dihydro-3H-1-thia-3,5,8-triazaacenaphthylene-2-carboxamide;
(R)-5-(*S)-(6-Isobutyl-4-methylpyridin-3-yl)-4-oxo-N-(pyrrolidin-3-yl)-4,5-dihydro-3H-1-thia-3,5,8-triazaacenaphthylene-2-carboxamide;
(R)-5-(*S)-(6-Isobutoxy-4-methylpyridin-3-yl)-4-oxo-N-(piperidin-3-yl)-4,5-dihydro-3H-1-thia-3,5,8-triazaacenaphthylene-2-carboxamide;
(R)-5-(*R)-(6-Isobutoxy-4-methylpyridin-3-yl)-4-oxo-N-(piperidin-3-yl)-4,5-dihydro-3H-1-thia-3,5,8-triazaacenaphthylene-2-carboxamide;
(R)-5-(*S)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide;
(R)-5-(*R)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide;
(R)-5-(*S)-(4-Methyl-2-phenoxypyrimidin-5-yl)-4-oxo-N-(piperidin-3-yl)-4,5-dihydro-3H-1-thia-3,5,8-triazaacenaphthylene-2-carboxamide;
(R)—N-(1-Acryloylpiperidin-3-yl)-5-(6-isobutyl-2-methylpyridin-3-yl)-4-oxo-4,5-dihydro-3H-1-thia-3,5,8-triazaacenaphthylene-2-carboxamide;
(R)-5-(*S)-(6-Isobutyl-4-methylpyridin-3-yl)-4-oxo-N-(1-propionylpiperidin-3-yl)-4,5-dihydro-3H-1-thia-3,5,8-triazaacenaphthylene-2-carboxamide;
(R)—N-(1-Acryloylpiperidin-3-yl)-5-(*S)-(6-isobutoxy-4-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(*R)-(6-isobutoxy-4-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(*R)-(6-(cyclopentyloxy)-4-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(2-methyl-6-((tetrahydro-2H-pyran-4-yl)oxy)pyridin-3-yl)-4-oxo-4,5-dihydro-3H-1-thia-3,5,8-triazaacenaphthylene-2-carboxamide;
(R)—N-(1-Acryloylpiperidin-3-yl)-5-(4-((2-methylpyridin-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-((6-methylpyridin-2-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-((2-methylpyridin-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(pyridin-3-yloxy)phenyl)-4,5-dihydro-3H-1-thia-3,5,8-triazaacenaphthylene-2-carboxamide;
(R)—N-(1-Acryloylpiperidin-3-yl)-5-(4-((6-methylpyridin-2-yl)oxy)phenyl)-4-oxo-4,5-dihydro-3H-1-thia-3,5,8-triazaacenaphthylene-2-carboxamide;
(R)—N-(1-Acryloylpyrrolidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(5-(2-fluorophenoxy)pyridin-2-yl)-4-oxo-4,5-dihydro-3H-1-thia-3,5,8-triazaacenaphthylene-2-carboxamide;
(R)—N-(1-Acryloylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide;
(R)—N-(1-Acryloylpyrrolidin-3-yl)-5S)-(6-isobutoxy-4-methylpyridin-3-yl)-4-oxo-4,5-dihydro-3H-1-thia-3,5,8-triazaacenaphthylene-2-carboxamide;
N1-(15-Oxo-19-((3 aR,4R,6aS)-2-oxohexahydro-1H-thieno[3,4-d]imidazol-4-yl)-4,7,10-trioxa-14-azanonadecyl)-N5-((E)-4-oxo-4-(3-(4-oxo-5-(5-phenoxypyridin-2-yl)-4,5-dihydro-3H-1-thia-3,5,8-triazaacenaphthylene-2-carboxamido)piperidin-1-yl)but-2-en-1-yl)glutaramide;
(R)—N-(1-Acryloylpyrrolidin-3-yl)-5-(2-methyl-4-(pyridin-2-yloxy)phenyl)-4-oxo-4,5-dihydro-3H-1-thia-3,5,8-triazaacenaphthylene-2-carboxamide;
(R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-((6-methylpyridin-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide;
N—((R)-1-Acryloylpiperidin-3-yl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(4-((5-methylpyridin-2-yl)oxy)phenyl)-4-oxo-4,5-dihydro-3H-1-thia-3,5,8-triazaacenaphthylene-2-carboxamide;
N—((R)-1-Acryloylpiperidin-3-yl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide;
1-Acryloyl-N-(5-(2-methyl-4-phenoxyphenyl)-4-oxo-4,5-dihydro-3H-1-thia-3,5,8-triazaacenaphthylen-2-yl)piperidine-3-carboxamide;
(R)—N-(1-Acryloylpiperidin-3-yl)-5-(*S)-(6-isopropoxy-4-methylpyridin-3-yl)-4-oxo-4,5-dihydro-3H-1-thia-3,5,8-triazaacenaphthylene-2-carboxamide;
(R)—N-(1-Acryloylpyrrolidin-3-yl)-5-(2-methyl-4-(pyridazin-3-yloxy)phenyl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide;
(R)—N-(1-Acryloylpiperidin-3-yl)-5-(*S)-(6-isobutyl-2-methylpyridin-3-yl)-4-oxo-4,5-dihydro-3H-1-thia-3,5,8-triazaacenaphthylene-2-carboxamide;
(R)-5-(*S)-(2-Methyl-6-phenoxypyridin-3-yl)-4-oxo-N-(tetrahydrofuran-3-yl)-4,5-dihydro-3H-1-thia-3,5,8-triazaacenaphthylene-2-carboxamide;
(R)-5-(*S)-(6-Isopropoxy-4-methylpyridin-3-yl)-4-oxo-N-(piperidin-3-yl)-4,5-dihydro-3H-1-thia-3,5,8-triazaacenaphthylene-2-carboxamide;
(S)—N-(1-Acryloylpiperidin-3-yl)-4-oxo-5-(5-phenoxypyridin-2-yl)-4,5-dihydro-3H-1-thia-3,5,8-triazaacenaphthylene-2-carboxamide;
2-(4-Acryloylpiperazin-1-yl)-5-(2-methyl-4-phenoxyphenyl)-3H-1-thia-3,5,8-triazaacenaphthylen-4(5H)-one;
(R)-5-(*S)-(6-(Cyclopentyloxy)-4-methylpyridin-3-yl)-4-oxo-N-(pyrrolidin-3-yl)-4,5-dihydro-3H-1-thia-3,5,8-triazaacenaphthylene-2-carboxamide;

(R)-5-(*S)-(6-Isobutoxy-4-methylpyridin-3-yl)-4-oxo-N-(pyrrolidin-3-yl)-4,5-dihydro-3H-1-thia-3,5,8-triazaacenaphthylene-2-carboxamide;
(R)-5-(2-Methyl-4-(pyridin-2-yloxy)phenyl)-4-oxo-N-(1-propionylpiperidin-3-yl)-4,5-dihydro-3H-1-thia-3,5,8-triazaacenaphthylene-2-carboxamide;
(R)—N-(1-Acetylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide;
(E)-1-(2-Cyano-3-cyclopropylacryloyl)-N-(5-(2-methyl-4-phenoxyphenyl)-4-oxo-4,5-dihydro-3H-1-thia-3,5,8-triazaacenaphthylen-2-yl)piperidine-3-carboxamide;
1-Cyano-N-(5-(2-methyl-4-phenoxyphenyl)-4-oxo-4,5-dihydro-3H-1-thia-3,5,8-triazaacenaphthylen-2-yl)piperidine-3-carboxamide;
(R)—N-(1-Acryloylpyrrolidin-3-yl)-4-oxo-5-(4-(pyridazin-3-yloxy)phenyl)-4,5-dihydro-3H-1-thia-3,5,8-triazaacenaphthylene-2-carboxamide;
(R)—N-(1-Acryloylpiperidin-3-yl)-5-(*R)-(6-isopropoxy-4-methylpyridin-3-yl)-4-oxo-4,5-dihydro-3H-1-thia-3,5,8-triazaacenaphthylene-2-carboxamide;
N-(5-(2-Methyl-4-phenoxyphenyl)-4-oxo-4,5-dihydro-3H-1-thia-3,5,8-triazaacenaphthylen-2-yl)-1-propionylpiperidine-4-carboxamide;
(R)-5-(*R)-(6-Isopropoxy-4-methylpyridin-3-yl)-4-oxo-N-(piperidin-3-yl)-4,5-dihydro-3H-1-thia-3,5,8-triazaacenaphthylene-2-carboxamide;
(R)-4-Oxo-N-(1-propionylpiperidin-3-yl)-5-(4-(pyridin-2-yloxy)phenyl)-4,5-dihydro-3H-1-thia-3,5,8-triazaacenaphthylene-2-carboxamide;
(R)—N-(1-Acetylpiperidin-3-yl)-5-(4-(pyridin-2-yloxy)phenyl)-4,5-dihydro-3H-1-thia-3,5,8-triazaacenaphthylene-2-carboxamide;
(R)-5-(2-Methyl-4-(pyridazin-3-yloxy)phenyl)-4-oxo-N-(1-propionylpiperidin-3-yl)-4,5-dihydro-3H-1-thia-3,5,8-triazaacenaphthylene-2-carboxamide;
(R)—N-(1-Acetylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide;
(R)—N-(1-Acetylpiperidin-3-yl)-4-oxo-5-(4-(pyridazin-3-yloxy)phenyl)-4,5-dihydro-3H-1-thia-3,5,8-triazaacenaphthylene-2-carboxamide;
(R)—N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(*R)-(6-isobutyl-2-methylpyridin-3-yl)-4-oxo-4,5-dihydro 3H-1-thia-3,5,8-triazaacenaphthylene-2-carboxamide;
(E)-1-(2-Cyano-4,4-dimethylpent-2-enoyl)-N-(5-(2-methyl-4-phenoxyphenyl)-4-oxo-4,5-dihydro-3H-1-thia-3,5,8-triazaacenaphthylen-2-yl)piperidine-3-carboxamide;
1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-3-carboxamide;
N-(5-(2-Methyl-4-phenoxyphenyl)-4-oxo-4,5-dihydro-3H-1-thia-3,5,8-triazaacenaphthylen-2-yl)-1-propionylpiperidine-3-carboxamide;
1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-4-carboxamide;
1-Acryloyl-N-(5-(2-methyl-4-phenoxyphenyl)-4-oxo-4,5-dihydro-3H-1-thia-3,5,8-triazaacenaphthylen-2-yl)piperidine-4-carboxamide;
1-Ethyl-N-(5-(2-methyl-4-phenoxyphenyl)-4-oxo-4,5-dihydro-3H-1-thia-3,5,8-triazaacenaphthylen-2-yl)piperidine-3-carboxamide;
1-Cyano-N-(5-(2-methyl-4-phenoxyphenyl)-4-oxo-4,5-dihydro-3H-1-thia-3,5,8-triazaacenaphthylen-2-yl)piperidine-4-carboxamide;
1-Methyl-N-(5-(2-methyl-4-phenoxyphenyl)-4-oxo-4,5-dihydro-3H-1-thia-3,5,8-triazaacenaphthylen-2-yl)piperidine-3-carboxamide;
5-(2-Methyl-4-phenoxyphenyl)-2-(4-methylpiperazin-1-yl)-3H-1-thia-3,5,8-triazaacenaphthylen-4(5H)-one;
(E)-4,4-Dimethyl-2-(4-(5-(2-methyl-4-phenoxyphenyl)-4-oxo-4,5-dihydro-3H-1-thia-3,5,8-triazaacenaphthylen-2-yl)piperazine-1-carbonyl)pent-2-enenitrile;
4-(5-(2-Methyl-4-phenoxyphenyl)-4-oxo-4,5-dihydro-3H-1-thia-3,5,8-triazaacenaphthylen-2-yl)piperazine-1-carbonitrile;
5-(2-Methyl-4-phenoxyphenyl)-2-(4-propionylpiperazin-1-yl)-3H-1-thia-3,5,8-triazaacenaphthylen-4(5H)-one;
N-(5-(2-Methyl-4-phenoxyphenyl)-4-oxo-4,5-dihydro-3H-1-thia-3,5,8-triazaacenaphthylen-2-yl)piperidine-3-carboxamide;
(E)-1-(2-Cyano-4,4-dimethylpent-2-enoyl)-N-(5-(2-methyl-4-phenoxyphenyl)-4-oxo-4,5-dihydro-3H-1-thia-3,5,8-triazaacenaphthylen-2-yl)piperidine-4-carboxamide;
(E)-1-(2-Cyano-3-cyclopropylacryloyl)-N-(5-(2-methyl-4-phenoxyphenyl)-4-oxo-4,5-dihydro-3H-1-thia-3,5,8-triazaacenaphthylen-2-yl)piperidine-4-carboxamide;
1-Methyl-N-(5-(2-methyl-4-phenoxyphenyl)-4-oxo-4,5-dihydro-3H-1-thia-3,5,8-triazaacenaphthylen-2-yl)piperidine-4-carboxamide;
1-Ethyl-N-(5-(2-methyl-4-phenoxyphenyl)-4-oxo-4,5-dihydro-3H-1-thia-3,5,8-triazaacenaphthylen-2-yl)piperidine-4-carboxamide;
N-(5-(2-Methyl-4-phenoxyphenyl)-4-oxo-4,5-dihydro-3H-1-thia-3,5,8-triazaacenaphthylen-2-yl)piperidine-4-carboxamide;
(R)-5-(*S)-(2-Methyl-4-phenoxyphenyl)-4-oxo-N-(1-(vinylsulfonyl)pyrrolidin-3-yl)-4,5-dihydro-3H-1-thia-3,5,8-triazaacenaphthylene-2-carboxamide;
(R,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide;
(R,E)-N-(1-(2-Cyano-3-cyclopropylacryloyl)piperidin-3-yl)-5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxamide;
(R)—N-(1-Cyanopyrrolidin-3-yl)-5-(2-methyl-4-phenoxyphenyl)-4-oxo-4,5-dihydro-3H-1-thia-3,5,8-triazaacenaphthylene-2-carboxamide;
(R)—N-(1-(2-Cyanoacetyl)pyrrolidin-3-yl)-5-(2-methyl-4-phenoxyphenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide;
(R,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide;

(R)—N-(1-(3-Methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2',3'-difluoro-4-methyl-[1,1'-biphenyl]-3-yl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide;

(R,E)-N-(1-(2-Cyano-3-cyclopropylacryloyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-5-(*S)-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide;

(R)—N-(1-Acryloylpiperidin-3-yl)-4-oxo-5-(4-(pyridin-2-yloxy)phenyl)-4,5-dihydro-3H-1-thia-3,5,8-triazaacenaphthylene-2-carboxamide;

(R)—N-(1-Acryloylpyrrolidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide;

5-(2-Methyl-4-phenoxyphenyl)-N—((R)-1-((R)-2-(methylamino)propanoyl)piperidin-3-yl)-4-oxo-4,5-dihydro-3H-1-thia-3,5,8-triazaacenaphthylene-2-carboxamide;

N—((R)-1-((R)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide;

(R)—N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N—((R)-1-((S)-2-(methylamino)propanoyl)piperidin-3-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide;

5-(4-(3-((2-Cyanophenoxy)methyl)phenoxy)-2-methylphenyl)-N-(1-methylpiperidin-4-yl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide;

5-(4-(3-((2-Cyanophenoxy)methyl)phenoxy)-2-methylphenyl)-4-oxo-N-(piperidin-4-yl)-4,5-dihydro-3H-1-thia-3,5,8-triazaacenaphthylene-2-carboxamide;

5-(2-Methyl-4-phenoxyphenyl)-N-(1-methylpiperidin-4-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide;

(R)-4-Oxo-5-(4-phenoxyphenyl)-N-(piperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

(S)—N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide;

(S)—N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-(piperidin-4-yl)-4,5-dihydro-3H-1-thia-3,5,8-triazaacenaphthylene-2-carboxamide;

(R,E)-N-(1-(2-Cyano-4,4-dimethylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide;

(R,E)-N-(1-(2-Cyano-4,4-dimethylpent-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(piperidin-3-yl)-4,5-dihydro-3H-1-thia-3,5,8-triazaacenaphthylene-2-carboxamide;

5-(4-(2-Methoxyphenoxy)-2-methylphenyl)-4-oxo-N-(piperidin-3-yl)-4,5-dihydro-3H-1-thia-3,5,8-triazaacenaphthylene-2-carboxamide;

(R)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

N-(1-Cyanopiperidin-4-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)—N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((R)-pyrrolidine-2-carbonyl)piperidin-3-yl)-4,5-dihydro-3H-1-thia-3,5,8-triazaacenaphthylene-2-carboxamide;

(E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

(S)—N-(1-Formylpiperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-4-oxo-5-(4-(pyridin-2-yloxy)phenyl)-4,5-dihydro-3H-1-thia-3,5,8-triazaacenaphthylene-2-carboxamide;

N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide;

N-(1-Cyanopiperidin-3-yl)-5-(4-(2-methoxyphenoxy)-2-methylphenyl)-4-oxo-4,5-dihydro-3H-1-thia-3,5,8-triazaacenaphthylene-2-carboxamide;

N-(1-Cyanopiperidin-4-yl)-5-(4-(2-methoxyphenoxy)-2-methylphenyl)-4-oxo-4,5-dihydro-3H-1-thia-3,5,8-triazaacenaphthylene-2-carboxamide;

(R)—N-(1-Formylpiperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide;

(S)—N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acetylpyrrolidin-3-yl)-4-oxo-5-(4-phenoxyphenyl)-4,5-dihydro-3H-1-thia-3,5,8-triazaacenaphthylene-2-carboxamide;

5-(2-Methyl-4-phenoxyphenyl)-4-oxo-N-(piperidin-3-yl)-4,5-dihydro-3H-1-thia-3,5,8-triazaacenaphthylene-2-carboxamide;

N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

(S)—N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((S)-pyrrolidine-2-carbonyl)piperidin-3-yl)-4,5-dihydro-3H-1-thia-3,5,8-triazaacenaphthylene-2-carboxamide;

(R)—N-(1-Acryloylpiperidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide;

(E)-N-(1-(2-Cyano-4,4-dimethylpent-2-enoyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide;

(E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-4-oxo-N-(1-(4-(piperidin-1-yl)but-2-enoyl)piperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-3-phenoxyphenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxamide;

5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

(S,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(S,E)-N-(1-(2-Cyano-3-cyclopropylacryloyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(3-Chloropropanoyl)piperidin-3-yl)-4-oxo-5-(5-phenoxypyridin-2-yl)-4,5-dihydro-3H-1-thia-3,5,8-triazaacenaphthylene-2-carboxamide;

5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-(2-(Azetidin-1-yl)acetyl)piperidin-3-yl)-5-(2-methyl-4-phenoxyphenyl)-4-oxo-4,5-dihydro-3H-1-thia-3,5,8-triazaacenaphthylene-2-carboxamide;

4-Oxo-5-(4-phenoxyphenyl)-N-(tetrahydro-2H-pyran-4-yl)-4,5-dihydro-3H-1-thia-3,5,8-triazaacenaphthylene-2-carboxamide;

(R)—N-(1-Methylpyrrolidin-3-yl)-4-oxo-5-(4-phenoxyphenyl)-4,5-dihydro-3H-1-thia-3,5,8-triazaacenaphthylene-2-carboxamide;

(R)-4-Oxo-5-(4-phenoxyphenyl)-N-(pyrrolidin-3-yl)-4,5-dihydro-3H-1-thia-3,5,8-triazaacenaphthylene-2-carboxamide;

(S)-5-(2-Methyl-4-phenoxyphenyl)-4-oxo-N-(piperidin-3-yl)-4,5-dihydro-3H-1-thia-3,5,8-triazaacenaphthylene-2-carboxamide;

(R,E)-N-(1-(4-(Dimethylamino)but-2-enoyl)piperidin-3-yl)-5-(4-isopropoxy-2-methylphenyl)-4-oxo-4,5-dihydro-3H-1-thia-3,5,8-triazaacenaphthylene-2-carboxamide;

(R)—N-(1-Benzoylpyrrolidin-3-yl)-4-oxo-5-(4-phenoxyphenyl)-4,5-dihydro-3H-1-thia-3,5,8-triazaacenaphthylene-2-carboxamide;

(R)-4-Oxo-5-(5-phenoxypyridin-2-yl)-N-(piperidin-3-yl)-4,5-dihydro-3H-1-thia-3,5,8-triazaacenaphthylene-2-carboxamide;

(E)-N-(1-(2-Cyano-3-cyclopropylacryloyl)piperidin-4-yl)-5-(2-methyl-4-phenoxyphenyl)-4-oxo-4,5-dihydro-3H-1-thia-3,5,8-triazaacenaphthylene-2-carboxamide;

5-(4-(2-Methoxyphenoxy)-2-methylphenyl)-4-oxo-N-(piperidin-4-yl)-4,5-dihydro-3H-1-thia-3,5,8-triazaacenaphthylene-2-carboxamide;

5-(4-(2-Methoxyphenoxy)-2-methylphenyl)-N-(1-methylpiperidin-4-yl)-4-oxo-4,5-dihydro-3H-1-thia-3,5,8-triazaacenaphthylene-2-carboxamide;

(R)-5-(4-(Cyclopentyloxy)-2-methylphenyl)-4-oxo-N-(piperidin-4-yl)-4,5-dihydro-3H-1-thia-3,5,8-triazaacenaphthylene-2-carboxamide;

N-(1-Methylpiperidin-4-yl)-4-oxo-5-(4-phenoxyphenyl)-4,5-dihydro-3H-1-thia-3,5,8-triazaacenaphthylene-2-carboxamide;

(E)-N-(1-(2-Cyano-4,4-dimethylpent-2-enoyl)piperidin-4-yl)-5-(2-methyl-4-phenoxyphenyl)-4-oxo-4,5-dihydro-3H-1-thia-3,5,8-triazaacenaphthylene-2-carboxamide;

(R)-4-Oxo-5-(6-phenoxypyridin-3-yl)-N-(piperidin-3-yl)-4,5-dihydro-3H-1-thia-3,5,8-triazaacenaphthylene-2-carboxamide;

(R)-5-(4-Isopropoxy-2-methylphenyl)-N-(1-(2-(methylamino)acetyl)piperidin-3-yl)-4-oxo-4,5-dihydro-3H-1-thia-3,5,8-triazaacenaphthylene-2-carboxamide;

(S)—N-(1-Acetylpyrrolidin-3-yl)-4-oxo-5-(4-phenoxyphenyl)-4,5-dihydro-3H-1-thia-3,5,8-triazaacenaphthylene-2-carboxamide;

(R)—N-(1-Benzylpyrrolidin-3-yl)-4-oxo-5-(4-phenoxyphenyl)-4,5-dihydro-3H-1-thia-3,5,8-triazaacenaphthylene-2-carboxamide;

4-Oxo-5-(4-phenoxyphenyl)-N-(piperidin-4-yl)-4,5-dihydro-3H-1-thia-3,5,8-triazaacenaphthylene-2-carboxamide;

4-Oxo-5-(4-phenoxyphenyl)-N-(2-(pyrrolidin-1-yl)ethyl)-4,5-dihydro-3H-1-thia-3,5,8-triazaacenaphthylene-2-carboxamide;

4-Oxo-5-(4-phenoxyphenyl)-N-(2-(piperazin-1-yl)ethyl)-4,5-dihydro-3H-1-thia-3,5,8-triazaacenaphthylene-2-carboxamide;

N-(1-Acryloylpiperidin-4-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(S)—N-(1-Methylpyrrolidin-3-yl)-4-oxo-5-(4-phenoxyphenyl)-4,5-dihydro-3H-1-thia-3,5,8-triazaacenaphthylene-2-carboxamide;

4-Oxo-5-(4-phenoxyphenyl)-N-(2-(piperidin-1-yl)ethyl)-4,5-dihydro-3H-1-thia-3,5,8-triazaacenaphthylene-2-carboxamide;

N-(2-Morpholinoethyl)-4-oxo-5-(4-phenoxyphenyl)-4,5-dihydro-3H-1-thia-3,5,8-triazaacenaphthylene-2-carboxamide;

(S)-4-Oxo-5-(4-phenoxyphenyl)-N-(pyrrolidin-3-yl)-4,5-dihydro-3H-1-thia-3,5,8-triazaacenaphthylene-2-carboxamide;

N-(2-(4-Methylpiperazin-1-yl)ethyl)-4-oxo-5-(4-phenoxyphenyl)-4,5-dihydro-3H-1-thia-3,5,8-triazaacenaphthylene-2-carboxamide;

(R)—N-(1-Acetylpiperidin-3-yl)-5-(4-isopropoxy-2-methylphenyl)-4-oxo-4,5-dihydro-3H-1-thia-3,5,8-triazaacenaphthylene-2-carboxamide;

(R)-4-Oxo-N-(piperidin-3-yl)-5-(3-(pyridin-3-yl)phenyl)-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide;

(S)—N-(1-Benzoylpyrrolidin-3-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-5-(3,5-dichlorophenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide;

(R)—N-(1-Acryloylpiperidin-3-yl)-5-(3-(dimethylamino)phenyl)-4-oxo-4,5-dihydro-3H-1-thia-3,5,8-triazaacenaphthylene-2-carboxamide;

N-(1-(2-Cyanoacetyl)piperidin-4-yl)-5-(2-methyl-4-phenoxyphenyl)-4-oxo-4,5-dihydro-3H-1-thia-3,5,8-triazaacenaphthylene-2-carboxamide;

(S)—N-(1-Benzylpyrrolidin-3-yl)-4-oxo-5-(4-phenoxyphenyl)-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

5-(2-Methyl-4-phenoxyphenyl)-4-oxo-N-(1-propionylpiperidin-4-yl)-4,5-dihydro-3H-1-thia-3,5,8-triazaacenaphthylene-2-carboxamide;

(R)—N-(1-Acryloylpiperidin-3-yl)-5-(4-aminophenyl)-4-oxo-4,5-dihydro-3H-1-thia-3,5,8-triazaacenaphthylene-2-carboxamide;

(R)-5-(4-(Dimethylamino)phenyl)-4-oxo-N-(piperidin-3-yl)-4,5-dihydro-3H-1-thia-3,5,8-triazaacenaphthylene-2-carboxamide;

(R)-4-Oxo-N-(piperidin-3-yl)-5-(m-tolyl)-4,5-dihydro-3H-1-thia-3,5,8-triazaacenaphthylene-2-carboxamide;

(R)-5-(4-Chlorophenyl)-4-oxo-N-(piperidin-3-yl)-4,5-dihydro-3H-1-thia-3,5,8-triazaacenaphthylene-2-carboxamide;

(R)-4-Oxo-N-(piperidin-3-yl)-5-(p-tolyl)-4,5-dihydro-3H-1-thia-3,5,8-triazaacenaphthylene-2-carboxamide;

(R)-5-(4-Fluorophenyl)-4-oxo-N-(piperidin-3-yl)-4,5-dihydro-3H-1-thia-3,5,8-triazaacenaphthylene-2-carboxamide;

(R)-5-(4-(tert-Butyl)phenyl)-4-oxo-N-(piperidin-3-yl)-4,5-dihydro-3H-1-thia-3,5,8-triazaacenaphthylene-2-carboxamide;

(R)-5-(4-Isopropoxy-3-methylphenyl)-4-oxo-N-(piperidin-3-yl)-4,5-dihydro-3H-1-thia-3,5,8-triazaacenaphthylene-2-carboxamide;

(R)-5-(4-Aminophenyl)-4-oxo-N-(piperidin-3-yl)-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-methyl-3-phenoxyphenyl)-4-oxo-4,5-dihydro-3H-1-thia-3,5,8-triazaacenaphthylene-2-carboxamide;

(R)-5-(*S)-(6-Isopropoxy-4-methylpyridin-3-yl)-4-oxo-N-(pyrrolidin-3-yl)-4,5-dihydro-3H-1-thia-3,5,8-triazaacenaphthylene-2-carboxamide;

(R)—N-(1-Acryloylpyrrolidin-3-yl)-5-(*S)-(6-isopropoxy-4-methylpyridin-3-yl)-4-oxo-4,5-dihydro-3H-1-thia-3,5,8-triazaacenaphthylene-2-carboxamide;

(R,E)-N-(1-(2-Cyano-3-(1-methylcyclobutyl)acryloyl)piperidin-3-yl)-5-(2-methyl-6-phenoxypyridin-3-yl)-4-oxo-4,5-dihydro-3H-1-thia-3,5,8-triazaacenaphthylene-2-carboxamide;

N1-((F)-4-((R)-3-(1-(2-Methyl-6-phenoxypyridin-3-yl)-2-oxo-1,2,3,5-tetrahydrocyclopenta[de]quinazoline-4-carboxamido)piperidin-1-yl)-4-oxobut-2-en-1-yl)-N5-(15-oxo-19-((3aR,4R,6aS)-2-oxooctahydrocyclopenta[d]imidazol-4-yl)-4,7,10-trioxa-14-azanonadecyl)glutaramide;

(R,E)-N-(1-(2-Cyano-4-ethoxy-4-methylpent-2-enoyl)piperidin-3-yl)-5-(2-methyl-6-phenoxypyridin-3-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-6-phenoxypyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(*R)-(2-methyl-4-(pyridin-2-yloxy)phenyl)-4-oxo-4,5-dihydro-3H-1-thia-3,5,8-triazaacenaphthylene-2-carboxamide;

(R)—N-(1 Acryloylpyrrolidin-3-yl)-5-(*S)-(2-methyl-4-(pyridin-2-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-2-methyl-4-(pyridin-2-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-(pyridin-2-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-((2-methylpyridin-3-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-(pyridazin-3-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-(pyridazin-3-yloxy)phenyl)-4-oxo-4,5-dihydro-3H-1-thia-3,5,8-triazaacenaphthylene-2-carboxamide;

(R)—N-(1-Acryloylpiperidin-3-yl)-4-oxo-5-(5-(pyridazin-3-yloxy)pyridin-2-yl)-4,5-dihydro-3H-1-thia-3,5,8-triazaacenaphthylene-2-carboxamide;

(R)—N-(1-Acryloylpyrrolidin-3-yl)-4-oxo-5-(5-(pyridazin-3-yloxy)pyridin-2-yl)-4,5-dihydro-3H-1-thia-3,5,8-triazaacenaphthylene-2-carboxamide;

(R)—N-(1-Acryloylpyrrolidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide;

(R)—N-(1-Acryloylpiperidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide;

(R)—N-(1-Acryloylpiperidin-3-yl)-5-(4-methyl-6-(pyridazin-3-yloxy)pyridin-3-yl)-4-oxo-4,5-dihydro-3H-1-thia-3,5,8-triazaacenaphthylene-2-carboxamide; and (R)—N-(1-Acryloylpyrrolidin-3-yl)-5-(4-methyl-6-(pyridazin-3-yloxy)pyridin-3-yl)-4-oxo-4,5-dihydro-3H-1-thia-3,5,8-triazaacenaphthylene-2-carboxamide;

and stereoisomers or isotopic variants thereof; and pharmaceutically acceptable salts thereof.

The disclosure also relates to methods of using the compounds described herein to treat subjects diagnosed with or suffering from a disease, disorder, or condition mediated by Bruton's tyrosine kinase. These methods are accomplished by administering to the subject a compound of the disclosure in an amount sufficient to inhibit Bruton's tyrosine kinase.

In a further aspect, provided herein are methods for inhibiting Bruton's tyrosine kinase in a subject in need of treatment by administering to the subject a composition containing a therapeutically effective amount of at least one compound of Formula (I)(as well as Formula (I'), Formula (II'), Formula (III'), Formula (IV') and Formula (V')). Some aspects of the disclosure are directed to methods of treating a subject suffering from an autoimmune disease by administering to the subject a composition containing a therapeutically effective amount of at least one compound of Formula (I)(as well as Formula (I'), Formula (II'), Formula (III'), Formula (IV') and Formula (V')). In some aspects, the autoimmune disease is, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia. When used for the treatment of an autoimmune disease, the compounds of Formula (I)(as well as Formula (I'), Formula (II'), Formula (III'), Formula (IV') and Formula (V')) can be administered as single agents. Alternatively, when used for the treatment of an autoimmune disease, the compounds of Formula (I)(as well as Formula (I'), Formula (II'), Formula (III'), Formula (IV') and Formula (V')) can be administered in combination with other agents known to be useful for the treatment of autoimmune diseases.

Other embodiments of the disclosure are directed to methods of treating a subject suffering from a heteroimmune condition by administering to the subject a composition containing a therapeutically effective amount of at least one compound of Formula (I)(as well as Formula (I'), Formula (II'), Formula (III'), Formula (IV') and Formula (V')). In some aspects, the heteroimmune condition or disease is, e.g., graft versus host disease, transplantation, transfusion, anaphylaxis, allergy, type I hypersensitivity, allergic conjunctivitis, allergic rhinitis, or atopic dermatitis. When used for the treatment of a heteroimmune condition, the compounds of Formula (I)(as well as Formula (I'), Formula (II'), Formula (III'), Formula (IV') and Formula (IV')) can be administered as single agents. Alternatively, when used for the treatment of a heteroimmune condition, the compounds of Formula (I)(as well as Formula (I'), Formula (II'), Formula (III'), Formula (IV') and Formula (V')) can be administered in combination with other agents known to be useful for the treatment of heteroimmune diseases.

Other embodiments of the disclosure are directed to methods of treating a subject suffering from an inflammatory disease by administering to the subject a composition containing a therapeutically effective amount of at least one compound of Formula (I)(as well as Formula (I'), Formula (II'), Formula (III'), Formula (IV') and Formula (V')). In certain embodiments, the inflammatory disease is, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. When used for the treatment of an inflammatory disease, the compounds of Formula (I)(as well as Formula (I'), Formula (II'), Formula (III'), Formula (IV') and Formula (V')) can be administered as single agents. Alternatively, when used for the treatment of an inflammatory disease, the compounds of Formula (I)(as well as Formula (I'), Formula (II'), Formula (III'), Formula (IV') and Formula (V')) can be administered in combination with other agents known to be useful for the treatment of inflammatory diseases.

Other embodiments of the disclosure are directed to methods of treating a subject suffering from cancer by administering to the subject a composition containing a therapeutically effective amount of at least one compound of Formula (I)(as well as Formula (I'), Formula (II'), Formula (III'), Formula (IV') and Formula (V')). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. Cancers that are particularly suited to being treated with compounds of the disclosure include mantle cell lymphoma and chronic lymphocytic leukemia and macroglobulinemia, as well as multiple myeloma. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002. When used for the treatment of cancer, the compounds of Formula (I)(as well as Formula (I'), Formula (II'), Formula (III'), Formula (IV') and Formula (V')) can be administered as single agents. Alternatively, when used for the treatment of cancer, the compounds of Formula (I)(as well as Formula (I'), Formula (II'), Formula (III'), Formula (IV') and Formula (V')) can be administered in combination with other agents known to be useful for the treatment of cancer.

Other embodiments of the disclosure are directed to methods of treating a subject suffering from a thromboembolic disorder by administering to the subject a composition containing a therapeutically effective amount of at least one compound of Formula (I)(as well as Formula (I'), Formula (II'), Formula (III'), Formula (IV') and Formula (V')). In further embodiments, thromboembolic disorder is, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis. When used for the treatment of a thromboembolic disorder, the compounds of Formula (I)(as well as Formula (I'), Formula (II'), Formula (III'), Formula (IV') and Formula (V')) can be administered as single agents. Alternatively, when used for the treatment of a thromboembolic disorder, the compounds of Formula (I)(as well as Formula (I'), Formula (II'), Formula (III'), Formula (IV') and Formula (V')) can be administered in combination with other agents known to be useful for the treatment of thromboembolic disorders.

Other embodiments of the disclosure are directed to methods of treating a subject suffering from a respiratory disease by administering to the subject a composition containing a therapeutically effective amount of at least one compound of Formula (I)(as well as Formula (I'), Formula (II'), Formula (III'), Formula (IV') and Formula (V')). In some aspects, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma. When used for the treatment of a respiratory disease, the compounds of Formula (I)(as well as Formula (I'), Formula (II'), Formula (III'), Formula (IV') and Formula (V')) can be administered as single agents. Alternatively, when used for the treatment of a respiratory disease, the compounds of Formula (I)(as well as Formula (I'), Formula (II'), Formula (III'), Formula (IV') and Formula (V')) can be administered in combination with other agents known to be useful for the treatment of respiratory diseases.

In another aspect are methods for preventing rheumatoid arthritis and osteoarthritis comprising administering to the subject, at least once, an effective amount of at least one compound of Formula (I)(as well as Formula (I'), Formula (II'), Formula (III'), Formula (IV') and Formula (V')). When used for the treatment of rheumatoid arthritis or osteoarthritis, the compounds of Formula (I) can be administered as single agents. Alternatively, when used for the treatment of rheumatoid arthritis or osteoarthritis, the compounds of Formula (I)(as well as Formula (I'), Formula (II'), Formula (III'), Formula (IV') and Formula (V')) can be administered in combination with other agents known to be useful for the treatment of rheumatoid arthritis or osteoarthritis.

In another aspect are methods for treating inflammatory responses of the skin comprising administering to the subject, at least once, an effective amount of at least one compound of Formula (I)(as well as Formula (I'), Formula (II'), Formula (III'), Formula (IV') and Formula (V')). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a compound of Formula (I)(as well as Formula (I'), Formula (II'), Formula (III'), Formula (IV') and Formula (V')). When used for the treatment of these conditions, the compounds of Formula (I)(as well as Formula (I'), Formula (II'), Formula (III'), Formula (IV') and Formula (V')) can be administered as single agents. Alternatively, when used for the treatment of these conditions, the compounds of Formula (I)(as well as Formula (I'), Formula (II'), Formula (III'), Formula (IV') and Formula (V')) can be administered in combination with other agents known to be useful for the treatment of these conditions.

In preferred aspects, compounds of the disclosure can be used to treat rheumatoid arthritis.

Compounds of the disclosure can also be used to treat systemic lupus erythematosus.

Compounds of the disclosure can also be used to treat pemphigus disorders and pemphigoid disorders.

In some aspects, the compounds of Formula (I)(as well as Formula (I'), Formula (II'), Formula (III'), Formula (IV') and Formula (V')) can be administered in combination with a CYP 3A4 inhibitor, according to methods known in the art.

In treatment methods according to the disclosure, an effective amount of a pharmaceutical agent according to the disclosure is administered to a subject suffering from or diagnosed as having such a disease, disorder, or condition. An "effective amount" means an amount or dose sufficient to generally bring about the desired therapeutic benefit in patients in need of such treatment for the designated disease, disorder, or condition. Effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

In addition, the compounds of the disclosure may be used in combination with additional active ingredients in the treatment of the above conditions. The additional active ingredients may be coadministered separately with a compound of the disclosure or included with such an agent in a pharmaceutical composition according to the disclosure. The combination may serve to increase efficacy (e.g., by including in the combination a compound potentiating the potency or effectiveness of an active agent according to the disclosure), decrease one or more side effects, or decrease the required dose of the active agent according to the disclosure.

The compounds of the disclosure are used, alone or in combination with one or more additional active ingredients, to formulate pharmaceutical compositions of the disclosure. A pharmaceutical composition of the disclosure comprises: (a) an effective amount of at least one compound in accordance with the disclosure; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the disclosure can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the disclosure may be mixed with a solid, semisolid, or liquid diluent. Soft gelatin capsules may be prepared by mixing the compound of the disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this disclosure may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the disclosure may utilize a patch formulation to affect transdermal delivery.

Compounds of the disclosure may alternatively be administered in methods of this disclosure by inhalation, via the nasal or oral routes, e.g., in a spray formulation also containing a suitable carrier.

Exemplary compounds useful in methods of the disclosure will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I)(as well as Formula (I'), Formula (II'), Formula (III'), Formula (IV') and Formula (IV')). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Compounds of the disclosure can be prepared using the knowledge of one skilled in the art in combination with the present disclosure. For example, compounds of the disclosure can be prepared according to the following schemes and examples.

ABBREVIATIONS

Table 1. Abbreviations and acronyms used herein include the following.

TABLE 1

| Term | Acronym/Abbreviation |
| --- | --- |
| Acetonitrile | ACN, MeCN |
| tert-Butylcarbamoyl | BOC |
| Di-tert-butyl dicarbonate | (Boc)$_2$O |
| Benzotriazol-1-yloxytris(dimethylamino)-phosphonium hexafluorophosphate | BOP |
| 1,1'-Carbonyldiimidazole | CDI |
| Diatomaceous Earth | Celite® 545, |
| (1-Cyano-2-ethoxy-2-oxoethylidenaminooxy)dimethylamino-morpholino-carbenium hexafluorophosphate | COMU® |
| 1,8-Diazabicyclo[5.4.0]undec-7-ene | DBU |
| Methylene chloride, dichloromethane | DCM |
| Diisopropyl azodiformate | DIAD |
| N,N-Diisopropylethylamine | DIPEA, DIEA, Hunig's base |
| N,N-Dimethylformamide | DMF |
| 4-Dimethylaminopyridine | DMAP |
| Dimethyl sulfoxide | DMSO |
| Deutero-dimethyl sulfoxide | DMSO-d$_6$ |
| Diphenylphosphino ferrocene | dppf |
| Bis[(2-diphenylphosphino)phenyl] ether | DPEphos |
| Di-tert-butylphosphino ferrocene | dtbpf |
| 1-Ethyl-3-(3-dimethylaminopropyl)carbodiimide | EDCI, EDC, EDAC |
| Electrospray Ionisation | ESI |
| Ethyl Acetate | EtOAc, or EA, or AcOEt |
| Ethanol | EtOH |
| Flash Column Chromatography | FCC |
| 2-(1H-9-Azobenzotriazole-1-yl)-1,1,3,3-tetramethylaminium hexafluorophosphate | HATU |
| Acetic Acid | HOAc, AcOH |
| 1-Hydroxy-7-azabenzotriazole | HOAT, HOAt |
| 1-Hydroxy-benzotriazole | HOBt |
| High-pressure liquid chromatography | HPLC |
| Isopropyl Alcohol | IPA |
| Deteromethanol | MeOD-d$_4$ |
| Methanol | MeOH |
| Methanesulfonyl chloride | MsCl |
| Methyl tert-butyl ether | MTBE |
| Sodium methoxide | NaOMe |
| Tetrakis(triphenylphosphine)palladium(0) | Pd(PPh$_3$)$_4$ |
| Palladium(II) acetate | Pd(OAc)$_2$ |
| [1,1'-Bis(diphenylphosphino)ferrocene]dichloropalladium(II) | Pd(dppf)Cl$_2$ |
| Palladium(II)bis(triphenylphosphine) dichloride, bis(triphenylphosphine)palladium(II) dichloride | PdCl$_2$(PPh$_3$)$_2$ |
| Triphenylphosphine | PPh$_3$ |
| Precipitate | ppt |
| p-Toluenesulfonic acid | p-TsOH, PTSA |
| (benzotriazol-1-yl-oxytripyrrolidinophosphonium hexafluorophosphate) | PyBOP |
| Bromotripyrrolidinophosphonium hexafluorophosphate | PyBrOP® |
| Room temperature | rt |
| Supercritical Fluid Chromatography | SFC |
| Thionyl chloride | SOCl$_2$ |
| Tetrabutylammonium fluoride | TBAF |
| tert-Butyl(chloro)dimethylsilane | TBSCl |
| Triethyl amine | TEA |
| Trifluoroacetic acid | TFA |
| Trifluoroacetic anhydride | TFAA |
| Tetrahydrofuran | THF |
| Thin Layer Chromatography | TLC |

PREPARATIVE EXAMPLES

Exemplary compounds useful in methods of the disclosure will now be described by reference to the illustrative synthetic schemes for their general preparation below and the specific examples to follow.

SCHEME 1

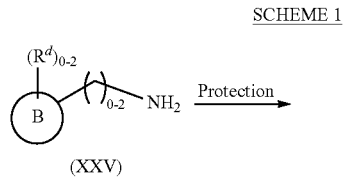

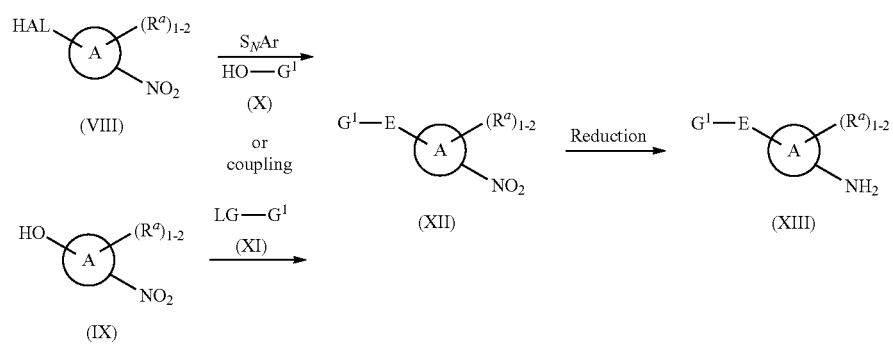

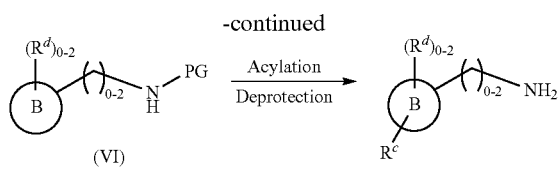

-continued

According to SCHEME 1, a compound of formula (VI), where ring B is a $C_{4-10}$heterocycloalkyl such as azetidinyl, pyrrolidinyl, piperidinyl, and the like; and PG is a suitable nitrogen protecting group such as BOC, is commercially available or is synthetically accessible employing conditions known to one skilled in the art, from a compound of formula (XXV). Acylation of a heterocycloalkyl compound of formula (VI), is achieved with a suitable acylating agent such as the anhydrides and halides of carboxylic acids such as acetic anhydride, propionic anhydride, prop-2-enoyl chloride, $C_{1-6}$alkyl(C=O)Cl, and the like, in the presence of a suitable base such as TEA, DIPEA, and the like, with or without the presence of a reagent such as DMAP, in a suitable solvent such as THF, DCM, and the like, at temperatures ranging from 0° C. to 25° C., for a period of 2 to 6 h. Subsequent deprotection of the tert-butylcarbamate (BOC) protecting group (PG), is accomplished by using an acid such as HCl, TFA, p-toluenesulfonic acid, in a solvent such as MeOH, dioxane, or DCM. In a preferred embodiment, deprotection is achieved with HCl/MeOH or TFA/DCM, to provide a compound of formula (VII).

A compound of formula (VI), where ring B is a $C_{5-6}$cycloalkyl, and Y is $NH_2$ is prepared from a compound of formula (VI), where ring B is a $C_{5-6}$cycloalkyl, and Y is OH under Mitsonobu conditions. In two steps, reaction of a compound of formula (VI), where Y is OH, with triphenylphosphane, DIAD, and, phthalimide, followed by hydrazinolysis with hydrazine hydrate in a solvent such as EtOH, provides a compound of formula (VI), where ring B is a $C_{5-6}$cycloalkyl, PG is BOC, and Y is $NH_2$.

A compound of formula (VI), where ring B is a $C_{5-6}$cycloalkyl, PG is BOC, and Y is $CO_2H$, is reacted with diphenyl phosphorazidate (DPPA), phenylmethanol, and a base such as TEA, in a solvent such as toluene, at a temperature of about 100° C., for a period of 18-24 h, to provide a compound (VI) where PG is BOC, and Y is NH—(C=O)OCH$_2$phenyl. Deprotection of the CBz, under conditions known to one skilled in the art, for example, hydrogenation using ($H_2$, 30 psi) using Pd(OH)$_2$, affords a compound of formula (VI), where PG is BOC, and Y is $NH_2$.

According to SCHEME 2, a synthetically accessible or commercially available compound of formula (VIII), where A is phenyl, or a six membered heteroaryl ring containing one or two nitrogen members, HAL is Br or F, and $R^a$ is independently H, halogen, and $CH_3$, is reacted in an aromatic nucleophilic substitution reaction with a commercially available or synthetically accessible alcohol of formula $G^1$-OH (X), where $G^1$ is phenyl, $C_{3-6}$cycloalkyl, or $C_{1-6}$alkyl, a suitable base such as NaH, $Na_2CO_3$, $NaHCO_3$, $K_2CO_3$, $Cs_2CO_3$, and the like, in a suitable solvent such as DMF, DMA, THF, dioxane, and the like, to provide a compound of formula (XII), where E is O.

In an alternate method, a compound of formula (XII), where E is O, is prepared from a compound of formula (VIII), where HAL is F, and $R^a$ is OH, in a coupling reaction. For example, reaction of a compound of formula (VIII) with a commercially available or synthetically accessible aryl or heteroaryl boronic acid or ester such as phenyl boronic acid a metal catalyst such as copper (II) acetate, a base such as trimethylamine, in a solvent such as DCM, and the like, for a period of about 16 h, provides a compound of formula (XII) where $R^a$ is F and E is O.

A compound of formula (IX), where $R^a$ is $C_{1-6}$alkyl, is reacted with a commercially available or synthetically accessible compound of formula LG-$G^1$ (XI), where LG is a leaving group such as Cl, Br, I, or methanesulfonate, and $G^1$ is $C_{1-6}$alkyl, $C_{3-6}$cycloalkyl or $C_{3-6}$heterocycloalkyl, a suitable base such as NaH, $Na_2CO_3$, $NaHCO_3$, $K_2CO_3$, $Cs_2CO_3$, and the like, in a suitable solvent such as DMF, DMA, THF, dioxane, and the like, to provide a compound of formula (XII), where E is O, and $G^1$ is $C_{1-6}$alkyl, $C_{3-6}$cycloalkyl or $C_{3-6}$heterocycloalkyl.

A compound of formula (XII), where ring A is pyridyl, E is N-PG, and $G^1$ is $C_{1-6}$alkyl, is prepared from a compound of formula (VII), where HAL is Cl, and $R^a$ is $C_{1-6}$alkyl. For example, 2-chloro-4-methyl-5-nitropyridine is reacted with an amine such as propan-2-amine, followed by reaction with DMAP, di-tert-butyl dicarbonate, in a solvent such as THF, to provide a compound of formula (XII), where ring A is pyridyl, E is N, substituted with a protecting group (BOC), and $G^1$ is $C_{1-6}$alkyl.

Reduction of the nitro moiety of a compound of formula (XII), where E is O or N-PG, $G^1$ is phenyl, $C_{1-6}$alkyl, $C_{3-6}$cycloalkyl, pyridyl, employing conditions known to one skilled in the art, for example, reduction with iron (Fe), in a solvent such as EtOH/water, in the presence of $NH_4Cl$ or concentrated HCl, at a temperatures ranging from 0° C. to 25° C., for a period of 2 to 6 h, provides the corresponding aniline of formula (XIII). Reduction of a nitro compound of formula (VII), is also achieved using hydrogenation conditions, for example, reaction with a palladium catalyst such as Pd/C, $Pd(OH)_2$, Pt/C and the like, in a suitable solvent such as THF, MeOH, EtOAc, or a mixture thereof, in the presence of $H_2$ (for example at atmospheric pressure or at 30 to 50 PSI), at temperatures ranging from rt to 50° C., to provide an amine compound of formula (XIII). Reduction of a nitro compound of formula (XII), is also achieved employing Zn, ammonium chloride, in a suitable solvent or solvent mixture such as acetone/water, at a temperature ranging from 0° C. to rt, for a period of about 2-6 h, to provide an amine compound of formula (XIII).

SCHEME 3

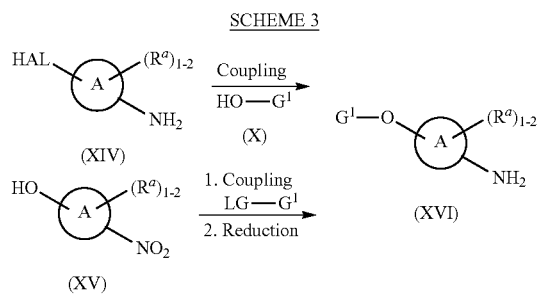

According to SCHEME 3, a compound of formula (XIV), where ring A is a suitably substituted phenyl or heteroaryl containing 1-2 nitrogen members, and HAL is I, Cl, or Br, and $R^a$ is $C_{1-6}$alkyl, is reacted in a Copper-Catalyzed Cross-Coupling reaction with a compound of formula $G^1$-OH, where $G^1$ is phenyl, or heteroaryl containing 1-2 nitrogen members. For example, a compound of formula (XV) such as 2-chloro-4-methylpyrimidin-5-amine, is reacted with a compound of formula (X), such as phenol, a copper catalyst such as Cu, CuI, and the like, N,N-dimethylglycine, a base such as $K_2CO_3$, $Cs_2CO_3$, and the like, in a suitable solvent such as dioxane, DMSO, and the like, at a temperature of about 90° C., for a period of 1 to 3 days, provides 4-methyl-2-phenoxypyrimidin-5-amine. In an alternate method, coupling reactions are performed in the absence of a catalyst, employing microwave or conventional heating, with a base such as $K_2CO_3$, in a solvent such as DMSO.

A compound of formula (XVI) is also prepared from a compound of formula (IX) in two steps. In a first step, coupling with a compound of formula (IX), where ring A is phenyl, or a heteroaryl ring containing 1-2 nitrogen members, $R^a$ is $C_{1-6}$alkyl, is reacted with a compound of formula LG-$G^1$, where LG is Cl, and $G^1$ is $C_{1-6}$alkyl, phenyl, or 6 membered heteroaryl ring containing 1 to 2 nitrogen members as previously described. In a second step, reduction of the nitro moiety employing conditions known to one of skill in the art provides a compound of formula (XVI).

SCHEME 4

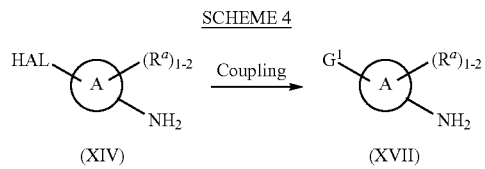

According to SCHEME 4, an aryl halide compound of formula (XIV), where ring A is phenyl, or a heteroaryl ring containing 1-2 nitrogen members, HAL is Cl, Br, and $R^a$ is H or $C_{1-6}$alkyl, undergo a transition metal catalyzed cross-coupling reaction such as Suziki, Negishi, and Grignard reactions. For example, reaction of a compound of formula (XIV) with a commercially available or synthetically accessible alkyl or aryl boronic acid or ester, in the presence of a suitable palladium catalyst such as $Pd(PPh_3)_4$, $Pd(OAc)_2$, $Pd(dppf)Cl_2$, and the like, a base such as $Cs_2CO_3$, $K_2CO_3$, $Na_2CO_3$, and the like, in a suitable solvent such as ACN, THF, MeOH, EtOH, toluene, dioxane, water, or a mixture thereof, employing conventional or microwave heating, at temperatures ranging from 80° C. to 120° C., for a period of 12, to 24 h, to provide a compound of formula (XVII), where $G^1$ is $C_{1-6}$alkyl, or phenyl.

In a similar fashion, an aryl an aryl halide compound of formula (XIV), where ring A is phenyl, or a heteroaryl ring containing 1-2 nitrogen members, HAL is Cl, Br, and $R^a$ is H or $C_{1-6}$alkyl, is reacted with a Grignard reagent such as such as isopropylmagnisium chloride, or an organozinc reagent such as isobutylzinc(II) bromide, cyclobutylzinc(II) bromide, and the like, in the presence of a palladium catalyst such as $Pd(dppf)Cl_2$.DCM, $Pd(dppf)_2Cl_2$, and the like, in a suitable solvent such THF, at temperatures ranging from −78° C. to the reflux temperature of the solvent, to provide a compound of formula (XVII), where $G^1$ is $C_{1-6}$alkyl.

SCHEME 5

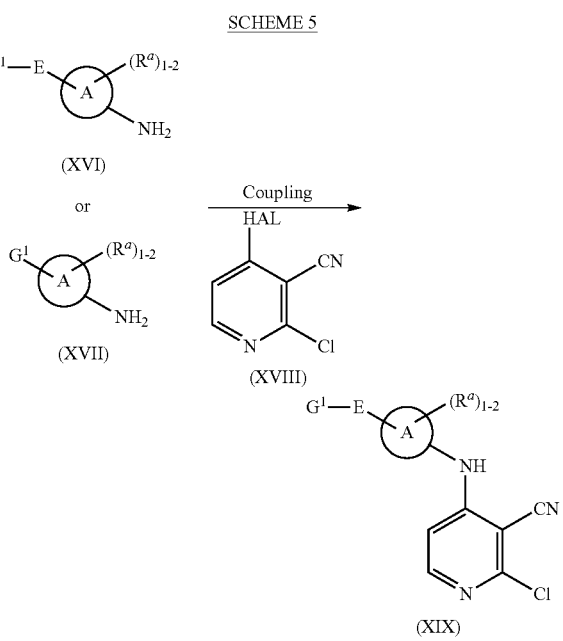

According to SCHEME 5, aryl halides of formula (XVIII), where HAL is I, Cl or Br, undergo a palladium catalyzed arylation with a compound of formula (XVI) or (XVII), where $G^1$ is phenyl, and $C_{3-6}$cycloalkyl, $R^a$ is H or $C_{1-6}$alkyl, in the presence of a palladium catalyst such as $Pd(OAc)_2$, $Pd_2(dba)_3$, and the like, a ligand such as Xantphos, S-Phos, BINAP, DPEPhos, a suitable base such as NaOtBu, $Cs_2CO_3$, $K_3PO_4$, and the like, in a suitable solvent such as ACN, THF, toluene, dioxane, and the like, employing conventional or microwave heating, at temperatures ranging from 60 to 120° C., to provide a compound of formula (XIX), where E is a bond, or O.

late compound of formula (XX). A compound of formula (XXI) is prepared in two steps from a compound of formula (XX). In a first step, reaction of a compound of formula (XX) with CDI; in suitable solvent such as 1, dioxane, and the like; at reflux temperature; for a period of 12-24 h. In a second step, hydrolysis of the ester moiety, with a suitable base such as NaOH, LiOH, and the like, in a solvent such as MeOH, and the like, at temperatures ranging from rt to 50° C., for a period of 12 to 24 h, affords an acid compound of formula (XXI).

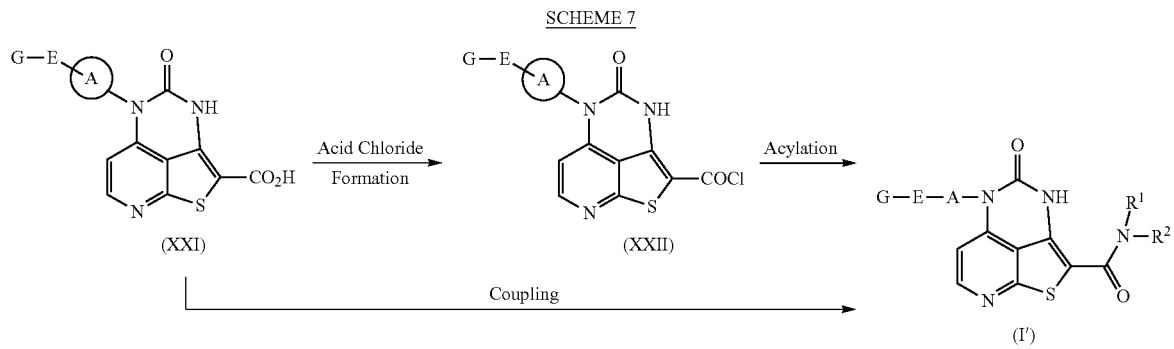

SCHEME 7

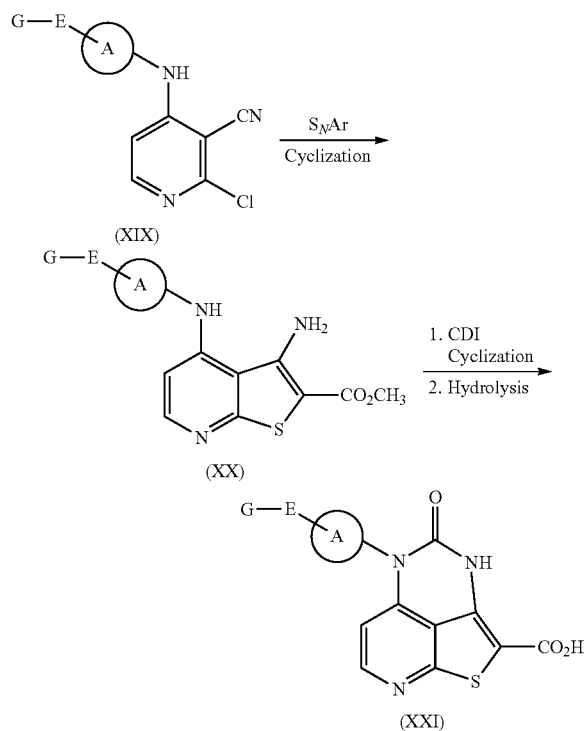

SCHEME 6

According to SCHEME 6, a nitrile compound of formula (XIX) is reacted in a nucleophilic aromatic substitution reaction with ethyl thioacetate, under basic conditions, followed by ring closure, to afford a thienopyridine-carboxy- According to SCHEME 7, an acid compound of formula (XXI), as described above, is first converted to an acid chloride compound of formula (XXII). For example, a compound of formula (XXI) is treated with a chlorinating agent such as thionyl chloride and the like; in a solvent such as toluene, and the like, to form a compound of formula (XXII).

Coupling reactions are achieved by conventional amide bond forming techniques which are well known to one of skill in the art as depicted in SCHEME 5. For example, an acyl halide (eg, chloride) compound of formula (XXI), is reacted with a suitably substituted commercially available or synthetically accessible amine of formula (XXV), (VI), or (VII) in the presence of an excess of a tertiary amine, such as TEA, pyridine, and the like, optionally in the presence of a suitable catalyst such as DMAP, in a suitable solvent such as DCM or THF, at a temperature ranging from room temperature to the reflux temperature of the solvent, to provide a compound of Formula (I'). A variety of other amino acid coupling methodologies are used to couple the compounds of formula (XXI). Reaction of a suitably substituted commercially available or synthetically accessible amine of formula (XXV), (VI), or (VII); with a suitably substituted acid of formula (XXI) under amide bond forming conditions provides a compound of Formula (I'). In a preferred embodiment, a compound of formula (XXV), (VI), or (VII), either as a free base or as an acid salt, is reacted with an acid compound of formula (XXI), in the presence of a dehydrating agent such as HOBt/EDAC, HATU, HOAT, T3P®, and the like; a suitably selected base such as DIPEA, TEA, and the like; in an organic solvent or mixture thereof such as toluene, acetonitrile, ethyl acetate, DMF, THF, methylene chloride, and the like; to afford a compound of Formula (I'). In a particularly preferred embodiment, the dehydrating agent is HATU and the base is TEA or DIPEA. In cases where the amine compound of formula (XXV), (VI), or (VII) has a tert-butylcarbamate (BOC) protecting group (PG), removal of the tert-butylcarbamate (BOC) protecting group (PG), is accomplished by using an acid such as HCl, TFA, p-toluenesulfonic acid, in a solvent such as MeOH, dioxane, or DCM. In a preferred embodiment, deprotection is achieved with HCl/MeOH or TFA/DCM.

A compound of Formula (I'), where $R^2$ is a suitably substituted $C_{4-10}$heterocycloalkyl, is reacted under reductive amination conditions with an suitable aldehyde such as formaldehyde, paraformaldehyde, a reducing agent such as $NaBH_4$, $NaBH(OAc)_3$, and the like, in a suitable solvent such as DCM, MeOH, THF, and the like, to afford a compound of Formula (I'), where $R^2$ is $C_{4-10}$heterocycloalkyl substituted with $CH_3$.

A compound of Formula (I'), where $R^2$ is $C_{4-10}$heterocycloalkyl, is reacted with acylating agent such as the anhydrides and halides of carboxylic acids such as acetic anhydride, prop-2-enoyl prop-2-enoate, propionic anhydride, $C_{1-6}$alkyl(C=O)Cl, and the like, under conditions previously described, to provide a compound of Formula (I'), where $R^2$ is $C_{4-10}$heterocycloalkyl substituted with (C=O)$C_{1-3}$alkyl, and (C=O)$C_{1-3}$alkenyl.

A compound of Formula (I'), where $R^2$ is $C_{4-10}$heterocycloalkyl is reacted with a suitable acid of such as $CO_2H$—$C_{1-6}$alkyl-$N(R^6R^7)$, 2-(dimethylamino)acetic acid, cyanoacetic acid, Boc-sarcosine, 2-(tert-butoxycarbonylamino)acetic acid, (E)-4-(dimethylamino)but-2-enoic acid, acrylic acid, and the like, under amide bond forming conditions previously described conditions to provide a compound of Formula (I'). A deprotection step, employing conditions previously described is employed where applicable.

SCHEME 8

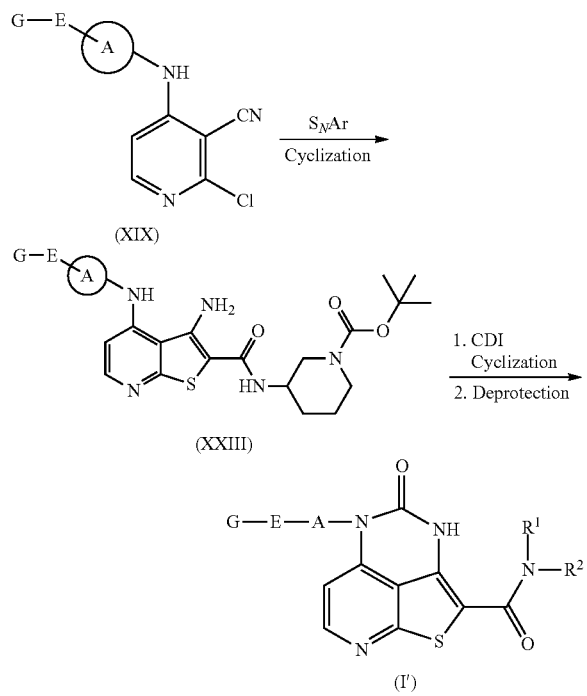

(XIX)

(XXIII)

(I')

According to SCHEME 8, a nitrile compound of formula (XIX) is reacted in a nucleophilic aromatic substitution reaction with tert-butyl-[(2-sulfanylacetyl)amino]piperidine-1-carboxylate, in a sealed vessel under high heat such as 150° C. for a period of time form 15 min to 1 hr, followed by ring closure, to afford a thienopyridine-carboxamide compound of formula (XXIII). A compound of Formula (I') is prepared in two steps from a compound of formula (XXIII). In a first step, reaction of a compound of formula (XXIII) with CDI; in suitable solvent such as dioxane, and the like; at reflux temperature; for a period of 12-24 h. In a second step, deprotection of the amine moiety, with a suitable acid such as HCl or TFA, and the like, in a solvent such as dioxane, and the like, at temperatures ranging from rt to 40° C., for a period of 30 min to 24 h, affords an amine compound of Formula (I').

Compounds of Formula (I') may be converted to their corresponding salts using methods known to one of ordinary skill in the art. For example, an amine of Formula (I') is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I') may be obtained in crystalline form by recrystallization from polar solvents (including mixtures of polar solvents and aqueous mixtures of polar solvents) or from non-polar solvents (including mixtures of non-polar solvents).

Where the compounds according to this disclosure have at least one chiral center, they may accordingly exist as enantiomers. Where the compounds possess two or more chiral centers, they may additionally exist as diastereomers. It is to be understood that all such isomers and mixtures thereof are encompassed within the scope of the present disclosure.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the disclosure and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

Normal-phase silica gel chromatography (FCC) was performed on silica gel ($SiO_2$) using prepacked cartridges.

Preparative reverse-phase high performance liquid chromatography (RP HPLC) was performed on either: An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM NH$_4$OH was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 m, 30×100 mm, T=45° C.), mobile phase of 5% ACN in H$_2$O (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 μm, 50×100 mm), mobile phase of 5% ACN in H$_2$O (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 μm, 100×50 mm), mobile phase of 5-99% ACN in 20 mM NH$_4$OH over 10 min and then hold at 99 ACN for 2 min, at a flow rate of 80 mL/min.

Quality control testing includes identity, chemical, and radiochemical purity by HPLC using an XBridge C18 (5 m, 4.6×250 mm) column eluted with a mixture of methanol/ammonium acetate 5 mM, 65/35, v/v at a flow rate of 1 mL/min equipped with serial UV (280 nm) and gamma detection.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Chiral Resolution Method A.

The atropisomers were chromatographed to isolate the two separate atropisomers, with the respective single atropisomers arbitrarily labeled as *S or *R to indicate that the compound is a single atropisomer of unknown absolute configuration. In cases for which absolute configuration of a single atropisomeric compound was determined, the atropisomers are named as either S or R throughout (with S corresponding to the alternate designations aS, S$_a$, or P; and with R corresponding to the alternate designations aR, R$_a$, or M). The purification was performed on a chiral SFC column (Stationary phase: Whelk O1 (S,S), 5 μm, 250×21.1 mm column. The mobile phase was: 40% CO$_2$, 60% MeOH (0.2% formic acid).

Intermediate 1: tert-Butyl
(3R,5R)-3-amino-5-fluoropiperidine-1-carboxylate

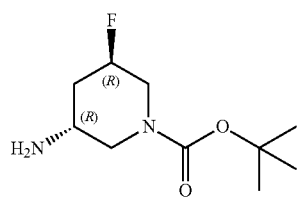

A mixture of (3R,5S)-tert-butyl 3-azido-5-hydroxypiperidine-1-carboxylate (Intermediate 2, Step I) (1.5 g, 6.19 mmol) in DCM at −78° C. was reacted by slow addition of DAST (1.2 g, 7.43 mmol). The reaction solution was stirred at −78° C. for 2 h and at rt for 16 h. The reaction was quenched by the addition of saturated aqueous NaHCO$_3$. The organic layer was separated, washed with aqueous NaHCO$_3$ solution, water, dried over anhydrous Na$_2$SO$_4$, and concentrated to dryness. The residue was reduced using conditions analogous to step J of Intermediate 2 to yield the title compound (660 mg, 44%) MS (ESI): mass calcd. for C$_{10}$H$_{19}$FN$_2$O$_2$, 218.1; m/z found, 219.1 [M+H]$^+$.

Intermediate 2: tert-Butyl
(3R,5S)-3-amino-5-hydroxypiperidine-1-carboxylate

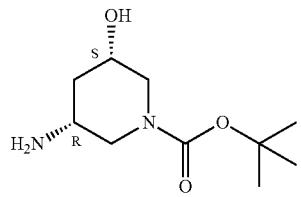

Step A: (2R,4S)-Methyl
1-benzyl-4-hydroxypyrrolidine-2-carboxylate

To a round bottom flask were added methyl (2R,4S)-4-hydroxypyrrolidine-2-carboxylate (12 g, 83 mmol) and DCM (150 mL). To the reaction mixture were added triethylamine (33.3 g, 330 mmol) and benzylbromide (17 g, 99 mmol) at rt, and then was heated to reflux for 16 h. The reaction mixture was washed with saturated NaHCO$_3$, extracted with EtOAc, and dried over anhydrous Na$_2$SO$_4$, filtered, and concentrated to dryness. The residue was purified by flash column chromatography to yield the title compound (9.2 g, 42%) as a colorless oil. MS (ESI): mass calcd. for C$_{10}$H$_{20}$N$_2$O$_3$, 216.1; m/z found, 217.1 [M+H]$^+$.

Step B: (2R,4S)-Methyl 1-benzyl-4-((tert-butyldimethylsilyl)oxy)pyrrolidine-2-carboxylate To a round bottom flask were added (2R,4S)-methyl 1-benzyl-4-hydroxypyrrolidine-2-carboxylate (9.2 g, 39 mmol), DCM (200 mL), triethylamine (7.90 g, 7.82 mmol), TBSCl (7.07 g, 47.0 mmol), and DMAP (48 mg, 0.39 mmol) at rt. The reaction mixture was heated to reflux for 16 h, cooled to rt, washed with saturated NaHCO$_3$, extracted with EtOAc, dried over anhydrous Na$_2$SO$_4$, filtered, and concentrated to dryness. The residue was purified by flash column chromatography to yield the title compound (13 g, 40%) as a colorless oil. MS (ESI): mass calcd. for C$_{19}$H$_{31}$NO$_3$Si, 349.2; m/z found, 350.1 [M+H]$^+$.

Step C: ((2R,4S)-1-Benzyl-4-((tert-butyldimethylsilyl)oxy)pyrrolidin-2-yl)methanol To a round bottom flask were added (2R,4S)-methyl 1-benzyl-4-((tert-butyldimethylsilyl)oxy)pyrrolidine-2-carboxylate (13 g, 37 mmol), THF (50 mL), and LiBH$_4$ (2.0 g, 93 mmol) at 0° C. The reaction was allowed to warm to rt and was stirred for an additional 16 hrs at rt. The reaction mixture was washed with saturated NaHCO$_3$, extracted with EtOAc, dried over anhydrous Na$_2$SO$_4$, filtered, and concentrated to dryness. The residue was purified by flash column chromatography to obtain the title compound (6 g, 50%) as a yellow oil. MS (ESI): mass calcd. for C$_{18}$H$_{31}$NO$_2$Si, 321.2; m/z found, 322.1 [M+H]$^+$.

Step D: (3S,5S)-1-Benzyl-5-((tert-butyldimethylsilyl)oxy)piperidin-3-ol

To a round bottom flask were added ((2R,4S)-1-benzyl-4-((tert-butyldimethylsilyl)oxy)pyrrolidin-2-yl)methanol (6.0 g, 19 mmol), THF (20 mL), and triethylamine (5.7 mL, 28 mmol). The reaction mixture was cooled to 0° C. and to this was added TFAA (5.9 g, 28 mmol). The reaction mixture was allowed to warm to rt and was reacted at rt for 16 h. The reaction mixture was washed with saturated NaHCO$_3$, extracted with EtOAc, dried over anhydrous Na$_2$SO$_4$, filtered, and concentrated to dryness. The residue was purified by flash column chromatography to yield the title compound (3 g, 50%) as a yellow oil. MS (ESI): mass calcd. for C$_{18}$H$_{31}$NO$_2$Si, 321.2.1; m/z found, 322.0 [M+H]$^+$.

Step E: (3S,5S)-5-((tert-Butyldimethylsilyl)oxy)piperidin-3-ol

To a round bottom flask were added (3S,5S)-1-benzyl-5-((tert-butyldimethylsilyl)oxy)piperidin-3-ol (3.0 g, 9.3 mmol), EtOH (20 mL), and Pd/C (10% on activated carbon, 600 mg). To the reaction mixture was added H$_2$ and was reacted at rt for 16 h. The reaction mixture was filtered and concentrated to dryness to yield the title compound (2.4 g, quantitative) as a yellow oil. MS (ESI): mass calcd. for C$_{11}$H$_{25}$NO$_2$Si, 231.2; m/z found, 232.2 [M+H]$^+$.

Step F: tert-Butyl (3S,5S)-3-[tert-butyl(dimethyl)silyl]ox-5-hydroxypiperidine-1-carboxylate To a round bottom flask were added (3S,5S)-5-((tert-butyldimethylsilyl)oxy)piperidin-3-ol (2.4 g, 10 mmol), DCM (20 mL), triethylamine (2.1 g, 21 mmol), and (Boc)$_2$O (2.7 g, 12 mmol) at 0° C. and was reacted at rt for 1 h. The reaction was quenched with saturated NaHCO$_3$, extracted with EtOAc, dried over anhydrous Na$_2$SO$_4$, filtered, and concentrated to dryness. The residue was purified by flash column chromatography to yield the title compound (3.3 g, 96%) as a yellow oil. MS (ESI): mass calcd. for C$_{16}$H$_{33}$NO$_4$Si, 331.2; m/z found, 332.1 [M+H]$^+$.

Step G: tert-Butyl (3S,5S)-3-[tert-butyl(dimethyl)silyl]oxy-5-methylsulfonyloxypiperidine-1-carboxylate To a round bottom flask were added tert-butyl (3S,5S)-3-[tert-butyl(dimethyl)silyl]oxy-5-hydroxypiperidine-1-carboxylate (3.3 g, 10 mmol), DCM (20 mL), triethylamine (3 g, 29 mmol), and MsCl (1.7 g, 14.5 mmol) at 0° C. The reaction mixture was allowed to warm to rt and was reacted at rt for 2 h. The reaction was quenched with saturated NaHCO$_3$, extracted with EtOAc, dried over anhydrous Na$_2$SO$_4$, filtered, and concentrated to dryness to yield the title compound (4 g, 98%) as a yellow oil. MS (ESI): mass calcd. for C$_{17}$H$_{35}$NO$_6$SSi, 409.2; m/z found, 410.1 [M+H]$^+$.

Step H: (3R,5S)-tert-Butyl 3-azido-5-((tert-butyldimethylsilyl)oxy)piperidine-1-carboxylate To a round bottom flask were added tert-butyl (3S,5S)-3-[tert-butyl(dimethyl)silyl]oxy-5-methylsulfonyloxypiperidine-1-carboxylate (3.6 g, 8.8 mmol), DMF (20 mL), and NaN$_3$ (1.7 g, 26 mmol) at rt. The reaction was reacted at 70° C. for 72 h. The reaction was quenched with saturated NaHCO$_3$, extracted with EtOAc, dried over anhydrous Na$_2$SO$_4$, filtered, and concentrated to dryness. The residue was purified by flash column chromatography to yield the title compound (3.0 g, 96%) as a yellow oil.

Step I: (3R,5S)-tert-Butyl 3-azido-5-hydroxypiperidine-1-carboxylate

To a round bottom flask were added (3R,5S)-tert-butyl 3-azido-5-((tert-butyldimethylsilyl)oxy)piperidine-1-carboxylate (3.0 g, 8.4 mmol), THF (10 mL), and TBAF (1 M solution, 10 mL, 10 mmol) in sequence at 0° C. The reaction solution was warmed to rt and reacted at rt for 16 h. The reaction was quenched by the addition of water, extracted with EtOAc, dried over anhydrous Na$_2$SO$_4$, filtered, concentrated to dryness, and purified by flash column chromatography to yield the title compound (1.4 g, 69%) as a yellow oil. Mass calcd. for C$_{10}$H$_{18}$N$_4$O$_3$, 242.1. $^1$H NMR (400 MHz, CDCl$_3$): δ 9.89-3.62 (m, 3H), 3.58-3.31 (m, 1H), 3.08-3.88 (m, 2H), 2.25-2.10 (m, 1H), 1.64-1.51 (m, 1H), 1.42 (s, 9H).

Step J: (3R,5S)-tert-Butyl 3-amino-5-hydroxypiperidine-1-carboxylate

A mixture of (3R,5S)-tert-butyl 3-azido-5-hydroxypiperidine-1-carboxylate (500 mg, 2.06 mmol), Pd/C (10% on activated carbon, 200 mg), and MeOH (5 mL) were reacted at rt under H$_2$ for 16 h. The reaction mixture was filtered and concentrated to dryness. No further purification (407 mg, 91% yield). MS (ESI): mass calcd. for C$_{10}$H$_{20}$N$_2$O$_3$, 216.1; m/z found, 217.0 [M+H]$^+$.

Intermediate 3: tert-Butyl (3R,5S)-3-amino-5-fluoropiperidine-1-carboxylate

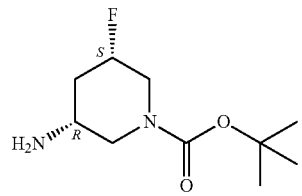

Step A: (3R,5R)-tert-Butyl 3-azido-5-hydroxypiperidine-1-carboxylate

The title compound was prepared using analogous conditions described in steps A-I of Intermediate 2, and using methyl (2R,4R)-4-hydroxypyrrolidine-2-carboxylate in place of methyl (2R,4S)-4-hydroxypyrrolidine-2-carboxylate in step A.

Step B: (3R,5S)-tert-Butyl 3-azido-5-fluoropiperidine-1-carboxylate

To a solution of (3R,5R)-tert-butyl 3-azido-5-hydroxypiperidine-1-carboxylate (1.5 g, 6.2 mmol) in dry DCM (50 mL) at −78° C. was added DAST (1.2 g, 7.4 mmol) slowly. The reaction solution was stirred at −78° C. for 2 h and at rt for 16 h. The reaction was quenched by addition of saturated aqueous NaHCO$_3$ solution and the organic layer was separated and washed with aqueous NaHCO$_3$ solution and water, dried over anhydrous Na$_2$SO$_4$, and concentrated to dryness. The residue was purified by flash column chromatography to yield the title compound as a colorless oil (660 mg, 44% yield). C$_{10}$H$_{17}$FN$_4$O$_2$. $^1$H NMR (400 MHz, CDCl$_3$): δ 4.80 (d, J=46.5 Hz, 1H), 4.32-3.95 (m, 1H), 3.95-3.71 (m, 2H), 3.39-2.63 (m, 2H), 2.41-2.12 (m, 1H), 1.86-1.57 (m, 1H), 1.46 (s, 9H).

Step C: (3R,5S)-tert-Butyl 3-amino-5-fluoropiperidine-1-carboxylate

To a solution of (3R,5S)-tert-butyl 3-azido-5-fluoropiperidine-1-carboxylate (660 mg, 2.7 mmol) in MeOH (60 mL) was added Pd/C (10% Pd on C, 130 mg) and the mixture was stirred at rt under H$_2$ overnight, then filtered and concentrated to dryness to yield the title compound as a yellow oil (450 mg, 76% yield). MS (ESI): mass calcd. for C$_{10}$H$_{19}$FN$_2$O$_2$, 218.1; m/z found, 219.1 [M+H]$^+$.

Intermediate 4: tert-Butyl (3R,5R)-3-amino-5-hydroxypiperidine-1-carboxylate

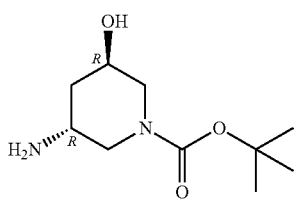

The title compound was prepared using conditions analogous to Intermediate 2, steps A-J, and using (2R,4R)-4-hydroxypyrrolidine-2-carboxylic acid in place of methyl (2R,4S)-4-hydroxypyrrolidine-2-carboxylate in step A. MS (ESI): mass calcd. for C$_{10}$H$_{20}$N$_2$O$_3$, 216.1; m/z found, 217.1 [M+H]$^+$.

Intermediate 5: 1-[(3R)-3-Aminopyrrolidin-1-yl]prop-2-en-1-one

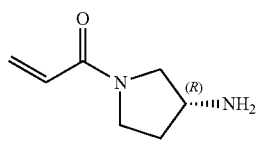

A solution of tert-butyl N-[(3R)-pyrrolidin-3-yl]carbamate (5.0 g, 27 mmol) and DIEA (4.156 g, 32.21 mmol) in DCM (60 mL) was cooled to 0° C. and prop-2-enoyl chloride (2.43 g, 26.8 mmol) was added portion wise and stirred at rt for 1 h. The mixture was concentrated to dryness and purified by flash column chromatography to get pure product, which was dissolved in concentrated HCl (30 mL) and MeOH (30 mL) and was stirred at rt for 0.5 h. The mixture was concentrated to dryness to give the title compound as a yellow oil (3.98 g, 83.9% yield). MS (ESI): mass calcd. for C$_7$H$_{12}$N$_2$O, 140.1; m/z found, 141.1 [M+H]$^+$.

Intermediate 6: tert-Butyl (3R,5R)-3-amino-5-methoxypiperidine-1-carboxylate

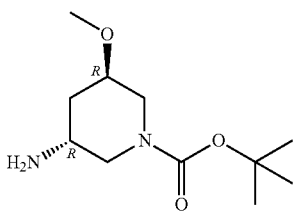

The title compound was prepared using Method 2, steps A-J, and using (1R,3S)-3-hydroxycyclopentane carboxylic acid in place of methyl (2R,4S)-4-hydroxypyrrolidine-2-carboxylate in step A, and at step J, first the methyl ester is formed, followed by reduction to obtain tert-butyl (3R,5R)-3-amino-5-hydroxypiperidine-1-carboxylate. MS (ESI): mass calcd. for C$_{10}$H$_{20}$N$_2$O$_3$: 216.1; m/z found, 217.1 [M+H]$^+$.

Intermediate 7: 4-Isopropyl-2-methyl-aniline

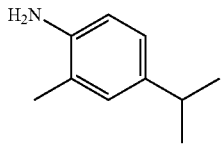

To a solution of 4-iodo-2-methyl-aniline (4.0 g, 17 mmol) and Pd(dppf)$_2$Cl$_2$ (140 mg, 0.17 mmol) in THF (50 mL) was added isopropylmagnisium chloride (25.5 mL, 51.0 mmol) at −78° C. and was reacted at reflux for 4 h. The reaction was quenched with a saturated solution of NH$_4$Cl, extracted with EtOAc, dried over anhydrous Na$_2$SO$_4$, filtered, and concentrated to dryness. The residue was purified by flash column chromatography to give the title compound as a brown solid (320 mg, 12%). MS (ESI): mass calcd. for C$_{10}$H$_{15}$N, 149.1; m/z found, 150.0 [M+H]$^+$.

Intermediate 8: Benzofuran-7-ol

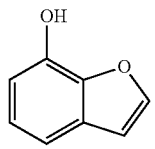

Step A: 7-Methoxybenzofuran

To a round bottom flask were added 7-methoxy-2-benzofuran-2-carboxylic acid (5.0 g, 0.026 mol), copper (0.2 g, 3 mmol), and quinoline (30 mL). The reaction mixture was heated at reflux for 2 h. The mixture was filtered through Celite and washed with EtOAc, concentrated to dryness, and purified by flash column chromatography to yield the title compound (2.45 g, 64% yield) as a yellow oil. MS (ESI): mass calcd. for $C_9H_8O_2$, 148.1; m/z found, 149.0 $[M+H]^+$.

Step B: Benzofuran-7-ol

To a round bottom flask containing 7-methoxybenzofuran (2.45 g, 16.5 mmol) and anhydrous DCM (25 mL) was carefully added a solution of boron tribromide in DCM (1 M, 33 mL) at 0° C. The reaction was allowed to warm to rt and stir at rt for 4 h. The reaction was quenched with water (20 mL), extracted with $Et_2O$, concentrated to dryness, and purified by flash column chromatography to yield the title compound (1.23 g, 55% yield) as a light-brown oil. MS (ESI): mass calcd. for $C_8H_6O_2$, 134.0.1; m/z found, 135.1 $[M+H]^+$.

Intermediate 9: 2-Fluoro-6-methyl-4-phenoxyaniline

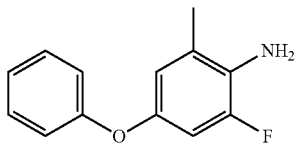 [SMILES: Cc1cc(Oc2ccccc2)cc(F)c1N]

Step A: 4-Bromo-2-fluoro-6-methylaniline

To a round bottom flask were added 2-fluoro-6-methylaniline (7 g, 56 mmol) and anhydrous DMF (100 mL). The reaction mixture was cooled in an ice bath, placed under a nitrogen atmosphere, and treated with N-bromosuccinimide (10 g, 56 mmol). The reaction was allowed to warm to rt and was stirred at rt for 10 min. The reaction mixture was poured into a water solution of diluted brine and extracted with EtOAc. The combined organic extracts were washed with diluted brine (3×), dried over anhydrous $MgSO_4$, filtered through a pad of silica, and concentrated to dryness. The residue was purified by flash column chromatography to yield the title compound (6.84 g, 60% yield) as a yellow foam. MS (ESI): mass calcd. for $C_7H_7BrFN$, 203.0; m/z found, 204 $[M+H]^+$.

Step B: 2-Fluoro-6-methyl-4-phenoxyaniline

A mixture of 4-Bromo-2-fluoro-6-methylaniline (4.73 g, 23 mmol), phenol (4.4 g, 48 mmol), 1-Butylimidazole (1.4 g, 11 mmol), CuCl (230 mg, 2.3 mmol) and $K_2CO_3$ (6.5 g, 47 mmol) was degassed and heated at 120° C. overnight. The mixture was cooled to room temperature, The mixture was concentrated and purified by ISCO using MeOH/$H_2O$ as eluent to get the title compound as brown oil (2.23 g, 44%). MS (ESI): mass calcd. for $C_{13}H_{12}FNO$, 217.1; m/z found, 218 $[M+H]^+$.

Intermediate 10: (E)-4-[tert-Butoxycarbonyl(methyl)amino]but-2-enoic Acid

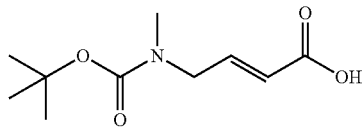

Step A: Methyl (E)-4-(methylamino)but-2-enoate

To a solution of methyl (E)-4-bromobut-2-enoate (1.79 g, 10 mmol) in THF (3 mL) was added methylamine (0.776 g, 25.0 mmol) at −20° C. over 30 min and then stirred at −5° C. for 2 h, filtered, and washed with THF. The filtrate was concentrated to dryness to give the title compound as a brown oil (0.96 g, 74%), which was used in the next step directly.

Step B: Methyl (E)-4-[tert-butoxycarbonyl(methyl)amino]but-2-enoate

To a solution of methyl (E)-4-(methylamino)but-2-enoate (0.96 g, 7.4 mmol) and $Na_2CO_3$ (1.58 g, 14.9 mmol) in THF (20 mL) and $H_2O$ (20 mL) was added $Boc_2O$ (3.24 g, 14.9 mmol) and the mixture was stirred at 25° C. for 3 h. The mixture was diluted with DCM, washed with brine several times, dried over anhydrous $Na_2SO_4$, filtered, and concentrated to dryness. The residue was purified by flash column chromatography to give the title compound as yellow liquid (0.68 g, 40% yield).

Step C: (E)-4-[tert-Butoxycarbonyl(methyl)amino]but-2-enoic Acid

To a solution of methyl (E)-4-[tert-butoxycarbonyl (methyl)amino]but-2-enoate (0.68 g, 3.0 mmol) in THF (15 mL) and water (15 mL) was added $LiOH.H_2O$ (0.498 g, 11.9 mmol) and the mixture was stirred at rt for 12 h. The pH of the mixture was adjusted to about 2, extracted with EtOAc, dried over anhydrous $Na_2SO_4$, filtered, and concentrated to dryness to give the title compound as light yellow liquid (0.41 g, 64% yield), which was used in the next step directly. MS (ESI): mass calcd. for $C_{11}H_{19}NO_4$, 229.1; m/z found, 130.0 $[M-Boc+H]^+$.

Intermediate 11: tert-Butyl (3S,4R)-3-amino-4-methoxypyrrolidine-1-carboxylate

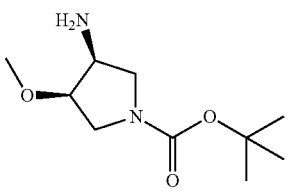

A mixture of tert-butyl (3S,4R)-3-amino-4-hydroxy-pyrrolidine-1-carboxylate (500 mg, 2.47 mmol), phthalic anhydride (439 mg, 2.97 mmol), triethylamine (500 mg, 4.94 mmol), and DMAP (60 mg, 0.49 mmol) in THF (20 mL) was stirred at reflux overnight. The reaction mixture was concentrated to dryness and the residue was purified by flash column chromatography to yield the intermediate as a white solid. This material was reacted with Ag₂O (1.142 g, 4.944 mmol) in MeI (10 mL) was stirred at reflux overnight. The reaction mixture was concentrated to dryness and the residue was purified by flash column chromatography to give the intermediate as a white solid. A solution of this material and NH₂NH₂.H₂O (1 mL, 85%) in EtOH (5 mL) was stirred at reflux for 2 h. The solid was filtered off and the solvent was removed to give the title compound as an oil which was used without further purification in the next reaction.

Intermediate 12: (E)-4-(tert-Butoxycarbonylamino)but-2-enoic Acid

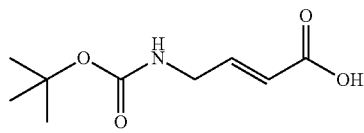

Step A: (E)-4-Aminobut-2-enoic Acid

To a round bottom flask were added (E)-4-bromobut-2-enoic acid (1 g, 6 mmol) and aqueous ammonia (10 mL) and was stirred at rt for 7 h. The mixture was concentrated to dryness to yield the title compound (0.61 g, 100%), which was used in the next step without purification.

Step B: (E)-4-(tert-Butoxycarbonylamino)but-2-enoic Acid

To a round bottom flask containing a solution of (E)-4-aminobut-2-enoic acid (0.61 g, 6 mmol), Na₂CO₃ (1.3 g, 12 mmol), THF (15 mL), and H₂O (15 mL) was added Boc₂O (2.6 g, 12 mmol). The reaction mixture was stirred at 25° C. for 15 h. Then the mixture was extracted with EtOAc and the pH of the aqueous layer was adjusted to 2 with 1 M HCl. The acidic aqueous layer was extracted with EtOAc, washed with brine (3×), dried over anhydrous Na₂SO₄, filtered, and concentrated to dryness to yield the title compound (0.24 g, 20% yield) as a white solid. MS (ESI): mass calcd. for C₉H₁₅NO₄; 201.1; m/z found, 102 [M-Boc+H]⁺.

Intermediate 13: (E)-4-Hydroxybut-2-enoic Acid

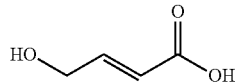

Step A: Ethyl (E)-4-bromobut-2-enoate

To a round bottom flask containing ethyl (2E)-but-2-enoate (10.9 g, 87.6 mmol) and CCl₄ (100 mL) were added NBS (17 g, 96 mmol) and AIBN (4.3 g, 26 mmol). The reaction mixture was stirred at 80° C. for 12 h. The reaction mixture was diluted with DCM and extracted with saturated NaHCO₃, water, and brine. The organic layer was dried over anhydrous Na₂SO₄ and evaporated to dryness to yield the title compound (7.5 g, 44% yield) as an oil.

Step B: (E)-4-Hydroxybut-2-enoic Acid

To a round bottom flask were added ethyl (E)-4-bromobut-2-enoate (2 g, 10 mmol), KOH (1.2 g, 21 mmol), and water (10 mL). The reaction mixture was stirred at 100° C. for 2 h, then acidified with 1 M HCl, and extracted with EtOAc (3×). The combined organic layers were washed with brine, dried over anhydrous MgSO₄, and concentrated to dryness to yield the title compound (560 mg, 53% yield) as a brown oil.

Intermediate 14: 2-Chloro-4-(4-hydroxy-2-methylanilino)pyridine-3-carbonitrile

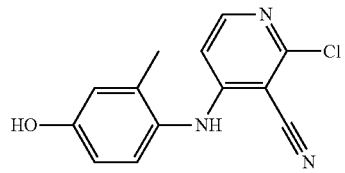 [SMILES: Cc1cc(O)ccc1Nc1ccnc(Cl)c1C#N]

Step A: 2-Chloro-4-(4-methoxy-2-methylanilino)pyridine-3-carbonitrile

To a round bottom flask were added 2-chloro-4-iodopyridine-3-carbonitrile (1.7 g, 6.4 mmol), 4-methoxy-2-methylaniline (880 mg, 6.4 mmol), DPEPhos [bis(2-diphenylphosphinophenyl)ether] (690 mg, 1.3 mmol), palladium(II) acetate (145 mg, 0.646 mmol), K₃PO₄ (3.7 g, 0.017 mmol), and dioxane (15 mL). The reaction mixture was degassed and heated at 120° C. overnight. The mixture was cooled to rt, concentrated to dryness, and purified by flash column chromatography to yield the title compound (1.1 g, 63% yield) as a brown solid. MS (ESI): mass calcd. for C₁₄H₁₂ClN₃O, 273.1; m/z found, 274 [M+H]⁺.

Step B: 2-Chloro-4-(4-hydroxy-2-methylanilino)pyridine-3-carbonitrile

To a round bottom flask containing a solution of 2-chloro-4-(4-methoxy-2-methylanilino)pyridine-3-carbonitrile (1.1 g, 4 mmol) in anhydrous DCM (15 mL) was carefully added a solution of boron tribromide in DCM (1 M, 4 mL, 4 mmol) at 0° C. The reaction mixture was allowed to stir at rt for 4 h. The reaction was quenched with water (20 mL), extracted with ethyl ether, and concentrated to dryness. The residue was purified by flash column chromatography to yield the title compound (900 mg, 86% yield) as a yellow solid. MS (ESI): mass calcd. for C₁₃H₁₀ClN₃O, 259.1; m/z found, 260.0 [M+H]⁺.

Intermediate 15: 1-[(3R)-3-Amino-1-piperidyl]prop-2-en-1-one

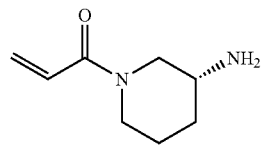

Step A: (R)-tert-Butyl (1-acryloylpiperidin-3-yl)carbamate

To a solution of tert-butyl N-[(3R)-3-piperidyl]carbamate (2 g, 10 mmol) in DCM (30 mL) was added triethylamine (5 g, 50 mmol) and the reaction mixture was cooled to 0° C. Prop-2-enoyl chloride (2.7 g, 30 mmol) was added slowly and was stirred overnight at rt. The reaction was extracted with H$_2$O and DCM, the organic layer was washed with brine, dried over anhydrous Na$_2$SO$_4$, and concentrated to dryness. The crude product was used crude in the next step without further purification.

Step B: 1-[(3R)-3-Amino-1-piperidyl]prop-2-en-1-one (R)-tert-Butyl (1-acryloylpiperidin-3-yl)carbamate (from Step A) was dissolved in MeOH and concentrated to dryness. Concentrated aqueous HCl was added, and the mixture was stirred for 2 h at rt. The reaction mixture was concentrated to dryness and the residue was used directly in the next step. MS (ESI): mass calcd. for C$_8$H$_{14}$N$_2$O, 154.1; m/z found, 155.1 [M+H]$^+$.

Intermediate 16: 5-(*S)-(2-Methyl-4-phenoxyphenyl)-4-oxo-4,5-dihydro-3H-1-thia-3,5,8-triazaacenaphthylene-2-carboxylic Acid

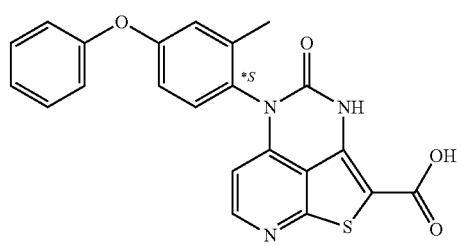 [SMILES: Cc1cc(Oc2ccccc2)ccc1N1C(=O)Nc2c(C(=O)O)sc3nccc1c23]

The title compound was prepared using Method 1, steps A-F in Example 1 (including Chiral Resolution Step A to obtain the *S atropisomer). MS (ESI): mass calcd. for C$_{22}$H$_{15}$N$_3$O$_4$S, 417.1; m/z found, 418.2 [M+H]$^+$.

Intermediate 17: (E)-2-Cyano-3-cyclopropylprop-2-enoic Acid

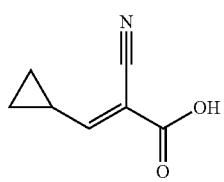

A solution of cyanoacetic acid (1.34 g, 15.7 mmol), cyclopropanecarboxaldehyde (1.0 mL, 13 mmol), NH$_4$OAc (101 mg, 1.31 mmol), and HOAc (10 mL) in a 50 mL round bottom flask fitted with a stir bar under N$_2$ was warmed in a sand bath set at 110° C. The reaction was run until LCMS and TLC showed the reaction had gone to completion. The reaction mixture was concentrated to dryness and water (20 mL) was added to the white solid. This mixture was concentrated dryness and repeated one time more. Water was added and the precipitate was filtered off to yield the title compound as a white solid (1.3 g, 72% yield). MS (ESI): mass calcd. for C$_7$H$_7$NO$_2$, 137.0; m/z found, 138.0 [M+H]$^+$.

Intermediate 18: (R)-5-(3-Fluoro-2-methyl-4-phenoxyphenl)-4-oxo-N-(piperidin-3-yl)-4,5-dihydro-3H-1-thia-3,5,8-triazaacenaphthylene-2-carboxamide

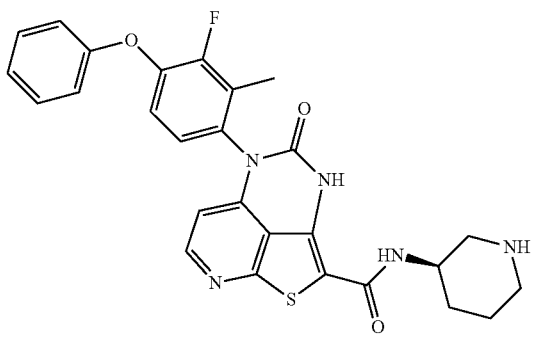 [SMILES: Cc1c(N2C(=O)Nc3c(C(=O)N[C@@H]4CCCNC4)sc4nccc2c34)ccc(Oc2ccccc2)c1F]

Step A: 2-Bromo-3-fluoro-1-nitro-4-phenoxybenzene

To a mixture of a 2-bromo-3,4-difluoro-1-nitrobenzene (15.8 g, 66.4 mmol) and potassium carbonate (18.3 g, 132.8 mmol) in DMF (50 mL) was added phenol (6.25 g, 66.4 mmol) followed by stirring at 80° C. overnight. The title compound was collected by adding water to the reaction mixture and filtering to isolate a yellow solid (18 g, 87%).

Step B: 2-Fluoro-3-methyl-4-nitro-1-phenoxybenzene

Dimethylzinc as a 2 M solution in toluene (80.1 mL, 96.1 mmol) was slowly added to a mixture of 2-bromo-3-fluoro-1-nitro-4-phenoxybenzene (10 g, 32.0 mmol) and palladium-(diphenylphosphineoferrocenyl)-dichloride-methylene dichloride complex (1.33 g, 1.60 mmol) in dioxane (200 mL) at 40° C. The mixture was stirred at 55° C. for 2 hours. After cooling to room temperature, methanol was slowly added followed by a saturated solution of ammonium chloride. The resulting mixture was extracted into ethyl acetate. The organic phase was washed with brine, dried over anhydrous sodium sulphate, filtered and concentrated under reduced pressure. The crude oil was purified by flash chromatography on silica gel (PE/ethyl acetate, 9/1) to provide the crude as a yellow solid which is carried on to the next step without determining a yield.

Step C: 3-Fluoro-2-methyl-4-phenoxyaniline

Iron powder (4.5 g, 80.6 mmol) and NH$_4$Cl (4.5 g, 84.1 mmol) were added portion wise to a solution of 2-fluoro-3-methyl-4-nitro-1-phenoxybenzene (product from step B) in EtOH (60 mL) and H$_2$O (20 mL) at rt. The resulting brown suspension was stirred at reflux during 2 hours. The reaction mixture was quenched with water and extracted with ethyl acetate. The organic phase was washed with water and brine, dried over Na$_2$SO$_4$ anhydrous, filtered and concentrated under reduced pressure followed by purification by flash chromatography (silica gel, PE/ethyl acetate, 10/1) to obtain the title compound as a yellow solid (2.42 g, 35%) MS (ESI): mass calcd. for $C_{13}H_{12}FNO$, 217.1; m/z found, 217.9 $[M+H]^+$.

Step D: 2-Chloro-4-((3-fluoro-2-methyl-4-phenoxyphenyl)amino)nicotinonitrile A mixture of 3-fluoro-2-methyl-4-phenoxyaniline (2.4 g, 11.0 mmol), 2-chloro-4-iodonicotinonitrile (2.9 g, 11.0 mmol), DPEPhos (1.19 g, 2.2 mmol), $Pd(AcO)_2$ (247.5 mg, 1.1 mmol), $K_3PO_4$ (4.68 g, 22.1 mmol) in dioxane (50 mL) was heated at reflux under $N_2$ for 4 hr, then concentrated and purified by flash chromatography (silica gel, PE/ethyl acetate, 10/1) to give the title compound as a yellow solid. (3.9 g, 99.8%) MS (ESI): mass calcd. for $C_{19}H_{13}ClFN_3O$, 353.1; m/z found, 354.0 $[M+H]^+$.

Step E: Methyl 3-amino-4-((3-fluoro-2-methyl-4-phenoxyphenyl)amino)thieno[2,3-b]pyridine-2-carboxylate A mixture of 2-chloro-4-((3-fluoro-2-methyl-4-phenoxyphenyl)amino)nicotinonitrile (3.9 g, 11.0 mmol), methyl 2-mercaptoacetate (2.3 g, 22.0 mmol) and NaOMe (1.17 g, 22.0 mmol) in MeOH (30 mL) was stirred at reflux for 16 hours. The precipitate was collected by filtration, dried under vacuo to give the title compound without purification. (3.2 g, 69%). MS (ESI): mass calcd. for $C_{22}H_{18}FN_3O_3S$, 423.1; m/z found, 524.0 $[M+H]^+$.

Step F: Methyl 5-(3-fluoro-2-methyl-4-phenoxyphenyl)-4-oxo-4,5-dihydro-3H-1-thia-3,5,8-triazaacenaphthylene-2-carboxylate CDI (4.9 g, 30.2 mmol) and $Et_3N$ (0.5 mL) were added to a suspension of Methyl 3-amino-4-((3-fluoro-2-methyl-4-phenoxyphenyl)amino)thieno[2,3-b]pyridine-2-carboxylate (3.2 g, 7.56 mmol) in 1,4-dioxane (25 mL) at rt. The mixture was stirred at reflux for 3 hr, then concentrated and washed with MeOH to give the title compound as a yellow solid. (3.0 g, 99%) MS (ESI): mass calcd. for $C_{23}H_{16}FN_3O_4S$, 449.4; m/z found, 449.9 $[M+H]^+$.

Step G: 5-(3-Fluoro-2-methyl-4-phenoxyphenyl)-4-oxo-4,5-dihydro-3H-1-thia-3,5,8-triazaacenaphthylene-2-carboxylic Acid A mixture of Methyl 5-(3-fluoro-2-methyl-4-phenoxyphenyl)-4-oxo-4,5-dihydro-3H-1-thia-3,5,8-triazaacenaphthylene-2-carboxylate (3.0 g, 6.68 mmol) in MeOH/THF/$H_2O$ (30/30/25 mL) was added $LiOH.H_2O$ (1.4 g, 33.4 mmol) and stirred at 60° C. overnight. The solvent was removed and acidified with 1N HCl. The title compound was collected by filtration to give a tan solid. (2.6 g, 90%) MS (ESI): mass calcd. for $C_{22}H_{14}FN_3O_4S$, 435.4; m/z found, 435.9 $[M+H]^+$.

Step H: (R)-5-(3-Fluoro-2-methyl-4-phenoxyphenyl)-4-oxo-N-(piperidin-3-yl)-4,5-dihydro-3H-1-thia-3,5,8-triazaacenaphthylene-2-carboxamide A mixture of compound 5-(3-fluoro-2-methyl-4-phenoxyphenyl)-4-oxo-4,5-dihydro-3H-1-thia-3,5,8-triazaacenaphthylene-2-carboxylic acid (650 mg, 1.49 mmol), tert-butyl (R)-3-aminopiperidine-1-carboxylate (598.03 mg, 2.99 mmol), $Et_3N$ (301.6 mg, 2.99 mmol) and HATU (1.13 g, 2.99 mmol) in DMF (5 mL) was stirred at rt for 3 hr. Water was added and the precipitate isolated by filtration to give a pale yellow solid. The solid was dissolved in MeOH (8 mL) and acidified using HCl (8 mL). The resulting mixture was heated to 50° C. and stirred for 30 min, and then the solvent was removed to give the title compound as a yellow solid without further purification (680 mg, 82%). MS (ESI): mass calcd. for $C_{27}H_{24}FN_5O_3S$, 517.2; m/z found, 518.0 $[M+H]^+$.

Intermediate 19: (S)-2,3-Dimethoxypropanoic Acid

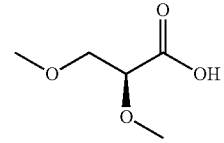

Step A: Methyl (S)-2-hydroxy-3-methoxypropanoate

To a solution of methyl (S)-oxirane-2-carboxylate (1 g, 9.80 mmol) in methanol (0.48 mL) was added was added Magnesium trifluoromethanesulfonate (790 mg, 2.45 mmol) at rt, and warmed to 40° C. for 16 hrs. Filtered and rinsed with DCM followed by concentration to obtain the title compound as a colorless oil (1.0 g, 76% yield).

Step B: Methyl (S)-2,3-diethoxypropanoate

A mixture of Methyl (S)-2-hydroxy-3-methoxypropanoate (900 mg, 6.7 mmol) in DCM (10 mL) was treated with methyl iodide (1.90 g, 13.4 mmol) and silver oxide (2.32 g, 10 mmol) at rt. The mixture was warmed to 40° C. for 16 hours. Filtered and rinsed with DCM followed by concentration to give the title compound as a colorless oil (400 mg, 2.7 mmol, 40% yield).

Step C: (S)-2,3-Dimethoxypropanoic Acid

A mixture of methyl (S)-2,3-diethoxypropanoate (400 mg, 2.7 mmol), and lithium hydroxide hydrate (454 mg, 11 mmol) in DME (4 mL) and water (1 mL) stirred at rt for 16 hrs. Adjusted pH to <7, extracted with DCM, and concentrated to give the title compound as a colorless oil without further purification or yield determination.

Intermediate 20: Benzyl 5-amino-2-methylpiperidine-1-carboxylate

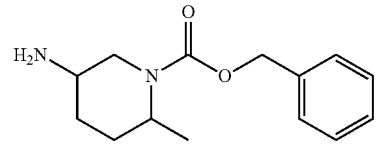 [SMILES: CC1CCC(N)CN1C(=O)OCc1ccccc1]

Step A: Benzyl 5-((tert-butoxycarbonyl)amino)-2-methylpiperidine-1-carboxylate To a mixture of tert-butyl (6-methylpiperidin-3-yl)carbamate (900 mg, 4.2 mmol) in DCM, was added triethylamine (848 mg, 8.4 mmol) and benzoyl chloride (1.07 g, 6.3 mmol) which was allowed to stir at rt for 2 hrs. The crude reaction mixture was concentrated to a give the title compound without further purification (900 mg, 61% yield). MS (ESI): mass calcd. for $C_{19}H_{28}N_2O_4$, 348.2; m/z found, 349.1 $[M+H]^+$.

Step B: Benzyl 5-amino-2-methylpiperidine-1-carboxylate

A mixture of Benzyl 5-((tert-butoxycarbonyl)amino)-2-methylpiperidine-1-carboxylate (900 mg, 2.58 mmol), in methanol (5 mL), was added 1M HCl in methanol (5 mL). The mixture was allowed to stir at rt for 2 h. The crude reaction mixture was concentrated to a give the title compound without further purification (600 mg, 94% yield). MS (ESI): mass calcd. for $C_{14}H_{19}NO_2$, 233.1; m/z found, 234.0 $[M+H]^+$.

Intermediate 21: 2-[tert-Butoxycarbonyl(methyl)amino]acetic Acid

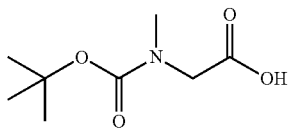

Sodium hydride (6.85 g, 171 mmol) was added to a mixture of (tert-butoxycarbonyl)glycine (10 g, 57.1 mmol) and methyl iodide (75 g, 528 mmol) in THF (600 mL) at 0° C. The mixture was slowly allowed to warm to rt overnight. Water (300 mL) was added and extracted into ethyl acetate (2×500 mL). The aqueous layer was acidified to pH 3 with 1 M HCl extracted with ethyl acetate (2×500 mL). The combined organic layer was extracted with saturated aqueous sodium chloride (500 mL), dried (MgSO₄), filtration and concentrated to give the title compound as an oil (10 g, 91%).

Intermediate 22: tert-Butyl (3R)-3-[(2-sulfanylacetyl)amino]piperidine-1-carboxylate

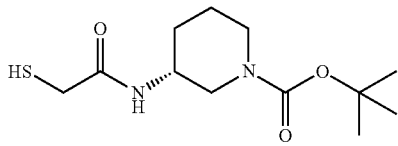 [SMILES: CC(C)(C)OC(=O)N1CCC[C@@H](NC(=O)CS)C1]

A 20 mL microwave vial was charged with (R)-1-boc-3-aminopiperdine (5.0 g, 25 mmol). The vial was sealed, evacuated, and back-filled with argon three times. Methyl 2-mercaptoacetate (6.7 mL, 170 mmol) was added via syringe in one portion and was heated to 150° C. in an oil bath. After 1 h 35 minutes, the mixture was cooled to rt and purified by flash column chromatography to yield a colorless oil (6.15 g. 90%).

Intermediate 23: (E)-2-Cyano-3-cyclopropylprop-2-enoyl chloride

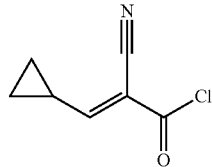

Step A: (E)-2-Cyano-3-cyclopropylacrylic Acid

Combined cyanoacetic acid (1.34 g, 15.7 mmol), cyclopropanecarboxyaldehyde (1.0 mL, 13 mmol), ammonium acetate (101 mg, 13.1 mmol) in acetic acid (10 ml) and warmed in a sand bath set at 110° C. for 2 hrs. The reaction mixture was concentrate to a solid and suspend in water (20 mL). The title compound was isolated by filtration and dried under vacuum to give the title compound (1.3 g, 72%) as a white solid.

Step B: (E)-2-Cyano-3-cyclopropylprop-2-enoyl chloride

To a suspension of (E)-2-cyano-3-cyclopropylacrylic acid (72.3 mg, 0.527 mmol) in CDCl₃ (5.2 mL) was added 1-chloro-N,N,2-trimethylpropenylamine (0.084 mL, 1.01 g/mL, 0.635 mmol). The resulting clear colorless solution was mixed for 5 minutes before direct use in subsequent reactions.

Intermediate 24: tert-Butyl (3S,4R)-3-amino-4-hydroxypyrrolidine-1-carboxylate

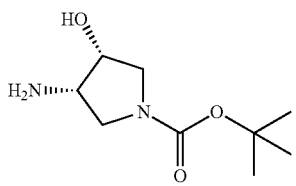

Step A: (3S,4R)-tert-Butyl 3-azido-4-((tert-butyldimethylsilyl)oxy)pyrrolidine-1-carboxylate A solution of methanesulfonyl chloride (11.66 g, 101.8 mmol) in DCM was added to a mixture of tert-butyl (3R,4R)-3-[tert-butyl(dimethyl)silyl]oxy-4-hydroxy-pyrrolidine-1-carboxylate (26.9 g, 84.8 mmol) and triethylamine (16.6 mL, 119 mmol) in DCM dropwise at 0° C. The reaction mixture was stirred for 1.5 h at room temperature. The reaction mixture was taken up in water and extracted with DCM. The organic layer was washed with brine, dried over anhydrous Na₂SO₄, and concentrated to dryness. The residue and sodium azide (11.2 g, 170 mmol) in DMF was heated at 120° C. for 13 h. The reaction mixture was poured into water and the mixture extracted with toluene. The organic layer was washed with brine, dried over anhydrous MgSO$_4$, and concentrated to dryness. The residue was purified by flash column chromatography to yield the title compound (13.5 g, 47%).

Step B: tert-Butyl (3S,4R)-3-amino-4-[tert-butyl (dimethyl)silyl]oxy-pyrrolidine-1-carboxylate A solution of (3S,4R)-tert-butyl 3-azido-4-((tert-butyldimethylsilyl)oxy)pyrrolidine-1-carboxylate (13.5 g, 39.4 mmol) and Pd/C (10% on carbon, 400 mg, 0.376 mmol) in ethanol (150 mL) was hydrogenated under H$_2$-gas for 2 hours. The reaction mixture was filtered over Celite and concentrated to dryness to yield the title compound (12.36 g, 99.08% yield).

Step C: tert-Butyl (3S,4R)-3-amino-4-hydroxy-pyrrolidine-1-carboxylate

To a solution of tert-butyl (3S,4R)-3-amino-4-[tert-butyl (dimethyl)silyl]oxy-pyrrolidine-1-carboxylate (12.15 g, 38.39 mmol) in THF was added TBAF (52.2 mL, 52.2 mmol). The reaction mixture was stirred at room temperature for 4 h. The reaction mixture was concentrated to dryness and water was added. The mixture was extracted with ethyl acetate and the organic layer was washed with water and brine several times. The water layer was extracted several times with chloroform. NaCl was added to the water layer and it was again extracted with chloroform. The combined organic layers were dried over anhydrous MgSO$_4$, filtered, and concentrated to dryness. The residue was purified by flash column chromatography to yield the title compound (7.8 g, 100% yield).

Intermediate 25: 4-((4-(2-((tert-Butyldimethylsilyl)oxy)phenoxy)-2-methylphenyl)amino)-2-chloronicotinonitrile

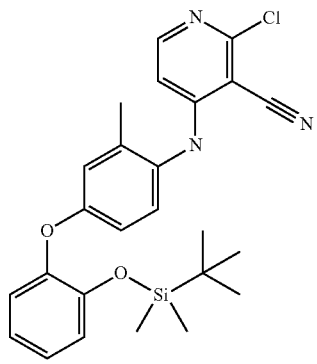 [SMILES: Cc1cc(Oc2ccccc2O[Si](C)(C)C(C)(C)C)ccc1Nc1ccnc(Cl)c1C#N]

Step A: 2-(3-Methyl-4-nitrophenoxy)phenol

The title compound was prepared in a manner analogous to Intermediate 27, Step A, using pyrocatechol.

Step B: tert-Butyldimethyl(2-(3-methyl-4-nitrophenoxy)phenoxy)silane

To a solution of 2-(3-methyl-4-nitrophenoxy)phenol (4.90 g, 20 mmol) in DCM (40 mL) were added Et$_3$N (3.03 g, 30 mmol) and TBSCl (3.31 g, 22 mmol) and stirred at room temperature for 3 hours. The reaction mixture was dispersed between DCM and saturated NH$_4$Cl aqueous solution. The organic layer was collected, condensed and purified by flash chromatography eluting with PE/EA to yield the title compound (4.10 g, 57% yield)

Step C: 4-((4-(2-((tert-Butyldimethylsilyl)oxy)phenoxy)-2-methylphenyl)amino)-2-chloronicotinonitrile The title compound was prepared in a manner analogous to Intermediate 27, Steps B-C, using tert-butyldimethyl(2-(3-methyl-4-nitrophenoxy)phenoxy)silane in step B. MS (ESI): mass calcd. for C$_{25}$H$_{28}$ClN$_3$O$_2$Si, 465.2; m/z found, 466.0 [M+H]+.

Intermediate 26: 3,5-Difluoro-4-nitrophenol

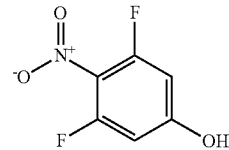

To a solution of 3,5-difluorophenol (20.45 g, 157.2 mmol) in DCM (225 mL) was added fuming nitric acid (>90%, 7.86 mL, 157 mmol) dropwise over 10 minutes. The resulting orange solution was stirred in an ice bath for 50 min. The mixture was poured into water (200 mL) and the phases separated. The aqueous phase was extracted with DCM (50 mL) and EtOAc (2×50 mL). The combined organic extracts were dried over anhydrous Na$_2$SO$_4$, filtered, and concentrated to dryness. The residue was purified by flash column chromatography to yield the title compound (11.24 g, 40.8% yield) as a yellow solid. MS (ESI): mass calcd. for C$_6$H$_3$F$_2$NO$_3$, 175.0; m/z found, 174 [M−H]−.

Intermediate 27: 5-(2-Methyl-4-phenoxyphenyl)-4-oxo-4,5-dihydro-3H-1-thia-3,5,8-triazaacenaphthylene-2-carboxylic Acid

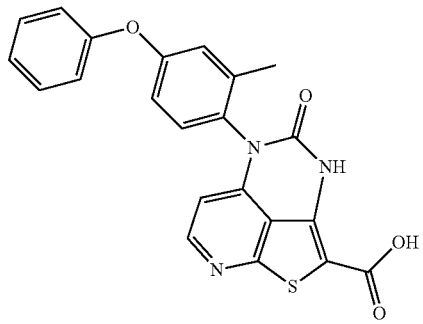 [SMILES: Cc1cc(Oc2ccccc2)ccc1N1C(=O)Nc2c(C(=O)O)sc3nccc1c23]

Step A: 2-Methyl-1-nitro-4-phenoxybenzene

To a round bottom flask were added phenol (42.5 g, 452 mmol), K$_2$CO$_3$ (125 g, 905 mmol), and DMF (500 mL). To the reaction mixture was added 5-fluoro-2-nitrotoluene (70.2 g, 452 mmol) and the reaction was stirred at 80° C. for 16 h under N$_2$. The reaction was diluted with saturated NH$_4$Cl and extracted with MTBE (3×400 mL). The organic layers were combined, dried over anhydrous Na$_2$SO$_4$, filtered, and concentrated to dryness to yield the title compound (100 g, 92% yield) as a brown oil.

Step B: 2-Methyl-4-phenoxyaniline

To a solution of 2-methyl-1-nitro-4-phenoxybenzene (100 g, 436 mmol) in EtOH/H$_2$O (3:1 ratio, 2000 mL) were sequentially added NH$_4$Cl (117 g, 2180 mmol) and Fe (97 g, 1700 mmol). The reaction mixture was heated to reflux for 2 h, then the reaction was cooled to 25° C. and concentrated to dryness. To the residue was added water and EtOAc and the organic layer was separated, washed with saturated NaHCO$_3$ and saturated brine, dried over anhydrous MgSO$_4$, filtered, and concentrated to dryness to yield the title compound (82 g, 90% yield).

Step C: 2-Chloro-4-(2-methyl-4-phenoxyanilino)pyridine-3-carbonitrile

To a round bottom flask under a N$_2$ atmosphere were added 2-methyl-4-phenoxyaniline (30 g, 150 mmol), 2-chloro-4-iodopyridine-3-carbonitrile (51.6 g, 195 mmol), and dioxane (200 mL), followed by bis(2-diphenylphosphinophenyl)ether (DPEphos) (16 g, 30 mmol), Pd(OAc)$_2$ (3.36 g, 15 mmol), and K$_3$PO$_4$ (89 g, 420 mmol). The reaction mixture was stirred at 100° C. overnight. The reaction mixture was filtered and purified flash column chromatography to yield the title compound (32 g, 63% yield) as a yellow solid.

Step D: Methyl 3-amino-4-(2-methyl-4-phenoxyanilino)thieno[2,3-b]pyridine-2-carboxylate To a round bottom flask were added 2-chloro-4-(2-methyl-4-phenoxyanilino)pyridine-3-carbonitrile (36 g, 107 mmol) in MeOH (150 mL). To this solution was added NaOMe (14.5 g, 268 mmol) in MeOH (30 mL), followed by methyl 2-sulfanylacetate (23 g, 217 mmol). The reaction mixture was refluxed overnight. The reaction mixture was cooled and the yellow precipitate was filtered off, washed with MeOH, and dried to yield the title compound (30 g, 75% yield) as a yellow solid.

Step E: Methyl 5-(2-methyl-4-phenoxyphenyl)-4-oxo-4,5-dihydro-3H-1-thia-3,5,8-triazaacenaphthylene-2-carboxylate To a round bottom flask were added methyl 3-amino-4-(2-methyl-4-phenoxyanilino)thieno[2,3-b]pyridine-2-carboxylate (30.6 g, 75.5 mmol), carbonyldiimidazole (49 g, 300 mmol), and 1,4-dioxane (500 ml). The reaction was stirred at reflux overnight. Then the reaction mixture was concentrated to dryness and to the residue was added to MeOH (200 mL) and the precipitate that formed was filtered off and dried to yield the title compound (28.1 g, 86%) as a yellow solid.

Step F: 5-(2-Methyl-4-phenoxyphenyl)-4-oxo-4,5-dihydro-3H-1-thia-3,5,8-triazaacenaphthylene-2-carboxylic Acid To a round bottom flask were added methyl 5-(2-methyl-4-phenoxyphenyl)-4-oxo-4,5-dihydro-3H-1-thia-3,5,8-triazaacenaphthylene-2-carboxylate (9.2 g, 21 mmol), lithium hydroxide (4.47 g, 106 mmol), THF (200 mL), MeOH (200 mL), and water (50 mL). The reaction mixture was stirred at 50° C. for 15 h. The mixture was concentrated to dryness and diluted with H$_2$O. The pH was adjusted to 2 with 1 M HCl and the precipitate was filtered and dried to yield the title compound (8.1 g, 91% yield) as yellow solid. MS (ESI): mass calcd. for C$_{22}$H$_{15}$N$_3$O$_4$S, 417.1; m/z found, 418.1 [M+H]$^+$.

Intermediate 28: 2-((3-(3-Methyl-4-nitrophenoxy)benzyl)oxy)benzonitrile

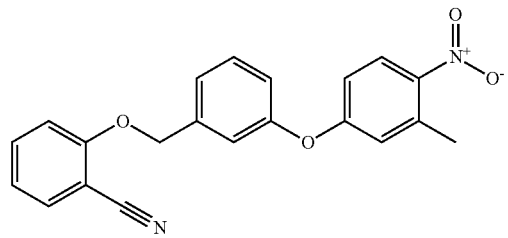 [SMILES: Cc1cc(Oc2cccc(COc3ccccc3C#N)c2)ccc1[N+](=O)[O-]]

Step A: 3-(3-Methyl-4-nitrophenoxy)benzaldehyde 4-fluoro-2-methyl-1-nitrobenzene (13 mL, 106.6 mmol), 3-hydroxybenzaldehyde (19.8 mL, 162 mmol) and K$_2$CO$_3$ (30.1 g, 217.9 mmol) were dissolved in DMF (123 mL) at rt under an atmosphere of argon. The mixture was warmed in a sand bath at 110° C. under N$_2$ for 5 hours. Cooled, filtered and extracted into ether partitioning away from a brine solution. The title compound was purified by silica chromatography (ethyl acetate/hexanes followed by DCM/methanol) (9.83 g, 36%) MS (ESI): mass calcd. for C$_{14}$H$_{11}$NO$_4$, 257.1; m/z found, 258.0 [M+H]$^+$.

Step B: (3-(3-Methyl-4-nitrophenoxy)phenyl)methanol

To a scintillation vial containing 3-(3-methyl-4-nitrophenoxy)benzaldehyde (13 g, 50.5 mmol) was added a stir bar and the vessel was purged with N2. Dry MeOH (125 mL, dried over hot 3A sieves) was added via a syringe filter and the suspension was cooled to −10° C. Sodium borohydride (1.1 g, 29 mmol) was added in one portion with mixing and the reaction was allowed to warm to rt over 30 min. The title compound was isolated by extracting into ethyl acetate from a solution of saturated aqueous NH$_4$Cl followed by drying over Na$_2$SO$_4$, filtration and concentration. (8.66 g, 66%) C$_{14}$H$_{13}$NO$_4$. $^1$H NMR (500 MHz, Methanol-d4): δ 8.08-8.01 (m, 1H), 7.46-7.37 (m, 1H), 7.26-7.20 (m, 1H), 7.14-7.08 (m, 1H), 7.04-6.97 (m, 1H), 6.97-6.92 (m, 1H), 6.92-6.87 (m, 1H), 4.62 (s, 2H), 2.55 (s, 3H).

Step C: 2-((3-(3-Methyl-4-nitrophenoxy)benzyl)oxy)benzonitrile (3-(3-methyl-4-nitrophenoxy)phenyl)methanol (8.13 g, 31.4 mmol), triphenylphosphine (9.97 g, 37.6 mmol) and DIAD (6.5 mL, 31.4 mmol) were dissolved in dry THF (118 mL) under an atmosphere of N2. The suspension was cooled to −10° C. and 2-hydroxybenzonitrile (4.5 g, 37.6 mmol) was added in one portion with mixing. The reaction was allowed to warm to rt, followed by heating to 80° C. for 3 hours, 40° C. for 33 hours and 80° C. for 1.5 hours. Concentrated crude reaction mixture onto silica and eluted through a plug of silica in a fritted funnel with ethyl acetate/hexanes, 4/1 to give the title compound. (8.65 g, 77%) MS (ESI): mass calcd. for $C_{21}H_{16}N_2O_4$, 360.1; m/z found, 361.0 [M+H]$^+$. $^1$H NMR (500 MHz, Methanol-d4): δ 8.02 (d, J=9.0 Hz, 1H), 7.68-7.55 (m, 2H), 7.53-7.41 (m, 1H), 7.41-7.29 (m, 1H), 7.29-7.14 (m, 2H), 7.14-7.01 (m, 2H), 6.99-6.85 (m, 2H), 5.27 (s, 2H), 2.53 (s, 3H).

Intermediate 29: tert-Butyl (3R,5S)-3-amino-5-methoxypiperidine-1-carboxylate

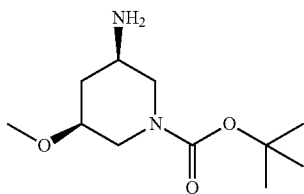 [SMILES: CO[C@H]1C[C@@H](N)CN(C(=O)OC(C)(C)C)C1]

Step A: (3R,5S)-tert-Butyl 3-azido-5-hydroxypiperidine-1-carboxylate

The title compound was prepared using the method for Intermediate 2, steps A-J. Mass calcd. for $C_{10}H_{18}N_4O_3$, 242.1.1; $^1$H NMR (400 MHz, CDCl$_3$): δ 3.85-3.68 (m, 3H), 3.60-3.49 (m, 1H), 3.16-3.00 (m, 2H), 2.38-2.07 (m, 3H), 1.65-1.59 (m, 1H), 1.44 (s, 9H).

Step B: tert-Butyl (3R,5S)-3-azido-5-methoxypiperidine-1-carboxylate

A solution of (3R,5S)-tert-butyl 3-azido-5-hydroxypiperidine-1-carboxylate (200 mg, 0.83 mmol) and Ag$_2$O (152 mg, 1.24 mmol) in CH$_3$I (4 mL) was reacted at 60° C. for 16 h, filtered, and concentrated to dryness to give the title compound as a colorless oil (200 mg, 95%). Mass calcd. for $C_{11}H_{20}N_4O_3$, 256.2; $^1$H NMR (400 MHz, CDCl$_3$): δ 4.39-4.00 (m, 3H), 3.37 (s, 3H), 3.36-3.29 (m, 1H), 3.24-3.15 (m, 1H), 2.68-2.31 (m, 3H), 1.44 (s, 9H), 1.37-1.29 (m, 1H).

Step C: tert-Butyl (3R,5S)-3-amino-5-methoxypiperidine-1-carboxylate

A solution of tert-butyl (3R,5S)-3-azido-5-methoxypiperidine-1-carboxylate (200 mg, 0.78 mmol) and Pd/C (10% on carbon, 20 mg) in MeOH (10 mL) was reacted at rt under H$_2$ for 16 h. The reaction mixture was filtered and concentrated to dryness to give the title compound (170 mg, 95%), which was used in the next step without purification. MS (ESI): mass calcd. for $C_{11}H_{22}N_2O_3$, 230.30; m/z found, 231.1 [M+H]$^+$.

Intermediate 30: 2-Fluoro-3-methylbut-2-enoic Acid

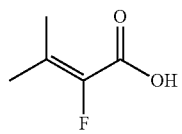

Step A: Ethyl 2-diethoxyphosphoryl-2-fluoroacetate

Ethyl 2-bromo 2-fluoroacetate (5.0 g, 27 mmol) was added to triethylphosphite (13 mL) and heated at 130° C. for 23 h. The resulting mixture was distilled under low pressure (1.4 mbar, 75-110° C.) to give the title compound as a yellowish oil (6.0 g, 92%).

Step B: Ethyl 2-fluoro-3-methylbut-2-enoate

To a dry 250 mL 2-neck round bottom flask that was purged with N$_2$ was added ethyl 2-diethoxyphosphoryl-2-fluoroacetate (500 mg, 2.07 mmol). Anhydrous THF (20 mL) was added and the reaction mixture was cooled to −70° C., then BuLi (2.5 M in Hexane, 1 mL) was added dropwise. The reaction mixture was stirred for 2 h at −70° C., then acetone (1 mL) was added and the reaction was warmed to rt and stirred overnight. The reaction was quenched by addition of an NH$_4$Cl solution and extracted with EtOAc. The organic layers was washed with brine, dried over anhydrous Na$_2$SO$_4$, and concentrated to dryness to give the title compound as a yellow oil (266 mg, 88.1% yield).

Step C: 2-Fluoro-3-methylbut-2-enoic Acid

To a solution of ethyl 2-fluoro-3-methylbut-2-enoate (266 mg, 1.82 mmol) in dioxane (5 mL) and water (5 mL) was added NaOH (291.3 mg, 7.281 mmol) and was stirred for 10 min at 60° C. The mixture was acidified with 2 M HCl to pH 2 and extracted with DCM. The organic phase was washed with brine, dried over anhydrous MgSO$_4$, and concentrated to dryness to give the title compound as a yellow oil (181 mg, 84%).

Intermediate 31: 2-Chloro-4-(2-methyl-4-tetrahydropyran-4-yloxyanilino)pyridine-3-carbonitrile

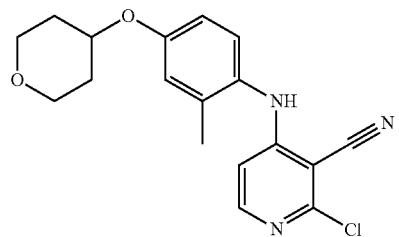 [SMILES: Cc1cc(OC2CCOCC2)ccc1Nc1ccnc(Cl)c1C#N]

Step A: Tetrahydro-2H-pyran-4-yl methanesulfonate

To a solution of tetrahydro-2H-pyran-4-ol (2 g, 20 mmol) in DCM (20 mL) at 0° C. was added DIEA (3 g, 23.5 mmol), and methanesulfonyl chloride (2.46 g, 21.5 mmol). The reaction mixture was stirred at 0° C. for 1 hr, then at room temperature for 1.5 hrs. The mixture was poured into water, extracted into DCM. The organic layer was separated, washed with water, brine, dried over Na$_2$SO$_4$, and concentrated to give the title compound. (3.72 mg, quantitative).

Step B: 4-(3-Methyl-4-nitrophenoxy)tetrahydro-2H-pyran

Tetrahydro-2H-pyran-4-yl methanesulfonate (3.53 g, 19.6 mmol) was dissolved in DMF (40 mL), followed by the addition of Cs$_2$CO$_3$ (9.57 g, 29.4 mmol) and 3-methyl-4-nitrophenol (3 g, 19.6 mmol). The mixture was heated at 120° C. for 3 h, then cooled to rt, and diluted with water and extracted into EA. The combined organic layers were washed with brine and concentrated, then purified by chromatography with DCM/MeOH to get the target compound as a white solid. (2.87 g, 62%) MS (ESI): mass calcd. for $C_{12}H_{15}NO_4$, 237.1; m/z found, 238.3 $[M+H]^+$.

Step C: 2-Methyl-4-((tetrahydro-2H-pyran-4-yl)oxy) aniline 4-(3-methyl-4-nitrophenoxy)tetrahydro-2H-pyran (1.1 g, 4.6 mmol) was treated with Palladium on carbon (25 mg, 0.2 mmol) in methanol (20 mL) with a positive pressure of hydrogen gas at rt for 18 hours. The title compound was isolated after filtering through a pad of Celite and concentrating to give a brown solid. (0.81 g, 84%) MS (ESI): mass calcd. for $C_{12}H_{17}NO_2$, 207.1; m/z found, 208.1 $[M+H]^+$.

Step D: 2-Chloro-4-(2-methyl-4-tetrahydropyran-4-yloxyanilino)pyridine-3-carbonitrile 2-methyl-4-((tetrahydro-2H-pyran-4-yl)oxy)aniline (0.81 g, 3.9 mmol), 2-chloro-4-iodonicotinonitrile (1.3 g, 5.1 mmol), $Cs_2CO_3$ (2.54 g, 7.8 mmol), DPEPhos (0.42 g, 0.8 mmol), $Pd(OAc)_2$ (87.5 mg, 0.4 mmol) were dissolved in 1,4-dioxane (30 mL). The mixture was stirred at 80° C. overnight. The title compound was purified by flash chromatography (PE/EA) to give a yellow solid. (1.03 g, 80%) MS (ESI): mass calcd. for $C_{18}H_{18}ClN_3O_2$, 343.1; m/z found, 344.1 $[M+H]^+$.

Intermediate 32: 5-(2-Methyl-4-phenoxyphenyl)-4-oxo-4,5-dihydro-3H-1-thia-3,5,8-triazaacenaphthylene-2-carbonyl chloride

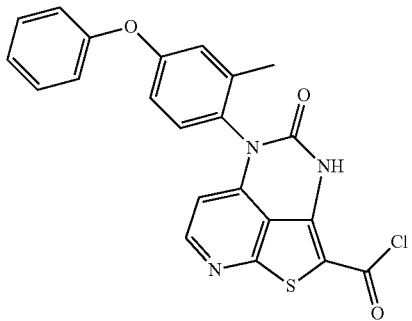 [SMILES: Cc1cc(Oc2ccccc2)ccc1N1C(=O)Nc2c(C(=O)Cl)sc3nccc1c23]

To a solution of 5-(2-methyl-4-phenoxyphenyl)-4-oxo-4,5-dihydro-3H-1-thia-3,5,8-triazaacenaphthylene-2-carboxylic acid (Intermediate 27) (500 mg, 1.2 mmol) in anhydrous DCM (20 mL) was added 2-drops of DMF and it was cooled to 0° C. Next, oxalyl dichloride (762 mg, 6 mmol) was added slowly and it was stirred at 40° C. overnight, concentrated to dryness, and the residue was used in the next step without further purification or determined yield.

Intermediate 33: (Z)-3-Acetamidoprop-2-enoic Acid

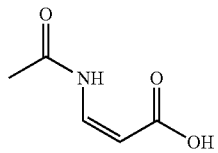

Step A: Ethyl (Z)-3-acetamidoprop-2-enoate

To a solution of ethyl prop-2-ynoate (1.246 g, 12.70 mmol), acetamide (500 mg, 8.5 mmol), TFA (4.8 g, 42 mmol), and NaOAc (1.46 g, 16.9 mmol) in toluene (15 mL) was added $Pd(OAc)_2$ (95 mg, 0.42 mmol) at rt under $N_2$ and stirred at 70° C. overnight, concentrated to dryness, and purified by flash column chromatography to give the title compound as an oil (470 mg, 35% yield).

Step B: (Z)-3-Acetamidoprop-2-enoic Acid

A solution of ethyl (Z)-3-acetamidoprop-2-enoate and $LiOH.H_2O$ in $THF/H_2O$ (1/1) was stirred at 50° C. for 1 h, then the solution was acidified with 1 M HCl and extracted with EtOAc, combining the organic layers, and concentrated to dryness to give the title compound, which was used without further purification in the next step.

Intermediate 34: 2-Chloro-4-((4-cyclobutoxy-2-methylphenyl)amino)nicotinonitrile

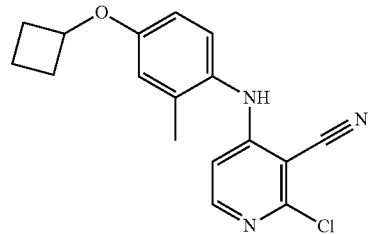 [SMILES: Cc1cc(OC2CCC2)ccc1Nc1ccnc(Cl)c1C#N]

The title compound was prepared using Method 1, steps A-C in Example 1, and using 3-methyl-4-nitro-phenol and bromocyclobutane in place of phenol and 5-fluoro-2-nitro-toluene in step A, to yield the title compound. MS (ESI): mass calcd. for $C_{17}H_{16}ClN_3O$, 313.1; m/z found, 314.0 $[M+H]^+$.

Intermediate 35: (4-Phenoxyphenyl)methanamine

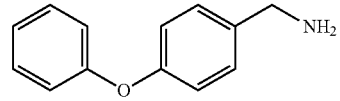 [SMILES: NCc1ccc(Oc2ccccc2)cc1]

A solution of 4-phenoxybenzaldehyde (2.0 g, 10 mmol), hydroxylamine hydrochloride (700 mg, 10 mmol), EtOH (20 ml), and water (1 ml) was stirred at room temperature overnight. To the reaction mixture were added 10 N HCl (1 ml) and of Pd/C (10% on carbon, 320 mg) and was stirred under hydrogen for 30 min. The reaction mixture was filtrated through Celite and concentrated to dryness. The residue was purified by flash column chromatography to give the title compound as a white solid (1.5 g, 75% yield).

Intermediate 36: (R)-5-(*S)-(2-Methyl-4-phenoxy-phenyl)-4-oxo-N-(pyrrolidin-3-yl)-4,5-dihydro-3H-1-thia-3,5,8-triazaacenaphthylene-2-carboxamide

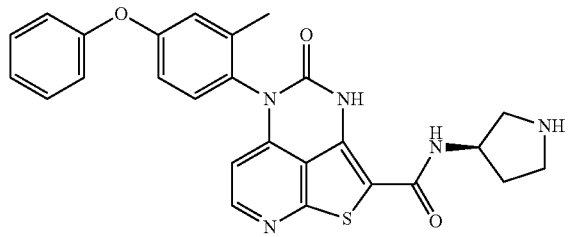 [SMILES: Cc1cc(Oc2ccccc2)ccc1N1C(=O)Nc2c(C(=O)N[C@@H]3CCNC3)sc3nccc1c23]

The title compound was prepared using Method 1, steps A-H (including Chiral Resolution Method A after step F to obtain the *S atropisomer) in Example 1, and using tert-butyl (3R)-3-aminocyclopentanecarboxylate in place of tert-butyl (3R,5R)-3-amino-5-fluoro-piperidine-1-carboxylate in step G, to yield the title compound. MS (ESI): mass calcd. for $C_{26}H_{23}N_5O_3S$, 485.2; m/z found, 486.1 [M+H]$^+$.

Intermediate 37: (E)-4-Methylsulfanylbut-2-enoic Acid

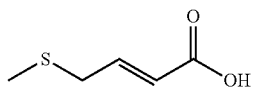

Step A: Methyl (E)-4-methylsulfanylbut-2-enoate

To a solution of methyl (E)-4-bromobut-2-enoate (1.507 g, 8.418 mmol) in MeCN (50 mL) was added 15% aqueous solution of NaSMe (0.59 g, 8.4 mmol) in water (4 mL) at −40° C. The resulting mixture was warmed at 0° C. over a period of 1 h. The reaction was dispersed between EtOAc and water, the organic layer was collected, and concentrated to dryness to give the title compound (1.231 g, 100.0% yield) and was used in the next step without further purification.

Step B: (E)-4-Methylsulfanylbut-2-enoic Acid

A solution of methyl (E)-4-methylsulfanylbut-2-enoate (1.231 g 8.418 mmol) and LiOH.H$_2$O (1.413 g, 33.67 mmol) in THF (15 mL) and water (15 mL) was stirred at room temperature for 6 hours. The reaction was adjusted to pH=3 using a 1 M aqueous solution of HCl and was dispersed between EtOAc and water. The organic layer was collected and concentrated to dryness to give the title compound (0.556 g, 50.0% yield), which was used in the next step without further purification.

Intermediate 38: (Z)-4-[tert-Butoxycarbonyl(methyl)amino]-2-fluoro-but-2-enoic Acid

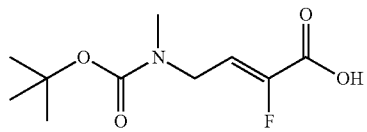 [SMILES: CN(C/C=C(\F)C(=O)O)C(=O)OC(C)(C)C]

Step A: Ethyl 2-diethoxyphosphoryl-2-fluoro-acetate

A solution of ethyl 2-bromo 2-fluoroacetate (5.0 g, 27 mmol) in triethylphosphite (13 mL) was heated at 130° C. for 23 h. The resulting mixture was distilled under low pressure (1.4 mbar, 75-110° C.) to give the title compound as a yellowish oil (6.0 g, 92%).

Step B: (Z)-4-[tert-Butoxycarbonyl(methyl)amino]-2-fluoro-but-2-enoic Acid

Ethyl 2-(diethoxyphosphoryl)-2-fluoroacetate (2.0 g, 8.3 mmol) was placed in THF (5 mL) and cooled to 0° C. in ice-bath. Next, NaH (198 mg, 8.26 mmol) was added and stirred for 30 min at 0° C. tert-Butyl N-methyl-N-(2-oxo-ethyl)carbamate (0.579 g, 3.34 mmol) was added to the reaction mixture slowly and the reaction mixture was allowed to warm to room temperature over 2 h. The reaction was quenched by the addition of DCM and water. The organic layer was collected and washed with brine, dried over anhydrous MgSO$_4$, and concentrated to dryness. The residue was dissolved in dioxane (5 mL) and water (5 mL), and NaOH (1.321 g, 33.03 mmol) was added and was reacted for 10 min at rt. The mixture was acidified with 2 M HCl to pH-2 and extracted with DCM. The organic layers were washed with brine, dried over anhydrous MgSO$_4$, and concentrated to dryness to give the title compound (500 mg, 26%).

Intermediate 39: (E/Z)-2-Chloro-3-cyclopropyl-prop-2-enoic Acid

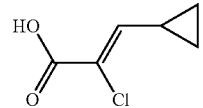

Step A: Ethyl 2,2-dichloro-2-diethoxyphosphoryl-acetate

A solution of 5% sodium hypochlorite (185 mL) was adjusted to pH 7.1 with 3 N HCl (10 mL) and ethyl 2-diethoxyphosphorylacetate (5.60 g, 25.0 mmol) was added drop wise at 0° C. with vigorous stirring over 30 min. After complete addition, the mixture was stirred for 5 min at rt and extracted with hexanes. The reaction mixture was concentrated to dryness gave the title compound as a colorless oil (0.86 g, 12% yield).

Step B: Ethyl 2-chloro-2-diethoxyphosphoryl-acetate

A solution of ethyl 2,2-dichloro-2-diethoxyphosphoryl-acetate (0.86 g, 2.9 mmol) in EtOH (6 mL) was cooled to 0° C. A solution of sodium sulfite (0.74 g, 5.9 mmol) in water (20 mL) was added at a rate that the temperature could be kept around 15° C. After the end of the addition the turbid solution was stirred at room temperature for 20 minutes before being extracted with chloroform (4×15 mL). The combined extracts were dried over anhydrous MgSO$_4$ and concentrated to dryness to give the title compound as a yellow oil (0.47 g, 62% yield).

Step C: Ethyl (E/Z)-2-chloro-3-cyclopropyl-prop-2-enoate

To a solution of NaH (60% in oil, 87 mg, 3.6 mmol) in THF (10 mL) at 0° C. was added ethyl 2-chloro-2-diethoxyphosphoryl-acetate (0.47 g, 1.8 mmol) dropwise and stirred at 0° C. for 1 h. Then cyclopropanecarbaldehyde (127 mg, 1.82 mmol) was added dropwise and stirred at 0° C. for 1 h. The mixture was quenched with saturated NH₄Cl, extracted with EtOAc, washed with brine, dried over anhydrous MgSO₄, and concentrated to dryness to give the title compound as a yellow liquid (0.24 g, 76% yield).

Step D: (E/Z)-2-Chloro-3-cyclopropyl-prop-2-enoic Acid

To a solution of ethyl (EZ)-2-chloro-3-cyclopropyl-prop-2-enoate (0.24 g, 1.4 mmol) in dioxane (5 mL) and water (5 mL) was added KOH (0.385 g, 6.87 mmol) and the mixture was stirred at 60° C. for 2 h. The pH of the mixture was adjusted to about 2, extracted with EtOAc, dried over anhydrous Na₂SO₄, filtered, and concentrated to dryness to give the title compound as a light yellow solid (0.13 g, 65% yield), which was used in the next step directly.

Intermediate 40: 4-Oxo-5-(4-phenoxyphenyl)-4,5-dihydro-3H-1-thia-3,5,8-triazaacenaphthylene-2-carbonyl chloride

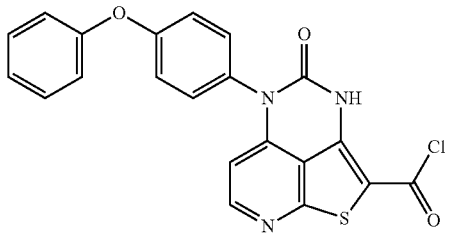 [SMILES: O=C(Cl)c1sc2nccc3c2c1NC(=O)N3c1ccc(Oc2ccccc2)cc1]

To a 50 mL flask with a stir bar were added 4-oxo-5-(4-phenoxyphenyl)-4,5-dihydro-3H-1-thia-3,5,8-triazaacenaphthylene-2-carboxylic acid (Intermediate 58) (1.0 g, 2.5 mmol) and thionyl chloride (10.0 mL, 137 mmol) and was warmed in a sand bath to reflux for 1 hour. The reaction mixture was concentrated to dryness and added DCM was added and the reaction was concentrated to dryness to give the title compound (1.046 g, 100.0% yield), which was used without further purification.

Intermediate 41: (R)-5-(2-Methyl-4-(2,3,4,5,6-pentadeuteriophenoxy)phenyl)-4-oxo-N-(piperidin-3-yl)-4,5-dihydro-3H-1-thia-3,5,8-triazaacenaphthylene-2-carboxamide

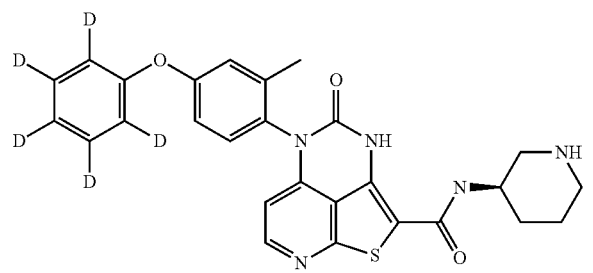 [SMILES: [2H]c1c([2H])c([2H])c(Oc2ccc(N3C(=O)Nc4c(C(=O)N[C@@H]5CCCNC5)sc5nccc3c45)c(C)c2)c([2H])c1[2H]]

The title compound was prepared using analogous conditions described in Method 1, steps A-H in Example 1, and using 2,3,4,5,6-pentadeuteriophenol in place of phenol in step A and using tert-butyl (3R)-3-aminopiperidine-1-carboxylate in place of tert-butyl (3R,5R)-3-amino-5-fluoro-piperidine-1-carboxylate in step G.

Intermediate 42: (E)-3-Cyclopropyl-2-methyl-prop-2-enoic Acid

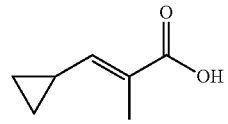

Step A: Ethyl (E)-3-cyclopropyl-2-methyl-prop-2-enoate

A solution of ethyl 2-diethoxyphosphorylpropanoate (2.38 g, 10.0 mmol) in THF (30 mL) was cooled to −78° C. and n-BuLi (2.4 N, 4.58 mL) was added dropwise and stirred at −78° C. for 1 h. Then cyclopropanecarbaldehyde (0.70 g, 10 mmol) was added dropwise and stirred at −78° C. for 1 h. The mixture was quenched with saturated aqueous NH₄Cl and extracted with EtOAc, washed with brine, dried over anhydrous Na₂SO₄, and concentrated to dryness to give the title compound as a yellow liquid (1.13 g, 73.3% yield). MS (ESI): mass calcd. for $C_9H_{14}O_2$, 154.1; m/z found, 155.1 $[M+H]^+$.

Step B: (E)-3-Cyclopropyl-2-methyl-prop-2-enoic Acid

To a solution of ethyl (E)-3-cyclopropyl-2-methyl-prop-2-enoate (1.13 g, 7.33 mmol) in dioxane (15 mL) and water (15 mL) was added KOH (2.056 g, 36.64 mmol) and the mixture was stirred at 60° C. for 2 h. The pH of the mixture was adjusted to about 2, then extracted with EtOAc, dried over anhydrous Na₂SO₄, filtered, and concentrated to dryness to give the title compound as light yellow solid (0.77 g, 83% yield), which was used in the next step directly. MS (ESI): mass calcd. for $C_7H_{10}O_2$, 126.1; m/z found, 127.1 $[M+H]^+$.

Intermediate 43: 1-[(3R)-3-Amino-1-piperidyl]-2-(dimethylamino)ethanone

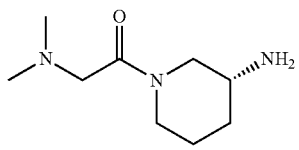

Step A: tert-Butyl N-[(3R)-1-[2-(dimethylamino)acetyl]-3-piperidyl]carbamate A solution of tert-butyl (3R)-3-aminopiperidine-1-carboxylate (400 mg, 2.0 mmol), 2-(dimethylamino)acetic acid (226 mg, 2.19 mmol), HATU (911 mg, 2.40 mmol), and triethylamine (0.557 mL, 4.00 mmol) in DMF (5 mL) was stirred at rt overnight, then poured into water. The mixture was extracted with EtOAc, the combined organic layers were washed with brine, dried over anhydrous $Na_2SO_4$, filtered, and concentrated to dryness to give the title compound as a yellow oil (399 mg, 70%).

Step B: 1-[(3R)-3-Amino-1-piperidyl]-2-(dimethyl-amino)ethanone

A solution of tert-butyl N-[(3R)-1-[2-(dimethylamino)acetyl]-3-piperidyl]carbamate (200 mg, 0.70 mmol) in 2 M HCl in MeOH (2 mL) was stirred at rt overnight. The reaction was concentrated to dryness and the residue was used in next step without further purification (150 mg, quantitative). MS (ESI): mass calcd. for $C_9H_{19}N_3O$, 185.2; m/z found, 186.1 $[M+H]^+$.

Intermediate 44: (E)-2-Cyano-4,4-dimethyl-pent-2-enoic acid or (E)-2-cyano-4,4-dimethylpent-2-enoic Acid

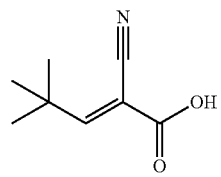

A stirred solution of 2-cyanoacetic acid (1.70 g, 20 mmol), pivalaldehyde (1.72 g, 20 mmol) and $NH_4OAc$ (60 mg, 0.8 mmol) in toluene was heated to reflux with Dean-Stark removal of water. When generation of water ceased, the mixture was cooled to room temperature and concentrated under reduced pressure to yield the title product as a yellow solid (2.13 g, 69% yield).

Intermediate 45:
1-Bromo-2-fluoro-5-methyl-4-nitrobenzene

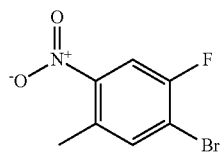

A solution of 4-bromo-5-fluoro-2-methylaniline (10.2 g, 50 mmol) and 3-chlorobenzenecarboperoxoic acid (34.5 g, 200 mmol) in DCE (10 mL) was stirred under nitrogen at reflux for 2 hours. After cooling to rt, the mixture was dispersed between DCM and saturated aqueous $Na_2SO_3$ solution. The organic layer was collected, concentrated to dryness and purified by flash column chromatography to give the title compound as a brown oil (7.02 g, 60.0% yield).

Intermediate 46: [1,1'-Biphenyl]-3-amine

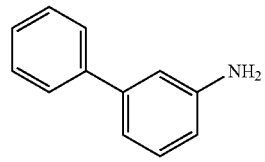 [SMILES: Nc1cccc(-c2ccccc2)c1]

To a solution of phenylboronic acid (12.193 g, 100.00 mmol) in MeOH (150 mL) were added sequentially $Na_2CO_3$ (21.198 g, 200.00 mmol) and 3-bromoaniline (17.202 g, 100.00 mmol), and then $Pd(OAc)_2$ (562 mg, 2.50 mmol) was added and the reaction was heated to reflux until a black suspension appeared. The reaction was cooled to room temperature, diluted with MeOH, and the black precipitate was removed by filtration. The filtrate was concentrated to dryness and the residue was added to water and DCM. The organic phase was collected, dried over anhydrous $Na_2SO_4$, and concentrated to dryness to give the title compound (18.373 g, 100.00% yield) as a brown oil. MS (ESI): mass calcd. for $C_{12}H_{11}N$, 169.22; m/z found, 170.0 $[M+H]^+$.

Intermediate 47:
3-(Tetrahydro-2H-pyran-4-yl)aniline

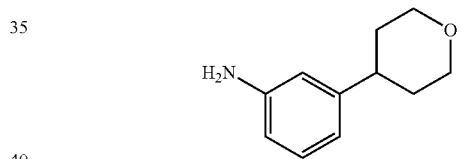

Step A: 3-(3,6-Dihydro-2H-pyran-4-yl)aniline

A solution of 3-bromoaniline (0.9 mL, 8.10 mmol), 3,6-Dihydro-2H-pyran-4-boronic acid pinacol ester (5.11 g, 24.3 mmol) and X-phos-palladium precatalyst generation 1 (163 mg, 0.203 mmol) in dioxane (6.1 mL) and 0.5 M $K_3PO_4H_2O$ (12.2 mL) was stirred at 90° C. for 16 h. The reaction mixture was concentrated to dryness and the residue was purified by FCC ($SiO_2$, 0-10% MeOH (2 N NH3)/DMC) to give the title compound (320 mg, 17%).

Step B: 3-(Tetrahydro-2H-pyran-4-yl)aniline

A solution of 3-(3,6-dihydro-2H-pyran-4-yl)aniline (2.0 g, 4.87 mmol) in 1:1 MeOH:DCM (97 mL) was passed through an H-Cube® hydrogenation flow reactor (recycling @ 80° C., 1 atm, 1.5 mL/min, 10% Pd/C) for 16 h. The solution as concentrated then purified (FCC, EtOAc-hexanes) to give the title compound (548 mg, 63%) as a white solid. MS (ESI): mass calcd. for $C_{21}H_{21}N_5O_2S$, 407.1; m/z found, 408 $[M+H]^+$.

Intermediate 48: 3-Methyl-2-phenylpyridin-4-amine

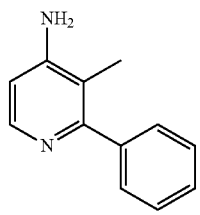

Step A: 3-Methyl-2-phenylpyridin-4-amine

To a solution of 4-bromo-2-chloro-3-methylpyridine (2.20 g, 10.7 mmol), tert-butyl carbamate (1.248 g, 10.66 mmol), Pd(dppf)Cl$_2$ (435 mg, 0.533 mmol), Xantphos (616 mg, 1.07 mmol), and Cs$_2$CO$_3$ (6.926 g, 21.31 mmol) in dioxane (60 mL) was heated at reflux under N$_2$ overnight. The reaction was concentrated to dryness and the residue was purified by flash column chromatography to give white solid that was used directly in the next step.

Step B: 3-Methyl-2-phenylpyridin-4-amine

3-Methyl-2-phenylpyridin-4-amine was dissolved in dioxane and H$_2$O, Pd(dppf)Cl$_2$ (435 mg, 0.533 mmol), and Na$_2$CO$_3$ (2.259 g, 21.31 mmol) were added and stirred at reflux overnight. The reaction was concentrated to dryness and the residue was purified by flash column chromatography to give yellow solid. The yellow solid was dissolved in HCl and MeOH and stirred at 60° C. for 30 min. Then 1 M NaOH was added and was extracted with EtOAc (30 mL×3) and concentrated to dryness to give the title compound (700 mg, 36% yield) as a pale yellow solid. MS (ESI): mass calcd. for C$_{12}$H$_{12}$N$_2$, 184.24; m/z found, 185.1 [M+H]$^+$.

Intermediate 49: 2-Methyl-6-phenoxypyridin-3-amine

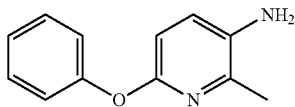

Step A: 2-methyl-3-nitro-6-phenoxypyridine

A round bottom flask containing 6-chloro-2-methyl-3-nitropyridine (50.1 g, 290 mmol) and CH$_3$CN (230 mL) was cooled at 0° C. Phenol (41.0 g, 436 mmol) was added followed by Cs$_2$CO$_3$ (148 g, 454 mmol). The reaction mixture was allowed to warm to room temperature and stirred for 15 h. The mixture was transferred to a 2 L Erlenmeyer flask, then diluted with water to a total volume of 1.8 L. The resulting suspension was stirred at room temperature for 10 min, then the solid was isolated by filtration, rinsed with water and dried to yield the title compound (64.7 g, 97% yield) as a brown solid. MS (ESI): mass calcd. for C$_{12}$H$_{10}$N$_2$O$_3$, 230.07; m/z found, 231.0 [M+H]$^+$.

Step B: 2-methyl-6-phenoxypyridin-3-amine

A round bottom flask containing 2-methyl-3-nitro-6-phenoxypyridine (64.7 g, 281 mmol) was treated with EtOH (500 mL) and a suspension of 10% Pd/C (4.17 g) in EtOH (300 mL). The mixture was degassed under vacuum and vented to an atmosphere of H$_2$. The reaction was stirred vigorously at room temperature for 7 h. The reaction mixture was filtered through celite, the filtrate was concentrated to about 400 mL, then water was added slowly until the total volume was 1.5 L. The resulting precipitate was filtered, and the filter cake was rinsed with water then dried under vacuum to provide the title compound (50.5 g, 90%) as an off-white solid. MS (ESI): mass calcd. for C$_{12}$H$_{12}$N$_2$O, 200.09; m/z found, 201.0 [M+H]$^+$.

Intermediate 50: (2R)-1-[(3R)-3-Amino-1-piperidyl]-3-methoxy-2-methyl-propan-1-one

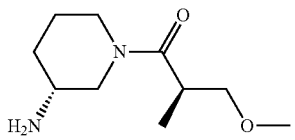

Step A: tert-Butyl N-[(3R)-1-[(2S)-2-hydroxypropanoyl]-3-piperidyl]carbamate

To a solution of (2R)-3-hydroxy-2-methyl-propanoic acid (78 mg, 0.75 mmol), HATU (342 mg, 0.90 mmol), and triethylamine (0.157 mL, 1.12 mmol) in DMF (3 mL) was added tert-butyl N-[(3R)-3-piperidyl]carbamate and the reaction was stirred at rt overnight. The reaction mixture was purified using flash column chromatography to give the title compound as a colorless liquid (138 mg, 68%).

Step B: tert-Butyl N-[(3R)-1-[(2R)-3-methoxy-2-methyl-propanoyl]-3-piperidyl]carbamate A solution of tert-butyl N-[(3R)-1-[(2S)-2-hydroxypropanoyl]-3-piperidyl]carbamate (128 mg, 0.447 mmol), Ag$_2$O (311 mg, 1.34 mmol), MeI (1 mL), and DCM (2 mL) was sparged with N2 and stirred at 40° C. for 3 days. The mixture was filtered through a pad of Celite and the filtrated was concentrated to dryness to give the title compound (121 mg, 91%), was used in next step without further purification.

Step C: (2R)-1-[(3R)-3-Amino-1-piperidyl]-3-methoxy-2-methyl-propan-1-one

To a solution of 2 M HCl in MeOH (2 mL) was added tert-butyl N-[(3R)-1-[(2R)-3-methoxy-2-methyl-propanoyl]-3-piperidyl]carbamate (121 mg, 0.403 mmol). The reaction mixture was stirred at rt overnight. The reaction mixture was concentrated to dryness to give the title compound (73 mg, 90%), was used in next step without further purification. MS (ESI): mass calcd. for C$_{10}$H$_{20}$N$_2$O$_2$, 200.2; m/z found, 201.2 [M+H]$^+$.

Intermediate 51: 3-Methyl-5-phenoxy-pyrazin-2-amine

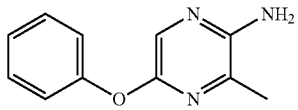

A solution of 5-bromo-3-methyl-pyrazin-2-amine (1000 mg, 5.32 mmol), phenol (650 mg, 6.91 mmol), Cs$_2$CO$_3$ (2600 mg, 7.98 mmol), CuI (203 mg, 1.06 mmol), and N,N-dimethylglycine (110 mg, 1.06 mmol) in dioxane (5 mL) was degassed and heated to 90° C. under N$_2$ for 12 h. After cooling to room temperature, the mixture was diluted with EtOAc (100 mL) and water (100 mL) and the organic phase collected. The aqueous layer was extracted again with EtOAc (100 mL) and the combined organic layers were dried over anhydrous MgSO$_4$ and concentrated to dryness. The residue was purified by flash column chromatography to give the title compound as a yellow oil (533 mg, 49.8% yield). MS (ESI): mass calcd. for C$_{11}$H$_{11}$N$_3$O, 201.1; m/z found, 202.1 [M+H]$^+$.

Intermediate 52: (E)-4-(tert-Butoxycarbonylamino)-2-fluoro-but-2-enoic Acid

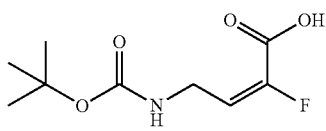

Step A: Ethyl (E)-4-((tert-Butoxycarbonyl)amino)-2-fluorobut-2-enoate

A solution of ethyl 2-(diethoxyphosphoryl)-2-fluoroacetate (500 mg, 2.07 mmol) in THF (5 mL) was cooled to 0° C. in ice-batch and NaH (60%, 50.0 mg, 2.07 mmol) was added and was stirred for 30 min. tert-Butyl (2-oxoethyl) carbamate was added to the reaction mixture slowly and the reaction mixture was allowed to warm to room temperature and stirred for 2 h. The reaction was worked up with DCM and water. The organic layer was washed with brine, dried over anhydrous MgSO$_4$, and concentrated to dryness to give the title compound.

Step B: (E)-4-(tert-Butoxycarbonylamino)-2-fluoro-but-2-enoic Acid

The intermediate ethyl (E)-4-((tert-butoxycarbonyl) amino)-2-fluorobut-2-enoate was dissolved in dioxane (5 mL) and water (5 mL), and NaOH was added and was reacted for 10 min. The mixture was acidified with 2 M HCl to pH~2 and extracted with DCM. The organics were washed with brine, dried over anhydrous MgSO$_4$, and concentrated to dryness to give the title compound as a white solid (210 mg, 46% yield).

Intermediate 53: (Z)-4-(tert-Butoxycarbonylamino)-2-chloro-but-2-enoic Acid

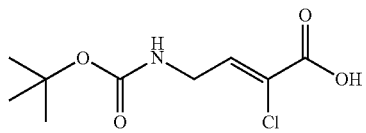

Step A: Ethyl (Z)-4-(tert-butoxycarbonylamino)-2-chloro-but-2-enoate

A solution of NaH (60%, 0.186 g, 7.73 mmol) and THF (15 mL) was cooled to 0° C. and ethyl 2-chloro-2-diethoxy-phosphoryl-acetate (1.0 g, 3.9 mmol) was added drop wise and stirred at 0° C. for 1 h. Then tert-butyl N-(2-oxoethyl) carbamate (0.615 g, 3.87 mmol) was added dropwise and stirred at 0° C. for 1 h. The mixture was quenched with saturated aqueous NH$_4$Cl, extracted with EtOAc, washed with brine, dried over anhydrous Na$_2$SO$_4$, and concentrated to dryness to give the title compound as yellow liquid (0.59 g, 58%).

Step B: (Z)-4-(tert-Butoxycarbonylamino)-2-chloro-but-2-enoic Acid

To a solution of ethyl (Z)-4-(tert-butoxycarbonylamino)-2-chloro-but-2-enoate (0.590 g, 2.24 mmol) in dioxane (10 mL) and H$_2$O (10 mL) was added KOH (0.628 g, 11.2 mmol) and the mixture was stirred at 60° C. for 2 h. Then the pH of the mixture was adjusted to about 2, extracted with EtOAc, dried over anhydrous Na$_2$SO$_4$, filtered, and concentrated to dryness to give the title compound as a light yellow solid (0.37 g, 70% yield), which was used in the next step directly.

Intermediate 54: 4-Oxo-5-(o-tolyl)-4,5-dihydro-3H-1-thia-3,5,8-triazaacenaphthylene-2-carboxylic Acid

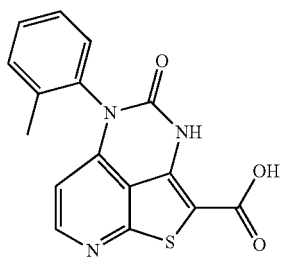 [SMILES: Cc1ccccc1N1C(=O)Nc2c(C(=O)O)sc3nccc1c23]

The title compound was prepared using Method 1, steps C-F in Example 1, using o-toluidine in place of 2-methyl-4-phenoxyaniline in step C. MS (ESI): mass calcd. for C$_{16}$H$_{11}$N$_3$O$_3$S, 325.1; m/z found, 326.0 [M+H]$^+$.

Intermediate 55: 5-(4-Methoxy-2-methylphenyl)-4-oxo-4,5-dihydro-3H-1-thia-3,5,8-triazaacenaphthylene-2-carboxylic Acid

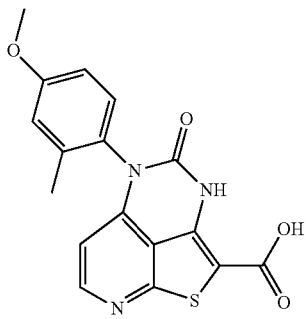 [SMILES: COc1ccc(N2C(=O)Nc3c(C(=O)O)sc4nccc2c34)c(C)c1]

The title compound was prepared using Method 1, steps C-F, in Example 1, using 4-methoxy-2-methylaniline in place of 2-methyl-4-phenoxyaniline in step C. MS (ESI): mass calcd. for $C_{17}H_{13}N_3O_4S$, 355.1; m/z found, 356.0 $[M+H]^+$.

Intermediate 56: 2-Amino-5-(2-methyl-4-phenoxyphenyl)-3H-1-thia-3,5,8-triazaacenaphthylen-4(5H)-one

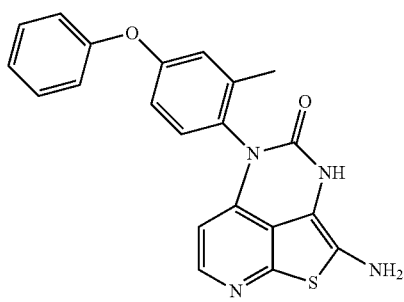 [SMILES: Cc1cc(Oc2ccccc2)ccc1N1C(=O)Nc2c(N)sc3nccc1c23]

Step A: tert-Butyl (5-(2-methyl-4-phenoxyphenyl)-4-oxo-4,5-dihydro-3H-1-thia-3,5,8-triazaacenaphthylen-2-yl)carbamate 5-(2-Methyl-4-phenoxyphenyl)-4-oxo-4,5-dihydro-3H-1-thia-3,5,8-triazaacenaphthylene-2-carboxylic acid (Intermediate 16) (200 mg, 0.479 mmol) was heated under reflux in redistilled thionyl chloride (0.50 mL) for 5 h. The thionyl chloride was removed under reduced pressure and the residue was taken up in dry acetone (2 mL), cooled to 0° C., and sodium azide (500 mg, 7.69 mmol) was added dropwise with stirring and the solution was allowed to warm to 20° C. over 10 min. The reaction was diluted with water, extracted with EtOAc, and the solvent was removed under reduced pressure. The residue was taken up into t-butyl alcohol (37.5 mL) and was heated at reflux for 5 h. The reaction was concentrated to dryness to give the title compound (180 mg, 53.9% yield). MS (ESI): mass calcd. for $C_{26}H_{24}N_4O_4S$, 488.56; m/z found, 489.0 $[M+H]^+$.

Step B: 2-Amino-5-(2-methyl-4-phenoxyphenyl)-3H-1-thia-3,5,8-triazaacenaphthylen-4(5H)-one To a solution of tert-butyl (5-(2-methyl-4-phenoxyphenyl)-4-oxo-4,5-dihydro-3H-1-thia-3,5,8-triazaacenaphthylen-2-yl)carbamate (180 mg, 0.258 mmol) in DCM (10 mL) were added 2,6-lutidine (166 mg, 1.55 mmol) and trimethylsilyl trifluoromethanesulfonate (344 mg, 1.55 mmol) and was stirred at 20° C. for 2 h. The reaction was quenched by the addition of $NaHCO_3$ in ice water. The organic layer was separated and the aqueous layer was extracted with ethyl acetate (2×50 mL). The organic layers were combined, washed with brine, dried over anhydrous $MgSO_4$, filtered, and concentrated to dryness. The residue was purified by preparative HPLC (column: YMC-Actus Triart C18 150×30 mm, 5 μm, mobile phase A: water (0.075% TFA (aq.), V/V; B: acetonitrile, B in A from 35% to 65%, flow rate: 35 mL/min) to give the title compound (40 mg, 28% yield). MS (ESI): mass calcd. for $C_{21}H_{16}N_4O_2S$, 388.1; m/z found, 389.1 $[M+H]^+$.

Intermediate 57: 5-(3-Bromophenyl)-4-oxo-4,5-dihydro-3H-1-thia-3,5,8-triazaacenaphthylene-2-carboxylic Acid

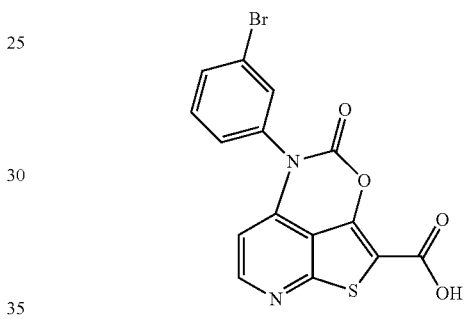

The title compound was prepared using Method 1, steps C-F in Example 1, and using 3-bromoaniline in place of 2-methyl-4-phenoxy-aniline in step C. MS (ESI): mass calcd. for $C_{15}H_8BrN_3O_3S$, 388.9; m/z found, 390.2 $[M+H]^+$.

Intermediate 58: 4-Oxo-5-(4-phenoxyphenyl)-4,5-dihydro-3H-1-thia-3,5,8-triazaacenaphthylene-2-carboxylic Acid

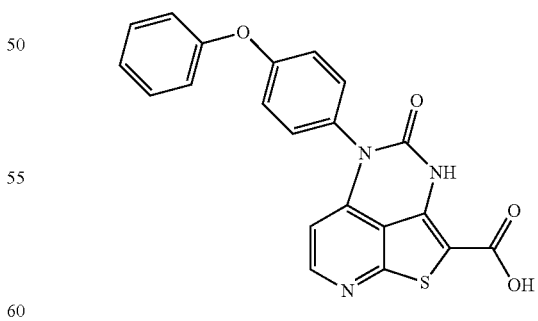

The title compound was prepared using Method 1, steps A-F in Example 1, using 4-fluoronitrobenzene in place of 5-fluoro-2-nitrotoluene in step A. MS (ESI): mass calcd. for $C_{21}H_{13}N_3O_4S$, 403.1; m/z found, 404.0 $[M+H]^+$. $^1H$ NMR (500 MHz, DMSO-d6): δ 8.36 (d, J=5.5 Hz, 1H), 7.52-7.42 (m, 4H), 7.25-7.11 (m, 6H), 6.09 (d, J=5.5 Hz, 1H).

Intermediate 59: 4-Oxo-5-(3-phenoxyphenyl)-4,5-dihydro-3H-1-thia-3,5,8-triazaacenaphthylene-2-carboxylic Acid

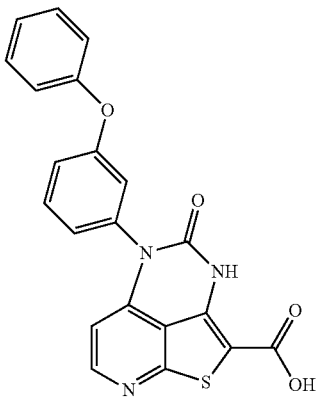 [SMILES: O=C(O)c1sc2nccc3c2c1NC(=O)N3c1cccc(Oc2ccccc2)c1]

The title compound was prepared using Method 1, steps C-F, in Example 1, using 3-phenoxyaniline in place of 2-methyl-4-phenoxyaniline in step C. MS (ESI): mass calcd. for $C_{21}H_{13}N_3O_4S$, 403.1; m/z found, 404.1 $[M+H]^+$.

Intermediate 60: 4-Oxo-5-(5-phenoxypyridin-2-yl)-4,5-dihydro-3H-1-thia-3,5,8-triazaacenaphthylene-2-carboxylic Acid

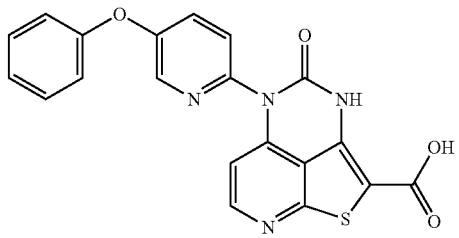 [SMILES: O=C(O)c1sc2nccc3c2c1NC(=O)N3c1ccc(Oc2ccccc2)cn1]

Step A: 2-Nitro-5-phenoxypyridine

A round bottom flask containing 5-bromo-2-nitropyridine (300 g, 1480 mmol) and DMSO (1200 mL) was treated with phenol (167 g, 1770 mmol) followed by $Cs_2CO_3$ (722 g, 2220 mmol). The reaction mixture was stirred at 50° C. for 4 h. The mixture was transferred to a flask containing ice-water (5 L). The resulting precipitate was collected by filtration, rinsed with water, and dried at 70° C. under vacuum to yield the title compound (230 g, 72% yield) as a grey solid. MS (ESI): mass calcd. for $C_{11}H_8N_2O_3$, 216.05; m/z found, 217.0 $[M+H]^+$.

Step B: 5-Phenoxypyridin-2-amine

To a solution of 2-nitro-5-phenoxypyridine (100 g, 463 mmol) in MeOH (1.5 L) was added 10% Pd—C (10 g). The reaction mixture was stirred under an atmosphere of $H_2$ at room temperature for 24 hours. The mixture was filtered, and the filtrate was concentrated to dryness under vacuo to yield the title compound (85 g, 99% yield) as a yellow solid. MS (ESI): mass calcd. for $C_{11}H_{10}N_2O$, 186.08; m/z found, 187.1 $[M+H]^+$.

Step C: Methyl 3-amino-4-((5-phenoxypyridin-2-yl)amino)thieno[2,3-b]pyridine-2-carboxylate To a round bottom flask containing 2-chloro-4-iodopyridine-3-carbonitrile (148 g, 559 mmol) and 5-phenoxypyridin-2-amine (80.0 g, 430 mmol) were added $Pd(OAc)_2$ (9.62 g, 43.0 mmol), followed by bis(2-diphenylphosphinophenyl)ether (DPEphos, 46.2 g, 85.9 mmol), and cesium carbonate (350.0 g, 107.0 mmol). The reaction mixture was treated with 1,4-dioxane (2 L), the vessel was purged with $N_2$, then stirred at 105° C. for 3 h. Methyl 2-sulfanylacetate (68.4 g, 644 mmol) was added, and the reaction was heated for an additional 16 h at 105° C. The reaction mixture was filtered, the filtrate was concentrated to dryness, and the residue was treated with MeOH (800 mL). The resulting solid was isolated by filtration and dried under vacuum to give the title compound (130 g, 77%) as a yellow solid. MS (ESI): mass calcd. for $C_{20}H_{16}N_4O_3S$, 392.09; m/z found, 393.2 $[M+H]^+$.

Step D: Methyl 4-oxo-5-(5-phenoxypyridin-2-yl)-4,5-dihydro-3H-1-thia-3,5,8-triazaacenaphthylene-2-carboxylate To a round bottom flask were added methyl 3-amino-4-((5-phenoxypyridin-2-yl)amino)thieno[2,3-b]pyridine-2-carboxylate (28.3 g, 72.1 mmol), carbonyldiimidazole (58.5 g, 361 mmol), and 1,4-dioxane (200 ml). The reaction was heated at reflux for 16 h. Then the reaction mixture was concentrated to dryness and the residue was treated with MeOH (200 mL). The resulting precipitate was isolated by filtration, rinsed with cold MeOH, and dried under vacuum to yield the title compound (21.0 g, 70% yield) as a yellow solid. MS (ESI): mass calcd. for $C_{21}H_{14}N_4O_4S$, 418.07; m/z found, 419.0 $[M+H]^+$.

Step E: 4-Oxo-5-(5-phenoxypyridin-2-yl)-4,5-dihydro-3H-1-thia-3,5,8-triazaacenaphthylene-2-carboxylic Acid To a round bottom flask were added methyl 4-oxo-5-(5-phenoxypyridin-2-yl)-4,5-dihydro-3H-1-thia-3,5,8-triazaacenaphthylene-2-carboxylate (20.0 g, 47.8 mmol), lithium hydroxide (20.0 g, 476 mmol), THF (250 mL), MeOH (100 mL), and water (100 mL). The reaction mixture was stirred at 80° C. for 4 h. The mixture was concentrated to dryness and diluted with $H_2O$ (100 mL). The pH was adjusted to 1 with 1 M HCl and the precipitate was filtered and dried to yield the title compound (18.0 g, 93% yield) as yellow solid. MS (ESI): mass calcd. for $C_{20}H_{12}N_4O_4S$, 404.06; m/z found, 405.0 $[M+H]^+$.

Intermediate 61: 4-Oxo-N-(piperidin-3-yl)-5-(o-tolyl)-4,5-dihydro-3H-1-thia-3,5,8-triazaacenaphthylene-2-carboxamide

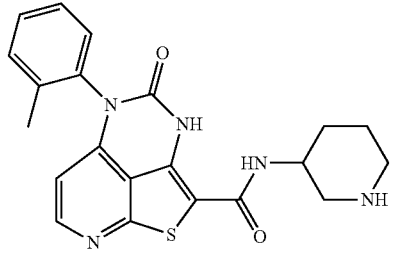 [SMILES: Cc1ccccc1N1C(=O)Nc2c(C(=O)NC3CCCNC3)sc3nccc1c23]

The title compound was prepared using Method 1, step G-H in Example 1, using using 4-oxo-5-(o-tolyl)-4,5-dihydro-3H-1-thia-3,5,8-triazaacenaphthylene-2-carboxylic acid (Intermediate 54) and tert-butyl-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid and tert-butyl (3R,5R)-3-amino-5-fluoropiperidine-1-carboxylate. MS (ESI): mass calcd. for $C_{21}H_{21}N_5O_2S$, 407.1; m/z found, 408.1 $[M+H]^+$.

Intermediate 62: 5-(2-Methyl-3-phenoxyphenyl)-4-oxo-4,5-dihydro-3H-1-thia-3,5,8-triazaacenaphthylene-2-carboxylic Acid

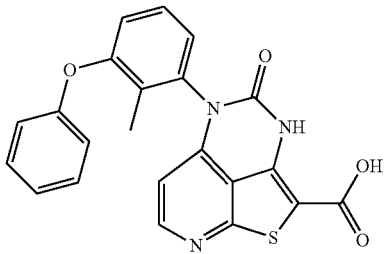 [SMILES: Cc1c(Oc2ccccc2)cccc1N1C(=O)Nc2c(C(=O)O)sc3nccc1c23]

The title compound was prepared using Method 1, steps A-F, in Example 1, using 1-bromo-2-methyl-3-nitrobenzene in place of 4-fluoro-2-methyl-1-nitrobenzene in step A. MS (ESI): mass calcd. for $C_{22}H_{15}N_3O_4S$, 417.1; m/z found, 418.0 $[M+H]^+$.

Intermediate 63: (*R)-5-(2-Methyl-4-phenoxyphenyl)-4-oxo-4,5-dihydro-3H-1-thia-3,5,8-triazaacenaphthylene-2-carboxylic Acid

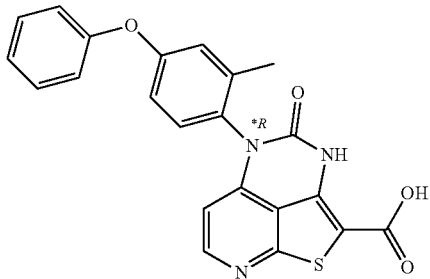 [SMILES: Cc1cc(Oc2ccccc2)ccc1N1C(=O)Nc2c(C(=O)O)sc3nccc1c23]

The title compound was prepared using Method 1, steps A-F in Example 1 (including Chiral resolution Method A after Step F to obtain the *R atropisomer). MS (ESI): mass calcd. for $C_{22}H_{15}N_3O_4S$, 417.1; m/z found, 418.0 $[M+H]^+$.

Intermediate 64: 5-(2-Methyl-5-phenoxyphenyl)-4-oxo-4,5-dihydro-3H-1-thia-3,5,8-triazaacenaphthylene-2-carboxylic Acid

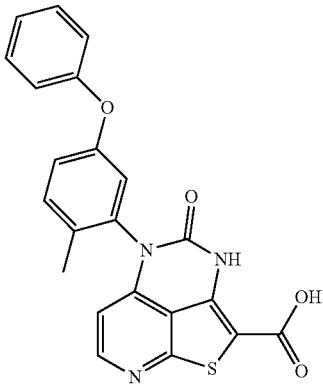 [SMILES: Cc1ccc(Oc2ccccc2)cc1N1C(=O)Nc2c(C(=O)O)sc3nccc1c23]

Step A: 1-Methyl-2-nitro-4-phenoxybenzene

A mixture of 4-methyl-3-nitrophenol (3.06 g, 20 mmol), phenylboronic acid (4.88 g, 40 mmol), Cu(AcO)$_2$ (5.20 g, 40 mmol) and 4A MS (1.5 g) in DCM was stirred at rt under oxygen overnight, then the reaction was filtrated and concentrated. The crude was purified using with ISCO eluting with PE/EA to give the title compound (3.16 g, 67%).

Step B: 5-(2-Methyl-5-phenoxyphenyl)-4-oxo-4,5-dihydro-3H-1-thia-3,5,8-triazaacenaphthylene-2-carboxylic Acid The title compound was prepared using Method 1, steps B-F, in Example 1, using 1-methyl-2-nitro-4-phenoxybenzene in place of 2-methyl-1-nitro-4-phenoxybenzene in step B. MS (ESI): mass calcd. for $C_{22}H_{15}N_3O_4S$, 417.1; m/z found, 418.0 $[M+H]^+$.

Intermediate 65: 5-(2-Fluoro-4-phenoxyphenyl)-4-oxo-4,5-dihydro-3H-1-thia-3,5,8-triazaacenaphthylene-2-carboxylic Acid

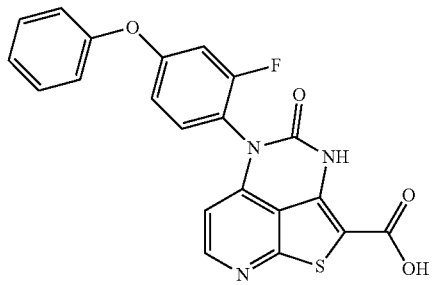 [SMILES: O=C(O)c1sc2nccc3c2c1NC(=O)N3c1ccc(Oc2ccccc2)cc1F]

The title compound was prepared using conditions analogous to Intermediate 64, steps A-B, using 3-fluoro-4-nitrophenol in place of 4-methyl-3-nitrophenol. MS (ESI): mass calcd. for $C_{21}H_{12}FN_3O_4S$, 421.1; m/z found, 422.0 $[M+H]^+$.

Intermediate 66: 5-(4-Methoxy-2-methylphenyl)-4-oxo-N-(piperidin-3-yl)-4,5-dihydro-3H-1-thia-3,5,8-triazaacenaphthylene-2-carboxamide

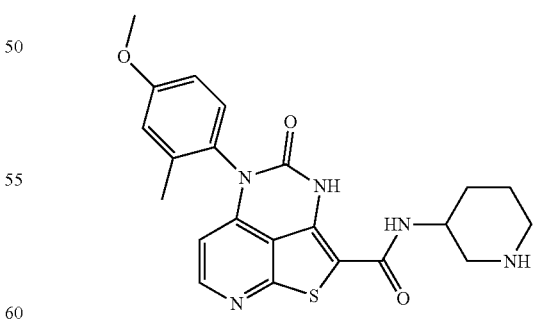

The title compound was prepared using Method 1, step G in Example 1, and using 5-(4-methoxy-2-methylphenyl)-4-oxo-4,5-dihydro-3H-1-thia-3,5,8-triazaacenaphthylene-2-carboxylic acid (Intermediate 55) and tert-butyl-3-aminopiperidine-1-carboxylate in place of 5-(2-methyl-4-phenoxyphenyl)-4-oxo-4,5-dihydro-3H-1-thia-3,5,8- triazaacenaphthylene-2-carboxylic acid and tert-butyl (3R,5R)-3-amino-5-fluoropiperidine-1-carboxylate. MS (ESI): mass calcd. for $C_{22}H_{23}N_5O_3S$, 437.2; m/z found, 438.1 $[M+H]^+$.

Intermediate 67: 5-(4-(2-Methoxyphenoxy)-2-methylphenyl)-4-oxo-4,5-dihydro-3H-1-thia-3,5,8-triazaacenaphthylene-2-carboxylic Acid

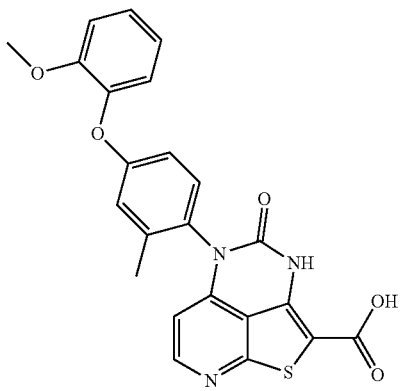 [SMILES: COc1ccccc1Oc1ccc(N2C(=O)Nc3c(C(=O)O)sc4nccc2c34)c(C)c1]

Step A: Methyl 5-(4-bromo-2-methylphenyl)-4-oxo-4,5-dihydro-3H-1-thia-3,5,8-triazaacenaphthylene-2-carboxylate The title compound was prepared using Method 1, steps C-E, in Example 1, using 4-bromo-2-methylaniline in place of 2-methyl-4-phenoxyaniline in step C as a yellow solid.

Step B: Methyl 5-(4-(2-methoxyphenoxy)-2-methylphenyl)-4-oxo-4,5-dihydro-3H-1-thia-3,5,8-triazaacenaphthylene-2-carboxylate The mixture of methyl 5-(4-bromo-2-methylphenyl)-4-oxo-4,5-dihydro-3H-1-thia-3,5,8-triazaacenaphthylene-2-carboxylate (1.0 g, 2.2 mmol), 2-methoxyphenol (1.1 g, 8.9 mmol), $Cs_2CO_3$ (1.4 g, 4.4 mmol), CuCl (44 mg, 0.44 mmol), quinolin-8-ol (64 mg, 0.44 mmol) in NMP (10 mL) was stirred at 165° C. in sealed tube for 35 minutes. Then was purified by flash column chromatography eluting with PE/EA to yield the title compound (634 mg, 62% yield) as a grey solid.

Step C: 5-(4-(2-Methoxyphenoxy)-2-methylphenyl)-4-oxo-4,5-dihydro-3H-1-thia-3,5,8-triazaacenaphthylene-2-carboxylic Acid The title compound was prepared using Method 1, step F, in Example 1, using methyl 5-(4-(2-methoxyphenoxy)-2-methylphenyl)-4-oxo-4,5-dihydro-3H-1-thia-3,5,8-triazaacenaphthylene-2-carboxylate in place of methyl 5-(2-methyl-4-phenoxyphenyl)-4-oxo-4,5-dihydro-3H-1-thia-3,5,8-triazaacenaphthylene-2-carboxylate as a grey solid. MS (ESI): mass calcd. for $C_{23}H_{17}N_3O_5S$, 447.1; m/z found, 448.0 $[M+H]^+$.

Intermediate 68: Methyl 5-(3-chloro-4-phenoxyphenyl)-4-oxo-4,5-dihydro-3H-1-thia-3,5,8-triazaacenaphthylene-2-carboxylate

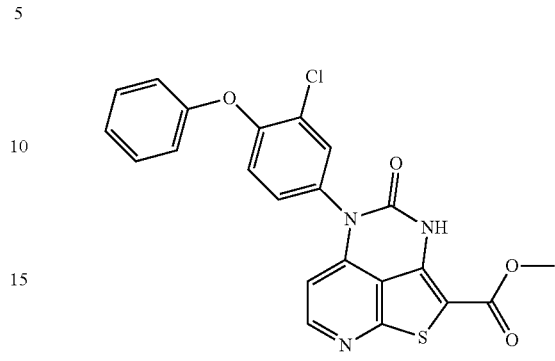

Step A: 3-Chloro-4-phenoxyaniline

The title compound was prepared using analogous conditions described in Method 1, steps A-B in Example 1, and using 2-chloro-1-fluoro-4-nitrobenzene in place of 5-fluoro-2-nitrotoluene in step A, to give the title compound. MS (ESI): mass calcd. for $C_{12}H_{10}ClNO$, 219.67; m/z found, 220.1 $[M+H]^+$.

Step B: Methyl 5-(3-chloro-4-phenoxyphenyl)-4-oxo-4,5-dihydro-3H-1-thia-3,5,8-triazaacenaphthylene-2-carboxylate The title compound was prepared using analogous conditions described in Example 534, step A, and using 3-chloro-4-phenoxyaniline and methyl 2-sulfanylacetate in place of 3-cyclobutylaniline and tert-butyl (3R)-3-[(2-sulfanylacetyl)amino]piperidine-1-carboxylate (Intermediate 22), to give the title compound. MS (ESI): mass calcd. for $C_{12}H_{10}ClNO$, 219.0; m/z found, 220.1 $[M+H]^+$.

Intermediate 69: 5-(4-Methoxybenzyl)-4-oxo-4,5-dihydro-3H-1-thia-3,5,8-triazaacenaphthylene-2-carboxylic Acid

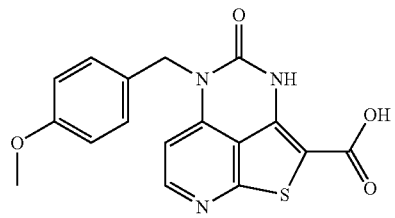 [SMILES: COc1ccc(CN2C(=O)Nc3c(C(=O)O)sc4nccc2c34)cc1]

The title compound was prepared using Method 1, steps C-F in Example 1, using (4-methoxyphenyl)methanamine in place of 2-methyl-4-phenoxyaniline and DIPEA in place of $Cs_2CO_3$, $Pd(AcO)_2$ and DPEphos in step C. MS (ESI): mass calcd. for $C_{17}H_{13}N_3O_4S$, 355.1; m/z found, 356.0 $[M+H]^+$.

Intermediate 70: (R)-5-(4-Isopropoxy-2-methylphenyl)-4-oxo-N-(piperidin-3-yl)-4,5-dihydro-3H-1-thia-3,5,8-triazaacenaphthylene-2-carboxamide

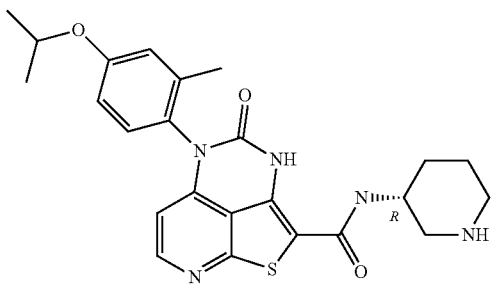

The title compound was prepared using Method 1, steps B-H in Example 1, and using 4-isopropoxy-2-methyl-1-nitrobenzene in place of 2-methyl-1-nitro-4-phenoxybenzene in step B, and using tert-butyl (3R)-3-aminopiperidine-1-carboxylate in place of tert-butyl (3R,5R)-3-amino-5-fluoropiperidine-1-carboxylate in step G. MS (ESI): mass calcd. for $C_{24}H_{27}N_5O_3S$, 465.2; m/z found, 466.2 [M+H]$^+$.

Intermediate 71: (S)-5-(2-Methyl-4-phenoxyphenyl)-4-oxo-N-(pyrrolidin-3-yl)-4,5-dihydro-3H-1-thia-3,5,8-triazaacenaphthylene-2-carboxamide

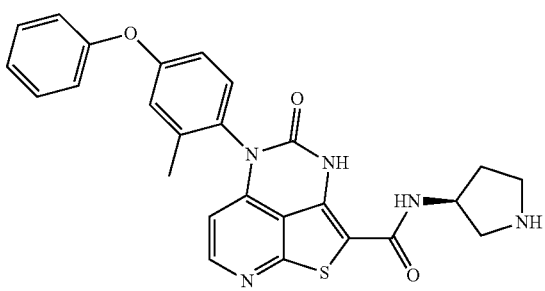 [SMILES: Cc1cc(Oc2ccccc2)ccc1N1C(=O)Nc2c(C(=O)N[C@H]3CCNC3)sc3nccc1c23]

The title compound was prepared using Method 1, step G-H, in Example 1, using tert-butyl (S)-3-aminopyrrolidine-1-carboxylate in place of tert-butyl (3R,5R)-3-amino-5-fluoropiperidine-1-carboxylate in step G. MS (ESI): mass calcd. for $C_{26}H_{23}N_5O_3S$, 485.2; m/z found, 486.5 [M+H]$^+$.

Intermediate 72: (E)-4-((4aR,7aS)-Hexahydro-6H-[1,4]dioxino[2,3-c]pyrrol-6-yl)but-2-enoic Acid

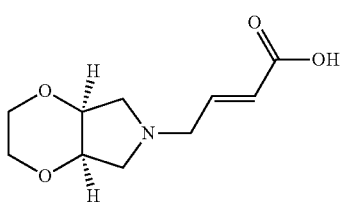 [SMILES: O=C(O)/C=C/CN1C[C@@H]2OCCO[C@@H]2C1]

Step A: Benzyl 3,4-dihydroxypyrrolidine-1-carboxylate

Benzyl 2,5-dihydro-1H-pyrrole-1-carboxylate (5.0 g, 25 mmol) was taken up in THF (40 mL) and water (15 mL) and to this solution were added OsO$_4$ (63 mg, 0.25 mmol) and 4-methylmorpholine 4-oxide (3.75 g, 32.0 mmol). The reaction was stirred at room temperature for 15 h. The reaction was concentrated to dryness and the crude was partitioned between EtOAc and water. The layers were separated and the aqueous layer was extracted with EtOAc. The combined organic layers were dried over anhydrous Na$_2$SO$_4$, concentrated to dryness, and purified by normal phase flash column chromatography (SiO$_2$) to give the title compound (4.8 g, 82% yield). MS (ESI): mass calcd. for $C_{12}H_{15}NO_4$, 237.25; m/z found, 238.1 [M+H]$^+$.

Step B: (4aR,7aS)-Benzyl tetrahydro-2H-[1,4]dioxino[2,3-c]pyrrole-6(3H)-carboxylate To a solution of NaOH (9.00 g, 225 mmol) in water (30 mL) were added benzyl 3,4-dihydroxypyrrolidine-1-carboxylate (4.8 g, 20 mmol), and dichloroethane (30 mL). To this solution was added tetrabutylammonium fluoride (2.65 g, 10.1 mmol) and the mixture was stirred at 55° C. for 48 h. The mixture was extracted with DCM, concentrated to dryness, and purified by normal phase flash column chromatography (SiO$_2$) to give the title compound as a white solid (0.96 g, 18% yield). MS (ESI): mass calcd. for $C_{14}H_{17}NO_4$, 263.29; m/z found, 264.1 [M+H]$^+$.

Step C: (4aR,7aS)-3,4a,5,6,7,7a-Hexahydro-2H-[1,4]dioxino[2,3-c]pyrrole

A solution of (4aR,7aS)-benzyl tetrahydro-2H-[1,4]dioxino[2,3-c]pyrrole-6(3H)-carboxylate (0.96 g, 3.6 mmol), Pd(OH)$_2$ (51 mg, 0.36 mmol), and MeOH (10 mL) were reacted at room temperature for 3 h under H$_2$. The mixture was filtered and concentrated to dryness to give the title compound as a light yellow solid (0.43 g, 91% yield). MS (ESI): mass calcd. for $C_6H_{11}NO_2$, 129.16; m/z found, 130.4 [M+H]$^+$.

Step D: (E)-Methyl 4-((4aR,7aS)-tetrahydro-2H-[1,4]dioxino[2,3-c]pyrrol-6(3H)-yl)but-2-enoate To a solution of methyl (E)-4-bromobut-2-enoate (42 mg, 0.23 mmol) and diisopropylethylamine (30 mg, 0.23 mmol) in THF (10 mL) was added (4aR,7aS)-3,4a,5,6,7,7a-hexahydro-2H-[1,4]dioxino[2,3-c]pyrrole (30 mg, 0.23 mmol), and was stirred at room temperature for 15 h. The mixture was concentrated to dryness to give the title compound (55 mg), which was used in the next step without further purification. MS (ESI): mass calcd. for $C_{11}H_{17}NO_4$, 227.26; m/z found, 228.1 [M+H]$^+$.

Step E: (E)-4-((4aR,7aS)-Tetrahydro-2H-[1,4]dioxino[2,3-c]pyrrol-6(3H)-yl)but-2-enoic Acid A solution of (E)-methyl 4-((4aR,7aS)-tetrahydro-2H-[1,4]dioxino[2,3-c]pyrrol-6(3H)-yl)but-2-enoate (55 mg, 0.24 mmol) and aqueous 4 M HCl (5 mL) was reacted at reflux for 1 h. The mixture was concentrated to dryness to give the title compound (55 mg, 106%), which was used without further purification.

Intermediate 73: Methyl 5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxylate

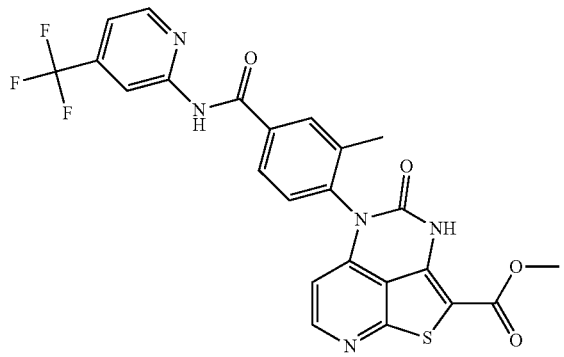 [SMILES: COC(=O)c1sc2nccc3c2c1NC(=O)N3c1ccc(C(=O)Nc2cc(C(F)(F)F)ccn2)cc1C]

Step A: 3-Methyl-4-nitro-N-(4-(trifluoromethyl)pyridin-2-yl)benzamide

To a solution of 3-methyl-4-nitrobenzoic acid (3.0 g, 16.6 mmol) in DCM (100 mL) was added one drop of DMF and oxalyl dichloride (10.5 g, 82.8 mmol). The mixture was stirred at room temperature for 30 minutes, then concentrated and diluted in DCM, then added to a solution of 4-(trifluoromethyl)pyridin-2-amine (2.7 g, 16.6 mmol), triethylamine in DCM under ice-bath, stirred for 1 hour. The mixture was concentrated to yield the title compound as a yellow solid, which was used forward next step without further purification.

Step B: Methyl 5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxylate The title compound was prepared using Method 1, steps B-E, in Example 1, using 3-methyl-4-nitro-N-(4-(trifluoromethyl)pyridin-2-yl)benzamide in place of 2-methyl-1-nitro-4-phenoxybenzene in step B.

Intermediate 74: Methyl 5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxylate

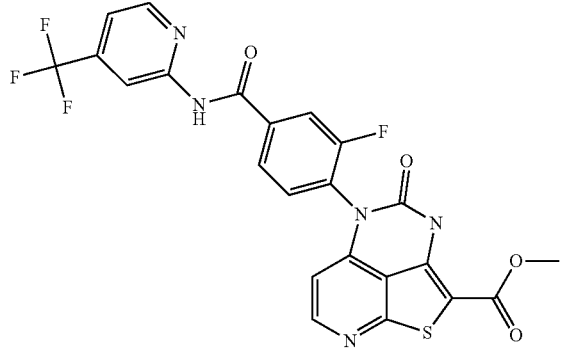 [SMILES: COC(=O)c1sc2nccc3c2c1NC(=O)N3c1ccc(C(=O)Nc2cc(C(F)(F)F)ccn2)cc1F]

Step A: 3-Fluoro-4-nitro-N-(4-(trifluoromethyl)pyridin-2-yl)benzamide

To the suspension of 3-fluoro-4-nitrobenzoic acid acid (4.1 g, 22.1 mmol) in 30 ml of DCM was added Oxalyl chloride (3.0 g, 24.4 mmol) and 1 drop of DMF, then was stirred at room temperature for 4 hours. After concentration under vacuo to dryness, the residue was dissolved in 10 ml of DCM and was added a solution of 4-(trifluoromethyl)pyridin-2-amine (3.6 g, 22.1 mmol) in 30 ml of DCM, stirred at room temperature for 5 mins. The mixture was concentrated and purified by ISCO using MeOH/H$_2$O as eluent to get the title compound as yellow solid acid (5.0 g, 69% yield).

Step B: Methyl 5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxylate The title compound was prepared using Method 1, steps B-E in Example 1, using 3-fluoro-4-nitro-N-(4-(trifluoromethyl)pyridin-2-yl)benzamide in place of 2-methyl-1-nitro-4-phenoxybenzene in step B.

Intermediate 75: 5-(4-(3-((2-Cyanophenoxy)methyl)phenoxy)-2-methylphenyl)-4-oxo-4,5-dihydro-3H-1-thia-3,5,8-triazaacenaphthylene-2-carboxylic Acid

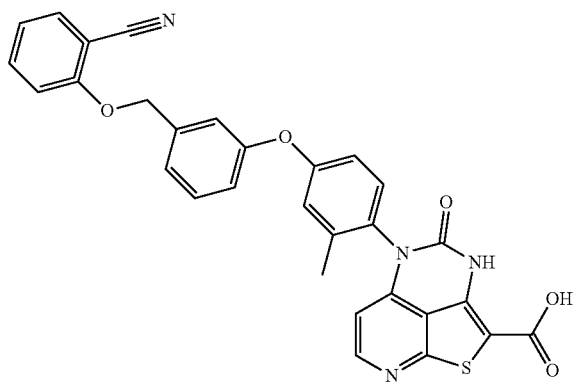

The title compound was prepared using Method 1, step F in Example 1, using methyl 5-(4-(3-((2-cyanophenoxy)methyl)phenoxy)-2-methylphenyl)-4-oxo-4,5-dihydro-3H-1-thia-3,5,8-triazaacenaphthylene-2-carboxylate (Intermediate 76) in place of methyl 5-(2-methyl-4-phenoxyphenyl)-4-oxo-4,5-dihydro-3H-1-thia-3,5,8-triazaacenaphthylene-2-carboxylate. MS (ESI): mass calcd. for $C_{30}H_{20}N_4O_5S$, 548.1; m/z found, 549.0 [M+H]$^+$.

Intermediate 76: Methyl 5-(4-(3-((2-cyanophenoxy)methyl)phenoxy)-2-methylphenyl)-4-oxo-4,5-dihydro-3H-1-thia-3,5,8-triazaacenaphthylene-2-carboxylate

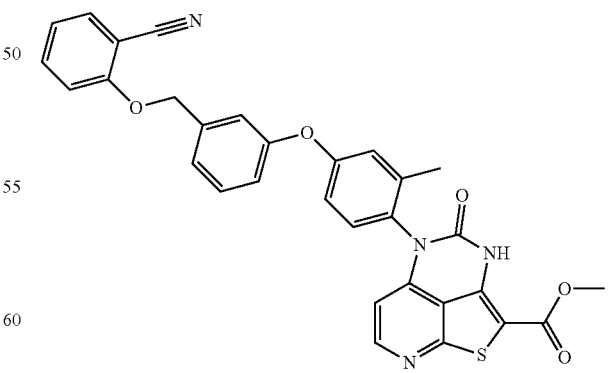

Step A: 3-((tert-Butldimethylsilyl)oxy)benzaldehyde

To a mixture of 3-hydroxybenzaldehyde (24.4 g, 200 mmol) in DCM (500 mL) was added Et$_3$N (30.3 g, 300 mmol) and TBSCl (33.1 g, 220 mmol) and stirred room temperature for 3 hours. The reaction was dispersed between DCM and saturated NH$_4$Cl aq solution. The organic layer was collected, condensed and was purified by flash column chromatography (PE/EA) to give the title compound (47.3 g, 100% yield). $^1$H NMR (400 MHz, DMSO-d6): δ ppm 10.01 (s, 1H), 7.50-7.63 (m, 2H), 7.37 (s, 1H), 7.25 (d, J=7.50 Hz, 1H), 1.01 (s, 9H), 0.26 (s, 6H)

Step B: (3-((tert-Butyldimethylsilyl)oxy)phenyl)methanol

To a mixture of 3-((tert-butyldimethylsilyl)oxy)benzaldehyde (47.3 g, 200 mmol) in MeOH (30 mL) cooled to 0° C. was added portion wise NaBH$_4$ (3.78 g, 100 mmol). After the addition was completed the reaction was stirred at room temperature for 2 hours. Volatiles were removed under vacuo. Water and EtOAc were added to the residue, the organic layer was separated, washed with brine, dried over Na$_2$SO$_4$, filtered and concentrated under vacuo to provide target product as yellow oil, which was used forward next step without further purification. Mass calcd. for C$_{13}$H$_{22}$O$_2$Si, 238.1. $^1$H NMR (400 MHz, DMSO-d6): δ ppm 0.18-0.27 (m, 6H) 0.99 (s, 9H) 4.48 (s, 2H) 5.23 (br. s., 1H) 6.69-6.78 (m, 1H) 6.85 (s, 1H) 6.93 (d, J=7.50 Hz, 1H) 7.23 (t, J=7.94 Hz, 1H).

Step C: 2-((3-((tert-Butyldimethylsilyl)oxy)benzyl)oxy)benzonitrile

To a mixture of (3-((tert-butyldimethylsilyl)oxy)phenyl)methanol (13.94 g, 60 mmol) in THF (200 mL) were sequentially added 2-hydroxybenzonitrile (8.58 g, 72 mmol), Ph$_3$P (18.88 g, 72 mmol) and DIAD (14.56 g, 72 mmol): dropwise at room temperature and the reaction was stirred for 1 hour. Saturated aqueous NH$_4$Cl and EtOAc were added, the organic layer was separated, washed with brine, dried over Na$_2$SO$_4$, filtered, condensed under vacuo and was purified by flash column chromatography (PE/EA) to give the title compound (17.0 g, 83% yield).

Step D: 2-((3-Hydroxybenzyl)oxy)benzonitrile

To a mixture of 2-((3-((tert-butyldimethylsilyl)oxy)benzyl)oxy)benzonitrile (17.0 g, 50 mmol) in THF (250 mL) was added a 1M solution TBAF (60 mL, 60 mmol) and the reaction was stirred at room temperature for 30 minutes. A saturated aqueous NH$_4$Cl solution and EtOAc were added, the organic layer was separated, washed with brine, dried over Na$_2$SO$_4$, filtered, condensed and was purified by flash column chromatography (MeOH/DCM) to give the title compound (11.3 g, 100% yield).

Step E: 2-((3-(3-Methyl-4-nitrophenoxy)benzyl)oxy)benzonitrile

To a mixture of 2-((3-hydroxybenzyl)oxy)benzonitrile (11.3 g, 50 mmol), 4-fluoro-2-methyl-1-nitrobenzene (7.8 g, 50 mmol), K$_2$CO$_3$ (13.8 g, 100 mmol) in 200 mL of DMSO was stirred under N$_2$ at 150° C. for 4 hours. The mixture was condensed and was purified by flash column chromatography (PE/EA) to give the title compound (15.1 g, 84% yield). MS (ESI): mass calcd. for C$_{21}$H$_{16}$N$_2$O$_4$, 360.1; m/z found, 361.0 [M+H]$^+$. $^1$H NMR (400 MHz, CDCl$_3$): δ 8.11-7.98 (m, 1H), 7.74-7.62 (m, 1H), 7.62-7.39 (m, 6H), 7.39-7.31 (m, 1H), 7.22-7.17 (m, 1H), 7.09-6.97 (m, 3H), 6.85 (d, J=8.4 Hz, 2H), 6.55 (s, 1H), 5.21 (s, 2H), 2.58 (s, 3H).

Step F: 2-((3-(4-Amino-3-methylphenoxy)benzyl)oxy)benzonitrile

To a mixture of 2-((3-(3-methyl-4-nitrophenoxy)benzyl)oxy)benzonitrile (15.1 g, 42 mmol) in EtOH (420 mL) and water (140 mL) were sequentially added NH$_4$Cl (11.2 g, 210 mmol), iron (9.38 g, 168 mmol) and the reaction mixture was stirred at reflux for 4 hours and then cooled to room temperature, The mixture was diluted with DCM (500 mL) and water (200 mL), the organic layer was collected, condensed and was purified by flash column chromatography (MeOH/water) to give the title compound (13.9 g, 100% yield). MS (ESI): mass calcd. for C$_{21}$H$_{18}$N$_2$O$_2$, 330.1; m/z found, 331.1 [M+H]$^+$. $^1$H NMR (400 MHz, CDCl$_3$): δ 7.57 (dd, J=7.6, 1.7 Hz, 1H), 7.53-7.45 (m, 1H), 7.33-7.24 (m, 1H), 7.15-7.08 (m, 1H), 7.04-6.84 (m, 5H), 6.82-6.72 (m, 2H), 6.67 (d, J=8.4 Hz, 1H), 5.14 (s, 2H), 2.15 (s, 3H).

Step G: Methyl 5-(4-(3-((2-cyanophenoxy)methyl)phenoxy)-2-methylphenyl)-4-oxo-4,5-dihydro-3H-1-thia-3,5,8-triazaacenaphthylene-2-carboxylate The title compound was prepared using Method 1, steps C-E in Example 1, using 2-((3-(4-amino-3-methylphenoxy)benzyl)oxy)benzonitrile in place of 2-methyl-4-phenoxyaniline in step C. MS (ESI): mass calcd. for C$_{31}$H$_{22}$N$_4$O$_5$S, 562.1; m/z found, 563.2 [M+H]$^+$.

Intermediate 77: (R)—N-(1-(2-Cyanoacetyl)piperidin-3-yl)-5-(2-methyl-6-phenoxypyridin-3-yl)-4-oxo-4,5-dihydro-3H-1-thia-3,5,8-triazaacenaphthylene-2-carboxamide

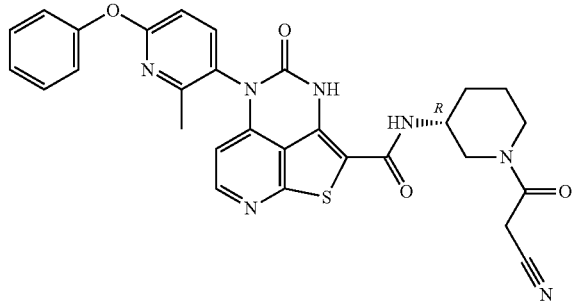

To a solution of (R)-5-(2-methyl-6-phenoxypyridin-3-yl)-4-oxo-N-(piperidin-3-yl)-4,5-dihydro-3H-1-thia-3,5,8-triazaacenaphthylene-2-carboxamide (Example 711) (3.4 g, 6.8 mmol) in DCM (50 mL) was added triethylamine (2.06 g, 20.4 mmol) and was cooled to 0° C. Next 2,5-dioxopyrrolidin-1-yl 2-cyanoacetate (1.86 g, 10.2 mmol) was added slowly and after the addition was complete, it was stirred at room temperature for 1 h. The reaction was washed with 1% HCl, NaHCO$_3$, and brine, dried over anhydrous Na$_2$SO$_4$, and concentrated to dryness. The residue was washed with DCM, the solid was collected by filtration and dried in a vacuum to give the title compound (3.0 g, 58% yield) as a yellow solid. MS (ESI): mass calcd. for C$_{29}$H$_{25}$N$_7$O$_4$S, 567.62; m/z found, 568.1 [M+H]$^+$.

Intermediate 78: (R)-5-(4-(3-((2-Cyanophenoxy)methyl)phenoxy)-2-methylphenyl)-4-oxo-N-(piperidin-3-yl)-4,5-dihydro-3H-1-thia-3,5,8-triazaacenaphthylene-2-carboxamide

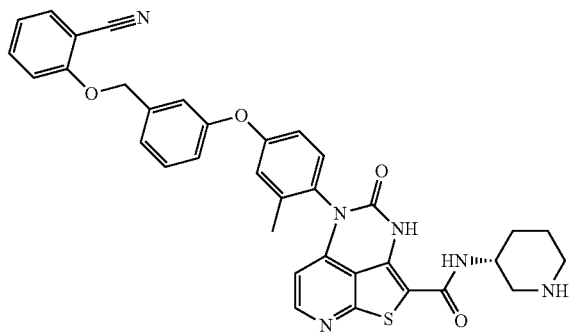 [SMILES: Cc1cc(Oc2cccc(COc3ccccc3C#N)c2)ccc1N1C(=O)Nc2c(C(=O)N[C@@H]3CCCNC3)sc3nccc1c23]

The title compound was prepared using Method 1, step G-H in Example 1, and using 5-(4-(3-((2-cyanophenoxy)methyl)phenoxy)-2-methylphenyl)-4-oxo-4,5-dihydro-3H-1-thia-3,5,8-triazaacenaphthylene-2-carboxylic acid (Intermediate 75) and tert-butyl (R)-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid and tert-butyl (3R,5R)-3-amino-5-fluoropiperidine-1-carboxylate. MS (ESI): mass calcd. for $C_{35}H_{30}N_6O_4S$, 630.2; m/z found, 631.0 $[M+H]^+$.

Intermediate 79: 1-Acryloylpiperidin-3-one

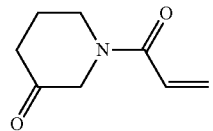

A solution of tert-butyl 3-oxopiperidine-1-carboxylate (1.00 g, 5.0 mmol) in 6 M HCl in MeOH (25 mL) was stirred at rt for 30 min, then concentrated to dryness. The residue was diluted in acetone/water (50 mL), and triethylamine (1.02 g, 10.0 mmol) and $K_2CO_3$ (1.39 g, 10.0 mmol) were added, followed by addition of prop-2-enoyl chloride (454 mg, 5.0 mmol). The mixture was stirred at rt for 18 h, extracted with EtOAc, the organic layers washed with water and brine, dried over anhydrous $Na_2SO_4$, and concentrated to dryness. The residue was purified by flash column chromatography to give the title compound as a white solid (480 mg, 62% yield). MS (ESI): mass calcd. for $C_8H11NO2$, 153.1; m/z found, 154.1 $[M+H]^+$.

Intermediate 80: 1-Acryloylpiperidin-4-one

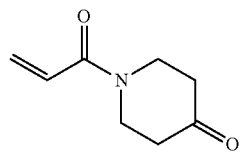

A solution of tert-butyl 4-oxopiperidine-1-carboxylate (1.5 g, 7.5 mmol) in 6 M HCl in MeOH (25 mL) was stirred at rt for 30 min, then concentrated to dryness. The residue was diluted in acetone/water (30 mL), and triethylamine (2.28 g, 22.6 mmol) and $K_2CO_3$ (2.08 g, 15.1 mmol) were added, followed by the addition of prop-2-enoyl chloride (681 mg, 7.53 mmol). The mixture was stirred at rt for 18 h, then extracted with EtOAc and the organic layers were washed with water and brine, dried over anhydrous $Na_2SO_4$, and concentrated to dryness. The residue was purified by flash column chromatography to give the title compound as a white solid (500 mg, 43%). MS (ESI): mass calcd. for $C_8H11NO2$, 153.1; m/z found, 154.1 $[M+H]^+$.

Intermediate 81: 5-(6-Isobutyl-4-methylpyridin-3-yl)-4-oxo-4,5-dihydro-3H-1-thia-3,5,8-triazaacenaphthylene-2-carboxylic Acid

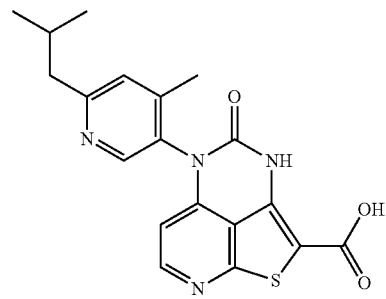 [SMILES: Cc1cc(CC(C)C)ncc1N1C(=O)Nc2c(C(=O)O)sc3nccc1c23]

Step A: 6-Isobutyl-4-methylpyridin-3-amine

To a 200 mL round bottom flask was were added 6-bromo-4-methylpyridin-3-amine (5.42 g, 29.0 mmol), a stir bar, and 1,1'-bis(diphenylphosphino)ferrocene-palladium(II)dichloride dichloromethane complex (520 mg, 0.6 mmol). The vessel was evacuated then back filled with nitrogen. THF (20 mL) was added, followed by isobutylzinc (II) bromide (80 mL, 40 mmol) via syringe, then the reaction mixture was heated to 60° C. for 2 h. The reaction mixture was treated with saturated aqueous sodium bicarbonate (300 mL) and extracted with EtOAc (2×300 mL). The combined organic layers were dried (MgSO₄), concentrated to dryness, and the residue purified by flash column chromatography to give the title compound (3.65 g, 77% yield) as a brown solid. MS (ESI): mass calcd. for $C_{10}H_{16}N_2$, 164.1; m/z found, 165.1 $[M+H]^+$.

Step B: Methyl 3-amino-4-((6-isobutyl-4-methylpyridin-3-yl)amino)thieno[2,3-b]pyridine-2-carboxylate To a round bottom flask under a $N_2$ atmosphere were added 6-isobutyl-4-methylpyridin-3-amine (53.5 g, 326 mmol), 2-chloro-4-iodopyridine-3-carbonitrile (94.8 g, 358 mmol), and dioxane (1000 mL), followed by bis(2-diphenylphosphinophenyl)ether (DPEphos) (10.5 g, 19.5 mmol), Pd(OAc)₂ (2.92 g, 13.0 mmol), and Cs₂CO₃ (265 g, 814 mmol). The reaction mixture was stirred at 105° C. overnight. The reaction mixture was filtered and concentrated. The residue was suspended in MeOH (400 mL) and stirred for 2 h at room temperature. The resulting precipitate was isolated by filtration and dried under vacuum to give the title compound (75.3 g, 62% yield) as a yellow solid.

Step C: Methyl 5-(6-isobutyl-4-methylpyridin-3-yl)-4-oxo-4,5-dihydro-3H-1-thia-3,5,8-triazaacenaphthylene-2-carboxylate To a round bottom flask were added Methyl 3-amino-4-((6-isobutyl-4-methylpyridin-3-yl)amino)thieno[2,3-b]pyridine-2-carboxylate (30.0 g, 81 mmol), carbonyldiimidazole (CDI, 39.4 g, 243 mmol), trimethylamine (24.6 g, 243 mmol) and 1,4-dioxane (300 mL). The reaction was stirred at 100° C. for 6 h, then cooled to 50° C. The resulting precipitate was collected by filtration, rinsed with MeOH and dried under vacuum to yield the title compound (27 g, 84%) as an off-white solid.

Step D: 5-(6-Isobutyl-4-methylpyridin-3-yl)-4-oxo-4,5-dihydro-3H-1-thia-3,5,8-triazaacenaphthylene-2-carboxylic Acid To a round bottom flask were added methyl 5-(6-isobutyl-4-methylpyridin-3-yl)-4-oxo-4,5-dihydro-3H-1-thia-3,5,8-triazaacenaphthylene-2-carboxylate (68.0 g, 172 mmol), lithium hydroxide (36.0 g, 858 mmol), and a mixture of 5:2:2 THF:MeOH:H$_2$O (4 L). The reaction mixture was stirred at 80° C. for 4.5 h. The mixture was concentrated to dryness and diluted with H$_2$O. The solution was acidified by the addition of 1 M HCl and the resulting precipitate was filtered and dried under vacuum to yield the title compound (63 g, 96% yield) as yellow solid. MS (ESI): mass calcd. for C$_{19}$H$_{18}$N$_4$O$_3$S, 382.11; m/z found, 383.1 [M+H]$^+$.

Intermediate 82: 5-(*S)-(6-Isobutyl-4-methylpyridin-3-yl)-4-oxo-4,5-dihydro-3H-1-thia-3,5,8-triazaacenaphthylene-2-carboxylic Acid

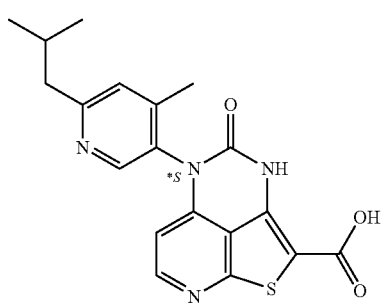 [SMILES: Cc1cc(CC(C)C)ncc1N1C(=O)Nc2c(C(=O)O)sc3nccc1c23]

5-(6-Isobutyl-4-methylpyridin-3-yl)-4-oxo-4,5-dihydro-3H-1-thia-3,5,8-triazaacenaphthylene-2-carboxylic acid (Intermediate 81) was resolved using Chiral resolution Method B to obtain the title compound (*S atropisomer). MS (ESI): mass calcd. for C$_{19}$H$_{18}$N$_4$O$_3$S, 382.1; m/z found, 383.0 [M+H]$^+$.

Intermediate 83: 5-(*R)-(6-Isobutyl-4-methylpyridin-3-yl)-4-oxo-4,5-dihydro-3H-1-thia-3,5,8-triazaacenaphthylene-2-carboxylic Acid

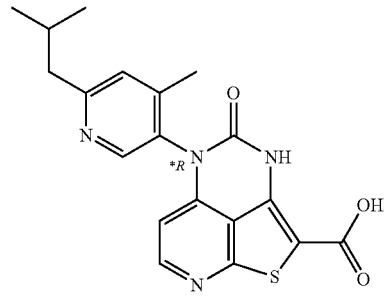 [SMILES: Cc1cc(CC(C)C)ncc1N1C(=O)Nc2c(C(=O)O)sc3nccc1c23]

5-(6-Isobutyl-4-methylpyridin-3-yl)-4-oxo-4,5-dihydro-3H-1-thia-3,5,8-triazaacenaphthylene-2-carboxylic acid (Intermediate 81) was resolved using Chiral resolution Method B to obtain the title compound (*R atropisomer). MS (ESI): mass calcd. for C$_{19}$H$_{18}$N$_4$O$_3$S, 382.1; m/z found, 383.0 [M+H]$^+$.

Example 1: N-((3R,5R)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide

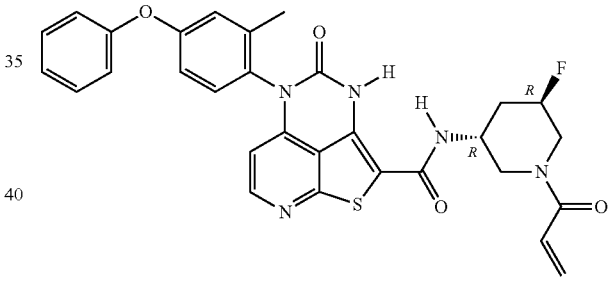

Method 1. Step A: 2-Methyl-1-nitro-4-phenoxybenzene

To a round bottom flask were added phenol (42.5 g, 452 mmol), K$_2$CO$_3$ (125 g, 905 mmol), and DMF (500 mL). To the reaction mixture was added 5-fluoro-2-nitrotoluene (70.2 g, 452 mmol) and the reaction was stirred at 80° C. for 16 h under N$_2$. The reaction was diluted with saturated NH$_4$Cl and extracted with MTBE (3×400 mL). The organic layers were combined, dried over anhydrous Na$_2$SO$_4$, filtered, and concentrated to dryness to yield the title compound (100 g, 92% yield) as a brown oil.

Method 1, Step B: 2-Methyl-4-phenoxyaniline

To a solution of 2-methyl-1-nitro-4-phenoxybenzene (100 g, 436 mmol) in EtOH/H$_2$O (3:1 ratio, 2000 mL) were sequentially added NH$_4$Cl (117 g, 2180 mmol) and Fe (97 g, 1700 mmol). The reaction mixture was heated to reflux for 2 h, then the reaction was cooled to 25° C. and concentrated to dryness. To the residue was added water and EtOAc and the organic layer was separated, washed with saturated NaHCO$_3$ and saturated brine, dried over anhydrous MgSO$_4$, filtered, and concentrated to dryness to yield the title compound (82 g, 90% yield).

Method 1, Step C: 2-Chloro-4-(2-methyl-4-phenoxyanilino)pyridine-3-carbonitrile To a round bottom flask under a N$_2$ atmosphere were added 2-methyl-4-phenoxyaniline (30 g, 150 mmol), 2-chloro-4-iodopyridine-3-carbonitrile (51.6 g, 195 mmol), and dioxane (200 mL), followed by bis(2-diphenylphosphinophenyl)ether (DPEphos) (16 g, 30 mmol), Pd(OAc)$_2$ (3.36 g, 15 mmol), and K$_3$PO$_4$ (89 g, 420 mmol). The reaction mixture was stirred at 100° C. overnight. The reaction mixture was filtered and purified flash column chromatography to yield the title compound (32 g, 63% yield) as a yellow solid.

Method 1, Step D: Methyl 3-amino-4-(2-methyl-4-phenoxyanilino)thieno[2,3-b]pyridine-2-carboxylate To a round bottom flask were added 2-chloro-4-(2-methyl-4-phenoxyanilino)pyridine-3-carbonitrile (36 g, 107 mmol) in MeOH (150 mL). To this solution was added NaOMe (14.5 g, 268 mmol) in MeOH (30 mL), followed by methyl 2-sulfanylacetate (23 g, 217 mmol). The reaction mixture was refluxed overnight. The reaction mixture was cooled and the yellow precipitate was filtered off, washed with MeOH, and dried to yield the title compound (30 g, 75% yield) as a yellow solid.

Method 1, Step E: Methyl 5-(2-methyl-4-phenoxyphenyl)-4-oxo-4,5-dihydro-3H-1-thia-3,5,8-triazaacenaphthylene-2-carboxylate To a round bottom flask were added methyl 3-amino-4-(2-methyl-4-phenoxyanilino)thieno[2,3-b]pyridine-2-carboxylate (30.6 g, 75.5 mmol), carbonyldiimidazole (CDI, 49 g, 300 mmol), and 1,4-dioxane (500 ml). The reaction was stirred at reflux overnight. Then the reaction mixture was concentrated to dryness and to the residue was added to MeOH (200 mL) and the precipitate that formed was filtered off and dried to yield the title compound (28.1 g, 86% yield) as a yellow solid.

Method 1, Step F: 5-(2-Methyl-4-phenoxyphenyl)-4-oxo-4,5-dihydro-3H-1-thia-3,5,8-triazaacenaphthylene-2-carboxylic Acid To a round bottom flask were added Methyl 5-(2-methyl-4-phenoxyphenyl)-4-oxo-4,5-dihydro-3H-1-thia-3,5,8-triazaacenaphthylene-2-carboxylate (9.2 g, 21 mmol), lithium hydroxide (4.47 g, 106 mmol), THF (200 mL), MeOH (200 mL), and water (50 mL). The reaction mixture was stirred at 50° C. for 15 h. The mixture was concentrated to dryness and diluted with H$_2$O. The pH was adjusted to 2 with 1 M aqueous HCl and the precipitate was filtered and dried to yield the title compound (8.1 g, 91% yield) as yellow solid.

Method 1, Step G: tert-Butyl (3R,5R)-3-fluoro-5-(5-(2-methyl-4-phenoxyphenyl)-4-oxo-4,5-dihydro-3H-1-thia-3,58-triazaacenaphthylene-2-carboxamido)piperidine-1-carboxylate To a round bottom flask were added 5-(2-methyl-4-phenoxyphenyl)-4-oxo-4,5-dihydro-3H-1-thia-3,5,8-triazaacenaphthylene-2-carboxylic acid (Intermediate 27, 191 mg, 0.458 mmol), tert-butyl (3R,5R)-3-amino-5-fluoropiperidine-1-carboxylate (Intermediate 1, 100 mg, 0.458 mmol), triethylamine (93 mg, 0.916 mmol), HATU (348 mg, 0.916 mmol), and DMF (3 mL). The reaction mixture was stirred at rt for 3 h. Water was added and the precipitate was collected by filtration to yield a pale yellow solid.

Method 1, Step H: N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide tert-Butyl (3R,5R)-3-fluoro-5-(5-(2-methyl-4-phenoxyphenyl)-4-oxo-4,5-dihydro-3H-1-thia-3,5,8-triazaacenaphthylene-2-carboxamido)piperidine-1-carboxylate was dissolved in MeOH (3 mL) and saturated aqueous HCl (3 mL) was added. The resulting mixture was heated to 50° C. for 30 min. The reaction mixture was concentrated to dryness and the residue was purified by flash column chromatography to yield the title compound (Example 138, 80 mg, 31% yield over 2 steps) as a yellow solid.

Method 1, Step I: N-((3R,5R)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide To a round bottom flask were added N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide (Example 138, 40 mg, 0.077 mmol), triethylamine (23 mg, 0.054 mmol), and DCM (3 mL). Next, prop-2-enoyl chloride (5.0 mg, 0.054 mmol) was added dropwise at 0° C., then stirred at rt for 1 h. The reaction mixture was concentrated to dryness and the residue purified by flash column chromatography to yield the title compound (22 mg, 48% yield) as a pale yellow solid. MS (ESI): mass calcd. for C$_{30}$H$_{26}$FN$_5$O$_4$S, 571.6; m/z found, 572.3 [M+H]$^+$. $^1$H NMR (400 MHz, CD$_3$OD): δ 8.28 (d, J=5.5 Hz, 1H), 7.42-7.30 (m, 2H), 7.30-7.22 (m, 1H), 7.16-7.08 (m, 1H), 7.08-6.97 (m, 3H), 6.95-6.87 (m, 1H), 6.80-6.61 (m, 1H), 6.19-6.05 (m, 1H), 5.98 (d, J=5.5 Hz, 1H), 5.72-5.60 (m, 1H), 4.82-4.57 (m, 1H), 4.17-4.05 (m, 1H), 4.02-3.85 (m, 2H), 3.55-3.28 (m, 2H), 2.39-2.18 (m, 1H), 2.04 (s, 3H), 2.0-1.91 (m, 1H).

Example 2: N-((3R,5S)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide

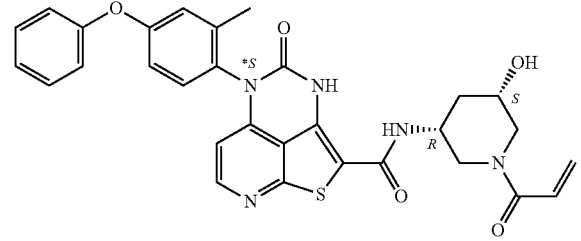

The title compound was prepared in a manner analogous to Method 1, steps A-I (including Chiral Resolution Step A to obtain the *S atropisomer) in Example 1, and using tert-butyl (3R,5S)-3-amino-5-hydroxypiperidine-1-carboxylate (Intermediate 2) in place of tert-butyl (3R,5R)-3-amino-5-fluoropiperidine-1-carboxylate (Intermediate 1) in step G. MS (ESI): mass calcd. for $C_{30}H_{27}N_5O_5S$, 569.6; m/z found, 570.2 [M+H]$^+$. $^1$H NMR (400 MHz, CD$_3$OD): δ 8.36-8.27 (m, 1H), 7.45-7.37 (m, 2H), 7.33-7.26 (m, 1H), 7.21-7.14 (m, 1H), 7.11-7.02 (m, 3H), 7.00-6.92 (m, 1H), 6.85-6.65 (m, 1H), 6.21-6.09 (m, 1H), 6.06-6.02 (m, 1H), 5.75-5.61 (m, 1H), 4.20-3.75 (m, 4H), 3.66-3.55 (m, 2H), 2.21-2.12 (m, 1H), 2.11 (s, 3H), 1.90-1.77 (m, 1H).

Example 3: N-((3R,5S)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide

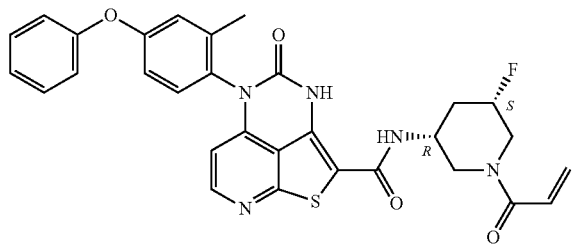

The titled compound was prepared using Method 1, steps A-I in Example 1, and using tert-butyl (3R,5S)-3-amino-5-fluoropiperidine-1-carboxylate (Intermediate 3) in place of tert-butyl (3R,5R)-3-amino-5-fluoropiperidine-1-carboxylate (Intermediate 1) in step G. MS (ESI): mass calcd. for $C_{30}H_{26}FN_5O_4S$, 571.6; m/z found, 572.4 [M+H]$^+$. $^1$H NMR (400 MHz, DMSO-d$_6$): δ 10.26 (s, 1H), 8.31 (d, J=4.7 Hz, 1H), 8.26-8.00 (m, 1H), 7.57-7.29 (m, 3H), 7.29-6.91 (m, 5H), 6.88-6.65 (m, 1H), 6.11 (d, J=16.7 Hz, 1H), 6.03-5.87 (m, 1H), 5.77-5.60 (m, 1H), 5.15-4.85 (m, 1H), 4.70-4.47 (m, 1H), 4.35-4.38 (m, 2H), 3.06-2.61 (m, 2H), 2.30-2.12 (m, 1H), 2.05 (s, 3H), 1.97-1.78 (m, 1H).

Example 4: (R)—N-(1-Acryloylpiperidin-3-yl)-5-(3-fluoro-2-methyl-4-phenoxyphenyl)-4-oxo-4,5-dihydro-3H-1-thia-3,5,8-triazaacenaphthylene-2-carboxamide

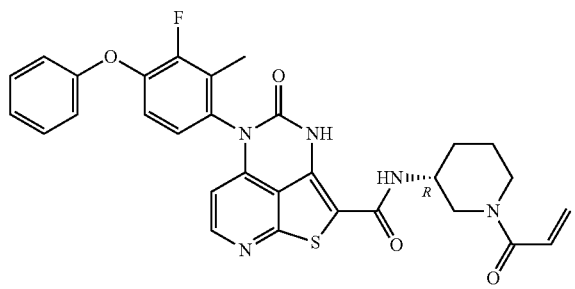

The title compound was prepared using analogous conditions described in Method 1, steps B-I in Example 1, and using 2-fluoro-3-methyl-4-nitro-1-phenoxybenzene (Intermediate 18, step B) in place of 2-methyl-4-phenoxyaniline in step B, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{26}FN_5O_4S$, 571.6; m/z found, 572.1 [M+H]$^+$. $^1$H NMR (400 MHz, CD$_3$OD): δ 8.34 (d, J=5.4 Hz, 1H), 7.41-7.34 (m, 2H), 7.22-7.11 (m, 2H), 7.10-7.04 (m, 3H), 6.84-6.72 (m, 1H), 6.19 (d, J=17.0 Hz, 1H), 6.12 (d, J=5.4 Hz, 1H), 5.76-5.69 (m, 1H), 4.56-4.48 (m, 0.5H), 4.32-4.25 (m, 0.5H), 4.4.20-4.13 (m, 0.5H), 4.02-3.88 (m, 1.5H), 3.22-3.12 (m, 1H), 2.95-2.83 (m, 1H), 2.12 (s, 3H), 2.07-2.00 (m, 1H), 1.90-1.82 (m, 1H), 1.78-1.66 (m, 1H), 1.63-1.54 (m, 1H).

Example 5: (R)—N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide

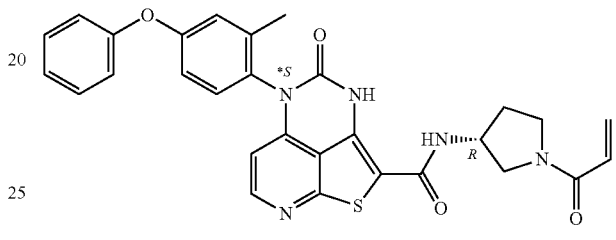

The title compound was prepared in a manner analogous to Method 1, steps A-I (including Chiral resolution Method A after Step F to obtain the *S atropisomer) in Example 1, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{25}N_5O_4S$, 539.6; m/z found, 540.30 [M+H]$^+$. $^1$H NMR (400 MHz, DMSO-d$_6$): δ 10.24 (s, 1H), 8.43-8.22 (m, 2H), 7.57-7.29 (m, 3H), 7.25-7.04 (m, 4H), 7.03-6.90 (m, 1H), 6.70-6.45 (m, 1H), 6.13 (d, J=16.4 Hz, 1H), 6.05-6.88 (m, 1H), 5.73-5.57 (m, 1H), 4.60-4.30 (m, 1H), 3.91-3.36 (m, 4H), 2.24-1.89 (m, 5H).

Example 6: N-((3R,5R)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide

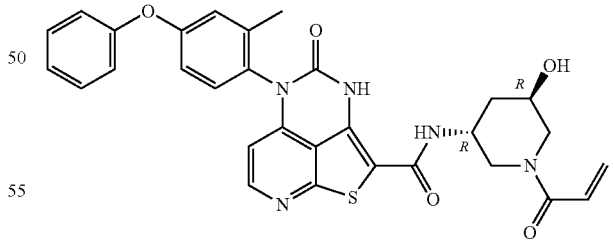

The title compound was prepared in a manner analogous to Method 1, steps A-I in Example 1, and using tert-butyl (3R,5R)-3-amino-5-hydroxypiperidine-1-carboxylate (Intermediate 4) in place of tert-butyl (3R,5R)-3-amino-5-fluoropiperidine-1-carboxylate (Intermediate 1) in step G. MS (ESI): mass calcd. for $C_{30}H_{27}N_5O_5S$, 569.6; m/z found, 570.3 [M+H]$^+$. $^1$H NMR (400 MHz, CD$_3$OD): δ 8.34-8.18 (m, 1H), 7.46-7.36 (m, 2H), 7.33-7.22 (m, 1H), 7.20-7.13 (m, 1H), 7.13-7.02 (m, 3H), 7.00-6.94 (m, 1H), 6.88-6.70

(m, 1H), 6.25-6.10 (m, 1H), 6.05-5.92 (m, 1H), 5.76-5.67 (m, 1H), 4.66-4.28 (m, 2H), 4.23-3.83 (m, 2.5H), 3.45-3.34 (m, 1H), 3.02-2.87 (m, 0.5H), 2.12 (s, 3H), 2.09-1.88 (m, 2H).

Example 7: (R)—N-(1-Acryloylpyrrolidin-3-yl)-5-(3-fluoro-2-methyl-4-phenoxyphenyl)-4-oxo-4,5-dihydro-3H-1-thia-3,5,8-triazaacenaphthylene-2-carboxamide

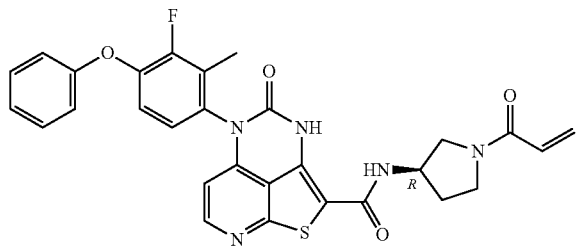

The title compound was prepared in a manner analogous to Method 1, steps A-G in Example 1, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{29}H_{24}FN_5O_4S$, 557.6; m/z found, 558.4 [M+H]⁺. ¹H NMR (400 MHz, a mixture of DMSO-$d_6$ and CD₃OD): δ 8.26 (d, J=5.5 Hz, 1H), 7.7.39-7.29 (m, 2H), 7.20-7.13 (m, 1H), 7.12-6.97 (m, 4H), 6.60-6.43 (m, 1H), 6.19-6.09 (m, 1H), 6.02 (d, J=5.4 Hz, 1H), 5.66-5.58 (m, 1H), 4.55-4.42 (m, 1H), 3.89-3.80 (m, 1H), 3.72-3.66 (m, 1H), 3.60-3.49 (m, 1H), 3.48-3.38 (m, 1H), 2.22-2.08 (m, 1H), 2.01 (s, 3H), 1.99-1.87 (m, 1H).

Example 8: N-((3R,5R)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide

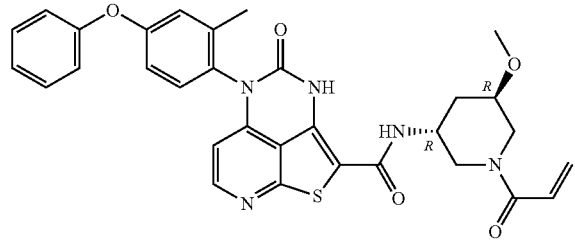

The title compound was prepared in a manner analogous to Method 1, steps A-I in Example 1, and using tert-butyl (3R,5R)-3-amino-5-methoxypiperidine-1-carboxylate (Intermediate 6) in place of tert-butyl (3R,5R)-3-amino-5-fluoropiperidine-1-carboxylate (Intermediate 1) in step G. MS (ESI): mass calcd. for $C_{31}H_{29}N_5O_5S$, 583.7; m/z found, 584.2 [M+H]⁺. ¹H NMR (400 MHz, CD₃OD): δ 8.33 (d, J=5.5 Hz, 1H), 7.52-7.37 (m, 2H), 7.38-7.26 (m, 1H), 7.22-7.14 (m, 1H), 7.13-7.03 (m, 3H), 7.01-6.94 (m, 1H), 6.89-6.68 (m, 1H), 6.25-6.13 (m, 1H), 6.07 (d, J=5.6 Hz, 1H), 5.79-5.68 (m, 1H), 4.70-4.51 (m, 1H), 4.35-4.06 (m, 2H), 3.76-3.55 (m, 1H), 3.41-3.33 (m, 3H), 3.27-3.08 (m, 1H), 3.02-2.69 (m, 1H), 2.33-2.10 (m, 4H), 2.07-1.74 (m, 1H).

Example 9: (R)—N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide

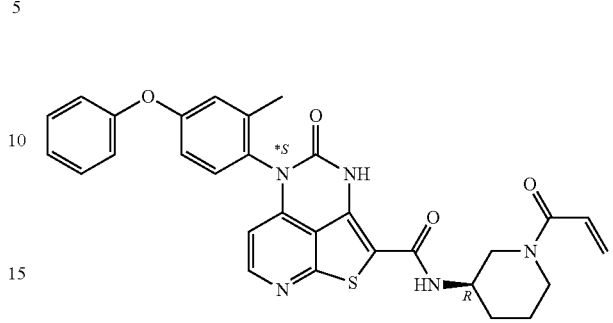

The title compound was prepared in a manner analogous to Method 1, steps A-I (including Chiral resolution Method A after Step F to obtain the *S atropisomer) in Example 1, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.40 [M+H]⁺. ¹H NMR (400 MHz, CD₃OD): δ 8.33 (d, J=5.5 Hz, 1H), 7.47-7.35 (m, 2H), 7.33-7.26 (m, 1H), 7.122-7.16 (m, 1H), 7.13-7.02 (m, 3H), 7.00-6.93 (m, 1H), 6.85-6.70 (m, 1H), 6.20 (d, J=16.6 Hz, 1H), 6.14-6.04 (m, 1H), 5.77-5.67 (m, 1H), 4.58-3.88 (m, 3H), 3.25-3.10 (m, 1H), 2.99-2.84 (m, 1H), 2.13 (s, 3H), 2.09-1.97 (m, 1H), 1.91-1.82 (m, 1H), 1.79-1.65 (m, 1H), 1.64-1.50 (m, 1H).

Example 10: (R)—N-(1-Acryloylpiperidin-3-yl)-5-(2-fluoro-4-phenoxyphenyl)-4-oxo-4,5-dihydro-3H-1-thia-3,5,8-triazaacenaphthylene-2-carboxamide

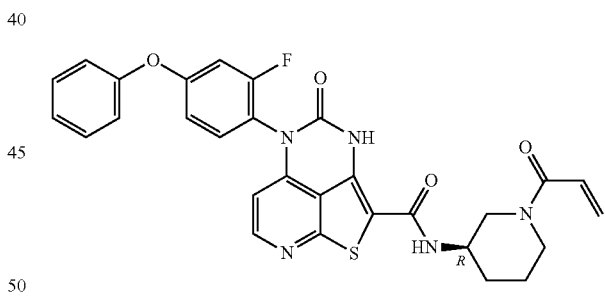

The title compound was prepared in a manner analogous to Method 1, steps C-I in Example 1, and using 2-fluoro-4-phenoxyaniline in place of 2-methyl-4-phenoxyaniline in step C and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{29}H_{24}FN_5O_4S$, 557.6; m/z found, 558.2 [M+H]⁺. ¹H NMR (400 MHz, DMSO-$d_6$): δ 10.37 (s, 1H), 8.33 (d, J=5.4 Hz, 1H), 8.22-8.05 (m, 1H), 7.64-7.51 (m, 1H), 7.51-7.38 (m, 2H), 7.28-7.20 (m, 1H), 7.20-7.09 (m, 3H), 6.99-6.90 (m, 1H), 6.86-6.63 (m, 1H), 6.17 (d, J=5.4 Hz, 1H), 6.07 (d, J=16.6 Hz, 1H), 5.65 (d, J=11.1 Hz, 1H), 4.53-4.07 (m, 1H), 4.08-3.88 (m, 1H), 3.84-3.65 (m, 1H), 3.11-2.91 (m, 1H), 2.78-2.56 (m, 1H), 2.00-1.83 (m, 1H), 1.80-1.69 (m, 1H), 1.68-1.54 (m, 1H), 1.47-1.30 (m, 1H).

Example 11: (R)—N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide

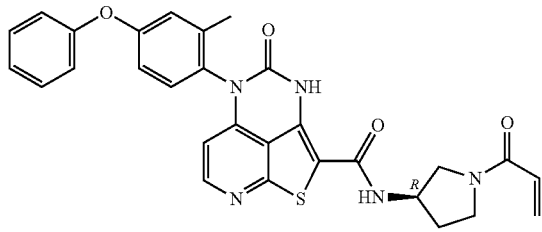

The title compound was prepared in a manner analogous to Method 1, steps A-I in Example 1, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{25}N_5O_4S$, 539.6; m/z found, 540.3 [M+H]$^+$. $^1$H NMR (400 MHz, DMSO-d$_6$): δ 10.33-10.21 (m, 1H), 8.45-8.31 (m, 2H), 7.50-7.42 (m, 2H), 7.42-7.36 (m, 1H), 7.25-7.18 (m, 1H), 7.16-7.07 (m, 3H), 7.02-6.95 (m, 1H), 6.67-6.52 (m, 1H), 6.21-6.10 (m, 1H), 6.04-5.96 (m, 1H), 5.72-5.64 (m, 1H), 4.57-4.42 (m, 1H), 3.92-3.59 (m, 4H), 3.24-1.93 (m, 5H).

Example 12: (R)—N-(1-Acryloylpyrrolidin-3-yl)-5-(2-chloro-4-phenoxyphenyl)-4-oxo-4,5-dihydro-3H-1-thia-3,5,8-triazaacenaphthylene-2-carboxamide

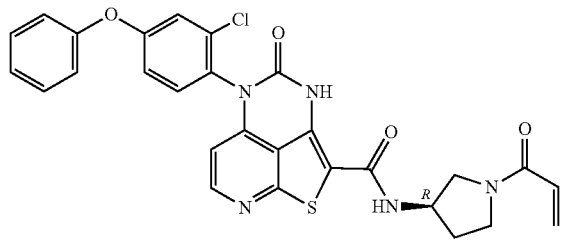

The title compound was prepared in a manner analogous to Method 1, steps A-G in Example 1 and using 2-chloro-4-fluoro-1-nitrobenzene in place of 2-methyl-4-fluoro-1-nitrobenzene for step A, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{28}H_{22}ClN_5O_4S$, 560.0; m/z found, 560.3 [M+H]$^+$. $^1$H NMR (400 MHz, DMSO-d$_6$): δ 10.40 (s, 1H), 8.53-8.39 (m, 1H), 8.36-8.31 (m, 1H), 7.62 (d, J=8.6 Hz, 1H), 7.51-7.45 (m, 2H), 7.35-7.31 (m, 1H), 7.26 (t, J=7.1 Hz, 1H), 7.22-7.16 (m, 2H), 7.16-7.12 (m, 1H), 6.65-6.52 (m, 1H), 6.17-6.10 (m, 1H), 6.08-6.02 (m, 1H), 5.70-5.63 (m, 1H), 4.57-4.40 (m, 1H), 3.90-3.70 (m, 1H), 3.69-3.60 (m, 1H), 3.58-3.49 (m, 1H), 3.45-3.39 (m, 1H), 2.25-2.09 (m, 1H), 2.02-1.92 (m, 1H).

Example 13: N-((3R,5S)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide

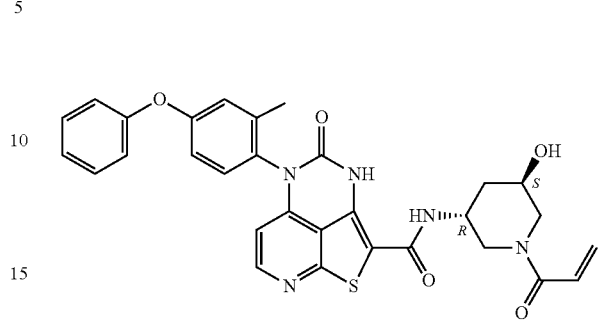

The title compound was prepared in a manner analogous to Method 1, steps A-I in Example 1, and using tert-butyl (3R,5S)-3-amino-5-hydroxypiperidine-1-carboxylate (Intermediate 2) in place of tert-butyl (3R,5R)-3-amino-5-fluoropiperidine-1-carboxylate (Intermediate 1) in step G. MS (ESI): mass calcd. for $C_{30}H_{27}N_5O_5S$, 569.17; m/z found, 570.4 [M+H]$^+$. $^1$H NMR (400 MHz, DMSO-d6): δ 10.31-10.09 (m, 1H), 8.36 (d, J=5.3 Hz, 1H), 8.19-7.98 (m, 1H), 7.53-7.35 (m, 3H), 7.27-7.16 (m, 1H), 7.18-7.06 (m, 3H), 7.04-6.94 (m, 1H), 6.85-6.67 (m, 1H), 6.18-6.04 (m, 1H), 6.01 (d, J=5.3 Hz, 1H), 5.77-5.62 (m, 1H), 4.33-4.13 (m, 1H), 4.06-3.79 (m, 2H), 3.10-2.87 (m, 2H), 2.70-2.52 (m, 1H), 2.13-1.95 (m, 4H), 1.70-1.56 (m, 1H).

Example 14: N-((3R,5S)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide

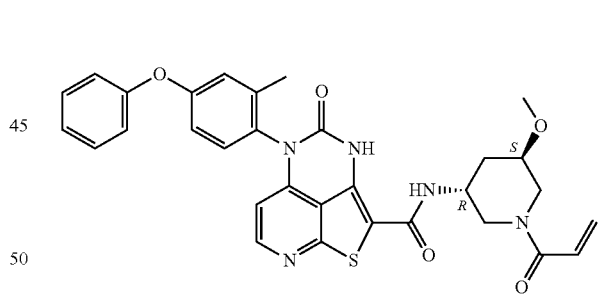

The title compound was prepared in a manner analogous to Method 1, steps A-I in Example 1 and using tert-Butyl (3R,5S)-3-amino-5-methoxypiperidine-1-carboxylate (Intermediate 29) in place of tert-butyl (3R,5R)-3-amino-5-fluoropiperidine-1-carboxylate (Intermediate 1) in step G. MS (ESI): mass calcd. for $C_{31}H_{29}N_5O_5S$, 583.7; m/z found, 584.2 [M+H]$^+$. $^1$H NMR (400 MHz, CD$_3$OD): δ 8.39-8.29 (m, 1H), 7.47-7.36 (m, 2H), 7.30-7.27 (m, 1H), 7.20-7.15 (m, 1H), 7.12-7.03 (m, 3H), 7.02-6.93 (m, 1H), 6.85-6.60 (m, 1H), 6.17-6.05 (m, 2H), 5.79-5.60 (m, 1H), 4.44-4.26 (m, 1H), 4.23-4.12 (m, 1H), 4.03-3.92 (m, 1H), 3.68-3.55 (m, 2H), 3.53-3.45 (m, 3H), 3.44-3.35 (m, 1H), 2.17-2.09 (m, 4H), 2.02-1.96 (m, 1H).

Example 15: (R)—N-(1-Acryloylpiperidin-3-yl)-5-(2-chloro-4-phenoxyphenyl)-4-oxo-4,5-dihydro-3H-1-thia-3,5,8-triazaacenaphthylene-2-carboxamide

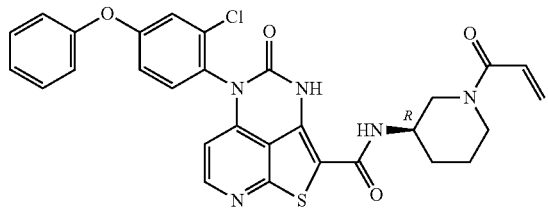

The title compound was prepared in a manner analogous to Method 1, steps A-I in Example 1 and using 2-chloro-4-fluoro-1-nitrobenzene in place of 5-fluoro-2-nitrotoluene in step A and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{29}H_{24}ClN_5O_4S$, 574.1; m/z found, 574.3 [M+H]$^+$. $^1$H NMR (400 MHz, CD$_3$OD): δ 8.33 (d, J=5.6 Hz, 1H), 7.78-7.73 (m, 1H), 7.52-7.45 (m, 1H), 7.36-7.21 (m, 2H), 7.10-7.02 (m, 2H), 7.00-6.88 (m, 2H), 6.88-6.70 (m, 1H), 6.28-6.14 (m, 1H), 6.07 (d, J=5.6 Hz, 1H), 5.81-5.66 (m, 1H), 4.63-3.87 (m, 3H), 3.25-3.10 (m, 1H), 3.01-2.82 (m, 1H), 2.14 (s, 3H), 2.09-2.01 (m, 1H), 1.94-1.83 (m, 1H), 1.81-1.68 (m, 1H), 1.65-1.52 (m, 1H).

Example 16: (R)—N-(1-Acryloylpiperidin-3-yl)-5-(4-(benzofuran-7-yloxy)-2-methylphenyl)-4-oxo-4,5-dihydro-3H-1-thia-3,5,8-triazaacenaphthylene-2-carboxamide

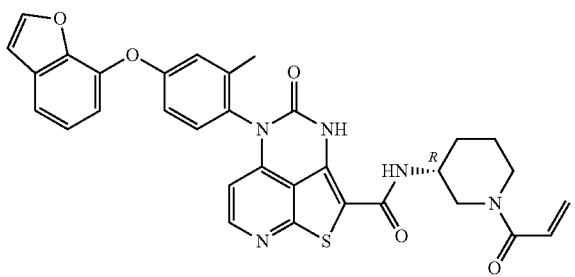

The title compound was prepared in a manner analogous to Method 1, steps A-I in Example 1, and using benzofuran-7-ol (Intermediate 8) in place of phenol in step A, and using (R)-tert-butyl 3-aminopiperidine-1-carboxylate place of tert-butyl (3R,5R)-3-amino-5-fluoropiperidine-1-carboxylate (Intermediate 1) in step G. MS (ESI): mass calcd. for $C_{32}H_{27}N_5O_5S$, 593.7; m/z found, 594.2 [M+H]$^+$. $^1$H NMR (400 MHz, CD$_3$OD): δ 8.33 (d, J=5.6 Hz, 1H), 7.78-7.73 (m, 1H), 7.52-7.45 (m, 1H), 7.36-7.21 (m, 2H), 7.10-7.02 (m, 2H), 7.00-6.88 (m, 2H), 6.88-6.70 (m, 1H), 6.28-6.14 (m, 1H), 6.07 (d, J=5.6 Hz, 1H), 5.81-5.66 (m, 1H), 4.63-3.87 (m, 3H), 3.25-3.10 (m, 1H), 3.01-2.82 (m, 1H), 2.14 (s, 3H), 2.09-2.01 (m, 1H), 1.94-1.83 (m, 1H), 1.81-1.68 (m, 1H), 1.65-1.52 (m, 1H).

Example 17: (R)—N-(1-Acryloylpyrrolidin-3-yl)-5-(4-(2,6-difluorophenoxy)-2-methylphenyl)-4-oxo-4,5-dihydro-3H-1-thia-3,5,8-triazaacenaphthylene-2-carboxamide

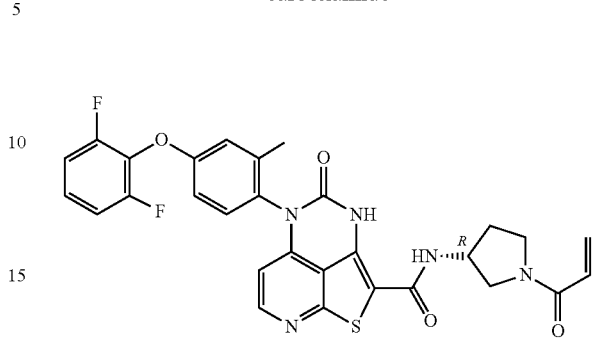

The title compound was prepared in a manner analogous to Method 1, steps A-I in Example 1, and using 2,6-difluorophenol in place of phenol in step A, and using (R)-tert-butyl 3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{23}F_2N_5O_4S$, 575.6; m/z found, 576.1 [M+H]$^+$. $^1$H NMR (400 MHz, CD$_3$OD): δ 8.32 (d, J=5.6 Hz, 1H), 7.38-7.27 (m, 2H), 7.22-7.11 (m, 2H), 7.04-6.99 (m, 1H), 6.96-6.89 (m, 1H), 6.73-6.51 (m, 1H), 6.34-6.20 (m, 1H), 6.08-6.00 (m, 1H), 5.80-5.64 (m, 1H), 4.71-4.54 (m, 1H), 4.02-3.49 (m, 4H), 2.41-2.01 (m, 5H).

Example 18: (R)—N-(1-Acryloylpiperidin-3-yl)-4-oxo-5-(4-phenoxyphenyl)-4,5-dihydro-3H-1-thia-3,5,8-triazaacenaphthylene-2-carboxamide

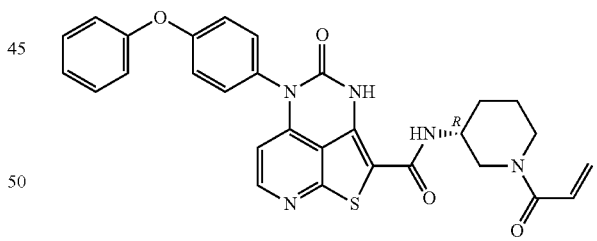

The title compound was prepared in a manner analogous to Method 1, steps A-I in Example 1, and using 4-fluoronitrobenzene in place of 5-fluoro-2-nitrotoluene in step A, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{29}H_{25}N_5O_4S$, 539.6; m/z found, 540.2 [M+H]$^+$. $^1$H NMR (500 MHz, CD$_3$OD): δ 8.33 (d, J=5.6 Hz, 1H), 7.48-7.32 (m, 4H), 7.27-7.07 (m, 5H), 6.90-6.68 (m, 1H), 6.21 (dd, J=14.0, 5.4 Hz, 2H), 5.79-5.69 (m, 1H), 4.60-3.87 (m, 3H), 3.24-3.12 (m, 1H), 2.99-2.81 (m, 1H), 2.15-1.46 (m, 4H).

Example 19: (R)—N-(1-Acryloylpiperidin-3-yl)-5-(4-(2-ethylphenoxy)-2-methylphenyl)-4-oxo-4,5-dihydro-3H-1-thia-3,5,8-triazaacenaphthylene-2-carboxamide

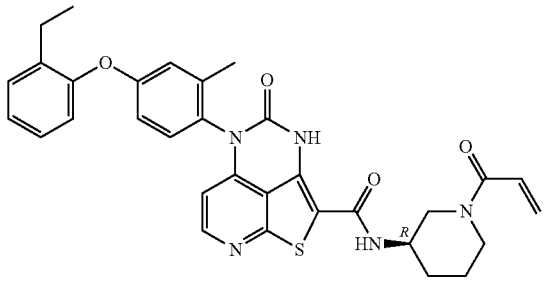

The title compound was prepared in a manner analogous to Method 1, steps A-I in Example 1, and using 2-ethylphenol in place of phenol in step A, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{32}H_{31}N_5O_4S$, 581.7; m/z found, 582.1 [M+H]$^+$. $^1$H NMR (400 MHz, CD$_3$OD): δ 8.32 (d, J=5.6 Hz, 1H), 7.36-7.30 (m, 1H), 7.27-7.20 (m, 2H), 7.18-7.12 (m, 1H), 7.00-6.93 (m, 2H), 6.88-6.83 (m, 1H), 6.83-6.71 (m, 1H), 6.25-6.12 (m, 1H), 6.05 (d, J=5.6 Hz, 1H), 5.78-5.66 (m, 1H), 4.62-4.11 (m, 2H), 3.98-3.88 (m, 1H), 3.23-3.13 (m, 1H), 2.99-2.82 (m, 1H), 2.71-2.57 (m, 2H), 2.12-2.05 (m, 4H), 1.91-1.81 (m, 1H), 1.76-1.55 (m, 2H), 1.23-1.13 (m, 3H).

Example 20: (R)—N-(1-Acryloylpiperidin-3-yl)-5-(2-fluoro-6-methyl-4-phenoxyphenyl)-4-oxo-4,5-dihydro-3H-1-thia-3,5,8-triazaacenaphthylene-2-carboxamide

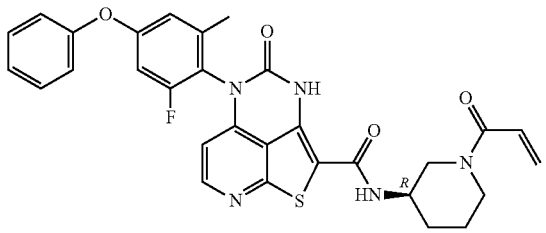

The title compound was prepared in a manner analogous to Method 1, steps C-I in Example 1, and using 2-fluoro-6-methyl-4-phenoxyaniline (Intermediate 9) in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{26}FN_5O_4S$, 571.6; m/z found, 572.5 [M+H]$^+$. $^1$H NMR (400 MHz, CD$_3$OD): δ 8.37 (d, J=5.5 Hz, 1H), 7.53-7.39 (m, 2H), 7.30-7.19 (m, 1H), 7.17-7.09 (m, 2H), 6.93-6.68 (m, 3H), 6.26-6.11 (m, 2H), 5.84-5.63 (m, 1H), 4.62-3.83 (m, 3H), 3.25-3.10 (m, 1H), 3.03-2.83 (m, 1H), 2.16 (s, 3H), 2.11-2.02 (m, 1H), 1.95-1.52 (m, 3H).

Example 21: (R,E)-N-(1-(2-cyano-3-(3-methyloxetan-3-yl)acryloyl)piperidin-3-yl)-5-(2-methyl-4-phenoxyphenyl)-4-oxo-4,5-dihydro-3H-1-thia-3,5,8-triazaacenaphthylene-2-carboxamide

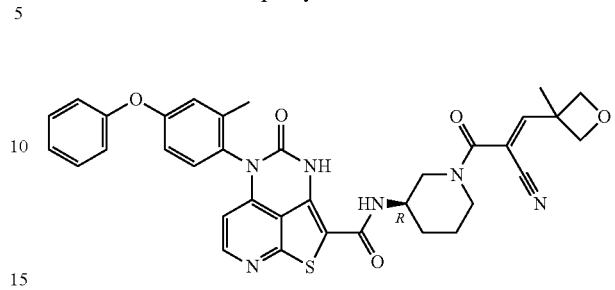

To a round bottom flask were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 120 mg, 0.212 mmol), 3-methyloxetane-3-carbaldehyde (64 mg, 0.64 mmol), piperidine (0.3 mL), acetic acid (0.1 mL), dioxane (10 mL), and 4A molecular sieves (1 g) and the reaction mixture was stirred at 100° C. for 1 h under N2. The mixture was concentrated to dryness and purified by flash column chromatography to yield the title compound (69 mg, 50% yield) as a white solid. MS (ESI): mass calcd. for $C_{35}H_{32}N_6O_5S$, 648.7; m/z found, 649.0 [M+H]$^+$. $^1$H NMR (400 MHz, CD$_3$OD): δ 8.33-8.27 (m, 1H), 7.42-7.35 (m, 2H), 7.33-7.23 (m, 2H), 7.20-7.12 (m, 1H), 7.10-7.01 (m, 3H), 6.99-6.92 (m, 1H), 6.07-6.01 (m, 1H), 5.08-4.92 (m, 1H), 4.68-4.54 (m, 1H), 4.53-4.37 (m, 2H), 4.35-4.22 (m, 1H), 4.09-3.70 (m, 3H), 3.65-3.36 (m, 1H), 2.15-2.01 (m, 4H), 1.99-1.73 (m, 2H), 1.69-1.57 (m, 4H).

Example 22: (R)—N-(1-Acryloylpyrrolidin-3-yl)-5-(4-(benzofuran-7-yloxy)-2-methylphenyl)-4-oxo-4,5-dihydro-3H-1-thia-3,5,8-triazaacenaphthylene-2-carboxamide

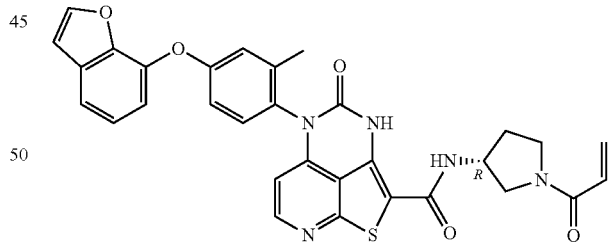

The title compound was prepared in a manner analogous to Method 1, steps A-I in Example 1, and using benzofuran-7-ol (Intermediate 8) in place of phenol in step A, and using (R)-tert-butyl 3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{31}H_{25}N_5O_5S$, 579.6; m/z found, 580.2 [M+H]$^+$. $^1$H NMR (400 MHz, CD$_3$OD): δ 8.36 (d, J=5.7 Hz, 1H), 7.77-7.73 (m, 1H), 7.52-7.46 (m, 1H), 7.32-7.21 (m, 2H), 7.08-7.02 (m, 2H), 7.00-6.87 (m, 2H), 6.70-6.53 (m, 1H), 6.33-6.24 (m, 1H), 6.12 (d, J=5.7 Hz, 1H), 5.80-5.69 (m, 1H), 4.70-4.57 (m, 1H), 4.03-3.48 (m, 4H), 2.37-2.04 (m, 5H).

Example 23: (R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide

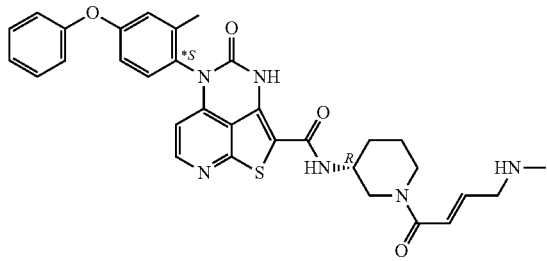

Step A: tert-butyl (R,E)-methyl(4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate The title compound was prepared in a manner analogous to Example 104 (including Chiral resolution Method A after Step F to obtain the *S atropisomer), and using (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98) and (E)-4-[tert-Butoxycarbonyl(methyl)amino]but-2-enoic Acid (Intermediate 10).

Step B: (R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide To a flask containing tert-butyl (R,E)-methyl(4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate (52 mg, 0.075 mmol) was added MeOH (4.0 mL) and concentrated aqueous HCl (4.0 mL). The reaction mixture was stirred at rt for 1 h, then the mixture was concentrated under reduced pressure and purified by silica gel chromatography to give the title compound (32 mg, 65%) as a white solid. MS (ESI): mass calcd. for $C_{32}H_{32}N_6O_4S$, 596.7; m/z found, 597.3 [M+H]$^+$. $^1$H NMR (400 MHz, CD$_3$OD): δ 8.40 (s, 1H), 8.37-8.30 (m, 1H), 7.44-7.37 (m, 2H), 7.34-7.27 (m, 1H), 7.21-7.14 (m, 1H), 7.13-7.04 (m, 3H), 7.01-6.95 (m, 1H), 6.92-6.82 (m, 1H), 6.74-6.60 (m, 1H), 6.12-6.05 (m, 1H), 4.54-3.91 (m, 3H), 3.84-3.75 (m, 2H), 3.25-3.08 (m, 1H), 3.00-2.81 (m, 1H), 2.71 (s, 3H), 2.18-2.02 (m, 4H), 1.94-1.83 (m, 1H), 1.82-1.67 (m, 1H), 1.66-1.53 (m, 1H).

Example 24: (R)-5-(4-(3-((2-Cyanophenoxy)methyl)phenoxy)-2-methylphenyl)-N-(1-methylpiperidin-3-yl)-4-oxo-4,5-dihydro-3H-1-thia-3,5,8-triazaacenaphthylene-2-carboxamide

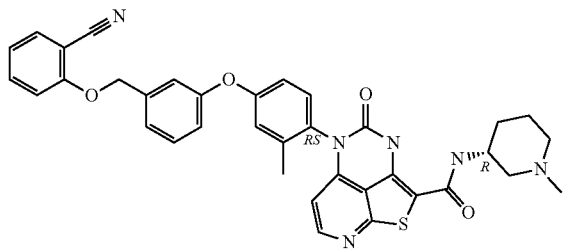

The title compound was prepared using the method from Example 52 Step B, and using (R)-5-(4-(3-((2-cyanophenoxy)methyl)phenoxy)-2-methylphenyl)-4-oxo-N-(piperidin-3-yl)-4,5-dihydro-3H-1-thia-3,5,8-triazaacenaphthylene-2-carboxamide (Intermediate 78) in place of (R)-5-(4-(2,6-difluorophenoxy)-2-methylphenyl)-4-oxo-N-(piperidin-3-yl)-4,5-dihydro-3H-1-thia-3,5,8-triazaacenaphthylene-2-carboxamide. MS (ESI): mass calcd. for $C_{36}H_{32}N_6O_4S$, 644.7; m/z found, 645 [M+H]$^+$. $^1$H NMR (400 MHz, DMSO-d$_6$): δ 8.30 (d, J=5.4 Hz, 1H), 8.07 (d, J=7.7 Hz, 1H), 7.80-7.70 (m, 1H), 7.69-7.60 (m, 1H), 7.53-7.44 (m, 1H), 7.37-7.23 (m, 3H), 7.17-7.05 (m, 3H), 7.04-6.93 (m, 1H), 5.95 (d, J=5.5 Hz, 1H), 5.33 (s, 2H), 4.05-3.92 (m, 1H), 2.95-2.84 (m, 1H), 2.80-2.68 (m, 1H), 2.27 (s, 3H), 2.05 (s, 3H), 2.03-1.93 (m, 2H), 1.85-1.65 (m, 2H), 1.61-1.47 (m, 1H), 1.45-1.30 (m, 1H).

Example 25: (S,E)-N-(1-(4-Hydroxybut-2-enoyl)piperidin-3-yl)-5-(2-methyl-4-phenoxyphenl)-4-oxo-4,5-dihydro-3H-1-thia-3,5,8-triazaacenaphthylene-2-carboxamide

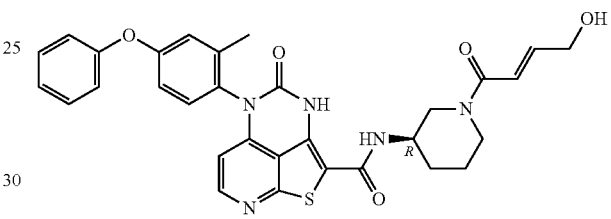

The title compound was prepared in a manner analogous to Method 1, steps A-I in Example 1, and using tert-butyl (3R)-3-aminopiperidine-1-carboxylate in place of tert-butyl (3R,5R)-3-amino-5-fluoropiperidine-1-carboxylate (Intermediate 1) in step G, and using (E)-4-hydroxybut-2-enoic acid (Intermediate 13) in place of prop-2-enoyl chloride in step I. MS (ESI): mass calcd. for $C_{31}H_{29}N_5O_5S$, 583.7; m/z found, 584.6 [M+H]$^+$. $^1$H NMR (400 MHz, CD$_3$OD): δ 8.33-8.29 (m, 1H), 7.42-7.35 (m, 2H), 7.33-7.28 (m, 1H), 7.19-7.12 (m, 1H), 7.10-7.02 (m, 3H), 6.99-6.94 (m, 1H), 6.88-6.77 (m, 1H), 6.71-6.61 (m, 1H), 6.08-6.03 (m, 1H), 4.53-3.90 (m, 5H), 3.24-3.12 (m, 1H), 2.97-2.84 (m, 1H), 2.11 (s, 3H), 2.09-2.00 (m, 1H), 1.89-1.81 (m, 1H), 1.77-1.65 (m, 1H), 1.63-1.50 (m, 1H).

Example 26: (R)—N-(1-(2-Chloroacryloyl)piperidin-3-yl)-5-(2-methyl-4-phenoxyphenyl)-4-oxo-4,5-dihydro-3H-1-thia-3,5,8-triazaacenaphthylene-2-carboxamide

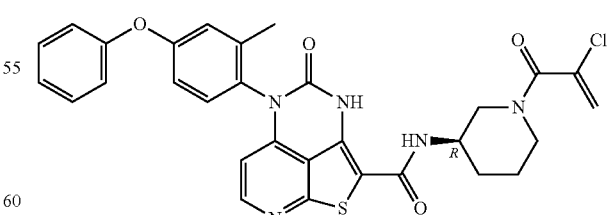

The title compound was prepared in a manner analogous to Example 104, using 2-chloroprop-2-enic acid and (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869). MS (ESI): mass calcd. for $C_{30}H_{26}ClN_5O_4S$, 588.1; m/z found, 588.3 [M+H]$^+$. $^1$H NMR (400 MHz, CD$_3$OD): δ 8.42-8.37 (m, 1H), 7.44-7.35 (m, 2H), 7.33-7.28 (m, 1H), 7.20-7.13 (m, 1H), 7.11-7.03 (m, 3H), 7.00-6.93 (m, 1H), 6.22-6.06 (m, 1H), 5.70 (s, 2H), 4.48-4.13 (m, 1H), 4.12-3.83 (m, 2H), 3.25-3.12 (m, 1H), 2.99-2.82 (m, 1H), 2.12 (s, 3H), 2.10-2.01 (m, 1H), 1.93-1.83 (m, 1H), 1.80-1.67 (m, 1H), 1.65-1.52 (m, 1H).

Example 27: (R,E)-N-(1-(4-Aminobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

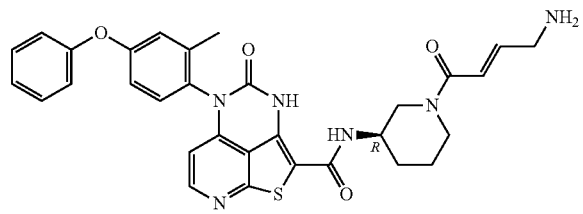

Step A: tert-butyl (R,E)-(4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate The title compound was prepared in a manner analogous to Example 104, using tert-butyl (3R)-3-aminopiperidine-1-carboxylate and (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869).

Step B: (R,E)-N-(1-(4-Aminobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide The title compound was prepared using the conditions described in Step B of Example 131 using tert-butyl (R,E)-(4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate. MS (ESI): mass calcd. for C$_{31}$H$_{30}$N$_6$O$_4$S, 582.7; m/z found, 583.4 [M+H]$^+$. $^1$H NMR (400 MHz, CD$_3$OD): δ 8.48 (s, 1H), 8.38-8.31 (m, 1H), 7.45-7.37 (m, 2H), 7.33-7.27 (m, 1H), 7.22-7.14 (m, 1H), 7.14-7.03 (m, 3H), 7.02-6.95 (m, 1H), 6.85-6.78 (m, 1H), 6.77-6.67 (m, 1H), 6.12-6.06 (m, 1H), 4.57-3.89 (m, 3H), 3.78-3.71 (m, 2H), 3.25-3.08 (m, 1H), 2.97-2.80 (m, 1H), 2.17-2.01 (m, 4H), 1.96-1.84 (m, 1H), 1.83-1.70 (m, 1H), 1.67-1.53 (m, 1H).

Example 28: N-((3S,4R)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide

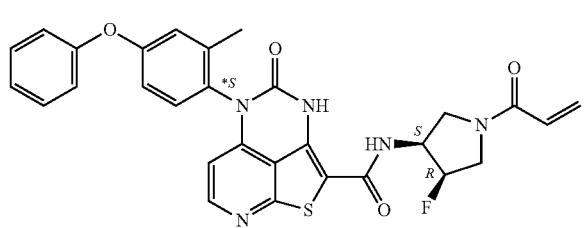

The title compound was prepared in a manner analogous to Method 1, steps A-I (including Chiral resolution Method A after Step F to obtain the *S atropisomer) in Example 1, and using tert-butyl (3S,4R)-3-amino-4-fluoropyrrolidine-1-carboxylate in place of tert-butyl (3R,5R)-3-amino-5-fluoropiperidine-1-carboxylate (Intermediate 1) in step G. MS (ESI): mass calcd. for C$_{29}$H$_{24}$FN$_5$O$_4$S, 557.6; m/z found, 558.2 [M+H]$^+$. $^1$H NMR (400 MHz, CD$_3$OD): δ 8.37-8.30 (m, 1H), 7.45-7.37 (m, 2H), 7.33-7.26 (m, 1H), 7.21-7.14 (m, 1H), 7.11-7.02 (m, 3H), 7.00-6.92 (m, 1H), 6.67-6.53 (m, 1H), 6.36-6.26 (m, 1H), 6.12-6.05 (m, 1H), 5.81-5.74 (m, 1H), 5.39-5.16 (m, 1H), 4.19-3.84 (m, 3H), 3.81-3.52 (m, 2H), 2.12 (s, 3H).

Example 29: (R,EZ)—N-(1-(2-Cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

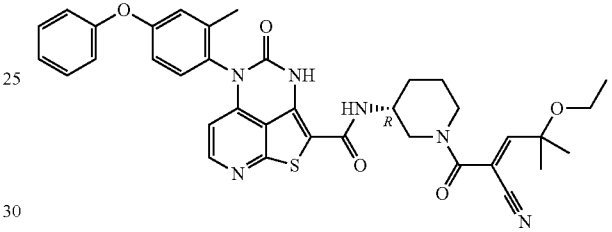

To a round bottom flask were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 200 mg, 0.35 mmol), 2-ethoxy-2-methylpropanal (123 mg, 1.1 mmol), piperdine (0.3 mL), and EtOH (5 mL) and was stirred at rt for 15 h. Then the reaction mixture was concentrated to dryness and purified by flash column chromatography to yield the title compound (154 mg, 63.0% yield) as a light yellow solid. MS (ESI): mass calcd. for C$_{36}$H$_{36}$N$_6$O$_5$S, 664.8; m/z found, 665.8 [M+H]$^+$. $^1$H NMR (400 MHz, CD$_3$OD): δ 8.35-8.31 (m, 1H), 7.43-7.37 (m, 2H), 7.33-7.27 (m, 1H), 7.20-7.14 (m, 1H), 7.11-7.03 (m, 3H), 7.00-6.95 (m, 1H), 6.92-6.69 (m, 1H), 6.12-6.05 (m, 1H), 4.62-3.89 (m, 3H), 3.60-3.34 (m, 3H), 3.19-2.86 (m, 1H), 2.21-2.20 (m, 4H), 1.96-1.85 (m, 1H), 1.80-1.62 (m, 2H), 1.50-1.21 (m, 9H).

Example 30: (R,E)-N-(1-(4-Hydroxybut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide

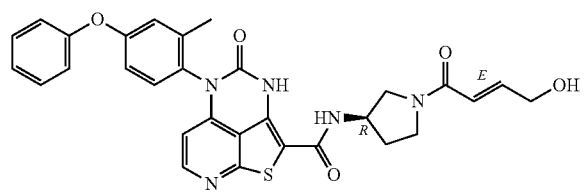

The title compound was prepared using the method in Example 104, and using (E)-4-hydroxybut-2-enoic acid (Intermediate 13) in place of methylsulfonylpropanoic acid.

MS (ESI): mass calcd. for $C_{30}H_{27}N_5O_5S$, 569.6; m/z found, 570.5 [M+H]$^+$. $^1$H NMR (400 MHz, DMSO-d$_6$): δ 10.24 (s, 1H), 8.32 (d, J=5.4 Hz, 1H), 7.49-7.40 (m, 2H), 7.36 (d, J=8.6 Hz, 1H), 7.23-7.15 (m, 1H), 7.14-7.03 (m, 3H), 7.02-6.90 (m, 1H), 6.81-6.67 (m, 1H), 6.46-6.25 (m, 1H), 5.96 (d, J=5.2 Hz, 1H), 5.09-4.90 (m, 1H), 4.57-4.37 (m, 1H), 4.21-4.05 (m, 2H), 3.88-3.38 (m, 4H), 2.22-2.08 (m, 1H), 2.05 (s, 3H), 2.01-1.90 (m, 1H).

Example 31: N-(4-Cyano-1,4-oxazepan-6-yl)-5-(2-methyl-4-phenoxyphenyl)-4-oxo-4,5-dihydro-3H-1-thia-3,5,8-triazaacenaphthylene-2-carboxamide

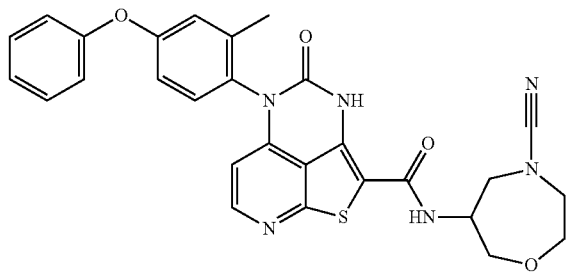 [SMILES: Cc1cc(Oc2ccccc2)ccc1N1C(=O)Nc2c(C(=O)NC3COCCN(C#N)C3)sc3nccc1c23]

The title compound was prepared in a manner analogous to Method 1, steps A-I in Example 1, and using tert-butyl 6-amino-1,4-oxazepane-4-carboxylate in place of tert-butyl (3R,5R)-3-amino-5-fluoropiperidine-1-carboxylate (Intermediate 1) in step G, and using bromocyanide in place of prop-2-enoyl chloride in step I. MS (ESI): mass calcd. for $C_{28}H_{24}N_6O_4S$, 540.6; m/z found, 541.5 [M+H]$^+$. $^1$H NMR (400 MHz, DMSO-d6): δ 10.26 (s, 1H), 8.40-8.26 (m, 1H), 8.19 (s, 1H), 7.49-7.37 (m, 2H), 7.37-7.28 (m, 1H), 7.21-7.14 (m, 1H), 7.14-7.02 (m, 3H), 6.99-6.91 (m, 1H), 6.04-5.86 (m, 1H), 4.38-4.22 (m, 1H), 3.90-3.81 (m, 1H), 3.80-3.66 (m, 3H), 3.57-3.50 (m, 1H), 3.41-3.35 (m, 3H), 2.03 (s, 3H).

Example 32: (R)—N-(1-Acryloylpiperidin-3-yl)-5-(4-(cyclohexloxy)-2-methylphenyl)-4-oxo-4,5-dihydro-3H-1-thia-3,5,8-triazaacenaphthylene-2-carboxamide

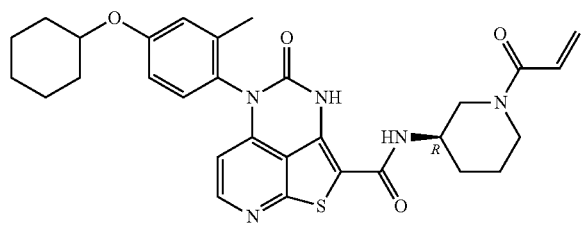

Step A: 2-Chloro-4-[4-(cyclohexoxy)-2-methylanilino]pyridine-3-carbonitrile

To a round bottom flask containing 2-chloro-4-(4-hydroxy-2-methylanilino)pyridine-3-carbonitrile (Intermediate 14) (1 g, 4 mmol), cyclohexanol (1.16 g, 11.6 mmol), PPh$_3$ (1.5 g, 5.7 mmol), and THF (20 mL) at 0° C. was added DIAD (1.17 g, 5.79 mmol). The mixture was stirred at rt overnight. The mixture was concentrated to dryness and the residue was purified by flash column chromatography to yield the title compound (400 mg, 30% yield) as a yellow solid.

Step B: (R)—N-(1-Acryloylpiperidin-3-yl)-5-(4-(cyclohexyloxy)-2-methylphenyl)-4-oxo-4,5-dihydro-3H-1-thia-3,5,8-triazaacenaphthylene-2-carboxamide The title compound was prepared in a manner analogous to Method 1, steps D-I in Example 1, and using 2-chloro-4-[4-(cyclohexoxy)-2-methylanilino]pyridine-3-carbonitrile in place of 2-chloro-4-(2-methyl-4-phenoxyanilino)pyridine-3-carbonitrile in step D, and using tert-butyl (3R)-3-aminopiperidine-1-carboxylate in place of tert-butyl (3R, 5R)-3-amino-5-fluoropiperidine-1-carboxylate (Intermediate 1) in step G. MS (ESI): mass calcd. for $C_{30}H_{33}N_5O_4S$, 559.7; m/z found, 560.1 [M+H]$^+$. $^1$H NMR (400 MHz, CD$_3$OD): δ 8.43 (s, 1H), 8.30 (d, J=5.5 Hz, 1H), 7.23-7.15 (m, 1H), 7.02-6.95 (m, 1H), 6.94-6.89 (m, 1H), 6.87-6.71 (m, 1H), 6.27-6.14 (m, 1H), 6.03 (d, J=5.5 Hz, 1H), 5.79-5.67 (m, 1H), 4.55-3.88 (m, 4H), 3.25-3.11 (m, 1H), 3.01-2.80 (m, 1H), 2.10 (s, 3H), 2.06-1.94 (m, 3H), 1.90-1.69 (m, 4H), 1.65-1.36 (m, 7H).

Example 33: (R)—N-(1-Acryloylpiperidin-3-yl)-5-(4-isopropoxy-2-methylphenyl)-4-oxo-4,5-dihydro-3H-1-thia-3,5,8-triazaacenaphthylene-2-carboxamide

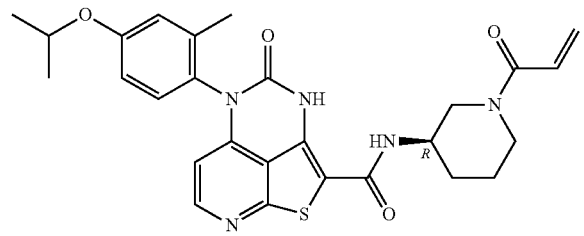

Step A: 4-Isopropoxy-2-methyl-1-nitrobenzene

To a round bottom flask were added 3-methyl-4-nitrophenol (5.0 g, 33 mmol), K$_2$CO$_3$ (9.0 g, 65 mmol), DMF (20 mL), and 2-iodopropane (8.3 g, 460 mmol) and the reaction was stirred at 80° C. overnight. Water was added to the mixture and a yellow precipitate formed. The mixture was filtered and the precipitate was washed with water and dried under vacuum to yield the title compound (5.0 g, 78% yield).

Step B: 4-Isopropoxy-2-methylaniline

To a round bottom flask were added 4-isopropoxy-2-methyl-1-nitrobenzene (5.0 g, 26 mmol) and MeOH (100 mL). The reaction mixture was evacuated under reduced pressure and filled with N$_2$ (3×) and Pd/C (10% on carbon; 500 mg) was added. The mixture was evacuated under reduced pressure and filled with N$_2$ (3×), then evacuated under reduced pressure and filled with H$_2$. The mixture was stirred under H$_2$ atmosphere overnight. The mixture was filtered over diatomaceous earth and concentrated to dryness to yield the title compound (3.5 g, 83% yield).

Step C: 2-Chloro-4-(4-isopropoxy-2-methylanilino) pyridine-3-carbonitrile

To a round bottom flask were added 4-isopropoxy-2-methylaniline (1 g, 6 mmol), 2-chloro-4-iodopyridine-3-carbonitrile (2.0 g, 7.6 mmol), DPEPhos[bis(2-diphenylphosphinophenyl)ether] (650 mg, 1.2 mmol), palladium(II) acetate (135 mg, 0.600 mmol), and $K_3PO_4$ (3.5 g, 16 mmol). The reaction mixture was degassed and heated at 120° C. overnight. The mixture was cooled to rt, concentrated to dryness, and purified by flash column chromatography to yield the title compound (2.34 g, 65.0% yield) as a yellow solid.

Step D: (R)—N-(1-Acryloylpiperidin-3-yl)-5-(4-isopropoxy-2-methylphenyl)-4-oxo-4,5-dihydro-3H-1-thia-3,5,8-triazaacenaphthylene-2-carboxamide The title compound was prepared in a manner analogous to Method 1, steps D-I in Example 1, and using 2-chloro-4-(4-isopropoxy-2-methylanilino)pyridine-3-carbonitrile in place of 2-chloro-4-(2-methyl-4-phenoxyanilino)pyridine-3-carbonitrile in step D, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{27}H_{29}N_5O_4S$, 519.6; m/z found, 520.2 [M+H]$^+$. $^1$H NMR (400 MHz, DMSO-d$_6$): δ 10.18 (s, 1H), 8.30 (d, J=5.4 Hz, 1H), 8.18-8.01 (m, 1H), 7.33-7.15 (m, 1H), 7.04-6.87 (m, 2H), 6.85-6.67 (m, 1H), 6.22-6.02 (m, 1H), 5.89 (d, J=5.4 Hz, 1H), 5.74-5.60 (m, 1H), 4.78-4.56 (m, 1H), 4.57-3.86 (m, 2H), 3.84-3.68 (m, 1H), 3.17-2.90 (m, 1H), 2.85-2.59 (m, 1H), 2.03 (s, 3H), 1.98-1.88 (m, 1H), 1.82-1.55 (m, 2H), 1.52-1.36 (m, 1H), 1.35-1.24 (m, 6H).

Example 34: N-((3S,4R)-1-Acryloyl-4-methoxypyrrolidin-3-yl)-5-(2-methyl-4-phenoxyphenl)-4-oxo-4,5-dihydro-3H-1-thia-3,5,8-triazaacenaphthylene-2-carboxamide

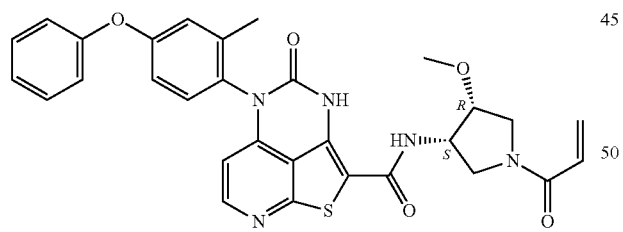

The title compound was prepared in a manner analogous to Method 1, steps A-I in Example 1, and using tert-butyl (3S,4R)-3-amino-4-methoxypyrrolidine-1-carboxylate (Intermediate 11) in place of tert-butyl (3R,5R)-3-amino-5-fluoropiperidine-1-carboxylate (Intermediate 1) in step G. MS (ESI): mass calcd. for $C_{30}H_{27}N_5O_5S$, 569.6; m/z found, 570.4 [M+H]$^+$. $^1$H NMR (400 MHz, CD$_3$OD and DMSO-d$_6$): δ 8.29 (d, J=5.4 Hz, 1H), 7.44-7.35 (m, 2H), 7.32-7.26 (m, 1H), 7.18-7.10 (m, 1H), 7.10-7.00 (m, 3H), 6.98-6.90 (m, 1H), 6.62-6.47 (m, 1H), 6.23-6.10 (m, 1H), 5.98 (d, J=5.5 Hz, 1H), 5.72-5.63 (m, 1H), 4.75-4.49 (m, 1H), 4.05-3.90 (m, 2H), 3.82-3.60 (m, 1H), 3.52-3.41 (m, 1H), 3.36-3.27 (m, 3H), 2.05 (s, 3H).

Example 35: (R)—N-(1-Cyanopiperidin-3-yl)-5-(*S)-(2-methyl-4-phenoxyphenyl)-4-oxo-4,5-dihydro-3H-1-thia-3,5,8-triazaacenaphthylene-2-carboxamide

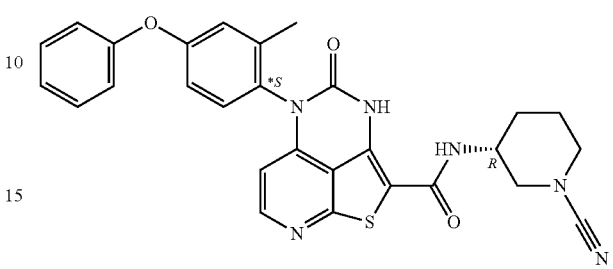

The title compound was prepared in a manner analogous to Method 1, steps A-I (including Chiral resolution Method A after Step F to obtain the *S atropisomer) in Example 1, and using tert-butyl (3R)-3-aminopiperidine-1-carboxylate in place of tert-butyl (3R,5R)-3-amino-5-fluoropiperidine-1-carboxylate (Intermediate 1) in step G, and using bromocyanide in place of prop-2-enoyl chloride in step I. MS (ESI): mass calcd. for $C_{28}H_{24}N_6O_3S$, 524.6; m/z found, 525.3 [M+H]$^+$. $^1$H NMR (400 MHz, DMSO-d$_6$): δ 10.18 (br, 1H), 8.36-8.25 (m, 1H), 8.23-8.08 (br, 1H), 7.46-7.39 (m, 2H), 7.37-7.30 (m, 1H), 7.20-7.16 (m, 1H), 7.13-7.05 (m, 3H), 6.99-6.92 (m, 1H), 6.00-5.86 (m, 1H), 3.97-3.90 (m, 1H), 2.98-2.90 (m, 2H), 2.03 (s, 3H), 2.01-1.90 (m, 1H), 1.90-1.83 (m, 1H), 1.82-1.73 (m, 1H), 1.66-1.51 (m, 2H), 1.51-1.34 (m, 1H).

Example 36: N-((3S,4S)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide

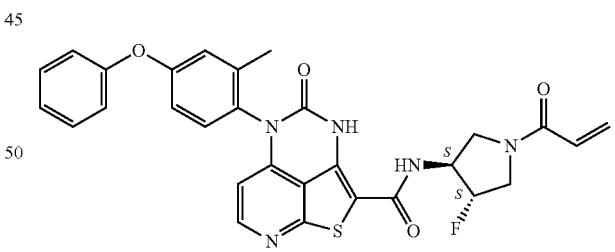

The title compound was prepared in a manner analogous to Method 1, steps A-I in Example 1, and using tert-butyl (3S,4S)-3-amino-4-fluoropyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{24}FN_5O_4S$, 557.6; m/z found, 558.1 [M+H]$^+$. $^1$H NMR (400 MHz, CD$_3$OD): δ 8.33 (d, J=5.5 Hz, 1H), 7.47-7.37 (m, 2H), 7.34-7.27 (m, 1H), 7.24-7.13 (m, 1H), 7.13-7.02 (m, 3H), 7.02-6.94 (m, 1H), 6.70-6.56 (m, 1H), 6.39-6.28 (m, 1H), 6.08 (d, J=5.5 Hz, 1H), 5.83-5.74 (m, 1H), 5.35-5.16 (m, 1H), 4.76-4.65 (m, 1H), 4.10-3.74 (m, 4H), 2.12 (s, 3H).

Example 37: N-((3S,4R)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide

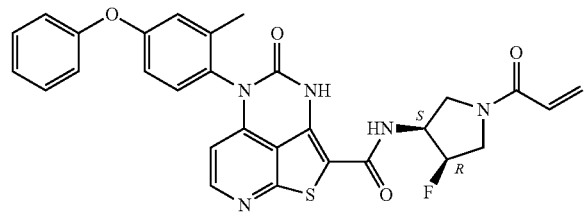

The title compound was prepared in a manner analogous to Method 1, steps A-I in Example 1, and using tert-butyl (3S,4R)-3-amino-4-fluoropyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{24}FN_5O_4S$, 557.6; m/z found, 558.1 $[M+H]^+$. $^1H$ NMR (400 MHz, DMSO-$d_6$ and $CD_3OD$): δ 8.28 (d, J=5.2 Hz, 1H), 7.42-7.21 (m, 3H), 7.16-7.07 (m, 1H), 7.07-6.97 (m, 3H), 6.95-6.88 (m, 1H), 6.61-6.45 (m, 1H), 6.25-6.15 (m, 1H), 5.98 (d, J=5.4 Hz, 1H), 5.74-5.64 (m, 1H), 5.35-5.10 (m, 1H), 4.81-4.61 (m, 1H), 4.06-3.84 (m, 2H), 3.80-3.47 (m, 2H), 2.04 (s, 3H).

Example 38: (R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide

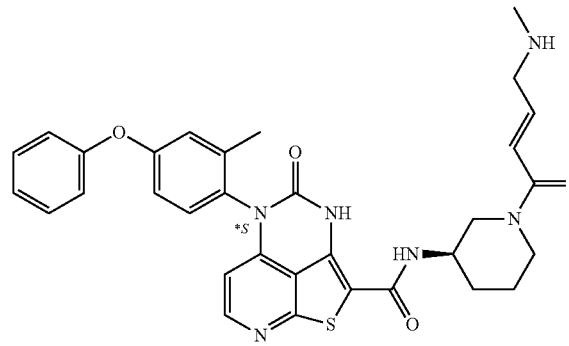

The title compound was prepared in a manner analogous to Example 104, using (E)-4-[tert-Butoxycarbonyl(methyl)amino]but-2-enoic acid (Intermediate 10) and (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98). MS (ESI): mass calcd. for $C_{32}H_{32}N_6O_4S$, 596.7; m/z found, 597.4 $[M+H]^+$. $^1H$ NMR (400 MHz, $CD_3OD$): δ 8.46 (s, 1H), 8.38-8.31 (m, 1H), 7.45-7.37 (m, 2H), 7.33-7.27 (m, 1H), 7.22-7.14 (m, 1H), 7.14-7.03 (m, 3H), 7.02-6.95 (m, 1H), 6.92-6.83 (m, 1H), 6.74-6.61 (m, 1H), 6.12-6.06 (m, 1H), 4.57-3.89 (m, 3H), 3.86-3.76 (m, 2H), 3.25-3.08 (m, 1H), 2.97-2.83 (m, 1H), 2.71 (s, 3H), 2.17-2.01 (m, 4H), 1.96-1.84 (m, 1H), 1.83-1.70 (m, 1H), 1.67-1.53 (m, 1H).

Example 39: (R)—N-(1-Acryloylpyrrolidin-3-yl)-5-(4-(cyclohexyloxy)-2-methylphenyl)-4-oxo-4,5-dihydro-3H-1-thia-3,5,8-triazaacenaphthylene-2-carboxamide

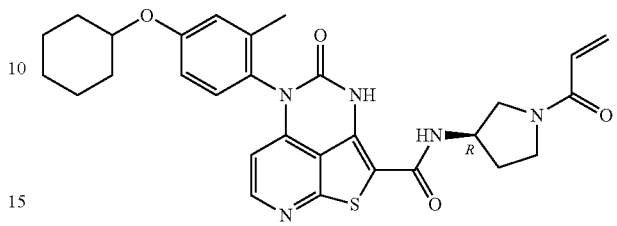

The title compound was prepared as for using steps A-I in Example 33, and using iodocyclohexane in place of 2-iodopropane in Step 1 and tert-butyl (3R)-3-aminopyrrolidine-1-carboxylate in place of tert-butyl (R)-3-aminopiperidine-1-carboxylate in Step G. MS (ESI): mass calcd. for $C_{29}H_{31}N_5O_4S$, 545.7; m/z found, 546.1 $[M+H]^+$. $^1H$ NMR (400 MHz, $CD_3OD$): δ 8.33 (d, J=5.6 Hz, 1H), 7.30-7.20 (m, 1H), 7.04-6.99 (m, 1H), 6.98-6.93 (m, 1H), 6.73-6.55 (m, 1H), 6.37-6.26 (m, 1H), 6.06 (d, J=5.6 Hz, 1H), 5.85-5.71 (m, 1H), 4.73-4.58 (m, 1H), 4.47-4.36 (m, 1H), 4.07-3.52 (m, 4H), 2.43-2.11 (m, 5H), 2.07-2.00 (m, 2H), 1.89-1.80 (m, 2H), 1.68-1.41 (m, 6H).

Example 40: (R,E)-N-(1-(2-Cyano-4-methoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

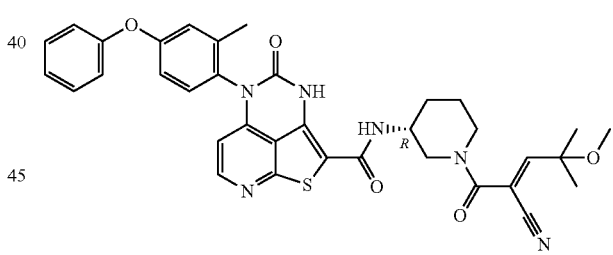

To a round bottom flask were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 250 mg, 0.44 mmol), 2-methoxy-2-methylpropanal (225 mg, 2.2 mmol), EtOH (5 mL), and piperdine (75 mL) The reaction mixture was stirred at rt for 1 h, concentrated to dryness, and purified by flash column chromatography to yield the title compound (80 mg, 28% yield) as a white solid. MS (ESI): mass calcd. for $C_{35}H_{34}N_6O_5S$, 650.7; m/z found, 651.3 $[M+H]^+$. $^1H$ NMR (400 MHz, $CD_3OD$): δ 8.32 (d, J=5.6 Hz, 1H), 7.47-7.36 (m, 2H), 7.34-7.26 (m, 1H), 7.22-7.14 (m, 1H), 7.12-7.02 (m, 3H), 7.01-6.94 (m, 1H), 6.92-6.69 (m, 1H), 6.06 (d, J=5.5 Hz, 1H), 4.56-3.83 (m, 3H), 3.6-3.32 (m, 1H), 3.29-3.22 (m, 3H), 3.18-2.82 (m, 1H), 2.17-2.02 (m, 4H), 1.98-1.84 (m, 1H), 1.81-1.57 (m, 2H), 1.51-1.32 (m, 6H).

Example 41: (R,E)-N-(1-(2-Cyano-3-¹³C-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide

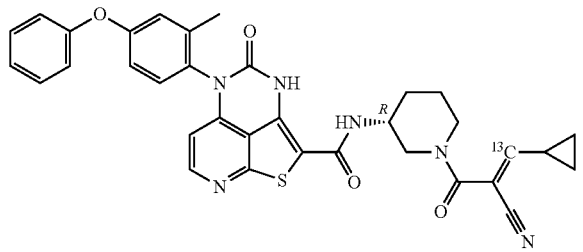

Step A: ¹³C-Cyclopropanecarbaldehyde

A solution of ¹³C-DMF (500 mg, 6.75 mmol) in THF (10 mL) was slowly added to cyclopropane magnesium bromide in THF (0.5 M, 14.8 mL, 7.42 mmol) cooled in an ice bath under $N_2$ over a period of 5 minutes. The mixture was brought to room temperature and stirred for 1 h. The mixture was acidified with 3 M aqueous HCl, extracted with $Et_2O$, dried over anhydrous $Na_2SO_4$, and concentrated to dryness to give the title compound as a pale yellow oil, which was used in the next step without purification.

Step B: (R,E)-N-(1-(2-Cyano-3-¹³C-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide To a solution of (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 200 mg, 0.35 mmol) and ¹³C-cyclopropanecarbaldehyde (100 mg, 1.4 mmol) in EtOH (5 mL) was added piperidine (60 mg, 0.70 mmol) and was stirred at room temperature overnight. The reaction was concentrated to dryness and purified by normal phase flash column chromatography ($SiO_2$) to give the title compound (22 mg, 91% yield) as a yellow solid. MS (ESI): mass calcd. for $C_{34}H_{30}N_6O_4S$, 619.7; m/z found, 620.2 [M+H]⁺. ¹H NMR (400 MHz, $CD_3OD$): δ 8.28 (d, J=5.6 Hz, 1H), 7.39-7.31 (m, 2H), 7.28-7.21 (m, 1H), 7.16-7.07 (m, 1H), 7.07-6.96 (m, 3H), 6.95-6.85 (m, 1H), 6.72-6.19 (m, 1H), 5.98 (d, J=5.6 Hz, 1H), 4.24-4.08 (m, 3H), 3.99-3.83 (m, 2H), 2.04 (s, 3H), 1.98-1.88 (m, 2H), 1.83-1.74 (m, 1H), 1.69-1.60 (m, 1H), 1.54-1.45 (m, 1H), 1.16-1.05 (m, 2H), 0.95-0.83 (m, 1H), 0.81-0.74 (m, 1H).

Example 42: (R)—N-(1-(But-2-ynoyl)piperidin-3-yl)-5-(2-methyl-4-phenoxyphenyl)-4-oxo-4,5-dihydro-3H-1-thia-3,5,8-triazaacenaphthylene-2-carboxamide

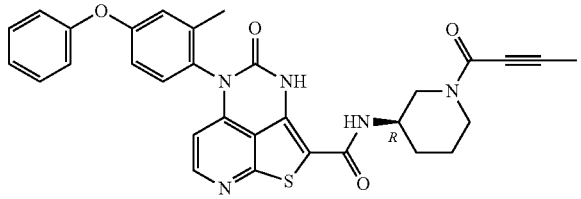

The title compound was prepared using the method in Example 104, and using but-2-ynoic acid in place of 3-methylsulfonylpropanoic acid. MS (ESI): mass calcd. for $C_{31}H_{27}N_5O_4S$, 565.6; m/z found, 566.2 [M+H]⁺. ¹H NMR (400 MHz, $CD_3OD$ and DMSO-$d_6$): δ 8.32-8.27 (m, 1H), 7.40-7.33 (m, 2H), 7.31-7.26 (m, 1H), 7.17-7.10 (m, 1H), 7.09-7.00 (m, 3H), 6.96-6.89 (m, 1H), 6.00-5.95 (m, 1H), 4.40-3.73 (m, 3H), 3.29-3.02 (m, 1H), 2.92-2.64 (m, 1H), 2.07 (s, 3H), 1.99-1.91 (m, 4H), 1.85-1.73 (m, 1H), 1.69-1.59 (m, 1H), 1.53-1.37 (m, 1H).

Example 43: (R,E)-N-(1-(2-Cyano-4-methyl-4-morpholinopent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

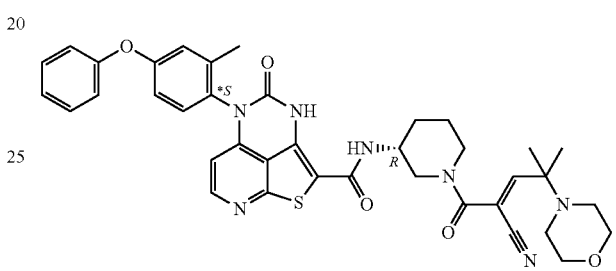

Step A: (R)—N-(1-(2-Cyanoacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Example 104, using 2-cyanoacetic acid and (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98).

Step B: (R,E)-N-(1-(2-Cyano-4-methyl-4-morpholinopent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide To a sealed tube were added (R)—N-(1-(2-cyanoacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide (50 mg, 0.09 mmol), 2-methyl-2-morpholinopropanal (20 mg, 0.13 mmol), piperidine (9 mg, 0.1 mmol), and EtOH (3 mL). The sealed tube was heated to 105° C. overnight, cooled to rt, and the residue purified by flash column chromatography to yield the title compound (39 mg, 63% yield) as a yellow solid. MS (ESI): mass calcd. for $C_{38}H_{39}N_7O_5S$, 705.8; m/z found, 706.3 [M+H]⁺. ¹H NMR (400 MHz, $CD_3OD$): δ 8.33 (d, J=5.5 Hz, 1H), 7.47-7.37 (m, 2H), 7.33-7.26 (m, 1H), 7.23-7.14 (m, 1H), 7.12-7.03 (m, 3H), 7.01-6.94 (m, 1H), 6.90-6.78 (m, 1H), 6.07 (d, J=5.6 Hz, 1H), 4.55-3.82 (m, 3H), 3.81-3.63 (m, 4H), 3.47-3.35 (m, 0.5H), 3.29-2.86 (m, 1.5H), 2.71-2.51 (m, 4H), 2.12 (s, 3H), 2.07-1.60 (m, 4H), 1.41-1.24 (m, 6H).

Example 44: (S)—N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide

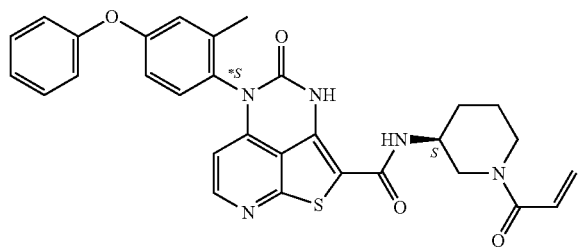

The title compound was prepared in a manner analogous to Method 1, steps A-I in Example 1 (including Chiral resolution Method A after Step F to obtain the *S atropisomer), and using tert-butyl (3S)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.0 [M+H]$^+$. $^1$H NMR (500 MHz, CD$_3$OD): δ 8.29 (d, J=6.5 Hz, 1H), 7.47-7.33 (m, 2H), 7.29 (d, J=8.4 Hz, 1H), 7.24-6.94 (m, 5H), 6.88-6.73 (m, 1H), 6.20 (d, J=17.3 Hz, 1H), 6.13-5.97 (m, 1H), 5.80-5.62 (m, 1H), 4.64-3.88 (m, 3H), 3.26-3.12 (m, 1H), 3.04-2.89 (m, 1H), 2.18-2.02 (m, 4H), 1.99-1.47 (m, 3H).

Example 45: (R)—N-(1-Acryloylpyrrolidin-3-yl)-5-(2-fluoro-6-methyl-4-phenoxyphenyl)-4-oxo-4,5-dihydro-3H-1-thia-3,5,8-triazaacenaphthylene-2-carboxamide

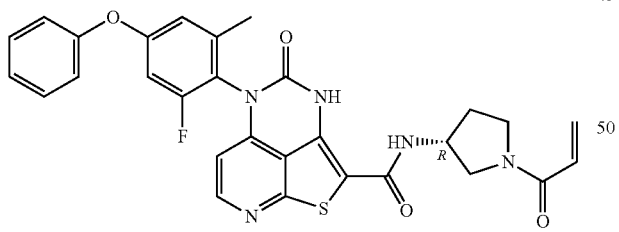

The title compound was prepared in a manner analogous to Method 1, steps C-G in Example 1, and using 2-fluoro-6-methyl-4-phenoxyaniline (Intermediate 9) in place of 2-methyl-4-phenoxyaniline in step C, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{29}H_{24}FN_5O_4S$, 557.6; m/z found, 558.5 [M+H]$^+$. $^1$H NMR (400 MHz, CD$_3$OD): δ 8.36-8.28 (br, 1H), 7.57-7.41 (m, 2H), 7.34-7.10 (m, 3H), 6.95-6.85 (m, 1H), 6.83-6.76 (m, 1H), 6.75-6.55 (m, 1H), 6.42-6.25 (m, 1H), 6.17-6.04 (m, 1H), 5.86-5.70 (m, 1H), 4.77-4.57 (m, 1H), 4.18-3.51 (m, 4H), 2.48-1.94 (m, 5H).

Example 46: (R)-5-(*S)-(2-methyl-4-phenoxyphenyl)-4-oxo-N-(1-propioloylpiperidin-3-yl)-4,5-dihydro-3H-1-thia-3,5,8-triazaacenaphthylene-2-carboxamide

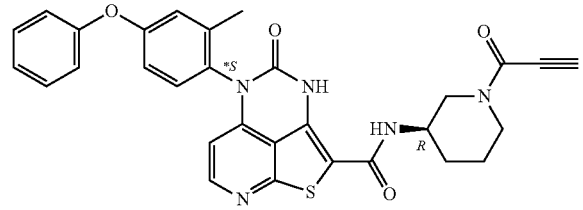

The title compound was prepared using a method analogous to Example 75, using prop-2-ynoic acid and (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98). MS (ESI): mass calcd. for $C_{30}H_{25}N_5O_4S$, 551.6; m/z found, 552.4 [M+H]$^+$. $^1$H NMR (400 MHz, CD$_3$OD): δ 8.40-8.26 (m, 1H), 7.43-7.34 (m, 2H), 7.29-7.21 (m, 1H), 7.20-7.13 (m, 1H), 7.12-7.03 (m, 3H), 7.00-6.93 (m, 1H), 6.09-6.03 (m, 1H), 4.50-4.36 (m, 1H), 4.33-4.13 (m, 1H), 4.05-3.77 (m, 2H), 3.38-3.19 (m, 1H), 3.06-2.85 (m, 1H), 2.16-2.01 (m, 4H), 1.95-1.84 (m, 1H), 1.79-1.67 (m, 1H), 1.64-1.49 (m, 1H).

Example 47: (R,E)-N-(1-(2-Cyano-3-cyclopropylacryloyl)piperidin-3-yl)-4-oxo-5-(4-phenoxyphenyl)-4,5-dihydro-3H-1-thia-3,5,8-triazaacenaphthylene-2-carboxamide

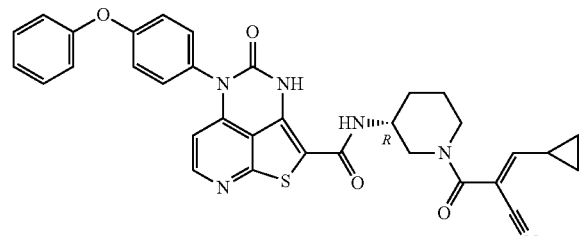

The title compound was prepared using a method analogous to Example 75, using (E)-2-cyano-3-cyclopropylprop-2-enoic acid (Intermediate 17) and (R)-4-oxo-5-(4-phenoxyphenyl)-N-(piperidin-3-yl)-4,5-dihydro-3H-1-thia-3,5,8-triazaacenaphthylene-2-carboxamide (Example 860). MS (ESI): mass calcd. for $C_{33}H_{28}N_6O_4S$, 604.7; m/z found, 605.1 [M+H]$^+$. $^1$H NMR (500 MHz, CD$_3$OD): δ 8.32 (dd, J=5.7, 1.6 Hz, 1H), 7.50-7.31 (m, 4H), 7.29-6.99 (m, 5H), 6.63-6.46 (m, 1H), 6.28-6.10 (m, 1H), 5.48 (d, J=1.4 Hz, 1H), 4.53-3.87 (m, 3H), 2.21-0.70 (m, 11H).

Example 48: (R)—N-(1-(2-Fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide

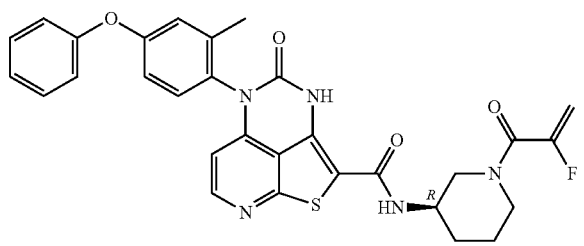

The title compound was prepared using a method analogous to Example 75, using 2-fluoroprop-2-enoic acid and (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869). MS (ESI): mass calcd. for $C_{30}H_{26}FN_5O_4S$, 571.6; m/z found, 572.2 [M+H]$^+$. $^1$H NMR (400 MHz, DMSO-$d_6$): δ 8.32 (d, J=5.6 Hz, 1H), 7.46-7.35 (m, 2H), 7.32-7.23 (m, 1H), 7.21-7.12 (m, 1H), 7.12-7.02 (m, 3H), 7.00-6.91 (m, 1H), 6.09-6.05 (m, 1H), 5.28-5.06 (m, 2H), 4.51-3.84 (m, 3H), 3.25-2.85 (m, 2H), 2.11 (s, 3H), 2.09-1.99 (m, 1H), 1.96-1.82 (m, 1H), 1.77-1.53 (m, 2H).

Example 49: (R)—N-(1-(2-Fluoroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide

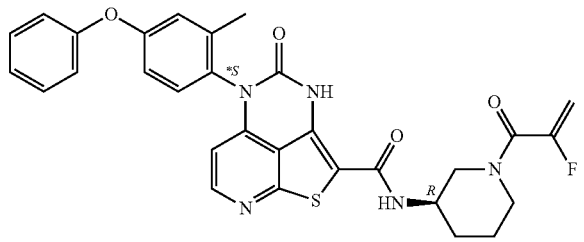

To a round bottom flask were added (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98, 31 mg, 0.062 mmol), were added DMF (3 mL), 2-fluoroacrylic acid (9 mg, 0.01 mmol), triethylamine (21 mg, 0.188 mmol), HATU (47 mg, 0.124 mmol). The reaction mixture was stirred at rt for 2 h. Water was added and the precipitate was collected by filtration, then purified by silica gel chromatograph to give the title compound as a light yellow solid. MS (ESI): mass calcd. for $C_{30}H_{26}FN_5O_4S$, 571.6; m/z found, 572.2 [M+H]$^+$. $^1$H NMR (400 MHz, CD$_3$OD): δ 8.34 (d, J=5.5 Hz, 1H), 7.47-7.36 (m, 2H), 7.33-7.25 (m, 1H), 7.22-7.14 (m, 1H), 7.13-7.03 (m, 3H), 7.02-6.94 (m, 1H), 6.08 (d, J=5.6 Hz, 1H), 5.30-5.10 (m, 2H), 4.63-3.77 (m, 3H), 3.29-2.75 (m, 2H), 2.15 (s, 3H), 2.10-2.00 (m, 1H), 1.95-1.84 (m, 1H), 1.80-1.69 (m, 1H), 1.67-1.55 (m, 1H).

Example 50: N-((3S,4S)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide

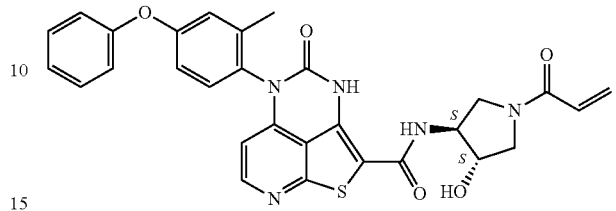

The title compound was prepared in a manner analogous to Method 1, steps A-I in Example 1, and using tert-butyl (3S,4S)-3-amino-4-hydroxypyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{25}N_5O_5S$, 555.6; m/z found, 556.1 [M+H]$^+$. $^1$H NMR (400 MHz, CD$_3$OD): δ 8.31 (d, J=5.5 Hz, 1H), 7.45-7.35 (m, 2H), 7.35-7.27 (m, 1H), 7.21-7.12 (m, 1H), 7.11-7.00 (m, 3H), 7.00-6.93 (m, 1H), 6.66-6.54 (m, 1H), 6.34-6.24 (m, 1H), 6.06 (d, J=5.5 Hz, 1H), 5.76 (dt, J=10.5, 1.9, 1H), 4.50-4.32 (m, 2H), 4.09-3.49 (m, 4H), 2.11 (s, 3H).

Example 51: (R)—N-(1-Acryloylpiperidin-3-yl)-5-(4-cyclopropoxy-2-methylphenyl)-4-oxo-4,5-dihydro-3H-1-thia-3,5,8-triazaacenaphthylene-2-carboxamide

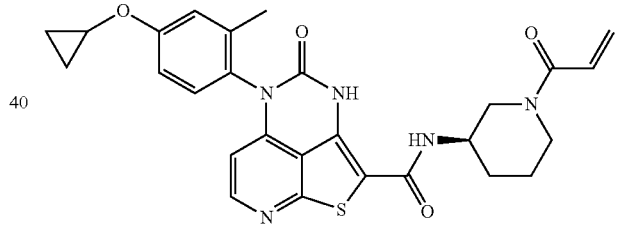

Step A: 4-(Cyclopropoxy)-2-methyl-1-nitrobenzene

To a reaction vial were added 3-methyl-4-nitrophenol (3.1 g, 20 mmol), bromocyclopropane (4.9 g, 40 mmol), KI (3.4 g, 20 mmol), cesium carbonate (6.6 g, 20 mmol), and NMP (20 mL) and was heated to 170° C. for 2 h in the microwave. The mixture was diluted with EtOAc, washed with brine, dried over anhydrous Na$_2$SO$_4$, concentrated to dryness, and purified by flash column chromatography to yield the title compound (0.85 g, 22% yield) as a brown liquid.

Step B: 4-(Cyclopropoxy)-2-methylaniline

A mixture of 4-(cyclopropoxy)-2-methyl-1-nitrobenzene (450 mg, 2.3 mmol) and Pd/C (24 mg, 0.23 mmol) in MeOH (15 mL) was stirred for 5 h under H$_2$. The reaction was filtered and the filtrate was concentrated to dryness to yield the title compound (310 mg, 82% yield) as a brown liquid, which was used in the next step without purification.

Step C: 2-Chloro-4-[4-(cyclopropoxy)-2-methyl-anilino]pyridine-3-carbonitrile To a round bottom flask were added 4-(cyclopropoxy)-2-methylaniline (420 mg, 2.6 mmol), 2-chloro-4-iodopyridine-3-carbonitrile (885 mg, 3.35 mmol), Pd(OAc)$_2$ (58 mg, 0.26 mmol), DPEphos (280 mg, 0.51 mmol), cesium carbonate (1.7 g, 5.2 mmol), and dioxane (20 mL) and was stirred at 110° C. for 15 h under N2. The mixture was concentrated to dryness and purified by flash column chromatography to yield the title compound (530 mg, 69% yield) as a light yellow solid.

Step D: (R)—N-(1-Acryloylpiperidin-3-yl)-5-(4-cyclopropoxy-2-methylphenyl)-4-oxo-4,5-dihydro-3H-1-thia-3,5,8-triazaacenaphthylene-2-carboxamide The title compound was prepared in a manner analogous to Method 1, steps D-I in Example 1, and using 2-chloro-4-[4-(cyclopropoxy)-2-methylanilino]pyridine-3-carbonitrile in place 2-chloro-4-(2-methyl-4-phenoxyanilino)pyridine-3-carbonitrile in step D, and using tert-butyl (3R)-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) in step G. MS (ESI): mass calcd. for C$_{27}$H$_{27}$N$_5$O$_4$S, 517.6; m/z found, 518.3 [M+H]$^+$. $^1$H NMR (400 MHz, CD$_3$OD): δ 8.35-8.26 (m, 1H), 7.27-7.20 (m, 1H), 7.15-7.04 (m, 2H), 6.85-6.71 (m, 1H), 6.24-6.13 (m, 1H), 6.07-6.00 (m, 1H), 5.77-5.67 (m, 1H), 4.61-3.87 (m, 3H), 3.87-3.76 (m, 1H), 3.22-3.08 (m, 1H), 2.96-2.81 (m, 1H), 2.16-1.98 (m, 4H), 1.92-1.80 (m, 1H), 1.79-1.65 (m, 1H), 1.64-1.50 (m, 1H), 0.88-0.77 (m, 2H), 0.76-0.67 (m, 2H).

Example 52: (R)-5-(4-(2,6-Difluorophenoxy)-2-methylphenyl)-N-(1-methylpiperidin-3-yl)-4-oxo-4,5-dihydro-3H-1-thia-3,5,8-triazaacenaphthylene-2-carboxamide

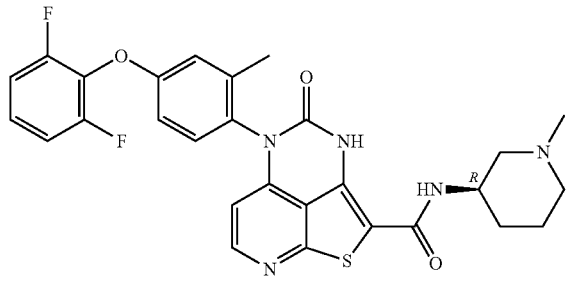

Step A: (R)-5-(4-(2,6-Difluorophenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, using 2,6-difluorophenol in place of phenol in step A, and using tert-butyl (3R)-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) in step G.

Step B: (R)-5-(4-(2,6-Difluorophenoxy)-2-methylphenyl)-N-(1-methylpiperidin-3-yl)-4-oxo-4,5-dihydro-3H-1-thia-3,5,8-triazaacenaphthylene-2-carboxamide To a round bottom flask were added (R)-5-(4-(2,6-difluorophenoxy)-2-methylphenyl)-4-oxo-N-(piperidin-3-yl)-4,5-dihydro-3H-1-thia-3,5,8-triazaacenaphthylene-2-carboxamide (120 mg, 0.22 mmol) and DCM (5 mL) and was treated with formaldehyde (0.5 mL, 37 wt. % in H$_2$O). To the stirred reaction was added NaBH(AcO)$_3$ (95 mg, 0.45 mmol) and the reaction was maintained at rt for 1 h. The reaction was concentrated to dryness and the residue purified by flash column chromatography to yield the title compound (59 mg, 43% yield) as a yellow solid. MS (ESI): mass calcd. for C$_{28}$H$_{25}$F$_2$N$_5$O$_3$S, 549.6; m/z found, 550.1 [M+H]$^+$. $^1$H NMR (400 MHz, DMSO-d6): δ 8.33-8.25 (m, 1H), 8.12-8.00 (m, 1H), 7.48-7.29 (m, 4H), 7.11-7.05 (m, 1H), 6.99-6.89 (m, 1H), 5.94-5.84 (m, 1H), 4.01-3.93 (m, 1H), 2.90-2.84 (m, 1H), 2.76-2.69 (m, 1H), 2.25 (s, 3H), 2.07 (s, 3H), 2.01-1.96 (m, 2H), 1.91 (s, 3H), 1.84-1.76 (m, 1H), 1.76-1.67 (m, 1H), 1.62-1.49 (m, 1H), 1.44-1.32 (m, 1H).

Example 53: (R)—N-(1-Acryloylpiperidin-3-yl)-5-(*S)-(5-chlorobenzo[d][1,3]dioxol-4-yl)-4-oxo-4,5-dihydro-3H-1-thia-3,5,8-triazaacenaphthylene-2-carboxamide

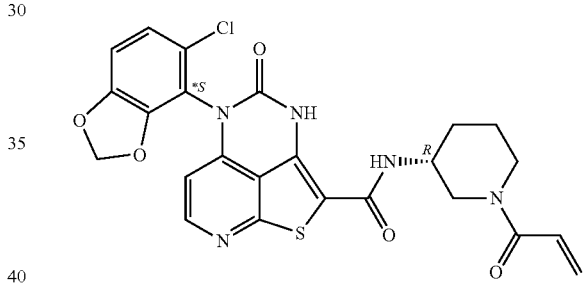

Step A: 2-Chloro-4-[(5-chloro-1,3-benzodioxol-4-yl)amino]pyridine-3-carbonitrile A mixture of 2,4-dichloropyridine-3-carbonitrile (1.6 g, 9.3 mmol), 5-chloro-1,3-benzodioxol-4-amine (1.6 g, 9.3 mmol), DPEphos (1.0 g, 1.9 mmol), Pd(AcO)$_2$ (0.21 g, 0.93 mmol), and K$_3$PO$_4$ (5.0 g, 23 mmol) in dioxane (80 mL) was heated at reflux under N$_2$ overnight. The reaction was concentrated to dryness and the residue was purified by flash column chromatography to yield the title compound (2.2 g, 77% yield) as a yellow solid.

Step B: (R)—N-(1-Acryloylpiperidin-3-yl)-5-(*S)-(5-chlorobenzo[d][1,3]dioxol-4-yl)-4-oxo-4,5-dihydro-3H-1-thia-3,5,8-triazaacenaphthylene-2-carboxamide The title compound was prepared in a manner analogous to Method 1, steps D-I in Example 1 (including Chiral resolution Method A after Step F to obtain the *S atropisomer), and using 2-chloro-4-[(5-chloro-1,3-benzodioxol-4-yl)amino]pyridine-3-carbonitrile in place of 2-chloro-4-(2-methyl-4-phenoxyanilino)pyridine-3-carbonitrile in step D, and using tert-butyl (3R)-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) in step G. MS (ESI): mass calcd. for $C_{24}H_{20}ClN_5O_5S$, 526.0; m/z found, 526.2 [M+H]$^+$. $^1$H NMR (400 MHz, CD$_3$OD): δ 8.38 (d, J=5.5 Hz, 1H), 7.11 (d, J=8.4 Hz, 1H), 7.00 (d, J=8.4 Hz, 1H), 6.85-6.70 (m, 1H), 6.25 (d, J=5.5 Hz, 1H), 6.23-6.15 (m, 1H), 6.11-6.07 (m, 2H), 5.78-5.65 (m, 1H), 4.56-4.48 (m, 0.5H), 4.31-4.23 (m, 0.5H), 4.20-4.12 (m, 0.5H), 4.05-3.87 (m, 1.5H), 3.25-3.11 (m, 1H), 2.97-2.85 (m, 1H), 2.12-2.01 (m, 1H), 1.91-1.82 (m, 1H), 1.79-1.65 (m, 1H), 1.63-1.52 (m, 1H).

Example 54: N-((3S,4S)-1-Acryloyl-4-methoxypyrrolidin-3-yl)-5-(2-methyl-4-phenoxyphenyl)-4-oxo-4,5-dihydro-3H-1-thia-3,5,8-triazaacenaphthylene-2-carboxamide

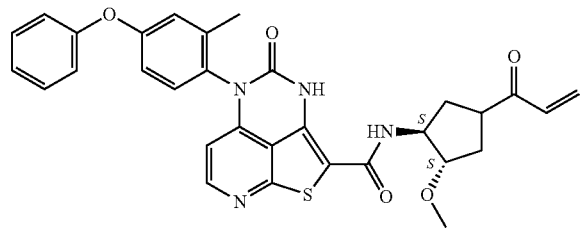

The title compound was prepared in a manner analogous to Method 1, steps A-I in Example 1, and using tert-butyl (3S,4S)-3-amino-4-methoxypyrrolidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_5S$, 569.6; m/z found, 570.0 [M+H]$^+$. $^1$H NMR (400 MHz, CD$_3$OD): δ 8.33 (d, J=5.3 Hz, 1H), 7.46-7.36 (m, 2H), 7.35-7.26 (m, 1H), 7.22-7.13 (m, 1H), 7.13-7.02 (m, 3H), 7.02-6.94 (m, 1H), 6.68-6.53 (m, 1H), 6.37-6.23 (m, 1H), 6.08 (d, J=5.5 Hz, 1H), 5.83-5.71 (m, 1H), 4.66-4.56 (m, 1H), 4.08-3.77 (m, 3H), 3.75-3.62 (m, 2H), 3.52-3.45 (m, 3H), 2.12 (s, 3H).

Example 55: (R)—N-(1-(But-2-ynoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

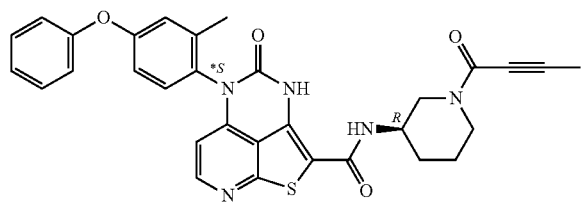

Step A: (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1 (including Chiral resolution Method A after Step F to obtain the *S atropisomer), and using tert-butyl (3S,4S)-3-amino-4-methoxypyrrolidine-1-carboxylate in place of tert-butyl (3R,5R)-3-amino-5-fluoropiperidine-1-carboxylate (Intermediate 1) in step G.

Step B: (R)—N-(1-(But-2-ynoyl)piperidin-3-yl)-5-(*S)-(2-methyl-4-phenoxyphenyl)-4-oxo-4,5-dihydro-3H-1-thia-3,5,8-triazaacenaphthylene-2-carboxamide A mixture of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 25 mg, 0.050 mmol), but-2-ynoic acid (25 mg, 0.30 mmol), HATU (50 mg, 0.13 mmol), and triethylamine (20 mg, 0.20 mmol) in DMF (2 mL) was reacted at rt for 2 h. The reaction was quenched with H$_2$O (20 mL), extracted with DCM, dried over anhydrous Na$_2$SO$_4$, filtered, and concentrated to dryness. The residue was purified by flash column chromatography to yield the title compound as a white solid. MS (ESI): mass calcd. for $C_{31}H_{27}N_5O_4S$, 565.6; m/z found, 566.4 [M+H]$^+$. $^1$H NMR (400 MHz, CD$_3$OD): δ 8.38-8.27 (m, 1H), 7.46-7.36 (m, 2H), 7.33-7.26 (m, 1H), 7.22-7.14 (m, 1H), 7.12-7.04 (m, 3H), 7.00-6.92 (m, 1H), 6.11-6.04 (m, 1H), 4.48-4.22 (m, 2H), 4.13-3.92 (m, 1H), 3.40-3.16 (m, 1H), 3.06-2.80 (m, 1H), 2.12 (s, 3H), 2.08-1.97 (m, 4H), 1.94-1.80 (m, 1H), 1.79-1.67 (m, 1H), 1.66-1.51 (m, 1H).

Example 56: (R)—N-(1-(2-(Dimethylamino)acetyl)piperidin-3-yl)-5-(*S)-(2-methyl-4-phenoxyphenyl)-4-oxo-4,5-dihydro-3H-1-thia-3,5,8-triazaacenaphthylene-2-carboxamide

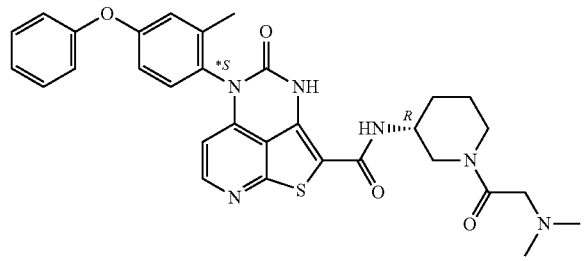

Step A: tert-Butyl N-[(3R)-1-[2-(dimethylamino)acetyl]-3-piperidyl]carbamate

A solution of tert-butyl N-[(3R)-3-piperidyl]carbamate (400 mg, 2 mmol), 2-(dimethylamino)acetic acid (226 mg, 2.19 mmol), HATU (0.91 mg, 2.4 mmol), and triethylamine (0.56 mL, 4.0 mmol) in DMF (5 mL) was stirred at rt overnight, then poured into water. The mixture was extracted with EtOAc and the combined organic layers were washed with brine, dried over anhydrous Na$_2$SO$_4$, filtered, and concentrated to dryness to yield the title compound as a yellow oil.

Step B: (R)—N-(1-(2-(Dimethylamino)acetyl)piperidin-3-yl)-5-(*S)-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-G in Example 1 (including Chiral resolution Method A after Step F to obtain the *S atropisomer), and using 1-[(3R)-3-amino-1-piperidyl]-2-(dimethylamino)ethanone (Intermediate 43) in place of tert-butyl (3R,5R)-3-amino-5-fluoropiperidine-1-carboxylate (Intermediate 1) in step G. MS (ESI): mass calcd. for C$_{31}$H$_{32}$N$_6$O$_4$S, 584.7; m/z found, 585.3 [M+H]$^+$. $^1$H NMR (400 MHz, CD$_3$OD): δ 8.26 (d, J=5.5 Hz, 1H), 7.43-7.34 (m, 2H), 7.29-7.21 (m, 1H), 7.20-7.13 (m, 1H), 7.12-7.03 (m, 3H), 7.00-6.93 (m, 1H), 6.00 (d, J=5.5 Hz, 1H), 4.26-3.74 (m, 3H), 3.61-3.40 (m, 2H), 3.27-3.04 (m, 2H), 2.49-2.34 (m, 6H), 2.12 (s, 3H), 2.05-1.96 (m, 1H), 1.93-1.70 (m, 2H), 1.68-1.52 (m, 1H).

Example 57: (R)-5-(4-(2-Fluorophenoxy)-2-methylphenyl)-N-(1-methylpiperidin-3-yl)-4-oxo-4,5-dihydro-3H-1-thia-3,5,8-triazaacenaphthylene-2-carboxamide

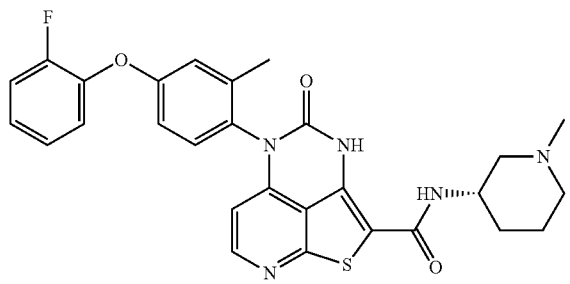 [SMILES: Cc1cc(Oc2ccccc2F)ccc1N1C(=O)Nc2c(C(=O)N[C@H]3CCCN(C)C3)sc3nccc1c23]

Step A: (R)-5-(4-(2-Fluorophenoxy)-2-methylphenyl)-4-oxo-N-(piperidin-3-yl)-4,5-dihydro-3H-1-thia-3,5,8-triazaacenaphthylene-2-carboxamide A solution of 5-(4-(2-fluorophenoxy)-2-methylphenyl)-4-oxo-4,5-dihydro-3H-1-thia-3,5,8-triazaacenaphthylene-2-carboxylic acid (218 mg, 0.501 mmol), tert-butyl (3R)-3-aminopiperidine-1-carboxylate (100 mg, 0.5 mmol), and HATU (380 mg, 1.0 mmol) in DMF (3 mL) was stirred at rt for 3 hr. Water was added and the precipitate that formed was filtered to give a pale yellow solid. The solid was dissolved in MeOH (4 mL) and HCl (4 mL), and the resulting mixture was heated to 50° C. for 30 min. The reaction was concentrated to dryness to yield the title compound (200 mg, 72% yield) as a yellow solid, which was used in the next step reaction without further purification.

Step B: (R)-5-(4-(2-Fluorophenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-fluorophenoxy)-2-methylphenyl)-4-oxo-N-(piperidin-3-yl)-4,5-dihydro-3H-1-thia-3,5,8-triazaacenaphthylene-2-carboxamide (110 mg, 0.21 mmol) and formaldehyde (0.3 mL, 37 wt. % in H$_2$O) in MeOH (5 mL) was added NaBH(OAc)$_3$ (135 mg, 0.640 mmol) and was stirred at rt for 1 h. The reaction was concentrated to dryness and purified by flash column chromatography to yield the title compound (67 mg, 54% yield) as a white solid. MS (ESI): mass calcd. for C$_{28}$H$_{26}$FN$_5$O$_3$S, 531.6; m/z found, 532.4 [M+H]$^+$. $^1$H NMR (400 MHz, CD$_3$OD): δ 8.54 (s, 1H), 8.33-8.21 (m, 1H), 7.39-7.31 (m, 1H), 7.31-7.18 (m, 4H), 7.06-6.98 (m, 1H), 6.98-6.88 (m, 1H), 6.06-5.97 (m, 1H), 4.32-4.19 (m, 1H), 3.44-3.33 (m, 1H), 3.22-3.08 (m, 1H), 2.77-2.60 (m, 5H), 2.15-2.06 (m, 3H), 2.04-1.90 (m, 2H), 1.88-1.74 (m, 1H), 1.69-1.55 (m, 1H).

Example 58: N-((3S,4R)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide

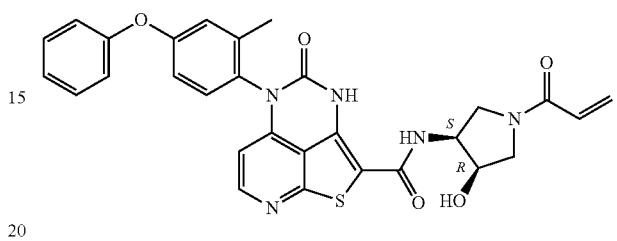

The title compound was prepared in a manner analogous to Method 1, steps A-I in Example 1, and using tert-butyl (3S,4R)-3-amino-4-hydroxypyrrolidine-1-carboxylate (Intermediate 24) in place of tert-butyl (3R,5R)-3-amino-5-fluoropiperidine-1-carboxylate (Intermediate 1) in step G. MS (ESI): mass calcd. for C$_{29}$H$_{25}$N$_5$O$_5$S, 555.6; m/z found, 556.4 [M+H]$^+$. $^1$H NMR (400 MHz, CD$_3$OD): δ 8.30 (d, J=5.5 Hz, 1H), 7.44-7.35 (m, 2H), 7.33-7.27 (m, 1H), 7.19-7.12 (m, 1H), 7.12-7.01 (m, 3H), 7.00-6.93 (m, 1H), 6.67-6.51 (m, 1H), 6.32-6.22 (m, 1H), 6.05 (d, J=5.5 Hz, 1H), 5.80-5.68 (m, 1H), 4.65-4.52 (m, 1H), 4.51-4.38 (m, 1H), 4.06-3.85 (m, 1H), 3.73-3.49 (m, 3H), 2.10 (s, 3H).

Example 59: (R)-5-(3-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide

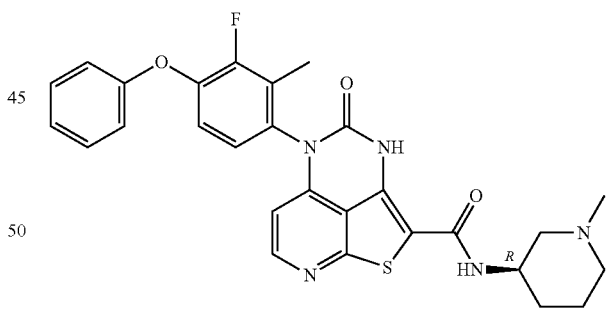

To a mixture of (R)-5-(3-fluoro-2-methyl-4-phenoxyphenyl)-4-oxo-N-(piperidin-3-yl)-4,5-dihydro-3H-1-thia-3,5,8-triazaacenaphthylene-2-carboxamide (Intermediate 18) (50 mg, 0.1 mmol) and formaldehyde (0.3 mL, 37 wt. % in H$_2$O) in MeOH (6 mL) was added NaBH(OAc)$_3$ (62 mg, 0.29 mmol). The reaction mixture was stirred at rt for 1 h, concentrated to dryness, and purified by flash column chromatography to yield the title compound (36 mg, 64% yield) as a white solid. MS (ESI): mass calcd. for C$_{28}$H$_{26}$FN$_5$O$_3$S, 531.6; m/z found, 532.0 [M+H]$^+$. $^1$H NMR (400 MHz, CD$_3$OD): δ 8.48 (s, 1H), 8.39-8.29 (m, 1H), 7.43-7.34 (m, 2H), 7.23-7.11 (m, 2H), 7.11-7.03 (m, 3H), 6.18-6.10 (m, 1H), 4.31-4.21 (m, 1H), 3.50-3.36 (m, 1H), 3.26-3.16 (m, 1H), 2.82-2.64 (m, 5H), 2.12 (s, 3H), 2.04-1.96 (m, 2H), 1.88-1.77 (m, 1H), 1.70-1.57 (m, 1H).

Example 60: (R)-5-(2-Methyl-4-phenoxyphenyl)-4-oxo-N-(1-propylpiperidin-3-yl)-4,5-dihydro-3H-1-thia-3,5,8-triazaacenaphthylene-2-carboxamide

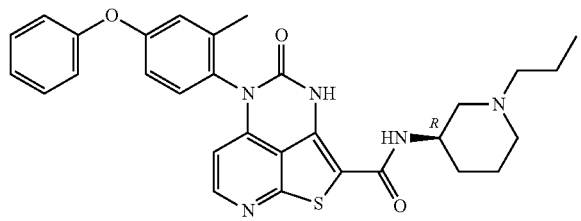

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) in MeOH (5 mL) was added propanal (0.045 mL, 0.6 mmol). It was stirred at rt for 10 min, then NaBH(OAc)$_3$ (190 mg, 0.90 mmol) was added and the mixture was stirred at rt overnight. The pH was adjusted to pH>7 with 2 M aqueous NaOH and concentrated to dryness. The residue was purified by flash column chromatography to yield the title compound (75 mg, 46% yield) as a yellow solid. MS (ESI): mass calcd. for $C_{30}H_{31}N_5O_3S$, 541.7; m/z found, 542.2 [M+H]$^+$. $^1$H NMR (400 MHz, DMSO-d$_6$ and CD$_3$OD): δ 8.25 (d, J=5.0 Hz, 1H), 7.47-7.32 (m, 2H), 7.32-7.22 (m, 1H), 7.19-7.11 (m, 1H), 7.10-6.99 (m, 3H), 6.97-6.86 (m, 1H), 5.93 (d, J=4.7 Hz, 1H), 4.06-3.95 (m, 1H), 2.96-2.83 (m, 1H), 2.79-2.64 (m, 1H), 2.38-2.25 (m, 2H), 2.15-1.98 (m, 5H), 1.86-1.77 (m, 1H), 1.74-1.65 (m, 1H), 1.62-1.53 (m, 1H), 1.53-1.38 (m, 3H), 0.84 (t, J=7.0 Hz, 3H).

Example 61: (S)-5-(3-Fluoro-2-methyl-4-phenoxyphenyl)-4-oxo-N-(tetrahydro-2H-pyran-3-1)-4,5-dihydro-3H-1-thia-3,5,8-triazaacenaphthylene-2-carboxamide

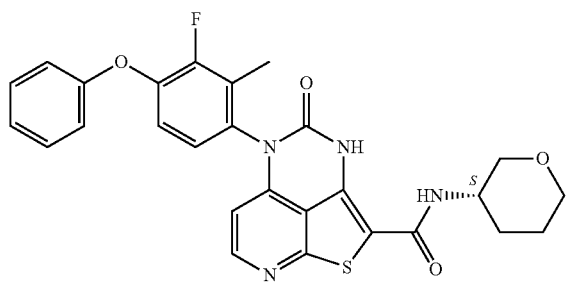

The title compound was prepared using analogous conditions described in Method 1, steps B-I in Example 1, and using 2-fluoro-3-methyl-4-nitro-1-phenoxybenzene (Intermediate 18, step B) in place of 2-methyl-4-phenoxyaniline in step B, and using (3S)-tetrahydropyran-3-amine in place of tert-butyl (3R,5R)-3-amino-5-fluoropiperidine-1-carboxylate (Intermediate 1) in step G. MS (ESI): mass calcd. for $C_{27}H_{23}FN_4O_4S$, 518.6; m/z found, 519.0 [M+H]$^+$. $^1$H NMR (400 MHz, DMSO-d$_6$): δ 8.27 (d, J=5.0 Hz, 1H), 7.42-7.27 (m, 2H), 7.25-7.16 (m, 1H), 7.14-6.98 (m, 4H), 6.03 (d, J=5.2 Hz, 1H), 392-3.84 (m, 1H), 3.80-3.70 (m, 2H), 3.30-3.12 (m, 2H), 2.02 (s, 3H), 1.92-1.83 (m, 1H), 1.67-1.49 (m, 3H).

Example 62: (R)—N-(1-Acryloylpiperidin-3-yl)-5-(4-ethyl-2-methylphenyl)-4-oxo-4,5-dihydro-3H-1-thia-3,5,8-triazaacenaphthylene-2-carboxamide

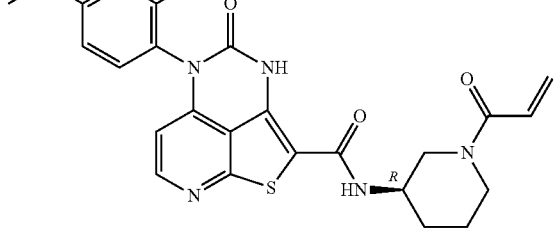

Step A: 4-Ethyl-2-methylaniline

To a mixture of 4-bromo-2-methylaniline (1.86 g, 10 mmol), Cs$_2$CO$_3$ (10 g, 30 mmol), and Pd(dppf)Cl$_2$ (146 mg, 0.200 mmol) in a Schlenk tube under a N$_2$ atmosphere was added dry THF (30 mL). To the stirred suspension was added trialkylborane (3.0 mL, 1 M in THF, 3.0 mmol) in one portion, and the mixture was refluxed for 5 h. The reaction was cooled to 0° C. and quenched by the addition of 10% aqueous NaOH and 30% aqueous H$_2$O$_2$. After stirring for 30 min at rt, the mixture was extracted with EtOAc. The combined organic layers were washed with aqueous FeSO$_4$ and brine, dried over anhydrous Na$_2$SO$_4$, filtered, and concentrated to dryness. The residue was purified by flash column chromatography to yield the title compound (1.1 g, 83% yield) as a white solid.

Step B: (R)—N-(1-Acryloylpiperidin-3-yl)-5-(4-ethyl-2-methylphenyl)-4-oxo-4,5-dihydro-3H-1-thia-3,5,8-triazaacenaphthylene-2-carboxamide The title compound was prepared in a manner analogous to Method 1, steps C-I in Example 1, and using 4-ethyl-2-methylaniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{27}N_5O_3S$, 489.6; m/z found, 490.1 [M+H]$^+$. $^1$H NMR (400 MHz, DMSO-d$_6$): δ 10.23 (s, 1H), 8.30 (d, J=5.5 Hz, 1H), 8.08 (s, 1H), 7.36-7.14 (m, 3H), 6.89-6.64 (m, 1H), 6.09 (d, J=16.7 Hz, 1H), 5.85 (d, J=5.5 Hz, 1H), 5.67 (d, J=10.5 Hz, 1H), 4.52-4.14 (m, 1H), 4.08-3.92 (m, 1H), 3.80-3.60 (m, 1H), 3.15-2.88 (m, 1H), 2.79-2.59 (m, 3H), d 2.80-2.60 (m, 3H), 1.99-1.89 (m, 1H), 1.78-1.58 (m, 2H), 1.50-1.32 (m, 1H), 1.23 (t, J=7.6 Hz, 3H).

Example 63: (R,E)-N-(1-(2-Cyano-4-methyl-4-(tetrahydro-2H-pyran-4-yl)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

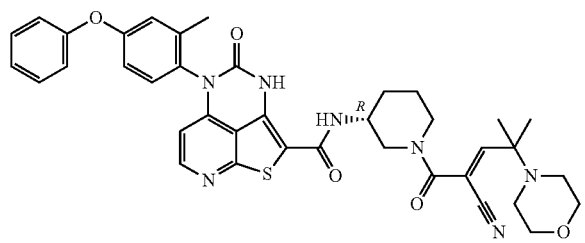

To a sealed tube were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 150 mg, 0.27 mmol), 2-methyl-2-morpholinopropanal (65 mg, 0.41 mmol), piperidine (30 mg, 0.35 mmol), and EtOH (3 mL) and was heated to 105° C. overnight, cooled to rt, concentrated to dryness, and the residue purified by flash column chromatography to yield the title compound (37 mg, 96% yield) as yellow solid. MS (ESI): mass calcd. for $C_{38}H_{39}N_7O_5S$, 705.8; m/z found, 706.3 $[M+H]^+$. $^1H$ NMR (400 MHz, $CD_3OD$): δ 8.31 (d, J=5.5 Hz, 1H), 7.47-7.36 (m, 2H), 7.35-7.26 (m, 1H), 7.21-7.14 (m, 1H), 7.12-7.04 (m, 3H), 7.01-6.93 (m, 1H), 6.89-6.78 (m, 1H), 6.08-6.02 m, 1H), 4.52-3.87 (m, 3H), 3.80-3.61 (m, 4H), 3.52-3.35 (m, 1H), 3.25-2.85 (m, 1H), 2.74-2.51 (m, 4H), 2.15-2.10 (m, 3H), 2.08-1.57 (m, 4H), 1.36-1.26 (m, 6H).

Example 64: (R)—N-(1-Acryloylpiperidin-3-yl)-5-(4-(2,6-difluorophenoxy)-2-methylphenyl)-4-oxo-4,5-dihydro-3H-1-thia-3,5,8-triazaacenaphthylene-2-carboxamide

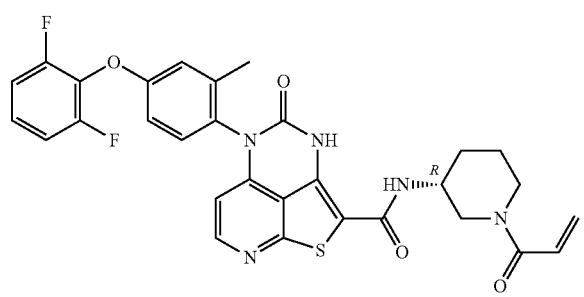

The title compound was prepared in a manner analogous to Method 1, steps A-I in Example 1, and using 2,6-difluorophenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{25}F_2N_5O_4S$, 589.6; m/z found, 590.2 $[M+H]^+$. $^1H$ NMR (400 MHz, $CD_3OD$): δ 8.29 (d, J=5.6 Hz, 1H), 7.40-7.26 (m, 2H), 7.21-7.10 (m, 2H), 7.04-6.98 (m, 1H), 6.95-6.88 (m, 1H), 6.85-6.70 (m, 1H), 6.27-6.12 (m, 1H), 6.05-5.98 (m, 1H), 5.78-5.64 (m, 1H), 4.61-3.84 (m, 3H), 3.24-3.07 (m, 1H), 2.98-2.79 (m, 1H), 2.15-2.10 (m, 3H), 2.09-1.98 (m, 1H), 1.94-1.48 (m, 3H).

Example 65: (R)—N-(1-Acryloylpiperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide

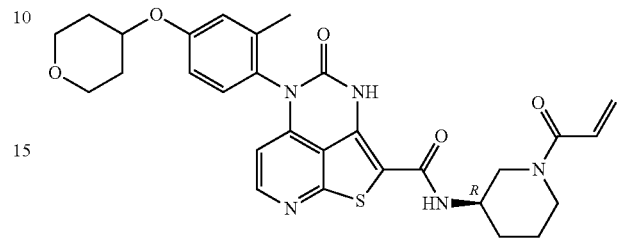

The title compound was prepared in a manner analogous to Method 1, steps D-I in Example 1, and using 2-chloro-4-(2-methyl-4-tetrahydropyran-4-yloxyanilino)pyridine-3-carbonitrile (Intermediate 31) in place of 2-chloro-4-(2-methyl-4-phenoxyanilino)pyridine-3-carbonitrile in step D, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{29}H_{31}N_5O_5S$, 561.7; m/z found, 562.5 $[M+H]^+$. $^1H$ NMR (400 MHz, $CD_3OD$): δ 8.31-8.27 (m, 1H), 7.25-7.20 (m, 1H), 7.05-7.01 (m, 1H), 6.99-6.95 (m, 1H), 6.81-6.77 (m, 1H), 6.22-6.17 (m, 1H), 6.04-6.00 (m, 1H), 5.74-5.69 (m, 1H), 4.68-4.58 (m, 1H), 4.33-4.11 (m, 1H), 4.07-3.85 (m, 4H), 3.65-3.57 (m, 2H), 3.21-3.18 (m, 1H), 2.93-2.86 (m, 1H), 2.11 (s, 3H), 2.09-2.02 (m, 3H), 1.89-1.83 (m, 1H), 1.80-1.69 (m, 3H), 1.55-1.50 (m, 1H).

Example 66: (R)—N-(1-Acryloylpiperidin-3-yl)-5-(4-ethoxy-2-methylphenyl)-4-oxo-4,5-dihydro-3H-1-thia-3,5,8-triazaacenaphthylene-2-carboxamide

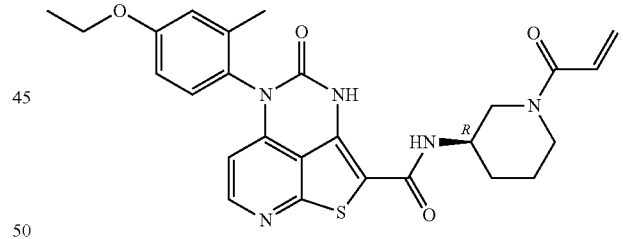

Step A: 4-Ethoxy-2-methyl-1-nitrobenzene

To a mixture of 3-methyl-4-nitrophenol (5.0 g, 33 mmol) and $K_2CO_3$ (13.6 g, 98.6 mmol) in DMF (25 mL) was added bromoethane (8.9 g, 82 mmol) and the reaction was stirred at 80° C. overnight. Water was added to the reaction mixture and a yellow solid was precipitated. The precipitate was filtered, washed with water, and dried to yield the title compound (4.5 g, 76% yield) as a yellow solid.

Step B: (R)—N-(1-Acryloylpiperidin-3-yl)-5-(4-ethoxy-2-methylphenyl)-4-oxo-4,5-dihydro-3H-1-thia-3,5,8-triazaacenaphthylene-2-carboxamide The title compound was prepared in a manner analogous to Method 1, steps B-I in Example 1, using 4-ethoxy-2- methyl-1-nitrobenzene in place of 2-methyl-1-nitro-4-phenoxybenzene in step B, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{27}N_5O_4S$, 505.6; m/z found, 506.0 [M+H]+. $^1$H NMR (400 MHz, $CD_3OD$): δ 8.33-8.22 (m, 1H), 7.29-7.16 (m, 1H), 7.01-6.88 (m, 2H), 6.87-6.70 (m, 1H), 6.26-6.12 (m, 1H), 6.04-5.94 (m, 1H), 5.77-5.65 (m, 1H), 4.57-3.89 (m, 5H), 3.21-3.05 (m, 1H), 2.96-2.77 (m, 1H), 2.10 (s, 3H), 2.07-1.99 (m, 1H), 1.88-1.80 (m, 1H), 1.78-1.49 (m, 2H), 1.44-1.35 (m, 3H).

Example 67: (S)-5-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide

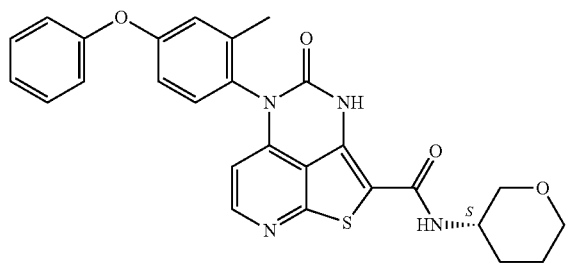

The title compound was prepared in a manner analogous to Method 1, steps A-G in Example 1, and using (3S)-tetrahydropyran-3-amine in place of tert-butyl (3R,5R)-3-amino-5-fluoropiperidine-1-carboxylate (Intermediate 1) in step G. MS (ESI): mass calcd. for $C_{27}H_{24}N_4O_4S$, 500.6; m/z found, 501.1 [M+H]+. $^1$H NMR (400 MHz, DMSO-$d_6$): δ 10.23 (s, 1H), 8.33 (d, J=5.5 Hz, 1H), 7.96 (d, J=7.4 Hz, 1H), 7.51-7.41 (m, 2H), 7.41-7.33 (m, 1H), 7.26-7.16 (m, 1H), 7.15-7.04 (m, 3H), 7.03-6.90 (m, 1H), 5.97 (d, J=5.4 Hz, 1H), 4.00-3.84 (m, 1H), 3.84-3.69 (m, 2H), 3.25-3.12 (m, 2H), 2.06 (s, 3H), 1.97-1.85 (m, 1H), 1.78-1.50 (m, 3H).

Example 68: (S)-5-(*S)-(2-Methyl-4-phenoxyphenyl)-4-oxo-N-(tetrahydrofuran-3-yl)-4,5-dihydro-3H-1-thia-3,5,8-triazaacenaphthylene-2-carboxamide

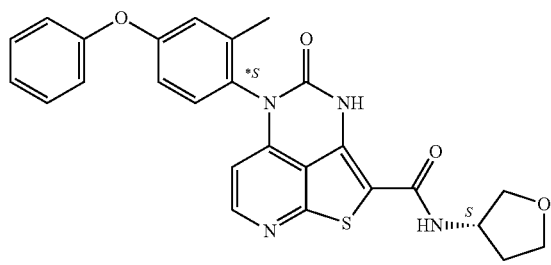

The title compound was prepared in a manner analogous to Method 1, steps A-G (including Chiral resolution Method A after Step F to obtain the *S atropisomer) in Example 1, and using (3S)-tetrahydrofuran-3-amine in place of tert-butyl (3R,5R)-3-amino-5-fluoropiperidine-1-carboxylate (Intermediate 1) in step G. MS (ESI): mass calcd. for $C_{26}H_{22}N_4O_4S$, 486.5; m/z found, 487.0 [M+H]+. $^1$H NMR (400 MHz, $CD_3OD$): δ 8.40-8.27 (m, 1H), 7.40-7.35 (m, 2H), 7.34-7.24 (m, 1H), 7.23-7.14 (m, 1H), 7.13-7.02 (m, 3H), 7.00-6.92 (m, 1H), 6.08 (d, J=4.7 Hz, 1H), 4.65-4.50 (m, 1H), 4.06-3.90 (m, 2H), 3.88-3.65 (m, 2H), 2.35-2.21 (m, 1H), 2.13 (s, 3H), 2.06-1.95 (m, 1H).

Example 69: (R)—N-(1-Acryloylpiperidin-3-yl)-5-(2,6-difluoro-4-phenoxyphenyl)-4-oxo-4,5-dihydro-3H-1-thia-3,5,8-triazaacenaphthylene-2-carboxamide

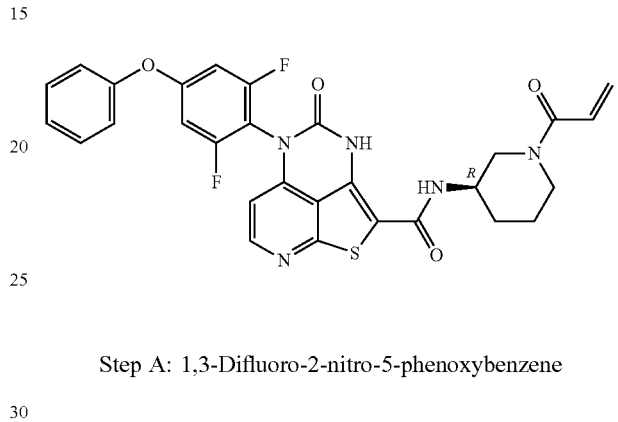

Step A: 1,3-Difluoro-2-nitro-5-phenoxybenzene 3,5-Difluoro-4-nitrophenol (Intermediate 26) (493 mg, 2.82 mmol) was dissolved in $CH_3CN$ (45 mL, 860 mmol) and (2-trimethylsilylphenyl) trifluoromethanesulfonate (1.0 mL, 4.2 mmol) was added, followed by cesium fluoride (1.28 g, 8.45 mmol). The reaction was stirred at rt overnight under argon. The reaction was washed with saturated aqueous NaCl (50 mL) and the aqueous phase was extracted with $Et_2O$ (50 mL). The combined organic extracts were dried over anhydrous $Na_2SO_4$, filtered, and concentrated to dryness. The product was purified by flash column chromatography to yield the title compound (450.7 mg, 63.70% yield) as a yellow oil.

Step B: (R)—N-(1-Acryloylpiperidin-3-yl)-5-(2,6-difluoro-4-phenoxyphenyl)-4-oxo-4,5-dihydro-3H-1-thia-3,5,8-triazaacenaphthylene-2-carboxamide The title compound was prepared in a manner analogous to Method 1, steps B-I in Example 1, using 1,3-difluoro-2-nitro-5-phenoxybenzene in place of 2-methyl-4-phenoxyaniline in step B and tert-butyl (R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{29}H_{23}F_2N_5O_4S$, 575.6; m/z found, 576.3 [M+H]+. 1H NMR (400 MHz, $CDCl_3$) δ9.51 (s, 1H), 8.43 (d, J=5.05 Hz, 1H), 7.46 (t, J=7.83 Hz, 2H), 7.28-7.31 (m, 1H), 7.12-7.16 (m, 2H), 6.69 (d, J=9.09 Hz, 2H), 6.62 (dd, J=16.67, 10.61 Hz, 1H), 6.25-6.51 (m, 1H), 6.16-6.24 (m, 1H), 5.70-5.82 (m, 1H), 5.38-5.52 (m, 1H), 3.87-4.22 (m, 2H), 3.27-3.77 (m, 3H), 1.87-2.13 (m, 2H), 1.62-1.85 (m, 2H).

Example 70: (R)-5-(4-(Benzofuran-7-yloxy)-2-methylphenyl)-N-(1-methylpiperidin-3-yl)-4-oxo-4,5-dihydro-3H-1-thia-3,5,8-triazaacenaphthylene-2-carboxamide

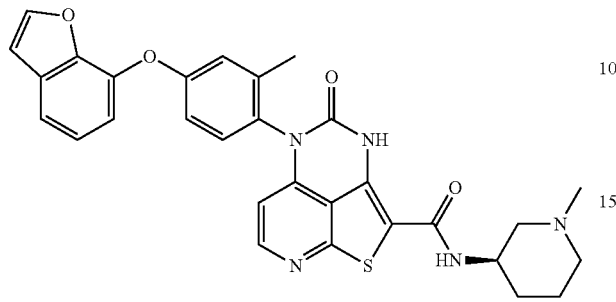

The title compound was prepared in a manner analogous to Method 1, steps A-G in Example 1, and using benzofuran-7-ol (Intermediate 8) in place of phenol in step A, and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.0 $[M+H]^+$. $^1$H NMR (400 MHz, CD$_3$OD): δ 8.41 (s, 1H), 8.35-8.29 (m, 1H), 7.77-7.72 (m, 1H), 7.51-7.45 (m, 1H), 7.31-7.22 (m, 2H), 7.07-7.02 (m, 2H), 6.98-6.93 (m, 1H), 6.92-6.88 (m, 1H), 6.10-6.05 (m, 1H), 4.33-4.18 (m, 1H), 3.47-3.36 (m, 1H), 3.26-3.14 (m, 1H), 2.91-2.68 (m, 5H), 2.10 (s, 3H), 2.06-1.96 (m, 2H), 1.89-1.74 (m, 1H), 1.73-1.59 (m, 1H).

Example 71: (R)-5-(3-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide

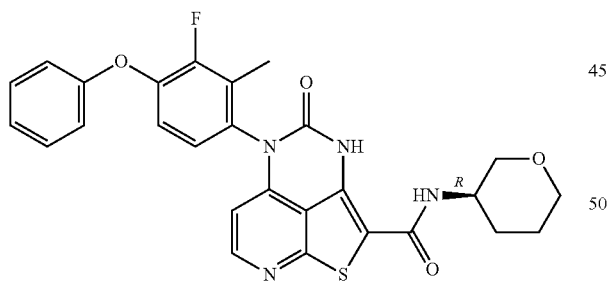

The title compound was prepared using analogous conditions described in Method 1, steps B-I in Example 1, and using 2-fluoro-3-methyl-4-nitro-1-phenoxybenzene (Intermediate 18, step B) in place of 2-methyl-4-phenoxyaniline in step B, and using (3R)-tetrahydropyran-3-amine in place of tert-butyl (3R,5R)-3-amino-5-fluoropiperidine-1-carboxylate (Intermediate 1) in step G. MS (ESI): mass calcd. for $C_{27}H_{23}FN_4O_4S$, 518.6; m/z found, 519 $[M+H]^+$. $^1$H NMR (400 MHz, DMSO-d$_6$ and CD$_3$OD): δ 8.27 (d, J=5.5 Hz, 1H), 7.42-7.28 (m, 2H), 7.23-7.15 (m, 1H), 7.13-6.96 (m, 4H), 6.03 (d, J=5.5 Hz, 1H), 3.93-3.83 (m, 1H), 3.80-3.69 (m, 2H), 3.28-3.12 (m, 2H), 2.02 (s, 3H), 1.92-1.84 (m, 1H), 1.66-1.50 (m, 3H).

Example 72: (R)—N-(1-(3-Methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide

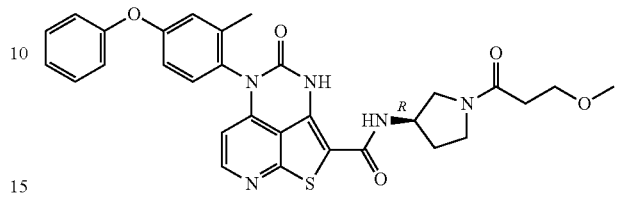

The title compound was prepared using the method in Example 104, and using 3-methoxypropanoic acid in place of 3-methylsulfonylpropanoic acid. MS (ESI): mass calcd. for $C_{30}H_{29}N_5O_5S$, 571.6; m/z found, 572.2 $[M+H]^+$. $^1$H NMR (400 MHz, CD$_3$OD): δ 8.32 (d, J=5.6, 1H), 7.43-7.35 (m, 2H), 7.33-7.25 (m, 1H), 7.21-7.12 (m, 1H), 7.12-7.03 (m, 3H), 7.01-6.92 (m, 1H), 6.07 (d, J=5.6, 1H), 4.66-4.53 (m, 1H), 3.82-3.70 (m, 1H), 3.68-3.60 (m, 3H), 3.56-3.38 (m, 2H), 3.34-3.30 (m, 3H), 2.62-2.54 (m, 2H), 2.35-2.17 (m, 1H), 2.16-1.99 (m, 4H).

Example 73: (R)-5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide

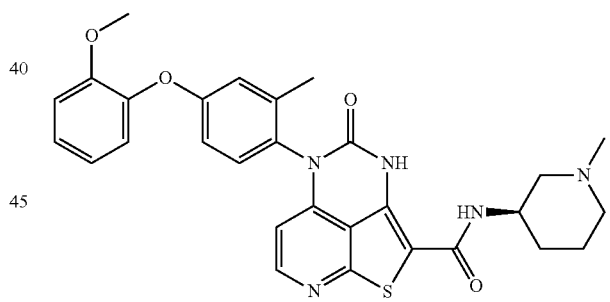

Step A: (R)-5-(4-(2-methoxyphenoxy)-2-methylphenyl)-4-oxo-N-(piperidin-3-yl)-4,5-dihydro-3H-1-thia-3,5,8-triazaacenaphthylene-2-carboxamide To a solution of 5-(4-(2-methoxyphenoxy)-2-methylphenyl)-4-oxo-4,5-dihydro-3H-1-thia-3,5,8-triazaacenaphthylene-2-carboxylic acid (Intermediate 67, 200 mg, 0.45 mmol) in DCM (50 mL) was added a drop of DMF and then oxalyl chloride (284 mg, 2.24 mmol). The reaction was stirred at rt for 3 h, concentrated to dryness, and diluted in DCM. Triethylamine (226 mg, 2.24 mmol) and tert-butyl (3R)-3-aminopiperidine-1-carboxylate (107 mg, 0.536 mmol) were added, stirred at rt for 1 h, concentrated to dryness, and purified by flash column chromatography to a yellow solid. The solid was diluted in MeOH, concentrated HCl was added and the solution was concentrated to dryness to yield the title compound (150 mg, 59% yield) as a yellow solid.

Step B: (R)-5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide To a mixture of (R)-5-(4-(2-methoxyphenoxy)-2-methylphenyl)-4-oxo-N-(piperidin-3-yl)-4,5-dihydro-3H-1-thia-3,5,8-triazaacenaphthylene-2-carboxamide (98 mg, 0.17 mmol) and formaldehyde (0.5 mL, 37 wt. % in H$_2$O) in MeOH (15 mL) was added NaBH(OAc)$_3$ (110 mg, 0.52 mmol), then stirred at rt for 1 h, concentrated to dryness, and purified by flash column chromatography to yield the title compound as a white solid (52 mg, 56% yield). MS (ESI): mass calcd. for C$_{29}$H$_{29}$N$_5$O$_4$S, 543.6; m/z found, 544.0 [M+H]$^+$. $^1$H NMR (400 MHz, DMSO-d6): δ 8.29 (d, J=5.3 Hz, 1H), 8.08 (d, J=7.5 Hz, 1H), 7.28-7.20 (m, 2H), 7.16-7.08 (m, 1H), 7.05-6.97 (m, 1H), 6.96-6.86 (m, 1H), 6.82-6.68 (m, 1H), 5.88 (d, J=5.3 Hz, 1H), 3.42-3.90 (m, 1H), 3.78 (s, 3H), 2.97-2.85 (m, 1H), 2.81-2.66 (m, 1H), 2.28 (s, 3H), 2.11-1.95 (m, 5H), 1.82-1.65 (m, 2H), 1.61-1.48 (m, 1H), 1.46-1.30 (m, 1H).

Example 74: (R)—N-(1-Ethylpiperidin-3-yl)-5-(2-methyl-4-phenoxyphenyl)-4-oxo-4,5-dihydro-3H-1-thia-3,5,8-triazaacenaphthylene-2-carboxamide

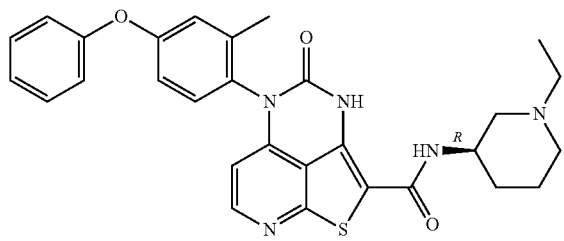

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) in DCM (10 mL) was added acetaldehyde (99 mg, 2.3 mmol). After stirring at rt for 10 min, NaBH(OAc)$_3$ (190 mg, 0.90 mmol) was added. The mixture was stirred at rt overnight and the pH was adjusted to pH>7 with 2 M aqueous NaOH. The reaction mixture was concentrated to dryness and the residue was purified using flash column chromatography to yield the title compound (44 mg, 27% yield) as a yellow solid. MS (ESI): mass calcd. for C$_{29}$H$_{29}$N$_5$O$_3$S, 527.6; m/z found, 528.2 [M+H]$^+$. $^1$H NMR (400 MHz, a mixture of DMSO-d6 and CD3OD): δ 8.23 (d, J=5.4 Hz, 1H), 7.42-7.31 (m, 2H), 7.30-7.20 (m, 1H), 7.16-7.10 (m, 1H), 7.08-7.98 (m, 3H), 6.95-6.83 (m, 1H), 5.91 (d, J=5.4 Hz, 1H), 4.03-3.95 (m, 1H), 2.99-2.88 (m, 1H), 2.78-2.71 (m, 1H), 2.46-2.38 (m, 2H), 2.09-1.97 (m, 5H), 1.85-1.75 (m, 1H), 1.75-1.65 (m, 1H), 1.60-1.48 (m, 1H), 1.46-1.38 (m, 1H), 1.01 (t, J=7.1 Hz, 3H).

Example 75: (R)—N-(1-(3-Hydroxypropanoyl)piperidin-3-yl)-5-(2-methyl-4-phenoxyphenyl)-4-oxo-4,5-dihydro-3H-1-thia-3,5,8-triazaacenaphthylene-2-carboxamide

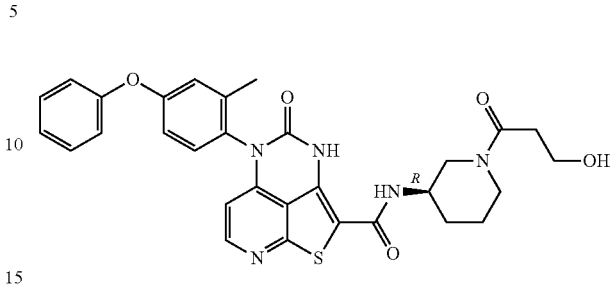

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 120 mg, 0.22 mmol), 3-hydroxypropanoic acid (40 mg, 0.45 mmol), HATU (110 mg, 0.29 mmol), diisopropylethylamine (58 mg, 0.45 mmol) in DMF (5 mL) was stirred at rt for 2 h. The reaction was purified by HPLC to yield the title compound (58 mg, 44% yield) as white solid. MS (ESI): mass calcd. for C$_{30}$H$_{29}$N$_5$O$_5$S, 571.6; m/z found, 572.4 [M+H]$^+$. $^1$H NMR (400 MHz, CD$_3$OD): δ 8.34-8.25 (m, 1H), 7.43-7.35 (m, 2H), 7.35-7.28 (m, 1H), 7.19-7.12 (m, 1H), 7.11-7.02 (m, 3H), 7.00-6.93 (m, 1H), 6.09-6.02 (m, 1H), 4.54-4.03 (m, 2H), 3.98-3.78 (m, 3H), 3.18-3.00 (m, 1H), 2.88-2.46 (m, 3H), 2.11 (s, 3H), 2.08-1.98 (m, 1H), 1.90-1.78 (m, 1H), 1.76-1.60 (m, 1H), 1.62-1.45 (m, 1H).

Example 76: (R,E)-N-(1-(2-Cyano-3-cyclopropylacrylol)piperidin-3-yl)-5-(4-(2-ethylphenoxy)-2-methylphenyl)-4-oxo-4,5-dihydro-3H-1-thia-3,5,8-triazaacenaphthylene-2-carboxamide

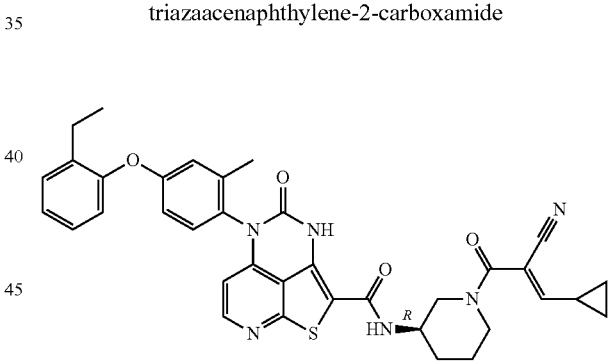

Step A: R)-5-(4-(2-Ethylphenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 2-ethylphenol in place of phenol in step A, and using tert-butyl (3R)-3-aminopyrrolidine-1-carboxylate in place of tert-butyl (3R,5R)-3-amino-5-fluoropiperidine-1-carboxylate (Intermediate 1) in step G.

Step B: (R,E)-N-(1-(2-Cyano-3-cyclopropylacryloyl)piperidin-3-yl)-5-(4-(2-ethylphenoxy)-2-methylphenyl)-4-oxo-4,5-dihydro-3H-1-thia-3,5,8-triazaacenaphthylene-2-carboxamide To a mixture of (R)-5-(4-(2-ethylphenoxy)-2-methylphenyl)-4-oxo-N-(piperidin-3-yl)-4,5-dihydro-3H-1-thia-3,5,8- triazaacenaphthylene-2-carboxamide (70 mg, 0.13 mmol) and triethylamine (28 mg, 0.28 mmol) in DMF (2 mL) were added (E)-2-cyano-3-cyclopropylprop-2-enoic acid (Intermediate 17) (36 mg, 0.26 mmol) and HATU (100 mg, 0.27 mmol) and was reacted at rt for 20 min. The reaction was quenched with H$_2$O (10 mL), extracted with DCM, dried over anhydrous Na$_2$SO$_4$, filtered, and concentrated to dryness. The residue was purified by flash column chromatography to obtain the title compound (60 mg, 97% yield) as a white solid. MS (ESI): mass calcd. for C$_{36}$H$_{34}$N$_6$O$_4$S, 646.8; m/z found, 647.0 [M+H]$^+$. $^1$H NMR (400 MHz, CD$_3$OD): δ 8.37-8.29 (m, 1H), 7.35-7.29 (m, 1H), 7.27-7.20 (m, 2H), 7.18-7.12 (m, 1H), 7.00-6.93 (m, 2H), 6.88-6.83 (m, 1H), 6.57-6.47 (m, 1H), 6.07-6.03 (m, 1H), 4.33-4.06 (m, 1H), 4.15-3.93 (m, 2H), 3.28-2.98 (m, 2H), 2.68-2.59 (m, 2H), 2.10 (s, 3H), 2.08-1.94 (m, 2H), 1.92-1.85 (m, 1H), 1.84-1.56 (m, 2H), 1.27-1.56 (m, 5H), 1.07-1.78 (m, 2H).

Example 77: (R)—N-(1-Acryloylpyrrolidin-3-yl)-5-(2,3-dimethyl-4-phenoxyphenyl)-4-oxo-4,5-dihydro-3H-1-thia-3,5,8-triazaacenaphthylene-2-carboxamide

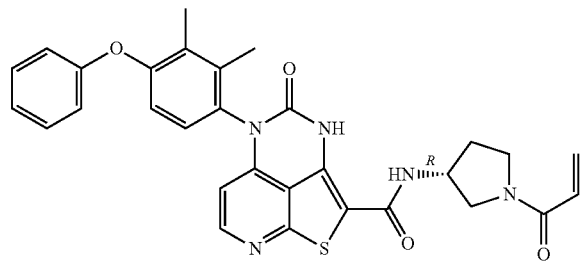

The title compound was prepared in a manner analogous to Method 1, steps A-I in Example 1, and using 1-fluoro-2,3-dimethyl-4-nitrobenzene in place of 5-fluoro-2-nitrotoluene in step A, and using tert-butyl (R)-3-aminopyrrolidine-1-carboxylate in place of tert-butyl (3R,5R)-3-amino-5-fluoropiperidine-1-carboxylate (Intermediate 1) in step G. MS (ESI): mass calcd. for C$_{30}$H$_{27}$N$_5$O$_4$S, 553.6; m/z found, 554.3 [M+H]$^+$. $^1$H NMR (400 MHz, CD$_3$OD and DMSO-d$_6$): δ 8.26-8.11 (br, 1H), 7.34-7.28 (m, 2H), 7.09 (d, J=8.3 Hz, 1H), 7.06-7.00 (m, 1H), 6.95-6.88 (m, 2H), 6.84 (d, J=8.6 Hz, 1H), 6.60-6.47 (m, 1H), 6.17-6.10 (m, 1H), 5.94-5.79 (m, 1H), 5.66-5.60 (m, 1H), 4.55-4.44 (m, 1H), 3.75-3.67 (m, 1H), 3.64-3.57 (m, 1H), 3.55-3.45 (m, 1H), 3.45-3.36 (m, 1H), 2.16 (s, 3H), 2.15-2.06 (m, 1H), 2.01 (s, 3H), 1.96-1.91 (m, 1H).

Example 78: (R)—N-(1-(2-(Dimethylamino)acetyl)piperidin-3-yl)-5-(2-methyl-4-phenoxyphenyl)-4-oxo-4,5-dihydro-3H-1-thia-3,5,8-triazaacenaphthylene-2-carboxamide

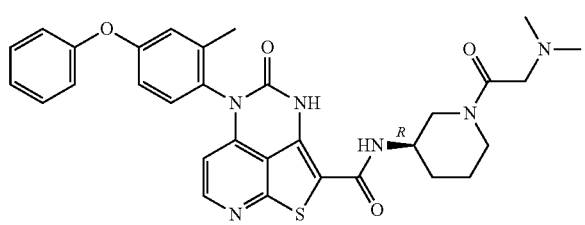

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 120 mg, 0.22 mmol) in DMF (2 mL) was added 2-(dimethylamino)acetic acid (47 mg, 0.34 mmol), HATU (102 mg, 0.268 mmol), and triethylamine (0.128 mL, 0.896 mmol). The mixture was stirred at rt overnight, then purified by flash column chromatography to yield the title compound (36 mg, 26% yield) as a yellow solid. MS (ESI): mass calcd. for C$_{31}$H$_{32}$N$_6$O$_4$S, 584.7; m/z found, 585.2 [M+H]$^+$. $^1$H NMR (400 MHz, CD$_3$OD): δ 8.26 (d, J=5.5, 1H), 7.45-7.35 (m, 2H), 7.32-7.23 (m, 1H), 7.20-7.12 (m, 1H), 7.11-7.00 (m, 3H), 7.00-6.90 (m, 1H), 6.00 (d, J=4.9, 1H), 4.06-3.91 (m, 2H), 3.79-3.59 (m, 1H), 3.50-3.39 (m, 2H), 3.23-3.06 (m, 2H), 2.52-2.31 (m, 6H), 2.10 (s, 3H), 2.06-1.97 (m, 1H), 1.79-1.89 (m, 1H), 1.74-1.49 (m, 2H).

Example 79: (R,E)-N-(1-(2-Cyano-3-cyclopropylacryloyl)piperidin-3-yl)-5-(2-fluoro-4-phenoxyphenyl)-4-oxo-4,5-dihydro-3H-1-thia-3,5,8-triazaacenaphthylene-2-carboxamide

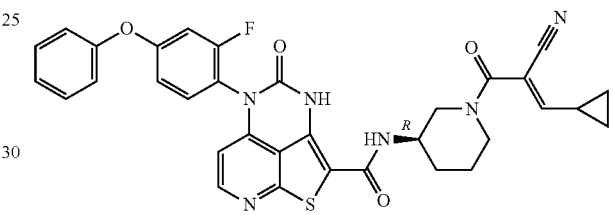

Step A: 2-Fluoro-1-nitro-4-phenoxybenzene

To a mixture of 3-fluoro-4-nitrophenol (2.0 g, 13 mmol), phenylboronic acid (2.33 g, 19.1 mmol), Cu(OAc)$_2$ (4.6 g, 25 mmol), and triethylamine (6.4 g, 64 mmol) in DCM (60 mL) was added molecular sieves (4A powder<50 μm, 2 g). The mixture was stirred at rt under N$_2$ overnight, filtered, concentrated to dryness, and purified by flash column chromatography to yield the title compound (2.7 g, 91% yield) as a yellow solid.

Step B: (R)-5-(2-Fluoro-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps B-H in Example 1, and using 2-fluoro-1-nitro-4-phenoxybenzene in place of 2-methyl-1-nitro-4-phenoxybenzene in step B and tert-butyl (3R)-3-aminopiperidine-1-carboxylate in place of tert-butyl (3R,5R)-3-amino-5-fluoropiperidine-1-carboxylate (Intermediate 1) in step G.

Step C: (R,E)-N-(1-(2-Cyano-3-cyclopropylacryloyl)piperidin-3-yl)-5-(2-fluoro-4-phenoxyphenyl)-4-oxo-4,5-dihydro-3H-1-thia-3,5,8-triazaacenaphthylene-2-carboxamide A solution of (R)-5-(2-fluoro-4-phenoxyphenyl)-4-oxo-N-(piperidin-3-yl)-4,5-dihydro-3H-1-thia-3,5,8-triazaacenaphthylene-2-carboxamide (150 mg, 0.30 mmol), (E)-2-cyano-3-cyclopropylprop-2-enoic acid (Intermediate 17) (61 mg, 45 mmol), HATU (2.27 g, 5.96 mmol), and triethylamine (150 mg, 1.5 mmol) in DMF (4 mL) was stirred at rt for 2 h, then purified by flash column chromatography to yield the title compound (124 mg, 67% yield) as a white solid. MS (ESI): mass calcd. for $C_{33}H_{27}FN_6O_4S$, 622.7; m/z found, 623.0 [M+H]+. 1H NMR (400 MHz, DMSO-d6): δ 8.32 (d, J=5.5 Hz, 1H), 8.21 (s, 1H), 7.62-7.50 (m, 1H), 7.50-7.39 (m, 2H), 7.28-7.19 (m, 1H), 7.19-7.08 (m, 3H), 6.99-6.89 (m, 1H), 6.66-6.47 (m, 1H), 6.15 (d, J=5.4 Hz, 1H), 4.04-4.00 (m, 1H), 3.99-3.72 (m, 2H), 3.10-2.68 (m, 2H), 2.00-1.71 (m, 3H), 1.70-1.58 (m, 1H), 1.56-1.37 (m, 1H), 1.18-1.05 (m, 2H), 1.02-0.68 (m, 2H).

Example 80: (R)-5-(*S)-(2-Methyl-4-phenoxyphenyl)-4-oxo-N-(tetrahydrofuran-3-1)-4,5-dihydro-3H-1-thia-3,5,8-triazaacenaphthylene-2-carboxamide

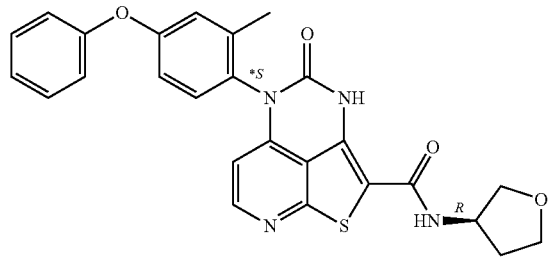

A solution of 5-(*S)-(2-methyl-4-phenoxyphenyl)-4-oxo-4,5-dihydro-3H-1-thia-3,5,8-triazaacenaphthylene-2-carboxylic acid (Intermediate 16) (30 mg, 0.072 mmol), HATU (55 mg, 0.15 mmol), and triethylamine (22 mg, 0.22 mmol) in anhydrous DMF (3 mL) was stirred at rt. After 10 min, (3R)-tetrahydrofuran-3-amine (10 mg, 0.12 mmol) was added and the mixture was stirred for 2 h. The crude mixture was purified by flash column chromatography to yield the title compound (27 mg, 99% yield) as a slight yellow solid. MS (ESI): mass calcd. for $C_{26}H_{22}N_4O_4S$, 486.5; m/z found, 487.1 [M+H]+. 1H NMR (400 MHz, CD3OD): δ 8.33 (d, J=5.5 Hz, 1H), 7.46-7.35 (m, 2H), 7.29 (d, J=8.6 Hz, 1H), 7.21-7.13 (m, 1H), 7.12-7.03 (m, 3H), 7.00-6.94 (m, 1H), 6.07 (d, J=5.5 Hz, 1H), 4.65-4.53 (m, 1H), 4.03-3.88 (m, 2H), 3.87-3.76 (m, 1H), 3.75-3.66 (m, 1H), 2.36-2.22 (m, 1H), 2.12 (s, 3H), 2.06-1.97 (m, 1H).

Example 81: (R)—N-(1-Acryloylpyrrolidin-3-yl)-5-(2,6-dimethyl-4-phenoxyphenyl)-4-oxo-4,5-dihydro-3H-1-thia-3,5,8-triazaacenaphthylene-2-carboxamide

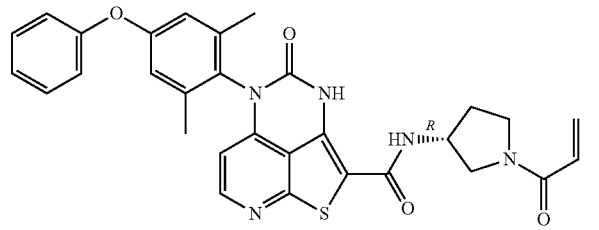

The title compound was prepared in a manner analogous to Method 1, steps A-I in Example 1, using 5-fluoro-1,3-dimethyl-2-nitrobenzene in place of 5-fluoro-2-nitrotoluene in step A and tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.2 [M+H]+. 1H NMR (400 MHz, CD3OD and DMSO-d6): δ 8.36-8.27 (m, 1H), 7.41-7.31 (m, 2H), 7.17-7.10 (m, 1H), 7.08-7.01 (m, 2H), 6.84 (s, 2H), 6.61-6.48 (m, 1H), 6.20-6.13 (m, 1H), 5.98-5.92 (m, 1H), 5.69-5.61 (m, 1H), 4.59-4.46 (m, 1H), 3.96-3.84 (m, 1H), 3.75-3.69 (m, 1H), 3.63-3.45 (m, 2H), 2.27-2.02 (m, 2H), 2.01 (s, 6H).

Example 82: (S)—N-(1-acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide

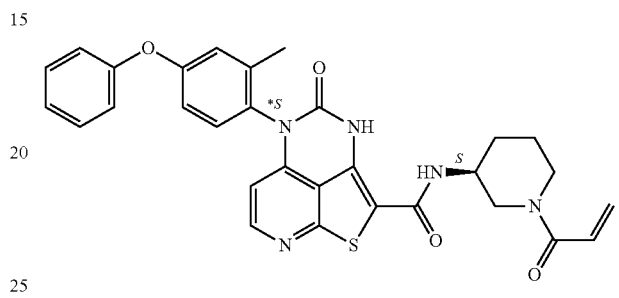

The title compound was prepared in a manner analogous to Method 1, steps A-I in Example 1 (including Chiral resolution Method A after Step F to obtain the *S atropisomer), and using tert-butyl (3S)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.2 [M+H]+. 1H NMR (400 MHz, CD3OD): δ 8.34-8.22 (m, 1H), 7.45-7.36 (m, 2H), 7.33-7.23 (m, 1H), 7.21-7.13 (m, 1H), 7.13-7.03 (m, 3H), 7.01-6.93 (m, 1H), 6.87-6.72 (m, 1H), 6.29-6.14 (m, 1H), 6.08-5.96 (m, 1H), 5.79-5.68 (m, 1H), 4.53-3.95 (m, 3H), 3.28-3.10 (m, 1H), 3.04-2.84 (m, 1H), 2.15-2.02 (m, 4H), 1.96-1.83 (m, 1H), 1.82-1.68 (m, 1H), 1.63-1.49 (m, 1H).

Example 83: (R)—N-(1-Acryloylpiperidin-3-yl)-5-(2-methyl-4-(pentafluorothio)phenyl)-4-oxo-4,5-dihydro-3H-1-thia-3,5,8-triazaacenaphthylene-2-carboxamide

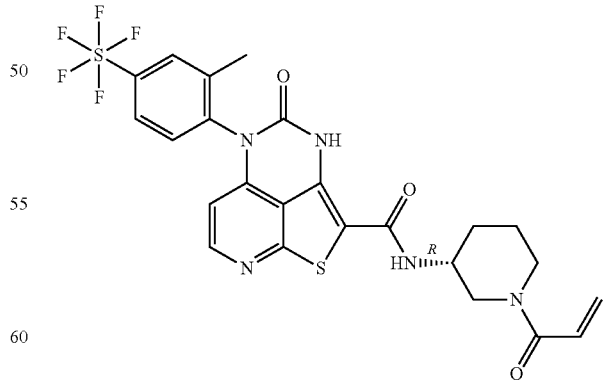

Step A: 2-Methyl-4-(pentafluorosulfanyl)aniline

To a stirred solution of 2-methyl-4-(pentafluorosulfanyl) nitrobenzene (1.5 g, 5.7 mmol) in ethanol (50 mL) was added Fe powder (1.28 g, 22.8 mmol), followed by the slow addition of concentrated HCl (2.5 mL) at 0° C. The mixture was stirred at rt for 1 h and the reaction was quenched by pouring into ice water and neutralized with sodium carbonate. The reaction was extracted with DCM, dried over anhydrous $Na_2SO_4$, filtered, and concentrated to dryness to yield the title compound (1.13 g, 85% yield) as a yellow oil.

Step B: (R)—N-(1-Acryloylpiperidin-3-yl)-5-(2-methyl-4-(pentafluorothio)phenyl)-4-oxo-4,5-dihydro-3H-1-thia-3,5,8-triazaacenaphthylene-2-carboxamide The title compound was prepared in a manner analogous to Method 1, steps C-G in Example 1, and using 2-methyl-4-(pentafluorosulfanyl)aniline in place of 2-methyl-4-phenoxyaniline in step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{24}H_{22}F_5N_5O_3S_2$, 587.6; m/z found, 588.3 [M+H]$^+$. $^1$H NMR (400 MHz, $CD_3OD$): δ 8.36-8.28 (m, 1H), 8.02-7.96 (m, 1H), 7.93-7.85 (m, 1H), 7.66-7.58 (m, 1H), 6.85-6.73 (m, 1H), 6.25-6.15 (m, 1H), 6.06-6.00 (m, 1H), 5.79-5.68 (m, 1H), 4.59-3.89 (m, 3H), 3.25-3.12 (m, 1H), 3.00-2.84 (m, 1H), 2.28 (s, 3H), 2.12-1.99 (m, 1H), 1.92-1.82 (m, 1H), 1.80-1.66 (m, 1H), 1.66-1.53 (m, 1H).

Example 84: (R)-5-(*S)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide

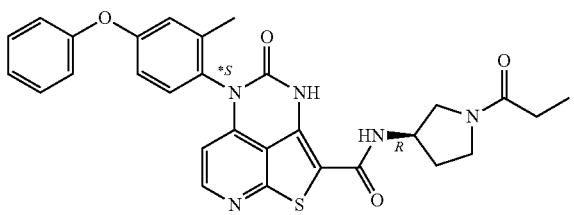

To a solution of (R)-5-(*S)-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36, 60 mg, 0.12 mmol), DCM (2 mL), and triethylamine (30 mg, 0.3 mmol) was added propanoyl propanoate (39 mg, 0.3 mmol) in DCM (2 mL) dropwise and stirred at room temperature for 2 h. The reaction mixture was concentrated to dryness and purified by normal phase flash column chromatography ($SiO_2$), then by preparative TLC to yield the title compound (27 mg, 42%) as a yellow solid. MS (ESI): mass calcd. for $C_{29}H_{27}N_5O_4S$, 541.6; m/z found, 542.2 [M+H]$^+$. $^1$H NMR (400 MHz, $CDCl_3$): δ 9.45 (s, 1H), 8.39-8.33 (m, 1H), 7.43-7.34 (m, 2H), 7.21-7.13 (m, 2H), 7.13-7.07 (m, 2H), 7.03-7.00 (m, 1H), 6.98-6.93 (m, 1H), 6.06-6.00 (m, 1H), 5.76-5.63 (m, 1H), 4.73-4.59 (m, 1H), 3.91-3.78 (m, 1H), 3.74-3.35 (m, 3H), 2.41-2.20 (m, 3H), 2.14-2.10 (m, 3H), 2.09-1.86 (m, 1H), 1.22-1.13 (m, 3H).

Example 85: (R)-Tetrahydro-2H-pyran-3-yl 5-(2-methyl-4-phenoxyphenyl)-4-oxo-4,5-dihydro-3H-1-thia-3,5,8-triazaacenaphthylene-2-carboxylate

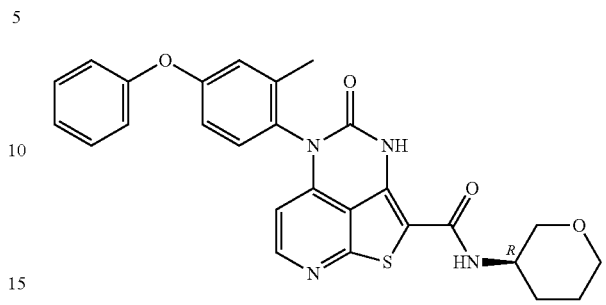

To a solution of 5-(2-methyl-4-phenoxyphenyl)-4-oxo-4,5-dihydro-3H-1-thia-3,5,8-triazaacenaphthylene-2-carboxylic acid (Intermediate 27, 150 mg, 0.36 mmol) in DCM (60 mL) was added a drop of DMF, then oxalyl chloride (230 mg, 1.8 mmol) was added. The reaction was stirred at rt for 3 h, concentrated to dryness, and diluted in DCM. Next, triethylamine (180 mg, 1.8 mmol) and (3R)-tetrahydropyran-3-amine (54 mg, 0.54 mmol) were added and the reaction was stirred at rt for 1 h, then concentrated to dryness, and purified by flash column chromatography to yield the title compound (115 mg, 64.1% yield) as a white solid. MS (ESI): mass calcd. for $C_{27}H_{24}N_4O_4S$, 500.6; m/z found, 501.1 [M+H]$^+$. $^1$H NMR (400 MHz, DMSO-d6): δ 8.31 (d, J=5.5 Hz, 1H), 7.98 (d, J=7.5 Hz, 1H), 7.50-7.38 (m, 2H), 7.37-7.30 (m, 1H), 7.24-7.15 (m, 1H), 7.15-7.03 (m, 3H), 7.00-6.92 (m, 1H), 5.95 (d, J=5.4 Hz, 1H), 3.94-3.85 (m, 1H), 3.85-3.70 (m, 2H), 3.25-3.12 (m, 2H), 2.04 (s, 3H), 1.96-1.85 (m, 1H), 1.73-1.51 (m, 3H).

Example 86: (R)—N-(1-Acryloylpiperidin-3-yl)-5-(2,4-dimethylphenyl)-4-oxo-4,5-dihydro-3H-1-thia-3,5,8-triazaacenaphthylene-2-carboxamide

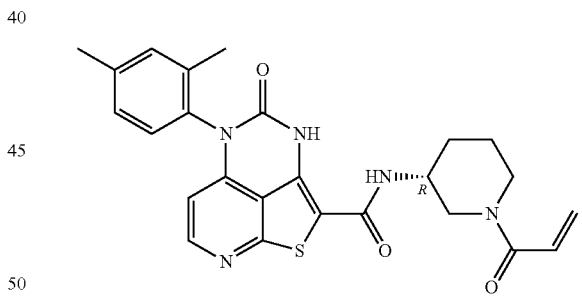

Step A: 5-(2,4-Dimethylphenyl)-4-oxo-4,5-dihydro-3H-1-thia-3,5,8-triazaacenaphthylene-2-carboxylic Acid The title compound was prepared in a manner analogous to Method 1, steps C-F in Example 1, and using 2,4-dimethylaniline in place of 2-methyl-4-phenoxyaniline in step C.

Step B: (R)—N-(1-Acryloylpiperidin-3-yl)-5-(2,4-dimethylphenyl)-4-oxo-4,5-dihydro-3H-1-thia-3,5,8-triazaacenaphthylene-2-carboxamide To a solution of 5-(2,4-dimethylphenyl)-4-oxo-4,5-dihydro-3H-1-thia-3,5,8-triazaacenaphthylene-2-carboxylic acid (200 mg, 0.59 mmol) and 1-[(3R)-3-amino-1-piperidyl]prop-2-en-1-one (Intermediate 15, 300 mg, 1.9 mmol) in anhydrous DMF were added HATU (570 mg, 1.5 mmol) and diisopropylethylamine (260 mg, 2.0 mmol) and the mixture stirred overnight at rt. The reaction mixture was purified by flash column chromatography, then preparative TLC to yield the title compound as a yellow solid. MS (ESI): mass calcd. for $C_{25}H_{25}N_5O_3S$, 475.6; m/z found, 476.1 [M+H]$^+$. $^1$H NMR (400 MHz, DMSO-d$_6$): δ 10.31-10.12 (m, 1H), 8.30 (d, J=5.5 Hz, 1H), 8.14-8.00 (m, 1H), 7.28-7.25 (m, 1H), 7.25-7.17 (m, 2H), 6.85-6.69 (m, 1H), 6.14-6.02 (m, 1H), 5.86 (d, J=5.5 Hz, 1H), 5.71-5.62 (m, 1H), 4.51-4.14 (m, 1H), 4.07-3.91 (m, 1H), 3.83-3.69 (m, 1H), 3.13-2.91 (m, 1H), 2.79-2.60 (m, 1H), 2.35 (s, 3H), 2.04 (s, 3H), 1.97-1.87 (m, 1H), 1.81-1.71 (m, 1H), 1.71-1.56 (m, 1H), 1.50-1.32 (m, 1H).

Example 87: (R)—N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide

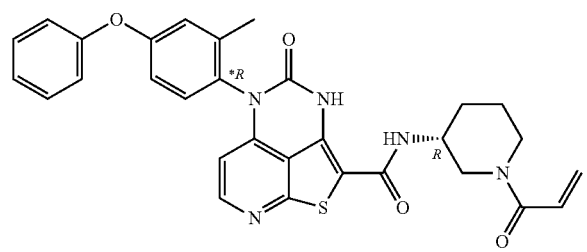

The title compound was prepared in a manner analogous to Method 1, steps A-I in Example 1 (including Chiral resolution Method A after Step F to obtain the *R atropisomer), and using tert-butyl (R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.3 [M+H]$^+$. $^1$H NMR (400 MHz, CD$_3$OD): δ 8.32 (d, J=5.6 Hz, 1H), 7.49-7.36 (m, 2H), 7.30 (d, J=8.6 Hz, 1H), 7.22-7.16 (m, 1H), 7.13-7.02 (m, 3H), 7.00-6.93 (m, 1H), 6.87-6.70 (m, 1H), 6.25-6.13 (m, 1H), 6.07 (d, J=5.5 Hz, 1H), 5.79-5.67 (m, 1H), 4.57-3.89 (m, 3H), 3.25-3.10 (m, 1H), 2.99-2.80 (m, 1H), 2.12 (s, 3H), 2.08-2.00 (m, 1H), 1.94-1.82 (m, 1H), 1.79-1.66 (m, 1H), 1.65-1.52 (m 1H).

Example 88: (S)-5-(*S)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide

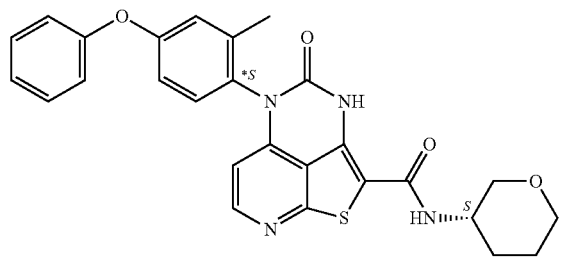

The title compound was prepared in a manner analogous to Method 1, steps A-G in Example 1 (including Chiral resolution Method A after Step F to obtain the *S atropisomer), and using (S)-tetrahydro-2H-pyran-3-amine in place of tert-butyl (3R,5R)-3-amino-5-fluoropiperidine-1-carboxylate in step G. MS (ESI): mass calcd. for $C_{27}H_{24}N_4O_4S$, 500.6; m/z found, 501.1 [M+H]$^+$. $^1$H NMR (400 MHz, CD$_3$OD and DMSO-d$_6$): δ 8.27 (d, J=5.5 Hz, 1H), 7.43-7.32 (m, 2H), 7.27 (d, J=8.6 Hz, 1H), 7.17-7.09 (m, 1H), 7.08-6.97 (m, 3H), 6.95-6.86 (m, 1H), 5.96 (d, J=5.5 Hz, 1H), 3.96-3.87 (m, 1H), 3.84-3.78 (m, 1H), 3.77-3.69 (m, 1H), 3.33-3.25 (m, 1H), 3.24-3.15 (m, 1H), 2.04 (s, 3H), 1.98-1.87 (m, 1H), 1.70-1.54 (m, 3H).

Example 89: (R)-5-(3-Fluoro-2-methyl-4-phenoxyphenl)-N-(1-(3-methoxypropanoyl)piperidin-3-yl)-4-oxo-4,5-dihydro-3H-1-thia-3,5,8-triazaacenaphthylene-2-carboxamide

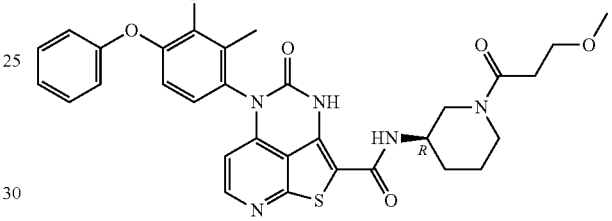

A solution of (R)-5-(3-fluoro-2-methyl-4-phenoxyphenyl)-4-oxo-N-(piperidin-3-yl)-4,5-dihydro-3H-1-thia-3,5,8-triazaacenaphthylene-2-carboxamide (Intermediate 18) (80 mg, 0.16 mmol), 3-methoxypropanoic acid (32 mg, 0.31 mmol), triethylamine (31 mg, 0.31 mmol), and HATU (118 mg, 0.310 mmol) in DMF (2 mL) was stirred at rt for 1 hr. Water was added and the precipitate was filtered to give a crude product, which was purified by flash column chromatography to yield the title compound (73 mg, 77% yield) as a white solid. MS (ESI): mass calcd. for $C_{31}H_{30}FN_5O_5S$, 603.7; m/z found, 604.2 [M+H]$^+$. $^1$H NMR (400 MHz, CD$_3$OD): δ 8.39-8.26 (m, 1H), 7.45-7.31 (m, 2H), 7.24-7.18 (m, 1H), 7.17-7.10 (m, 1H), 7.09-7.02 (m, 3H), 6.16-6.07 (m, 1H), 4.53-4.29 (m, 1H), 4.13-3.85 (m, 2H), 3.70-3.60 (m, 2H), 3.32 (s, 3H), 3.17-2.98 (m, 1H), 2.86-2.63 (m, 3H), 2.12 (s, 3H), 2.07-1.97 (m, 1H), 1.88-1.75 (m, 1H), 1.1.73-1.46 (m, 2H).

Example 90: (S)-5-(2-Methyl-4-phenoxyphenl)-4-oxo-N-(tetrahydrofuran-3-yl)-4,5-dihydro-3H-1-thia-3,5,8-triazaacenaphthylene-2-carboxamide

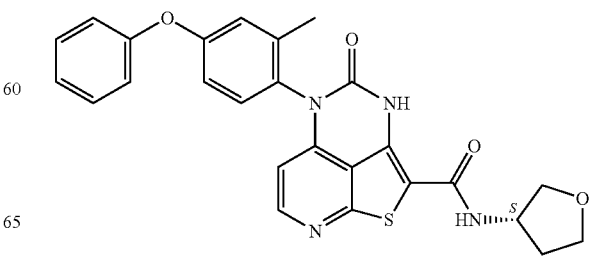

To a solution of 5-(2-methyl-4-phenoxyphenyl)-4-oxo-4,5-dihydro-3H-1-thia-3,5,8-triazaacenaphthylene-2-carboxylic acid (Intermediate 27, 100 mg, 0.24 mmol) in DCM (25 mL) was added a drop of DMF, then oxalyl chloride (150 mg, 1.2 mmol) was added. The reaction was stirred at rt for 3 h, concentrated to dryness, and diluted in DCM again. Next, triethylamine (120 mg, 1.2 mmol) and (3S)-tetrahydrofuran-3-amine (31 mg, 0.36 mmol) were added and stirred at rt for 1 h. The reaction mixture was concentrated dryness and purified by flash column chromatography to yield the title compound (60 mg, 51% yield) as a yellow solid. MS (ESI): mass calcd. for $C_{26}H_{22}N_4O_4S$, 486.5; m/z found, 487.0 [M+H]$^+$. $^1$H NMR (400 MHz, DMSO-$d_6$): δ 10.25 (s, 1H), 8.37-8.27 (m, 2H), 7.49-7.39 (m, 2H), 7.37 (d, J=8.6 Hz, 1H), 7.24-7.15 (m, 1H), 7.13-7.04 (m, 3H), 7.02-6.93 (m, 1H), 5.96 (d, J=5.5 Hz, 1H), 4.52-4.37 (m, 1H), 3.90-3.78 (m, 2H), 3.74-3.65 (m, 1H), 3.63-3.57 (m, 1H), 2.20-2.08 (m, 1H), 2.05 (s, 3H), 1.98-1.87 (m, 1H).

Example 91: (R)-5-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide

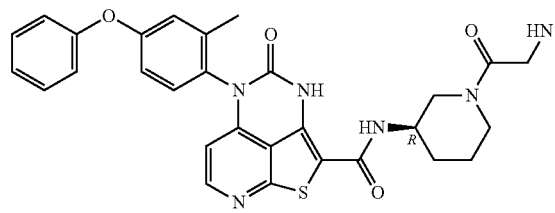

Step A: (R)-tert-Butyl methyl(2-(3-(5-(2-methyl-4-phenoxyphenyl)-4-oxo-4,5-dihydro-3H-1-thia-3,5,8-triazaacenaphthylene-2-carboxamido)piperidin-1-yl)-2-oxoethyl)carbamate To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.40 mmol) in DMF (3 mL) were added 2-[tert-butoxycarbonyl(methyl)amino]acetic acid (Intermediate 21, 114 mg, 0.603 mmol), HATU (230 mg, 0.60 mmol), and triethylamine (0.23 mL, 1.6 mmol). The mixture was stirred at rt overnight, then purified by flash column chromatography to yield the title compound (198 mg, 73.0% yield) as a yellow solid.

Step B: (R)-5-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide To a round bottom flask were added (R)-tert-butyl methyl (2-(3-(5-(2-methyl-4-phenoxyphenyl)-4-oxo-4,5-dihydro-3H-1-thia-3,5,8-triazaacenaphthylene-2-carboxamido)piperidin-1-yl)-2-oxoethyl)carbamate (198 mg, 0.300 mmol) and HCl in MeOH (3 M, 3 mL) and was stirred at rt for 4 h, then the pH was adjusted to pH>7 with 2 M aqueous NaOH. The mixture was purified by flash column chromatography to yield the title compound as a yellow solid (95 mg, 56% yield). MS (ESI): mass calcd. for $C_{30}H_{30}N_6O_4S$, 570.7; m/z found, 571.2 [M+H]$^+$. $^1$H NMR (400 MHz, a mixture solution of DMSO-$d_6$ and CD$_3$OD): δ 8.02-7.98 (m, 1H), 7.39-7.32 (m, 2H), 7.14-7.08 (m, 2H), 7.07-7.01 (m, 2H), 6.99-6.96 (m, 1H), 6.92-6.84 (m, 1H), 5.69-5.62 (m, 1H), 4.10-3.92 (m, 1H), 3.92-3.83 (m, 1H), 3.72-3.52 (m, 2H), 3.52-3.36 (m, 2H), 3.32-3.21 (m, 1H), 2.31-2.23 (m, 3H), 2.01 (s, 3H), 1.95-1.86 (m, 1H), 1.81-1.59 (m, 2H), 1.54-1.41 (m, 1H).

Example 92: N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide

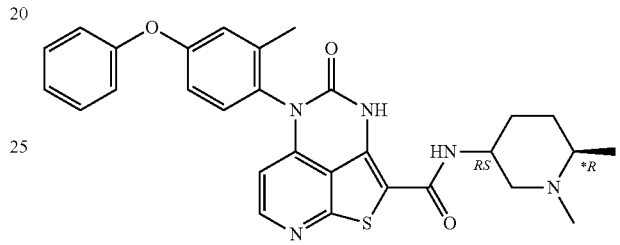

A mixture of 5-(2-Methyl-4-phenoxyphenyl)-N-((6R)-6-methylpiperidin-3-yl)-4-oxo-4,5-dihydro-3H-1-thia-3,5,8-triazaacenaphthylene-2-carboxamide (Example 173, 150 mg, 0.29 mmol), NaBH(OAc)$_3$ (123 mg, 0.580 mmol), and formaldehyde (1 mL, 37 wt. % in H$_2$O) in DCM (5 mL) was reacted at 80° C. for 2 h. The reaction mixture was concentrated to dryness, saturated aqueous NaHCO$_3$ was added, extracted with DCM, dried over anhydrous Na$_2$SO$_4$, filtered, and concentrated to dryness. The residue was purified by flash column chromatography to yield the title compound as a yellow solid. MS (ESI): mass calcd. for $C_{29}H_{29}N_5O_3S$, 527.6; m/z found, 528.2 [M+H]$^+$. $^1$H NMR (400 MHz, CD$_3$OD): δ 8.42 (s, 1H), 8.37-8.30 (m, 1H), 7.45-7.37 (m, 2H), 7.33-7.26 (m, 1H), 7.21-7.14 (m, 1H), 7.11-7.02 (m, 3H), 7.00-6.92 (m, 1H), 6.12-6.05 (m, 1H), 4.36-4.23 (m, 1H), 3.63-3.56 (m, 1H), 3.06-2.95 (m, 1H), 2.89-2.79 (m, 4H), 2.11 (s, 3H), 2.12-1.99 (m, 2H), 1.81-1.63 (m, 2H), 1.41-1.32 (m, 3H).

Example 93: (R)—N-(1-Isopropylpyrrolidin-3-yl)-5-(*S)-(2-methyl-4-phenoxyphenyl)-4-oxo-4,5-dihydro-3H-1-thia-3,5,8-triazaacenaphthylene-2-carboxamide

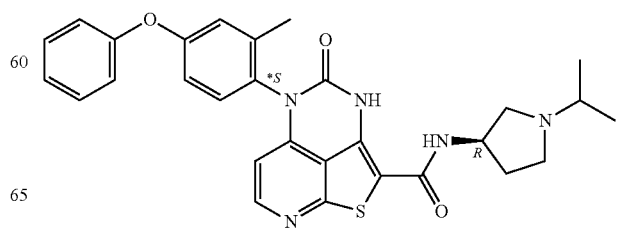

A solution of (R)-5-(*S)-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36, 60 mg, 0.12 mmol) dissolved in acetone was stirred for 10 min, then NaBH(OAc)$_3$ (100 mg, 0.5 mmol) was added slowly and the mixture was stirred for 2 h. Next, NaOH (2 mL) was added and the mixture was purified by flash column chromatography, then preparative TLC to yield the title compound as a yellow solid (11 mg, 17%). MS (ESI): mass calcd. for C$_{29}$H$_{29}$N$_5$O$_3$S, 527.6; m/z found, 528.2 [M+H]$^+$. —H NMR (400 MHz, DMSO-d6): δ 8.42 (s, 1H), 8.25 (d, J=5.4 Hz, 1H), 7.47-7.39 (m, 2H), 7.33-7.27 (m, 1H), 7.21-7.15 (m, 1H), 7.12-7.08 (m, 2H), 7.07-7.04 (m, 1H), 6.98-6.92 (m, 1H), 5.87 (d, J=5.4 Hz, 1H), 4.45-4.31 (m, 1H), 2.95-2.75 (m, 2H), 2.64-2.55 (m, 2H), 2.20-2.09 (m, 1H), 2.03 (s, 3H), 2.01-1.92 (m, 1H), 1.84-1.73 (m, 1H), 1.09-1.00 (m, 6H).

Example 94: N-((3S,4R)-4-Fluoro-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide

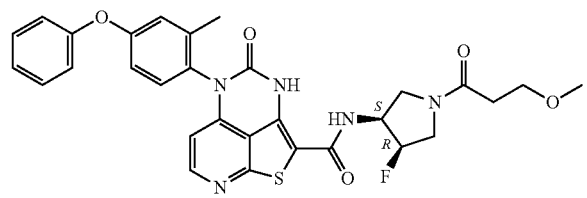

Step A: N-((3S,4R)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl (3S,4R)-3-amino-4-fluoropyrrolidine-1-carboxylate in place of tert-butyl (3R,5R)-3-amino-5-fluoropiperidine-1-carboxylate (Intermediate 1) in step G.

Step B: N-((3S,4R)-4-Fluoro-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide A mixture of N-((3S,4R)-4-fluoropyrrolidin-3-yl)-5-(2-methyl-4-phenoxyphenyl)-4-oxo-4,5-dihydro-3H-1-thia-3,5,8-triazaacenaphthylene-2-carboxamide (80 mg, 0.16 mmol), 3-methoxypropanoic acid (33 mg, 0.32 mmol), triethylamine (32 mg, 0.32 mmol), and HATU (120 mg, 0.32 mmol) in DMF (3 mL) was stirred at rt for 1 h, then water was added and the precipitate was collected by filtration and purified by flash column chromatography to yield the title compound as a white solid (75 mg, 78% yield). MS (ESI): mass calcd. for C$_{30}$H$_{28}$FN$_5$O$_5$S, 589.6; m/z found, 590.1 [M+H]$^+$. $^1$H NMR (400 MHz, CD$_3$OD): δ 8.33 (d, J=5.3 Hz, 1H), 7.43-7.34 (m, 2H), 7.34-7.26 (m, 1H), 7.20-7.12 (m, 1H), 7.12-7.02 (m, 3H), 6.99-6.94 (m, 1H), 6.07 (d, J=5.2 Hz, 1H), 5.36-5.14 (m, 1H), 4.80-4.63 (m, 1H), 4.07-3.45 (m, 6H), 3.33 (s, 3H), 2.68-2.51 (m, 2H), 2.11 (s, 3H).

Example 95: (R)—N-(1-(2-Methoxyacetyl)piperidin-3-yl)-5-(2-methyl-4-phenoxyphenyl)-4-oxo-4,5-dihydro-3H-1-thia-3,5,8-triazaacenaphthylene-2-carboxamide

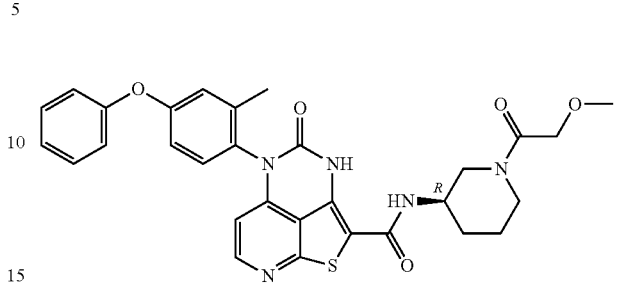

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 120 mg, 0.22 mmol) in DMF (2 mL) were added 2-methoxyacetic acid (0.026 mL, 0.34 mmol), HATU (100 mg, 0.27 mmol), and DMF (2 mL). The mixture was stirred at rt overnight, then purified by flash column chromatography to yield the title compound as a yellow solid (83 mg, 63%). MS (ESI): mass calcd. for C$_{30}$H$_{29}$N$_5$O$_5$S, 571.6; m/z found, 572.2 [M+H]$^+$. $^1$H NMR (400 MHz, CD$_3$OD): δ 8.32 (d, J=5.5, 1H), 7.45-7.35 (m, 2H), 7.33-7.27 (m, 1H), 7.20-7.12 (m, 1H), 7.12-7.02 (m, 3H), 7.02-6.93 (m, 1H), 6.07 (d, J=5.3, 1H), 4.29-4.09 (m, 3H), 4.02-3.85 (m, 2H), 3.39 (s, 3H), 3.11-3.01 (m, 1H), 2.86-2.74 (m, 1H), 2.11 (s, 3H), 2.09-2.00 (m, 1H), 1.88-1.78 (m, 1H), 1.76-1.52 (m, 2H).

Example 96: (R)-5-(*S)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide

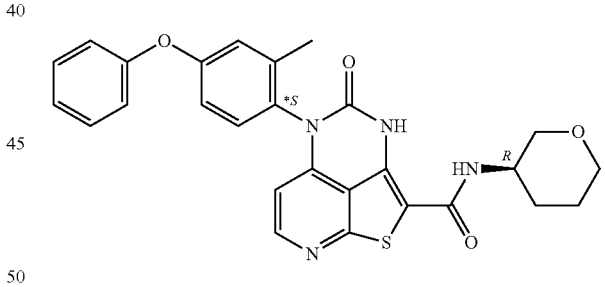

A solution of 5-(*S)-(2-methyl-4-phenoxyphenyl)-4-oxo-4,5-dihydro-3H-1-thia-3,5,8-triazaacenaphthylene-2-carboxylic acid (Intermediate 16) (30 mg, 0.07 mmol), HBTU (55 mg, 0.15 mmol), and triethylamine (22 mg, 0.22 mmol) in anhydrous DMF (3 mL) was stirred at rt. After 10 min, (3R)-tetrahydropyran-3-amine (11 mg, 0.11 mmol) was added and the mixture was stirred for 2 h at rt. The crude mixture was purified by flash column chromatography to yield the title compound as a slight yellow solid (25 mg, 69% yield). MS (ESI): mass calcd. for C$_{27}$H$_{24}$N$_4$O$_4$S, 500.6; m/z found, 501.1 [M+H]$^+$. $^1$H NMR (400 MHz, CD$_3$OD and DMSO-d$_6$): δ 8.28 (d, J=5.5 Hz, 1H), 7.41-7.33 (m, 2H), 7.28 (d, J=8.7 Hz, 1H), 7.18-7.10 (m, 1H), 7.09-6.97 (m, 3H), 6.96-6.86 (m, 1H), 5.96 (d, J=5.5 Hz, 1H), 3.98-3.91 (m, 1H), 3.85-3.69 (m, 2H), 3.35-3.24 (m, 1H), 3.25-3.17 (m, 1H), 2.04 (s, 3H), 1.96-1.87 (m, 1H), 1.74-1.53 (m, 3H).

Example 97: N-(1-Cyanoazepan-3-yl)-5-(2-methyl-4-phenoxyphenyl)-4-oxo-4,5-dihydro-3H-1-thia-3,5,8-triazaacenaphthylene-2-carboxamide

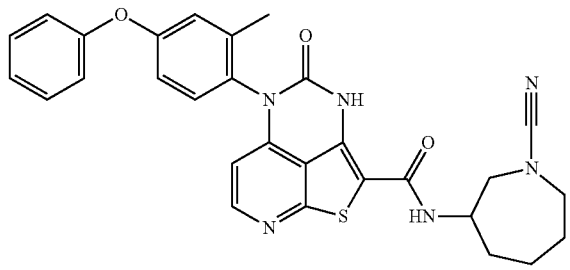 [SMILES: Cc1cc(Oc2ccccc2)ccc1N1C(=O)Nc2c(C(=O)NC3CCCCN(C#N)C3)sc3nccc1c23]

The title compound was prepared in a manner analogous to Method 1, steps A-I in Example 1, and using tert-butyl 3-aminoazepane-1-carboxylate in place of tert-butyl (3R,5R)-3-amino-5-fluoropiperidine-1-carboxylate (Intermediate 1) in step G, and using bromocyanide in place of prop-2-enoyl chloride in step I. MS (ESI): mass calcd. for $C_{29}H_{26}N_6O_3S$, 538.6; m/z found, 539.6 [M+H]$^+$. $^1$H NMR (400 MHz, DMSO-d$_6$ and CD$_3$OD): δ 8.28 (d, J=5.5 Hz, 1H), 7.41-7.32 (m, 2H), 7.28 (d, J=8.6 Hz, 1H), 7.16-7.08 (m, 1H), 7.09-6.99 (m, 3H), 6.94-6.90 (m, 1H), 5.99 (d, J=5.5 Hz, 1H), 4.18-4.09 (m, 1H), 3.48-3.37 (m, 1H), 3.36-3.27 (m, 1H), 3.25-3.17 (m, 2H), 2.05 (s, 3H), 1.95-1.80 (m, 3H), 1.72-1.60 (m, 2H), 1.55-1.42 (m, 1H).

Example 98: (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide

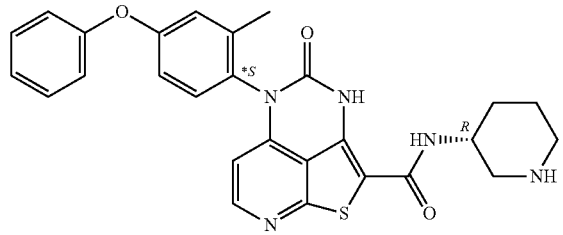

The title compound was prepared in a manner analogous to Method 1, steps A-H in Example 1 (including Chiral resolution Method A after Step F to obtain the *S atropisomer), and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 500.2 [M+H]$^+$. $^1$H NMR (400 MHz, CD$_3$OD): δ 8.20 (d, J=5.6 Hz, 1H), 7.48-7.34 (m, 2H), 7.27-7.21 (m, 1H), 7.19-7.13 (m, 1H), 7.11-7.03 (m, 3H), 7.00-6.94 (m, 1H), 5.94 (d, J=5.6 Hz, 1H), 4.19-4.06 (m, 1H), 3.29-3.21 (m, 1H), 3.15-3.00 (m, 1H), 2.89-2.70 (m, 2H), 2.11 (s, 3H), 2.08-1.86 (m, 2H), 1.79-1.64 (m, 2H).

Example 99: (R)—N-(1-(3-Hydroxypropanoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

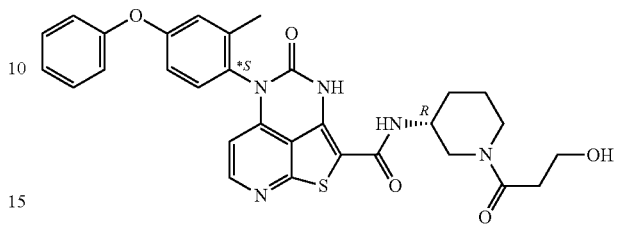

A solution containing (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 39 mg, 0.073 mmol), 3-hydroxypropanoic acid (13 mg, 0.14 mmol), HATU (36 mg, 0.095 mmol), and diisopropylethylamine (24 mg, 0.18 mmol) in DMF (5 mL) was stirred at rt for 2 h. The mixture was purified by flash column chromatography to yield the title compound as a white solid (15 mg, 36% yield). MS (ESI): mass calcd. for $C_{30}H_{29}N_5O_5S$, 571.6; m/z found, 572.4 [M+H]$^+$. $^1$H NMR (400 MHz, CD$_3$OD): δ 8.36-8.30 (m, 1H), 7.44-7.37 (m, 2H), 7.33-7.27 (m, 1H), 7.21-7.14 (m, 1H), 7.12-7.03 (m, 3H), 7.01-6.95 (m, 1H), 6.11-6.05 (m, 1H), 4.51-3.90 (m, 3H), 3.88-3.79 (m, 2H), 3.20-3.05 (m, 1H), 2.90-2.75 (m, 1H), 2.73-2.58 (m, 2H), 2.12 (s, 3H), 2.09-2.01 (m, 1H), 1.91-1.77 (m, 1H), 1.77-1.64 (m, 1H), 1.64-1.45 (m, 1H).

Example 100: (R,E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

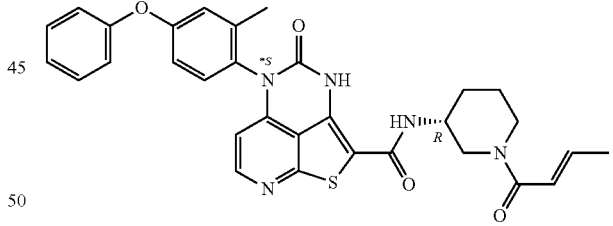

A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 45 mg, 0.090 mmol), (E)-but-2-enoic acid (15.5 mg, 0.18 mmol), HATU (68 mg, 0.18 mmol), triethylamine (18 mg, 0.18 mmol) in DMF (1 mL) was stirred at rt for 4 h. The mixture was purified by flash column chromatography to yield the title compound as a yellow solid (51 mg, 100% yield). MS (ESI): mass calcd. for $C_{31}H_{29}N_5O_4S$, 567.7; m/z found, 568.4 [M+H]$^+$. $^1$H NMR (400 MHz, DMSO-d$_6$): δ 10.21 (br, 1H), 8.35-8.26 (m, 1H), 8.22-8.02 (br, 1H), 7.45-7.40 (m, 2H), 7.36-7.31 (m, 1H), 7.20-7.16 (m, 1H), 7.12-7.08 (m, 2H), 7.08-7.05 (m, 1H), 6.98-6.93 (m, 1H), 6.69-6.59 (m, 1H), 6.55-6.35 (m, 1H), 5.97-5.89 (m, 1H), 4.49-4.04 (m, 1H), 4.04-3.90 (m, 1H), 3.77-3.72 (m, 1H), 2.92-2.85 (m, 1H), 2.76-2.60 (m, 1H), 2.03 (s, 3H), 1.94-1.88 (m, 1H), 1.83-1.77 (m, 3H), 1.76-1.70 (m, 1H), 1.66-1.57 (m, 1H), 1.47-1.37 (s, 1H).

Example 101: (R)—N-(1-Isopropylpiperidin-3-yl)-5-(2-methyl-4-phenoxyphenyl)-4-oxo-4,5-dihydro-3H-1-thia-3,5,8-triazaacenaphthylene-2-carboxamide

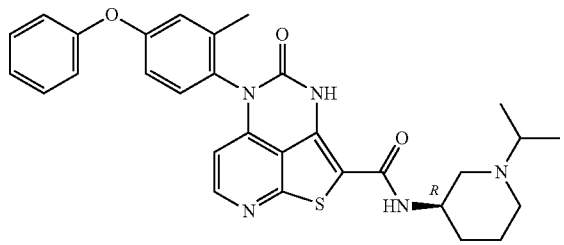

A mixture of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) in acetone (10 mL) was stirred at rt for 10 min, then NaBH(OAc)₃ (190 mg, 0.90 mmol) was added. The mixture was stirred at rt overnight and adjusted to pH>7 with 2 M aqueous NaOH. The reaction mixture was concentrated to dryness and the residue purified by flash column chromatography to yield the title compound as a yellow solid (52 mg, 32% yield). MS (ESI): mass calcd. for $C_{30}H_{31}N_5O_3S$, 541.7; m/z found, 542.1 [M+H]⁺. ¹H NMR (400 MHz, DMSO-d₆ and CD₃OD): δ 8.23 (d, J=4.7, 1H), 7.43-7.31 (m, 2H), 7.31-7.21 (m, 1H), 7.19-7.11 (m, 1H), 7.11-6.97 (m, 3H), 6.96-6.85 (m, 1H), 5.91 (d, J=4.7, 1H), 4.04-3.95 (m, 1H), 2.98-2.71 (m, 3H), 2.32-2.19 (m, 2H), 2.03 (s, 3H), 1.86-1.77 (m, 1H), 1.77-1.67 (m, 1H), 1.60-1.47 (m, 1H), 1.47-1.37 (m, 1H), 1.01 (d, J=5.7, 6H).

Example 102: (R,E)-N-(1-(2-Cyano-3-cyclopropylacryloyl)piperidin-3-yl)-5-(4-isopropoxy-2-methylphenyl)-4-oxo-4,5-dihydro-3H-1-thia-3,5,8-triazaacenaphthylene-2-carboxamide

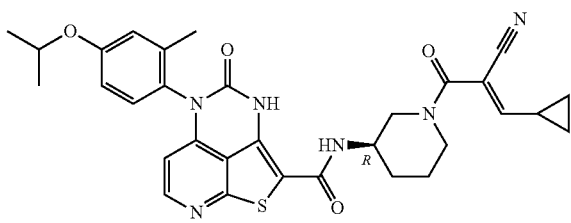

Step A: 4-Isopropoxy-2-methyl-1-nitrobenzene

To a mixture of 3-methyl-4-nitrophenol (5.0 g, 33 mmol) and K₂CO₃ (9.0 g, 65 mmol) in DMF (20 mL) was added 2-iodopropane (8.3 g, 49 mmol) and the reaction was stirred at 80° C. overnight. Water was added to the mixture to yield a precipitate, then filtered, washed with water, and dried to yield the title compound as a yellow solid (5.0 g, 78% yield).

Step B: (R,E)-N-(1-(2-Cyano-3-cyclopropylacryloyl)piperidin-3-yl)-5-(4-isopropoxy-2-methylphenyl)-4-oxo-4,5-dihydro-3H-1-thia-3,5,8-triazaacenaphthylene-2-carboxamide To a stirred solution of (R)-5-(4-Isopropoxy-2-methylphenyl)-4-oxo-N-(piperidin-3-yl)-4,5-dihydro-3H-1-thia-3,5,8-triazaacenaphthylene-2-carboxamide (Intermediate 70, 80 mg, 0.17 mmol) in DMF (3 mL) were added (E)-2-cyano-3-cyclopropylprop-2-enoic acid (Intermediate 17) (28 mg, 0.20 mmol), HATU (78 mg, 0.20 mmol), and diisopropylethylamine (0.05 mL) and was stirred at rt overnight. The reaction was concentrated to dryness and the residue was partitioned between ethyl acetate and water. The organic layer was separated, shaken with brine, and dried over anhydrous Na₂SO₄. The residue was purified by flash column chromatography to yield the title compound as yellow solid (37 mg, 37% yield). MS (ESI): mass calcd. for $C_{31}H_{32}N_6O_4S$, 584.7; m/z found, 585.1 [M+H]⁺. ¹H NMR (400 MHz, DMSO-d6): δ 8.45-8.28 (m, 1H), 8.22-8.05 (m, 1H), 7.34-7.18 (m, 1H), 7.11-6.87 (m, 2H), 6.71-6.54 (m, 1H), 6.01-5.85 (m, 1H), 4.82-4.57 (m, 1H), 3.98-3.77 (m, 2H), 3.07-2.87 (m, 1H), 2.05 (s, 3H), 1.98-1.44 (m, 6H), 1.41-1.21 (m, 6H), 1.26-1.11 (m, 3H), 1.09-0.75 (m, 2H).

Example 103: N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide

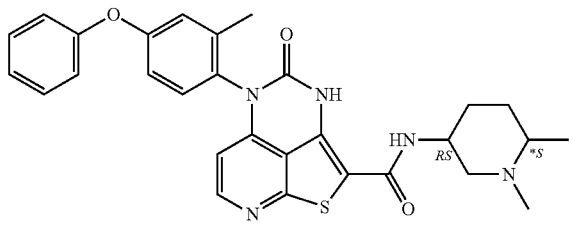

The title compound was made as described in Example 92, and in Step B the other isomer was isolated by flash column chromatography to yield the title compound as a yellow solid. MS (ESI): mass calcd. for $C_{29}H_{29}N_5O_3S$, 527.6; m/z found, 528.2 [M+H]⁺. ¹H NMR (400 MHz, CD₃OD): δ 8.45 (s, 1H), 8.37-8.30 (m, 1H), 7.45-7.37 (m, 2H), 7.33-7.26 (m, 1H), 7.21-7.14 (m, 1H), 7.11-7.02 (m, 3H), 7.00-6.92 (m, 1H), 6.12-6.05 (m, 1H), 4.39-4.28 (m, 1H), 3.48-3.35 (m, 1H), 3.29-3.17 (m, 2H), 2.85-2.75 (m, 3H), 2.11 (s, 3H), 2.01-1.86 (m, 4H), 1.43-1.35 (m, 3H).

Example 104: (R)-5-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide

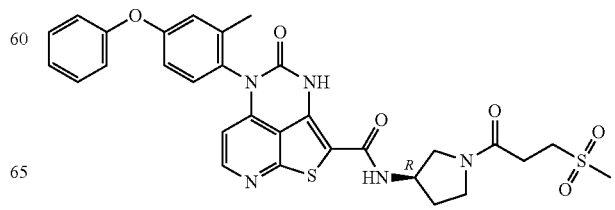

A solution of (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 100 mg, 0.21 mmol), 3-methylsulfonylpropanoic acid (35 mg, 0.23 mmol), HATU (160 mg, 0.42 mmol), and triethylamine (42 mg, 0.42 mmol) in DMF (2 mL) was stirred at rt for 2 h, then purified by flash column chromatography to yield the title compound as a white solid (41 mg, 32% yield). MS (ESI): mass calcd. for $C_{30}H_{29}N_5O_6S_2$, 619.7; m/z found, 620.0 [M+H]$^+$. $^1$H NMR (400 MHz, DMSO-d$_6$): δ 10.23 (s, 1H), 8.43-8.23 (m, 2H), 7.48-7.40 (m, 2H), 7.37 (d, J=8.6 Hz, 1H), 7.23-7.15 (m, 1H), 7.14-7.06 (m, 3H), 7.02-6.90 (m, 1H), 5.97 (dd, J=5.4, 2.4 Hz, 1H), 4.61-4.35 (m, 1H), 3.87-3.32 (m, 6H), 3.00 (s, 3H), 2.78-2.65 (m, 2H), 2.24-2.08 (m, 1H), 2.05 (s, 3H), 2.03-1.87 (m, 1H).

Example 105: (R,E)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide

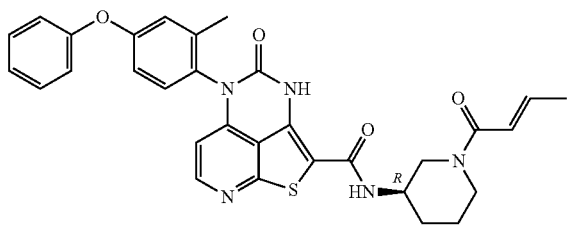

To a mixture of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) and (E)-but-2-enoic acid (52 mg, 0.60 mmol) in DMF (2 mL) were added HATU (230 mg, 0.60 mmol), and triethylamine (60 mg, 0.60 mmol) and was stirred at rt for 4 h. The mixture was purified by flash column chromatography to yield the title compound as yellow solid (124 mg, 73.0% yield). MS (ESI): mass calcd. for $C_{31}H_{29}N_5O_4S$, 567.7; m/z found, 568.2 [M+H]$^+$. $^1$H NMR (400 MHz, DMSO-d$_6$): δ 10.23 (s, 1H), 8.31 (d, J=5.4 Hz, 1H), 8.06 (br, 1H), 7.45-7.38 (m, 2H), 7.38-7.33 (m, 1H), 7.20-7.14 (m, 1H), 7.13-7.03 (m, 3H), 6.98-6.92 (m, 1H), 6.71-6.58 (m, 1H), 6.52-6.39 (m, 1H), 5.95 (d, J=5.4 Hz, 1H), 4.47-4.12 (m, 1H), 4.06-3.90 (m, 1H), 3.78-3.68 (m, 1H), 3.11-2.87 (m, 1H), 2.73-2.55 (m, 1H), 2.03 (s, 3H), 1.93-1.87 (m, 1H), 1.83-1.76 (m, 3H), 1.76-1.69 (m, 1H), 1.67-1.55 (m, 1H), 1.43-1.31 (m, 1H).

Example 106: (R)-5-(2-Methyl-4-phenoxyphenyl)-N-(1-(3-(methylamino)propanoyl)piperidin-3-yl)-4-oxo-4,5-dihydro-3H-1-thia-3,5,8-triazaacenaphthylene-2-carboxamide

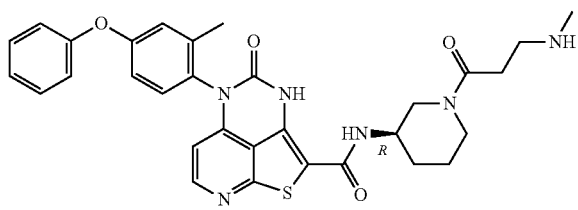

To a stirred suspension of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.40 mmol) in DMF (3 mL) were added 3-[tert-butoxycarbonyl(methyl)amino]propanoic acid (165 mg, 0.812 mmol), HATU (230 mg, 0.61 mmol), and diisopropylethylamine (105 mg, 0.812 mmol). The resulting mixture was stirred at rt overnight. The solvent was removed and the residue was partitioned between ethyl acetate and water. The organic layer was separated, shaken with brine, and dried over anhydrous Na$_2$SO$_4$. The residue was purified by flash column chromatography to yield the intermediate compound as a yellow solid. The intermediate compound was treated with concentrated HCl (2 mL) in MeOH (15 mL) at rt for about 2 h. After concentrating to dryness, the crude material was purified by flash column chromatography to yield the title compound as a yellow solid (150 mg, 59% yield). MS (ESI): mass calcd. for $C_{31}H_{32}N_6O_4S$, 584.7; m/z found, 585.1 [M+H]$^+$. $^1$H NMR (400 MHz, CD$_3$OD): δ 8.43 (s, 1H), 8.37-8.30 (m, 1H), 7.45-7.36 (m, 2H), 7.33-7.26 (m, 1H), 7.22-7.14 (m, 1H), 7.13-7.04 (m, 3H), 7.01-6.93 (m, 1H), 6.11-6.04 (m, 1H), 4.58-4.32 (m, 1H), 4.12-3.72 (m, 2H), 3.27-2.78 (m, 6H), 2.74-2.67 (m, 3H), 2.12 (s, 3H), 2.08-1.99 (m, 1H), 1.93-1.49 (m, 3H).

Example 107: (R)-5-(2-Fluoro-4-phenoxyphenyl)-4-oxo-N-(piperidin-3-yl)-4,5-dihydro-3H-1-thia-3,5,8-triazaacenaphthylene-2-carboxamide

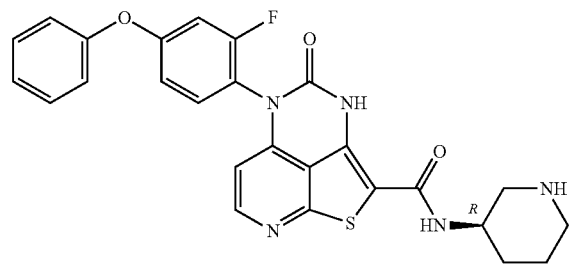

Step A: 2-Fluoro-1-nitro-4-phenoxybenzene

To a mixture of 3-fluoro-4-nitrophenol (2.0 g, 13 mmol), phenylboronic acid (2.3 g, 19 mmol), Cu(OAc)$_2$ (4.6 g, 25 mmol), and triethylamine (6.4 g, 64 mmol) in DCM (60 mL) was added molecular sieves (4A powder<50 µm, 2 g). The mixture was stirred at rt under N$_2$ overnight, filtered, concentrated to dryness, and purified by normal phase flash column chromatography (SiO$_2$) to yield the title compound as a yellow solid (2.7 g, 91% yield).

Step B: (R)-5-(2-Fluoro-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps B-H in Example 1, and using 2-Fluoro-1-nitro-4-phenoxybenzene in place 2-methyl-1-nitro-4-phenoxybenzene in Step B and and tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{22}FN_5O_3S$, 503.5; m/z found, 623.0 [M+H]$^+$. $^1$H NMR (400 MHz, DMSO-d$_6$): δ 9.07 (s, 1H), 8.42-8.34 (m, 1H), 8.30 (d, J=7.0 Hz, 1H), 7.65-7.54 (m, 1H), 7.53-7.41 (m, 2H), 7.32-7.22 (m, 1H), 7.21-7.12 (m, 3H), 7.02-6.94 (m, 1H), 6.21 (d, J=5.4 Hz, 1H), 4.26-4.05 (m, 1H), 3.25-3.08 (m, 2H), 2.93-2.72 (m, 2H), 1.97-1.80 (m, 2H), 1.79-1.52 (m, 2H).

Example 108: (R)-5-(2-Methyl-4-phenoxyphenyl)-4-oxo-N-(tetrahydrofuran-3-yl)-4,5-dihydro-3H-1-thia-3,5,8-triazaacenaphthylene-2-carboxamide

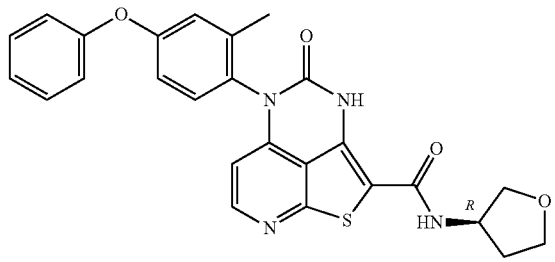

To a solution of 5-(2-methyl-4-phenoxyphenyl)-4-oxo-4,5-dihydro-3H-1-thia-3,5,8-triazaacenaphthylene-2-carboxylic acid (Intermediate 27, 150 mg, 0.36 mmol) in DCM (60 mL) was added a drop of DMF, then oxalyl chloride (230 mg, 1.8 mmol) was added. The reaction was stirred at rt for 3 h, concentrated to dryness, and diluted in DCM. To this solution was added triethylamine (180 mg, 1.8 mmol) and (3R)-tetrahydrofuran-3-amine (55 mg, 0.63 mmol) and was stirred at rt for 1 h, concentrated to dryness, and purified by flash column chromatography to yield the title compound as a yellow solid (61 mg, 34% yield). MS (ESI): mass calcd. for $C_{26}H_{22}N_4O_4S$, 486.5; m/z found, 487.0 [M+H]$^+$. $^1$H NMR (400 MHz, DMSO-d$_6$): δ 10.27 (s, 1H), 8.39-8.25 (m, 2H), 7.55-7.32 (m, 3H), 7.27-7.17 (m, 1H), 7.17-7.05 (m, 3H), 7.04-6.91 (m, 1H), 5.98 (d, J=5.4 Hz, 1H), 4.55-4.37 (m, 1H), 3.96-3.81 (m, 2H), 3.75-3.66 (m, 1H), 3.65-3.55 (m, 1H), 2.22-2.12 (m, 1H), 2.07 (s, 3H), 1.99-1.87 (m, 1H).

Example 109: N-(1-Acryloylazetidin-3-yl)-5-(2-methyl-4-phenoxyphenyl)-4-oxo-4,5-dihydro-3H-1-thia-3,5,8-triazaacenaphthylene-2-carboxamide

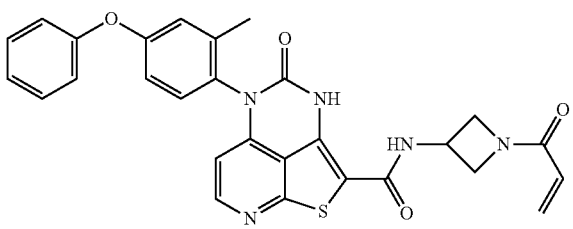 [SMILES: C=CC(=O)N1CC(NC(=O)c2sc3nccc4c3c2NC(=O)N4c2ccc(Oc3ccccc3)cc2C)C1]

The title compound was prepared in a manner analogous to Method 1, steps A-I in Example 1, and using tert-butyl 3-aminoazetidine-1-carboxylate in place of tert-butyl (3R, 5R)-3-amino-5-fluoropiperidine-1-carboxylate (Intermediate 1) in step G. MS (ESI): mass calcd. for $C_{28}H_{23}N_5O_4S$, 525.6; m/z found, 526.1 [M+H]$^+$. $^1$H NMR (400 MHz, DMSO-d$_6$ and CD$_3$OD): δ 8.29 (d, J=5.5 Hz, 1H), 7.43-7.33 (m, 2H), 7.31-7.23 (m, 1H), 7.17-7.09 (m, 1H), 7.08-6.98 (m, 3H), 6.97-6.89 (m, 1H), 6.37-6.23 (m, 1H), 6.20-6.08 (m, 1H), 5.98 (d, J=5.5 Hz, 1H), 5.71-5.60 (m, 1H), 4.81-4.69 (m, 1H), 4.58-4.47 (m, 1H), 4.24-4.17 (m, 2H), 4.04-3.97 (m, 1H), 2.04 (s, 3H).

Example 110: (R)—N-(1-$^{13}$C-Acryloylpiperidin-3-yl)-5-(4-methoxy-2-methylphenyl)-4-oxo-4,5-dihydro-3H-1-thia-3,5,8-triazaacenaphthylene-2-carboxamide

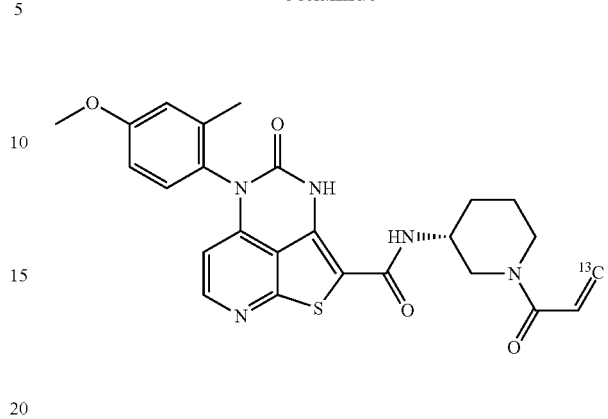

Step A: $^{13}$C-Acrylic Acid

To a round bottom flask were added malonic acid (1.7 g, 16 mmol), $^{13}$C-formaldehyde (0.50 g, 16 mmol, 37 wt. % in H$_2$O), and dry pyridine (7 mL) and stirred at reflux for 2 h. Concentrated H$_2$SO$_4$ was added dropwise to neutralize the cooled reaction mixture. The mixture was diluted with H$_2$O, extracted with Et$_2$O, dried over anhydrous Na$_2$SO$_4$, and concentrated to dryness to yield the title compound as a yellow liquid.

Step B: (R)-5-(4-Methoxy-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps C-H in Example 1, and using 4-methoxy-2-methylaniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G.

Step C: (R)—N-(1-$^{13}$C-Acryloylpiperidin-3-yl)-5-(4-methoxy-2-methylphenyl)-4-oxo-4,5-dihydro-3H-1-thia-3,5,8-triazaacenaphthylene-2-carboxamide A mixture of (R)-5-(4-methoxy-2-methylphenyl)-4-oxo-N-(piperidin-3-yl)-4,5-dihydro-3H-1-thia-3,5,8-triazaacenaphthylene-2-carboxamide (500 mg, 1.1 mmol), $^{13}$C-acrylic acid (154 mg, 2.11 mmol), EDCI (300 mg, 1.6 mmol), HOBt (210 mg, (1.6 mmol), and triethylamine (270 mg, 2.6 mmol) in DMF (8 mL) was stirred at rt for 2 h. The reaction mixture was first purified by HPLC, then by flash column chromatography, and finally by TLC to yield the title compound as a pink solid (8 mg, 1.5%). MS (ESI): mass calcd. for $C_{25}H_{25}N_5O_4S$, 492.6; m/z found, 493.2 [M+H]$^+$. $^1$H NMR (400 MHz, CD$_3$OD): δ 8.33-8.27 (m, 1H), 7.27-7.20 (m, 1H), 7.04-6.98 (m, 1H), 6.98-6.91 (m, 1H), 6.86-6.73 (m, 1H), 6.45-5.47 (m, 3H), 4.54-3.91 (m, 3H), 3.85 (s, 3H), 3.24-3.09 (m, 1H), 2.97-2.80 (m, 1H), 2.13 (s, 3H), 2.12-2.00 (m, 1H), 1.92-1.82 (m, 1H), 1.80-1.67 (m, 1H), 1.67-1.51 (m, 1H).

Example 111: N—((R)-1-((R)-2-Amino-3-methoxy-propanoyl)piperidin-3-yl)-5-(2-methyl-4-phenoxyphenyl)-4-oxo-4,5-dihydro-3H-1-thia-3,5,8-triazaacenaphthylene-2-carboxamide

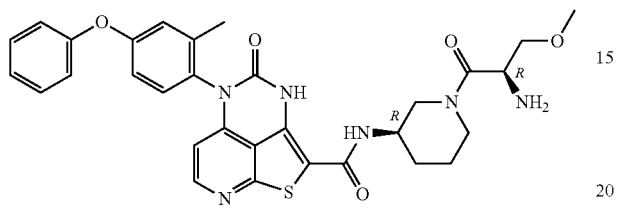

Step A: tert-Butyl ((R)-3-methoxy-1-((R)-3-(5-(2-methyl-4-phenoxyphenyl)-4-oxo-4,5-dihydro-3H-1-thia-3,5,8-triazaacenaphthylene-2-carboxamido)piperidin-1-yl)-1-oxopropan-2-yl)carbamate To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) in DMF (3 mL) were added 2-(tert-butoxycarbonylamino)-3-methoxy-propanoic acid (99 mg, 0.45 mmol), HATU (140 mg, 0.36 mmol), and triethylamine (0.086 mL, 0.62 mmol). The reaction mixture was stirred at rt for 4 h. The reaction mixture was purified by flash column chromatography to yield the title compound as a yellow solid (186 mg, 88% yield).

Step B: N—((R)-1-((R)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide A solution of tert-butyl ((R)-3-methoxy-1-((R)-3-(5-(2-methyl-4-phenoxyphenyl)-4-oxo-4,5-dihydro-3H-1-thia-3,5,8-triazaacenaphthylene-2-carboxamido)piperidin-1-yl)-1-oxopropan-2-yl)carbamate (186 mg, 0.265 mmol) and HCl/MeOH (2 M in MeOH, 4 mL). The reaction mixture was stirred at rt for 4 h, then the pH was adjusted pH>7 with 2 M aqueous NaOH. The mixture was purified by flash column chromatography to yield the title compound as a yellow solid (71 mg, 44% yield). MS (ESI): mass calcd. for $C_{31}H_{32}N_6O_5S$, 600.7; m/z found, 601.2 $[M+H]^+$. $^1H$ NMR (400 MHz, $CD_3OD$): δ 8.30-8.15 (m, 1H), 7.46-7.35 (m, 2H), 7.31-7.21 (m, 1H), 7.19-7.12 (m, 1H), 7.12-7.01 (m, 3H), 7.00-6.91 (m, 1H), 6.04-5.89 (m, 1H), 4.38-4.26 (m, 1H), 4.18-4.04 (m, 1H), 4.01-3.89 (m, 1H), 3.63-3.44 (m, 3H), 3.41-3.33 (m, 2H), 3.18-2.76 (m, 1H), 2.11 (s, 3H), 2.02-1.91 (m, 1H), 1.86-1.76 (m, 1H), 1.68-1.54 (m, 1H).

Example 112: (R,E)-N-(1-(2-Cyano-4-methyl-4-morpholinopent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

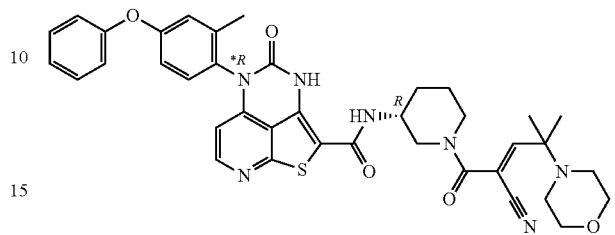

Step A: (R)—N-(1-(2-Cyanoacetyl)piperidin-3-yl)-5-(*R)-(2-methyl-4-phenoxyphenyl)-4-oxo-4,5-dihydro-3H-1-thia-3,5,8-triazaacenaphthylene-2-carboxamide To a stirred solution of (R)-5-(*R)-(2-methyl-4-phenoxyphenyl)-4-oxo-N-(piperidin-3-yl)-4,5-dihydro-3H-1-thia-3,5,8-triazaacenaphthylene-2-carboxamide (Example 300, 80 mg, 0.16 mmol) in DMF (3 mL) were added 2-cyanoacetic acid (30 mg, 0.35 mmol), HATU (120 mg, 0.54 mmol), and diisopropylethylamine (45 mg, 0.35 mmol). The resulting mixture was stirred at rt overnight, concentrated to dryness, and the residue was partitioned between ethyl acetate and water. The organic layer was separated, shaken with brine, and dried over anhydrous $Na_2SO_4$. The residue was purified by flash column chromatography to yield the title compound as a yellow solid (68 mg, 75% yield).

Step B: (R,E)-N-(1-(2-Cyano-4-methyl-4-morpholinopent-2-enoyl)piperidin-3-yl)-5-(*R)-(2-methyl-4-phenoxyphenl)-4-oxo-4,5-dihydro-3H-1-thia-3,5,8-triazaacenaphthylene-2-carboxamide To a sealed reaction tube were added (R)—N-(1-(2-cyanoacetyl)piperidin-3-yl)-5-(*R)-(2-methyl-4-phenoxyphenyl)-4-oxo-4,5-dihydro-3H-1-thia-3,5,8-triazaacenaphthylene-2-carboxamide (68 mg, 0.12 mmol), 2-methyl-2-morpholinopropanal (28 g, 0.18 mmol), piperidine (15 mg, 0.18 mmol), and EtOH (2 mL). The tube was sealed and heated to 105° C. overnight, cooled to rt, and the residue purified by flash column chromatography to yield the title compound as yellow solid (39 mg, 46% yield). MS (ESI): mass calcd. for $C_{38}H_{39}N_7O_5S$, 705.8; m/z found, 706.3 $[M+H]^+$. $^1H$ NMR (400 MHz, $CD_3OD$): δ 8.40-8.25 (m, 1H), 7.48-7.34 (m, 2H), 7.33-7.23 (m, 1H), 7.25-7.14 (m, 1H), 7.13-7.04 (m, 3H), 7.01-6.94 (m, 1H), 6.90-6.80 (m, 1H), 6.13-6.05 (m, 1H), 4.64-3.96 (m, 3H), 3.81-3.60 (m, 4H), 3.24-2.83 (m, 2H), 2.69-2.51 (m, 4H), 2.12 (s, 3H), 2.05-1.52 (m, 4H), 1.34-1.26 (m, 6H).

Example 113: (R)-5-(3-Fluoro-2-methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide

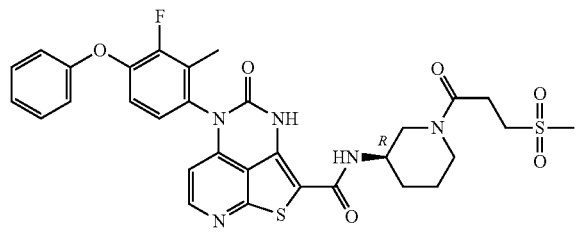

A mixture of (R)-5-(3-fluoro-2-methyl-4-phenoxyphenyl)-4-oxo-N-(piperidin-3-yl)-4,5-dihydro-3H-1-thia-3,5,8-triazaacenaphthylene-2-carboxamide (Intermediate 18) (80 mg, 0.16 mmol), 3-methylsulfonylpropanoic acid (47 mg, 0.31 mmol), triethylamine (31 mg, 0.31 mmol), and HATU (118 mg, 0.31 mmol) in DMF (2 mL) was stirred at rt for 1 h, then water was added and the precipitate was collected by filtration. The residue was purified by flash column chromatography to yield the title compound as a white solid (70 mg, 68% yield). MS (ESI): mass calcd. for $C_{31}H_{30}FN_5O_6S_2$, 651.7; m/z found, 652.0 [M+H]$^+$. $^1$H NMR (400 MHz, CD$_3$OD): δ 8.39-8.29 (m, 1H), 7.44-7.33 (m, 2H), 7.22-7.09 (m, 2H), 7.09-7.04 (m, 3H), 6.16-6.08 (m, 1H), 4.44-4.14 (m, 1H), 4.10-3.79 (m, 2H), 3.49-3.38 (m, 2H), 3.24-3.11 (m, 1H), 3.06-2.89 (m, 6H), 2.12 (s, 3H), 2.09-2.01 (m, 1H), 1.92-1.78 (m, 1H), 1.75-1.52 (m, 2H).

Example 114: (R)-5-(3-Fluoro-2-methyl-4-phenoxyphenyl)-N-(1-(2-hydroxyacetyl)piperidin-3-yl)-4-oxo-4,5-dihydro-3H-1-thia-3,5,8-triazaacenaphthylene-2-carboxamide

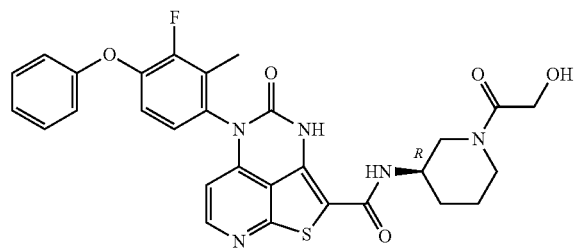

A solution of (R)-5-(3-fluoro-2-methyl-4-phenoxyphenyl)-4-oxo-N-(piperidin-3-yl)-4,5-dihydro-3H-1-thia-3,5,8-triazaacenaphthylene-2-carboxamide (Intermediate 18) (80 mg, 0.16 mmol), 2-hydroxyacetic acid (24 mg, 0.31 mmol), triethylamine (31 mg, 0.31 mmol), and HATU (118 mg, 0.310 mmol) in DMF (2 mL) was stirred at rt for 1 h, then water was added and the precipitate was collected by filtration. The residue was purified by flash column chromatography to yield the title compound as a white solid (60 mg, 67% yield). MS (ESI): mass calcd. for $C_{29}H_{26}FN_5O_5S$, 575.6; m/z found, 576.2 [M+H]$^+$. $^1$H NMR (400 MHz, CD$_3$OD): δ 8.37-8.25 (m, 1H), 7.43-7.32 (m, 2H), 7.23-7.17 (m, 1H), 7.16-7.10 (m, 1H), 7.09-7.02 (m, 3H), 6.18-6.04 (m, 1H), 4.56-4.17 (m, 3H), 3.97-3.58 (m, 2H), 3.08-2.96 (m, 1H), 2.91-2.75 (m, 1H), 2.11 (s, 3H), 2.08-1.97 (m, 1H), 1.88-1.76 (m, 1H), 1.73-1.49 (m, 2H).

Example 115: (R)-5-(3-Fluoro-2-methyl-4-phenoxyphenyl)-N-(1-(2-methoxyacetyl)piperidin-3-yl)-4-oxo-4,5-dihydro-3H-1-thia-3,5,8-triazaacenaphthylene-2-carboxamide

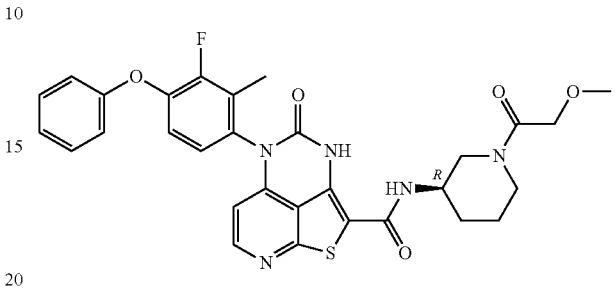

A mixture of (R)-5-(3-fluoro-2-methyl-4-phenoxyphenyl)-4-oxo-N-(piperidin-3-yl)-4,5-dihydro-3H-1-thia-3,5,8-triazaacenaphthylene-2-carboxamide (Intermediate 18) (80 mg, 0.16 mmol), 2-methoxyacetic acid (28 mg, 0.31 mmol), triethylamine (31 mg, 0.31 mmol), and HATU (118 mg, 0.310 mmol) in DMF (2 mL) was stirred at rt for 1 h, then water was added and the precipitate was collected by filtration. The residue was purified by flash column chromatography to yield the title compound as a white solid (60 mg, 66% yield). MS (ESI): mass calcd. for $C_{30}H_{28}FN_5O_5S$, 589.6; m/z found, 590.2 [M+H]$^+$. $^1$H NMR (400 MHz, CD$_3$OD): δ 8.40-8.24 (m, 1H), 7.44-7.31 (m, 2H), 7.24-7.17 (m, 1H), 7.16-7.10 (m, 1H), 7.09-7.01 (m, 3H), 6.16-6.06 (m, 1H), 4.52-4.10 (m, 3H), 3.99-3.69 (m, 2H), 3.38 (s, 3H), 3.12-2.96 (m, 1H), 2.87-2.70 (m, 1H), 2.11 (s, 3H), 2.07-1.97 (m, 1H), 1.87-1.76 (m, 1H), 1.75-1.47 (m, 2H).

Example 116: (R,Z)—N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide

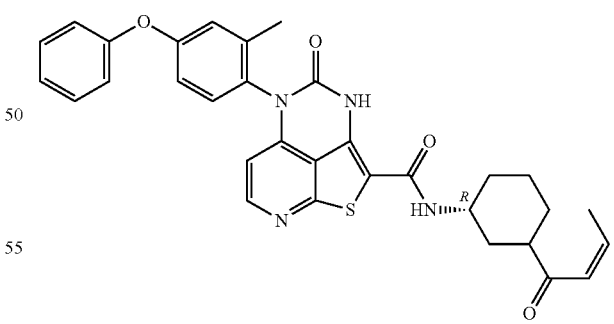

Step A: 1,3-Dibromobutan-2-one

To a solution butan-2-one (0.72 g, 10 mmol) in hydrobromic acid (3 mL) in a 3-neck flask equipped with a condenser and a bubble trap filled with sodium hydroxide was added bromine (3.2 g, 20 mmol) at 0° C. over 20 minutes. The mixture was stirred 1 h before the heavier organic phase was separated. The product was used without further purification (2.30 g, 100% yield).

Step B: (Z)-But-2-enoic Acid 1,3-Dibromobutan-2-one (2.3 g, 10.0 mmol) was added to a 2 M aqueous solution of potassium carbonate (100 mL) at 0° C. The mixture was stirred for 16 h at rt using a condenser. The aqueous solution was extracted with diethyl ether to remove unreacted material. The aqueous phase was then acidified with 37% hydrochloric acid to a pH of 2 and extracted with diethyl ether. The ether layers were dried over anhydrous MgSO$_4$ and filtered. The product was used without further purification (166 mg, 19% yield).

Step C: (R,Z)—N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide A mixture of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 300 mg, 0.58 mmol), (Z)-but-2-enoic acid (100 mg, 1.2 mmol), HATU (290 mg, 0.76 mmol), and diisopropylethylamine (190 mg, 1.5 mmol) in DMF (5 mL) was stirred at rt for 2 h. The mixture was purified by HPLC to yield the title compound as white solid (45 mg, 13% yield). MS (ESI): mass calcd. for C$_{31}$H$_{29}$N$_5$O$_4$S, 567.7; m/z found, 568.3 [M+H]$^+$. $^1$H NMR (400 MHz, CD$_3$OD): δ 8.37-8.30 (m, 1H), 7.45-7.36 (m, 2H), 7.35-7.26 (m, 1H), 7.21-7.13 (m, 1H), 7.13-7.02 (m, 3H), 7.02-6.93 (m, 1H), 6.88-6.38 (m, 1H), 6.15-5.99 (m, 2H), 4.60-3.85 (m, 3H), 3.21-3.04 (m, 1H), 2.97-2.80 (m, 1H), 2.38-1.96 (m, 5H), 1.90-1.78 (m, 3H), 1.78-1.63 (m, 1H), 1.63-1.50 (m, 1H)

Example 117: (R)-5-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide

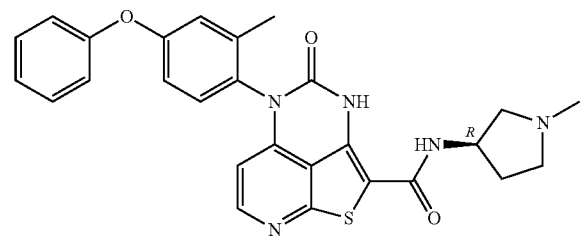

The title compound was prepared in a manner analogous to Method 1, steps A-G in Example 1, and using (R)-1-methylpyrrolidin-3-amine in place of tert-butyl (3R,5R)-3-amino-5-fluoropiperidine-1-carboxylate (Intermediate 1) in step G. MS (ESI): mass calcd. for C$_{27}$H$_{25}$N$_5$O$_3$S, 499.6; m/z found, 500.0 [M+H]$^+$. $^1$H NMR (400 MHz, DMSO-d$_6$ and CD$_3$OD): δ 8.23 (d, J=5.5 Hz, 1H), 7.42-7.34 (m, 2H), 7.29-7.23 (m, 1H), 7.17-7.10 (m, 1H), 7.08-7.04 (m, 2H), 7.03-7.00 (m, 1H), 6.95-6.88 (m, 1H), 5.90 (d, J=5.5 Hz, 1H), 4.47-4.37 (m, 1H), 2.86-2.76 (m, 2H), 2.68-2.61 (m, 1H), 2.58-2.50 (m, 1H), 2.36 (s, 3H), 2.25-2.15 (m, 1H), 2.03 (s, 3H), 1.88-1.80 (m, 1H).

Example 118: (R)—N-(1-Isopropylpyrrolidin-3-yl)-5-(2-methyl-4-phenoxyphenyl)-4-oxo-4,5-dihydro-3H-1-thia-3,5,8-triazaacenaphthylene-2-carboxamide

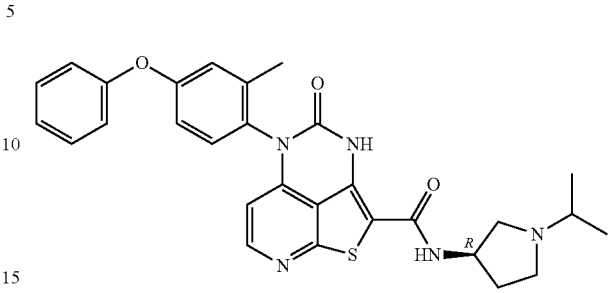

A solution of (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 150 mg, 0.31 mmol) in acetone was stirred for 10 min, then NaBH(OAc)$_3$ (130 mg, 0.60 mmmol) was added slowly and the mixture was stirred for 2 h. Next, NaOH (2 mL) was added and the mixture was purified by flash column chromatography, then preparative TLC to yield the title compound as a yellow solid (47 mg, 30% yield). MS (ESI): mass calcd. for C$_{29}$H$_{29}$N$_5$O$_3$S, 527.6; m/z found, 528.1 [M+H]$^+$. $^1$H NMR (400 MHz, CDCl3): δ 8.34 (d, J=5.2 Hz, 1H), 7.44-7.34 (m, 2H), 7.20-7.14 (m, 2H), 7.13-7.06 (m, 2H), 7.00 (s, 1H), 6.98-6.93 (m, 1H), 6.25-6.11 (m, 1H), 6.00 (d, J=5.2 Hz, 1H), 4.68-4.58 (br, 1H), 3.10-3.01 (m, 1H), 2.90-2.80 (m, 1H), 2.74-2.64 (m, 1H), 2.49-2.31 (m, 3H), 2.12 (s, 3H), 1.83-1.70 (m, 1H), 1.23-1.07 (m, 6H).

Example 119: (R)—N-(1-Acryloylpyrrolidin-3-yl)-5-(4-ethyl-2-methylphenyl)-4-oxo-4,5-dihydro-3H-1-thia-3,5,8-triazaacenaphthylene-2-carboxamide

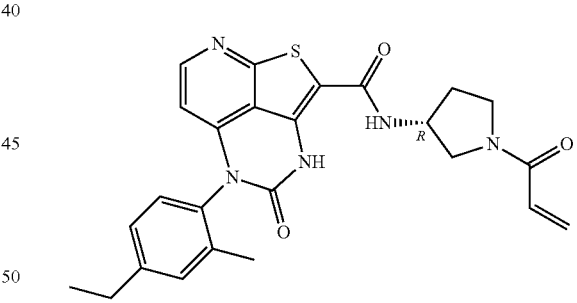

Step A: 4-Ethyl-2-methylaniline

To a mixture of 4-bromo-2-methylaniline (1.86 g, 10.0 mmol), Cs$_2$CO$_3$ (9.8 g, 30 mmol), and Pd(dppf)Cl$_2$ (146 mg, 0.200 mmol) in a Schlenk tube under a N$_2$ atmosphere was added dry THF (30 mL). To the stirred suspension was added trialkylborane (30 mL, 1 M solution in THF, 30 mmol) in one portion, and the mixture was refluxed for 5 h. The reaction was cooled to 0° C. and quenched by the addition of 10% aqueous NaOH and 30% aqueous H$_2$O$_2$. After stirring for 30 min at rt, the mixture was extracted with EtOAc. The combined organic layers were washed successively with aqueous FeSO$_4$ and brine, dried over anhydrous Na$_2$SO$_4$, filtered, and concentrated to dryness. The residue was purified by flash column chromatography to yield the title compound as a white solid (1.1 g, 83% yield).

Step B: 5-(4-Ethyl-2-methylphenyl)-4-oxo-4,5-dihydro-3H-1-thia-3,5,8-triazaacenaphthylene-2-carboxylic Acid The title compound was prepared in a manner analogous to Method 1, steps C-F in Example 1, and using 4-ethyl-2-methylaniline in place of 2-methyl-4-phenoxyaniline in step C.

Step C: (R)—N-(1-Acryloylpyrrolidin-3-yl)-5-(4-ethyl-2-methylphenyl)-4-oxo-4,5-dihydro-3H-1-thia-3,5,8-triazaacenaphthylene-2-carboxamide A solution of 5-(4-ethyl-2-methylphenyl)-4-oxo-4,5-dihydro-3H-1-thia-3,5,8-triazaacenaphthylene-2-carboxylic acid (150 mg, 0.42 mmol), 1-[(3R)-3-aminopyrrolidin-1-yl]prop-2-en-1-one (Intermediate 5, 119 mg, 0.850 mmol), HATU (320 mg, 0.85 mmol), and triethylamine (214 mg, 2.12 mmol) in DMF (4 mL) was stirred at rt for 2 h. The residue was purified by flash column chromatography to yield the title compound as a yellow solid (50 mg, 25% yield). MS (ESI): mass calcd. for $C_{25}H_{25}N_5O_3S$, 475.6; m/z found, 476.0 [M+H]$^+$. $^1$H NMR (400 MHz, DMSO-$d_6$): δ 10.25 (s, 1H), 8.42-8.22 (m, 2H), 7.35-7.16 (m, 3H), 6.71-6.48 (m, 1H), 6.23-6.05 (m, 1H), 5.85 (d, J=5.5 Hz, 1H), 5.73-5.60 (m, 1H), 4.60-4.37 (m, 1H), 3.91-3.38 (m, 4H), 2.65 (q, J=7.5 Hz, 2H), 2.24-2.07 (m, 1H), 2.05 (s, 3H), 2.03-1.89 (m, 1H), 1.23 (t, J=7.6 Hz, 3H).

Example 120: N—((R)-1-((S)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide

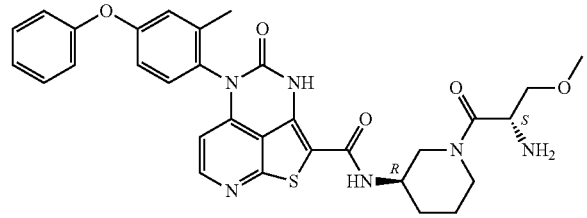

Step A: tert-Butyl ((S)-3-methoxy-1-((R)-3-(5-(2-methyl-4-phenoxyphenyl)-4-oxo-4,5-dihydro-3H-1-thia-3,5,8-triazaacenaphthylene-2-carboxamido)piperidin-1-yl)-1-oxopropan-2-yl)carbamate A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol), (2S)-2-(tert-butoxycarbonylamino)-3-methoxypropanoic acid (99 mg, 0.45 mmol), HATU (137 mg, 0.360 mmol), and triethylamine (0.086 mL, 0.62 mmol) in DMF (3 mL) was stirred at rt overnight, then purified by flash column chromatography to yield the title compound as a yellow solid (188 mg, 89%).

Step B: N—((R)-1-((S)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide A solution of tert-butyl ((S)-3-methoxy-1-((R)-3-(5-(2-methyl-4-phenoxyphenyl)-4-oxo-4,5-dihydro-3H-1-thia-3, 5,8-triazaacenaphthylene-2-carboxamido)piperidin-1-yl)-1-oxopropan-2-yl)carbamate (188 mg, 0.268 mmol) in HCl/MeOH (3 mL) was stirred at rt overnight, then the pH was adjusted to pH>7 with 2 M aqueous NaOH, and purified by flash column chromatography to yield the title compound as a yellow solid (83 mg, 99% yield). MS (ESI): mass calcd. for $C_{31}H_{32}N_6O_5S$, 600.7; m/z found, 601.1 [M+H]$^+$. $^1$H NMR (400 MHz, CD$_3$OD): δ 8.06 (d, J=5.5, 1H), 7.43-7.31 (m, 2H), 7.22-7.05 (m, 4H), 7.04-7.00 (m, 1H), 6.99-6.91 (m, 1H), 5.79 (d, J=5.6, 1H), 4.13-3.94 (m, 3H), 3.56-3.51 (m, 1H), 3.46-3.39 (m, 1H), 3.39-3.34 (m, 2H), 3.33-3.37 (m, 3H), 3.25-3.20 (m, 1H), 2.16-2.01 (m, 4H), 1.96-1.78 (m, 2H), 1.68-1.51 (m, 1H).

Example 121: (R)—N-(1-Acryloylpiperidin-3-yl)-4-oxo-5-(6-phenoxypyridazin-3-yl)-4,5-dihydro-3H-1-thia-3,5,8-triazaacenaphthylene-2-carboxamide

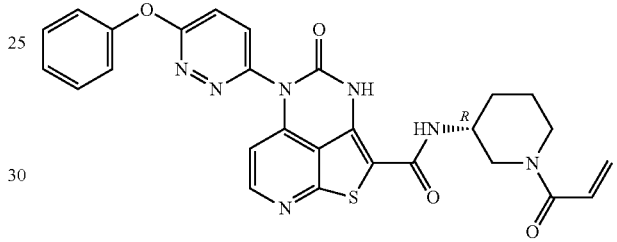

Step A: 6-Phenoxypyridazin-3-amine

A solution of 6-chloropyridazin-3-amine (1.3 g, 10 mmol), phenol (3.8 g, 40 mmol), and NaOH (1.6 g, 40 mmol) in water (10 mL) was stirred at 190° C. in a sealed tube for 16 h. The mixture was dispersed between EtOAc and water. Another reaction on the same scale was carried out. The organic layers were combined, concentrated to dryness, and purified by flash column chromatography to yield the title compound (0.50 g, 27% yield).

Step B: (R)—N-(1-Acryloylpiperidin-3-yl)-4-oxo-5-(6-phenoxypyridazin-3-yl)-4,5-dihydro-3H-1-thia-3, 5,8-triazaacenaphthylene-2-carboxamide The title compound was prepared in a manner analogous to Method 1, steps C-G in Example 1, and using 6-phenoxypyridazin-3-amine in place of 2-methyl-4-phenoxyaniline in step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{27}H_{23}N_7O_4S$, 541.6; m/z found, 542.4 [M+H]$^+$. $^1$H NMR (400 MHz, CD$_3$OD): δ 8.23-8.15 (m, 1H), 7.93-7.84 (m, 1H), 7.58 (d, J=9.2 Hz, 1H), 7.51-7.44 (m, 2H), 7.33-7.25 (m, 3H), 6.83-6.74 (m, 1H), 6.28-6.14 (m, 2H), 5.75-5.67 (m, 1H), 4.22-4.11 (m, 1H), 3.98-3.91 (m, 1H), 3.07-2.93 (m, 1H), 2.15-1.95 (m, 2H), 1.94-1.78 (m, 2H), 1.67-1.49 (m, 2H).

Example 122: N—((R)-1-((S)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide

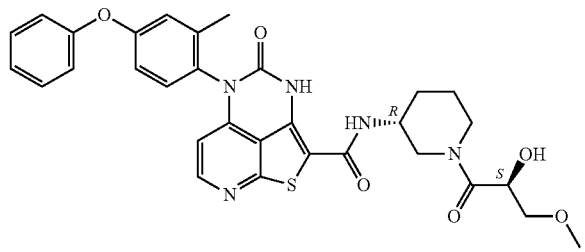

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol), (2S)-2-hydroxy-3-methoxy-propanoic acid (54 mg, 0.45 mmol), HATU (170 mg, 0.45 mmol), and triethylamine (0.084 mL, 0.60 mmol) in DMF (3 mL) was stirred at rt for 4 h, then purified by flash column chromatography and preparative TLC to yield the title compound as a yellow solid (24 mg, 13%). MS (ESI): mass calcd. for $C_{31}H_{31}N_5O_6S$, 601.7; m/z found, 602.3 [M+H]$^+$. $^1$H NMR (400 MHz, CD$_3$OD): δ 8.33 (d, J=5.6 Hz, 1H), 7.44-7.36 (m, 2H), 7.35-7.28 (m, 1H), 7.21-7.15 (m, 1H), 7.13-7.03 (m, 3H), 7.03-6.95 (m, 1H), 6.07 (d, J=5.6 Hz, 1H), 4.69-4.61 (m, 1H), 4.44-4.17 (m, 1H), 4.13-3.89 (m, 2H), 3.71-3.64 (m, 1H), 3.61-3.50 (m, 1H), 3.47-3.35 (m, 3H), 3.22-3.10 (m, 1H), 2.01-1.86 (m, 1H), 2.12 (s, 3H), 2.07-1.99 (m, 1H), 1.88-1.80 (m, 1H), 1.79-1.49 (m, 2H).

Example 123: 5-(2-Methyl-4-phenoxyphenyl)-4-oxo-N-(tetrahydro-2H-pyran-4-yl)-4,5-dihydro-3H-1-thia-3,5,8-triazaacenaphthylene-2-carboxamide

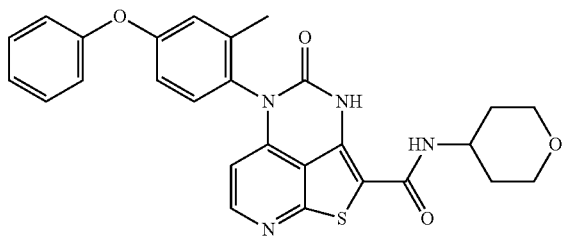 [SMILES: Cc1cc(Oc2ccccc2)ccc1N1C(=O)Nc2c(C(=O)NC3CCOCC3)sc3nccc1c23]

The title compound was prepared in a manner analogous to Method 1, steps A-G in Example 1, and using tetrahydropyran-4-amine in place of tert-butyl (3R,5R)-3-amino-5-fluoropiperidine-1-carboxylate (Intermediate 1) in step G. MS (ESI): mass calcd. for $C_{27}H_{24}N_4O_4S$, 500.6; m/z found, 501.1 [M+H]$^+$. $^1$H NMR (400 MHz, DMSO-d$_6$ and CD$_3$OD): δ 8.29-8.25 (m, 1H), 7.39-7.32 (m, 2H), 7.28-7.23 (m, 1H), 7.16-7.09 (m, 1H), 7.07-6.99 (m, 3H), 6.94-6.89 (m, 1H), 5.99-5.95 (m, 1H), 4.02-3.97 (m, 1H), 3.91-3.83 (m, 2H), 3.42-3.32 (m, 2H), 2.05 (s, 3H), 1.79-1.70 (m, 2H), 1.67-1.55 (m, 2H).

Example 124: (R)—N-(1-(2-Hydroxyacetyl)piperidin-3-yl)-5-(2-methyl-4-phenoxyphenyl)-4-oxo-4,5-dihydro-3H-1-thia-3,5,8-triazaacenaphthylene-2-carboxamide

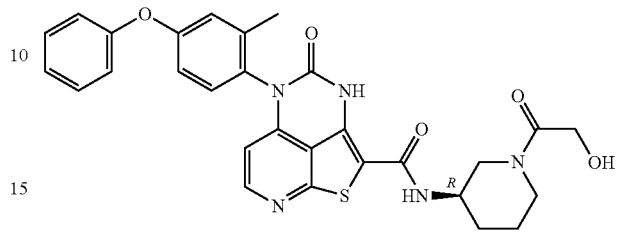

Step A: Benzyl N-[(3R)-1-(2-hydroxyacetyl)-3-piperidyl]carbamate

A mixture of benzyl N-[(3R)-3-piperidyl]carbamate (1.0 g, 3.3 mmol), 2-hydroxyacetic acid (225 mg, 3.00 mmol), HATU (1.24 g, 3.26 mmol), and triethylamine (0.450 mL, 3.26 mmol) in MeCN (10 mL) was stirred at 30° C. for 3 h. The reaction mixture was diluted with EtOAc, washed with 1 M aqueous HCl (3×), saturated aqueous NaHCO$_3$ (3×) and saturated brine (1×). After filtration and concentration to dryness, the residue was purified by flash column chromatography to yield the title compound as a clear oil (400 mg, 42%).

Step B: 1-[(3R)-3-Amino-1-piperidyl]-2-hydroxyethanone

A mixture of benzyl N-[(3R)-1-(2-hydroxyacetyl)-3-piperidyl]carbamate (400 mg, 1.4 mmol) and Pd/C (10%, 50 mg) in MeOH (10 mL) was reacted at rt overnight under H$_2$. The reaction mixture was filtered and concentrated to dryness to yield the title compound as a clear oil (210 mg, 95%), which is used in the next step without further purification.

Step C: (R)—N-(1-(2-Hydroxyacetyl)piperidin-3-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-G in Example 1, and using 1-[(3R)-3-amino-1-piperidyl]-2-hydroxyethanone in place of tert-butyl (3R)-3-aminopyrrolidine-1-carboxylate in step G. MS (ESI): mass calcd. for $C_{29}H_{27}N_5O_5S$, 557.6; m/z found, 558.1 [M+H]$^+$. $^1$H NMR (400 MHz, DMSO-d$_6$): δ 10.20 (s, 1H), 8.32 (d, J=5.4 Hz, 1H), 8.11 (s, 1H), 7.46-7.40 (m, 2H), 7.36 (d, J=8.5 Hz, 1H), 7.21-7.17 (m, 1H), 7.12-7.06 (m, 3H), 6.99-6.95 (m, 1H), 5.96 (d, J=5.2 Hz, 1H), 4.61-4.28 (m, 1H), 4.13-4.05 (m, 3H), 3.81-3.77 (m, 1H), 3.72-3.53 (m, 1H), 2.99-2.64 (m, 2H), 2.05 (s, 3H), 1.93-1.89 (m, 1H), 1.75-1.71 (m, 1H), 1.67-1.55 (m, 1H), 1.50-1.36 (m, 1H).

Example 125: 5-(2-Methyl-4-phenoxyphenyl)-N—((R)-1-((S)-1-methylpyrrolidine-3-carbonyl)piperidin-3-yl)-4-oxo-4,5-dihydro-3H-1-thia-3,5,8-triazaacenaphthylene-2-carboxamide

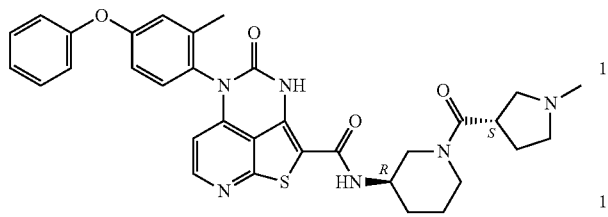

To a solution of 5-(2-methyl-4-phenoxyphenyl)-4-oxo-N—((R)-1-((S)-pyrrolidine-3-carbonyl)piperidin-3-yl)-4,5-dihydro-3H-1-thia-3,5,8-triazaacenaphthylene-2-carboxamide (120 mg, 0.20 mmol) in DCM (2 mL) were added formaldehyde (0.5 mL, 37 wt. % in $H_2O$) and sodium $NaBH(OAc)_3$ (200 mg, 0.94 mmol) and was reacted at rt overnight. The reaction was quenched with $H_2O$ (10 mL), extracted with DCM, dried over anhydrous $Na_2SO_4$, filtered, and concentrated to dryness. The residue was purified by flash column chromatography to yield the title compound as a yellow solid (54 mg, 44% yield). MS (ESI): mass calcd. for $C_{33}H_{34}N_6O_4S$, 610.7; m/z found, 611.2 $[M+H]^+$. $^1H$ NMR (400 MHz, $CD_3OD$): δ 8.30-8.22 (m, 1H), 7.44-7.34 (m, 2H), 7.30-7.23 (m, 1H), 7.19-7.12 (m, 1H), 7.10-7.02 (m, 3H), 7.00-6.93 (m, 1H), 6.04-5.94 (m, 1H), 4.35-4.19 (m, 1H), 4.17-3.81 (m, 2H), 3.60-3.46 (m, 1H), 3.27-3.19 (m, 1H), 3.16-2.95 (m, 2H), 2.95-2.84 (m, 2H), 2.80-2.70 (m, 1H), 2.59-2.44 (m, 3H), 2.15-2.00 (m, 6H), 1.93-1.71 (m, 2H), 1.66-1.50 (m, 1H).

Example 126: (R)—N-(1-Acryloylpyrrolidin-3-yl)-5-(4-isopropoxy-2-methylphenyl)-4-oxo-4,5-dihydro-3H-1-thia-3,5,8-triazaacenaphthylene-2-carboxamide

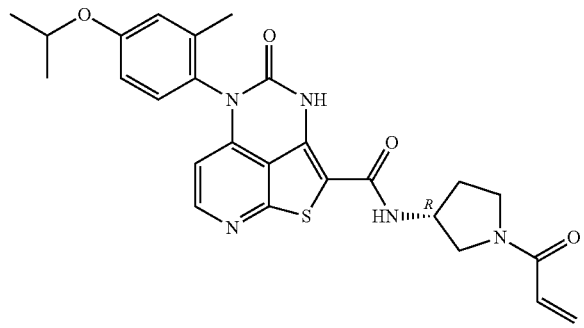

The title compound was prepared in a manner analogous to Method 1, steps A-I in Example 1, and using 3-methyl-4-nitrophenol and 2-iodopropane in place of phenol and 5-fluoro-2-nitrotoluene in step A, and using tert-butyl (3R)-3-aminopiperidine-1-carboxylate in place of tert-butyl (3R)-3-aminopyrrolidine-1-carboxylate in step. MS (ESI): mass calcd. for $C_{26}H_{27}N_5O_4S$, 505.6; m/z found, 506.2 $[M+H]^+$. $^1H$ NMR (400 MHz, $CD_3OD$): δ 8.28 (d, J=5.4 Hz, 1H), 7.26-7.18 (m, 1H), 7.00-6.87 (m, 2H), 6.69-6.51 (m, 1H), 6.34-6.21 (m, 1H), 6.06-5.97 (m, 1H), 5.79-5.69 (m, 1H), 4.74-4.53 (m, 2H), 4.04-3.48 (m, 4H), 2.43-1.98 (m, 5H), 1.42-1.29 (m, 6H).

Example 127: (R)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide

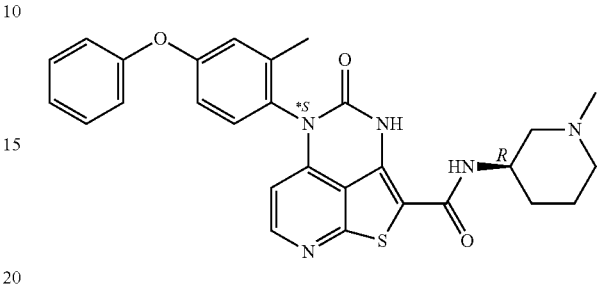

The title compound was prepared using an analogous method to Example 52 Step B using (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98). MS (ESI): mass calcd. for $C_{28}H_{27}N_5O_3S$, 513.6; m/z found, 514.2 $[M+H]^+$. $^1H$ NMR (400 MHz, $CD_3OD$): δ 8.30 (d, J=5.6, 1H), 7.43-7.35 (m, 2H), 7.31-7.26 (m, 1H), 7.20-7.14 (m, 1H), 7.12-7.08 (m, 2H), 7.08-7.03 (m, 1H), 7.01-6.95 (m, 1H), 6.05 (d, J=5.6, 1H), 4.24-4.11 (m, 1H), 3.02-2.90 (m, 1H), 2.78-2.68 (m, 1H), 2.36 (s, 3H), 2.29-2.16 (m, 2H), 2.12 (s, 3H), 1.95-1.78 (m, 2H), 1.74-1.63 (m, 1H), 1.57-1.45 (m, 1H).

Example 128: (R)-5-(3-Fluoro-2-methyl-4-phenoxyphenyl)-N-(1-(3-hydroxypropanoyl)piperidin-3-yl)-4-oxo-4,5-dihydro-3H-1-thia-3,5,8-triazaacenaphthylene-2-carboxamide

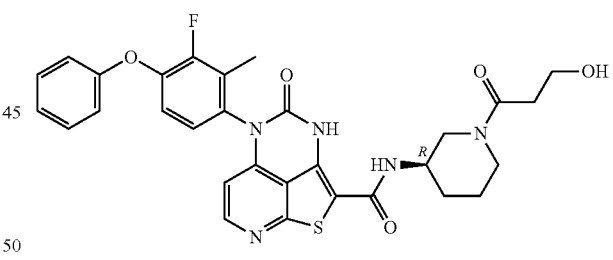

A solution of (R)-5-(3-fluoro-2-methyl-4-phenoxyphenyl)-4-oxo-N-(piperidin-3-yl)-4,5-dihydro-3H-1-thia-3,5,8-triazaacenaphthylene-2-carboxamide (Intermediate 18) (80 mg, 0.16 mmol), 3-hydroxypropanoic acid (28 mg, 0.31 mmol), triethylamine (31 mg, 0.31 mmol), and HATU (120 mg, 0.31 mmol) in DMF (2 mL) was stirred at rt for 1 h. The reaction was quenched by the addition of water and the precipitate collected by filtration. The residue was purified by flash column chromatography to yield the title compound as a white solid (32 mg, 35% yield). MS (ESI): mass calcd. for $C_{30}H_{28}FN_5O_5S$, 589.6; m/z found, 590.1 $[M+H]^+$. $^1H$ NMR (400 MHz, $CD_3OD$): δ 8.43-8.23 (m, 1H), 7.45-7.32 (m, 2H), 7.25-7.17 (m, 1H), 7.16-7.10 (m, 1H), 7.09-7.01 (m, 3H), 6.18-6.06 (m, 1H), 4.52-4.07 (m, 2H), 3.95-3.76 (m, 3H), 3.18-3.00 (m, 1H), 2.80-2.47 (m, 3H), 2.11 (s, 3H), 2.07-1.98 (m, 1H), 1.88-1.76 (m, 1H), 1.74-1.47 (m, 2H).

251

Example 129: N-(4-Methyl-1,4-oxazepan-6-yl)-5-(2-methyl-4-phenoxyphenyl)-4-oxo-4,5-dihydro-3H-1-thia-3,5,8-triazaacenaphthylene-2-carboxamide

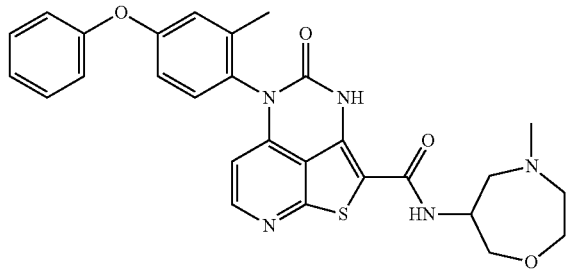 [SMILES: Cc1cc(Oc2ccccc2)ccc1N1C(=O)Nc2c(C(=O)NC3COCCN(C)C3)sc3nccc1c23]

Step A: 5-(2-Methyl-4-phenoxyphenyl)-N-(1,4-oxazepan-6-yl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl 6-amino-1,4-oxazepane-4-carboxylate in place of tert-butyl (3R,5R)-3-amino-5-fluoropiperidine-1-carboxylate (Intermediate 1) in step G.

Step B: N-(4-Methyl-14-oxazepan-6-yl)-5-(2-methyl-4-phenoxyphenyl)-4-oxo-4,5-dihydro-3H-1-thia-3,5,8-triazaacenaphthylene-2-carboxamide To a solution of 5-(2-methyl-4-phenoxyphenyl)-N-(1,4-oxazepan-6-yl)-4-oxo-4,5-dihydro-3H-1-thia-3,5,8-triazaacenaphthylene-2-carboxamide (259 mg, 0.502 mmol) in DCM (10 mL) were added formaldehyde (2 mL, 37 wt. % in H$_2$O) and NaBH(OAc)$_3$ (213 mg, 1.00 mmol) and stirred at rt for 4 h. To the reaction mixture were added DCM (50 mL), MeOH (5 mL), water (30 mL), and an aqueous solution of NH$_4$OH (2 mL). The organic layer was collected, concentrated to dryness, and purified by flash column chromatography, then by preparative TLC to yield the title compound as a yellow solid (156 mg, 56.0% yield). MS (ESI): mass calcd. for C$_{28}$H$_{27}$N$_5$O$_4$S, 529.6; m/z found, 530.0 [M+H]$^+$. $^1$H NMR (400 MHz, DMSO-d6): δ 8.29 (d, J=5.3 Hz, 1H), 8.14-8.00 (m, 1H), 7.45-7.38 (m, 2H), 7.34 (d, J=8.6 Hz, 1H), 7.20-7.15 (m, 1H), 7.13-7.03 (m, 3H), 6.99-6.92 (m, 1H), 5.99-5.89 (d, J=5.4 Hz, 1H), 4.34-4.25 (m, 1H), 3.83-3.77 (m, 1H), 2.78-2.53 (m, 4H), 2.33 (s, 3H), 2.03 (s, 3H).

Example 130: (R)—N-(1-(3-(Dimethylamino)propanoyl)piperidin-3-yl)-5-(2-methyl-4-phenoxyphenyl)-4-oxo-4,5-dihydro-3H-1-thia-3,5,8-triazaacenaphthylene-2-carboxamide

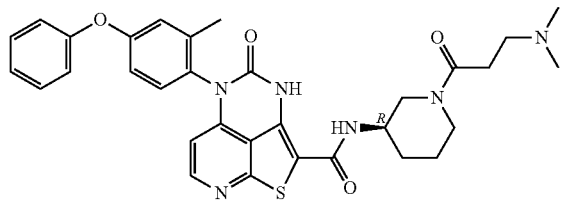

252

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.4 mmol) in DMF (3 mL) were added 3-(dimethylamino)propanoic acid (95 mg, 0.81 mmol), HATU (230 mg, 0.61 mmol), and diisopropylethylamine (105 mg, 0.812 mmol) and stirred at rt overnight. The reaction was concentrated to dryness and the residue was partitioned between EtOAc and water. The organic layer was separated, shaken with brine, dried over anhydrous Na$_2$SO$_4$, and purified by flash column chromatography to yield the title compound as a yellow solid (95 mg, 40% yield). MS (ESI): mass calcd. for C$_{32}$H$_{34}$N$_6$O$_4$S, 598.7; m/z found, 599.1 [M+H]$^+$. $^1$H NMR (400 MHz, CD$_3$OD): δ 8.32-8.21 (m, 1H), 7.46-7.35 (m, 2H), 7.32-7.24 (m, 1H), 7.21-7.13 (m, 1H), 7.12-7.03 (m, 3H), 7.01-6.92 (m, 1H), 6.07-5.97 (m, 1H), 4.47-4.11 (m, 1H), 4.07-3.69 (m, 2H), 3.24-3.03 (m, 3H), 3.02-2.75 (m, 3H), 2.66-2.59 (m, 6H), 2.11 (s, 3H), 2.07-1.99 (m, 1H), 1.95-1.53 (m, 3H).

Example 131: 5-(2-Methyl-4-phenoxyphenyl)-4-oxo-N—((R)-1-((S)-pyrrolidine-3-carbonyl)piperidin-3-yl)-4,5-dihydro-3H-1-thia-3,5,8-triazaacenaphthylene-2-carboxamide

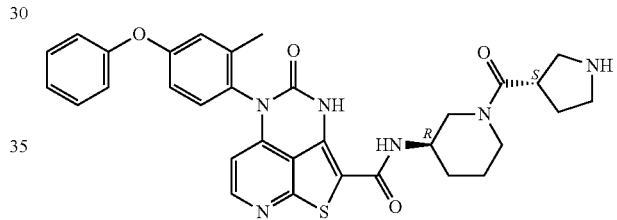

Step A: (S)-tert-Butyl 3-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)pyrrolidine-1-carboxylate A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 300 mg, 0.6 mmol), (3S)-1-tert-butoxycarbonylpyrrolidine-3-carboxylic acid (260 mg, 1.2 mmol), HATU (456 mg, 1.20 mmol), and triethylamine (120 mg. 1.2 mmol) in DMF (5 mL) was reacted at rt for 2 h, then quenched with H$_2$O (10 mL), extracted with DCM, dried over anhydrous Na$_2$SO$_4$, filtered, and concentrated to dryness. The residue was purified by flash column chromatography to yield the title compound as a yellow solid (300 mg, 72% yield).

Step B: 5-(2-Methyl-4-phenoxyphenyl)-4-oxo-N—((R)-1-((S)-pyrrolidine-3-carbonyl)piperidin-3-yl)-4,5-dihydro-3H-1-thia-3,5,8-triazaacenaphthylene-2-carboxamide To a solution of (S)-tert-butyl 3-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)

pyrrolidine-1-carboxylate (300 mg, 0.43 mmol) in MeOH (6 mL) was added HCl (37%, 2 mL) and was reacted at rt for 1 h, then quenched with a saturated solution of NaHCO$_3$ (20 mL), extracted with DCM, dried over anhydrous Na$_2$SO$_4$, filtered, and concentrated to dryness to yield the title compound as a yellow solid (200 mg, 78% yield). MS (ESI): mass calcd. for C$_{32}$H$_{32}$N$_6$O$_4$S, 596.7; m/z found, 597.2 [M+H]$^+$. $^1$H NMR (400 MHz, CD$_3$OD): δ 8.48 (s, 1H), 8.35-8.26 (m, 1H), 7.46-7.35 (m, 2H), 7.35-7.28 (m, 1H), 7.19-7.12 (m, 1H), 7.08-7.04 (m, 3H), 7.00-6.93 (m, 1H), 6.09-6.02 (m, 1H), 4.53-4.31 (m, 1H), 4.21-3.86 (m, 2H), 3.75-3.47 (m, 3H), 3.41-3.34 (m, 2H), 3.26-2.68 (m, 2H), 2.46-2.21 (m, 1H), 2.13-2.01 (m, 5H), 1.94-1.54 (m, 3H).

Example 132: N-((3S,4R)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide

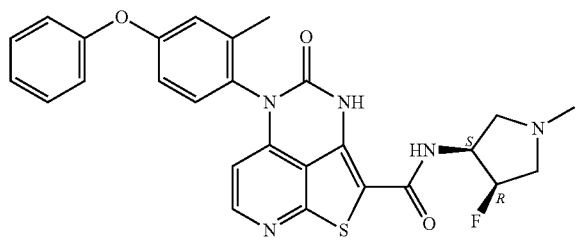

Step A: N-((3S,4R)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl (3S,4R)-3-amino-4-fluoropyrrolidine-1-carboxylate in place of tert-butyl (3R,5R)-3-amino-5-fluoropiperidine-1-carboxylate (Intermediate 1) in step G.

Step B: N-((3S,4R)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide To a solution of N-((3S,4R)-4-fluoropyrrolidin-3-yl)-5-(2-methyl-4-phenoxyphenyl)-4-oxo-4,5-dihydro-3H-1-thia-3,5,8-triazaacenaphthylene-2-carboxamide (100 mg, 0.2 mmol) and formaldehyde (0.3 mL, 37 wt. % in H$_2$O) in MeOH (4 mL) was added NaBH(OAc)$_3$ (126 mg, 0.597 mmol) and stirred at rt for 1 h, concentrated to dryness, and purified by flash column chromatography to yield the title compound as a white solid (100 mg, 95% yield). MS (ESI): mass calcd. for C$_{27}$H$_{24}$FN$_5$O$_3$S, 517.6; m/z found, 518.0 [M+H]$^+$. $^1$H NMR (400 MHz, CD$_3$OD): δ 8.32 (d, J=5.5 Hz, 1H), 7.44-7.34 (m, 2H), 7.29 (d, J=8.6 Hz, 1H), 7.20-7.12 (m, 1H), 7.12-7.03 (m, 3H), 6.96 (dd, J=8.6, 2.8 Hz, 1H), 6.06 (d, J=5.5 Hz, 1H), 5.26-5.05 (m, 1H), 4.73-4.61 (m, 1H), 3.15-3.00 (m, 1H), 2.98-2.81 (m, 3H), 2.44 (s, 3H), 2.11 (s, 3H).

Example 133: (R)-5-(2-Chloro-4-phenoxyphenyl)-N-(1-methylpiperidin-3-yl)-4-oxo-4,5-dihydro-3H-1-thia-3,5,8-triazaacenaphthylene-2-carboxamide

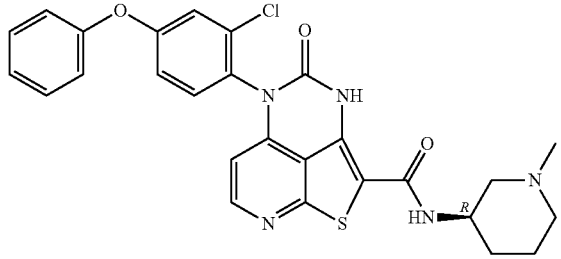

Step A: (R)-5-(2-Chloro-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 2-chloro-4-fluoro-1-nitrobenzene in place of 5-fluoro-2-nitrotoluene in step A, and using tert-butyl (3R)-3-aminopyrrolidine-1-carboxylate in place of tert-butyl (3R,5R)-3-amino-5-fluoropiperidine-1-carboxylate (Intermediate 1) in step G.

Step B: (R)-5-(2-Chloro-4-phenoxyphenyl)-N-(1-methylpiperidin-3-yl)-4-oxo-4,5-dihydro-3H-1-thia-3,5,8-triazaacenaphthylene-2-carboxamide To a solution of (R)-5-(2-chloro-4-phenoxyphenyl)-4-oxo-N-(piperidin-3-yl)-4,5-dihydro-3H-1-thia-3,5,8-triazaacenaphthylene-2-carboxamide (104 mg, 0.20 mmol) in DCM (5 mL) were added formaldehyde (0.5 mL, 37 wt. % in H$_2$O) and NaBH(OAc)$_3$ (85 mg, 0.4 mmol) and stirred at rt for 4 h. To the reaction mixture were added DCM (50 mL), MeOH (5 mL), and water (30 mL). The organic layer was collected, concentrated to dryness, and purified by flash column chromatography to yield the title compound as yellow solid (15 mg, 14% yield). MS (ESI): mass calcd. for C$_{27}$H$_{24}$ClN$_5$O$_3$S, 534.0; m/z found, 534.4 [M+H]$^+$. $^1$H NMR (400 MHz, DMSO-d6): δ 8.85-8.75 (m, 1H), 8.01 (d, J=5.5 Hz, 1H), 7.49-7.43 (m, 2H), 7.36-7.32 (m, 1H), 7.26-7.20 (m, 2H), 7.19-7.15 (m, 2H), 7.07-7.02 (m, 1H), 5.62 (d, J=5.4 Hz, 1H), 3.95-3.83 (m, 1H), 2.81-2.69 (m, 1H), 2.14 (s, 3H), 2.02-1.91 (m, 2H), 1.86-1.76 (m, 2H), 1.71-1.64 (m, 1H), 1.56-1.29 (m, 2H).

Example 134: (R,Z)—N-(1-(2-Cyano-4-(dimethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

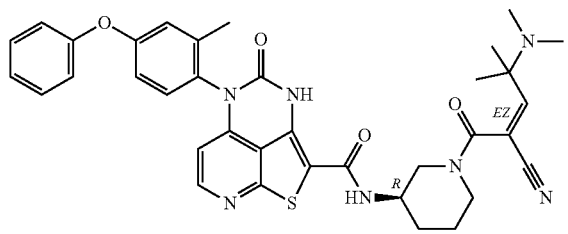

To a round bottom flask were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 150 mg, 0.26 mmol), 2-(dimethylamino)-2-methylpropanal (92 mg, 0.80 mmol), piperidine (0.3 mL), AcOH (0.1 mL), dioxane (10 mL), and 4A molecular sieves (1 g) and was stirred at 100° C. for 1 h under $N_2$. The mixture was concentrated to dryness and purified by flash column chromatography to yield the title compound as a yellow solid (103 mg, 52.8% yield). MS (ESI): mass calcd. for $C_{36}H_{37}N_7O_4S$, 663.8; m/z found, 664.4 [M+H]$^+$. $^1$H NMR (400 MHz, $CD_3OD$): δ 8.37 (s, 1H), 8.34-8.30 (m, 1H), 7.42-7.35 (m, 2H), 7.32-7.25 (m, 1H), 7.20-7.12 (m, 1H), 7.11-7.02 (m, 3H), 6.99-6.94 (m, 1H), 6.92-6.76 (m, 1H), 6.09-6.04 (m, 1H), 4.44-3.80 (m, 3H), 3.25-2.87 (m, 2H), 2.49-2.31 (m, 6H), 2.13-2.00 (m, 4H), 1.96-1.85 (m, 1H), 1.80-1.58 (m, 2H), 1.45-1.30 (m, 6H).

Example 135: (R)-5-(2-Fluoro-4-phenoxyphenyl)-N-(1-methylpiperidin-3-yl)-4-oxo-4,5-dihydro-3H-1-thia-3,5,8-triazaacenaphthylene-2-carboxamide

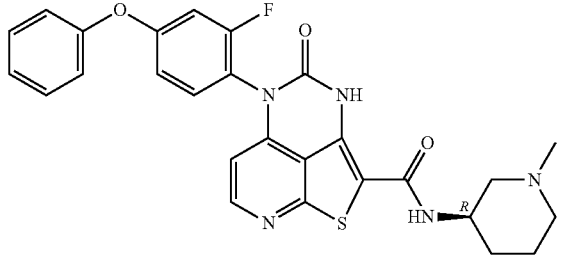

Step A: 2-Fluoro-1-nitro-4-phenoxybenzene

To a solution of 3-fluoro-4-nitrophenol (2.33 g, 19.1 mmol), phenylboronic acid (2.00 g, 12.7 mmol), $Cu(OAc)_2$ (4.624 g, 25.46 mmol), and triethylamine (6.435 g, 63.65 mmol) in DCM (60 mL) was added molecular sieves (4A powder, <50 μm, 2.0 g). The mixture was stirred at room temperature under $N_2$ overnight. The reaction was filtered and concentrated to dryness. The residue was purified by normal phase flash column chromatography ($SiO_2$) to yield the title compound as a yellow solid (2.7 g, 91% yield). MS (ESI): mass calcd. for $C_{12}H_8FNO_3$, 233.20; m/z found, 233.9 [M+H]$^+$.

Step B: (R)-5-(2-Fluoro-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps B-H in Example 1, and using 2-fluoro-1-nitro-4-phenoxybenzene, Pd/C, and MeOH in place of -methyl-1-nitro-4-phenoxybenzene, Fe, EtOH/$H_2O$, and $NH_4Cl$ 2 in step B, and using 2-fluoro-4-phenoxyaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G.

Step C: (R)-5-(2-Fluoro-4-phenoxyphenyl)-N-(1-methylpiperidin-3-yl)-4-oxo-4,5-dihydro-3H-1-thia-3,5,8-triazaacenaphthylene-2-carboxamide A solution of (R)-5-(2-fluoro-4-phenoxyphenyl)-4-oxo-N-(piperidin-3-yl)-4,5-dihydro-3H-1-thia-3,5,8-triazaacenaphthylene-2-carboxamide (100 mg, 0.2 mmol) and formaldehyde (1 mL, 37 wt. % in $H_2O$) in MeOH (10 mL) was added $NaBH(OAc)_3$ (212 mg, 1.00 mmol) and then stirred at room temperature for 1 h, concentrated to dryness, and purified by normal phase flash column chromatography ($SiO_2$) to yield the title compound as a yellow solid (62 mg, 60% yield). MS (ESI): mass calcd. for $C_{27}H_{24}FN_5O_3S$, 517.6; m/z found, 517.9 [M+H]$^+$. $^1$H NMR (400 MHz, DMSO-$d_6$): δ 8.32 (d, J=7.5 Hz, 1H), 8.23-8.17 (m, 2H), 7.55-7.37 (m, 3H), 7.31-7.14 (m, 3H), 7.14-7.06 (m, 1H), 6.98-6.87 (m, 1H), 6.02 (d, J=5.4 Hz, 1H), 3.98-3.86 (m, 1H), 2.88-2.77 (m, 1H), 2.72-2.57 (m, 1H), 2.22 (s, 3H), 2.05-1.88 (m, 2H), 1.84-1.63 (m, 2H), 1.58-1.43 (m, 1H), 1.39-1.25 (m, 1H).

Example 136: (R)-5-(2-Methyl-4-phenoxyphenl)-N-(1-(oxetane-3-carbonyl)piperidin-3-yl)-4-oxo-4,5-dihydro-3H-1-thia-3,5,8-triazaacenaphthylene-2-carboxamide

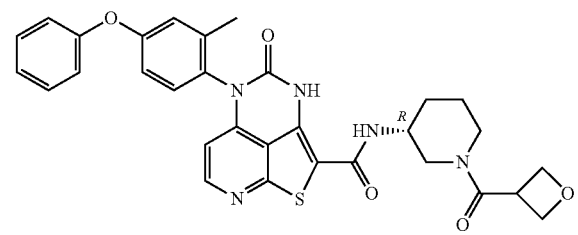

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 100 mg, 0.2 mmol), oxetane-3-carboxylic acid (30 mg, 0.29 mmol), triethylamine (40 mg, 0.40 mmol), and HATU (150 mg, 0.40 mmol) in DMF (5 mL) was reacted at rt for 2 h, quenched with $H_2O$ (10 mL), extracted with DCM, dried over anhydrous $Na_2SO_4$, filtered, and concentrated to dryness. The residue was purified by flash column chromatography to yield the title compound as an off white solid (48 mg, 41% yield). MS (ESI): mass calcd. for $C_{31}H_{29}N_5O_5S$, 583.7; m/z found, 584.2 [M+H]$^+$. $^1$H NMR (400 MHz, $CD_3OD$ and DMSO-$d_6$): δ 8.41-8.34 (m, 1H), 7.50-7.41 (m, 2H), 7.38-7.33 (m, 1H), 7.27-7.18 (m, 1H), 7.17-7.09 (m, 3H), 7.06-6.97 (m, 1H), 6.12-6.05 (m, 1H), 5.08-4.89 (m, 1H), 4.89-4.75 (m, 4H), 4.28-4.18 (m, 1H), 4.04-3.78 (m, 1H), 3.68-3.38 (m, 1H), 3.01-2.93 (m, 1H), 2.85-2.75 (m, 1H), 2.20-2.11 (m, 3H), 2.09-2.03 (m, 1H), 1.93-1.81 (m, 1H), 1.76-1.64 (m, 1H), 1.63-1.52 (m, 1H).

Example 137: (R)—N-(1-Acryloylpyrrolidin-3-yl)-N-methyl-5-(2-methyl-4-phenoxyphenl)-4-oxo-4,5-dihydro-3H-1-thia-3,5,8-triazaacenaphthylene-2-carboxamide

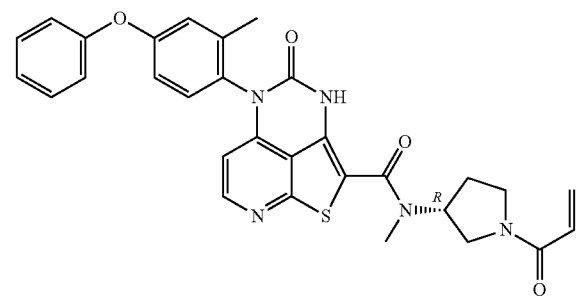

The title compound was prepared in a manner analogous to Method 1, steps A-I in Example 1, and using tert-butyl (3R)-3-(methylamino)pyrrolidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.9 [M+H]$^+$. $^1$H NMR (400 MHz, DMSO-d$_6$): δ 10.84 (s, 1H), 8.37-8.17 (m, 1H), 7.48-7.41 (m, 2H), 7.36 (d, J=8.6 Hz, 1H), 7.26-7.15 (m, 1H), 7.14-7.04 (m, 3H), 7.03-6.89 (m, 1H), 6.64-6.48 (m, 1H), 6.19-6.04 (m, 1H), 6.00-5.89 (m, 1H), 5.75-5.58 (m, 1H), 4.98-4.73 (m, 1H), 3.89-3.34 (m, 4H), 3.08-2.95 (m, 3H), 2.29-2.09 (m, 2H), 2.06 (s, 3H).

Example 138: N-((3R,5R)-5-Fluoropiperidin-3-yl)-5-(2-methyl-4-phenoxyphenyl)-4-oxo-4,5-dihydro-3H-1-thia-3,5,8-triazaacenaphthylene-2-carboxamide

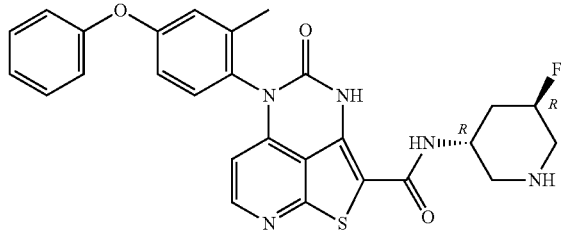

A solution of 5-(2-methyl-4-phenoxyphenyl)-4-oxo-4,5-dihydro-3H-1-thia-3,5,8-triazaacenaphthylene-2-carboxylic acid (Method 1, Example 1, Steps A-F, 191 mg, 0.458 mmol), tert-butyl (3R,5R)-3-amino-5-fluoropiperidine-1-carboxylate (100 mg, 0.458 mmol), triethylamine (92 mg, 0.92 mmol), and HATU (348 mg, 0.916 mmol) in DMF (3 mL) was stirred at rt for 3 h. The reaction was quenched by the addition of water and the precipitate collected by filtration. The solid was dissolved in MeOH (3 mL) and HCl (3 mL) and the solution was heated with stirring at 50° C. for 30 min, concentrated to dryness, and the residue purified by flash column chromatography to yield the title compound as a yellow solid (80 mg, 31% yield). MS (ESI): mass calcd. for $C_{27}H_{24}FN_5O_3S$, 517.6; m/z found, 518.3 [M+H]$^+$. $^1$H NMR (400 MHz, CD$_3$OD): δ 8.33 (d, J=5.5 Hz, 1H), 7.47-7.36 (m, 2H), 7.34-7.27 (m, 1H), 7.21-7.13 (m, 1H), 7.14-7.03 (m, 3H), 7.02-6.94 (m, 1H), 1H), 6.07 (d, J=5.5 Hz, 1H), 4.76-4.54 (m, 1H), 4.18-4.08 (m, 1H), 3.17-3.01 (m, 2H), 2.79-2.59 (m, 2H), 2.36-2.24 (m, 1H), 2.12 (s, 3H), 1.94-1.83 (m, 1H).

Example 139: N-((3S,4S)-4-Hydroxy-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide

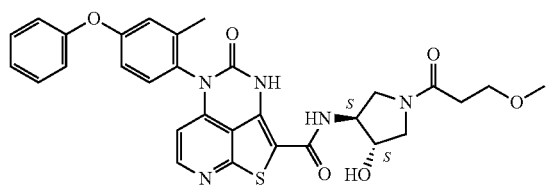

A solution of N-((3S,4S)-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide (Example 236) (100 mg, 0.2 mmol), 3-methoxypropanoic acid (41 mg, 0.40 mmol), triethylamine (40 mg, 0.40 mmol), and HATU (151 mg, 0.398 mmol) in DMF (3 mL) was stirred at rt for 1 h. Water was added and the precipitate was filtered to give a crude, which was purified by flash column chromatography to yield the title compound as a white solid (65 mg, 54% yield). MS (ESI): mass calcd. for $C_{30}H_{29}N_5O_6S$, 587.6; m/z found, 588.2 [M+H]$^+$. $^1$H NMR (400 MHz, CD$_3$OD): δ 8.31 (d, J=5.4 Hz, 1H), 7.44-7.35 (m, 2H), 7.33-7.27 (m, 1H), 7.20-7.12 (m, 1H), 7.11-7.02 (m, 3H), 7.00-6.93 (m, 1H), 6.06 (d, J=5.5 Hz, 1H), 4.44-4.29 (m, 2H), 4.01-3.84 (m, 1H), 3.74-3.57 (m, 4H), 3.52-3.41 (m, 1H), 3.32 (s, 3H), 2.65-2.55 (m, 2H), 2.11 (s, 3H).

Example 140: (R)—N-(1-(2-Cyano-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

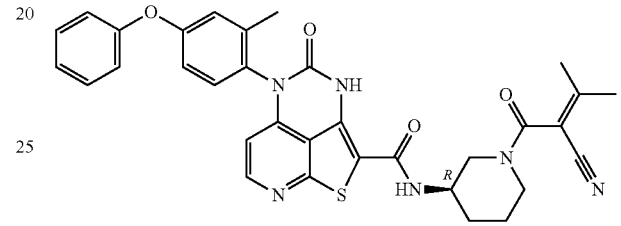

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) and 2-cyano-3-methylbut-2-enoic acid (75 mg, 0.60 mmol) in DMF (2 mL) were added HATU (228 mg, 0.600 mmol) and triethylamine (61 mg, 0.60 mmol) and stirred at rt for 4 h. The mixture was purified by flash column chromatography to yield the title product as a yellow solid (105 mg, 58.0% yield). MS (ESI): mass calcd. for $C_{33}H_{30}N_6O_4S$, 606.7; m/z found, 607.1 [M+H]$^+$. $^1$H NMR (400 MHz, DMSO-d$_6$): δ 10.23 (br, 1H), 8.37-8.25 (m, 1H), 8.21-8.04 (m, 1H), 7.47-7.38 (m, 2H), 7.38-7.30 (m, 1H), 7.20-7.14 (m, 1H), 7.14-7.03 (m, 3H), 7.00-6.91 (m, 1H), 6.02-5.87 (m, 1H), 4.39-4.09 (m, 1H), 3.82-3.62 (m, 2H), 3.16-3.02 (m, 1H), 2.88-2.73 (m, 1H), 2.11-2.01 (m, 6H), 1.97-1.92 (m, 1H), 1.92-1.87 (m, 3H), 1.83-1.75 (m, 1H), 1.70-1.59 (m, 1H), 1.48-1.38 (m, 1H).

Example 141: (R)—N-(1-Ethylpyrrolidin-3-yl)-5-(2-methyl-4-phenoxyphenyl)-4-oxo-4,5-dihydro-3H-1-thia-3,5,8-triazaacenaphthylene-2-carboxamide

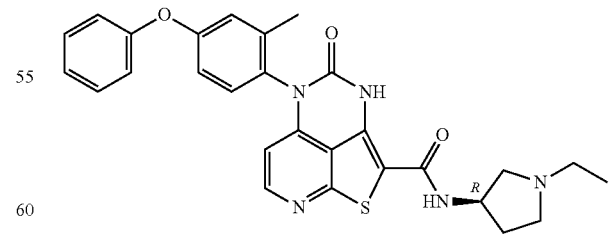

To a solution of (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 150 mg, 0.31 mmol) in MeOH (5 mL) was added acetaldehyde (1 mL) slowly and was stirred for 10 min. Then NaBH(OAc)$_3$ (127 mg, 0.600 mmol) was added slowly and the mixture was stirred for 2 h. NaOH (2 mL) was added and the mixture was purified by flash column chromatography, then preparative TLC to yield the title compound as a yellow solid (58 mg, 36% yield). MS (ESI): mass calcd. for $C_{28}H_{27}N_5O_3S$, 513.6; m/z found, 514.1 [M+H]$^+$. $^1$H NMR (400 MHz, CDCl3): δ 8.41-8.31 (m, 1H), 7.49-7.34 (m, 2H), 7.22-7.15 (m, 2H), 7.15-7.08 (m, 2H), 7.02 (s, 1H), 7.00-6.94 (m, 1H), 6.33-6.11 (m, 1H), 6.02 (d, J=3.9 Hz, 1H), 4.76-4.56 (m, 1H), 3.13-3.03 (m, 1H), 2.92-2.85 (m, 1H), 2.67-2.55 (m, 3H), 2.47-2.39 (m, 1H), 2.35-2.28 (m, 1H), 2.14 (s, 3H), 1.88-1.77 (m, 1H), 1.24-1.13 (m, 3H).

Example 142: N—((R)-1-((S)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide

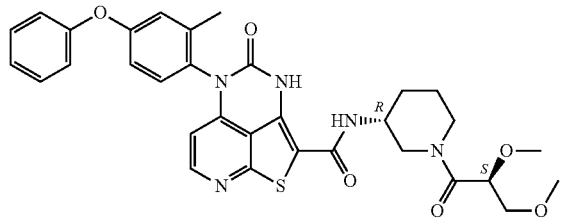

To a solution of (S)-2,3-dimethoxypropanoic acid (Intermediate 19) (50 mg, 0.37 mmol) in DCM (5 mL) was added oxalyl dichloride (2 mL) and was stirred at 60° C. overnight. The reaction was concentrated to dryness and dissolved in DCM (5 mL). This mixture was added to a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 80 mg, 0.16 mmol) and triethylamine (40 mg, 0.40 mmol) in DCM (5 mL) and reacted at room temperature for 30 minutes. The reaction was quenched with H$_2$O, extracted with DCM, dried over anhydrous Na$_2$SO$_4$, filtered, concentrated to dryness, and purified by normal phase flash column chromatography (SiO$_2$) to yield the title compound (35 mg, 36%) as an off white solid. MS (ESI): mass calcd. for $C_{32}H_{33}N_5O_6S$, 615.7; m/z found, 616.2 [M+H]$^+$. $^1$H NMR (400 MHz, CD$_3$OD and DMSO-d$_6$): δ 8.43-8.30 (m, 1H), 7.50-7.38 (m, 2H), 7.37-7.27 (m, 1H), 7.27-7.17 (m, 1H), 7.17-7.07 (m, 3H), 7.04-6.95 (m, 1H), 6.14-6.07 (m, 1H), 4.53-4.36 (m, 3H), 4.34-3.84 (m, 3H), 3.72-3.56 (m, 2H), 3.44-3.34 (m, 4H), 3.22-3.03 (m, 1H), 3.01-2.77 (m, 1H), 2.19-2.11 (m, 3H), 2.10-2.01 (m, 1H), 1.93-1.81 (m, 1H), 1.78-1.49 (m, 2H).

Example 143: N—((R)-1-((R)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide

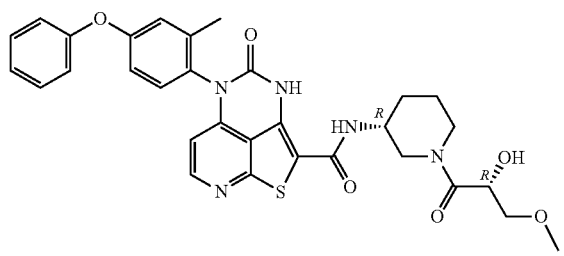

Step A: (2R)-Oxirane-2-carboxylic acid, sodium salt

To a solution of methyl (2R)-oxirane-2-carboxylate (170 mg, 1.7 mmol) in MeOH (1 mL) in an ice-salt bath was added a solution of NaOH (73 mg, 1.8 mmol) in MeOH (2 mL) dropwise over 10 min. The reaction mixture was stirred at rt overnight, then ether (5 mL) was added. The mixture was left to stand at −10° C. for 1 h, and the precipitate was collected, washed with ether, dried in vacuo to yield the title compound as a white solid (170 mg, 92%).

Step B: 5-(2-methyl-4-phenoxyphenyl)-N—((R)-1-((R)-oxirane-2-carbonyl)piperidin-3-yl)-4-oxo-4,5-dihydro-3H-1-thia-3,5,8-triazaacenaphthylene-2-carboxamide A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.40 mmol), (2R)-oxirane-2-carboxylic acid (89 mg, 0.80 mmol), HATU (115 mg, 0.600 mmol), and diisopropylethylamine (0.219 mL, 1.20 mmol) in DMF (3 mL) was stirred at rt for 15 min, then purified by flash column chromatography to yield the title compound as a yellow solid (160 mg, 70% yield).

Step C: N—((R)-1-((R)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide A mixture of (R)—N-(1-(cyclopropanecarbonyl)piperidin-3-yl)-5-(2-methyl-4-phenoxyphenyl)-4-oxo-4,5-dihydro-3H-1-thia-3,5,8-triazaacenaphthylene-2-carboxamide (150 mg, 0.26 mmol) and NaOMe in MeOH (0.5 M, 9 mL) was stirred at 100° C. in a microwave tube for 5 min, concentrated to dryness, and the residue purified by flash column chromatography to yield the title compound as a yellow solid (40 mg, 25% yield). MS (ESI): mass calcd. for $C_{31}H_{31}N_5O_6S$, 601.7; m/z found, 602.8 [M+H]$^+$. $^1$H NMR (400 MHz, CD$_3$OD): δ 8.33 (d, J=5.6 Hz, 1H), 7.44-7.36 (m, 2H), 7.35-7.26 (m, 1H), 7.20-7.13 (m, 1H), 7.11-7.04 (m, 3H), 7.00-6.95 (m, 1H), 6.07 (d, J=5.5 Hz, 1H), 4.75-4.60 (m, 1H), 4.48-4.17 (m, 1H), 4.10-3.89 (m, 2H), 3.72-3.52 (m, 2H), 3.44-3.33 (m, 3H), 3.23-3.09 (m, 1H), 3.00-2.79 (m, 1H), 2.12 (s, 3H), 2.09-2.01 (m, 1H), 1.91-1.80 (m, 1H), 1.79-1.49 (m, 2H).

Example 144: (R)-5-(2-Methyl-4-phenoxyphenyl)-4-oxo-N-(1-(2-(trifluoromethyl)acryloyl)piperidin-3-yl)-4,5-dihydro-3H-1-thia-3,5,8-triazaacenaphthylene-2-carboxamide

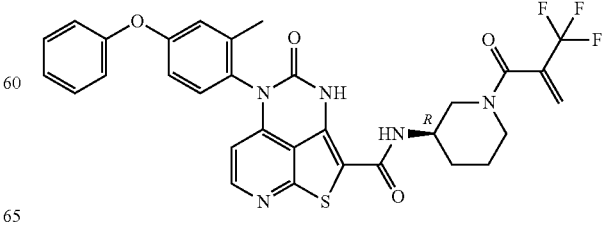

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), 2-(trifluoromethyl)prop-2-enoic acid (78 mg, 0.56 mmol), HATU (138 mg, 0.364 mmol), and diisopropylethylamine (72 mg, 0.56 mmol) in DMF (5 mL) was stirred at rt for 2 h. The mixture was purified first by HPLC and then by flash column chromatography to yield the title compound as white solid (18 mg, 10% yield). MS (ESI): mass calcd. for $C_{31}H_{26}F_3N_5O_4S$, 621.6; m/z found, 622.0 $[M+H]^+$. $^1H$ NMR (400 MHz, $CD_3OD$): δ 8.34-8.27 (m, 1H), 7.42-7.34 (m, 2H), 7.33-7.26 (m, 1H), 7.19-7.12 (m, 1H), 7.10-7.01 (m, 3H), 6.98-6.92 (m, 1H), 6.22-6.14 (m, 1H), 6.08-6.03 (m, 1H), 5.99-5.87 (m, 1H), 4.57-4.32 (m, 1H), 4.12-3.78 (m, 2H), 3.22-3.06 (m, 1H), 2.95-2.80 (m, 1H), 2.11-2.05 (m, 4H), 1.97-1.79 (m, 1H), 1.79-1.65 (m, 1H), 1.63-1.53 (m, 1H).

Example 145: 5-(2-Methyl-4-phenoxyphenyl)-N—((R)-1-((R)-1-methylpyrrolidine-3-carbonyl)piperidin-3-yl)-4-oxo-4,5-dihydro-3H-1-thia-3,5,8-triazaacenaphthylene-2-carboxamide

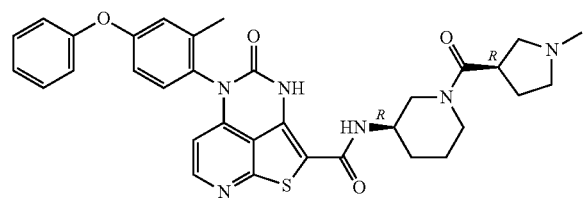

Step A: (R)-tert-Butyl 3-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)pyrrolidine-1-carboxylate A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 300 mg, 0.6 mmol), (3R)-1-tert-butoxycarbonylpyrrolidine-3-carboxylic acid (260 mg, 1.2 mmol), HATU (456 mg, 1.20 mmol), and triethylamine (121 mg, 1.20 mmol) in DMF (5 mL) was reacted at rt for 2 h. The reaction was quenched with $H_2O$ (10 mL), extracted with DCM, dried over anhydrous $Na_2SO_4$, filtered, and concentrated to dryness. The residue was purified by flash column chromatography to yield the title compound as a yellow solid (350 mg, 83% yield).

Step B: 5-(2-Methyl-4-phenoxyphenyl)-4-oxo-N—((R)-1-((R)-pyrrolidine-3-carbonyl)piperidin-3-yl)-4,5-dihydro-3H-1-thia-3,5,8-triazaacenaphthylene-2-carboxamide To a solution of (R)-tert-butyl 3-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)pyrrolidine-1-carboxylate (350 mg, 0.50 mmol) in MeOH (5 mL) was added HCl (37%, 2 mL) and was reacted at rt for 1 h. The reaction was quenched by the addition of a saturated solution of $NaHCO_3$ (20 mL), extracted with DCM, dried over anhydrous $Na_2SO_4$, filtered, and concentrated to dryness to yield the title compound as a yellow solid (200 mg, 67% yield).

Step C: 5-(2-Methyl-4-phenoxyphenyl)-N—((R)-1-((R)-1-methylpyrrolidine-3-carbonyl)piperidin-3-yl)-4-oxo-4,5-dihydro-3H-1-thia-3,5,8-triazaacenaphthylene-2-carboxamide To a solution of 5-(2-methyl-4-phenoxyphenyl)-4-oxo-N—((R)-1-((R)-pyrrolidine-3-carbonyl)piperidin-3-yl)-4,5-dihydro-3H-1-thia-3,5,8-triazaacenaphthylene-2-carboxamide (150 mg, 0.25 mmol) in DCM (2 mL) were added formaldehyde (0.5 mL, 37 wt. % in $H_2O$) and $NaBH(OAc)_3$ (200 mg, 0.94 mmol) and was stirred at rt overnight. The reaction was quenched with $H_2O$ (10 mL), extracted with DCM, dried over anhydrous $Na_2SO_4$, filtered, and concentrated to dryness. The residue was purified by flash column chromatography to yield the title compound as a yellow solid (120 mg, 78% yield). MS (ESI): mass calcd. for $C_{33}H_{34}N_6O_4S$, 610.7; m/z found, 611.2 $[M+H]^+$. $^1H$ NMR (400 MHz, $CD_3OD$): δ 8.43 (s, 1H), 8.35-8.27 (m, 1H), 7.43-7.35 (m, 2H), 7.34-7.27 (m, 1H), 7.19-7.12 (m, 1H), 7.10-7.00 (m, 3H), 6.99-6.92 (m, 1H), 6.11-6.00 (m, 1H), 4.57-4.32 (m, 1H), 4.26-3.81 (m, 2H), 3.81-3.60 (m, 2H), 3.53-3.31 (m, 3H), 3.22-3.00 (m, 1H), 2.96-2.89 (m, 3H), 2.88-2.41 (m, 2H), 2.22-1.98 (m, 5H), 1.93-1.47 (m, 3H).

Example 146: (R)-5-(2-Methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide

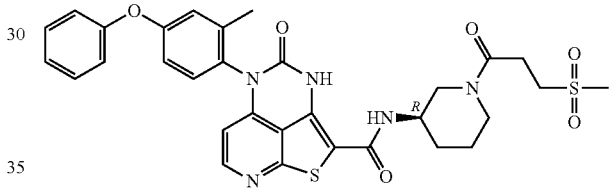

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 120 mg, 0.22 mmol), 3-methylsulfonylpropanoic acid (68 mg, 0.45 mmol), HATU (110 mg, 0.29 mmol), and diisopropylethylamine (58 mg, 0.45 mmol) in DMF (5 mL) was stirred at rt for 2 h. The mixture was purified by HPLC to yield the title compound as white solid (85 mg, 60% yield). MS (ESI): mass calcd. for $C_{31}H_{31}N_5O_6S_2$, 633.7; m/z found, 634.0 $[M+H]^+$. $^1H$ NMR (400 MHz, $CD_3OD$): δ 8.34-8.30 (m, 1H), 7.42-7.36 (m, 2H), 7.32-7.27 (m, 1H), 7.19-7.13 (m, 1H), 7.10-7.03 (m, 3H), 6.99-6.95 (m, 1H), 6.08-6.04 (m, 1H), 4.44-4.13 (m, 1H), 4.08-3.79 (m, 2H), 3.50-3.39 (m, 2H), 3.24-3.11 (m, 1H), 3.08-2.83 (m, 6H), 2.12 (s, 3H), 2.08-2.00 (m, 1H), 1.91-1.76 (m, 1H), 1.77-1.52 (m, 2H).

Example 147: (R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide

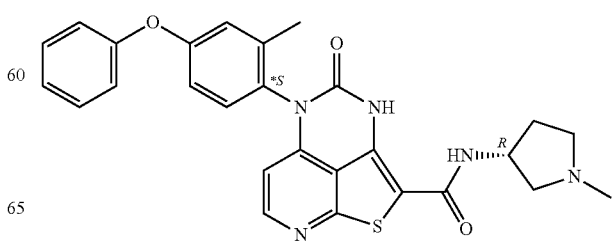

Step A: tert-butyl N-[(3R)-1-Methylpyrrolidin-3-yl]carbamate

To a solution of tert-butyl N-[(3R)-pyrrolidin-3-yl]carbamate (500 mg, 2.68 mmol) in MeOH (5 mL) was added formaldehyde (0.4 mL, 37 wt. % in $H_2O$) and was stirred at rt for 5 min. Next, sodium cyanoborohydride (506 mg, 8.05 mmol) was added and was stirred at rt overnight. The reaction mixture was concentrated to dryness and the residue was added to EtOAc and $H_2O$, and extracted with EtOAc. The combined organic layers were washed with brine, dried over anhydrous $MgSO_4$, filtered, and concentrated to dryness to yield the title compound as a yellow oil (536 mg, 100%).

Step B: (3R)-1-Methylpyrrolidin-3-amine

A solution of tert-butyl N-[(3R)-1-methylpyrrolidin-3-yl]carbamate (536 mg, 2.84 mmol) in HCl and MeOH (2 M, 2 mL) was stirred at rt for 4 h. The reaction mixture was concentrated to dryness to yield the title compound (322 mg, 88%), which was used in next step without further purification.

Step C: (R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide The title compound was prepared in a manner analogous to Method 1, steps A-G in Example 1 (including Chiral resolution Method A after Step F to obtain the *S atropisomer), and using (3R)-1-methylpyrrolidin-3-amine in place of tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 500.1 [M+H]$^+$. $^1H$ NMR (400 MHz, $CD_3OD$): δ 8.29 (d, J=5.6 Hz, 1H), 7.47-7.35 (m, 2H), 7.31-7.25 (m, 1H), 7.21-7.14 (m, 1H), 7.12-7.04 (m, 3H), 7.02-6.94 (m, 1H), 6.03 (d, J=5.6 Hz, 1H), 4.61-4.53 (m, 1H), 3.02-2.91 (m, 2H), 2.85-2.78 (m, 1H), 2.69-2.63 (m, 1H), 2.50 (s, 3H), 2.43-2.35 (m, 1H), 2.12 (s, 3H), 1.99-1.88 (m, 1H).

Example 148: (R)-5-(2-Methyl-4-(o-tolyloxy)phenyl)-N-(1-methylpiperidin-3-yl)-4-oxo-4,5-dihydro-3H-1-thia-3,5,8-triazaacenaphthylene-2-carboxamide

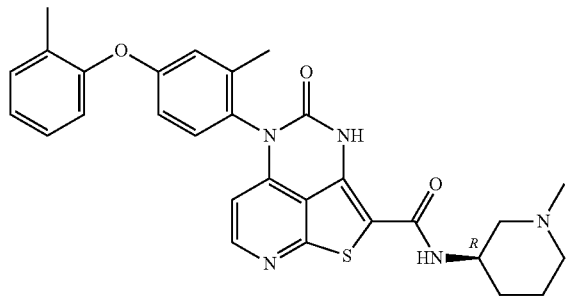

Step A: (R)-5-(2-Methyl-4-(o-tolyloxy)phenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using o-cresol in place of phenol in step A, and using (R)-tert-butyl 3-aminopiperidine-1-carboxylate in place of tert-butyl (3R,5R)-3-amino-5-fluoropiperidine-1-carboxylate (Intermediate 1) in step G to yield the title compound.

Step B: (R)-5-(2-Methyl-4-(o-tolyloxy)phenyl)-N-(1-methylpiperidin-3-yl)-4-oxo-4,5-dihydro-3H-1-thia-3,5,8-triazaacenaphthylene-2-carboxamide To a solution of (R)-5-(2-methyl-4-(o-tolyloxy)phenyl)-4-oxo-N-(piperidin-3-yl)-4,5-dihydro-3H-1-thia-3,5,8-triazaacenaphthylene-2-carboxamide (80 mg, 0.16 mmol) in DCM (5 mL), were added formaldehyde (0.5 ml, 37 wt. % in $H_2O$) and $NaBH(OAc)_3$ (100 mg, 0.47 mmol) and reacted at rt for 20 min. The reaction was quenched with $H_2O$ (10 mL), extracted with EtOAc, dried over anhydrous $Na_2SO_4$, filtered, and concentrated to dryness. The residue was purified by flash column chromatography to yield the title compound as a yellow solid (26 mg, 31% yield). MS (ESI): mass calcd. for $C_{29}H_{29}N_5O_3S$, 527.6; m/z found, 528.0 [M+H]$^+$. $^1H$ NMR (400 MHz, $CD_3OD$): δ 8.38-8.27 (m, 1H), 7.32-7.27 (m, 1H), 7.27-7.19 (m, 2H), 7.18-7.07 (m, 1H), 7.03-6.90 (m, 2H), 6.88-6.80 (m, 1H), 6.11-6.02 (m, 1H), 4.35-4.15 (m, 1H), 3.45-3.34 (m, 1H), 3.26-3.13 (m, 1H), 2.81-2.65 (m, 5H), 2.22 (s, 3H), 2.09 (s, 3H), 2.03-1.96 (m, 2H), 1.86-1.75 (m, 1H), 1.66-1.57 (m, 1H).

Example 149: (R)—N-(1-Cyclopropylpyrrolidin-3-yl)-5-(2-methyl-4-phenoxyphenyl)-4-oxo-4,5-dihydro-3H-1-thia-3,5,8-triazaacenaphthylene-2-carboxamide

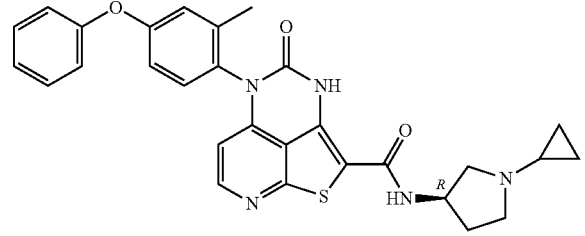

To a solution of (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 200 mg, 0.41 mmol) in MeOH (5 mL) was added (1-ethoxycyclopropoxy)-trimethylsilane (209 mg, 1.20 mmol) slowly and was stirred for 10 min, then $NaBH_4CN$ (77 mg, 1.2 mmol) and AcOH (6 mg, 0.1 mmol) was added slowly and the mixture was stirred for 2 h. NaOH (2 mL) was added and the mixture was purified first by flash column chromatography, then by preparative TLC to yield the title compound as a yellow solid (65 mg, 29% yield). MS (ESI): mass calcd. for $C_{29}H_{27}N_5O_3S$, 525.6; m/z found, 526.2 [M+H]$^+$. $^1H$ NMR (400 MHz, $CDCl_3$): δ 9.50-9.35 (m, 1H), 8.33 (d, J=5.4 Hz, 1H), 7.46-7.33 (m, 2H), 7.20-7.13 (m, 2H), 7.13-7.05 (m, 2H), 6.99 (s, 1H), 6.97-6.91 (m, 1H), 5.96 (d, J=5.4 Hz, 1H), 5.18-4.95 (m, 1H), 3.99-3.60 (m, 2H), 3.37-2.92 (m, 2H), 2.72-2.58 (m, 1H), 2.49-2.25 (m, 2H), 2.11 (d, J=2.4, 3H), 1.51-1.28 (m, 2H), 1.01-0.75 (m, 2H).

Example 150: (R,E)-N-(1-(2-Cyano-4-methyl-4-(piperidin-1-yl)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

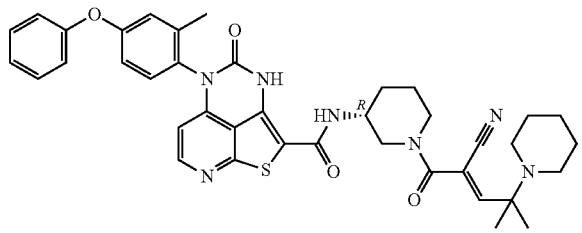

To a sealed tube were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 150 mg, 0.265 mmol), 2-methyl-2-(1-piperidyl)propanal (65 mg, 0.42 mmol), piperidine (30 mg, 0.35 mmol), and EtOH (3 mL) and the tube was sealed and heated to 105° C. overnight, cooled to rt, and the residue purified by flash column chromatography to yield the title compound as a yellow solid (78 mg, 42% yield). MS (ESI): mass calcd. for $C_{39}H_{41}N_7O_4S$, 703.9; m/z found, 704.30 [M+H]$^+$. $^1$H NMR (400 MHz, CD$_3$OD): δ 8.32 (d, J=5.6 Hz, 1H), 7.46-7.37 (m, 2H), 7.33-7.26 (m, 1H), 7.22-7.15 (m, 1H), 7.14-7.05 (m, 3H), 7.02-6.95 (m, 1H), 6.94-6.75 (m, 1H), 6.09-6.03 (m, 1H), 4.52-3.71 m, 3H), 3.57-3.34 (m, 1H), 3.24-2.91 (m, 1H), 266-2.41 (m, 4H), 2.16-2.10 (m, 3H), 2.09-1.86 (m, 2H), 1.85-1.53 (m, 6H), 1.50-1.36 (m, 2H), 1.35-1.24 (m, 6H).

Example 151: (R)—N-(1-(2-Aminoacetyl)piperidin-3-yl)-5-(2-methyl-4-phenoxyphenyl)-4-oxo-4,5-dihydro-3H-1-thia-3,5,8-triazaacenaphthylene-2-carboxamide

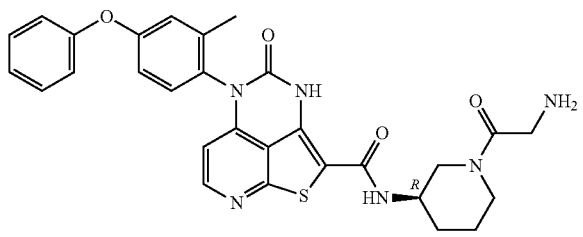

Step A: (R)-tert-Butyl (2-(3-(5-(2-methyl-4-phenoxyphenyl)-4-oxo-4,5-dihydro-3H-1-thia-3,5,8-triazaacenaphthylene-2-carboxamido)piperidin-1-yl)-2-oxoethyl)carbamate To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) in DMF (3 mL) were added 2-(tert-butoxycarbonylamino)acetic acid (79 mg, 0.45 mmol), HATU (137 mg, 0.360 mmol), and triethylamine (0.167 mL, 1.20 mmol). The reaction mixture was stirred at rt for 4 h and was purified by flash column chromatography to yield the title compound as a yellow solid (171 mg, 86% yield).

Step B: (R)—N-(1-(2-Aminoacetyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)-tert-butyl (2-(3-(5-(2-methyl-4-phenoxyphenyl)-4-oxo-4,5-dihydro-3H-1-thia-3,5,8-triazaacenaphthylene-2-carboxamido)piperidin-1-yl)-2-oxoethyl) carbamate (171 mg, 0.260 mmol) and HCl/MeOH (2 M, 3 mL) was stirred at rt for 4 h, then the pH was adjusted to pH>7 with 2 M aqueous NaOH, and purified by flash column chromatography to yield the title compound as a yellow solid (95 mg, 65% yield). MS (ESI): mass calcd. for $C_{29}H_{28}N_6O_4S$, 556.6; m/z found, 557.2 [M+H]$^+$. $^1$H NMR (400 MHz, CD$_3$OD): δ 8.09-8.01 (m, 1H), 7.42-7.31 (m, 2H), 7.20-7.05 (m, 4H), 7.04-6.99 (m, 1H), 6.99-6.93 (m, 1H), 5.83-5.73 (m, 1H), 4.16-4.02 (m, 1H), 3.99-3.91 (m, 1H), 3.86-3.73 (m, 1H), 3.62-3.48 (m, 2H), 3.42-3.30 (m, 1H), 3.27-3.16 (m, 1H), 2.10 (s, 3H), 2.07-2.00 (m, 1H), 1.93-1.76 (m, 2H), 1.65-1.51 (m, 1H).

Example 152: (R,E)-N-(1-(2-Cyano-4-(cyclopropylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

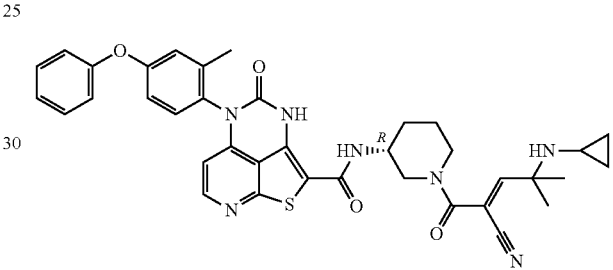

Step A: 3-Bromo-3-methylbutanal

To a solution of 3-methylbutanal (500 mg, 5.80 mmol) in Et$_2$O (3 mL) was added slowly a bromine/dioxane complex (720 mg, 2.90 mmol) while cooling with ice-water. The reaction mixture was stirred at rt for 4 h, and then 10% aqueous Na$_2$S$_2$O$_4$ was added. After stirring at rt for 15 min, the mixture was extracted with Et$_2$O/H$_2$O, the organic layer was collected, washed with brine (10 mL), dried over anhydrous MgSO$_4$, filtered, and concentrated to dryness to yield the title compound as a pale yellow liquid (510 mg, 52%).

Step B: 2-(Cyclopropylamino)-2-methylpropanal

To a solution of 3-bromo-3-methylbutanal (450 mg, 2.73 mmol) in Et$_2$O (10 mL) was added cyclopropanamine (545 mg, 9.55 mmol). The reaction mixture was stirred at rt overnight, then extracted with an Et$_2$O/water mixture. The organic layer was collected, washed with Et$_2$O, dried over anhydrous Mg$_2$SO$_4$, filtered, and concentrated to dryness to yield the title compound as a pale yellow liquid (197 mg, 57%).

Step C: (R,E)-N-(1-(2-Cyano-4-(cyclopropylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide To a solution of (R)—N-(1-(2-cyanoacetyl)piperidin-3-yl)-5-(2-methyl-4-phenoxyphenyl)-4-oxo-4,5-dihydro-3H-

1-thia-3,5,8-triazaacenaphthylene-2-carboxamide (Example 874, 163 mg, 0.288 mmol) and 2-(cyclopropylamino)-2-methylpropanal (110 mg, 0.86 mmol) in iPrOH (5 mL) was added piperdine (0.014 mL, 0.14 mmol) and was stirred at 40° C. overnight, concentrated to dryness, and the residue purified by flash column chromatography to yield the title compound as a yellow solid (19 mg, 10% yield). MS (ESI): mass calcd. for $C_{37}H_{37}N_7O_4S$, 675.8; m/z found, 676.3 [M+H]$^+$. $^1$H NMR (400 MHz, CD$_3$OD): δ 8.25-8.18 (m, 1H), 7.73-7.64 (m, 1H), 7.44-7.35 (m, 2H), 7.26-7.20 (m, 1H), 7.19-7.14 (m, 1H), 7.11-7.07 (m, 2H), 7.07-7.03 (m, 1H), 6.99-6.94 (m, 1H), 6.03-5.90 (m, 1H), 4.07-3.81 (m, 2H), 3.64-3.43 (m, 1H), 3.06-3.08 (m, 1H), 2.71-2.57 (m, 1H), 2.15-2.01 (m, 5H), 1.98-1.88 (m, 1H), 1.76-1.68 (m, 1H), 1.65-1.53 (m, 6H), 1.34-1.29 (m, 1H), 1.11-0.89 (m, 4H).

Example 153: 5-(2-Methyl-4-phenoxyphenyl)-N-((6S)-6-methylpiperidin-3-yl)-4-oxo-4,5-dihydro-3H-1-thia-3,5,8-triazaacenaphthylene-2-carboxamide

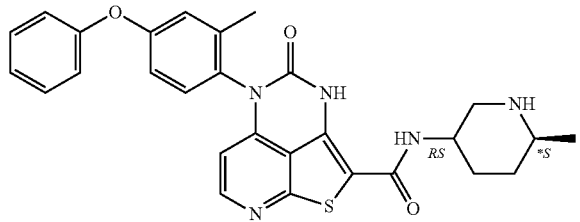 [SMILES: Cc1cc(Oc2ccccc2)ccc1N1C(=O)Nc2c(C(=O)NC3CC[C@H](C)NC3)sc3nccc1c23]

The title compound was prepared in a manner analogous to Method 1, steps A-H in Example 1, and using benzyl 5-amino-2-methylpiperidine-1-carboxylate (Intermediate 20) in place of tert-butyl (3R,5R)-3-amino-5-fluoropiperidine-1-carboxylate (Intermediate 1) in step G and TFA in place of MeOH and aqueous HCl in Step H. Example 153 and Example 173 were separated from the same reaction mixture by flash column chromatography (C-18, MeOH/H$_2$O) followed by preparative TLC. MS (ESI): mass calcd. for $C_{28}H_{27}N_5O_3S$, 513.6; m/z found, 544.2 [M+H]$^+$. $^1$H NMR (400 MHz, CD$_3$OD): δ 8.40-8.32 (m, 1H), 7.45-7.37 (m, 2H), 7.33-7.26 (m, 1H), 7.21-7.14 (m, 1H), 7.11-7.02 (m, 3H), 7.00-6.92 (m, 1H), 6.12-6.05 (m, 1H), 4.39-4.28 (m, 1H), 3.63-3.50 (m, 1H), 3.46-3.37 (m, 1H), 3.37-3.33 (m, 1H), 2.11 (s, 3H), 2.06-1.83 (m, 4H), 1.43-1.35 (m, 3H).

Example 154: N-((3S,4R)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide

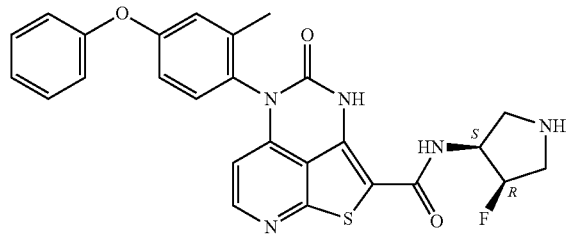

The title compound was prepared in a manner analogous to Method 1, steps A-H in Example 1, and using tert-butyl (3S,4R)-3-amino-4-fluoropyrrolidine-1-carboxylate in place of tert-butyl (3R,5R)-3-amino-5-fluoropiperidine-1-carboxylate (Intermediate 1) in step G. MS (ESI): mass calcd. for $C_{26}H_{22}FN_5O_3S$, 503.5; m/z found, 504.1 [M+H]$^+$. $^1$H NMR (400 MHz, DMSO-d$_6$ and CD$_3$OD): δ 8.37-8.25 (m, 1H), 7.42-7.30 (m, 2H), 7.29-7.21 (m, 1H), 7.16-7.09 (m, 1H), 7.08-6.98 (m, 3H), 6.95-6.88 (m, 1H), 6.06-5.96 (m, 1H), 5.39-5.18 (m, 1H), 4.83-4.66 (m, 1H), 3.67-3.54 (m, 3H), 3.44-3.35 (m, 1H), 2.04 (s, 3H).

Example 155: N-((3R)-1-(3-Methoxybutanoyl)piperidin-3-yl)-5-(2-methyl-4-phenoxyphenyl)-4-oxo-4,5-dihydro-3H-1-thia-3,5,8-triazaacenaphthylene-2-carboxamide

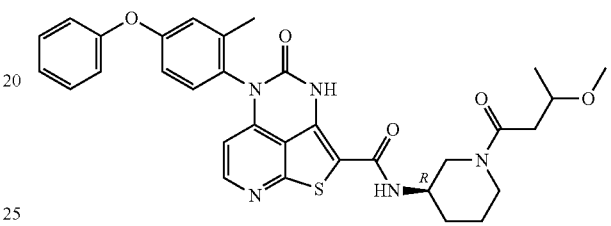

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) and 3-methoxybutanoic acid (265 mg, 0.900 mmol) in anhydrous DMF (2 mL) were added HATU (342 mg, 0.900 mmol) and diisopropylethylamine (156 mg, 1.20 mmol) and the mixture was stirred overnight at rt. The reaction mixture was purified by flash column chromatography, then preparative TLC to yield the title compound (41 mg, 23%) as a white solid. MS (ESI): mass calcd. for $C_{32}H_{33}N_5O_5S$, 599.7; m/z found, 600.3 [M+H]$^+$. $^1$H NMR (400 MHz, DMSO-d$_6$): δ 10.26 (s, 1H), 8.35-8.09 (m, 2H), 7.48-7.42 (m, 2H), 7.38-7.31 (m, 1H), 7.23-7.17 (m, 1H), 7.16-7.10 (m, 2H), 7.10-7.08 (m, 1H), 7.01-6.95 (m, 1H), 5.93 (s, 1H), 4.49-4.11 (m, 1H), 3.99-3.64 (m, 3H), 3.23-3.16 (m, 3H), 3.09-2.90 (m, 1H), 2.75-2.54 (m, 2H), 2.38-2.22 (m, 1H), 2.06 (s, 3H), 1.99-1.88 (m, 1H), 1.81-1.70 (m, 1H), 1.69-1.54 (m, 1H), 1.52-1.31 (m, 1H), 1.14-1.07 (m, 3H).

Example 156: N—((R)-1-((S)-3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide

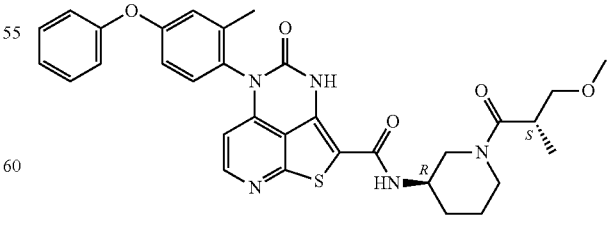

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), (2S)-3-methoxy-2-methylpropanoic acid (43 mg, 0.36 mmol), HATU (137 mg, 0.360 mmol), and triethylamine (0.125 mL, 0.897 mmol) in DMF (3 mL) was stirred at rt overnight. The reaction mixture was purified by flash column chromatography to yield the title compound as a white solid (120 mg, 70% yield). MS (ESI): mass calcd. for $C_{32}H_{33}N_5O_5S$, 599.7; m/z found, 600.2 [M+H]⁺. ¹H NMR (400 MHz, CD₃OD): δ 8.34 (d, J=5.5, 1H), 7.45-7.38 (m, 2H), 7.34-7.27 (m, 1H), 7.23-7.14 (m, 1H), 7.12-7.03 (m, 3H), 7.01-6.94 (m, 1H), 6.08 (d, J=5.5, 1H), 4.36-4.27 (m, 1H), 4.20-3.87 (m, 2H), 3.65-3.55 (m, 1H), 3.36 (s, 3H), 3.27-3.17 (m, 2H), 3.15-2.75 (m, 2H), 2.13 (s, 3H), 2.09-2.00 (m, 1H), 1.92-1.70 (m, 2H), 1.63-1.49 (m, 1H), 1.10-0.99 (m, 3H).

Example 157: (R)-5-(4-(2-Ethoxyphenoxy)-2-methylphenyl)-N-(1-methylpiperidin-3-yl)-4-oxo-4,5-dihydro-3H-1-thia-3,5,8-triazaacenaphthylene-2-carboxamide

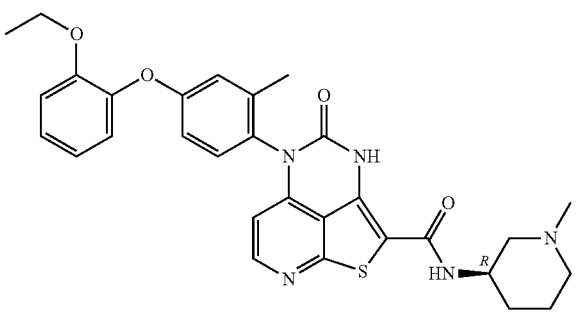

Step A: (R)-5-(4-(2-Ethoxyphenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 2-ethoxyphenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(2-Ethoxyphenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-ethoxyphenoxy)-2-methylphenyl)-4-oxo-N-(piperidin-3-yl)-4,5-dihydro-3H-1-thia-3,5,8-triazaacenaphthylene-2-carboxamide (542 mg, 0.997 mmol) in DCM (10 mL) were added formaldehyde (1 mL, 37 wt. % in H₂O) and NaBH(OAc)₃ (423 mg, 2.00 mmol) and stirred at rt for 4 h. To the reaction mixture were added DCM (50 mL), MeOH (5 mL), water (30 mL), and an aqueous solution of NH₄OH (2 mL). The organic layer was separated, concentrated to dryness, and purified by flash column chromatography, then by preparative TLC to yield the title compound as a yellow solid (90 mg, 26% yield). MS (ESI): mass calcd. for $C_{30}H_{31}N_5O_4S$, 557.7; m/z found, 558.5 [M+H]⁺. ¹H NMR (400 MHz, DMSO-d6): δ 8.29 (d, J=5.5 Hz, 1H), 8.09-7.97 (m, 1H), 7.26 (d, J=8.7 Hz, 1H), 7.22-7.15 (m, 2H), 7.14-7.10 (m, 1H), 7.01-6.96 (m, 1H), 6.94-6.91 (m, 1H), 6.79 (dd, J=8.6, 2.9 Hz, 1H), 5.86 (d, J=5.5 Hz, 1H), 4.04 (q, J=7.0 Hz, 2H), 3.99-3.93 (m, 1H), 2.91-2.84 (m, 1H), 2.76-2.68 (m, 1H), 2.26 (s, 3H), 2.01 (s, 3H), 2.02-1.92 (m, 2H), 1.82-1.74 (m, 1H), 1.74-1.66 (m, 1H), 1.59-1.48 (m, 1H), 1.42-1.32 (m, 1H), 1.19 (t, J=7.0 Hz, 3H).

Example 158: N-((3R)-1-(3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide

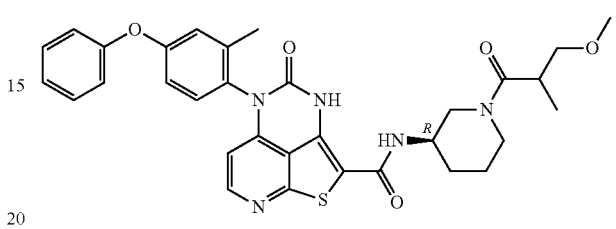

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 110 mg, 0.22 mmol) in DMF (3 mL) were added 3-methoxy-2-methylpropanoic acid (39 mg, 0.33 mmol), HATU (100 mg, 0.26 mmol) and triethylamine (0.123 mL, 0.880 mmol) and was stirred at rt for 4 h. The reaction mixture was purified by flash column chromatography to yield the title compound as a white solid (70 mg, 52% yield). MS (ESI): mass calcd. for $C_{32}H_{33}N_5O_5S$, 599.7; m/z found, 600.2 [M+H]⁺. ¹H NMR (400 MHz, CD₃OD): δ 8.32 (d, J=5.5, 1H), 7.46-7.36 (m, 2H), 7.33-7.28 (m, 1H), 7.21-7.15 (m, 1H), 7.11-7.03 (m, 3H), 7.00-6.94 (m, 1H), 6.07 (d, J=5.5, 1H), 4.38-4.23 (m, 1H), 4.20-3.88 (m, 2H), 3.62-3.52 (m, 1H), 3.38-3.31 (m, 3H), 3.26-3.19 (m, 2H), 3.15-3.01 (m, 1H), 2.86-2.73 (m, 1H), 2.12 (s, 3H), 2.07-2.01 (m, 1H), 1.89-1.79 (m, 1H), 1.76-1.66 (m, 1H), 1.61-1.45 (s, 1H), 1.15-1.01 (m, 3H).

Example 159: (R)-5-(2-Methyl-4-phenoxyphenyl)-4-oxo-N-(pyrrolidin-3-yl)-4,5-dihydro-3H-1-thia-3,5,8-triazaacenaphthylene-2-carboxamide

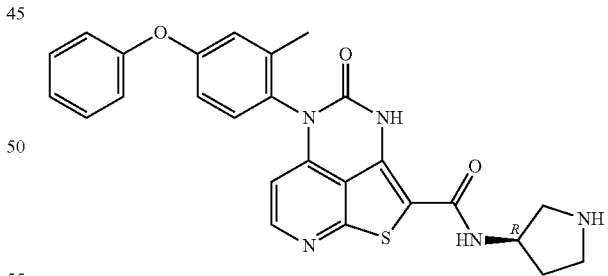

The title compound was prepared in a manner analogous to Method 1, steps A-H in Example 1, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{26}H_{23}N_5O_3S$, 485.6; m/z found, 486.1 [M+H]⁺. ¹H NMR (400 MHz, CDCl3): δ 8.31 (d, J=5.5 Hz, 1H), 7.41-7.33 (m, 2H), 7.19-7.12 (m, 2H), 7.11-7.05 (m, 2H), 7.01-6.97 (m, 1H), 6.97-6.91 (m, 1H), 6.44-6.27 (m, 1H), 5.97 (d, J=5.5 Hz, 1H), 4.64-4.50 (m, 1H), 3.25-3.10 (m, 2H), 3.06-2.89 (m, 2H), 2.30-2.17 (m, 1H), 2.11 (s, 3H), 1.84-1.72 (m, 1H).

Example 160: N-((3R,5R)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide

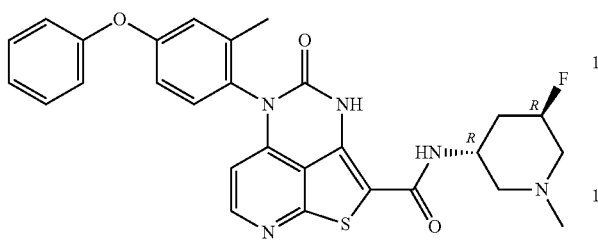

To a solution of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide (Example 138, 23 mg, 0.044 mmol) and formaldehyde (0.3 mL, 37 wt. % in H$_2$O) in MeOH (2 mL) was added NaBH(OAc)$_3$ (3.2 mg, 0.015 mmol) and stirred at rt overnight, concentrated to dryness, and purified by flash column chromatography to yield the title compound as a white solid (21 mg, 86% yield). MS (ESI): mass calcd. for C$_{28}$H$_{26}$FN$_5$O$_3$S, 531.6; m/z found, 532.2 [M+H]$^+$. $^1$H NMR (400 MHz, CD$_3$OD): δ 8.27 (d, J=5.5 Hz, 1H), 7.39-7.30 (m, 2H), 7.25 (d, J=8.6 Hz, 1H), 7.15-7.07 (m, 1H), 7.06-6.98 (m, 3H), 6.91 (dd, J=8.6, 2.8 Hz, 1H), 5.98 (d, J=5.5 Hz, 1H), 4.76-4.56 (m, 1H), 4.16-4.08 (m, 1H), 2.79-2.64 (m, 2H), 2.28 (s, 1H), 2.26 (s, 3H), 2.19-2.06 (m, 2H), 2.04 (s, 3H), 1.75-1.63 (m, 1H).

Example 161: (R)-5-(2-Methyl-4-phenoxyphenyl)-4-oxo-N-(1-propioloylpiperidin-3-yl)-4,5-dihydro-3H-1-thia-3,5,8-triazaacenaphthylene-2-carboxamide

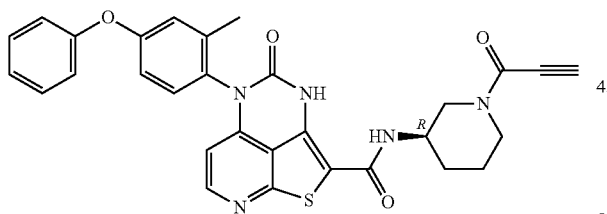

A solution of (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), prop-2-ynoic acid (42 mg, 0.60 mmol), HATU (148 mg, 0.390 mmol), and diisopropylethylamine (77 mg, 0.60 mmol) in DMF (5 mL) was stirred at rt for 2 h. The reaction mixture was purified by HPLC to yield the title compound as a yellow solid (82 mg, 49% yield). MS (ESI): mass calcd. for C$_{30}$H$_{25}$N$_5$O$_4$S, 551.6; m/z found, 552.6 [M+H]$^+$. $^1$H NMR (400 MHz, CD$_3$OD and DMSO-d$_6$): δ 8.30-8.24 (m, 1H), 7.40-7.32 (m, 2H), 7.31-7.25 (m, 1H), 7.15-7.08 (m, 1H), 7.07-6.98 (m, 3H), 6.93-6.88 (m, 1H), 5.98-5.93 (m, 1H), 4.39-3.74 (m, 4H), 3.26-3.05 (m, 1H), 2.86-2.67 (m, 1H), 2.03 (s, 3H), 1.98-1.89 (m, 1H), 1.84-1.70 (m, 1H), 1.69-1.57 (m, 1H), 1.53-1.33 (m, 1H).

Example 162: 5-(2-Methyl-4-phenoxyphenyl)-N-(1-methyl-6-oxopiperidin-3-yl)-4-oxo-4,5-dihydro-3H-1-thia-3,5,8-triazaacenaphthylene-2-carboxamide

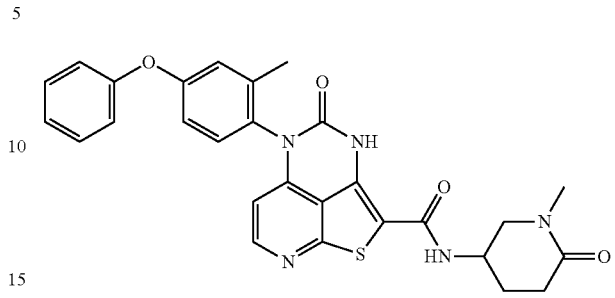

The title compound was prepared in a manner analogous to Method 1, steps A-G in Example 1, and using 5-amino-1-methylpiperidin-2-one in place of tert-butyl (3R,5R)-3-amino-5-fluoropiperidine-1-carboxylate (Intermediate 1) in step G. MS (ESI): mass calcd. for C$_{28}$H$_{25}$N$_5$O$_4$S, 527.6; m/z found, 528.3 [M+H]$^+$. $^1$H NMR (400 MHz, DMSO-d6): δ 8.36-8.25 (m, 2H), 7.50-7.39 (m, 2H), 7.35 (d, J=8.6 Hz, 1H), 7.25-7.15 (m, 1H), 7.14-7.04 (m, 3H), 7.00-6.92 (m, 1H), 5.95 (d, J=5.5 Hz, 1H), 4.31-4.15 (m, 1H), 3.50-3.36 (m, 2H), 2.79 (s, 3H), 2.37-2.25 (m, 2H), 2.05 (s, 3H), 1.97-1.83 (m, 2H).

Example 163: (R)—N-(1-(3-Aminopropanoyl)piperidin-3-yl)-5-(2-methyl-4-phenoxyphenyl)-4-oxo-4,5-dihydro-3H-1-thia-3,5,8-triazaacenaphthylene-2-carboxamide

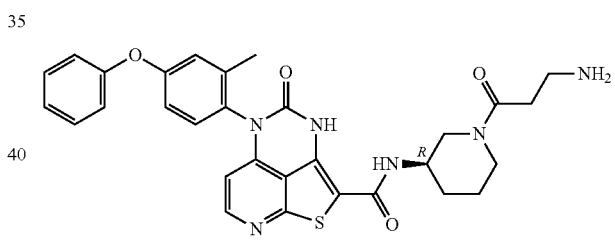

Step A: 3-(tert-Butoxycarbonylamino)propanoic Acid

To a solution of 3-aminopropanoic acid (1.0 g, 11 mmol) in DCM (50 mL) at 0° C. under a N$_2$ atmosphere were added DMAP (137 mg, 1.12 mmol) and tert-butoxycarbonyl tert-butyl carbonate (3.0 g, 14 mmol). The reaction was warmed to rt overnight. The reaction mixture was concentrated to dryness and was used in the next step without purification (1.5 g, 70% yield).

Step B: (R)-tert-Butyl (3-(3-(5-(2-methyl-4-phenoxyphenyl)-4-oxo-4,5-dihydro-3H-1-thia-3,5,8-triazaacenaphthylene-2-carboxamido)piperidin-1-yl)-3-oxopropyl)carbamate To a stirred solution of (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) in DMF (3 mL) were added 3-(tert-butoxycarbonylamino)propanoic acid (170 mg, 0.90 mmol), HATU (230 mg, 0.60 mmol), and diisopropylethylamine (120 mg, 0.93 mmol) and stirred at rt overnight. The solvent was removed and the residue was partitioned between ethyl acetate and water. The organic layer was separated, shaken with brine, and dried over anhydrous $Na_2SO_4$. The residue was purified by flash column chromatography to yield the title compound as brown solid (50 mg, 25% yield).

Step C: (R)—N-(1-(3-Aminopropanoyl)piperidin-3-yl)-5-(2-methyl-4-phenoxyphenyl)-4-oxo-4,5-dihydro-3H-1-thia-3,5,8-triazaacenaphthylene-2-carboxamide To a solution of (R)-tert-Butyl (3-(3-(5-(2-methyl-4-phenoxyphenyl)-4-oxo-4,5-dihydro-3H-1-thia-3,5,8-triazaacenaphthylene-2-carboxamido)piperidin-1-yl)-3-oxopropyl)carbamate (50 mg, 0.075 mmol) in MeOH (15 mL) was added concentrated HCl (1 mL) and was stirred at rt for about 2 h. The reaction was concentrated to dryness and purified by flash column chromatography to yield the title compound as a yellow solid (26 mg, 57% yield). MS (ESI): mass calcd. for $C_{30}H_{30}N_6O_4S$, 570.7; m/z found, 571.2 [M+H]$^+$. $^1$H NMR (400 MHz, $CD_3OD$): δ 8.49 (s, 1H), 8.29-8.21 (m, 1H), 7.44-7.33 (m, 2H), 7.28-7.22 (m, 1H), 7.18-7.10 (m, 1H), 7.10-7.01 (m, 3H), 6.99-6.91 (m, 1H), 6.04-5.94 (m, 1H), 4.29-4.06 (m, 1H), 4.05-3.60 (m, 2H), 3.20-3.09 (m, 3H), 3.00-2.74 (m, 2H), 2.13-2.06 (m, 3H), 2.05-1.52 (m, 5H).

Example 164: N-((3R,5S)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide

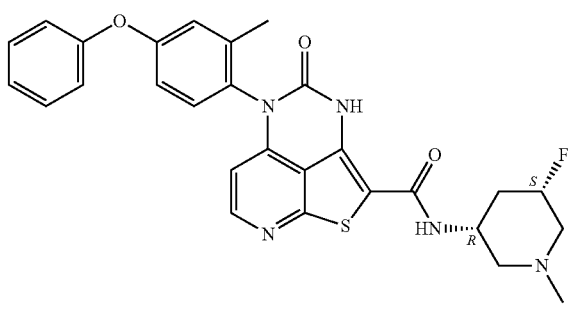

To a solution of N-((3R,5S)-5-fluoropiperidin-3-yl)-5-(2-methyl-4-phenoxyphenyl)-4-oxo-4,5-dihydro-3H-1-thia-3,5,8-triazaacenaphthylene-2-carboxamide (Example 167, 90 mg, 0.16 mmol) and formaldehyde (0.5 mL, 37 wt. % in $H_2O$) in methanol (25 mL) was added $NaBH(OAc)_3$ (102 mg, 0.481 mmol) and was stirred at rt for 16 h, concentrated to dryness, and purified by flash column chromatography to yield the title compound as a white solid (78 mg, 84% yield). MS (ESI): mass calcd. for $C_{28}H_{26}FN_5O_3S$, 531.6; m/z found, 532.2 [M+H]$^+$. $^1$H NMR (400 MHz, DMSO-d$_6$): δ 8.29 (d, J=5.5 Hz, 1H), 8.15 (s, 1H), 8.06 (d, J=8.1 Hz, 1H), 7.48-7.39 (m, 2H), 7.37-7.30 (m, 1H), 7.23-7.15 (m, 1H), 7.14-7.05 (m, 3H), 7.00-6.95 (m, 1H), 5.93 (d, J=5.4 Hz, 1H), 4.91 (d, J=47.4 Hz, 1H), 4.27-4.15 (m, 1H), 2.91-2.80 (m, 2H), 2.19 (s, 3H), 2.15-1.88 (m, 6H), 1.78-1.50 (m, 1H).

Example 165: N-(1,3-Dimethylpiperidin-4-yl)-5-(2-methyl-4-phenoxyphenyl)-4-oxo-4,5-dihydro-3H-1-thia-3,5,8-triazaacenaphthylene-2-carboxamide

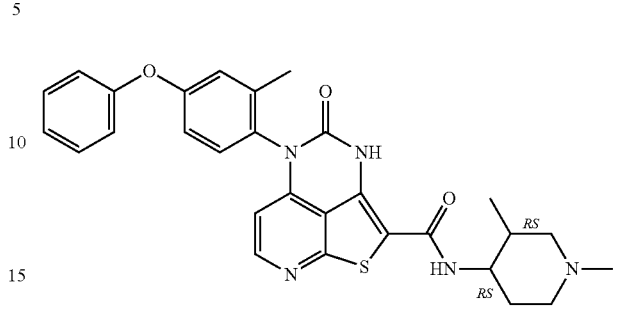

To a solution of 5-(2-methyl-4-phenoxyphenyl)-N-(3-methylpiperidin-4-yl)-4-oxo-4,5-dihydro-3H-1-thia-3,5,8-triazaacenaphthylene-2-carboxamide (Example 172, 90 mg, 0.18 mmol) and formaldehyde (0.5 mL, 37 wt. % in $H_2O$) in methanol (15 mL) was added $NaBH(OAc)_3$ (111 mg, 0.524 mmol) and was stirred at rt for 3 h, concentrated to dryness, and purified by flash column chromatography to yield the title compound as a yellow solid (71 mg, 77% yield). MS (ESI): mass calcd. for $C_{29}H_{29}N_5O_3S$, 527.6; m/z found, 528.3 [M+H]$^+$. $^1$H NMR (400 MHz, $CD_3OD$): δ 8.37-8.20 (m, 1H), 7.45-7.34 (m, 2H), 7.34-7.20 (m, 1H), 7.20-7.11 (m, 1H), 7.11-7.02 (m, 3H), 6.99-6.93 (m, 1H), 6.10-5.94 (m, 1H), 4.35-4.15 (m, 0.5H), 3.74-3.55 (m, 0.5H), 3.10-2.68 (m, 3H), 2.65-2.37 (m, 3H), 2.35-2.20 (m, 1H), 2.12 (s, 3H), 2.05-1.70 (m, 3H), 1.08-0.91 (m, 3H).

Example 166: 5-(2-Methyl-4-phenoxyphenyl)-4-oxo-N-(2-oxopiperidin-4-yl)-4,5-dihydro-3H-1-thia-3,5,8-triazaacenaphthylene-2-carboxamide

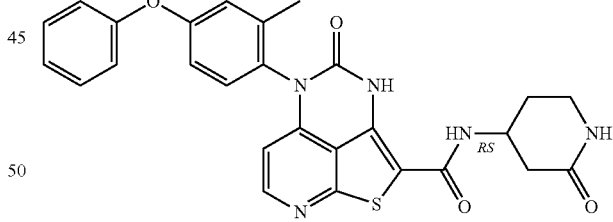

The title compound was prepared in a manner analogous to Method 1, steps A-G in Example 1, and using 4-aminopiperidin-2-one in place of tert-butyl (3R,5R)-3-amino-5-fluoropiperidine-1-carboxylate (Intermediate 1) in step G. MS (ESI): mass calcd. for $C_{27}H_{23}N_5O_4S$, 513.6; m/z found, 514.9 [M+H]$^+$. $^1$H NMR (400 MHz, DMSO-d6): δ 8.46-8.30 (br, 1H), 8.30-8.20 (m, 1H), 7.60-7.54 (m, 1H), 7.45-7.39 (m, 2H), 7.34-7.26 (m, 1H), 7.20-7.15 (m, 1H), 7.12-7.07 (m, 2H), 7.07-7.03 (m, 1H), 6.97-6.92 (m, 1H), 5.93-5.83 (m, 1H), 4.20-4.13 (m, 1H), 3.22-3.13 (m, 2H), 2.45-2.41 (m, 1H), 2.31-2.23 (m, 1H), 2.03 (s, 3H), 1.96-1.91 (m, 1H), 1.77-1.68 (m, 1H).

Example 167: N-((3R,5S)-5-fluoropiperidin-3-yl)-5-(2-methyl-4-phenoxyphenyl)-4-oxo-4,5-dihydro-3H-1-thia-3,5,8-triazaacenaphthylene-2-carboxamide

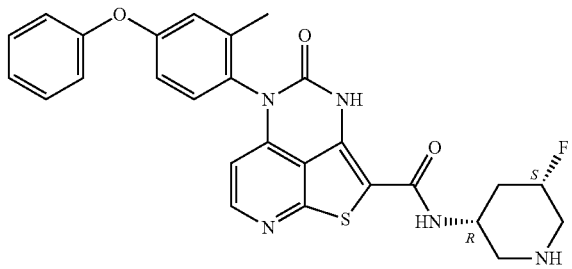

The title compound was prepared in a manner analogous to Method 1, steps A-H in Example 1, and using tert-butyl (3R,5S)-3-amino-5-fluoropiperidine-1-carboxylate (Intermediate 3) in place of tert-butyl (3R,5R)-3-amino-5-fluoropiperidine-1-carboxylate (Intermediate 1) in step G. MS (ESI): mass calcd. for $C_{27}H_{24}FN_5O_3S$, 517.6; m/z found, 518.3 [M+H]$^+$. $^1$H NMR (400 MHz, DMSO-d6): δ 8.29 (d, J=5.5 Hz, 1H), 8.15 (s, 1H), 8.05 (d, J=8.1 Hz, 1H), 7.52-7.38 (m, 2H), 7.34 (d, J=8.6 Hz, 1H), 7.24-7.15 (m, 1H), 7.15-7.03 (m, 3H), 7.02-6.91 (m, 1H), 5.93 (d, J=5.5 Hz, 1H), 4.90 (s, 0.5H), 4.78 (s, 0.5H), 4.20-4.09 (m, 1H), 3.05-2.90 (m, 2H), 2.79-2.51 (m, 2H), 2.20-2.07 (m, 1H), 2.04 (s, 3H), 1.98-1.72 (m, 1H).

Example 168: N-((3R,5R)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide

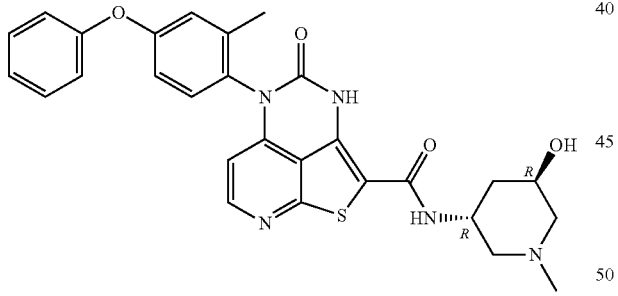

A solution of N-((3R,5R)-5-hydroxypiperidin-3-yl)-5-(2-methyl-4-phenoxyphenyl)-4-oxo-4,5-dihydro-3H-1-thia-3,5,8-triazaacenaphthylene-2-carboxamide (Example 179, 80 mg, 0.16 mmol) in DCM (5 mL) was treated with formaldehyde (0.5 mL, 37 wt. % in H$_2$O). To the stirred reaction mixture was added NaBH(OAc)$_3$ (100 mg, 0.47 mmol) and the reaction mixture was maintained at rt for 1 h, and then concentrated to dryness. The residue was purified by flash column chromatography to yield the title compound as a yellow solid (53 mg, 59% yield). MS (ESI): mass calcd. for $C_{28}H_{27}N_5O_4S$, 529.6; m/z found, 530.2 [M+H]$^+$. $^1$H NMR (400 MHz, CD$_3$OD): δ 8.44 (s, 1H), 8.36-8.30 (m, 1H), 7.46-7.37 (m, 2H), 7.34-7.27 (m, 1H), 7.21-7.14 (m, 1H), 7.13-7.04 (m, 3H), 7.01-6.94 (m, 1H), 6.11-6.04 (m, 1H), 4.76-4.61 (m, 1H), 4.28-4.21 (m, 1H), 3.48-3.36 (m, 1H), 3.24-3.10 (m, 1H), 3.08-2.95 (m, 1H), 2.84-2.75 (m, 4H), 2.12 (s, 3H), 2.09-1.99 (m, 1H), 1.96-1.82 (m, 1H).

Example 169: (R)—N-(1-Acryloylpyrrolidin-3-yl)-5-(*R)-(2-methyl-4-phenoxyphenyl)-4-oxo-4,5-dihydro-3H-1-thia-3,5,8-triazaacenaphthylene-2-carboxamide

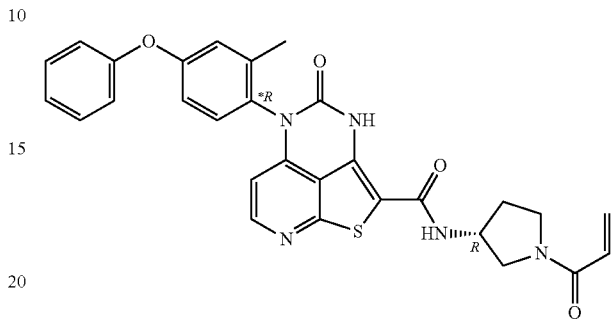

The title compound was prepared in a manner analogous to Method 1, steps A-I in Example 1 (including Chiral resolution Method A after Step F to obtain the *R atropisomer), and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{25}N_5O_4S$, 539.6; m/z found, 540.3 [M+H]$^+$. $^1$H NMR (400 MHz, DMSO-d$_6$): δ 10.23 (s, 1H), 8.42-8.25 (m, 2H), 7.52-7.31 (m, 3H), 7.24-7.05 (m, 4H), 7.02-6.90 (m, 1H), 6.68-6.48 (m, 1H), 6.13 (d, J=18.0 Hz, 1H), 6.03-5.93 (m, 1H), 5.72-5.57 (m, 1H), 4.60-4.32 (m, 1H), 3.91-3.35 (m, 4H), 2.24-1.91 (m, 5H).

Example 170: (R)-5-(4-(2-Ethylphenoxy)-2-methylphenyl)-N-(1-methylpiperidin-3-yl)-4-oxo-4,5-dihydro-3H-1-thia-3,5,8-triazaacenaphthylene-2-carboxamide

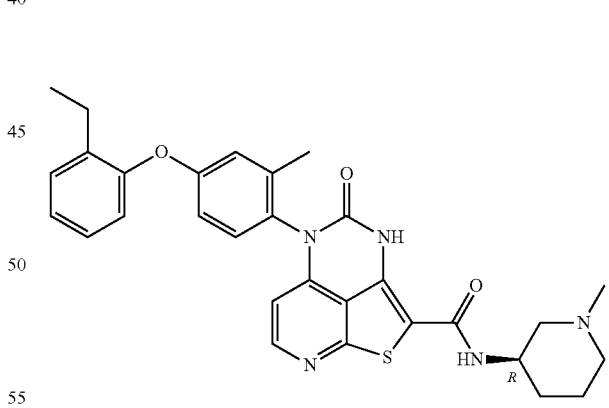

Step A: (R)-5-(4-(2-Ethylphenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 2-ethylphenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(2-Ethylphenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-ethylphenoxy)-2-methylphenyl)-4-oxo-N-(piperidin-3-yl)-4,5-dihydro-3H-1-thia-3,5,8-triazaacenaphthylene-2-carboxamide (60 mg, 0.11 mmol) in DCM (2 mL) were added formaldehyde (0.5 mL, 37 wt. % in $H_2O$) and $NaBH(OAc)_3$ (70 mg, 0.33 mmol) and was reacted at rt for 20 min. The reaction was quenched by the addition of $H_2O$ (10 mL), extracted with DCM, dried over anhydrous $Na_2SO_4$, filtered, and concentrated to dryness. The residue was purified by flash column chromatography and preparative TLC to yield the title compound as a yellow solid (51 mg, 82% yield). MS (ESI): mass calcd. for $C_{30}H_{31}N_5O_3S$, 541.7; m/z found, 544.2 $[M+H]^+$. $^1H$ NMR (400 MHz, $CD_3OD$): δ 8.28 (d, J=5.6 Hz, 1H), 7.35-7.29 (m, 1H), 7.27-7.20 (m, 2H), 7.18-7.12 (m, 1H), 7.00-6.93 (m, 2H), 6.88-6.83 (m, 1H), 6.02 (d, J=5.6 Hz, 1H), 4.21-4.06 (m, 1H), 2.96-2.87 (m, 1H), 2.76-2.68 (m, 1H), 2.66-2.56 (m, 2H), 2.33 (s, 3H), 2.26-2.13 (m, 2H), 2.09 (s, 3H), 1.91-1.78 (m, 2H), 1.72-1.63 (m, 1H), 1.55-1.48 (m, 1H), 1.22-1.16 (m, 3H).

Example 171: 5-(2-Methyl-4-phenoxyphenyl)-4-oxo-N-(quinuclidin-2-yl)-4,5-dihydro-3H-1-thia-3,5,8-triazaacenaphthylene-2-carboxamide

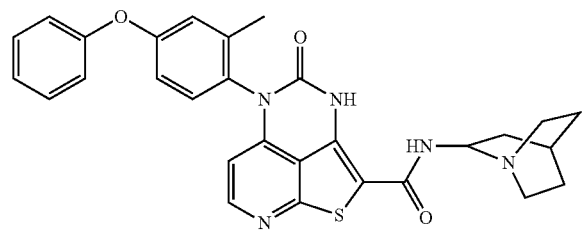 [SMILES: Cc1cc(Oc2ccccc2)ccc1N1C(=O)Nc2c(C(=O)NC3CC4CCN3CC4)sc3nccc1c23]

The title compound was prepared in a manner analogous to Method 1, steps A-G in Example 1, and using 3-aminoquinuclidine and THF in place of tert-butyl (3R,5R)-3-amino-5-fluoropiperidine-1-carboxylate and DMF in step G. MS (ESI): mass calcd. for $C_{29}H_{27}N_5O_3S$, 525.6; m/z found, 526.0 $[M+H]^+$. 1H NMR (500 MHz, DMSO-d6) δ 8.82 (s, 1H), 8.42-8.08 (m, 1H), 7.59-7.40 (m, 2H), 7.40-7.07 (m, 6H), 7.07-6.90 (m, 1H), 6.05-5.70 (m, 1H), 4.08 (s, 1H), 3.10-2.69 (m, 5H), 2.14-1.93 (m, 6H), 1.86-1.67 (m, 2H), 1.67-1.47 (m, 1H).

Example 172: 5-(2-Methyl-4-phenoxyphenyl)-N-(3-methylpiperidin-4-yl)-4-oxo-4,5-dihydro-3H-1-thia-3,5,8-triazaacenaphthylene-2-carboxamide

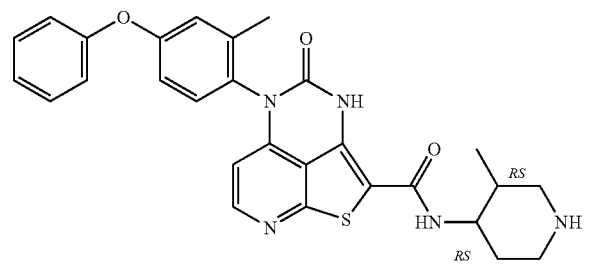

The title compound was prepared in a manner analogous to Method 1, steps A-H in Example 1, and using tert-butyl 4-amino-3-methylpiperidine-1-carboxylate and THF in place of tert-butyl (3R,5R)-3-amino-5-fluoropiperidine-1-carboxylate and DMF in step G. MS (ESI): mass calcd. for $C_{28}H_{27}N_5O_3S$, 513.6; m/z found, 514.3 $[M+H]^+$. $^1H$ NMR (400 MHz, $CD_3OD$ and DMSO-$d_6$): δ 8.34-8.24 (m, 1H), 7.44-7.33 (m, 2H), 7.28 (d, J=8.5 Hz, 1H), 7.18-7.09 (m, 1H), 7.10-6.99 (m, 3H), 6.97-6.86 (m, 1H), 5.99-5.90 (m, 1H), 4.38-4.15 (m, 0.5H), 3.86-3.78 (m, 0.5H), 3.35-3.14 (m, 2H), 3.12-2.92 (m, 2H), 2.77-2.62 (m, 0.5H), 2.33-2.18 (m, 0.5H), 2.03 (s, 3H), 1.97-1.77 (m, 2H), 0.98-0.85 (m, 3H).

Example 173: 5-(2-Methyl-4-phenoxyphenyl)-N-((6R)-6-methylpiperidin-3-yl)-4-oxo-4,5-dihydro-3H-1-thia-3,5,8-triazaacenaphthylene-2-carboxamide

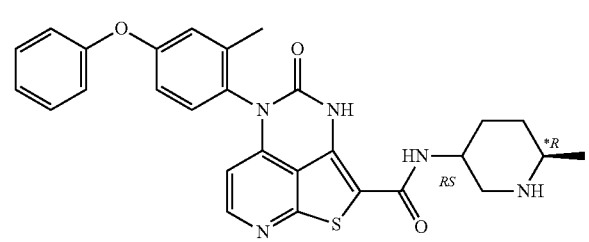

The title compound was prepared in a manner analogous to Method 1, steps A-H in Example 1, and using benzyl 5-amino-2-methylpiperidine-1-carboxylate (Intermediate 20) in place of tert-butyl (3R,5R)-3-amino-5-fluoropiperidine-1-carboxylate (Intermediate 1) in step G and TFA in place of MeOH and aqueous HCl in Step H. Example 153 and Example 173 were separated from the same reaction mixture by flash column chromatography (C-18, MeOH/$H_2O$) followed by preparative TLC. MS (ESI): mass calcd. for $C_{28}H_{27}N_5O_3S$, 513.6; m/z found, 544.2 $[M+H]^+$. $^1H$ NMR (400 MHz, $CD_3OD$): δ 8.40-8.33 (m, 1H), 7.45-7.37 (m, 2H), 7.33-7.26 (m, 1H), 7.21-7.14 (m, 1H), 7.11-7.02 (m, 3H), 7.00-6.92 (m, 1H), 6.12-6.05 (m, 1H), 4.33-4.17 (m, 1H), 3.60-3.48 (m, 1H), 3.23-3.15 (m, 1H), 2.97-2.84 (m, 1H), 2.15-2.04 (m, 5H), 1.84-1.73 (m, 1H), 1.67-1.58 (m, 1H), 1.41-1.32 (m, 3H).

Example 174: (R)—N-(5,5-Difluoropiperidin-3-yl)-5-(2-methyl-4-phenoxyphenyl)-4-oxo-4,5-dihydro-3H-1-thia-3,5,8-triazaacenaphthylene-2-carboxamide

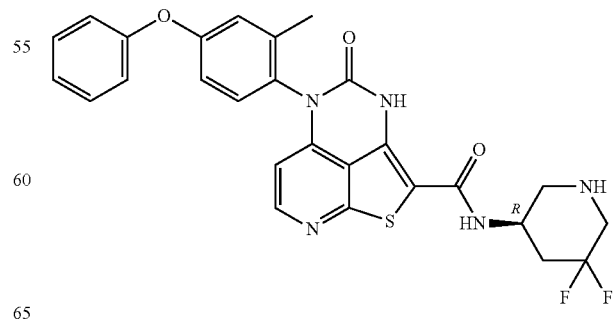

The title compound was prepared in a manner analogous to Method 1, steps A-H in Example 1, and using tert-butyl (5R)-5-amino-3,3-difluoropiperidine-1-carboxylate in place of tert-butyl (3R,5R)-3-amino-5-fluoropiperidine-1-carboxylate (Intermediate 1) in step G. MS (ESI): mass calcd. for $C_{27}H_{23}F_2N_5O_3S$, 535.6; m/z found, 535.9 [M+H]$^+$. $^1$H NMR (400 MHz, DMSO-d6): δ 8.32 (d, J=5.5 Hz, 1H), 8.07 (d, J=8.0 Hz, 1H), 7.47-7.41 (m, 2H), 7.36 (d, J=8.6 Hz, 1H), 7.22-7.18 (m, 1H), 7.16-7.05 (m, 3H), 7.01-6.95 (m, 1H), 5.96 (d, J=5.5 Hz, 1H), 4.10-4.00 (m, 1H), 3.03-2.90 (m, 2H), 2.80-2.66 (m, 1H), 2.45-2.40 (m, 1H), 2.37-2.27 (m, 1H), 2.05 (s, 3H), 2.02-1.94 (m, 1H).

Example 175: (R,E)-N-(1-(2-Cyano-3-cyclopropylacryloyl)piperidin-3-yl)-5-(2,6-difluoro-4-phenoxyphenyl)-4-oxo-4,5-dihydro-3H-1-thia-3,5,8-triazaacenaphthylene-2-carboxamide

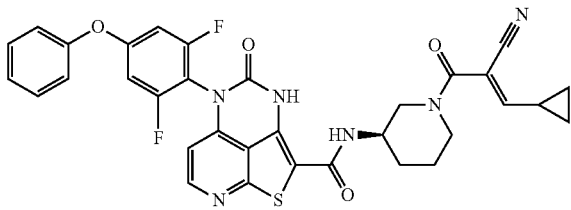 [SMILES: N#C/C(=C\C1CC1)C(=O)N1CCC[C@@H](NC(=O)c2sc3nccc4c3c2NC(=O)N4c2c(F)cc(Oc3ccccc3)cc2F)C1]

Step A: 1,3-Difluoro-2-nitro-5-phenoxybenzene

To a solution of 3,5-difluoro-4-nitrophenol (Intermediate 26) (493 mg, 2.82 mmol) in CH$_3$CN (45 mL) was added (2-trimethylsilylphenyl) trifluoromethanesulfonate (1.0 mL, 4.2 mmol), followed by cesium fluoride (1.28 g, 8.45 mmol). The mixture was stirred at rt overnight (argon needle inlet). The reaction mixture was washed with saturated aqueous NaCl (50 mL) and the aqueous phase was extracted once with Et$_2$O (50 mL). The combined organic extracts were dried over anhydrous Na$_2$SO$_4$, filtered, concentrated to dryness, and purified by flash column chromatography to yield the title compound as a yellow oil mass (450.7 mg. 64%)

Step B: 2,6-difluoro-4-phenoxyaniline

The title compound was prepared in a manner analogous to Method 1, step B in Example 1, and using 1,3-difluoro-2-nitro-5-phenoxybenzene in place of 2-Methyl-1-nitro-4-phenoxybenzene in step B.

Step C: 2-Chloro-4-(2,6-difluoro-4-phenoxyanilino) pyridine-3-carbonitrile

The title compound was prepared in a manner analogous to Method 1, step C in Example 1, and using 2,6-difluoro-4-phenoxyaniline in place of 2-Methyl-4-phenoxyaniline in step C.

Step D: tert-Butyl (3R)-3-[(2-sulfanylacetyl)amino] piperidine-1-carboxylate

A 20 mL microwave vial was charged with (R)-1-boc-3-aminopiperdine (5.0 g, 25 mmol). The vial was sealed, evacuated, and back-filled with argon three times. Methyl 2-mercaptoacetate (6.7 mL, 170 mmol) was added via syringe in one portion and was heated to 150° C. in an oil bath. After 1 h 35 minutes, the mixture was cooled to rt and purified by flash column chromatography to yield a colorless oil (6.15 g. 90%).

Step E: (R)-tert-Butyl 3-(3-amino-4-((2,6-difluoro-4-phenoxyphenyl)amino)thieno[2,3-b]pyridine-2-carboxamido)piperidine-1-carboxylate To the sealed tube containing 2-chloro-4-(2,6-difluoro-4-phenoxyanilino)pyridine-3-carbonitrile (580 mg, 1.6 mmol) was added a 0.56 M solution of tert-butyl (3R)-3-[(2-sulfanylacetyl)amino]piperidine-1-carboxylate in dioxane (3.5 mL, 1.9 mmol). The resulting brown suspension was heated in the sealed tube under argon at 150° C. in an oil bath for 15 minutes. The mixture was cooled to rt and was used directly in the next reaction.

Step F: (R)-tert-butyl 3-(5-(2,6-difluoro-4-phenoxyphenyl)-4-oxo-4,5-dihydro-3H-1-thia-3,5,8-triazaacenaphthylene-2-carboxamido)piperidine-1-carboxylate To a solution of (R)-tert-butyl 3-(3-amino-4-((2,6-difluoro-4-phenoxyphenyl)amino)thieno[2,3-b]pyridine-2-carboxamido)piperidine-1-carboxylate (966 mg, 1.62 mmol) in dioxane (3.5 mL) was added CDI (1.05 g, 6.49 mmol) and was heated at 150° C. in an oil bath for 10 minutes. The mixture was cooled to rt and was partitioned between EtOAc (50 mL) and water (50 mL). The aqueous phase was extracted with EtOAc (2×50 mL) and the combined organic extracts were washed with saturated aqueous NaCl (50 mL). The organic phase was dried over anhydrous Na$_2$SO$_4$ and filtered. The filtrate was concentrated to dryness and the residue was purified by flash column chromatography to yield the title compound as a tan solid (562 mg, 56%).

Step G: (R,E)-N-(1-(2-Cyano-3-cyclopropylacryloyl)piperidin-3-yl)-5-(2,6-difluoro-4-phenoxyphenyl)-4-oxo-4,5-dihydro-3H-1-thia-3,5,8-triazaacenaphthylene-2-carboxamide A suspension of (R)-5-(2,6-difluoro-4-phenoxyphenyl)-4-oxo-N-(piperidin-3-yl)-4,5-dihydro-3H-1-thia-3,5,8-triazaacenaphthylene-2-carboxamide (Example 235) (28.6 mg, 0.0548 mmol) in THF (2 mL) was sonicated to produce a milky suspension. To this suspension was added triethylamine (11 µL, 0.082 mmol) followed by a solution of (E)-2-cyano-3-cyclopropylprop-2-enoyl chloride (Intermediate 23) (0.060 mmol) in CHCl$_3$ (from step H above). The reaction mixture was stirred at rt for 1 h, concentrated to dryness, and purified by flash column chromatography and HPLC to yield the title compound as a white solid (17.9 mg, 51%). MS (ESI): mass calcd. for $C_{33}H_{26}F_2N_6O_4S$, 640.7; m/z found, 641.3 [M+H]$^+$. 1H NMR (400 MHz, CDCl$_3$) δ 9.42-9.68 (m, 1H), 8.45 (d, J=5.56 Hz, 1H), 7.39-7.55 (m, 2H), 7.29 (t, J=7.33 Hz, 1H), 7.14 (d, J=7.58 Hz, 2H), 6.70 (d, J=9.09 Hz, 2H), 6.28 (d, J=6.06 Hz, 1H), 4.13-4.22 (m, 1H), 3.39-4.02 (m, 3H), 1.65-2.16 (m, 6H), 1.21-1.33 (m, 3H), 0.92-1.04 (m, 1H).

Example 176: $^{13}C$—(R,Z)—N-(1-(2-Cyano-3-cyclo-proplacryloyl)piperidin-3-yl)-5-(4-methoxy-2-methylphenyl)-4-oxo-4,5-dihydro-3H-1-thia-3,5,8-triazaacenaphthylene-2-carboxamide

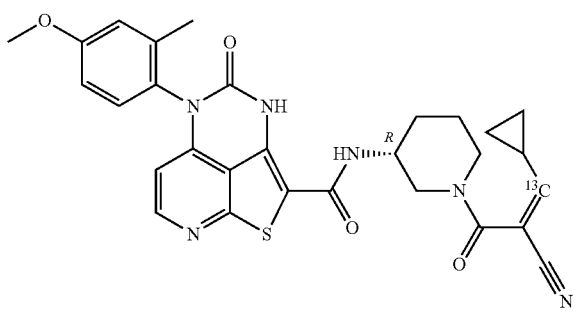

Step A: $^{13}C$-Cyclopropanecarbaldehyde

A solution of $^{13}C$—N,N-dimethylformamide (500 mg, 6.75 mmol) in THF (10 mL) was slowly added to cyclopropylmagnesiumbromide in THF (0.5 M, 15 mL, 7.4 mmol) in an ice bath under $N_2$ over a period of 5 min. The mixture was brought to rt and stirred for 1 h, then the mixture was acidified with 3 M aqueous HCl, extracted with $Et_2O$, dried over anhydrous $Na_2SO_4$, and concentrated to dryness to yield the title compound as a pale yellow oil (320 mg, 62%), which was used without purification in next step.

Step B: $^{13}C$—(R,Z)—N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide A solution of (R)-5-(4-methoxy-2-methylphenyl)-4-oxo-N-(piperidin-3-yl)-4,5-dihydro-3H-1-thia-3,5,8-triazaacenaphthylene-2-carboxamide (prepared as in Example 110, Step B, 250 mg, 0.57 mmol), 2-cyanoacetic acid (97 mg, 1.1 mmol), triethylamine (115 mg, 1.14 mmol), and HATU (434 mg, 1.14 mmol) in DMF (3 mL) was stirred at rt for 3 h. The reaction was quenched by the addition of water and the precipitate was filtered to give a pale yellow solid. To a mixture of this solid and $^{13}C$-cyclopropanecarbaldehyde (122 mg, 1.71 mmol) in EtOH (5 mL) was added piperidine (97 mg, 1.1 mmol) and was stirred at rt for 1 h, concentrated to dryness, and purified by by flash chromatography (C-18, MeOH/$H_2O$) to yield the title compound as a white solid (12 mg, 4%). MS (ESI): mass calcd. for $C_{29}H_{28}N_6O_4S$, 557.6; m/z found, 558.4 $[M+H]^+$. $^1H$ NMR (400 MHz, DMSO-$d_6$ and $CD_3OD$): δ 8.25 (d, J=5.3 Hz, 1H), 7.19 (d, J=8.8 Hz, 1H), 6.97 (s, 1H), 6.89 (d, J=8.8 Hz, 1H), 6.53-6.01 (m, 1H), 5.86 (d, J=5.3 Hz, 1H), 4.39-4.21 (m, 1H), 3.90-3.84 (m, 1H), 3.78 (s, 3H), 3.72-3.63 (m, 1H), 3.30-3.13 (m, 1H), 2.95-2.84 (m, 1H), 2.03 (s, 3H), 2.00-1.89 (m, 2H), 1.86-1.78 (m, 1H), 1.68-1.63 (m, 1H), 1.52-1.44 (m, 1H), 1.09-0.97 (m, 2H), 0.82-0.75 (m, 2H).

Example 177: $^{13}C$—(R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide

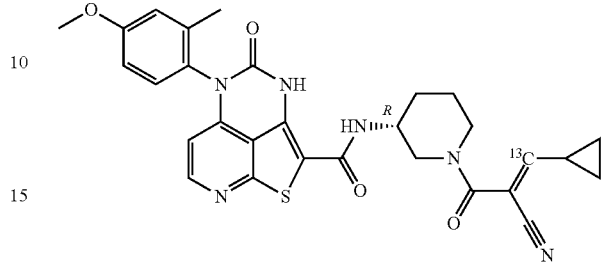

The title compound was made using the same procedure as described in Example 176, but the other isomer was isolated by flash chromatography (C-18, MeOH/$H_2O$). MS (ESI): mass calcd. for $C_{29}H_{28}N_6O_4S$, 557.6; m/z found, 558.4 $[M+H]^+$. $^1H$ NMR (400 MHz, DMSO-$d_6$ and $CD_3OD$): δ 8.26 (d, J=5.4 Hz, 1H), 7.20 (d, J=8.7 Hz, 1H), 6.97 (s, 1H), 6.90 (d, J=8.6 Hz, 1H), 6.77-6.24 (m, 1H), 5.88 (d, J=5.4 Hz, 1H), 3.95-3.82 (m, 2H), 3.78 (s, 3H), 3.71-3.57 (m, 1H), 3.10-2.76 (m, 2H), 2.03 (s, 3H), 1.97-1.86 (m, 2H), 1.82-1.75 (m, 1H), 1.71-1.61 (m, 1H), 1.503-1.43 (m, 1H), 1.16-1.09 (m, 2H), 1.00-0.88 (m, 1H), 0.84-0.77 (m, 1H).

Example 178: (R,E)-N-(1-(2-Cyano-3-cyclopropylacryloyl)piperidin-3-yl)-5-(4-(cyclohexyloxy)-2-methylphenyl)-4-oxo-4,5-dihydro-3H-1-thia-3,5,8-triazaacenaphthylene-2-carboxamide

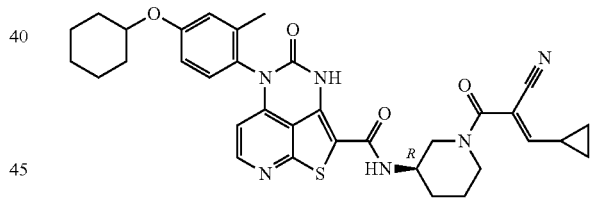

Step A: 2-Chloro-4-[4-(cyclohexoxy)-2-methylanilino]pyridine-3-carbonitrile To a cold (0° C.) solution of 2-chloro-4-(4-hydroxy-2-methylanilino)pyridine-3-carbonitrile (Intermediate 14) (1.0 g, 3.8 mmol), cyclohexanol (1.16 g, 11.6 mmol), and $PPh_3$ (1.5 g, 5.7 mmol) in THF (20 mL) was added DIAD (1.17 g, 5.79 mmol) and was stirred at rt overnight. The mixture was concentrated to dryness and the residue was purified by flash column chromatography to yield the title compound as a yellow solid (400 mg, 30% yield).

Step B: (R)-5-(4-(Cyclohexyloxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps D-H in Example 1, and using 2-chloro- 4-[4-(cyclohexoxy)-2-methylanilino]pyridine-3-carbonitrile in place of 2-chloro-4-(2-methyl-4-phenoxyanilino)pyridine-3-carbonitrile in step D, and using tert-butyl (3R)-3-aminopiperidine-1-carboxylate in place of tert-butyl (3R,5R)-3-amino-5-fluoropiperidine-1-carboxylate (Intermediate 1) in step G.

Step C: (R,E)-N-(1-(2-Cyano-3-cyclopropylacryloyl)piperidin-3-yl)-5-(4-(cyclohexyloxy)-2-methylphenyl)-4-oxo-4,5-dihydro-3H-1-thia-3,5,8-triazaacenaphthylene-2-carboxamide To a stirred solution of (R)-5-(4-(cyclohexyloxy)-2-methylphenyl)-4-oxo-N-(piperidin-3-yl)-4,5-dihydro-3H-1-thia-3,5,8-triazaacenaphthylene-2-carboxamide (100 mg, 0.20 mmol) in DMF (3 mL) were added (E)-2-cyano-3-cyclopropylprop-2-enoic acid (Intermediate 17) (43 mg, 0.31 mmol), HATU (120 mg, 0.32 mmol), and diisopropylethylamine (67 mg, 0.52 mmol) and was stirred at rt overnight, concentrated to dryness, and the residue partitioned between ethyl acetate and water. The organic layer was separated, shaken with brine, and dried over anhydrous $Na_2SO_4$. The residue was purified by flash column chromatography to yield the title compound as a brown solid (26 mg, 16% yield). MS (ESI): mass calcd. for $C_{34}H_{36}N_6O_4S$, 624.8; m/z found, 625.1 [M+H]$^+$. $^1$H NMR (400 MHz, CD$_3$OD): δ 8.46 (s, 1H), 8.31 (d, J=5.5 Hz, 1H), 7.22-7.14 (m, 1H), 7.01-6.95 (m, 1H), 6.95-6.88 (m, 1H), 6.60-6.48 (m, 1H), 6.03 (d, J=5.5 Hz, 1H), 4.44-4.33 (m, 1H), 4.11-3.94 (m, 2H), 2.10 (s, 3H), 2.06-1.95 (m, 4H), 1.94-1.65 (m, 5H), 1.64-1.26 (m, 10H), 1.25-1.14 (m, 2H), 1.06-0.77 (m, 2H).

Example 179: N-((3R,5R)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide

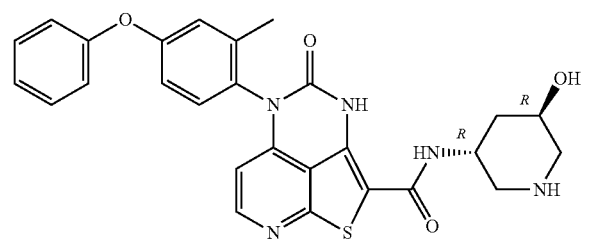

The title compound was prepared in a manner analogous to Method 1, steps A-H in Example 1, and using tert-butyl (3R,5R)-3-amino-5-hydroxypiperidine-1-carboxylate (Intermediate 4) in place of tert-butyl (3R,5R)-3-amino-5-fluoropiperidine-1-carboxylate (Intermediate 1) in step G. MS (ESI): mass calcd. for $C_{27}H_{25}N_5O_4S$, 515.6; m/z found, 516.3 [M+H]$^+$. $^1$H NMR (400 MHz, CD$_3$OD): δ 8.24 (d, J=5.6 Hz, 1H), 7.45-7.35 (m, 2H), 7.29-7.23 (m, 1H), 7.20-7.13 (m, 1H), 7.12-7.04 (m, 3H), 7.00-6.94 (m, 1H), 5.98 (d, J=5.6 Hz, 1H), 4.52-4.37 (m, 1H), 4.09-3.98 (m, 1H), 3.22-3.11 (m, 1H), 2.91-2.81 (m, 2H), 2.76-2.65 (m, 1H), 2.12 (s, 3H), 2.07-1.87 (m, 2H).

Example 180: (R)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide

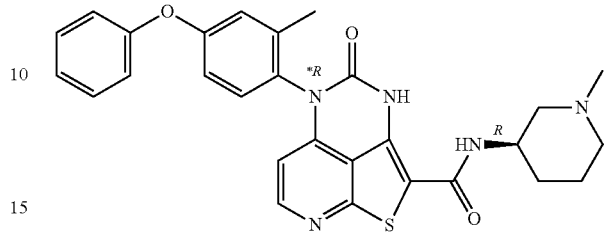

The title compound was prepared in a manner analogous to Method 1, steps A-G in Example 1 (including Chiral resolution Method A after Step F to obtain the *R atropisomer), and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{28}H_{27}N_5O_3S$, 513.6; m/z found, 514.2 [M+H]$^+$. $^1$H NMR (400 MHz, CD$_3$OD): δ 8.31 (d, J=5.5, 1H), 7.46-7.36 (m, 2H), 7.33-7.24 (m, 1H), 7.22-7.14 (m, 1H), 7.12-7.02 (m, 3H), 7.02-6.93 (m, 1H), 6.05 (d, J=5.6, 1H), 4.24-4.11 (m, 1H), 3.02-2.89 (m, 1H), 2.80-2.66 (m, 1H), 2.36 (s, 3H), 2.31-2.17 (m, 2H), 2.12 (s, 3H), 1.94-1.80 (m, 2H), 1.75-1.61 (m, 1H), 1.56-1.45 (m, 1H).

Example 181: (R)—N-(1-(2-Cyanoacetyl)piperidin-3-yl)-4-oxo-5-(4-phenoxyphenyl)-4,5-dihydro-3H-1-thia-3,5,8-triazaacenaphthylene-2-carboxamide

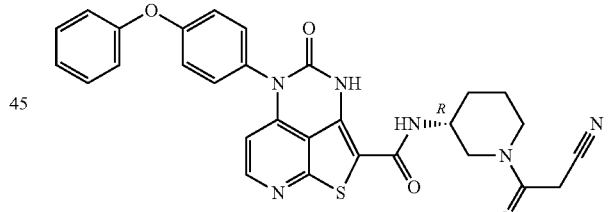

To an oven dried microwave vial with a stir bar under Ar were added (R)-4-oxo-5-(4-phenoxyphenyl)-N-(piperidin-3-yl)-4,5-dihydro-3H-1-thia-3,5,8-triazaacenaphthylene-2-carboxamide (Example 860, 313.4 mg, 0.523 mmol), cyanoacetic acid (72 mg, 0.84 mmol), HATU (258 mg, 0.680 mmol), and triethylamine (0.147 mL, 1.04 mmol) in THF (2.1 mL) and was warmed in the microwave for 5 min at 100° C. The reaction mixture was filtered and purified by HPLC to yield the title compound (203 mg, 58% yield). MS (ESI): mass calcd. for $C_{29}H_{24}N_6O_4S$, 552.6; m/z found, 553.0 [M+H]$^+$. $^1$H NMR (500 MHz, CD$_3$OD): δ 8.42-8.24 (m, 1H), 7.50-7.37 (m, 4H), 7.24-7.05 (m, 5H), 6.27-6.13 (m, 1H), 4.53-4.30 (m, 1H), 4.03-3.60 (m, 4H), 3.23-2.68 (m, 2H), 2.16-1.48 (m, 4H).

Example 182: (R)—N-(1-Methylpiperidin-3-yl)-4-oxo-5-(4-phenoxyphenyl)-4,5-dihydro-3H-1-thia-3,5,8-triazaacenaphthylene-2-carboxamide

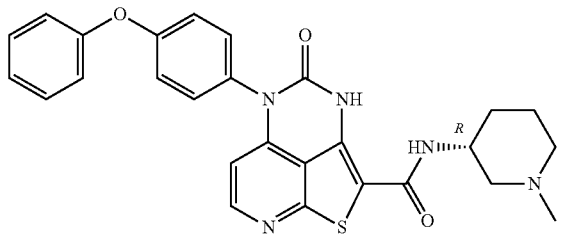

To an oven dried microwave vial with a stir bar under Ar were added (R)-4-oxo-5-(4-phenoxyphenyl)-N-(piperidin-3-yl)-4,5-dihydro-3H-1-thia-3,5,8-triazaacenaphthylene-2-carboxamide (Example 860, 69.5 mg, 0.143 mmol), sodium cyanoborohydride (19.7 mg, 0.313 mmol), and MeOH (3 mL) and was cooled to 0° C. in an ice bath. Next, was added via a syringe was aqueous formaldehyde (0.01 mL, 37 wt. % in H$_2$O) and allowed to slowly warm to rt. The reaction mixture was filtered and purified by HPLC to yield the title compound as a white fluffy solid (25.3 mg, 35% yield). MS (ESI): mass calcd. for C$_{27}$H$_{25}$N$_5$O$_3$S, 499.6; m/z found, 500.1 [M+H]$^+$. $^1$H NMR (500 MHz, CD$_3$OD): δ 8.27 (d, J=5.6 Hz, 1H), 7.50-7.31 (m, 4H), 7.24-7.03 (m, 6H), 6.14 (d, J=5.6 Hz, 1H), 4.27-4.05 (m, 1H), 2.99-2.63 (m, 2H), 2.33 (s, 3H), 2.25-2.07 (m, 2H), 1.97-1.41 (m, 4H).

Example 183: (R)-5-(*S)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide

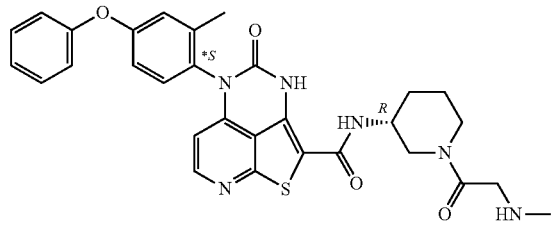

Step A: (R)-tert-Butyl methyl(2-(3-(5-(*S)-(2-methyl-4-phenoxyphenyl)-4-oxo-4,5-dihydro-3H-1-thia-3,5,8-triazaacenaphthylene-2-carboxamido)piperidin-1-yl)-2-oxoethyl)carbamate To a solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 30 mg, 0.056 mmol), 2-[tert-butoxycarbonyl(methyl)amino]acetic acid (Intermediate 21) (16 mg, 0.085 mmol), HATU (28 mg, 0.074 mmol), and triethylamine (0.031 mL, 0.22 mmol) were added to DMF (1.5 mL). The reaction mixture was stirred at rt overnight, then purified by flash column chromatography and preparative TLC to yield the title compound as a yellow solid.

Step B: (R)-5-(*S)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide A solution of (R)-tert-butyl methyl(2-(3-(5-(*S)-(2-methyl-4-phenoxyphenyl)-4-oxo-4,5-dihydro-3H-1-thia-3,5,8-triazaacenaphthylene-2-carboxamido)piperidin-1-yl)-2-oxoethyl)carbamate (25 mg, 0.037 mmol) in HCl/MeOH (2 M, 2 mL) was stirred at rt for 4 h, then the pH was adjusted to pH>7 with saturated NaHCO$_3$, and purified by flash column chromatography and preparative TLC to yield the title compound as a yellow solid (5 mg, 24% yield). MS (ESI): mass calcd. for C$_{30}$H$_{30}$N$_6$O$_4$S, 570.7; m/z found, 571.2 [M+H]$^+$. $^1$H NMR (400 MHz, CD$_3$OD): δ 8.16-8.07 (m, 1H), 7.43-7.35 (m, 2H), 7.23-7.12 (m, 2H), 7.11-7.05 (m, 2H), 7.04-7.01 (m, 1H), 7.01-6.91 (m, 1H), 5.90-5.75 (m, 1H), 4.26-4.09 (m, 2H), 3.97-3.89 (m, 1H), 3.84-3.78 (m, 1H), 3.73-3.55 (m, 2H), 3.48-3.41 (m, 1H), 2.60-2.49 (m, 3H), 2.15-2.08 (m, 3H), 2.02-1.87 (m, 3H), 1.85-1.73 (m, 1H), 1.67-1.56 (m, 1H).

Example 184: (R)-5-(*S)-(2-Methyl-4-phenoxyphenyl)-4-oxo-N-(1-propionylpiperidin-3-yl)-4,5-dihydro-3H-1-thia-3,5,8-triazaacenaphthylene-2-carboxamide

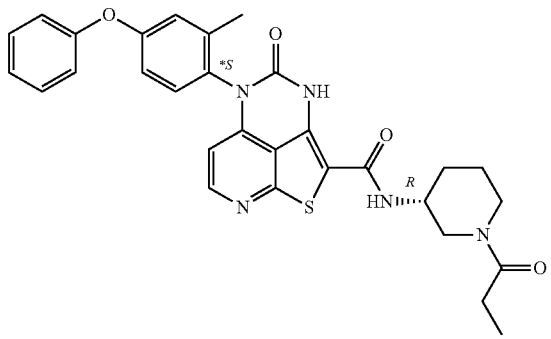

A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 30 mg, 0.06 mmol), triethylamine (15 mg, 0.015 mmol), and propanoyl propanoate (15 mg, 0.12 mmol) in DCM (15 mL) was stirred for 30 min at rt. The mixture was purified by flash column chromatography to yield the title compound as yellow solid (19 mg, 57% yield). MS (ESI): mass calcd. for C$_{30}$H$_{29}$N$_5$O$_4$S, 555.6; m/z found, 556.6 [M+H]$^+$. $^1$H NMR (400 MHz, CD$_3$OD): δ 8.34-8.28 (m, 1H), 7.51-7.35 (m, 2H), 7.34-7.27 (m, 1H), 7.21-7.13 (m, 1H), 711-7.02 (m, 3H), 7.00-6.93 (m, 1H), 6.09-6.01 (m, 1H), 4.54-3.83 (m, 3H), 3.16-2.97 (m, 1H), 2.85-2.65 (m, 1H), 2.59-2.36 (m, 2H), 2.15-2.09 (m, 3H), 2.09-2.00 (m, 1H), 1.91-1.51 (m, 3H), 1.17-1.09 (m, 3H).

Example 185: (R,E)-N-(1-(2-Cyano-3-cyclopropylacryloyl)piperidin-3-yl)-5-(4-cyclopropoxy-2-methylphenyl)-4-oxo-4,5-dihydro-3H-1-thia-3,5,8-triazaacenaphthylene-2-carboxamide

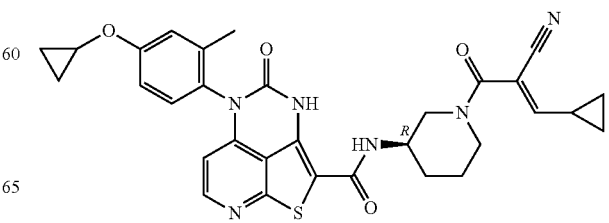

Step A: 4-cyclopropoxy-2-methyl-1-nitrobenzene

The title compound was prepared using the method from Example 33, Step A, using bromocyclopropane in place of 2-iodopropane.

Step B: (R)-5-(4-Cyclopropoxy-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps B-H in Example 1, and using 4-cyclopropoxy-2-methyl-1-nitrobenzene in place of 2-methyl-1-nitro-4-phenoxybenzene in Step B, and using tert-butyl (3R)-3-aminopiperidine-1-carboxylate in place of tert-butyl (3R,5R)-3-amino-5-fluoropiperidine-1-carboxylate (Intermediate 1) in step G.

Step C: (R,E)-N-(1-(2-Cyano-3-cyclopropylacryloyl)piperidin-3-yl)-5-(4-cyclopropoxy-2-methylphenyl)-4-oxo-4,5-dihydro-3H-1-thia-3,5,8-triazaacenaphthylene-2-carboxamide A solution of (R)-5-(4-cyclopropoxy-2-methylphenyl)-4-oxo-N-(piperidin-3-yl)-4,5-dihydro-3H-1-thia-3,5,8-triazaacenaphthylene-2-carboxamide (80 mg, 0.17 mmol), (E)-2-cyano-3-cyclopropylprop-2-enoic acid (Intermediate 17) (48 mg, 0.35 mmol), HATU (85 mg, 0.22 mmol), and diisopropylethylamine (44 mg, 0.35 mmol) in DMF (5 mL) was stirred at rt for 2 h. The mixture was purified by HPLC to yield the title compound as a white solid (27 mg, 27% yield). MS (ESI): mass calcd. for $C_{31}H_{30}N_6O_4S$, 582.7; m/z found, 583.1 [M+H]$^+$. $^1$H NMR (400 MHz, CD$_3$OD): δ 8.33-8.27 (m, 1H), 7.25-7.20 (m, 1H), 7.14-7.10 (m, 1H), 7.10-7.04 (m, 1H), 6.57-6.49 (m, 1H), 6.04-5.99 (m, 1H), 4.14-3.93 (m, 3H), 3.89-3.79 (m, 1H), 3.25-3.05 (m, 2H), 2.12 (s, 3H), 2.09-1.95 (m, 2H), 1.93-1.83 (m, 1H), 1.82-1.70 (m, 1H), 1.68-1.59 (m, 1H), 1.25-1.15 (m, 2H), 1.01-0.91 (m, 1H), 0.87-0.77 (m, 3H), 0.75-0.69 (m, 2H).

Example 186: N-((3S,4S)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide

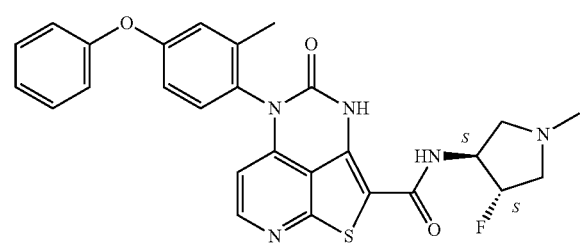

To a solution of N-((3S,4S)-4-fluoropyrrolidin-3-yl)-5-(2-methyl-4-phenoxyphenyl)-4-oxo-4,5-dihydro-3H-1-thia-3,5,8-triazaacenaphthylene-2-carboxamide (Example 218, 100 mg, 0.2 mmol) and formaldehyde (0.5 mL, 37 wt. % in H$_2$O) in MeOH (5 mL) was added NaBH(OAc)$_3$ (127 mg, 0.597 mmol) and was stirred at rt for 1 h, concentrated to dryness, and purified by flash column chromatography to yield the title compound as a white solid (86 mg, 80% yield). MS (ESI): mass calcd. for $C_{27}H_{24}FN_5O_3S$, 517.6; m/z found, 518.0 [M+H]$^+$. $^1$H NMR (400 MHz, CD$_3$OD): δ 8.28 (d, J=5.5 Hz, 1H), 7.42-7.35 (m, 2H), 7.35-7.30 (m, 1H), 7.18-7.12 (m, 1H), 7.09-7.01 (m, 3H), 6.99-6.92 (m, 1H), 6.04 (d, J=5.5 Hz, 1H), 5.39-5.18 (m, 1H), 4.66-4.51 (m, 1H), 3.64-3.53 (m, 1H), 3.43-3.37 (m, 1H), 3.36-3.30 (m, 1H), 3.05-2.95 (m, 1H), 2.70 (s, 3H), 2.08 (s, 3H).

Example 187: 5-(2-Methyl-4-phenoxyphenyl)-N-(1-methylazepan-4-yl)-4-oxo-4,5-dihydro-3H-1-thia-3,5,8-triazaacenaphthylene-2-carboxamide

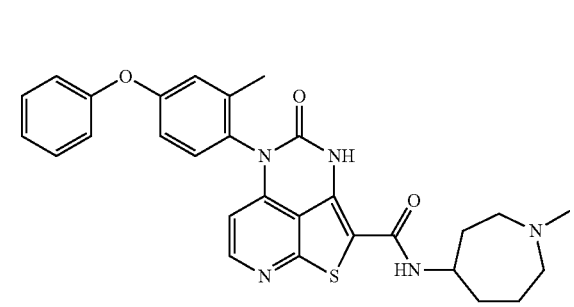 [SMILES: Cc1cc(Oc2ccccc2)ccc1N1C(=O)Nc2c(C(=O)NC3CCCN(C)CC3)sc3nccc1c23]

Step A: N-(Azepan-4-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl 4-aminoazepane-1-carboxylate in place of tert-butyl (3R,5R)-3-amino-5-fluoropiperidine-1-carboxylate (Intermediate 1) in step G.

Step B: 5-(2-Methyl-4-phenoxyphenyl)-N-(1-methylazepan-4-yl)-4-oxo-4,5-dihydro-3H-1-thia-3,5,8-triazaacenaphthylene-2-carboxamide To a solution of N-(azepan-4-yl)-5-(2-methyl-4-phenoxyphenyl)-4-oxo-4,5-dihydro-3H-1-thia-3,5,8-triazaacenaphthylene-2-carboxamide (100 mg, 0.2 mmol) and formaldehyde (0.4 mL, 37 wt. % in H$_2$O) in MeOH (5 mL) was added NaBH(OAc)$_3$ (124 mg, 0.585 mmol) and was stirred at rt for 1 h, concentrated to dryness, and purified by flash column chromatography to yield the title compound as a yellow solid (70 mg, 68% yield). MS (ESI): mass calcd. for $C_{29}H_{29}N_5O_3S$, 527.6; m/z found, 528.2 [M+H]$^+$. $^1$H NMR (400 MHz, CD$_3$OD): δ 8.24 (d, J=5.4 Hz, 1H), 7.45-7.33 (m, 2H), 7.32-7.22 (m, 1H), 7.22-12 (m, 1H), 7.11-7.01 (m, 3H), 7.01-6.92 (m, 1H), 5.98 (d, J=5.4 Hz, 1H), 4.27-4.15 (m, 1H), 3.09-2.98 (m, 1H), 2.96-2.79 (m, 3H), 2.54 (s, 3H), 2.16-2.06 (m, 5H), 2.02-1.87 (m, 2H), 1.83-1.70 (m, 2H).

Example 188: (R)—N-(1-(3-Methoxy-2,2-dimethylpropanoyl)piperidin-3-yl)piperidin-3-yl)-5-(2-methyl-4-phenoxyphenyl)-4-oxo-4,5-dihydro-3H-1-thia-3,5,8-triazaacenaphthylene-2-carboxamide

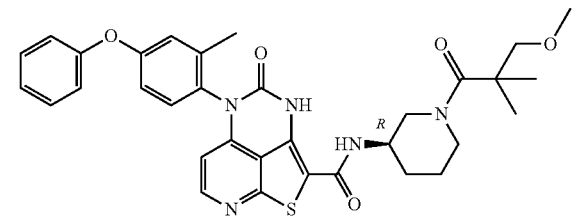

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 110 mg, 0.22 mmol) in DMF (3 mL) were added 3-methoxy-2,2-dimethylpropanoic acid (44 mg, 0.33 mmol), HATU (100 mg, 0.26 mmol), and triethylamine (0.123 mL, 0.880 mmol) and was stirred at rt for 4 h. The reaction mixture was purified by flash column chromatography to yield the title compound as a yellow solid 50 mg, 36% yield). MS (ESI): mass calcd. for $C_{33}H_{35}N_5O_5S$, 613.7; m/z found, 614.3 [M+H]$^+$. $^1$H NMR (400 MHz, CD$_3$OD): δ 8.33 (d, J=5.6, 1H), 7.46-7.36 (m, 2H), 7.34-7.26 (m, 1H), 7.20-7.13 (m, 1H), 7.12-7.02 (m, 3H), 7.00-6.91 (m, 1H), 6.13-6.02 (m, 1H), 4.44-4.23 (m, 2H), 4.03-3.92 (m, 1H), 3.60-3.51 (m, 1H), 3.47-3.39 (m, 1H), 3.36 (s, 3H), 3.01-2.92 (m, 1H), 2.92-2.83 (m, 1H), 2.12 (s, 3H), 2.08-2.01 (m, 1H), 1.85-1.79 (m, 1H), 1.77-1.65 (m, 1H), 1.63-1.50 (m, 1H), 1.30 (s, 6H).

Example 189: N-(1-Cyanoazepan-4-yl)-5-(2-methyl-4-phenoxyphenyl)-4-oxo-4,5-dihydro-3H-1-thia-3,5,8-triazaacenaphthylene-2-carboxamide

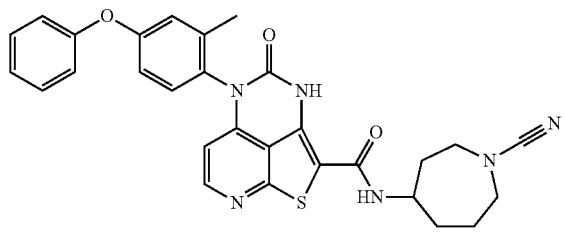 [SMILES: Cc1cc(Oc2ccccc2)ccc1N1C(=O)Nc2c(C(=O)NC3CCCN(C#N)CC3)sc3nccc1c23]

The title compound was prepared in a manner analogous to Method 1, steps A-I in Example 1, and using tert-butyl 4-aminoazepane-1-carboxylate in place of tert-butyl (3R, 5R)-3-amino-5-fluoropiperidine-1-carboxylate (Intermediate 1) in step G, and using bromocyanide in place of prop-2-enoyl chloride in step I. MS (ESI): mass calcd. for $C_{29}H_{26}N_6O_3S$, 538.6; m/z found, 539.1 [M+H]$^+$. $^1$H NMR (400 MHz, CD$_3$OD): δ 8.32 (d, J=5.6 Hz, 1H), 7.44-7.36 (m, 2H), 7.28 (d, J=8.6 Hz, 1H), 7.21-7.13 (m, 1H), 7.12-7.03 (m, 3H), 7.01-6.92 (m, 1H), 6.07 (d, J=5.6 Hz, 1H), 4.12-4.00 (m, 1H), 3.50-3.38 (m, 2H), 3.33-3.30 (m, 1H), 3.28-3.24 (m, 1H), 2.14-2.08 (m, 4H), 2.05-1.88 (m, 3H), 1.85-1.69 (m, 2H).

Example 190: N—((R)-1-((R)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide

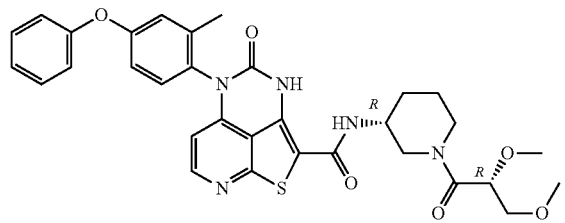

Step A: Methyl (2R)-2-hydroxy-3-methoxypropanoate

To a solution of methyl cyclopropanecarboxylate (1.0 g, 9.8 mmol) in MeOH (1 mL) was added Mg$_2$(SO$_3$CF$_3$)$_2$ (4.05 g, 11.7 mmol) at rt and warmed to 40° C. for 16 h. The reaction mixture was filtered, washed with DCM, and concentrated to dryness to yield the title compound as a colorless oil (900 mg, 69%).

Step B: Methyl (2R)-2,3-dimethoxypropanoate

To a solution of methyl (2R)-2-hydroxy-3-methoxypropanoate (900 mg, 6.7 mmol) in DCM (10 mL) were added methyl iodide (1.90 g, 13.4 mmol) and Ag$_2$O (2.32 g, 10.0 mmol) at rt. The reaction was warmed to 40° C. for 16 h, filtered, washed with DCM, and concentrated to dryness to yield the title compound as a colorless oil (400 mg, 40%).

Step C: (2R)-2,3-Dimethoxypropanoic Acid

A solution of methyl (2R)-2,3-dimethoxypropanoate (400 mg, 2.7 mmol), LiOH.H$_2$O (454 mg, 10.8 mmol) in dimethoxymethane (4 mL) and H$_2$O (1 mL) was reacted at rt for 16 h. The pH was adjusted to pH<7, extracted with DCM, concentrated to remove the DCM, which yielded the title compound as a colorless oil as a solution in dimethoxymethane (3.0 g).

Step D: N—((R)-1-((R)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide To a solution of (2R)-2,3-dimethoxypropanoic acid (50 mg, 0.37 mmol) in DCM (5 mL) was added oxalyl dichloride (2 mL) and reacted at 60° C. overnight. The reaction mixture was concentrated to dryness and dissolved in DCM (5 mL). The mixture was added to solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 80 mg, 0.16 mmol) and triethylamine (40 mg, 0.40 mmol) in DCM (5 mL) and reacted at rt for 30 min. The reaction was quenched with H$_2$O, extracted with DCM, dried over anhydrous Na$_2$SO$_4$, filtered, and concentrated to dryness. The residue was purified by flash column chromatography to yield the title compound as an off white solid (30 mg, 30%). MS (ESI): mass calcd. for $C_{32}H_{33}N_5O_6S$, 615.7; m/z found, 616.2 [M+H]$^+$. $^1$H NMR (400 MHz, CD$_3$OD): δ 8.41-8.27 (m, 1H), 7.46-7.34 (m, 2H), 7.33-7.26 (m, 1H), 7.27-7.17 (m, 1H), 7.15-7.02 (m, 3H), 7.02-6.95 (m, 1H), 6.12-6.03 (m, 1H), 4.68-4.47 (m, 3H), 4.41-3.89 (m, 3H), 3.77-3.55 (m, 2H), 3.44-3.36 (m, 4H), 3.52-3.12 (m, 1H), 3.01-2.77 (m, 1H), 2.19-2.11 (m, 3H), 2.07-2.01 (m, 1H), 1.93-1.81 (m, 1H), 1.78-1.49 (m, 2H).

Example 191: 5-(2-Methyl-4-phenoxyphenyl)-4-oxo-N—((R)-1-((R)-pyrrolidine-3-carbonyl)piperidin-3-yl)-4,5-dihydro-3H-1-thia-3,5,8-triazaacenaphthylene-2-carboxamide

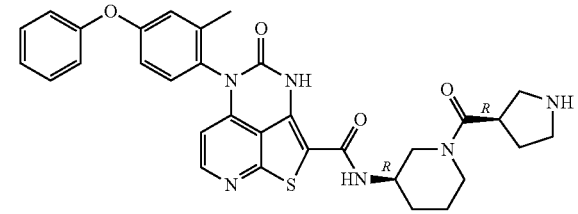

Step A: (R)-tert-butyl 3-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)pyrrolidine-1-carboxylate A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 300 mg, 0.60 mmol), (3R)-1-tert-butoxycarbonylpyrrolidine-3-carboxylic acid (258 mg, 1.20 mmol), HATU (456 mg, 1.20 mmol), and triethylamine (121 mg, 1.20 mmol) in DMF (5 mL) was reacted at rt for 2 h. The reaction was quenched with H$_2$O (10 mL), extracted with DCM, dried over anhydrous Na$_2$SO$_4$, filtered, and concentrated to dryness. The residue was purified by flash column chromatography to yield the title compound as a yellow solid (350 mg, 83% yield).

Step B: 5-(2-Methyl-4-phenoxyphenyl)-4-oxo-N—((R)-1-((R)-pyrrolidine-3-carbonyl)piperidin-3-yl)-4,5-dihydro-3H-1-thia-3,5,8-triazaacenaphthylene-2-carboxamide To a solution of (R)-tert-butyl 3-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)pyrrolidine-1-carboxylate (350 mg, 0.50 mmol) in MeOH (5 mL) was added HCl (37%, 2 mL) and was reacted at rt for 1 h. The reaction was quenched by the addition of a saturated solution of NaHCO$_3$ (20 mL), extracted with DCM, dried over anhydrous Na$_2$SO$_4$, filtered, and concentrated to dryness to yield the title compound as a yellow solid (200 mg, 67% yield). MS (ESI): mass calcd. for C$_{32}$H$_{32}$N$_6$O$_4$S, 596.7; m/z found, 597.1 [M+H]$^+$. $^1$H NMR (400 MHz, CD$_3$OD): δ 8.43 (s, 1H), 8.36-8.30 (m, 1H), 7.44-7.34 (m, 2H), 7.33-7.25 (m, 1H), 7.20-7.13 (m, 1H), 7.11-7.02 (m, 3H), 7.00-6.92 (m, 1H), 6.13-6.03 (m, 1H), 4.52-4.33 (m, 1H), 4.24-3.87 (m, 2H), 3.75-3.61 (m, 2H), 3.44-3.31 (m, 3H), 3.09-2.62 (m, 2H), 2.40-2.15 (m, 1H), 2.15-1.99 (m, 5H), 1.92-1.50 (m, 3H).

Example 192: N-(4-(Hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide

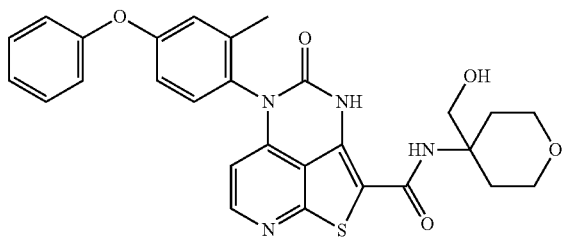 [SMILES: Cc1cc(Oc2ccccc2)ccc1N1C(=O)Nc2c(C(=O)NC3(CO)CCOCC3)sc3nccc1c23]

The title compound was prepared in a manner analogous to Method 1, steps A-G in Example 1, and using (4-amino-tetrahydropyran-4-yl)methanol in place of tert-butyl (3R,5R)-3-amino-5-fluoropiperidine-1-carboxylate (Intermediate 1) in step G. MS (ESI): mass calcd. for C$_{28}$H$_{26}$N$_4$O$_5$S, 530.6; m/z found, 531.7 [M+H]$^+$. $^1$H NMR (400 MHz, DMSO-d6): δ 10.14 (s, 1H), 8.35-8.23 (m, 1H), 7.48-7.41 (m, 2H), 7.38-7.30 (m, 1H), 7.24-7.17 (m, 1H), 7.16-7.06 (m, 3H), 7.01-6.94 (m, 1H), 6.00-5.86 (m, 1H), 5.08-4.90 (m, 1H), 3.71-3.52 (m, 6H), 2.29-2.12 (m, 2H), 2.06 (s, 3H), 1.68-1.56 (m, 2H).

Example 193: (R,E)-N-(1-(2-Cyano-3-cyclopropylacryloyl)piperidin-3-yl)-5-(4-ethoxy-2-methylphenyl)-4-oxo-4,5-dihydro-3H-1-thia-3,5,8-triazaacenaphthylene-2-carboxamide

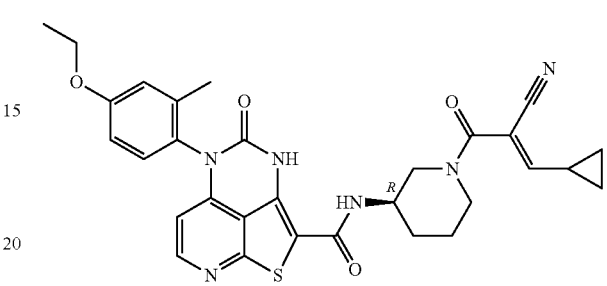

Step A: Step A: 4-Ethoxy-2-methyl-1-nitrobenzene

To a mixture of 3-methyl-4-nitrophenol (5.0 g, 33 mmol) and K$_2$CO$_3$ (13.6 g, 98.6 mmol) in DMF (25 mL) was added bromoethane (8.9 g, 82 mmol) and the reaction was stirred at 80° C. overnight. Water was added to the reaction mixture and a yellow solid was precipitated. The precipitate was filtered, washed with water, and dried to yield the title compound (4.5 g, 76% yield) as a yellow solid.

Step B: (R)-5-(4-Ethoxy-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps B-H in Example 1, and using 4-ethoxy-2-methyl-1-nitrobenzene in place of 2-methyl-1-nitro-4-phenoxybenzene Step B, and using tert-butyl (3R)-3-aminopiperidine-1-carboxylate in place of tert-butyl (3R,5R)-3-amino-5-fluoropiperidine-1-carboxylate (Intermediate 1) in step G.

Step C: (R,E)-N-(1-(2-Cyano-3-cyclopropylacryloyl)piperidin-3-yl)-5-(4-ethoxy-2-methylphenyl)-4-oxo-4,5-dihydro-3H-1-thia-3,5,8-triazaacenaphthylene-2-carboxamide To a stirred suspension of (R)-5-(4-ethoxy-2-methylphenyl)-4-oxo-N-(piperidin-3-yl)-4,5-dihydro-3H-1-thia-3,5,8-triazaacenaphthylene-2-carboxamide (100 mg, 0.22 mmol) in DMF (3 mL) were added (E)-2-cyano-3-cyclopropylprop-2-enoic acid (Intermediate 17) (36 mg, 0.26 mmol), HATU (100 mg, 0.26 mmol), and diisopropylethylamine (60 mg, 0.46 mmol) and was stirred at rt overnight. The reaction mixture was concentrated to dryness and the residue was partitioned between ethyl acetate and water. The organic layer was separated, shaken with brine, dried over anhydrous Na$_2$SO$_4$, and purified by flash column chromatography to yield the title compound as a brown solid (73 mg, 56% yield). MS (ESI): mass calcd. for C$_{30}$H$_{30}$N$_6$O$_4$S, 570.7; m/z found, 571.9 [M+H]$^+$. $^1$H NMR (400 MHz, CD$_3$OD): δ 8.29 (d, J=5.2 Hz, 1H), 7.26-7.16 (m, 1H), 7.01-6.94 (m, 1H), 6.93-6.87 (m, 1H), 6.60-6.47 (m, 1H), 6.04-5.97 (m, 1H), 4.27-3.88 (m, 5H), 3.25-3.00 (m, 1H), 2.14-2.09 (m, 3H), 2.09-1.49 (m, 6H), 1.46-1.35 (m, 3H), 1.25-1.13 (m, 2H), 1.04-0.70 (m, 2H).

Example 194: (R)—N-(1-Acryloylpiperidin-3-yl)-5-(2-fluorophenyl)-4-oxo-4,5-dihydro-3H-1-thia-3,5,8-triazaacenaphthylene-2-carboxamide

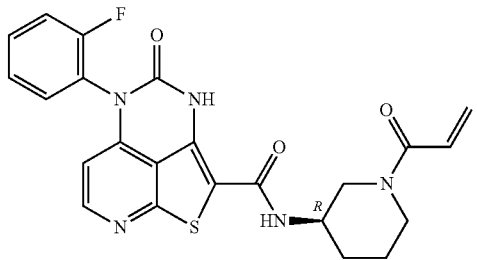

The title compound was prepared in a manner analogous to Method 1, steps C-I in Example 1, and using 2-fluoroaniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{23}H_{20}FN_5O_3S$, 465.5; m/z found, 466.1 [M+H]$^+$. $^1$H NMR (400 MHz, DMSO-d$_6$): δ 10.37 (s, 1H), 8.33 (d, J=5.4 Hz, 1H), 8.24-8.03 (m, 1H), 7.68-7.54 (m, 2H), 7.54-7.46 (m, 1H), 7.44-7.33 (m, 1H), 6.87-6.64 (m, 1H), 6.15-5.97 (m, 2H), 5.65 (d, J=10.6 Hz, 1H), 4.55-4.11 (m, 1H), 4.10-3.88 (m, 1H), 3.79-3.69 (br, 1H), 3.14-2.90 (m, 1H), 2.83-2.57 (m, 1H), 2.05-1.85 (m, 1H), 1.83-1.52 (m, 2H), 1.52-1.29 (m, 1H).

Example 195: (R,Z)—N-(1-(4-Amino-2-cyano-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

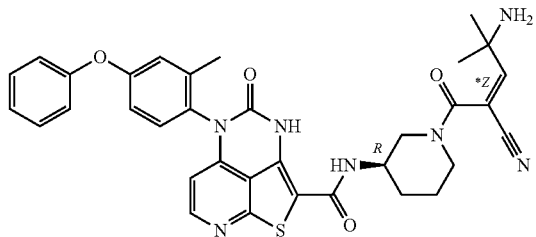

Step A: (R,Z)-tert-Butyl (4-cyano-2-methyl-5-(3-(5-(2-methyl-4-phenoxyphenyl)-4-oxo-4,5-dihydro-3H-1-thia-3,5,8-triazaacenaphthylene-2-carboxamido)piperidin-1-yl)-5-oxopent-3-en-2-yl)carbamate A solution of ((R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 300 mg, 0.53 mmol), tert-butyl N-(1,1-dimethyl-2-oxoethyl)carbamate (297 mg, 1.59 mmol), piperdine (0.5 mL), acetic acid (0.2 mL), dioxane (15 mL), and 4A molecular sieves (1 g) were added to a flask and stirred at 100° C. for 1 h under N2. The mixture was concentrated to dryness and purified by flash column chromatography to yield the title compound as a light yellow solid (188 mg, 48.2% yield).

Step B: (R,Z)—N-(1-(4-Amino-2-cyano-4-methyl-pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide To a solution of (R,Z)-tert-butyl (4-cyano-2-methyl-5-(3-(5-(2-methyl-4-phenoxyphenyl)-4-oxo-4,5-dihydro-3H-1-thia-3,5,8-triazaacenaphthylene-2-carboxamido)piperidin-1-yl)-5-oxopent-3-en-2-yl)carbamate (188 mg, 0.255 mmol) in MeOH (5 mL) was added concentrated HCl (5 mL) and stirred at rt for 10 min. The mixture was concentrated to dryness, diluted with DCM, washed with saturated NaHCO$_3$ and brine, concentrated to dryness, and purified by flash column chromatography to yield the title compound as a yellow solid (151 mg, 90.6% yield). MS (ESI): mass calcd. for $C_{34}H_{33}N_7O_4S$, 635.7; m/z found, 636.1 [M+H]$^+$. $^1$H NMR (400 MHz, CD$_3$OD): δ 8.28-8.20 (m, 1H), 7.83-7.63 (m, 1H), 7.42-7.34 (m, 2H), 7.28-7.21 (m, 1H), 7.18-7.11 (m, 1H), 7.09-7.00 (m, 3H), 6.98-6.92 (m, 1H), 6.01-5.95 (m, 1H), 4.30-3.73 (m, 3H), 3.36-3.25 (m, 2H), 2.14-2.04 (m, 4H), 2.01-1.83 (m, 2H), 1.75-1.62 (m, 1H), 1.60-1.46 (m, 6H).

Example 196: (R,E)-N-(1-(3-(1-Aminocyclopropyl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide

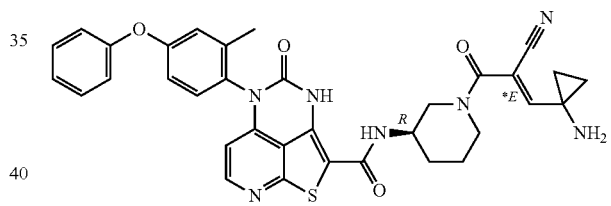

Step A: (R,E)-tert-butyl (1-(2-cyano-3-(3-(5-(2-methyl-4-phenoxyphenyl)-4-oxo-4,5-dihydro-3H-1-thia-3,5,8-triazaacenaphthylene-2-carboxamido)piperidin-1-yl)-3-oxoprop-1-en-1-yl)cyclopropyl) carbamate A solution of ((R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 150 mg, 0.26 mmol), tert-butyl N-(1-formylcyclopropyl)carbamate (147 mg, 0.795 mmol), piperidine (0.3 mL), acetic acid (0.1 mL), dioxane (10 mL), and 4A molecular sieves (1 g) was stirred at 100° C. for 1 h under N2. The mixture was concentrated to dryness and purified by flash column chromatography to yield the title compound as a light yellow solid (153 mg, 78.5% yield).

Step B: (R,E)-N-(1-(3-(1-Aminocyclopropyl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide To a solution of (R,E)-tert-butyl (1-(2-cyano-3-(3-(5-(2-methyl-4-phenoxyphenyl)-4-oxo-4,5-dihydro-3H-1-thia-3, 5,8-triazaacenaphthylene-2-carboxamido)piperidin-1-yl)-3-oxoprop-1-en-1-yl)cyclopropyl)carbamate (153 mg, 0.21 mmol) in MeOH (4 mL) was added TFA (1 mL) and was stirred at rt for 20 min. The mixture was concentrated to dryness, diluted with DCM, washed with saturated NaHCO$_3$ and brine, concentrated to dryness, and purified by flash column chromatography to yield the title compound as a brown solid (68 mg, 51% yield). MS (ESI): mass calcd. for C$_{34}$H$_{31}$N$_7$O$_4$S, 633.7; m/z found, 634.0 [M+H]$^+$. $^1$H NMR (400 MHz, CD$_3$OD and DMSO-d$_6$): δ 8.36-8.18 (m, 1H), 7.59-7.18 (m, 4H), 7.18-6.85 (m, 5H), 6.03-5.84 (m, 1H), 4.66-4.39 (m, 1H), 4.12-3.69 (m, 2H), 3.07-2.67 (m, 2H), 2.10-1.77 (m, 6H), 1.77-1.48 (m, 3H), 1.39-1.11 (m, 2H).

Example 197: N-((3R,5S)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide

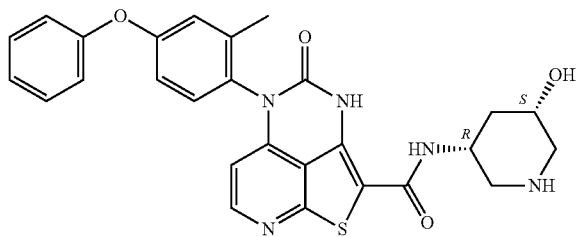

The title compound was prepared using using Method 1, steps A-H in Example 1, using tert-butyl (3R,5S)-3-amino-5-hydroxypiperidine-1-carboxylate (Intermediate 2) in place of tert-butyl (3R,5R)-3-amino-5-fluoropiperidine-1-carboxylate (Intermediate 1) in step G. MS (ESI): mass calcd. for C$_{27}$H$_{25}$N$_5$O$_4$S, 515.6; m/z found, 516.2 [M+H]$^+$. $^1$H NMR (400 MHz, CD$_3$OD): δ 8.37-8.27 (m, 1H), 7.47-7.35 (m, 2H), 7.35-7.28 (m, 1H), 7.23-7.12 (m, 1H), 7.13-7.03 (m, 3H), 7.02-6.94 (m, 1H), 6.07 (d, J=5.6 Hz, 1H), 4.41-4.25 (m, 1H), 4.12-4.00 (m, 1H), 3.29-3.19 (m, 2H), 3.14-3.02 (m, 1H), 3.00-2.89 (m, 1H), 2.26-2.15 (m, 1H), 2.14-2.07 (m, 3H), 1.90-1.80 (m, 1H).

Example 198: 5-(2-Methyl-4-phenoxyphenyl)-4-oxo-N—((R)-1-((R)-tetrahydrofuran-3-carbonyl)piperidin-3-yl)-4,5-dihydro-3H-1-thia-3,5,8-triazaacenaphthylene-2-carboxamide

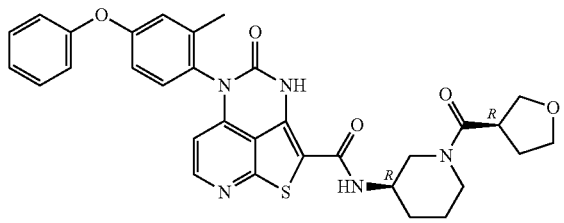

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 90 mg, 0.18 mmol), (3R)-tetrahydrofuran-3-carboxylic acid (88 mg, 0.76 mmol), HATU (168 mg, 0.44 mmol), and triethylamine (45 mg, 0.45 mmol) in DMF (5 mL) was reacted at rt for 2 h. The reaction was quenched by the addition of H$_2$O (10 mL), extracted with DCM, dried over anhydrous Na$_2$SO$_4$, filtered, and concentrated to dryness. The residue was purified by flash column chromatography to yield the title compound as a yellow solid (52 mg, 48% yield). MS (ESI): mass calcd. for C$_{32}$H$_{31}$N$_5$O$_5$S, 597.7; m/z found, 598.3 [M+H]$^+$. $^1$H NMR (400 MHz, CD$_3$OD): δ 8.35-8.27 (m, 1H), 7.43-7.35 (m, 2H), 7.32-7.28 (m, 1H), 7.19-7.12 (m, 1H), 7.12-7.00 (m, 3H), 6.99-6.92 (m, 1H), 6.11-6.00 (m, 1H), 4.52-4.29 (m, 1H), 4.21-3.79 (m, 6H), 3.52-3.38 (m, 1H), 3.22-3.00 (m, 1H), 2.87-2.69 (m, 1H), 2.39-2.14 (m, 1H), 2.14-2.09 (m, 3H), 2.09-1.97 (m, 2H), 1.88-1.50 (m, 3H).

Example 199: (R,E)-N-(1-(3-Cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide

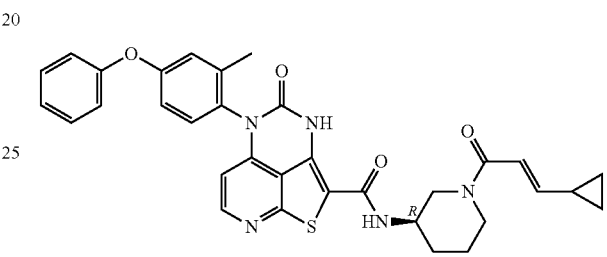

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 100 mg, 0.2 mmol) and (E)-3-cyclopropylprop-2-enoic acid (500 mg, 4.5 mmol) in anhydrous DMF (5 mL) were added HATU (228 mg, 0.600 mmol) and diisopropylethylamine (130 mg, 1.0 mmol) and was stirred overnight at rt. The reaction mixture was purified by flash column chromatography, then preparative TLC to yield the title compound as a yellow solid (41 mg, 34% yield). MS (ESI): mass calcd. for C$_{33}$H$_{31}$N$_5$O$_4$S, 593.7; m/z found, 594.1 [M+H]$^+$. $^1$H NMR (400 MHz, CDCl$_3$): δ9.51-9.41 (m, 1H), 8.34 (d, J=5.4 Hz, 1H), 7.42-7.35 (m, 2H), 7.20-7.13 (m, 2H), 7.12-7.06 (m, 2H), 7.01-6.98 (m, 1H), 6.97-6.92 (m, 1H), 6.52-6.33 (m, 2H), 6.00 (d, J=5.4 Hz, 1H), 4.16-4.06 (m, 1H), 4.01-3.78 (m, 1H), 3.63-3.27 (m, 2H), 2.14-2.09 (m, 3H), 2.05-1.92 (m, 1H), 1.81-1.58 (m, 5H), 0.96-0.82 (m, 2H), 0.76-0.42 (m, 2H).

Example 200: N-((3S,4R)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide

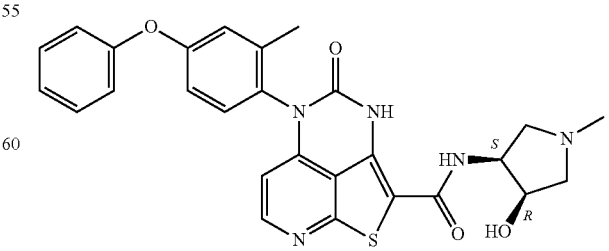

To a solution of N-((3S,4R)-4-hydroxypyrrolidin-3-yl)-5-(2-methyl-4-phenoxyphenyl)-4-oxo-4,5-dihydro-3H-1-thia- 3,5,8-triazaacenaphthylene-2-carboxamide (Example 241, 100 mg, 0.2 mmol) and formaldehyde (0.5 mL, 37 wt. % in H$_2$O) in MeOH (5 mL) was added NaBH(OAc)$_3$ (127 mg, 0.597 mmol) and stirred at rt overnight, concentrated to dryness, and purified by flash column chromatography to yield the title compound as a yellow solid (53 mg, 50% yield). MS (ESI): mass calcd. for C$_{27}$H$_{25}$N$_5$O$_4$S, 515.6; m/z found, 516.4 [M+H]$^+$. $^1$H NMR (400 MHz, CD$_3$OD): δ 8.33-8.17 (m, 1H), 7.43-7.33 (m, 2H), 7.33-7.23 (m, 1H), 7.18-7.09 (m, 1H), 7.10-7.00 (m, 3H), 7.00-6.90 (m, 1H), 6.04-5.93 (m, 1H), 4.57-4.37 (m, 2H), 3.14-2.94 (m, 2H), 2.87-2.69 (m, 2H), 2.47 (s, 3H), 2.09 (s, 3H).

Example 201: (R)-5-(4-(2-Cyclopropylphenoxy)-2-methylphenyl)-N-(1-methylpiperidin-3-yl)-4-oxo-4,5-dihydro-3H-1-thia-3,5,8-triazaacenaphthylene-2-carboxamide

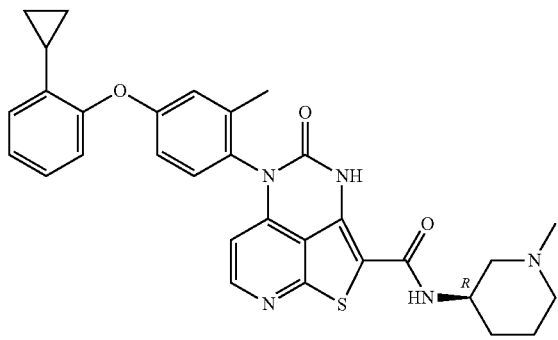

Step A: (R)-5-(4-(2-Cyclopropylphenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 2-cyclopropylphenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(2-Cyclopropylphenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-cyclopropylphenoxy)-2-methylphenyl)-4-oxo-N-(piperidin-3-yl)-4,5-dihydro-3H-1-thia-3,5,8-triazaacenaphthylene-2-carboxamide (100 mg, 0.19 mmol) in DCM (10 mL) was added formaldehyde (30 mg, 1.0 mmol, 37 wt. % in H$_2$O) and after stirring at rt for 10 min, NaBH(OAc)$_3$ (78 mg, 0.37 mmol) was added. The mixture was stirred at rt overnight, then the pH was adjusted to pH>7 with 2 M aqueous NaOH, and concentrated to dryness. The residue was purified by flash column chromatography to yield the title compound as a yellow solid (45 mg, 44% yield). MS (ESI): mass calcd. for C$_{31}$H$_{31}$N$_5$O$_3$S, 553.7; m/z found, 554.4 [M+H]$^+$. $^1$H NMR (400 MHz, DMSO-d$_6$ and CD$_3$OD): δ 8.24 (d, J=5.5, 1H), 7.29-7.20 (m, 1H), 7.19-7.06 (m, 2H), 7.02-6.89 (m, 3H), 6.86-6.76 (m, 1H), 5.89 (d, J=5.5, 1H), 4.06-3.93 (m, 1H), 2.91-2.76 (m, 1H), 2.70-2.59 (m, 1H), 2.23 (s, 3H), 2.08-1.92 (m, 6H), 1.82-1.66 (m, 2H), 1.59-1.48 (m, 1H), 1.43-1.32 (m, 1H), 0.90-0.80 (m, 2H), 0.67-0.57 (m, 2H).

Example 202: 5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide

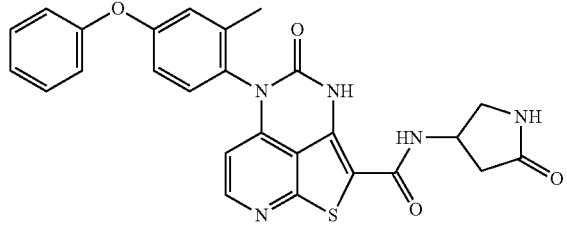 [SMILES: Cc1cc(Oc2ccccc2)ccc1N1C(=O)Nc2c(C(=O)NC3CNC(=O)C3)sc3nccc1c23]

The title compound was prepared in a manner analogous to Method 1, steps A-G in Example 1, and using 4-aminopyrrolidin-2-one in place of tert-butyl (3R,5R)-3-amino-5-fluoropiperidine-1-carboxylate (Intermediate 1) in step G. MS (ESI): mass calcd. for C$_{26}$H$_{21}$N$_5$O$_4$S, 499.5; m/z found, 500.7 [M+H]$^+$. $^1$H NMR (400 MHz, a mixture of CD3OD and DMSO-d6): δ 8.25-8.16 (m, 1H), 7.40-7.32 (m, 2H), 7.27-7.18 (m, 1H), 7.15-7.08 (m, 1H), 7.07-7.01 (m, 2H), 7.01-7.98 (m, 1H), 6.92-6.88 (m, 1H), 5.93-5.84 (m, 1H), 4.67-4.52 (m, 1H), 3.63-3.57 (m, 1H), 3.25-3.19 (m, 1H), 2.58-2.51 (m, 1H), 2.36-2.29 (m, 1H), 2.01 (s, 3H).

Example 203: N-(1,2-Dimethylpiperidin-4-yl)-5-(2-methyl-4-phenoxyphenyl)-4-oxo-4,5-dihydro-3H-1-thia-3,5,8-triazaacenaphthylene-2-carboxamide

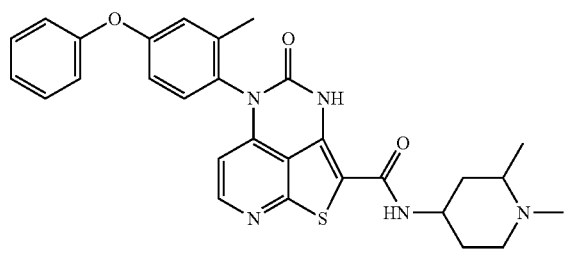 [SMILES: Cc1cc(Oc2ccccc2)ccc1N1C(=O)Nc2c(C(=O)NC3CCN(C)C(C)C3)sc3nccc1c23]

To a solution of 5-(2-methyl-4-phenoxyphenyl)-N-(2-methylpiperidin-4-yl)-4-oxo-4,5-dihydro-3H-1-thia-3,5,8-triazaacenaphthylene-2-carboxamide (Example 258, 150 mg, 0.29 mmol) and formaldehyde (0.6 mL, 37 wt. % in H$_2$O) in MeOH (30 mL) was added NaBH(OAc)$_3$ (186 mg, 0.878 mmol) and was stirred at rt for 3 h, concentrated to dryness, and purified by flash column chromatography to yield the title compound as a yellow solid (110 mg, 71% yield). MS (ESI): mass calcd. for C$_{29}$H$_{29}$N$_5$O$_3$S, 527.6; m/z found, 528.7 [M+H]$^+$. $^1$H NMR (400 MHz, CD$_3$OD and DMSO-d$_6$): δ 8.23 (d, J=5.5 Hz, 1H), 7.46-7.32 (m, 2H), 7.27 (d, J=8.5 Hz, 1H), 7.19-7.10 (m, 1H), 7.09-6.98 (m, 3H), 6.97-6.85 (m, 1H), 5.89 (d, J=5.4 Hz, 1H), 3.90-3.64 (m, 2H), 2.98-2.75 (m, 1H), 2.24 (s, 3H), 2.20-2.11 (m, 1H), 2.03 (s, 3H), 1.89-1.72 (m, 2H), 1.69-1.53 (m, 1H), 1.43-1.28 (m, 1H), 1.05 (d, J=6.2 Hz, 3H).

Example 204: (R)—N-(1-Methacryloylpiperidin-3-yl)-5-(2-methyl-4-phenoxyphenyl)-4-oxo-4,5-dihydro-3H-1-thia-3,5,8-triazaacenaphthylene-2-carboxamide

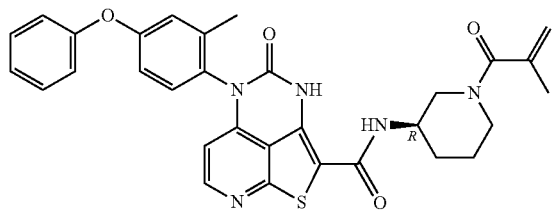

A solution (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), 2-methylprop-2-enoic acid (52 mg, 0.60 mmol), HATU (148 mg, 0.390 mmol), and diisopropylethylamine (77 mg, 0.60 mmol) in DMF (5 mL) was stirred at rt for 2 h. The mixture was purified by HPLC to yield the title compound as a brown solid (105 mg, 66.1% yield). MS (ESI): mass calcd. for $C_{31}H_{29}N_5O_4S$, 567.7; m/z found, 568.7 [M+H]$^+$. $^1$H NMR (400 MHz, CD$_3$OD and DMSO-d$_6$): δ 8.27-8.22 (m, 1H), 7.38-7.31 (m, 2H), 7.31-7.24 (m, 1H), 7.14-7.07 (m, 1H), 7.07-6.98 (m, 3H), 6.94-6.87 (m, 1H), 5.97-5.91 (m, 1H), 5.17-4.93 (m, 2H), 4.05-3.89 (m, 1H), 3.86-3.74 (m, 2H), 3.08-2.62 (m, 2H), 2.05-1.99 (m, 3H), 1.96-1.88 (m, 1H), 1.84 (s, 3H), 1.78-1.69 (m, 1H), 1.67-1.58 (m, 1H), 1.49-1.39 (m, 1H).

Example 205: N-(1-(Cyclopropanecarbonyl)piperidin-3-yl)-5-(2-methyl-4-phenoxyphenyl)-4-oxo-4,5-dihydro-3H-1-thia-3,5,8-triazaacenaphthylene-2-carboxamide

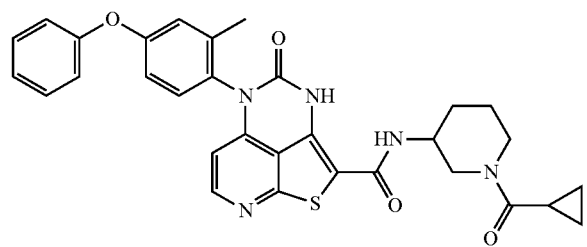 [SMILES: Cc1cc(Oc2ccccc2)ccc1N1C(=O)Nc2c(C(=O)NC3CCCN(C(=O)C4CC4)C3)sc3nccc1c23]

The title compound was prepared in a manner analogous to Method 1, steps A-G in Example 1, and using 1-(cyclopropylcarbonyl)-3-piperidinamine HCl in place of tert-butyl (3R,5R)-3-amino-5-fluoropiperidine-1-carboxylate (Intermediate 1) in step G. MS (ESI): mass calcd. for $C_{31}H_{29}N_5O_4S$, 567.7; m/z found, 568.0 [M+H]$^+$. $^1$H NMR (500 MHz, Methanol-d4) δ 8.34 (d, J=5.5 Hz, 1H), 7.46-7.36 (m, 2H), 7.30 (d, J=8.5 Hz, 1H), 7.21-7.13 (m, 1H), 7.13-7.03 (m, 3H), 6.98 (dd, J=8.5, 2.8 Hz, 1H), 6.09 (d, J=5.5 Hz, 1H), 4.51 (d, J=63.3 Hz, 1H), 4.34 (s, 1H), 4.20 (d, J=13.6 Hz, 1H), 3.97 (d, J=38.8 Hz, 1H), 3.30-3.15 (m, 1H), 2.99-2.81 (m, 1H), 2.13 (s, 3H), 2.00 (s, 1H), 1.95-1.08 (m, 3H), 0.99-0.69 (m, 4H).

Example 206: 5-(2-Methyl-4-phenoxyphenyl)-N-(1-methylazepan-3-yl)-4-oxo-4,5-dihydro-3H-1-thia-3,5,8-triazaacenaphthylene-2-carboxamide

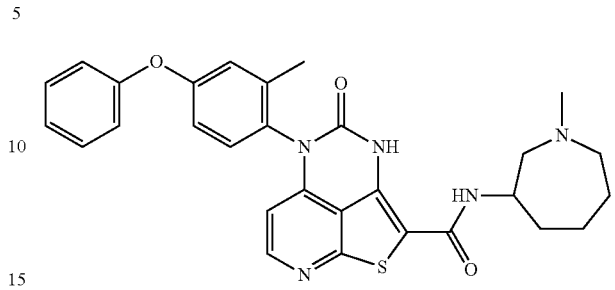

Step A: N-(Azepan-3-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl 3-aminoazepane-1-carboxylate in place of tert-butyl (3R,5R)-3-amino-5-fluoropiperidine-1-carboxylate (Intermediate 1) in step G.

Step B: 5-(2-Methyl-4-phenoxyphenyl)-N-(1-methylazepan-3-yl)-4-oxo-4,5-dihydro-3H-1-thia-3,5,8-triazaacenaphthylene-2-carboxamide To a solution of N-(azepan-3-yl)-5-(2-methyl-4-phenoxyphenyl)-4-oxo-4,5-dihydro-3H-1-thia-3,5,8-triazaacenaphthylene-2-carboxamide (100 mg, 0.2 mmol) and formaldehyde (0.3 mL, 37 wt. % in H$_2$O) in MeOH was added NaBH(OAc)$_3$ (124 mg, 0.585 mmol) and stirred at rt for 1 h, concentrated to dryness, and purified by flash column chromatography to yield the title compound as a white solid (70 mg, 63% yield). MS (ESI): mass calcd. for $C_{29}H_{29}N_5O_3S$, 527.6; m/z found, 528.5 [M+H]$^+$. $^1$H NMR (400 MHz, CD$_3$OD): δ 8.50 (s, 1H), 8.31 (d, J=5.6 Hz, 1H), 7.42-7.36 (m, 2H), 7.31-7.27 (m, 1H), 7.19-7.12 (m, 1H), 7.11-7.03 (m, 3H), 6.97 (dd, J=8.6, 2.8 Hz, 1H), 6.06 (d, J=5.6 Hz, 1H), 4.31-4.21 (m, 1H), 3.43-3.30 (m, 2H), 3.27-3.12 (m, 2H), 2.84 (s, 3H), 2.15-2.04 (m, 1H), 2.08 (s, 3H), 2.01-1.83 (m, 4H), 1.74-1.62 (m, 1H).

Example 207: 5-(2-Methyl-4-phenoxyphenyl)-4-oxo-N—((R)-1-((S)-tetrahydrofuran-3-carbonyl)piperidin-3-yl)-4,5-dihydro-3H-1-thia-3,5,8-triazaacenaphthylene-2-carboxamide

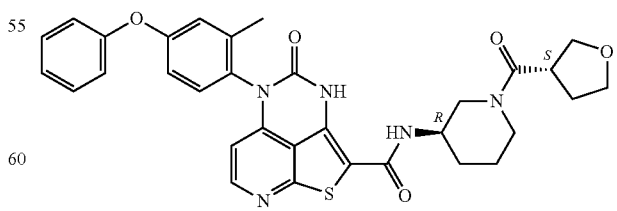

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 120 mg, 0.24 mmol), (3S)-tetrahydrofuran-3-carboxylic acid (100 mg, 0.86 mmol), HATU (150 mg, 0.40 mmol), and triethylamine (80 mg, 0.79 mmol) in DMF (5 mL) was reacted at rt for 2 h. The reaction was quenched with H₂O (10 mL), extracted with DCM, dried over anhydrous Na₂SO₄, filtered, and concentrated to dryness. The residue was purified by flash column chromatography to yield the title compound as an off white solid (57 mg, 40% yield). MS (ESI): mass calcd. for C₃₂H₃₁N₅O₅S, 597.7; m/z found, 598.2 [M+H]⁺. ¹H NMR (400 MHz, CD₃OD): δ 8.32-8.27 (m, 1H), 7.42-7.29 (m, 3H), 7.19-7.09 (m, 1H), 7.09-7.00 (m, 3H), 6.97-6.90 (m, 1H), 6.04-5.98 (m, 1H), 4.60-4.31 (m, 1H), 4.26-4.08 (m, 1H), 3.94-3.85 (m, 1H), 3.85-3.66 (m, 4H), 3.52-3.37 (m, 1H), 3.15-2.92 (m, 1H), 2.81-2.59 (m, 1H), 2.15-1.97 (m, 6H), 1.89-1.73 (m, 1H), 1.73-1.41 (m, 2H).

Example 208: N-((3S,4R)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide

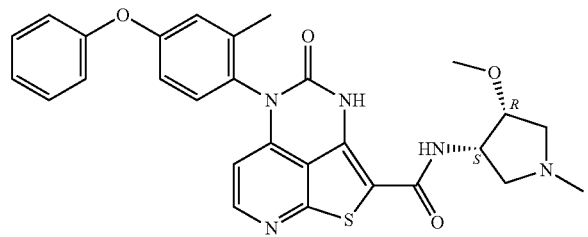

To a solution of N-((3S,4R)-4-methoxypyrrolidin-3-yl)-5-(2-methyl-4-phenoxyphenyl)-4-oxo-4,5-dihydro-3H-1-thia-3,5,8-triazaacenaphthylene-2-carboxamide (Example 211, 100 mg, 0.19 mmol) and formaldehyde (0.4 mL, 37 wt. % in H₂O) in MeOH (5 mL) was added NaBH(OAc)₃ (123 mg, 0.582 mmol) and was stirred at rt for 1 h. The reaction mixture was concentrated to dryness and purified by flash column chromatography to yield the title compound as a yellow solid (54 mg, 52% yield). MS (ESI): mass calcd. for C₂₈H₂₇N₅O₄S, 529.6; m/z found, 530.2 [M+H]⁺. ¹H NMR (400 MHz, CD₃OD and DMSO-d₆): δ 8.23 (d, J=5.4 Hz, 1H), 7.41-7.28 (m, 2H), 7.28-7.18 (m, 1H), 7.14-7.06 (m, 1H), 7.06-6.95 (m, 3H), 6.94-6.85 (m, 1H), 5.94 (d, J=5.4 Hz, 1H), 4.60-4.51 (m, 1H), 3.96-3.86 (m, 1H), 3.27 (s, 3H), 2.92-2.78 (m, 2H), 2.71-2.59 (m, 2H), 2.32 (s, 3H), 2.03 (s, 3H).

Example 209: (R)—N-(1-Acryloylpyrrolidin-3-yl)-5-(5-chlorobenzo[d][1,3]dioxol-4-yl)-4-oxo-4,5-dihydro-3H-1-thia-3,5,8-triazaacenaphthylene-2-carboxamide

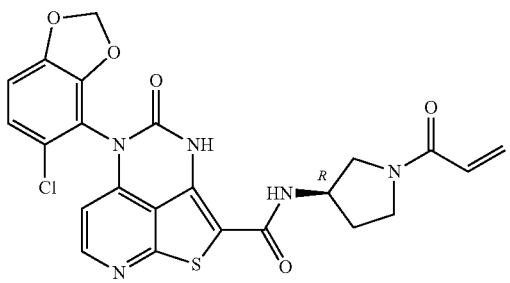

The title compound was prepared in a manner analogous to Method 1, steps C-I in Example 1, and using 5-chloro-1,3-benzodioxol-4-amine and 2,4-dichloropyridine-3-carbonitrile in place of 2-methyl-4-phenoxyaniline and 2-chloro-4-iodopyridine-3-carbonitrile in step C, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for C₂₃H₁₈ClN₅O₅S, 511.9; m/z found, 512.3 [M+H]⁺. ¹H NMR (400 MHz, CD₃OD): δ 8.37 (d, J=5.5 Hz, 1H), 7.12 (d, J=8.4 Hz, 1H), 7.01 (d, J=8.4 Hz, 1H), 6.70-6.52 (m, 1H), 6.32-6.23 (m, 2H), 6.13-6.07 (m, 2H), 5.82-5.67 (m, 1H), 4.67-4.57 (m, 1H), 4.01-3.51 (m, 4H), 2.40-2.21 (m, 1H), 2.19-2.03 (m, 1H).

Example 210: (R)-5-(2-Methyl-4-(m-tolyloxy)phenyl)-N-(1-methylpiperidin-3-yl)-4-oxo-4,5-dihydro-3H-1-thia-3,5,8-triazaacenaphthylene-2-carboxamide

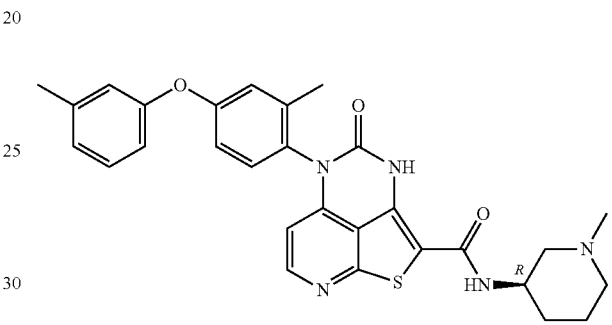

Step A: (R)-5-(2-Methyl-4-(m-tolyloxy)phenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using m-cresol in place of phenol in step A, and using tert-butyl (3R)-3-aminopiperidine-1-carboxylate in place of tert-butyl (3R, 5R)-3-amino-5-fluoropiperidine-1-carboxylate (Intermediate 1) in step G.

Step B: (R)-5-(2-Methyl-4-(m-tolyloxy)phenyl)-N-(1-methylpiperidin-3-yl)-4-oxo-4,5-dihydro-3H-1-thia-3,5,8-triazaacenaphthylene-2-carboxamide To a solution of (R)-5-(2-methyl-4-(m-tolyloxy)phenyl)-4-oxo-N-(piperidin-3-yl)-4,5-dihydro-3H-1-thia-3,5,8-triazaacenaphthylene-2-carboxamide (88 mg, 0.17 mmol) in DCM (5 mL) was added formaldehyde (0.5 mL, 37 wt. % in H₂O) and NaBH(OAc)₃ (73 mg, 0.34 mmol) and stirred at rt for 4 h. The mixture was diluted with DCM (50 mL), MeOH (5 mL), and water (30 mL). The organic layer was collected, concentrated to dryness, and purified by flash column chromatography to yield the title compound as a yellow solid (62 mg, 65% yield). MS (ESI): mass calcd. for C₂₉H₂₉N₅O₃S, 527.6; m/z found, 528.0 [M+H]⁺. ¹H NMR (400 MHz, DMSO-d6): δ 8.26 (d, J=5.3 Hz, 1H), 8.05 (br, 1H), 7.33-7.26 (m, 2H), 7.05-7.01 (m, 1H), 7.00-6.97 (m, 1H), 6.95-6.90 (m, 2H), 6.89-6.85 (m, 1H), 5.88 (d, J=5.4 Hz, 1H), 3.95-3.87 (m, 1H), 2.84-2.78 (m, 1H), 2.70-2.61 (m, 1H), 2.30 (s, 3H), 2.18 (s, 3H), 2.02 (s, 3H), 1.93-1.83 (m, 2H), 1.79-1.73 (m, 1H), 1.69-1.63 (m, 1H), 1.54-1.45 (m, 1H), 1.35-1.27 (m, 1H).

Example 211: N-((3S,4R)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide

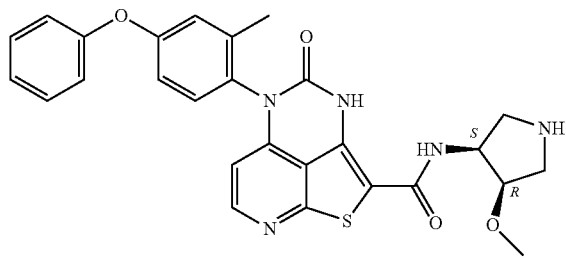

The title compound was prepared using steps A-H in Example 1, and using tert-butyl (3S,4R)-3-amino-4-methoxypyrrolidine-1-carboxylate (Intermediate 11) in place of tert-butyl (3R,5R)-3-amino-5-fluoropiperidin-1-carboxylate (Intermediate 1) in step G. MS (ESI): mass calcd. for $C_{27}H_{25}N_5O_4S$, 515.6; m/z found, 516.3 [M+H]$^+$. $^1$H NMR (400 MHz, CD$_3$OD and DMSO-d$_6$): δ 8.29 (d, J=5.5 Hz, 1H), 7.43-7.30 (m, 2H), 7.26 (d, J=8.6 Hz, 1H), 7.15-7.08 (m, 1H), 7.07-6.99 (m, 3H), 6.92 (dd, J=8.6, 2.8 Hz, 1H), 6.00 (d, J=5.5 Hz, 1H), 4.67-4.60 (m, 1H), 4.10-4.03 (m, 1H), 3.53-3.45 (m, 2H), 3.36 (s, 3H), 3.35-3.27 (m, 2H), 2.04 (s, 3H).

Example 212: (R,E)-N-(1-(2-Cyano-4-(ethylamino)-4-methylpent-2-enoyl)piperidin-3-yl)-5-(2-methyl-4-phenoxyphenl)-4-oxo-4,5-dihydro-3H-1-thia-3,5,8-triazaacenaphthylene-2-carboxamide

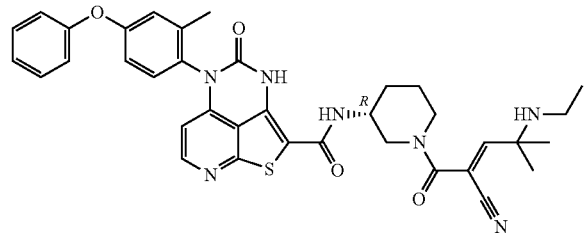

Step A: 3-Bromo-3-methylbutanal

To a solution of 3-methylbutanal (1.0 g, 12 mmol) in Et$_2$O (10 mL) was slowly added bromine-1,4-dioxane complex (1.44 g, 5.81 mmol) while cooling with ice water. The reaction mixture was stirred at rt overnight, then 10% aqueous Na$_2$S$_2$O$_4$ was added. After stirring at rt for 30 min, the mixture was extracted with Et$_2$O. The organic layer was washed with brine, dried over anhydrous MgSO$_4$, filtered, and concentrated to dryness to yield the title compound as a yellow liquid (1.1 g, 56%)

Step B: 3-(Ethylamino)-3-methylbutanal

To a solution of 3-bromo-3-methylbutanal (650 mg, 3.94 mmol) in Et$_2$O (10 mL) was added ethyl amine (0.773 mL, 11.8 mmol) while cooling with ice-water. The reaction mixture was stirred at rt overnight, then concentrated to dryness and the residue used in next step without purification.

Step C: (R,E)-N-(1-(2-Cyano-4-(ethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 98 mg, 0.17 mmol), 3-(ethylamino)-3-methylbutanal (60 mg, 0.52 mmol), and piperidine (0.0085 mL, 0.086 mmol) in CH$_3$CN (5 mL) was stirred at 60° C. overnight, concentrated to dryness, and the residue purified by flash column chromatography to yield the title compound as a yellow solid (20 mg, 17% yield). MS (ESI): mass calcd. for $C_{36}H_{37}N_7O_4S$, 663.8; m/z found, 664.3 [M+H]$^+$. $^1$H NMR (400 MHz, CD$_3$OD): δ 8.12-8.03 (m, 1H), 7.63-7.51 (m, 1H), 7.42-7.35 (m, 2H), 7.19-7.12 (m, 2H), 7.11-7.07 (m, 2H), 7.06-7.02 (m, 1H), 6.98-6.93 (m, 1H), 5.84-5.78 (m, 1H), 4.05-3.95 (m, 1H), 3.76-3.69 (m, 1H), 3.64-3.56 (m, 2H), 3.54-3.45 (m, 1H), 3.24-3.17 (m, 1H), 2.16-2.08 (m, 5H), 2.08-1.97 (m, 2H), 1.75-1.70 (m, 1H), 1.58-1.45 (m, 6H), 1.18-1.12 (m, 3H).

Example 213: (R)—N-(1-Cyclopropylpiperidin-3-yl)-5-(2-methyl-4-phenoxyphenyl)-4-oxo-4,5-dihydro-3H-1-thia-3,5,8-triazaacenaphthylene-2-carboxamide

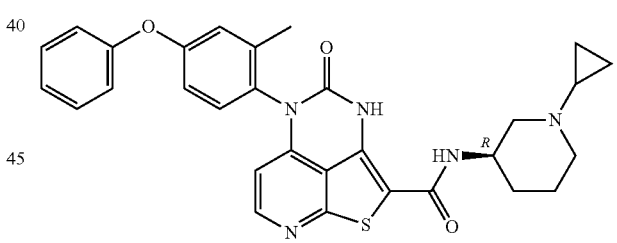

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol), (1-ethoxycyclopropoxy)trimethylsilane (209 mg, 1.20 mmol), NaBH$_3$CN (38 mg, 0.60 mmol), and acetic acid (2 drops) in MeOH (10 mL) was heated at 55° C. overnight. The product was purified by flash column chromatography to yield the title compound as a white solid (76 mg, 41% yield). MS (ESI): mass calcd. for $C_{30}H_{29}N_5O_3S$, 539.6; m/z found, 540.5 [M+H]$^+$. $^1$H NMR (400 MHz, CD$_3$OD): δ 8.34-8.30 (m, 1H), 8.21 (s, 1H), 7.43-7.36 (m, 2H), 7.31-7.26 (m, 1H), 7.19-7.13 (m, 1H), 7.11-7.03 (m, 3H), 6.99-6.94 (m, 1H), 6.09-6.06 (m, 1H), 4.20-4.09 (m, 1H), 4.34-4.30 (m, 1H), 3.16-3.06 (m, 1H), 2.66-2.53 (m, 2H), 2.22-2.12 (m, 1H), 2.11 (s, 3H), 1.98-1.80 (m, 2H), 1.74-1.52 (m, 2H), 0.71-0.59 (m, 4H).

Example 214: (R)-5-(4-(3-Fluorophenoxy)-2-methylphenyl)-N-(1-methylpiperidin-3-yl)-4-oxo-4,5-dihydro-3H-1-thia-3,5,8-triazaacenaphthylene-2-carboxamide

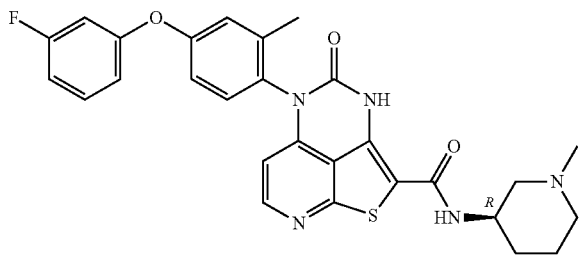

Step A: (R)-5-(4-(3-Fluorophenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 3-fluorophenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(3-Fluorophenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(3-fluorophenoxy)-2-methylphenyl)-4-oxo-N-(piperidin-3-yl)-4,5-dihydro-3H-1-thia-3,5,8-triazaacenaphthylene-2-carboxamide (96 mg, 0.19 mmol) in DCM (5 mL) were added formaldehyde (0.5 mL, 37 wt. % in $H_2O$) and $NaBH(OAc)_3$ (78 mg, 0.37 mmol) and was stirred at rt for 4 h. To the mixture was added DCM (50 mL), MeOH (5 mL), and water (30 mL) and the organic layer was collected, concentrated to dryness, and purified by flash column chromatography to yield the title compound as a yellow solid (58 mg, 56% yield). MS (ESI): mass calcd. for $C_{28}H_{26}FN_5O_3S$, 531.6; m/z found, 532.0 $[M+H]^+$. $^1H$ NMR (400 MHz, DMSO-d6): δ 8.24 (d, J=5.2 Hz, 1H), 8.11 (br, 1H), 7.47-7.39 (m, 1H), 7.38-7.28 (m, 1H), 7.16-7.08 (m, 1H), 7.05-6.95 (m, 3H), 6.94-6.88 (m, 1H), 5.90 (d, J=5.1 Hz, 1H), 3.95-3.87 (m, 1H), 2.84-2.77 (m, 1H), 2.69-2.60 (m, 1H), 2.18 (s, 3H), 2.03 (s, 3H), 1.95-1.84 (m, 2H), 1.80-1.71 (m, 1H), 1.70-1.62 (m, 1H), 1.53-1.43 (m, 1H), 1.36-1.25 (m, 1H).

Example 215: (R)-5-(2-Fluoro-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide

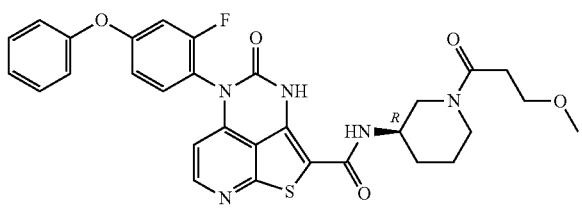

Step A: 2-Fluoro-1-nitro-4-phenoxybenzene

To a solution of 3-fluoro-4-nitrophenol (2.0 g, 13 mm01), phenylboronic acid (2.33 g, 19.1 mmol), $Cu(OAc)_2$ (4.62 g, 25.5 mmol), and triethylamine (6.44 g, 6.37 mmol) in DCM (60 mL) was added 4A molecular sieves (powder<50 µm, 2 g). The mixture was stirred at rt under $N_2$ overnight, then filtered, concentrated to dryness, and purified by flash column chromatography to yield the title compound as a yellow solid (2.7 g, 91% yield).

Step B: (R)-5-(2-Fluoro-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps B-H in Example 1, and using 2-fluoro-1-nitro-4-phenoxybenzene in place of 2-methyl-1-nitro-4-phenoxybenzene in step B, and using tert-butyl (3R)-3-aminopiperidine-1-carboxylate in place of tert-butyl (3R,5R)-3-amino-5-fluoropiperidine-1-carboxylate (Intermediate 1) in step G.

Step C: (R)-5-(2-Fluoro-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide A solution of (R)-5-(2-fluoro-4-phenoxyphenyl)-4-oxo-N-(piperidin-3-yl)-4,5-dihydro-3H-1-thia-3,5,8-triazaacenaphthylene-2-carboxamide (150 mg, 0.30 mmol), 3-methoxypropanoic acid (27 mg, 0.26 mmol), HATU (227 mg, 0.596 mmol), and triethylamine (60 mg, 0.60 mmol) in DMF (4 mL) was stirred at rt for 2 h, then purified by flash column chromatography to yield the title compound as a white solid (103 mg, 58.1% yield). MS (ESI): mass calcd. for $C_{30}H_{28}FN_5O_5S$, 589.6; m/z found, 590.0 $[M+H]^+$. $^1H$ NMR (400 MHz, DMSO-d$_6$): δ 10.39 (s, 1H), 8.34 (d, J=5.5 Hz, 1H), 8.22-7.89 (m, 1H), 7.65-7.51 (m, 1H), 7.51-7.40 (m, 2H), 7.30-7.22 (m, 1H), 7.21-7.09 (m, 3H), 6.99-6.89 (m, 1H), 6.17 (d, J=5.4 Hz, 1H), 4.49-4.08 (m, 1H), 3.97-3.62 (m, 2H), 3.58-3.46 (m, 2H), 3.22-3.15 (m, 3H), 3.05-2.80 (m, 1H), 2.68-2.49 (m, 3H), 1.98-1.83 (m, 1H), 1.81-1.51 (m, 2H), 1.49-1.26 (m, 1H).

Example 216: (R)—N-(1-Acryloylpiperidin-3-yl)-4-oxo-5-(o-tolyl)-4,5-dihydro-3H-1-thia-3,5,8-triazaacenaphthylene-2-carboxamide

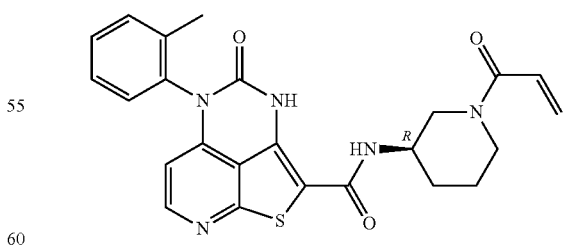

The title compound was prepared in a manner analogous to Method 1, steps C-G in Example 1, and using 2-methylaniline in place of 2-methyl-4-phenoxyaniline for step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G.

MS (ESI): mass calcd. for C₂₄H₂₃N₅O₃S, 461.5; m/z found, 462.1 [M+H]⁺. ¹H NMR (400 MHz, CD₃OD): δ 8.29 (d, J=5.5, 1H), 7.48-7.39 (m, 3H), 7.35-7.30 (m, 1H), 6.86-6.71 (m, 1H), 6.25-6.14 (m, 1H), 5.96 (d, J=5.5, 1H), 5.76-5.67 (m, 1H), 4.56-4.26 (m, 1H), 4.21-3.90 (m, 2H), 3.20-3.11 (m, 1H), 2.65-2.82 (m, 1H), 2.16 (s, 3H), 2.09-2.01 (m, 1H), 1.90-1.82 (m, 1H), 1.80-1.22 (m, 1H), 1.63-1.52 (m, 1H).

Example 217: 5-(2-Methyl-4-phenoxyphenyl)-4-oxo-N-(2-(2-oxoimidazolidin-1-yl)ethyl)-4,5-dihydro-3H-1-thia-3,5,8-triazaacenaphthylene-2-carboxamide

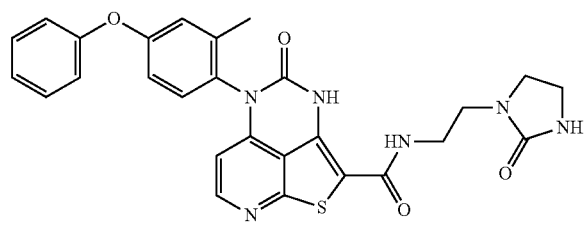 [SMILES: Cc1cc(Oc2ccccc2)ccc1N1C(=O)Nc2c(C(=O)NCCN3CCNC3=O)sc3nccc1c23]

The title compound was prepared using analogous conditions described in Method 1, steps A-G in Example 1, and using 1-(2-aminoethyl)imidazolidin-2-one in place of tert-butyl (3R,5R)-3-amino-5-fluoropiperidine-1-carboxylate (Intermediate 1) in step G. MS (ESI): mass calcd. for C₂₇H₂₄N₆O₄S, 528.6; m/z found, 528.9 [M+H]⁺. ¹H NMR (500 MHz, CDCl₃): δ 9.55 (s, 1H), 8.32 (s, 1H), 7.44-7.35 (m, 2H), 7.23-7.15 (m, 3H), 7.14-7.07 (m, 2H), 7.00 (d, J=2.7 Hz, 1H), 6.99-6.91 (m, 1H), 5.97 (d, J=5.2 Hz, 1H), 4.94 (s, 1H), 3.70-3.56 (m, 4H), 3.56-3.40 (m, 4H), 2.13 (s, 3H).

Example 218: N-((3S,4S)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide

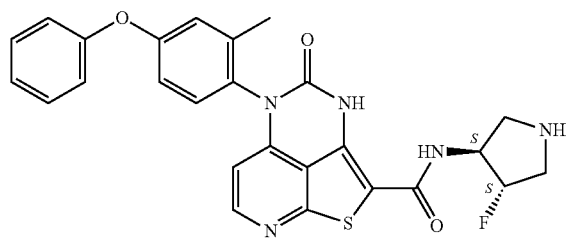

The title compound was prepared using analogous conditions described in Method 1, steps A-H in Example 1, and using tert-butyl (3S,4S)-3-amino-4-fluoropyrrolidine-1-carboxylate in place of tert-butyl (3R,5R)-3-amino-5-fluoropiperidine-1-carboxylate (Intermediate 1) in step G. MS (ESI): mass calcd. for C₂₆H₂₂FN₅O₃S, 503.5; m/z found, 504.1 [M+H]⁺. ¹H NMR (400 MHz, CD₃OD): δ 8.26 (d, J=5.5 Hz, 1H), 7.46-7.35 (m, 2H), 7.28 (d, J=8.6 Hz, 1H), 7.19-7.12 (m, 1H), 7.12-0.02 (m, 3H), 7.00-6.92 (m, 1H), 6.01 (d, J=5.5 Hz, 1H), 5.28-5.11 (m, 1H), 4.56-4.46 (m, 1H), 3.49-3.42 (m, 1H), 3.41-3.34 (m, 1H), 3.25-3.15 (m, 1H), 3.06-2.99 (m, 1H), 2.11 (s, 3H).

Example 219: (R)-5-(2-Methyl-4-phenoxyphenyl)-4-oxo-N-(1-(tetrahydro-2H-pyran-4-carbonyl)piperidin-3-yl)-4,5-dihydro-3H-1-thia-3,5,8-triazaacenaphthylene-2-carboxamide

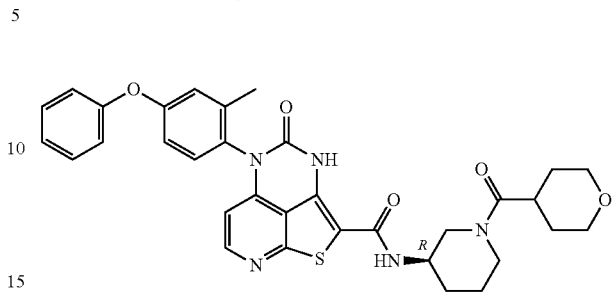

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 90 mg, 0.18 mmol), tetrahydropyran-4-carboxylic acid (88 mg, 0.67 mmol), HATU (168 mg, 0.442 mmol), and triethylamine (45 mg, 0.45 mmol) in DMF (5 mL) was reacted at rt for 2 h. The reaction was quenched by the addition of H₂O (10 mL), extracted with DCM, dried over anhydrous Na₂SO₄, filtered, and concentrated to dryness. The residue was purified by flash column chromatography to give the title compound as an off white solid (57 mg, 53% yield). MS (ESI): mass calcd. for C₃₃H₃₃N₅O₅S, 611.7; m/z found, 612.2 [M+H]⁺. ¹H NMR (400 MHz, CD₃OD): δ 8.35-8.31 (m, 1H), 7.43-7.36 (m, 2H), 7.35-7.27 (m, 1H), 7.22-7.12 (m, 1H), 7.11-7.02 (m, 3H), 7.00-6.92 (m, 1H), 6.10-6.05 (m, 1H), 4.56-4.26 (m, 1H), 4.21-3.81 (m, 4H), 3.61-3.38 (m, 2H), 3.20-2.93 (m, 2H), 2.83-2.67 (m, 1H), 2.14-2.08 (m, 3H), 2.08-1.98 (m, 1H), 1.91-1.82 (m, 1H), 1.82-1.63 (m, 4H), 1.63-1.48 (m, 2H).

Example 220: (R)-5-(4-(2-Hydroxyphenoxy)-2-methylphenyl)-N-(1-methylpiperidin-3-yl)-4-oxo-4,5-dihydro-3H-1-thia-3,5,8-triazaacenaphthylene-2-carboxamide

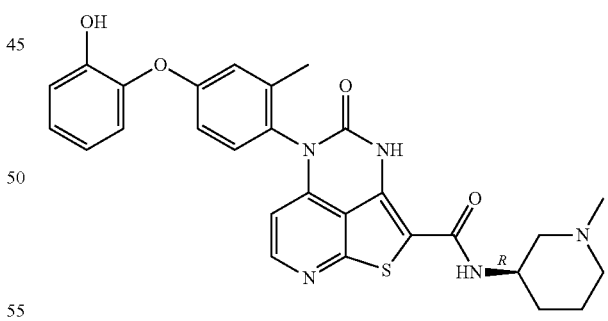

Step A: Methyl 3-amino-4-((4-(2-((tert-butyldimethylsilyl)oxy)phenoxy)-2-methylphenyl)amino)thieno[2,3-b]pyridine-2-carboxylate A solution of 4-((4-(2-((tert-butyldimethylsilyl)oxy)phenoxy)-2-methylphenyl)amino)-2-chloronicotinonitrile (Intermediate 25) (2.54 g, 5.45 mmol), methyl 2-sulfanylacetate (1.157 g, 10.90 mmol), and NaOMe (589 mg, 10.9 mmol) in MeOH (15 mL) was stirred at reflux for 16 hours. The mixture was concentrated to dryness and dispersed between DCM and water. The organic layer was collected, concentrated to dryness, and was used in the next step without further purification (1.345 g, 46% yield).

Step B: Methyl 5-(4-(2-((tert-butyldimethylsilyl)oxy)phenoxy)-2-methylphenyl)-4-oxo-4,5-dihydro-3H-1-thia-3,5,8-triazaacenaphthylene-2-carboxylate A solution of methyl 4-((4-(2-((tert-butyldimethylsilyl)oxy)phenoxy)-2-methylphenyl)amino)-3-methylthieno[2,3-b]pyridine-2-carboxylate (1.345 g, 2.511 mmol) and CDI (1.221 g, 7.530 mmol) in dioxane (15 mL) was stirred at reflux for 3 hours, concentrated to dryness, and purified by normal phase flash column chromatography (SiO$_2$) to give the title compound (1.03 g, 73.0% yield).

Step C: 5-(4-(2-Hydroxyphenoxy)-2-methylphenyl)-4-oxo-4,5-dihydro-3H-1-thia-3,5,8-triazaacenaphthylene-2-carboxylic Acid A solution of methyl 5-(4-(2-((tert-butyldimethylsilyl)oxy)phenoxy)-2-methylphenyl)-4-oxo-4,5-dihydro-3H-1-thia-3,5,8-triazaacenaphthylene-2-carboxylate (1.03 g, 1.83 mmol) and LiOH.H$_2$O (385 mg, 9.18 mmol) in THF/MeOH/water (10 mL/4 mL/4 mL) was stirred at reflux for 4 hours, concentrated under vacuum to half volume, and the pH was adjusted to pH=6 using AcOH. The precipitate was collected by filtration and dried under vacuum to give the title compound (702 mg, 88.0% yield), which was used in the next step without further purification.

Step D: (R)-5-(4-(2-Hydroxyphenoxy)-2-methylphenyl)-4-oxo-N-(piperidin-3-yl)-4,5-dihydro-3H-1-thia-3,5,8-triazaacenaphthylene-2-carboxamide To a solution of 5-(4-(2-hydroxyphenoxy)-2-methylphenyl)-4-oxo-4,5-dihydro-3H-1-thia-3,5,8-triazaacenaphthylene-2-carboxylic acid (702 mg, 1.62 mmol) and tert-butyl (3R)-3-aminopiperidine-1-carboxylate (649 mg, 3.24 mmol) in DMF (3 mL) were added HATU (1.232 g, 3.240 mmol) and triethylamine (328 mg, 3.24 mmol) and was stirred at room temperature for 4 hours. The mixture was concentrated to dryness and the residue dissolved in MeOH (20 mL) and concentrated HCl (2 mL). The mixture was concentrated to dryness and dispersed between DCM and 10% aqueous NH$_3$, the organic layer collected, concentrated to dryness, and used in the next step without further purification (610 mg, 73% yield).

Step E: (R)-5-(4-(2-Hydroxyphenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-hydroxyphenoxy)-2-methylphenyl)-4-oxo-N-(piperidin-3-yl)-4,5-dihydro-3H-1-thia-3,5,8-triazaacenaphthylene-2-carboxamide (316 mg, 0.613 mmol) in DCM (10 mL) were added formaldehyde (1 mL, 37 wt. % in H$_2$O) and NaBH(OAc)$_3$ (260 mg, 1.23 mmol) and was stirred at room temperature for 4 hours. To the mixture were added DCM (50 mL), MeOH (5 mL), water (30 mL), and an aqueous NH$_4$OH solution (2 mL). The organic layer was separated, concentrated to dryness, and purified by normal phase flash column chromatography (SiO$_2$) to give the title compound as yellow solid (82 mg, 25% yield). MS (ESI): mass calcd. for C$_{28}$H$_{27}$N$_5$O$_4$S, 529.6; m/z found, 530.4 [M+H]$^+$. $^1$H NMR (400 MHz, DMSO-d$_6$): δ 9.64 (br, 1H), 8.36-8.24 (m, 1H), 8.14-7.94 (m, 1H), 7.30-7.22 (m, 1H), 7.12-7.04 (m, 2H), 7.03-6.97 (m, 1H), 6.93-6.83 (m, 2H), 6.83-6.75 (m, 1H), 5.94-5.82 (m, 1H), 3.98-3.91 (m, 1H), 2.87-2.81 (m, 1H), 2.71-2.65 (m, 1H), 2.22 (s, 3H), 2.02 (s, 3H), 1.97-1.88 (m, 2H), 1.81-1.75 (m, 1H), 1.73-1.66 (m, 1H), 1.56-1.48 (m, 1H), 1.39-1.30 (m, 1H).

Example 221: (R,E)-N-(1-(3-Ethoxyacryloyl)piperidin-3-yl)-5-(2-methyl-4-phenoxyphenl)-4-oxo-4,5-dihydro-3H-1-thia-3,5,8-triazaacenaphthylene-2-carboxamide

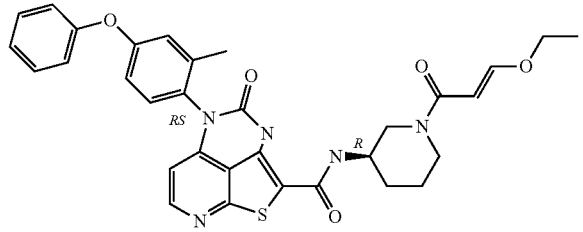

Step A: (E)-3-Ethoxyprop-2-enoic Acid

A solution of ethyl (E)-3-ethoxyprop-2-enoate (5.0 g, 0.035 mmol) was dissolved in a 2 M NaOH (40 mL) solution and refluxed for 4 hours. The mixture was cooled to rt, the pH adjusted to pH 3 with 4 M aqueous HCl, and extracted with ethyl acetate. The organic phase was treated with activated charcoal and sodium sulphate, filtered, and concentrated to dryness to give the title compound as a tan solid (1.8 g, 44% yield).

Step B: (R,E)-N-(1-(3-Ethoxyacryloyl)piperidin-3-yl)-5-(2-methyl-4-phenoxyphenyl)-4-oxo-4,5-dihydro-3H-1-thia-3,5,8-triazaacenaphthylene-2-carboxamide A solution of (EZ)-3-ethoxyprop-2-enoic acid (81 mg, 0.70 mmol) and thionyl chloride (1 mL) was refluxed for 2 h and concentrated to dryness to give the (EZ)-3-ethoxyprop-2-enoyl chloride crude product. To a cold stirred solution of (EZ)-3-ethoxyprop-2-enoyl chloride in DCM (5 mL) was added (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 300 mg, 0.60 mmol) and triethylamine (182 mg, 1.80 mmol). The mixture was warmed and stirred at rt for 1 h. Water was added and the solution was extracted with DCM. The organic layer was concentrated to dryness and the resulting residue was purified by flash column chromatography to give the title compound as a yellow solid (80 mg, 22% yield). MS (ESI): mass calcd. for C$_{32}$H$_{31}$N$_5$O$_5$S, 597.7; m/z found, 598.5 [M+H]$^+$. $^1$H NMR (400 MHz, CD$_3$OD): δ 8.35-8.20 (m, 1H), 7.60-7.42 (m, 1H), 7.41-7.30 (m, 3H), 7.19-7.10 (m, 1H), 7.07-6.98 (m, 3H), 6.98-6.90 (m, 1H), 6.09-5.98 (m, 1H), 5.88-5.76 (m, 1H), 4.63-4.13 (m, 1H), 4.09-3.72 (m, 4H), 3.18-3.01 (m, 1H), 3.00-2.66 (m, 1H), 2.12-2.04 (m, 3H), 2.03-1.95 (m, 1H), 1.86-1.75 (m, 1H), 1.74-1.62 (m, 1H), 1.57-1.43 (m, 1H), 1.33-1.21 (m, 3H).

Example 222: (R)-5-(2-Fluoro-6-methyl-4-phenoxyphenyl)-N-(1-methylpiperidin-3-yl)-4-oxo-4,5-dihydro-3H-1-thia-3,5,8-triazaacenaphthylene-2-carboxamide

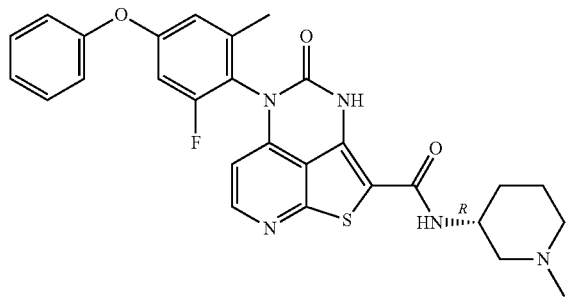

The title compound was prepared using analogous conditions described in Method 1, steps C-G in Example 1, and using 2-fluoro-6-methyl-4-phenoxyaniline (Intermediate 9) in place of 2-methyl-4-phenoxyaniline in step C, and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{28}H_{26}FN_5O_3S$, 531.6; m/z found, 532.3 $[M+H]^+$. $^1$H NMR (400 MHz, CD$_3$OD): δ 8.31 (d, J=5.6 Hz, 1H), 7.48-7.40 (m, 2H), 7.26-7.18 (m, 1H), 7.16-7.08 (m, 2H), 6.90-6.83 (m, 1H), 6.81-6.72 (m, 1H), 6.10 (d, J=5.5 Hz, 1H), 4.26-4.11 (m, 1H), 3.05-2.92 (m, 1H), 2.83-2.69 (m, 1H), 2.38-2.35 (m, 3H), 2.30-2.18 (m, 2H), 2.15 (s, 3H), 1.97-1.78 (m, 2H), 1.74-1.62 (m, 1H), 1.59-1.44 (m, 1H).

Example 223: (R)-5-(4-(2-Isopropylphenoxy)-2-methylphenyl)-N-(1-methylpiperidin-3-yl)-4-oxo-4,5-dihydro-3H-1-thia-3,5,8-triazaacenaphthylene-2-carboxamide

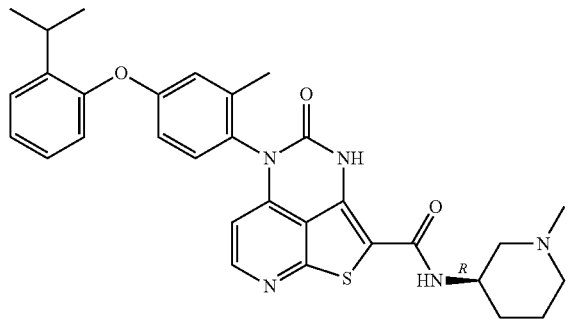

Step A: (R)-5-(4-(2-isopropylphenoxy)-2-methylphenyl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 2-isopropylphenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(2-Isopropylphenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-isopropylphenoxy)-2-methylphenyl)-4-oxo-N-(piperidin-3-yl)-4,5-dihydro-3H-1-thia-3,5,8-triazaacenaphthylene-2-carboxamide (100 mg, 0.19 mmol) and formaldehyde (0.3 mL, 37 wt. % in H$_2$O) in MeOH (6 mL) was added NaBH(OAc)$_3$ (118 mg, 0.555 mmol) and was stirred at rt for 1 h, concentrated to dryness, and purified by flash column chromatography to give the title compound as a white solid (63 mg, 54% yield). MS (ESI): mass calcd. for $C_{31}H_{33}N_5O_3S$, 555.7; m/z found, 556.1 $[M+H]^+$. $^1$H NMR (400 MHz, CD$_3$OD): δ 8.49 (s, 1H), 8.35-8.21 (m, 1H), 7.46-7.34 (m, 1H), 7.35-7.25 (m, 1H), 7.24-7.14 (m, 2H), 7.01-6.92 (m, 2H), 6.91-6.82 (m, 1H), 6.08-5.96 (m, 1H), 4.35-4.22 (m, 1H), 3.52-3.38 (m, 1H), 3.28-3.17 (m, 2H), 2.90-2.66 (m, 5H), 2.14-2.06 (m, 3H), 2.05-1.94 (m, 2H), 1.90-1.78 (m, 1H), 1.72-1.60 (m, 1H), 1.22 (d, J=6.9 Hz, 6H).

Example 224: N-((3R,5R)-5-Methoxypiperidin-3-yl)-5-(2-methyl-4-phenoxyphenyl)-4-oxo-4,5-dihydro-3H-1-thia-3,5,8-triazaacenaphthylene-2-carboxamide

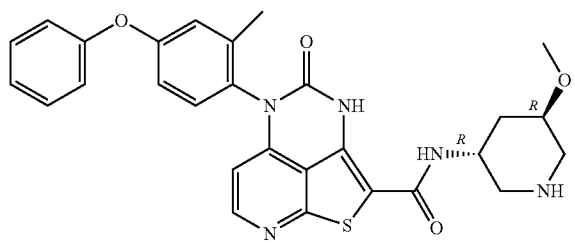

The title compound was prepared using analogous conditions described in Method 1, steps A-H in Example 1, and using tert-butyl (3R,5R)-3-amino-5-methoxypiperidine-1-carboxylate (Intermediate 6) in place of tert-butyl (3R,5R)-3-amino-5-fluoropiperidine-1-carboxylate (Intermediate 1) in step G. MS (ESI): mass calcd. for $C_{28}H_{27}N_5O_4S$, 529.6; m/z found, 530.3 $[M+H]^+$. $^1$H NMR (400 MHz, CD$_3$OD): δ 8.24 (d, J=5.6 Hz, 1H), 7.45-7.35 (m, 2H), 7.29-7.23 (m, 1H), 7.19-7.12 (m, 1H), 7.11-7.02 (m, 3H), 7.01-6.93 (m, 1H), 5.98 (d, J=5.6 Hz, 1H), 4.41-4.25 (m, 1H), 3.62-3.54 (m, 1H), 3.41-3.37 (m, 3H), 3.22-3.13 (m, 1H), 3.10-3.01 (m, 1H), 2.80-2.72 (m, 1H), 2.70-2.59 (m, 1H), 2.28-2.15 (m, 1H), 2.11 (s, 3H), 1.87-1.75 (m, 1H).

Example 225: (R)-5-(2-Methyl-4-phenoxyphenyl)-N-(1-(3-methylbut-2-enoyl)piperidin-3-yl)-4-oxo-4,5-dihydro-3H-1-thia-3,5,8-triazaacenaphthylene-2-carboxamide

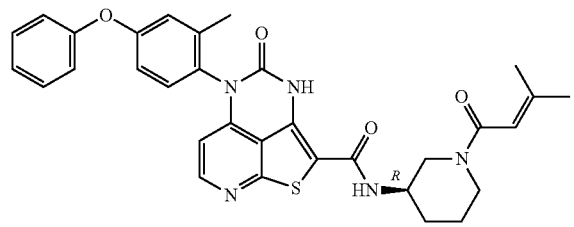

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.30 mmol) and 3-methylbut-2-enoic acid (60 mg, 0.60 mmol) in DMF (2 mL) were added HATU (228 mg, 0.600 mmol) and triethylamine (61 mg, 0.60 mmol) and was stirred at rt for 4 hours. The mixture was purified by flash column chromatography, then by preparative TLC to give the title compound as a yellow solid (117 mg, 66.0% yield). MS (ESI): mass calcd. for $C_{32}H_{31}N_5O_4S$, 581.7; m/z found, 582.2 $[M+H]^+$. $^1H$ NMR (400 MHz, DMSO-$d_6$): δ 10.22 (s, 1H), 8.30 (d, J=5.2 Hz, 1H), 8.11-8.00 (m, 1H), 7.47-7.38 (m, 2H), 7.38-7.32 (m, 1H), 7.20-7.14 (m, 1H), 7.13-7.02 (m, 3H), 6.99-6.92 (m, 1H), 5.94 (d, J=5.1 Hz, 1H), 5.90-5.81 (m, 1H), 4.44-4.10 (m, 1H), 3.90-3.69 (m, 2H), 3.05-2.85 (m, 1H), 2.69-2.52 (m, 1H), 2.03 (s, 3H), 1.95-1.86 (m, 1H), 1.79-1.72 (m, 6H), 172-1.51 (m, 2H), 1.42-1.30 (m, 1H).

Example 226: (R)-5-(4-(3-(Methoxymethyl)phenoxy)-2-methylphenyl)-N-(1-methylpiperidin-3-yl)-4-oxo-4,5-dihydro-3H-1-thia-3,5,8-triazaacenaphthylene-2-carboxamide

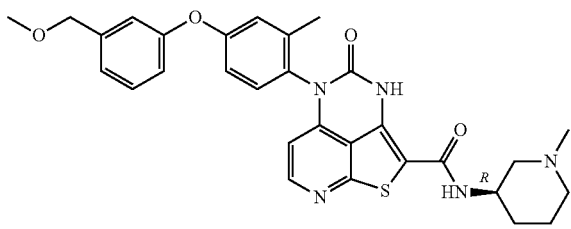

Step A: 4-[3-(Methoxymethyl)phenoxy]-2-methylaniline

To a solution of 1-bromo-3-(methoxymethyl)benzene (2.6 g, 13 mmol) and 4-amino-3-methylphenol (1.6 g, 13 mmol) in $CH_3CN$ (50 mL) were added $K_2CO_3$ (7.10 g, 51.5 mmol), (1R,2R)—$N^1,N^2$-dimethylcyclohexane-1,2-diamine (369 mg, 2.59 mmol), and CuI (247 mg, 1.30 mmol) and it was charged with $N_2$ and was stirred at 80° C. overnight. The reaction mixture was concentrated to dryness, extracted with EtOAc/$H_2O$, the organic layer was collected and purified by flash column chromatography to give the title compound as a black solid (500 mg, 16% yield).

Step B: (R)-5-(4-(3-(Methoxymethyl)phenoxy)-2-methylphenyl)-N-(1-methylpiperidin-3-yl)-4-oxo-4,5-dihydro-3H-1-thia-3,5,8-triazaacenaphthylene-2-carboxamide The title compound was prepared using analogous conditions described in Method 1, steps C-G in Example 1, and using 4-[3-(methoxymethyl)phenoxy]-2-methylaniline in place of 2-methyl-4-phenoxyaniline in step C, and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{30}H_{31}N_5O_4S$, 557.7; m/z found, 558.2 $[M+H]^+$. $^1H$ NMR (400 MHz, $CDCl_3$): δ 9.71-9.44 (m, 1H), 8.33 (d, J=5.4 Hz, 1H), 8.25-8.04 (m, 1H), 7.40-7.30 (m, 1H), 7.23-7.11 (m, 2H), 7.09 (s, 1H), 7.04-6.97 (m, 2H), 6.97-6.90 (m, 1H), 5.95 (d, J=5.4 Hz, 1H), 4.79-4.61 (m, 1H), 4.46 (s, 2H), 3.59-3.47 (m, 1H), 3.40 (s, 3H), 3.73-3.41 (m, 2H), 2.83 (s, 3H), 2.76-2.61 (m, 1H), 2.60-2.28 (m, 1H), 2.18-1.99 (m, 4H), 2.00-1.83 (m, 1H), 1.83-1.62 (m, 1H).

Example 227: (R)-5-(2-Methyl-4-(2-(trifluoromethoxy)phenoxy)phenyl)-N-(1-methylpiperidin-3-yl)-4-oxo-4,5-dihydro-3H-1-thia-3,5,8-triazaacenaphthylene-2-carboxamide

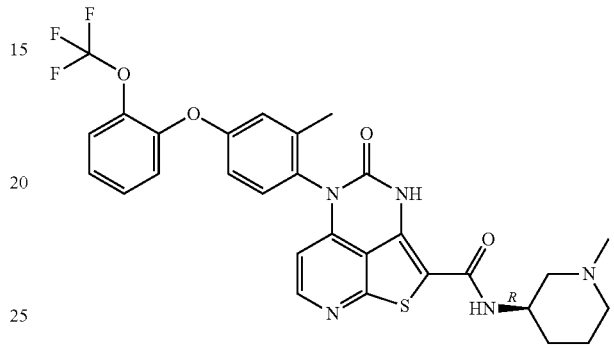

Step A: (R)-5-(2-Methyl-4-(2-(trifluoromethoxy)phenoxy)phenyl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 2-(trifluoromethoxy)phenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(2-Methyl-4-(2-(trifluoromethoxy)phenoxy)phenyl)-N-(1-methylpiperidin-3-yl)-4-oxo-4,5-dihydro-3H-1-thia-3,5,8-triazaacenaphthylene-2-carboxamide To a solution of (R)-5-(2-methyl-4-(2-(trifluoromethoxy)phenoxy)phenyl)-4-oxo-N-(piperidin-3-yl)-4,5-dihydro-3H-1-thia-3,5,8-triazaacenaphthylene-2-carboxamide (107 mg, 0.183 mmol) in DCM (5 mL) were added formaldehyde (0.5 mL, 37 wt. % in $H_2O$) and $NaBH(OAc)_3$ (78 mg, 0.37 mmol) and was stirred at rt for 4 hours. To the mixture were added DCM (50 mL), MeOH (5 mL), and water (30 mL). The organic layer was collected, concentrated to dryness, and purified by flash column chromatography to give the title compound as a yellow solid (66 mg, 60% yield). MS (ESI): mass calcd. for $C_{29}H_{26}F_3N_5O_4S$, 597.6; m/z found, 598.0 $[M+H]^+$. $^1H$ NMR (400 MHz, DMSO-d6): δ 8.26 (d, J=5.5 Hz, 1H), 8.12-7.99 (m, 1H), 7.58-7.50 (m, 1H), 7.46-7.40 (m, 1H), 7.37-7.32 (m, 1H), 7.32-7.27 (m, 1H), 7.26-7.22 (m, 1H), 7.11-7.07 (m, 1H), 6.98-6.93 (m, 1H), 5.88 (d, J=5.5 Hz, 1H), 3.95-3.88 (m, 1H), 2.87-2.87 (m, 1H), 2.72-2.61 (m, 1H), 2.20 (s, 3H), 2.04 (s, 3H), 1.96-1.84 (m, 2H), 1.79-1.72 (m, 1H), 1.70-1.63 (m, 1H), 1.54-1.44 (m, 1H), 1.37-1.27 (m, 1H).

Example 228: (R,Z)—N-(1-(3-Cyclopropyl-2-fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide

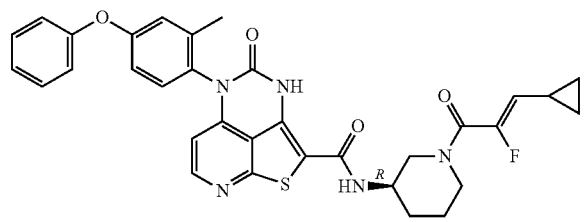

Step A: Ethyl 2-diethoxyphosphoryl-2-fluoroacetate

A solution of ethyl 2-bromo 2-fluoroacetate (5.0 g, 27 mmol) and triethylphosphite (13 mL) was heated at 130° C. for 23 h. The resulting mixture was distilled under reduced pressure (1.4 mbar, 75-110° C.) to give the title compound as a yellowish oil (6 g, 92%).

Step B: (Z)-3-Cyclopropyl-2-fluoroprop-2-enoic Acid

A solution of ethyl 2-(diethoxyphosphoryl)-2-fluoroacetate (2.0 g, 8.3 mmol) in THF (5 mL) was cooled to 0° C. in an ice-batch. NaH (198 mg, 8.26 mmol) was added and stirred for 30 min, then cyclopropanecarbaldehyde (0.579 g, 8.26 mmol) was slowly added to the reaction mixture and the reaction mixture was allowed to warm to rt for 2 h. The reaction was worked up by the addition of DCM and water. The organic layer was separated and washed with brine, dried over anhydrous MgSO$_4$, and concentrated to dryness. The residue was dissolved in dioxane (5 mL), and water (5 mL) and NaOH (1.321 g, 33.03 mmol) were added and stirred for 10 min, then it was acidified with 2 M aqueous HCl to pH~2 and extracted with DCM. The organic layers were washed with brine, dried over anhydrous MgSO$_4$, and concentrated to dryness to give the title compound (0.72 g, 67% yield).

Step C: (R,Z)—N-(1-(3-Cyclopropyl-2-fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), (Z)-3-cyclopropyl-2-fluoroprop-2-enoic acid (73 mg, 0.56 mmol), HATU (213 mg, 0.560 mmol), and triethylamine (142 mg, 1.40 mmol) in DMF (3 mL) was stirred at rt for 2 h. The reaction mixture was purified by flash column chromatography to give the title compound as a white solid (50 mg, 29% yield). MS (ESI): mass calcd. for C$_{33}$H$_{30}$FN$_5$O$_4$S, 611.7; m/z found, 612.5 [M+H]$^+$. $^1$H NMR (400 MHz, DMSO-d$_6$): δ 10.21 (s, 1H), 8.33 (d, J=5.5 Hz, 1H), 8.07 (s, 1H), 7.49-7.40 (m, 2H), 7.39-7.33 (m, 1H), 7.24-7.15 (m, 1H), 7.15-7.05 (m, 3H), 7.02-6.93 (m, 1H), 5.97 (d, J=5.5 Hz, 1H), 5.16 (dd, J=21.0, 10.5 Hz, 1H), 4.35-4.05 (m, 1H), 3.96-3.71 (m, 2H), 2.05 (s, 3H), 2.02-1.90 (m, 2H), 1.87-1.76 (m, 1H), 1.74-1.62 (m, 1H), 1.52-1.41 (m, 2H), 1.31-1.23 (m, 1H), 0.87-0.72 (m, 2H), 0.50-0.31 (m, 2H).

Example 229: (E)-N-(1-(2-Cyano-3-cyclopropylacryloyl)azetidin-3-yl)-5-(2-methyl-4-phenoxyphenyl)-4-oxo-4,5-dihydro-3H-1-thia-3,5,8-triazaacenaphthylene-2-carboxamide

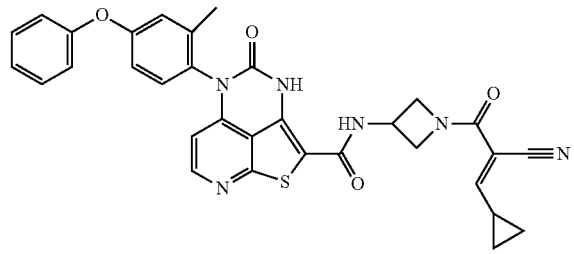 [SMILES: Cc1cc(Oc2ccccc2)ccc1N1C(=O)Nc2c(C(=O)NC3CN(C(=O)/C(C#N)=C/C4CC4)C3)sc3nccc1c23]

To a solution of DMF (2 mL) was added N-(azetidin-3-yl)-5-(2-methyl-4-phenoxyphenyl)-4-oxo-4,5-dihydro-3H-1-thia-3,5,8-triazaacenaphthylene-2-carboxamide (Example 252, 100 mg, 0.21 mmol), (E)-2-cyano-3-cyclopropylprop-2-enoic acid (Intermediate 17) (58 mg, 0.42 mmol), HATU (121 mg, 0.318 mmol), and diisopropylethylamine (0.072 mL, 0.42 mmol). The mixture was stirred at rt overnight, then purified by flash column chromatography to give the title compound as a white solid (63 mg, 50% yield). MS (ESI): mass calcd. for C$_{32}$H$_{26}$N$_6$O$_4$S, 590.7; m/z found, 591.0 [M+H]$^+$. $^1$H NMR (400 MHz, DMSO-d$_6$ and CD$_3$OD): δ 8.28 (d, J=5.5 Hz, 1H), 7.41-7.34 (m, 2H), 7.32-7.26 (m, 1H), 7.17-7.10 (m, 1H), 7.09-7.00 (m, 3H), 6.94-6.91 (m, 1H), 6.91-6.86 (m, 1H), 5.95 (d, J=5.5 Hz, 1H), 4.75-4.65 (m, 2H), 4.47-4.37 (m, 1H), 4.32-4.23 (m, 1H), 4.06-3.97 (m, 1H), 2.03 (s, 3H), 1.96-1.86 (m, 1H), 1.21-1.18 (m, 2H), 0.96-0.89 (m, 2H).

Example 230: N-(1-Cyclopropylazetidin-3-yl)-5-(2-methyl-4-phenoxyphenyl)-4-oxo-4,5-dihydro-3H-1-thia-3,5,8-triazaacenaphthylene-2-carboxamide

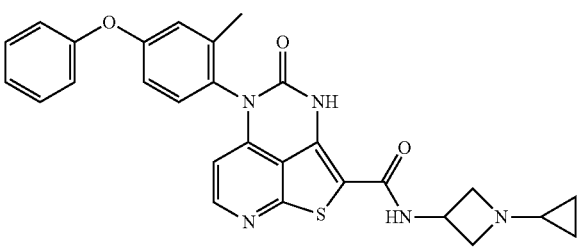 [SMILES: Cc1cc(Oc2ccccc2)ccc1N1C(=O)Nc2c(C(=O)NC3CN(C4CC4)C3)sc3nccc1c23]

To a solution of N-(azetidin-3-yl)-5-(2-methyl-4-phenoxyphenyl)-4-oxo-4,5-dihydro-3H-1-thia-3,5,8-triazaacenaphthylene-2-carboxamide (Example 252, 150 mg, 0.30 mmol) and (1-ethoxycyclopropoxy)trimethylsilane (0.5 mL) in MeOH (10 mL) was added acetic acid (1 mL), followed by sodium cyanoborohydride (93 mg, 1.5 mmol). The resulting mixture was heated to reflux for 3 h, the reaction was made basic to pH 14 with a 6 M aqueous NaOH solution, then concentrated to dryness, and purified by flash column chromatography to get the title compound as a yellow solid (61 mg, 40% yield). MS (ESI): mass calcd. for C$_{28}$H$_{25}$N$_5$O$_3$S, 511.6; m/z found, 512.4 [M+H]$^+$. $^1$H NMR (400 MHz, CD$_3$OD): δ 8.45-8.25 (m, 1H), 7.51-7.38 (m, 2H), 7.37-7.28 (m, 1H), 7.27-7.17 (m, 1H), 7.16-7.07 (m, 3H), 7.05-6.95 (m, 1H), 6.18-6.06 (m, 1H), 4.70-4.52 (m, 1H), 3.89-3.69 (m, 2H), 3.45-3.37 (m, 2H), 2.16 (s, 3H), 2.12-2.05 (m, 1H), 0.57-0.48 (m, 2H), 0.46-0.37 (m, 2H).

Example 231: (R,EZ)—N-(1-(2-Cyano-3-methoxy-acryloyl)piperidin-3-yl)-5-(2-methyl-4-phenoxyphenyl)-4-oxo-4,5-dihydro-3H-1-thia-3,5,8-triazaacenaphthylene-2-carboxamide

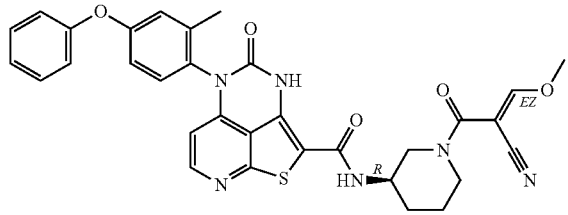

Step A: (EZ)-2-Cyano-3-methoxyprop-2-enoic Acid

A solution of 2-cyanoacetic acid (800 mg, 9.4 mmol) in trimethoxymethane (10 mL) and acetic anhydride (2 mL) was heated at reflux under $N_2$ overnight, and then it was concentrated to dryness. The residue was dissolved in THF/$H_2O$ (10 mL/10 mL) and LiOH.$H_2O$ (790 mg, 18.8 mmol) was added and was stirred at rt for 2 h. The reaction was extracted with EtOAc and concentrated to dryness to give to title compound as a yellow solid (500 mg, 42% yield).

Step B: (R,EZ)—N-(1-(2-Cyano-3-methoxyacryloyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.40 mmol), (EZ)-2-cyano-3-methoxyprop-2-enoic acid (102 mg, 0.800 mmol), triethylamine (81 mg, 0.80 mmol), and HATU (304 mg, 0.800 mmol) in DMF (4 mL) was stirred at rt for 1 h. Water was added and the precipitate was collected by filtration. The residue was purified by flash column chromatography to give the title compound as a white solid (40 mg, 17% yield). MS (ESI): mass calcd. for $C_{32}H_{28}N_6O_5S$, 608.7; m/z found, 609.1 $[M+H]^+$. $^1H$ NMR (400 MHz, $CD_3OD$): δ 8.38-8.26 (m, 1H), 7.94-7.81 (m, 1H), 7.44-7.35 (m, 2H), 7.35-7.28 (m, 1H), 7.20-7.13 (m, 1H), 7.12-7.02 (m, 3H), 7.01-6.93 (m, 1H), 6.12-6.00 (m, 1H), 4.20-4.06 (m, 1H), 3.99-3.80 (m, 1H), 3.70 (s, 3H), 3.48-3.30 (m, 3H), 2.16-2.05 (m, 4H), 2.01-1.91 (m, 1H), 1.83-1.68 (m, 2H).

Example 232: (R,E)-5-(*S)-(5-Chlorobenzo[d][1,3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide

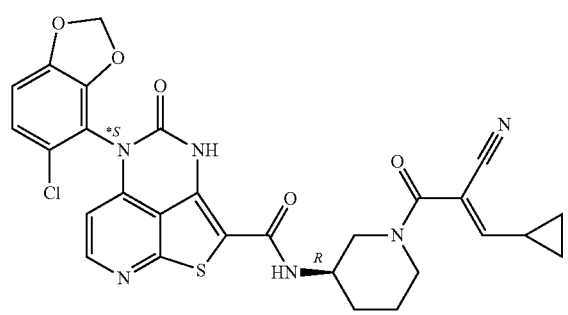

Step A: (R)-5-(5-chlorobenzo[d][1,3]dioxol-4-yl)-4-oxo-N-(piperidin-3-yl)-4,5-dihydro-3H-1-thia-3,5,8-triazaacenaphthylene-2-carboxamide The title compound was prepared using analogous conditions described in Method 1, steps C-H in Example 1, and using 5-chlorobenzo[d][1,3]dioxol-4-amine in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G and Chiral resolution Method A after Step F to give the *S atropisomer. MS (ESI): mass calcd. for $C_{21}H_{18}ClN_5O_4S$, 471.92; m/z found, 472.0 $[M+H]^+$.

Step B: (R,E)-5-(*S)-(5-Chlorobenzo[d][1.3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide A solution of (R)-5-(5-chlorobenzo[d][1,3]dioxol-4-yl)-4-oxo-N-(piperidin-3-yl)-4,5-dihydro-3H-1-thia-3,5,8-triazaacenaphthylene-2-carboxamide (110 mg, 0.23 mmol), (E)-2-cyano-3-cyclopropylprop-2-enoic acid (Intermediate 17) (32 mg, 0.23 mmol), triethylamine (94 mg, 0.93 mmol), and HATU (177 mg, 0.466 mmol) in DMF (4 mL) was stirred at room temperature for 3 h, then concentrated to dryness, and purified by normal phase flash column chromatography ($SiO_2$) to give the title compound as a white solid (27 mg, 19% yield). MS (ESI): mass calcd. for $C_{28}H_{23}N_6O_5S$, 591.04; m/z found, 591.5 $[M+H]^+$. $^1H$ NMR (400 MHz, DMSO-$d_6$ and $CD_3OD$): δ 8.55-8.31 (m, 1H), 7.17 (d, J=7.9 Hz, 1H), 7.07 (d, J=7.9 Hz, 1H), 6.68-6.46 (m, 1H), 6.30-6.20 (m, 1H), 6.20-6.07 (m, 2H), 4.18-4.03 (m, 2H), 4.03-3.96 (m, 1H), 3.26-3.07 (m, 2H), 2.11-1.97 (m, 2H), 1.93-1.75 (m, 2H), 1.69-1.58 (m, 1H), 1.27-1.15 (m, 2H), 0.97-0.83 (m, 2H).

Example 233: (R,E)-N-(1-(2-Cyano-3-cyclopropylacryloyl)piperidin-3-yl)-5-(2-methyl-4-((tetrahydro-2H-pyran-4-yl)oxy)phenyl)oxo-4,5-dihydro-3H-1-thia-3,5,8-triazaacenaphthylene-2-carboxamide

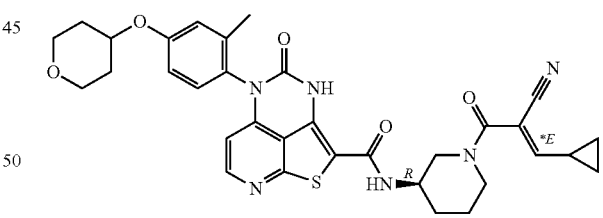

Step A: (R)-5-(2-methyl-4-((tetrahydro-2H-pyran-4-yl)oxy)phenyl)-4-oxo-N-(piperidin-3-vi)-4,5-dihydro-3H-1-thia-3,5,8-triazaacenaphthylene-2-carboxamide The title compound was prepared analogous conditions described in Method 1, steps D-H in Example 1, and using 2-chloro-4-(2-methyl-4-tetrahydropyran-4-yloxyanilino)pyridine-3-carbonitrile (Intermediate 31) in place of 2-chloro-4-(2-methyl-4-phenoxyanilino)pyridine-3-carbonitrile in step D, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R,E)-N-(1-(2-Cyano-3-cyclopropylacryloyl)piperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide A solution of (R)-5-(2-methyl-4-((tetrahydro-2H-pyran-4-yl)oxy)phenyl)-4-oxo-N-(piperidin-3-yl)-4,5-dihydro-3H-1-thia-3,5,8-triazaacenaphthylene-2-carboxamide (100 mg, 0.197 mmol), (E)-2-cyano-3-cyclopropylprop-2-enoic acid (Intermediate 17) (54 mg, 0.39 mmol), HATU (97 mg, 0.26 mmol), and DIPEA (68 μL, 0.39 mmol) in DMF (5 mL) was stirred at rt for 2 h, then purified by flash column chromatography to yield the title compound as a white solid (77 mg, 62% yield). MS (ESI): mass calcd. for $C_{33}H_{34}N_6O_5S$, 626.7; m/z found, 627.1 [M+H]$^+$. $^1$H NMR (400 MHz, CD$_3$OD): δ 8.36-8.27 (m, 1H), 7.26-7.18 (m, 1H), 7.06-7.00 (m, 1H), 7.01-6.94 (m, 1H), 6.58-6.49 (m, 1H), 6.07-6.00 (m, 1H), 4.69-4.59 (m, 1H), 4.27-4.10 (m, 1H), 4.04-3.89 (m, 4H), 3.66-3.56 (m, 2H), 3.23-3.03 (m, 1H), 2.13 (s, 3H), 2.10-1.95 (m, 5H), 1.93-1.84 (m, 1H), 1.82-1.69 (m, 3H), 1.68-1.56 (m, 1H), 1.25-1.16 (m, 2H), 1.03-0.90 (m, 1H), 0.90-0.76 (m, 1H).

Example 234: (R,EZ)—N-(1-(2-Cyano-4-((2-methoxyethyl)amino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

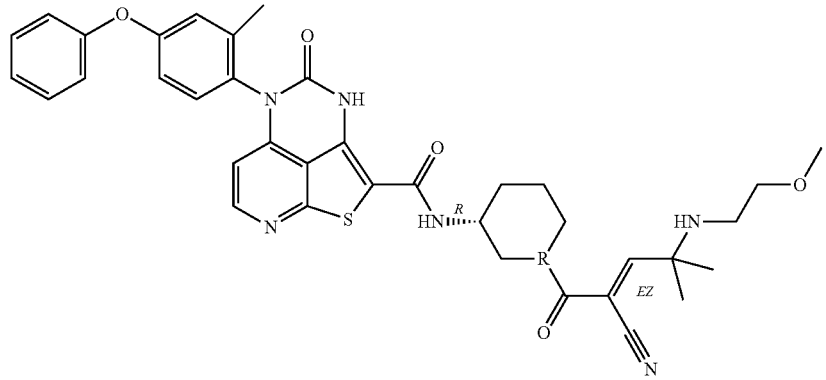

Step A:
2-(2-Methoxyethylamino)-2-methylpropan-1-ol

To a round bottom flask were added 2-amino-2-methylpropan-1-ol (1.0 g, 11 mmol), 1-bromo-2-methoxy-ethane (1.6 g, 11 mmol), NaI (168 mg, 1.12 mmol), K$_2$CO$_3$ (3.10 g, 22.4 mmol), and CH$_3$CN (20 mL) and the mixture was refluxed for 6 h. The solvent was removed under reduced pressure and the residue was used in the next step without purification (1.22 g, 75% yield).

Step B: tert-butyl N-(2-hydroxy-1,1-dimethylethyl)-N-(2-methoxyethyl)carbamate

To a round bottom flask were added 2-(2-methoxyethylamino)-2-methylpropan-1-ol (1.22 g, 8.29 mmol), di-tert-butyl dicarbonate (2.17 g, 9.94 mmol), Na$_2$CO$_3$ (1.318 g, 12.43 mmol), THF (20 mL), and water (20 mL) and was stirred at rt for 5 h. The mixture was extracted with EtOAc, washed with 1 M aqueous HCl, saturated NaHCO$_3$ and brine, dried over anhydrous Na$_2$SO$_4$, filtered, and concentrated to dryness to give the title compound as a yellow liquid (462 mg, 23% yield).

Step C: tert-Butyl N-(1,1-dimethyl-2-oxo-ethyl)-N-(2-methoxyethyl)carbamate

A solution of DMSO (219 mg, 2.80 mmol) in DCM (10 mL) was cooled to −78° C. and oxalyl dichloride (284 mg, 2.24 mmol) was added dropwise and the mixture was stirred at −78° C. for 30 min, then tert-butyl N-(2-hydroxy-1,1-dimethylethyl)-N-(2-methoxyethyl)carbamate (462 mg, 1.87 mmol) dissolved in DCM (10 mL) was added dropwise and the mixture was stirred at −78° C. for another 30 min. The reaction was quenched with triethylamine at −78° C. and stirred at −78° C. for 30 min. The mixture was warmed to rt and diluted with DCM, washed with saturated NaHCO$_3$ and brine, dried over anhydrous Na$_2$SO$_4$, filtered, and concentrated to dryness to give the title compound as a colorless liquid (401 mg, 87% yield).

Step D: (R,EZ)-tert-Butyl (4-cyano-2-methyl-5-(3-(5-(2-methyl-4-phenoxyphenyl)-4-oxo-4,5-dihydro-3H-1-thia-3,5,8-triazaacenaphthylene-2-carboxamido)piperidin-1-yl)-5-oxopent-3-en-2-yl)(2-methoxyethyl)carbamate A solution of tert-butyl N-(1,1-dimethyl-2-oxo-ethyl)-N-(2-methoxyethyl)carbamate (200 mg, 0.815 mmol), (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 231 mg, 0.407 mmol), piperidine (0.3 mL), AcOH (0.1 mL), dioxane (10 mL), and 4A molecular sieves (1 g) was stirred at 100° C. for 1 h under N2. The mixture was concentrated to dryness and purified by flash column chromatography to give the title compound as a yellow solid (29 mg, 9% yield).

Step E: (R,EZ)—N-(1-(2-Cyano-4-((2-methoxyethyl)amino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide To a round bottom flask were added (R,EZ)-tert-butyl (4-cyano-2-methyl-5-(3-(5-(2-methyl-4-phenoxyphenyl)-4-oxo-4,5-dihydro-3H-1-thia-3,5,8-triazaacenaphthylene-2-carboxamido)piperidin-1-yl)-5-oxopent-3-en-2-yl)(2-methoxyethyl)carbamate (29 mg, 0.036 mmol), concentrated HCl (2 mL), and MeOH (2 mL) and was stirred at rt for 1 h under N2. The mixture was concentrated to dryness and purified by flash column chromatography to give the title compound as a white solid (11 mg, 41% yield). MS (ESI): mass calcd. for $C_{37}H_{39}N_7O_5S$, 693.8; m/z found, 694.3 [M+H]$^+$. $^1$H NMR (400 MHz, CD$_3$OD): δ 8.35-8.29 (m, 1H), 7.93-7.63 (m, 1H), 7.44-7.38 (m, 2H), 7.31-7.24 (m, 1H), 7.21-7.14 (m, 1H), 7.12-7.04 (m, 3H), 7.01-6.95 (m, 1H), 6.11-6.04 (m, 1H), 4.60-3.95 (m, 3H), 3.89-3.75 (m, 2H), 3.70-3.56 (m, 2H), 3.41-3.25 (m, 4H), 3.25-3.05 (m, 1H), 2.24-2.06 (m, 4H), 2.06-1.83 (m, 2H), 1.78-1.65 (m, 1H), 1.65-1.49 (m, 6H).

Example 235: (R)-5-(2,6-Difluoro-4-phenoxyphenyl)-4-oxo-N-(piperidin-3-yl)-4,5-dihydro-3H-1-thia-3,5,8-triazaacenaphthylene-2-carboxamide

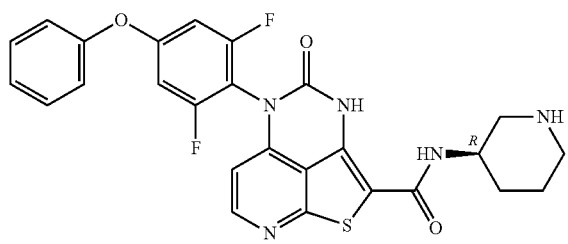

The title compound was prepared using conditions described in steps A-G in Example 175. MS (ESI): mass calcd. for $C_{26}H_{21}F_2N_5O_3S$, 521.5; m/z found, 522.2 [M+H]$^+$. $^1$H NMR (400 MHz, DMSO-d$_6$) δ 8.90 (d, J=5.56 Hz, 1H), 8.16 (d, J=5.56 Hz, 1H), 7.45-7.55 (m, 2H), 7.27-7.34 (m, 1H), 7.24 (d, J=7.58 Hz, 2H), 6.95 (d, J=8.08 Hz, 2H), 6.00 (d, J=5.05 Hz, 1H), 4.03-4.16 (m, 1H), 3.32-3.39 (m, 1H), 3.12-3.20 (m, 1H), 2.78-2.94 (m, 2H), 1.85-2.02 (m, 2H), 1.54-1.78 (m, 2H).

Example 236: N-((3S,4S)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide

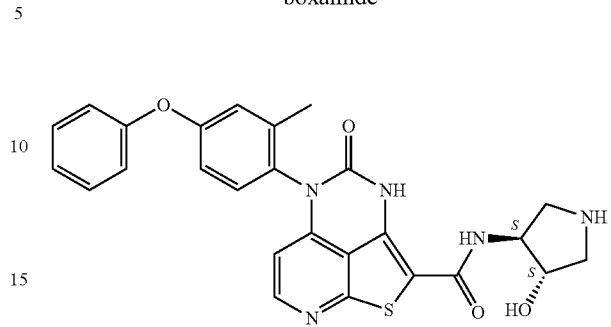

The title compound was prepared using analogous conditions described in Method 1, steps A-H in Example 1, and using tert-butyl (3S,4S)-3-amino-4-hydroxypyrrolidine-1-carboxylate in place of tert-butyl (3R,5R)-3-amino-5-fluoropiperidine-1-carboxylate (Intermediate 1) in step G. MS (ESI): mass calcd. for $C_{26}H_{23}N_5O_4S$, 501.6; m/z found, 502.1 [M+H]$^+$. $^1$H NMR (400 MHz, CD$_3$OD): δ 8.32 (d, J=5.6 Hz, 1H), 7.46-7.33 (m, 2H), 7.31-7.23 (m, 1H), 7.19-7.13 (m, 1H), 7.11-7.03 (m, 3H), 7.00-6.93 (m, 1H), 6.06 (d, J=5.5 Hz, 1H), 4.54-4.45 (m, 1H), 4.40-4.30 (m, 1H), 3.79-3.68 (m, 1H), 3.60-3.51 (m, 1H), 3.51-3.41 (m, 1H), 3.27-3.23 (m, 1H), 2.11 (s, 3H).

Example 237: N$^1$-((E)-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)-N5-(15-oxo-19-((3aS,4R,6aR)-2-oxohexahydro-1H-thieno[3,4-d]imidazol-4-yl)-4,7,10-trioxa-14-azanonadecyl)glutaramide

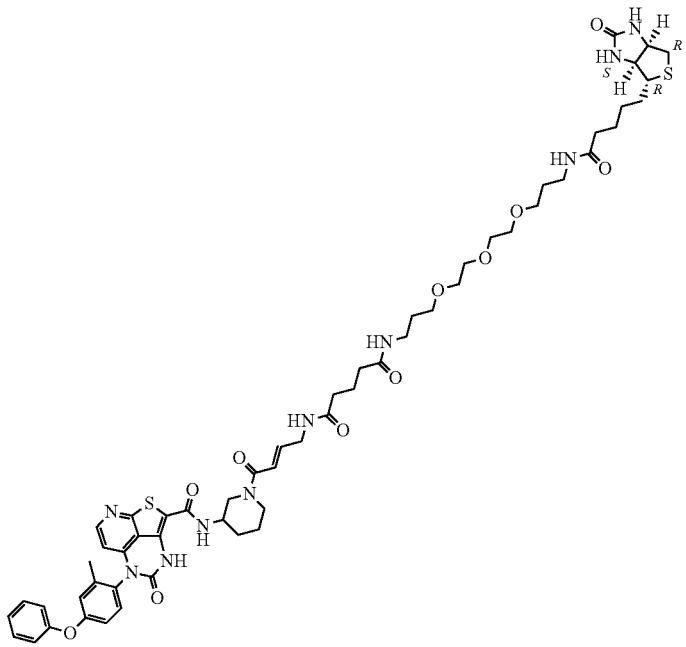

Step A: N-(3-(2-(2-(3-aminopropoxy)ethoxy)ethoxy)propyl)-5-((3aS,4R,6aR)-2-oxohexahydro-1H-thieno[3,4-d]imidazol-4-yl)pentanamide To a solution of tert-butyl (15-oxo-19-((3aS,4S,6aR)-2-oxohexahydro-1H-thieno[3,4-d]imidazol-4-yl)-4,7,10-trioxa-14-azanonadecyl)carbamate (5.80 g, 10.6 mmol) in 5 M aqueous HCl/MeOH (30 mL) was concentrated under vacuum at 50° C. to get the target compound as a yellow oil (5.2 g, 100% yield). MS (ESI): mass calcd. for $C_{20}H_{38}N_4O_5S$, 446.61; m/z found, 447.3 $[M+H]^+$.

Step B: Methyl 5,21-dioxo-25-((3aS,4S,6aR)-2-oxohexahydro-1H-thieno[3,4-d]imidazol-4-yl)-10,13,16-trioxa-6,20-diazapentacosan-1-oate A solution of 5-methoxy-5-oxo-pentanoic acid (1.57 g, 10.8 mmol), HATU (4.91 g, 12.9 mmol), and triethylamine (4.35 g, 43.1 mmol) in anhydrous DMF (50 mL) was stirred at room temperature for 10 minutes, then N-(3-(2-(2-(3-aminopropoxy)ethoxy)ethoxy)propyl)-5-((3aS,4R,6aR)-2-oxohexahydro-1H-thieno[3,4-d]imidazol-4-yl)pentanamide (5.20 g, 10.8 mmol) was added and the mixture was stirred for 16 h. The crude mixture was concentrated to dryness and purified by normal phase flash column chromatography (SiO$_2$) to give the title compound (3.3 g, 53% yield). MS (ESI): mass calcd. for $C_{26}H_{46}N_4O_8S$, 574.73; m/z found, 575.3 $[M+H]^+$.

Step C: 5,21-dioxo-25-((3aS,4S,6aR)-2-oxohexahydro-1H-thieno[3,4-d]imidazol-4-yl)-10,13,16-trioxa-6,20-diazapentacosan-1-oic Acid To a solution of methyl 5,21-dioxo-25-((3aS,4S,6aR)-2-oxohexahydro-1H-thieno[3,4-d]imidazol-4-yl)-10,13,16-trioxa-6,20-diazapentacosan-1-oate (3.3 g, 5.7 mmol) and CaCl$_2$ (9.6 g, 86 mmol) in i-PrOH/H$_2$O (7:3, 108 mL) was added 0.5 M NaOH (14 mL) at room temperature. After 5 h, the reaction mixture was neutralized with 5 M aqueous HCl and extracted with DCM (3×100 mL), dried over anhydrous Na$_2$SO$_4$, concentrated to dryness, and purified by normal phase flash column chromatography (SiO$_2$) to give the title compound as a colorless viscous foam (2.0 g, 42% yield). MS (ESI): mass calcd. for $C_{25}H_{44}N_4O_8S$, 560.70; m/z found, 561.3 $[M+H]^+$.

Step D: N$^1$-((E)-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)-N5-(15-oxo-19-((3aS,4R,6aR)-2-oxohexahydro-1H-thieno[3,4-d]imidazol-4-yl)-4,7,10-trioxa-14-azanonadecyl)glutaramide A solution of 5,21-dioxo-25-((3aS,4S,6aR)-2-oxohexahydro-1H-thieno[3,4-d]imidazol-4-yl)-10,13,16-trioxa-6,20-diazapentacosan-1-oic acid (193 mg, 3.44 mmol), HATU (261 mg, 0.687 mmol), and triethylamine (70 mg, 0.69 mmol) in anhydrous DMF (10 mL) was stirred at room temperature for 10 minutes, then (R,E)-N-(1-(4-aminobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 27, 200 mg, 0.34 mmol) was added and the mixture stirred for 2 h. The crude mixture was concentrated to dryness and purified by normal phase flash column chromatography (SiO$_2$) to give the title compound as a slight yellow solid (153 mg, 40% yield). MS (ESI): mass calcd. for $C_{56}H_{72}N_{10}O_{11}S_2$, 1125.4; m/z found, 1125.5 $[M+H]^+$. $^1$H NMR (400 MHz, CD$_3$OD): δ 8.40-8.20 (m, 1H), 7.47-7.25 (m, 3H), 7.23-6.88 (m, 5H), 6.78-6.63 (m, 1H), 6.62-6.47 (m, 1H), 6.06 (s, 1H), 4.55-4.42 (m, 1H), 4.35-4.06 (m, 2H), 4.03-3.85 (m, 3H), 3.70-3.41 (m, 12H), 3.27-3.10 (m, 6H), 3.05-2.84 (m, 2H), 2.75-2.60 (m, 1H), 2.34-2.00 (m, 10H), 1.95-1.81 (m, 3H), 1.80-1.51 (m, 10H), 1.46-1.25 (m, 3H).

Example 238: (R,E)-N-(1-(2-Cyano-4-methyl-4-(methylamino)pent-2-enoyl)piperidin-3-yl)-5-(2-methyl-4-phenoxyphenl)-4-oxo-4,5-dihydro-3H-1-thia-3,5,8-triazaacenaphthylene-2-carboxamide

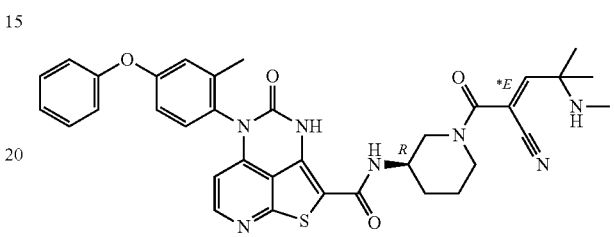

Step A: 2-(tert-Butoxycarbonylamino)-2-methylpropanoic Acid

To a solution of 2-amino-2-methylpropanoic acid (4.0 g, 39 mmol), NaOH (1.55 g, 38.8 mmol), water (50 mL), and THF (20 mL) was added (Boc)$_2$O (10.16 g, 46.55 mmol) portion wise at rt. The mixture was stirred overnight at rt, then concentrated to dryness, and extracted with EtOAc. The pH of the aqueous layer was adjusted to 3-4 with 1 M aqueous HCl, extracted with EtOAc, washed with brine, dried over anhydrous Na$_2$SO$_4$, and concentrated to dryness to give the title compound as a white solid (3.21 g, 40.7% yield).

Step B: Methyl 2-(tert-butoxycarbonylamino)-2-methylpropanoate

To a round bottom flask were added 2-(tert-butoxycarbonylamino)-2-methylpropanoic acid (2.0 g, 9.8 mmol), concentrated H$_2$SO$_4$ (0.1 mL), and MeOH (20 mL) and stirred at 60° C. for 5 h. The mixture was concentrated to dryness, the residue was diluted with EtOAc, washed with saturated NaHCO$_3$ and brine, dried over anhydrous Na$_2$SO$_4$, filtered, and concentrated to dryness to give the title compound as a white solid 1.78 g, 83.3% yield).

Step C: Methyl 2-[tert-butoxycarbonyl(methyl)amino]-2-methylpropanoate

To a solution of methyl 2-(tert-butoxycarbonylamino)-2-methylpropanoate (0.89 g, 4.10 mmol) in DMF (12 mL) was added NaH (353 mg, 14.7 mmol) portion wise at 0° C. The mixture was stirred for 5 min at this temperature then methyl iodide (2.089 g, 14.72 mmol) was added dropwise at 0° C. The resulting mixture was stirred at rt overnight, then quenched with H$_2$O, and extracted with EtOAc. The organic phases were combined and washed with brine, dried over anhydrous Na$_2$SO$_4$, filtered, and concentrated to dryness. The residue was purified by flash column chromatography to give the title compound as a colorless oil (0.72 g, 76% yield).

Step D: tert-Butyl N-(2-hydroxy-1,1-dimethylethyl)-N-methylcarbamate

To a suspension of LiAlH₄ (0.118 g, 3.11 mmol) in THF (15 mL) was added methyl 2-[tert-butoxycarbonyl(methyl) amino]-2-methylpropanoate (0.72 g, 3.1 mmol) at 0° C. under N2. The mixture was stirred for 4 h at this temperature, then it was quenched with ice/water at 0° C., extracted with EtOAc, the organic layers washed with brine, dried over anhydrous Na₂SO₄, and concentrated to dryness to give the title compound as a yellow liquid (0.33 g, 51% yield).

Step E: tert-butyl methyl(2-methyl-1-oxopropan-2-yl)carbamate

A solution of DMSO (0.19 g, 2.4 mmol) and DCM (10 mL) was cooled to −78° C. and oxalyl dichloride (0.247 g, 1.95 mmol) was added dropwise and the mixture was stirred at −78° C. for 30 min. Next, tert-butyl N-(2-hydroxy-1,1-dimethylethyl)-N-methylcarbamate (0.33 g, 1.6 mmol) in DCM (5 mL) was added dropwise and the mixture was stirred at −78° C. for another 30 min. The reaction was quenched by the addition of triethylamine (0.328 g, 3.25 mmol) at −78° C. and stirred at −78° C. for 30 min. The mixture was warmed to rt and diluted with DCM, washed with saturated NaHCO₃ and brine, dried over anhydrous Na₂SO₄, filtered, and concentrated to dryness to give the title compound as a colorless liquid (0.27 g, 81% yield).

Step F: (R,E)-tert-Butyl (4-cyano-2-methyl-5-(3-(5-(2-methyl-4-phenoxyphenyl)-4-oxo-4,5-dihydro-3H-1-thia-3,5,8-triazaacenaphthylene-2-carboxamido)piperidin-1-yl)-5-oxopent-3-en-2-yl)(methyl)carbamate To a round bottom flask were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 0.253 g, 0.447 mmol), tert-butyl methyl(2-methyl-1-oxopropan-2-yl)carbamate (0.27 g, 1.3 mmol), piperidine (0.3 mL), AcOH (0.1 mL), dioxane (10 mL), and 4A molecular sieves (1 g) and was stirred at 100° C. for 1 h under N2. The mixture was concentrated to dryness and purified by flash column chromatography to give the title compound as a white solid (79 mg, 24% yield).

Step G: (R,E)-N-(1-(2-Cyano-4-methyl-4-(methylamino)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide To a solution of (R,E)-tert-butyl (4-cyano-2-methyl-5-(3-(5-(2-methyl-4-phenoxyphenyl)-4-oxo-4,5-dihydro-3H-1-thia-3,5,8-triazaacenaphthylene-2-carboxamido)piperidin-1-yl)-5-oxopent-3-en-2-yl)(methyl)carbamate (79.0 mg, 0.105 mmol) in MeOH (3 mL) was added concentrated HCl (3 mL) and was stirred at rt for 30 min. The mixture was concentrated to dryness, diluted with DCM, washed with saturated NaHCO₃ and brine, concentrated to dryness and purified by flash column chromatography to give the title compound as a yellow solid (44 mg, 65% yield). MS (ESI): mass calcd. for C₃₅H₃₅N₇O₄S, 649.8; m/z found, 650.3 [M+H]⁺. ¹H NMR (400 MHz, CD₃OD): δ 8.35-8.30 (m, 1H), 7.92-7.61 (m, 1H), 7.42-7.35 (m, 2H), 7.32-7.25 (m, 1H), 7.20-7.12 (m, 1H), 7.11-7.02 (m, 3H), 6.99-6.94 (m, 1H), 6.09-6.04 (m, 1H), 4.40-3.90 (m, 3H), 3.25-2.87 (m, 5H), 2.14-2.04 (m, 4H), 1.96-1.80 (m, 2H), 1.80-1.58 (m, 1H), 1.58-1.47 (m, 6H)

Example 239: (R,E)-5-(5-Chlorobenzo[d][1,3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide

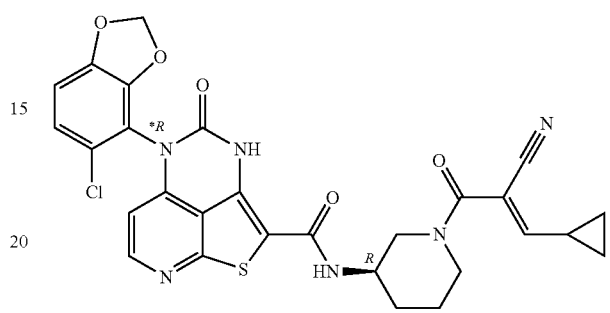

The title compound was prepared using the same synthesis as Example 232, except that Chiral resolution Method A after Step F was used to isolate the *R. MS (ESI): mass calcd. for C₂₈H₂₃ClN₆O₅S, 591.0; m/z found, 591.5 [M+H]⁺. ¹H NMR (400 MHz, a mixture of DMSO-d₆ and CD₃OD): δ 8.52-8.34 (m, 1H), 7.18 (d, J=8.6 Hz, 1H), 7.08 (d, J=8.6 Hz, 1H), 6.65-6.49 (m, 1H), 6.30-6.20 (m, 1H), 6.20-6.08 (m, 2H), 4.15-4.03 (m, 2H), 4.02-3.94 (m, 1H), 3.26-3.10 (m, 2H), 2.12-1.98 (m, 2H), 1.94-1.72 (m, 2H), 1.68-1.58 (m, 1H), 1.28-1.15 (m, 2H), 0.98-0.85 (m, 2H).

Example 240: 5-(2-Methyl-4-phenoxyphenyl)-N-(1-(3-(methyl(sulfonyl)propanoyl)azetidin-3-yl)-4-oxo-4,5-dihydro-3H-1-thia-3,5,8-triazaacenaphthylene-2-carboxamide

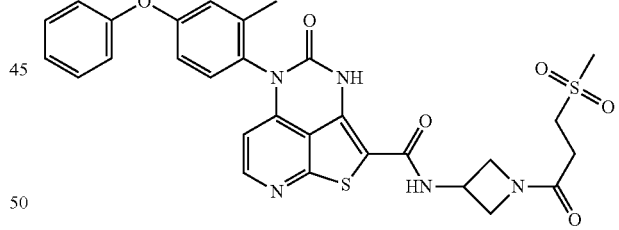

A solution of N-(azetidin-3-yl)-5-(2-methyl-4-phenoxyphenyl)-4-oxo-4,5-dihydro-3H-1-thia-3,5,8-triazaacenaphthylene-2-carboxamide (Example 252, 100 mg, 0.21 mmol), 3-methylsulfonylpropanoic acid (36 mg, 0.23 mmol), HATU (161 mg, 0.424 mmol), and triethylamine (43 mg, 0.42 mmol) in DMF (3 mL) was stirred at rt for 2 h, then purified by flash column chromatography to give the title compound as a white solid (65 mg, 51% yield). MS (ESI): mass calcd. for C₂₉H₂₇N₅O₆S₂, 605.7; m/z found, 606.0 [M+H]⁺. ¹H NMR (400 MHz, DMSO-d6): δ 8.78 (d, J=6.6 Hz, 1H), 8.31 (d, J=5.5 Hz, 1H), 7.47-7.40 (m, 2H), 7.35 (d, J=8.6 Hz, 1H), 7.23-7.16 (m, 1H), 7.16-7.05 (m, 3H), 6.99-6.92 (m, 1H), 5.95 (d, J=5.5 Hz, 1H), 4.77-4.62 (m, 1H), 4.52-4.40 (m, 1H), 4.23-4.10 (m, 2H), 4.01-3.85 (m, 1H), 2.99 (s, 3H), 2.60-2.51 (m, 2H), 2.05 (s, 3H).

Example 241: N-((3S,4R)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide

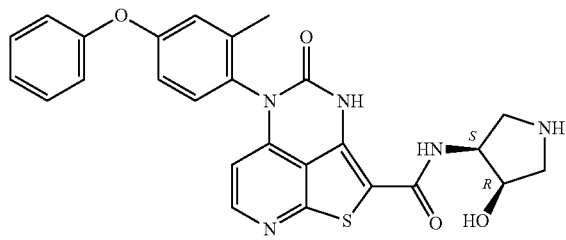

The title compound was prepared using analogous conditions described in Method 1, steps A-H in Example 1, and using tert-butyl (3S,4R)-3-amino-4-hydroxypyrrolidine-1-carboxylate (Intermediate 24) in place of tert-butyl (3R,5R)-3-amino-5-fluoropiperidine-1-carboxylate (Intermediate 1) in step G. MS (ESI): mass calcd. for $C_{26}H_{23}N_5O_4S$, 501.6; m/z found, 502.2 [M+H]$^+$. $^1$H NMR (400 MHz, CD$_3$OD): δ 8.28 (d, J=5.6 Hz, 1H), 7.46-7.33 (m, 2H), 7.33-7.23 (m, 1H), 7.21-7.12 (m, 1H), 7.12-7.01 (m, 3H), 6.99-6.93 (m, 1H), 6.03 (d, J=5.4 Hz, 1H), 4.61-4.56 (m, 1H), 4.49-4.45 (m, 1H), 3.59-3.54 (m, 1H), 3.45-3.39 (m, 1H), 3.37-3.33 (m, 1H), 3.24-3.12 (m, 1H), 2.10 (s, 3H).

Example 242: (R)-5-(2-Methyl-4-(2-(trifluoromethyl)phenoxy)phenyl)-N-(1-methylpiperidin-3-yl)-4-oxo-4,5-dihydro-3H-1-thia-3,5,8-triazaacenaphthylene-2-carboxamide

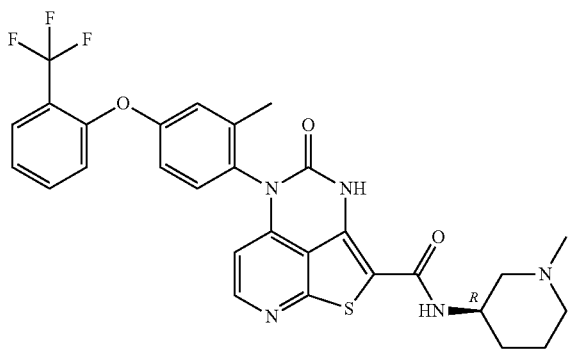

Step A: (R)-5-(2-Methyl-4-(2-(trifluoromethyl)phenoxy)phenyl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 2-(trifluoromethyl)phenol in place of phenol in step A, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{28}H_{24}F_3N_5O_3S$, 567.58; m/z found, 568.0 [M+H]$^+$.

Step B: (R)-5-(2-Methyl-4-(2-(trifluoromethyl)phenoxy)phenyl)-N-(1-methylpiperidin-3-1)-4-oxo-4,5-dihydro-3H-1-thia-3,5,8-triazaacenaphthylene-2-carboxamide To a solution of (R)-5-(2-methyl-4-(2-(trifluoromethyl)phenoxy)phenyl)-4-oxo-N-(piperidin-3-yl)-4,5-dihydro-3H-1-thia-3,5,8-triazaacenaphthylene-2-carboxamide (505 mg, 0.890 mmol) in DCM (10 mL) was added formaldehyde (1 mL, 37 wt. % in H$_2$O) and NaBH(OAc)$_3$ (377 mg, 1.78 mmol) and was stirred at rt for 4 hours. To the mixture was added DCM (50 mL), MeOH (5 mL), water (30 mL), and aqueous NH$_4$OH (2 mL). The organic layer was collected, concentrated to dryness, and purified by flash column chromatography to give the title compound as a yellow solid (77 mg, 13% yield). MS (ESI): mass calcd. for $C_{29}H_{26}F_3N_5O_3S$, 581.6; m/z found, 582.4 [M+H]$^+$. $^1$H NMR (400 MHz, DMSO-d6): δ 8.29 (d, J=5.5 Hz, 1H), 8.12-8.02 (m, 1H), 7.82-7.77 (m, 1H), 7.73-7.66 (m, 1H), 7.41-7.33 (m, 2H), 7.21-7.18 (d, J=8.3 Hz, 1H), 7.17-7.15 (m, 1H), 7.05-7.00 (m, 1H), 5.94 (d, J=5.5 Hz, 1H), 4.01-3.94 (m, 1H), 2.94-2.85 (m, 1H), 2.77-2.68 (m, 1H), 2.27 (s, 3H), 2.07 (s, 3H), 2.06-1.94 (m, 2H), 1.82-1.75 (m, 1H), 1.74-1.67 (m, 1H), 1.60-1.49 (m, 1H), 1.42-1.33 (m, 1H).

Example 243: N-((3S,4S)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide

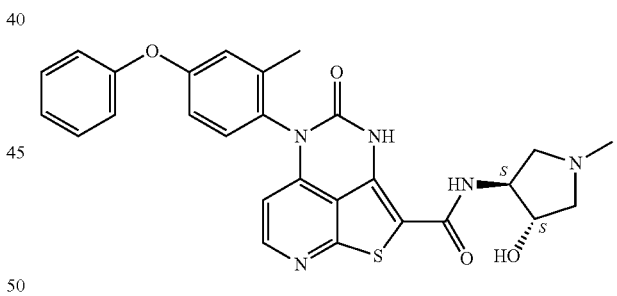

To a solution of N-((3S,4S)-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide (Example 236, 100 mg, 0.2 mmol) and formaldehyde (0.5 mL, 37 wt. % in H$_2$O) in MeOH (5 mL) was added NaBH(OAc)$_3$ (127 mg, 0.597 mmol) and was stirred at rt for 1 h, concentrated to dryness, and purified by flash column chromatography to give the title compound as a white solid (68 mg, 66% yield). MS (ESI): mass calcd. for $C_{27}H_{25}N_5O_4S$, 515.6; m/z found, 516.0 [M+H]$^+$. $^1$H NMR (400 MHz, CD$_3$OD): δ 8.26 (dd, J=5.6 Hz, 1.0, 1H), 7.44-7.33 (m, 2H), 7.31-7.25 (m, 1H), 7.19-7.11 (m, 1H), 7.11-7.02 (m, 3H), 7.00-6.91 (m, 1H), 6.01 (d, J=5.6 Hz, 1H), 4.35-4.25 (m, 2H), 3.15-3.03 (m, 2H), 2.74-2.65 (m, 1H), 2.64-2.57 (m, 1H), 2.45 (s, 3H), 2.10 (s, 3H).

Example 244: N-((3S,4S)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide

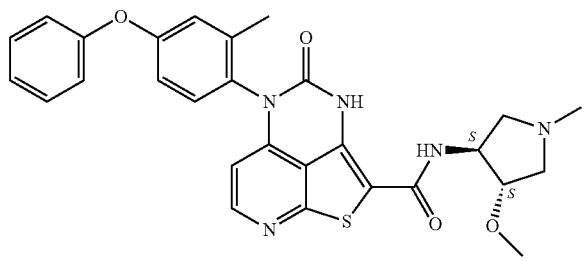

To a solution of N-((3S,4S)-4-methoxypyrrolidin-3-yl)-5-(2-methyl-4-phenoxyphenyl)-4-oxo-4,5-dihydro-3H-1-thia-3,5,8-triazaacenaphthylene-2-carboxamide (Example 245, 100 mg, 0.19 mmol) and formaldehyde (0.5 mL, 37 wt. % in H$_2$O) in MeOH (5 mL) was added NaBH(OAc)$_3$ (123 mg, 0.582 mmol) and was stirred at rt for 1 h, concentrated to dryness, and purified by flash column chromatography to give the title compound as a white solid (63 mg, 60% yield). MS (ESI): mass calcd. for C$_{28}$H$_{27}$N$_5$O$_4$S, 529.6; m/z found, 530.0 [M+H]$^+$. $^1$H NMR (400 MHz, CD$_3$OD): δ 8.30 (d, J=5.4 Hz, 1H), 7.48-7.35 (m, 2H), 7.35-7.28 (m, 1H), 7.23-7.13 (m, 1H), 7.13-7.02 (m, 3H), 7.03-6.93 (m, 1H), 6.05 (d, J=5.4 Hz, 1H), 4.53-4.39 (m, 1H), 4.01-3.87 (m, 1H), 3.41 (s, 3H), 3.18-2.97 (m, 2H), 2.78-2.57 (m, 2H), 2.44 (s, 3H), 2.19-2.07 (m, 3H).

Example 245: N-((3S,4S)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide

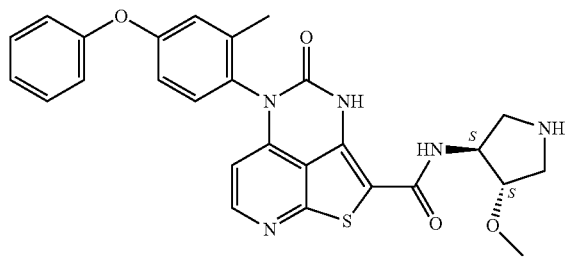

The title compound was prepared using analogous conditions described in Method 1, steps A-H in Example 1, and using tert-butyl (3S,4S)-3-amino-4-methoxypyrrolidine-1-carboxylate in place of tert-butyl (3R,5R)-3-amino-5-fluoropiperidine-1-carboxylate (Intermediate 1) in step G. MS (ESI): mass calcd. for C$_{27}$H$_{25}$N$_5$O$_4$S, 515.6; m/z found, 516.0 [M+H]$^+$. $^1$H NMR (400 MHz, CD$_3$OD): δ 8.17 (d, J=5.6 Hz, 1H), 7.39-7.32 (m, 2H), 7.25-7.19 (m, 1H), 7.16-7.09 (m, 1H), 7.08-7.00 (m, 3H), 6.98-6.90 (m, 1H), 5.91 (d, J=5.6 Hz, 1H), 4.53-4.46 (m, 1H), 4.04-3.96 (m, 1H), 3.49-3.44 (m, 1H), 3.43 (s, 3H), 3.41-3.37 (m, 1H), 3.22-3.12 (m, 2H), 2.07 (s, 3H).

Example 246: N-(1-(3-Methoxypropanoyl)azetidin-3-yl)-5-(2-methyl-4-phenoxyphenyl)-4-oxo-4,5-dihydro-3H-1-thia-3,5,8-triazaacenaphthylene-2-carboxamide

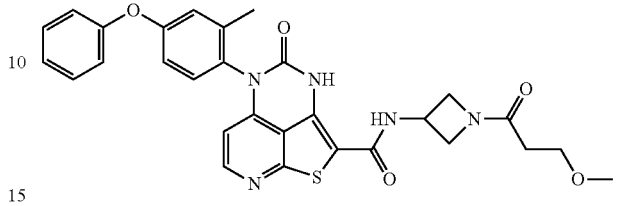

To a solution of N-(1-Acryloylazetidin-3-yl)-5-(2-methyl-4-phenoxyphenyl)-4-oxo-4,5-dihydro-3H-1-thia-3,5,8-triazaacenaphthylene-2-carboxamide (Example 109, 95 mg, 0.18 mmol) in MeOH (10 mL), was added NaOCH$_3$ (49 mg, 0.91 mmol) and was stirred at 60° C. for 2 h, concentrated to dryness, and the residue purified by flash column chromatography to give the title compound as a yellow solid (33 mg, 32% yield). MS (ESI): mass calcd. for C$_{29}$H$_{27}$N$_5$O$_5$S, 557.6; m/z found, 558.1 [M+H]$^+$. $^1$H NMR (400 MHz, CD$_3$OD): δ 8.32 (d, J=5.5, 1H), 7.44-7.35 (m, 2H), 7.32-7.26 (m, 1H), 7.22-7.13 (m, 1H), 7.11-7.03 (m, 3H), 7.00-6.94 (m, 1H), 6.06 (d, J=5.5, 1H), 4.79-4.74 (m, 1H), 4.60-4.52 (m, 1H), 4.36-4.29 (m, 1H), 4.29-4.19 (m, 1H), 4.08-3.98 (m, 1H), 3.64 (t, J=6.0, 2H), 3.33 (s, 3H), 2.40 (t, J=6.1, 2H), 2.12 (s, 3H).

Example 247: (R,E)-5-(2-Methyl-4-phenoxyphenyl)-N-(1-(4-methylpent-2-enoyl)piperidin-3-yl)-4-oxo-4,5-dihydro-3H-1-thia-3,5,8-triazaacenaphthylene-2-carboxamide

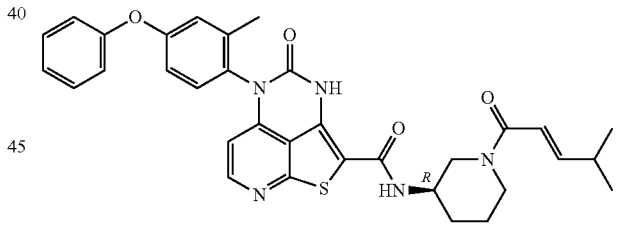

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 100 mg, 0.2 mmol) and (E)-4-methylpent-2-enoic acid (500 mg, 4.4 mmol) in anhydrous DMF (5 mL) were added HATU (228 mg, 0.600 mmol) and diisopropylethylamine (130 mg, 1.0 mmol) and was stirred overnight at rt. The reaction mixture was purified by flash column chromatography to give the title compound as a yellow solid (16 mg, 13% yield). MS (ESI): mass calcd. for C$_{33}$H$_{33}$N$_5$O$_4$S, 595.7; m/z found, 596.1 [M+H]$^+$. $^1$H NMR (400 MHz, CDCl3): δ 9.61-9.34 (m, 1H), 8.34 (d, J=5.3 Hz, 1H), 7.43-7.34 (m, 2H), 7.20-7.13 (m, 2H), 7.12-7.05 (m, 2H), 7.00 (s, 1H), 6.96-6.93 (m, 1H), 6.26-6.15 (m, 1H), 6.04-5.94 (m, 1H), 4.17-4.04 (m, 1H), 3.96-3.79 (m, 1H), 3.69-3.55 (m, 1H), 2.56-2.35 (m, 1H), 2.10 (s, 3H), 2.08-1.83 (m, 2H), 1.81-1.59 (m, 5H), 1.161-0.96 (m, 6H).

Example 248: 5-(2-Methyl-4-phenoxyphenyl)-N-(1-methylazetidin-3-yl)-4-oxo-4,5-dihydro-3H-1-thia-3,5,8-triazaacenaphthylene-2-carboxamide

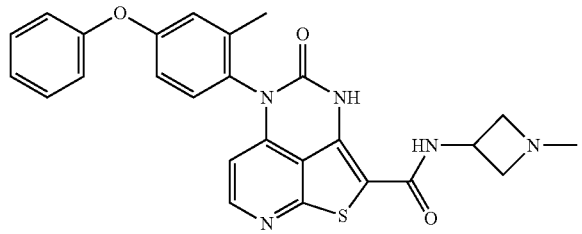 [SMILES: Cc1cc(Oc2ccccc2)ccc1N1C(=O)Nc2c(C(=O)NC3CN(C)C3)sc3nccc1c23]

To a solution of N-(azetidin-3-yl)-5-(2-methyl-4-phenoxyphenyl)-4-oxo-4,5-dihydro-3H-1-thia-3,5,8-triazaacenaphthylene-2-carboxamide (Example 252, 100 mg, 0.2 mmol) and formaldehyde (33 mg, 1.1 mmol, 37 wt. % in H$_2$O) in DCM (5 mL) was added NaBH(OAc)$_3$ (135 mg, 0.637 mmol) and was stirred at rt overnight. The pH was adjusted to pH>7 with 2 M NaOH, then concentrated to dryness, and purified by flash column chromatography to give the title compound as a yellow solid (41 mg, 39% yield). MS (ESI): mass calcd. for C$_{26}$H$_{23}$N$_5$O$_3$S, 485.6; m/z found, 486.1 [M+H]$^+$. $^1$H NMR (400 MHz, a mixture of DMSO-d$_6$ and CD$_3$OD): δ 8.22 (d, J=4.9, 1H), 7.44-7.32 (m, 2H), 7.30-7.21 (m, 1H), 7.19-7.10 (m, 1H), 7.10-6.98 (m, 3H), 6.97-6.84 (m, 1H), 5.89 (d, J=5.4, 1H), 4.57-4.41 (m, 1H), 3.79-3.69 (m, 2H), 3.37-3.25 (m, 2H), 2.41 (s, 3H), 2.03 (s, 3H).

Example 249: (S)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide

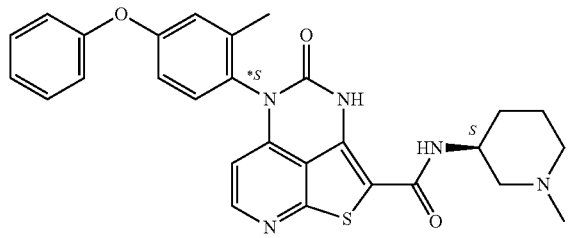

Step A: (S)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H (including Chiral resolution Method A after Step F to obtain the *S atropisomer) in Example 1, and using tert-butyl (3S)-3-aminopiperidine-1-carboxylate in place of tert-butyl (3R,5R)-3-amino-5-fluoropiperidine-1-carboxylate (Intermediate 1) in step G.

Step B: (S)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide To an oven dried microwave vial with a stir bar under Ar were added (S)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (103.2 mg, 0.168 mmol), sodium cyanoborohydride (25.5 mg, 0.407 mmol), and MeOH (4 mL) and was cooled to 0° C. in an ice bath. Next, aqueous formaldehyde (0.014 mL, 37 wt. % in H$_2$O) was added via syringe through the septum cap. The reaction was allowed to slowly warm to rt and stirred for an additional 30 min at rt. The crude reaction mixture was filtered and purified by HPLC to give the title compound (16.2 mg, 18.8% yield). MS (ESI): mass calcd. for C$_{28}$H$_{27}$N$_5$O$_3$S, 513.6; m/z found, 514.0 [M+H]$^+$. $^1$H NMR (500 MHz, CD$_3$OD): δ 8.28 (d, J=5.6 Hz, 1H), 7.45-7.33 (m, 2H), 7.29 (d, J=8.5 Hz, 1H), 7.21-6.89 (m, 5H), 6.03 (d, J=5.5 Hz, 1H), 4.24-4.05 (m, 1H), 3.03-2.85 (m, 1H), 2.79-2.59 (m, 1H), 2.34 (s, 3H), 2.28-2.04 (m, 5H), 1.98-1.39 (m, 4H).

Example 250: (R)-5-(4-(Cyclohexyloxy)-2-methylphenyl)-N-(1-methylpiperidin-3-yl)-4-oxo-4,5-dihydro-3H-1-thia-3,5,8-triazaacenaphthylene-2-carboxamide

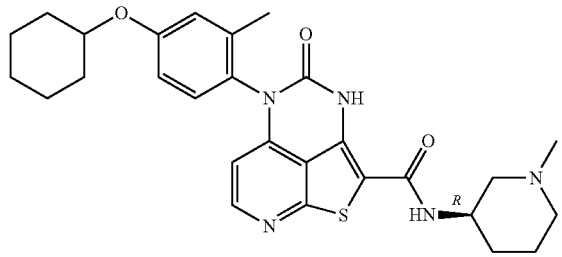

Step A: 2-Chloro-4-[4-(cyclohexoxy)-2-methylanilino]pyridine-3-carbonitrile

To a cold solution (0° C.) of 2-chloro-4-(4-hydroxy-2-methylanilino)pyridine-3-carbonitrile (Intermediate 14) (1.0 g, 3.9 mmol), cyclohexanol (1.16 g, 11.5 mmol), and PPh$_3$ (1.5 g, 5.7 mmol) in THF (20 mL) was added DIAD (1.17 g, 5.79 mmol) and was stirred at rt overnight. The mixture was concentrated to dryness and the residue was purified by flash column chromatography to give the title compound as a yellow solid (400 mg, 30% yield). MS (ESI): mass calcd. for C$_{19}$H$_{20}$ClN$_3$O, 341.84; m/z found, 342.0 [M+H]$^+$.

Step B: (R)-5-(4-(Cyclohexyloxy)-2-methylphenyl)-N-(1-methylpiperidin-3-yl)-4-oxo-4,5-dihydro-3H-1-thia-3,5,8-triazaacenaphthylene-2-carboxamide The title compound was prepared in a manner analogous to Method 1, steps D-G in Example 1, and using 2-chloro-4-[4-(cyclohexoxy)-2-methylanilino]pyridine-3-carbonitrile in place of 2-chloro-4-(2-methyl-4-phenoxyanilino)pyridine-3-carbonitrile for step D, and using (3R)-1-methylpiperidin-3-amine in place of tert-butyl (3R,5R)-3-amino-5-fluoropiperidine-1-carboxylate (Intermediate 1) in step G. MS (ESI): mass calcd. for C$_{28}$H$_{33}$N$_5$O$_3$S, 519.7; m/z found, 520.1 [M+H]$^+$. $^1$H NMR (400 MHz, CD$_3$OD): δ 8.48 (s, 1H), 8.37-8.32 (m, 1H), 7.26-7.19 (m, 1H), 7.06-7.00 (m, 1H), 6.99-6.94 (m, 1H), 6.11-6.05 (m, 1H), 4.52-4.37 (m, 1H), 4.37-4.25 (m, 1H), 3.49-3.40 (m, 1H), 3.28-3.20 (m, 1H), 2.86-2.73 (m, 5H), 2.14 (s, 3H), 2.08-2.00 (m, 4H), 1.89-1.81 (m, 3H), 1.72-1.50 (m, 5H), 1.46-1.37 (m, 2H).

Example 251: N-(1-Ethylazetidin-3-yl)-5-(2-methyl-4-phenoxyphenyl)-4-oxo-4,5-dihydro-3H-1-thia-3,5,8-triazaacenaphthylene-2-carboxamide

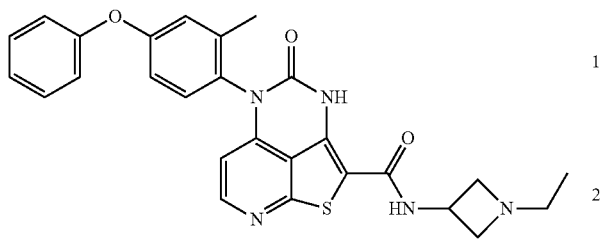

To a solution of N-(azetidin-3-yl)-5-(2-methyl-4-phenoxyphenyl)-4-oxo-4,5-dihydro-3H-1-thia-3,5,8-triazaacenaphthylene-2-carboxamide (Example 252, 100 mg, 0.20 mmol) and acetaldehyde (0.5 mL) in MeOH (10 mL) was added NaBH(OAc)$_3$ (209 mg, 0.985 mmol) and was stirred at rt for 1 h, concentrated to dryness, and purified by flash column chromatography to give the title compound as a white solid (50 mg, 51% yield). MS (ESI): mass calcd. for C$_{27}$H$_{25}$N$_5$O$_3$S, 499.6; m/z found, 500.4 [M+H]$^+$. 1H NMR (400 MHz, DMSO-d6): δ 8.67 (s, 1H), 8.27 (d, J=4.9 Hz, 1H), 7.49-7.38 (m, 2H), 7.36-7.27 (m, 1H), 7.23-7.15 (m, 1H), 7.15-7.03 (m, 3H), 7.00-6.90 (m, 1H), 5.90 (d, J=5.3 Hz, 1H), 4.52-4.38 (m, 1H), 3.68-3.60 (m, 2H), 3.11-3.20 (m, 2H), 2.61-2.50 (m, 2H), 2.05 (s, 3H), 0.95-0.83 (m, 3H).

Example 252: N-(Azetidin-3-yl)-5-(2-methyl-4-phenoxyphenyl)-4-oxo-4,5-dihydro-3H-1-thia-3,5,8-triazaacenaphthylene-2-carboxamide

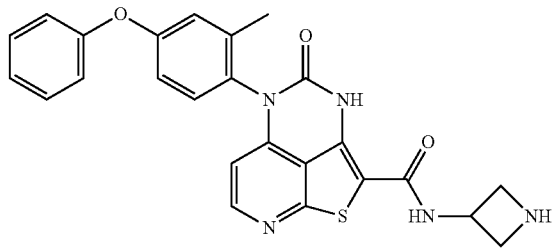 [SMILES: Cc1cc(Oc2ccccc2)ccc1N1C(=O)Nc2c(C(=O)NC3CNC3)sc3nccc1c23]

The title compound was prepared in a manner analogous to Method 1, steps A-H in Example 1, and using tert-butyl 3-aminoazetidine-1-carboxylate in place of tert-butyl (3R,5R)-3-amino-5-fluoropiperidine-1-carboxylate (Intermediate 1) in step G. MS (ESI): mass calcd. for C$_{25}$H$_{21}$N$_5$O$_3$S, 471.5; m/z found, 472.4 [M+H]$^+$. 1H NMR (400 MHz, DMSO-d6): δ 8.95 (s, 1H), 8.86 (d, J=6.5 Hz, 1H), 8.36 (d, J=5.5 Hz, 1H), 7.52-7.34 (m, 3H), 7.24-7.15 (m, 1H), 7.15-7.08 (m, 3H), 7.04-6.95 (m, 1H), 6.01 (d, J=5.4 Hz, 1H), 4.88-4.66 (m, 1H), 4.21-4.02 (m, 4H), 2.06 (s, 3H).

Example 253: (R)-5-(*R)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide

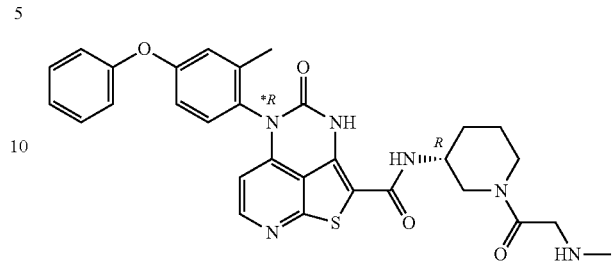

Step A: (R)-tert-Butyl methyl(2-(3-(5-(*R)-(2-methyl-4-phenoxyphenyl)-4-oxo-4,5-dihydro-3H-1-thia-3,5,8-triazaacenaphthylene-2-carboxamido)piperidin-1-yl)-2-oxoethyl)carbamate A solution of (R)-5-(*R)(2-methyl-4-phenoxyphenyl)-4-oxo-N-(piperidin-3-yl)-4,5-dihydro-3H-1-thia-3,5,8-triazaacenaphthylene-2-carboxamide (Example 300, 104 mg, 0.194 mmol), 2-[tert-butoxycarbonyl(methyl)amino]acetic acid (Intermediate 21) (44 mg, 0.23 mmol), HATU (96 mg, 0.25 mmol), and triethylamine (0.108 mL, 0.776 mmol) in DMF (3 mL) was stirred at rt overnight, then purified by flash column chromatography to give the title compound as a white solid (100 mg, 77%).

Step B: (R)-5-(*R)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide A solution of (R)-tert-butyl methyl(2-(3-(5-(*R)-(2-methyl-4-phenoxyphenyl)-4-oxo-4,5-dihydro-3H-1-thia-3,5,8-triazaacenaphthylene-2-carboxamido)piperidin-1-yl)-2-oxoethyl)carbamate (100 mg, 0.15 mmol) in HCl/MeOH (2 M, 3 mL) was stirred at rt for 4 h and concentrated to dryness. The pH was adjusted to pH>7 with saturated NaHCO$_3$ and purified by flash column chromatography to give the title compound as a yellow solid (60 mg, 70% yield). MS (ESI): mass calcd. for C$_{30}$H$_{30}$N$_6$O$_4$S, 570.7; m/z found, 571.3 [M+H]$^+$. 1H NMR (400 MHz, CD$_3$OD): δ 8.09-7.96 (m, 1H), 7.41-7.34 (m, 2H), 7.20-7.11 (m, 2H), 7.10-7.05 (m, 2H), 7.04-7.00 (m, 1H), 6.98-6.92 (m, 1H), 5.84-5.71 (m, 1H), 4.24-3.90 (m, 2H), 3.86-3.77 (m, 1H), 3.66-3.55 (m, 1H), 3.53-3.42 (m, 2H), 3.27-3.20 (m, 1H), 2.40-2.30 (m, 3H), 2.14-2.03 (m, 4H), 1.95-1.76 (m, 2H), 1.66-1.53 (m, 1H).

Example 254: (R)—N-(1-Acryloylpiperidin-3-yl)-5-(4-methoxy-2-methylphenyl)-4-oxo-4,5-dihydro-3H-1-thia-3,5,8-triazaacenaphthylene-2-carboxamide

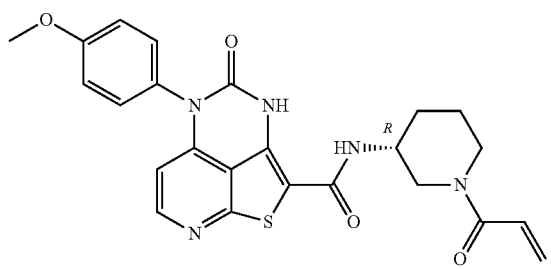

The title compound was prepared in a manner analogous to Method 1, steps C-I in Example 1, and using 4-methoxyaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{24}H_{23}N_5O_4S$, 477.5; m/z found, 477.9 [M+H]$^+$. $^1$H NMR (400 MHz, DMSO-d$_6$): δ 10.15 (d, J=16.5 Hz, 1H), 8.33 (d, J=5.5 Hz, 1H), 8.13-8.02 (m, 1H), 7.38 (d, J=8.9 Hz, 2H), 7.14 (d, J=9.0 Hz, 2H), 6.90-6.72 (m, 1H), 6.12 (d, J=16.7 Hz, 1H), 6.02 (d, J=5.5 Hz, 1H), 5.70 (d, J=11.0 Hz, 1H), 4.50-4.21 (m, 1H), 4.09-3.99 (m, 1H), 3.85 (s, 3H), 3.79 (s, 1H), 3.17-2.94 (m, 1H), 2.82-2.60 (m, 1H), 1.96-1.94 (m, 1H), 1.81-1.78 (m, 1H), 1.74-1.59 (m, 1H), 1.44 (brs, 1H).

Example 255: (R)—N-(1-Acryloylpiperidin-3-yl)-5-(4-fluorophenyl)-4-oxo-4,5-dihydro-3H-1-thia-3,5,8-triazaacenaphthylene-2-carboxamide

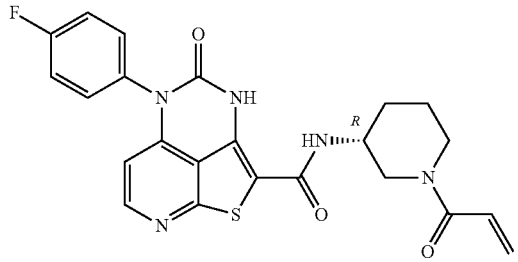

The title compound was prepared in a manner analogous to Method 1, steps C-I in Example 1, and using 4-fluoroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{23}H_{20}FN_5O_3S$, 465.5; m/z found, 466.1 [M+H]$^+$. $^1$H NMR (400 MHz, DMSO-d$_6$): δ 10.27 (s, 1H), 8.33 (d, J=5.5 Hz, 1H), 8.16-8.07 (m, 1H), 7.56-7.53 (m, 2H), 7.47-7.43 (m, 2H), 6.90-6.70 (m, 1H), 6.11 (d, J=17.0 Hz, 1H), 6.03 (d, J=5.5 Hz, 1H), 5.69 (d, J=12.2 Hz, 1H), 4.53-4.16 (m, 1H), 4.12-3.95 (m, 1H), 3.79 (brs, 1H), 3.17-2.94 (m, 1H), 2.83-2.65 (m, 1H), 1.97-1.94 (m, 1H), 1.81-1.78 (m, 1H), 1.74-1.59 (m, 1H), 1.44 (brs, 1H).

Example 256: (R)—N-(1-Acryloylpiperidin-3-yl)-5-(4-chlorophenyl)-4-oxo-4,5-dihydro-3H-1-thia-3,5,8triazaacenaphthylene-2-carboxamide

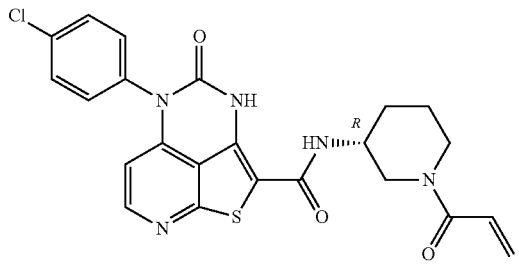

The title compound was prepared in a manner analogous to Method 1, steps C-I in Example 1, and using 4-chloroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{23}H_{20}ClN_5O_3S$, 482.0; m/z found, 482.1 [M+H]$^+$. $^1$H NMR (400 MHz, DMSO-d$_6$): δ 10.27 (s, 1H), 8.31 (d, J=5.5 Hz, 1H), 8.15 (s, 1H), 7.68 (d, J=8.7 Hz, 2H), 7.51 (d, J=8.5 Hz, 2H), 6.89-6.71 (m, 1H), 6.11 (d, J=16.6 Hz, 1H), 6.04 (d, J=5.4 Hz, 1H), 5.69 (dd, J=10.5, 2.2 Hz, 1H), 4.52-4.12 (m, 1H), 4.09-3.95 (m, 1H), 3.79 (s, 1H), 3.16-2.97 (m, 1H), 2.85-2.63 (m, 1H), 2.00-1.90 (m, 1H), 1.81-1.77 (m, 1H), 1.72-1.62 (m, 1H), 1.43 (s, 1H).

Example 257: (R)—N-(1-Acryloylpiperidin-3-yl)-4-oxo-5-phenyl-4,5-dihydro-3H-1-thia-3,5,8-triazaacenaphthylene-2-carboxamide

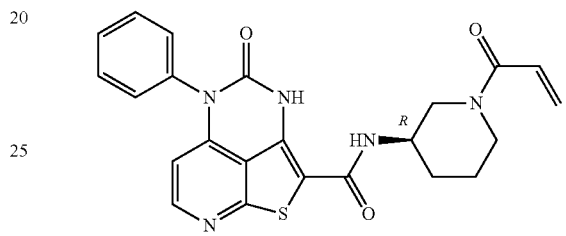

The title compound was prepared in a manner analogous to Method 1, steps C-I in Example 1, and using aniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{23}H_{21}N_5O_3S$, 447.5; m/z found, 448.1 [M+H]$^+$. $^1$H NMR (400 MHz, CD$_3$OD): δ 8.30-8.23 (m, 1H), 7.65-7.50 (m, 3H), 7.49-7.38 (m, 2H), 6.85-6.69 (m, 1H), 6.26-6.13 (m, 1H), 6.11-6.02 (m, 1H), 5.79-5.64 (m, 1H), 4.61-4.23 (m, 1H), 4.21-3.86 (m, 2H), 3.20-3.09 (m, 1H), 2.95-2.80 (m, 1H), 2.10-1.97 (m, 1H), 1.91-1.80 (m, 1H), 1.77-1.66 (m, 1H), 1.62-1.47 (m, 1H).

Example 258: 5-(2-Methyl-4-phenoxyphenyl)-N-(2-methylpiperidin-4-yl)-4-oxo-4,5-dihydro-3H-1-thia-3,5,8-triazaacenaphthylene-2-carboxamide

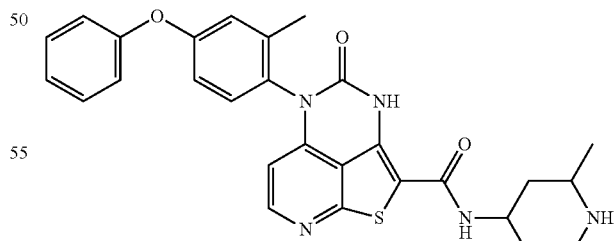

The title compound was prepared in a manner analogous to Method 1, steps A-H in Example 1, and using tert-butyl 4-amino-2-methylpiperidine-1-carboxylate in place of tert-butyl (3R,5R)-3-amino-5-fluoropiperidine-1-carboxylate (Intermediate 1) in step G. MS (ESI): mass calcd. for $C_{28}H_{27}N_5O_3S$, 513.6; m/z found, 514.7 [M+H]$^+$. $^1$H NMR (400 MHz, CD$_3$OD and DMSO-d$_6$): δ 8.30 (d, J=5.5 Hz, 1H), 7.46-7.34 (m, 2H), 7.30 (d, J=8.6 Hz, 1H), 7.18-7.10 (m, 1H), 7.09-6.97 (m, 3H), 6.96-6.86 (m, 1H), 5.97 (d, J=5.5 Hz, 1H), 4.09-3.99 (m, 1H), 3.37-3.17 (m, 2H), 3.06-2.85 (m, 1H), 2.09-1.92 (m, 5H), 1.78-1.62 (m, 1H), 1.60-1.50 (m, 1H), 1.23 (d, J=6.5 Hz, 3H).

Example 259: N-((3R,5R)-5-Methoxy-1-methylpiperidin-3-yl)-4-oxo-5-(4-phenoxyphenyl)-4,5-dihydro-3H-1-thia-3,5,8-triazaacenaphthylene-2-carboxamide

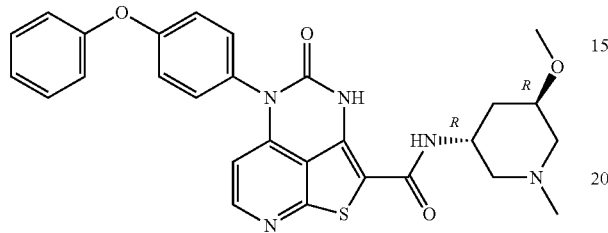

Step A: (3R,5R)-tert-Butyl 3-methoxy-5-(5-(2-methyl-4-phenoxyphenyl)-4-oxo-4,5-dihydro-3H-1-thia-3,5,8-triazaacenaphthylene-2-carboxamido)piperidine-1-carboxylate The title compound was prepared in a manner analogous to Method 1, steps A-G in Example 1 using tert-Butyl (3R,5S)-3-amino-5-methoxypiperidine-1-carboxylate (Intermediate 29) in place of tert-butyl (3R,5R)-3-amino-5-fluoropiperidine-1-carboxylate (Intermediate 1) in step G. MS (ESI): mass calcd. for $C_{33}H_{35}N_5O_6S$, 629.73; m/z found, 630.3 [M+H]$^+$.

Step B: N-((3R,5R)-5-Methoxypiperidin-3-yl)-5-(2-methyl-4-phenoxyphenyl)-4-oxo-4,5-dihydro-3H-1-thia-3,5,8-triazaacenaphthylene-2-carboxamide (3R,5R)-tert-Butyl 3-methoxy-5-(5-(2-methyl-4-phenoxyphenyl)-4-oxo-4,5-dihydro-3H-1-thia-3,5,8-triazaacenaphthylene-2-carboxamido)piperidine-1-carboxylate (250 mg, 0.397 mmol) was treated with concentrated HCl (2 mL) in MeOH (15 mL) at room temperature for about 2 hours. The reaction was concentrated to dryness to give the title compound (150 mg, 97% yield), which was carried forward to next step without any further purification. MS (ESI): mass calcd. for $C_{28}H_{27}N_5O_4S$, 629.73; m/z found, 630.3 [M+H]$^+$. $^1$H NMR (400 MHz, CD$_3$OD): δ 8.24 (d, J=5.6 Hz, 1H), 7.45-7.35 (m, 2H), 7.29-7.23 (m, 1H), 7.19-7.12 (m, 1H), 7.11-7.02 (m, 3H), 7.01-6.93 (m, 1H), 5.98 (d, J=5.6 Hz, 1H), 4.41-4.25 (m, 1H), 3.62-3.54 (m, 1H), 3.41-3.37 (m, 3H), 3.22-3.13 (m, 1H), 3.10-3.01 (m, 1H), 2.80-2.72 (m, 1H), 2.70-2.59 (m, 1H), 2.28-2.15 (m, 1H), 2.11 (s, 3H), 1.87-1.75 (m, 1H).

Step C: N-((3R,5R)-5-Methoxy-1-methylpiperidin-3-yl)-4-oxo-5-(4-phenoxyphenyl)-4,5-dihydro-3H-1-thia-3,5,8-triazaacenaphthylene-2-carboxamide.

A solution of N-((3R,5R)-5-methoxypiperidin-3-yl)-5-(2-methyl-4-phenoxyphenyl)-4-oxo-4,5-dihydro-3H-1-thia-3,5,8-triazaacenaphthylene-2-carboxamide (80 mg, 0.15 mmol) in DCM (5 mL) was treated with formaldehyde (1.0 mL, 37 wt. % in H$_2$O). To the stirred reaction mixture was added NaBH(OAc)$_3$ (65 mg, 0.31 mmol) and was stirred at room temperature for 1 h, then concentrated to dryness, and the residue was purified by normal phase flash column chromatography (SiO$_2$) to give the title compound as yellow solid (38 mg, 46% yield). MS (ESI): mass calcd. for $C_{29}H_{29}N_5O_4S$, 543.6; m/z found, 544.3 [M+H]$^+$. $^1$H NMR (400 MHz, CD$_3$OD): δ 8.29 (d, J=5.5 Hz, 1H), 7.47-7.35 (m, 2H), 7.34-7.25 (m, 1H), 7.21-7.13 (m, 1H), 7.12-7.01 (m, 3H), 7.00-6.93 (m, 1H), 6.04 (d, J=5.5 Hz, 1H), 4.51-4.36 (m, 1H), 3.65-3.55 (m, 1H), 3.37 (s, 3H), 2.95-2.69 (m, 2H), 2.45-2.31 (m, 4H), 2.28-2.19 (m, 1H), 2.11 (s, 3H), 2.05-1.93 (m, 1H), 1.80-1.67 (m, 1H).

Example 260: (R)—N-(1-(2-chloro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

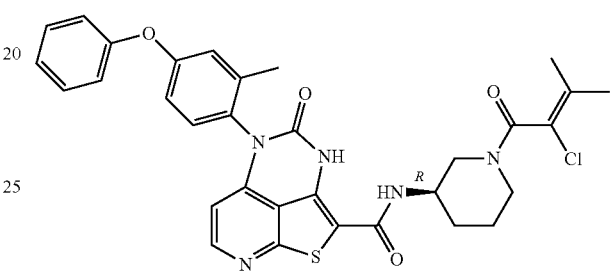

A solution of (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), 2-chloro-3-methylbut-2-enoic acid (75 mg, 0.56 mmol), HATU (138 mg, 0.364 mmol), and diisopropylethylamine (90 mg, 0.70 mmol) in DMF (5 mL) was stirred at rt for 2 h. The mixture was purified by HPLC to give the title compound as a white solid (103 mg, 59.6% yield). MS (ESI): mass calcd. for $C_{32}H_{30}ClN_5O_4S$, 616.1; m/z found, 616.3 [M+H]$^+$. $^1$H NMR (400 MHz, CD$_3$OD): δ 8.36-8.31 (m, 1H), 7.44-7.37 (m, 2H), 7.34-7.28 (m, 1H), 7.21-7.14 (m, 1H), 7.12-7.04 (m, 3H), 7.01-6.95 (m, 1H), 6.11-6.06 (m, 1H), 4.52-4.23 (m, 1H), 4.05-3.71 (m, 2H), 3.23-3.09 (m, 1H), 3.00-2.87 (m, 1H), 2.15-2.03 (m, 4H), 1.94-1.78 (m, 7H), 1.76-1.54 (m, 2H).

Example 261: (R,Z)—N-(1-(2-Fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

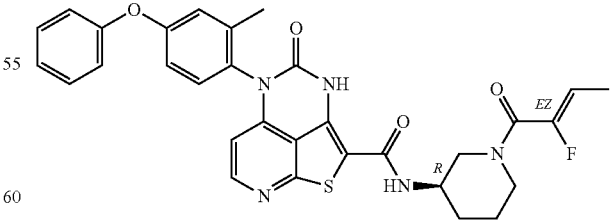

The title compound was prepared in a manner analogous to Method 1, steps A-H in Example 1, and using tert-butyl (3R)-3-aminopiperidine-1-carboxylate in place of tert-butyl (3R,5R)-3-amino-5-fluoropiperidine-1-carboxylate (Intermediate 1) in step G, and using analogous methods found in Example 260, using (EZ)-2-fluorobut-2-enoic acid in place of 2-chloro-3-methylbut-2-enoic acid. MS (ESI): mass calcd. for $C_{31}H_{28}FN_5O_4S$, 585.6; m/z found, 586.2 [M+H]$^+$. 1H NMR (400 MHz, DMSO-d6): δ 8.29 (d, J=5.5 Hz, 1H), 8.16 (s, 1H), 7.47-7.37 (m, 2H), 7.36-7.27 (m, 1H), 7.21-7.14 (m, 1H), 7.13-7.02 (m, 3H), 6.98-6.90 (m, 1H), 5.92 (d, J=5.2 Hz, 1H), 5.68-5.45 (m, 1H), 4.30-3.95 (m, 1H), 3.93-3.73 (m, 2H), 3.15-2.70 (m, 2H), 2.03 (s, 3H), 1.96-1.88 (m, 1H), 1.84-1.71 (m, 1H), 1.69-1.60 (m, 3H), 1.59-1.49 (m, 1H), 1.48-1.37 (m, 1H).

Example 262: N-(1-Methyl-5-oxopyrrolidin-3-yl)-4-oxo-5-(4-phenoxyphenyl)-4,5-dihydro-3H-1-thia-3,5,8-triazaacenaphthylene-2-carboxamide

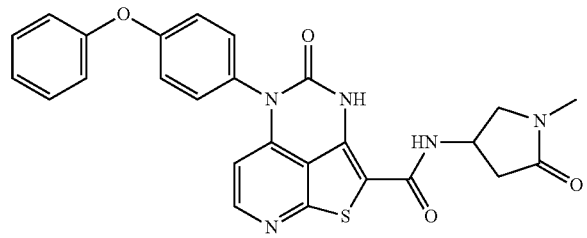 [SMILES: CN1CC(NC(=O)c2sc3nccc4c3c2NC(=O)N4c2ccc(Oc3ccccc3)cc2)CC1=O]

The title compound was prepared in a manner analogous to Method 1, steps A-G in Example 1, and using 4-amino-1-methylpyrrolidin-2-one in place of tert-butyl (3R,5R)-3-amino-5-fluoropiperidine-1-carboxylate (Intermediate 1) in step G. MS (ESI): mass calcd. for $C_{27}H_{23}N_5O_4S$, 513.6; m/z found, 514.7 [M+H]$^+$. $^1$H NMR (400 MHz, DMSO-d$_6$/CD$_3$OD): δ 8.28-8.21 (m, 1H), 7.41-7.32 (m, 2H), 7.28-7.23 (m, 1H), 7.15-7.09 (m, 1H), 7.08-7.02 (m, 2H), 7.02-6.98 (m, 1H), 6.93-6.89 (m, 1H), 5.96-5.88 (m, 1H), 4.57-4.50 (m, 1H), 3.71-3.66 (m, 1H), 3.33-3.26 (m, 1H), 2.73 (s, 3H), 2.67-2.60 (m, 1H), 2.42-2.34 (m, 1H), 2.02 (s, 3H).

Example 263: (R)—N-(1-(2-Fluoro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

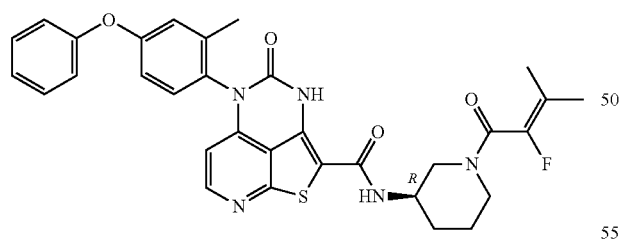

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.37 mmol), 2-fluoro-3-methylbut-2-enoic acid (Intermediate 30, 88 mg, 0.75 mmol), HATU (284 mg, 0.746 mmol), and triethylamine (75 mg, 0.75 mmol) in DMF (4 mL) was stirred at rt for 2 h, then purified by flash column chromatography to give the title compound as a yellow solid (135 mg, 60.3% yield). MS (ESI): mass calcd. for $C_{32}H_{30}FN_5O_4S$, 599.7; m/z found, 600.3 [M+H]$^+$. $^1$H NMR (400 MHz, DMSO-d$_6$): δ 10.50-10.01 (br, 1H), 8.31 (d, J=5.4 Hz, 1H), 8.15-8.00 (m, 1H), 7.48-7.38 (m, 2H), 7.37-7.31 (m, 1H), 7.21-7.13 (m, 1H), 7.12-7.04 (m, 3H), 7.01-6.88 (m, 1H), 5.95 (d, J=5.5 Hz, 1H), 4.45-3.98 (m, 1H), 3.88-3.53 (m, 2H), 3.17-2.93 (m, 1H), 2.85-2.63 (m, 1H), 2.03 (s, 3H), 1.97-1.85 (m, 1H), 1.85-1.72 (m, 1H), 1.71-1.55 (m, 7H), 1.47-1.33 (m, 1H).

Example 264: (R)—N-(1-Acryloylpyrrolidin-3-yl)-5-(2-methyl-4-(pentafluorothio)phenyl)-4-oxo-4,5-dihydro-3H-1-thia-3,5,8-triazaacenaphthylene-2-carboxamide

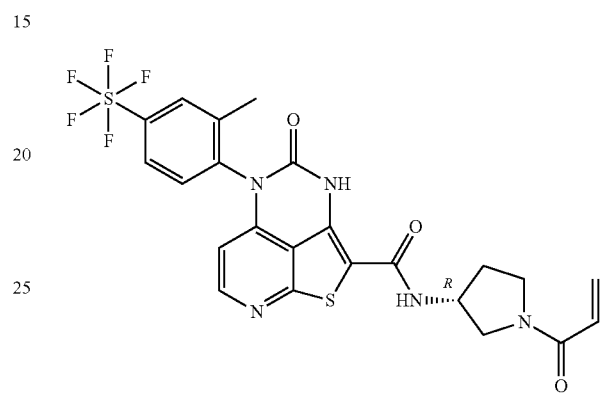

Step A: 2-Methyl-4-(pentafluoro-{6}-sulfanyl)aniline

To a stirred solution of pentafluoro-(3-methyl-4-nitrophenyl)-{6}-sulfane (1.5 g, 5.7 mmol) in ethanol (50 mL) was added Fe powder (1.27 g, 22.8 mmol) followed by the slow addition of concentrated HCl (2.5 mL) at 0° C. The mixture was stirred at rt for another 1 h, then the reaction was poured into ice water and neutralized with sodium carbonate, extracted with DCM, dried over anhydrous Na$_2$SO$_4$, filtered, and concentrated to dryness to give the title compound as a yellow oil (1.13 g, 85.0% yield).

Step B: (R)—N-(1-Acryloylpyrrolidin-3-yl)-5-(2-methyl-4-(pentafluorothio)phenyl)-4-oxo-4,5-dihydro-3H-1-thia-3,5,8-triazaacenaphthylene-2-carboxamide The title compound was prepared in a manner analogous to Method 1, steps C-I in Example 1, and using 2-methyl-4-(pentafluoro-{6}-sulfanyl)aniline in place of 2-methyl-4-phenoxyaniline in step C, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{23}H_{20}F_5N_5O_3S_2$, 573.6; m/z found, 574.2 [M+H]$^+$. $^1$H NMR (400 MHz, CD$_3$OD): δ 8.37-8.30 (m, 1H), 8.03-7.97 (m, 1H), 7.93-7.86 (m, 1H), 7.65-7.57 (m, 1H), 6.69-6.54 (m, 1H), 6.33-6.22 (m, 1H), 6.08-6.01 (m, 1H), 5.80-5.72 (m, 1H), 4.65-4.54 (m, 1H), 4.04-3.53 (m, 4H), 2.40-1.99 (m, 5H).

Example 265: (S)-5-(2-Methyl-4-phenoxyphenl)-N-((1-methylpyrrolidin-2-yl)methyl)-4-oxo-4,5-dihydro-3H-1-thia-3,5,8-triazaacenaphthylene-2-carboxamide

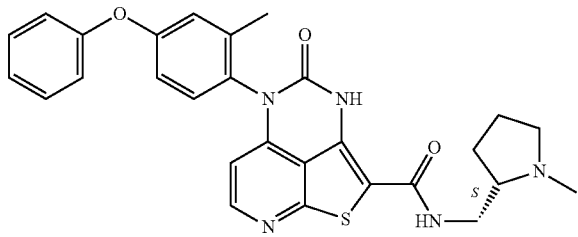

Step A: (S)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide The title compound was prepared in a manner analogous to Method 1, steps A-H in Example 1, and using tert-butyl (2S)-2-(aminomethyl)pyrrolidine-1-carboxylate in place of tert-butyl (3R,5R)-3-amino-5-fluoropiperidine-1-carboxylate (Intermediate 1) in step G.

Step B: (S)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide To a solution of (S)-5-(2-methyl-4-phenoxyphenyl)-4-oxo-N-(pyrrolidin-2-ylmethyl)-4,5-dihydro-3H-1-thia-3,5,8-triazaacenaphthylene-2-carboxamide (150 mg, 0.30 mmol) in MeOH (2 mL) was added formaldehyde (1 mL, 37 wt. % in H$_2$O) slowly and stirred for 10 min. Next, NaBH(OAc)$_3$ (127 mg, 0.600 mmol) was added slowly and the mixture was stirred for 2 h, then NaOH was added and the mixture was purified by flash column chromatography, then preparative TLC to give the title compound as a yellow solid (43 mg, 28% yield). MS (ESI): mass calcd. for C$_{28}$H$_{27}$N$_5$O$_3$S, 513.6; m/z found, 514.0 [M+H]$^+$. 1H NMR (400 MHz, CDCl3): δ 8.34 (d, J=5.5 Hz, 1H), 7.45-7.34 (m, 2H), 7.20-7.14 (m, 2H), 7.12-7.07 (m, 2H), 7.02-6.99 (m, 1H), 6.97-6.93 (m, 1H), 5.99 (d, J=5.5 Hz, 1H), 3.81-3.66 (m, 1H), 3.43-3.28 (m, 1H), 3.28-3.12 (m, 1H), 2.73-2.53 (m, 1H), 2.43 (s, 3H), 2.39-2.30 (m, 1H), 2.12 (s, 3H), 2.05-1.90 (m, 1H), 1.85-1.72 (m, 2H), 1.71-1.62 (m, 1H).

Example 266: N-((3R,5S)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide

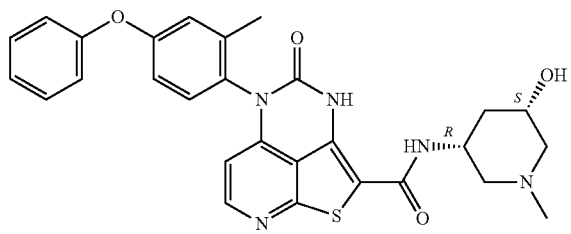

Step A: N-((3R,5S)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl (3R,5S)-3-amino-5-hydroxypiperidine-1-carboxylate (Intermediate 2) in place of tert-butyl (3R,5R)-3-amino-5-fluoropiperidine-1-carboxylate (Intermediate 1) in step G.

Step B: N-((3R,5S)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide To a solution of N-((3R,5S)-5-hydroxypiperidin-3-yl)-5-(2-methyl-4-phenoxyphenyl)-4-oxo-4,5-dihydro-3H-1-thia-3,5,8-triazaacenaphthylene-2-carboxamide (80 mg, 0.16 mmol) and formaldehyde (0.3 mL, 37 wt. % in H$_2$O) in MeOH (2 mL) was added NaBH(OAc)$_3$ (67 mg, 0.32 mmol) and was stirred at rt overnight, concentrated to dryness and purified by flash column chromatography to give the title compound as a yellow solid (70 mg 85% yield). MS (ESI): mass calcd. for C$_{28}$H$_{27}$N$_5$O$_4$S, 529.6; m/z found, 530.2 [M+H]$^+$. $^1$H NMR (400 MHz, CD$_3$OD): δ 8.34 (d, J=5.6 Hz, 1H), 7.44-7.36 (m, 2H), 7.33-7.28 (m, 1H), 7.21-7.14 (m, 1H), 7.12-7.05 (m, 3H), 7.02-7.95 (m, 1H), 6.09 (d, J=5.6 Hz, 1H), 4.41-4.27 (m, 1H), 4.10-4.39 (m, 1H), 3.13-2.97 (m, 2H), 2.87-2.47 (m, 5H), 2.16-2.04 (m, 4H), 1.78-1.64 (m, 1H).

Example 267: (S)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide

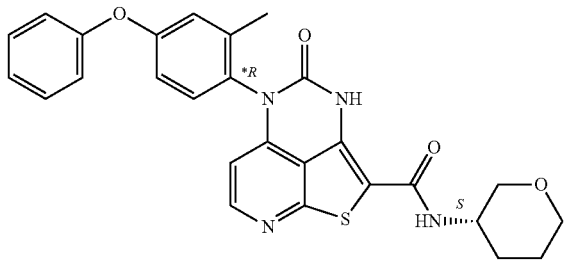

The title compound was prepared in a manner analogous to Method 1, steps A-G (including Chiral Resolution Method A after step F to obtain the *R atropisomer) in Example 1, and using (3S)-tetrahydropyran-3-amine in place of tert-butyl (3R,5R)-3-amino-5-fluoropiperidine-1-carboxylate (Intermediate 1) in step G. MS (ESI): mass calcd. for C$_{27}$H$_{24}$N$_4$O$_4$S, 500.6; m/z found, 501.3 [M+H]$^+$. $^1$H NMR (400 MHz, CD$_3$OD and DMSO-d$_6$): δ 8.42 (d, J=5.5 Hz, 1H), 7.56-7.47 (m, 2H), 7.45-7.37 (m, 1H), 7.32-7.24 (m, 1H), 7.22-7.14 (m, 3H), 7.09-7.05 (m, 1H), 6.11 (d, J=5.5 Hz, 1H), 4.09-4.02 (m, 1H), 3.98-3.95 (m, 1H), 3.94-3.84 (m, 1H), 3.47-3.38 (m, 1H), 3.37-3.31 (m, 1H), 2.19 (s, 3H), 2.11-2.01 (m, 1H), 1.86-1.67 (m, 3H).

Example 268: N-((3R,5S)-5-Methoxypiperidin-3-yl)-5-(2-methyl-4-phenoxyphenyl)-4-oxo-4,5-dihydro-3H-1-thia-3,5,8-triazaacenaphthylene-2-carboxamide

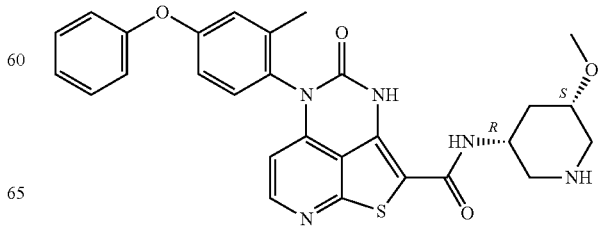

The title compound was prepared in a manner analogous to Method 1, steps A-H in Example 1, and using tert-butyl (3R,5S)-3-amino-5-methoxypiperidine-1-carboxylate (Intermediate 29) in place of tert-butyl (3R,5R)-3-amino-5-fluoropiperidine-1-carboxylate (Intermediate 1) in step G. MS (ESI): mass calcd. for $C_{28}H_{27}N_5O_4S$, 529.6; m/z found, 530.2 [M+H]$^+$. $^1$H NMR (400 MHz, CD$_3$OD): δ 8.38-8.31 (m, 1H), 7.45-7.36 (m, 2H), 7.33-7.26 (m, 1H), 7.22-7.12 (m, 1H), 7.12-7.04 (m, 3H), 7.02-6.93 (m, 1H), 6.14-6.05 (m, 1H), 4.48-4.38 (m, 1H), 3.82-3.72 (m, 1H), 3.52 (s, 3H), 3.40-3.31 (m, 2H), 3.28-3.19 (m, 2H), 2.27-2.17 (m, 1H), 2.16-2.08 (m, 3H), 2.07-2.00 (m, 1H).

Example 269: (S)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide

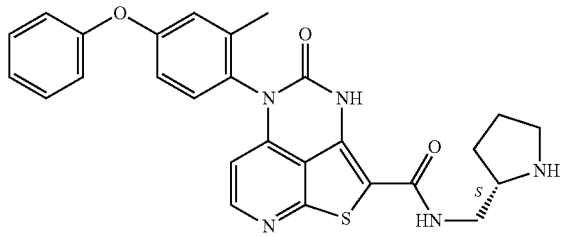

The title compound was prepared in a manner analogous to Method 1, steps A-H in Example 1, and using tert-butyl (2S)-2-(aminomethyl)pyrrolidine-1-carboxylate in place of tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 500.1 [M+H]$^+$. 1H NMR (400 MHz, CDCl3): δ 8.33-8.26 (m, 1H), 7.42-7.35 (m, 2H), 7.23-7.14 (m, 2H), 7.12-7.06 (m, 2H), 7.02-6.98 (m, 1H), 6.98-6.92 (m, 1H), 6.54 (br, 1H), 6.03-5.90 (m, 1H), 3.59-3.51 (m, 1H), 3.47-3.39 (m, 1H), 3.29-3.19 (m, 1H), 3.02-2.92 (m, 2H), 2.15-2.08 (m, 3H), 1.97-1.90 (m, 1H), 1.88-1.79 (m, 1H), 1.78-1.69 (m, 1H), 1.51-1.41 (m, 1H).

Example 270: (R)—N-(1-Acryloylpyrrolidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide

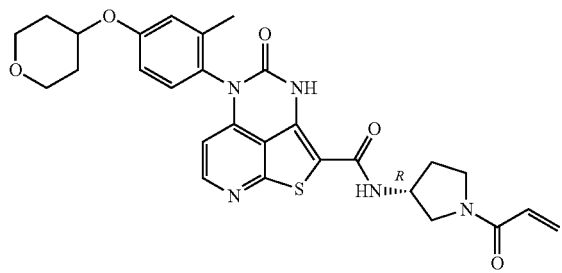

The title compound was prepared in a manner analogous to Method 1, steps D-I in Example 1, and using 2-chloro-4-(2-methyl-4-tetrahydropyran-4-yloxyanilino)pyridine-3-carbonitrile (Intermediate 31) in place of 2-chloro-4-(2-methyl-4-phenoxyanilino)pyridine-3-carbonitrile in step D, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{28}H_{29}N_5O_5S$, 547.6; m/z found, 548.1 [M+H]$^+$. $^1$H NMR (400 MHz, CD$_3$OD): δ 8.31-8.25 (m, 1H), 7.25-7.20 (m, 1H), 7.05-7.01 (m, 1H), 6.99-6.95 (m, 1H), 6.65-6.49 (m, 1H), 6.31-6.22 (m, 1H), 6.04-5.97 (m, 1H), 5.77-5.69 (m, 1H), 4.67-4.55 (m, 2H), 4.01-3.90 (m, 2H), 3.87-3.76 (m, 1H), 3.76-3.65 (m, 1H), 3.65-3.56 (m, 3H), 3.56-3.45 (m, 1H), 2.37-2.17 (m, 1H), 2.10 (s, 3H), 2.08-2.00 (m, 3H), 1.81-1.68 (m, 2H).

Example 271: (R)—N-(1-Acryloylpiperidin-3-yl)-4-oxo-5-(p-tolyl)-4,5-dihydro-3H-1-thia-3,5,8-triazaacenaphthylene-2-carboxamide

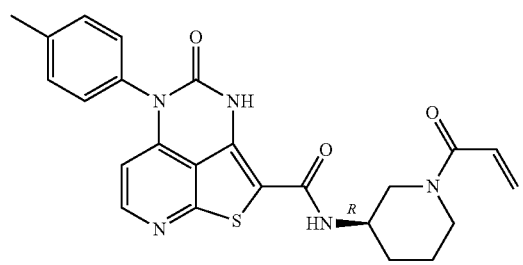

The title compound was prepared in a manner analogous to Method 1, steps C-I in Example 1, and using p-toluidine in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{24}H_{23}N_5O_3S$, 461.5; m/z found, 461.9 [M+H]$^+$. $^1$H NMR (400 MHz, DMSO-d$_6$): δ 10.17 (d, J=16.2 Hz, 1H), 8.33 (d, J=5.5 Hz, 1H), 8.17-8.03 (m, 1H), 7.41 (d, J=8.2 Hz, 2H), 7.34 (d, J=8.3 Hz, 2H), 6.89-6.72 (m, 1H), 6.12 (d, J=16.6 Hz, 1H), 6.01 (d, J=5.5 Hz, 1H), 5.70 (d, J=11.2 Hz, 1H), 4.50-4.21 (m, 1H), 4.12-3.96 (m, 1H), 3.79 (s, 1H), 3.16-2.94 (m, 1H), 2.77-2.63 (m, 1H), 2.42 (s, 3H), 1.96-1.93 (m, 1H), 1.81-1.78 (m, 1H), 1.74-1.60 (m, 1H), 1.44 (brs, 1H).

Example 272: (R)—N-(5,5-Difluoro-1-methylpiperidin-3-yl)-5-(2-methyl-4-phenoxyphenyl)-4-oxo-4,5-dihydro-3H-1-thia-3,5,8-triazaacenaphthylene-2-carboxamide

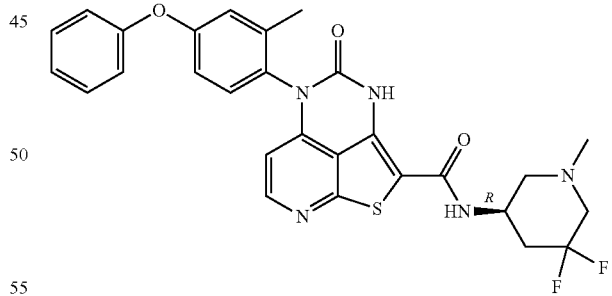

Step A: (R)—N-(5,5-Difluoropiperidin-3-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl (5R)-5-amino-3,3-difluoropiperidine-1-carboxylate in place of tert-butyl (3R,5R)-3-amino-5-fluoropiperidine-1-carboxylate (Intermediate 1) in step G.

Step B: (R)—N-(5,5-Difluoro-1-methylpiperidin-3-yl)-5-(2-methyl-4-phenoxyphenyl)-4-oxo-4,5-dihydro-3H-1-thia-3,5,8-triazaacenaphthylene-2-carboxamide To a solution of (R)—N-(5,5-difluoropiperidin-3-yl)-5-(2-methyl-4-phenoxyphenyl)-4-oxo-4,5-dihydro-3H-1-thia-3,5,8-triazaacenaphthylene-2-carboxamide (110 mg, 0.21 mmol) and formaldehyde (1 mL, 37 wt. % in H$_2$O) in MeOH (20 mL) was added NaBH(OAc)$_3$ (218 mg, 1.03 mmol) and was stirred at rt for 16 h, concentrated to dryness, and purified by flash column chromatography to give the title compound as a yellow solid (70 mg, 62% yield). MS (ESI): mass calcd. for C$_{28}$H$_{25}$F$_2$N$_5$O$_3$S, 549.6; m/z found, 550.3 [M+H]$^+$. $^1$H NMR (400 MHz, DMSO-d$_6$): δ 10.21 (s, 1H), 8.34 (d, J=5.5 Hz, 1H), 8.05 (d, J=7.7 Hz, 1H), 7.48-7.42 (m, 2H), 7.38 (d, J=8.6 Hz, 1H), 7.24-7.15 (m, 1H), 7.14-7.03 (m, 3H), 7.02-6.93 (m, 1H), 5.98 (d, J=5.5 Hz, 1H), 4.26-4.08 (m, 1H), 3.03-2.93 (m, 1H), 2.92-2.80 (m, 1H), 2.35-2.20 (m, 5H), 2.06 (s, 3H), 2.04-1.88 (m, 2H).

Example 273: N-(1-Isopropylazetidin-3-yl)-5-(2-methyl-4-phenoxyphenyl)-4-oxo-4,5-dihydro-3H-1-thia-3,5,8-triazaacenaphthylene-2-carboxamide

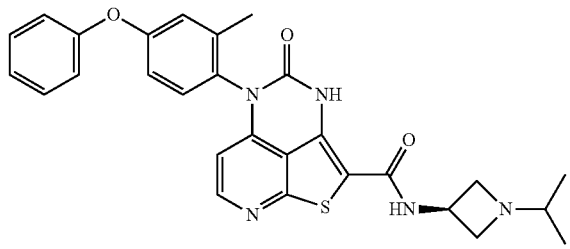

To a solution of N-(azetidin-3-yl)-5-(2-methyl-4-phenoxyphenyl)-4-oxo-4,5-dihydro-3H-1-thia-3,5,8-triazaacenaphthylene-2-carboxamide (Example 252, 150 mg, 0.30 mmol) and acetone (1 mL) in MeOH (10 mL) was added NaBH(OAc)$_3$ (188 mg, 0.885 mmol) and was stirred at rt for 1 h, concentrated to dryness, and purified by flash column chromatography to give the title compound as a white solid (103 mg, 68.1% yield). MS (ESI): mass calcd. for C$_{28}$H$_{27}$N$_5$O$_3$S, 513.6; m/z found, 514.4 [M+H]$^+$. 1H NMR (400 MHz, DMSO-d6): δ 8.65-8.53 (m, 1H), 8.28 (d, J=5.5 Hz, 1H), 7.48-7.38 (m, 2H), 7.36-7.28 (m, 1H), 7.24-7.15 (m, 1H), 7.14-7.03 (m, 3H), 6.99-6.92 (m, 1H), 5.92 (d, J=5.4 Hz, 1H), 4.48-4.29 (m, 1H), 3.63-3.55 (m, 2H), 3.13-3.06 (m, 2H), 2.46-2.39 (m, 1H), 2.04 (s, 3H), 0.89 (d, J=6.2 Hz, 6H).

Example 274: (R,E)-N-(1-(4,4-Dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

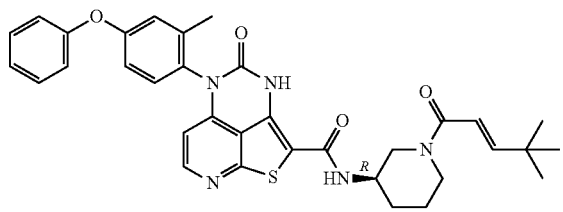

Step A: (E)-4,4-Dimethylpent-2-enoic Acid

To a solution of malonic acid (2000 mg, 19 mmol) and 2,2-dimethylpropanal (827 mg, 9.60 mmol) in pyridine 20 mL was added piperidine (0.5 mg) and the mixture was refluxed overnight. The reaction mixture was washed with 1 M aqueous HCl, extracted with DCM, and concentrated to dryness to give the title compound as a brown oil (1200 mg), which was used in the next step without further purification.

Step B: (R,E)-N-(1-(4,4-Dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 100 mg, 0.2 mmol) and (E)-4,4-dimethylpent-2-enoic acid (500 mg, 3.9 mmol) in anhydrous DMF (5 mL) were added HATU (228 mg, 0.600 mmol) and diisopropylethylamine (130 mg, 1.0 mmol) and the mixture was stirred overnight at rt. It was purified by flash column chromatography, then TLC to give the title compound as a yellow solid (15 mg, 12% yield). MS (ESI): mass calcd. for C$_{34}$H$_{35}$N$_5$O$_4$S, 609.7; m/z found, 610.2 [M+H]$^+$. 1H NMR (400 MHz, CDCl3): δ 9.54-9.38 (m, 1H), 8.42-8.28 (m, 1H), 7.42-7.36 (m, 2H), 7.21-7.14 (m, 2H), 7.12-7.06 (m, 2H), 7.00 (s, 1H), 6.97-6.94 (m, 1H), 6.19-6.11 (m, 1H), 6.08-5.93 (m, 1H), 4.16-4.10 (m, 1H), 3.81-3.43 (m, 4H), 2.12 (s, 3H), 1.81-1.63 (m, 5H), 1.13-1.01 (m, 9H).

Example 275: 5-(2-Methyl-4-phenoxyphenyl)-N-(2-morpholinoethyl)-4-oxo-4,5-dihydro-3H-1-thia-3,5,8-triazaacenaphthylene-2-carboxamide

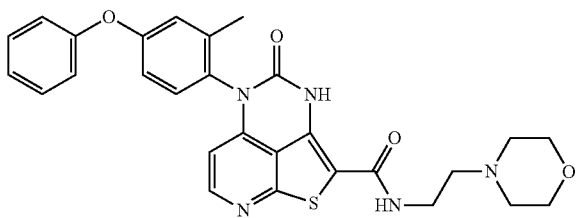 [SMILES: Cc1cc(Oc2ccccc2)ccc1N1C(=O)Nc2c(C(=O)NCCN3CCOCC3)sc3nccc1c23]

To a solution of 2-morpholinoethanamine (200 mg, 1.5 mmol) and triethylamine (500 mg, 5.0 mmol) in DCM/THF (1/1) was added dropwise a solution of 5-(2-methyl-4-phenoxyphenyl)-4-oxo-4,5-dihydro-3H-1-thia-3,5,8-triazaacenaphthylene-2-carbonyl chloride (Intermediate 32, 260 mg, 0.60 mmol) in DCM/THF(1/1). The reaction was stirred at rt for 2 h, then it was concentrated to dryness, and purified by flash column chromatography to give the title compound as a yellow solid (53 mg, 17% yield). MS (ESI): mass calcd. for C$_{28}$H$_{27}$N$_5$O$_4$S, 529.6; m/z found, 530.4 [M+H]$^+$. $^1$H NMR (400 MHz, CDCl$_3$): δ 9.44 (br, 1H), 8.35 (d, J=5.5 Hz, 1H), 7.42-7.35 (m, 2H), 7.20-7.13 (m, 2H), 7.12-7.07 (m, 2H), 7.02-6.99 (m, 1H), 6.97-6.93 (m, 1H), 6.45-6.23 (m, 1H), 6.00 (d, J=5.5 Hz, 1H), 3.84-3.69 (m, 4H), 3.59-3.49 (m, 2H), 2.73-2.37 (m, 6H), 2.12 (s, 3H).

Example 276: (R)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide

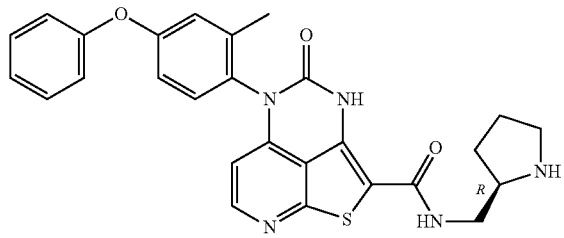

The title compound was prepared in a manner analogous to Method 1, steps A-H in Example 1, and using (R)-tert-butyl 2-(aminomethyl)pyrrolidine-1-carboxylate in place of tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 500.1 [M+H]$^+$. 1H NMR (400 MHz, CDCl3): δ 8.31-8.24 (m, 1H), 7.43-7.34 (m, 2H), 7.25-7.20 (m, 1H), 7.20-7.14 (m, 1H), 7.11-7.07 (m, 2H), 7.00-6.98 (m, 1H), 6.98-6.94 (m, 1H), 6.78 (br, 1H), 5.96-5.92 (m, 1H), 3.62-3.45 (m, 2H), 3.34-3.22 (m, 1H), 3.04-2.93 (m, 2H), 2.14-2.07 (m, 3H), 1.99-1.91 (m, 1H), 1.90-1.81 (m, 1H), 1.79-1.70 (m, 1H), 1.53-1.40 (m, 1H).

Example 277: (R,Z)—N-(1-(2-Chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

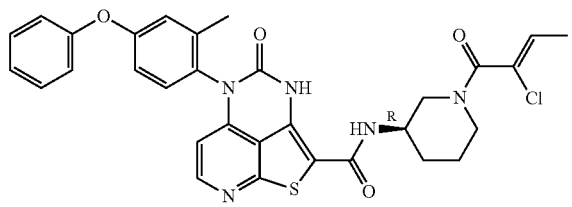

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), (Z)-2-chlorobut-2-enoic acid (67 mg, 0.56 mmol), HATU (138 mg, 0.364 mmol), and diisopropylethylamine (90 mg, 0.7 mmol) in DMF (5 mL) was stirred at rt for 2 h. The mixture was purified by HPLC to give the title compound as light yellow solid (118 mg, 70.0% yield). MS (ESI): mass calcd. for $C_{31}H_{28}ClN_5O_4S$, 602.1; m/z found, 602.4 [M+H]$^+$. $^1$H NMR (400 MHz, CD$_3$OD): δ 8.37-8.30 (m, 1H), 7.45-7.35 (m, 2H), 7.33-7.26 (m, 1H), 7.21-7.14 (m, 1H), 7.13-7.03 (m, 3H), 7.02-6.95 (m, 1H), 6.22-6.13 (m, 1H), 6.11-6.05 (m, 1H), 4.58-3.94 (m, 3H), 3.23-2.92 (m, 2H), 2.17-2.02 (m, 4H), 1.94-1.81 (m, 4H), 1.79-1.56 (m, 2H).

Example 278: (R)—N-(1-Acryloylpiperidin-3-yl)-4-oxo-5-(4-phenoxy-2-(trifluoromethyl)phenyl)-4,5-dihydro-3H-1-thia-3,5,8-triazaacenaphthylene-2-carboxamide

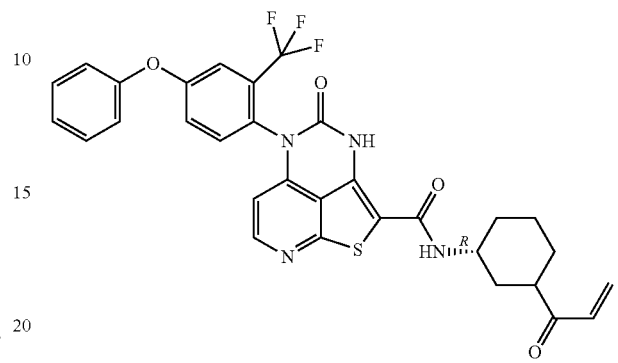

The title compound was prepared in a manner analogous to Method 1, steps A-I in Example 1, and using 4-fluoro-1-nitro-2-(trifluoromethyl)benzene in place of 5-fluoro-2-nitrotoluene in step A, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{24}F_3N_5O_4S$, 607.6; m/z found, 608.3 [M+H]$^+$. $^1$H NMR (400 MHz, DMSO-d$_6$): □ 10.38 (s, 1H), 8.34 (d, J=5.5 Hz, 1H), 8.20-8.02 (m, 1H), 7.74 (d, J=8.7 Hz, 1H), 7.59-7.38 (m, 4H), 7.35-7.14 (m, 3H), 6.90-6.65 (m, 1H), 6.20-6.00 (m, 2H), 5.66 (d, J=12.2 Hz, 1H), 4.52-4.12 (m, 1H), 4.10-3.89 (m, 1H), 3.84-3.63 (m, 1H), 3.16-2.88 (m, 1H), 2.83-2.55 (m, 1H), 2.05-1.85 (m, 1H), 1.85-1.51 (m, 2H), 1.50-1.30 (m, 1H).

Example 279: (R)—N-(1-Acryloylpiperidin-3-yl)-4-oxo-5-(m-tolyl)-4,5-dihydro-3H-1-thia-3,5,8-triazaacenaphthylene-2-carboxamide

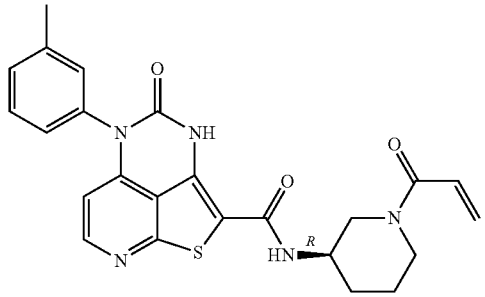

The title compound was prepared in a manner analogous to Method 1, steps C-I in Example 1, and using m-toluidine in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{24}H_{23}N_5O_3S$, 461.5; m/z found, 461.9 [M+H]$^+$. $^1$H NMR (400 MHz, DMSO-d$_6$): δ 10.18 (d, J=16.6 Hz, 1H), 8.33 (d, J=5.5 Hz, 1H), 8.16-8.05 (m, 1H), 7.52-7.48 (m, 1H), 7.37 (d, J=7.5 Hz, 1H), 7.33-7.23 (m, 2H), 6.90-6.73 (m, 1H), 6.12 (d, J=16.6 Hz, 1H), 6.01 (d, J=5.5 Hz, 1H), 5.70 (d, J=10.6 Hz, 1H), 4.51-4.21 (m, 1H), 4.09-4.00 (m, 1H), 3.79 (s, 1H), 3.14-2.96 (m, 1H), 2.80-2.63 (m, 1H), 2.40 (s, 3H), 1.97-1.93 (m, 1H), 1.81-1.78 (m, 1H), 1.75-1.59 (m, 1H), 1.44 (brs, 1H).

Example 280: (R)-5-(4-Chloro-3-(trifluoromethyl) phenyl)-4-oxo-N-(piperidin-3-yl)-4,5-dihydro-3H-1-thia-3,5,8-triazaacenaphthylene-2-carboxamide

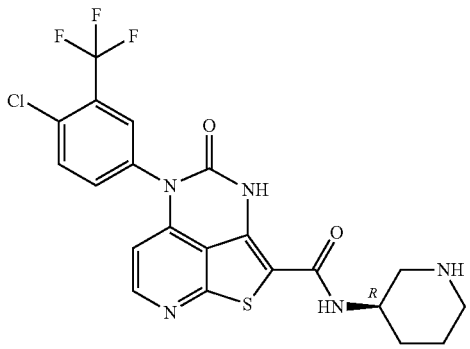

The title compound was prepared in a manner analogous to Method 1, steps C-H in Example 1, and using 4-chloro-3-(trifluoromethyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{21}H_{17}ClF_3N_5O_2S$, 495.9; m/z found, 495.8 [M+H]$^+$. 1H NMR (400 MHz, DMSO-d6) δ 8.71 (d, J=7.1 Hz, 1H), 8.23 (s, 1H), 8.15 (d, J=5.5 Hz, 1H), 7.92-7.90 (m, 2H), 7.72 (dd, J=8.5, 1.9 Hz, 1H), 5.97 (d, J=5.5 Hz, 1H), 4.07 (s, 1H), 3.32-3.28 (m, 1H), 3.14-3.11 (m, 1H), 2.85-2.74 (m, 2H), 1.96-1.85 (m, 2H), 1.72-1.51 (m, 2H).

Example 281: (R)-5-(2,3-Dimethyl-4-phenoxyphenyl)-N-(1-methylpiperidin-3-yl)-4-oxo-4,5-dihydro-3H-1-thia-3,5,8-triazaacenaphthylene-2-carboxamide

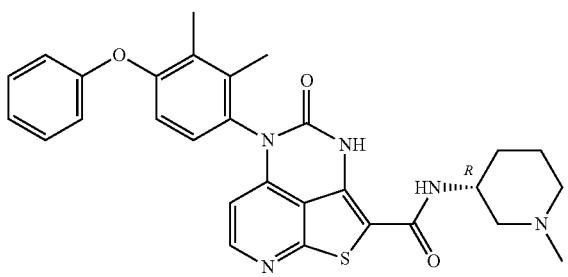

Step A: (R)-5-(23-Dimethyl-4-phenoxyphenyl-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 1-fluoro-2,3-dimethyl-4-nitrobenzene in place of 5-fluoro-2-nitrotoluene in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(2,3-Dimethyl-4-phenoxyphenyl)-N-(1-methylpiperidin-3-yl)-4-oxo-4,5-dihydro-3H-1-thia-3,5,8-triazaacenaphthylene-2-carboxamide To a solution of (R)-5-(2,3-dimethyl-4-phenoxyphenyl)-4-oxo-N-(piperidin-3-yl)-4,5-dihydro-3H-1-thia-3,5,8-triazaacenaphthylene-2-carboxamide (167 mg, 0.326 mmol) in DCM (10 mL) were added formaldehyde (3 mL, 37 wt. % in H$_2$O) and NaBH(OAc)$_3$ (276 mg, 1.30 mmol) and was stirred at rt for 4 h. To the mixture were added DCM (50 mL), MeOH (5 mL), and water (30 mL). The organic layer was collected, concentrated to dryness, and purified by TLC to give the title compound as a yellow solid (75 mg, 44% yield). MS (ESI): mass calcd. for $C_{29}H_{29}N_5O_3S$, 527.6; m/z found, 528.2 [M+H]$^+$. 1H NMR (400 MHz, DMSO-d6): δ 8.32-8.22 (m, 1H), 8.14-8.00 (br, 1H), 7.41-7.35 (m, 2H), 7.19 (d, J=7.9 Hz, 1H), 7.13-7.07 (m, 1H), 7.01-6.93 (m, 2H), 6.90 (d, J=8.7 Hz, 1H), 5.97-5.84 (m, 1H), 3.96-3.90 (m, 1H), 2.85-2.79 (m, 1H), 2.69-2.62 (m, 1H), 2.20 (s, 3H), 2.18 (s, 3H), 2.03 (s, 3H), 1.95-1.86 (m, 2H), 1.81-1.74 (m, 1H), 1.72-1.64 (m, 1H), 1.56-1.46 (m, 1H), 1.38-1.29 (m, 1H).

Example 282: 5-(2-Methyl-4-phenoxyphenyl)-N-((1-methylpyrrolidin-3-yl)methyl)-4-oxo-4,5-dihydro-3H-1-thia-3,5,8-triazaacenaphthylene-2-carboxamide

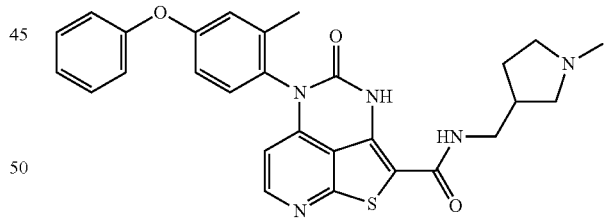

The title compound was prepared in a manner analogous to Method 1, steps C-G in Example 1, and using (1-methylpyrrolidin-3-yl)methanamine in place of tert-butyl (3R, 5R)-3-amino-5-fluoropiperidine-1-carboxylate (Intermediate 1) in step G. MS (ESI): mass calcd. for $C_{28}H_{27}N_5O_3S$, 513.6; m/z found, 514.0 [M+H]$^+$. $^1$H NMR (500 MHz, CD$_3$OD): δ 8.46 (s, 1H), 8.34 (d, J=5.5 Hz, 1H), 7.48-7.35 (m, 2H), 7.31 (dd, J=8.6, 1.3 Hz, 1H), 7.22-7.13 (m, 1H), 7.13-7.02 (m, 3H), 6.98 (dd, J=8.6, 2.8 Hz, 1H), 6.09 (d, J=5.5 Hz, 1H), 3.56-3.33 (m, 5H), 3.27-3.14 (m, 1H), 2.92 (s, 3H), 2.88-2.74 (m, 1H), 2.33-2.20 (m, 1H), 2.12 (s, 3H), 2.00-1.86 (m, 1H).

Example 283: (R)-5-(4-(2-Isopropoxyphenoxy)-2-methylphenyl)-N-(1-methylpiperidin-3-yl)-4-oxo-4,5-dihydro-3H-1-thia-3,5,8-triazaacenaphthylene-2-carboxamide

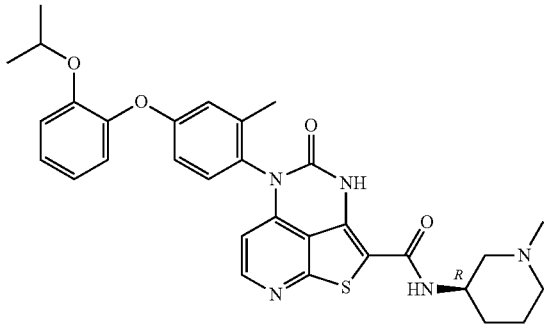

Step A: (R)-5-(4-(2-Isopropoxyphenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 2-isopropoxyphenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(2-Isopropoxyphenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-isopropoxyphenoxy)-2-methylphenyl)-4-oxo-N-(piperidin-3-yl)-4,5-dihydro-3H-1-thia-3,5,8-triazaacenaphthylene-2-carboxamide (187 mg, 0.315 mmol) and formaldehyde (1 mL, 37 wt. % in $H_2O$) in MeOH (10 mL) was added $NaBH(OAc)_3$ (200 mg, 0.95 mmol) and was stirred at rt for 1 h, concentrated to dryness, and purified by flash column chromatography to give the title compound as a white solid (122 mg, 67.3% yield). MS (ESI): mass calcd. for $C_{31}H_{33}N_5O_4S$, 571.7; m/z found, 572.5 [M+H]$^+$. $^1$H NMR (400 MHz, DMSO-d$_6$): δ 8.30 (d, J=5.5 Hz, 1H), 8.15 (s, 1H), 8.01 (d, J=7.5 Hz, 1H), 7.32-7.23 (m, 1H), 7.22-7.07 (m, 3H), 7.03-6.88 (m, 2H), 6.86-6.75 (m, 1H), 5.86 (d, J=5.5 Hz, 1H), 4.62-4.51 (m, 1H), 4.00-3.93 (m, 1H), 2.95-2.84 (m, 1H), 2.77-2.64 (m, 1H), 2.27 (s, 3H), 2.02 (s, 5H), 1.83-1.66 (m, 2H), 1.57-1.48 (m, 1H), 1.48-1.33 (m, 1H), 1.15 (d, J=6.0 Hz, 6H).

Example 284: (R)-5-(4-Cyclobutoxy-2-methylphenyl)-N-(1-methylpiperidin-3-yl)-4-oxo-4,5-dihydro-3H-1-thia-3,5,8-triazaacenaphthylene-2-carboxamide

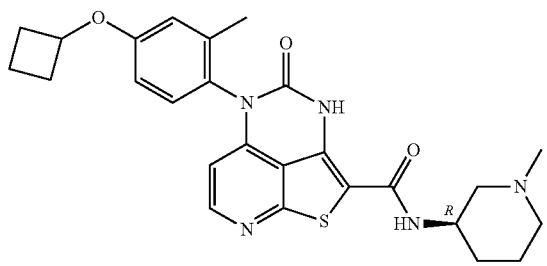

To a solution of (R)-5-(4-cyclobutoxy-2-methylphenyl)-4-oxo-N-(piperidin-3-yl)-4,5-dihydro-3H-1-thia-3,5,8-triazaacenaphthylene-2-carboxamide (Example 605) (150 mg, 0.31 mmol) and formaldehyde (0.5 mL, 37 wt. % in $H_2O$) in DCM (2 mL) was added $NaBH(OAc)_3$ (200 mg, 0.95 mmol) and was stirred at rt for overnight. The reaction was quenched by the addition of water (10 mL), extracted with DCM, dried over anhydrous $Na_2SO_4$, filtered, concentrated to dryness, and purified by flash column chromatography to give the title compound as a yellow solid (65 mg, 42% yield). MS (ESI): mass calcd. for $C_{26}H_{29}N_5O_3S$, 491.6; m/z found, 492.0 [M+H]$^+$. $^1$H NMR (400 MHz, CD$_3$OD): δ 8.32-8.27 (m, 1H), 7.24-7.17 (m, 1H), 6.92-6.86 (m, 1H), 6.86-6.78 (m, 1H), 6.02-5.94 (m, 1H), 4.80-4.66 (m, 1H), 4.33-4.19 (m, 1H), 3.49-3.36 (m, 1H), 3.27-3.17 (m, 1H), 2.84-2.69 (m, 5H), 2.56-2.40 (m, 2H), 2.19-2.06 (m, 5H), 2.06-1.95 (m, 2H), 1.92-1.58 (m, 4H).

Example 285: (R)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide

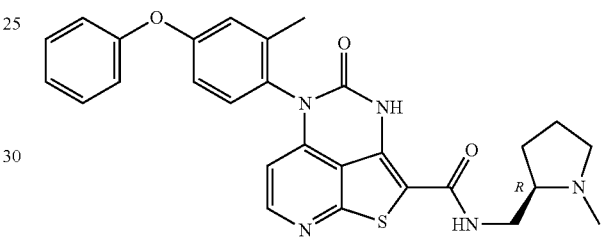

Step A: (R)-5-(2-Methyl-4-phenoxyphenyl)-4-oxo-N-(pyrrolidin-2-yl)methyl)-4,5-dihydro-3H-1-thia-3,5,8-triazaacenaphthylene-2-carboxamide The title compound was prepared in a manner analogous to Method 1, steps A-H in Example 1, and using tert-butyl (2R)-2-aminopyrrolidine-1-carboxylate in place of tert-butyl (3R,5R)-3-amino-5-fluoropiperidine-1-carboxylate (Intermediate 1) in step G.

Step B: (R)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide To a solution of (R)-5-(2-methyl-4-phenoxyphenyl)-4-oxo-N-(pyrrolidin-2-ylmethyl)-4,5-dihydro-3H-1-thia-3,5,8-triazaacenaphthylene-2-carboxamide (150 mg, 0.3 mmol) in MeOH (2 mL) was added formaldehyde (1 mL, 37 wt. % in $H_2O$) slowly and was stirred for 10 min, then $NaBH(OAc)_3$ (127 mg, 0.6 mmol) was added slowly and the mixture was stirred for 2 h, then NaOH (2 mL) was added and the mixture was purified by flash column chromatography, then by preparative TLC to give the title compound as a yellow solid (75 mg, 47% yield). MS (ESI): mass calcd. for $C_{28}H_{27}N_5O_3S$, 513.6; m/z found, 514.0 [M+H]$^+$. $^1$H NMR (400 MHz, CDCl$_3$): δ 9.05-8.96 (m, 1H), 8.61-8.56 (m, 1H), 8.34 (d, J=5.5 Hz, 1H), 7.41-7.36 (m, 2H), 7.19-7.14 (m, 2H), 7.11-7.07 (m, 2H), 7.02-6.98 (m, 1H), 6.96-6.92 (m, 1H), 5.97 (d, J=5.5 Hz, 1H), 3.86-3.79 (m, 1H), 3.78-3.67 (m, 2H), 3.51-3.39 (m, 1H), 2.87-2.74 (m, 4H), 2.29-2.20 (m, 1H), 2.12 (s, 3H), 2.10-2.02 (m, 2H), 1.95-1.83 (m, 1H).

Example 286: (R)-5-(4-(3,5-Difluorophenoxy)-2-methylphenyl)-N-(1-methylpiperidin-3-yl)-4-oxo-4,5-dihydro-3H-1-thia-3,5,8-triazaacenaphthylene-2-carboxamide

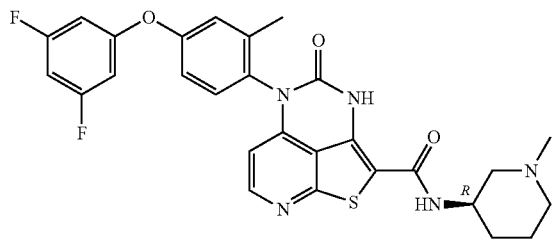

Step A: (R)-5-(4-(3,5-Difluorophenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 3,5-difluorophenol and 4-fluoro-2-methyl-1-nitrobenzene in place of 5-fluoro-2-nitrotoluene and phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(3,5-Difluorophenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(3,5-difluorophenoxy)-2-methylphenyl)-4-oxo-N-(piperidin-3-yl)-4,5-dihydro-3H-1-thia-3,5,8-triazaacenaphthylene-2-carboxamide (120 mg, 0.22 mmol) in DCM (1 mL) were added formaldehyde (0.5 mL, 37 wt. % in H$_2$O) and NaBH(OAc)$_3$ (140 mg, 0.66 mmol) and was stirred at rt for 20 min. The reaction was quenched by the addition of water (10 mL), extracted with DCM, dried over anhydrous Na$_2$SO$_4$, filtered, concentrated to dryness, and purified by flash column chromatography to give the title compound as a white solid (75 mg, 60% yield). MS (ESI): mass calcd. for C$_{28}$H$_{25}$F$_2$N$_5$O$_3$S, 549.6; m/z found, 550.1 [M+H]$^+$. $^1$H NMR (400 MHz, CD$_3$OD): δ 8.29 (d, J=5.5 Hz, 1H), 7.42-7.33 (m, 1H), 7.21-7.14 (m, 1H), 7.12-7.02 (m, 1H), 6.74-6.61 (m, 3H), 6.05 (d, J=5.5 Hz, 1H), 4.22-4.09 (m, 1H), 3.02-2.85 (m, 1H), 2.77-2.64 (m, 1H), 2.34 (s, 3H), 2.27-2.17 (m, 2H), 2.16 (s, 3H), 1.94-1.77 (m, 2H), 1.75-1.62 (m, 1H), 1.56-1.42 (m, 1H).

Example 287: (R)—N-(1-(2-(Dimethylamino)acetyl)piperidin-3-yl)-5-(*R)-(2-methyl-4-phenoxyphenyl)-4-oxo-4,5-dihydro-3H-1-thia-3,5,8-triazaacenaphthylene-2-carboxamide

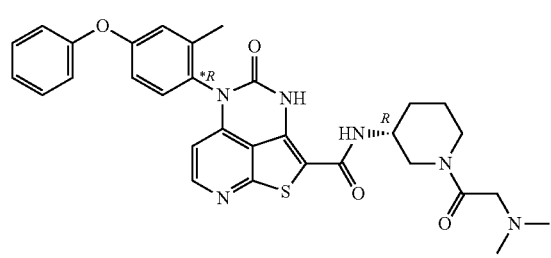

The title compound was prepared in a manner analogous to Method 1, steps C-G (including Chiral Resolution Method A after step F to obtain the *R atropisomer) in Example 1, and using 1-[(3R)-3-amino-1-piperidyl]-2-(dimethylamino)ethanone (Intermediate 43) in place of tert-butyl (3R,5R)-3-amino-5-fluoropiperidine-1-carboxylate (Intermediate 1) in step G. MS (ESI): mass calcd. for C$_{31}$H$_{32}$N$_6$O$_4$S, 584.7; m/z found, 585.4 [M+H]$^+$. $^1$H NMR (400 MHz, CD$_3$OD): δ 8.33-8.21 (m, 1H), 7.48-7.34 (m, 2H), 7.31-7.24 (m, 1H), 7.20-7.14 (m, 1H), 7.12-7.04 (m, 3H), 7.02-6.92 (m, 1H), 6.05-5.98 (m, 1H), 4.37-3.79 (m, 3H), 3.63-3.40 (m, 2H), 3.26-2.96 (m, 2H), 2.50-2.37 (m, 6H), 2.12 (s, 3H), 2.02-1.98 (m, 1H), 1.88-1.68 (m, 2H), 1.68-1.51 (m, 1H).

Example 288: (R)—N-(1-Acryloylpiperidin-3-yl)-4-oxo-5-(3-(trifluoromethyl)phenyl)-4,5-dihydro-3H-1-thia-3,5,8-triazaacenaphthylene-2-carboxamide

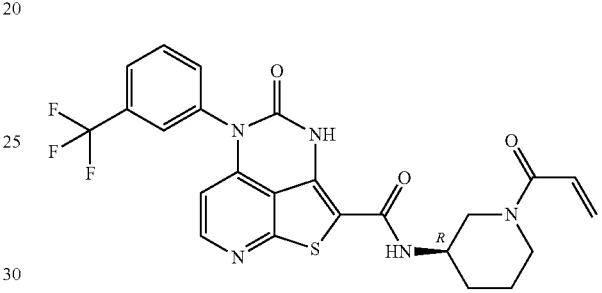

The title compound was prepared in a manner analogous to Method 1, steps C-I in Example 1, and using 3-(trifluoromethyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for C$_{24}$H$_{20}$F$_3$N$_5$O$_3$S, 515.5; m/z found, 516.0 [M+H]$^+$. $^1$H NMR (400 MHz, DMSO-d$_6$): δ 10.25 (s, 1H), 8.34 (d, J=5.4 Hz, 1H), 8.12 (s, 1H), 7.98 (s, 1H), 7.94 (d, J=7.4 Hz, 1H), 7.90-7.81 (m, 2H), 6.90-6.72 (m, 1H), 6.12 (d, J=16.6 Hz, 1H), 6.03 (d, J=5.5 Hz, 1H), 5.69 (d, J=12.4 Hz, 1H), 4.53-4.15 (m, 1H), 4.12-3.95 (m, 1H), 3.80 (brs, 1H), 3.18-2.94 (m, 1H), 2.85-2.61 (m, 1H), 1.97-1.94 (m, 1H), 1.81-1.79 (m, 1H), 1.75-1.59 (m, 1H), 1.44 (brs, 1H).

Example 289: (S)—N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide

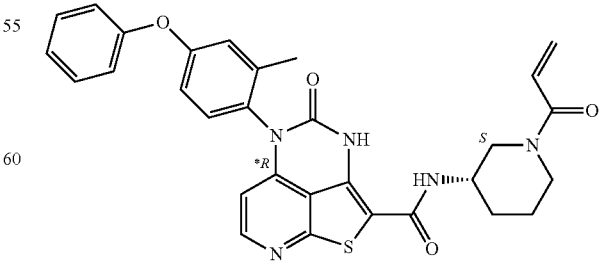

The title compound was prepared in a manner analogous to Method 1, steps A-I (including Chiral Resolution Method A after step F to obtain the *R atropisomer) in Example 1, and using tert-butyl (3S)-3-aminopiperidine-1-carboxylate in place of tert-butyl (3R,5R)-3-amino-5-fluoropiperidine-1-carboxylate (Intermediate 1) in step G. MS (ESI): mass calcd. for C₃₀H₂₇N₅O₄S, 553.6; m/z found, 554.0 [M+H]⁺. ¹H NMR (500 MHz, CD₃OD): δ 8.27 (dd, J=7.7, 5.3 Hz, 1H), 7.46-7.35 (m, 2H), 7.29 (dd, J=8.7, 2.6 Hz, 1H), 7.23-6.93 (m, 5H), 6.86-6.73 (m, 1H), 6.25-6.12 (m, 1H), 6.08-5.95 (m, 1H), 5.82-5.66 (m, 1H), 4.69-4.46 (m, 1H), 4.39-4.09 (m, 1H), 4.06-3.83 (m, 1H), 3.27-3.11 (m, 1H), 2.98-2.85 (m, 1H), 2.22-2.01 (m, 4H), 1.97-1.42 (m, 3H).

Example 290: (R)-5-(2-Methyl-4-(p-tolyloxy)phenyl)-N-(1-methylpiperidin-3-yl)-4-oxo-4,5-dihydro-3H-1-thia-3,5,8-triazaacenaphthylene-2-carboxamide

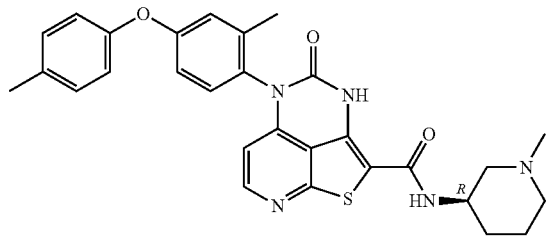

Step A: (R)-5-(2-Methyl-4-(p-tolyloxy)phenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using p-cresol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(2-Methyl-4-(p-tolyloxy)phenyl)-N-(1-methylpiperidin-3-yl)-4-oxo-4,5-dihydro-3H-1-thia-3,5,8-triazaacenaphthylene-2-carboxamide To a solution of (R)-5-(2-methyl-4-(p-tolyloxy)phenyl)-4-oxo-N-(piperidin-3-yl)-4,5-dihydro-3H-1-thia-3,5,8-triazaacenaphthylene-2-carboxamide (92 mg, 0.18 mmol) in DCM (5 mL) were added formaldehyde (0.5 mL, 37 wt. % in H₂O) and NaBH(OAc)₃ (76 mg, 0.36 mmol) and was stirred at rt for 4 hours. To the mixture was added DCM (50 mL), MeOH (5 mL), and water (30 mL). The organic layer was collected, concentrated to dryness, and purified by flash column chromatography to give the title compound as a yellow solid (54 mg, 56% yield). MS (ESI): mass calcd. for C₂₉H₂₉N₅O₃S, 527.6; m/z found, 528.0 [M+H]⁺. 1H NMR (400 MHz, DMSO-d6): δ 8.26 (d, J=5.5 Hz, 1H), 8.09-7.97 (m, 1H), 7.32-7.27 (m, 1H), 7.23-7.19 (m, 2H), 7.01-6.97 (m, 3H), 6.92-6.87 (m, 1H), 5.88 (d, J=5.5 Hz, 1H), 3.95-3.88 (m, 1H), 2.85-2.78 (m, 1H), 2.70-2.61 (m, 1H), 2.28 (s, 3H), 2.19 (s, 3H), 2.01 (s, 3H), 1.94-1.84 (m, 2H), 1.78-1.72 (m, 1H), 1.70-1.63 (m, 1H), 1.53-1.44 (m, 1H), 1.36-1.27 (m, 1H).

Example 291: (S)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide

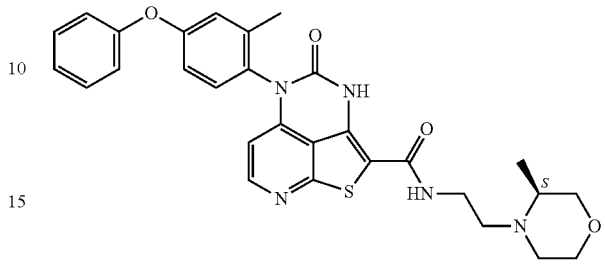

To a solution of 2-[(3S)-3-methylmorpholin-4-yl]ethanamine (260 mg, 1.8 mmol) in DCM/THF (1/1) and triethylamine (312 mg, 2.4 mmol) was added 5-(2-methyl-4-phenoxyphenyl)-4-oxo-4,5-dihydro-3H-1-thia-3,5,8-triazaacenaphthylene-2-carbonyl chloride (Intermediate 32, 261 mg, 0.600 mmol) in DCM/THF(1/1) dropwise, and it was stirred for 2 h at rt. The reaction mixture was concentrated to dryness and purified by flash column chromatography, then preparative TLC to give the title compound as a yellow solid (15 mg, 4.5% yield). MS (ESI): mass calcd. for C₂₉H₂₉N₅O₄S, 543.6; m/z found, 544.0 [M+H]⁺. 1H NMR (400 MHz, CDCl3): δ 8.33 (d, J=5.1 Hz, 1H), 7.44-7.34 (m, 2H), 7.21-7.12 (m, 2H), 7.12-7.05 (m, 2H), 7.01-6.97 (m, 1H), 6.97-6.90 (m, 1H), 6.39-6.31 (m, 1H), 5.99 (d, J=5.1 Hz, 1H), 3.85-3.78 (m, 1H), 3.74-3.63 (m, 2H), 3.61-3.54 (m, 1H), 3.42-3.34 (m, 1H), 3.33-3.26 (m, 1H), 3.02-2.91 (m, 1H), 2.85-2.76 (m, 1H), 2.59-2.48 (m, 1H), 2.43-2.31 (m, 2H), 2.11 (s, 3H), 1.05-0.96 (m, 3H).

Example 292: (R,E)-5-(*R)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide

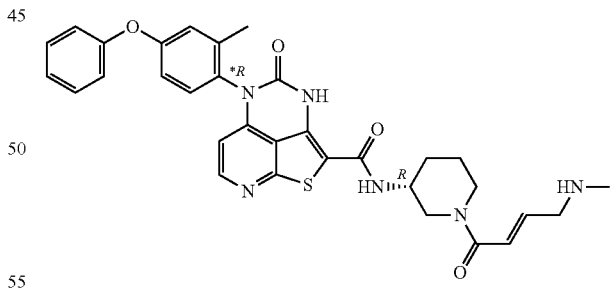

Step A: (R,E)-tert-Butyl methyl(4-(3-(5-(*R)-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate A solution of (R)-5-(*R)-(2-methyl-4-phenoxyphenyl)-4-oxo-N-(piperidin-3-yl)-4,5-dihydro-3H-1-thia-3,5,8-triazaacenaphthylene-2-carboxamide (Example 300, 80 mg, 0.16 mmol), (E)-4-[tert-butoxycarbonyl(methyl)amino]but-2-enoic acid (Intermediate 10, 52 mg, 0.24 mmol), HATU (79 mg, 0.21 mmol), and diisopropylethylamine (52 mg, 0.40 mmol) in DMF (3 mL) was stirred at rt for 2 h. The mixture was purified by HPLC, then by flash column chromatography to give the title compound as a white solid (59 mg, 53% yield). MS (ESI): mass calcd. for $C_{37}H_{40}N_6O_6S$, 696.82; m/z found, 697.3 $[M+H]^+$.

Step B: (R,E)-5-(*R)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide To a round bottom flask were added (R,E)-tert-butyl methyl(4-(3-(5-(*R)-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate (59 mg, 0.085 mmol), concentrated HCl (3 mL), and MeOH (3 mL) and was stirred at rt for 1 h. The mixture was concentrated to dryness and was purified by flash column chromatography to give the title compound as a white solid (27 mg, 49% yield). MS (ESI): mass calcd. for $C_{32}H_{32}N_6O_4S$, 596.7; m/z found, 597.3 $[M+H]^+$. $^1H$ NMR (400 MHz, $CD_3OD$): δ 8.47 (s, 1H), 8.37-8.30 (m, 1H), 7.44-7.37 (m, 2H), 7.34-7.27 (m, 1H), 7.21-7.14 (m, 1H), 7.13-7.04 (m, 3H), 7.01-6.95 (m, 1H), 6.92-6.82 (m, 1H), 6.74-6.60 (m, 1H), 6.12-6.05 (m, 1H), 4.54-3.91 (m, 3H), 3.84-3.75 (m, 2H), 3.25-3.08 (m, 1H), 3.00-2.81 (m, 1H), 2.71 (s, 3H), 2.18-2.02 (m, 4H), 1.94-1.83 (m, 1H), 1.82-1.67 (m, 1H), 1.66-1.53 (m, 1H).

Example 293: (R)-5-(2-Methyl-4-(pyridin-3-yloxy)phenyl)-N-(1-methylpiperidin-3-yl)-4-oxo-4,5-dihydro-3H-1-thia-3,5,8-triazaacenaphthylene-2-carboxamide

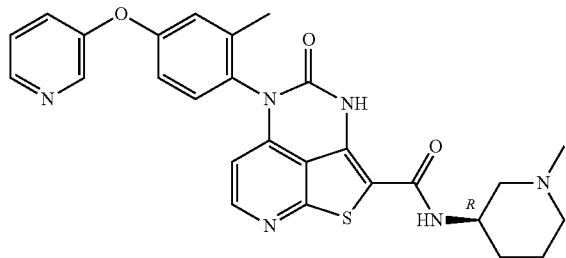

Step A: (R)-5-(2-Methyl-4-(pyridin-3-yloxy)phenyl)-4-oxo-N-(piperidin-3-yl)-4,5-dihydro-3H-1-thia-3,5,8-triazaacenaphthylene-2-carboxamide The title compound was prepared in a manner analogous to Method 1, steps C-H in Example 1, and using 2-methyl-4-(3-pyridyloxy)aniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{24}N_6O_3S$, 500.57; m/z found, 501.1 $[M+H]^+$.

Step B: (R)-5-(2-Methyl-4-(pyridin-3-yloxy)phenyl)-N-(1-methylpiperidin-3-yl)-4-oxo-4,5-dihydro-3H-1-thia-3,5,8-triazaacenaphthylene-2-carboxamide To a solution of (R)-5-(2-methyl-4-(pyridin-3-yloxy)phenyl)-4-oxo-N-(piperidin-3-yl)-4,5-dihydro-3H-1-thia-3,5,8-triazaacenaphthylene-2-carboxamide (100 mg, 0.2 mmol) and formaldehyde (0.3 mL, 37 wt. % in $H_2O$) in MeOH (5 mL) was added $NaBH(OAc)_3$ (127 mg, 0.6 mmol) and was stirred at rt for 1 h, concentrated to dryness, and purified by flash column chromatography to give the title compound as a tan solid (59 mg, 56% yield). MS (ESI): mass calcd. for $C_{27}H_{26}N_6O_3S$, 514.6; m/z found, 515.0 $[M+H]^+$. $^1H$ NMR (400 MHz, $CD_3OD$): δ 8.43-8.38 (m, 1H), 8.38-8.32 (m, 1H), 8.32-8.26 (m, 1H), 7.63-7.54 (m, 1H), 7.53-7.43 (m, 1H), 7.41-7.33 (m, 1H), 7.21-7.12 (m, 1H), 7.11-7.03 (m, 1H), 6.13-597 (m, 1H), 4.21-4.10 (m, 1H), 3.03-2.88 (m, 1H), 2.82-2.65 (m, 1H), 2.36 (s, 3H), 2.29-2.18 (m, 2H), 2.15 (s, 3H), 1.94-1.77 (m, 2H), 1.75-1.63 (m, 1H), 1.57-1.44 (m, 1H).

Example 294: (R)—N-(1-Acryloylpiperidin-3-yl)-5-(3-chlorophenyl)-4-oxo-4,5-dihydro-3H-1-thia-3,5,8-triazaacenaphthylene-2-carboxamide

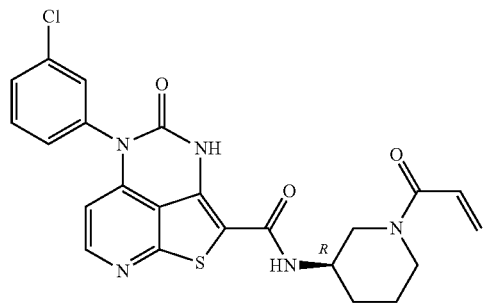

The title compound was prepared in a manner analogous to Method 1, steps C-I in Example 1, and using 3-chloroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{23}H_{20}ClN_5O_3S$, 481.1; m/z found, 482.1 $[M+H]^+$. $^1H$ NMR (400 MHz, DMSO-$d_6$): δ 10.26 (d, J=14.5 Hz, 1H), 8.35 (d, J=5.5 Hz, 1H), 8.14-8.09 (m, 1H), 7.68 (s, 1H), 7.66-7.65 (m, 2H), 7.54-7.45 (m, 1H), 6.90-6.71 (m, 1H), 6.12 (d, J=17.1 Hz, 1H), 6.08 (d, J=5.5 Hz, 1H), 5.70 (d, J=11.1 Hz, 1H), 4.50-4.48 (m, 1H), 3.99 (s, 1H), 3.81 (s, 1H), 3.16-2.95 (m, 1H), 2.81-2.63 (m, 1H), 1.98-1.94 (m, 1H), 1.86-1.59 (m, 2H), 1.44 (s, 1H).

Example 295: (R)-5-(4-(4-Fluorophenoxy)-2-methylphenyl)-N-(1-methylpiperidin-3-yl)-4-oxo-4,5-dihydro-3H-1-thia-3,5,8-triazaacenaphthylene-2-carboxamide

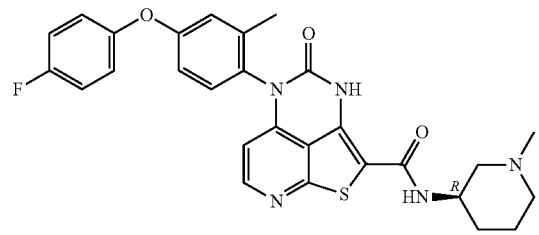

Step A: (R)-5-(4-(4-Fluorophenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 4-fluorophenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(4-Fluorophenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(4-fluorophenoxy)-2-methylphenyl)-4-oxo-N-(piperidin-3-yl)-4,5-dihydro-3H-1-thia-3,5,8-triazaacenaphthylene-2-carboxamide (84 mg, 0.16 mmol) in DCM (5 mL) were added formaldehyde (0.5 mL, 37 wt. % in H$_2$O) and NaBH(OAc)$_3$ (69 mg, 0.33 mmol) and was stirred at rt for 4 hours. To the mixture was added DCM (50 mL), MeOH (5 mL), and water (30 mL). The organic layer was collected, concentrated to dryness, and purified by flash column chromatography to give the title compound as a yellow solid (52 mg, 60% yield). MS (ESI): mass calcd. for C$_{28}$H$_{26}$FN$_5$O$_3$S, 531.6; m/z found, 532.0 [M+H]$^+$. 1H NMR (400 MHz, DMSO-d6): δ 8.26 (d, J=5.4 Hz, 1H), 8.04 (br, 1H), 7.33-7.29 (m, 1H), 7.28-7.22 (m, 2H), 7.18-7.13 (m, 2H), 7.05-7.01 (m, 1H), 6.94-6.90 (m, 1H), 5.88 (d, J=5.5 Hz, 1H), 3.95-3.87 (m, 1H), 2.86-2.78 (m, 1H), 2.70-2.62 (m, 1H), 2.19 (s, 3H), 2.02 (s, 3H), 1.94-1.84 (m, 2H), 1.79-1.72 (m, 1H), 1.70-1.63 (m, 1H), 1.53-1.43 (m, 1H), 1.36-1.26 (m, 1H).

Example 296: (R)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide

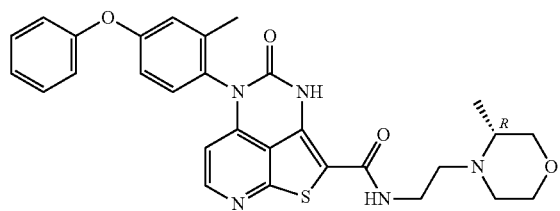

To a solution of 2-[(3R)-3-methylmorpholin-4-yl]ethanamine (260 mg, 1.8 mmol) in DMF (5 mL) and triethylamine (312 mg, 2.40 mmol) was added 5-(2-methyl-4-phenoxyphenyl)-4-oxo-4,5-dihydro-3H-1-thia-3,5,8-triazaacenaphthylene-2-carbonyl chloride (Intermediate 32, 261 mg, 0.600 mmol) in DCM/THF(1/1) was added dropwise. The reaction was stirred for 2 h at rt, concentrated to dryness, and purified by flash column chromatography, then preparative TLC to give the title compound as a yellow solid (30 mg, 9% yield). MS (ESI): mass calcd. for C$_{29}$H$_{29}$N$_5$O$_4$S, 543.6; m/z found, 544.0 [M+H]$^+$. 1H NMR (400 MHz, CDCl3): δ 8.33 (d, J=5.5 Hz, 1H), 7.42-7.34 (m, 2H), 7.21-7.13 (m, 2H), 7.12-7.06 (m, 2H), 7.01-6.98 (m, 1H), 6.97-6.91 (m, 1H), 6.38-6.31 (m, 1H), 5.99 (d, J=5.5 Hz, 1H), 3.84-3.77 (m, 1H), 3.75-3.70 (m, 1H), 3.69-3.62 (m, 1H), 3.62-3.54 (m, 1H), 3.42-3.32 (m, 1H), 3.32-3.26 (m, 1H), 3.02-2.90 (m, 1H), 2.84-2.76 (m, 1H), 2.59-2.47 (m, 1H), 2.43-2.32 (m, 2H), 2.12 (s, 3H), 1.04-0.97 (m, 3H).

Example 297: (R)-5-(4-(Cyclopentyloxy)-2-methylphenyl)-N-(1-methylpiperidin-3-yl)-4-oxo-4,5-dihydro-3H-1-thia-3,5,8-triazaacenaphthylene-2-carboxamide

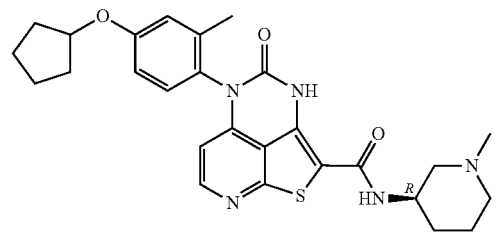

To a solution of (R)-5-(4-(cyclopentyloxy)-2-methylphenyl)-4-oxo-N-(piperidin-3-yl)-4,5-dihydro-3H-1-thia-3,5,8-triazaacenaphthylene-2-carboxamide (Example 919, 80 mg, 0.16 mmol) in DCM (2 mL) were added formaldehyde (0.5 mL, 37 wt. % in H$_2$O) and NaBH(OAc)$_3$ (200 mg) and was reacted at rt overnight. The reaction was quenched with H$_2$O (10 mL), extracted with DCM, dried over anhydrous Na$_2$SO$_4$, filtered, and concentrated to dryness. The residue was purified by flash column chromatography to give the title compound as a yellow solid (48 mg, 58% yield). MS (ESI): mass calcd. for C$_{27}$H$_{31}$N$_5$O$_3$S, 505.6; m/z found, 506.2 [M+H]$^+$. $^1$H NMR (400 MHz, CD$_3$OD): δ 8.35-8.27 (m, 1H), 7.24-7.15 (m, 1H), 6.97-6.91 (m, 1H), 6.90-6.86 (m, 1H), 6.08-6.00 (m, 1H), 4.89-4.85 (m, 1H), 4.39-4.18 (m, 1H), 3.65-3.50 (m, 1H), 3.48-3.33 (m, 1H), 3.04-2.90 (m, 2H), 2.88-2.86 (m, 3H), 2.09 (s, 3H), 2.08-1.99 (m, 2H), 199-1.91 (m, 2H), 1.89-1.83 (m, 2H), 1.82-1.69 (m, 4H), 1.68-1.59 (m, 2H).

Example 298: 5-(2-Methyl-4-phenoxyphenyl)-N-(2-(1-methylpyrrolidin-2-yl)ethyl)-4-oxo-4,5-dihydro-3H-1-thia-3,5,8-triazaacenaphthylene-2-carboxamide

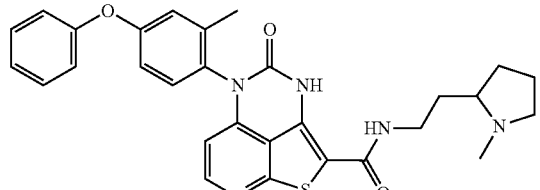

The title compound was prepared in a manner analogous to Method 1, steps A-G in Example 1, and using 2-(1-methylpyrrolidin-2-yl)ethanamine in place of tert-butyl (3R, 5R)-3-amino-5-fluoropiperidine-1-carboxylate (Intermediate 1) in step G. MS (ESI): mass calcd. for C$_{29}$H$_{29}$N$_5$O$_3$S, 527.6; m/z found, 528.0 [M+H]$^+$. 1H NMR (500 MHz, DMSO-d6) δ 8.54-8.35 (m, 1H), 8.35-8.17 (m, 1H), 7.56-6.88 (m, 9H), 6.01-5.79 (m, 1H), 3.13-2.96 (m, 1H), 2.35-1.50 (m, 16H).

Example 299: (R)—N-(1-Acryloylpyrrolidin-3-yl)-5-(4-methoxy-2-methylphenyl)-4-oxo-4,5-dihydro-3H-1-thia-3,5,8-triazaacenaphthylene-2-carboxamide

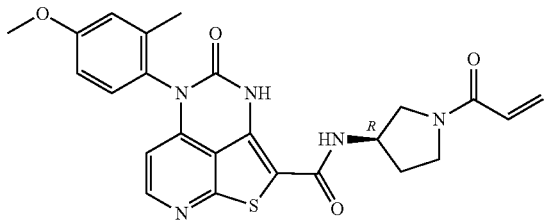

Step A: (R)-5-(4-Methoxy-2-methylphenyl)-4-oxo-N-(pyrrolidin-3-yl)-4,5-dihydro-3H-1-thia-3,5,8-triazaacenaphthylene-2-carboxamide The title compound was prepared in a manner analogous to Method 1, steps B-I in Example 1, and using 4-methoxy-2-methyl-1-nitrobenzene in place of 2-methyl-1-nitro-4-phenoxybenzene in step B, and using tert-butyl (3R)-3-aminopyrrolidine-1-carboxylate in place of tert-butyl (3R,5R)-3-amino-5-fluoropiperidine-1-carboxylate (Intermediate 1) in step G.

Step B: (R)—N-(1-Acryloylpyrrolidin-3-yl)-5-(4-methoxy-2-methylphenyl)-4-oxo-4,5-dihydro-3H-1-thia-3,5,8-triazaacenaphthylene-2-carboxamide To a solution of triethylamine (0.105 mL, 0.756 mmol) in THF (5 mL) was added (R)-5-(4-methoxy-2-methylphenyl)-4-oxo-N-(pyrrolidin-3-yl)-4,5-dihydro-3H-1-thia-3,5,8-triazaacenaphthylene-2-carboxamide (160 mg, 0.38 mmol). After stirring at rt for 5 min, acrylic acid (30 mg, 0.42 mmol), EDCI (87 mg, 0.45 mmol), and HOBt (61 mg, 0.45 mmol) were added. The reaction mixture was stirred at rt for 30 min, concentrated to dryness, and the residue was purified by flash column chromatography to give the title compound as a yellow solid (27 mg, 14% yield). MS (ESI): mass calcd. for $C_{24}H_{23}N_5O_4S$, 477.5; m/z found, 478.2 [M+H]+. 1H NMR (400 MHz, DMSO-$d_6$ and CD$_3$OD): δ 8.24 (d, J=5.5, 1H), 7.21-7.11 (m, 1H), 6.98-6.91 (m, 1H), 6.91-6.84 (m, 1H), 6.60-6.43 (m, 1H), 6.20-6.11 (m, 1H), 5.90 (d, J=5.5, 1H), 5.69-5.62 (m, 1H), 4.60-4.45 (m, 6.2, 1H), 3.93-3.83 (m, 1H), 3.77 (s, 3H), 3.75-3.67 (m, 1H), 3.65-3.56 (m, 1H), 3.45-3.39 (m, 1H), 2.26-2.08 (m, 1H), 2.08-1.91 (m, 4H).

Example 300: (R)-5-(*R)-(2-Methyl-4-phenoxyphenl)-4-oxo-N-(piperidin-3-yl)-4,5-dihydro-3H-1-thia-3,5,8-triazaacenaphthylene-2-carboxamide

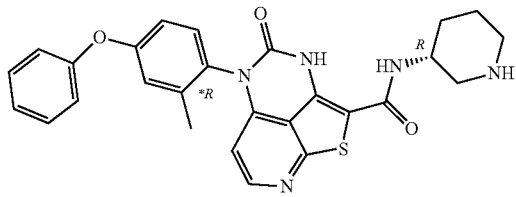

The title compound was prepared in a manner analogous to Method 1, steps G-H in Example 1, and using 5-(*R)-(2-methyl-4-phenoxyphenyl)-4-oxo-4,5-dihydro-3H-1-thia-3,5,8-triazaacenaphthylene-2-carboxylic acid (Intermediate 63) and tert-butyl (3R)-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 500.2 [M+H]+. 1H NMR (400 MHz, CD$_3$OD): δ 8.21 (d, J=5.5 Hz, 1H), 7.44-7.35 (m, 2H), 7.28-7.21 (m, 1H), 7.19-7.13 (m, 1H), 7.13-7.03 (m, 3H), 7.00-6.92 (m, 1H), 5.95 (d, J=5.6 Hz, 1H), 4.24-4.07 (m, 1H), 3.28-3.23 (m, 1H), 3.13-3.03 (m, 1H), 2.91-2.73 (m, 2H), 2.11 (s, 3H), 2.07-1.98 (m, 1H), 1.96-1.88 (m, 1H), 1.80-1.64 (m, 2H).

Example 301: (R)—N-(1-Acryloylpyrrolidin-3-yl)-5-(2-fluorophenyl)-4-oxo-4,5-dihydro-3H-1-thia-3,5,8-triazaacenaphthylene-2-carboxamide

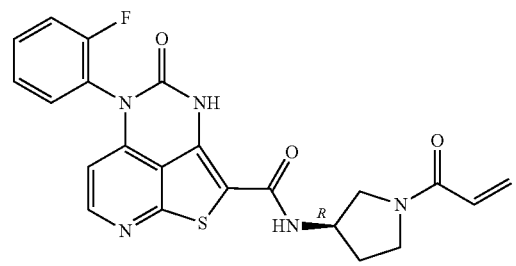

The title compound was prepared in a manner analogous to Method 1, steps C-I in Example 1, and using 2-fluoroaniline in place of 2-methyl-4-phenoxyaniline in step C, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{22}H_{18}FN_5O_3S$, 451.5; m/z found, 452.0 [M+H]+. 1H NMR (400 MHz, DMSO-$d_6$): δ 10.38 (s, 1H), 8.50-8.34 (m, 1H), 8.32 (d, J=5.4 Hz, 1H), 7.70-7.56 (m, 2H), 7.55-7.35 (m, 2H), 6.69-6.42 (m, 1H), 6.20-6.08 (m, 1H), 6.05 (d, J=5.2 Hz, 1H), 5.72-5.57 (m, 1H), 4.59-4.33 (m, 1H), 3.88-3.59 (m, 2H), 3.57-3.39 (m, 2H), 2.23-1.91 (m, 2H).

Example 302: (R)-5-(4-(2,4-Difluorophenoxy)-2-methylphenyl)-N-(1-methylpiperidin-3-yl)-4-oxo-4,5-dihydro-3H-1-thia-3,5,8-triazaacenaphthylene-2-carboxamide

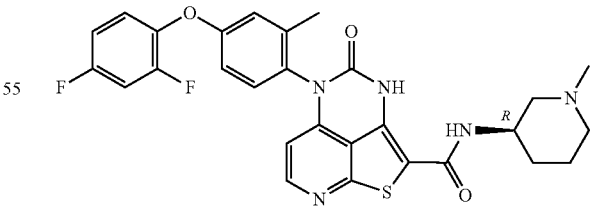

Step A: (R)-5-(4-(2,4-difluorophenoxy)-2-methylphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 2,4- difluorophenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(2,4-Difluorophenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2,4-difluorophenoxy)-2-methylphenyl)-4-oxo-N-(piperidin-3-yl)-4,5-dihydro-3H-1-thia-3,5,8-triazaacenaphthylene-2-carboxamide (210 mg, 0.39 mmol) and formaldehyde (0.5 mL, 37 wt. % in $H_2O$) in MeOH (10 mL) was added $NaBH(OAc)_3$ (249 mg, 1.18 mmol) and was stirred at rt for 1 h, concentrated to dryness, and purified by flash column chromatography to give the title compound as a white solid 190 mg, 87% yield). MS (ESI): mass calcd. for $C_{28}H_{25}F_2N_5O_3S$, 549.6; m/z found, 549.9 $[M+H]^+$. $^1H$ NMR (400 MHz, $CD_3OD$): δ 8.33-8.25 (m, 1H), 7.37-7.21 (m, 2H), 7.21-7.10 (m, 1H), 7.08-6.97 (m, 2H), 6.96-6.87 (m, 1H), 6.10-5.96 (m, 1H), 4.28-4.15 (m, 1H), 3.28-3.17 (m, 1H), 3.07-2.94 (m, 1H), 2.66-2.48 (m, 5H), 2.11 (s, 3H), 2.00-1.88 (m, 2H), 1.83-1.70 (m, 1H), 1.65-1.52 (m, 1H).

Example 303: (R)-5-(5-Fluoro-2-methyl-4-phenoxyphenl)-N-(1-methylpiperidin-3-yl)-4-oxo-4,5-dihydro-3H-1-thia-3,5,8-triazaacenaphthylene-2-carboxamide

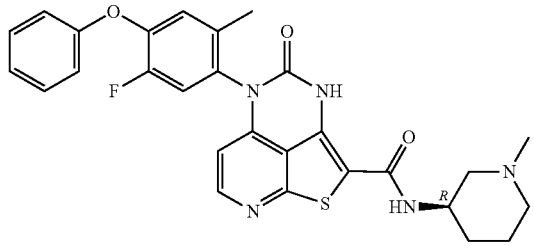

Step A: (R)-5-(5-Fluoro-2-methyl-4-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using 1-bromo-2-fluoro-5-methyl-4-nitrobenzene (Intermediate 45) in place of 5-fluoro-2-nitrotoluene in step A, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{27}H_{24}FN_5O_3S$, 517.58; m/z found, 518.0 $[M+H]^+$.

Step B: (R)-5-(5-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide To a solution of (R)-5-(5-fluoro-2-methyl-4-phenoxyphenyl)-4-oxo-N-(piperidin-3-yl)-4,5-dihydro-3H-1-thia-3,5,8-triazaacenaphthylene-2-carboxamide (115 mg, 0.222 mmol) in DCM (5 mL) was added formaldehyde (0.5 mL, 37 wt. % in $H_2O$) and $NaBH(OAc)_3$ (94 mg, 0.44 mmol) and was stirred at rt for 4 hours. To the mixture was added DCM (50 mL), MeOH (5 mL), and water (30 mL). The organic layer was collected, concentrated to dryness, and purified by flash column chromatography to give the title compound as a yellow solid (68 mg, 57% yield). MS (ESI): mass calcd. for $C_{28}H_{26}FN_5O_3S$, 531.6; m/z found, 532.0 $[M+H]^+$. 1H NMR (400 MHz, DMSO-d6): δ 8.34-8.22 (m, 1H), 8.15 (br, 1H), 7.55-7.45 (m, 1H), 7.44-7.35 (m, 2H), 7.24-7.18 (m, 1H), 7.18-7.12 (m, 1H), 7.12-7.01 (m, 2H), 6.06-5.93 (m, 1H), 3.98-3.85 (m, 1H), 2.87-2.78 (m, 1H), 2.72-2.59 (m, 1H), 2.20 (s, 3H), 1.99 (s, 3H), 1.95-1.87 (m, 2H), 1.80-1.72 (m, 1H), 1.70-1.64 (m, 1H), 1.55-1.45 (m, 1H), 1.36-1.26 (m, 1H).

Example 304: (R)—N-(1-Acryloylpyrrolidin-3-yl)-5-(2,4-dimethylphenyl)-4-oxo-4,5-dihydro-3H-1-thia-3,5,8-triazaacenaphthylene-2-carboxamide

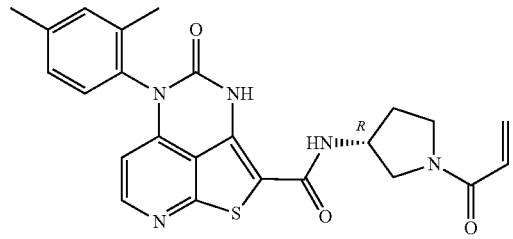

(R)—N-(1-Acryloylpyrrolidin-3-yl)-5-(2,4-dimethylphenyl)-4-oxo-4,5-dihydro-3H-1-thia-3,5,8-triazaacenaphthylene-2-carboxamide The title compound was prepared in a manner analogous to Method 1, steps C-G in Example 1, and using 2,4-dimethylaniline in place of 2-methyl-4-phenoxyaniline in step C, and using 1-[(3R)-3-Aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{24}H_{23}N_5O_3S$, 461.5; m/z found, 462.2 $[M+H]^+$. $^1H$ NMR (400 MHz, DMSO-$d_6$): δ 10.29-10.12 (m, 1H), 8.48-8.34 (m, 1H), 8.31-8.19 (m, 1H), 7.28-7.25 (m, 1H), 7.23-7.13 (m, 2H), 6.66-6.49 (m, 1H), 6.19-6.07 (m, 1H), 5.87-5.77 (m, 1H), 5.71-5.60 (m, 1H), 4.57-4.35 (m, 1H), 3.90-3.40 (m, 4H), 2.34 (s, 3H), 2.20-2.08 (m, 1H), 2.03 (s, 3H), 2.00-1.89 (m, 1H).

Example 305: (R)-5-(5-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide

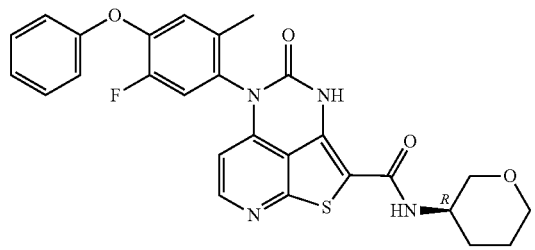

The title compound was prepared in a manner analogous to Method 1, steps A-G in Example 1, and using 1-bromo-2-fluoro-5-methyl-4-nitrobenzene (Intermediate 45) in place of 5-fluoro-2-nitrotoluene in step A, and using (3R)-tetrahydropyran-3-amine in place of tert-butyl (3R,5R)-3-amino-5-fluoropiperidine-1-carboxylate (Intermediate 1) in step G. MS (ESI): mass calcd. for $C_{27}H_{23}FN_4O_4S$, 518.6; m/z found, 519.0 [M+H]$^+$. $^1$H NMR (400 MHz, DMSO-d$_6$): δ 10.25 (br, 1H), 8.36-8.29 (m, 1H), 8.01 (br, 1H), 7.59-7.52 (m, 1H), 7.44-7.40 (m, 2H), 7.23 (d, J=8.8 Hz, 1H), 7.19-7.14 (m, 1H), 7.11-7.07 (m, 2H), 6.13-6.03 (m, 1H), 3.93-3.85 (m, 1H), 3.82-3.73 (m, 2H), 3.27-3.24 (m, 1H), 3.21-3.15 (m, 1H), 2.02 (s, 3H), 1.93-1.88 (m, 1H), 1.71-1.55 (m, 3H).

Example 306: (R)-5-(2-Methyl-4-(pyridin-2-yloxy)phenyl)-N-(1-methylpiperidin-3-yl)-4-oxo-4,5-dihydro-3H-1-thia-3,5,8-triazaacenaphthylene-2-carboxamide

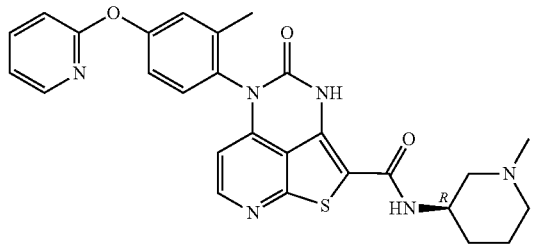

Step A: (R)-5-(2-Methyl-4-(pyridin-2-yloxy)phenyl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H in Example 1, and using pyridin-2-ol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(2-Methyl-4-(pyridin-2-yloxy)phenyl)-N-(1-methylpiperidin-3-yl)-4-oxo-4,5-dihydro-3H-1-thia-3,5,8-triazaacenaphthylene-2-carboxamide To a solution of (R)-5-(2-methyl-4-(pyridin-2-yloxy)phenyl)-4-oxo-N-(piperidin-3-yl)-4,5-dihydro-3H-1-thia-3,5,8-triazaacenaphthylene-2-carboxamide (150 mg, 0.30 mmol) in MeOH (5 mL) was added formaldehyde (1 mL, 37 wt. % in H$_2$O) slowly and stirred for 10 min, then NaBH(OAc)$_3$ (127 mg, 0.600 mmol) was added slowly and the mixture was stirred for 2 h, then NaOH (2 mL) was added and the mixture was purified by flash column chromatography, then preparative TLC to give the title compound as a yellow solid (81 mg, 52% yield). MS (ESI): mass calcd. for $C_{27}H_{26}N_6O_3S$, 514.6; m/z found, 515.1 [M+H]$^+$. 1H NMR (400 MHz, CDCl3): δ 8.35 (d, J=5.4 Hz, 1H), 8.29-8.18 (m, 1H), 7.80-7.67 (m, 1H), 7.25-7.21 (m, 1H), 7.18 (s, 1H), 7.16-7.11 (m, 1H), 7.09-7.03 (m, 1H), 7.00-6.94 (m, 1H), 6.36-6.15 (m, 1H), 6.07 (d, J=5.4 Hz, 1H), 4.31-4.17 (m, 1H), 2.65-2.37 (m, 3H), 2.28 (s, 3H), 2.22-2.10 (m, 4H), 1.81-1.58 (m, 4H).

Example 307: (R)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide

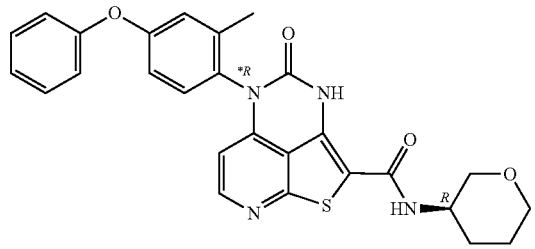

The title compound was prepared in a manner analogous to Method 1, steps A-G (including Chiral Resolution Method A after step F to obtain the *R atropisomer) in Example 1, and using (3R)-tetrahydropyran-3-amine in place of tert-butyl (3R,5R)-3-amino-5-fluoropiperidine-1-carboxylate (Intermediate 1) in step G. MS (ESI): mass calcd. for $C_{27}H_{24}N_4O_4S$, 500.6; m/z found, 501.3 [M+H]$^+$. $^1$H NMR (400 MHz, CD$_3$OD and DMSO-d$_6$): δ 8.42 (d, J=5.5 Hz, 1H), 7.56-7.47 (m, 2H), 7.44-7.34 (m, 1H), 7.32-7.25 (m, 1H), 7.23-7.13 (m, 3H), 7.07-7.01 (m, 1H), 6.11 (d, J=5.5 Hz, 1H), 4.12-4.00 (m, 1H), 3.99-3.83 (m, 2H), 3.48-3.37 (m, 1H), 3.36-3.31 (m, 1H), 2.18 (s, 3H), 2.10-1.97 (m, 1H), 1.86-1.66 (m, 3H).

Example 308: (S)-5-(5-Fluoro-2-methyl-4-phenoxyphenl)-4-oxo-N-(tetrahydro-2H-pyran-3-yl)-4,5-dihydro-3H-1-thia-3,5,8-triazaacenaphthylene-2-carboxamide

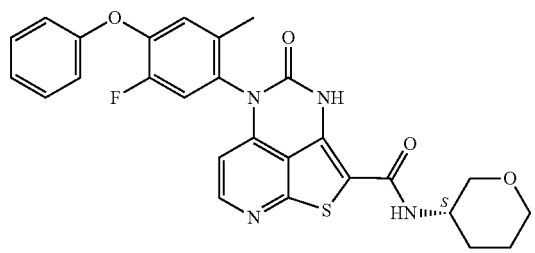

The title compound was prepared in a manner analogous to Method 1, steps A-G in Example 1, and using 1-bromo-2-fluoro-5-methyl-4-nitrobenzene (Intermediate 45) in place of 5-fluoro-2-nitrotoluene in step A, and using (3S)-tetrahydropyran-3-amine in place of tert-butyl (3R,5R)-3-amino-5-fluoropiperidine-1-carboxylate (Intermediate 1) in step G. MS (ESI): mass calcd. for $C_{27}H_{23}FN_4O_4S$, 518.6; m/z found, 519.0 [M+H]$^+$. $^1$H NMR (400 MHz, DMSO-d$_6$): δ 10.25 (br, 1H), 8.34 (d, J=5.4 Hz, 1H), 7.97 (br, 1H), 7.60-7.52 (m, 1H), 7.44-7.39 (m, 2H), 7.23 (d, J=8.8 Hz, 1H), 7.19-7.14 (m, 1H), 7.11-7.07 (m, 2H), 6.09 (d, J=5.5 Hz, 1H), 3.94-3.85 (m, 1H), 3.82-3.74 (m, 2H), 3.27-3.23 (m, 1H), 3.21-3.15 (m, 1H), 2.02 (s, 3H), 1.94-1.88 (m, 1H), 1.70-1.54 (m, 3H).

Example 309: (S)—N-(1-Benzyl-2-oxoazepan-3-yl)-5-(2-methyl-4-phenoxyphenyl)-4-oxo-4,5-dihydro-3H-1-thia-3,5,8-triazaacenaphthylene-2-carboxamide

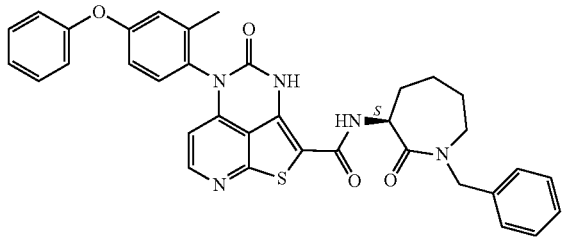

The title compound was prepared in a manner analogous to Method 1, steps A-G in Example 1, and using (3S)-3-amino-1-benzyl-azepan-2-one in place of tert-butyl (3R,5R)-3-amino-5-fluoropiperidine-1-carboxylate (Intermediate 1) in step G. MS (ESI): mass calcd. for $C_{35}H_{31}N_5O_4S$, 617.7; m/z found, 618.0 [M+H]⁺. 1H NMR (400 MHz, Methanol-d4) δ 8.31 (s, 1H), 7.51-7.37 (m, 2H), 7.37-7.26 (m, 6H), 7.23-7.14 (m, 1H), 7.14-7.03 (m, 3H), 7.03-6.95 (m, 1H), 6.09-5.99 (m, 1H), 4.75-4.70 (m, 1H), 4.62-4.57 (m, 1H), 3.77-3.54 (m, 1H), 3.03-2.83 (m, 2H), 2.13 (s, 3H), 1.99-1.87 (m, 2H), 1.79-1.65 (m, 3H), 1.36-1.18 (m, 1H).

Example 310: (S)-5-(2-Methyl-4-phenoxyphenyl)-4-oxo-N-(piperidin-2-ylmethyl)-4,5-dihydro-3H-1-thia-3,5,8-triazaacenaphthylene-2-carboxamide

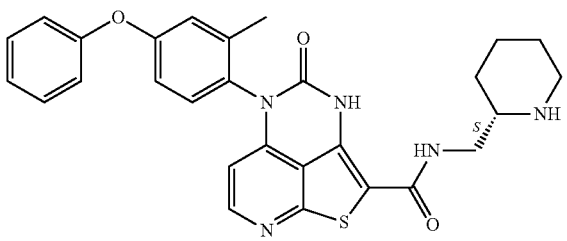

The title compound was prepared in a manner analogous to Method 1, steps A-H in Example 1, and using (S)-2-aminomethyl-1-N-Boc-piperidine in place of tert-butyl (3R,5R)-3-amino-5-fluoropiperidine-1-carboxylate (Intermediate 1) in step G. MS (ESI): mass calcd. for $C_{28}H_{27}N_5O_3S$, 513.62; m/z found, 514.0 [M+H]⁺. ¹H NMR (400 MHz, CDCl₃): δ 8.45-8.22 (m, 1H), 7.48-7.36 (m, 2H), 7.25-6.91 (m, 6H), 6.40-6.15 (m, 1H), 6.09-5.82 (m, 1H), 3.60-2.53 (m, 7H), 2.23-2.07 (m, 3H), 1.92-1.15 (m, 6H).

Example 311: (R)—N-(1-Acryloylpyrrolidin-3-yl)-4-oxo-5-(6-phenoxypyridazin-3-yl)-4,5-dihydro-3H-1-thia-3,5,8-triazaacenaphthylene-2-carboxamide

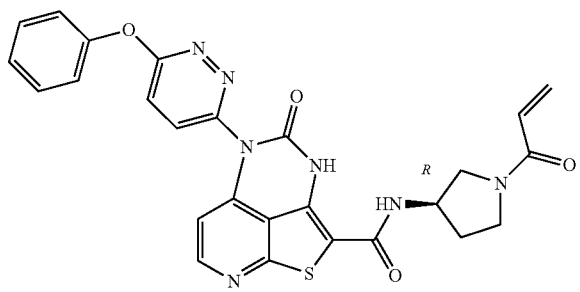

Step A: 6-Phenoxypyridazin-3-amine

A solution of 6-chloropyridazin-3-amine (1.295 g, 10.00 mmol), phenol (3.764 g, 40.00 mmol) and NaOH (1.6 g, 40 mmol) in water (10 mL) was stirred at 190° C. in a sealed tube for 16 hours. The mixture was dispersed between EtOAc and water. The organic layer was collected, concentrated to dryness, and purified by flash column chromatography to give the title compound (0.5 g, 27% yield). MS (ESI): mass calcd. for $C_{10}H_9N_3O$, 187.20; m/z found, 188.0 [M+H]⁺.

Step B: (R)—N-(1-acryloylpyrrolidin-3-yl)-4-oxo-5-(6-phenoxypyridazin-3-yl)-4,5-dihydro-3H-1-thia-3,5,8-triazaacenaphthylene-2-carboxamide The title compound was prepared in a manner analogous to Method 1, steps C-G in Example 1, and using 6-phenoxy-pyridazin-3-amine in place of 2-methyl-4-phenoxyaniline in step C, and using 1-[(3R)-3-aminopyrrolidin-1-yl]prop-2-en-1-one (intermediate 5) in place of tert-butyl (3R,5R)-3-amino-5-fluoropiperidine-1-carboxylate (Intermediate 1) in step G. MS (ESI): mass calcd. for $C_{26}H_{21}N_7O_4S$, 527.6; m/z found, 528.3 [M+H]⁺. ¹H NMR (400 MHz, CD₃OD): δ 8.24-8.18 (m, 1H), 7.92-7.86 (m, 1H), 7.59 (d, J=9.2 Hz, 1H), 7.51-7.44 (m, 2H), 7.32-7.24 (m, 3H), 6.67-6.54 (m, 1H), 6.30-6.23 (m, 2H), 5.77-5.72 (m, 1H), 4.65-4.57 (m, 1H), 3.90-3.83 (m, 1H), 3.76-3.69 (m, 1H), 3.65-3.50 (m, 2H), 2.36-2.25 (m, 1H), 2.22-2.12 (m, 1H).

Example 312: N-((3R,5S)-5-Methoxy-1-methylpiperidin-3-yl)-5-(2-methyl-4-phenoxyphenyl)-4-oxo-4,5-dihydro-3H-1-thia-3,5,8-triazaacenaphthylene-2-carboxamide

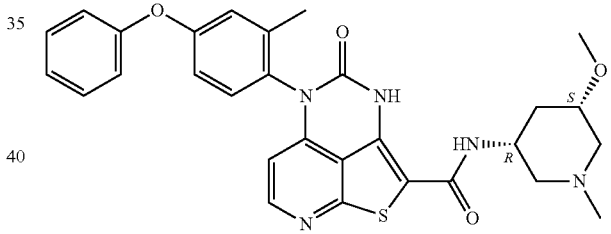

Step A: N-((3R,5S)-5-Methoxypiperidin-3-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-H in Example 1, and using tert-butyl (3R,5S)-3-amino-5-methoxypiperidine-1-carboxylate (Intermediate 29) in place of tert-butyl (3R,5R)-3-amino-5-fluoropiperidine-1-carboxylate (Intermediate 1) in step G. MS (ESI): mass calcd. for $C_{28}H_{27}N_5O_4S$, 529.61; m/z found, 530.2 [M+H]⁺. ¹H NMR (400 MHz, CD₃OD): δ 8.38-8.31 (m, 1H), 7.45-7.36 (m, 2H), 7.33-7.26 (m, 1H), 7.22-7.12 (m, 1H), 7.12-7.04 (m, 3H), 7.02-6.93 (m, 1H), 6.14-6.05 (m, 1H), 4.48-4.38 (m, 1H), 3.82-3.72 (m, 1H), 3.52 (s, 3H), 3.40-3.31 (m, 2H), 3.28-3.19 (m, 2H), 2.27-2.17 (m, 1H), 2.16-2.08 (m, 3H), 2.07-2.00 (m, 1H).

Step B: N-((3R,5S)-5-Methoxy-1-methylpiperidin-3-yl)-5-(2-methyl-4-phenoxyphenyl)-4-oxo-4,5-dihydro-3H-1-thia-3,5,8-triazaacenaphthylene-2-carboxamide To a solution of N-((3R,5S)-5-methoxypiperidin-3-yl)-5-(2-methyl-4-phenoxyphenyl)-4-oxo-4,5-dihydro-3H-1-thia- 3,5,8-triazaacenaphthylene-2-carboxamide (50 mg, 0.09 mmol) in DCM (5 mL) were added formaldehyde (1 mL, 37 wt. % in $H_2O$) and $NaBH(OAc)_3$ (40 mg, 0.19 mmol) and was reacted at rt for 30 min. The reaction was quenched by the addition of $H_2O$ (10 mL), extracted with DCM, dried over anhydrous $Na_2SO_4$, filtered, and concentrated to dryness. The residue was purified by flash column chromatography to give the title compound as a yellow solid (40 mg, 82%). MS (ESI): mass calcd. for $C_{29}H_{29}N_5O_4S$, 543.6; m/z found, 544.2 [M+H]$^+$. $^1H$ NMR (400 MHz, $CD_3OD$): δ 8.37-8.30 (m, 1H), 7.45-7.37 (m, 2H), 7.33-7.26 (m, 1H), 7.21-7.14 (m, 1H), 7.11-7.02 (m, 3H), 7.00-6.92 (m, 1H), 6.12-6.05 (m, 1H), 4.38-4.26 (m, 1H), 3.71-3.58 (m, 1H), 3.46 (s, 3H), 3.01-2.62 (m, 4H), 2.53 (s, 3H), 2.18-2.08 (m, 3H), 2.07-2.00 (m, 1H), 1.86-1.72 (m, 1H).

Example 313: (R,EZ)—N-(1-(3-Cyclopropyl-2-(trifluoromethyl)acryloyl)piperidin-3-yl)-5-(2-methyl-4-phenoxyphenyl)-4-oxo-4,5-dihydro-3H-1-thia-3,5,8-triazaacenaphthylene-2-carboxamide

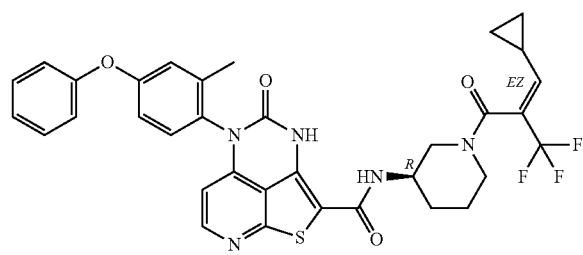

Step A:
(EZ)-3-Cyclopropyl-2-(trifluoromethyl)prop-2-enoic Acid

To a round bottom flask were added 3,3,3-trifluoropropanoic acid (500 mg, 3.9 mmol), cyclopropanecarbaldehyde (274 mg, 3.91 mmol), piperidine (33 mg, 0.39 mmol), and pyridine (8 mL) and was stirred at 100° C. for 2 h under $N_2$. The mixture was purified by HPLC to give the title compound as a brown solid (53 mg, 7.5% yield). MS (ESI): mass calcd. for $C_7H_7F_3O_2$, 180.12; m/z found, 180.1 [M+H]$^+$.

Step B: (R,EZ)—N-(1-(3-Cyclopropyl-2-(trifluoromethyl)acryloyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), (EZ)-3-cyclopropyl-2-(trifluoromethyl)prop-2-enoic acid (53 mg, 0.29 mmol), HATU (148 mg, 0.390 mmol), and diisopropylethylamine (77 mg, 0.60 mmol) in DMF (5 mL) was stirred at rt for 2 h. The mixture was purified by HPLC, then by preparative TLC to give the title compound as a white solid (15 mg, 8.2% yield), a mixture of two isomer (16.81% and 83.19%). MS (ESI): mass calcd. for $C_{34}H_{30}F_3N_5O_4S$, 661.7; m/z found, 662.0 [M+H]$^+$. $^1H$ NMR (400 MHz, $CD_3OD$): δ 8.40-8.30 (m, 1H), 7.48-7.37 (m, 2H), 7.36-7.28 (m, 1H), 7.23-7.15 (m, 1H), 7.14-7.04 (m, 3H), 7.03-6.94 (m, 1H), 6.15-6.03 (m, 1H), 5.94-5.07 (m, 1H), 4.56-4.21 (m, 1H), 4.10-3.77 (m, 2H), 3.24-2.89 (m, 2H), 2.13 (s, 3H), 2.12-2.03 (m, 1H), 1.98-1.83 (m, 2H), 1.82-1.51 (m, 2H), 1.14-0.99 (m, 2H), 0.95-0.63 (m, 2H).

Example 314: (R)—N-(1-Acryloylpyrrolidin-3-yl)-4-oxo-5-(o-tolyl)-4,5-dihydro-3H-1-thia-3,5,8-triazaacenaphthylene-2-carboxamide

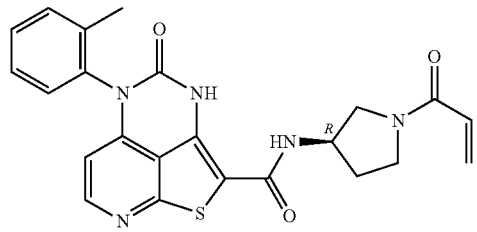

The title compound was prepared in a manner analogous to Method 1, steps C-I in Example 1, and using 2-methylaniline in place of 2-methyl-4-phenoxyaniline in step C, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{23}H_{21}N_5O_3S$, 447.5; m/z found, 448.1 [M+H]$^+$. $^1H$ NMR (400 MHz, DMSO-$d_6$ and $CD_3OD$): δ 8.26 (d, J=5.5, 1H), 7.46-7.26 (m, 4H), 6.63-6.47 (m, 1H), 6.22-6.11 (m, 1H), 5.86 (d, J=5.5, 1H), 5.69-5.57 (m, 1H), 4.61-4.44 (m, 1H), 3.91-3.40 (m, 4H), 2.25-2.10 (m, 1H), 2.08 (s, 3H), 2.06-1.95 (m, 1H).

Example 315: 5-(2-Methyl-4-phenoxyphenyl)-N-(2-morpholino-2-oxoethyl)-4-oxo-4,5-dihydro-3H-1-thia-3,5,8-triazaacenaphthylene-2-carboxamide

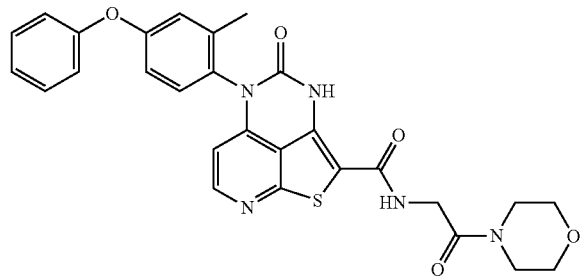 [SMILES: Cc1cc(Oc2ccccc2)ccc1N1C(=O)Nc2c(C(=O)NCC(=O)N3CCOCC3)sc3nccc1c23]

Step A: Methyl 2-(5-(2-methyl-4-phenoxyphenyl)-4-oxo-4,5-dihydro-3H-1-thia-3,5,8-triazaacenaphthylene-2-carboxamido)acetate The title compound was prepared using analogous conditions described in Method 1, steps A-G in Example 1, and using methyl 2-aminoacetate in place of tert-butyl (3R,5R)-3-amino-5-fluoropiperidine-1-carboxylate (Intermediate 1) in step G.

Step B: 2-(5-(2-Methyl-4-phenoxyphenyl)-4-oxo-4,5-dihydro-3H-1-thia-3,5,8-triazaacenaphthylene-2-carboxamido)acetic Acid A solution of methyl 2-(5-(2-methyl-4-phenoxyphenyl)-4-oxo-4,5-dihydro-3H-1-thia-3,5,8-triazaacenaphthylene-2- carboxamido)acetate (1017 mg, 2.082 mmol) and NaOH (250 mg, 6.25 mmol) in MeOH/water (5 mL/5 mL) was stirred at reflux for 4 hours. The reaction was concentrated under vacuo to half volume and the pH was adjusted to pH=6 with AcOH. The precipitate was collected by filtration and dried under vacuo to give the title compound (949 mg), which was used in the next step without further purification.

Step C: 5-(2-Methyl-4-phenoxyphenyl)-N-(2-morpholino-2-oxoethyl)-4-oxo-4,5-dihydro-3H-1-thia-3,5,8-triazaacenaphthylene-2-carboxamide To a solution of 2-(5-(2-methyl-4-phenoxyphenyl)-4-oxo-4,5-dihydro-3H-1-thia-3,5,8-triazaacenaphthylene-2-carboxamido)acetic acid (150 mg, 0.32 mmol) and morpholine (42 mg, 0.48 mmol) in DMF (3 mL) were added HATU (240 mg, 0.63 mmol) and triethylamine (96 mg, 0.95 mmol) and was stirred at rt for 16 hours. The mixture was purified by flash column chromatography to give the title compound (139 mg, 89% yield). MS (ESI): mass calcd. for $C_{28}H_{25}N_5O_5S$, 543.6; m/z found, 544.2 [M+H]$^+$. 1H NMR (400 MHz, DMSO-d6): δ 8.35 (br, 1H), 8.30 (d, J=5.4 Hz, 1H), 7.47-7.39 (m, 2H), 7.35 (d, J=8.7 Hz, 1H), 7.21-7.16 (m, 1H), 7.14-7.08 (m, 2H), 7.08-7.05 (m, 1H), 6.96 (dd, J=8.7, 2.8 Hz, 1H), 5.93 (d, J=5.2 Hz, 1H), 4.11 (d, J=5.8 Hz, 2H), 3.62-3.53 (m, 4H), 3.51-3.42 (m, 4H), 2.05 (s, 3H).

Example 316: (R)—N-(1-Methylpiperidin-3-yl)-4-oxo-4,5-dihydro-3H-1-thia-3,5,8-triazaacenaphthylene-2-carboxamide

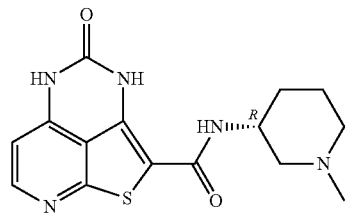

Step A: tert-butyl (R)-3-(5-(4-methoxybenzyl)-4-oxo-4,5-dihydro-3H-1-thia-3,5,8-triazaacenaphthylene-2-carboxamido)piperidine-1-carboxylate The title compound was prepared in a manner analogous to Method 1, Step G (2) in Example 1 by using 5-(4-methoxybenzyl)-4-oxo-4,5-dihydro-3H-1-thia-3,5,8-triazaacenaphthylene-2-carboxylic acid (Intermediate 84) and tert-butyl (R)-3-aminopiperidine-1-carboxylate in place of 5-(2-Methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate.

Step B: (R)-4-oxo-N-(piperidin-3-yl)-4,5-dihydro-3H-1-thia-3,5,8-triazaacenaphthylene-2-carboxamide To a solution of tert-butyl (R)-3-(5-(4-methoxybenzyl)-4-oxo-4,5-dihydro-3H-1-thia-3,5,8-triazaacenaphthylene-2-carboxamido)piperidine-1-carboxylate (13 g, 24.2 mmol) in TFA (100 mL) was stirred at rt for 30 min, then heated at 160° C. for 8 hr in a sealed tube, cooled to room temperature and concentrated to give a yellow solid used in the next step without further purification (7.6 g).

Step C: (R)—N-(1-methylpiperidin-3-yl)-4-oxo-4,5-dihydro-3H-1-thia-3,5,8-triazaacenaphthylene-2-carboxamide formate A mixture of (R)-4-oxo-N-(piperidin-3-yl)-4,5-dihydro-3H-1-thia-3,5,8-triazaacenaphthylene-2-carboxamide (7.6 g, 23.9 mmol) and formaldehyde (10 mL, 37 wt. % in H$_2$O) in methanol (50 mL) was added NaBH(OAc)$_3$ (25.4 g, 119.7 mmol) then stirred at room temperature for 16 hr, concentrated and purified by flash chromatography eluting with MeOH/water (containing 0.1% HCOOH) to get the target compound as a yellow solid (5.8 g, 75%). MS (ESI): mass calcd. for $C_{16}H_{19}N_5O_4S$, 377.4; m/z found, 322.0 [M−HCOOH+H]$^+$. $^1$H NMR (400 MHz, D$_2$O): δ 8.46 (s, 1H), 8.04 (d, J=5.5 Hz, 1H), 6.39 (d, J=5.5 Hz, 1H), 4.30-4.03 (m, 1H), 3.72-3.53 (m, 2H), 3.05-2.93 (m, 4H), 2.93-2.81 (m, 1H), 2.25-2.02 (m, 2H), 2.00-1.80 (m, 1H), 1.72-1.50 (m, 1H).

Example 317: (R)-5-(2,6-Dimethyl-4-phenoxyphenyl)-N-(1-methylpiperidin-3-yl)-4-oxo-4,5-dihydro-3H-1-thia-3,5,8-triazaacenaphthylene-2-carboxamide

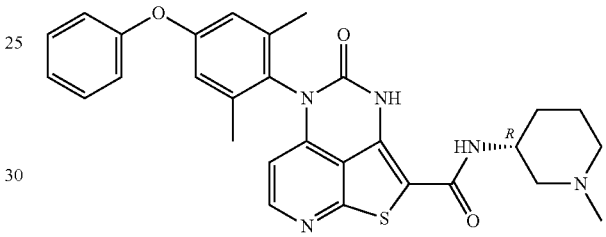

The title compound was prepared in a manner analogous to Method 1, steps A-G in Example 1, and using 5-fluoro-1,3-dimethyl-2-nitrobenzene in place of 5-fluoro-2-nitrotoluene in step A, and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{29}H_{29}N_5O_3S$, 527.6; m/z found, 528.7 [M+H]$^+$. 1H NMR (400 MHz, a mixture of CD$_3$OD and DMSO-d6): δ 8.32 (d, J=5.5 Hz, 1H), 7.41-7.34 (m, 2H), 7.17-7.10 (m, 1H), 7.08-7.02 (m, 2H), 6.87-6.82 (m, 2H), 5.96 (d, J=5.5 Hz, 1H), 4.20-4.17 (m, 1H), 4.00-3.88 (m, 1H), 3.41-3.28 (m, 1H), 3.26-3.16 (m, 1H), 2.83-2.67 (m, 4H), 2.01 (s, 6H), 1.97-1.86 (m, 2H), 1.81-1.69 (m, 1H), 1.67-1.52 (m, 1H).

Example 318: (R)—N-(1-(3-Hydroxypropanoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

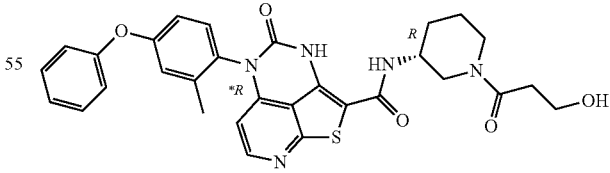

A solution of (R)-5-(*R)-(2-Methyl-4-phenoxyphenl)-4-oxo-N-(piperidin-3-yl)-4,5-dihydro-3H-1-thia-3,5,8-triazaacenaphthylene-2-carboxamide (Example 300, 60 mg, 0.11 mmol), 3-hydroxypropanoic acid (20 mg, 0.22 mmol), HATU (55 mg, 0.15 mmol), and diisopropylethylamine (35 mg, 0.28 mmol) in DMF (5 mL) was stirred at rt for 2 h. The mixture was purified by flash column chromatography to give the title compound as a white solid (29 mg, 46% yield).

MS (ESI): mass calcd. for $C_{30}H_{29}N_5O_5S$, 571.6; m/z found, 572.4 [M+H]$^+$. $^1$H NMR (400 MHz, CD$_3$OD): δ 8.37-8.30 (m, 1H), 7.44-7.37 (m, 2H), 7.33-7.27 (m, 1H), 7.21-7.14 (m, 1H), 7.12-7.03 (m, 3H), 7.01-6.95 (m, 1H), 6.11-6.05 (m, 1H), 4.51-3.90 (m, 3H), 3.88-3.79 (m, 2H), 3.20-3.05 (m, 1H), 2.90-2.75 (m, 1H), 2.73-2.60 (m, 2H), 2.12 (s, 3H), 2.09-2.01 (m, 1H), 1.91-1.77 (m, 1H), 1.77-1.64 (m, 1H), 1.64-1.49 (m, 1H).

Example 319: (R)-5-(*S)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide

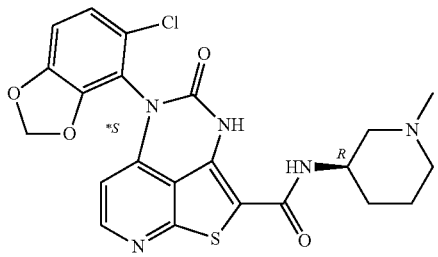

The title compound was prepared in a manner analogous to Method 1, steps C-H in Example 1, and using 5-chlorobenzo[d][1,3]dioxol-4-amine in place of in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G, and using analogous conditions as described in Example 52, step B, and using (R)-5-(*S)-(5-chlorobenzo[d][1,3]dioxol-4-yl)-4-oxo-N-(piperidin-3-yl)-4,5-dihydro-3H-1-thia-3,5,8-triazaacenaphthylene-2-carboxamide in place of (R)-5-(4-(2,6-difluorophenoxy)-2-methylphenyl)-4-oxo-N-(piperidin-3-yl)-4,5-dihydro-3H-1-thia-3,5,8-triazaacenaphthylene-2-carboxamide. MS (ESI): mass calcd. for $C_{22}H_{20}ClN_5O_4S$, 485.94; m/z found, 486.5 [M+H]$^+$. $^1$H NMR (400 MHz, CD$_3$OD): δ 8.40 (d, J=5.3 Hz, 1H), 7.14 (d, J=8.4 Hz, 1H), 7.02 (d, J=8.4 Hz, 1H), 6.27 (d, J=5.4 Hz, 1H), 6.10 (d, J=2.2 Hz, 2H), 4.34-4.21 (m, 1H), 3.52-3.42 (m, 1H), 3.28-3.21 (m, 1H), 2.92-2.82 (m, 2H), 2.79 (s, 3H), 2.08-1.99 (m, 2H), 1.91-1.80 (m, 1H), 1.78-1.64 (m, 1H).

Example 320: (R)—N-(1-Ethylpiperidin-3-yl)-5-(4-(2-isopropylphenoxy)-2-methylphenyl)-4-oxo-4,5-dihydro-3H-1-thia-3,5,8-triazaacenaphthylene-2-carboxamide

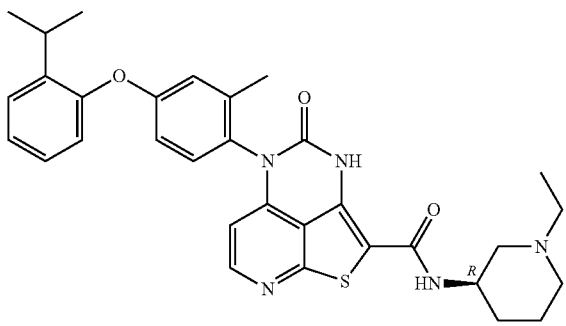

Step A: (R)-5-(4-(2-Isopropylphenoxy)-2-methylphenyl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 2-isopropylphenol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{31}N_5O_3S$, 541.66; m/z found, 542.2 [M+H]$^+$.

Step B: (R)—N-(1-Ethylpiperidin-3-yl)-5-(4-(2-isopropylphenoxy)-2-methylphenyl)-4-oxo-4,5-dihydro-3H-1-thia-3,5,8-triazaacenaphthylene-2-carboxamide To a solution of (R)-5-(4-(2-isopropylphenoxy)-2-methylphenyl)-4-oxo-N-(piperidin-3-yl)-4,5-dihydro-3H-1-thia-3,5,8-triazaacenaphthylene-2-carboxamide (100 mg, 0.19 mmol) and acetaldehyde (0.3 mL) in MeOH (6 mL) was added NaBH(OAc)$_3$ (118 mg, 0.555 mmol) and was stirred at rt for 1 h, concentrated to dryness and purified by flash column chromatography to give the title compound as a white solid (72 mg, 60% yield). MS (ESI): mass calcd. for $C_{32}H_{35}N_5O_3S$, 569.7; m/z found, 570.1 [M+H]$^+$. $^1$H NMR (400 MHz, CD$_3$OH): δ 8.49 (s, 1H), 8.36-8.25 (m, 1H), 7.45-7.34 (m, 1H), 7.32-7.24 (m, 1H), 7.24-7.15 (m, 2H), 7.03-6.92 (m, 2H), 6.91-6.83 (m, 1H), 6.10-5.97 (m, 1H), 4.35-4.22 (m, 1H), 3.58-3.42 (m, 1H), 3.29-3.20 (m, 2H), 3.12-2.97 (m, 2H), 2.85-2.64 (m, 2H), 2.09 (s, 3H), 2.06-1.98 (m, 2H), 1.90-1.77 (m, 1H), 1.74-1.61 (m, 1H), 1.34-1.27 (m, 3H), 1.23 (d, J=6.9 Hz, 6H).

Example 321: (R)—N-(1-Acryloylpiperidin-3-yl)-5-(*R)-(5-chlorobenzo[d][1,3]dioxol-4-yl)-4-oxo-4,5-dihydro-3H-1-thia-3,5,8-triazaacenaphthylene-2-carboxamide

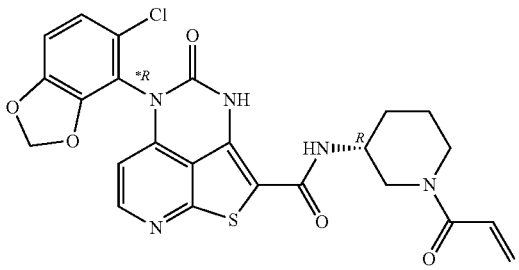

The title compound was prepared using analogous conditions described in Method 1, steps C-I in Example 1 (including Chiral Resolution Method A after step F to obtain the *R atropisomer), and using 5-chlorobenzo[d][1,3]dioxol-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{24}H_{20}ClN_5O_5S$, 526.0; m/z found, 526.2 [M+H]$^+$. $^1$H NMR (400 MHz, CD$_3$OD): δ 8.37 (d, J=5.5 Hz, 1H), 7.11 (d, J=8.4 Hz, 1H), 7.00 (d, J=8.4 Hz, 1H), 6.85-6.70 (m, 1H), 6.24 (d, J=5.5 Hz, 1H), 6.23-6.13 (m, 1H), 6.10-6.06 (m, 2H), 5.77-5.66 (m, 1H), 4.55-4.49 (m, 0.5H), 4.31-4.24 (m, 0.5H), 4.20-4.12 (m, 0.5H), 4.03-3.90 (m, 1.5H), 3.23-3.11 (m, 1H), 2.97-2.84 (m, 1H), 2.10-2.01 (m, 1H), 1.91-1.82 (m, 1H), 1.79-1.67 (m, 1H), 1.62-1.49 (m, 1H).

Example 322: (R)-5-(4-Cyclopropoxy-2-methylphenyl)-N-(1-methylpiperidin-3-yl)-4-oxo-4,5-dihydro-3H-1-thia-3,5,8-triazaacenaphthylene-2-carboxamide

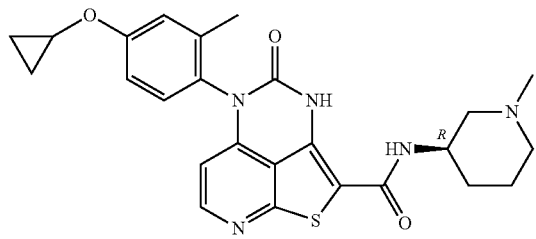

Step A: (R)-5-(4-Cyclopropoxy-2-methylphenyl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 3-methyl-4-nitrophenol and bromocyclopropane in place of phenol and 5-fluoro-2-nitrotoluene in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-Cyclopropoxy-2-methylphenyl)-N-(1-methylpiperidin-3-yl)-4-oxo-4,5-dihydro-3H-1-thia-3,5,8-triazaacenaphthylene-2-carboxamide A solution of (R)-5-(4-cyclopropoxy-2-methylphenyl)-4-oxo-N-(piperidin-3-yl)-4,5-dihydro-3H-1-thia-3,5,8-triazaacenaphthylene-2-carboxamide (120 mg, 0.26 mmol), formaldehyde (0.5 mL, 37 wt. % in $H_2O$), and $NaBH(OAc)_3$ (83 mg, 0.39 mmol) in DCM (5 mL) was stirred at rt for 5 h. The mixture was concentrated to dryness and purified by flash column chromatography to give the title compound as a light yellow solid (45 mg, 36%). MS (ESI): mass calcd. for $C_{25}H_{27}N_5O_3S$, 477.6; m/z found, 478.0 $[M+H]^+$. $^1H$ NMR (400 MHz, $CD_3OD$): δ 8.41 (s, 1H), 8.32-8.27 (m, 1H), 7.26-7.20 (m, 1H), 7.13-7.10 (m, 1H), 7.10-7.05 (m, 1H), 6.04-5.99 (m, 1H), 4.34-4.24 (m, 1H), 3.88-3.79 (m, 1H), 3.53-3.43 (m, 1H), 3.28-3.22 (m, 1H), 2.92-2.82 (m, 2H), 2.82-2.75 (m, 3H), 2.11 (s, 3H), 2.06-1.95 (m, 2H), 1.92-1.78 (m, 1H), 1.76-1.63 (m, 1H), 0.85-0.78 (m, 2H), 0.75-0.68 (m, 2H).

Example 323: (S)-5-(*R)-(2-Methyl-4-phenoxyphenyl)-4-oxo-N-(tetrahydrofuran-3-yl)-4,5-dihydro-3H-1-thia-3,5,8-triazaacenaphthylene-2-carboxamide

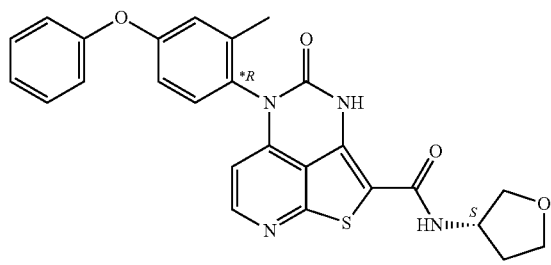

The title compound was prepared using analogous conditions described in Method 1, steps A-G in Example 1 (including Chiral Resolution Method A after step F to obtain the *R atropisomer), and using (3S)-tetrahydrofuran-3-amine in place of tert-butyl (3R,5R)-3-amino-5-fluoropiperidine-1-carboxylate (Intermediate 1) in step G. MS (ESI): mass calcd. for $C_{26}H_{22}N_4O_4S$, 486.5; m/z found, 487.2 $[M+H]^+$. $^1H$ NMR (400 MHz, $CD_3OD$): δ 8.28 (d, J=5.5 Hz, 1H), 7.44-7.35 (m, 2H), 7.34-7.25 (m, 1H), 7.20-7.11 (m, 1H), 7.09-7.00 (m, 3H), 6.97-6.90 (m, 1H), 6.03 (d, J=5.5 Hz, 1H), 4.62-4.48 (m, 1H), 4.02-3.89 (m, 2H), 3.85-3.75 (m, 1H), 3.74-3.65 (m, 1H), 2.35-2.20 (m, 1H), 2.09 (s, 3H), 2.05-1.94 (m, 1H).

Example 324: (R)—N-(1-Acryloylpyrrolidin-3-yl)-4-oxo-5-(4-phenoxy-2-(trifluoromethyl)phenyl)-4,5-dihydro-3H-1-thia-3,5,8-triazaacenaphthylene-2-carboxamide

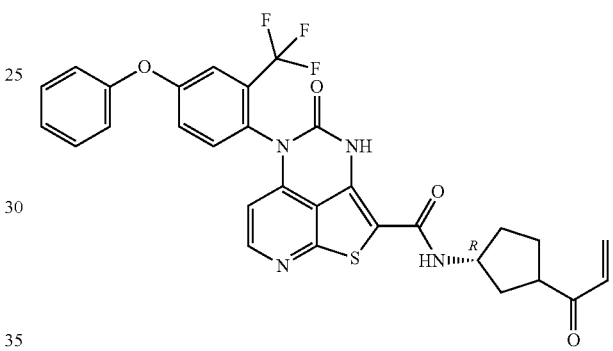

The title compound was prepared using analogous conditions described in Method 1, steps A-I in Example 1, and using 4-fluoro-1-nitro-2-(trifluoromethyl)benzene in place of 5-fluoro-2-nitrotoluene in step A, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{22}F_3N_5O_4S$, 593.6; m/z found, 594.3 $[M+H]^+$. $^1H$ NMR (400 MHz, DMSO-$d_6$): δ 10.39 (s, 1H), 8.54-8.18 (m, 2H), 7.74 (d, J=8.7 Hz, 1H), 7.60-7.37 (m, 4H), 7.34-7.14 (m, 3H), 6.70-6.45 (m, 1H), 6.23-5.97 (m, 2H), 5.74-5.55 (m, 1H), 4.63-4.35 (m, 1H), 3.95-3.38 (m, 4H), 2.27-1.87 (m, 2H).

Example 325: (R)-5-(*R)-(2-Methyl-4-phenoxyphenl)-4-oxo-N-(1-propionylpyrrolidin-3-yl)-4,5-dihydro-3H-1-thia-3,5,8-triazaacenaphthylene-2-carboxamide

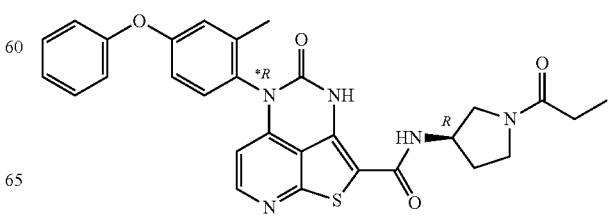

Step A: (R)-5-(*R)-(2-Methyl-4-phenoxyphenyl)-4-oxo-N-(pyrrolidin-3-yl)-4,5-dihydro-3H-1-thia-3,5,8-triazaacenaphthylene-2-carboxamide The title compound was prepared using analogous conditions described in Method 1, steps A-H in Example 1 (including Chiral Resolution Method A after step F to obtain the *R atropisomer), and using tert-butyl (3R)-3-aminopyrrolidine-1-carboxylate in place of tert-butyl (3R,5R)-3-amino-5-fluoropiperidine-1-carboxylate (Intermediate 1) in step G.

Step B: (R)-5-(*R)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide To a solution of (R)-5-(*R)-(2-methyl-4-phenoxyphenyl)-4-oxo-N-(pyrrolidin-3-yl)-4,5-dihydro-3H-1-thia-3,5,8-triazaacenaphthylene-2-carboxamide (60 mg, 0.12 mmol) and triethylamine (30 mg, 0.3 mmol) in DCM (2 mL) was added propanoyl propanoate (39 mg, 0.3 mmol) in DCM was added dropwise and was stirred for 2 h at rt, then it was concentrated to dryness. The residue was purified by flash column chromatography, then preparative TLC to give the title compound as a yellow solid (14 mg). MS (ESI): mass calcd. for $C_{29}H_{27}N_5O_4S$, 541.6; m/z found, 542.2 [M+H]$^+$. $^1$H NMR (400 MHz, DMSO-d$_6$): δ 10.24 (s, 1H), 8.72-8.48 (br, 1H), 8.30-8.17 (m, 1H), 7.48-7.41 (m, 2H), 7.32-7.24 (m, 1H), 7.23-7.17 (m, 1H), 7.15-7.10 (m, 2H), 7.09-7.05 (m, 1H), 6.99-6.94 (m, 1H), 5.92-5.77 (m, 1H), 4.56-4.35 (m, 1H), 3.81-3.31 (m, 4H), 2.30-2.22 (m, 2H), 2.21-2.08 (m, 1H), 2.05 (s, 3H), 2.01-1.87 (m, 1H), 1.02-0.96 (m, 3H).

Example 326: (R)-5-(4-(2-Carbamoylphenoxy)-2-methylphenyl)-N-(1-methylpiperidin-3-yl)-4-oxo-4,5-dihydro-3H-1-thia-3,5,8-triazaacenaphthylene-2-carboxamide

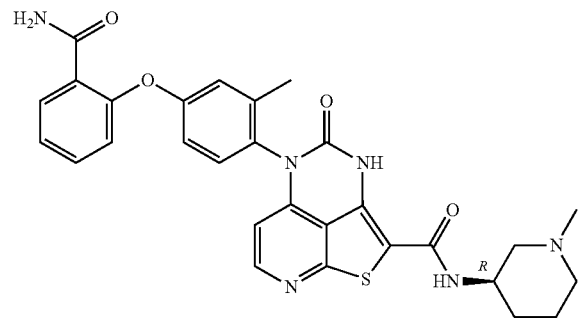

Step A: (R)-5-(4-(2-Carbamoylphenoxy)-2-methylphenyl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 2-hydroxybenzamide in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-(2-Carbamoylphenoxy)-2-methylphenyl)-N-(1-methylpiperidin-3-yl)-4-oxo-4,5-dihydro-3H-1-thia-3,5,8-triazaacenaphthylene-2-carboxamide To a solution of (R)-5-(4-(2-carbamoylphenoxy)-2-methylphenyl)-4-oxo-N-(piperidin-3-yl)-4,5-dihydro-3H-1-thia-3,5,8-triazaacenaphthylene-2-carboxamide (315 mg, 0.116 mmol) in DCM were added formaldehyde (1.0 mL, 37 wt. % in H$_2$O) and NaBH(OAc)$_3$ (49 mg, 0.23 mmol) and was stirred at room temperature for 4 hours. To the mixture were added DCM (50 mL), MeOH (5 mL), water (30 mL), and an aqueous solution of NH$_4$OH (2 mL). The organic layer was collected, concentrated to dryness, and purified by flash column chromatography to give the title compound as a yellow solid (17 mg, 26% yield). MS (ESI): mass calcd. for $C_{29}H_{28}N_6O_4S$, 556.6; m/z found, 557.4 [M+H]$^+$. 1H NMR (400 MHz, DMSO-d6): δ 10.82 (br, 1H), 8.25 (d, J=5.3 Hz, 1H), 8.18-8.03 (m, 1H), 7.95 (d, J=6.9 Hz, 1H), 7.85-7.76 (m, 1H), 7.76-7.67 (m, 1H), 7.45-7.36 (m, 1H), 7.30 (d, J=8.4 Hz, 1H), 6.97 (d, J=8.3 Hz, 1H), 6.92 (t, J=7.6 Hz, 1H), 5.86 (d, J=5.4 Hz, 1H), 3.96-3.91 (m, 1H), 2.85-2.79 (m, 1H), 2.68-2.62 (m, 1H), 2.20 (s, 3H), 2.08 (s, 3H), 1.95-1.86 (m, 2H), 1.82-1.74 (m, 1H), 1.72-1.65 (m, 1H), 1.57-1.47 (m, 1H), 1.37-1.29 (m, 1H).

Example 327: 5-(2-Methyl-4-phenoxyphenyl)-2-(piperazin-1-yl)-3H-1-thia-3,5,8-triazaacenaphthylen-4(5H)-one

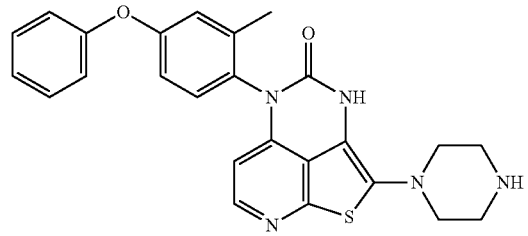 [SMILES: Cc1cc(Oc2ccccc2)ccc1N1C(=O)Nc2c(N3CCNCC3)sc3nccc1c23]

To a solution of 5-(2-methyl-4-phenoxyphenyl)-4-oxo-4,5-dihydro-3H-1-thia-3,5,8-triazaacenaphthylene-2-carboxylic acid (Intermediate 27, 1.50 g, 3.59 mmol) in 1-methyl-2-pyrrolidinone (15 mL) was added silver acetate (120 mg, 0.72 mmol) and potassium carbonate (149 mg, 1.08 mmol) and was stirred at 120° C. for 30 minutes. The reaction was filtered and the organic layer was collected and concentrated to dryness. The residue was purified by flash column chromatography (SiO$_2$) to give the title compound (1.2 g, 89% yield).

Step C: 2-Chloro-5-(2-methyl-4-phenoxyphenyl)-3H-1-thia-3,5,8-triazaacenaphthylen-4(5H)-one To a solution of 5-(2-methyl-4-phenoxyphenyl)-3H-1-thia-3,5,8-triazaacenaphthylen-4(5H)-one (1000 mg, 2.68 mmol) in CHCl$_3$ (20 mL) was added NCS (358 mg, 2.68 mmol) and was stirred overnight at 15° C. The reaction was poured into aqueous NaHCO$_3$ (25 mL) and extracted with DCM (30 mL×3). The combined organic layers were washed with brine (50 mL), dried over anhydrous Na$_2$SO$_4$, filtered, and concentrated to dryness. The residue was purified by flash column chromatography (SiO$_2$) to give the title compound (1.0 g, 92% yield).

Step D: tert-Butyl 4-(5-(2-methyl-4-phenoxyphenyl)-4-oxo-4,5-dihydro-3H-1-thia-3,5,8-triazaacenaphthylen-2-yl)piperazine-1-carboxylate To a solution of 2-chloro-5-(2-methyl-4-phenoxyphenyl)-3H-1-thia-3,5,8-triazaacenaphthylen-4(5H)-one (200 mg, 0.49 mmol) in DMSO (3 mL) were added 1-Boc-piperazine (913 mg, 4.90 mmol), Cu (6.4 mg, 0.10 mmol), copper(I) iodide (19 mg, 0.10 mmol), and potassium phosphate (312 mg, 1.47 mmol) and was irradiated using a microwave at 120° C. for 2.5 h. The reaction was poured into citric acid (25 mL, 4 M in water) and extracted with dichloromethane (30 mL×3). The combined organic layers were concentrated to dryness and the residue was purified by preparative RP-C18 HPLC to give the title compound (40 mg).

Step E: 5-(2-Methyl-4-phenoxyphenyl)-2-(piperazin-1-yl)-3H-1-thia-3,5,8-triazaacenaphthylen-4(5H)-one A solution of tert-butyl 4-(5-(2-methyl-4-phenoxyphenyl)-4-oxo-4,5-dihydro-3H-1-thia-3,5,8-triazaacenaphthylen-2-yl)piperazine-1-carboxylate (30 mg, 0.054 mmol) in MeOH (1 mL) and concentrated HCl (1 mL) and was stirred at room temperature for 3 h. The mixture was poured into aqueous NaHCO$_3$ (50 mL), extracted with DCM (3×30 mL), the organic phases washed with saturated brine (50 mL), dried over anhydrous Na$_2$SO$_4$, filtered, and concentrated to dryness. The residue was purified by preparative RP-C18 HPLC to give the title compound as a trifluoroacetic acid salt (12 mg, 96% yield). MS (ESI): mass calcd. for C$_{25}$H$_{23}$N$_5$O$_2$S, 457.5; m/z found, 458.1 [M+H]$^+$. $^1$H NMR (400 MHz, DMSO-d$_6$): δ 10.67 (s, 1H), 8.77 (br, 2H), 8.17 (d, J=5.4 Hz, 1H), 7.45 (t, J=7.8 Hz, 2H), 7.33 (d, J=8.5 Hz, 1H), 7.20 (t, J=7.3 Hz, 1H), 7.15-7.05 (m, 3H), 6.98 (dd, J=2.8, 8.4 Hz, 1H), 5.85 (d, J=5.4 Hz, 1H), 3.36-3.18 (m, 4H), 3.16-2.98 (m, 4H), 2.06 (s, 3H).

Example 328: (R)-6-Methyl-4-oxo-5-(4-phenoxyphenyl)-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 2-chloro-4-iodo-5-methylpyridine-3-carbonitrile and 4-phenoxyaniline in place of 2-chloro-4-iodopyridine-3-carbonitrile and 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for C$_{27}$H$_{25}$N$_5$O$_3$S, 499.6; m/z found, 500.3 [M+H]$^+$. $^1$H NMR (400 MHz, CD$_3$OD): δ 8.20 (s, 1H), 7.38-7.47 (m, 4H), 7.16-7.21 (m, 1H), 7.08-7.13 (m, 4H), 4.21-4.31 (m, 1H), 3.53 (dd, J=4.04, 12.13 Hz, 1H), 3.33-3.40 (m, 1H), 2.88-3.01 (m, 2H), 2.01-2.13 (m, 2H), 1.67-1.91 (m, 2H), 1.61 (s, 3H).

Example 329: (R)—N-(1-Cyanopiperidin-3-yl)-5-(*R)-(2-methyl-4-phenoxyphenyl)-4-oxo-4,5-dihydro-3H-1-thia-3,5,8-triazaacenaphthylene-2-carboxamide To a solution of (R)-5-(*R)-(2-methyl-4-phenoxyphenyl)-4-oxo-N-(piperidin-3-yl)-4,5-dihydro-3H-1-thia-3,5,8-triazaacenaphthylene-2-carboxamide (Example 300, 52.5 mg, 0.105 mmol), BrCN (13.4 mg, 0.126 mmol), and triethylamine (21 mg, 0.21 mmol) in DCM (5 mL) was stirred at rt for 4 hours. The reaction mixture was concentrated to dryness and purified by flash column chromatography to give the title compound as a yellow solid (30 mg, 53% yield). MS (ESI): mass calcd. for C$_{28}$H$_{24}$N$_6$O$_3$S, 524.6; m/z found, 525.3 [M+H]$^+$. $^1$H NMR (400 MHz, CD3OD and DMSO-d$_6$): δ 8.29-8.22 (m, 1H), 7.39-7.31 (m, 2H), 7.28-7.22 (m, 1H), 7.14-7.08 (m, 1H), 7.07-7.01 (m, 2H), 7.01-6.98 (m, 1H), 6.92-6.88 (m, 1H), 5.98-5.90 (m, 1H), 3.99-3.95 (m, 2H), 3.44-3.39 (m, 1H), 3.27-3.21 (m, 1H), 2.97-2.87 (m, 2H), 2.02 (s, 3H), 1.90-1.84 (m, 1H), 1.79-1.72 (m, 1H), 1.68-1.60 (m, 1H), 1.56-1.48 (m, 1H).

Example 330: (R)-5-(3,5-Dichlorophenyl)-4-oxo-N-(piperidin-3-yl)-4,5-dihydro-3H-1-thia-3,5,8-triazaacenaphthylene-2-carboxamide

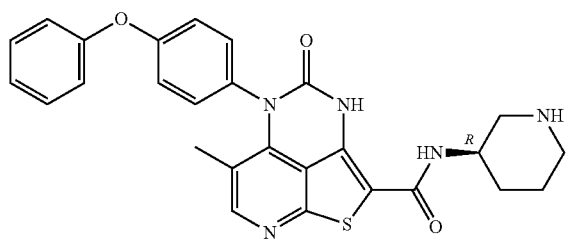

The title compound was prepared in a manner analogous to Method 1, steps C-H in Example 1, and using 3,5-dichloroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for C$_{20}$H$_{17}$Cl$_2$N$_5$O$_2$S, 462.4; m/z found, 461.9 [M+H]$^+$. 1H NMR (400 MHz, DMSO-d6) δ 8.73 (d, J=7.2 Hz, 1H), 8.22 (s, 1H), 8.15 (d, J=5.5 Hz, 1H), 7.73 (t, J=1.7

Hz, 1H), 7.51 (s, 2H), 5.95 (d, J=5.6 Hz, 1H), 4.06 (s, 1H), 3.31-3.27 (m, 1H), 3.14-3.10 (m, 1H), 2.87-2.73 (m, 2H), 1.96-1.93 (m, 1H), 1.88-1.84 (m, 1H), 1.71-1.52 (m, 2H).

Example 331: (R)—N-Methyl-5-(2-methyl-4-phenoxyphenyl)-4-oxo-N-(pyrrolidin-3-yl)-4,5-dihydro-3H-1-thia-3,5,8-triazaacenaphthylene-2-carboxamide

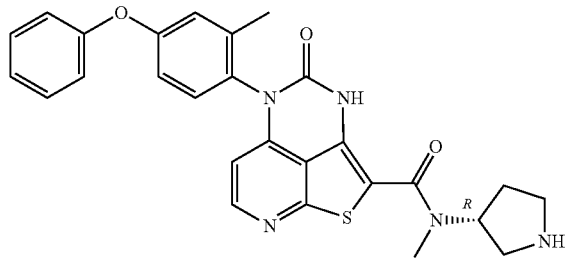

The title compound was prepared using analogous conditions as described in Method 1, steps A-H in Example 1, and using (R)-tert-butyl 3-(methylamino)pyrrolidine-1-carboxylate in place of tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 500.2 [M+H]$^+$. $^1$H NMR (400 MHz, CD3OD and DMSO-d$_6$): δ 8.27 (d, J=5.5 Hz, 1H), 7.45-7.33 (m, 2H), 7.28 (d, J=8.6 Hz, 1H), 7.17-7.12 (m, 1H), 7.11-7.00 (m, 3H), 6.97-6.87 (m, 1H), 5.96 (d, J=5.5 Hz, 1H), 4.75-4.53 (m, 1H), 3.53-3.41 (m, 1H), 3.40-3.30 (m, 2H), 3.14 (s, 3H), 2.32-1.86 (m, 6H).

Example 332: (R)-5-(4-Isopropoxy-2-methylphenyl)-N-(1-methylpiperidin-3-yl)-4-oxo-4,5-dihydro-3H-1-thia-3,5,8-triazaacenaphthylene-2-carboxamide

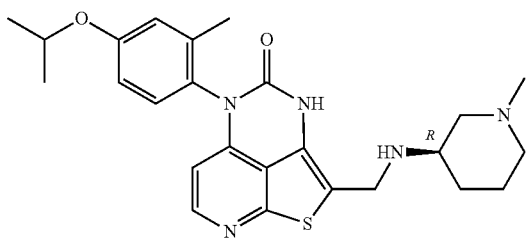

A solution of (R)-5-(4-isopropoxy-2-methylphenyl)-4-oxo-N-(piperidin-3-yl)-4,5-dihydro-3H-1-thia-3,5,8-triazaacenaphthylene-2-carboxamide (Intermediate 70, 100 mg, 0.22 mmol) in DCM (5 mL) and was treated with formaldehyde (0.5 mL, 37 wt. % in H$_2$O). To the stirred reaction mixture was added NaBH(OAc)$_3$ (91 mg, 0.43 mmol) and was stirred at rt for 1 h, then concentrated to dryness. The residue was purified by flash column chromatography to give the title compound as a yellow solid (27 mg, 26% yield). MS (ESI): mass calcd. for $C_{25}H_{29}N_5O_3S$, 479.6; m/z found, 480.2 [M+H]$^+$. 1H NMR (400 MHz, DMSO-d6): δ 8.24 (d, J=5.4 Hz, 1H), 8.04 (s, 1H), 7.25-7.13 (m, 1H), 6.99-6.93 (m, 1H), 6.92-6.83 (m, 1H), 5.89-5.78 (m, 1H), 4.73-4.59 (m, 1H), 3.96-3.88 (m, 1H), 2.85-2.76 (m, 1H), 2.68-2.61 (m, 1H), 2.18 (s, 3H), 2.01 (s, 3H), 1.92-1.64 (m, 5H), 1.55-1.45 (m, 1H), 1.31-1.26 (m, 6H).

Example 333: (R)-5-(4-Ethoxy-2-methylphenyl)-N-(1-methylpiperidin-3-yl)-4-oxo-4,5-dihydro-3H-1-thia-3,5,8-triazaacenaphthylene-2-carboxamide

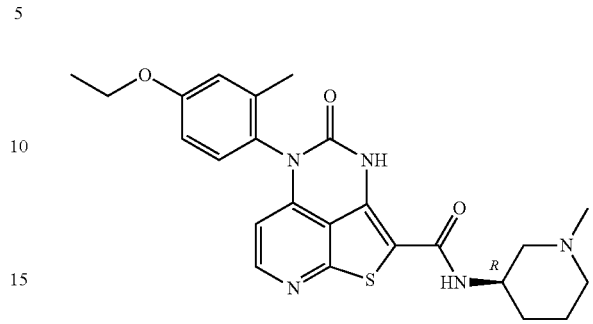

The title compound was prepared using analogous conditions as described in Method 1, steps A-G in Example 1, and using 3-methyl-4-nitrophenol and bromoethane in place of phenol and 5-fluoro-2-nitrotoluene in step A, and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{24}H_{27}N_5O_3S$, 465.6; m/z found, 466.1 [M+H]$^+$. $^1$H NMR (400 MHz, CD$_3$OD): δ 8.44 (s, 1H), 8.30 (d, J=5.5 Hz, 1H), 7.26-7.15 (m, 1H), 7.01-6.95 (m, 1H), 6.95-6.87 (m, 1H), 6.02 (d, J=5.5 Hz, 1H), 4.33-4.18 (m, 1H), 4.14-4.03 (m, 2H), 3.51-3.37 (m, 1H), 3.27-3.14 (m, 1H), 2.85-2.65 (m, 5H), 2.10 (s, 3H), 2.06-1.94 (m, 2H), 1.90-1.73 (m, 1H), 1.72-1.57 (m, 1H), 1.45-1.37 (m, 3H).

Example 334: (R)—N-(1-Acryloylpiperidin-3-yl)-5-(4-(tert-butyl)phenyl)-4-oxo-4,5-dihydro-3H-1-thia-3,5,8-triazaacenaphthylene-2-carboxamide

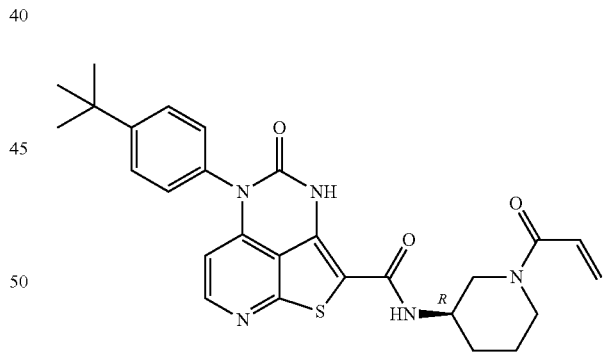

The title compound was prepared in a manner analogous to Method 1, steps C-I in Example 1, and using 4-(tert-butyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{27}H_{29}N_5O_3S$, 503.6; m/z found, 504.1 [M+H]$^+$. $^1$H NMR (400 MHz, DMSO-d$_6$): δ 10.21 (d, J=15.1 Hz, 1H), 8.34 (d, J=5.5 Hz, 1H), 8.18-8.05 (m, 1H), 7.63 (d, J=8.6 Hz, 2H), 7.38 (d, J=8.5 Hz, 2H), 6.90-6.73 (m, 1H), 6.12 (d, J=17.0 Hz, 1H), 6.00 (d, J=5.5 Hz, 1H), 5.70 (d, J=10.7 Hz, 1H), 4.53-4.19 (m, 1H), 4.11-3.95 (m, 1H), 3.80 (s, 1H), 3.18-2.93 (m, 1H), 2.82-2.63 (m, 1H), 2.01-1.91 (m, 1H), 1.85-1.58 (m, 2H), 1.44 (s, 1H), 1.36 (s, 9H).

Example 335: (R)-5-(*S)-(2-Methyl-4-((tetrahydro-2H-pyran-4-yl)oxy)phenyl)-N-(1-methylpiperidin-3-yl)-4-oxo-4,5-dihydro-3H-1-thia-3,5,8-triazaacenaphthylene-2-carboxamide

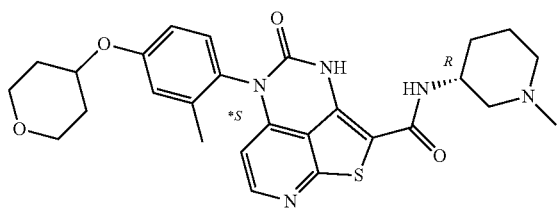

The title compound was prepared using analogous conditions described in Example 343, steps A-B, and by obtaining the *S atropisomer instead of the *R atropisomer in step A. MS (ESI): mass calcd. for C27H31N5O4S, 521.63; m/z found, 522.1 [M+H]+. 1H NMR (400 MHz, CD3OD): δ 8.41 (s, 1H), 8.34-8.28 (m, 1H), 7.25-7.16 (m, 1H), 7.06-7.01 (m, 1H), 7.00-6.95 (m, 1H), 6.06-6.01 (m, 1H), 4.70-4.61 (m, 1H), 4.34-4.22 (m, 1H), 4.03-3.90 (m, 2H), 3.68-3.56 (m, 2H), 3.52-3.40 (m, 1H), 2.90-2.70 (m, 5H), 2.16-1.95 (m, 8H), 1.88-1.81 (m, 1H), 1.81-1.63 (m, 3H).

Example 336: (R)-5-(3-Chlorophenyl)-4-oxo-N-(piperidin-3-yl)-4,5-dihydro-3H-1-thia-3,5,8-triazaacenaphthylene-2-carboxamide

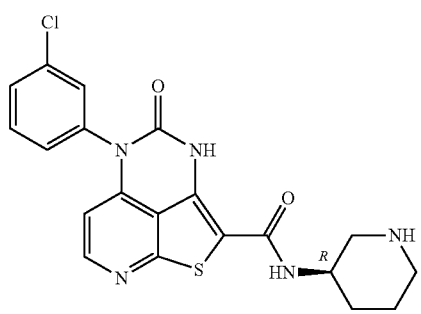

The title compound was prepared in a manner analogous to Method 1, steps C-H in Example 1, and using 3-chloroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for C20H18ClN5O2S, 427.9; m/z found, 427.8 [M+H]+. 1H NMR (400 MHz, DMSO-d6) δ 8.65 (d, J=7.3 Hz, 1H), 8.22 (s, 1H), 8.16 (d, J=5.6 Hz, 1H), 7.61-7.54 (m, 2H), 7.48 (s, 1H), 7.34 (d, J=7.5 Hz, 1H), 5.88 (d, J=5.6 Hz, 1H), 4.06 (s, 1H), 3.30-3.26 (m, 1H), 3.12-3.09 (m, 1H), 2.82-2.73 (m, 2H), 1.95-1.93 (m, 1H), 1.87-1.83 (m, 1H), 1.72-1.53 (m, 2H).

Example 337: (R)—N-(1-Acryloylpyrrolidin-3-yl)-4-oxo-5-phenyl-4,5-dihydro-3H-1-thia-3,5,8-triazaacenaphthylene-2-carboxamide

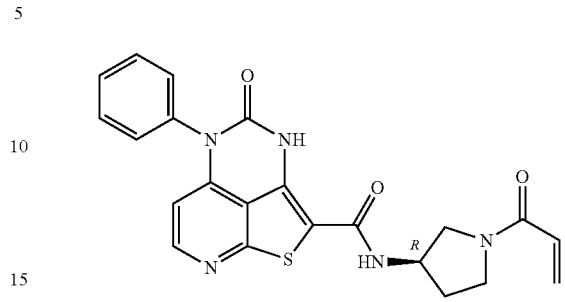

Step A: 4-Oxo-5-phenyl-4,5-dihydro-3H-1-thia-3,5,8-triazaacenaphthylene-2-carboxylic Acid The title compound was prepared using analogous conditions as described in Method 1, steps C-F in Example 1, and using aniline in place of 2-methyl-4-phenoxyaniline in step C.

Step B: 4-Oxo-5-phenyl-4,5-dihydro-3H-1-thia-3,5,8-triazaacenaphthylene-2-carbonyl chloride To a solution of 4-oxo-5-phenyl-4,5-dihydro-3H-1-thia-3,5,8-triazaacenaphthylene-2-carboxylic acid (200 mg, 0.64 mmol) in DCM (10 mL) was added oxalyl dichloride (4 mL) and was stirred at 60° C. overnight. The reaction mixture was concentrated to dryness to give the title compound as a brown solid (200 mg, 95% yield).

Step C: (R)-tert-Butyl 3-(4-oxo-5-phenyl-4,5-dihydro-3H-1-thia-3,5,8-triazaacenaphthylene-2-carboxamido)pyrrolidine-1-carboxylate To a solution of 4-oxo-5-phenyl-4,5-dihydro-3H-1-thia-3,5,8-triazaacenaphthylene-2-carbonyl chloride (200 mg, 0.61 mmol) in DCM (4 mL) were added tert-butyl (3R)-3-aminopyrrolidine-1-carboxylate (200 mg, 1.07 mmol) and triethylamine (100 mg, 0.99 mmol) and was reacted at rt for 20 min. The reaction was quenched with H2O (10 mL), extracted with DCM, dried over anhydrous Na2SO4, filtered, and concentrated to dryness. The residue was purified by flash column chromatography and preparative TLC to give the title compound as a yellow solid 150 mg, 52% yield).

Step D: (R)-4-Oxo-5-phenyl-N-(pyrrolidin-3-yl)-4,5-dihydro-3H-1-thia-3,5,8-triazaacenaphthylene-2-carboxamide To a solution of (R)-tert-butyl 3-(4-oxo-5-phenyl-4,5-dihydro-3H-1-thia-3,5,8-triazaacenaphthylene-2-carboxamido)pyrrolidine-1-carboxylate (150 mg, 0.31 mmol) in MeOH (5 mL) was added concentrated HCl (2 mL) and was reacted at rt for 20 min. The reaction was quenched by the addition of H2O (10 mL), extracted with DCM, dried over anhydrous Na2SO4, filtered, and concentrated to dryness. The residue was purified by flash column chromatography and preparative TLC to give the title compound as a red solid (100 mg, 84% yield).

Step E: (R)—N-(1-Acryloylpyrrolidin-3-yl)-4-oxo-5-phenyl-4,5-dihydro-3H-1-thia-3,5,8-triazaacenaphthylene-2-carboxamide To a solution of (R)-4-oxo-5-phenyl-N-(pyrrolidin-3-yl)-4,5-dihydro-3H-1-thia-3,5,8-triazaacenaphthylene-2-carboxamide (100 mg, 0.26 mmol) in DCM (4 mL) were added prop-2-enoyl chloride (25 mg, 0.28 mmol) and triethylamine (45 mg, 0.45 mmol) and was reacted at rt for 20 min. The reaction was quenched by the addition of H$_2$O (10 mL), extracted with DCM, dried over anhydrous Na$_2$SO$_4$, filtered, and concentrated to dryness. The residue was purified by flash column chromatography and preparative TLC to give the title compound as a red solid (105 mg, 91.6% yield). MS (ESI): mass calcd. for C$_{22}$H$_{19}$N$_5$O$_3$S, 433.5; m/z found, 434.1 [M+H]$^+$. $^1$H NMR (400 MHz, CD$_3$OD): δ 8.28-8.24 (m, 1H), 7.62-7.54 (m, 3H), 7.46-7.40 (m, 2H), 6.66-6.52 (m, 1H), 6.32-6.22 (m, 1H), 6.09-6.05 (m, 1H), 5.78-5.69 (m, 1H), 4.68-4.56 (m, 1H), 4.03-3.68 (m, 3H), 3.59-3.49 (m, 1H), 2.32-2.07 (m, 2H).

Example 338: (R)—N-Methyl-5-(2-methyl-4-phenoxyphenyl)-N-(1-methylpyrrolidin-3-yl)-4-oxo-4,5-dihydro-3H-1-thia-3,5,8-triazaacenaphthylene-2-carboxamide

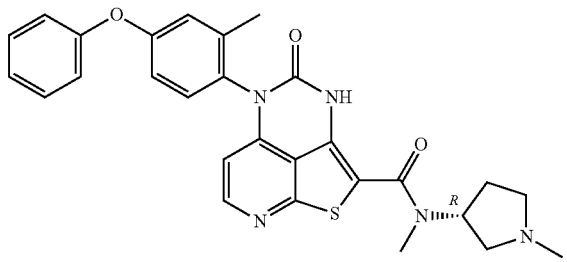

Step A: (R)—N-Methyl-5-(2-methyl-4-phenoxyphenyl)-4-oxo-N-(pyrrolidin-3-yl)-4,5-dihydro-3H-1-thia-3,5,8-triazaacenaphthylene-2-carboxamide The title compound was prepared using analogous conditions as described in Method 1, steps A-H in Example 1, and using tert-butyl (3R)-3-(methylamino)pyrrolidine-1-carboxylate in place of tert-butyl (3R,5R)-3-amino-5-fluoropiperidine-1-carboxylate (Intermediate 1) in step G.

Step B: (R)—N-Methyl-5-(2-methyl-4-phenoxyphenyl)-N-(1-methylpyrrolidin-3-yl)-4-oxo-4,5-dihydro-3H-1-thia-3,5,8-triazaacenaphthylene-2-carboxamide To a solution of (R)—N-methyl-5-(2-methyl-4-phenoxyphenyl)-4-oxo-N-(pyrrolidin-3-yl)-4,5-dihydro-3H-1-thia-3,5,8-triazaacenaphthylene-2-carboxamide (100 mg, 0.19 mmol) and formaldehyde (0.5 mL, 37 wt. % in H$_2$O) in MeOH (30 mL) was added NaBH(OAc)$_3$ (120 mg, 0.57 mmol) and was stirred at rt for 3 h, concentrated to dryness, and purified by flash column chromatography to give the title compound as a white solid (67 mg, 99% yield). MS (ESI): mass calcd. for C$_{28}$H$_{27}$N$_5$O$_3$S, 513.6; m/z found, 514.6 [M+H]$^+$. 1H NMR (400 MHz, DMSO-d6): δ 8.29 (d, J=5.4 Hz, 1H), 7.50-7.40 (m, 2H), 7.37 (d, J=8.6 Hz, 1H), 7.22-7.15 (m, 1H), 7.13-7.05 (m, 3H), 6.98-6.92 (m, 1H), 5.95 (d, J=5.4 Hz, 1H), 4.95-4.77 (m, 1H), 3.05 (s, 3H), 2.81-2.69 (m, 2H), 2.46-2.35 (m, 1H), 2.22 (s, 3H), 2.20-2.07 (m, 2H), 2.05 (s, 3H), 1.92-1.77 (m, 1H).

Example 339: (S)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide

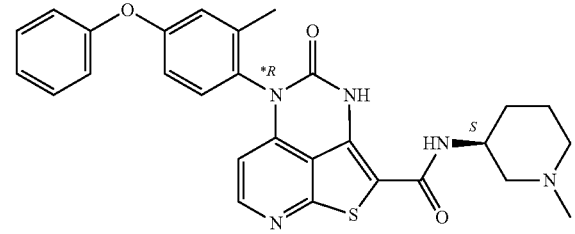

Step A: (S)-5-(*R)-(2-Methyl-4-phenoxyphenyl)-4-oxo-N-(piperidin-3-yl)-4,5-dihydro-3H-1-thia-3,5,8-triazaacenaphthylene-2-carboxamide The title compound was prepared using analogous conditions as described in Method 1, steps A-H in Example 1 (including Chiral Resolution Method A after step F to obtain the *R atropisomer), and using (S)-1-boc-3-aminopiperidine in place of tert-butyl (3R,5R)-3-amino-5-fluoropiperidine-1-carboxylate (Intermediate 1) in step G.

Step B: (S)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide To an oven dried microwave vial containing a stir bar under Ar were added (S)-5-(*R)-(2-methyl-4-phenoxyphenyl)-4-oxo-N-(piperidin-3-yl)-4,5-dihydro-3H-1-thia-3,5,8-triazaacenaphthylene-2-carboxamide (59.9 mg, 0.12 mmol), sodium cyanoborohydride (18 mg, 0.29 mmol), and MeOH (4 mL) and the flask was cooled to 0° C. in an ice bath. Next, aqueous formaldehyde (0.01 mL, 37 wt. % in H$_2$O) was added via syringe through the septum cap and the reaction was allowed to slowly warm to rt and stir at rt for 30 min. The reaction mixture was purified by HPLC to give the title compound (14.7 mg, 23.9% yield). MS (ESI): mass calcd. for C$_{28}$H$_{27}$N$_5$O$_3$S, 513.6; m/z found, 514.0 [M+H]$^+$. $^1$H NMR (500 MHz, CD$_3$OD): δ 8.16 (d, J=5.6 Hz, 1H), 7.29 (s, 2H), 7.18 (d, J=8.6 Hz, 1H), 7.12-6.80 (m, 5H), 5.90 (d, J=5.5 Hz, 1H), 4.13-3.51 (m, 2H), 2.92-2.74 (m, 1H), 2.69-2.52 (m, 1H), 2.23 (s, 3H), 2.12-1.98 (m, 5H), 1.90-1.30 (m, 5H).

Example 340: (R)-5-(4-Methoxy-2-methylphenyl)-N-(1-methylpiperidin-3-yl)-4-oxo-4,5-dihydro-3H-1-thia-3,5,8-triazaacenaphthylene-2-carboxamide

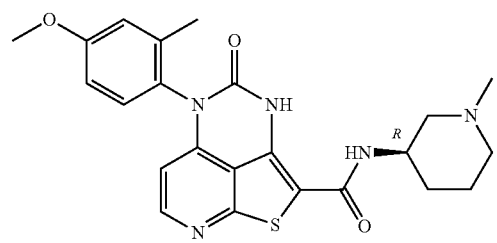

The title compound was prepared using analogous conditions as described in Method 1, steps C-G in Example 1, and using 4-methoxy-2-methylaniline in place of 2-methyl-4-phenoxyaniline in step C, and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{23}H_{25}N_5O_3S$, 451.5; m/z found, 452.2 [M+H]$^+$. $^1$H NMR (400 MHz, cd3od) δ 8.28 (d, J=5.5 Hz, 1H), 7.27-7.17 (m, 1H), 7.06-6.97 (m, 1H), 6.97-6.88 (m, 1H), 6.05-5.91 (d, J=5.6 Hz, 1H), 4.24-4.09 (m, 1H), 3.85 (s, 3H), 3.01-2.85 (m, 1H), 2.78-2.62 (m, 1H), 2.34 (s, 3H), 2.25-2.14 (m, 2H), 2.12 (s, 3H), 1.93-1.76 (m, 2H), 1.73-1.61 (m, 1H), 1.57-1.43 (m, 1H).

Example 341: (R)-4-Oxo-N-(piperidin-3-yl)-5-(4-(trifluoromethyl)phenyl)-4,5-dihydro-3H-1-thia-3,5,8-triazaacenaphthylene-2-carboxamide

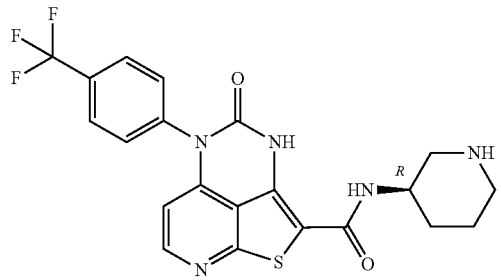

The title compound was prepared in a manner analogous to Method 1, steps C-H in Example 1, and using 4-(trifluoromethyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{21}H_{18}F_3N_5O_2S$, 461.5; m/z found, 462.0 [M+H]$^+$. $^1$H NMR (400 MHz, DMSO-d6) δ 10.32 (s, 1H), 9.31 (s, 1H), 9.11 (s, 1H), 8.37-8.33 (m, 2H), 8.02 (d, J=8.4 Hz, 2H), 7.76 (d, J=8.2 Hz, 2H), 6.11 (d, J=5.6 Hz, 1H), 4.21 (s, 1H), 3.32-3.30 (m, 1H), 3.21-3.18 (m, 1H), 2.94-2.81 (m, 2H), 1.92-1.89 (m, 2H), 1.81-1.58 (m, 2H).

Example 342: (R)-5-(4-Methoxyphenyl)-4-oxo-N-(piperidin-3-yl)-4,5-dihydro-3H-1-thia-3,5,8-triazaacenaphthylene-2-carboxamide

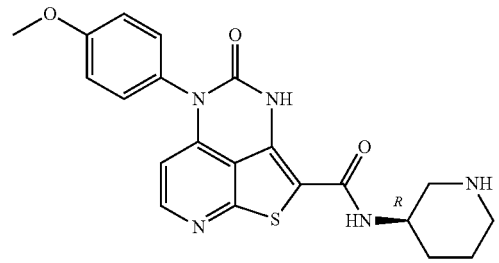

The title compound was prepared in a manner analogous to Method 1, steps C-H in Example 1, and using 4-methoxyaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{21}H_{21}N_5O_3S$, 423.5; m/z found, 423.9 [M+H]$^+$. 1H NMR (400 MHz, DMSO-d6) δ 8.48 (s, 1H), 8.28-8.20 (m, 2H), 7.28 (d, J=7.2 Hz, 2H), 7.11 (d, J=8.7 Hz, 2H), 5.89 (s, 1H), 4.05 (s, 1H), 3.83 (s, 3H), 3.25-3.22 (m, 1H), 3.09-3.06 (m, 1H), 2.74 (brs, 2H), 1.94-1.91 (m, 1H), 1.82 (brs, 1H), 1.60 (brs, 2H).

Example 343: (R)-5-(R)-(2-Methyl-4-((tetrahydro-2H-pyran-4-yl)oxy)phenyl)-N-(1-methylpiperidin-3-yl)-4-oxo-4,5-dihydro-3H-1-thia-3,5,8-triazaacenaphthylene-2-carboxamide

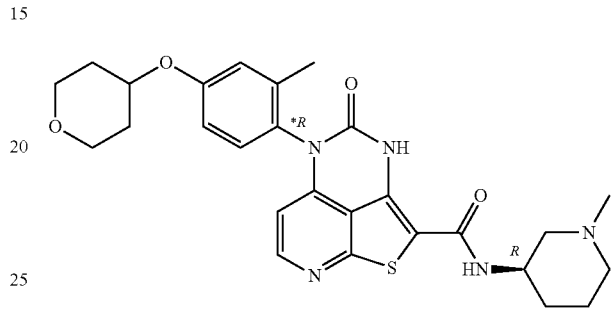

Step A: R)-5-(R)-(2-Methyl-4-((tetrahydro-2H-pyran-4-yl)oxy)phenyl)-4-oxo-N-(piperidin-3-yl)-4,5-dihydro-3H-1-thia-3,5,8-triazaacenaphthylene-2-carboxamide The title compound was prepared using analogous conditions as described in Method 1, steps D-H in Example 1 (including Chiral Resolution Method A after step F to obtain the *R atropisomer), and using 2-chloro-4-(2-methyl-4-tetrahydropyran-4-yloxyanilino)pyridine-3-carbonitrile (Intermediate 31 in place of 2-chloro-4-(2-methyl-4-phenoxyanilino)pyridine-3-carbonitrile in step D, and using tert-butyl (3R)-3-aminopiperidine-1-carboxylate in place of tert-butyl (3R,5R)-3-amino-5-fluoropiperidine-1-carboxylate (Intermediate 1) in step G (216 mg).

Step B: (R)-5-(*R)-(2-Methyl-4-((tetrahydro-2H-pyran-4-yl)oxy)phenyl)-N-(1-methylpiperidin-3-yl)-4-oxo-4,5-dihydro-3H-1-thia-3,5,8-triazaacenaphthylene-2-carboxamide A solution of (R)-5-(*R)-(2-methyl-4-((tetrahydro-2H-pyran-4-yl)oxy)phenyl)-4-oxo-N-(piperidin-3-yl)-4,5-dihydro-3H-1-thia-3,5,8-triazaacenaphthylene-2-carboxamide (80 mg, 0.16 mmol), formaldehyde (0.5 mL, 37 wt. % in H$_2$O), and NaBH(OAc)$_3$ (50 mg, 0.24 mmol) in DCM (5 mL) was stirred at rt for 5 h. The mixture was concentrated to dryness and purified by flash column chromatography to give the title compound as a yellow solid (25 mg, 29% yield). MS (ESI): mass calcd. for $C_{27}H_{31}N_5O_4S$, 521.6; m/z found, 522.0 [M+H]$^+$. $^1$H NMR (400 MHz, CD$_3$OD): δ 8.47 (s, 1H), 8.36-8.28 (m, 1H), 7.27-7.16 (m, 1H), 7.09-6.95 (m, 2H), 6.08-6.01 (m, 1H), 4.70-4.61 (m, 1H), 4.34-4.22 (m, 1H), 4.03-3.90 (m, 2H), 3.68-3.56 (m, 2H), 3.47-3.37 (m, 1H), 2.81-2.70 (m, 5H), 2.16-1.95 (m, 8H), 1.87-1.63 (m, 4H).

Example 344: (R)-5-([1,1'-Biphenyl]-4-yl)-4-oxo-N-(piperidin-3-yl)-4,5-dihydro-3H-1-thia-3,5,8-triazaacenaphthylene-2-carboxamide

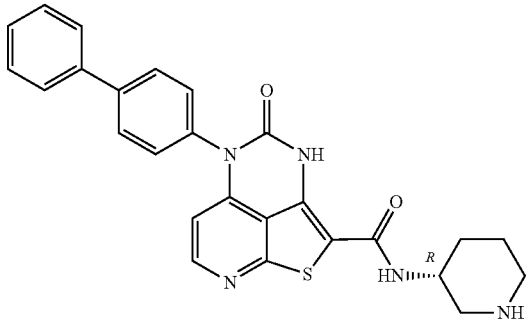

Step A: (R)-tert-Butyl 3-(5-([1,1'-biphenyl]-4-yl)-4-oxo-4,5-dihydro-3H-1-thia-3,5,8-triazaacenaphthylene-2-carboxamido)piperidine-1-carboxylate To a 2-5 mL microwave vial with stir bar were added 1,1'-bis(diphenylphosphino)ferrocene-palladium(II)dichloride dichloromethane complex (5.4 mg, 0.0066 mmol), 2-chloro-4-iodonicotinonitrile (86.7 mg, 0.328 mmol), 4-aminobiphenyl (56.8 mg, 0.336 mmol), and Cs$_2$CO$_3$ (151 mg, 0.463 mmol) at rt. The vial was sealed, charged with dioxane (0.66 mL) via syringe, and quickly evacuated/flushed with argon (4×). The mixture was stirred at 150° C. under argon for 30 min. The reaction was treated with (R)-tert-butyl 3-(2-mercaptoacetamido)piperidine-1-carboxylate (Intermediate 22) (0.51 mL, 0.65 M, 0.33 mmol) via syringe at rt, and stirred under argon at 150° C. for 15 min. The mixture was then cooled to rt, opened, and treated with CDI (218 mg, 1.34 mmol) in one portion under air. The microwave vial was resealed, evacuated/flushed with argon (4×), and stirred at 150° C. under argon for 15 min. The reaction was then cooled to rt, diluted with EtOAc (10 mL), and washed with 0.5 M citric acid (1×10 mL; final pH~4-5), 0.1 M citric acid (1×10 mL; final pH~2), and 2 M K$_2$CO$_3$ (1×10 mL; final pH>10). The organic phase was dried over anhydrous Na$_2$SO$_4$, filtered, and concentrated to dryness. The residue was purified by flash column chromatography to give the title compound as a yellow foam (89.7 mg, 48%).

Step C: (R)-5-([1,1'-Biphenyl]-4-yl)-4-oxo-N-(piperidin-3-yl)-4,5-dihydro-3H-1-thia-3,5,8-triazaacenaphthylene-2-carboxamide A solution of (R)-tert-butyl 3-(5-([1,1'-biphenyl]-4-yl)-4-oxo-4,5-dihydro-3H-1-thia-3,5,8-triazaacenaphthylene-2-carboxamido)piperidine-1-carboxylate (86.6 mg, 0.152 mmol) in dioxane (0.76 mL, 0.2 M, 0.152 mmol) in an 8 mL reaction vial was stirred under air at rt while HCl (4 M in dioxane, 2 mL, 8 mmol) was added dropwise over ~1 min and then capped and stirred at rt for 1 h, filtered to collect the precipitate, washed with dioxane (1×2 mL), and concentrated to dryness to give the title compound as an off-white powder (65.4 mg, 85.0%). MS (ESI): mass calcd. for C$_{26}$H$_{23}$N$_5$O$_2$S, 469.6; m/z found, 470.2 [M+H]$^+$. $^1$H NMR (400 MHz, CD$_3$OD): δ ppm 8.47 (d, J=6.1 Hz, 1H), 7.90 (d, J=8.6 Hz, 2H), 7.71 (d, J=7.1 Hz, 2H), 7.46-7.57 (m, 4H), 7.38-7.45 (m, 1H), 6.45 (d, J=6.6 Hz, 1H), 4.24-4.35 (m, 1H), 3.55 (dd, J=12.1, 4.0 Hz, 1H), 3.37 (d, J=12.6 Hz, 1H), 2.92-3.04 (m, 2H), 2.04-2.16 (m, 2H), 1.71-1.93 (m, 2H)

Example 345: (R)-5-(*R)-(2-Methyl-4-phenoxyphenyl)-4-oxo-N-(1-propionylpiperidin-3-yl)-4,5-dihydro-3H-1-thia-3,5,8-triazaacenaphthylene-2-carboxamide

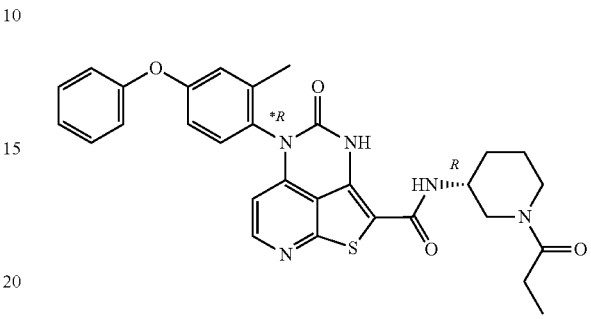

To a solution of (R)-5-(*R)(2-methyl-4-phenoxyphenyl)-4-oxo-N-(piperidin-3-yl)-4,5-dihydro-3H-1-thia-3,5,8-triazaacenaphthylene-2-carboxamide (Example 300, 50 mg, 0.10 mmol) in DCM (15 mL) were added triethylamine (30 mg) and acroyl chloride (26 mg, 0.20 mmol) and the mixture was stirred for 30 min at rt. The mixture was purified by flash column chromatography to give the title compound as yellow solid (31 mg, 56% yield). MS (ESI): mass calcd. for C$_{30}$H$_{29}$N$_5$O$_4$S, 555.6; m/z found, 556.1 [M+H]$^+$. $^1$H NMR (400 MHz, CD$_3$OD): δ 8.30 (d, J=5.5 Hz, 1H), 7.45-7.36 (m, 2H), 7.34-7.26 (m, 1H), 7.22-7.13 (m, 1H), 7.12-7.01 (m, 3H), 7.01-6.93 (m, 1H), 6.05 (d, J=5.5 Hz, 1H), 4.58-3.77 (m, 3H), 3.19-2.98 (m, 1H), 2.83-2.66 (m, 1H), 2.58-2.17 (m, 2H), 2.12 (s, 3H), 2.08-2.00 (m, 1H), 1.92-1.43 (m, 3H), 1.14-1.06 (m, 3H).

Example 346: (R)-5-(3,4-Dichlorophenyl)-4-oxo-N-(piperidin-3-yl)-4,5-dihydro-3H-1-thia-3,5,8-triazaacenaphthylene-2-carboxamide

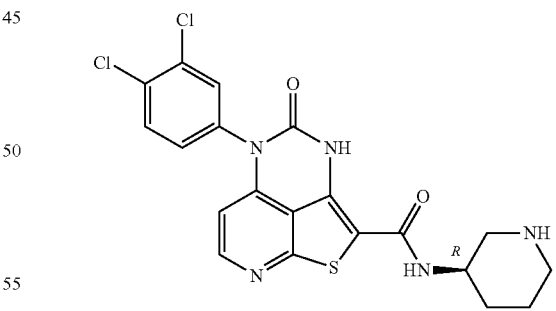

The title compound was prepared in a manner analogous to Method 1, steps C-H in Example 1, and using 3,4-dichloroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for C$_{20}$H$_{17}$Cl$_2$N$_5$O$_2$S, 462.4; m/z found, 461.8 [M+H]$^+$. $^1$H NMR (400 MHz, DMSO-d6): 8.72 (d, J=7.6 Hz, 1H), 8.20 (s, 1H), 8.13 (d, J=4.6 Hz, 1H), 7.81 (d, J=8.5 Hz, 1H), 7.70 (s, 1H), 7.37 (dd, J=8.5, 1.5 Hz, 1H), 5.94 (d, J=5.1 Hz, 1H), 4.05 (s, 1H), 3.31-3.27 (m, 1H), 3.13-3.10 (m, 1H), 2.86-2.71 (m, 2H), 1.95-1.84 (m, 2H), 1.71-1.51 (m, 2H).

Example 347: (R)-4-Oxo-N-(piperidin-3-yl)-5-(3-(trifluoromethyl)phenyl)-4,5-dihydro-3H-1-thia-3,5,8-triazaacenaphthylene-2-carboxamide

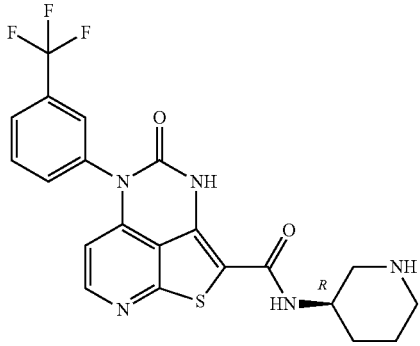

The title compound was prepared in a manner analogous to Method 1, steps C-H in Example 1, and using 3-(trifluoromethyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{21}H_{18}F_3N_5O_2S$, 461.5; m/z found, 461.9 [M+H]$^+$. 1H NMR (400 MHz, DMSO-d6) δ 8.72 (s, 1H), 8.22 (s, 1H), 8.15 (d, J=5.1 Hz, 1H), 7.88-7.72 (m, 3H), 7.68 (d, J=6.9 Hz, 1H), 5.85 (d, J=5.2 Hz, 1H), 4.06 (s, 1H), 3.31-3.28 (m, 1H), 3.13-3.10 (m, 1H), 2.83-2.73 (m, 2H), 1.97-1.94 (m, 1H), 1.88-1.84 (m, 1H), 1.72-1.51 (m, 2H).

Example 348: (R)-4-Oxo-5-phenyl-N-(piperidin-3-yl)-4,5-dihydro-3H-1-thia-3,5,8-triazaacenaphthylene-2-carboxamide

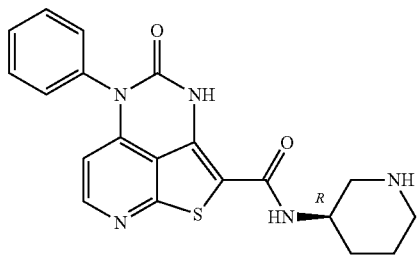

The title compound was prepared in a manner analogous to Method 1, steps C-H in Example 1, and using aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{20}H_{19}N_5O_2S$, 393.5; m/z found, 394.0 [M+H]$^+$. 1H NMR (400 MHz, DMSO-d6) δ 8.56 (s, 1H), 8.27 (s, 1H), 8.19-8.15 (m, 1H), 7.59-7.56 (m, 2H), 7.51-7.47 (m, 1H), 7.36 (d, J=7.5 Hz, 2H), 5.85-5.82 (m, 1H), 4.06 (s, 1H), 3.27-3.25 (m, 1H), 3.10-3.07 (m, 1H), 2.75 (s, 2H), 1.95-1.93 (m, 1H), 1.86-1.83 (m, 1H), 1.66-1.57 (m, 2H).

Example 349: (R)—N-(1-Methylpiperidin-3-yl)-4-oxo-5-(4-phenoxy-2-(trifluoromethyl)phenyl)-4,5-dihydro-3H-1-thia-3,5,8-triazaacenaphthylene-2-carboxamide

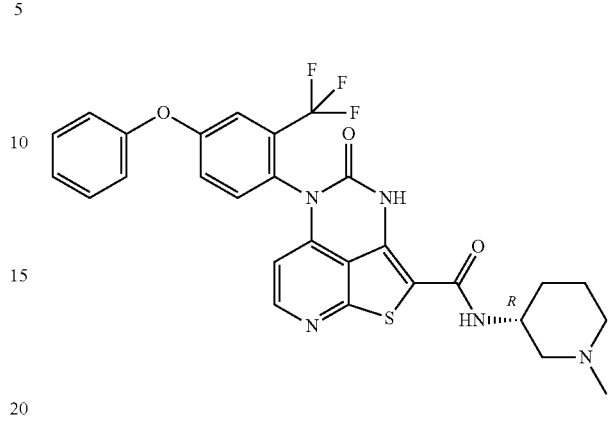

Step A: (R)-4-Oxo-5-(4-phenoxy-2-(trifluoromethyl)phenyl)-N-(piperidin-3-yl)-4,5-dihydro-3H-1-thia-3,5,8-triazaacenaphthylene-2-carboxamide The title compound was prepared using analogous conditions as described in Method 1, steps A-H in Example 1, and using 4-fluoro-1-nitro-2-(trifluoromethyl)benzene in place of 5-fluoro-2-nitrotoluene in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)—N-(1-Methylpiperidin-3-yl)-4-oxo-5-(4-phenoxy-2-(trifluoromethyl)phenyl)-4,5-dihydro-3H-1-thia-3,5,8-triazaacenaphthylene-2-carboxamide To a solution of (R)-4-oxo-5-(4-phenoxy-2-(trifluoromethyl)phenyl)-N-(piperidin-3-yl)-4,5-dihydro-3H-1-thia-3,5,8-triazaacenaphthylene-2-carboxamide (150 mg, 0.25 mmol) and formaldehyde (1.0 mL, 37 wt. % in H$_2$O) in MeOH (20 mL) was added NaBH(OAc)$_3$ (162 mg, 0.764 mmol) and was stirred at rt for 16 h, concentrated to dryness, and purified by flash column chromatography to give the title compound as a light yellow solid (116 mg, 80.3% yield). MS (ESI): mass calcd. for $C_{28}H_{24}F_3N_5O_3S$, 567.6; m/z found, 568.2 [M+H]$^+$. $^1$H NMR (400 MHz, DMSO-d$_6$): δ 8.35-8.25 (m, 1H), 8.22-8.16 (m, 2H), 7.75-7.60 (m, 1H), 7.57-7.37 (m, 4H), 7.33-7.17 (m, 3H), 6.00-5.90 (m, 1H), 4.10-3.83 (m, 1H), 3.00-2.85 (m, 1H), 2.83-2.63 (m, 1H), 2.28 (s, 3H), 2.18-1.91 (m, 2H), 1.85-1.65 (m, 2H), 1.64-1.46 (m, 1H), 1.46-1.28 (m, 1H).

Example 350: (R)-5-(4-Methyl-6-phenoxypyridazin-3-yl)-N-(1-methylpiperidin-3-yl)-4-oxo-4,5-dihydro-3H-1-thia-3,5,8-triazaacenaphthylene-2-carboxamide

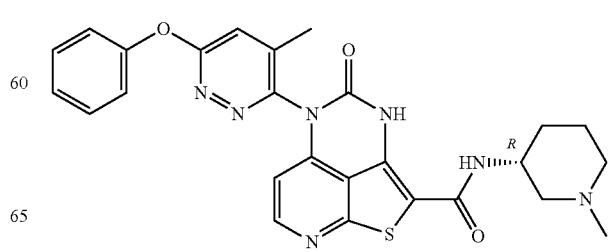

Step A: (R)-5-(4-methyl-6-phenoxypyridazin-3-yl)-4-oxo-N-(piperidin-3-yl)-4,5-dihydro-3H-1-thia-3,5,8-triazaacenaphthylene-2-carboxamide The title compound was prepared using analogous conditions as described in Method 1, steps A, and C-H in Example 1, and using 6-chloro-4-methylpyridazin-3-amine in place of 5-fluoro-2-nitrotoluene in step A (with no step B), and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(4-Methyl-6-phenoxypyridazin-3-yl)-N-(1-methylpiperidin-3-yl)-4-oxo-4,5-dihydro-3H-1-thia-3,5,8-triazaacenaphthylene-2-carboxamide To a solution of (R)-5-(4-methyl-6-phenoxypyridazin-3-yl)-4-oxo-N-(piperidin-3-yl)-4,5-dihydro-3H-1-thia-3,5,8-triazaacenaphthylene-2-carboxamide (20 mg, 0.040 mmol) in DCM (5 mL) were added formaldehyde (0.5 mL, 37 wt. % in $H_2O$) and $NaBH(OAc)_3$ (34 mg, 0.16 mmol) and was stirred at room temperature for 4 hours. To the mixture was added DCM (50 mL), MeOH (5 mL), and water (30 mL). The organic layer was collected, concentrated to dryness, and purified by TLC to give the title compound as a yellow solid (8 mg, 38% yield). MS (ESI): mass calcd. for $C_{26}H_{25}N_7O_3S$, 515.6; m/z found, 516.4 $[M+H]^+$. 1H NMR (400 MHz, DMSO-d6): δ 8.55 (br, 1H), 8.16-8.10 (br, 1H), 7.74 (s, 1H), 7.50-7.44 (m, 2H), 7.34-7.24 (m, 3H), 6.11-6.05 (br, 1H), 3.95-3.90 (m, 1H), 2.88-2.78 (m, 1H), 2.68-2.59 (m, 1H), 2.40 (s, 3H), 2.22 (s, 3H), 2.05-1.93 (m, 2H), 1.84-1.76 (m, 1H), 1.74-1.66 (m, 1H), 1.57-1.48 (m, 1H), 1.31-1.26 (m, 1H).

Example 351: (R)—N-(1-Acryloylpyrrolidin-3-yl)-5-(4-methyl-6-phenoxypyridazin-3-yl)-4-oxo-4,5-dihydro-3H-1-thia-3,5,8-triazaacenaphthylene-2-carboxamide

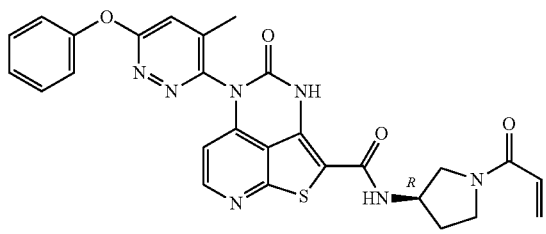

The title compound was prepared using analogous conditions as described in Method 1, steps A, and C-G in Example 1, and using 6-chloro-4-methylpyridazin-3-amine in place of 5-fluoro-2-nitrotoluene in step A (with no step B), and using 1-[(3R)-3-aminopyrrolidin-1-yl]prop-2-en-1-one (intermediate 5) in place of tert-butyl (3R,5R)-3-amino-5-fluoropiperidine-1-carboxylate (Intermediate 1) in step G. MS (ESI): mass calcd. for $C_{27}H_{23}N_7O_4S$, 541.6; m/z found, 542.4 $[M+H]^+$. 1H NMR (400 MHz, DMSO-d6): δ 8.24-8.14 (br, 1H), 7.78 (s, 1H), 7.53-7.42 (m, 2H), 7.36-7.22 (m, 3H), 6.66-6.50 (m, 1H), 6.24-6.03 (m, 2H), 5.71-5.60 (m, 1H), 4.53-4.40 (m, 1H), 3.91-3.82 (m, 1H), 3.74-3.62 (m, 3H), 2.40 (s, 3H), 2.21-1.85 (m, 2H).

Example 352: (R)—N-(1-Methylpiperidin-3-yl)-4-oxo-5-(o-tolyl)-4,5-dihydro-3H-1-thia-3,5,8-triazaacenaphthylene-2-carboxamide

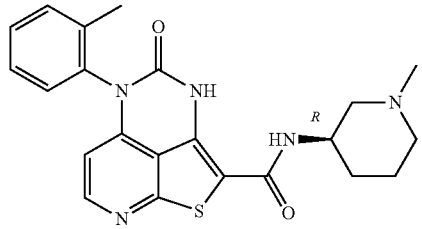

The title compound was prepared using analogous conditions as described in Method 1, steps C-G in Example 1, and using 2-methylaniline in place of 2-methyl-4-phenoxyaniline in step C, and using (3R)-1-methylpiperidin-3-amine in place of tert-butyl (3R,5R)-3-amino-5-fluoropiperidine-1-carboxylate (Intermediate 1) in step G. MS (ESI): mass calcd. for $C_{22}H_{23}N_5O_2S$, 421.5; m/z found, 422.1 $[M+H]^+$. 1H NMR (400 MHz, DMSO-d6 and CD3OD): δ 8.20 (d, J=5.1 Hz, 1H), 7.45-7.29 (m, 3H), 7.28-7.21 (m, 1H), 5.83 (d, J=5.3 Hz, 1H), 4.09-3.99 (m, 1H), 2.90-2.77 (m, 1H), 2.69-2.58 (m, 1H), 2.24 (s, 3H), 2.15-2.00 (m, 5H), 1.84-1.65 (m, 2H), 1.62-1.49 (m, 1H), 1.46-1.33 (m, 1H).

Example 353: (R)-5-(*R)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide

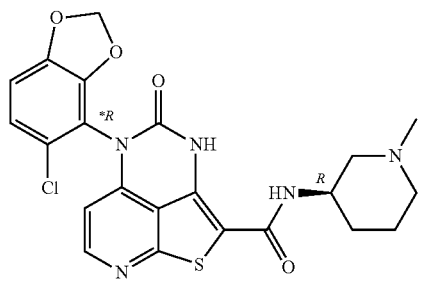

Step A: (R)-5-(*R)-(5-Chlorobenzo[d][1,3]dioxol-4-yl)-4-oxo-N-(piperidin-3-yl)-4,5-dihydro-3H-1-thia-3,5,8-triazaacenaphthylene-2-carboxamide The title compound was prepared using analogous conditions as described in Method 1, steps C-H in Example 1 (including Chiral Resolution Method A after step F to obtain the *R atropisomer), and using 2,4-dichloropyridine-3-carbonitrile and 5-chloro-1,3-benzodioxol-4-amine in place of 2-methyl-4-phenoxyaniline and 2-chloro-4-iodopyridine-3-carbonitrile in step C, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{21}H_{18}ClN_5O_4S$, 471.92; m/z found, 472.0 $[M+H]^+$.

Step B: (R)-5-(*R)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide To a solution of (R)-5-(*R)-(5-chlorobenzo[d][1,3]dioxol-4-yl)-4-oxo-N-(piperidin-3-yl)-4,5-dihydro-3H-1-thia- 3,5,8-triazaacenaphthylene-2-carboxamide (103 mg, 0.218 mmol) and formaldehyde (0.3 mL, 37 wt. % in $H_2O$) in MeOH (6 mL) was added $NaBH(OAc)_3$ (92 mg, 0.44 mmol) and was stirred at rt for 1 h, concentrated to dryness, and purified by flash column chromatography to give the title compound as a white solid (18 mg, 17% yield). MS (ESI): mass calcd. for $C_{22}H_{20}ClN_5O_4S$, 485.9; m/z found, 486.5 [M+H]+. $^1$H NMR (400 MHz, $CD_3OD$): δ 8.39 (d, J=5.4 Hz, 1H), 7.13 (d, J=8.4 Hz, 1H), 7.02 (d, J=8.4 Hz, 1H), 6.26 (d, J=5.5 Hz, 1H), 6.10 (d, J=2.3 Hz, 2H), 4.33-4.20 (m, 1H), 3.45-3.34 (m, 1H), 3.25-3.13 (m, 1H), 2.86-2.67 (m, 5H), 2.06-1.95 (m, 2H), 1.90-1.76 (m, 1H), 1.76-1.60 (m, 1H).

Example 354: (R)-5-(2-Methyl-4-(pyridin-4-yloxy) phenyl)-N-(1-methylpiperidin-3-yl)-4-oxo-4,5-dihydro-3H-1-thia-3,5,8-triazaacenaphthylene-2-carboxamide

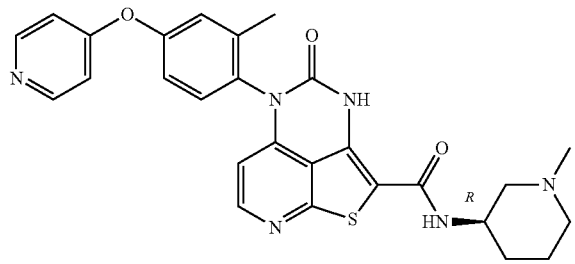

Step A: (R)-5-(2-Methyl-4-(pyridin-4-yloxy)phenyl)-4-oxo-N-(piperidin-3-yl)-4,5-dihydro-3H-1-thia-3,5,8-triazaacenaphthylene-2-carboxamide The title compound was prepared using analogous conditions as described in Method 1, steps A-H in Example 1, and using pyridin-4-ol in place of phenol in step A, and using tert-butyl (3R)-3-aminopiperidine-1-carboxylate in place of tert-butyl (3R,5R)-3-amino-5-fluoropiperidine-1-carboxylate (Intermediate 1) in step G.

Step B: (R)-5-(2-Methyl-4-(pyridin-4-yloxy)phenyl)-N-(1-methylpiperidin-3-yl)-4-oxo-4,5-dihydro-3H-1-thia-3,5,8-triazaacenaphthylene-2-carboxamide To a solution of (R)-5-(2-methyl-4-(pyridin-4-yloxy)phenyl)-4-oxo-N-(piperidin-3-yl)-4,5-dihydro-3H-1-thia-3,5,8-triazaacenaphthylene-2-carboxamide (110 mg, 0.22 mmol) and formaldehyde (0.3 mL, 37 wt. % in $H_2O$) in MeOH (5 mL) was added $NaBH(OAc)_3$ (140 mg, 0.66 mmol) and was stirred at rt for 1 h, concentrated to dryness, and purified by flash column chromatography to give the title compound as a white solid (72 mg, 64% yield). MS (ESI): mass calcd. for $C_{27}H_{26}N_6O_3S$, 514.6; m/z found, 515.5 [M+H]+. $^1$H NMR (400 MHz, $CD_3OD$): δ 8.40-8.24 (m, 1H), 8.17 (d, J=7.1 Hz, 2H), 7.70 (s, 1H), 7.74-7.52 (m, 2H), 6.59 (d, J=7.1 Hz, 2H), 6.16-5.94 (m, 1H), 4.30-4.14 (m, 1H), 3.29-3.17 (m, 1H), 3.09-2.09 (m, 1H), 2.72-2.44 (m, 5H), 2.27 (s, 3H), 2.04-1.86 (m, 2H), 1.84-1.70 (m, 1H), 1.65-1.49 (m, 1H).

Example 355: (R)—N-(1-Acryloylpiperidin-3-yl)-4-oxo-5-(4-(trifluoromethyl)phenyl)-4,5-dihydro-3H-1-thia-3,5,8-triazaacenaphthylene-2-carboxamide

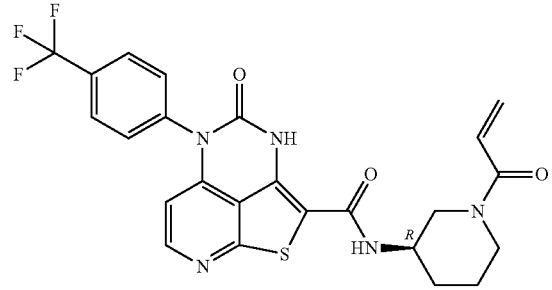

The title compound was prepared in a manner analogous to Method 1, steps C-I in Example 1, and using 4-(trifluoromethyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{24}H_{20}F_3N_5O_3S$, 515.5; m/z found, 516.0 [M+H]+. $^1$H NMR (400 MHz, DMSO-$d_6$): δ 10.29 (d, J=16.5 Hz, 1H), 8.33 (d, J=5.5 Hz, 1H), 8.14-8.08 (m, 1H), 8.01 (d, J=8.5 Hz, 2H), 7.75 (d, J=8.2 Hz, 2H), 6.78 (brs, 1H), 6.13-6.07 (m, 2H), 5.69 (d, J=10.1 Hz, 1H), 4.54-4.16 (m, 1H), 4.10-3.74 (m, 2H), 3.05-2.94 (m, 1H), 2.80-2.73 (m, 1H), 1.96-1.93 (m, 1H), 1.80-1.77 (m, 1H), 1.72-1.63 (m, 1H), 1.43 (s, 1H).

Example 356: (R)-5-(3-(Dimethylamino)phenyl)-4-oxo-N-(piperidin-3-yl)-4,5-dihydro-3H-1-thia-3,5,8-triazaacenaphthylene-2-carboxamide

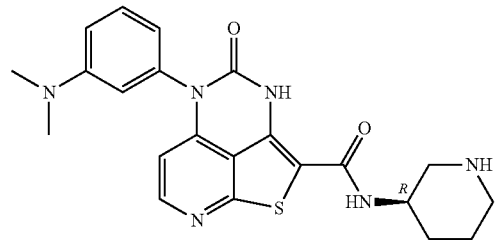

The title compound was prepared in a manner analogous to Method 1, steps C-H in Example 1, and using 3-(dimethylamino)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{22}H_{24}N_6O_2S$, 436.5; m/z found, 437.0 [M+H]+. 1H NMR (400 MHz, DMSO-d6) δ 8.44 (d, J=7.6 Hz, 1H), 8.32 (s, 1H), 8.22 (d, J=5.5 Hz, 1H), 7.38-7.34 (m, 1H), 6.83 (dd, J=8.4, 2.2 Hz, 1H), 6.73-6.66 (m, 1H), 6.61 (d, J=7.5 Hz, 1H), 5.94 (d, J=5.5 Hz, 1H), 4.09 (s, 1H), 3.26-3.22 (m, 1H), 3.13-3.03 (m, 1H), 2.92 (s, 6H), 2.80-2.74 (m, 2H), 1.93-1.83 (m, 2H), 1.66-1.58 (m, 2H).

397

Example 357: (R)—N-(1-Acryloylpiperidin-3-yl)-5-isopropyl-4-oxo-4,5-dihydro-3H-1-thia-3,5,8-triaz-aacenaphthylene-2-carboxamide

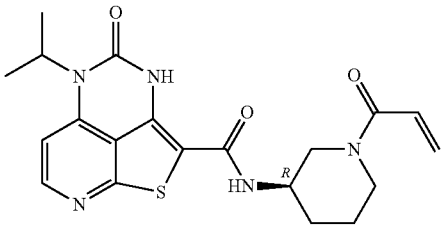

The title compound was prepared in a manner analogous to Method 1, steps C-I in Example 1, and using propan-2-amine in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{20}H_{23}N_5O_3S$, 413.5; m/z found, 414.0 [M+H]$^+$. $^1$H NMR (400 MHz, DMSO-d$_6$): δ 8.43-8.33 (m, 3H), 6.94 (d, J=8.5 Hz, 1H), 6.85-6.74 (m, 1H), 6.13-6.07 (m, 1H), 5.68 (d, J=10.6 Hz, 1H), 4.88 (s, 1H), 4.43-4.10 (m, 1H), 4.04-3.89 (m, 1H), 3.76 (s, 1H), 3.13-2.85 (m, 3H), 1.95-1.93 (m, 1H), 1.80-1.77 (m, 1H), 1.61 (s, 1H), 1.45 (d, J=6.8 Hz, 6H).

Example 358: (R)—N-(1-Acryloylpiperidin-3-yl)-5-(2-methylpyridin-3-yl)-4-oxo-4,5-dihydro-3H-1-thia-3,5,8-triazaacenaphthylene-2-carboxamide

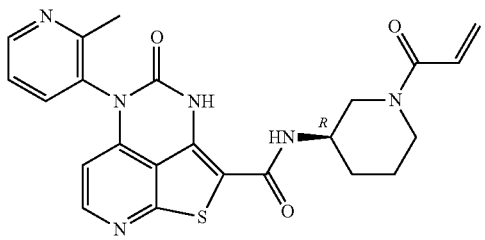

Step A: 2-Chloro-4-[(2-methyl-3-pyridyl)amino]pyridine-3-carbonitrile

To a 10-20 mL microwave vial were added sequentially 2,4-dichloropyridine-3-carbonitrile (429 mg, 1.62 mmol), 2-methylpyridin-3-amine (175 mg, 1.62 mmol), palladium (II) acetate (7.3 mg, 0.032 mmol), bis(2-diphenylphosphinophenyl)ether (26 mg, 0.049 mmol), and Cs$_2$CO$_3$ (740 mg, 2.27 mmol). The vial was sealed and was evacuated and refilled with argon three times and dioxane (3.2 mL) was added. The vial was evacuated and refilled with argon once. The suspension was heated for 5 minutes in a 50° C. oil bath under argon and then the sealed vial was heated for 30 minutes in a 150° C. oil bath. The suspension was removed from the heating bath and stored at room temperature overnight. The crude reaction mixture was used directly in the next step.

398

Step B: tert-butyl (3R)-3-[[3-amino-4-[(2-methyl-3-pyridyl)amino]thieno[2,3-b]pyridine-2-carbonyl]amino]piperidine-1-carboxylate To a sealed tube containing 2-chloro-4-[(2-methyl-3-pyridyl)amino]pyridine-3-carbonitrile (397 mg, 1.62 mmol) was added a 0.5 M solution of tert-butyl (3R)-3-[(2-sulfanylacetyl)amino]piperidine-1-carboxylate (Intermediate 22) in dioxane (3.89 mL, 1.95 mmol) and was heated in the sealed tube in a 150° C. oil bath for 15 minutes. The mixture was cooled to rt to give the title compound, which was used directly in the next reaction.

Step C: (R)-tert-Butyl 3-(5-(2-methylpyridin-3-yl)-4-oxo-4,5-dihydro-3H-1-thia-3,5,8-triazaacenaphthylene-2-carboxamido)piperidine-1-carboxylate To a reaction vial containing of tert-butyl (3R)-3-[[3-amino-4-[(2-methyl-3-pyridyl)amino]thieno[2,3-b]pyridine-2-carbonyl]amino]piperidine-1-carboxylate (783 mg, 1.62 mmol) was added CDI (1.052 g, 6.488 mmol). The reaction vial was sealed and the vessel was evacuated and refilled with argon twice. The mixture was heated for 5 minutes in a 50° C. oil bath under argon, then it was heated at 150° C. for 10 minutes, then the mixture was cooled to room temperature. The mixture was partitioned between EtOAc (50 mL) and water (50 mL). The aqueous phase was extracted with EtOAc (2×50 mL) and the combined organic extracts were washed with saturated aqueous NaCl (50 mL). The organic phase was dried over anhydrous Na$_2$SO$_4$, filtered, and concentrated to dryness. The residue was purified by flash column chromatography to give the title compound as a yellow solid (699.7 mg, 84.82% yield).

Step D: (R)-5-(2-Methylpyridin-3-yl)-4-oxo-N-(piperidin-3-yl)-4,5-dihydro-3H-1-thia-3,5,8-triazaacenaphthylene-2-carboxamide To a solution of (R)-tert-butyl 3-(5-(2-methylpyridin-3-yl)-4-oxo-4,5-dihydro-3H-1-thia-3,5,8-triazaacenaphthylene-2-carboxamido)piperidine-1-carboxylate (699.7 mg, 1.376 mmol) in dioxane (5 mL) was added HCl in dioxane (5 mL, 4 M, 20 mmol). The suspension was stirred at rt for 30 min. The reaction mixture was filtered, the precipitate washed with dioxane and was air-dried. The gummy solid was dissolved in a mixture of MeOH and DCM and the resulting solution was concentrated to dryness and dried under vacuum to yield a yellow foamy solid (689.3 mg). Part of the residue (200 mg) was purified by HPLC to give the title compound as a white powder (36.9 mg).

Step E: (R)—N-(1-Acryloylpiperidin-3-yl)-5-(2-methylpyridin-3-yl)-4-oxo-4,5-dihydro-3H-1-thia-3,5,8-triazaacenaphthylene-2-carboxamide To a suspension of crude (R)-5-(2-methylpyridin-3-yl)-4-oxo-N-(piperidin-3-yl)-4,5-dihydro-3H-1-thia-3,5,8-triazaacenaphthylene-2-carboxamide (127 mg, 0.264 mmol) in THF (2.5 mL) was added triethylamine (147 µL, 1.06 mmol). To the resulting suspension was added a solution of acryloyl chloride in DCM (2.9 mL, 0.10 M, 0.29 mmol). The suspension was stirred at rt for 15 min. The reaction mixture was concentrated to dryness, the residue dissolved in MeOH, and purified by HPLC to give the title compound as a white powder (15.6 mg). MS (ESI): mass calcd. for $C_{23}H_{22}N_6O_3S$, 462.5; m/z found, 463.2 [M+H]$^+$. 1H NMR (400 MHz, MeOH, 1:1 mixture of rotamers) δ 8.72-8.77 (m, 1H), 8.38 (d, J=5.56 Hz, 1H), 8.16-8.24 (m, 1H), 7.70-7.78 (m, 1H), 6.75-6.86 (m, 1H), 6.21 (dd, J=4.04, 16.67 Hz, 1H), 6.15 (d, J=5.56 Hz, 1H), 5.75 (t, J=9.09 Hz, 1H), 4.51-4.59 (m, 0.5H), 4.26-4.35 (m, 0.5H), 4.14-4.21 (m, 0.5H), 3.92-4.06 (m, 1.5H), 3.13-3.26 (m, 1H), 2.83-2.99 (m, 1H), 2.03-2.12 (m, 1H), 1.83-1.94 (m, 1H), 1.66-1.83 (m, 1H), 1.53-1.66 (m, 1H).

Example 359: (R)-5-(2-Methylpyridin-3-yl)-4-oxo-N-(piperidin-3-yl)-4,5-dihydro-3H-1-thia-3,5,8-triazaacenaphthylene-2-carboxamide

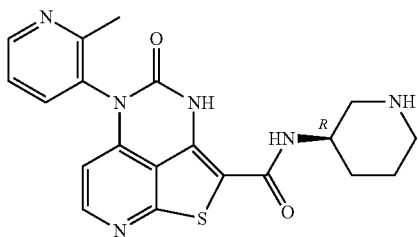

The title compound was prepared using the conditions described in Example 358, steps A-D. MS (ESI): mass calcd. for $C_{20}H_{20}N_6O_2S$, 408.5; m/z found, 409.2 [M+H]$^+$. $^1$H NMR (400 MHz, CD$_3$OD): δ 8.70 (d, J=3.54 Hz, 1H), 8.39 (d, J=5.56 Hz, 1H), 8.05 (d, J=8.08 Hz, 1H), 7.65 (dd, J=5.05, 8.08 Hz, 1H), 6.13 (d, J=5.56 Hz, 1H), 4.28 (tt, J=3.85, 10.80 Hz, 1H), 3.54 (dd, J=4.04, 12.13 Hz, 1H), 3.37 (d, J=12.63 Hz, 1H), 2.87-3.04 (m, 2H), 2.47 (s, 3H), 2.00-2.20 (m, 2H), 1.62-1.95 (m, 2H).

Example 360: (R)—N-(1-Acryloylpiperidin-3-yl)-5-(3,4-dichlorophenyl)-4-oxo-4,5-dihydro-3H-1-thia-3,5,8-triazaacenaphthylene-2-carboxamide

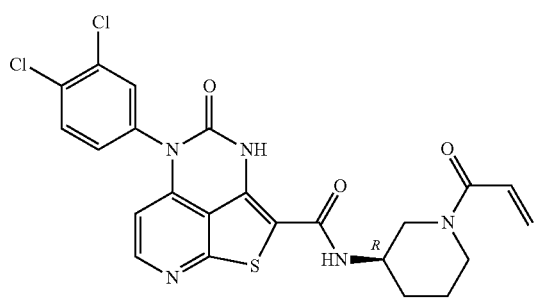

The title compound was prepared in a manner analogous to Method 1, steps C-I in Example 1, and using 3,4-dichloroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{23}H_{19}Cl_2N_5O_3S$, 516.4; m/z found, 515.8 [M+H]$^+$. $^1$H NMR (400 MHz, CD$_3$OD): δ 8.46 (d, J=6.1 Hz, 1H), 7.83 (d, J=8.5 Hz, 1H), 7.78 (s, 1H), 7.47 (d, J=8.6 Hz, 1H), 6.82 (dd, J=16.7, 10.6 Hz, 1H), 6.40 (s, 1H), 6.23 (dd, J=16.5, 7.4 Hz, 1H), 5.79-5.74 (m, 1H), 4.59-4.24 (m, 1H), 4.21-3.94 (m, 2H), 3.26-3.14 (m, 1H), 2.98-2.88 (m, 1H), 2.12-2.09 (m, 1H), 1.92-1.89 (m, 1H), 1.78 (brs, 1H), 1.63 (brs, 1H).

Example 361: (R)-5-Isopropyl-4-oxo-N-(piperidin-3-yl)-4,5-dihydro-3H-1-thia-3,5,8-triazaacenaphthylene-2-carboxamide

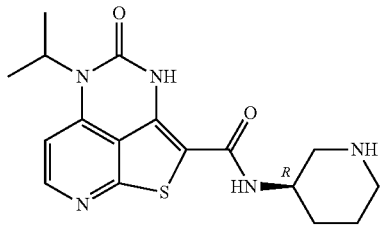

The title compound was prepared in a manner analogous to Method 1, steps C-H in Example 1, and using propan-2-amine in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{17}H_{21}N_5O_2S$, 359.4; m/z found, 360.1 [M+H]$^+$. 1H NMR (400 MHz, DMSO-d6) δ 9.99 (s, 1H), 9.28 (s, 1H), 9.11 (s, 1H), 8.50 (d, J=5.8 Hz, 1H), 8.29 (d, J=7.5 Hz, 1H), 7.17 (d, J=5.9 Hz, 1H), 4.76 (s, 1H), 4.25-4.11 (m, 1H), 3.33-3.23 (m, 1H), 3.19-3.16 (m, 1H), 2.95-2.74 (m, 2H), 1.91-1.88 (m, 2H), 1.79-1.57 (m, 2H), 1.48 (d, J=6.9 Hz, 6H).

Example 362: (R)—N-(1-Acryloylpiperidin-3-yl)-5-(4-chloro-3-(trifluoromethyl)phenyl)-4-oxo-4,5-dihydro-3H-1-thia-3,5,8-triazaacenaphthylene-2-carboxamide

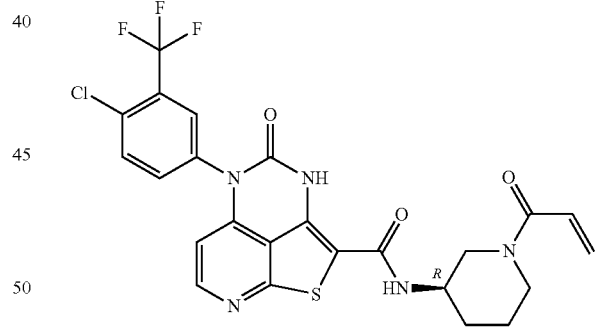

The title compound was prepared in a manner analogous to Method 1, steps C-I in Example 1, and using 4-chloro-3-(trifluoromethyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{24}H_{19}ClF_3N_5O_3S$, 550.0; m/z found, 549.9 [M+H]$^+$. $^1$H NMR (400 MHz, DMSO-d$_6$): δ 10.29 (d, J=15.3 Hz, 1H), 8.35 (d, J=5.5 Hz, 1H), 8.14-8.10 (m, 2H), 8.01 (d, J=8.5 Hz, 1H), 7.88 (dd, J=8.5, 2.3 Hz, 1H), 6.87-6.72 (m, 1H), 6.18 (d, J=5.5 Hz, 1H), 6.12 (d, J=16.5 Hz, 1H), 5.69 (dd, J=10.5, 2.3 Hz, 1H), 4.53-4.17 (m, 1H), 4.11-3.98 (m, 1H), 3.19-2.94 (m, 2H), 2.85-2.62 (m, 1H), 2.01-1.91 (m, 1H), 1.86-1.59 (m, 2H), 1.44 (s, 1H).

Example 363: (R)—N-(1-(3-Methoxy-3-methylbutanoyl)piperidin-3-yl)-5-(2-methyl-4-phenoxyphenyl)-4-oxo-4,5-dihydro-3H-1-thia-3,5,8-triazaacenaphthylene-2-carboxamide

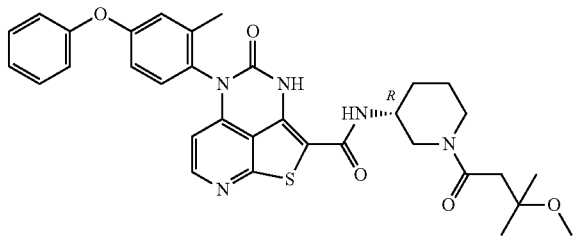

Step A: 3-Methoxy-3-methylbutanoic Acid

To a cold solution of sodium hypobromite [prepared from NaOH (1.6 g, 40 mmol), bromine (3.2 g, 20 mmol), and water (6 g)] was added with stirring 4-methoxy-4-methylpentan-2-one (650 mg, 5.0 mmol), keeping the temperature below 20° C. After the addition of the ketone was complete, the reaction mixture was stirred an additional 3 h, the bromoform layer was removed and the aqueous layer washed repeatedly with dilute sulfuric acid, and sodium bisulfite was added to destroy excess bromine. The acid was isolated by ether extraction, washed with brine, and dried over anhydrous MgSO$_4$, filtered, and concentrated to dryness to give the title compound as a yellow oil (201 mg).

Step B: (R)—N-(1-(3-Methoxy-3-methylbutanoyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), 3-methoxy-3-methylbutanoic acid (45 mg, 0.34 mmol), HATU (138 mg, 0.363 mmol), and triethylamine (0.156 mL, 1.12 mmol) in DMF (3 mL) was stirred at rt overnight, then purified by flash column chromatography and preparative TLC to give the title compound as a white solid (80 mg, 46% yield). MS (ESI): mass calcd. for C$_{33}$H$_{35}$N$_5$O$_5$S, 613.7; m/z found, 614.3 [M+H]$^+$. $^1$H NMR (400 MHz, CD$_3$OD): δ 8.37-8.29 (m, 1H), 7.46-7.36 (m, 2H), 7.34-7.27 (m, 1H), 7.21-7.13 (m, 1H), 7.13-7.03 (m, 3H), 7.01-6.94 (m, 1H), 6.15-6.00 (m, 1H), 4.45-4.32 (m, 1H), 4.26-3.91 (m, 2H), 3.23 (s, 3H), 3.18-3.03 (m, 1H), 2.96-2.68 (m, 1H), 2.66-2.58 (m, 2H), 2.12 (s, 3H), 2.08-1.98 (m, 1H), 1.88-1.79 (m, 1H), 1.72-1.47 (m, 2H), 1.34-1.24 (m, 6H).

Example 364: (R,Z)—N-(1-(3-Acetamidoacryloyl)piperidin-3-yl)-5-(2-methyl-4-phenoxyphenyl)-4-oxo-4,5-dihydro-3H-1-thia-3,5,8-triazaacenaphthylene-2-carboxamide

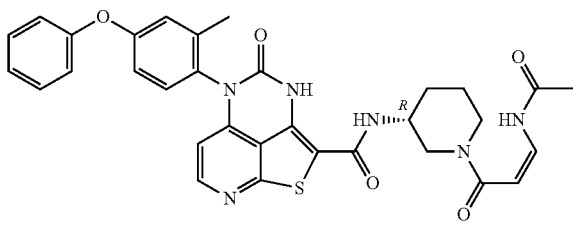

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.4 mmol), (Z)-3-acetamidoprop-2-enoic acid (Intermediate 33, 129 mg, 1.00 mmol), triethylamine (101 mg, 1.00 mmol), and HATU (380 mg, 1.0 mmol) in DMF (3 mL) was stirred at rt for 3 h. Water was added and the precipitate was collected by filtration. The residue was purified by flash column chromatography to give the title compound as a yellow solid (13 mg, 5.2% yield). MS (ESI): mass calcd. for C$_{32}$H$_{30}$N$_6$O$_5$S, 610.7; m/z found, 611.2 [M+H]$^+$. $^1$H NMR (400 MHz, CD$_3$OD): δ 8.32 (d, J=5.5 Hz, 1H), 7.46-7.27 (m, 4H), 7.21-7.13 (m, 1H), 7.14-7.03 (m, 3H), 7.02-6.94 (m, 1H), 6.07 (d, J=5.5 Hz, 1H), 5.64 (d, J=8.8 Hz, 1H), 4.51-4.33 (m, 1H), 4.16-3.88 (m, 3H), 3.15-2.94 (m, 1H), 2.16-2.02 (m, 7H), 1.93-1.84 (m, 1H), 1.82-1.71 (m, 1H), 1.63-1.54 (m, 1H).

Example 365: (R,E)-N-(1-(2-Cyano-3-cyclopropylacryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide

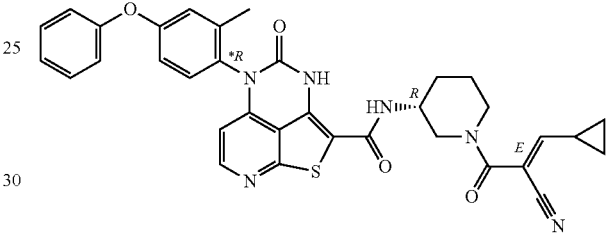

A solution of (R)-5-(*R)-(2-methyl-4-phenoxyphenyl)-4-oxo-N-(piperidin-3-yl)-4,5-dihydro-3H-1-thia-3,5,8-triazaacenaphthylene-2-carboxamide (Example 300, 60 mg, 0.12 mmol), (E)-2-cyano-3-cyclopropylprop-2-enoic acid (Intermediate 17) (23 mg, 0.17 mmol), HATU (55 mg, 0.15 mmol), and triethylamine (0.062 mL 0.45 mmol) in DMF (2 mL) was stirred at rt overnight. The reaction mixture was purified by flash column chromatography and preparative TLC to give the title compound as a yellow solid (13 mg, 18% yield). MS (ESI): mass calcd. for C$_{34}$H$_{30}$N$_6$O$_4$S, 618.7; m/z found, 619.2 [M+H]$^+$. $^1$H NMR (400 MHz, CD$_3$OD): δ 8.34 (d, J=5.5 Hz, 1H), 7.45-7.35 (m, 2H), 7.33-7.26 (m, 1H), 7.21-7.14 (m, 1H), 7.13-7.03 (m, 3H), 7.00-6.95 (m, 1H), 6.61-6.49 (m, 1H), 6.08 (d, J=5.6 Hz, 1H), 4.61-4.51 (m, 2H), 4.10-3.96 (m, 2H), 3.20-3.16 (m, 1H), 2.13 (s, 3H), 2.10-1.96 (m, 2H), 1.94-1.85 (m, 1H), 1.80-1.59 (m, 2H), 1.26-1.15 (m, 2H), 1.02-0.82 (m, 2H).

Example 366: (R)—N-(1-(2-Chloroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide

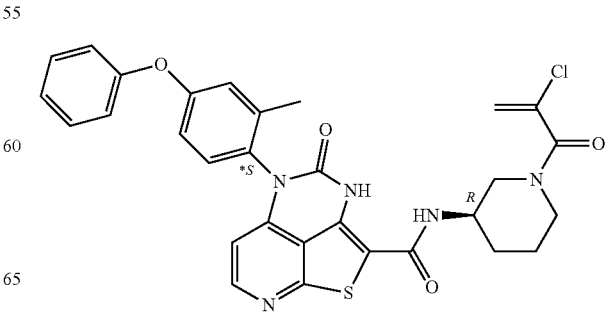

To a solution of (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98, 50 mg, 0.09 mmol), 2-chloroprop-2-enoic acid (20 mg, 0.19 mmol), HATU (46 mg, 0.12 mmol), and diisopropylethylamine (30 mg, 0.23 mmol) in DMF (5 mL) was stirred at rt for 2 h. The mixture was purified by flash column chromatography, and by preparative TLC to give the title compound as a white solid (10 mg, 18% yield). MS (ESI): mass calcd. for $C_{30}H_{26}ClN_5O_4S$, 588.1; m/z found, 588.2 $[M+H]^+$. $^1H$ NMR (400 MHz, $CD_3OD$): δ 8.36-8.30 (m, 1H), 7.44-7.37 (m, 2H), 7.33-7.27 (m, 1H), 7.21-7.14 (m, 1H), 7.12-7.03 (m, 3H), 7.01-6.95 (m, 1H), 6.11-6.05 (m, 1H), 5.72 (m, 2H), 4.45-3.88 (m, 3H), 3.25-2.90 (m, 2H), 2.17-2.02 (m, 4H), 1.95-1.84 (m, 1H), 1.81-1.69 (m, 1H), 1.66-1.57 (m, 1H).

Example 367: (R,E)-N-(1-(4-Aminobut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

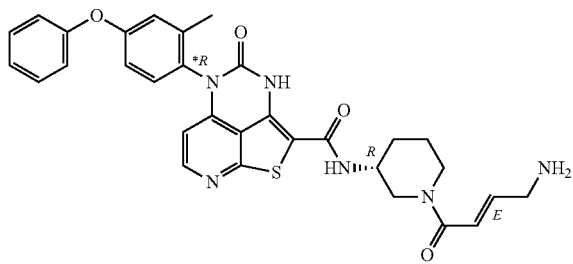

Step A: (R,E)-tert-Butyl (4-(3-(5-(*R)-(2-methyl-4-phenoxyphenl)-4-oxo-4,5-dihydro-3H-1-thia-3,5,8-triazaacenaphthylene-2-carboxamido)piperidin-1-yl)-4-oxobut-2-en-1-yl)carbamate A solution of (R)-5-(*R)-(2-methyl-4-phenoxyphenyl)-4-oxo-N-(piperidin-3-yl)-4,5-dihydro-3H-1-thia-3,5,8-triazaacenaphthylene-2-carboxamide (Example 300, 60 mg, 0.11 mmol), (E)-4-(tert-butoxycarbonylamino)but-2-enoic acid (Intermediate 12, 45 mg, 0.22 mmol), HATU (56 mg, 0.15 mmol), and diisopropylethylamine (36 mg, 0.28 mmol) in DMF (5 mL) was stirred at rt for 2 h. The mixture was purified by flash column chromatography, then by preparative TLC to give the title compound as a white solid (43 mg, 56% yield).

Step B: (R,E)-N-(1-(4-Aminobut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide To a round bottom flask were added (R,E)-tert-butyl (4-(3-(5-(*R)-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate (43 mg, 0.063 mmol), concentrated HCl (5 mL), and MeOH (5 mL) and was stirred at rt for 1 h. The mixture was concentrated to dryness and was purified by flash column chromatography to give the title compound as a white solid (19 mg, 48% yield). MS (ESI): mass calcd. for $C_{31}H_{30}N_6O_4S$, 582.7; m/z found, 583.3 $[M+H]^+$. $^1H$ NMR (400 MHz, $CD_3OD$): δ 8.38-8.32 (m, 1H), 7.45-7.37 (m, 2H), 7.32-7.26 (m, 1H), 7.21-7.14 (m, 1H), 7.13-7.03 (m, 3H), 7.02-6.94 (m, 1H), 6.86-6.78 (m, 1H), 6.77-6.67 (m, 1H), 6.13-6.06 (m, 1H), 4.45-3.90 (m, 3H), 3.80-3.70 (m, 2H), 3.23-3.07 (m, 1H), 2.91-2.80 (m, 1H), 2.16-2.02 (m, 4H), 1.94-1.84 (m, 1H), 1.81-1.69 (m, 1H), 1.65-1.52 (m, 1H).

Example 368: (R,E)-N-(1-(4-(Dimethylamino)but-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide

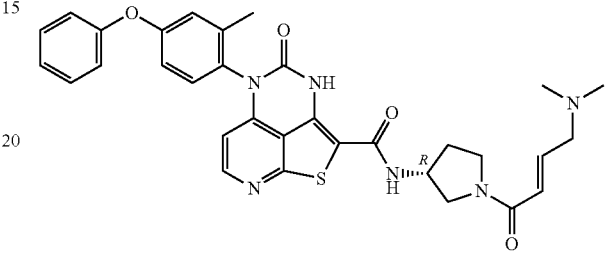

Step A: (R,E)-tert-Butyl (4-(3-(5-(2-methyl-4-phenoxyphenyl)-4-oxo-4,5-dihydro-3H-1-thia-3,5,8-triazaacenaphthylene-2-carboxamido)pyrrolidin-1-yl)-4-oxobut-2-en-1-yl)carbamate A solution of (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 300 mg, 0.58 mmol), (E)-4-(tert-butoxycarbonylamino)but-2-enoic acid (Intermediate 12, 231 mg, 1.15 mmol), HATU (284 mg, 0.747 mmol), and DIEA (186 mg, 1.44 mmol) in DMF (6 mL) was stirred at rt for 2 h. The mixture was purified by flash column chromatography using two different methods to give the title compound as a white solid (265 mg, 68.9% yield).

Step B: (R,E)-N-(1-(4-Aminobut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide To a round bottom flask were added (R,E)-tert-butyl (4-(3-(5-(2-methyl-4-phenoxyphenyl)-4-oxo-4,5-dihydro-3H-1-thia-3,5,8-triazaacenaphthylene-2-carboxamido)pyrrolidin-1-yl)-4-oxobut-2-en-1-yl)carbamate (265 mg, 0.396 mmol), concentrated HCl (8 mL), and MeOH (8 mL) and was stirred at rt for 1 h. The mixture was concentrated to dryness and purified by flash column chromatography to give the title compound as white solid (188 mg, 75.5% yield).

Step C: (R,E)-N-(1-(4-(Dimethylamino)but-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide A solution of (R,E)-N-(1-(4-aminobut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide (135 mg, 0.220 mmol), formaldehyde (0.2 mL, 37 wt. % in $H_2O$), and $NaBH(OAc)_3$ (93 mg, 0.44 mmol) in DCM (8 mL) was stirred at rt for 5 h. The mixture was concentrated to dryness and purified by flash column chromatography to give the title compound as a white solid (63 mg, 43% yield). MS (ESI): mass calcd. for $C_{32}H_{32}N_6O_4S$, 596.7; m/z found, 597.3 [M+H]$^+$. 1H NMR (400 MHz, CD3OD): δ 8.45 (s, 1H), 8.37-8.32 (m, 1H), 7.44-7.36 (m, 2H), 7.32-7.26 (m, 1H), 7.21-7.14 (m, 1H), 7.12-7.03 (m, 3H), 7.01-6.95 (m, 1H), 6.84-6.74 (m, 1H), 6.68-6.56 (m, 1H), 6.11-6.05 (m, 1H), 4.09-3.69 (m, 4H), 3.64-3.58 (m, 2H), 3.56-3.44 (m, 1H), 2.63 (s, 6H), 2.40-2.15 (m, 2H), 2.12 (s, 3H)

Example 369: (R)-5-(2-Methyl-4-phenoxyphenyl)-4-oxo-N-(1-(vinylsulfonyl)pyrrolidin-3-yl)-4,5-dihydro-3H-1-thia-3,5,8-triazaacenaphthylene-2-carboxamide

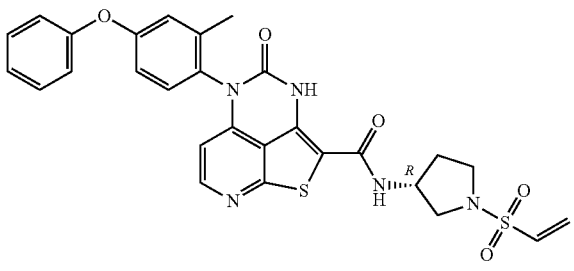

The title compound was prepared using analogous conditions described in Method 1, steps A-I in Example 1, and using tert-butyl (3R)-3-aminopyrrolidine-1-carboxylate in place of tert-butyl (3R,5R)-3-amino-5-fluoro-piperidine-1-carboxylate in step G and using ethenesulfonyl chloride in place of prop-2-enoyl chloride in step I to yield the title compound. MS (ESI): mass calcd. for $C_{28}H_{25}N_5O_5S_2$, 575.7; m/z found, 576.3 [M+H]$^+$. $^1$H NMR (400 MHz, CD$_3$OD): δ 8.33 (d, J=5.5 Hz, 1H), 7.45-7.35 (m, 2H), 7.34-7.25 (m, 1H), 7.21-7.13 (m, 1H), 7.12-7.03 (m, 3H), 6.99-6.93 (m, 1H), 6.80-6.64 (m, 1H), 6.21 (d, J=16.5 Hz, 1H), 6.14-6.03 (m, 2H), 4.61-4.45 (m, 1H), 3.66-3.55 (m, 1H), 3.53-3.45 (m, 1H), 3.38-3.31 (m, 1H), 3.29-3.20 (m, 1H), 2.32-2.20 (m, 1H), 2.12 (s, 3H), 2.08-2.00 (m, 1H).

Example 370: (R)-5-(2-Methyl-4-phenoxyphenl)-N-(1-trideuteriomethylpiperidin-3-yl)-4-oxo-4,5-dihydro-3H-1-thia-3,5,8-triazaacenaphthylene-2-carboxamide

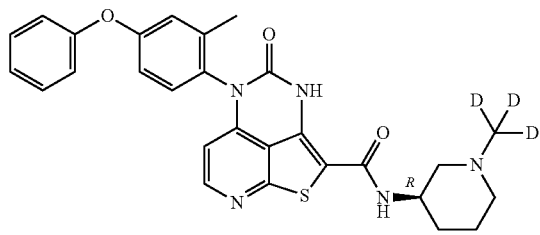

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 100 mg, 0.19 mmol) and deuterated-formaldehyde (12 mg, 0.38 mmol, 37 wt. % in H$_2$O) were added to MeOH (3 mL). After stirring at rt for 5 min, sodium cyanoborodeuteride (36 mg, 0.55 mmol) was added. The mixture was stirred at rt for 2 h. The reaction was concentrated to dryness and the residue was purified by flash column chromatography to give the title compound as a yellow solid (38 mg, 37% yield). MS (ESI): mass calcd. for $C_{28}H_{24}D_3N_5O_3S$, 516.6; m/z found, 517.2 [M+H]$^+$. $^1$H NMR (400 MHz, CD$_3$OD): δ 8.26 (d, J=4.9 Hz, 1H), 7.46-7.33 (m, 2H), 7.31-7.24 (m, 1H), 7.19-7.11 (m, 1H), 7.11-7.01 (m, 3H), 7.00-6.90 (m, 1H), 6.00 (d, J=5.1 Hz, 1H), 4.20-4.06 (m, 1H), 2.99-2.88 (m, 1H), 2.75-2.61 (m, 1H), 2.25-2.02 (m, 5H), 1.92-1.75 (m, 2H), 1.71-1.61 (m, 1H), 1.54-1.44 (m, 1H).

Example 371: (R,E)-N-(1-(4-(Dimethylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide

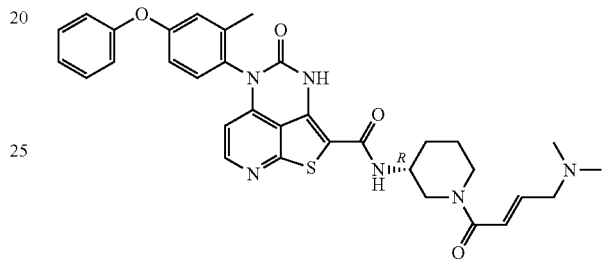

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 250 mg, 0.45 mmol), (E)-4-[tert-butoxycarbonyl(methyl)amino]but-2-enoic acid (Intermediate 10, 200 mg, 0.93 mmol), HATU (230 mg, 0.61 mmol), and DIEA (150 mg, 1.17 mmol) in DMF (6 mL) was stirred at rt for 2 h. The mixture was purified by HPLC and by flash column chromatography to give the title compound as a white solid (228 mg, 70.2% yield).

Step F: (R,E)-5-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide A solution of (R,E)-tert-butyl methyl(4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate (228 mg, 0.327 mmol), concentrated HCl (5 mL), and MeOH (5 mL) was stirred at rt for 1 h under N2. The mixture was concentrated to dryness and purified by flash column chromatography to give the title compound as a white solid (120 mg, 57% yield).

Step G: (R,E)-N-(1-(4-(Dimethylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide A solution of (R,E)-5-(2-methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide (68 mg, 0.11 mmol), formaldehyde (0.5 mL, 37 wt. % in H$_2$O), and NaBH(OAc)$_3$ (45 mg, 0.21 mmol) in DCM (8 mL) was stirred at rt for 5 h. The mixture was concentrated to dryness and purified by flash column chromatography to give the title compound as a white solid (37 mg, 52% yield). MS (ESI): mass calcd. for $C_{33}H_{34}N_6O_4S$, 610.7; m/z found, 611.3 [M+H]$^+$. 1H NMR (400 MHz, CD3OD): δ 8.41 (s, 1H), 8.37-8.30 (m, 1H), 7.45-7.36 (m, 2H), 7.34-7.26 (m, 1H), 7.21-7.14 (m, 1H), 7.12-7.03 (m, 3H), 7.01-6.95 (m, 1H), 6.93-6.86 (m, 1H), 6.75-6.64 (m, 1H), 6.11-6.05 (m, 1H), 4.54-4.50 (m, 1H), 4.42-3.89 (m, 3H), 3.83-3.73 (m, 2H), 3.25-3.14 (m, 1H), 2.97-2.87 (m, 1H), 2.76 (s, 6H), 2.16-2.02 (m, 4H), 1.94-1.82 (m, 1H), 1.82-1.70 (m, 1H), 1.66-1.53 (m, 1H)

Example 372: (R)-5-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide

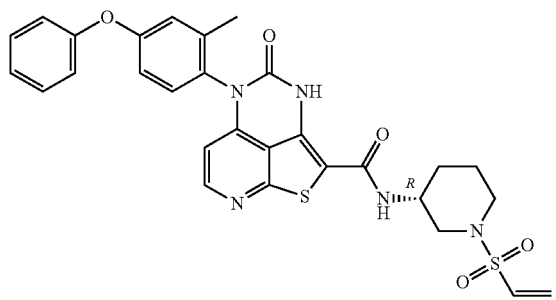

The title compound was prepared using analogous conditions described in Method 1, steps A-I in Example 1, and using tert-butyl (3R)-3-aminopiperidine-1-carboxylate in place of tert-butyl (3R,5R)-3-amino-5-fluoro-piperidine-1-carboxylate in step G and using ethenesulfonyl chloride in place of prop-2-enoyl chloride in step I to yield the title compound. MS (ESI): mass calcd. for $C_{29}H_{27}N_5O_5S_2$, 589.7; m/z found, 590.2 [M+H]$^+$. $^1$H NMR (400 MHz, CD$_3$OD): δ 8.32 (d, J=5.6 Hz, 1H), 7.44-7.35 (m, 2H), 7.30 (d, J=8.6 Hz, 1H), 7.21-7.13 (m, 1H), 7.11-7.03 (m, 3H), 7.01-6.92 (m, 1H), 6.72-6.60 (m, 1H), 6.22-6.04 (m, 3H), 4.16-3.98 (m, 1H), 3.84-3.69 (m, 1H), 3.63-3.47 (m, 1H), 2.81-2.55 (m, 2H), 2.12 (s, 3H), 2.04-1.95 (m, 1H), 1.93-1.83 (m, 1H), 1.77-1.63 (m, 1H), 1.62-1.50 (m, 1H).

Example 373: (R,E)-N-(1-(4-(Dimethylamino)but-2-enoyl)piperidin-3-yl)-4-oxo-5-(4-phenoxyphenyl)-4,5-dihydro-3H-1-thia-3,5,8-triazaacenaphthylene-2-carboxamide

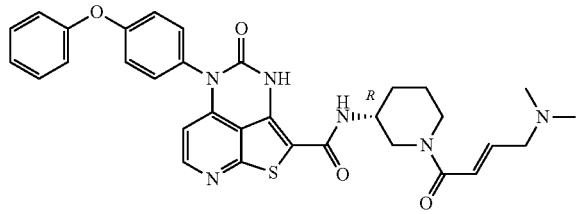

To an oven dried microwave vial with a stir bar under Ar were added (R)-4-oxo-5-(4-phenoxyphenyl)-N-(piperidin-3-yl)-4,5-dihydro-3H-1-thia-3,5,8-triazaacenaphthylene-2-carboxamide (Example 860, 62 mg, 0.10 mmol), trans-4-dimethylaminocrotonic acid hydrochloride (37.6 mg, 0.227 mmol), HATU (202 mg, 0.531 mmol), THF (3.0 mL), and triethylamine (0.20 mL, 1.4 mmol). The reaction vial was capped and allowed to warm in the microwave for 5 min at 100° C. The reaction mixture was concentrated to dryness, filtered, and purified by HPLC to give the title compound (27 mg, 44% yield). MS (ESI): mass calcd. for $C_{32}H_{32}N_6O_4S$, 596.7; m/z found, 597.2 [M+H]$^+$. $^1$H NMR (500 MHz, CD$_3$OD): δ 8.39-8.21 (m, 1H), 7.45-7.33 (m, 4H), 7.25-7.06 (m, 5H), 6.83-6.57 (m, 2H), 6.24-6.08 (m, 1H), 4.57-3.87 (m, 3H), 3.27-2.83 (m, 4H), 2.36-2.20 (m, 6H), 2.12-1.46 (m, 4H).

Example 374: (R,E)-5-(2-Methyl-4-phenoxyphenyl)-N-(1-(4-(methylsulfonyl)but-2-enoyl)piperidin-3-yl)-4-oxo-4,5-dihydro-3H-1-thia-3,5,8-triazaacenaphthylene-2-carboxamide

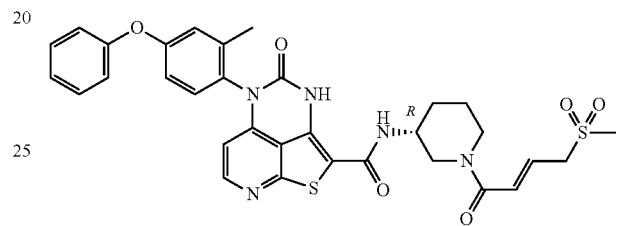

Step A: (R,E)-5-(2-Methyl-4-phenoxyphenyl)-N-(1-(4-(methylthio)but-2-enoyl)piperidin-3-yl)-4-oxo-4,5-dihydro-3H-1-thia-3,5,8-triazaacenaphthylene-2-carboxamide To a solution of (E)-4-methylsulfanylbut-2-enoic acid (Intermediate 37, 0.556 g, 4.201 mmol), HATU (1.0 g, 2.6 mmol), and triethylamine (1.0 g, 9.9 mmol) in DMF (10 mL) was added (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 0.75 g, 1.5 mmol) and was stirred at rt for 4 hours. The mixture was purified by flash column chromatography to give the title compound (300 mg, 33% yield).

Step B: (R,E)-5-(2-Methyl-4-phenoxyphenyl)-N-(1-(4-(methylsulfonyl)but-2-enoyl)piperidin-3-yl)-4-oxo-4,5-dihydro-3H-1-thia-3,5,8-triazaacenaphthylene-2-carboxamide To a mixture of (R,E)-5-(2-methyl-4-phenoxyphenyl)-N-(1-(4-(methylthio)but-2-enoyl)piperidin-3-yl)-4-oxo-4,5-dihydro-3H-1-thia-3,5,8-triazaacenaphthylene-2-carboxamide (300 mg, 0.49 mmol) in DCM (10 mL) was added 3-chlorobenzenecarboperoxoic acid (169 mg, 0.735 mmol) and was stirred at rt for 4 hours. The mixture was dispersed between DCM and a 1 M aqueous Na$_2$CO$_3$ solution. The organic layer was collected, concentrated to dryness, and purified by flash column chromatography, then by preparative TLC to give the title compound (58 mg, 17% yield). MS (ESI): mass calcd. for $C_{32}H_{31}N_5O_6S_2$, 645.7; m/z found, 646.2 [M+H]$^+$. 1H NMR (400 MHz, DMSO-d6): δ 8.60-8.26 (m, 1H), 8.25-8.10 (m, 1H), 7.45-7.39 (m, 2H), 7.29-7.20 (m, 1H), 7.19-7.15 (m, 1H), 7.12-7.07 (m, 2H), 7.06-7.02 (m, 1H), 6.96-6.91 (m, 1H), 6.89-6.78 (m, 1H), 6.59-6.48 (m, 1H), 5.88-5.69 (m, 1H), 4.45-4.12 (m, 1H), 4.11-4.04 (m, 2H), 4.01-3.85 (m, 1H), 3.82-3.75 (m, 1H), 3.13-

3.02 (m, 1H), 2.96-2.90 (m, 3H), 2.86-2.63 (m, 1H), 2.02 (s, 3H), 1.97-1.93 (m, 1H), 1.81-1.72 (m, 1H), 1.67-1.56 (m, 1H), 1.49-1.39 (m, 1H).

Example 375: (R)—N-(1-Acryloylpiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide

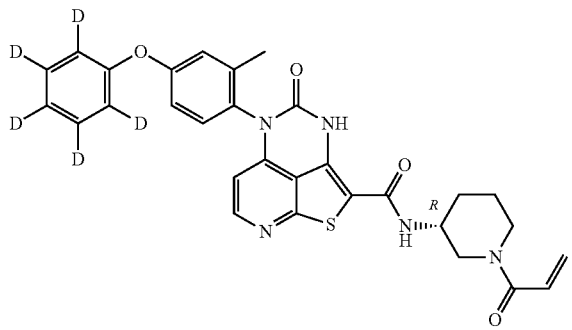

The title compound was prepared using analogous conditions described in Method 1, steps A-I in Example 1, and using 2,3,4,5,6-pentadeuteriophenol in place of phenol in step A and using tert-butyl (3R)-3-aminopiperidine-1-carboxylate in place of tert-butyl (3R,5R)-3-amino-5-fluoropiperidine-1-carboxylate in step G to yield the title compound. MS (ESI): mass calcd. for $C_{30}H_{22}D_5N_5O_4S$, 558.7; m/z found, 559.3 [M+H]$^+$. $^1$H NMR (400 MHz, CD$_3$OD): δ 8.35-8.30 (m, 1H), 7.32-7.27 (m, 1H), 7.07-7.03 (m, 1H), 7.00-6.94 (m, 1H), 6.85-6.72 (m, 1H), 6.24-6.14 (m, 1H), 6.09-6.05 (m, 1H), 5.76-5.68 (m, 1H), 4.56-3.89 (m, 3H), 3.26-2.82 (m, 2H), 2.15-2.00 (m, 4H), 1.92-1.81 (m, 1H), 1.78-1.66 (m, 1H), 1.63-1.52 (m, 1H).

Example 376: (R)—N-(1-Acryloylpyrrolidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide

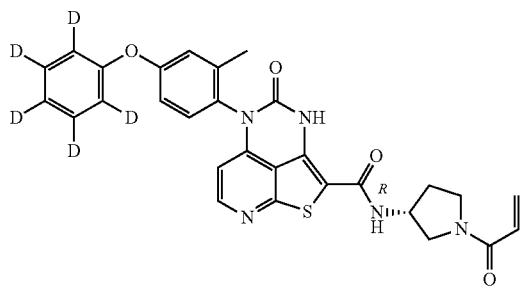

The title compound was prepared using analogous conditions described in Method 1, steps A-G in Example 1, and using 2,3,4,5,6-pentadeuteriophenol in place of phenol in step A and using 1-[(3R)-3-aminopyrrolidin-1-yl]prop-2-en-1-one (intermediate 5) in place of tert-butyl (3R,5R)-3-amino-5-fluoro-piperidine-1-carboxylate in step G to yield the title compound. MS (ESI): mass calcd. for $C_{29}H_{20}D_5N_5O_4S$, 544.6; m/z found, 545.2 [M+H]$^+$. $^1$H NMR (400 MHz, DMSO-d$_6$): δ 10.30-10.19 (m, 1H), 8.41-8.29 (m, 2H), 7.43-7.35 (m, 1H), 7.13-7.07 (m, 1H), 7.04-6.94 (m, 1H), 6.69-6.49 (m, 1H), 6.21-6.08 (m, 1H), 6.05-5.95 (m, 1H), 5.75-5.63 (m, 1H), 4.59-4.41 (m, 1H), 3.96-3.45 (m, 4H), 2.27-1.92 (m, 5H).

Example 377: (R,E)-5-(2-Methyl-4-phenoxyphenyl)-N-(1-(4-(methylamino)but-2-enoyl)pyrrolidin-3-yl)-4-oxo-4,5-dihydro-3H-1-thia-3,58-triazaacenaphthylene-2-carboxamide

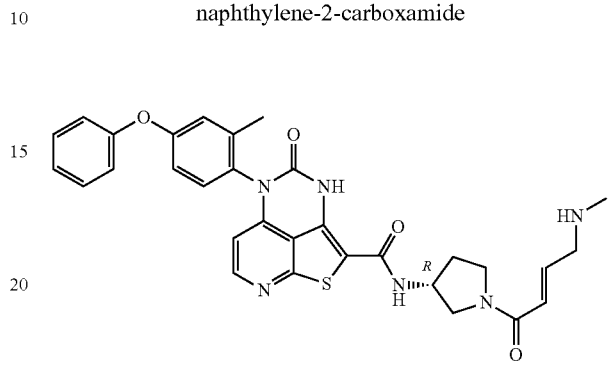

Step A: (R,E)-tert-Butyl methyl(4-(3-(5-(2-methyl-4-phenoxyphenyl)-4-oxo-4,5-dihydro-3H-1-thia-3,5,8-triazaacenaphthylene-2-carboxamido)pyrrolidin-1-yl)-4-oxobut-2-en-1-yl)carbamate A solution of (E)-4-[tert-butoxycarbonyl(methyl)amino]but-2-enoic acid (Intermediate 10, 165 mg, 0.766 mmol), (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 200 mg, 0.38 mmol), HATU (112 mg, 0.295 mmol), and DIEA (247 mg, 1.92 mmol) in DMF (5 mL) was stirred at rt for 1 h. The mixture was purified by flash column chromatography using two different methods to give the title compound as a light yellow solid (93 mg, 36% yield).

Step B: (R,E)-5-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide To a round bottom flask were added (R,E)-tert-butyl methyl(4-(3-(5-(2-methyl-4-phenoxyphenyl)-4-oxo-4,5-dihydro-3H-1-thia-3,5,8-triazaacenaphthylene-2-carboxamido)pyrrolidin-1-yl)-4-oxobut-2-en-1-yl)carbamate (93 mg, 0.14 mmol), concentrated HCl (5 mL), and MeOH (5 mL) and was stirred at rt for 1 h. The mixture was concentrated to dryness and the residue was purified by flash column chromatography to give the title compound as a white solid (48 mg, 60% yield). MS (ESI): mass calcd. for $C_{31}H_{30}N_6O_4S$, 582.7; m/z found, 583.2 [M+H]$^+$. 1H NMR (400 MHz, CD3OD): δ 8.35-8.31 (m, 1H), 7.44-7.37 (m, 2H), 7.32-7.26 (m, 1H), 7.20-7.15 (m, 1H), 7.12-7.04 (m, 3H), 7.00-6.95 (m, 1H), 6.82-6.58 (m, 2H), 6.10-6.06 (m, 1H), 4.16-3.42 (m, 7H), 2.72-2.66 (m, 3H), 2.43-2.03 (m, 5H)

Example 378: (R,E)-N-(1-(2-Cyano-3-cyclopropylacryloyl)piperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide

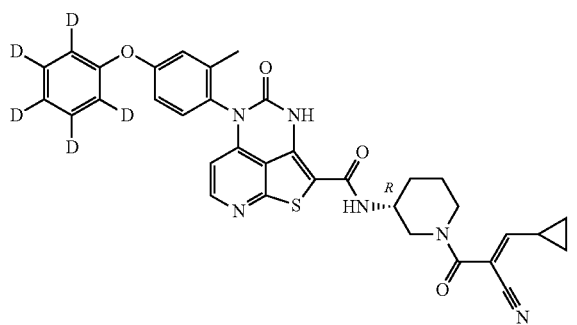

A solution of (R)-5-(2-methyl-4-(2,3,4,5,6-pentadeuteriophenoxy)phenyl)-4-oxo-N-(piperidin-3-yl)-4,5-dihydro-3H-1-thia-3,5,8-triazaacenaphthylene-2-carboxamide (Intermediate 41, 150 mg, 0.28 mmol), (E)-2-cyano-3-cyclopropyl-prop-2-enoic acid (Intermediate 17) (76 mg, 0.55 mmol), HATU (137 mg, 0.360 mmol), and DIEA (107 mg, 0.831 mmol) in DMF (5 mL) was stirred at room temperature for 1 h. Then the reaction mixture was purified by normal phase flash column chromatography (SiO$_2$) using two different methods to give the title compound as a white solid (71 mg, 41% yield). MS (ESI): mass calcd. for C$_{34}$H$_{25}$D$_5$N$_6$O$_4$S, 623.7; m/z found, 624.3 [M+H]$^+$. $^1$H NMR (400 MHz, CD$_3$OD): δ 8.35-8.30 (m, 1H), 7.32-7.27 (m, 1H), 7.07-7.03 (m, 1H), 7.00-6.95 (m, 1H), 6.57-6.50 (m, 1H), 6.10-6.05 (m, 1H), 4.08-3.93 (m, 2H), 3.67-3.62 (m, 2H), 3.22-3.10 (m, 1H), 2.12 (s, 3H), 2.10-1.95 (m, 2H), 1.93-1.84 (m, 1H), 1.80-1.68 (m, 1H), 1.68-1.56 (m, 1H), 1.25-1.16 (m, 2H), 1.01-0.93 (m, 1H), 0.90-0.78 (m, 1H).

Example 379: (R)—N-(1-Cyanopiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide

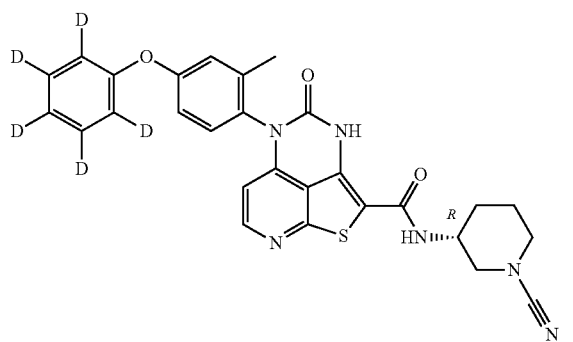

The title compound was prepared using analogous conditions described in Method 1, steps A-I in Example 1, and using 2,3,4,5,6-pentadeuteriophenol in place of phenol in step A and using tert-butyl (3R)-3-aminopiperidine-1-carboxylate in place of tert-butyl (3R,5R)-3-amino-5-fluoropiperidine-1-carboxylate in step G and using carbononitridic bromide in place of prop-2-enoyl chloride in step I to yield the title compound. MS (ESI): mass calcd. for C$_{28}$H$_{19}$D$_5$N$_6$O$_3$S, 529.6; m/z found, 530.3 [M+H]$^+$. $^1$H NMR (400 MHz, CD$_3$OD): δ 8.35-8.31 (m, 1H), 7.32-7.27 (m, 1H), 7.07-7.03 (m, 1H), 7.00-6.94 (m, 1H), 6.09-6.04 (m, 1H), 4.16-4.07 (m, 1H), 3.61-3.52 (m, 1H), 3.40-3.30 (m, 1H), 3.10-2.94 (m, 2H), 2.12 (s, 3H), 2.07-1.98 (m, 1H), 1.90-1.81 (m, 1H), 1.81-1.70 (m, 1H), 1.66-1.54 (m, 1H).

Example 380: (R)-5-(2-Methyl-4-(2,3,4,5,6-pentadeuteriophenoxy)phenyl)-N-(1-(trideuteriomethyl)piperidin-3-yl)-4-oxo-4,5-dihydro-3H-1-thia-3,5,8-triazaacenaphthylene-2-carboxamide

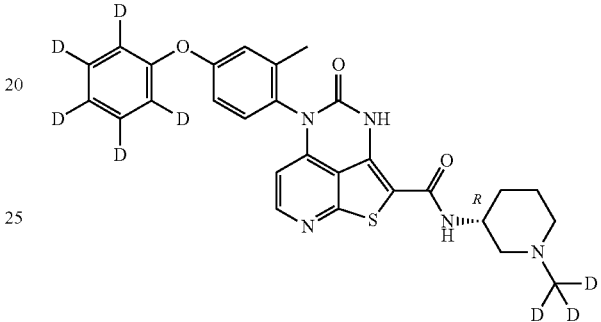

A solution of (R)-5-(2-methyl-4-(2,3,4,5,6-pentadeuteriophenoxy)phenyl)-4-oxo-N-(piperidin-3-yl)-4,5-dihydro-3H-1-thia-3,5,8-triazaacenaphthylene-2-carboxamide (Intermediate 41, 155 mg. 0.286 mmol) and deuterated-formaldehyde (18 mg, 0.56 mmol, 37 wt. % in H$_2$O) in MeOH (4 mL) was stirred at rt for 30 min, then sodium cyanoborodeuteride (57 mg, 0.86 mmol) was added. The reaction mixture was stirred at rt overnight. The reaction was concentrated to dryness and the residue was purified by flash column chromatography to give the title compound as a yellow solid (66 mg, 43% yield). MS (ESI): mass calcd. for C$_{28}$H$_{19}$D$_8$N$_5$O$_3$S, 521.7; m/z found, 522.2 [M+H]$^+$. $^1$H NMR (400 MHz, CD$_3$OD): δ 8.39-8.15 (m, 1H), 7.38-7.19 (m, 1H), 7.11-6.88 (m, 2H), 6.16-5.88 (m, 1H), 4.24-4.06 (m, 1H), 3.01-2.82 (s, 1H), 2.78-2.61 (m, 1H), 2.32-2.01 (m, 5H), 1.93-1.76 (m, 2H), 1.72-1.59 (m, 1H), 1.55-1.42 (m, 1H).

Example 381: (R)-5-(2-Methyl-4-(2,3,4,5,6-pentadeuteriophenoxy)phenyl)-N-(1-methylpiperidin-3-yl)-4-oxo-4,5-dihydro-3H-1-thia-3,5,8-triazaacenaphthylene-2-carboxamide

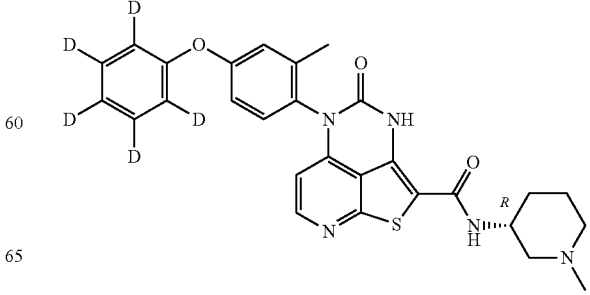

A solution (R)-5-(2-methyl-4-(2,3,4,5,6-pentadeuteriophenoxy)phenyl)-4-oxo-N-(piperidin-3-yl)-4,5-dihydro-3H-1-thia-3,5,8-triazaacenaphthylene-2-carboxamide (Intermediate 41, 150 mg, 0.28 mmol), aqueous formaldehyde (1 mL, 37 wt. % in H$_2$O), and NaBH(OAc)$_3$ (117 mg, 0.554 mmol) in DCM (10 mL) was stirred at rt for 5 h. The mixture was concentrated to dryness and purified by flash column chromatography to give the title compound as a light yellow solid (90 mg, 57% yield). MS (ESI): mass calcd. for C$_{28}$H$_{22}$D$_5$N$_5$O$_3$S, 518.6; m/z found, 519.2 [M+H]$^+$. 1H NMR (400 MHz, CD$_3$OD): δ 8.35-8.28 (m, 1H), 7.33-7.27 (m, 1H), 7.07-7.03 (m, 1H), 7.01-6.94 (m, 1H), 6.09-6.04 (m, 1H), 4.34-4.22 (m, 1H), 3.48-3.37 (m, 1H), 3.27-3.18 (m, 1H), 2.88-2.71 (m, 5H), 2.11 (s, 3H), 2.07-1.96 (m, 2H), 1.90-1.76 (m, 1H), 1.74-1.59 (m, 1H)

Example 382: (R,E)-N-(1-(4-Aminobut-2-enoyl) pyrrolidin-3-yl)-5-(2-methyl-4-phenoxyphenyl)-4-oxo-4,5-dihydro-3H-1-thia-3,5,8-triazaacenaphthylene-2-carboxamide

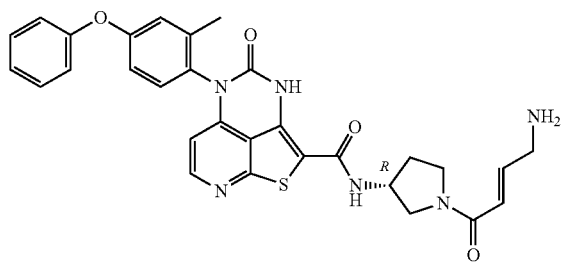

The title compound was prepared using analogous conditions described in Example 368, steps A-B. MS (ESI): mass calcd. for C$_{30}$H$_{28}$N$_6$O$_4$S, 568.6; m/z found, 569.3 [M+H]$^+$. 1H NMR (400 MHz, CD$_3$OD): δ 8.42 (s, 1H), 8.37-8.32 (m, 1H), 7.44-7.36 (m, 2H), 7.32-7.26 (m, 1H), 7.21-7.14 (m, 1H), 7.12-7.03 (m, 3H), 7.01-6.95 (m, 1H), 6.84-6.74 (m, 1H), 6.68-6.56 (m, 1H), 6.11-6.05 (m, 1H), 4.08-3.44 (m, 7H), 2.44-2.13 (m, 2H), 2.12 (s, 3H)

Example 383: (R,E)-5-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide

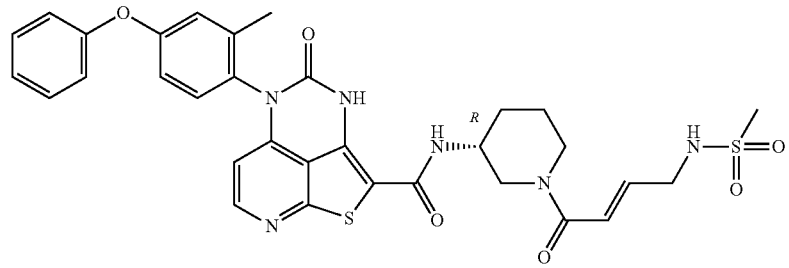

To a solution of (R,E)-N-(1-(4-aminobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 27, 300 mg, 0.52 mmol) and triethylamine (104 mg, 1.03 mmol) in DCM (5 mL) was added ClSO$_2$Me (59 mg, 0.52 mmol) and was stirred at room temperature for 15 minutes. The mixture was dispersed between DCM and water and the organic layer was collected, concentrated to dryness, and purified by flash column chromatography, then by preparative TLC to give the title compound (52 mg, 15% yield). MS (ESI): mass calcd. for C$_{32}$H$_{32}$N$_6$O$_6$S$_2$, 660.8; m/z found, 661.2 [M+H]$^+$. 1H NMR (400 MHz, DMSO-d6): δ 8.54-8.26 (m, 1H), 8.26-8.13 (m, 1H), 7.47-7.38 (m, 2H), 7.36-7.21 (m, 2H), 7.20-7.14 (m, 1H), 7.13-7.07 (m, 2H), 7.07-7.03 (m, 1H), 6.97-6.91 (m, 1H), 6.66-6.53 (m, 2H), 5.90-5.73 (m, 1H), 4.45-4.07 (m, 1H), 4.04-3.87 (m, 1H), 3.82-3.71 (m, 3H), 3.15-2.99 (m, 1H), 2.88 (s, 3H), 2.85-2.61 (m, 1H), 2.03 (s, 3H), 1.97-1.90 (m, 1H), 1.82-1.70 (m, 1H), 1.69-1.55 (m, 1H), 1.47-1.35 (m, 1H).

Example 384: (R)—N-(1-(2-(Dimethylamino) acetyl)pyrrolidin-3-yl)-5-(2-methyl-4-phenoxyphenyl)-4-oxo-4,5-dihydro-3H-1-thia-3,5,8-triazaacenaphthylene-2-carboxamide

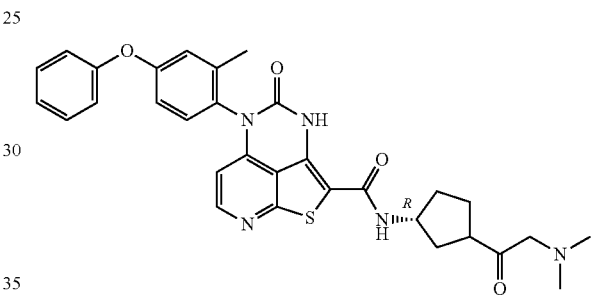

To a round bottom flask were added (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 150 mg, 0.29 mmol), 2-(dimethylamino)acetic acid (59 mg, 0.57 mmol), HATU (142 mg, 0.373 mmol), and DIEA (111 mg, 0.861 mmol) in DMF (5 mL) and was stirred at rt for 1 h. The mixture was purified by flash column chromatography to give the title compound as a white solid (130 mg, 74% yield). MS (ESI): mass calcd. for C$_{30}$H$_{30}$N$_6$O$_4$S, 570.7; m/z found, 571.3 [M+H]$^+$. 1H NMR (400 MHz, CD3OD): δ 8.35-8.30 (m, 1H), 7.43-7.37 (m, 2H), 7.32-7.28 (m, 1H), 7.20-7.14 (m, 1H), 7.11-7.04 (m, 3H), 7.00-6.94 (m, 1H), 6.10-6.04 (m, 1H), 4.67-4.57 (m, 1H), 4.03-3.96 (m, 2H), 3.91-3.81 (m, 1H), 3.74-3.62 (m, 1H), 3.60-3.41 (m, 2H), 2.88-2.84 (m, 6H), 2.39-2.14 (m, 2H), 2.11 (s, 3H).

Example 385: (R,E)-N-(1-(2-Cyanobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

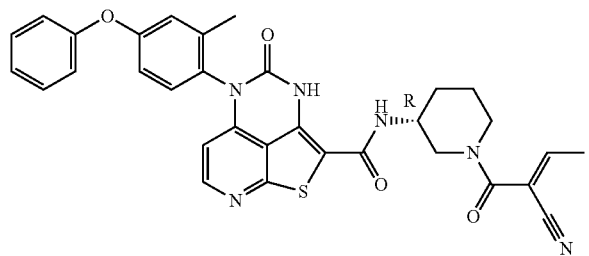

To a round bottom flask were added (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874) (300 mg, 0.53 mmol), acetaldehyde (116 mg, 2.65 mmol), piperidine (0.1 ml), and EtOH (10 mL) and was stirred at rt for 0.5 h. The mixture was diluted with DCM, washed with 1 N HCl and saturated aqueous NaHCO$_3$, dried over anhydrous Na$_2$SO$_4$, concentrated to dryness, and purified by flash column chromatography to give the title compound as a yellow solid (46 mg, 15% yield). MS (ESI): mass calcd. for C$_{32}$H$_{28}$N$_6$O$_4$S, 592.7; m/z found, 593.2 [M+H]$^+$. $^1$H NMR (400 MHz, DMSO-d$_6$): δ 10.18 (s, 1H), 8.35-8.31 (m, 1H), 8.14-8.02 (m, 1H), 7.47-7.40 (m, 2H), 7.39-7.33 (m, 1H), 7.22-7.15 (m, 1H), 7.13-7.03 (m, 4H), 6.99-6.93 (m, 1H), 5.99-5.94 (m, 1H), 3.89-3.78 (m, 1H), 3.18-2.82 (m, 4H), 2.09-2.00 (m, 6H), 1.97-1.89 (m, 1H), 1.83-1.74 (m, 1H), 1.73-1.61 (m, 1H), 1.54-1.43 (m, 1H).

Example 386: N—((R)-1-((S)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide

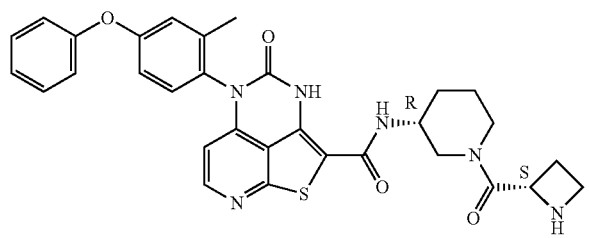

Step A: (S)-tert-butyl 2-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)azetidine-1-carboxylate A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 100 mg, 0.19 mmol), (2S)-1-tert-butoxycarbonylazetidine-2-carboxylic acid (63 mg, 0.28 mmol), HATU (107 mg, 0.281 mmol), and triethylamine (0.104 mL, 0.748 mmol) in DMF (3 mL) was stirred at rt overnight. The reaction mixture was purified by flash column chromatography to give the title compound as a white solid (115 mg, 90.0% yield).

Step B: N—((R)-1-((S)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide A solution of (S)-tert-butyl 2-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)azetidine-1-carboxylate (115 mg, 0.168 mmol) in 2 N HCl in MeOH (2 mL) was stirred at rt for 4 h, then concentrated to dryness. The residue was adjusted with 2 N NaHCO$_3$ to pH>7, then purified by flash column chromatography to give the title compound as a yellow solid (77 mg, 75% yield). MS (ESI): mass calcd. for C$_{31}$H$_{30}$N$_6$O$_4$S, 582.7; m/z found, 583.2 [M+H]$^+$. $^1$H NMR (400 MHz, DMSO-d$_6$ and CD$_3$OD): δ 8.06-8.02 (m, 1H), 7.40-7.26 (m, 2H), 7.16-7.06 (m, 2H), 7.05-6.99 (m, 2H), 6.98-6.92 (m, 1H), 6.92-6.83 (m, 1H), 5.72 (d, J=5.5 Hz, 1H), 5.08-4.51 (m, 1H), 3.98-3.81 (m, 1H), 3.66-3.58 (m, 1H), 3.58-3.43 (m, 2H), 3.43-3.32 (m, 1H), 3.18-3.09 (m, 2H), 2.81-2.56 (m, 1H), 2.48-2.34 (m, 1H), 2.01 (s, 3H), 1.92-1.80 (m, 2H), 1.77-1.66 (m, 1H), 1.54-1.42 (m, 1H).

Example 387: (R,E)-N-(1-(2-Cyano-3-(3-methyloxetan-3-yl)acryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide

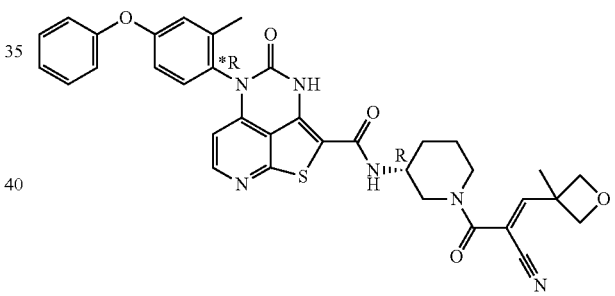

Step A: (R)—N-(1-(2-Cyanoacetyl)piperidin-3-yl)-5-(*R)-(2-methyl-4-phenoxyphenyl)-4-oxo-4,5-dihydro-3H-1-thia-3,5,8-triazaacenaphthylene-2-carboxamide A solution of (R)-5-(*R)-(2-methyl-4-phenoxyphenyl)-4-oxo-N-(piperidin-3-yl)-4,5-dihydro-3H-1-thia-3,5,8-triazaacenaphthylene-2-carboxamide (Example 300, 100 mg, 0.19 mmol), 2-cyanoacetic acid (32 mg, 0.37 mmol), HATU (92 mg, 0.24 mmol), and DIEA (60 mg, 0.47 mmol) in DMF (5 mL) was stirred at rt for 2 h. The reaction mixture was purified by flash column chromatography to give the title compound as a white solid (82 mg, 78% yield).

Step B: (R,E)-N-(1-(2-Cyano-3-(3-methyloxetan-3-yl)acryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide To a round bottom flask were added (R)—N-(1-(2-cyanoacetyl)piperidin-3-yl)-5-(*R)-(2-methyl-4-phenoxyphenyl)-4-oxo-4,5-dihydro-3H-1-thia-3,5,8-triazaacenaphthylene-2-carboxamide (100 mg, 0.18 mmol), 3-methyloxetane-3-carbaldehyde (53 mg, 0.53 mmol), piperidine (0.3 mL), AcOH (0.1 mL), 4A molecular sieves (0.5 g), and dioxane (10 mL) and was stirred at 100° C. for 1 h under N2. The mixture was concentrated to dryness and purified by flash column chromatography to give the title compound as a white solid (71 mg). MS (ESI): mass calcd. for $C_{35}H_{32}N_6O_5S$, 648.7; m/z found, 649.3 [M+H]$^+$. $^1$H NMR (400 MHz, CD$_3$OD): δ 8.33-8.28 (m, 1H), 7.42-7.35 (m, 2H), 7.31-7.23 (m, 2H), 7.19-7.12 (m, 1H), 7.11-7.01 (m, 3H), 6.98-6.92 (m, 1H), 6.07-6.02 (m, 1H), 5.04-6.91 (m, 1H), 4.73-4.26 (m, 4H), 4.06-3.86 (m, 2H), 3.56-2.76 (m, 2H), 2.16-2.01 (m, 4H), 1.97-1.85 (m, 1H), 1.82-1.57 (m, 5H).

Example 388: (R,Z)—N-(1-(2-Fluoro-4-(methylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide

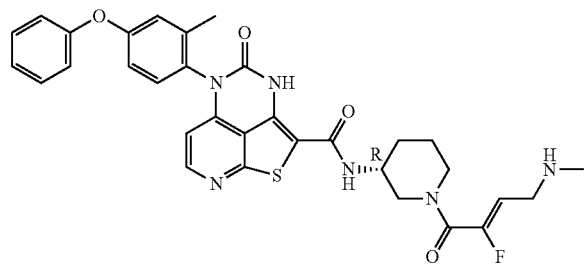

Step A: (R,Z)-tert-Butyl (3-fluoro-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)(methyl)carbamate A solution of (Z)-4-[tert-butoxycarbonyl(methyl)amino]-2-fluoro-but-2-enoic acid (Intermediate 38, 500 mg, 2.1 mmol), HBTU and triethylamine (236 mg, 2.33 mmol) in anhydrous DMF (5 mL) was stirred at room temperature for 10 min, then (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 250 mg, 0.47 mmol) was added and the mixture was stirred for 2 h. The crude mixture was purified by flash column chromatography to give the title compound as a slight yellow solid (21 mg, 6.2% yield).

Step B: (R,Z)—N-(1-(2-Fluoro-4-(methylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide A solution of (R,Z)-tert-butyl (3-fluoro-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)(methyl)carbamate (21 mg, 0.029 mmol) in 6 N HCl in MeOH (10 mL) was concentrated to dryness at 50° C. under vacuum to yield a yellow solid. The residue was purified by flash column chromatography to give the title compound as a yellow solid (15 mg, 76% yield). MS (ESI): mass calcd. for $C_{32}H_{31}FN_6O_4S$, 614.7; m/z found, 615.2 [M+H]$^+$. 1H NMR (400 MHz, CD3OD): δ 8.43 (s, 1H), 8.34 (d, J=3.6 Hz, 1H), 7.49-7.35 (m, 2H), 7.34-7.25 (m, 1H), 7.23-7.14 (m, 1H), 7.13-7.03 (m, 3H), 7.01-6.92 (m, 1H), 6.08 (d, J=5.4 Hz, 1H), 5.92-5.75 (m, 1H), 4.54-3.91 (m, 3H), 3.85-3.63 (m, 2H), 3.27-3.11 (m, 1H), 3.05-2.88 (m, 1H), 2.77-2.67 (m, 3H), 2.12 (s, 3H), 2.10-2.03 (m, 1H), 1.98-1.86 (m, 1H), 1.83-1.56 (m, 2H).

Example 389: (R)-5-(2-Methyl-4-phenoxyphenyl)-4-oxo-N-(1-(2-(pyrrolidin-1-yl)acetyl)piperidin-3-yl)-4,5-dihydro-3H-1-thia-3,5,8-triazaacenaphthylene-2-carboxamide

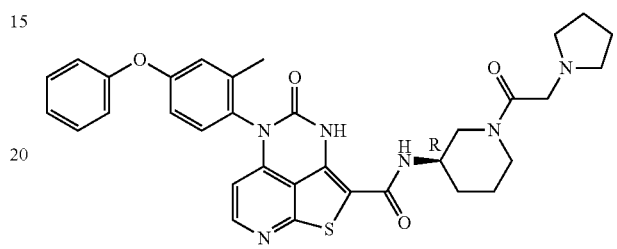

To a solution of (R)—N-(1-(2-chloroacetyl)piperidin-3-yl)-5-(2-methyl-4-phenoxyphenyl)-4-oxo-4,5-dihydro-3H-1-thia-3,5,8-triazaacenaphthylene-2-carboxamide (Example 396, 150 mg, 0.26 mmol) in DCM and triethylamine was added pyrrolidine (38 mg, 0.53 mmol) in DCM dropwise and was stirred at rt for 2 h. The reaction mixture was concentrated to dryness and purified by flash column chromatography, then preparative TLC to give the title compound as a yellow solid (68 mg). MS (ESI): mass calcd. for $C_{33}H_{34}N_6O_4S$, 610.7; m/z found, 611.2 [M+H]$^+$. 1H NMR (400 MHz, CDCl3): δ 8.33 (d, J=4.7 Hz, 1H), 7.44-7.34 (m, 2H), 7.21-7.12 (m, 2H), 7.12-7.06 (m, 2H), 7.03-6.97 (m, 1H), 6.97-6.91 (m, 1H), 5.98 (d, J=4.7 Hz, 1H), 4.22-4.03 (m, 1H), 3.94-3.75 (m, 1H), 3.69-3.61 (m, 1H), 3.56-3.37 (m, 3H), 3.34-3.19 (m, 1H), 2.73-2.53 (m, 4H), 2.14-2.09 (m, 3H), 1.99-1.89 (m, 2H), 1.83-1.73 (m, 6H).

Example 390: (R)-2-(((1-Acryloylpiperidin-3-yl)amino)methyl)-5-(2-methyl-4-phenoxyphenyl)-3H-1-thia-3,5,8-triazaacenaphthylen-4(5H)-one

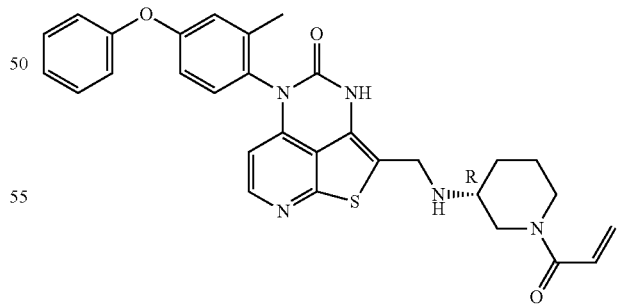

Step A: N-Methoxy-N-methyl-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-G in Example 1, and using N-methoxymethanamine in place of tert-butyl (3R,5R)-3-amino-5-fluoro-piperidine-1-carboxylate in step G to yield the title compound.

Step B: 5-(2-Methyl-4-phenoxyphenyl)-4-oxo-4,5-dihydro-3H-1-thia-3,5,8-triazaacenaphthylene-2-carbaldehyde To a solution of N-methoxy-N-methyl-5-(2-methyl-4-phenoxyphenyl)-4-oxo-4,5-dihydro-3H-1-thia-3,5,8-triazaacenaphthylene-2-carboxamide (1.7 g, 3.7 mmol) in anhydrous THF (30 mL) was added LiAlH$_4$ (210 mg, 5.5 mmol) and was stirred at rt for 72 h under N2. Next, an aqueous solution of 1 N KHSO$_4$ was added cautiously via an addition funnel, and then water was added followed by EtOAc. The organic layer was collected and washed with 1 N HCl, which caused a yellow solid to precipitate, which was collected by filtration. The residue was purified by flash column chromatography to give the title compound as a yellow sold (622 mg, 42.0% yield).

Step C: (R)-2-(((1-Acryloylpiperidin-3-yl)amino)methyl)-5-(2-methyl-4-phenoxyphenyl)-3H-1-thia-3,5,8-triazaacenaphthylen-4(5H)-one To a solution of 5-(2-methyl-4-phenoxyphenyl)-4-oxo-4,5-dihydro-3H-1-thia-3,5,8-triazaacenaphthylene-2-carbaldehyde (100 mg, 0.25 mmol) and 1-[(3R)-3-amino-1-piperidyl]prop-2-en-1-one (Intermediate 15, 71 mg, 0.37 mmol) in DCM/MeOH (20 mL) was added NaBH(AcO)$_3$ (158 mg, 0.745 mmol) and was stirred at rt for 18 h. To the reaction mixture was added NaBH$_4$ (19 mg, 0.50 mmol) and was stirred for 10 min, then water was added and the mixture was extracted with DCM, concentrated to dryness, and purified by flash column chromatography to give the title compound as a slight yellow solid (45 mg, 32% yield). MS (ESI): mass calcd. for C$_{30}$H$_{29}$N$_5$O$_3$S, 539.6; m/z found, 540.0 [M+H]$^+$. $^1$H NMR (400 MHz, CD$_3$OD): δ 8.20-8.03 (m, 1H), 7.48-7.32 (m, 2H), 7.29-7.20 (m, 1H), 7.19-7.11 (m, 1H), 7.11-7.02 (m, 3H), 6.99-6.90 (m, 1H), 6.82-6.65 (m, 1H), 6.29-6.06 (m, 1H), 5.97-5.87 (m, 1H), 5.77-5.63 (m, 1H), 4.25-4.10 (m, 1H), 4.11-3.73 (m, 3H), 3.41-3.33 (m, 0.5H), 3.19-2.92 (m, 1.5H), 2.80-2.61 (m, 1H), 2.12 (s, 3H), 2.07-1.95 (m, 1H), 1.88-1.70 (m, 1H), 1.62-1.40 (m, 2H).

Example 391: (R)-5-(2-Methyl-4-phenoxyphenyl)-N-(1-(2-(methylamino)acetyl)pyrrolidin-3-yl)-4-oxo-4,5-dihydro-3H-1-thia-3,5,8-triazaacenaphthylene-2-carboxamide

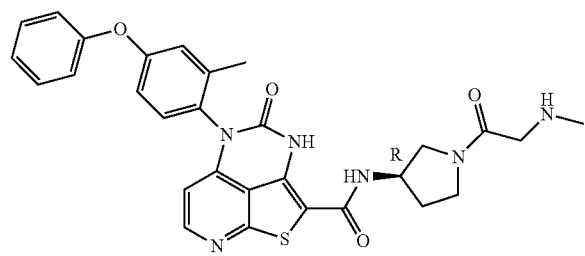

Step A: (R)-tert-Butyl methyl(2-(3-(5-(2-methyl-4-phenoxyphenyl)-4-oxo-4,5-dihydro-3H-1-thia-3,5,8-triazaacenaphthylene-2-carboxamido)pyrrolidin-1-yl)-2-oxoethyl)carbamate A solution of (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 150 mg, 0.29 mmol), N-Boc-N-methylglycine (109 mg, 0.574 mmol), HATU (142 mg, 0.373 mmol), and DIEA (111 mg, 0.861 mmol) in DMF (5 mL) was stirred at rt for 1 h. The reaction mixture was purified by flash column chromatography to give the title compound as a light yellow solid (159 mg, 84.3% yield).

Step B: (R)-5-(2-Methyl-4-phenoxyphenyl)-N-(1-(2-(methylamino)acetyl)pyrrolidin-3-yl)-4-oxo-4,5-dihydro-3H-1-thia-3,5,8-triazaacenaphthylene-2-carboxamide To a round bottom flask were added (R)-tert-butyl methyl (2-(3-(5-(2-methyl-4-phenoxyphenyl)-4-oxo-4,5-dihydro-3H-1-thia-3,5,8-triazaacenaphthylene-2-carboxamido)pyrrolidin-1-yl)-2-oxoethyl)carbamate (159 mg, 0.242 mmol), concentrated HCl (5 mL), and MEOH (5 mL) and was stirred at rt for 1 h. The mixture was concentrated to dryness and was purified by flash column chromatography to give the title compound as a white solid (118 mg, 81.0% yield). MS (ESI): mass calcd. for C$_{29}$H$_{28}$N$_6$O$_4$S, 556.6; m/z found, 557.3 [M+H]$^+$. 1H NMR (400 MHz, CD$_3$OD): δ 8.34-8.30 (m, 1H), 7.42-7.36 (m, 2H), 7.32-7.27 (m, 1H), 7.20-7.14 (m, 1H), 7.10-7.03 (m, 3H), 7.00-6.94 (m, 1H), 6.10-6.03 (m, 1H), 4.68-4.56 (m, 1H), 3.98-3.91 (m, 2H), 3.89-3.80 (m, 1H), 3.74-3.63 (m, 1H), 3.60-3.42 (m, 2H), 2.76-2.70 (m, 3H), 2.42-2.13 (m, 2H), 2.11 (s, 3H)

Example 392: (R)—N-(1-(2-Aminoacetyl)pyrrolidin-3-yl)-5-(2-methyl-4-phenoxyphenyl)-4-oxo-4,5-dihydro-3H-1-thia-3,5,8-triazaacenaphthylene-2-carboxamide

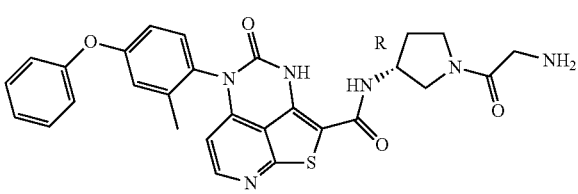

Step A: (R)-tert-Butyl (2-(3-(5-(2-methyl-4-phenoxyphenyl)-4-oxo-4,5-dihydro-3H-1-thia-3,5,8-triazaacenaphthylene-2-carboxamido)pyrrolidin-1-yl)-2-oxoethyl)carbamate A solution of (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159, 150 mg, 0.29 mmol), N-Boc-glycine (100 mg, 0.57 mmol), HATU (142 mg, 0.373 mmol), and DIEA (111 mg, 0.861 mmol) in DMF (5 mL) was stirred at rt for 1 h. The mixture was purified by flash column chromatography to give the title compound as a light yellow solid (151 mg, 81.9% yield).

Step B: (R)—N-(1-(2-Aminoacetyl)pyrrolidin-3-yl)-5-(2-methyl-4-phenoxyphenyl)-4-oxo-4,5-dihydro-3H-1-thia-3,5,8-triazaacenaphthylene-2-carboxamide To a round bottom flask were added (R)-tert-butyl (2-(3-(5-(2-methyl-4-phenoxyphenyl)-4-oxo-4,5-dihydro-3H-1-thia-3,5,8-triazaacenaphthylene-2-carboxamido)pyrrolidin-1-yl)-2-oxoethyl)carbamate (151 mg, 0.235 mmol), concentrated HCl (5 mL), and MeOH (5 mL) and was stirred at rt for 1 h. The reaction mixture was concentrated to dryness and the residue was purified by flash column chromatography to give the title compound as a white solid (116 mg, 83.8% yield). MS (ESI): mass calcd. for $C_{28}H_{26}N_6O_4S$, 542.6; m/z found, 543.3 [M+H]$^+$. 1H NMR (400 MHz, CD3OD): δ 8.34-8.30 (m, 1H), 7.42-7.36 (m, 2H), 7.32-7.27 (m, 1H), 7.20-7.14 (m, 1H), 7.10-7.03 (m, 3H), 7.00-6.94 (m, 1H), 6.10-6.03 (m, 1H), 4.68-4.56 (m, 1H), 3.90-3.78 (m, 3H), 3.74-3.63 (m, 1H), 3.60-3.42 (m, 2H), 2.42-2.13 (m, 2H), 2.11 (s, 3H)

Example 393: (R)-5-(2-Methyl-4-phenoxyphenyl)-4-oxo-N-(1-(2-(piperidin-1-yl)acetyl)piperidin-3-yl)-4,5-dihydro-3H-1-thia-3,5,8-triazaacenaphthylene-2-carboxamide

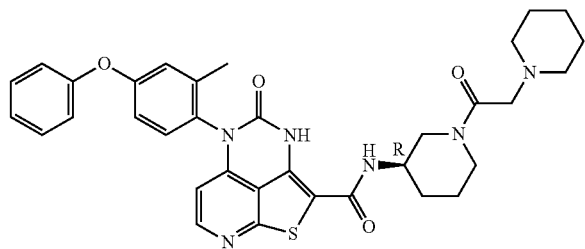

To a solution of (R)—N-(1-(2-chloroacetyl)piperidin-3-yl)-5-(2-methyl-4-phenoxyphenyl)-4-oxo-4,5-dihydro-3H-1-thia-3,5,8-triazaacenaphthylene-2-carboxamide (Example 396, 150 mg, 0.26 mmol) in DCM (2 mL) and triethylamine (52 mg, 0.52 mmol) was added piperidine (44 mg, 0.52 mmol) in DCM (2 mL) dropwise and it was stirred at rt for 2 h. The reaction mixture was concentrated to dryness and was purified by flash column chromatography and preparative TLC to give the title compound as a yellow solid (37 mg). MS (ESI): mass calcd. for $C_{34}H_{36}N_6O_4S$, 624.8; m/z found, 625.2 [M+H]$^+$. 1H NMR (400 MHz, DMSO-d6): δ 8.36 (br, 1H), 8.24 (d, J=5.3 Hz, 1H), 7.48-7.40 (m, 2H), 7.36-7.26 (m, 1H), 7.22-7.16 (m, 1H), 7.14-7.09 (m, 2H), 7.10-7.05 (m, 1H), 7.00-6.93 (m, 1H), 5.86 (d, J=5.3 Hz, 1H), 4.31-3.70 (m, 3H), 3.19-2.98 (m, 3H), 2.88-2.71 (m, 1H), 2.49-2.32 (m, 4H), 2.05 (s, 3H), 1.95-1.89 (m, 1H), 1.80-1.60 (m, 2H), 1.55-1.49 (m, 4H), 1.45-1.28 (m, 3H).

Example 394: (R)-5-(2-Methyl-4-phenoxyphenyl)-N-(1-(2-morpholinoacetyl)piperidin-3-yl)-4-oxo-4,5-dihydro-3H-1-thia-3,5,8-triazaacenaphthylene-2-carboxamide

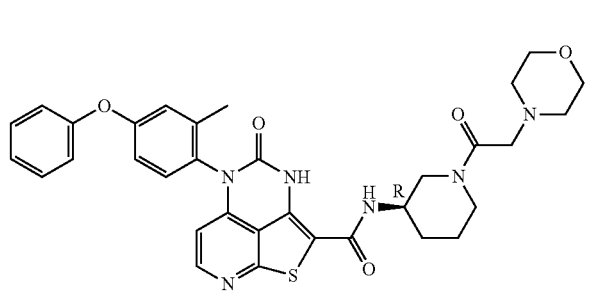

To a solution of (R)—N-(1-(2-chloroacetyl)piperidin-3-yl)-5-(2-methyl-4-phenoxyphenyl)-4-oxo-4,5-dihydro-3H-1-thia-3,5,8-triazaacenaphthylene-2-carboxamide (Example 396, 150 mg, 0.26 mmol) and triethylamine (43 mg, 0.43 mmol) in DCM (2 mL) was added morpholine (38 mg, 0.43 mmol) in DCM (2 mL) dropwise and was stirred at rt for 2 h. The reaction mixture was concentrated to dryness and was purified by flash column chromatography, then preparative TLC to give the title compound as a yellow solid (80 mg). MS (ESI): mass calcd. for $C_{33}H_{34}N_6O_5S$, 626.7; m/z found, 627.2 [M+H]$^+$. 1H NMR (400 MHz, DMSO-d6): δ 10.22 (br, 1H), 8.34-8.14 (m, 2H), 7.48-7.36 (m, 2H), 7.36-7.25 (m, 1H), 7.21-7.14 (m, 1H), 7.13-7.07 (m, 2H), 7.08-7.03 (m, 1H), 6.98-6.91 (m, 1H), 5.95-5.79 (m, 1H), 4.31-3.70 (m, 3H), 3.63-3.48 (m, 4H), 3.21-2.92 (m, 3H), 2.71-2.57 (m, 1H), 2.45-2.24 (m, 4H), 2.03 (s, 3H), 1.94-1.86 (m, 1H), 1.78-1.31 (m, 3H).

Example 395: (R)—N-(1-(2-Chloroacetyl)pyrrolidin-3-yl)-5-(2-methyl-4-phenoxyphenyl)-4-oxo-4,5-dihydro-3H-1-thia-3,5,8-triazaacenaphthylene-2-carboxamide

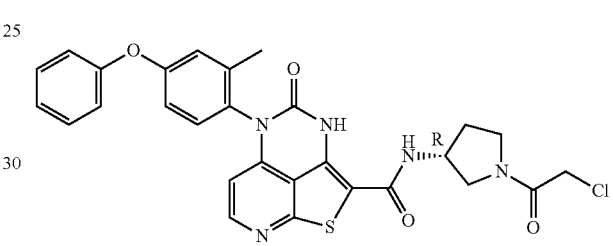

The title compound was prepared in a manner analogous to Method 1, steps A-I in Example 1, and using tert-butyl (3R)-3-aminopyrrolidine-1-carboxylate in place of tert-butyl (3R,5R)-3-amino-5-fluoro-piperidine-1-carboxylate in step G and using 2-chloroacetyl chloride in place of prop-2-enoyl chloride in step I to yield the title compound. MS (ESI): mass calcd. for $C_{28}H_{24}ClN_5O_4S$, 562.0; m/z found, 562.1 [M+H]$^+$. $^1$H NMR (400 MHz, DMSO-d$_6$): δ 10.31-10.14 (m, 1H), 8.43-8.25 (m, 2H), 7.47-7.39 (m, 2H), 7.39-7.34 (m, 1H), 7.22-7.15 (m, 1H), 7.14-7.06 (m, 3H), 7.00-6.94 (m, 1H), 6.04-5.92 (m, 1H), 4.57-4.39 (m, 1H), 4.35-4.23 (m, 2H), 3.84-3.36 (m, 4H), 2.22-2.10 (m, 1H), 2.05 (s, 3H), 2.04-1.89 (m, 1H).

Example 396: (R)—N-(1-(2-Chloroacetyl)piperidin-3-yl)-5-(2-methyl-4-phenoxyphenyl)-4-oxo-4,5-dihydro-3H-1-thia-3,5,8-triazaacenaphthylene-2-carboxamide

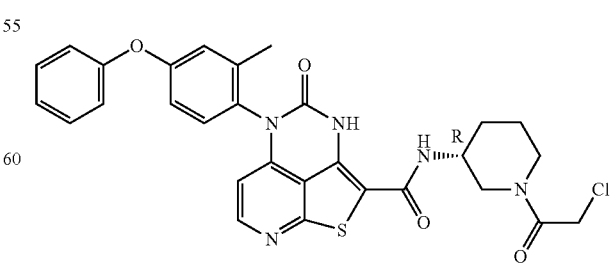

The title compound was prepared in a manner analogous to Method 1, steps A-I in Example 1, and using tert-butyl (3R)-3-aminopiperidine-1-carboxylate in place of tert-butyl (3R,5R)-3-amino-5-fluoro-piperidine-1-carboxylate in step G and using 2-chloroacetyl chloride in place of prop-2-enoyl chloride in step I to yield the title compound. MS (ESI): mass calcd. for $C_{29}H_{26}ClN_5O_4S$, 576.1; m/z found, 576.3 [M+H]$^+$. $^1$H NMR (400 MHz, DMSO-d$_6$): δ 10.29-10.12 (m, 1H), 8.33 (d, J=5.5 Hz, 1H), 8.17-7.96 (m, 1H), 7.49-7.39 (m, 2H), 7.39-7.34 (m, 1H), 7.22-7.15 (m, 1H), 7.14-7.05 (m, 3H), 7.00-6.94 (m, 1H), 5.98 (d, J=5.5 Hz, 1H), 4.42-4.10 (m, 3H), 3.94-3.70 (m, 2H), 3.13-2.94 (m, 1H), 2.78-2.58 (m, 1H), 2.05 (s, 3H), 1.96-1.90 (m, 1H), 1.79-1.71 (m, 1H), 1.65-1.38 (m, 2H).

Example 397: (R)—N-(1-Acryloylpiperidin-3-yl)-4-oxo-5-(4-(thiophen-2-yl)phenyl)-4,5-dihydro-3H-1-thia-3,5,8-triazaacenaphthylene-2-carboxamide

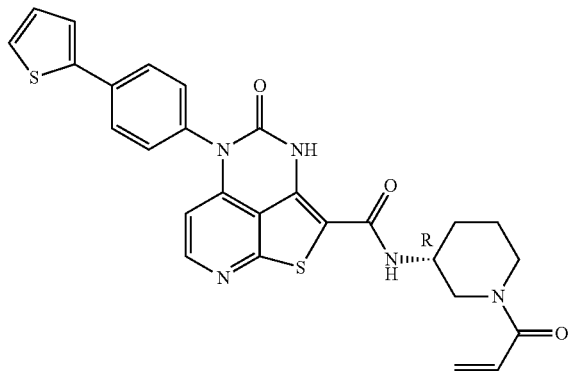

Step A: (R)-tert-Butyl 3-(4-oxo-5-(4-(thiophen-2-yl)phenyl)-4,5-dihydro-3H-1-thia-3,5,8-triazaacenaphthylene-2-carboxamido)piperidine-1-carboxylate To a 2-5 mL Biotage microwave vial with stir bar were added 1,1'-bis(diphenylphosphino)ferrocene-palladium(II)dichloride*DCM complex (2.3 mg, 0.0028 mmol), 2-chloro-4-iodonicotinonitrile (39.9 mg, 0.151 mmol), 4-thiophen-2-ylphenylamine (26.8 mg, 0.153 mmol), and Cs$_2$CO$_3$ (71 mg, 0.22 mmol) under air at room temperature. The vial was sealed, and 1,4-dioxane (0.3 mL) was added via syringe, and quickly evacuated/flushed with argon 4×. The mixture was stirred at 150° C. under argon for 30 min. The reaction was treated with (R)-tert-butyl 3-(2-mercaptoacetamido)piperidine-1-carboxylate (Intermediate 22) (0.24 mL, 0.156 mmol) via syringe at room temperature, and stirred under argon at 150° C. for 15 min. The amber mixture was then cooled to room temperature, opened, and treated with CDI (102 mg, 0.629 mmol) in one portion under air. The microwave vial was resealed, evacuated/flushed with argon 4×, and stirred at 150° C. under argon for 15 min. The reaction was then cooled to room temperature, diluted with EtOAc (10 mL), and washed with 0.5 M citric acid/brine (2×5 mL; final pH~1-2) and 2 M K$_2$CO$_3$ (1×5 mL; final pH>10). The clear amber organic phase was then dried over anhydrous Na$_2$SO$_4$, filtered, and concentrated to dryness. The residue was dissolved in DCM (0.75 mL) and purified by flash column chromatography to give the title compound as a yellow foam (48 mg, 55%).

Step B: (R)-4-Oxo-N-(piperidin-3-yl)-5-(4-(thiophen-2-yl)phenyl)-4,5-dihydro-3H-1-thia-3,5,8-triazaacenaphthylene-2-carboxamide A solution of (R)-tert-butyl 3-(4-oxo-5-(4-(thiophen-2-yl)phenyl)-4,5-dihydro-3H-1-thia-3,5,8-triazaacenaphthylene-2-carboxamido)piperidine-1-carboxylate (48 mg, 0.083 mmol) in 1,4-dioxane (0.417 mL) was treated with HCl (4.08 M in dioxane, 1.02 mL) in one portion at room temperature, and the resulting homogeneous solution was stirred at room temperature for 3 h. After 3 h, the opaque slurry was concentrated to dryness, and the residue was suspended in CH$_3$CN (3 mL) and the CH$_3$CN was removed by suction and the precipitate was dried under high vacuum to give the title compound as a light yellow powder (42.3 mg, 99%).

Step C: (R)—N-(1-Acryloylpiperidin-3-yl)-4-oxo-5-(4-(thiophen-2-yl)phenyl)-4,5-dihydro-3H-1-thia-3,5,8-triazaacenaphthylene-2-carboxamide A solution of (R)-4-oxo-N-(piperidin-3-yl)-5-(4-(thiophen-2-yl)phenyl)-4,5-dihydro-3H-1-thia-3,5,8-triazaacenaphthylene-2-carboxamide (34.5 mg, 0.0674 mmol) in triethylamine (0.066 mL, 0.48 mmol) and DCM (6.1 mL) under argon (evacuated/flushed 2×) was stirred at −40 to −45° C. (dry ice/CH$_3$CN bath temperature) while acryloyl chloride (0.64 mL, 0.064 mmol) was added dropwise over 3.5 min. After 20 min the cold reaction was quenched with an equal volume of 0.1 M NaH$_2$PO$_4$ (pH~5, 7 mL, 0.7 mmol; final pH~6-7). The organic layer was dried over anhydrous Na$_2$SO$_4$, filtered, and concentrated to dryness and dried under high vacuum to provide a crude residue as a dark yellow solid. This residue was purified by HPLC to give the title compound as a light beige foam (12.2 mg, 34.0% yield). MS (ESI): mass calcd. for $C_{27}H_{23}N_5O_3S_2$, 529.6; m/z found, 530.25 [M+H]$^+$. $^1$H NMR (400 MHz, CDCl$_3$): δ ppm (ROTAMERS) 9.49 (br. s., 1H), 8.31-8.41 (m, 1H), 7.81 (d, J=8.6 Hz, 2H), 7.31-7.42 (m, 4H), 7.13 (dd, J=5.1 Hz, J=3.8 Hz, 1H), 6.58-6.69 (m, 1H), 6.15-6.48 (m, 2.5H), 5.71-5.82 (m, 1H), 5.49-5.56 (m, 0.5H), 3.88-4.23 (m, 2.5H), 3.29-3.74 (m, 2.5H), 1.67-2.14 (m, 4H).

Example 398: (R,E)-N-(1-(2-Cyano-4,4-dimethylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

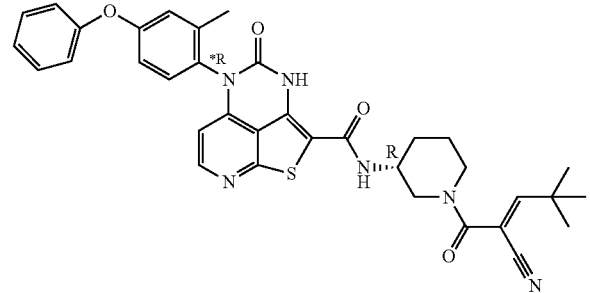

Step A: (R)-tert-Butyl 3-(5-(*R)-(2-methyl-4-phenoxyphenyl)-4-oxo-4,5-dihydro-3H-1-thia-3,5,8-triazaacenaphthylene-2-carboxamido)piperidine-1-carboxylate A solution of 5-(*R) (2-methyl-4-phenoxyphenyl)-4-oxo-4,5-dihydro-3H-1-thia-3,5,8-triazaacenaphthylene-2-carboxylic acid (Intermediate 63, 100 mg, 0.24 mmol), HATU (183 mg, 0.481 mmol), and triethylamine (73 mg, 0.72 mmol) in anhydrous DMF (3 mL) was stirred at room temperature for 10 min, then tert-butyl (3R)-3-aminopiperidine-1-carboxylate (72 mg, 0.36 mmol) was added and the mixture was stirred for 2 h. The crude mixture was purified by flash column chromatography to give the title compound as a slight yellow solid (110 mg, 76% yield).

Step B: (R,E)-N-(1-(2-Cyano-4,4-dimethylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide A solution of (R)-tert-butyl 3-(5-(*R)-(2-methyl-4-phenoxyphenyl)-4-oxo-4,5-dihydro-3H-1-thia-3,5,8-triazaacenaphthylene-2-carboxamido)piperidine-1-carboxylate (110 mg, 0.18 mmol) in HCl/MeOH (6 N, 15 mL) was concentrated at 50° C. to dryness to give a yellow solid. A solution of (E)-2-cyano-4,4-dimethyl-pent-2-enoic acid (Intermediate 44, 34 mg, 0.22 mmol), HATU (139 mg, 0.366 mmol), and triethylamine (56 mg, 0.55 mmol) in anhydrous DMF (3 mL) was stirred at room temperature for 10 min, then the yellow solid from above was added and the mixture was stirred for 2 h. The reaction mixture was purified by flash column chromatography to give the title compound as a slight yellow solid (75 mg, 64% yield). MS (ESI): mass calcd. for $C_{35}H_{34}N_6O_4S$, 634.7; m/z found, 635.3 [M+H]$^+$. $^1$H NMR (400 MHz, CD$_3$OD): δ 8.32 (d, J=5.5 Hz, 1H), 7.45-7.35 (m, 2H), 7.32-7.25 (m, 1H), 7.22-7.13 (m, 1H), 7.12-7.03 (m, 3H), 6.98-6.93 (m, 1H), 6.86 (s, 1H), 6.07 (d, J=5.5 Hz, 1H), 4.57-3.88 (m, 3H), 3.29-2.78 (m, 2H), 2.12 (s, 3H), 2.10-2.02 (m, 1H), 1.99-1.56 (m, 3H), 1.28 (s, 9H).

Example 399: (R,E)-N-(1-(2-Cyano-3-cyclopropylacryloyl)piperidin-3-yl)-5-(4-isopropoxyphenyl)-4-oxo-4,5-dihydro-3H-1-thia-3,5,8-triazaacenaphthylene-2-carboxamide

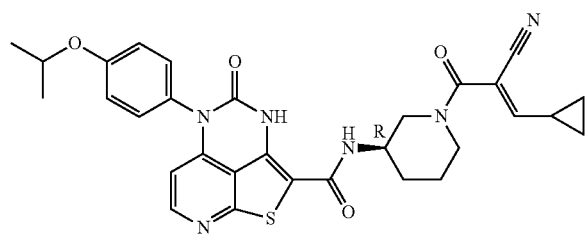

Step A: (E)-2-Cyano-3-cyclopropylacryloyl chloride

To a suspension of (E)-2-cyano-3-cyclopropyl-prop-2-enoic acid (Intermediate 17) (24 mg, 0.18 mmol) in CHCl$_3$ (0.5 mL) was added 1-chloro-N,N,2-trimethylpropenylamine (28 μL, 0.22 mmol) and was mixed for 5 minutes before being used directly in the next reaction.

Step B: (R,E)-N-(1-(2-Cyano-3-cyclopropylacryloyl)piperidin-3-yl)-5-(4-isopropoxyphenyl)-4-oxo-4,5-dihydro-3H-1-thia-3,5,8-triazaacenaphthylene-2-carboxamide A solution of triethylamine (68 μL, 0.49 mmol) and (R)-5-(4-isopropoxyphenyl)-4-oxo-N-(piperidin-3-yl)-4,5-dihydro-3H-1-thia-3,5,8-triazaacenaphthylene-2-carboxamide hydrochloride (79.3 mg, 0.162 mmol) in DCM (1 mL) was cooled in an ice water bath. To the reaction mixture was added a solution of (E)-2-cyano-3-cyclopropylacryloyl chloride (0.179 mmol) in CHCl$_3$ (0.5 mL) and the reaction mixture was stirred at 0° C. for 40 min. The reaction mixture was partitioned between DCM (10 mL) and saturated aqueous NaHCO$_3$ (10 mL). The aqueous phase was extracted once with EtOAc (10 mL) and the combined organic extracts were dried over anhydrous Na$_2$SO$_4$, filtered, and concentrated to dryness. The residue was purified by flash column chromatography to give the title compound as a light yellow powder (38.0 mg, 41% yield). MS (ESI): mass calcd. for $C_{30}H_{30}N_6O_4S$, 570.7; m/z found, 571.0 [M+H]$^+$. $^1$H NMR (400 MHz, DMSO-d$_6$): δ 10.12 (s, 1H), 8.33 (d, J=5.56 Hz, 1H), 8.11 (d, J=7.07 Hz, 1H), 7.34 (d, J=8.08 Hz, 2H), 7.10 (d, J=9.09 Hz, 2H), 6.62 (d, J=11.12 Hz, 1H), 6.04 (d, J=5.56 Hz, 1H), 4.70 (spt, J=6.06 Hz, 1H), 3.80-4.31 (m, 3H), 2.67-3.27 (m, 2H), 1.76-1.98 (m, 3H), 1.61-1.76 (m, 1H), 1.41-1.60 (m, 1H), 1.33 (d, J=6.06 Hz, 6H), 0.78-1.29 (m, 4H).

Example 400: (R)—N-(1-Acryloylpiperidin-3-yl)-5-(4-isopropoxyphenyl)-4-oxo-4,5-dihydro-3H-1-thia-3,5,8-triazaacenaphthylene-2-carboxamide

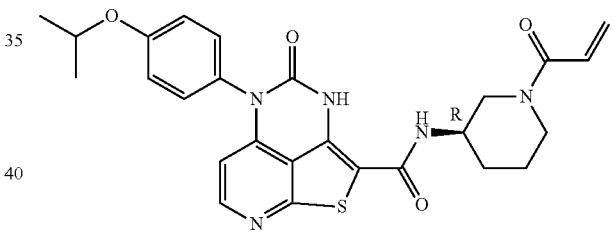

To a solution of (R)-5-(4-isopropoxyphenyl)-4-oxo-N-(piperidin-3-yl)-4,5-dihydro-3H-1-thia-3,5,8-triazaacenaphthylene-2-carboxamide*HCl (Example 405 step E, 93.2 mg, 0.191 mmol) in DCM (1 mL) was added triethylamine (79 μL, 0.57 mmol) followed by acryloyl chloride (15 μL, 0.19 mmol) dropwise via syringe. The resulting suspension was stirred under air at 0° C. for 40 min. The reaction mixture was partitioned between DCM (10 mL) and saturated aqueous NaHCO$_3$ (10 mL). The aqueous phase was extracted once with EtOAc (10 mL) and the combined organic extracts were dried over anhydrous Na$_2$SO$_4$, filtered, and concentrated to dryness. The residue was purified by flash column chromatography to give the title compound as a yellow powder (32.2 mg, 33.3% yield). MS (ESI): mass calcd. for $C_{26}H_{27}N_5O_4S$, 505.6; m/z found, 506.2 [M+H]$^+$. $^1$H NMR (400 MHz, CDCl3): δ 9.46 (s, 1H), 8.34 (br. s., 1H), 7.22 (d, J=7.58 Hz, 2H), 7.04 (d, J=8.59 Hz, 2H), 6.63 (dd, J=10.86, 16.93 Hz, 1H), 6.28-6.49 (m, 1H), 6.24 (br. s., 0.5H), 6.06-6.19 (m, 1H), 5.68-5.82 (m, 1H), 5.49 (br. s., 0.5H), 4.60 (spt, J=5.98 Hz, 1H), 3.84-4.24 (m, 2.5H), 3.28-3.77 (m, 2.5H), 1.68-2.14 (m, 4H), 1.39 (d, J=6.06 Hz, 6H).

Example 401: (R,E)-N-(1-(3-Cyclopropyl-2-methyl-acryloyl)piperidin-3-yl)-5-(2-methyl-4-phenoxyphenyl)-4-oxo-4,5-dihydro-3H-1-thia-3,5,8-triazaacenaphthylene-2-carboxamide

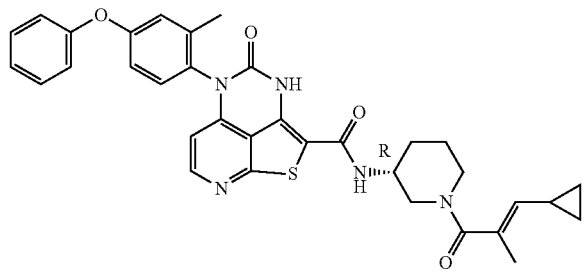

A solution of (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869, 150 mg, 0.28 mmol), (E)-3-cyclopropyl-2-methyl-prop-2-enoic acid (Intermediate 42, 71 mg, 0.56 mmol), HATU (138 mg, 0.364 mmol), and DIEA (108 mg, 0.840 mmol) in DMF (5 mL) was stirred at rt for 1 h. The mixture was purified by flash column chromatography to give the title compound as light yellow solid (58 mg, 34% yield). MS (ESI): mass calcd. for $C_{34}H_{33}N_5O_4S$, 607.7; m/z found, 608.3 $[M+H]^+$. $^1$H NMR (400 MHz, CD$_3$OD): δ 8.35-8.31 (m, 1H), 7.43-7.36 (m, 2H), 7.32-7.27 (m, 1H), 7.19-7.13 (m, 1H), 7.11-7.04 (m, 3H), 7.00-6.94 (m, 1H), 7.09-6.05 (m, 1H), 5.06-4.98 (m, 1H), 4.35-3.84 (m, 3H), 3.14-2.83 (m, 2H), 2.12 (s, 3H), 2.10-1.98 (m, 1H), 1.98-1.90 (m, 3H), 1.90-1.78 (m, 1H), 1.78-1.64 (m, 1H), 1.64-1.49 (m, 2H), 0.90-0.78 (m, 2H), 0.56-0.45 (m, 1H), 0.45-0.37 (m, 1H).

Example 402: (R,EZ)—N-(1-(2-Chloro-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide

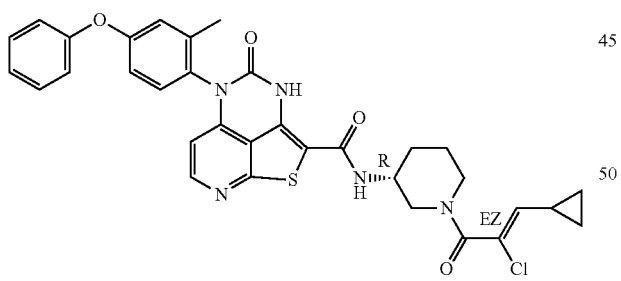

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 150 mg 0.28 mmol), (EZ)-2-chloro-3-cyclopropyl-prop-2-enoic acid (Intermediate 39, 82 mg, 0.56 mmol), HATU (138 mg, 0.364 mmol), and DIEA (108 mg, 0.840 mmol) in DMF (5 mL) was stirred at rt for 1 h. The mixture was purified by flash column chromatography to give the title compound as a light yellow solid (68 mg, 39% yield). MS (ESI): mass calcd. for $C_{33}H_{30}ClN_5O_4S$, 628.1; m/z found, 628.3 $[M+H]^+$. $^1$H NMR (400 MHz, CD$_3$OD): δ 8.34-8.28 (m, 1H), 7.42-7.33 (m, 2H), 7.33-7.26 (m, 1H), 7.19-7.11 (m, 1H), 7.10-7.01 (m, 3H), 6.99-6.92 (m, 1H), 6.09-6.02 (m, 1H), 5.60-5.36 (m, 1H), 4.35-3.84 (m, 3H), 3.19-2.83 (m, 2H), 2.15-1.98 (m, 4H), 1.95-1.78 (m, 2H), 1.77-1.67 (m, 1H), 1.67-1.51 (m, 1H), 0.96-0.78 (m, 2H), 0.70-0.60 (m, 1H), 0.60-0.47 (m, 1H).

Example 403: (R,E)-5-(2-Methyl-4-phenoxyphenyl)-N-(1-(4-morpholinobut-2-enoyl)piperidin-3-yl)-4-oxo-4,5-dihydro-3H-1-thia-3,5,8-triazaacenaphthylene-2-carboxamide

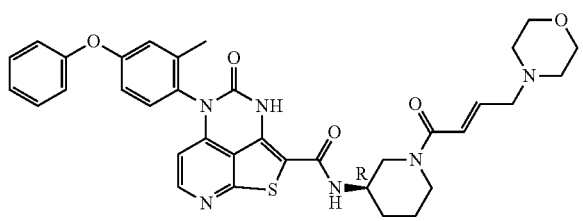

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869, 200 mg, 0.40 mmol) and (E)-4-morpholinobut-2-enoic acid (171 mg, 1.00 mmol) in anhydrous DMF (3 mL) were added HATU (228 mg, 0.600 mmol) and diisopropylethylamine (78 mg, 0.60 mmol) and the mixture was stirred at rt overnight. The reaction mixture was purified by flash column chromatography to give the title compound as a yellow solid (74 mg). MS (ESI): mass calcd. for $C_{35}H_{36}N_6O_5S$, 652.8; m/z found, 653.2 $[M+H]^+$. $^1$H NMR (400 MHz, DMSO-d$_6$): δ 10.33-10.13 (m, 1H), 8.33 (d, J=5.5 Hz, 1H), 8.18-8.08 (m, 1H), 7.46-7.40 (m, 2H), 7.40-7.33 (m, 1H), 7.21-7.16 (m, 1H), 7.14-7.05 (m, 3H), 7.00-6.93 (m, 1H), 6.67-6.50 (m, 2H), 5.97 (d, J=5.5 Hz, 1H), 4.46-3.73 (m, 4H), 3.65-3.35 (m, 6H), 3.15-2.58 (m, 3H), 2.43-2.28 (m, 2H), 2.05 (s, 3H), 1.94-1.87 (m, 1H), 1.83-1.54 (m, 2H), 1.46-1.36 (m, 1H).

Example 404: (R)—N-(1-Acryloylpiperidin-3-yl)-5-(benzo[b]thiophen-5-yl)-4-oxo-4,5-dihydro-3H-1-thia-3,5,8-triazaacenaphthylene-2-carboxamide

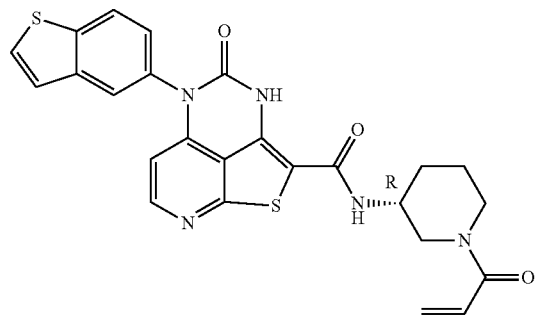

Step A: (R)-tert-Butyl 3-(5-(benzo[b]thiophen-5-yl)-4-oxo-4,5-dihydro-3H-1-thia-3,5,8-triazaacenaphthylene-2-carboxamido)piperidine-1-carboxylate The title compound was prepared using step A in Example 397, and using 1-benzothiophen-5-amine in place of 4-thiophen-2-ylphenylamine in step B to yield the title compound.

Step B: (R)-5-(Benzo[b]thiophen-5-yl)-4-oxo-N-(piperidin-3-yl)-4,5-dihydro-3H-1-thia-3,5,8-triazaacenaphthylene-2-carboxamide A solution of (R)-tert-butyl 3-(5-(benzo[b]thiophen-5-yl)-4-oxo-4,5-dihydro-3H-1-thia-3,5,8-triazaacenaphthylene-2-carboxamido)piperidine-1-carboxylate (54.4 mg, 0.0990 mmol) in dioxane (0.5 mL, 0.1 mmol) was treated with HCl (4.08 M in dioxane, 1.21 mL) in one portion at room temperature, and the resulting solution was stirred at room temperature for 3 h, then it was concentrated to dryness. The residue was suspended in $CH_3CN$ (3 mL) and the $CH_3CN$ supernatant was suctioned off by pipette, and the wet solids were dried under high vacuum to give the title compound as a light yellow powder (47 mg, 98% yield).

Step C: (R)—N-(1-Acryloylpiperidin-3-yl)-5-(benzo[b]thiophen-5-yl)-4-oxo-4,5-dihydro-3H-1-thia-3,5,8-triazaacenaphthylene-2-carboxamide A solution of (R)-5-(benzo[b]thiophen-5-yl)-4-oxo-N-(piperidin-3-yl)-4,5-dihydro-3H-1-thia-3,5,8-triazaacenaphthylene-2-carboxamide (36.6 mg, 0.0753 mmol) in triethylamine (34.1 mg, 0.337 mmol) and DCM (6.85 mL) under argon (evacuated/flushed 2×) was stirred at −40° C. to −45° C. (dry ice/$CH_3CN$ bath temperature) while acryloyl chloride (0.73 mL, 0.072 mmol) was added dropwise over 3.5 min. After 20 min, the cold reaction was quenched with an equal volume of 0.1 M $NaH_2PO_4$ (pH~5, 7 mL, 0.7 mmol; final pH~6-7). The organic layer was dried over anhydrous $Na_2SO_4$, filtered, and concentrated to dryness and dried under high vacuum to provide a crude residue. This residue was purified by HPLC to give the title compound as a light beige foam (10.7 mg, 28.2% yield). MS (ESI): mass calcd. for $C_{25}H_{21}N_5O_3S_2$, 503.6; m/z found, 504.3 [M+H]$^+$. $^1$H NMR (400 MHz, $CDCl_3$): δ (ROTAMERS) 9.51 (s, 1H), 8.32 (d, J=5.05 Hz, 1H), 8.07 (d, J=8.59 Hz, 1H), 7.82 (br. s., 1H), 7.60 (d, J=5.56 Hz, 1H), 7.36-7.43 (m, 1H), 7.27-7.32 (m, 1H), 6.57-6.70 (m, 1H), 6.25-6.49 (m, 1.5H), 6.11 (br. s., 1H), 5.69-5.82 (m, 1H), 5.62 (br. s., 0.5H), 3.85-4.24 (m, 2.5H), 3.27-3.79 (m, 2.5H), 1.90-2.14 (m, 2H), 1.73-1.87 (m, 2H). 3.24-3.18 (m, 2H), 2.05 (s, 3H), 1.78 (s, 3H).

Example 405: (R)-5-(4-Isopropoxyphenyl)-4-oxo-N-(piperidin-3-yl)-4,5-dihydro-3H-1-thia-3,5,8-triazaacenaphthylene-2-carboxamide

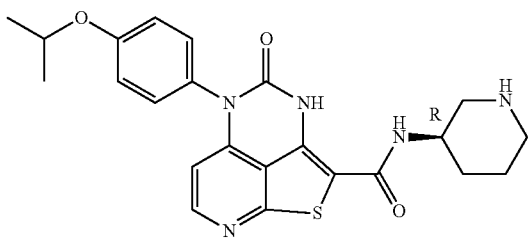

Step A: 2-Chloro-4-(4-isopropoxyanilino)pyridine-3-carbonitrile

To a 10-20 mL microwave vial was added sequentially 2-chloro-4-iodonicotinonitrile (300 mg, 1.13 mmol), 4-isopropoxyaniline (172 mg, 1.13 mmol), palladium(II) acetate (5.0 mg, 0.023 mmol), bis(2-diphenylphosphinophenyl) ether (18 mg, 0.034 mmol), and $Cs_2CO_3$ (517 mg, 1.59 mmol) and the vial was sealed and evacuated and refilled with argon three times. To this vial was added 1,4-dioxane (2.2 mL) and the vial was evacuated and refilled with argon once. The reaction mixture was heated for 5 minutes in a 50° C. oil bath under an argon inlet needle, then the inlet needle was removed and the sealed vial was heated for 30 minutes in a 150° C. oil bath. The crude reaction mixture was used directly in the next step (326 mg).

Step B: tert-Butyl (3R)-3-[(2-sulfanylacetyl)amino]piperidine-1-carboxylate

To a 10-20 mL microwave vial was added (R)-1-Boc-3-aminopiperidine (5.015 g, 25.04 mmol). The vial was sealed and evacuated and back-filled with argon three times and then methyl 2-mercaptoacetate (6.7 mL, 75 mmol) was added via syringe in one portion and the vial was heated in a 150° C. oil bath. After 1 h 35 minutes, the mixture was cooled to rt and was purified by flash column chromatography to give the title compound (5.54 g, 80.6% yield).

Step C: (R)-tert-Butyl 3-(3-amino-4-((4-isopropoxyphenyl)amino)thieno[2,3-b]pyridine-2-carboxamido)piperidine-1-carboxylate To the sealed tube containing 2-chloro-4-(4-isopropoxyanilino)pyridine-3-carbonitrile (326 mg, 1.13 mmol) was added a 0.5 M solution of tert-butyl (3R)-3-[(2-sulfanylacetyl)amino]piperidine-1-carboxylate in dioxane (0.5 M, 2.7 mL, 1.4 mmol). The resulting brown suspension was heated in the sealed tube in a 150° C. oil bath for 15 minutes. The mixture was cooled to room temperature to give the title compound as a crude mixture (596 mg), which was used in the next reaction without purification.

Step D: (R)-tert-Butyl 3-(5-(4-isopropoxyphenyl)-4-oxo-4,5-dihydro-3H-1-thia-3,5,8-triazaacenaphthylene-2-carboxamido)piperidine-1-carboxylate To the crude mixture of (R)-tert-butyl 3-(3-amino-4-((4-isopropoxyphenyl)amino)thieno[2,3-b]pyridine-2-carboxamido)piperidine-1-carboxylate (from above reaction) was added CDI (0.736 g, 4.54 mmol). The tube was sealed and the vessel was evacuated and refilled with argon twice. The mixture was heated for 5 minutes in a 50° C. oil bath under an argon inlet needle, then the argon inlet needle was removed and the mixture was heated at 150° C. for 10 minutes. The mixture was cooled to room temperature and the mixture was partitioned between EtOAc (50 mL) and water (50 mL). The aqueous phase was extracted with EtOAc (2×50 mL) and the combined organic extracts were washed with saturated aqueous NaCl (50 mL), followed by 1 N aqueous HCl (50 mL). The organic phase was dried over anhydrous $Na_2SO_4$, filtered, and concentrated to dryness. The residue was purified by flash column chromatography to give the title compound as a tan foamy solid (449 mg 71.8% yield).

Step E: (R)-5-(4-Isopropoxyphenyl)-4-oxo-N-(piperidin-3-yl)-4,5-dihydro-3H-1-thia-3,5,8-triazaacenaphthylene-2-carboxamide hydrochloride To a solution of (R)-tert-butyl 3-(5-(4-isopropoxyphenyl)-4-oxo-4,5-dihydro-3H-1-thia-3,5,8-triazaacenaphthylene-2-carboxamido)piperidine-1-carboxylate (421.8 mg, 0.765 mmol) in dioxane (4 mL) was added 4 M HCl in dioxane (4.0 mL, 4.0 M, 16 mmol) and was stirred at room temperature under air for 20 minutes. The reaction mixture was concentrated to dryness and the residue was dried under vacuum to give the title compound as a tan powder (459.2 mg, 123.1% yield).

Step F: (R)-5-(4-Isopropoxyphenyl)-4-oxo-N-(piperidin-3-yl)-4,5-dihydro-3H-1-thia-3,5,8-triazaacenaphthylene-2-carboxamide A portion of (R)-5-(4-isopropoxyphenyl)-4-oxo-N-(piperidin-3-yl)-4,5-dihydro-3H-1-thia-3,5,8-triazaacenaphthylene-2-carboxamide hydrochloride (52 mg, 0.11 mmol) was purified by HPLC to give the title compound as a light yellow powder (42.0 mg, 70% yield). MS (ESI): mass calcd. for $C_{23}H_{25}N_5O_3S$, 451.5; m/z found, 452.1 [M+H]$^+$. 1H NMR (400 MHz, DMSO-d6) δ 10.17 (s, 1H), 8.62-8.80 (m, 2H), 8.38 (d, J=5.56 Hz, 1H), 8.21 (d, J=7.07 Hz, 1H), 7.38 (d, J=7.58 Hz, 2H), 7.15 (d, J=9.09 Hz, 2H), 6.09 (d, J=5.56 Hz, 1H), 4.74 (spt, J=5.89 Hz, 1H), 4.14-4.26 (m, 1H), 3.24-3.43 (m, 2H), 2.80-2.95 (m, 2H), 1.88-2.02 (m, 2H), 1.60-1.82 (m, 2H), 1.37 (d, 6H).

Example 406: (R)-5-(4-Isopropoxyphenyl)-4-oxo-N-(1-propionylpiperidin-3-yl)-4,5-dihydro-3H-1-thia-3,5,8-triazaacenaphthylene-2-carboxamide

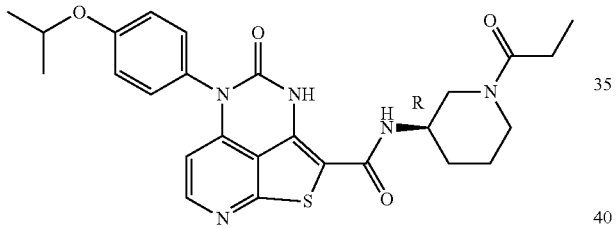

To a solution of (R)-5-(4-isopropoxyphenyl)-4-oxo-N-(piperidin-3-yl)-4,5-dihydro-3H-1-thia-3,5,8-triazaacenaphthylene-2-carboxamide (Example 405, 88.8 mg, 0.182 mmol) in DCM (1 mL) was added triethylamine (76 µL, 0.55 mmol). The resulting solution was cooled in an ice bath and propionyl chloride (16 µL, 0.18 mmol) was added dropwise via a microliter syringe and the resulting orange solution was stirred under air in the ice bath for 25 min. The reaction mixture was partitioned between DCM (10 mL) and saturated aqueous NaHCO$_3$ (10 mL). The aqueous phase was extracted once with EtOAc (10 mL) and the combined organic extracts were dried over anhydrous Na$_2$SO$_4$, filtered, and concentrated to dryness. The residue was purified by flash column chromatography to give the title compound as a light yellow powder (41.5 mg, 44.9% yield). MS (ESI): mass calcd. for $C_{26}H_{29}N_5O_4S$, 507.6; m/z found, 508.3 [M+H]$^+$. 1H NMR (400 MHz, DMSO-d$_6$, 1:1 mixture of rotamers): δ 10.18 (s, 0.5H), 10.12 (s, 0.5H), 8.33 (d, J=5.56 Hz, 1H), 8.10 (d, J=7.07 Hz, 0.5H), 8.02 (d, J=7.58 Hz, 0.5H), 7.34 (d, J=9.09 Hz, 2H), 7.10 (d, J=9.09 Hz, 2H), 6.01-6.05 (m, 1H), 4.70 (spt, J=5.98 Hz, 1H), 4.33-4.50 (m, 0.5H), 4.19-4.27 (m, 0.5H), 3.70-3.95 (m, 2H), 2.86-3.02 (m, 1H), 2.53-2.68 (m, 1H), 2.30-2.38 (m, 2H), 1.87-1.97 (m, 1H), 1.35-1.80 (m, 3H), 1.33 (d, J=6.06 Hz, 6H), 1.01 (q, J=7.07 Hz, 3H).

Example 407: (R)-4-Oxo-N-(piperidin-3-yl)-5-(4-(thiophen-2-yl)phenyl)-4,5-dihydro-3H-1-thia-3,5,8-triazaacenaphthylene-2-carboxamide

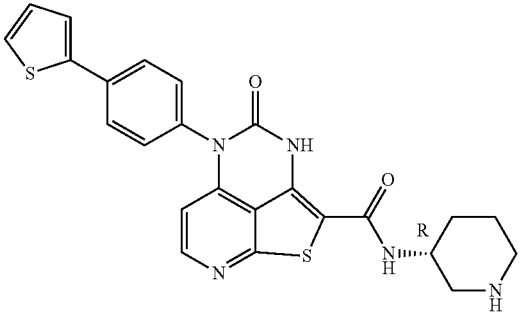

The title compound was prepared using step A-B in Example 397, to yield the title compound. MS (ESI): mass calcd. for $C_{24}H_{21}N_5O_2S_2$, 475.6; m/z found, 476.25 [M+H]$^+$. 1H NMR (400 MHz, CD$_3$OD): δ ppm 8.46 (d, J=6.6 Hz, 1H), 7.91 (d, J=8.6 Hz, 2H), 7.54 (d, J=2.5 Hz, 1H), 7.45-7.51 (m, 3H), 7.13-7.19 (m, 1H), 6.43 (d, J=6.6 Hz, 1H), 4.22-4.35 (m, 1H), 3.55 (dd, J=12.4, 4.3 Hz, 1H), 3.37 (d, J=12.6 Hz, 1H), 2.91-3.03 (m, 2H), 2.04-2.17 (m, 2H), 1.70-1.93 (m, 2H).

Example 408: (R)—N-(1-Acryloylpiperidin-3-yl)-4-oxo-5-(4-phenoxybenzyl)-4,5-dihydro-3H-1-thia-3,5,8-triazaacenaphthylene-2-carboxamide

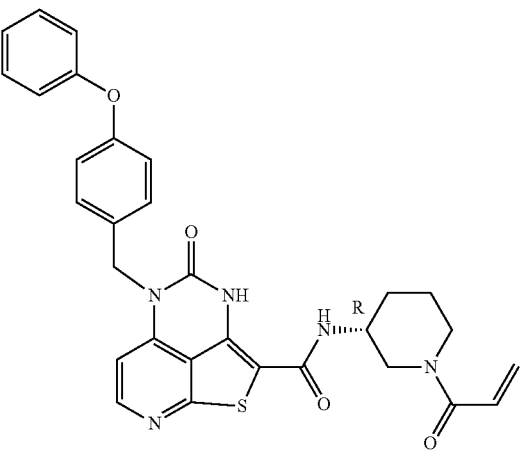

The title compound was prepared in a manner analogous to Method 1, steps C-I in Example 1, and using (4-phenoxyphenyl)methanamine (Intermediate 35) in place of 2-methyl-4-phenoxy-aniline in step C and using tert-butyl (3R)-3-aminopiperidine-1-carboxylate in place of tert-butyl (3R,5R)-3-amino-5-fluoro-piperidine-1-carboxylate in step G to yield the title compound. MS (ESI): mass calcd. for $C_{30}H_{27}N_5O_4S$, 553.6; m/z found, 554.3 [M+H]$^+$. 1H NMR (400 MHz, DMSO-d$_6$): δ 10.12 (s, 1H), 8.35 (d, J=5.4 Hz, 1H), 8.25-8.02 (m, 1H), 7.47-7.27 (m, 4H), 7.18-7.05 (m, 1H), 7.02-6.89 (m, 4H), 6.85-6.65 (m, 2H), 6.17-5.99 (m, 1H), 5.69-5.61 (m, 1H), 5.07 (s, 2H), 4.53-4.12 (m, 1H), 4.07-3.88 (m, 1H), 3.84-3.69 (m, 1H), 3.1-2.90 (m, 1H), 2.85-2.58 (m, 1H), 1.98-1.85 (m, 1H), 1.81-1.72 (m, 1H), 1.69-1.54 (m, 1H), 1.50-1.33 (m, 1H).

Example 409: (R)—N-(1-Methylpyrrolidin-3-yl)-4-oxo-5-(4-phenoxybenzyl)-4,5-dihydro-3H-1-thia-3,5,8-triazaacenaphthylene-2-carboxamide

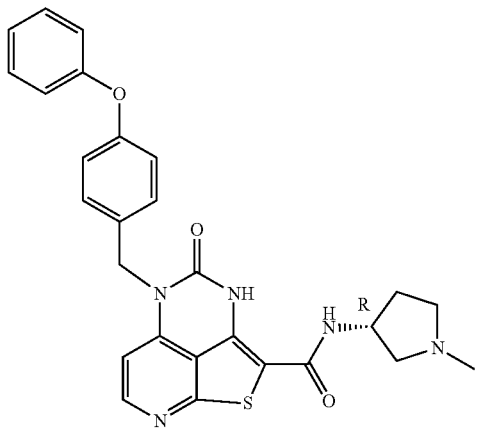

Step A: (R)-4-Oxo-5-(4-phenoxybenzyl)-N-(pyrrolidin-3-yl)-4,5-dihydro-3H-1-thia-3,5,8-triazaacenaphthylene-2-carboxamide The title compound was prepared in a manner analogous to Method 1, steps C-H in Example 1, and using (4-phenoxyphenyl)methanamine (Intermediate 35) in place of 2-methyl-4-phenoxy-aniline in step C and using tert-butyl (3R)-3-aminopyrrolidine-1-carboxylate in place of tert-butyl (3R,5R)-3-amino-5-fluoro-piperidine-1-carboxylate in step G to yield the title compound.

Step B: (R)—N-(1-Methylpyrrolidin-3-yl)-4-oxo-5-(4-phenoxybenzyl)-4,5-dihydro-3H-1-thia-3,5,8-triazaacenaphthylene-2-carboxamide To a solution of (R)-4-oxo-5-(4-phenoxybenzyl)-N-(pyrrolidin-3-yl)-4,5-dihydro-3H-1-thia-3,5,8-triazaacenaphthylene-2-carboxamide (100 mg, 0.21 mmol) in DCM (5 mL) were added formaldehyde (0.5 mL, 37 wt. % in $H_2O$) and $NaBH(OAc)_3$ (90 mg, 0.43 mmol) and was stirred at room temperature for 1 h. The reaction mixture was concentrated to dryness and the residue was purified by flash column chromatography to give the title compound as a yellow solid (40 mg, 36% yield). MS (ESI): mass calcd. for $C_{27}H_{25}N_5O_3S$, 499.6; m/z found, 500.2 [M+H]$^+$. 1H NMR (400 MHz, CD3OD): δ 8.30 (d, J=5.6 Hz, 1H), 7.35-7.22 (m, 4H), 7.09-7.02 (m, 1H), 6.90-6.84 (m, 4H), 6.72 (d, J=5.6 Hz, 1H), 5.08 (s, 2H), 4.65-4.55 (m, 1H), 3.63-3.37 (m, 3H), 3.26-3.16 (m, 1H), 2.90 (s, 3H), 2.58-2.32 (m, 1H), 2.29-2.16 (m, 1H).

Example 410: (R)-5-(Benzo[b]thiophen-5-yl)-4-oxo-N-(piperidin-3-yl)-4,5-dihydro-3H-1-thia-3,5,8-triazaacenaphthylene-2-carboxamide

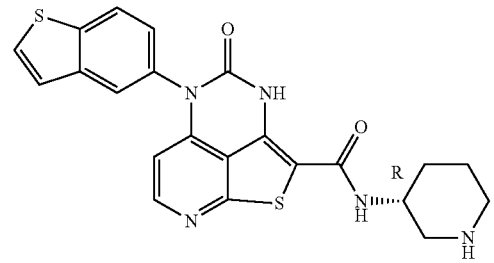

The title compound was prepared using steps A-B in Example 404, to yield the title compound. MS (ESI): mass calcd. for $C_{22}H_{19}N_5O_2S_2$, 449.6; m/z found, 450.25 [M+H]$^+$. $^1$H NMR (400 MHz, CD3OD): δ ppm 8.40 (d, J=6.6 Hz, 1H), 8.18 (d, J=8.6 Hz, 1H), 7.97 (s, 1H), 7.78 (d, J=5.6 Hz, 1H), 7.49 (d, J=5.6 Hz, 1H), 7.39 (d, J=8.6 Hz, 1H), 6.29 (d, J=6.1 Hz, 1H), 4.24-4.35 (m, 1H), 3.51-3.60 (m, 1H), 3.37 (d, J=12.6 Hz, 1H), 2.91-3.04 (m, 2H), 2.04-2.16 (m, 2H), 1.71-1.93 (m, 2H).

Example 411: (R)—N-(1-Methylpiperidin-3-yl)-4-oxo-5-(4-phenoxybenzyl)-4,5-dihydro-3H-1-thia-3,5,8-triazaacenaphthylene-2-carboxamide

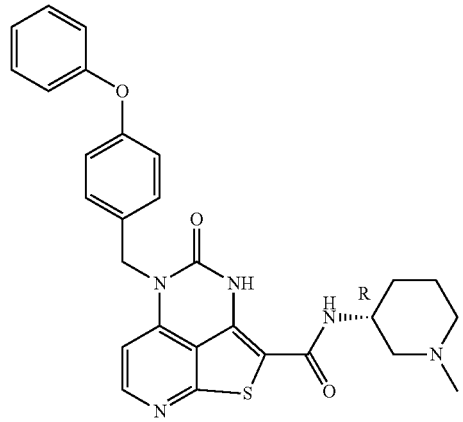

Step A: (R)-4-Oxo-5-(4-phenoxybenzyl)-N-(piperidin-3-yl)-4,5-dihydro-3H-1-thia-3,5,8-triazaacenaphthylene-2-carboxamide The title compound was prepared in a manner analogous to Method 1, steps C-H in Example 1, and using (4-phenoxyphenyl)methanamine (Intermediate 35) in place of 2-methyl-4-phenoxy-aniline in step C and using tert-butyl (3R)-3-aminopiperidine-1-carboxylate in place of tert-butyl (3R,5R)-3-amino-5-fluoro-piperidine-1-carboxylate in step G to yield the title compound.

Step B: (R)—N-(1-Methylpiperidin-3-yl)-4-oxo-5-(4-phenoxybenzyl)-4,5-dihydro-3H-1-thia-3,5,8-triazaacenaphthylene-2-carboxamide To a solution of (R)-4-oxo-5-(4-phenoxybenzyl)-N-(piperidin-3-yl)-4,5-dihydro-3H-1-thia-3,5,8-triazaacenaphthylene-2-carboxamide (73 mg, 0.15 mmol) in DCM (5 mL) were added formaldehyde (0.5 mL, 37 wt. % in H$_2$O) and NaBH(OAc)$_3$ (61 mg, 0.29 mmol) and was stirred at room temperature for 1 h. The reaction mixture was concentrated to dryness and the residue was purified by flash column chromatography to give the title compound as a yellow solid (54 mg, 66% yield). MS (ESI): mass calcd. for C$_{28}$H$_{27}$N$_5$O$_3$S, 513.6; m/z found, 514.2 [M+H]$^+$. 1H NMR (400 MHz, CD3OD): δ 8.41 (s, 1H), 8.33 (d, J=5.5 Hz, 1H), 7.40-7.24 (m, 4H), 7.11-7.02 (m, 1H), 6.95-6.85 (m, 4H), 6.75 (d, J=5.6 Hz, 1H), 5.11 (s, 2H), 4.37-4.18 (m, 1H), 3.55-3.42 (m, 1H), 3.29-3.23 (m, 1H), 2.90-2.83 (m, 2H), 2.80 (s, 3H), 2.10-1.97 (m, 2H), 1.92-1.78 (m, 1H), 1.72-1.60 (m, 1H).

Example 412: (R)-4-Oxo-5-(4-phenoxybenzyl)-N-(piperidin-3-yl)-4,5-dihydro-3H-1-thia-3,5,8-triazaacenaphthylene-2-carboxamide

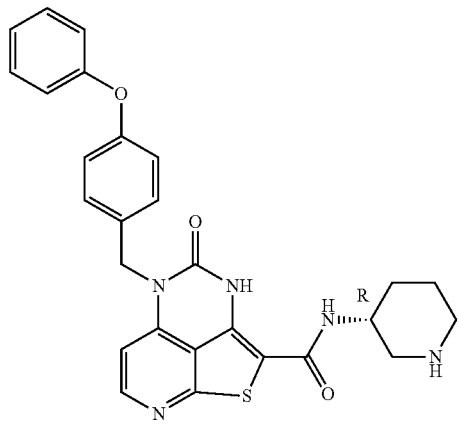

The title compound was prepared using steps A in Example 411, to yield the title compound. MS (ESI): mass calcd. for C$_{27}$H$_{25}$N$_5$O$_3$S, 499.6; m/z found, 500.2 [M+H]$^+$. $^1$H NMR (400 MHz, CD$_3$OD): δ 8.30 (d, J=5.5 Hz, 1H), 7.40-7.25 (m, 4H), 7.12-7.02 (m, 1H), 6.97-6.88 (m, 4H), 6.71 (d, J=5.7 Hz, 1H), 5.13 (s, 2H), 4.18-4.02 (m, 1H), 3.26-3.18 (m, 1H), 3.07-2.97 (m, 1H), 2.84-2.64 (m, 2H), 2.08-1.96 (m, 1H), 1.92-1.83 (m, 1H), 1.74-1.61 (m, 2H).

Example 413: (R)-5-(2-Methyl-4-(trifluoromethoxy)phenyl)-4-oxo-N-(piperidin-3-yl)-4,5-dihydro-3H-1-thia-3,5,8-triazaacenaphthylene-2-carboxamide

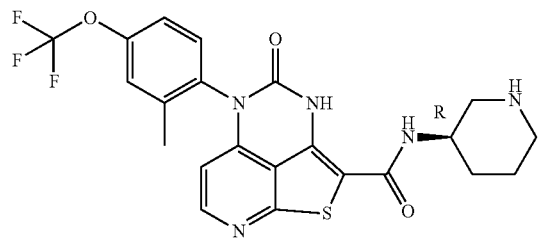

Step A: 2-Chloro-6-[2-methyl-4-(trifluoromethoxy)anilino]benzonitrile

To a 10-20 mL microwave vial were added sequentially 2-chloro-4-iodonicotinonitrile (300 mg, 1.14 mmol), 2-methyl-4-(trifluoromethoxy)aniline (217 mg, 1.14 mmol), palladium(II) acetate (5.0 mg, 0.023 mmol), bis(2-diphenylphosphinophenyl)ether (18 mg, 0.034 mmol), and Cs$_2$CO$_3$ (518 mg, 1.60 mmol). The vial was sealed and was evacuated and refilled with argon three times and dioxane (2.2 mL) was added. The vial was evacuated and refilled with argon once. The suspension was heated for 5 minutes in a 50° C. oil bath under the argon inlet needle, then the inlet needle was removed and the sealed vial was heated for 30 minutes in a 150° C. oil bath. The crude product was used directly in the next reaction (372 mg).

Step B: (R)-tert-Butyl 3-(3-amino-4-((2-methyl-4-(trifluoromethoxy)phenyl)amino)thieno[2,3-b]pyridine-2-carboxamido)piperidine-1-carboxylate To a sealed tube containing 2-chloro-6-[2-methyl-4-(trifluoromethoxy)anilino]benzonitrile (372 mg, 1.14 mmol) was added a 0.5 M solution of tert-butyl (3R)-3-[(2-sulfanylacetyl)amino]piperidine-1-carboxylate (Intermediate 22) (2.72 mL, 1.36 mmol) in dioxane. The reaction mixture was heated in the sealed tube in a 150° C. oil bath for 15 minutes. The mixture was cooled to room temperature and used directly in the next reaction (642 mg).

Step C: (R)-tert-butyl 3-(5-(2-methyl-4-(trifluoromethoxy)phenyl)-4-oxo-4,5-dihydro-3H-1-thia-3,5,8-triazaacenaphthylene-2-carboxamido)piperidine-1-carboxylate To the crude reaction mixture containing (R)-tert-butyl 3-(3-amino-4-((2-methyl-4-(trifluoromethoxy)phenyl)amino)thieno[2,3-b]pyridine-2-carboxamido)piperidine-1-carboxylate (642 mg, 1.14 mmol) was added CDI (0.745 g, 4.60 mmol). The tube was sealed and the vessel was evacuated and refilled with argon twice. The mixture was heated for 5 minutes in a 50° C. oil bath under an argon inlet needle, then the argon inlet needle was removed and the mixture was heated at 150° C. for 10 minutes. The mixture was cooled to room temperature, water was added, and the aqueous phase was extracted with EtOAc (2×50 mL) and the combined organic extracts were washed with 1 M aqueous HCl (50 mL) followed by saturated aqueous NaCl (50 mL). The organic phase was dried over anhydrous Na$_2$SO$_4$, filtered, and concentrated to dryness. The residue was purified by flash column chromatography to give the title compound as a tan solid (452.4 mg, 67.37% yield).

Step D: (R)-5-(2-Methyl-4-(trifluoromethoxy)phenyl)-4-oxo-N-(piperidin-3-yl)-4,5-dihydro-3H-1-thia-3,5,8-triazaacenaphthylene-2-carboxamide To a solution of (R)-tert-butyl 3-(5-(2-methyl-4-(trifluoromethoxy)phenyl)-4-oxo-4,5-dihydro-3H-1-thia-3,5,8-triazaacenaphthylene-2-carboxamido)piperidine-1-carboxylate (437 mg, 0.738 mmol) in dioxane (4 mL) was added 4 M HCl in dioxane (4 mL, 16 mmol) and was stirred at room temperature under air for 1.5 h. The reaction mixture was concentrated to dryness and the residue was purified by HPLC to give the title compound as a light yellow solid (53.4 mg, 11.9% yield). MS (ESI): mass calcd. for C$_{22}$H$_{20}$F$_3$N$_5$O$_3$S, 491.5; m/z found, 492.1 [M+H]$^+$. 1H NMR (400 MHz, MeOH) Shift 8.36 (d, J=5.56 Hz, 1H), 7.45-7.49 (m, 1H), 7.42-7.45 (m, 1H), 7.35 (d, J=8.59 Hz, 1H), 6.06 (d, J=5.56 Hz, 1H), 4.27 (tt, J=3.85, 10.80 Hz, 1H), 3.54 (dd, J=4.04, 12.63 Hz, 1H), 3.32-3.41 (m, 1H), 2.88-3.02 (m, 2H), 2.22 (s, 3H), 2.03-2.15 (m, 2H), 1.67-1.94 (m, 2H), 1.24-1.45 (m, 1H).

Example 414: (R)—N-(1-Acryloylpiperidin-3-yl)-5-(2-methyl-4-(trifluoromethoxy)phenyl)-4-oxo-4,5-dihydro-3H-1-thia-3,5,8-triazaacenaphthylene-2-carboxamide

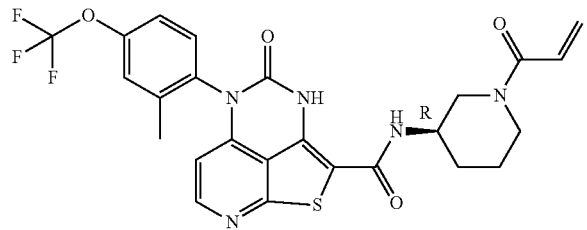

To a solution of (R)-5-(2-methyl-4-(trifluoromethoxy)phenyl)-4-oxo-N-(piperidin-3-yl)-4,5-dihydro-3H-1-thia-3,5,8-triazaacenaphthylene-2-carboxamide (Example 413, 150 mg, 0.30 mmol) in DCM (2 mL) was added triethylamine (125 μL, 0.900 mmol) and was cooled in an ice-water bath and to it was added acryloyl chloride (24 μL, 0.30 mmol) dropwise via syringe. The reaction mixture was stirred under air at 0° C. for 1 h. The reaction mixture was partitioned between DCM (10 mL) and saturated aqueous NaHCO$_3$ (10 mL). The aqueous phase was extracted once with EtOAc (10 mL) and the combined organic extracts were dried over anhydrous Na$_2$SO$_4$, filtered, and concentrated to dryness. The residue was purified by flash column chromatography to give the title compound as a light yellow solid (67.2 mg, 41.1% yield). MS (ESI): mass calcd. for C$_{25}$H$_{22}$F$_3$N$_5$O$_4$S, 545.5; m/z found, 546.2 [M+H]$^+$. $^1$H NMR (400 MHz, CD$_3$OD): δ 8.33 (d, J=5.56 Hz, 1H), 7.49 (d, J=8.59 Hz, 1H), 7.43 (s, 1H), 7.35 (d, J=8.59 Hz, 1H), 6.74-6.86 (m, 1H), 6.21 (dd, J=3.03, 16.67 Hz, 1H), 6.03 (d, J=5.56 Hz, 1H), 5.70-5.78 (m, 1H), 4.50-4.59 (m, 0.5H), 4.31 (d, J=12.63 Hz, 0.5H), 4.18 (d, J=14.65 Hz, 0.5H), 3.90-4.05 (m, 1.5H), 3.11-3.25 (m, 1H), 2.83-2.99 (m, 1H), 2.22 (s, 3H), 2.03-2.13 (m, 1H), 1.88 (dt, J=3.60, 13.52 Hz, 1H), 1.50-1.84 (m, 2H).

Example 415: (R)-4-Oxo-N-(piperidin-3-yl)-5-(4-(trifluoromethoxy)phenyl)-4,5-dihydro-3H-1-thia-3,5,8-triazaacenaphthylene-2-carboxamide

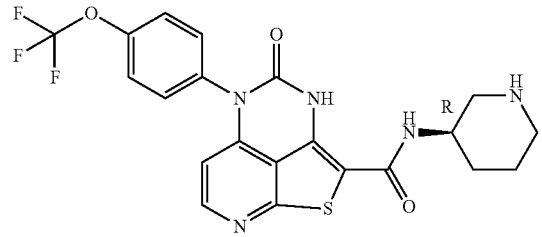

The title compound was prepared using analogous conditions described in Example 413 in steps A-D, using 4-(trifluoromethoxy)aniline in place of 2-methyl-4-(trifluoromethoxy)aniline in step A to yield the title compound. MS (ESI): mass calcd. for C$_{21}$H$_{18}$F$_3$N$_5$O$_3$S, 477.5; m/z found, 478.0 [M+H]$^+$. 1H NMR (400 MHz, MeOH) δ 8.35 (d, J=5.56 Hz, 1H), 7.51-7.62 (m, 4H), 6.18 (d, J=5.56 Hz, 1H), 4.27 (tt, J=4.04, 10.86 Hz, 1H), 3.53 (dd, J=4.04, 12.13 Hz, 1H), 3.36 (d, J=12.63 Hz, 1H), 2.89-3.02 (m, 2H), 2.02-2.15 (m, 2H), 1.69-1.93 (m, 2H), 1.25-1.45 (m, 1H).

Example 416: (R)—N-(1-Acryloylpiperidin-3-yl)-4-oxo-5-(4-(trifluoromethoxy)phenyl)-4,5-dihydro-3H-1-thia-3,5,8-triazaacenaphthylene-2-carboxamide

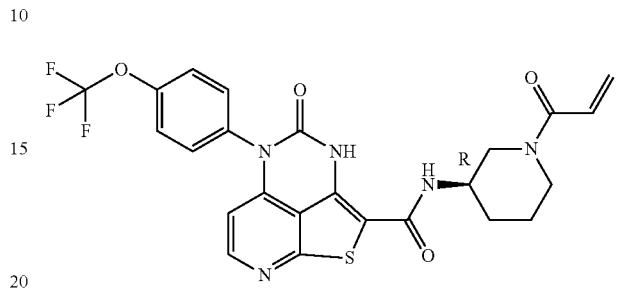

A solution of (R)-4-oxo-N-(piperidin-3-yl)-5-(4-(trifluoromethoxy)phenyl)-4,5-dihydro-3H-1-thia-3,5,8-triazaacenaphthylene-2-carboxamide (Example 415, 77 mg, 0.15 mmol) in DCM (1 mL) and triethylamine (62 μL, 0.45 mmol) was cooled in an ice-water bath and to it was added acryloyl chloride (12 μL, 0.15 mmol) dropwise via syringe. The reaction mixture was stirred under air at 0° C. for 1 h. The reaction mixture was partitioned between DCM (10 mL) and saturated aqueous NaHCO$_3$ (10 mL). The aqueous phase was extracted once with EtOAc (10 mL) and the combined organic extracts were dried over anhydrous Na$_2$SO$_4$, filtered, and concentrated to dryness. The residue was purified by flash column chromatography to give the title compound as a light yellow solid (25.4 mg, 31.9% yield). MS (ESI): mass calcd. for C$_{24}$H$_{20}$F$_3$N$_5$O$_4$S, 531.5; m/z found, 532.2 [M+H]$^+$. $^1$H NMR (400 MHz, CD$_3$OD): δ 8.32 (d, J=5.56 Hz, 1H), 7.56-7.62 (m, 2H), 7.50-7.56 (m, 2H), 6.73-6.86 (m, 1H), 6.21 (dd, J=3.54, 16.67 Hz, 1H), 6.15 (d, J=5.56 Hz, 1H), 5.74 (t, J=8.84 Hz, 1H), 4.51-4.60 (m, 0.5H), 4.31 (d, J=12.13 Hz, 0.5H), 4.14-4.22 (m, 0.5H), 3.91-4.05 (m, 1.5H), 3.10-3.23 (m, 1H), 2.82-2.99 (m, 1H), 2.02-2.13 (m, 1H), 1.88 (dt, J=3.66, 13.39 Hz, 1H), 1.50-1.83 (m, 2H).

Example 417: (R)—N-(1-Acryloylpiperidin-3-yl)-5-(*S)-(4-isopropoxy-2-methylphenyl)-4-oxo-4,5-dihydro-3H-1-thia-3,5,8-triazaacenaphthylene-2-carboxamide

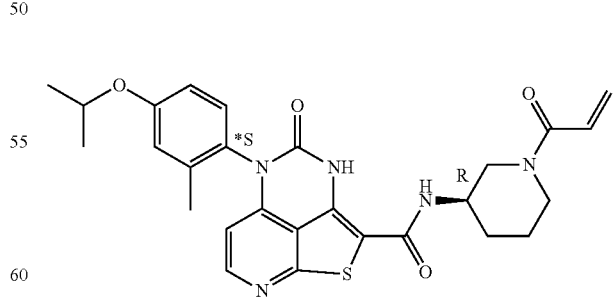

The title compound was prepared using analogous conditions described in steps A-D in Example 33 (including Chiral Resolution Method A after step F in Example 1 to obtain the *S atropisomer), to yield the title compound. MS (ESI): mass calcd. for C$_{27}$H$_{29}$N$_5$O$_4$S, 519.6; m/z found, 520.2 [M+H]⁺. ¹H NMR (400 MHz, CD₃OD): δ 8.31 (d, J=5.56 Hz, 1H), 7.21 (d, J=8.59 Hz, 1H), 6.98 (d, J=2.53 Hz, 1H), 6.93 (dd, J=2.53, 8.59 Hz, 1H), 6.74-6.86 (m, 1H), 6.21 (dd, J=3.03, 16.67 Hz, 1H), 6.04 (d, J=5.56 Hz, 1H), 5.74 (t, J=8.34 Hz, 1H), 4.67 (spt, J=6.06 Hz, 1H), 4.55 (dd, J=2.78, 13.39 Hz, 0.5H), 4.31 (d, J=13.14 Hz, 0.5H), 4.13-4.16 (m, 0.5H), 3.90-4.07 (m, 1.5H), 3.10-3.24 (m, 1H), 2.83-3.00 (m, 1H), 2.12 (s, 3H), 2.02-2.11 (m, 1H), 1.88 (dt, J=3.66, 13.39 Hz, 1H), 1.48-1.82 (m, 2H), 1.35 (d, J=6.06 Hz, 6H).

Example 418: (R)—N-(1-Acryloylpiperidin-3-yl)-5-(*R)-(4-isopropoxy-2-methylphenyl)-4-oxo-4,5-dihydro-3H-1-thia-3,5,8-triazaacenaphthylene-2-carboxamide

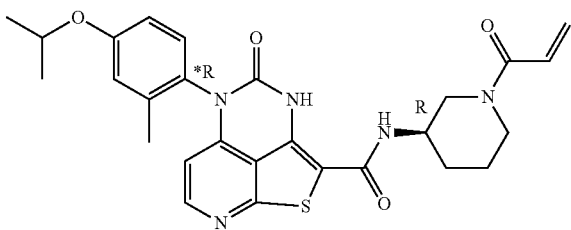

The title compound was prepared using analogous conditions described in steps A-D in Example 33 (including Chiral Resolution Method A after step F in Example 1 to obtain the *R atropisomer of the intermediate), to yield the title compound. Absolute stereochemical configuration of the title compound was confirmed via X-ray analysis after co-crystallization with BTK protein. MS (ESI): mass calcd. for C₂₇H₂₉N₅O₄S, 519.6; m/z found, 520.2 [M+H]⁺. ¹H NMR (400 MHz, CD₃OD): δ 8.31 (d, J=5.56 Hz, 1H), 7.21 (d, J=8.59 Hz, 1H), 6.98 (d, J=3.03 Hz, 1H), 6.92 (dd, J=2.53, 8.59 Hz, 1H), 6.80 (ddd, J=6.57, 10.48, 16.80 Hz, 1H), 6.21 (d, J=16.67 Hz, 1H), 6.03 (d, J=5.56 Hz, 1H), 5.74 (dd, J=4.55, 10.61 Hz, 1H), 4.67 (spt, J=6.06 Hz, 1H), 4.49-4.59 (m, 0.5H), 4.25-4.37 (m, 0.5H), 4.14-4.23 (m, 0.5H), 3.89-4.05 (m, 1.5H), 3.11-3.23 (m, 1H), 2.83-2.98 (m, 1H), 2.12 (s, 3H), 2.02-2.10 (m, 1H), 1.88 (dt, J=3.66, 13.39 Hz, 1H), 1.49-1.82 (m, 2H), 1.35 (d, J=6.06 Hz, 6H).

Example 419: (R)—N-(1-Acryloylpiperidin-3-yl)-5-(naphthalen-2-yl)-4-oxo-4,5-dihydro-3H-1-thia-3,5,8-triazaacenaphthylene-2-carboxamide

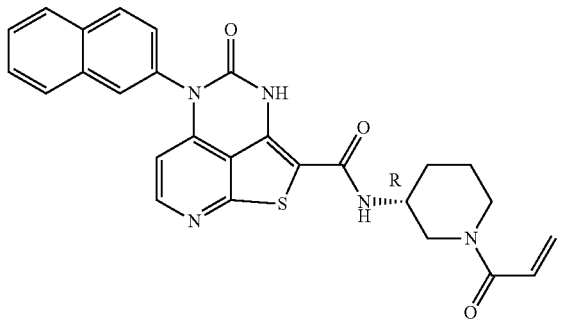

Step A: (R)-tert-Butyl 3-(5-(naphthalen-2-yl)-4-oxo-4,5-dihydro-3H-1-thia-3,5,8-triazaacenaphthylene-2-carboxamido)piperidine-1-carboxylate To a 10 mL Biotage microwave vial with a stir bar were added 2-aminonaphthalene (217.3 mg, 1.518 mmol), 2-chloro-4-iodonicotinonitrile (398.9 mg, 1.508 mmol), Pd(OAc)₂ (7.2 mg, 0.032 mmol), DPEPhos (25.4 mg, 0.0472 mmol), and Cs₂CO₃ (696 mg, 2.14 mmol). The vial was sealed, treated with dioxane (3 mL), evacuated/flushed with argon 4×, and stirred at 150° C. under argon for 30 min. The reaction was then cooled to room temperature, treated with tert-butyl (3R)-3-[(2-sulfanylacetyl)amino]piperidine-1-carboxylate (Intermediate 22) (2.35 mL, 0.65 M, 1.53 mmol) via syringe, evacuated/flushed with argon 4×, and stirred at 150° C. for 15 min. The reaction was cooled to room temperature, treated with solid CDI (974.4 mg, 6.009 mmol) in one portion under air, resealed and evacuated/flushed with argon 4×, and stirred at 150° C. for 15 min. The reaction was then diluted with EtOAc (10 mL), and washed with 0.5 M citric acid/brine (2×8 mL) and 2 M K₂CO₃ (1×5 mL). The clear amber organic phase was dried over anhydrous Na₂SO₄, filtered, and concentrated to dryness. The residue was purified by normal phase flash column chromatography (SiO2) to give the title compound as an orange-yellow foam (539 mg, 65.7% yield).

Step C: (R)-5-(Naphthalen-2-yl)-4-oxo-N-(piperidin-3-yl)-4,5-dihydro-3H-1-thia-3,5,8-triazaacenaphthylene-2-carboxamide A solution of (R)-tert-butyl 3-(5-(naphthalen-2-yl)-4-oxo-4,5-dihydro-3H-1-thia-3,5,8-triazaacenaphthylene-2-carboxamido)piperidine-1-carboxylate (534 mg, 0.982 mmol) in dioxane (4.9 mL) was treated with HCl (3.97 M in dioxane, 12.4 mL, 49.2 mmol) in one portion at room temperature, and the resulting mixture was stirred at room temperature for 1 h. The reaction was concentrated to dryness to give the title compound as a yellow-beige powder (538.2 mg, 100.2% yield).

Step D: (R)—N-(1-Acryloylpiperidin-3-yl)-5-(naphthalen-2-yl)-4-oxo-4,5-dihydro-3H-1-thia-3,5,8-triazaacenaphthylene-2-carboxamide A solution of (R)-5-(naphthalen-2-yl)-4-oxo-N-(piperidin-3-yl)-4,5-dihydro-3H-1-thia-3,5,8-triazaacenaphthylene-2-carboxamide (99.7 mg, 0.182 mmol) in DCM (1.25 mL) and MeOH (0.3 mL) was treated with triethylamine (76 µL, 0.55 mmol) at room temperature under air, and the resulting homogeneous orange solution was stirred at 0° C. under positive argon pressure while acryloyl chloride (14.8 µL, 0.182 mmol) was added dropwise over 50 sec. The resulting solution was stirred at 0° C. for 5 min and was then quenched with 1 M NaH₂PO₄ (3 mL) and extracted with DCM (1×5 mL). The organic layer was dried over anhydrous Na₂SO₄, filtered, and concentrated to dryness. The residue was purified by HPLC to give the title compound as an off-white powder (27.5 mg, 24.7%). MS (ESI): mass calcd. for C₂₇H₂₃N₅O₃S, 497.2; m/z found, 498.1 [M+H]⁺. 1H NMR (400 MHz, MeOH-d4) δ 8.30 (d, J=5.56 Hz, 1H), 8.11 (d, J=9.09 Hz, 1H), 7.94-8.04 (m, 3H), 7.56-7.66 (m, 2H), 7.50 (d, J=7.58 Hz, 1H), 6.80 (ddd, J=7.07, 10.36, 16.93 Hz, 1H), 6.14-6.26 (m, 1H), 6.14-6.26 (m, 1H), 5.70-5.77 (m, 1H), 4.27-4.60 (m, 1H), 3.93-4.23 (m, 2H), 3.12-3.26 (m, 1H), 2.85-2.97 (m, 1H), 2.04-2.12 (m, 1H), 1.84-1.93 (m, 1H), 1.67-1.81 (m, 1H), 1.53-1.64 (m, 1H).

Example 420: (R)—N-(1-Acryloylpiperidin-3-yl)-5-(1-benzyl-1H-pyrazol-3-yl)-4-oxo-4,5-dihydro-3H-1-thia-3,5,8-triazaacenaphthylene-2-carboxamide

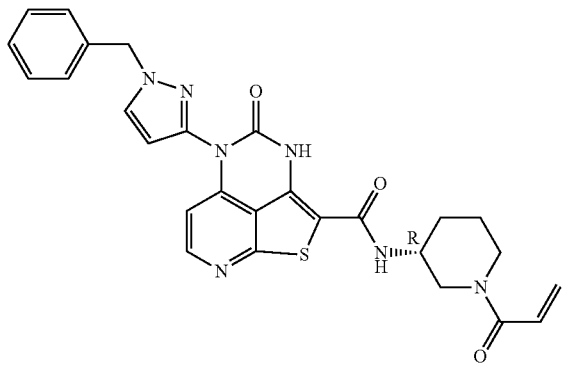

Step A: (R)-tert-Butyl 3-(5-(1-benzyl-1H-pyrazol-3-yl)-4-oxo-4,5-dihydro-3H-1-thia-3,5,8-triazaacenaphthylene-2-carboxamido)piperidine-1-carboxylate To a 2-5 mL Biotage microwave vial with a stir bar were added 1-benzyl-1H-pyrazol-3-amine (132.7 mg, 0.766 mmol), 2-chloro-4-iodonicotinonitrile (201 mg, 0.760 mmol), Pd(OAc)$_2$ (3.7 mg, 0.017 mmol), DPEPhos (12.5 mg, 0.0232 mmol), and Cs$_2$CO$_3$ (344 mg, 1.06 mmol). The vial was sealed, treated with dioxane (1.52 mL), evacuated/flushed with argon 4×, and stirred at 150° C. under argon for 30. The reaction was then cooled to room temp, treated with tert-butyl (3R)-3-[(2-sulfanylacetyl)amino]piperidine-1-carboxylate (Intermediate 22) (1.2 mL, 0.65 M, 0.78 mmol) via syringe, evacuated/flushed with argon 4×, and stirred at 150° C. for 15 min. The reaction was then cooled to room temperature, treated with solid CDI (492.6 mg, 3.038 mmol) in one portion under air, resealed and evacuated/flushed with argon 4×, and stirred at 150° C. for 15 min. The reaction was diluted with EtOAc (10 mL), and washed with 0.5 M citric acid/brine (2×8 mL) and 2 M K$_2$CO$_3$ (1×5 mL), dried over anhydrous Na$_2$SO$_4$, filtered, and concentrated to dryness. The reaction mixture was purified by normal phase flash column chromatography (SiO$_2$) to give the title compound as an orange-yellow foam (256.6 mg, 58.85% yield).

Step B: (R)-5-(1-benzyl-1H-pyrazol-3-yl)-4-oxo-N-(piperidin-3-yl)-4,5-dihydro-3H-1-thia-3,5,8-triazaacenaphthylene-2-carboxamide A solution of (R)-tert-butyl 3-(5-(1-benzyl-1H-pyrazol-3-yl)-4-oxo-4,5-dihydro-3H-1-thia-3,5,8-triazaacenaphthylene-2-carboxamido)piperidine-1-carboxylate (251.9 mg, 0.4390 mmol) in dioxane (2.2 mL) was treated with HCl (3.97 M in dioxane, 2.8 mL, 11 mmol) in one portion at room temperature, and the resulting mixture was stirred at room temperature for 1 h. The reaction was concentrated to dryness to give the title compound as a yellow-beige powder (253.1 mg, 100.8% yield).

Step C: (R)—N-(1-Acryloylpiperidin-3-yl)-5-(1-benzyl-1H-pyrazol-3-yl)-4-oxo-4,5-dihydro-3H-1-thia-3,5,8-triazaacenaphthylene-2-carboxamide A solution of (R)-5-(1-benzyl-1H-pyrazol-3-yl)-4-oxo-N-(piperidin-3-yl)-4,5-dihydro-3H-1-thia-3,5,8-triazaacenaphthylene-2-carboxamide (90.9 mg, 0.159 mmol) in DCM (1.05 mL) was treated with triethylamine (66 µL, 0.48 mmol) at room temperature under air and the solution was stirred at 0° C. under positive argon pressure while acryloyl chloride (13 µL, 0.16 mmol) was added dropwise over 50 sec and was stirred at 0° C. for 5 min. The reaction was quenched with 1 M NaH$_2$PO$_4$ (3 mL) and extracted with DCM (1×5 mL). The organic layer was dried over anhydrous Na$_2$SO$_4$, filtered, and concentrated to dryness. The residue was purified by HPLC and the combined fractions were neutralized with a few drops of 1M NaHCO$_3$ until pH>8, and concentrated to dryness. The residue was partitioned with water (2 mL) and DCM (4 mL), and the organic layer was dried over anhydrous Na$_2$SO$_4$, filtered, and concentrated to dryness to give the title compound as a yellow film (24.5 mg, 29.2% yield). MS (ESI): mass calcd. for C$_{27}$H$_{25}$N$_7$O$_3$S, 527.2; m/z found, 528.3 [M+H]$^+$. 1H NMR (400 MHz, CDCl3) δ 9.46 (br s, 1H), 8.36 (d, J=5.93 Hz, 1H), 7.53 (s, 1H), 7.28-7.43 (m, 5H), 6.53-6.71 (m, 1H), 6.27-6.45 (m, 3H), 5.69-5.90 (m, 1H), 5.52-5.69 (m, 1H), 5.35 (s, 2H), 3.84-4.26 (m, 3H), 3.42-3.80 (m, 1H), 3.18-3.40 (m, 1H), 1.98-2.14 (m, 1H), 1.63-1.86 (m, 3H).

Example 421: (R)-5-([1,1'-Biphenyl]-3-yl)-N-(1-acryloylpiperidin-3-yl)-4-oxo-4,5-dihydro-3H-1-thia-3,5,8-triazaacenaphthylene-2-carboxamide

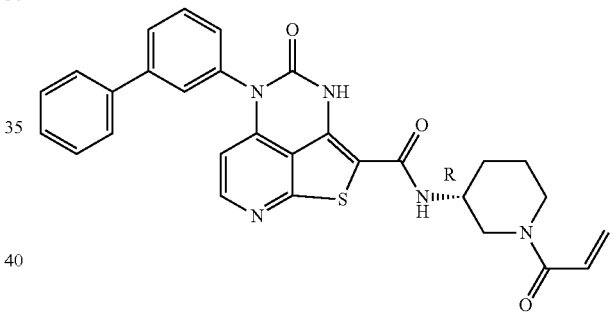

Step A: (R)-tert-Butyl 3-(5-([1,1'-biphenyl]-3-yl)-4-oxo-4,5-dihydro-3H-1-thia-3,5,8-triazaacenaphthylene-2-carboxamido)piperidine-1-carboxylate To a 2-5 mL Biotage microwave vial with a stir bar were added 3-aminobiphenyl (370.5 mg, 2.189 mmol), 2-chloro-4-iodonicotinonitrile (578 mg, 2.186 mmol), Pd(OAc)$_2$ (9.6 mg, 0.043 mmol), DPEPhos (36.1 mg, 0.0671 mmol), and Cs$_2$CO$_3$ (988 mg, 3.03 mmol). The vial was sealed and treated with dioxane (4.35 mL), evacuated/flushed with argon 4×, and stirred at 150° C. under argon for 30. The reaction was then cooled to room temperature, treated with tert-butyl (3R)-3-[(2-sulfanylacetyl)amino]piperidine-1-carboxylate (Intermediate 22) in dioxane (4.05 mL, 0.65 M, 2.63 mmol) via syringe, evacuated/flushed with argon 4×, and stirred at 150° C. for 15 min. The reaction was then cooled to room temperature, treated with solid CDI (1.409 g, 8.689 mmol) in one portion under air, resealed and evacuated/flushed with argon 4×, and stirred at 150° C. for 15 min. The reaction was diluted with EtOAc (10 mL), and washed with 0.5 M citric acid/brine (2×8 mL) and 2 M K$_2$CO$_3$ (1×5 mL), dried over anhydrous Na$_2$SO$_4$, filtered, and concentrated to dryness. The reaction mixture was purified by flash column chromatography to give the title compound as a beige foam (289 mg, 23.2% yield).

Step B: (R)-5-([1,1'-Biphenyl]-3-yl)-4-oxo-N-(piperidin-3-yl)-4,5-dihydro-3H-1-thia-3,5,8-triazaacenaphthylene-2-carboxamide A solution of (R)-tert-butyl 3-(5-([1,1'-biphenyl]-3-yl)-4-oxo-4,5-dihydro-3H-1-thia-3,5,8-triazaacenaphthylene-2-carboxamido)piperidine-1-carboxylate (283.8 mg, 0.498 mmol) in dioxane (2.5 mL) was treated with HCl (3.97 M in dioxane, 6.3 mL, 25 mmol) in one portion at room temperature, and the resulting mixture was stirred at room temperature for 1 h. The reaction was concentrated to dryness to give the title compound as a beige powder (290.4 mg, 102.7% yield).

Step C: (R)-5-([1,1'-Biphenyl]-3-yl)-N-(1-acryloylpiperidin-3-yl)-4-oxo-4,5-dihydro-3H-1-thia-3,5,8-triazaacenaphthylene-2-carboxamide A solution of (R)-5-([1,1'-biphenyl]-3-yl)-4-oxo-N-(piperidin-3-yl)-4,5-dihydro-3H-1-thia-3,5,8-triazaacenaphthylene-2-carboxamide (99.94 mg, 0.176 mmol) in DCM (1.2 mL) was treated with triethylamine (73 µL, 0.53 mmol) at room temperature under air, and the resulting was stirred at 0° C. under positive argon pressure while acryloyl chloride (14.3 µL, 0.176 mmol) was added dropwise over 50 sec. The solution was stirred at 0° C. for 5 min and was quenched with 1 M NaH$_2$PO$_4$ (3 mL) and extracted with DCM (1×5 mL). The organic layer was dried over anhydrous Na$_2$SO$_4$, filtered, and concentrated to dryness. The residue was purified by HPLC to give the title compound (23.8 mg, 21.2% yield). MS (ESI): mass calcd. for C$_{29}$H$_{25}$N$_5$O$_3$S, 523.2; m/z found, 524.1 [M+H]$^+$. 1H NMR (400 MHz, MeOH-d4) δ 8.33 (d, J=5.56 Hz, 1H), 7.83 (d, J=8.59 Hz, 1H), 7.62-7.77 (m, 4H), 7.32-7.50 (m, 1H), 7.32-7.50 (m, 1H), 7.32-7.50 (m, 2H), 6.80 (ddd, J=6.06, 10.61, 16.67 Hz, 1H), 6.17-6.24 (m, 2H), 5.70-5.75 (m, 1H), 4.25-4.59 (m, 1H), 3.90-4.23 (m, 2H), 3.19 (br dd, J=9.35, 12.88 Hz, 1H), 2.82-2.98 (m, 1H), 2.02-2.13 (m, 1H), 1.87 (td, J=3.66, 13.39 Hz, 1H), 1.68-1.81 (m, 1H), 1.53-1.63 (m, J=8.60 Hz, 1H).

Example 422: (R)—N-(1-Acryloylpiperidin-3-yl)-5-(4-benzylphenyl)-4-oxo-4,5-dihydro-3H-1-thia-3,5,8-triazaacenaphthylene-2-carboxamide

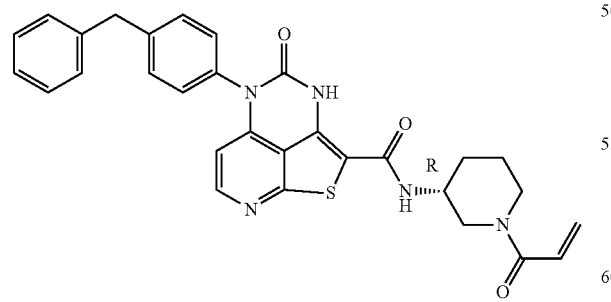

The title compound was prepared using analogous conditions described in steps A-C in Example 421, and using 4-benzylaniline in place of 3-aminobiphenyl in step A to yield the title compound. MS (ESI): mass calcd. for C$_{30}$H$_{27}$N$_5$O$_3$S, 537.2; m/z found, 538.0 [M+H]$^+$. 1H NMR (400 MHz, CDCl3) δ 9.46 (br s, 1H), 8.32 (br d, J=4.55 Hz, 1H), 7.31-7.41 (m, 4H), 7.22-7.25 (m, 4H), 6.57-6.68 (m, 1H), 6.21-6.48 (m, 2H), 6.11 (br s, 1H), 5.70-5.80 (m, 1H), 5.56 (br s, 1H), 3.94-4.10 (m, 4H), 3.28-3.78 (m, 3H), 2.04 (br d, J=14.15 Hz, 1H), 1.95 (br s, 1H), 1.69 (br s, 2H).

Example 423: (R)-5-([1,1'-Biphenyl]-4-yl)-N-(1-acryloylpiperidin-3-yl)-4-oxo-4,5-dihydro-3H-1-thia-3,5,8-triazaacenaphthylene-2-carboxamide

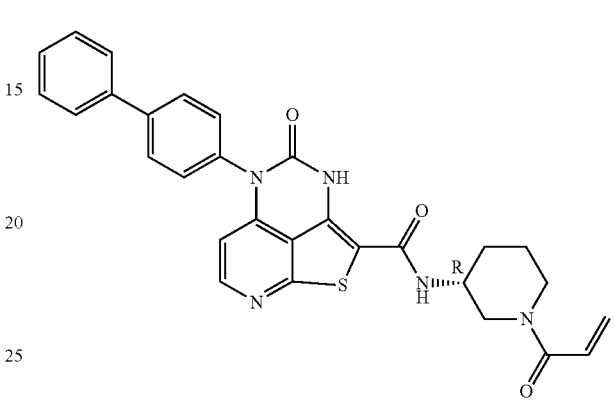

The title compound was prepared using analogous conditions described in steps A-C in Example 421, and using 4-aminobiphenyl in place of 3-aminobiphenyl in step A to yield the title compound. MS (ESI): mass calcd. for C$_{29}$H$_{25}$N$_5$O$_3$S, 523.2; m/z found, 524.3 [M+H]$^+$. 1H NMR (400 MHz, MeOH-d4) δ 8.34 (d, J=5.6 Hz, 1H), 7.87 (d, J=8.6 Hz, 2H), 7.70 (d, J=7.1 Hz, 2H), 7.44-7.57 (m, 4H), 7.35-7.44 (m, 1H), 6.73-6.88 (m, 1H), 6.25 (d, J=6.1 Hz, 1H), 6.21 (d, J=16.7 Hz, 1H), 5.70-5.80 (m, 1H), 4.60-4.27 (m, 1H), 4.17-4.03 (m, 1H), 3.89-3.99 (m, 1H), 3.09-3.24 (m, 1H), 2.90 (m, 1H), 2.06 (br. s., 1H), 1.83-1.93 (m, 1H), 1.74 (br. s., 1H), 1.60 (br. s., 1H).

Example 424: (R)—N-(1-(2-(Dimethylamino)acetyl)piperidin-3-yl)-4-oxo-5-(4-phenoxyphenyl)-4,5-dihydro-3H-1-thia-3,5,8-triazaacenaphthylene-2-carboxamide

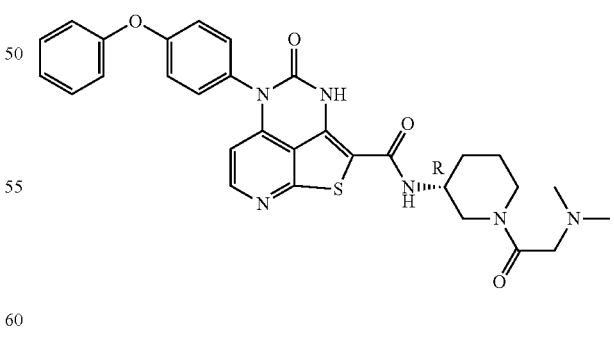

Step A: (R)-tert-Butyl 3-(4-oxo-5-(4-phenoxyphenyl)-4,5-dihydro-3H-1-thia-3,5,8-triazaacenaphthylene-2-carboxamido)piperidine-1-carboxylate To a 100 mL flask containing 4-oxo-5-(4-phenoxyphenyl)-4,5-dihydro-3H-1-thia-3,5,8-triazaacenaphthylene-2- carbonyl chloride (Intermediate 40, 1.046 g, 2.479 mmol) in THF (10 mL) was added with stirring triethylamine (10.0 mL, 123 mmol), (R)-1-Boc-3-aminopiperidine (768 mg, 3.72 mmol), and THF (10 mL) and was stirred for 15 hours. The reaction was quenched by pouring into a separatory funnel containing aqueous saturated NaHCO₃ and was extracted into ether and dried over anhydrous MgSO₄. The mixture was filtered and concentrated to dryness to give the title compound as a dark red solid (1.26 g, 86.8% yield).

Step B: (R)—N-(1-(2-(Dimethylamino)acetyl)piperidin-3-yl)-4-oxo-5-(4-phenoxyphenyl)-4,5-dihydro-3H-1-thia-3,5,8-triazaacenaphthylene-2-carboxamide To an oven dried microwave vial were added (R)-4-oxo-5-(4-phenoxyphenyl)-N-(piperidin-3-yl)-4,5-dihydro-3H-1-thia-3,5,8-triazaacenaphthylene-2-carboxamide (Example 860) (113 mg, 0.216 mmol), N,N-dimethylglycine (44.9 mg, 0.435 mmol), THF (3 mL), HATU (168 mg, 0.442 mmol), and triethylamine (2.0 mL, 14 mmol) and was capped and warmed in the microwave for 30 sec at 100° C. The reaction was concentrated to dryness and filtered through syringe filter. The residue was purified by HPLC to give the title compound (36.3 mg, 29.4% yield). MS (ESI): mass calcd. for C₃₀H₃₀N₆O₄S, 570.7; m/z found, 571.1 [M+H]⁺. 1H NMR (500 MHz, Methanol-d4) δ 8.52 (s, OH), 8.34-8.23 (m, 1H), 7.48-7.34 (m, 4H), 7.24-7.07 (m, 5H), 6.21-6.13 (m, 1H), 4.54-3.64 (m, 5H), 3.20-3.06 (m, 1H), 3.06-2.84 (m, 1H), 2.68-2.55 (m, 6H), 2.15-1.97 (m, 1H), 1.97-1.48 (m, 3H).

Example 425: (R)—N-(1-(2-(Dimethylamino)acetyl)pyrrolidin-3-yl)-4-oxo-5-(4-phenoxyphenyl)-4,5-dihydro-3H-1-thia-3,5,8-triazaacenaphthylene-2-carboxamide

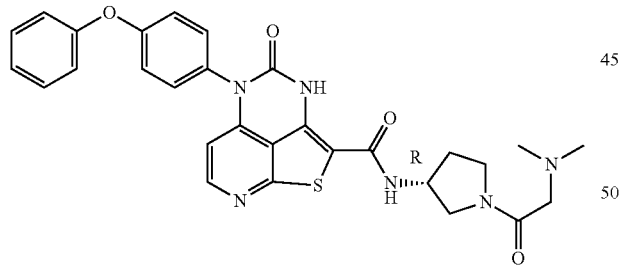

The title compound was prepared using analogous conditions described in steps A-C in Example 424, and using (R)-1-Boc-3-aminopyrrolidine and DIEA in place of (R)-1-Boc-3-aminopiperidine and triethylamine in step A to yield the title compound. MS (ESI): mass calcd. for C₂₉H₂₈N₆O₄S, 556.6; m/z found, 557.1 [M+H]⁺. ¹H NMR (500 MHz, CDCl₃): δ 8.45-8.32 (m, 1H), 7.44-7.33 (m, 2H), 7.33-7.25 (m, 1H), 7.24-7.08 (m, 5H), 6.27 (dd, J=29.7, 6.7 Hz, 1H), 6.20-6.10 (m, 1H), 4.72-4.60 (m, 1H), 3.86-3.53 (m, 4H), 3.40 (dd, J=14.4, 8.6 Hz, 1H), 3.16 (dd, J=46.1, 14.4 Hz, 1H), 2.56-2.48 (m, 6H), 2.43-2.14 (m, 1H), 2.09-1.91 (m, OH).

Example 426: (R)-5-([1,1'-Biphenyl]-3-yl)-4-oxo-N-(piperidin-3-yl)-4,5-dihydro-3H-1-thia-3,5,8-triazaacenaphthylene-2-carboxamide

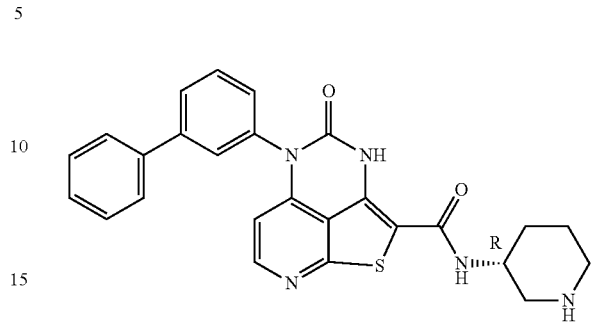

The title compound was prepared using analogous conditions described in steps A-B in Example 421. MS (ESI): mass calcd. for C₂₆H₂₃N₅O₂S, 469.2; m/z found, 470.2 [M+H]⁺. 1H NMR (400 MHz, 95:5 CDCl3/MeOH-d4) δ 8.31 (d, J=5.6 Hz, 1H), 7.77 (d, J=8.1 Hz, 1H), 7.67 (t, J=7.8 Hz, 1H), 7.61 (d, J=7.1 Hz, 2H), 7.57 (d, J=2.0 Hz, 1H), 7.46 (t, J=7.3 Hz, 2H), 7.36-7.42 (m, 1H), 7.30-7.35 (m, 1H), 6.18 (d, J=5.6 Hz, 1H), 4.11 (dt, J=7.1, 3.5 Hz, 1H), 3.12 (dd, J=12.4, 3.3 Hz, 1H), 2.83-2.91 (m, 1H), 2.66-2.82 (m, 2H), 1.92 (td, J=8.1, 4.0 Hz, 1H), 1.65-1.85 (m, 2H), 1.60 (td, J=8.6, 4.0 Hz, 1H)

Example 427: (R)—N-(1-Acryloylpiperidin-3-yl)-5-(benzo[b]thiophen-2-yl)-4-oxo-4,5-dihydro-3H-1-thia-3,5,8-triazaacenaphthylene-2-carboxamide

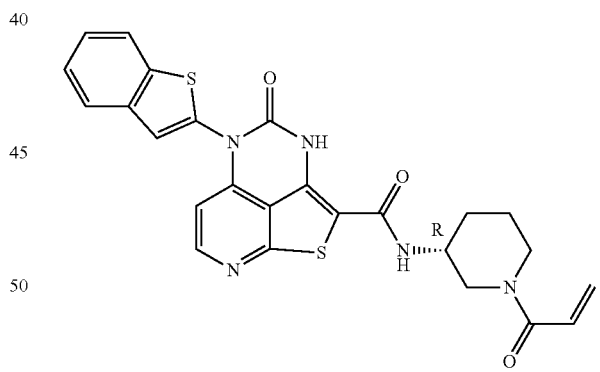

The title compound was prepared using analogous conditions described in steps A-C in Example 421, and using benzo[b]thiophen-2-amine in place of 3-aminobiphenyl in step A to yield the title compound. MS (ESI): mass calcd. for C₂₅H₂₁N₅O₃S₂, 503.1; m/z found, 504.1 [M+H]⁺. 1H NMR (400 MHz, CDCl3) δ 9.59 (br. s., 1H), 8.31-8.45 (m, 1H), 7.75-7.90 (m, 2H), 7.41-7.47 (m, 2H), 7.40 (s, 1H), 6.54-6.71 (m, 1H), 6.41 (br. s., 2H), 6.31 (d, J=16.7 Hz, 1H), 5.65-5.82 (m, 1H), 4.13 (br. s., 1H), 4.02 (d, J=13.1 Hz, 2H), 3.80 (br. s., 1H), 3.55 (br. s., 1H), 3.29 (br. s., 1H), 2.05 (br. s., 1H), 1.98 (br. s., 1H), 1.60-1.71 (m, 1H).

Example 428: (R)-5-(Benzo[b]thiophen-2-yl)-4-oxo-N-(piperidin-3-yl)-4,5-dihydro-3H-1-thia-3,5,8-triazaacenaphthylene-2-carboxamide

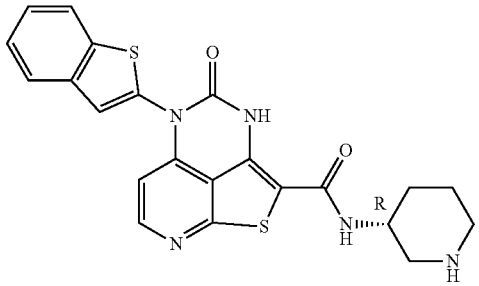

The title compound was prepared using analogous conditions described in steps A-B in Example 421, and using benzo[b]thiophen-2-amine in place of 3-aminobiphenyl in step A to yield the title compound. MS (ESI): mass calcd. for $C_{22}H_{19}N_5O_2S_2$, 449.1; m/z found, 450.1 [M+H]$^+$. 1H NMR (400 MHz, MeOH-d4) δ 8.19 (d, J=6.1 Hz, 1H), 7.82-7.93 (m, 2H), 7.45 (s, 1H), 7.38-7.44 (m, 2H), 6.28 (d, J=5.6 Hz, 1H), 4.10-4.24 (m, 1H), 3.06-3.16 (m, 1H), 2.81-3.00 (m, 2H), 1.91-2.10 (m, 2H), 1.66-1.83 (m, 2H), 1.24-1.44 (m, 1H).

Example 429: (R)-5-(Naphthalen-2-yl)-4-oxo-N-(piperidin-3-yl)-4,5-dihydro-3H-1-thia-3,5,8-triazaacenaphthylene-2-carboxamide

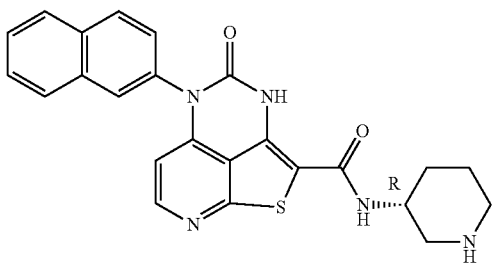

The title compound was prepared using analogous conditions described in steps A-B in Example 421, and using 2-aminonaphthalene in place of 3-aminobiphenyl in step A to yield the title compound. MS (ESI): mass calcd. for $C_{24}H_{21}N_5O_2S$, 443.1; m/z found, 444.1 [M+H]$^+$. 1H NMR (400 MHz, MeOH-d4) δ 8.47 (d, J=6.57 Hz, 1H), 8.16 (d, J=9.09 Hz, 1H), 8.01-8.07 (m, 2H), 7.98 (d, J=7.58 Hz, 1H), 7.58-7.69 (m, 2H), 7.52 (dd, J=2.02, 8.59 Hz, 1H), 6.43 (d, J=6.57 Hz, 1H), 4.26-4.37 (m, 1H), 3.52-3.58 (m, 1H), 3.33-3.40 (m, 1H), 2.96-3.05 (m, 2H), 2.05-2.16 (m, 2H), 1.74-1.93 (m, 2H).

Example 430: (R)-5-(4-Benzylphenyl)-4-oxo-N-(piperidin-3-yl)-4,5-dihydro-3H-1-thia-3,5,8-triazaacenaphthylene-2-carboxamide

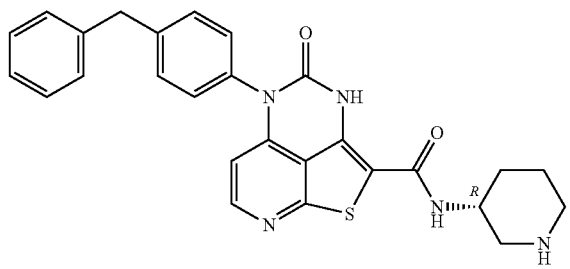

The title compound was prepared using analogous conditions described in steps A-B in Example 421, and using 4-benzylaniline in place of 3-aminobiphenyl in step A to yield the title compound. MS (ESI): mass calcd. for $C_{24}H_{23}N_7O_2S$, 483.2; m/z found, 484.2 [M+H]$^+$. 1H NMR (400 MHz, MeOH-d4) δ 8.45 (d, J=6.57 Hz, 1H), 7.46-7.53 (m, J=8.08 Hz, 2H), 7.34-7.40 (m, J=8.59 Hz, 2H), 7.24-7.34 (m, 4H), 7.17-7.24 (m, 1H), 6.37 (d, J=6.06 Hz, 1H), 4.23-4.34 (m, 1H), 4.10 (s, 2H), 3.54 (dd, J=4.29, 11.87 Hz, 1H), 3.33-3.39 (m, 1H), 2.92-3.03 (m, 2H), 2.04-2.15 (m, 2H), 1.70-1.92 (m, 2H).

Example 431: (R)-5-(1-Benzyl-1H-pyrazol-3-yl)-4-oxo-N-(piperidin-3-yl)-4,5-dihydro-3H-1-thia-3,5,8-triazaacenaphthylene-2-carboxamide

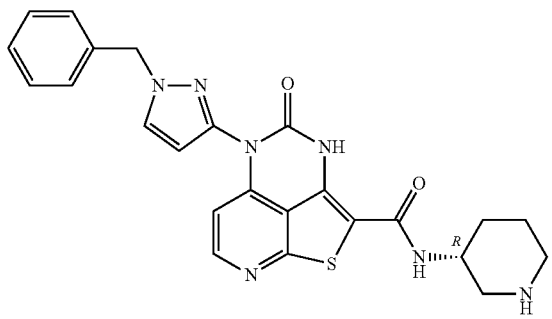

The title compound was prepared using analogous conditions described in steps A-B in Example 421, and using 1-benzyl-1H-pyrazol-3-amine in place of 3-aminobiphenyl in step A to yield the title compound. MS (ESI): mass calcd. for C24H23N7O2S, 473.2; m/z found, 474.1 [M+H]$^+$. 1H NMR (400 MHz, MeOH-d4) δ 8.53 (d, J=6.57 Hz, 1H), 7.95 (d, J=2.53 Hz, 1H), 7.28-7.41 (m, 5H), 6.60 (d, J=6.57 Hz, 1H), 6.50 (d, J=2.53 Hz, 1H), 5.43 (s, 2H), 4.23-4.35 (m, 1H), 3.53 (dd, J=4.04, 12.13 Hz, 1H), 3.32-3.39 (m, 1H), 2.93-3.04 (m, 2H), 2.04-2.13 (m, 2H), 1.71-1.93 (m, 2H).

Example 432: 5-(*S)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide

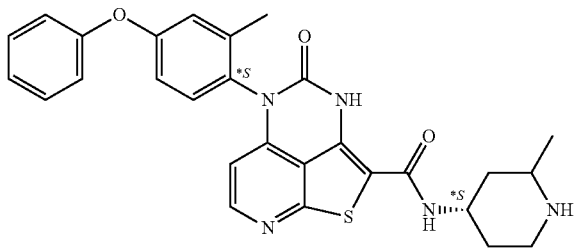 [SMILES: Cc1cc(Oc2ccccc2)ccc1N1C(=O)Nc2c(C(=O)N[C@H]3CCNC(C)C3)sc3nccc1c23]

A chiral purification was performed on 5-(2-methyl-4-phenoxyphenyl)-N-(2-methylpiperidin-4-yl)-4-oxo-4,5-dihydro-3H-1-thia-3,5,8-triazaacenaphthylene-2-carboxamide (Example 258, 841.57 mg) via chiral SFC (Stationary phase: CHIRALCEL OD-H 5 m 250×20 mm, Mobile phase: 55% $CO_2$, 45% iPOH (0.3% iPrNH$_2$)) and a second purification was performed via chiral SFC (Stationary phase: Whelk 01 (S,S) 5 μm 250×21.1 mm, Mobile phase: 45% $CO_2$, 55% MeOH (0.3% iPrNH$_2$)) to give the title compound (as the *S atropisomer; 15 mg). MS (ESI): mass calcd. for $C_{28}H_{27}N_5O_3S$, 513.6; m/z found, 513.2 [M+H]$^+$. 1H NMR (600 MHz, Chloroform-d) δ 8.35 (d, J=5.4 Hz, 1H), 7.48-7.35 (m, 2H), 7.22-6.91 (m, 6H), 6.02 (d, J=5.5 Hz, 1H), 5.58 (d, J=8.0 Hz, 1H), 4.09-3.96 (m, 1H), 3.39-2.68 (m, 3H), 2.18-1.96 (m, 6H), 1.47-1.20 (m, 2H), 1.13-1.00 (m, 3H).

Example 433: 5-(*R)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide

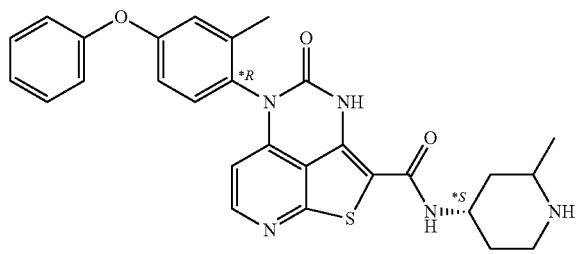 [SMILES: Cc1cc(Oc2ccccc2)ccc1N1C(=O)Nc2c(C(=O)N[C@H]3CCNC(C)C3)sc3nccc1c23]

A chiral purification was performed on 5-(2-methyl-4-phenoxyphenyl)-N-(2-methylpiperidin-4-yl)-4-oxo-4,5-dihydro-3H-1-thia-3,5,8-triazaacenaphthylene-2-carboxamide (Example 258, 841.57 mg) via chiral SFC (Stationary phase: CHIRALCEL OD-H 5 m 250×20 mm, Mobile phase: 55% $CO_2$, 45% iPOH (0.3% iPrNH$_2$)) and a second purification was performed via chiral SFC (Stationary phase: Whelk O1 (S,S) 5 m 250×21.1 mm, Mobile phase: 45% $CO_2$, 55% MeOH (0.3% iPrNH$_2$)) to give the title compound (as the *R atropisomer; 17 mg). MS (ESI): mass calcd. for $C_{28}H_{27}N_5O_3S$, 513.6; m/z found, 513.2 [M+H]$^+$. $^1$H NMR (600 MHz, CDCl$_3$): δ 8.36 (d, J=5.5 Hz, 1H), 7.48-7.33 (m, 2H), 7.23-6.93 (m, 7H), 6.02 (d, J=5.5 Hz, 1H), 5.52-5.41 (m, 1H), 4.08-3.95 (m, 1H), 3.21-3.13 (m, 1H), 2.92-2.75 (m, 2H), 2.13 (s, 3H), 2.10-1.98 (m, 2H), 1.44-1.32 (m, 1H), 1.30-1.22 (m, 1H), 1.14-1.03 (m, 4H).

Example 434: 5-(*S)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide

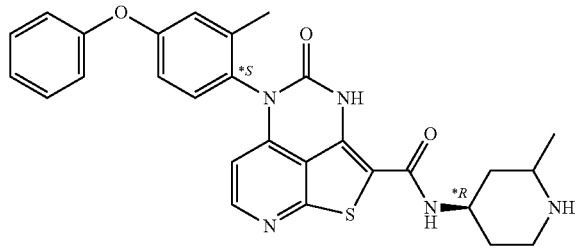 [SMILES: Cc1cc(Oc2ccccc2)ccc1N1C(=O)Nc2c(C(=O)N[C@@H]3CCNC(C)C3)sc3nccc1c23]

A chiral purification was performed on 5-(2-methyl-4-phenoxyphenyl)-N-(2-methylpiperidin-4-yl)-4-oxo-4,5-dihydro-3H-1-thia-3,5,8-triazaacenaphthylene-2-carboxamide (Example 258) via chiral SFC (Stationary phase: CHIRALCEL OD-H 5 m 250×20 mm, Mobile phase: 55% $CO_2$, 45% iPOH (0.3% iPrNH$_2$)) to give the title compound (as the *S atropisomer). MS (ESI): mass calcd. for $C_{28}H_{27}N_5O_3S$, 513.6; m/z found, 513.2 [M+H]$^+$. $^1$H NMR (600 MHz, CDCl$_3$): δ 8.35 (s, 1H), 7.47-7.34 (m, 2H), 7.23-6.89 (m, 6H), 6.16 (s, 1H), 6.01 (d, J=5.4 Hz, 1H), 4.21-4.04 (m, 1H), 3.41-3.20 (m, 1H), 3.03-2.78 (m, 2H), 2.13 (s, 4H), 1.69 (s, 1H), 1.46-1.22 (m, 7H).

Example 435: 5-(*R)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide

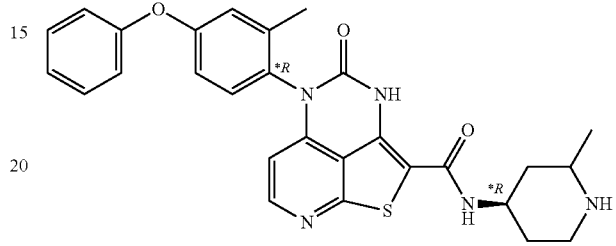

A chiral purification was performed on 5-(2-methyl-4-phenoxyphenyl)-N-(2-methylpiperidin-4-yl)-4-oxo-4,5-dihydro-3H-1-thia-3,5,8-triazaacenaphthylene-2-carboxamide (Example 258, 841.57) via chiral SFC (Stationary phase: CHIRALCEL OD-H 5 m 250×20 mm, Mobile phase: 55% $CO_2$, 45% iPOH (0.3% iPrNH$_2$)) to give the title compound (as the *R atropisomer; 12 mg). MS (ESI): mass calcd. for $C_{28}H_{27}N_5O_3S$, 513.6; m/z found, 513.2 [M+H]$^+$. 1H NMR (600 MHz, Chloroform-d) δ 8.31 (s, 1H), 7.40-7.36 (m, 2H), 7.32 (s, 1H), 7.20-7.15 (m, 2H), 7.11-7.06 (m, 2H), 6.99 (d, J=2.8 Hz, 1H), 6.94 (dd, J=8.5, 2.8 Hz, 1H), 5.98 (d, J=5.4 Hz, 1H), 4.26 (s, 1H), 3.67 (s, 1H), 3.54 (s, 1H), 3.38 (d, J=24.9 Hz, 1H), 3.10 (s, 1H), 2.21 (s, 2H), 2.11 (s, 3H), 1.95 (d, J=13.2 Hz, 1H), 1.54 (d, J=6.2 Hz, 3H), 1.25 (s, 2H).

Example 436: N-(4-(Hydroxymethyl)tetrahydro-2H-pyran-4-yl)-5-(*S)-(2-methyl-4-phenoxyphenyl)-4-oxo-4,5-dihydro-3H-1-thia-3,5,8-triazaacenaphthylene-2-carboxamide

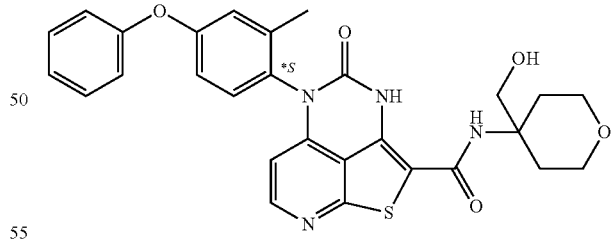

Step A: N-(4-(Hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-G in Example 1, and using (4-aminotetrahydropyran-4-yl)methanol in place of tert-butyl (3R,5R)-3-amino-5-fluoro-piperidine-1-carboxylate in step G to yield the title compound.

Step B: N-(4-(Hydroxymethyl)tetrahydro-2H-pyran-4-yl)-5-(*S)-(2-methyl-4-phenoxyphenyl)-4-oxo-4,5-dihydro-3H-1-thia-3,5,8-triazaacenaphthylene-2-carboxamide A chiral purification was performed on N-(4-(hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide (869 mg) via chiral SFC (Stationary phase: CHIRALCEL OD-H 5 m 250×20 mm, Mobile phase: 50% $CO_2$, 50% iPrOH) to give the title compound (as the *S atropisomer; 17 mg). MS (ESI): mass calcd. for $C_{28}H_{26}N_4O_5S$, 530.6; m/z found, 530.2 [M+H]$^+$. $^1$H NMR (600 MHz, CDCl$_3$): δ 9.65 (s, 1H), 8.32 (d, J=5.5 Hz, 1H), 7.44-7.35 (m, 2H), 7.25-7.16 (m, 2H), 7.14-7.08 (m, 2H), 7.03-6.92 (m, 2H), 6.00 (d, J=5.4 Hz, 1H), 5.54 (s, 1H), 4.49 (s, 1H), 3.99 (d, J=11.7 Hz, 1H), 3.87-3.76 (m, 3H), 3.76-3.67 (m, 2H), 2.14-2.00 (m, 5H), 1.95-1.81 (m, 2H).

Example 437: N-(4-(Hydroxymethyl)tetrahydro-2H-pyran-4-yl)-5-(*R)-(2-methyl-4-phenoxyphenyl)-4-oxo-4,5-dihydro-3H-1-thia-3,5,8-triazaacenaphthylene-2-carboxamide

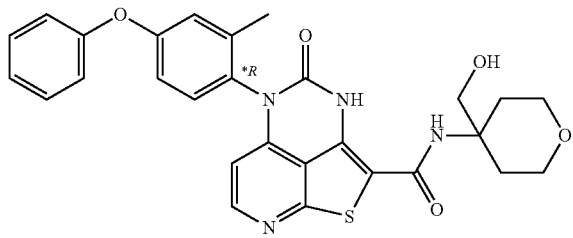 [SMILES: Cc1cc(Oc2ccccc2)ccc1N1C(=O)Nc2c(C(=O)NC3(CO)CCOCC3)sc3nccc1c23]

Step A: N-(4-(Hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide The title compound was prepared in a manner analogous to Method 1, steps A-G in Example 1, and using (4-aminotetrahydropyran-4-yl)methanol in place of tert-butyl (3R,5R)-3-amino-5-fluoro-piperidine-1-carboxylate in step G to yield the title compound.

Step B: N-(4-(Hydroxymethyl)tetrahydro-2H-pyran-4-yl)-5-(*R)-(2-methyl-4-phenoxyphenyl)-4-oxo-4,5-dihydro-3H-1-thia-3,5,8-triazaacenaphthylene-2-carboxamide A chiral purification was performed on N-(4-(hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide (869 mg) via chiral SFC (Stationary phase: CHIRALCEL OD-H 5 m 250×20 mm, Mobile phase: 50% $CO_2$, 50% iPrOH) to give the title compound (as the *R atropisomer; 19 mg). MS (ESI): mass calcd. for $C_{28}H_{26}N_4O_5S$, 530.6; m/z found, 530.2 [M+H]$^+$. 1H NMR (600 MHz, Chloroform-d) δ 9.59 (s, 1H), 8.33 (d, J=5.5 Hz, 1H), 7.49-7.34 (m, 2H), 7.24-7.17 (m, 2H), 7.13-7.09 (m, 2H), 7.02-6.96 (m, 2H), 6.01 (d, J=5.5 Hz, 1H), 5.52 (s, 1H), 4.43 (s, 1H), 4.00-3.93 (m, 1H), 3.88-3.79 (m, 3H), 3.71 (ddt, J=12.3, 9.3, 3.2 Hz, 2H), 2.13-2.10 (m, 3H), 1.96-1.87 (m, 2H), 1.23-1.19 (m, 2H).

Example 438: (R)—N-(1-(2-Chloro-3-methylbut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

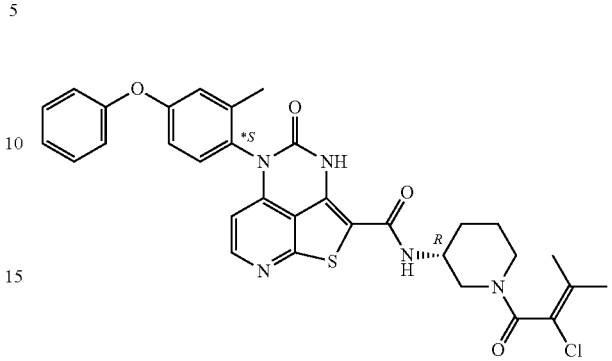

A chiral purification was performed on (R)—N-(1-(2-chloro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 260) via chiral SFC (Stationary phase: CHIRALCEL OJ-H 5 μm 250×20 mm, Mobile phase: 70% $CO_2$, 30% EtOH) to give the title compound (as the *S atropisomer; 39 mg). MS (ESI): mass calcd. for $C_{32}H_{30}ClN_5O_4S$, 616.1; m/z found, 615.2 [M+H]$^+$. 1H NMR (600 MHz, Chloroform-d) δ 9.50 (s, 1H), 8.48-8.27 (m, 1H), 7.48-7.33 (m, 2H), 7.23-7.14 (m, 2H), 7.14-7.07 (m, 2H), 7.05-6.99 (m, 1H), 6.99-6.92 (m, 1H), 6.12-6.06 (m, 1H), 6.06-5.99 (m, 1H), 5.89 (s, 1H), 4.23-4.11 (m, 1H), 4.01-3.81 (m, 1H), 3.81-3.68 (m, 1H), 3.50-3.45 (m, 1H), 3.32-3.20 (m, 1H), 2.14 (s, 4H), 2.07-1.94 (m, 2H), 1.89-1.82 (m, 4H), 1.78-1.63 (m, 2H).

Example 439: (R)—N-(1-(2-Chloro-3-methylbut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

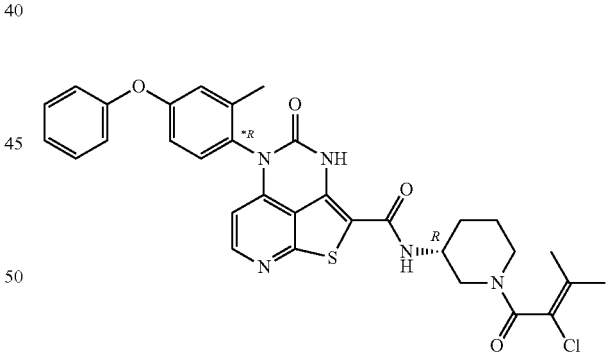

A chiral purification was performed on (R)—N-(1-(2-chloro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 260) via chiral SFC (Stationary phase: CHIRALCEL OJ-H 5 μm 250×20 mm, Mobile phase: 70% $CO_2$, 30% EtOH) to give the title compound (as the *R atropisomer; 39 mg). MS (ESI): mass calcd. for $C_{32}H_{30}ClN_5O_4S$, 616.1; m/z found, 615.2 [M+H]$^+$. $^1$H NMR (600 MHz, CDCl$_3$): δ 9.51 (s, 1H), 8.47-8.25 (m, 1H), 7.51-7.32 (m, 2H), 7.24-6.91 (m, 6H), 6.22-5.82 (m, 2H), 4.28-4.06 (m, 1H), 3.97-3.64 (m, 2H), 3.57-3.23 (m, 2H), 2.17-2.09 (m, 3H), 2.08-1.92 (m, 2H), 1.92-1.90 (m, 3H), 1.88-1.84 (m, 3H), 1.81-1.63 (m, 2H).

Example 440: (R,E)-N-(1-(4-(Dimethylamino)but-2-enoyl)pyrrolidin-3-yl)-4-oxo-5-(4-phenoxyphenl)-4,5-dihydro-3H-1-thia-3,5,8-triazaacenaphthylene-2-carboxamide

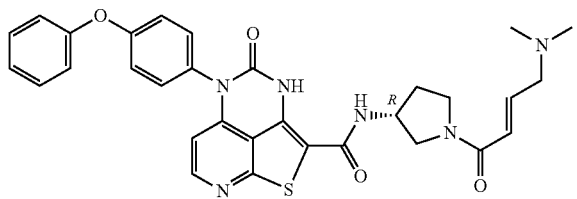

To a small oven dried microwave vial under Ar were added (R)-4-Oxo-5-(4-phenoxyphenyl)-N-(pyrrolidin-3-yl)-4,5-dihydro-3H-1-thia-3,5,8-triazaacenaphthylene-2-carbo (Example 91120 mm, 0 mg, 0.424 mmol), trans-4-dimethylaminocrotonic acid hydrochloride (151.3 mg, 0.9140 mmol), THF (6 mL), HATU (481.3 mg, 1.266 mmol), and triethylamine (0.8 m, 6 mmol) and the vial was capped and was heated in the microwave for 30 seconds at 100° C. The reaction mixture was concentrated to dryness and purified by flash column chromatography and then by HPLC to give the title compound (65 mg, 26% yield). MS (ESI): mass calcd. for $C_{31}H_{30}N_6O_4S$, 582.7; m/z found, 583.2 [M+H]$^+$. 1H NMR (400 MHz, DMSO-d6) δ 8.49-8.24 (m, 2H), 7.56-7.36 (m, 4H), 7.29-7.05 (m, 6H), 6.75-6.54 (m, 1H), 6.50-6.31 (m, 1H), 6.07 (d, J=5.5 Hz, 1H), 4.62-4.34 (m, 1H), 3.95-3.56 (m, 4H), 3.18-3.01 (m, 2H), 2.29-1.84 (m, 8H).

Example 441: (R)—N-(1-Acryloylpyrrolidin-3-yl)-N-methyl-5-(*S)-(2-methyl-4-phenoxyphenyl)-4-oxo-4,5-dihydro-3H-1-thia-3,5,8-triazaacenaphthylene-2-carboxamide

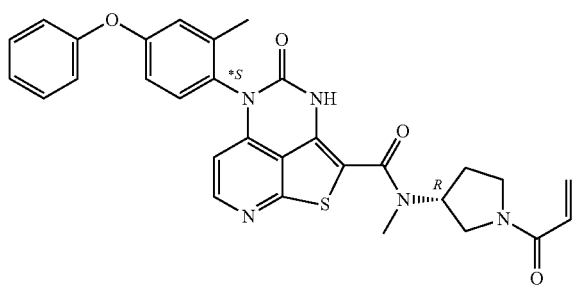

A purification was performed on (R)—N-(1-acryloylpyrrolidin-3-yl)-N-methyl-5-(2-methyl-4-phenoxyphenyl)-4-oxo-4,5-dihydro-3H-1-thia-3,5,8-triazaacenaphthylene-2-carboxamide (Example 137, 907 mg) via chiral SFC (Stationary phase: CHIRALCEL OJ-H 5 μm 250×20 mm, Mobile phase: 60% CO$_2$, 40% MeOH) to give the title compound (as the *S atropisomer; 30 mg). MS (ESI): mass calcd. for $C_{30}H_{27}N_5O_4S$, 553.6; m/z found, 553.2 [M+H]$^+$. $^1$H NMR (500 MHz, Chloroform-d) δ 9.79 (s, 1H), 8.51-8.24 (m, 1H), 7.47-7.34 (m, 2H), 7.24-7.04 (m, 4H), 7.06-6.88 (m, 2H), 6.54-6.36 (m, 2H), 6.11-5.97 (m, 1H), 5.80-5.66 (m, 1H), 5.37-5.16 (m, 1H), 4.08-3.73 (m, 2H), 3.72-3.40 (m, 2H), 3.24 (d, J=16.6 Hz, 3H), 2.32 (s, 1H), 2.26-2.02 (m, 4H).

Example 442: (R)—N-(1-Acryloylpyrrolidin-3-yl)-N-methyl-5-(*R)-(2-methyl-4-phenoxyphenl)-4-oxo-4,5-dihydro-3H-1-thia-3,5,8-triazaacenaphthylene-2-carboxamide

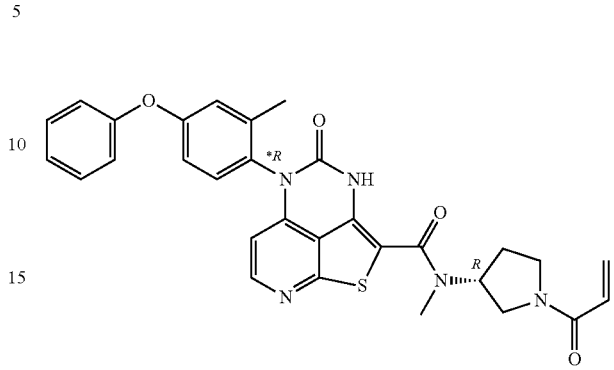

A purification was performed on (R)—N-(1-acryloylpyrrolidin-3-yl)-N-methyl-5-(2-methyl-4-phenoxyphenyl)-4-oxo-4,5-dihydro-3H-1-thia-3,5,8-triazaacenaphthylene-2-carboxamide (Example 137, 907 mg) via chiral SFC (Stationary phase: CHIRALCEL OJ-H 5 μm 250×20 mm, Mobile phase: 60% CO$_2$, 40% MeOH) to give the title compound (as the *R atropisomer; 29 mg). MS (ESI): mass calcd. for $C_{30}H_{27}N_5O_4S$, 553.6; m/z found, 553.2 [M+H]$^+$. $^1$H NMR (500 MHz, CDCl$_3$): δ 9.80 (s, 1H), 8.43-8.29 (m, 1H), 7.46-7.34 (m, 2H), 7.24-7.07 (m, 4H), 7.05-6.90 (m, 2H), 6.51-6.33 (m, 2H), 6.13-5.95 (m, 1H), 5.83-5.63 (m, 1H), 5.36-5.17 (m, 1H), 4.02-3.73 (m, 2H), 3.73-3.44 (m, 2H), 3.25 (d, J=13.9 Hz, 3H), 2.39-2.16 (m, 2H), 2.13 (s, 3H).

Example 443: (R)—N-(1-Acryloylpyrrolidin-3-yl)-4-oxo-5-(4-phenoxyphenyl)-4,5-dihydro-3H-1-thia-3,5,8-triazaacenaphthylene-2-carboxamide

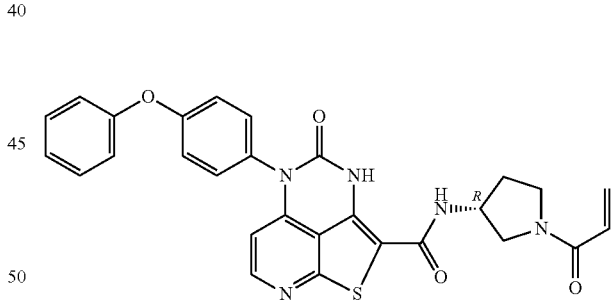

The title compound was prepared in a manner analogous to Method 1, steps A-I in Example 1, and using 4-fluoronitrobenzene in place of 5-fluoro-2-nitrotoluene in step A and using (R)-(+)-1-Boc-3-aminopyrrolidine in place of tert-butyl (3R,5R)-3-amino-5-fluoro-piperidine-1-carboxylate in step G to yield the title compound. MS (ESI): mass calcd. for $C_{28}H_{23}N_5O_4S$, 525.6; m/z found, 526.2 [M+H]$^+$. 1H NMR (500 MHz, Methanol-d4) δ 8.31 (d, J=6.0 Hz, 1H), 7.44-7.37 (m, 4H), 7.21-7.16 (m, 3H), 7.11 (d, J=7.7 Hz, 2H), 6.68-6.56 (m, 1H), 6.32-6.25 (m, 1H), 6.18 (d, J=5.0 Hz, 1H), 5.79-5.72 (m, 1H), 4.70-4.59 (m, 1H), 4.05-3.98 (m, 0.5H), 3.91-3.82 (m, 1H), 3.77-3.70 (m, 1H), 3.64-3.57 (m, 1H), 3.55-3.49 (m, 0.5H), 2.40-2.23 (m, 1H), 2.21-2.06 (m, 1H).

Example 444: (R)—N-(1-Acryloylpiperidin-3-yl)-5-(4-isopropyl-2-methylphenyl)-4-oxo-4,5-dihydro-3H-1-thia-3,5,8-triazaacenaphthylene-2-carboxamide

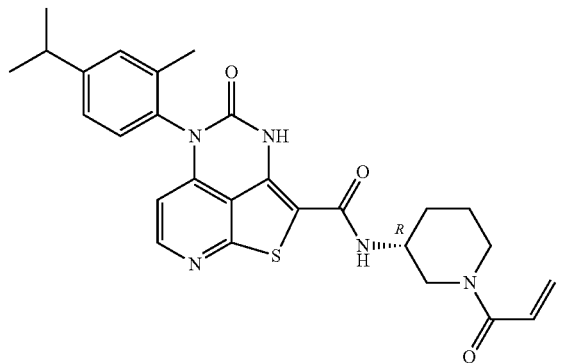

The title compound was prepared in a manner analogous to Method 1, steps C-I in Example 1, and using 4-isopropyl-2-methyl-aniline (Intermediate 7) in place of 2-methyl-4-phenoxy-aniline in step C and using tert-butyl (3R)-3-aminopiperidine-1-carboxylate in place of tert-butyl (3R,5R)-3-amino-5-fluoro-piperidine-1-carboxylate in step G to yield the title compound. MS (ESI): mass calcd. for $C_{27}H_{29}N_5O_3S$, 503.6; m/z found, 540.7 [M+H]$^+$. $^1$H NMR (400 MHz, CD$_3$OD): δ 8.33-8.25 (m, 1H), 7.35-7.31 (m, 1H), 7.30-7.25 (m, 1H), 7.24-7.19 (m, 1H), 6.84-6.72 (m, 1H), 6.23-6.15 (m, 1H), 6.00-5.95 (m, 1H), 5.77-5.69 (m, 1H), 4.56-4.25 (m, 1H), 4.20-3.90 (m, 2H), 3.25-3.11 (m, 1H), 2.99-2.46. (m, 2H), 2.17-2.10 (m, 3H), 2.09-2.03 (m, 1H), 1.94-1.81 (m, 1H), 1.76-1.59 (m, 2H), 1.30-0.99 (m, 6H).

Example 445: (R)—N-(1-Acryloylpyrrolidin-3-yl)-5-(4-isopropyl-2-methylphenyl)-4-oxo-4,5-dihydro-3H-1-thia-3,5,8-triazaacenaphthylene-2-carboxamide

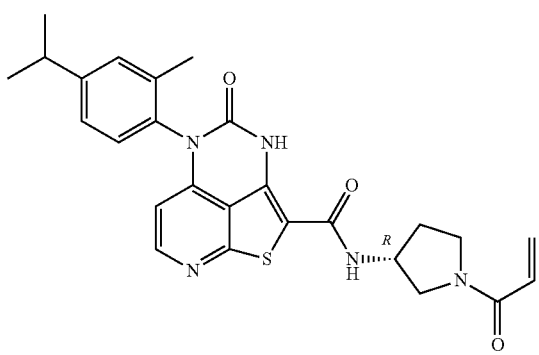

The title compound was prepared in a manner analogous to Method 1, steps C-G in Example 1, and using 4-isopropyl-2-methyl-aniline (Intermediate 7) in place of 2-methyl-4-phenoxy-aniline in step C and using 1-[(3R)-3-aminopyrrolidin-1-yl]prop-2-en-1-one (Intermediate 5) in place of tert-butyl (3R,5R)-3-amino-5-fluoro-piperidine-1-carboxylate in step G to yield the title compound. MS (ESI): mass calcd. for $C_{26}H_{27}N_5O_3S$, 489.6; m/z found, 490.2 [M+H]$^+$. $^1$H NMR (400 MHz, CD$_3$OD): δ 8.33-8.25 (m, 1H), 7.35-7.31 (m, 1H), 7.30-7.25 (m, 1H), 7.24-7.19 (m, 1H), 6.67-6.52 (m, 1H), 6.31-6.21 (m, 1H), 6.00-5.95 (m, 1H), 5.77-5.69 (m, 1H), 4.67-4.58 (m, 1H), 4.03-3.66 (m, 3H), 3.61-3.48 (m, 1H), 3.00-2.64 (m, 1H), 2.36-2.22 (m, 1H), 2.17-2.10 (m, 3H), 2.08-1.65 (m, 1H), 1.30-0.96 (m, 6H).

Example 446: (R)-5-(4-Isopropyl-2-methylphenyl)-4-oxo-N-(piperidin-3-yl)-4,5-dihydro-3H-1-thia-3,5,8-triazaacenaphthylene-2-carboxamide

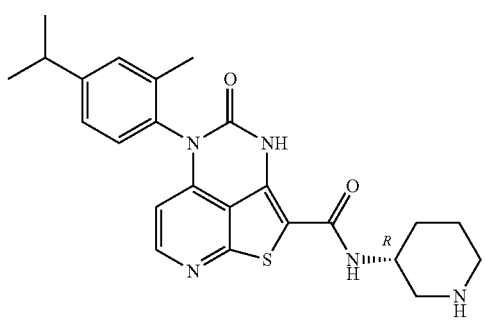

The title compound was prepared in a manner analogous to Method 1, steps C-H in Example 1, and using benzofuran-7-ol (Intermediate 8) in place of 2-methyl-4-phenoxy-aniline in step C and using tert-butyl (3R)-3-aminopiperidine-1-carboxylate in place of tert-butyl (3R,5R)-3-amino-5-fluoro-piperidine-1-carboxylate in step G to yield the title compound. MS (ESI): mass calcd. for $C_{24}H_{27}N_5O_2S$, 449.6; m/z found, 450.2 [M+H]$^+$. $^1$H NMR (400 MHz, CD$_3$OD): δ 8.35-8.28 (m, 1H), 7.35-7.31 (m, 1H), 7.30-7.25 (m, 1H), 7.24-7.19 (m, 1H), 6.00-5.95 (m, 1H), 4.55-4.25 (m, 1H), 3.85-3.50 (m, 1H), 3.40-3.33 (m, 1H), 3.00-249. (m, 3H), 2.17-2.10 (m, 3H), 2.08-1.99 (m, 2H), 1.83-1.68 (m, 2H), 1.30-0.96 (m, 6H).

Example 447: (R)-5-(4-Isopropyl-2-methylphenyl)-N-(1-methylpiperidin-3-yl)-4-oxo-4,5-dihydro-3H-1-thia-3,5,8-triazaacenaphthylene-2-carboxamide

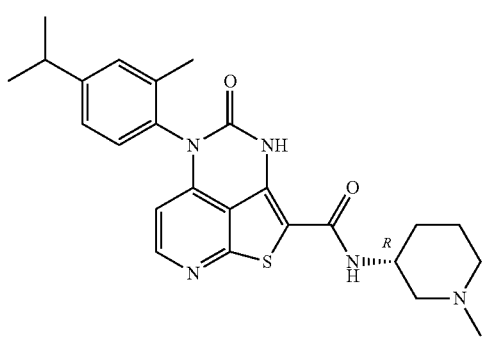

To a solution of (R)-5-(4-isopropyl-2-methylphenyl)-4-oxo-N-(piperidin-3-yl)-4,5-dihydro-3H-1-thia-3,5,8-triazaacenaphthylene-2-carboxamide (Example 446, 40 mg, 0.089 mmol) in DCM (2 mL) were added formaldehyde (1.0 mL, 37 wt. % in H$_2$O), and NaBH(OAc)$_3$ (40 mg, 0.19 mmol) and was reacted at rt for 20 min. The reaction mixture was concentrated to dryness and the residue was purified by flash column chromatography and preparative TLC to give the title compound as a yellow solid (35 mg). MS (ESI): mass calcd. for $C_{25}H_{29}N_5O_2S$, 463.6; m/z found, 464.2 [M+H]+. 1H NMR (400 MHz, $CD_3OD$): δ 8.35-8.28 (m, 1H), 7.35-7.31 (m, 1H), 7.30-7.25 (m, 1H), 7.24-7.19 (m, 1H), 6.00-5.95 (m, 1H), 4.41-4.19 (m, 1H), 3.67-3.52 (m, 1H), 3.46-3.35 (m, 1H), 3.02-2.94. (m, 2H), 2.89 (s, 3H), 2.74-2.43 (m, 1H), 2.17-2.10 (m, 3H), 2.08-2.03 (m, 2H), 1.90-1.71 (m, 2H), 1.30-0.96 (m, 6H).

Example 448: (R,*Z)—N-(1-(2-Cyano-4-methoxy-4-methylpent-2-enoyl)piperidin-3-yl)-5-(*)-(2-methyl-4-phenoxyphenyl)-4-oxo-4,5-dihydro-3H-1-thia-3,5,8-triazaacenaphthylene-2-carboxamide

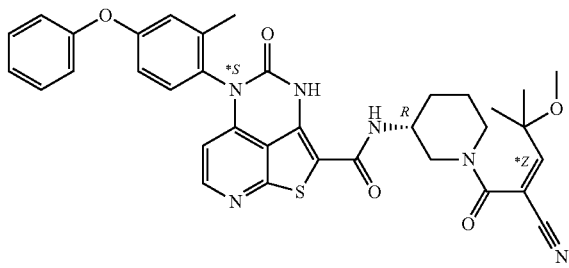

A chiral purification was performed on (R,ZE)-N-(1-(2-cyano-4-methoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 40; 55.5 mg) via chiral SFC (Stationary phase: CHIRALCEL OD-H 5 μm 250×20 mm, Mobile phase: 50% $CO_2$, 50% EtOH) and a second purification (25 mg from fraction 3, first purification) was performed via chiral SFC (Stationary phase: CHIRALCEL OJ-H 5 μm 250×20 mm, Mobile phase: 75% $CO_2$, 25% MeOH) to give the title compound (as the *S atropisomer and as the *Z configuration; 7 mg). MS (ESI): mass calcd. for $C_{35}H_{34}N_6O_5S$, 650.8; m/z found, 650.2 [M+H]+. 1H NMR (400 MHz, Methanol-d4) δ 8.51-8.24 (m, 1H), 7.49-7.35 (m, 2H), 7.35-7.25 (m, 1H), 7.25-6.92 (m, 5H), 6.73 (d, J=1.5 Hz, 1H), 6.15-5.94 (m, 1H), 4.69-4.27 (m, 1H), 4.20-3.74 (m, 2H), 3.27-3.23 (m, 2H), 3.21-2.72 (m, 2H), 2.21-2.07 (m, 3H), 1.95-1.70 (m, 2H), 1.44-1.28 (m, 8H), 1.15-0.70 (m, 1H).

Example 449: (R,*Z)—N-(1-(2-Cyano-4-methoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

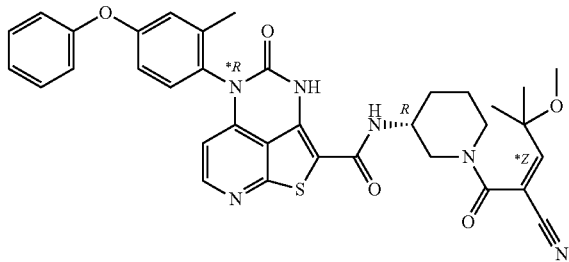

A chiral purification was performed on (R,EZ)—N-(1-(2-cyano-4-methoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 40; 55.5 mg) via chiral SFC (Stationary phase: CHIRALCEL OD-H 5 μm 250×20 mm, Mobile phase: 50% $CO_2$, 50% EtOH) and a second purification (25 mg from fraction 3, first purification) was performed via chiral SFC (Stationary phase: CHIRALCEL OJ-H 5 μm 250×20 mm, Mobile phase: 75% $CO_2$, 25% MeOH) to give the title compound (as the *R atropisomer and as the *Z configuration; 16 mg). MS (ESI): mass calcd. for $C_{35}H_{34}N_6O_5S$, 650.8; m/z found, 650.2 [M+H]+. 1H NMR (400 MHz, Methanol-d4) δ 8.32 (d, J=5.6 Hz, 1H), 7.46-7.34 (m, 2H), 7.32 (d, J=8.6 Hz, 1H), 7.25-7.14 (m, 1H), 7.14-7.03 (m, 3H), 1.38-1.34 (m, 1H), 6.98 (dd, J=8.6, 2.8 Hz, 1H), 6.95-6.82 (m, 1H), 6.07 (d, J=5.6 Hz, 1H), 4.54-3.36 (m, 3H), 3.29-2.74 (m, 5H), 2.27-2.00 (m, 4H), 1.99-1.84 (m, 1H), 1.87-1.57 (m, 3H), 1.43 (s, 6H).

Example 450: (R,*E)-N-(1-(2-Cyano-4-methoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

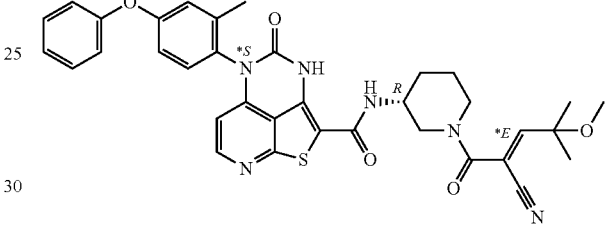

A chiral purification was performed on (R,EZ)—N-(1-(2-cyano-4-methoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 40; 55.5 mg) via chiral SFC (Stationary phase: CHIRALCEL OD-H 5 μm 250×20 mm, Mobile phase: 50% $CO_2$, 50% EtOH) and a second purification (25 mg from fraction 2, first purification) was performed via chiral SFC (Stationary phase: CHIRALCEL OJ-H 5 m 250×20 mm, Mobile phase: 75% $CO_2$, 25% MeOH) to give the title compound (as the *S atropisomer and as the *E configuration; 6 mg). MS (ESI): mass calcd. for $C_{35}H_{34}N_6O_5S$, 650.8; m/z found, 650.2 [M+H]+. 1H NMR (400 MHz, $CD_3OD$): δ 8.39-8.28 (m, 1H), 7.51-6.66 (m, 9H), 6.08 (d, J=5.5 Hz, 1H), 4.63-3.68 (m, 3H), 3.30-3.06 (m, 4H), 3.01-2.64 (m, 1H), 2.23-2.01 (m, 3H), 1.96-1.83 (m, 1H), 1.83-1.51 (m, 2H), 1.48-1.40 (m, 2H), 1.40-1.29 (m, 5H).

Example 451: (R,*E)-N-(1-(2-Cyano-4-methoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

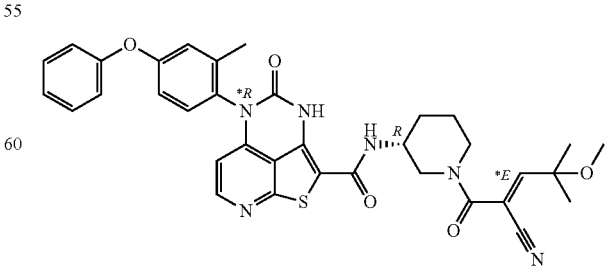

A chiral purification was performed on (R,EZ)—N-(1-(2-cyano-4-methoxy-4-methylpent-2-enoyl)piperidin-3-yl)-5-

(2-methyl-4-phenoxyphenyl)-4-oxo-4,5-dihydro-3H-1-thia-3,5,8-triazaacenaphthylene-2-carboxamide (Example 40; 55.5 mg) via chiral SFC (Stationary phase: CHIRALCEL OD-H 5 m 250×20 mm, Mobile phase: 50% CO$_2$, 50% EtOH) and a second purification (25 mg from fraction 2, first purification) was performed via chiral SFC (Stationary phase: CHIRALCEL OJ-H 5 μm 250×20 mm, Mobile phase: 75% CO$_2$, 25% MeOH) to give the title compound (as the *R atropisomer and as the *E configuration; 14 mg). MS (ESI): mass calcd. for C$_{35}$H$_{34}$N$_6$O$_5$S, 650.8; m/z found, 650.2 [M+H]$^+$. $^1$H NMR (400 MHz, CD$_3$OD): δ 8.34 (d, J=5.5 Hz, 1H), 7.47-6.83 (m, 9H), 6.08 (d, J=5.6 Hz, 1H), 4.17-3.94 (m, 2H), 3.30-3.28 (m, 3H), 3.22-2.82 (m, 1H), 2.19-2.02 (m, 4H), 2.00-1.86 (m, 1H), 1.86-1.51 (m, 2H), 1.51-1.36 (m, 7H), 1.29 (s, 1H).

Example 452: N-((1-Acryloylpyrrolidin-3-yl)methyl)-4-oxo-5-(4-phenoxyphenyl)-4,5-dihydro-3H-1-thia-3,5,8-triazaacenaphthylene-2-carboxamide

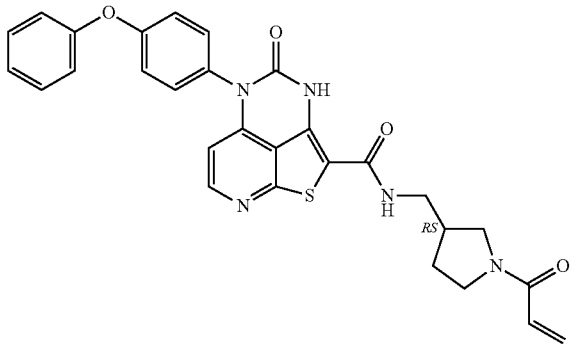

The title compound was prepared in a manner analogous to Method 1, steps A-I in Example 1, and using 4-fluoronitrobenzene in place of 5-fluoro-2-nitrotoluene in step A and using 2-(aminomethyl)-1-N-Boc-pyrrolidine in place of tert-butyl (3R,5R)-3-amino-5-fluoro-piperidine-1-carboxylate in step G to yield the title compound as an off-white solid. MS (ESI): mass calcd. for C$_{29}$H$_{25}$N$_5$O$_4$S, 539.6; m/z found, 540.1 [M+H]$^+$. $^1$H NMR (400 MHz, Chloroform-d) δ 9.51 (s, 1H), 8.32 (d, J=5.6 Hz, 1H), 8.21 (t, J=4.4 Hz, 1H), 7.39 (t, J=7.8 Hz, 2H), 7.30 (s, 1H), 7.15 (ddd, J=20.2, 13.2, 7.5 Hz, 5H), 6.60-6.39 (m, 2H), 6.10 (d, J=5.5 Hz, 1H), 5.78 (dd, J=9.5, 2.9 Hz, 1H), 4.53 (tt, J=6.9, 3.4 Hz, 1H), 3.73-3.58 (m, 3H), 3.40 (ddd, J=13.7, 10.1, 3.5 Hz, 1H), 2.06 (ddt, J=18.9, 15.0, 7.5 Hz, 4H), 1.85 (td, J=6.0, 5.6, 2.5 Hz, 1H).

Example 453: 4-Oxo-5-(4-phenoxyphenyl)-N-(pyrrolidin-3-ylmethyl)-4,5-dihydro-3H-1-thia-3,5,8-triazaacenaphthylene-2-carboxamide

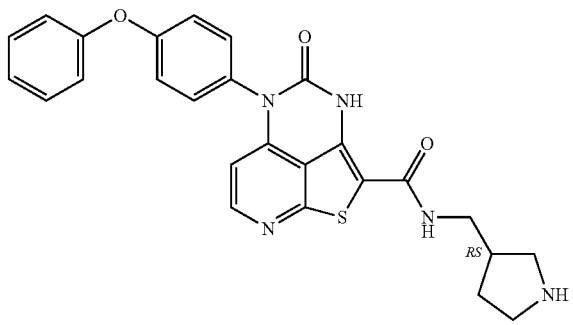

The title compound was prepared in a manner analogous to Method 1, steps A-H in Example 1, and using 4-fluoronitrobenzene in place of 5-fluoro-2-nitrotoluene in step A and using 2-(aminomethyl)-1-N-Boc-pyrrolidine in place of tert-butyl (3R,5R)-3-amino-5-fluoro-piperidine-1-carboxylate in step G to yield the title compound as an off-white solid. MS (ESI): mass calcd. for C$_{26}$H$_{23}$N$_5$O$_3$S, 485.5; m/z found, 486.1 [M+H]$^+$. 1H NMR (500 MHz, Chloroform-d) δ 9.68 (s, 1H), 9.50 (s, 2H), 8.42 (s, 1H), 8.17 (s, 1H), 7.49 (dt, J=8.7, 2.9 Hz, 1H), 7.44-7.35 (m, 2H), 7.32 (dt, J=8.6, 2.6 Hz, 1H), 7.22-7.05 (m, 3H), 6.04 (s, 1H), 4.39 (s, 1H), 3.95 (d, J=8.8 Hz, 1H), 3.84-3.77 (m, 1H), 3.47 (d, J=19.5 Hz, 2H), 3.34 (s, 1H), 3.28 (q, J=10.4, 8.3 Hz, 1H), 2.23-2.13 (m, 1H), 2.14-1.94 (m, 2H).

Example 454: (R)—N-(1-(1H-Imidazole-1-carbonyl)piperidin-3-yl)-5-(2,2-difluorobenzo[d][1,3]dioxol-5-yl)-4-oxo-4,5-dihydro-3H-1-thia-3,5,8-triazaacenaphthylene-2-carboxamide

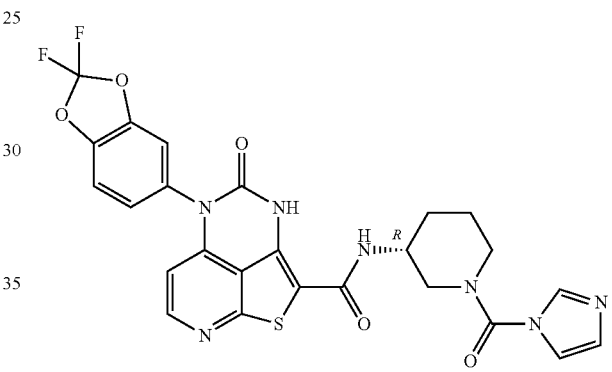

To a 40 mL microwave vial were added 2-chloro-4-iodonicotinonitrile (1.451 g, 5.488 mmol), bis(2-diphenylphosphinophenyl)ether (90 mg, 0.17 mmol), palladium(II) acetate (25 mg, 0.11 mmol), cesium carbonate (2.503 g, 7.683 mmol), 2,2-difluoro-5-aminobenzodioxole (1.0 g, in 1.0 mL dioxane), and dioxane (10 mL) and was purged with N$_2$ stream for 30 min. The reaction was heated in the microwave at 150° C. for 30 min. To the reaction mixture was added tert-butyl (3R)-3-[(2-sulfanylacetyl)amino]piperidine-1-carboxylate (Intermediate 22) (8.44 mL, 5.49 mmol) and was purged with N$_2$ stream for 15 min. The reaction was heated in microwave at 150° C. for 30 min. To the mixture was added CDI (3.6 g, 22 mmol) and was heated at 150° C. for 30 min. The reaction mixture was extracted with EtOAc and the organic phase was washed with water and brine. The precipitate was filtered off through Celite. The organic phase was over anhydrous Na$_2$SO$_4$, filtered, and concentrated to dryness. The reaction mixture was purified by flash column chromatography, then by HPLC to give the title compound as a brown solid (82.4 mg, 2.65% yield). MS (ESI): mass calcd. for C$_{25}$H$_{19}$F$_2$N$_7$O$_5$S, 567.5; m/z found, 568.0 [M+H]$^+$. $^1$H NMR (500 MHz, CD$_3$OD): δ 8.16-8.06 (m, 2H), 7.47 (s, 1H), 7.27-7.20 (m, 2H), 7.15-7.08 (m, 1H), 7.06 (s, 1H), 6.80 (d, J=5.9 Hz, 1H), 5.16-5.06 (m, 1H), 4.17 (t, J=12.0 Hz, 1H), 4.12-3.97 (m, 2H), 3.13 (t, J=12.4 Hz, 1H), 2.86-2.71 (m, 1H), 1.92 (t, J=13.3 Hz, 2H), 1.83-1.72 (m, 1H).

Example 455: (R)—N-(1-Acryloylpiperidin-3-yl)-5-(4-methoxy-3-(trifluoromethyl)phenyl)-4-oxo-4,5-dihydro-3H-1-thia-3,5,8-triazaacenaphthylene-2-carboxamide

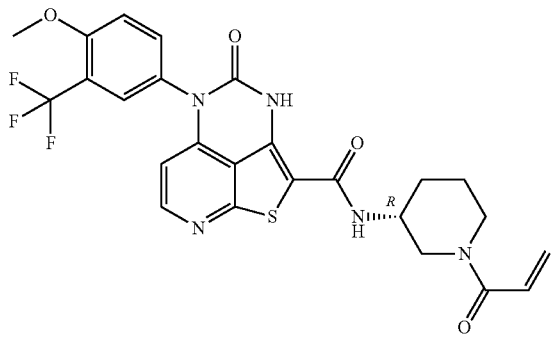

Step A: (R)-tert-Butyl 3-(5-(4-methoxy-3-(trifluoromethyl)phenyl)-4-oxo-4,5-dihydro-3H-1-thia-3,5,8-triazaacenaphthylene-2-carboxamido)piperidine-1-carboxylate To a microwave vial with a stir bar were added 2-chloro-4-iodonicotinonitrile (520 mg, 2.0 mmol), 4-methoxy-3-(trifluoromethyl)aniline (369 mg, 1.93 mmol), DPEPhos (31 mg, 0.058 mmol), Pd(OAc)$_2$ (9.9 mg, 0.044 mmol), and Cs$_2$CO$_3$ (924 mg, 2.84 mmol). The vial was treated with dioxane (4 mL) via syringe, and the entire mixture was degassed under vacuum for 1 minute, and then vented to nitrogen. The reaction mixture was heated in the microwave at 150° C. for 30 minutes. The reaction was then cooled to room temperature, treated with tert-butyl (3R)-3-[(2-sulfanylacetyl)amino]piperidine-1-carboxylate (Intermediate 22) (0.49 M in dioxane, 522 mg, 1.90 mmol) via syringe, evacuated and flushed with nitrogen, and stirred at 150° C. for 20 min. The reaction was then cooled to room temperature. The reaction mixture was then treated with solid CDI (1.195 g, 7.368 mmol) in one portion under air, resealed and evacuated and flushed with nitrogen, and stirred at 150° C. for 20 min. The reaction was diluted with EtOAc (100 mL) and saturated aqueous sodium bicarbonate (100 mL), and the organic phase was collected. The aqueous layer was extracted again with EtOAc (100 mL), and the combined organics were dried over anhydrous MgSO$_4$, concentrated to dryness, and purified by flash column chromatography to give the title compound (252 mg, 21.7% yield).

Step B: (R)-5-(4-Methoxy-3-(trifluoromethyl)phenyl)-4-oxo-N-(piperidin-3-yl)-4,5-dihydro-3H-1-thia-3,5,8-triazaacenaphthylene-2-carboxamide A solution of (R)-tert-butyl 3-(5-(4-methoxy-3-(trifluoromethyl)phenyl)-4-oxo-4,5-dihydro-3H-1-thia-3,5,8-triazaacenaphthylene-2-carboxamido)piperidine-1-carboxylate (500 mg, 0.85 mmol) in dioxane (4 mL) was treated with 4 N HCl-dioxane (12 mL). After 30 min at room temperature, a gummy precipitate had settled on the bottom of the vial. The dioxane was poured off, and the precipitate was treated with saturated aqueous sodium bicarbonate (20 mL) and extracted with DCM (2×50 mL). The combined organic layers were dried over anhydrous MgSO$_4$ and concentrated to dryness. The resulting crude product was purified by flash column chromatography to give the title compound as an off white solid (72 mg, 17% yield).

Step C: (R)—N-(1-Acryloylpiperidin-3-yl)-5-(4-methoxy-3-(trifluoromethyl)phenyl)-4-oxo-4,5-dihydro-3H-1-thia-3,5,8-triazaacenaphthylene-2-carboxamide A solution of (R)-5-(4-methoxy-3-(trifluoromethyl)phenyl)-4-oxo-N-(piperidin-3-yl)-4,5-dihydro-3H-1-thia-3,5,8-triazaacenaphthylene-2-carboxamide (52 mg, 0.087 mmol) in DCM (5 mL) was stirred at room temperature and triethylamine (36 μL, 0.26 mmol) was added via syringe, followed by very slow addition of acryloyl chloride (7.0 μL, 0.086 mmol) 1 microliter at a time over 20 min. The suspension gradually became a homogeneous solution. The reaction was closely monitored by LCMS, and when the starting material peak was the same size as a new impurity peak that was growing in, then the reaction mixture was quenched with saturated aqueous sodium bicarbonate (10 mL). The mixture was treated with DCM (10 mL), the mixture was extracted and the organic layer was separated. The aqueous layer was extracted again with DCM, and the combined organics were dried over anhydrous MgSO$_4$, and concentrated to dryness. The residue was purified by flash column chromatography to yield a product that was dissolved in DCM (2 mL), which was then was treated with hexanes (10 mL). The resulting solid was isolated by filtration to give the title compound as a tan solid (25 mg, 52% yield). MS (ESI): mass calcd. for C$_{25}$H$_{22}$F$_3$N$_5$O$_4$S, 545.5; m/z found, [M+H]$^+$. $^1$H NMR (400 MHz, DMSO-d$_6$): δ 10.24-10.12 (s, 1H), 8.39-8.26 (d, J=5.5 Hz, 1H), 8.14-8.02 (m, 1H), 7.85-7.80 (d, J=2.4 Hz, 1H), 7.79-7.72 (m, 1H), 7.53-7.44 (d, J=8.9 Hz, 1H), 6.88-6.71 (m, 1H), 6.15-6.08 (d, J=16.9 Hz, 1H), 6.07-6.03 (d, J=5.5 Hz, 1H), 5.73-5.63 (m, 1H), 4.53-4.15 (m, 1H), 4.12-4.01 (m, 1H), 4.01-3.94 (s, 3H), 3.87-3.73 (m, 1H), 3.19-2.92 (m, 1H), 2.83-2.61 (m, 1H), 2.00-1.90 (m, 1H), 1.84-1.58 (m, 2H), 1.52-1.36 (m, 1H).

Example 456: (R)—N-(1-Acryloylpiperidin-3-yl)-5-(4-cyclobutoxy-2-methylphenyl)-4-oxo-4,5-dihydro-3H-1-thia-3,5,8-triazaacenaphthylene-2-carboxamide

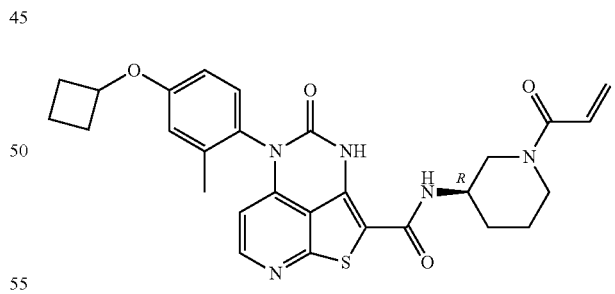

To a solution of (R)-5-(4-cyclobutoxy-2-methylphenyl)-4-oxo-N-(piperidin-3-yl)-4,5-dihydro-3H-1-thia-3,5,8-triazaacenaphthylene-2-carboxamide (Example 605, 180 mg, 0.35 mmol) in DCM (1 mL) was added triethylamine (146 μL, 1.05 mmol). The mixture was cooled in an ice-water bath and to it was added acryloyl chloride (28 μL, 0.35 mmol) dropwise via syringe. The reaction mixture was stirred under air at 0° C. for 30 minutes. The reaction mixture was partitioned between DCM (10 mL) and saturated aqueous NaHCO$_3$ (10 mL). The aqueous phase was extracted once with EtOAc (10 mL) and the combined organic extracts were dried over anhydrous Na$_2$SO$_4$, filtered, and concentrated to dryness. The residue was purified by flash column chromatography to give the title compound as a tan powder (56.3 mg, 30.3% yield). MS (ESI): mass calcd. for C$_{28}$H$_{29}$N$_5$O$_4$S, 531.6; m/z found, 532.0 [M+H]$^+$. $^1$H NMR (400 MHz, CDCl$_3$): δ 9.45 (br. s., 1H), 8.34 (d, J=4.04 Hz, 1H), 7.06-7.14 (m, 1H), 6.83 (s, 1H), 6.79 (dd, J=2.02, 8.59 Hz, 1H), 6.57-6.69 (m, 1H), 6.28-6.48 (m, 1H), 6.17-6.28 (m, 0.5H), 5.95-6.05 (m, 1H), 5.70-5.82 (m, 1H), 5.40-5.51 (m, 0.5H), 4.67 (quin, J=7.07 Hz, 1H), 3.87-4.22 (m, 2.5H), 3.23-3.74 (m, 2.5H), 2.42-2.54 (m, 2H), 1.99-2.28 (m, 6H), 1.61-1.99 (m, 5H).

Example 457: (R)—N-(1-Acryloylpiperidin-3-yl)-5-(4-cyclobutoxyphenyl)-4-oxo-4,5-dihydro-3H-1-thia-3,5,8-triazaacenaphthylene-2-carboxamide

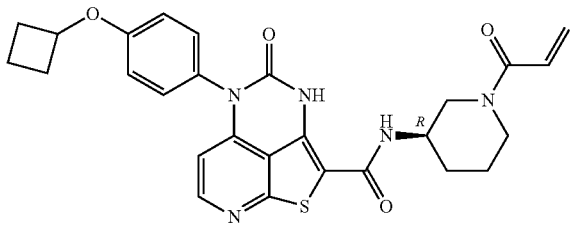

The title compound was prepared in a manner analogous to Method 1, step I in Example 1, and using (R)-5-(4-Cyclobutoxyphenyl)-4-oxo-N-(piperidin-3-yl)-4,5-dihydro-3H-1-thia-3,5,8-triazaacenaphthylene-2-carboxamide (Example 626) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide. MS (ESI): mass calcd. for C$_{27}$H$_{27}$N$_5$O$_4$S, 517.6; m/z found, 518.2 [M+H]$^+$. $^1$H NMR (400 MHz, CDCl$_3$): δ 9.45 (br. s., 1H), 8.35 (br. s., 1H), 7.21 (d, J=8.59 Hz, 2H), 6.97 (d, J=8.59 Hz, 2H), 6.58-6.69 (m, 1H), 6.27-6.50 (m, 1H), 6.18-6.26 (m, 0.5H), 6.08-6.18 (m, 1H), 5.69-5.82 (m, 1H), 5.41-5.51 (m, 0.5H), 4.68 (quin, J=7.07 Hz, 1H), 3.87-4.21 (m, 2H), 3.26-3.75 (m, 2H), 2.44-2.54 (m, 2H), 2.15-2.28 (m, 2H), 2.00-2.15 (m, 1H), 1.62-1.99 (m, 6H).

Example 458: 4-Oxo-N-(2-oxopiperidin-3-yl)-5-(4-phenoxyphenyl)-4,5-dihydro-3H-1-thia-3,5,8-triazaacenaphthylene-2-carboxamide

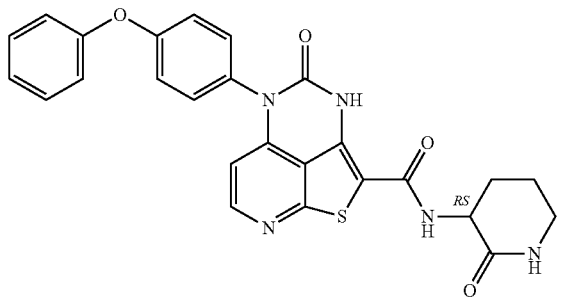

The title compound was prepared in a manner analogous to Method 1, steps A-G in Example 1, and using 4-fluoronitrobenzene in place of 5-fluoro-2-nitrotoluene in step A and using 3-aminopiperidin-2-one in place of tert-butyl (3R,5R)-3-amino-5-fluoro-piperidine-1-carboxylate in step G to yield the title compound as an off-white solid. MS (ESI): mass calcd. for C26H21N5O4S, 499.5; m/z found, 500.2 [M+H]$^+$. 1H NMR (500 MHz, Chloroform-d) δ 9.59 (s, 1H), 8.31 (d, J=5.5 Hz, 1H), 7.45-7.36 (m, 2H), 7.34-7.25 (m, 2H), 7.23-7.07 (m, 5H), 7.03 (d, J=6.2 Hz, 1H), 6.40 (s, 1H), 6.11 (d, J=5.5 Hz, 1H), 4.51 (dt, J=11.9, 6.1 Hz, 1H), 3.41 (ddd, J=8.5, 5.1, 2.3 Hz, 2H), 3.21 (q, J=7.3 Hz, 1H), 2.47 (dt, J=13.3, 5.1 Hz, 1H), 2.05-1.90 (m, 1H), 1.88-1.74 (m, 1H).

Example 459: (R)-5-(4-Methoxy-3-(trifluoromethyl)phenyl)-4-oxo-N-(piperidin-3-yl)-4,5-dihydro-3H-1-thia-3,5,8-triazaacenaphthylene-2-carboxamide

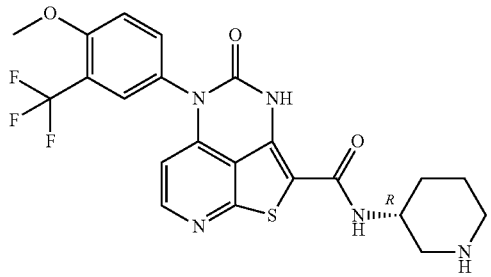

The title compound was prepared using steps A-B in Example 455, to yield the title compound as an off-white solid. MS (ESI): mass calcd. for C$_{22}$H$_{20}$F$_3$N$_5$O$_3$S, 491.5; m/z found, 492.0 [M+H]$^+$. 1H NMR (600 MHz, MeOD) δ 8.23 (d, J=5.6 Hz, 1H), 7.71-7.59 (m, 2H), 7.41 (d, J=8.7 Hz, 1H), 6.05 (d, J=5.6 Hz, 1H), 4.22-4.11 (m, 1H), 4.02 (s, 3H), 3.31-3.28 (m, 1H), 3.13-3.06 (m, 1H), 2.89-2.77 (m, 2H), 2.10-2.02 (m, 1H), 1.99-1.90 (m, 1H), 1.79-1.68 (m, 2H).

Example 460: (R)-5-(3-Chloro-4-methylphenyl)-4-oxo-N-(piperidin-3-yl)-4,5-dihydro-3H-1-thia-3,5,8-triazaacenaphthylene-2-carboxamide

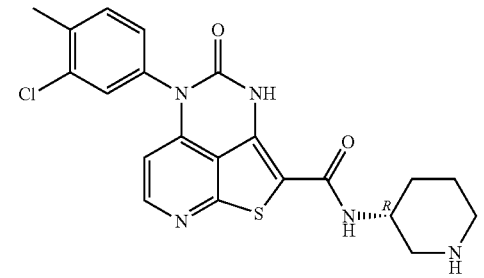

Step A: (R)-tert-Butyl 3-(5-(3-chloro-4-methylphenyl)-4-oxo-4,5-dihydro-3H-1-thia-3,5,8-triazaacenaphthylene-2-carboxamido)piperidine-1-carboxylate To a 2-5 mL Biotage microwave vial with a stir bar were added 3-chloro-4-methylaniline (69.3 mg, 0.489 mmol), 2-chloro-4-iodonicotinonitrile (129 mg, 0.487 mmol), Pd(OAc)$_2$ (2.3 mg, 0.010 mmol), DPEPhos (8.1 mg, 0.015 mmol), and Cs$_2$CO$_3$ (221 mg, 0.678 mmol). The vial was sealed, treated with dioxane (0.98 mL), evacuated and flushed with argon 4×, and stirred at 150° C. under argon for 30 min. The reaction was cooled to room temperature and was treated with tert-butyl (3R)-3-[(2-sulfanylacetyl)amino]piperidine-1-carboxylate (Intermediate 22) (0.49 M in dioxane, 1.0 mL, 0.49 mmol) via syringe. The vial was sealed and evacuated and flushed with argon 4×, and stirred at 150° C. for 15 min. The reaction was then cooled to room temperature, treated with solid CDI (308 mg, 1.90 mmol) in one portion under air, resealed and evacuated and flushed with argon 4×, and stirred at 150° C. for 15 min. The reaction was diluted with EtOAc (10 mL), and washed with 0.5 M citric acid and brine (2×8 mL) and 2 M $K_2CO_3$ (1×5 mL). The organic phase was dried over anhydrous $Na_2SO_4$, filtered, and concentrated to dryness. The residue was purified by normal phase flash column chromatography ($SiO_2$) to give the title compound as an orange-yellow foam (142.4 mg, 53.90% yield).

Step B: (R)-5-(3-Chloro-4-methylphenyl)-4-oxo-N-(piperidin-3-yl)-4,5-dihydro-3H-1-thia-3,5,8-triazaacenaphthylene-2-carboxamide A solution of (R)-tert-butyl 3-(5-(3-chloro-4-methylphenyl)-4-oxo-4,5-dihydro-3H-1-thia-3,5,8-triazaacenaphthylene-2-carboxamido)piperidine-1-carboxylate (142.4 mg, 0.263 mmol) in dioxane (1.5 mL) was treated with HCl (3.97 M in dioxane, 3.5 mL, 14 mmol) in one portion at room temperature, and the resulting solution was stirred at room temperature for 1 h. The reaction was concentrated to dryness to give the title compound as a yellow-beige powder (118.1 mg, 92.27% yield). MS (ESI): mass calcd. for $C_{21}H_{20}ClN_5O_2S$, 441.1; m/z found, 442.0 $[M+H]^+$. 1H NMR (400 MHz, MeOH-d4) δ 8.48 (d, J=6.57 Hz, 1H), 7.58 (d, J=8.36 Hz, 1H), 7.55 (s, 1H), 7.33 (dd, J=2.02, 8.08 Hz, 1H), 6.41 (d, J=6.06 Hz, 1H), 4.25-4.33 (m, 1H), 3.54 (br dd, J=3.79, 11.87 Hz, 1H), 3.34-3.40 (m, 1H), 2.93-3.03 (m, 2H), 2.49 (s, 3H), 1.99-2.14 (m, 2H), 1.72-1.91 (m, 2H).

Example 461: (R)-5-(4-Methyl-3-(trifluoromethyl)phenyl)-4-oxo-N-(piperidin-3-yl)-4,5-dihydro-3H-1-thia-3,5,8-triazaacenaphthylene-2-carboxamide

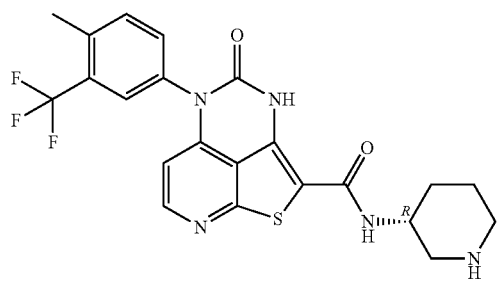

Step A: (R)-tert-Butyl 3-(5-(4-methyl-3-(trifluoromethyl)phenyl)-4-oxo-4,5-dihydro-3H-1-thia-3,5,8-triazaacenaphthylene-2-carboxamido)piperidine-1-carboxylate To a 2-5 mL Biotage microwave vial with a stir bar were added 4-methyl-3-(trifluoromethyl)aniline (80 mg, 0.41 mmol), 2-chloro-4-iodonicotinonitrile (107 mg, 0.405 mmol), $Pd(OAc)_2$ (1.8 mg, 0.0080 mmol), DPEPhos (6.8 mg, 0.013 mmol), and $Cs_2CO_3$ (184 mg, 0.565 mmol). The vial was sealed, treated with dioxane (0.81 mL), evacuated and flushed with argon 4×, and stirred at 150° C. under argon for 30 min. The reaction was cooled to room temperature and was treated with tert-butyl (3R)-3-[(2-sulfanylacetyl)amino]piperidine-1-carboxylate (Intermediate 22) (0.49 M in dioxane, 0.83 mL, 0.41 mmol) via syringe. The vial was sealed and evacuated and flushed with argon 4×, and stirred at 150° C. for 15 min. The reaction was then cooled to room temperature, treated with solid CDI (265 mg, 1.63 mmol) in one portion under air, resealed and evacuated and flushed with argon 4×, and stirred at 150° C. for 15 min. The reaction was diluted with EtOAc (10 mL), and washed with 0.5 M citric acid and brine (2×8 mL) and 2 M $K_2CO_3$ (1×5 mL). The organic phase was dried over anhydrous $Na_2SO_4$, filtered, and concentrated to dryness. The residue was purified by normal phase flash column chromatography (SiO2) to give the title compound as a light-beige solid (123 mg, 52.8% yield).

Step B: (R)-5-(4-Methyl-3-(trifluoromethyl)phenyl)-4-oxo-N-(piperidin-3-yl)-4,5-dihydro-3H-1-thia-3,5,8-triazaacenaphthylene-2-carboxamide A solution of (R)-tert-butyl 3-(5-(4-methyl-3-(trifluoromethyl)phenyl)-4-oxo-4,5-dihydro-3H-1-thia-3,5,8-triazaacenaphthylene-2-carboxamido)piperidine-1-carboxylate (117.3 mg, 0.204 mmol) in dioxane (1.0 mL) was treated with HCl (3.97 M in dioxane, 2.55 mL, 10.1 mmol) in one portion at room temperature, and the resulting solution was stirred at room temperature for 1 h. The reaction was concentrated to dryness to give the title compound as a yellow-beige powder (113.4 mg, 101.7% yield). MS (ESI): mass calcd. for $C_{22}H_{23}F_3N_5O_2S$, 475.1; m/z found, 476.0 $[M+H]^+$. 1H NMR (400 MHz, MeOH-d4) δ 8.42 (d, J=6.06 Hz, 1H), 7.79 (s, 1H), 7.60-7.68 (m, 2H), 6.29 (d, J=6.06 Hz, 1H), 4.24-4.32 (m, 1H), 3.54 (dd, J=4.04, 12.13 Hz, 1H), 3.34-3.40 (m, 1H), 2.92-3.02 (m, 2H), 2.58-2.63 (m, 3H), 2.05-2.14 (m, 2H), 1.71-1.91 (m, 2H).

Example 462: 4-Oxo-5-(4-phenoxyphenyl)-N-((tetrahydrofuran-2-yl)methyl)-4,5-dihydro-3H-1-thia-3,5,8-triazaacenaphthylene-2-carboxamide

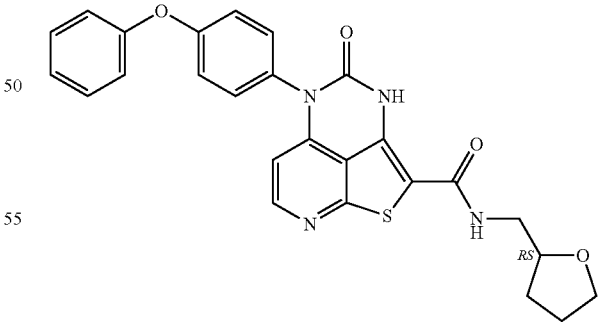

The title compound was prepared in a manner analogous to Method 1, steps A-G in Example 1, and using 4-fluoronitrobenzene in place of 5-fluoro-2-nitrotoluene in step A and using tetrahydrofurfurylamine in place of tert-butyl (3R,5R)-3-amino-5-fluoro-piperidine-1-carboxylate in step G to yield the title compound. MS (ESI): mass calcd. for $C_{26}H_{22}N_4O_4S$, 486.5; m/z found, 487.1 $[M+H]^+$. 1H NMR (500 MHz, Chloroform-d) δ 8.28 (d, J=5.4 Hz, 1H), 7.45-7.01 (m, 11H), 6.13 (d, J=5.4 Hz, 1H), 4.10 (dtt, J=10.4, 7.2, 3.0 Hz, 1H), 3.97 (q, J=7.0, 6.1 Hz, 1H), 3.81 (q, J=7.4 Hz, 1H), 3.65 (dt, J=14.0, 4.5 Hz, 1H), 3.41 (dq, J=17.6, 7.3, 5.7 Hz, 1H), 3.11-3.06 (m, 1H), 2.09-1.87 (m, 3H).

Example 463: N-((3S,4S)-1-Acryloyl-4-hydroxypyrrolidin-3-yl)-4-oxo-5-(4-phenoxyphenyl)-4,5-dihydro-3H-1-thia-3,5,8-triazaacenaphthylene-2-carboxamide

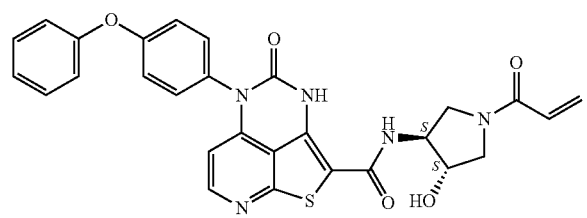

The title compound was prepared in a manner analogous to Method 1, steps A-I in Example 1, and using 4-fluoronitrobenzene in place of 5-fluoro-2-nitrotoluene in step A and using tert-buty (3S,4S)-3-amino-4-hydroxy-pyrrolidine-1-carboxylate in place of tert-butyl (3R,5R)-3-amino-5-fluoropiperidine-1-carboxylate in step G to yield the title compound. MS (ESI): mass calcd. for C28H23N5O5S, 541.5; m/z found, 542.2 [M+H]⁺. 1H NMR (400 MHz, Chloroform-d) 9.57 (s, 1H), 8.22-8.12 (m, 1H), 7.47-7.32 (m, 5H), 7.21-7.05 (m, 4H), 6.38-6.25 (m, 2H), 6.03-5.92 (m, 1H), 5.71-5.59 (m, 2H), 4.41 (s, 2H), 4.07 (t, J=9.4 Hz, 1H), 3.86 (s, 1H), 3.63-3.51 (m, 3H).

Example 464: N-((3S,4S)-4-Hydroxypyrrolidin-3-yl)-4-oxo-5-(4-phenoxyphenyl)-4,5-dihydro-3H-1-thia-3,5,8-triazaacenaphthylene-2-carboxamide

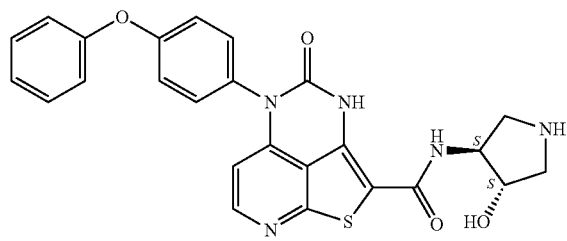

The title compound was prepared in a manner analogous to Method 1, steps A-H in Example 1, and using 4-fluoronitrobenzene in place of 5-fluoro-2-nitrotoluene in step A and using tert-butyl (3S,4S)-3-amino-4-hydroxy-pyrrolidine-1-carboxylate in place of tert-butyl (3R,5R)-3-amino-5-fluoropiperidine-1-carboxylate in step G to yield the title compound. MS (ESI): mass calcd. for C25H21N5O4S, 487.5; m/z found, 488.0 [M+H]⁺. 1H NMR (500 MHz, Methanol-d4) δ 8.30 (d, J=5.6 Hz, 1H), 7.46-7.37 (m, 4H), 7.22-7.14 (m, 3H), 7.14-7.07 (m, 2H), 6.17 (d, J=5.6 Hz, 2H), 6.00 (s, 1H), 4.53 (dt, J=4.2, 2.0 Hz, 1H), 4.39 (dddd, J=6.6, 3.1, 2.1, 0.9 Hz, 1H), 3.77 (dd, J=12.6, 6.9 Hz, 2H), 3.56 (ddd, J=30.3, 12.5, 3.7 Hz, 2H), 3.35 (s, 1H), 2.00 (s, 1H).

Example 465: (R)-5-(3-Benzylphenyl)-4-oxo-N-(piperidin-3-yl)-4,5-dihydro-3H-1-thia-3,5,8-triazaacenaphthylene-2-carboxamide

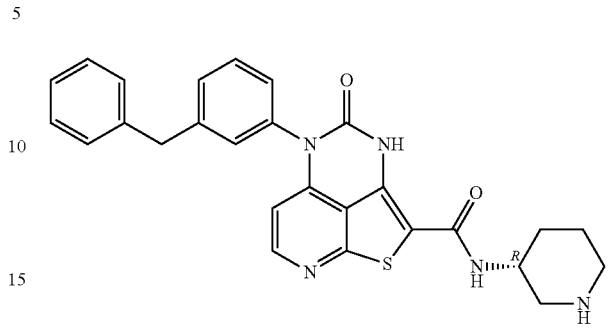

Step A: (R)-tert-butyl 3-(5-(3-benzylphenyl)-4-oxo-4,5-dihydro-3H-1-thia-3,5,8-triazaacenaphthylene-2-carboxamido)piperidine-1-carboxylate To a 2-5 mL Biotage microwave vial with a stir bar were added 3-benzylaniline (71.8 mg, 0.384 mmol), 2-chloro-4-iodonicotinonitrile (102 mg, 0.384 mmol), Pd(OAc)₂ (1.8 mg, 0.0080 mmol), DPEPhos (6.6 mg, 0.012 mmol), and Cs₂CO₃ (173 mg, 0.531 mmol). The vial was sealed, treated with dioxane (0.77 mL), evacuated and flushed with argon 4×, and stirred at 150° C. under argon for 30 min. The reaction was cooled to room temperature and was treated with tert-butyl (3R)-3-[(2-sulfanylacetyl)amino]piperidine-1-carboxylate (Intermediate 22) (0.49 M in dioxane, 0.79 mL, 0.39 mmol) via syringe. The vial was sealed and evacuated and flushed with argon 4×, and stirred at 150° C. for 15 min. The reaction was then cooled to room temperature, treated with solid CDI (252 mg, 1.55 mmol) in one portion under air, resealed and evacuated and flushed with argon 4×, and stirred at 150° C. for 15 min. The reaction was diluted with EtOAc (10 mL), and washed with 0.5 M citric acid and brine (2×8 mL) and 2 M K₂CO₃ (1×5 mL). The organic phase was dried over anhydrous Na₂SO₄, filtered, and concentrated to dryness. The residue was purified by normal phase flash column chromatography (SiO2) to give the title compound as a light-beige solid (122 mg, 54.5% yield).

Step B: (R)-5-(3-Benzylphenyl)-4-oxo-N-(piperidin-3-yl)-4,5-dihydro-3H-1-thia-3,5,8-triazaacenaphthylene-2-carboxamide A solution of (R)-tert-butyl 3-(5-(3-benzylphenyl)-4-oxo-4,5-dihydro-3H-1-thia-3,5,8-triazaacenaphthylene-2-carboxamido)piperidine-1-carboxylate (119.8 mg, 0.205 mmol) in dioxane (1.0 mL) was treated with HCl (3.97 M in dioxane, 2.55 mL, 10.1 mmol) in one portion at room temperature, and the resulting solution was stirred at room temperature for 1 h. The reaction was concentrated to dryness to give the title compound as a yellow powder (113.5 mg, 98.03% yield). MS (ESI): mass calcd. for C27H25N5O2S, 483.2; m/z found, 484.2 [M+H]⁺. 1H NMR (400 MHz, MeOH-d4) δ 8.44 (d, J=6.06 Hz, 1H), 7.56 (t, J=7.58 Hz, 1H), 7.45 (d, J=7.58 Hz, 1H), 7.16-7.33 (m, 7H), 6.32 (d, J=6.57 Hz, 1H), 4.24-4.33 (m, 1H), 4.08 (s, 2H), 3.54 (dd, J=4.04, 12.13 Hz, 1H), 3.33-3.39 (m, 1H), 2.93-3.03 (m, 2H), 2.04-2.14 (m, 2H), 1.72-1.91 (m, 2H).

Example 466: (R)-4-Oxo-5-(3-phenoxyphenyl)-N-(piperidin-3-yl)-4,5-dihydro-3H-1-thia-3,5,8-triazaacenaphthylene-2-carboxamide

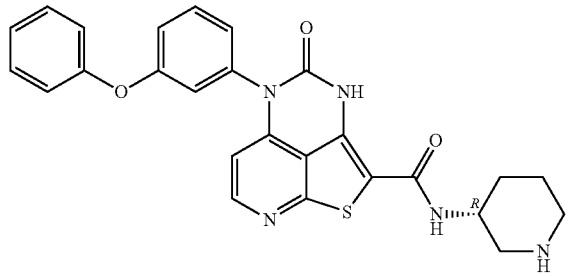

Step A: (R)-tert-Butyl 3-(4-oxo-5-(3-phenoxyphenyl)-4,5-dihydro-3H-1-thia-3,5,8-triazaacenaphthylene-2-carboxamido)piperidine-1-carboxylate To a 2-5 mL Biotage microwave vial with a stir bar were added 3-phenoxyaniline (82.8 mg, 0.447 mmol), 2-chloro-4-iodonicotinonitrile (117 mg, 0.443 mmol), Pd(OAc)$_2$ (2.1 mg, 0.0094 mmol), DPEPhos (7.3 mg, 0.014 mmol), and Cs$_2$CO$_3$ (201 mg, 0.617 mmol). The vial was sealed, treated with dioxane (0.89 mL), evacuated and flushed with argon 4×, and stirred at 150° C. under argon for 30 min. The reaction was cooled to room temperature and was treated with tert-butyl (3R)-3-[(2-sulfanylacetyl)amino]piperidine-1-carboxylate (Intermediate 22) (0.49 M in dioxane, 0.91 mL, 0.45 mmol) via syringe. The vial was sealed and evacuated and flushed with argon 4×, and stirred at 150° C. for 15 min. The reaction was then cooled to room temperature, treated with solid CDI (252 mg, 1.55 mmol) in one portion under air, resealed and evacuated and flushed with argon 4×, and stirred at 150° C. for 15 min. The reaction was diluted with EtOAc (10 mL), and washed with 0.5 M citric acid and brine (2×8 mL) and 2 M K$_2$CO$_3$ (1×5 mL). The organic phase was dried over anhydrous Na$_2$SO$_4$, filtered, and concentrated to dryness. The residue was purified by normal phase flash column chromatography (SiO$_2$) to give the title compound as a light-beige solid (168 mg, 64.7% yield).

Step B: (R)-4-Oxo-5-(3-phenoxyphenyl)-N-(piperidin-3-yl)-4,5-dihydro-3H-1-thia-3,5,8-triazaacenaphthylene-2-carboxamide A solution of ((R)-tert-butyl 3-(4-oxo-5-(3-phenoxyphenyl)-4,5-dihydro-3H-1-thia-3,5,8-triazaacenaphthylene-2-carboxamido)piperidine-1-carboxylate (168 mg, 0.287 mmol) in dioxane (1.4 mL) was treated with HCl (3.97 M in dioxane, 3.60 mL, 14.3 mmol) in one portion at room temperature, and the resulting solution was stirred at room temperature for 1 h. The reaction was concentrated to dryness to give the title compound as a yellow powder (143.5 mg, 85.71% yield). MS (ESI): mass calcd. for C$_{26}$H$_{23}$N$_5$O$_3$S, 485.2; m/z found, 486.1 [M+H]$^+$. 1H NMR (400 MHz, MeOH-d4) δ 8.47 (d, J=6.06 Hz, 1H), 7.61 (t, J=8.08 Hz, 1H), 7.39 (t, J=8.08 Hz, 2H), 7.07-7.22 (m, 6H), 6.43 (d, J=6.57 Hz, 1H), 4.23-4.32 (m, 1H), 3.49-3.59 (m, 1H), 3.34-3.40 (m, 1H), 2.91-3.03 (m, 2H), 2.00-2.12 (m, 2H), 1.71-1.91 (m, 2H).

Example 467: N-((3R,5S)-5-Methoxypiperidin-3-yl)-5-(*S)-(2-methyl-4-phenoxyphenyl)-4-oxo-4,5-dihydro-3H-1-thia-3,5,8-triazaacenaphthylene-2-carboxamide


A chiral purification was performed on N-((3R,5S)-5-Methoxypiperidin-3-yl)-5-(2-methyl-4-phenoxyphenyl)-4-oxo-4,5-dihydro-3H-1-thia-3,5,8-triazaacenaphthylene-2-carboxamide (Example 268, 868 mg) via chiral SFC (Stationary phase: CHIRALCEL OD-H 5 m 250×20 mm, Mobile phase: 55% CO$_2$, 45% MeOH) to give the title compound (as the *S atropisomer; 4 mg, 0.5% yield). MS (ESI): mass calcd. for C$_{28}$H$_{27}$N$_5$O$_4$S, 529.6; m/z found, 529.2 [M+H]$^+$. $^1$H NMR (600 MHz, CDCl$_3$): δ 8.34 (d, J=5.5 Hz, 1H), 7.52-7.34 (m, 3H), 7.21-7.06 (m, 4H), 7.05-6.90 (m, 2H), 6.00 (d, J=5.5 Hz, 1H), 4.26 (s, 1H), 3.60-3.40 (m, 4H), 3.36-3.12 (m, 1H), 2.89 (dd, J=73.7, 13.7 Hz, 2H), 2.21-2.03 (m, 4H), 1.92 (d, J=14.6 Hz, 1H), 1.25 (s, 3H).

Example 468: N-((3R,5S)-5-Methoxypiperidin-3-yl)-5-(*R)-(2-methyl-4-phenoxyphenyl)-4-oxo-4,5-dihydro-3H-1-thia-3,5,8-triazaacenaphthylene-2-carboxamide

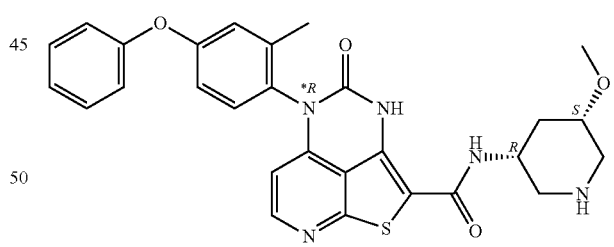

A chiral purification was performed on N-((3R,5S)-5-Methoxypiperidin-3-yl)-5-(2-methyl-4-phenoxyphenyl)-4-oxo-4,5-dihydro-3H-1-thia-3,5,8-triazaacenaphthylene-2-carboxamide (Example 268, 868 mg) via chiral SFC (Stationary phase: CHIRALCEL OD-H 5 m 250×20 mm, Mobile phase: 55% CO$_2$, 45% MeOH) to give the title compound (as the *R atropisomer; 4 mg, 0.5% yield). MS (ESI): mass calcd. for C$_{28}$H$_{27}$N$_5$O$_4$S, 529.6; m/z found, 529.2 [M+H]$^+$. $^1$H NMR (600 MHz, CDCl$_3$): δ 8.35 (d, J=5.6 Hz, 1H), 7.42-7.38 (m, 2H), 7.24-6.90 (m, 8H), 6.00 (s, 1H), 4.20-4.08 (m, 1H), 3.53-3.35 (m, 5H), 3.26-3.00 (m, 1H), 2.95-2.71 (m, 2H), 2.16-1.86 (m, 6H).

Example 469: (*S)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide

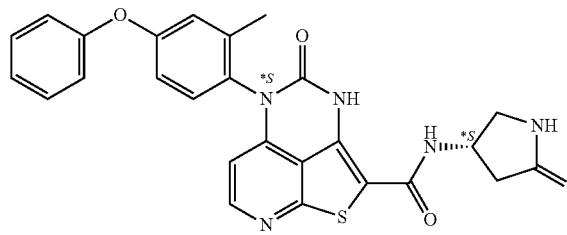

A chiral purification was performed on 5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide (Example 202, 818 mg) via chiral SFC (Stationary phase: CHIRALCEL OJ-H 5 m 250×20 mm, Mobile phase: 55% $CO_2$, 45% MeOH) and a and a second purification (30 mg from fraction 2, first purification) was performed via chiral SFC (Stationary phase: CHIRALCEL OJ-H 5 m 250×20 mm, Mobile phase: 70% $CO_2$, 30% EtOH) to give the title compound (as the *S atropisomer; 10 mg, 1.2% yield). MS (ESI): mass calcd. for $C_{26}H_{21}N_5O_4S$, 499.5; m/z found, 499.1 $[M+H]^+$. $^1H$ NMR (600 MHz, $CDCl_3$): δ 9.95 (s, 1H), 8.35 (d, J=5.4 Hz, 1H), 7.46-7.33 (m, 2H), 7.26-6.85 (m, 7H), 6.57 (s, 1H), 6.00 (d, J=5.5 Hz, 1H), 4.93-4.81 (m, 1H), 3.90-3.73 (m, 1H), 3.43 (dd, J=10.5, 2.6 Hz, 1H), 2.91-2.78 (m, 1H), 2.57 (dd, J=17.3, 3.2 Hz, 1H), 2.14 (s, 3H).

Example 470: (*S)-5-(*R)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide

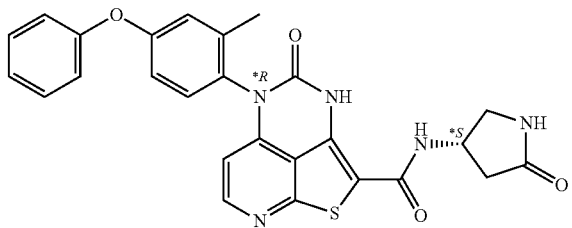 [SMILES: Cc1cc(Oc2ccccc2)ccc1N1C(=O)Nc2c(C(=O)N[C@@H]3CNC(=O)C3)sc3nccc1c23]

A chiral purification was performed on 5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide (Example 202, 818 mg) via chiral SFC (Stationary phase: CHIRALCEL OJ-H 5 m 250×20 mm, Mobile phase: 55% $CO_2$, 45% MeOH) and a and a second purification (30 mg from fraction 2, first purification) was performed via chiral SFC (Stationary phase: CHIRALCEL OJ-H 5 m 250×20 mm, Mobile phase: 70% $CO_2$, 30% EtOH) to give the title compound (as the *R atropisomer; 10 mg, 1.2% yield). MS (ESI): mass calcd. for $C_{26}H_{21}N_5O_4S$, 499.5; m/z found, 499.1 $[M+H]^+$. $^1H$ NMR (600 MHz, $CDCl_3$): δ 10.07 (s, 1H), 8.34 (d, J=5.5 Hz, 1H), 7.48-7.31 (m, 2H), 7.24-6.89 (m, 7H), 6.71 (s, 1H), 5.99 (d, J=5.3 Hz, 1H), 4.85 (s, 1H), 3.81 (dd, J=10.6, 5.9 Hz, 1H), 3.45 (d, J=10.7 Hz, 1H), 2.94-2.68 (m, 1H), 2.60 (d, J=17.2 Hz, 1H), 2.13 (s, 3H).

Example 471: (*R)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide

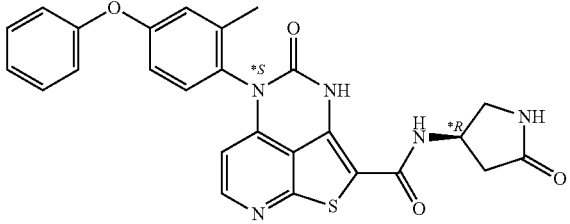

A chiral purification was performed on 5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide (Example 202, 818 mg) via chiral SFC (Stationary phase: CHIRALCEL OJ-H 5 m 250×20 mm, Mobile phase: 55% $CO_2$, 45% MeOH) to give the title compound (as the *S atropisomer; 16 mg, 2.0% yield). MS (ESI): mass calcd. for $C_{26}H_{21}N_5O_4S$, 499.5; m/z found, 499.1 $[M+H]^+$. 1H NMR (600 MHz, Chloroform-d) δ 8.34 (d, J=5.5 Hz, 1H), 7.49-7.34 (m, 2H), 7.24-6.85 (m, 7H), 6.61-6.46 (m, 1H), 6.01-5.90 (m, 1H), 4.85 (s, 1H), 3.92-3.75 (m, 1H), 3.50-3.36 (m, 1H), 2.90-2.76 (m, 1H), 2.56 (d, J=17.2 Hz, 1H), 2.13 (s, 3H).

Example 472: (*R)-5-(*R)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide

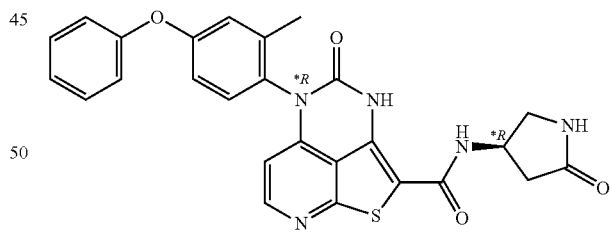

A chiral purification was performed on 5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide (Example 202, 818 mg) via chiral SFC (Stationary phase: CHIRALCEL OJ-H 5 m 250×20 mm, Mobile phase: 55% $CO_2$, 45% MeOH) to give the title compound (as the *R atropisomer; 17 mg, 2.1% yield). MS (ESI): mass calcd. for $C_{26}H_{21}N_5O_4S$, 499.5; m/z found, 499.1 $[M+H]^+$. $^1H$ NMR (600 MHz, $CDCl_3$): δ 10.03 (s, 1H), 8.32 (s, 1H), 7.47-7.29 (m, 3H), 7.21-6.66 (m, 7H), 5.97 (s, 1H), 4.84 (s, 1H), 3.93-3.65 (m, 1H), 3.50-3.28 (m, 1H), 2.79 (s, 1H), 2.59 (d, J=17.2 Hz, 1H), 2.12 (s, 3H).

Example 473: (R,*E)-N-(1-(But-2-enoyl)piperidin-3-yl)-5-(*S)-(2-methyl-4-phenoxyphenl)-4-oxo-4,5-dihydro-3H-1-thia-3,5,8-triazaacenaphthylene-2-carboxamide

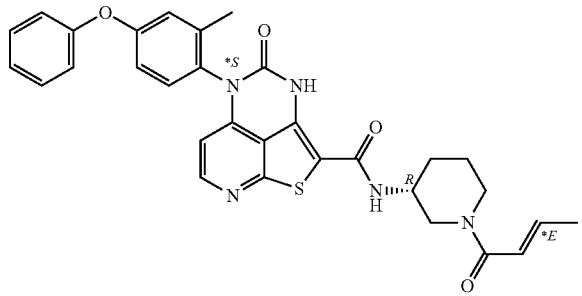

Step A: (R,ZE)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide The title compound was prepared as in Example 116 to yield the title compound.

Step B: (R,*E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide A chiral purification was performed on (R,ZE)-N-(1-(but-2-enoyl)piperidin-3-yl)-5-(2-methyl-4-phenoxyphenyl)-4-oxo-4,5-dihydro-3H-1-thia-3,5,8-triazaacenaphthylene-2-carboxamide (930 mg) via chiral SFC (Stationary phase: CHIRALCEL OD-H 5 μm 250×20 mm, Mobile phase: 55% $CO_2$, 45% MeOH) and a second purification (11 mg from fraction 2, first purification) was performed via chiral SFC (Stationary phase: CHIRALPAK AD-H 5 μm 250×20 mm, Mobile phase: 40% $CO_2$, 60% MeOH) to give the title compound (as the *E isomer and the *S atropisomer; 2 mg, 0.2% yield). MS (ESI): mass calcd. for $C_{31}H_{29}N_5O_4S$, 567.7; m/z found, 567.2 $[M+H]^+$. 1H NMR (600 MHz, Chloroform-d) δ 9.46 (s, 1H), 8.43-8.25 (m, 1H), 7.48-7.34 (m, 2H), 7.23-7.13 (m, 2H), 7.13-7.06 (m, 2H), 7.01 (s, 1H), 6.96 (dd, J=8.5, 2.8 Hz, 1H), 6.53-5.98 (m, 3H), 4.38-3.23 (m, 2H), 2.13 (s, 4H), 1.91 (s, 3H), 1.25 (s, 6H).

Example 474: (R,*E)-N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

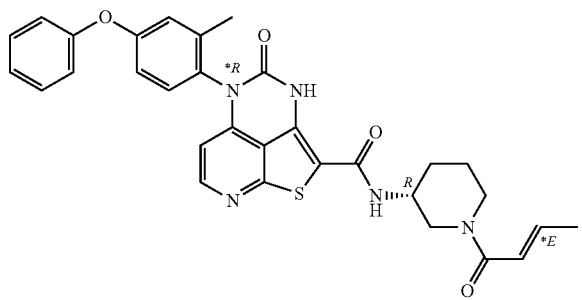

Step A: (R,ZE)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide The title compound was prepared as in Example 116 to yield the title compound.

Step B: (R,*E)-N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide A chiral purification was performed on (R,ZE)-N-(1-(but-2-enoyl)piperidin-3-yl)-5-(2-methyl-4-phenoxyphenyl)-4-oxo-4,5-dihydro-3H-1-thia-3,5,8-triazaacenaphthylene-2-carboxamide (930 mg) via chiral SFC (Stationary phase: CHIRALCEL OD-H 5 μm 250×20 mm, Mobile phase: 55% $CO_2$, 45% MeOH) to give the title compound (as the *E isomer and the *R atropisomer; 7 mg, 0.8% yield). MS (ESI): mass calcd. for $C_{31}H_{29}N_5O_4S$, 567.7; m/z found, 567.2 $[M+H]^+$. $^1H$ NMR (600 MHz, $CDCl_3$): δ 5.46 (d, J=7.3 Hz, 0H), 4.28-3.12 (m, 5H), 2.21-1.77 (m, 6H), 1.25 (s, 3H), 5.45-5.39 (m, OH), 9.48 (s, 1H), 8.36 (dd, J=11.1, 5.5 Hz, 1H), 7.48-7.32 (m, 2H), 7.24-6.86 (m, 7H), 6.31-5.95 (m, 3H).

Example 475: (R,*Z)—N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

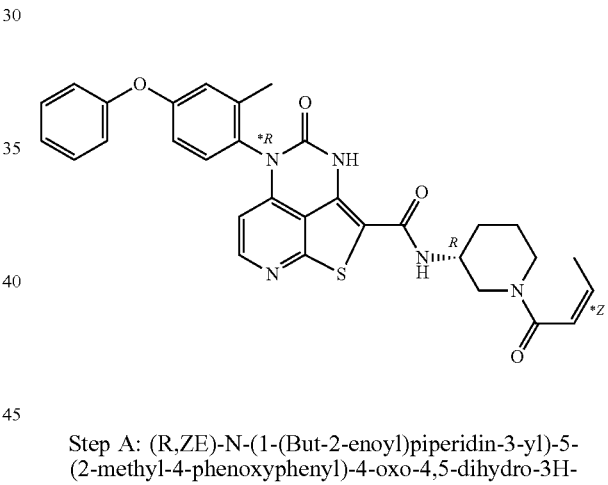

Step A: (R,ZE)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide The title compound was prepared as in Example 116 to yield the title compound.

Step B: (R,*Z)—N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide A chiral purification was performed on (R,ZE)-N-(1-(but-2-enoyl)piperidin-3-yl)-5-(2-methyl-4-phenoxyphenyl)-4-oxo-4,5-dihydro-3H-1-thia-3,5,8-triazaacenaphthylene-2-carboxamide (930 mg) via chiral SFC (Stationary phase: CHIRALCEL OD-H 5 m 250×20 mm, Mobile phase: 55% $CO_2$, 45% MeOH) and a second purification (11 mg from fraction 2, first purification) was performed via chiral SFC (Stationary phase: CHIRALPAK AD-H 5 m 250×20 mm, Mobile phase: 40% $CO_2$, 60% MeOH) to give the title compound (as the *Z isomer and the *R atropisomer; 4 mg, 0.4% yield). MS (ESI): mass calcd. for $C_{31}H_{29}N_5O_4S$, 567.7; m/z found, 567.2 [M+H]⁺. 1H NMR (600 MHz, Chloroform-d) δ 9.46 (s, 1H), 8.44-8.31 (m, 1H), 7.48-7.37 (m, 2H), 7.23-6.87 (m, 6H), 6.32-5.38 (m, 4H), 4.22-3.15 (m, 5H), 2.22-1.55 (m, 8H), 1.44-0.99 (m, 2H).

Example 476: (R,*Z)—N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

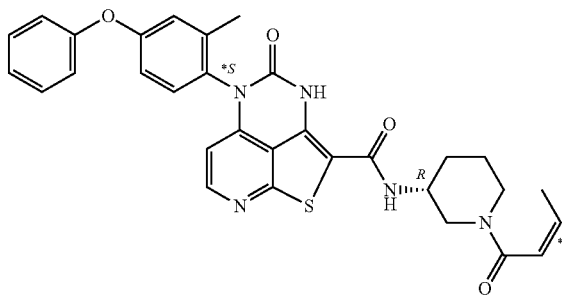

Step A: (R,ZE)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide The title compound was prepared as in Example 116 to yield the title compound.

Step B: (R,*Z)—N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide A chiral purification was performed on (R,ZE)-N-(1-(but-2-enoyl)piperidin-3-yl)-5-(2-methyl-4-phenoxyphenyl)-4-oxo-4,5-dihydro-3H-1-thia-3,5,8-triazaacenaphthylene-2-carboxamide (930 mg) via chiral SFC (Stationary phase: CHIRALCEL OD-H 5 μm 250×20 mm, Mobile phase: 55% CO₂, 45% MeOH) to give the title compound (as the *Z isomer and the *S atropisomer; 4 mg, 0.4% yield). MS (ESI): mass calcd. for $C_{31}H_{29}N_5O_4S$, 567.7; m/z found, 567.2 [M+H]⁺. ¹H NMR (600 MHz, CDCl₃): δ 9.47 (s, 1H), 8.36 (s, 1H), 7.47-7.34 (m, 2H), 7.22-6.84 (m, 7H), 6.43-6.23 (m, 1H), 6.10-5.79 (m, 1H), 4.52-3.22 (m, 6H), 2.22-1.65 (m, 6H), 1.45-0.93 (m, 4H).

Example 477: (R,*Z)—N-(1-(2-Cyano-4-ethoxy-4-methylpent-2-enoyl)piperidin-3-yl)-5-(*S)-(2-methyl-4-phenoxyphenl)-4-oxo-4,5-dihydro-3H-1-thia-3,5,8-triazaacenaphthylene-2-carboxamide

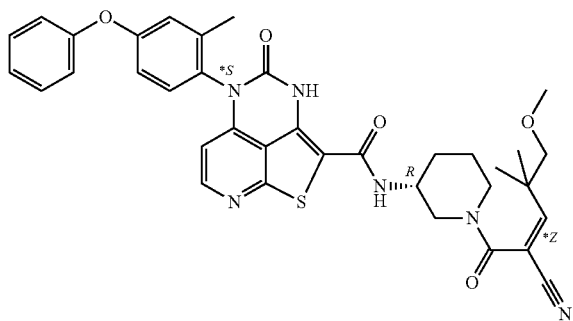

A chiral purification was performed on (R,EZ)—N-(1-(2-cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 29; 1089 mg) via chiral SFC (Stationary phase: CHIRALCEL OD-H 5 μm 250×20 mm, Mobile phase: 55% CO₂, 45% mixture of MeOH/iPrOH, 50/50, v/v) and a second purification (55 mg from fraction 3, first purification) was performed via chiral SFC (Stationary phase: CHIRALCEL OJ-H 5 m 250×20 mm, Mobile phase: 75% CO₂, 25% iPrOH) to give the title compound (as the *Z isomer and the *S atropisomer; 6 mg, 0.6% yield). MS (ESI): mass calcd. for $C_{36}H_{36}N_6O_5S$, 664.8; m/z found, 664.3 [M+H]⁺. ¹H NMR (600 MHz, CDCl₃): δ 9.48 (s, 1H), 8.36 (dd, J=5.3, 0.9 Hz, 1H), 7.48-7.36 (m, 2H), 7.22-6.92 (m, 6H), 6.56 (d, J=7.7 Hz, 1H), 6.02 (dd, J=5.5, 1.6 Hz, 1H), 5.77-5.54 (m, 1H), 4.28-4.13 (m, 1H), 4.08-3.57 (m, 1H), 3.57-3.30 (m, 3H), 2.19-2.10 (m, 3H), 2.11-1.65 (m, 2H), 1.65-1.54 (m, 4H), 1.51-1.27 (m, 5H), 1.23-1.19 (m, 1H), 1.16 (dt, J=19.0, 6.9 Hz, 3H).

Example 478: (R,*E)-N-(1-(2-Cyano-4-ethoxy-4-methylpent-2-enoyl)piperidin-3-yl)-5-(*)-(2-methyl-4-phenoxyphenyl)-4-oxo-4,5-dihydro-3H-1-thia-3,5,8-triazaacenaphthylene-2-carboxamide

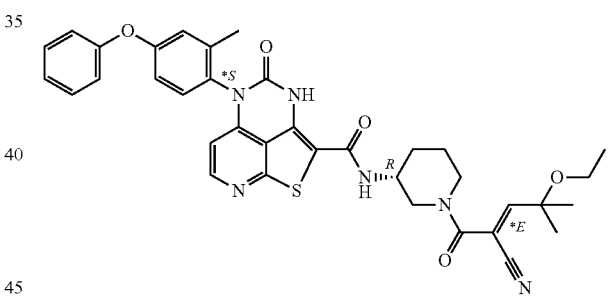

A chiral purification was performed on (R,EZ)—N-(1-(2-cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 29; 1089 mg) via chiral SFC (Stationary phase: CHIRALCEL OD-H 5 μm 250×20 mm, Mobile phase: 55% CO₂, 45% mixture of MeOH/iPrOH, 50/50, v/v) and a second purification (55 mg from fraction 3, first purification) was performed via chiral SFC (Stationary phase: CHIRALCEL OJ-H 5 μm 250×20 mm, Mobile phase: 75% CO₂, 25% iPrOH) to give the title compound (as the *E isomer and the *S atropisomer; 25 mg, 2.3% yield). MS (ESI): mass calcd. for $C_{36}H_{36}N_6O_5S$, 664.8; m/z found, 664.3 [M+H]⁺. ¹H NMR (600 MHz, CDCl₃): δ 9.44 (s, 1H), 8.36 (d, J=5.4 Hz, 1H), 7.46-7.34 (m, 2H), 7.23-6.90 (m, 6H), 6.10-5.53 (m, 2H), 4.23-4.07 (m, 1H), 4.02-3.78 (m, 1H), 3.69-3.30 (m, 5H), 2.14 (s, 3H), 2.10-1.91 (m, 2H), 1.91-1.63 (m, 4H), 1.57-1.39 (m, 4H), 1.28-1.24 (m, 4H).

Example 479: (R,*Z)—N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

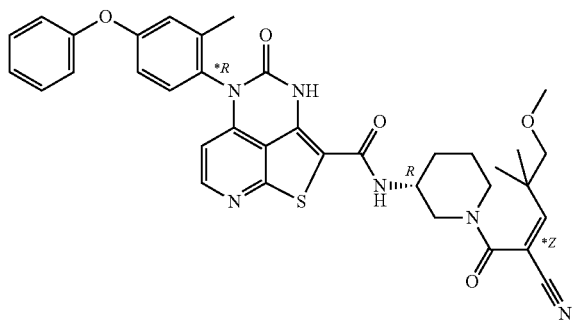

A chiral purification was performed on (R,EZ)—N-(1-(2-cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 29; 1089 mg) via chiral SFC (Stationary phase: CHIRALCEL OD-H 5 μm 250×20 mm, Mobile phase: 55% CO$_2$, 45% mixture of MeOH/iPrOH, 50/50, v/v) and a second purification (56 mg from fraction 2, first purification) was performed via chiral SFC (Stationary phase: CHIRALCEL OJ-H 5 μm 250×20 mm, Mobile phase: 75% CO$_2$, 25% iPrOH) to give the title compound (as the *Z isomer and the *R atropisomer; 6 mg, 0.6% yield). MS (ESI): mass calcd. for C$_{36}$H$_{36}$N$_6$O$_5$S, 664.8; m/z found, 664.3 [M+H]$^+$. $^1$H NMR (600 MHz, CDCl$_3$): δ 9.49 (s, 1H), 8.36 (d, J=5.5 Hz, 1H), 7.50-7.38 (m, 2H), 7.23-6.91 (m, 6H), 6.60-6.47 (m, 1H), 6.02 (d, J=5.5 Hz, 1H), 5.79-5.53 (m, 1H), 4.32-3.30 (m, 5H), 2.21-1.54 (m, 10H), 1.42-1.34 (m, 5H), 1.21-1.07 (m, 3H).

Example 480: (R,*E)-N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide

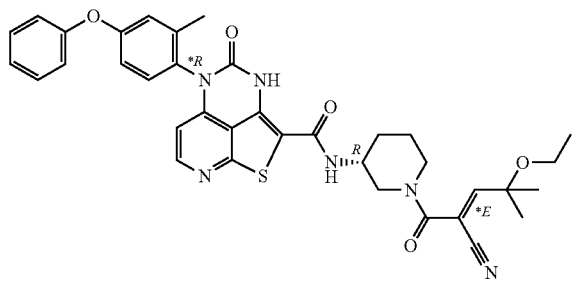

A chiral purification was performed on (R,EZ)—N-(1-(2-cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide (Example 29; 1089 mg) via chiral SFC (Stationary phase: CHIRALCEL OD-H 5 μm 250×20 mm, Mobile phase: 55% CO$_2$, 45% mixture of MeOH/iPrOH, 50/50, v/v) and a second purification (56 mg from fraction 2, first purification) was performed via chiral SFC (Stationary phase: CHIRALCEL OJ-H 5 μm 250×20 mm, Mobile phase: 75% CO$_2$, 25% iPrOH) to give the title compound (as the *E isomer and the *R atropisomer; 26 mg, 2.4% yield). MS (ESI): mass calcd. for C$_{36}$H$_{36}$N$_6$O$_5$S, 664.8; m/z found, 664.3 [M+H]$^+$. $^1$H NMR (600 MHz, CDCl$_3$): δ 9.44 (s, 1H), 8.37 (d, J=5.5 Hz, 1H), 7.46-7.35 (m, 2H), 7.24-6.87 (m, 7H), 6.03 (d, J=5.5 Hz, 2H), 4.39-3.08 (m, 5H), 2.23-1.57 (m, 8H), 1.55-1.05 (m, 10H).

Example 481: N-((3R,5R)-1-Acryl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide

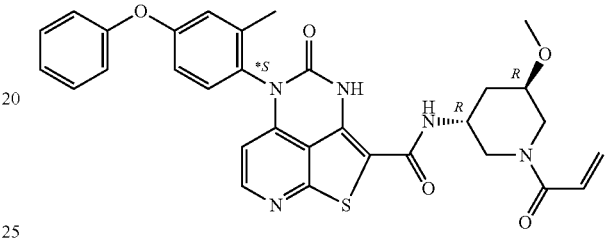

The title compound was prepared in a manner analogous to Method 1, steps G-I in Example 1, and using 5-(*S)-(2-methyl-4-phenoxyphenyl)-4-oxo-4,5-dihydro-3H-1-thia-3,5,8-triazaacenaphthylene-2-carboxylic acid (Intermediate 16) and tert-butyl (3R,5R)-3-amino-5-methoxypiperidine-1-carboxylate (Intermediate 6) in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for C$_{31}$H$_{29}$N$_5$O$_5$S, 583.7; m/z found, 584.5 [M+H]$^+$. $^1$H NMR (400 MHz, CD$_3$OD): δ 8.29 (d, J=5.5 Hz, 1H), 7.42-7.35 (m, 2H), 7.34-7.29 (m, 1H), 7.19-7.12 (m, 1H), 7.11-6.91 (m, 4H), 6.85-6.69 (m, 1H), 6.22-6.13 (m, 1H), 6.03 (d, J=5.6 Hz, 1H), 5.76-5.65 (m, 1H), 4.70-4.50 (m, 1H), 4.32-4.07 (m, 2H), 3.72-3.56 (m, 1H), 3.38-3.33 (m, 3H), 3.26-2.65 (m, 2H), 2.28-2.12 (m, 1H), 2.10 (s, 3H), 1.97-1.69 (m, 1H).

Example 482: N-((3R,5S)-1-Acryloyl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide

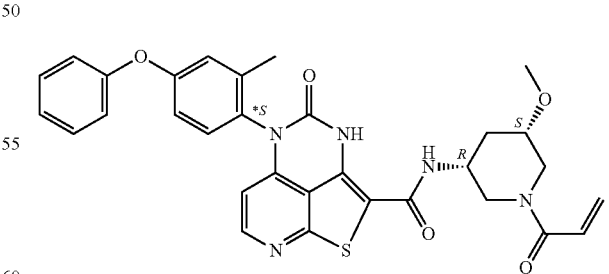

The title compound was prepared in a manner analogous to Method 1, steps G-I in Example 1, and using 5-(*S)-(2-methyl-4-phenoxyphenyl)-4-oxo-4,5-dihydro-3H-1-thia-3,5,8-triazaacenaphthylene-2-carboxylic acid (Intermediate 16) and tert-butyl (3R,5S)-3-amino-5-methoxypiperidine-1-carboxylate (Intermediate 29) in place of 5-(2-methyl-4- phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{31}H_{29}N_5O_5S$, 583.7; m/z found, 584.2 [M+H]$^+$. $^1$H NMR (400 MHz, CD$_3$OD): δ 8.39-8.29 (m, 1H), 7.47-7.36 (m, 2H), 7.30-7.27 (m, 1H), 7.20-7.15 (m, 1H), 7.12-7.03 (m, 3H), 7.02-6.93 (m, 1H), 6.85-6.60 (m, 1H), 6.17-6.05 (m, 2H), 5.79-5.60 (m, 1H), 4.44-4.26 (m, 1H), 4.23-4.12 (m, 1H), 4.03-3.92 (m, 1H), 3.68-3.55 (m, 2H), 3.53-3.45 (m, 3H), 3.44-3.35 (m, 1H), 2.17-2.09 (m, 4H), 2.02-1.96 (m, 1H).

Example 483: N-((3R,5R)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide

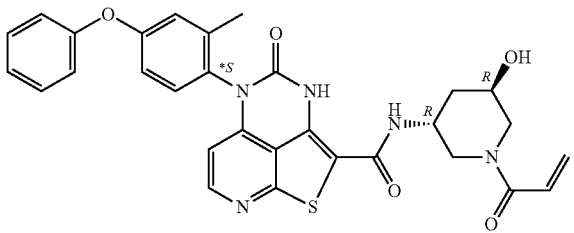

The title compound was prepared in a manner analogous to Method 1, steps G-I in Example 1, and using 5-(*S)-(2-methyl-4-phenoxyphenyl)-4-oxo-4,5-dihydro-3H-1-thia-3,5,8-triazaacenaphthylene-2-carboxylic acid (Intermediate 16) and tert-butyl (3R,5R)-3-amino-5-hydroxypiperidine-1-carboxylate (Intermediate 4) in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{30}H_{27}N_5O_5S$, 569.6; m/z found, 570.5 [M+H]$^+$. $^1$H NMR (400 MHz, CD$_3$OD): δ 8.30 (d, J=5.5 Hz, 1H), 7.46-7.36 (m, 2H), 7.32-7.26 (m, 1H), 7.21-7.13 (m, 1H), 7.12-7.03 (m, 3H), 7.00-6.92 (m, 1H), 6.85-6.68 (m, 1H), 6.26-6.12 (m, 1H), 6.05 (d, J=5.6 Hz, 1H), 5.78-5.66 (m, 1H), 4.59-4.54 (m, 1H), 4.44-4.32 (m, 1H), 4.16-4.02 (m, 2H), 3.96-3.87 (m, 0.5H), 3.38-3.33 (m, 1H), 2.95-2.83 (m, 0.5H), 2.11 (s, 3H), 2.07-1.84 (m, 2H).

Example 484: N-((3R,5S)-1-Acryloyl-5-fluoropiperidin-3-yl)-5-(*S)-(2-meth phenoxyphenyl)-4-oxo-4,5-dihydro-3H-1-thia-3,5,8-triazaacenaphthylene-2-carboxamide

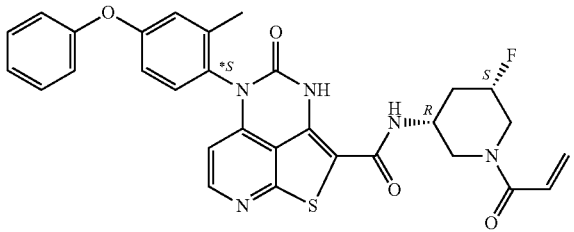

The title compound was prepared in a manner analogous to Method 1, steps G-I in Example 1, and using 5-(*S)-(2-methyl-4-phenoxyphenyl)-4-oxo-4,5-dihydro-3H-1-thia-3, 5,8-triazaacenaphthylene-2-carboxylic acid (Intermediate 16) and tert-butyl (3R,5S)-3-amino-5-fluoropiperidine-1-carboxylate (Intermediate 3) in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{30}H_{26}FN_5O_4S$, 571.6; m/z found, 572.4 [M+H]$^+$. $^1$H NMR (400 MHz, CD$_3$OD): δ 8.30 (d, J=5.5 Hz, 1H), 7.43-7.35 (m, 2H), 7.30 (d, J=8.6 Hz, 1H), 7.19-7.11 (m, 1H), 7.10-7.01 (m, 3H), 6.87-6.63 (m, 1H), 6.88-6.63 (m, 1H), 6.27-6.14 (m, 1H), 6.04 (d, J=5.5 Hz, 1H), 5.81-5.66 (m, 1H), 5.08-4.85 (m, 1H), 4.75-4.63 (m, 1H), 4.35-4.16 (m, 2H), 3.15-2.64 (m, 2H), 2.43-2.21 (m, 1H), 2.10 (s, 3H), 2.04-1.76 (m, 1H).

Example 485: N-(4-Cyano-1,4-oxazepan-6-yl)-5-(*S)-(2-methyl-4-phenoxyphenyl)-4-oxo-4,5-dihydro-3H-1-thia-3,5,8-triazaacenaphthylene-2-carboxamide

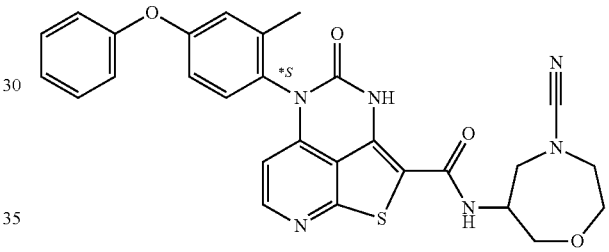

Step A: 5-(*)-(2-Methyl-4-phenoxyphenyl)-N-(1,4-oxazepan-6-yl)-4-oxo-4,5-dihydro-3H-1-thia-3,5,8-triazaacenaphthylene-2-carboxamide The title compound was prepared in a manner analogous to Method 1, steps A-H (including Chiral Resolution Method A after step F to obtain the *S atropisomer) in Example 1, and using tert-butyl 6-amino-1,4-oxazepane-4-carboxylate in place of tert-butyl (3R,5R)-3-amino-5-fluoropiperidine-1-carboxylate in step G, to yield the title compound (148 mg).

Step B: N-(4-Cyano-1,4-oxazepan-6-yl)-5-(*S)-(2-methyl-4-phenoxyphenyl)-4-oxo-4,5-dihydro-3H-1-thia-3,5,8-triazaacenaphthylene-2-carboxamide To a mixture of 5-(S)-(2-methyl-4-phenoxyphenyl)-N-(1, 4-oxazepan-6-yl)-4-oxo-4,5-dihydro-3H-1-thia-3,5,8-triazaacenaphthylene-2-carboxamide (123 mg, 0.239 mmol), triethylamine (49 mg, 0.48 mmol) in DCM (5 mL) was added BrCN (31 mg, 0.29 mmol) and was stirred at room temperature for 30 minutes. The mixture was concentrated to dryness and purified by flash column chromatography, and then by preparative TLC to yield the title compound (101 mg, 99.3% yield). MS (ESI): mass calcd. for $C_{28}H_{24}N_6O_4S$, 540.6; m/z found, 541.1 [M+H]$^+$. $^1$H NMR (400 MHz, DMSO-d$_6$): δ 10.22 (s, 1H), 8.34-8.29 (m, 1H), 8.17-8.10 (m, 1H), 7.45-7.39 (m, 2H), 7.37-7.33 (m, 1H), 7.20-7.15 (m, 1H), 7.12-7.08 (m, 2H), 7.08-7.05 (m, 1H), 6.97-6.94

(m, 1H), 5.98-5.94 (m, 1H), 4.35-4.25 (m, 1H), 3.90-3.82 (m, 1H), 3.81-3.65 (m, 3H), 3.57-3.50 (m, 1H), 3.40-3.32 (m, 3H), 2.04 (s, 3H).

Example 486: N-((3S,4S)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide

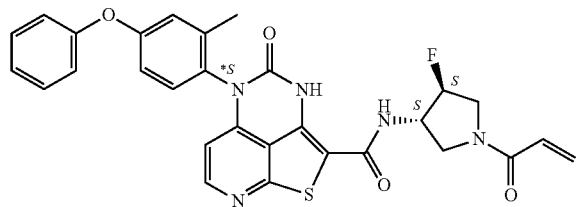

The title compound was prepared in a manner analogous to Method 1, steps A-I (including Chiral Resolution Method A after step F to obtain the *S atropisomer) in Example 1, and using tert-butyl (3S,4S)-3-amino-4-fluoro-pyrrolidine-1-carboxylate in place of tert-butyl (3R,5R)-3-amino-5-fluoro-piperidine-1-carboxylate in step G, to yield the title compound. MS (ESI): mass calcd. for $C_{29}H_{24}FN_5O_4S$, 557.6; m/z found, 558.5 [M+H]$^+$. $^1$H NMR (400 MHz, CD$_3$OD): δ 8.32 (d, J=5.6 Hz, 1H), 7.45-7.35 (m, 2H), 7.34-7.26 (m, 1H), 7.22-7.13 (m, 1H), 7.13-7.02 (m, 3H), 7.00-6.93 (m, 1H), 6.71-6.55 (m, 1H), 6.35-6.28 (m, 1H), 6.06 (d, J=5.6 Hz, 1H), 5.81-5.75 (m, 1H), 5.36-5.15 (m, 1H), 4.76-4.64 (m, 1H), 4.09-3.75 (m, 4H), 2.13-2.09 (m, 3H).

Example 487: (R,E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

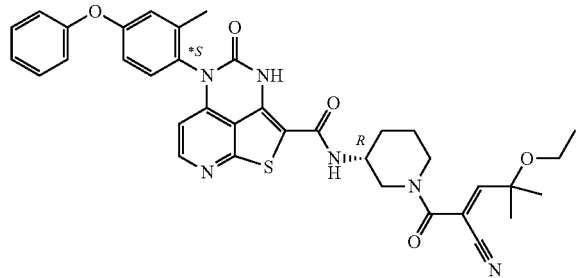

Step A: (R)—N-(1-(2-Cyanoacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 300 mg, 0.601 mmol), 2-cyanoacetic acid (102 mg, 1.20 mmol), HATU (297 mg, 0.780 mmol), and diisopropylethylamine (155 mg, 1.20 mmol) in DMF (5 mL) was stirred at rt for 1 h. The mixture was purified by flash column chromatography to yield the title compound as white solid (225 mg, 66.2% yield).

Step B: (R,E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide A solution of (R)—N-(1-(2-cyanoacetyl)piperidin-3-yl)-5-(1-(2-methyl-4-phenoxyphenyl)-4-oxo-4,5-dihydro-3H-1-thia-3,5,8-triazaacenaphthylene-2-carboxamide (70 mg, 0.12 mmol), 2-ethoxy-2-methyl-propanal (43 mg, 0.37 mmol), piperidine (0.3 mL), and ethanol (10 mL) was added to a flask and stirred at rt for 3 h. The mixture was concentrated to dryness and purified by flash column chromatography to yield the title compound as white solid (77 mg, 92% yield). MS (ESI): mass calcd. for $C_{36}H_{36}N_6O_5S$, 664.8; m/z found, 665.4 [M+H]$^+$. $^1$H NMR (400 MHz, CD$_3$OD): δ 8.33-8.26 (m, 1H), 7.42-7.35 (m, 2H), 7.35-7.28 (m, 1H), 7.19-7.12 (m, 1H), 7.10-7.01 (m, 3H), 7.01-6.93 (m, 1H), 6.91-6.83 (m, 1H), 6.07-6.01 (m, 1H), 4.48-3.81 (m, 3H), 3.59-3.34 (m, 3H), 3.24-2.86 (m, 1H), 2.15-1.99 (m, 4H), 1.96-1.84 (m, 1H), 1.83-1.58 (m, 2H), 1.50-1.32 (m, 6H), 1.25-1.11 (m, 3H).

Example 488: (R,E)-N-(1-(4-(Dimethylamino)but-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

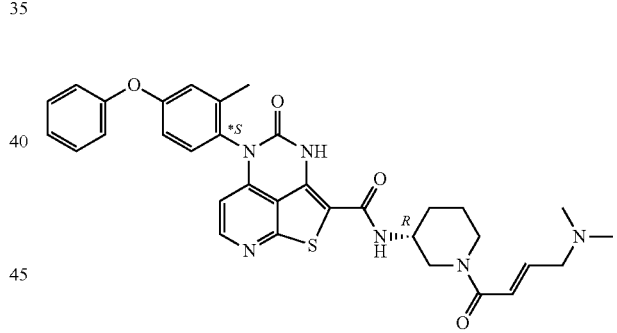

A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 90 mg, 0.18 mmol), (E)-4-(dimethylamino)but-2-enoic acid (46 mg, 0.36 mmol), HATU (89 mg, 0.23 mmol), and diisopropylethylamine (46 mg, 0.36 mmol) in DMF (5 mL) was stirred at rt for 1 h. The mixture was purified by flash column chromatography to yield the title compound as white solid (75 mg, 63% yield). MS (ESI): mass calcd. for $C_{33}H_{34}N_6O_4S$, 610.7; m/z found, 611.4 [M+H]$^+$. $^1$H NMR (400 MHz, CD$_3$OD): δ 8.44 (s, 1H), 8.34-8.28 (m, 1H), 7.43-7.34 (m, 2H), 7.34-7.27 (m, 1H), 7.20-7.11 (m, 1H), 7.11-7.01 (m, 3H), 7.01-6.91 (m, 1H), 6.89-6.79 (m, 1H), 6.76-6.62 (m, 1H), 6.10-6.01 (m, 1H), 4.38-3.85 (m, 3H), 3.77-3.63 (m, 2H), 3.24-3.10 (m, 1H), 2.99-2.83 (m, 1H), 2.76-2.63 (m, 6H), 2.16-2.00 (m, 4H), 1.92-1.81 (m, 1H), 1.81-1.65 (m, 1H), 1.65-1.48 (m, 1H).

Example 489: N-((3S,4R)-1-Acryloyl-4-hydroxy-pyrrolidin-3-yl)-5-(*S)-(2-methyl-4-phenoxyphenyl)-4-oxo-4,5-dihydro-3H-1-thia-3,5,8-triazaacenaphthylene-2-carboxamide

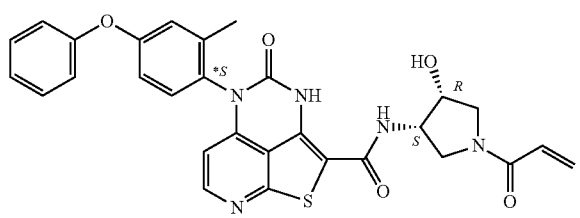

The title compound was prepared in a manner analogous to Method 1, steps A-I (including Chiral Resolution Method A after step F to obtain the *S atropisomer) in Example 1, and using tert-butyl (3S,4R)-3-amino-4-hydroxypyrrolidine-1-carboxylate (Intermediate 24) in place of tert-butyl (3R,5R)-3-amino-5-fluoro-piperidine-1-carboxylate in step G, to yield the title compound. MS (ESI): mass calcd. for $C_{29}H_{25}N_5O_5S$, 555.6; m/z found, 556.4 $[M+H]^+$. $^1$H NMR (400 MHz, CD$_3$OD): δ 8.29 (d, J=5.6 Hz, 1H), 7.43-7.36 (m, 2H), 7.34-7.27 (m, 1H), 7.19-7.13 (m, 1H), 7.11-7.03 (m, 3H), 7.01-6.93 (m, 1H), 6.67-6.50 (m, 1H), 6.32-6.22 (m, 1H), 6.04 (d, J=5.5 Hz, 1H), 5.79-5.69 (m, 1H), 4.66-4.39 (m, 2H), 4.07-3.50 (m, 4H), 2.10 (s, 3H).

Example 490: N-((3S,4S)-1-Acryloyl-4-methoxy-pyrrolidin-3-yl)-5-(*S)-(2-methyl-4-phenoxyphenyl)-4-oxo-4,5-dihydro-3H-1-thia-3,5,8-triazaacenaphthylene-2-carboxamide

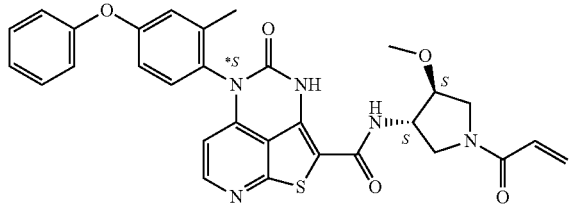

The title compound was prepared in a manner analogous to Method 1, steps A-I (including Chiral Resolution Method A after step F to obtain the *S atropisomer) in Example 1, and using tert-butyl (3S,4S)-3-amino-4-methoxy-pyrrolidine-1-carboxylate in place of tert-butyl (3R,5R)-3-amino-5-fluoro-piperidine-1-carboxylate in step G, to yield the title compound. MS (ESI): mass calcd. for $C_{30}H_{27}N_5O_5S$, 569.6; m/z found, 570.4 $[M+H]^+$. $^1$H NMR (400 MHz, CD$_3$OD): δ 8.38 (d, J=5.5 Hz, 1H), 7.53-7.42 (m, 2H), 7.39-7.31 (m, 1H), 7.26-7.20 (m, 1H), 7.17-7.08 (m, 3H), 7.08-6.98 (m, 1H), 6.76-6.57 (m, 1H), 6.39-6.28 (m, 1H), 6.12 (d, J=5.5 Hz, 1H), 5.86-5.76 (m, 1H), 4.69-4.62 (m, 1H), 4.13-3.93 (m, 2H), 3.92-3.66 (m, 3H), 3.57-3.50 (m, 3H), 2.17 (s, 3H).

Example 491: (R,E)-N-(1-(2-Cyano-3-cyclopropylacryloyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide

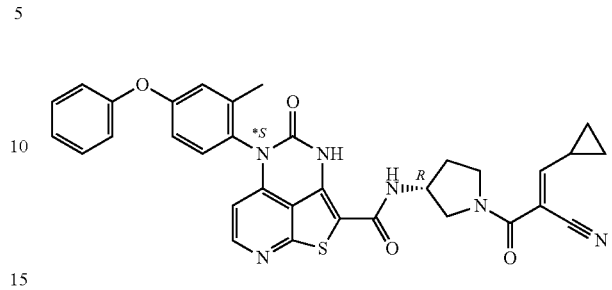

To a solution of (R)-5-(*S)-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36, 80 mg, 0.15 mmol) in DMF (3 mL) were added (E)-2-Cyano-3-cyclopropyl-prop-2-enoic acid (Intermediate 17) (32 mg, 0.23 mmol), HATU (70 mg, 0.18 mmol), and triethylamine (0.085 mL, 0.61 mmol). The reaction mixture was stirred at rt overnight, then purified using flash column chromatography to yield the title compound as a yellow solid (40 mg, 43% yield). MS (ESI): mass calcd. for $C_{33}H_{28}N_6O_4S$, 604.7; m/z found, 605.2 $[M+H]^+$. $^1$H NMR (400 MHz, DMSO-d$_6$ and CD$_3$OD): δ 8.27 (d, J=5.5 Hz, 1H), 7.42-7.32 (m, 2H), 7.30-7.21 (m, 1H), 7.17-7.07 (m, 1H), 7.07-7.01 (m, 2H), 7.01-6.99 (m, 1H), 6.94-6.88 (m, 1H), 6.74-6.65 (m, 1H), 5.97 (d, J=5.5 Hz, 1H), 4.58-4.47 (m, 1H), 4.09-3.99 (m, 1H), 3.95-3.77 (m, 1H), 3.75-3.67 (m, 1H), 3.64-3.56 (m, 1H), 3.52-3.41 (m, 1H), 2.22-2.12 (m, 1H), 2.04 (s, 3H), 1.96-1.88 (m, 1H), 1.20-1.14 (m, 2H), 0.90-0.83 (m, 2H).

Example 492: (R,E)-5-(*S)-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide

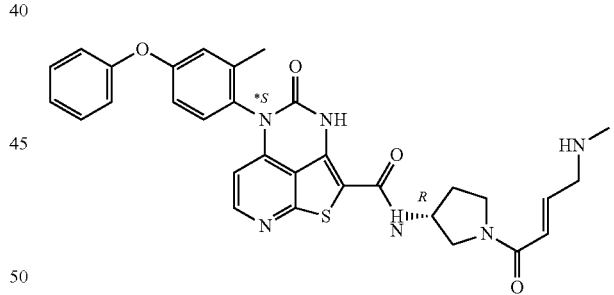

Step A: (R,E)-tert-Butyl methyl(4-(3-(5-(*S)-(2-methyl-4-phenoxyphenyl)-4-oxo-4,5-dihydro-3H-1-thia-3,5,8-triazaacenaphthylene-2-carboxamido)pyrrolidin-1-yl)-4-oxobut-2-en-1-yl)carbamate A solution of (R)-5-(*S)-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36, 90 mg, 0.19 mmol), (E)-4-[tert-butoxycarbonyl(methyl)amino]but-2-enoic acid (Intermediate 10, 80 mg, 0.37 mmol), HATU (91 mg, 0.24 mmol), and diisopropylethylamine (72 mg, 0.56 mmol) in DMF (5 mL) was stirred at rt for 1 h. The reaction mixture was purified by flash column chromatography to yield the title compound as white solid (98 mg, 79% yield).

Step B: (R,E)-5-(*S)-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide The reagents (R,E)-tert-butyl methyl(4-(3-(5-(*S)-(2-methyl-4-phenoxyphenyl)-4-oxo-4,5-dihydro-3H-1-thia-3,5,8-triazaacenaphthylene-2-carboxamido)pyrrolidin-1-yl)-4-oxobut-2-en-1-yl)carbamate (98 mg, 0.14 mmol), concentrated HCl (5 mL), and MeOH (5 mL) were added to a flask and stirred at rt for 1 h. The mixture was concentrated to dryness and the residue was purified by flash column chromatography to yield the title compound as white solid (64 mg, 71% yield). MS (ESI): mass calcd. for $C_{31}H_{30}N_6O_4S$, 582.7; m/z found, 583.4 [M+H]$^+$. $^1$H NMR (400 MHz, CD$_3$OD): δ 8.47 (s, 1H), 8.36-8.30 (m, 1H), 7.44-7.36 (m, 2H), 7.32-7.26 (m, 1H), 7.20-7.13 (m, 1H), 7.12-7.03 (m, 3H), 7.01-6.94 (m, 1H), 6.81-6.60 (m, 2H), 6.10-6.05 (m, 1H), 4.15-3.46 (m, 7H), 2.72-2.65 (m, 3H), 2.40-2.21 (m, 1H), 2.21-2.04 (m, 4H).

Example 493: (R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide

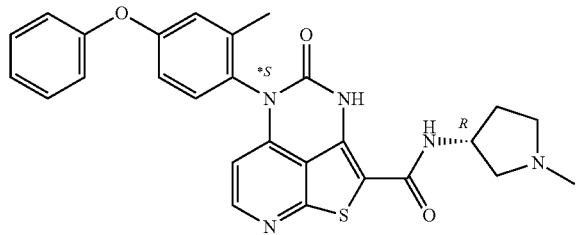

The title compound was prepared in a manner analogous to Method 1, steps A-G (including Chiral Resolution Method A after step F to obtain the *S atropisomer) in Example 1, and using (3R)-1-methylpyrrolidin-3-amine in place of tert-butyl (3R,5R)-3-amino-5-fluoro-piperidine-1-carboxylate in step G, to yield the title compound. MS (ESI): mass calcd. for $C_{27}H_{25}N_5O_3S$, 499.6; m/z found, 500.2 [M+H]$^+$. $^1$H NMR (400 MHz, CD$_3$OD): δ 8.49 (s, 1H), 8.32 (d, J=5.5 Hz, 1H), 7.46-7.36 (m, 2H), 7.32-7.26 (m, 1H), 7.20-7.14 (m, 1H), 7.13-7.03 (m, 3H), 7.00-6.94 (m, 1H), 6.07 (d, J=5.6 Hz, 1H), 4.66-4.53 (m, 1H), 3.68-3.55 (m, 1H), 3.52-3.42 (m, 2H), 3.26-3.15 (m, 1H), 2.89 (s, 3H), 2.6-2.46 (m, 1H), 2.29-2.17 (m, 1H), 2.10 (s, 3H).

Example 494: (R)-5-(*S)-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide

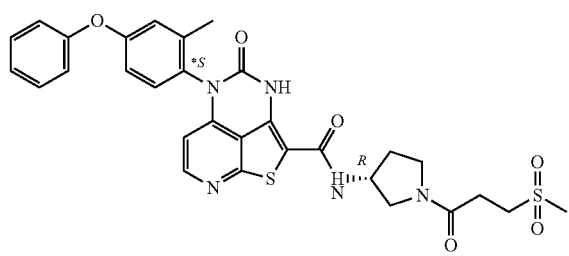

A solution of (R)-5-(*S)(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36, 100 mg, 0.19 mmol), 3-(methylsulfonyl)propanoic acid (29 mg, 0.19 mmol), HATU (146 mg, 0.384 mmol), and triethylamine (97 mg, 0.96 mmol) in DMF 3 mL) was stirred at rt for 2 h, then purified by flash column chromatography to yield the title compound as a white solid (62 mg, 99% yield). MS (ESI): mass calcd. for $C_{30}H_{29}N_5O_6S_2$, 619.7; m/z found, 620.3 [M+H]$^+$. 1H NMR (400 MHz, DMSO-d6): δ 10.22 (s, 1H), 8.34-8.29 (m, 1H), 7.46-7.39 (m, 2H), 7.36 (d, J=8.6 Hz, 1H), 7.22-7.15 (m, 1H), 7.13-7.04 (m, 3H), 6.99-6.93 (m, 1H), 5.98-5.91 (m, 1H), 4.55-4.35 (m, 1H), 3.85-3.30 (m, 6H), 2.98 (s, 3H), 2.78-2.65 (m, 2H), 2.24-2.06 (m, 1H), 2.04 (s, 3H), 2.03-1.89 (m, 1H).

Example 495: (R)—N-(1-(2-Methoxyacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide

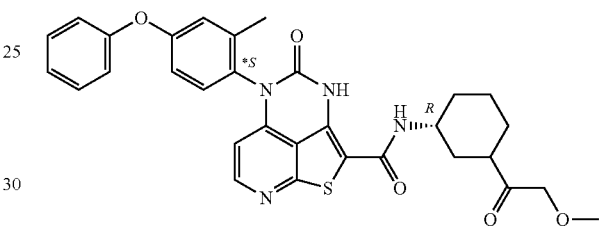

To a solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98, 80 mg, 0.15 mmol) in DMF (2 mL) were added 2-methoxyacetic acid (20 mg, 0.22 mmol), HATU (68 mg, 0.18 mmol), triethylamine (0.083 mL, 0.60 mmol). The reaction mixture was stirred at rt for 3 h. The reaction mixture was purified by flash column chromatography to yield the title compound as a yellow solid (67 mg, 98% yield). MS (ESI): mass calcd. for $C_{30}H_{29}N_5O_5S$, 571.6; m/z found, 572.2 [M+H]$^+$. $^1$H NMR (400 MHz, CD$_3$OD): δ 8.35-8.27 (m, 1H), 7.43-7.33 (m, 2H), 7.31-7.24 (m, 1H), 7.20-7.15 (m, 1H), 7.12-7.02 (m, 3H), 7.01-6.94 (m, 1H), 6.05 (d, J=5.4 Hz, 1H), 4.54 (s, 2H), 4.24-4.15 (m, 2H), 3.98-3.88 (m, 1H), 3.40 (s, 3H), 3.15-3.04 (m, 1H), 2.98-2.84 (m, 1H), 2.12 (s, 3H), 2.06-1.99 (m, 1H), 1.89-1.80 (m, 1H), 1.78-1.53 (m, 2H).

Example 496: N-(1-Acryloylazetidin-3-yl)-5-(*S)-(2-methyl-4-phenoxyphenyl)-4-oxo-4,5-dihydro-3H-1-thia-3,5,8-triazaacenaphthylene-2-carboxamide

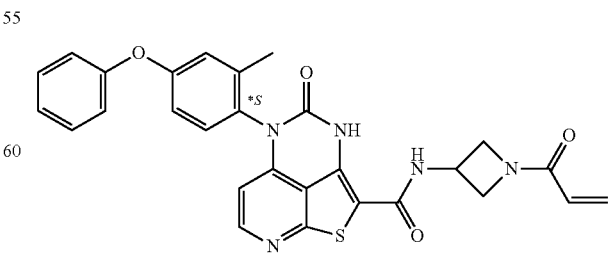

The title compound was prepared in a manner analogous to Method 1, steps A-I (including Chiral Resolution Method A after step F to obtain the *S atropisomer) in Example 1, and using tert-butyl 3-aminoazetidine-1-carboxylate in place of tert-butyl (3R,5R)-3-amino-5-fluoro-piperidine-1-carboxylate in step G, to yield the title compound. MS (ESI): mass calcd. for $C_{28}H_{23}N_5O_4S$, 525.6; m/z found, 526.7 [M+H]$^+$. $^1$H NMR (400 MHz, DMSO-d$_6$): δ 10.32 (s, 1H), 8.82 (s, 1H), 8.51-8.22 (m, 1H), 7.52-7.42 (m, 2H), 7.41-7.33 (m, 1H), 7.27-7.19 (m, 1H), 7.18-7.07 (m, 3H), 7.05-6.95 (m, 1H), 6.43-6.28 (m, 1H), 6.22-6.07 (m, 1H), 6.02-5.90 (m, 1H), 5.74-5.64 (m, 1H), 4.84-4.69 (m, 1H), 4.62-4.49 (m, 1H), 4.35-4.15 (m, 2H), 4.08-3.91 (m, 1H), 2.14-2.04 (m, 3H).

Example 497: (R)—N-(1-Acryloylpiperidin-3-yl)-5-(3-methyl-5-phenoxypyridin-2-yl)-4-oxo-4,5-dihydro-3H-1-thia-3,5,8-triazaacenaphthylene-2-carboxamide

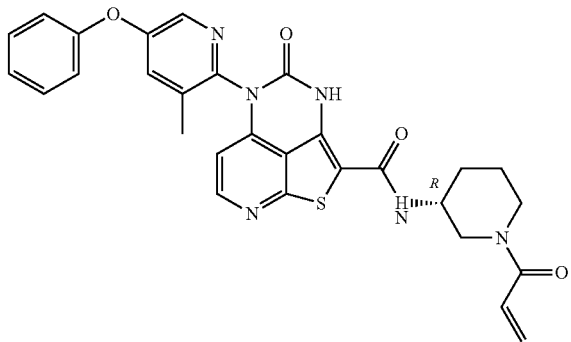

The title compound was prepared in a manner analogous to Method 1, step I in Example 1, using (R)-5-(3-Methyl-5-phenoxypyridin-2-yl)-4-oxo-N-(piperidin-3-yl)-4,5-dihydro-3H-1-thia-3,5,8-triazaacenaphthylene-2-carboxamide (Example 595) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide, to yield the title compound. MS (ESI): mass calcd. for $C_{29}H_{26}N_6O_4S$, 554.6; m/z found, 555.1 [M+H]$^+$. $^1$H NMR (500 MHz, CD$_3$OD): δ 8.37-8.33 (d, J=5.5 Hz, 1H), 8.24-8.18 (d, J=2.8 Hz, 1H), 7.55-7.50 (d, J=2.8 Hz, 1H), 7.49-7.43 (m, 2H), 7.29-7.23 (m, 1H), 7.21-7.15 (m, 2H), 6.85-6.75 (m, 1H), 6.25-6.17 (m, 1H), 6.12-6.08 (d, J=5.5 Hz, 1H), 5.79-5.70 (m, 1H), 4.59-4.25 (m, 1H), 4.23-3.92 (m, 2H), 3.26-3.12 (m, 1H), 3.01-2.82 (m, 1H), 2.26-2.18 (s, 3H), 2.13-2.04 (m, 1H), 1.93-1.83 (m, 1H), 1.80-1.68 (m, 1H), 1.66-1.51 (m, 1H).

Example 498: (R)—N-(1-Acryloylpiperidin-3-yl)-5-(2',3'-difluoro-[1'-biphenyl]-3-yl)-4-oxo-4,5-dihydro-3H-1-thia-3,5,8-triazaacenaphthylene-2-carboxamide

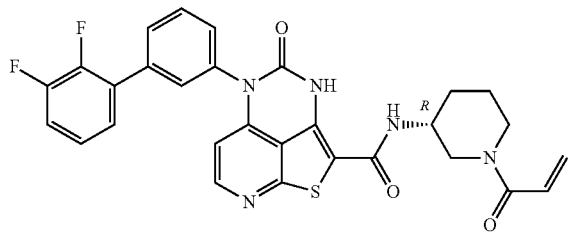

Step A: 5-(3-bromophenyl)-4-oxo-4,5-dihydro-3H-1-thia-3,5,8-triazaacenaphthylene-2-carboxylic Acid The title compound was prepared in a manner analogous to Method 1, steps C-F in Example 1, and using 3-bromoaniline in place of 2-methyl-4-phenoxy-aniline in step C, to yield the title compound.

Step B: (R)-tert-Butyl 3-(5-(3-bromophenyl)-4-oxo-4,5-dihydro-3H-1-thia-3,5,8-triazaacenaphthylene-2-carboxamido)piperidine-1-carboxylate To a stirred suspension of 5-(3-bromophenyl)-4-oxo-4,5-dihydro-3H-1-thia-3,5,8-triazaacenaphthylene-2-carboxylic acid (3.5 g, 9.0 mmol) in DMF (15 mL) were added tert-butyl (3R)-3-aminopiperidine-1-carboxylate (3.6 g, 18 mmol), HATU (5.1 g, 13 mmol), and diisopropylethylamine (2.3 g, 18 mmol). The resulting mixture was stirred at room temperature overnight. The solvent was removed and the residue was partitioned between ethyl acetate and water. The organic layer was separated, shaken with brine and dried over anhydrous Na$_2$SO$_4$. The residue was purified by flash column chromatography to yield the title compound as yellow solid (3.0 g, 58% yield).

Step C: (R)-tert-Butyl 3-(5-(2',3'-difluoro-[1,1'-biphenyl]-3-yl)-4-oxo-4,5-dihydro-3H-1-thia-3,5,8-triazaacenaphthylene-2-carboxamido)piperidine-1-carboxylate A mixture of (R)-tert-butyl 3-(5-(3-bromophenyl)-4-oxo-4,5-dihydro-3H-1-thia-3,5,8-triazaacenaphthylene-2-carboxamido)piperidine-1-carboxylate (180 mg, 0.314 mmol), (2,3-difluorophenyl)boronic Acid (75 mg, 0.48 mmol), Pd(dppf)Cl$_2$·CH$_2$Cl$_2$ (25 mg, 0.031 mmol), and Na$_2$CO$_3$ (85 mg, 0.80 mmol) in dioxane (7 mL) and H$_2$O (1 mL) was sparged with N$_2$ and stirred at 120° C. for 4 h. The reaction was cooled and the mixture was purified by flash column chromatography to yield the title compound as yellow solid (150 mg, 79% yield).

Step D: (R)—N-(1-Acryloylpiperidin-3-yl)-5-(2',3'-difluoro-[1'-biphenyl]-3-yl)-4-oxo-4,5-dihydro-3H-1-thia-3,5,8-triazaacenaphthylene-2-carboxamide The title compound was prepared in a manner analogous to Method 1, step I, in Example 1, using (R)-5-(2',3'-Difluoro-[1,1'-biphenyl]-3-yl)-4-oxo-N-(piperidin-3-yl)-4,5-dihydro-3H-1-thia-3,5,8-triazaacenaphthylene-2-carboxamide (Example 706) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide to yield the title compound (54 mg, 44% yield). MS (ESI): mass calcd. for $C_{29}H_{23}F_2N_5O_3S$, 559.6; m/z found, 560.4 [M+H]$^+$. $^1$H NMR (400 MHz, DMSO-d$_6$): δ 10.14 (s, 1H), 8.30 (d, J=5.4 Hz, 1H), 8.15-7.94 (m, 1H), 7.81-7.64 (m, 3H), 7.57-7.22 (m, 4H), 6.89-6.63 (m, 1H), 6.15-5.95 (m, 2H), 5.69-5.56 (m, 1H), 4.55-4.11 (m, 1H), 4.09-3.88 (m, 1H), 3.84-3.65 (m, 1H), 3.15-2.92 (m, 1H), 2.82-2.57 (m, 1H), 2.02-1.87 (m, 1H), 1.82-1.53 (m, 2H), 1.49-1.29 (m, 1H).

Example 499: N-((3R,5R)-1-Acryloyl-5-fluoropiperidin-3-yl)-5-(*S)-(2-methyl-4-phenoxyphenyl)-4-oxo-4,5-dihydro-3H-1-thia-3,5,8-triazaacenaphthylene-2-carboxamide

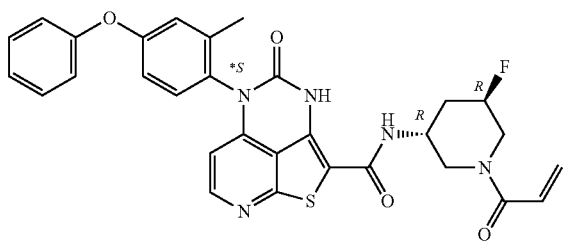

The title compound was prepared in a manner analogous to Method 1, steps G-I in Example 1, and using 5-(*S)-(2-methyl-4-phenoxyphenyl)-4-oxo-4,5-dihydro-3H-1-thia-3,5,8-triazaacenaphthylene-2-carboxylic acid (Intermediate 16) in place of 5-(2-methyl-4-phenoxyphenyl)-4-oxo-4,5-dihydro-3H-1-thia-3,5,8-triazaacenaphthylene-2-carboxylic acid (Intermediate 27) in step G. MS (ESI): mass calcd. for $C_{30}H_{26}FN_5O_4S$, 571.6; m/z found, 572.2 $[M+H]^+$. $^1H$ NMR (400 MHz, CD3OD and DMSO-$d_6$=2:1): δ 8.42-8.37 (m, 1H), 7.54-7.44 (m, 2H), 7.42-7.35 (m, 1H), 7.28-7.22 (m, 1H), 7.21-7.12 (m, 3H), 7.06-6.99 (m, 1H), 6.92-6.71 (m, 1H), 6.31-6.17 (m, 1H), 6.13-6.07 (m, 1H), 5.87-5.72 (m, 1H), 4.98-4.62 (m, 1H), 4.27-4.10 (m, 2H), 4.04-3.97 (m, 1H), 3.81-3.49 (m, 2H), 2.51-2.35 (m, 1H), 2.17 (s, 3H), 2.14-2.02 (m, 1H).

Example 500: (R)—N-(1-Acryloylpiperidin-3-yl)-5-(3'-fluoro-[1,1'-biphenyl]-3-yl)-4-oxo-4,5-dihydro-3H-1-thia-3,5,8-triazaacenaphthylene-2-carboxamide

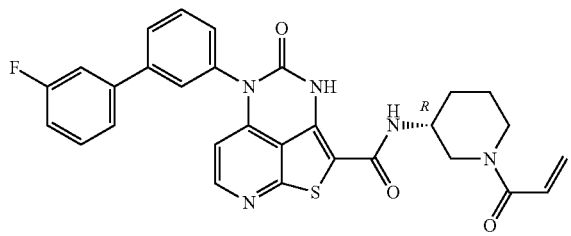

The title compound was prepared using the procedures found in Example 498, steps A-E, and using (3-fluorophenyl)boronic acid in place of (2,3-difluorophenyl)boronic acid in step C, to yield the title compound. MS (ESI): mass calcd. for $C_{29}H_{24}FN_5O_3S$, 541.6; m/z found, 542.5 $[M+H]^+$. $^1H$ NMR (400 MHz, DMSO-$d_6$): δ 10.15 (s, 1H), 8.29 (d, J=5.5 Hz, 1H), 8.13-7.98 (m, 1H), 7.93-7.81 (m, 2H), 7.73-7.62 (m, 1H), 7.61-7.38 (m, 4H), 7.25-7.14 (m, 1H), 6.86-6.64 (m, 1H), 6.16-5.98 (m, 2H), 5.69-5.60 (m, 1H), 4.58-4.11 (m, 1H), 4.07-3.89 (m, 1H), 3.84-3.70 (m, 1H), 3.16-2.89 (m, 1H), 2.83-2.57 (m, 1H), 2.01-1.87 (m, 1H), 1.81-1.56 (m, 2H), 1.48-1.31 (m, 1H).

Example 501: (R)—N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide

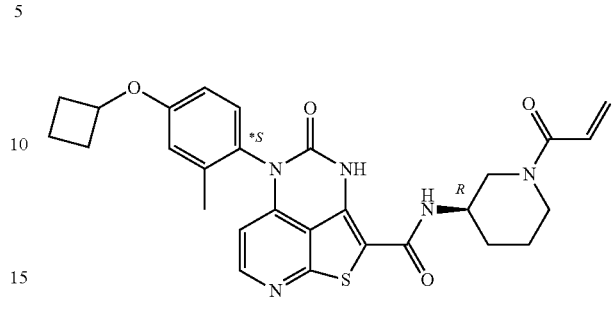

The title compound was prepared using a method analogous to Method 1, Step I in Example 1, using (R)-5-(4-cyclobutoxy-2-methylphenyl)-4-oxo-N-(piperidin-3-yl)-4,5-dihydro-3H-1-thia-3,5,8-triazaacenaphthylene-2-carboxamide (Example 605) instead of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide, followed by subjection to Chiral Resolution Method A to obtain the S* atropisomer. MS (ESI): mass calcd. for $C_{28}H_{29}N_5O_4S$, 531.6; m/z found, 532.2 $[M+H]^+$. $^1H$ NMR (400 MHz, CD$_3$OD, 1.3:1 mixture of rotamers): δ 8.30 (d, J=5.56 Hz, 1H), 7.20 (d, J=8.59 Hz, 1H), 6.91 (d, J=2.53 Hz, 1H), 6.75-6.87 (m, 2H), 6.20 (d, J=16.67 Hz, 1H), 6.02 (d, J=5.56 Hz, 1H), 5.71-5.79 (m, 1H), 4.75 (quin, J=7.07 Hz, 1H), 4.48-4.58 (m, 0.5H), 4.26-4.35 (m, 0.5H), 4.14-4.22 (m, 0.5H), 3.88-4.07 (m, 1.5H), 3.10-3.23 (m, 1H), 2.82-2.98 (m, 1H), 2.44-2.56 (m, 2H), 2.01-2.22 (m, 6H), 1.82-1.94 (m, 2H), 1.66-1.82 (m, 2H), 1.50-1.66 (m, 1H).

Example 502: (R,E)-N-(1-(4-(Dimethylamino)but-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide

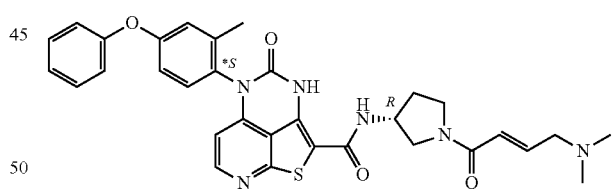

The title compound was prepared by treating a solution of (R)-5-(*S)-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36) (80 mg, 0.15 mmol) in DMF (3 mL) with (E)-4-(dimethylamino)but-2-enoic acid (30 mg, 0.23 mmol), HATU (70 mg, 0.18 mmol), and triethylamine (0.085 mL, 0.61 mmol). The reaction mixture was stirred at rt overnight, then purified by flash column chromatography to yield the title compound as a yellow solid (77 mg, 95% yield). MS (ESI): mass calcd. for $C_{32}H_{32}N_6O_4S$, 596.7; m/z found, 597.2 $[M+H]^+$. $^1H$ NMR (400 MHz, CD$_3$OD): δ 8.29-8.36 (m, 1H), 7.44-7.35 (m, 2H), 7.31-7.25 (m, 1H), 7.20-7.13 (m, 1H), 7.11-7.03 (m, 3H), 7.00-6.94 (m, 1H), 6.85-6.75 (m, 1H), 6.60-6.49 (m, 1H), 6.10-6.04 (m, 1H), 4.69-4.57 (m, 1H), 4.02-3.81 (m, 1H), 3.77-3.67 (m, 1H), 3.65-3.46 (m, 2H), 3.44-3.37 (m, 2H), 2.46 (s, 6H), 2.37-2.23 (m, 1H), 2.18-2.06 (m, 4H).

Example 503: (R,E)-N-(1-(4-Hydroxybut-2-enoyl) piperidin-3-yl)-5-(*S)-(2-methyl-4-phenoxyphenyl)-4-oxo-4,5-dihydro-3H-1-thia-3,5,8-triazaacenaphthylene-2-carboxamide

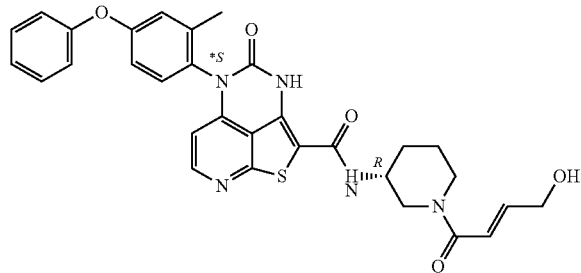

A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) (85 mg, 0.17 mmol), (E)-4-hydroxybut-2-enoic acid (Intermediate 13) (35 mg, 0.34 mmol), HATU (84 mg, 0.22 mmol), and diisopropylethylamine (66 mg, 0.51 mmol) in DMF (5 mL) was stirred at rt for 1 h. Then the mixture was purified by flash column chromatography to yield the title compound as white solid (56 mg, 56% yield). MS (ESI): mass calcd. for $C_{31}H_{29}N_5O_5S$, 583.7; m/z found, 584.4 [M+H]$^+$. $^1$H NMR (400 MHz, CD$_3$OD): δ 8.34-8.29 (m, 1H), 7.43-7.35 (m, 2H), 7.32-7.26 (m, 1H), 7.19-7.12 (m, 1H), 7.11-7.02 (m, 3H), 6.99-6.93 (m, 1H), 6.90-6.78 (m, 1H), 6.69-6.61 (m, 1H), 6.08-6.03 (m, 1H), 4.35-3.83 (m, 5H), 3.27-3.09 (m, 1H), 3.02-2.85 (m, 1H), 2.16-1.98 (m, 4H), 1.91-1.80 (m, 1H), 1.80-1.66 (m, 1H), 1.66-1.49 (m, 1H).

Example 504: (R)—N-(1-Acryloylpiperidin-3-yl)-5-(2'-methyl-[1,1'-biphenyl]-3-yl)-4-oxo-4,5-dihydro-3H-1-thia-3,5,8-triazaacenaphthylene-2-carboxamide

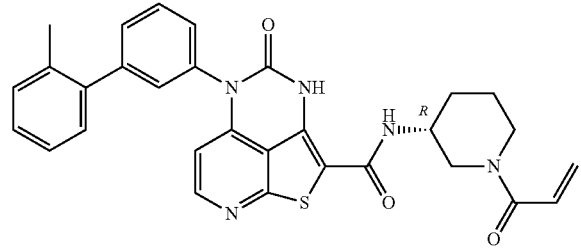

Step A: (R)-tert-Butyl 3-(5-(3-bromophenyl)-4-oxo-4,5-dihydro-3H-1-thia-3,5,8-triazaacenaphthylene-2-carboxamido)piperidine-1-carboxylate A mixture of compound 5-(3-bromophenyl)-4-oxo-4,5-dihydro-3H-1-thia-3,5,8-triazaacenaphthylene-2-carboxylic acid (Intermediate 57) (1.5 g, 3.8 mmol), tert-butyl (3R)-3-aminopiperidine-1-carboxylate (0.77 g, 3.8 mmol), triethylamine (0.78 g, 7.7 mmol), and HATU (1.5 g, 3.8 mmol) in DMF (5 mL) was stirred at rt for 3 h. Water was added and the precipitate was filtered off to yield the title compound as a pale yellow solid (1.6 g, 73% yield).

Step B: (R)-5-(2'-Methyl-[1,1'-biphenyl]-3-yl)-4-oxo-N-(piperidin-3-yl)-4,5-dihydro-3H-1-thia-3,5,8-triazaacenaphthylene-2-carboxamide A mixture of (R)-tert-butyl 3-(5-(3-bromophenyl)-4-oxo-4,5-dihydro-3H-1-thia-3,5,8-triazaacenaphthylene-2-carboxamido)piperidine-1-carboxylate (400 mg, 0.70 mmol), o-tolylboronic acid (105 mg, 0.770 mmol), Pd(dppf)Cl$_2$ (29 mg, 0.035 mmol), and Na$_2$CO$_3$ (148 mg, 1.40 mmol) in dioxane (10 mL) and H$_2$O (1.0 mL) was stirred at 110° C. for 2 h. The reaction was concentrated to dryness and the residue was purified flash column chromatography. The solid was dissolved in MeOH (4 mL) and HCl (4 mL), and the resulting mixture was heated to 50° C. and stirred for 30 min. The reaction was concentrated to dryness and the residue was purified by flash column chromatography to yield the title compound (320 mg, 95% yield).

Step C: (R)—N-(1-Acryloylpiperidin-3-yl)-5-(2'-methyl-[1,1'-biphenyl]-3-yl)-4-oxo-4,5-dihydro-3H-1-thia-3,5,8-triazaacenaphthylene-2-carboxamide The title compound was prepared in a manner analogous to Method 1, step I in Example 1, to yield 80 mg, 48% yield. MS (ESI): mass calcd. for $C_{30}H_{27}N_5O_3S$, 537.6; m/z found, 538.3 [M+H]$^+$. $^1$H NMR (400 MHz, CD$_3$OD): δ 8.27 (d, J=5.6 Hz, 1H), 7.68-7.60 (m, 1H), 7.51-7.38 (m, 3H), 7.27-7.18 (m, 4H), 6.782-6.70 (m, 1H), 6.24-6.11 (m, 2H), 5.76-5.61 (m, 1H), 4.55-4.25 (m, 1H), 4.22-3.96 (m, 1H), 3.96-3.88 (m, 1H), 3.19-3.06 (m, 1H), 2.90-2.78 (m, 1H), 2.27 (s, 3H), 2.07-1.99 (m, 1H), 1.87-1.79 (m, 1H), 1.74-1.62 (m, 1H), 1.59-1.47 (m, 1H).

Example 505: (R)—N-(1-Acryloylpiperidin-3-yl)-5-(*S)-(2-methyl-4-(trifluoromethoxy)phenyl)-4-oxo-4,5-dihydro-3H-1-thia-3,5,8-triazaacenaphthylene-2-carboxamide

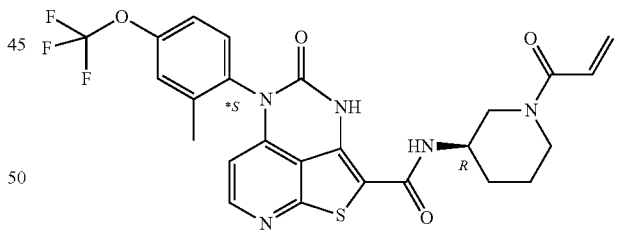

Step A: 2-Chloro-4-((2-methyl-4-(trifluoromethoxy) phenyl)amino)nicotinonitrile

A 10-20 mL microwave vial was charged sequentially with 2-chloro-4-iodonicotinonitrile (300.1 mg, 1.135 mmol), 2-methyl-4-(trifluoromethoxy)aniline (216.9 mg, 1.135 mmol), Pd(OAc)$_2$ (5.1 mg, 0.023 mmol), bis(2-diphenylphosphinophenyl)ether (18.3 mg, 0.0340 mmol), and Cs$_2$CO$_3$ (518 mg, 1.59 mmol). The vial was sealed and was evacuated and refilled with argon three times, and then dioxane (2.2 mL) was added. The vial was evacuated and refilled with argon once. The suspension was heated for 5 minutes in an oil bath at 50° C. under an argon inlet needle, then the inlet needle was removed and the sealed vial was heated for 30 minutes in an oil bath at 150° C. The crude product was used directly in the next reaction.

Step B: tert-Butyl (3R)-3-[2-sulfanylacetyl)amino] piperidine-1-carboxylate. A 10-20 mL microwave vial was charged with (R)-1-Boc-3-aminopiperidine (5.02 g, 25.0 mmol)

The vial was sealed and evacuated and back-filled with argon three times. Methyl 2-mercaptoacetate (6.72 mL, 75.1 mmol) was added via syringe in one portion and the vial was heated in an oil bath at 150° C. After 1 h 35 minutes, the mixture was cooled to rt and was purified by flash column chromatography to yield the title compound (5.54 g, 80.6% yield).

Step C: (R)-tert-Butyl 3-(3-amino-4-((2-methyl-4-(trifluoromethoxy)phenyl)amino)thieno[2,3-b]pyridine-2-carboxamido)piperidine-1-carboxylate To a sealed tube containing 2-chloro-4-((2-methyl-4-(trifluoromethoxy)phenyl)amino)nicotinonitrile (372 mg, 1.14 mmol) was added a 0.5 M solution of tert-butyl (3R)-3-[(2-sulfanylacetyl)amino]piperidine-1-carboxylate in dioxane. The suspension was heated in the sealed tube in an oil bath at 150° C. for 15 minutes. The mixture was cooled to room temperature and the reaction mixture was used directly in the next reaction.

Step D: (R)-tert-Butyl 3-(5-(2-methyl-4-(trifluoromethoxy)phenyl)-4-oxo-4,5-dihydro-3H-1-thia-3,5,8-triazaacenaphthylene-2-carboxamido)piperidine-1-carboxylate To (R)-tert-butyl 3-(3-amino-4-((2-methyl-4-(trifluoromethoxy)phenyl)amino)thieno[2,3-b]pyridine-2-carboxamido)piperidine-1-carboxylate in dioxane was added CDI (0.745 g, 4.60 mmol). The reaction tube was sealed and the vessel was evacuated and refilled with argon twice. The mixture was heated for 5 minutes in an oil bath at 50° C. under an argon inlet needle, then the argon inlet needle was removed and the mixture was heated at 150° C. for 10 minutes. The mixture was cooled to room temperature. The aqueous phase was extracted with EtOAc (2×50 mL) and the combined organic extracts were washed with 1 M aqueous HCl (50 mL), followed by saturated aqueous NaCl (50 mL). The organic phase was dried over anhydrous $Na_2SO_4$, filtered, and concentrated to dryness. The residue was purified by flash column chromatography to yield the title compound as a tan solid (452.4 mg, 67.37% yield).

Step E: (R)—N-(1-Acryloylpiperidin-3-yl)-5-(*S)-(2-methyl-4-(trifluoromethoxy)phenyl)-4-oxo-4,5-dihydro-3H-1-thia-3,5,8-triazaacenaphthylene-2-carboxamide The title compound was prepared using conditions analogous to Method 1, Step I, in Example 1, and using (R)-5-(2-methyl-4-(trifluoromethoxy)phenyl)-4-oxo-N-(piperidin-3-yl)-4,5-dihydro-3H-1-thia-3,5,8-triazaacenaphthylene-2-carboxamide (Example 413) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide. The resulting product was purified using chiral SFC (Stationary phase: Whelk 01 (S,S) 5 µm 250× 21.1 mm, Mobile phase: 60% $CO_2$, 40% MeOH) to give the *S atropisomer. MS (ESI): mass calcd. for $C_{25}H_{22}F_3N_5O_4S$, 545.5; m/z found, 545.1 [M+H]+. $^1$H NMR (400 MHz, DMSO-$d_6$): δ 10.34 (br. s., 1H), 8.33 (d, J=5.05 Hz, 1H), 8.06-8.24 (m, 1H), 7.51-7.61 (m, 2H), 7.44 (d, J=8.08 Hz, 1H), 6.70-6.89 (m, 1H), 6.11 (d, J=17.18 Hz, 1H), 5.92 (d, J=5.05 Hz, 1H), 5.69 (d, J=9.60 Hz, 1H), 4.42-4.55 (m, 0.5H), 4.17-4.28 (m, 0.5H), 3.94-4.12 (m, 1H), 3.71-3.86 (m, 1H), 2.92-3.14 (m, 1H), 2.60-2.82 (m, 1H), 2.15 (s, 3H), 1.89-2.02 (m, 1H), 1.56-1.85 (m, 2H), 1.33-1.53 (m, 1H).

Example 506: (R)—N-(1-Acryloylpiperidin-3-yl)-4-oxo-5-(6-phenoxypyridin-3-yl)-4,5-dihydro-3H-1-thia-3,5,8-triazaacenaphthylene-2-carboxamide

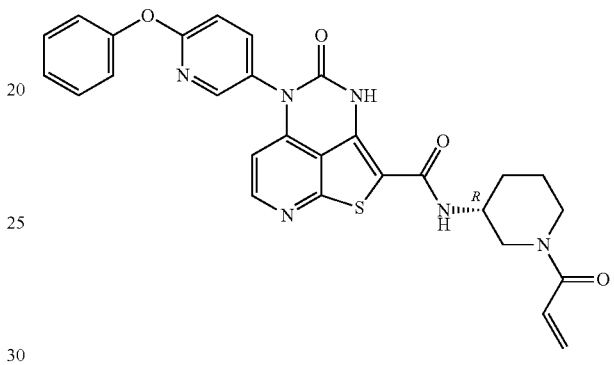

Step A: (R)-tert-Butyl 3-(4-oxo-5-(6-phenoxypyridin-3-yl)-4,5-dihydro-3H-1-thia-3,5,8-triazaacenaphthylene-2-carboxamido)piperidine-1-carboxylate To a 2-5 mL Biotage microwave vial containing a stir bar were added 6-phenoxypyridin-3-amine (182 mg, 0.0.980 mmol), 2-chloro-4-iodonicotinonitrile (256 mg, 0.971 mmol), Pd(OAc)$_2$ (4.7 mg, 0.021 mmol), DPEPhos (15.6 mg, 0.029 mmol), and $Cs_2CO_3$ (446 mg, 1.37 mmol). The vial was sealed, treated with dioxane (1.95 mL), evacuated and flushed with argon 4×, and stirred at 150° C. under argon for 30 min. The reaction was cooled to rt, treated with tert-butyl (3R)-3-[(2-sulfanylacetyl)amino]piperidine-1-carboxylate (Intermediate 22) (2.0 mL, 0.49 M, 0.98 mmol) via syringe, evacuated and flushed with argon 4×, and stirred at 150° C. for 15 min. The reaction was cooled to rt, treated with solid CDI (628 mg, 3.87 mmol) in one portion, resealed, and evacuated and flushed with argon 4×, and stirred at 150° C. for 15 min. The reaction was then diluted with EtOAc (10 mL), and washed with 0.5 M citric acid/brine solution (2×8 mL) and 2 M $K_2CO_3$ (1×5 mL). The organic phase was dried over anhydrous $Na_2SO_4$, filtered, and concentrated to dryness. The residue was dissolved in DCM (5 mL) and purified by flash column chromatography to yield the title compound as an orange-yellow foam (328 mg, 57.7% yield).

Step B: (R)-4-oxo-5-(6-phenoxypyridin-3-yl)-N-(piperidin-3-yl)-4,5-dihydro-3H-1-thia-3,5,8-triazaacenaphthylene-2-carboxamide A solution of (R)-tert-butyl 3-(4-oxo-5-(6-phenoxypyridin-3-yl)-4,5-dihydro-3H-1-thia-3,5,8-triazaacenaphthylene-2-carboxamido)piperidine-1-carboxylate (324 mg, 0.551 mmol) was dissolved in 9:1:0.05 MeOH/CH$_3$CN/TFA (1 mL) and purified by C18 HPLC to yield the title compound as a light yellow powder (302 mg, 94.3% yield).

Step C: (R)—N-(1-Acryloylpiperidin-3-yl)-4-oxo-5-(6-phenoxypyridin-3-yl)-4,5-dihydro-3H-1-thia-3,5,8-triazaacenaphthylene-2-carboxamide The title compound was prepared in a manner analogous to Method 1, step I, in Example 1, to yield the title compound (80 mg, 36% yield). MS (ESI): mass calcd. for $C_{28}H_{24}N_6O_4S$, 540.6; m/z found, 541.1 [M+H]$^+$. $^1$H NMR (500 MHz, CD$_3$OD): δ 8.31 (d, J=5.6 Hz, 1H), 8.24 (d, J=2.5 Hz, 1H), 7.94 (dd, J=8.7, 2.7 Hz, 1H), 7.49-7.41 (m, 2H), 7.28-7.23 (m, 1H), 7.21-7.18 (m, 2H), 7.15 (d, J=8.7 Hz, 1H), 6.84-6.73 (m, 1H), 6.25-6.13 (m, 2H), 5.72 (dd, J=23.1, 10.7 Hz, 1H), 4.60-4.49 (m, 0.5H), 4.32 (d, J=12.6 Hz, 0.5H), 4.19 (d, J=11.5 Hz, 0.5H), 4.02-3.86 (m, 1.5H), 3.15 (q, J=10.6, 10.1 Hz, 1H), 2.87 (q, J=12.0 Hz, 1H), 2.06 (d, J=12.5 Hz, 1H), 1.91-1.80 (m, 1H), 1.77-1.65 (m, 1H), 1.63-1.50 (m, 1H).

Example 507: (R)—N-(1-Acryloylpiperidin-3-yl)-5-(3'-chloro-[1,1'-biphenyl]-3-yl)-4-oxo-4,5-dihydro-3H-1-thia-3,5,8-triazaacenaphthylene-2-carboxamide

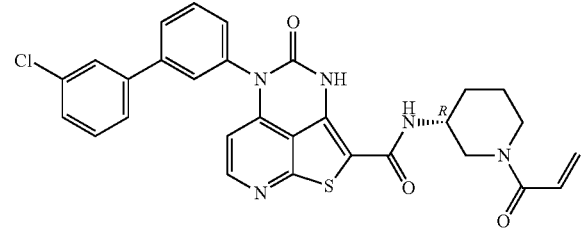

Step A: (R)-tert-butyl 3-(5-(3'-chloro-[1,1'-biphenyl]-3-yl)-4-oxo-4,5-dihydro-3H-1-thia-3,5,8-triazaacenaphthylene-2-carboxamido)piperidine-1-carboxylate A solution of (R)-tert-butyl 3-(5-(3-bromophenyl)-4-oxo-4,5-dihydro-3H-1-thia-3,5,8-triazaacenaphthylene-2-carboxamido)piperidine-1-carboxylate (Example 504, Step A) (170 mg, 0.30 mmol) (3-chlorophenyl)boronic acid (70 mg, 0.45 mmol), Pd(dppf)Cl$_2$.CH$_2$Cl$_2$ (25 mg, 0.031 mmol), and Na$_2$CO$_3$ 80 mg, (0.76 mmol) in dioxane (7 mL) and H$_2$O (1 mL) was sparged with N$_2$ and stirred at 120° C. for 4 h. The reaction mixture was cooled and purified by flash column chromatography to yield the title compound as yellow solid (140 mg, 78% yield).

Step B: (R)-5-(3'-chloro-[1,1'-biphenyl]-3-yl)-4-oxo-N-(piperidin-3-yl)-4,5-dihydro-3H-1-thia-3,5,8-triazaacenaphthylene-2-carboxamide A solution of (R)-tert-butyl 3-(5-(3'-chloro-[1,1'-biphenyl]-3-yl)-4-oxo-4,5-dihydro-3H-1-thia-3,5,8-triazaacenaphthylene-2-carboxamido)piperidine-1-carboxylate (140 mg, 0.232 mmol) and concentrated HCl (2 mL) and MeOH (15 mL) was stirred at room temperature for 2 hours. The reaction was concentrated to dryness and purified by flash column chromatography to yield the title compound as yellow solid (130 mg, 87% yield).

Step C: (R)—N-(1-Acryloylpiperidin-3-yl)-5-(3'-chloro-[1,1'-biphenyl]-3-yl)-4-oxo-4,5-dihydro-3H-1-thia-3,5,8-triazaacenaphthylene-2-carboxamide The title compound was prepared in a manner analogous to Method 1, step I in Example 1, to yield 43 mg (24% yield). MS (ESI): mass calcd. for $C_{29}H_{24}ClN_5O_3S$, 558.1; m/z found, 558.5 [M+H]$^+$. $^1$H NMR (400 MHz, DMSO-d$_6$): δ 10.15 (s, 1H), 8.29 (d, J=5.5 Hz, 1H), 8.15-8.00 (m, 1H), 7.93-7.83 (m, 2H), 7.79-7.72 (m, 1H), 7.70-7.63 (m, 2H), 7.55-7.37 (m, 3H), 6.88-6.62 (m, 1H), 6.14-5.95 (m, 2H), 5.69-5.58 (m, 1H), 4.49-4.10 (m, 1H), 4.08-3.89 (m, 1H), 3.86-3.70 (m, 1H), 3.15-2.90 (m, 1H), 2.84-2.60 (m, 1H), 1.99-1.87 (m, 1H), 1.82-1.55 (m, 2H), 1.51-1.32 (m, 1H).

Example 508: N-((3S,4R)-1-Acryloyl-4-methoxypyrrolidin-3-yl)-5-(*S)-(2-methyl-4-phenoxyphenyl)-4-oxo-4,5-dihydro-3H-1-thia-3,5,8-triazaacenaphthylene-2-carboxamide

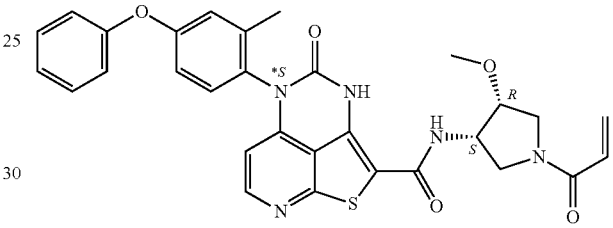

The title compound was prepared in a manner analogous to Method 1, steps A-I (including Chiral Resolution Method A to obtain the *S atropisomer after Step F) in Example 1, and using tert-butyl (3S,4R)-3-amino-4-methoxy-pyrrolidine-1-carboxylate in place of tert-butyl (3R,5R)-3-amino-5-fluoro-piperidine-1-carboxylate in step G. MS (ESI): mass calcd. for $C_{30}H_{27}N_5O_5S$, 569.6; m/z found, 570.4 [M+H]$^+$. $^1$H NMR (400 MHz, CD$_3$OD): δ 8.26 (d, J=5.4 Hz, 1H), 7.41-7.30 (m, 2H), 7.30-7.22 (m, 1H), 7.14-7.07 m, 1H), 7.06-6.98 (m, 3H), 6.94-6.87 (m, 1H), 6.58-6.46 (m, 1H), 6.24-6.11 (m, 1H), 6.02-5.91 (m, 1H), 5.69-5.61 (m, 1H), 4.70-4.56 (m, 1H), 4.05-3.72 (m, 3H), 3.70-3.54 (m, 1H), 3.49-3.41 (m, 1H), 3.36-3.30 (m, 3H), 2.04 (s, 3H).

Example 509: (R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide

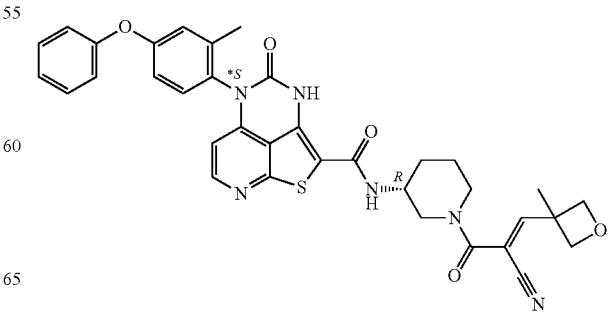

Step A: (R)—N-(1-(2-cyanoacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) (300 mg, 0.601 mmol), 2-cyanoacetic acid (102 mg, 1.20 mmol), HATU (297 mg, 0.780 mmol), and diisopropylethylamine (155 mg, 1.20 mmol) in DMF (5 mL) was stirred at rt for 1 h. The reaction mixture was purified by flash column chromatography to yield the title compound as white solid (225 mg, 66.2% yield).

Step B: (R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide A solution of (R)—N-(1-(2-cyanoacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide (85 mg, 0.15 mmol), 3-methyloxetane-3-carbaldehyde (45 mg, 0.45 mmol), piperidine (0.3 mL), AcOH (0.1 mL), dioxane (5 mL), and 4A molecular sieves (0.3 g) was stirred at 100° C. for 1 h under $N_2$. The mixture was concentrated to dryness and purified by flash column chromatography to give the title compound as white solid (91 mg, 93% yield). MS (ESI): mass calcd. for $C_{35}H_{32}N_6O_5S$, 648.7; m/z found, 649.4 [M+H]$^+$. $^1$H NMR (400 MHz, $CD_3OD$): δ 8.33-8.28 (m, 1H), 7.42-7.35 (m, 2H), 7.32-7.23 (m, 2H), 7.18-7.12 (m, 1H), 7.11-7.00 (m, 3H), 6.99-6.93 (m, 1H), 6.06-6.02 (m, 1H), 5.02-4.88 (m, 1H), 4.65-4.19 (m, 4H), 4.06-3.59 (m, 3H), 3.57-3.32 (m, 1H), 2.14-2.01 (m, 4H), 1.99-1.77 (m, 2H), 1.71-1.58 (m, 4H).

Example 510: (R)—N-(1-Acryloylpiperidin-3-yl)-5-(2'-chloro-[1,1'-biphenyl]-3-yl)-4-oxo-4,5-dihydro-3H-1-thia-3,5,8-triazaacenaphthylene-2-carboxamide

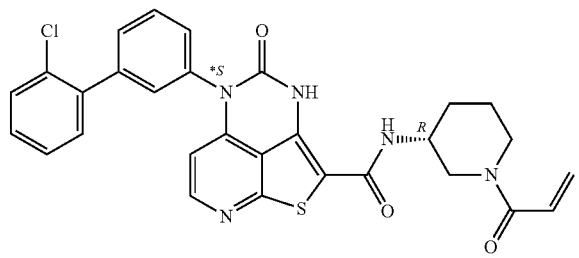

The title compound was prepared using the procedures found in Example 498, steps A-E, and using 2-(2-chlorophenyl)-4,4,5,5-tetramethyl-1,3,2-dioxaborolane in place of (2,3-difluorophenyl)boronic acid in step C. MS (ESI): mass calcd. for $C_{29}H_{24}ClN_5O_3S$, 558.1; m/z found, 558.1 [M+H]$^+$. 1H NMR (400 MHz, DMSO-d6): δ 8.27 (d, J=5.1 Hz, 1H), 8.24-8.08 (m, 1H), 7.73-7.61 (m, 1H), 7.60-7.53 (m, 2H), 7.52-7.35 (m, 5H), 6.88-6.62 (m, 1H), 6.13-5.99 (m, 2H), 5.70-5.58 (m, 1H), 4.53-4.06 (m, 1H), 4.04-3.87 (m, 1H), 3.82-3.69 (m, 1H), 3.10-2.94 (m, 1H), 2.87-2.59 (m, 1H), 2.00-1.85 (m, 1H), 1.81-1.52 (m, 2H), 1.46-1.32 (m, 1H).

Example 511: (R,E)-N-(1-(4-Aminobut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

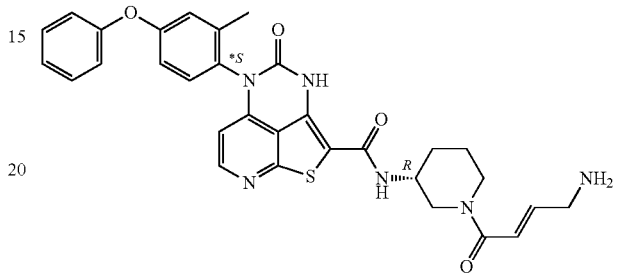

Step A: (R,E)-tert-buty (4-(3-(5-(S)-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) (90 mg, 0.18 mmol), (E)-4-(tert-butoxycarbonylamino)but-2-enoic acid (Intermediate 12) (72 mg, 0.36 mmol), HATU (89 mg, 0.23 mmol), and diisopropylethylamine (70 mg, 0.54 mmol) in DMF (5 mL) was stirred at rt for 1 h. The mixture was purified by flash column chromatography to give the title compound as white solid (101 mg, 82% yield).

Step B: (R,E)-N-(1-(4-Aminobut-2-enoyl)piperidin-3-yl)-5-(*S)-(2-methyl-4-phenoxyphenl)-4-oxo-4,5-dihydro-3H-1-thia-3,5,8-triazaacenaphthylene-2-carboxamide A solution of (R,E)-tert-butyl (4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate (101 mg, 0.148 mmol), concentrated HCl (5 mL), and MeOH (5 mL) was stirred at rt for 1 h. The mixture was concentrated to dryness and the residue was purified by flash column chromatography to give the title compound as white solid (67 mg, 95% yield). MS (ESI): mass calcd. for $C_{31}H_{30}N_6O_4S$, 582.7; m/z found, 583.4 [M+H]$^+$. $^1$H NMR (400 MHz, DMSO-d$_6$ and $CD_3OD$): δ 8.36 (s, 1H), 8.30-8.25 (m, 1H), 7.40-7.33 (m, 2H), 7.29-7.23 (m, 1H), 7.17-7.09 (m, 1H), 7.09-7.00 (m, 3H), 6.96-6.89 (m, 1H), 6.75-6.57 (m, 2H), 5.98-5.93 (m, 1H), 4.15-3.77 (m, 3H), 3.63-3.57 (m, 2H), 3.13-3.00 (m, 1H), 2.85-2.63 (m, 1H), 2.04 (s, 3H), 2.00-1.89 (m, 1H), 1.85-1.74 (m, 1H), 1.74-1.59 (m, 1H), 1.54-1.39 (m, 1H).

Example 512: (R)—N-(1-Acryloylpiperidin-3-yl)-4-oxo-5-(2-phenylpyridin-4-yl)-4,5-dihydro-3H-1-thia-3,5,8-triazaacenaphthylene-2-carboxamide

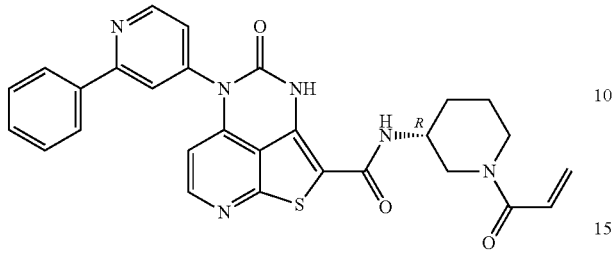

The title compound was prepared in a manner analogous to Method 1, steps C-I in Example 1, and using 2-phenylpyridin-4-amine in place of 2-methyl-4-phenoxy-aniline in step C and using tert-butyl (3R)-3-aminopiperidine-1-carboxylate in place of tert-butyl (3R,5R)-3-amino-5-fluoropiperidine-1-carboxylate in step G. MS (ESI): mass calcd. for $C_{28}H_{24}N_6O_3S$, 524.6; m/z found, 525.2 [M+H]$^+$. $^1$H NMR (400 MHz, DMSO-d$_6$): δ 10.27 (s, 1H), 8.92-8.83 (m, 1H), 8.35-8.26 (m, 1H), 8.18-8.04 (m, 4H), 7.53-7.42 (m, 4H), 6.84-6.66 (m, 1H), 6.26-6.15 (m, 1H), 6.12-6.01 (m, 1H), 5.70-5.59 (m, 1H), 4.50-4.09 (m, 1H), 4.06-3.90 (m, 1H), 3.82-3.72 (m, 1H), 3.16-2.92 (m, 1H), 2.84-2.59 (m, 1H), 1.96-1.88 (m, 1H), 1.80-1.72 (m, 1H), 1.72-1.55 (m, 1H), 1.47-1.34 (m, 1H).

Example 513: (R)—N-(1-Acryloylpiperidin-3-yl)-4-oxo-5-(5-phenoxypyridin-2-yl)-4,5-dihydro-3H-1-thia-3,5,8-triazaacenaphthylene-2-carboxamide

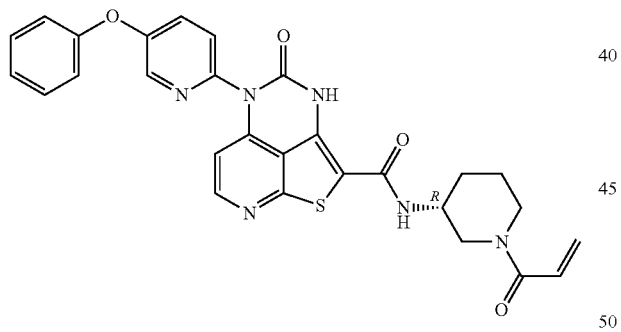

A round bottom flask containing a solution of 4-oxo-5-(5-phenoxypyridin-2-yl)-4,5-dihydro-3H-1-thia-3,5,8-triazaacenaphthylene-2-carboxylic acid (Intermediate 60, 60.0 g, 148 mmol) in DMF (500 mL) was treated with HATU (73.9 g, 193 mmol) and TEA (59.9 g, 593 mmol). The mixture was stirred for 30 minutes until all of the solids were dissolved. 1-[(3R)-3-amino-1-piperidyl]prop-2-en-1-one (Intermediate 15) (35.0 g, 233 mmol) was added as a suspension in DMF (200 mL). The reaction mixture was stirred at room temperature for 30 min. The mixture was treated with water (600 mL), the resulting precipitate was collected by filtration, dried under vacuum, then purified (FCC, SiO$_2$, MeOH/EtOAc/DCM=1/13/26) to give the title compound (40.0 g, 50%) as light yellow solid. MS (ESI): mass calcd. for $C_{28}H_{24}N_6O_4S$, 540.16; m/z found, 541.0 [M+H]$^+$. $^1$H NMR (600 MHz, DMSO) δ 10.24 (d, J=17.7 Hz, 1H), 8.47-8.41 (m, 1H), 8.36 (d, J=5.5 Hz, 1H), 8.16-8.01 (m, 1H), 7.73-7.68 (m, 1H), 7.66-7.61 (m, 1H), 7.54-7.46 (m, 2H), 7.29-7.19 (m, 3H), 6.85-6.73 (m, 1H), 6.22 (d, J=5.5 Hz, 1H), 6.11 (d, J=17.5 Hz, 1H), 5.72-5.63 (m, 1H), 4.52-4.17 (m, 1H), 4.11-3.94 (m, 1H), 3.85-3.75 (m, 1H), 3.17-2.95 (m, 1H), 2.81-2.63 (m, 1H), 2.00-1.92 (m, 1H), 1.82-1.75 (m, 1H), 1.74-1.59 (m, 1H), 1.50-1.37 (m, 1H).

Example 514: (R,E)-N-(1-(2-Cyano-3-cyclopropylacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide

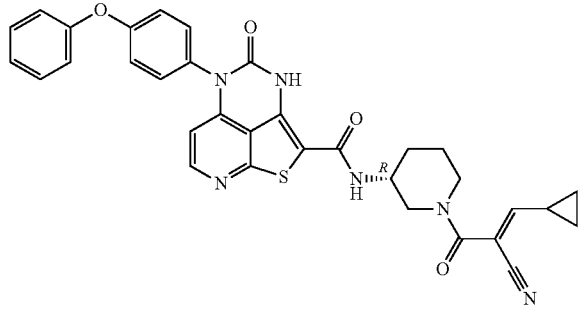

A solution of (100 mg, 0.2 mmol), (E)-2-cyano-3-cyclopropyl-prop-2-enoic acid (Intermediate 17) (55 mg, 0.40 mmol), HATU (99 mg, 0.26 mmol), and diisopropylethylamine (77 mg, 0.60 mmol) in DMF (5 mL) was stirred at rt for 1 h. The reaction mixture was purified by flash column chromatography to yield the title compound as white solid (63 mg, 98% yield). MS (ESI): mass calcd. for $C_{34}H_{30}N_6O_4S$, 618.7; m/z found, 619.3 [M+H]$^+$. $^1$H NMR (400 MHz, DMSO-d$_6$ and CD$_3$OD): δ 8.31-8.27 (m, 1H), 7.41-7.34 (m, 2H), 7.30-7.26 (m, 1H), 7.16-7.10 (m, 1H), 7.08-7.01 (m, 3H), 6.95-6.89 (m, 1H), 6.51-6.45 (m, 1H), 5.99-5.95 (m, 1H), 3.99-3.80 (m, 3H), 3.12-2.87 (m, 2H), 2.05 (s, 3H), 1.98-1.84 (m, 2H), 1.84-1.75 (m, 1H), 1.75-1.62 (m, 1H), 1.62-1.44 (m, 1H), 1.17-1.07 (m, 2H), 0.98-0.87 (m, 1H), 0.87-0.75 (m, 1H).

Example 515: (R)—N-(1-Acryloylpiperidin-3-yl)-5-(2',4'-difluoro-[1,1'-biphenyl]-3-yl)-4-oxo-4,5-dihydro-3H-1-thia-3,5,8-triazaacenaphthylene-2-carboxamide

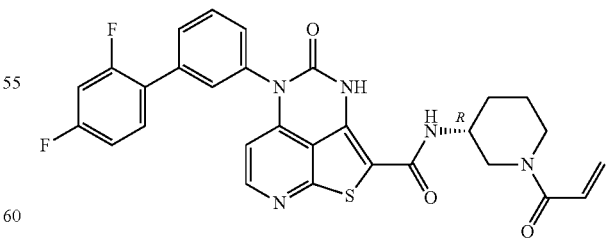

The title compound was prepared using the procedures found in Example 498, steps A-E, and using (2,4-difluorophenyl)boronic acid in place of (2,3-difluorophenyl)boronic acid in step C, to yield the title compound. MS (ESI): mass calcd. for $C_{29}H_{23}F_2N_5O_3S$, 559.6; m/z found, 560.6

[M+H]+. 1H NMR (400 MHz, DMSO-d6): δ10.13 (s, 1H), 8.29 (d, J=5.5 Hz, 1H), 8.14-7.98 (m, 1H), 7.76-7.57 (m, 4H), 7.52-7.44 (m, 1H), 7.4-7.30 (m, 1H), 7.25-7.13 (m, 1H), 6.87-6.62 (m, 1H), 6.19-6.01 (m, 2H), 5.68-5.55 (m, 1H), 4.56-4.10 (m, 1H), 4.05-3.87 (m, 1H), 3.82-3.71 (m, 1H), 3.18-2.88 (m, 1H), 2.83-2.57 (m, 1H), 2.01-1.83 (m, 1H), 1.80-1.55 (m, 2H), 1.48-1.29 (m, 1H).

Example 516: (R)—N-(1-Acryloylpiperidin-3-yl)-5-(3-benzylphenyl)-4-oxo-4,5-dihydro-3H-1-thia-3,5,8-triazaacenaphthylene-2-carboxamide

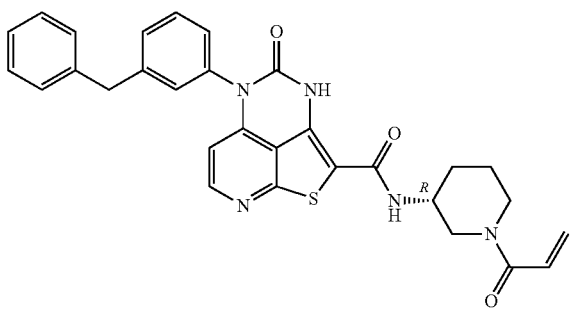

Step A: (R)-tert-Butyl 3-(5-(3-benzylphenyl)-4-oxo-4,5-dihydro-3H-1-thia-3,5,8-triazaacenaphthylene-2-carboxamido)piperidine-1-carboxylate The title compound was prepared using the procedure found in Example 506, step A, and using 3-benzylaniline in place of 6-phenoxypyridin-3-amine to yield the title compound (122 mg).

Step B: (R)-5-(3-Benzylphenyl)-4-oxo-N-(piperidin-3-yl)-4,5-dihydro-3H-1-thia-3,5,8-triazaacenaphthylene-2-carboxamide A solution of (R)-tert-butyl 3-(5-(3-benzylphenyl)-4-oxo-4,5-dihydro-3H-1-thia-3,5,8-triazaacenaphthylene-2-carboxamido)piperidine-1-carboxylate (119.8 mg, 0.205 mmol) in dioxane (1.0 mL) was treated with HCl (4 M in dioxane, 2.55 mL) in one portion at rt, and was stirred at rt for 1 h. The reaction mixture was concentrated to dryness to yield the title compound as a yellow-beige powder (114 mg, 98.0% yield).

Step C: (R)—N-(1-Acryloylpiperidin-3-yl)-5-(3-benzylphenyl)-4-oxo-4,5-dihydro-3H-1-thia-3,5,8-triazaacenaphthylene-2-carboxamide The title compound was prepared in a manner analogous to Method 1, step I, in Example 1. MS (ESI): mass calcd. for $C_{30}H_{27}N_5O_3S$, 537.6; m/z found, 538.2 [M+H]+. 1H NMR (400 MHz, DMSO-d6, 1.2:1 mixture of rotamers) δ 10.17 (br. s., 1H), 8.32 (d, J=5.56 Hz, 1H), 8.05-8.16 (m, 1H), 7.49-7.56 (m, 1H), 7.40 (d, J=7.58 Hz, 1H), 7.24-7.37 (m, 6H), 7.17-7.24 (m, 1H), 6.73-6.88 (m, 1H), 6.11 (d, J=16.17 Hz, 1H), 5.97 (d, J=5.56 Hz, 1H), 5.69 (d, J=12.13 Hz, 1H), 4.41-4.55 (m, 0.5H), 4.15-4.29 (m, 0.5H), 3.95-4.13 (m, 3H), 3.72-3.88 (m, 1H), 2.91-3.17 (m, 1H), 2.59-2.83 (m, 1H), 1.88-1.98 (m, 1H), 1.74-1.85 (m, 1H), 1.57-1.74 (m, 1H), 1.34-1.53 (m, 1H).

Example 517: (R)—N-(1-Acryloylpiperidin-3-yl)-5-(3'-methyl-[1,1'-biphenyl]-3-yl)-4-oxo-4,5-dihydro-3H-1-thia-3,5,8-triazaacenaphthylene-2-carboxamide


The title compound was prepared using the procedures found in Example 498, steps A-E, and using m-tolylboronic acid in place of (2,3-difluorophenyl)boronic acid in step C. MS (ESI): mass calcd. for $C_{30}H_{27}N_5O_3S$, 537.6; m/z found, 538.4 [M+H]+. 1H NMR (400 MHz, CD3OD): δ 8.28 (d, J=5.5 Hz, 1H), 7.80-7.75 (m, 1H), 7.70-7.62 (m, 2H), 7.50-7.35 (m, 3H), 7.34-7.26 (m, 1H), 7.19-7.13 (m, 1H), 6.83-6.69 (m, 1H), 6.24-6.11 (m, 2H), 5.76-5.64 m, 1H), 4.34-4.23 (m, 1H), 4.21-4.11 (m, 1H), 4.06-3.87 (m, 2H), 3.20-3.12 (m, 1H), 2.94-2.85 (m, 1H), 2.37 (s, 3H), 2.08-2.02 (m, 1H), 1.88-1.81 (m, 1H), 1.76-1.66 (m, 1H), 1.60-1.49 (m, 1H).

Example 518: (S)—N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide

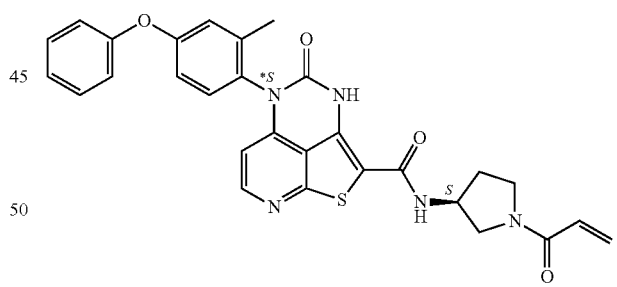

The title compound was prepared in a manner analogous to Method 1, steps A-I (including Chiral Resolution Method A to obtain the *S atropisomer after Step F) in Example 1, and using tert-butyl (3S)-3-aminopyrrolidine-1-carboxylate in place of tert-butyl (3R,5R)-3-amino-5-fluoro-piperidine-1-carboxylate in step G. MS (ESI): mass calcd. for $C_{29}H_{25}N_5O_4S$, 539.6; m/z found, 540.4 [M+H]+. 1H NMR (400 MHz, DMSO-d6 and CD3OD): δ 8.30-8.26 (m, 1H), 7.39-7.32 (m, 2H), 7.29-7.24 (m, 1H), 7.15-7.09 (m, 1H), 7.07-6.99 (m, 3H), 6.94-6.89 (m, 1H), 6.62-6.46 (m, 1H), 6.20-6.12 (m, 1H), 6.00-5.95 (m, 1H), 5.68-5.62 (m, 1H), 4.60-4.45 (m, 1H), 3.93-3.39 (m, 4H), 2.26-1.93 (m, 5H).

Example 519: (R)—N-(1-Acryloylpiperidin-3-yl)-5-(3-cyclohexylphenyl)-4-oxo-4,5-dihydro-3H-1-thia-3,5,8-triazaacenaphthylene-2-carboxamide

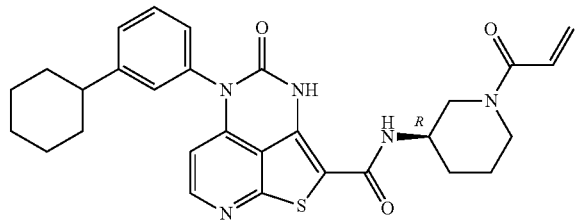

Step A: 3-Cyclohexylaniline

A solution of 1-bromo-3-nitro-benzene (2.50 g, 12.4 mmol), cyclohexen-1-ylboronic acid (1.56 g, 12.4 mmol), Pd(dppf)Cl$_2$ (505 mg, 0.619 mmol)), and Na$_2$CO$_3$ (2.62 g, 24.8 mmol) in dioxane (50 mL) and H$_2$O (5 mL) was stirred at 110° C. overnight. The reaction mixture was concentrated to dryness and the residue was purified by flash column chromatography to give the intermediate as a yellow solid. To the intermediate in EtOH (50 mL) at rt was added Pd/C (1.0 g). The mixture was flushed with H$_2$ (2×) and stirred at rt for 16 h. The reaction mixture was filtered and the filtrate was concentrated to dryness to give the title compound (1.6 g, 74% yield), which was used without further

Step B: Methyl 5-(3-cyclohexylphenyl)-4-oxo-4,5-dihydro-3H-1-thia-3,5,8-triazaacenaphthylene-2-carboxylate A solution of 2-chloro-4-iodo-pyridine-3-carbonitrile (1.60 g, 6.05 mmol), 3-cyclohexylaniline (1.06, 6.05 mmol), Pd(OAc)$_2$ (134 mg, 0.600 mmol), DPEphos (646 mg, 1.20 mmol), and Cs$_2$CO$_3$ (3.93 g, 12.1 mmol) in dioxane (100 mL) was heated at reflux under N$_2$ overnight. Methyl 2-sulfanylacetate (0.955 g, 9.00 mmol) was added and stirred at reflux overnight. CDI (2.92 g, 18.0 mmol) was added and stirred at reflux overnight. The reaction mixture was concentrated to dryness and the residue was purified by flash column chromatography to give the title compound as a pale yellow solid (900 mg, 36.5% yield).

Step C: (R)—N-(1-Acryloylpiperidin-3-yl)-5-(3-cyclohexylphenyl)-4-oxo-4,5-dihydro-3H-1-thia-3,5,8-triazaacenaphthylene-2-carboxamide The title compound was prepared in a manner analogous to Method 1, steps E-I in Example 1, using methyl 5-(3-cyclohexylphenyl)-4-oxo-4,5-dihydro-3H-1-thia-3,5,8-triazaacenaphthylene-2-carboxylate and using tert-butyl (3R)-3-aminopiperidine-1-carboxylate in place of tert-butyl (3R,5R)-3-amino-5-fluoro-piperidine-1-carboxylate in step G. MS (ESI): mass calcd. for C$_{29}$H$_{31}$N$_5$O$_3$S, 529.7; m/z found, 530.6 [M+H]$^+$. $^1$H NMR (400 MHz, CD$_3$OD): δ 8.19 (d, J=5.4 Hz, 1H), 7.50-7.44 (m, 1H), 7.38-7.34 (m, 1H), 7.32-7.27 (m, 1H), 7.26-7.19 (m, 1H), 6.82-6.68 (m, 1H), 6.22-6.09 (m, 1H), 5.99 (d, J=5.6 Hz, 1H), 5.74-5.59 (m, 1H), 4.55-4.28 (m, 1H), 4.25-3.87 (m, 2H), 3.19-3.03 (m, 1H), 2.88-2.75 (m, 1H), 2.62-2.52 (m, 1H), 2.08-1.99 (m, 1H), 1.91-1.78 (m, 5H), 1.75-1.64 (m, 2H), 1.56-1.34 (m, 5H), 1.30-1.20 (m, 1H).

Example 520: (R,E)-N-(1-(4-Aminobut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide

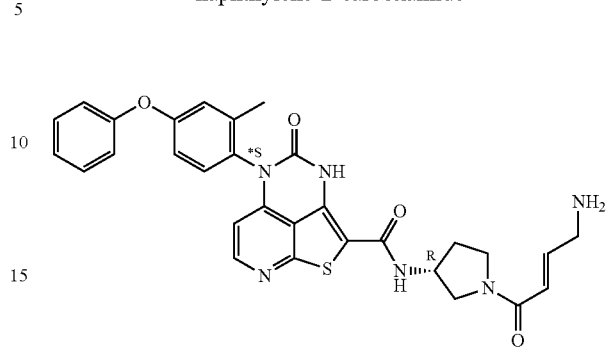

The title compound was prepared analogous to Example 511 using (R)-5-(*S)-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36) instead of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) to yield a white solid (67 mg, 71% yield). MS (ESI): mass calcd. for C$_{30}$H$_{28}$N$_6$O$_4$S, 568.6; m/z found, 569.4 [M+H]$^+$. $^1$H NMR (400 MHz, CD$_3$OD): δ 8.47 (s, 1H), 8.36-8.29 (m, 1H), 7.44-7.35 (m, 2H), 7.33-7.26 (m, 1H), 7.21-7.13 (m, 1H), 7.13-7.02 (m, 3H), 7.01-6.93 (m, 1H), 6.85-6.74 (m, 1H), 6.66-6.54 (m, 1H), 6.11-6.04 (m, 1H), 4.06-3.46 (m, 7H), 2.40-2.05 (m, 5H).

Example 521: (R)—N-(1-Acryloylpiperidin-3-yl)-5-(4'-methyl-[1,1'-biphenyl]-3-yl)-4-oxo-4,5-dihydro-3H-1-thia-3,5,8-triazaacenaphthylene-2-carboxamide

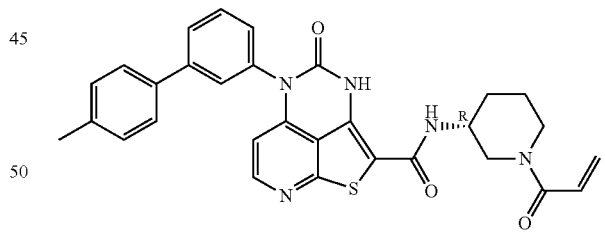

The title compound was prepared using the procedures found in Example 498, steps A-E, and using p-tolylboronic acid in place of (2,3-difluorophenyl)boronic acid in step C. MS (ESI): mass calcd. for C$_{30}$H$_{27}$N$_5$O$_3$S, 537.6; m/z found, 538.2 [M+H]$^+$. $^1$H NMR (400 MHz, CD$_3$OD): δ 8.25 (d, J=5.6 Hz, 1H), 7.79-7.73 (m, 1H), 7.70-7.60 (m, 2H), 7.56-7.49 (m, 2H), 7.39-7.32 (m, 1H), 7.27-7.19 (m, 2H), 6.83-6.70 (m, 1H), 6.24-6.11 (m, 2H), 5.78-5.64 (m, 1H), 4.52-4.45 (m, 1H), 4.34-4.11 (m, 1H), 4.00-3.88 (m, 1H), 3.21-3.10 (m, 1H), 2.96-2.82 (m, 1H), 2.34 (s, 3H), 2.12-1.99 (m, 1H), 1.90-1.80 (m, 1H), 1.79-1.65 (m, 1H), 1.62-1.49 (m, 1H).

Example 522: (R,E)-N-(1-(4-Hydroxybut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide

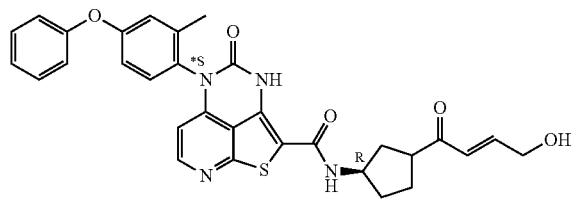

A solution of (R)-5-(*S)(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36, 100 mg, 0.192 mmol), (E)-4-hydroxybut-2-enoic acid (Intermediate 13, 29 mg, 0.286 mmol), HATU (146 mg, 0.384 mmol), and triethylamine (97 mg, 0.96 mmol) in DMF (3 mL) was stirred at rt for 2 h, then purified by flash column chromatography to give the title compound as a light yellow solid (55 mg, 49% yield). MS (ESI): mass calcd. for $C_{30}H_{27}N_5O_5S$, 569.6; m/z found, 570.5 [M+H]$^+$. $^1$H NMR (400 MHz, CD$_3$OD): δ 8.31 (d, J=5.5 Hz, 1H), 7.45-7.34 (m, 2H), 7.29 (d, J=8.6 Hz, 1H), 7.20-7.12 (m, 1H), 7.12-7.01 (m, 3H), 6.98-6.85 (m, 2H), 6.55-6.37 (m, 1H), 6.05 (d, J=5.6 Hz, 1H), 4.69-4.56 (m, 1H), 4.32-4.20 (m, 2H), 4.00-3.46 (m, 4H), 2.40-2.20

Example 523: N-((3S,4S)-1-Acryloyl-4-hydroxypyrrolidin-3-yl)-5-(*S)-(2-methyl-4-phenoxyphenyl)-4-oxo-4,5-dihydro-3H-1-thia-3,5,8-triazaacenaphthylene-2-carboxamide

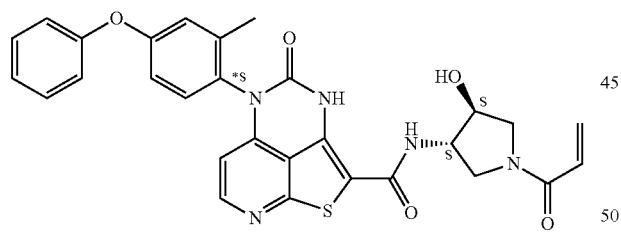

The title compound was prepared in a manner analogous to Method 1, steps A-I (including Chiral Resolution Method A to obtain the *S atropisomer after Step F) in Example 1, and using tert-butyl (3S,4S)-3-amino-4-hydroxypyrrolidine-1-carboxylate (Intermediate 24) in place of tert-butyl (3R,5R)-3-amino-5-fluoro-piperidine-1-carboxylate in step G, to yield the title compound. MS (ESI): mass calcd. for $C_{29}H_{25}N_5O_5S$, 555.6; m/z found, 556.4 [M+H]$^+$. $^1$H NMR (400 MHz, DMSO-d$_6$): δ 10.15 (br, 1H), 8.36-8.24 (m, 2H), 7.46-7.38 (m, 2H), 7.37-7.31 (m, 1H), 7.21-7.14 (m, 1H), 7.13-7.04 (m, 3H), 6.98-6.93 (m, 1H), 6.61-6.51 (m, 1H), 6.17-6.09 (m, 1H), 5.98-5.92 (m, 1H), 5.68-5.62 (m, 1H), 5.49-5.37 (m, 1H), 4.33-4.11 (m, 2H), 3.94-3.39 (m, 4H), 2.03 (s, 3H).

Example 524: 5-(*S)-(2-Methyl-4-phenoxyphenyl)-N—((R)-1-((S)-2-(methylamino)propanoyl)piperidin-3-yl)-4-oxo-4,5-dihydro-3H-1-thia-3,5,8-triazaacenaphthylene-2-carboxamide

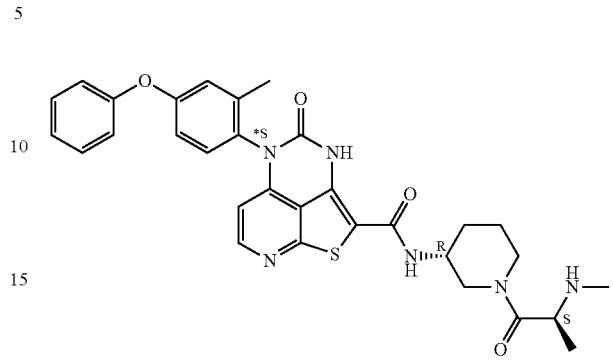

A solution of (2S)-2-[tert-butoxycarbonyl(methyl)amino]propanoic acid (98 mg, 0.48 mmol), HATU (182 mg, 0.48 mmol), and triethylamine (202 mg, 2.00 mmol) were dissolved in anhydrous DMF (5 mL) and stirred at room temperature. After 10 min, (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) (200 mg, 0.40 mmol) was added and the mixture was stirred for 2 h. The crude mixture was purified by flash column chromatography to get a white solid. The solid was diluted in 6.0 N HCl/MeOH, then concentrated to dryness. The residue was purified by flash column chromatography to give the title compound as a light yellow solid (125 mg, 48.0% yield). MS (ESI): mass calcd. for $C_{31}H_{32}N_6O_4S$, 584.7; m/z found, 585.6 [M+H]$^+$. $^1$H NMR (400 MHz, CD$_3$OD): δ 8.49 (s, 1H), 8.35-8.20 (m, 1H), 7.45-7.33 (m, 2H), 7.30-7.22 (m, 1H), 7.20-7.12 (m, 1H), 7.11-7.02 (m, 3H), 7.00-6.93 (m, 1H), 6.11-5.96 (m, 1H), 4.54-4.05 (m, 2H), 4.03-3.67 (m, 2H), 3.25-2.85 (m, 2H), 2.65-2.53 (m, 3H), 2.14-2.07 (m, 3H), 2.04-1.65 (m, 3H), 1.64-1.38 (m, 4H).

Example 525: (R)—N-(1-Acryloylpiperidin-3-yl)-5-(2,2-difluorobenzo[d][1,3]dioxol-5-yl)-4-oxo-4,5-dihydro-3H-1-thia-3,5,8-triazaacenaphthylene-2-carboxamide

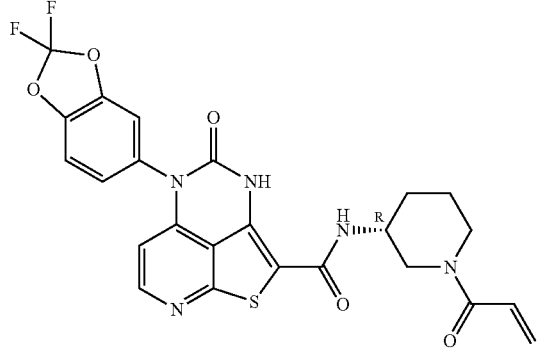

Step A: (R)-tert-Butyl 3-(3-amino-4-((2,2-difluorobenzo[d][1,3]dioxol-5-yl)amino)thieno[2,3-b]pyridine-2-carboxamido)piperidine-1-carboxylate To a Biotage vial were added 2-chloro-4-iodonicotinonitrile (1.03 g, 3.90 mmol), 2,2-difluoro-5-aminobenzodioxole (710 mg, 3.90 mmol), bis(2-diphenylphosphinophenyl)ether (64 mg, 0.12 mmol), palladium(II) acetate (17 mg, 0.078 mmol), Cs$_2$CO$_3$ (1.777 g, 5.453 mmol), and dioxane (7.8 mL) and was stirred at rt while purging with N$_2$ stream for 30 min, then it was placed in heating block at 110° C. for 1.5 h. Next, tert-butyl (3R)-3-[(2-sulfanylacetyl)amino]piperidine-1-carboxylate (Intermediate 22) (6.0 mL, 3.9 mmol) was added and it was purged with N$_2$ for 15 min, then was heated at 90° C. for 1.5 hr. The reaction mixture was diluted with EtOAc, filtered through Celite, concentrated to dryness, and purified by flash column chromatography to give the title compound as a yellow oil (1.715 g, 80.43% yield).

Step B: (R)-tert-Butyl 3-(5-(2,2-difluorobenzo[d][1,3]dioxol-5-yl)-4-oxo-4,5-dihydro-3H-1-thia-3,5,8-triazaacenaphthylene-2-carboxamido)piperidine-1-carboxylate. To a 40 mL vial were added (R)-tert-butyl 3-(3-amino-4-((2,2-difluorobenzo[d][1,3]dioxol-5-yl)amino)thieno[2,3-b]pyridine-2-carboxamido)piperidine-1-carboxylate (1.5 g, 2.7 mmol), acetonitrile (5.5 mL), Cs$_2$CO$_3$ (1.34 g, 4.11 mmol), CDI (888 mg, 5.48 mmol) and was stirred at 75° C. for 1.5 h. After 1.5 h, more CDI (888 mg, 5.48 mmol) was added and was heated for an additional 50 min. The reaction mixture was diluted with EtOAc and H$_2$O/brine, the organic layer was collected, dried over anhydrous Na$_2$SO$_4$, filtered, and concentrated to dryness. The residue was purified by flash column chromatography to give the title compound as a brown oil (1.587 g, 89.1% yield)

Step C: (R)-5-(2,2-difluorobenzo[d][1,3]dioxol-5-yl)-4-oxo-N-(piperidin-3-yl)-4,5-dihydro-3H-1-thia-3,5,8-triazaacenaphthylene-2-carboxamide To a 40 mL round bottom flask were added (R)-tert-butyl 3-(5-(2,2-difluorobenzo[d][1,3]dioxol-5-yl)-4-oxo-4,5-dihydro-3H-1-thia-3,5,8-triazaacenaphthylene-2-carboxamido)piperidine-1-carboxylate (562 mg, 0.98 mmol), DCM (1.96 mL), and TFA (0.38 mL, 5.0 mmol) and was stirred at rt for 15 min, then DCE (1.96 mL) was added and was heated at 40° C. for 20 min. Another 5 equivalents of TFA 0.38 mL) was added and was heated at 50° C. for 20 min. The reaction was quenched with saturated aqueous NaHCO$_3$, diluted with DCM, and the organic layer was collected. EtOAc was added to the aqueous phase and the organic phase collected. The aqueous phase was extracted again with 5% MeOH in EtOAc. The combined organic phases were dried over anhydrous Na$_2$SO$_4$, filtered, concentrated to dryness to yield the title compound as a yellow foam (6.60 mg).

Step D: (R)—N-(1-Acryloylpiperidin-3-yl)-5-(2,2-difluorobenzo[d][1,3]dioxol-5-yl)-4-oxo-4,5-dihydro-3H-1-thia-3,5,8-triazaacenaphthylene-2-carboxamide The title compound was prepared in a manner analogous to Method 1, step I in Example 1. MS (ESI): mass calcd. for C$_{24}$H$_{19}$F$_2$N$_5$O$_5$S, 527.5; m/z found, 528.0 [M+H]$^+$. $^1$H NMR (500 MHz, CD$_3$OD): δ 8.31 (d, J=5.6 Hz, 1H), 7.44 (d, J=8.4 Hz, 2H), 7.30 (dd, J=8.5, 2.0 Hz, 1H), 6.86-6.73 (m, 1H), 6.25-6.17 (m, 2H), 5.78-5.68 (m, 1H), 4.58-4.51 (m, 0.5H), 4.32 (d, J=13.5 Hz, 0.5H), 4.22-4.15 (m, 0.5H), 4.04-3.92 (m, 1.5H), 3.17 (t, J=11.5 Hz, 1H), 2.96-2.83 (m, 1H), 2.07 (d, J=12.8 Hz, 1H), 1.92-1.83 (m, 1H), 1.78-1.67 (m, 1H), 1.64-1.53 (m, 1H).

Example 526: (R)—N-(1-Acryloylpiperidin-3-yl)-4-oxo-5-(4-phenylpyridin-2-yl)-4,5-dihydro-3H-1-thia-3,5,8-triazaacenaphthylene-2-carboxamide

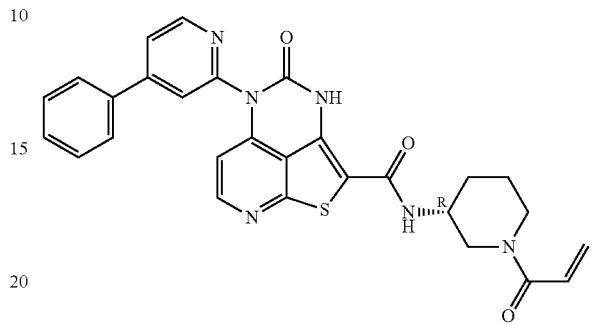

The title compound was prepared in a manner analogous to Method 1, steps C-I in Example 1, and using 4-phenylpyridin-2-amine in Step C and tert-butyl (3R)-3-aminopiperidine-1-carboxylate Step G. MS (ESI): mass calcd. for C$_{28}$H$_{24}$N$_6$O$_3$S, 524.6; m/z found, 525.2 [M+H]$^+$. $^1$H NMR (400 MHz, CD$_3$OD): δ 8.75-8.66 (m, 1H), 8.34-8.30 (m, 1H), 7.96-7.91 (m, 1H), 7.90-7.85 (m, 1H), 7.83-7.78 (m, 2H), 7.54-7.44 (m, 3H), 6.84-6.69 (m, 1H), 6.28-6.22 (m, 1H), 6.21-6.12 (m, 1H), 5.77-5.65 (m, 1H), 4.35-3.86 (m, 3H), 3.21-3.09 (m, 1H), 3.00-2.81 (m, 1H), 2.13-1.97 (m, 1H), 1.93-1.80 (m, 1H), 1.78-1.65 (m, 1H), 1.62-1.49 (m, 1H).

Example 527: (R)—N-(1-Acryloylpiperidin-3-yl)-4-oxo-5-(3-phenoxyphenyl)-4,5-dihydro-3H-1-thia-3,5,8-triazaacenaphthylene-2-carboxamide

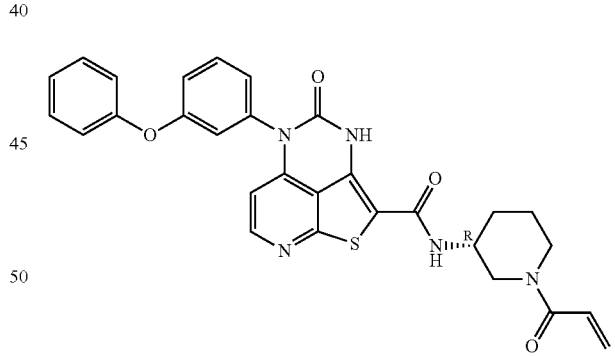

The title compound was prepared using analagous to Example 506, using 3-phenoxyaniline in place of 6-phenoxypyridin-3-amine in step A. MS (ESI): mass calcd. for C$_{29}$H$_{25}$N$_5$O$_4$S, 539.6; m/z found, 540.2 [M+H]$^+$. $^1$H NMR (400 MHz, DMSO-d$_6$): δ 10.18 (br. s., 1H), 8.35 (d, J=5.56 Hz, 1H), 8.03-8.15 (m, 1H), 7.61 (t, J=8.08 Hz, 1H), 7.40-7.47 (m, 2H), 7.24 (d, J=8.59 Hz, 1H), 7.15-7.22 (m, 3H), 7.09-7.15 (m, 2H), 6.72-6.88 (m, 1H), 6.06-6.16 (m, 2H), 5.65-5.73 (m, 1H), 4.43-4.52 (m, 0.5H), 4.17-4.27 (m, 0.5H), 3.94-4.11 (m, 1H), 3.72-3.84 (m, 1H), 3.04-3.15 (m, 0.5H), 2.92-3.04 (m, 0.5H), 2.71-2.84 (m, 0.5H), 2.60-2.70 (m, 0.5H), 1.88-1.98 (m, 1H), 1.73-1.84 (m, 1H), 1.57-1.73 (m, 1H), 1.35-1.51 (m, 1H).

Example 528: (R)—N-(1-Acryloylpiperidin-3-yl)-4-oxo-5-(5-phenoxypyrazin-2-yl)-4,5-dihydro-3H-1-thia-3,5,8-triazaacenaphthylene-2-carboxamide

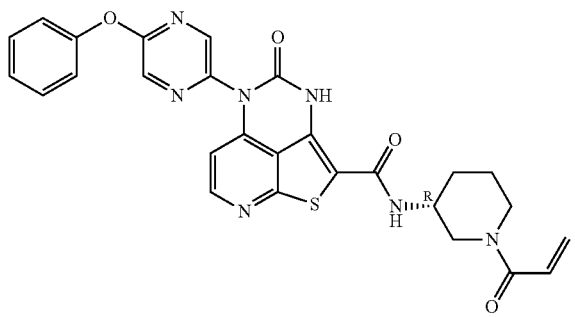

Step A: 5-Phenoxypyrazin-2-amine

A mixture of phenol (1.75 g, 18.6 mmol), 5-bromopyrazin-2-amine (3.0 g, 17 mmol), $Cs_2CO_3$ (7.85 g, 24.1 mmol), CuI (330 mg, 1.72 mmol), N,N-dimethylglycine (180 mg, 1.75 mmol) in dioxane was sparged with $N_2$ and heated to 115° C. under $N_2$ for 2 h. After cooling to room temperature, the mixture was purified by flash column chromatography to give the title compound as a yellow solid (2.0 g, 62% yield).

Step B: (R)—N-(1-Acryloylpiperidin-3-yl)-4-oxo-5-(5-phenoxypyrazin-2-yl)-4,5-dihydro-3H-1-thia-3,5,8-triazaacenaphthylene-2-carboxamide The title compound was prepared in a manner analogous to Method 1, steps C-I in Example 1, and using 5-phenoxypyrazin-2-amine in place of 2-methyl-4-phenoxy-aniline in step C, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{27}H_{23}N_7O_4S$, 541.6; m/z found, 542.7 [M+H]$^+$. $^1$H NMR (400 MHz, CD$_3$OD): δ 8.51-8.44 (m, 1H), 8.38-8.26 (m, 2H), 7.52-7.39 (m, 2H), 7.33-7.20 (m, 3H), 6.86-6.70 (m, 1H), 6.39-6.31 (m, 1H), 6.25-6.11 (m, 1H), 5.80-5.65 (m, 1H), 4.57-3.85 (m, 3H), 3.22-3.10 (m, 1H), 2.99-2.79 (m, 1H), 2.14-2.00 (m, 1H), 1.91-1.81 (m, 1H), 1.8-1.66 (m, 1H), 1.64-1.50 (m, 1H).

Example 529: (R)—N-(1-Acryloylpiperidin-3-yl)-5-(3-isopropylphenyl)-4-oxo-4,5-dihydro-3H-1-thia-3,5,8-triazaacenaphthylene-2-carboxamide

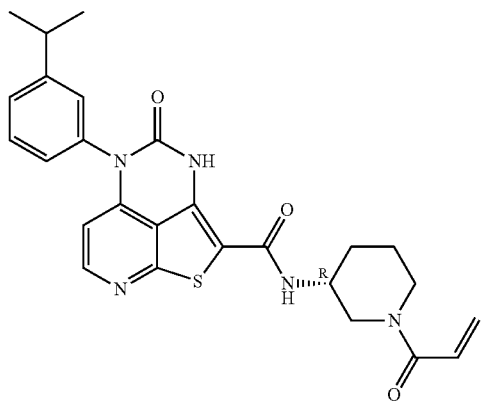

The title compound was prepared in a manner analogous to Method 1, steps E-I in Example 1, using 3-isopropylaniline in Step C, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{26}H_{27}N_5O_3S$, 489.6; m/z found, 490.2 [M+H]$^+$. $^1$H NMR (400 MHz, CD$_3$OD): δ 8.32-8.26 (m, 1H), 7.57-7.48 (m, 1H), 7.46-7.39 (m, 1H), 7.33-7.28 (m, 1H), 7.23-7.19 (m, 1H), 6.83-6.74 (m, 1H), 6.27-6.15 (m, 1H), 6.11-6.05 (m, 1H), 5.79-5.67 (m, 1H), 4.43-4.18 (m, 1H), 4.18-3.90 (m, 2H), 3.24-3.10 (m, 1H), 3.03-2.83 (m, 2H), 2.12-1.99 (m, 1H), 1.91-1.82 (m, 1H), 1.77-1.66 (m, 1H), 1.65-1.51 (m, 1H) 1.31-1.26 (m, 6H).

Example 530: (R)-5-(*S)-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide

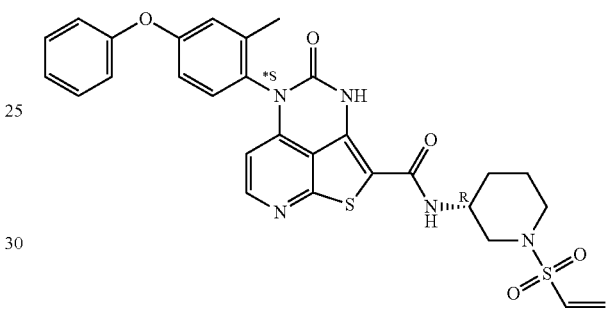

Step A: (R)-tert-butyl 3-(5-(*S)-(2-methyl-4-phenoxyphenyl)-4-oxo-4,5-dihydro-3H-1-thia-3,5,8-triazaacenaphthylene-2-carboxamido)piperidine-1-carboxylate The title compound was prepared in a manner analogous to Method 1, steps A-G (including Chiral Resolution Method A to obtain the *S atropisomer after Step F) in Example 1, and using tert-butyl (3R)-3-aminopiperidine-1-carboxylate in place of tert-butyl (3R,5R)-3-amino-5-fluoro-piperidine-1-carboxylate in step G.

Step B: (R)-5-(*S)-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide A solution of (R)-tert-butyl 3-(5-(*S)-(2-methyl-4-phenoxyphenyl)-4-oxo-4,5-dihydro-3H-1-thia-3,5,8-triazaacenaphthylene-2-carboxamido)piperidine-1-carboxylate (100 mg, 0.167 mmol) in 6 M HCl (15 mL, in MeOH) was concentrated to dryness to get a yellow solid. The residue was diluted in DCM (30 mL) and triethylamine (84 mg, 0.84 mmol) was added, followed by ethenesulfonyl chloride (21 mg, 0.17 mmol). The reaction was stirred at rt for 1 h, then concentrated to dryness and purified by flash column chromatography to give the title compound as a white yellow solid (54 mg, 54% yield). MS (ESI): mass calcd. for $C_{29}H_{27}N_5O_5S_2$, 589.7; m/z found, 590.4 [M+H]$^+$. $^1$H NMR (400 MHz, CD$_3$OD): δ 8.33 (d, J=5.6 Hz, 1H), 7.49-7.34 (m, 2H), 7.33-7.25 (m, 1H), 7.24-7.14 (m, 1H), 7.13-7.02 (m, 3H), 7.00-6.93 (m, 1H), 6.74-6.57 (m, 1H), 6.18 (d, J=16.6 Hz, 1H), 6.13-6.02 (m, 2H), 4.14-4.00 (m, 1H), 3.83-3.68 (m, 1H), 3.63-3.47 (m, 1H), 2.79-2.58 (m, 2H), 2.12 (s, 3H), 2.03-1.85 (m, 2H), 1.75-1.64 (m, 1H), 1.63-1.50 (m, 1H).

Example 531: (R)-5-([1,1'-Biphenyl]-3-yl)-N-(1-acryloylpyrrolidin-3-yl)-4-oxo-4,5-dihydro-3H-1-thia-3,5,8-triazaacenaphthylene-2-carboxamide

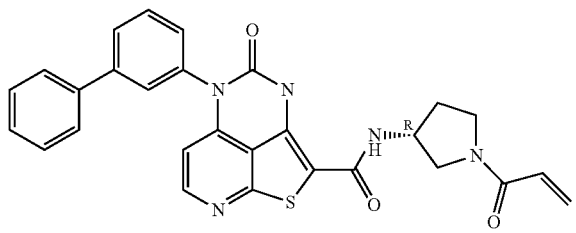

The title compound was prepared in a manner analogous to Method 1, steps C-I in Example 1, and using [1,1'-biphenyl]-3-amine (Intermediate 46) in place of 2-methyl-4-phenoxyaniline in step C, and using tert-butyl (3R)-3-aminopyrrolidine-1-carboxylate in place of tert-butyl (3R,5R)-3-amino-5-fluoro-piperidine-1-carboxylate in step G. MS (ESI): mass calcd. for $C_{28}H_{23}N_5O_3S$, 509.6; m/z found, 510.9 $[M+H]^+$. $^1H$ NMR (400 MHz, $CD_3OD$): δ 8.26 (d, J=5.6 Hz, 1H), 7.82-7.76 (m, 1H), 7.73-7.58 (m, 4H), 7.49-7.30 (m, 4H), 6.68-6.50 (m, 1H), 6.32-6.21 (m, 1H), 6.15 (d, J=5.6 Hz, 1H), 5.78-5.65 (m, 1H), 4.67-4.55 (m, 1H), 4.00-3.45 (m, 4H), 2.37-2.18 (m, 1H), 2.17-1.97 (m, 1H).

Example 532: (R,E)-5-(*S)-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide

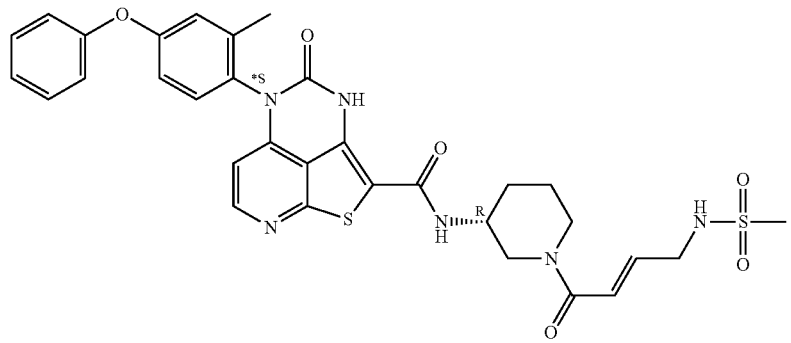

To a solution of (R,E)-N-(1-(4-aminobut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide (Example 520) (157 mg, 0.269 mmol) and triethylamine (55 mg, 0.54 mmol) in DCM (10 mL) was added methanesulfonyl chloride (31 mg, 0.27 mmol) and was stirred at room temperature for 15 minutes. The mixture was dispersed between DCM and water, and the organic layer was collected, concentrated to dryness, and purified by flash column chromatography, then by preparative TLC to give the title compound (137 mg, 76.0% yield). MS (ESI): mass calcd. for $C_{32}H_{32}N_6O_6S_2$, 660.8; m/z found, 661.2 $[M+H]^+$. $^1H$ NMR (400 MHz, DMSO-$d_6$): δ 10.17 (s, 1H), 8.35-8.28 (m, 1H), 8.13-7.99 (m, 1H), 7.45-7.39 (m, 2H), 7.38-7.33 (m, 1H), 7.32-7.27 (m, 1H), 7.20-7.15 (m, 1H), 7.13-7.08 (m, 2H), 7.08-7.04 (m, 1H), 6.99-6.92 (m, 1H), 6.64-6.55 (m, 1H), 6.00-5.91 (m, 1H), 4.51-4.12 (m, 1H), 4.04-3.92 (m, 1H), 3.79-3.71 (m, 3H), 3.11-2.90 (m, 1H), 2.88 (s, 3H), 2.76-2.58 (m, 1H), 2.04 (s, 3H), 1.95-1.88 (m, 1H), 1.80-1.70 (m, 1H), 1.69-1.56 (m, 1H), 1.46-1.33 (m, 1H).

Example 533: (R)—N-(1-Acryloylpiperidin-3-yl)-4-oxo-5-(3-propylphenyl)-4,5-dihydro-3H-1-thia-3,5,8-triazaacenaphthylene-2-carboxamide

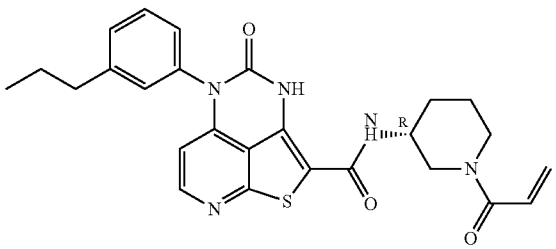

The title compound was prepared in a manner analogous to Method 1, steps C-I in Example 1, and using 3-propyl aniline in Step C tert-butyl (3R)-3-aminopiperidine-1-carboxylate in Step G. MS (ESI): mass calcd. for $C_{26}H_{27}N_5O_3S$, 489.6; m/z found, 491.1 $[M+H]^+$. $^1H$ NMR (400 MHz, $CD_3OD$): δ 8.29-8.26 (d, J=5.6 Hz, 1H), 7.53-7.47 (m, 1H), 7.39-7.35 (m, 1H), 7.27-7.20 (m, 2H), 6.84-6.74 (m, 1H), 6.23-6.15 (m, 1H), 6.09-6.06 (m, 1H), 5.76-5.68 (m, 1H), 4.56-4.26 (m, 1H), 4.20-3.92 (m, 2H), 3.21-3.12 (m, 1H), 2.95-2.83 (m, 1H), 2.68 (t, J=7.6 Hz, 2H), 2.10-2.02 (m, 1H), 1.90-1.82 (m, 1H), 1.77-1.63 (m, 3H), 1.62-1.53 (m, 1H), 0.96 (t, J=7.3 Hz, 3H).

Example 534: (R)—N-(1-Acryloylpiperidin-3-yl)-5-(3-cyclobutylphenyl)-4-oxo-4,5-dihydro-3H-1-thia-3,5,8-triazaacenaphthylene-2-carboxamide

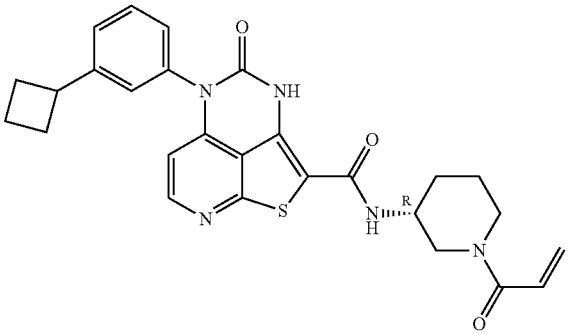

Step A: (R)-tert-Butyl 3-(5-(3-cyclobutylphenyl)-4-oxo-4,5-dihydro-3H-1-thia-3,5,8-triazaacenaphthylene-2-carboxamido)piperidine-1-carboxylate To a microwave vial containing a stir bar, 2-chloro-4-iodo-pyridine-3-carbonitrile (1.152 g, 4.356 mmol) and 3-cyclobutylaniline (636 mg, 4.32 mmol) were added DPEphos (126 mg, 0.234 mmol), Pd(OAc)$_2$ (40.6 mg, 0.181 mmol), and Cs$_2$CO$_3$ (2.22 g, 6.81 mmol). Dioxane (10 mL) was added to the reaction mixture via syringe and was degassed under vacuum for 1 minute, then vented to nitrogen. The reaction mixture was heated at 130° C. for 60 minutes. The reaction was cooled to rt and treated with tert-butyl (3R)-3-[(2-sulfanylacetyl)amino]piperidine-1-carboxylate (Intermediate 22) (1.5 g, 0.411 mmol) as a solution in dioxane (6 mL), and was evacuated and then flushed with nitrogen. The reaction was then stirred at 130° C. for 1 h followed by treatment with solid CDI (2.19 g, 13.5 mmol) in one portion, resealed, and stirred at 90° C. for 30 min. The reaction was diluted with EtOAc (100 mL) and saturated aqueous sodium bicarbonate (100 mL), and the organic phase collected. The aqueous layer was extracted with EtOAc (100 mL), and the combined organics were dried over anhydrous MgSO$_4$, concentrated to dryness, and purified by flash column chromatography to give the title compound as an off white solid (1.49 g, 62.3% yield).

Step B: (R)-5-(3-Cyclobutylphenyl)-4-oxo-N-(piperidin-3-yl)-4,5-dihydro-3H-1-thia-3,5,8-triazaacenaphthylene-2-carboxamide A solution of (R)-tert-butyl 3-(5-(3-cyclobutylphenyl)-4-oxo-4,5-dihydro-3H-1-thia-3,5,8-triazaacenaphthylene-2-carboxamido)piperidine-1-carboxylate (1.163 g, 2.124 mmol) in dioxane (11 mL) was treated with 4 M HCl-dioxane (11 mL). The reaction mixture was stirred at room temperature for 2.5 h. Et$_2$O (20 mL) was added and the yellow precipitate that formed was isolated by filtration and dried overnight under vacuum to give the title compound (858.5 mg, 77.68% yield).

Step C: (R)—N-(1-Acryloylpiperidin-3-yl)-5-(3-cyclobutylphenyl)-4-oxo-4,5-dihydro-3H-1-thia-3,5,8-triazaacenaphthylene-2-carboxamide The title compound was prepared in a manner analogous to Method 1, step I in Example 1. MS (ESI): mass calcd. for C$_{27}$H$_{27}$N$_5$O$_3$S, 501.6; m/z found, 502.1 [M+H]$^+$. $^1$H NMR (600 MHz, CD$_3$OD): δ 8.35-8.23 (d, J=5.5 Hz, 1H), 7.59-7.50 (m, 1H), 7.46-7.38 (d, J=7.8 Hz, 1H), 7.33-7.27 (s, 1H), 7.25-7.19 (d, J=7.8 Hz, 1H), 6.85-6.74 (m, 1H), 6.26-6.17 (m, 1H), 6.15-6.07 (d, J=5.6 Hz, 1H), 5.80-5.68 (m, 1H), 4.60-4.27 (m, 1H), 4.23-3.92 (m, 2H), 3.71-3.62 (m, 1H), 3.24-3.12 (m, 1H), 3.00-2.83 (m, 1H), 2.45-2.32 (m, 2H), 2.27-2.16 (m, 2H), 2.14-2.02 (m, 2H), 1.96-1.83 (m, 2H), 1.81-1.70 (m, 1H), 1.67-1.52 (m, 1H).

Example 535: (R)-5-(*S)-(2-Methyl-4-phenoxyphenyl)-N-(1-trideuteriomethylpiperidin-3-yl)-4-oxo-4,5-dihydro-3H-1-thia-3,5,8-triazaacenaphthylene-2-carboxamide A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) (100 mg, 0.187 mmol) and dideuterioformaldehyde (1.1 mL, 37 wt. % in H$_2$O) in MeOH (2.5 mL) was stirred at rt for 3 h. Sodium cyanoborodeuteride (49 mg, 0.74 mmol) was added and the mixture was stirred at rt for 2 h. The concentrated to dryness and the residue was purified by preparative TLC to give the title compound as a yellow solid (65 mg, 97% yield). MS (ESI): mass calcd. for C$_{28}$H$_{24}$D$_3$N$_5$O$_3$S, 516.6; m/z found, 517.2 [M+H]$^+$. $^1$H NMR (400 MHz, CD$_3$OD): δ 8.32 (d, J=5.6 Hz, 1H), 7.45-7.33 (m, 2H), 7.33-7.25 (m, 1H), 7.23-7.12 (m, 1H), 7.10-7.02 (m, 3H), 6.99-6.91 (m, 1H), 6.06 (d, J=5.5 Hz, 1H), 4.28-4.16 (m, 1H), 3.37-3.32 (m, 1H), 3.18-3.05 (m, 1H), 2.76-2.58 (m, 2H), 2.10 (s, 3H), 2.03-1.93 (m, 2H), 1.84-1.72 (m, 1H), 1.70-1.58 (m, 1H).

Example 536: (R)—N-(1-Acryloylpiperidin-3-yl)-5-(3-methyl-4-phenoxyphenyl)-4-oxo-4,5-dihydro-3H-1-thia-3,5,8-triazaacenaphthylene-2-carboxamide

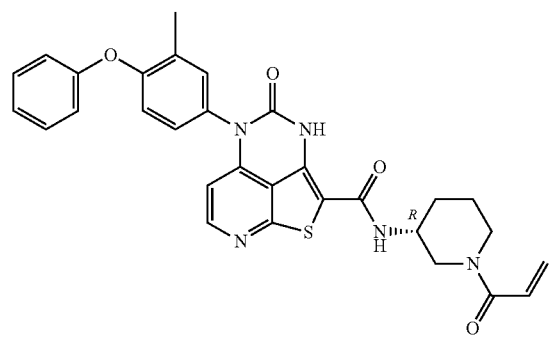

The title compound was prepared using the procedures found in Example 534, steps A-C, and using 2-methyl-4-phenoxy-aniline in place of 3-cyclobutylaniline in step A. MS (ESI): mass calcd. for C$_{30}$H$_{27}$N$_5$O$_4$S, 553.6; m/z found, 554.1 [M+H]$^+$. 1H NMR (400 MHz, MeOD) δ 8.33 (d, J=5.6 Hz, 1H), 7.43-7.33 (m, 3H), 7.22 (d, J=8.5 Hz, 1H), 7.17-7.09 (m, 1H), 7.06-7.00 (m, 3H), 6.87-6.75 (m, 1H), 6.27-6.15 (m, 2H), 5.80-5.70 (m, 1H), 4.59-4.27 (m, 1H), 4.22-3.92 (m, 2H), 3.24-3.12 (m, 1H), 3.01-2.85 (m, 1H), 2.32 (s, 3H), 2.15-2.03 (m, 1H), 1.95-1.51 (m, 3H).

Example 537: (R)—N-(1-Acryloylpiperidin-3-yl)-4-oxo-5-(5-phenylpyridin-3-yl)-4,5-dihydro-3H-1-thia-3,5,8-triazaacenaphthylene-2-carboxamide

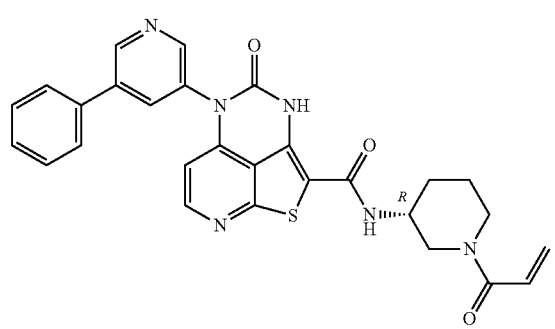

The title compound was prepared using step A in the procedure found in Example 526, using 5-phenylpyridin-3-amine in place of 4-phenylpyridin-2-amine, and using Method 1, steps E-I in Example 1, and using tert-butyl (3R)-3-aminopiperidine-1-carboxylate in place of tert-butyl (3R,5R)-3-amino-5-fluoro-piperidine-1-carboxylate in step G, to yield the title compound. MS (ESI): mass calcd. for $C_{28}H_{24}N_6O_3S$, 524.6; m/z found, 525.2 [M+H]$^+$. $^1$H NMR (400 MHz, CD$_3$OD): δ 9.05-8.92 (m, 1H), 8.70-8.54 (m, 1H), 8.40-8.28 (m, 1H), 8.28-8.22 (m, 1H), 7.77-7.66 (m, 2H), 7.55-7.41 (m, 3H), 6.83-6.69 (m, 1H), 6.29-6.22 (m, 1H), 6.21-6.15 (m, 1H), 5.79-5.65 (m, 1H), 4.31-3.88 (m, 3H), 3.22-3.06 (m, 1H), 2.96-2.82 (m, 1H), 2.10-1.98 (m, 1H), 1.93-1.81 (m, 1H), 176-1.65 (m, 1H), 1.61-1.51 (m, 1H).

Example 538: (R)—N-(1-Acryloylpiperidin-3-yl)-4-oxo-5-(3-(pyridin-3-yl)phenyl)-4,5-dihydro-3H-1-thia-3,5,8-triazaacenaphthylene-2-carboxamide

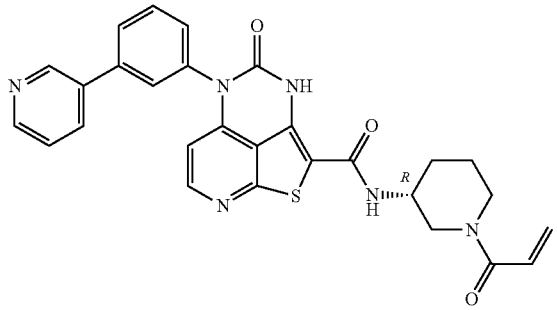

The title compound was prepared in a manner analogous to Method 1, steps C-I in Example 1, and using 3-(3-pyridyl)aniline in place of 2-methyl-4-phenoxy-aniline in step C, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{28}H_{24}N_6O_3S$, 524.6; m/z found, 525.4 [M+H]$^+$. $^1$H NMR (400 MHz, CD$_3$OD): δ 8.87 (s, 1H), 8.61-8.47 (m, 1H), 8.37-8.25 (m, 1H), 8.22-8.08 (m, 1H), 7.95-7.68 (m, 3H), 7.60-7.46 (m, 2H), 6.89-6.69 (m, 1H), 6.27-6.12 (m, 2H), 5.82-5.64 (m, 1H), 4.56-4.49 (m, 1H), 4.36-4.13 (m, 1H), 4.02-3.90 (m, 1H), 3.24-3.10 (m, 1H), 2.98-2.83 (m, 1H), 2.13-1.96 (m, 1H), 1.92-1.83 (m, 1H), 1.79-1.67 (m, 1H), 1.64-1.51 (m, 1H).

Example 539: (R)—N-(1-(Ethylsulfonyl)piperidin-3-yl)-5-(*S)-(2-methyl-4-phenoxyphenyl)-4-oxo-4,5-dihydro-3H-1-thia-3,5,8-triazaacenaphthylene-2-carboxamide

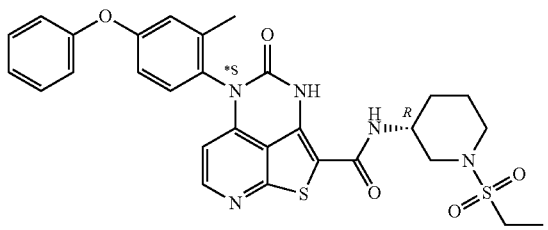

The title compound was prepared using steps A-B in the procedure found in Example 530, using ethanesulfonyl chloride in step B. MS (ESI): mass calcd. for $C_{29}H_{29}N_5O_5S_2$, 591.7; m/z found, 592.2 [M+H]$^+$. $^1$H NMR (400 MHz, CD$_3$OD and DMSO-d$_6$): δ 8.29-8.23 (m, 1H), 7.39-7.33 (m, 2H), 7.29-7.24 (m, 1H), 7.14-7.09 (m, 1H), 7.06-7.02 (m, 2H), 7.02-6.99 (m, 1H), 6.92-6.89 (m, 1H), 5.95-5.91 (m, 1H), 3.92-3.84 (m, 1H), 3.72-3.67 (m, 1H), 3.54-3.47 (m, 1H), 2.97 (q, J=7.4 Hz, 2H), 2.78-2.71 (m, 1H), 2.71-2.65 (m, 1H), 2.02 (s, 3H), 1.92-1.85 (m, 1H), 1.81-1.73 (m, 1H), 1.57-1.48 (m, 2H), 1.18 (t, J=7.3 Hz, 3H).

Example 540: (R)—N-(1-Acryloylpiperidin-3-yl)-4-oxo-5-(3-(pyridin-2-yl)phenyl)-4,5-dihydro-3H-1-thia-3,5,8-triazaacenaphthylene-2-carboxamide

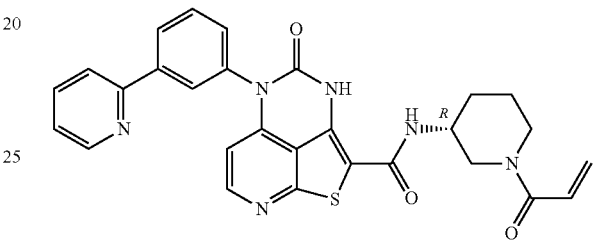

Step A: (R)-tert-Butyl 3-(5-(3-bromophenyl)-4-oxo-4,5-dihydro-3H-1-thia-3,5,8-triazaacenaphthylene-2-carboxamido)piperidine-1-carboxylate A solution of 5-(3-bromophenyl)-4-oxo-4,5-dihydro-3H-1-thia-3,5,8-triazaacenaphthylene-2-carboxylic acid (Intermediate 57) (1.5 g, 3.8 mmol), tert-butyl (3R)-3-aminopiperidine-1-carboxylate (0.77 g, 3.8 mmol), triethylamine (0.78 g, 7.7 mmol), and HATU (1.46 g, 3.84 mmol) in DMF (5 mL) was stirred at rt for 3 h. Water was added and the precipitate was filtered to give the title compound a pale yellow solid (1.6 g, 73% yield).

Step B: (R)-4-Oxo-N-(piperidin-3-yl)-5-(3-(pyridin-2-yl)phenyl)-4,5-dihydro-3H-1-thia-3,5,8-triazaacenaphthylene-2-carboxamide A solution of (R)-tert-butyl 3-(5-(3-bromophenyl)-4-oxo-4,5-dihydro-3H-1-thia-3,5,8-triazaacenaphthylene-2-carboxamido)piperidine-1-carboxylate (400 mg, 0.70 mmol), trimethyl(2-pyridyl)silane (186 mg, 0.770 mmol), and Pd(PPh$_3$)$_4$ (40 mg, 0.035 mmol) in DMF (5 mL) was stirred at 110° C. for 2 h. The reaction mixture was concentrated to dryness and the residue was purified by flash column chromatography to get the intermediate as a yellow solid. The solid was dissolved in MeOH (4 mL) and saturated aqueous HCl (4 mL), and the resulting mixture was heated to 50° C. for 30 min. The reaction mixture was concentrated to dryness and was purified by flash column chromatography to give the title compound (240 mg, 73% yield).

Step C: (R)—N-(1-Acryloylpiperidin-3-yl)-4-oxo-5-(3-(pyridin-2-yl)phenyl)-4,5-dihydro-3H-1-thia-3,5,8-triazaacenaphthylene-2-carboxamide The title compound was prepared in a manner analogous to Method 1, step I in Example 1, using (R)-4-oxo-N-

(piperidin-3-yl)-5-(3-(pyridin-2-yl)phenyl)-4,5-dihydro-3H-1-thia-3,5,8-triazaacenaphthylene-2-carboxamide to yield the title compound. MS (ESI): mass calcd. for $C_{28}H_{24}N_6O_3S$, 524.6; m/z found, 525.4 [M+H]$^+$. $^1$H NMR (400 MHz, CD$_3$OD): δ 8.61-8.54 (m, 1H), 8.20 (d, J=5.6 Hz, 1H), 8.16-8.07 (m, 2H), 7.91-7.77 (m, 2H), 7.71-7.63 (m, 1H), 7.56-7.48 (m, 1H), 7.35-7.25 (m, 1H), 6.82-6.68 (m, 1H), 6.23-6.09 (m, 2H), 5.76-5.60 (m, 1H), 4.58-4.16 (m, 2H), 3.97-3.89 (m, 1H), 3.17-3.04 (m, 1H), 2.93-2.74 (m, 1H), 2.08-2.01 (m, 1H), 1.85-1.76 (m, 1H), 1.74-1.62 (m, 1H), 1.56-1.44 (m, 1H).

Example 541: (R,E)-5-(3-Chloro-4-phenoxyphenyl)-N-(1-(4-(dimethylamino)but-2-enol)piperidin-3-yl)-4-oxo-4,5-dihydro-3H-1-thia-3,5,8-triazaacenaphthylene-2-carboxamide

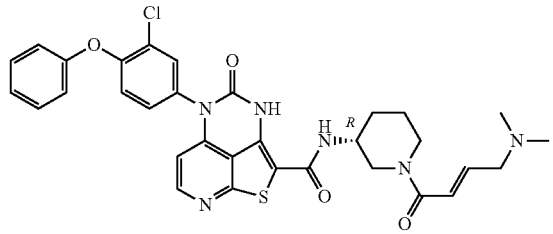

The title compound was prepared using a method analogous to Example 75, using (E)-4-(dimethylamino)but-2-enoic acid and (R)-5-(3-Chloro-4-phenoxyphenyl)-4-oxo-N-(piperidin-3-yl)-4,5-dihydro-3H-1-thia-3,5,8-triazaacenaphthylene-2-carboxamide (Example 581) to yield the title compound. MS (ESI): mass calcd. for $C_{32}H_{31}ClN_6O_4S$, 631.1; m/z found, 631.6 [M+H]$^+$. $^1$H NMR (400 MHz, CD$_3$OD): δ 8.41 (s, 1H), 8.37-8.27 (m, 1H), 7.77-7.60 (m, 1H), 7.48-7.31 (m, 3H), 7.25-7.10 (m, 2H), 7.09-6.89 (m, 2H), 6.92-6.78 (m, 1H), 6.77-6.60 (m, 1H), 6.32-6.18 (m, 1H), 4.54-3.86 (m, 3H), 3.78-3.60 (m, 2H), 3.25-3.06 (m, 1H), 2.98-2.80 (m, 1H), 2.77-2.60 (m, 6H), 2.15-1.97 (m, 1H), 1.95-1.83 (m, 1H), 1.81-1.46 (m, 2H).

Example 542: (R)—N-(1-Isopropylpiperidin-3-yl)-5-(*S)-(2-methyl-4-phenoxyphenyl)-4-oxo-4,5-dihydro-3H-1-thia-3,5,8-triazaacenaphthylene-2-carboxamide

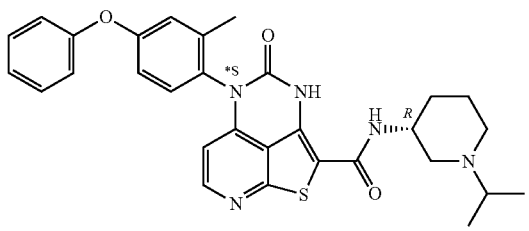

To a solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) (90 mg, 0.18), MeOH (2 mL), and acetone (3 mL) was added sodium triacetoxyborohydride (76 mg, 0.36 mmol). The reaction mixture was maintained at room temperature overnight, then concentrated to dryness, and purified by flash column chromatography to give the title compound as yellow solid (75 mg, 71% yield). MS (ESI): mass calcd. for $C_{30}H_{31}N_5O_3S$, 541.7; m/z found, 542.3 [M+H]$^+$. $^1$H NMR (400 MHz, CD$_3$OD): δ 8.48 (s, 1H), 8.33 (d, J=5.6 Hz, 1H), 7.46-7.36 (m, 2H), 7.33-7.26 (m, 1H), 7.21-7.14 (m, 1H), 7.12-7.04 (m, 3H), 7.01-6.93 (m, 1H), 6.07 (d, J=5.6 Hz, 1H), 4.40-4.26 (m, 1H), 3.54-3.40 (m, 2H), 3.36-3.31 (m, 1H), 3.01-2.79 (m, 2H), 2.11 (s, 3H), 2.09-2.01 (m, 2H), 1.95-1.80 (m, 1H), 1.76-1.64 (m, 1H), 1.39-1.31 (m, 6H).

Example 543: N-((3S,4S)-1-Acryloyl-4-fluoropyrrolidin-3-yl)-4-oxo-5-(4-phenoxyphenyl)-4,5-dihydro-3H-1-thia-3,5,8-triazaacenaphthylene-2-carboxamide

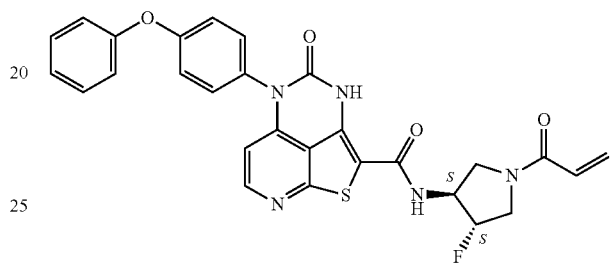

Step A: (3S,4S)-tert-Butyl 3-fluoro-4-(4-oxo-5-(4-phenoxyphenyl)-4,5-dihydro-3H-1-thia-3,5,8-triazaacenaphthylene-2-carboxamido)pyrrolidine-1-carboxylate To a solution of (3S,4S)-tert-butyl 3-amino-4-fluoropyrrolidine-1-carboxylate (11.85 mL, 1.185 mmol), diisopropylethylamine (0.622 mL, 3.56 mmol), and THF (5 mL) at 0° C. was added 4-oxo-5-(4-phenoxyphenyl)-4,5-dihydro-3H-1-thia-3,5,8-triazaacenaphthylene-2-carbonyl chloride (Intermediate 40) (0.500 g, 1.19 mmol) dropwise and stirred for 30 min. The reaction was quenched with saturated NaHCO$_3$, extracted with DCM, concentrated to dryness, and the residue was purified by flash column chromatography to give the title compound as an off white solid (480 mg, 69% yield).

Step B: N-((3S,4S)-4-Fluoropyrrolidin-3-yl)-4-oxo-5-(4-phenoxyphenyl)-4,5-dihydro-3H-1-thia-3,5,8-triazaacenaphthylene-2-carboxamide To a solution of (3S,4S)-tert-butyl 3-fluoro-4-(4-oxo-5-(4-phenoxyphenyl)-4,5-dihydro-3H-1-thia-3,5,8-triazaacenaphthylene-2-carboxamido)pyrrolidine-1-carboxylate (400 mg, 0.68 mmol) in DCM (20 mL) was added TFA (11 mL) dropwise at rt and was stirred at rt for an additional 30 min. The reaction was concentrated to dryness and the residue was purified by flash column chromatography to give the title compound as an off white solid (300 mg, 90% yield).

Step C: N-((3S,4S)-1-Acryloyl-4-fluoropyrrolidin-3-yl)-4-oxo-5-(4-phenoxyphenyl)-4,5-dihydro-3H-1-thia-3,5,8-triazaacenaphthylene-2-carboxamide The title compound was prepared in a manner analogous to Method 1, step I in Example 1, using N-((3S,4S)-4-fluoropyrrolidin-3-yl)-4-oxo-5-(4-phenoxyphenyl)-4,5-dihydro-3H-1-thia-3,5,8-triazaacenaphthylene-2-carboxamide. MS (ESI): mass calcd. for $C_{28}H_{22}FN_5O_4S$, 543.6; m/z found, 544.0 [M+H]$^+$. $^1$H NMR (400 MHz, CDCl$_3$): δ 9.63 (s, 1H), 8.28 (dd, J=5.5, 2.1 Hz, 1H), 8.03-7.96 (m, 1H), 7.44-7.28 (m, 4H), 7.22-7.06 (m, 5H), 6.36 (dd, J=7.2, 5.0 Hz, 1H), 6.10 (d, J=5.5 Hz, 1H), 5.72 (td, J=8.3, 4.5 Hz, 1H), 5.34-5.22 (m, 1H), 4.84 (dt, J=11.5, 6.0 Hz, 1H), 4.67 (dt, J=10.8, 5.2 Hz, 1H), 4.05-3.69 (m, 4H).

Example 544: (S)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide

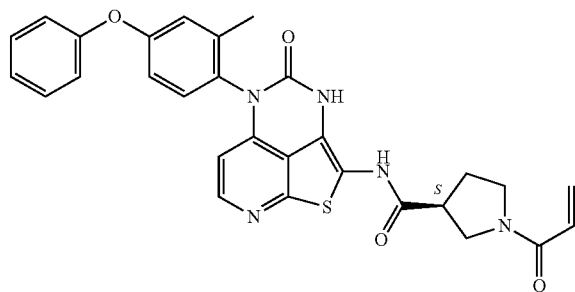

Step A: (S)-tert-Butyl 3-((5-(2-methyl-4-phenoxyphenyl)-4-oxo-4,5-dihydro-3H-1-thia-3,5,8-triazaacenaphthylen-2-yl)carbamoyl)pyrrolidine-1-carboxylate A solution of (3S)-1-tert-butoxycarbonylpyrrolidine-3-carboxylic acid (33.3 mg, 0.155 mmol), HATU (73.6 mg, 0.194 mmol), and triethylamine (39 mg, 0.39 mmol) in anhydrous DMF (3 mL) was stirred at room temperature for 10 min, then 2-amino-5-(2-methyl-4-phenoxyphenyl)-3H-1-thia-3,5,8-triazaacenaphthylen-4(5H)-one (Intermediate 56) (50 mg, 0.13 mmol) was added and the mixture was stirred for 2 h. The mixture was purified by flash column chromatography to give the title compound as a white solid (42 mg, 56% yield).

Step B: (S)—N-(5-(2-Methyl-4-phenoxyphenyl)-4-oxo-4,5-dihydro-3H-1-thia-3,5,8-triazaacenaphthylen-2-yl)pyrrolidine-3-carboxamide To a solution of (S)-tert-butyl 3-((5-(2-methyl-4-phenoxyphenyl)-4-oxo-4,5-dihydro-3H-1-thia-3,5,8-triazaacenaphthylen-2-yl)carbamoyl)pyrrolidine-1-carboxylate (42 mg, 0.072 mmol) in 6 M HCl in MeOH (12 mL) was concentrated to dryness to give the title compound as a yellow solid (35 mg, 100% yield), which used in the next step without further purification.

Step C: (S)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide The title compound was prepared in a manner analogous to Method 1, step I in Example 1. MS (ESI): mass calcd. for $C_{29}H_{25}N_5O_4S$, 539.6; m/z found, 540.4 [M+H]$^+$. $^1$H NMR (400 MHz, CD$_3$OD): δ 8.17-8.07 (m, 1H), 7.44-7.32 (m, 2H), 7.28-7.21 (m, 1H), 7.18-7.11 (m, 1H), 7.11-7.00 (m, 3H), 6.97-6.89 (m, 1H), 6.68-6.54 (m, 1H), 6.32-6.23 (m, 1H), 5.98-5.88 (m, 1H), 5.78-5.68 (m, 1H), 3.99-3.79 (m, 2H), 3.78-3.61 (m, 2H), 3.58-3.49 (m, 0.5H), 3.25-3.17 (m, 0.5H), 2.38-2.16 (m, 2H), 2.12 (s, 3H).

Example 545: (R)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide

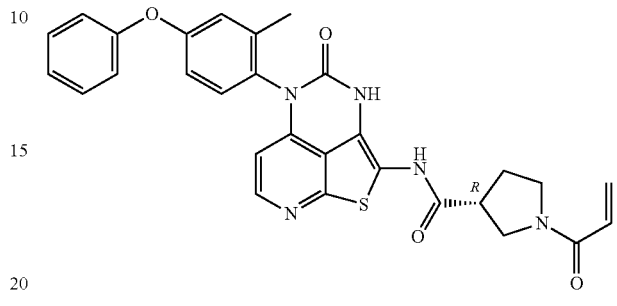

The title compound was prepared using steps A-C in the procedure found in Example 544, and using (3R)-1-tert-butoxycarbonylpyrrolidine-3-carboxylic acid in place of (3S)-1-tert-butoxycarbonylpyrrolidine-3-carboxylic acid in step A, to yield the title compound. MS (ESI): mass calcd. for $C_{29}H_{25}N_5O_4S$, 539.6; m/z found, 540.4 [M+H]$^+$. $^1$H NMR (400 MHz, CD$_3$OD): δ 8.21-8.06 (m, 1H), 7.44-7.32 (m, 2H), 7.25 (d, J=8.3 Hz, 1H), 7.20-7.15 (m, 1H), 7.12-7.01 (m, 3H), 7.00-6.93 (m, 1H), 6.68-6.54 (m, 1H), 6.34-6.20 (m, 1H), 5.97-5.87 (m, 1H), 5.80-5.68 (m, 1H), 3.99-3.80 (m, 2H), 3.79-3.65 (m, 2H), 3.59-3.48 (m, 0.5H), 3.27-3.18 (m, 0.5H), 2.37-2.16 (m, 2H), 2.13 (s, 3H).

Example 546: (R)—N-(1-(2-(Methylamino)acetyl)piperidin-3-yl)-4-oxo-5-(4-phenoxyphenyl)-4,5-dihydro-3H-1-thia-3,5,8-triazaacenaphthylene-2-carboxamide

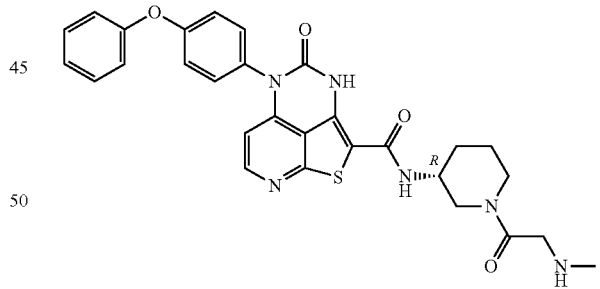

To a microwave vial was added (R)-4-oxo-5-(4-phenoxyphenyl)-N-(piperidin-3-yl)-4,5-dihydro-3H-1-thia-3,5,8-triazaacenaphthylene-2-carboxamide (Example 860) (150 mg, 0.309 mmol), sarcosine (41.3 mg, 0.463 mmol), THF (4 mL), and HATU (352 mg, 0.927 mmol) and the reaction mixture was heated in microwave at 100° C. for 5 min. The reaction was diluted with DCM, washed with water, and purified by flash column chromatography to give the title compound (125 mg, 72.7% yield). MS (ESI): mass calcd. for $C_{29}H_{28}N_6O_4S$, 556.6; m/z found, 557.0 [M+H]$^+$. $^1$H NMR (500 MHz, CDCl$_3$): δ 8.15 (dd, J=29.9, 5.6 Hz, 1H), 7.48 (s, 1H), 7.34-7.26 (m, 4H), 7.24-6.96 (m, 7H), 5.95 (dd, J=22.3, 5.5 Hz, 1H), 5.31 (s, 3H), 3.75-3.68 (m, 1H), 3.58-3.45 (m, 2H), 3.44-3.19 (m, 4H), 1.89 (p, J=6.3, 5.6 Hz, 2H), 1.81-1.59 (m, 2H).

Example 547: N—((R)-1-((S)-3-Hydroxy-2-methyl-propanoyl)piperidin-3-yl)-5-(2-methyl-4-phenoxyphenyl)-4-oxo-4,5-dihydro-3H-1-thia-3,5,8-triazaacenaphthylene-2-carboxamide

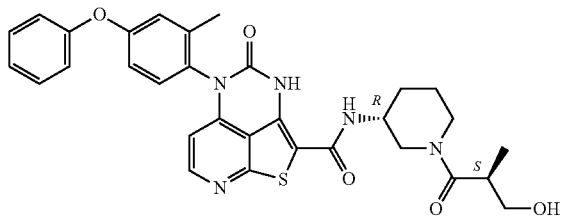

A solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) (100 mg, 0.187 mmol), (2S)-3-hydroxy-2-methyl-propanoic acid (35.0 mg, 0.279 mmol), HATU (106 mg, 0.279 mmol), and triethylamine (0.052 mL, 0.37 mmol) in DMF (3 mL) was stirred at rt overnight, then purified using flash column chromatography to give the title compound as a yellow solid (40 mg, 100% yield). MS (ESI): mass calcd. for $C_{31}H_{31}N_5O_5S$, 585.7; m/z found, 586.2 [M+H]$^+$. $^1$H NMR (400 MHz, CD$_3$OD): δ 8.32 (d, J=5.5 Hz, 1H), 7.44-7.36 (m, 2H), 7.33-7.24 (m, 1H), 7.20-7.12 (m, 1H), 7.12-7.02 (m, 3H), 7.02-6.93 (m, 1H), 6.07 (d, J=5.5 Hz, 1H), 4.39-4.26 (m, 1H), 4.24-3.89 (m, 2H), 3.79-3.66 (m, 1H), 3.58-3.47 (m, 1H), 3.17-2.96 (m, 2H), 2.95-2.68 (m, 1H), 2.11 (s, 3H), 2.07-1.99 (m, 1H), 1.94-1.78 (m, 1H), 1.75-1.52 (m, 2H), 1.11-0.99 (m, 3H).

Example 548: N-((3S,4S)-1-Acryloyl-4-methoxy-pyrrolidin-3-yl)-4-oxo-5-(4-phenoxyphenyl)-4,5-dihydro-3H-1-thia-3,5,8-triazaacenaphthylene-2-carboxamide

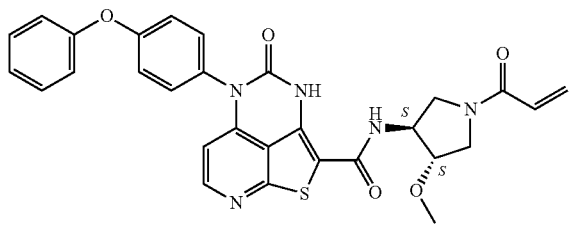

The title compound was prepared in a manner analogous to Method 1, steps A-I in Example 1, and using 4-fluoronitrobenzene in place of 5-fluoro-2-nitrotoluene in step A, and using tert-butyl (3S,4S)-3-amino-4-methoxy-cyclopentanecarboxylate in place of tert-butyl (3R,5R)-3-amino-5-fluoro-piperidine-1-carboxylate in step G, to yield the title compound. MS (ESI): mass calcd. for $C_{29}H_{25}N_5O_5S$, 555.6; m/z found, 556.15 [M+H]$^+$. $^1$H NMR (600 MHz, CDCl$_3$): δ 9.67 (s, 1H), 9.60 (s, 1H), 8.30 (dd, J=5.5, 1.6 Hz, 1H), 7.97-7.92 (m, 1H), 7.44-7.34 (m, 2H), 7.32 (ddt, J=10.1, 7.9, 3.3 Hz, 2H), 7.21-7.07 (m, 5H), 6.41-6.30 (m, 2H), 6.10 (dd, J=5.4, 1.1 Hz, 1H), 5.69 (td, J=7.8, 4.8 Hz, 1H), 4.07 (d, J=4.3 Hz, 1H), 4.00-3.92 (m, 1H), 3.84-3.70 (m, 2H), 3.67-3.53 (m, 1H), 3.49 (d, J=32.6 Hz, 3H).

Example 549: (R,Z)—N-(1-(4-Amino-2-fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

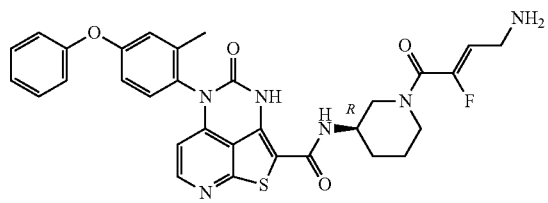

Step A: (R,Z)-tert-butyl (3-fluoro-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate A solution of (E)-4-(tert-butoxycarbonylamino)-2-fluoro-but-2-enoic acid (Intermediate 52) (105 mg, 0.480 mmol), HATU (182 mg, 0.480 mmol), and triethylamine (202 mg, 2.00 mmol) in anhydrous DMF (5 mL) was stirred at room temperature for 10 min, then (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) (200 mg, 0.40 mmol) was added and the mixture was stirred for 2 hr. The reaction mixture was purified by flash column chromatography to give the title compound as a light yellow solid (124 mg, 24.0% yield).

Step B: (R,Z)—N-(1-(4-Amino-2-fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide A solution of (R,Z)-tert-butyl (3-fluoro-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)carbamate (124 mg, 0.0973 mmol) in 6 M HCl in MeOH (10 mL) was concentrated to dryness at 50° C., and was purified by flash column chromatography to give the title compound as a light yellow solid (25 mg, 98% yield). MS (ESI): mass calcd. for $C_{31}H_{29}FN_6O_4S$, 600.7; m/z found, 601.4 [M+H]$^+$. $^1$H NMR (400 MHz, CD$_3$OD): δ 8.32-8.19 (m, 1H), 7.42-7.33 (m, 2H), 7.30-7.21 (m, 1H), 7.18-7.12 (m, 1H), 7.11-7.01 (m, 3H), 6.99-6.90 (m, 1H), 6.07-5.93 (m, 1H), 5.80-5.64 (m, 1H), 4.35-3.88 (m, 3H), 3.65-3.40 (m, 2H), 3.27-2.94 (m, 2H), 2.11 (s, 3H), 2.07-1.86 (m, 2H), 1.85-1.69 (m, 1H), 1.67-1.52 (m, 1H).

Example 550: (R,Z)—N-(1-(4-Amino-2-chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide

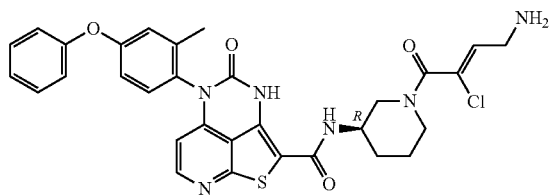

The title compound was prepared using a method analogous to Example 75 using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) and using (Z)-4-(tert-butoxycarbonylamino)-2-chloro-but-2-enoic acid (Intermediate 53). MS (ESI): mass calcd. for $C_{31}H_{29}ClN_6O_4S$, 617.1; m/z found, 617.4 $[M+H]^+$. $^1H$ NMR (400 MHz, $CD_3OD$): δ 8.40-8.29 (m, 2H), 7.44-7.36 (m, 2H), 7.32-7.26 (m, 1H), 7.22-7.14 (m, 1H), 7.12-7.03 (m, 3H), 7.01-6.95 (m, 1H), 6.36-6.15 (m, 1H), 6.12-6.05 (m, 1H), 4.31-3.70 (m, 5H), 3.09-2.78 (m, 2H), 2.19-2.04 (m, 4H), 1.97-1.86 (m, 1H), 1.85-1.73 (m, 1H), 1.72-1.57 (m, 1H).

Example 551: (R)-5-([1,1'-Biphenyl]-3-yl)-N-(1-(2-(methylamino)acetyl)piperidin-3-yl)-4-oxo-4,5-dihydro-3H-1-thia-3,5,8-triazaacenaphthylene-2-carboxamide

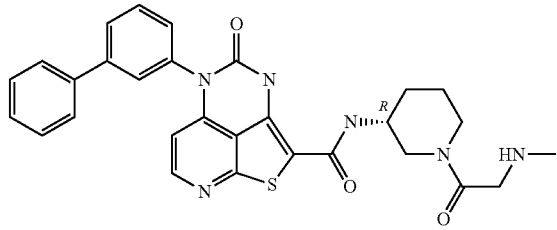

Step A: (R)-5-([1,1'-Biphenyl]-3-yl)-4-oxo-N-(piperidin-3-yl)-4,5-dihydro-3H-1-thia-3,5,8-triazaacenaphthylene-2-carboxamide The title compound was prepared using analogous conditions described in Method 1, steps C-H, in Example 1, and using [1,1'-biphenyl]-3-amine (Intermediate 46) in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{23}N_5O_2S$, 469.56; m/z found, 470.3 $[M+H]^+$.

Step B: (R)-tert-Butyl (2-(3-(5-([1,1'-biphenyl]-3-yl)-4-oxo-4,5-dihydro-3H-1-thia-3,5,8-triazaacenaphthylene-2-carboxamido)piperidin-1-yl)-2-oxoethyl)(methyl)carbamate To a solution of 2-[tert-butoxycarbonyl(methyl)amino]acetic acid (Intermediate 21) (0.189 g, 1.00 mmol), HATU (0.38 g, 1.0 mmol), and triethylamine (0.202 g, 2.00 mmol) in DMF (5 mL) was added (R)-5-([1,1'-biphenyl]-3-yl)-4-oxo-N-(piperidin-3-yl)-4,5-dihydro-3H-1-thia-3,5,8-triazaacenaphthylene-2-carboxamide (0.47 g, 1.0 mmol) and was stirred at room temperature for 30 minutes. The reaction was purified by normal phase flash column chromatography ($SiO_2$) to give the title compound (0.577 g, 90.0% yield).

Step C: (R)-5-([1,1'-Biphenyl]-3-yl)-N-(1-(2-(methylamino)acetyl)piperidin-3-yl)-4-oxo-4,5-dihydro-3H-1-thia-3,5,8-triazaacenaphthylene-2-carboxamide To a solution of (R)-tert-butyl (2-(3-(5-([1,1'-biphenyl]-3-yl)-4-oxo-4,5-dihydro-3H-1-thia-3,5,8-triazaacenaphthylene-2-carboxamido)piperidin-1-yl)-2-oxoethyl)(methyl)carbamate (0.256 g, 0.400 mmol) in MeOH (15 mL) was added saturated aqueous HCl (1.5 mL). The mixture was concentrated to dryness and the residue was dispersed between DCM and 10% aqueous $NH_3$. The organic layer was collected and purified by preparative TLC to give the title compound (86 mg, 39% yield). MS (ESI): mass calcd. for $C_{29}H_{28}N_6O_3S$, 540.6; m/z found, 541.2 $[M+H]^+$. $^1H$ NMR (400 MHz, DMSO-$d_6$): δ 8.95-8.60 (br, 1H), 8.36-8.27 (m, 1H), 8.27-8.10 (m, 1H), 7.88-7.79 (m, 1H), 7.79-7.73 (m, 1H), 7.70-7.62 (m, 3H), 7.48-7.34 (m, 4H), 6.11-6.02 (m, 1H), 4.46-3.94 (m, 3H), 3.92-3.73 (m, 1H), 3.72-3.50 (m, 1H), 3.20-2.92 (m, 2H), 2.87-2.63 (m, 1H), 2.53 (s, 3H), 1.97-1.87 (m, 1H), 1.80-1.60 (m, 2H), 1.55-1.35 (m, 1H).

Example 552: (R)-5-([1,1'-Biphenyl]-3-yl)-N-(1-methylpiperidin-3-yl)-4-oxo-4,5-dihydro-3H-1-thia-3,5,8-triazaacenaphthylene-2-carboxamide

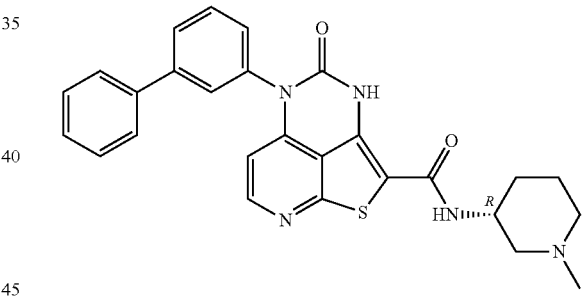

Step A: (R)-5-([1,1'-Biphenyl]-3-yl)-4-oxo-N-(piperidin-3-yl)-4,5-dihydro-3H-1-thia-3,5,8-triazaacenaphthylene-2-carboxamide The title compound was prepared using analogous conditions described in Method 1, steps C-H, in Example 1, and using [1,1'-biphenyl]-3-amine (Intermediate 46) in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{23}N_5O_2S$, 469.56; m/z found, 470.3 $[M+H]^+$.

Step B: (R)-5-([1,1'-Biphenyl]-3-yl)-N-(1-methylpiperidin-3-yl)-4-oxo-4,5-dihydro-3H-1-thia-3,5,8-triazaacenaphthylene-2-carboxamide To a solution of (R)-5-([1,1'-biphenyl]-3-yl)-4-oxo-N-(piperidin-3-yl)-4,5-dihydro-3H-1-thia-3,5,8-triazaacenaphthylene-2-carboxamide (188 mg, 0.400 mmol) in DCM (10 mL) were added formaldehyde (2 mL, 37 wt. % in $H_2O$) and NaBH(OAc)₃ (339 mg, 1.60 mmol) and was stirred at room temperature for 4 hours. To the mixture were added DCM (50 mL), MeOH (5 mL), and water (30 mL). The organic layer was collected, concentrated to dryness, and purified by TLC (MeOH/DCM=1/20) to give the title compound (69 mg, 35% yield) as a yellow solid. MS (ESI): mass calcd. for C₂₇H₂₅N₅O₂S, 483.6; m/z found, 484.3 [M+H]⁺. ¹H NMR (400 MHz, DMSO-d₆): δ 8.29-8.23 (m, 1H), 8.08-7.98 (m, 1H), 7.84-7.79 (m, 1H), 7.77-7.73 (m, 1H), 7.70-7.63 (m, 3H), 7.49-7.43 (m, 2H), 7.43-7.34 (m, 2H), 6.07-5.99 (m, 1H), 3.97-3.89 (m, 1H), 3.43 (br, 1H), 2.86-2.80 (m, 1H), 2.70-2.63 (m, 1H), 2.20 (s, 3H), 1.99-1.85 (m, 2H), 1.80-1.73 (m, 1H), 1.72-1.64 (m, 1H), 1.56-1.45 (m, 1H), 1.39-1.28 (m, 1H).

Example 553: (R)-5-(3'-Methyl-[1,1'-biphenyl]-3-yl)-4-oxo-N-(piperidin-3-yl)-4,5-dihydro-3H-1-thia-3,5,8-triazaacenaphthylene-2-carboxamide

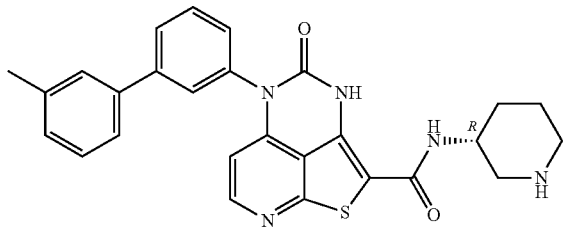

A solution of (R)-tert-butyl 3-(5-(3-bromophenyl)-4-oxo-4,5-dihydro-3H-1-thia-3,5,8-triazaacenaphthylene-2-carboxamido)piperidine-1-carboxylate (Example 540, Step A) (400 mg, 0.70 mmol), m-tolylboronic acid (105 mg, 0.770 mmol), Pd(dppf)Cl₂ (29 mg, 0.035 mmol), and Na₂CO₃ (148 mg, 1.40 mmol) in dioxane (10 mL) and H₂O (1 mL) was stirred at 110° C. for 2 h. The reaction mixture was concentrated to dryness and the residue was purified by flash column chromatography. The solid was dissolved in MeOH (4 mL) and saturated aqueous HCl (4 mL), and the mixture was heated to 50° C. and stirred for 30 min. The reaction mixture was concentrated to dryness and the residue was purified by flash column chromatography to give the title compound (280 mg, 80% yield). MS (ESI): mass calcd. for C₂₇H₂₅N₅O₂S, 483.6; m/z found, 484.3 [M+H]⁺. ¹H NMR (400 MHz, CD₃OD): δ 8.21 (d, J=5.6 Hz, 1H), 7.79-7.74 (m, 1H), 7.68-7.61 (m, 2H), 7.48-7.45 (m, 1H), 7.44-7.41 (m, 1H), 7.37-7.28 (m, 2H), 7.19-7.14 (m, 1H), 6.10 (d, J=5.6 Hz, 1H), 4.19-4.10 (m, 1H), 3.28-3.25 (m, 1H), 3.13-3.03 (m, 1H), 2.85-2.73 (m, 2H), 2.38 (s, 3H), 2.06-1.97 (m, 1H), 1.97-1.87 (m, 1H), 1.75-1.66 (m, 2H).

Example 554: (R)-5-(2'-Methyl-[1,1'-biphenyl]-3-yl)-4-oxo-N-(piperidin-3-yl)-4,5-dihydro-3H-1-thia-3,5,8-triazaacenaphthylene-2-carboxamide

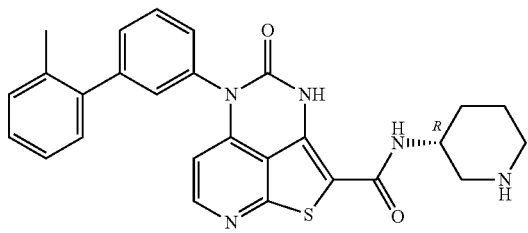

The title compound was prepared using using the procedure found in Example 553, step B, and using o-tolylboronic acid in place of m-tolylboronic acid, to yield the title compound. MS (ESI): mass calcd. for C₂₇H₂₅N₅O₂S, 483.6; m/z found, 484.3 [M+H]⁺. ¹H NMR (400 MHz, CD₃OD): δ 8.21 (d, J=5.6 Hz, 1H), 7.68-7.61 (m, 1H), 7.52-7.43 (m, 1H), 7.43-7.30 (m, 2H), 7.29-7.19 (m, 4H), 6.10 (d, J=5.6 Hz, 1H), 4.16-4.04 (m, 1H), 3.27-3.21 (m, 1H), 3.08-3.00 (m, 1H), 2.83-2.69 (m, 2H), 2.29 (s, 3H), 2.06-1.98 (m, 1H), 1.95-1.85 (m, 1H), 1.75-1.63 (m, 2H).

Example 555: 5-(*S)-(2-Methyl-4-phenoxyphenyl)-4-oxo-N—((R)-1-((E)-4-((4aR,7aS)-tetrahydro-2H-[1,4]dioxino[2,3-c]pyrrol-6(3H)-yl)but-2-enoyl)pyrrolidin-3-yl)-4,5-dihydro-3H-1-thia-3,5,8-triazaacenaphthylene-2-carboxamide

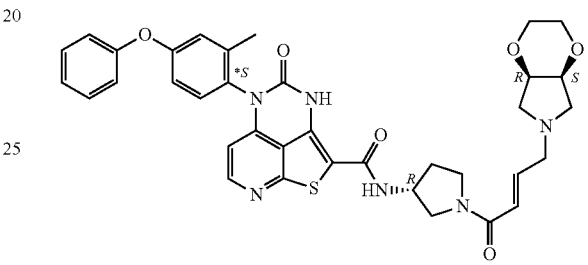

The title compound was prepared using a method analogous to Example 75 using (R)-5-(*S)-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 36) and (E)-4-((4aR,7aS)-tetrahydro-2H-[1,4]dioxino[2,3-c]pyrrol-6(3H)-yl)but-2-enoic acid (Intermediate 72). MS (ESI): mass calcd. for C₃₆H₃₆N₆O₆S, 680.8; m/z found, 681.5 [M+H]⁺. ¹H NMR (400 MHz, CD₃OD): δ 8.35-8.27 (m, 1H), 7.45-7.26 (m, 3H), 7.20-6.93 (m, 5H), 6.87-6.73 (m, 1H), 6.62-6.45 (m, 1H), 6.11-6.01 (m, 1H), 4.68-4.55 (m, 1H), 4.20-4.07 (m, 2H), 4.00-3.71 (m, 4H), 3.62-3.41 (m, 6H), 3.14-3.01 (m, 2H), 3.01-2.88 (m, 2H), 2.39-2.01 (m, 5H).

Example 556: (R)—N-(1-Acryloylpiperidin-3-yl)-4-oxo-5-(2-phenoxypyrimidin-5-yl)-4,5-dihydro-3H-1-thia-3,5,8-triazaacenaphthylene-2-carboxamide

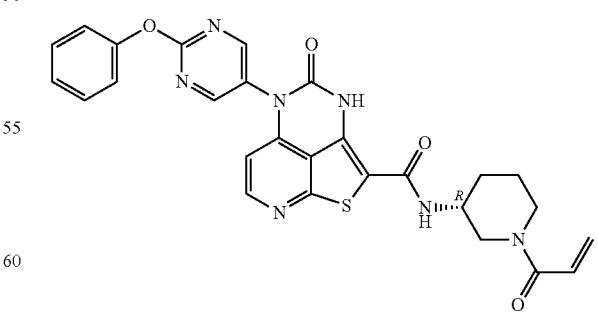

The title compound was prepared in a manner analogous to Method 1, steps A-G in Example 1, and using 2-chloro-5-nitro-pyrimidine in place of 5-fluoro-2-nitrotoluene in step A, and using 1-[(3R)-3-amino-1-piperidyl]prop-2-en-1-one (Intermediate 15) in place of tert-butyl (3R,5R)-3-amino-5-fluoro-piperidine-1-carboxylate in step G, to yield the title compound. MS (ESI): mass calcd. for C$_{27}$H$_{23}$N$_{7}$O$_{4}$S, 541.6; m/z found, 542.2 [M+H]$^{+}$. $^{1}$H NMR (400 MHz, CD$_{3}$OD): δ 8.71 (s, 2H), 8.36-8.31 (m, 1H), 7.49-7.39 (m, 2H), 7.31-7.20 (m, 3H), 6.83-6.68 (m, 1H), 6.38-6.32 (m, 1H), 6.22-6.12 (m, 1H), 5.77-5.64 (m, 1H), 4.35-3.86 (m, 3H), 3.18-3.12 (m, 1H), 2.96-2.80 (m, 1H), 2.11-1.99 (m, 1H), 1.90-1.80 (m, 1H), 1.79-1.64 (m, 1H), 1.62-1.48 (m, 1H).

Example 557: N-((3R,5R)-1-Acryloyl-5-hydroxypiperidin-3-yl)-5-(4-isopropoxy-2-methylphenyl)-4-oxo-4,5-dihydro-3H-1-thia-3,5,8-triazaacenaphthylene-2-carboxamide

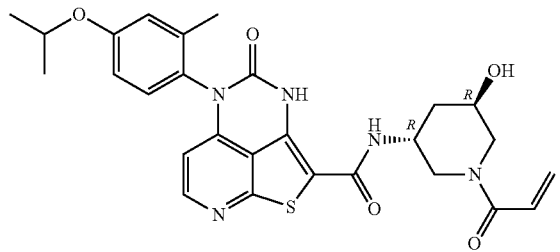

The title compound was prepared as in Example 33, steps A-D, and using (3R,5S)-tert-butyl 3-amino-5-hydroxypiperidine-1-carboxylate in place tert-butyl (3R)-3-aminopiperidine-1-carboxylate in step D. MS (ESI): mass calcd. for C$_{27}$H$_{29}$N$_{5}$O$_{5}$S, 535.6; m/z found, 536.2 [M+H]$^{+}$. $^{1}$H NMR (400 MHz, CD$_{3}$OD): δ 8.37 (d, J=5.9 Hz, 1H), 7.27-7.14 (m, 1H), 7.03-6.95 (m, 1H), 6.94-6.87 (m, 1H), 6.84-6.69 (m, 1H), 6.28-6.01 (m, 2H), 5.78-5.62 (m, 1H), 4.71-4.62 (m, 1H), 4.60-3.81 (m, 4H), 3.25-3.15 (m, 1H), 3.02-2.94 (m, 1H), 2.19-1.83 (m, 5H), 1.39-1.29 (m, 6H).

Example 558: (R)—N-(1-Acryloylpyrrolidin-3-yl)-5-(3-chloro-4-phenoxyphenyl)-4-oxo-4,5-dihydro-3H-1-thia-3,5,8-triazaacenaphthylene-2-carboxamide

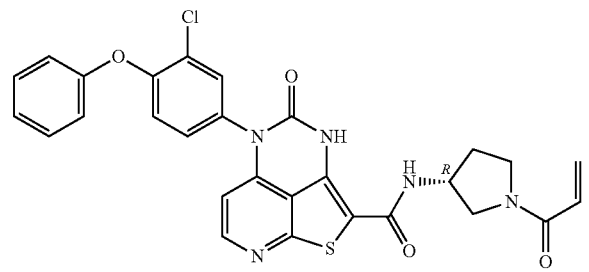

The title compound was prepared in a manner analogous to Method 1, steps A-I in Example 1, and using 2-chloro-1-fluoro-4-nitro-benzene in place of 5-fluoro-2-nitrotoluene in step A, and using tert-butyl (3R)-3-aminopyrrolidine-1-carboxylate in place of tert-butyl (3R,5R)-3-amino-5-fluoropiperidine-1-carboxylate in step G, to yield the title compound. MS (ESI): mass calcd. for C$_{28}$H$_{22}$ClN$_{5}$O$_{4}$S, 560.0; m/z found, 560.1 [M+H]$^{+}$. $^{1}$H NMR (400 MHz, CD$_{3}$OD): δ 8.35-8.30 (m, 1H), 7.69-7.65 (m, 1H), 7.44-7.32 (m, 3H), 7.20-7.11 (m, 2H), 7.09-7.02 (m, 2H), 6.67-6.52 (m, 1H), 6.31-6.24 (m, 1H), 6.24-6.20 (m, 1H), 5.78-5.69 (m, 1H), 4.66-4.55 (m, 1H), 4.02-3.47 (m, 4H), 2.38-2.20 (m, 1H), 2.19-2.01 (m, 1H).

Example 559: (R,E)-N-(1-(2-Cyano-3-cyclopropylacryloyl)piperidin-3-yl)-4-oxo-5-(2-phenylpyridin-4-yl)-4,5-dihydro-3H-1-thia-3,5,8-triazaacenaphthylene-2-carboxamide

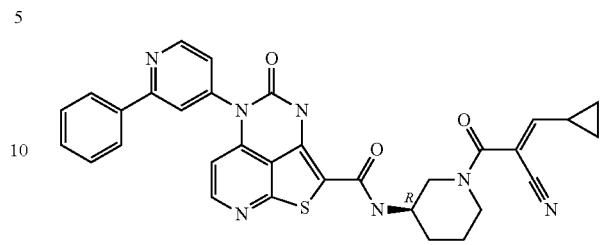

Step A: 2-Phenylpyridin-4-amine

To a stirred solution of 2-chloropyridin-4-amine (64.0 g, 498 mmol) in toluene (800 mL) were added phenylboronic acid (72.9 g, 597 mmol), Pd(PPh$_{3}$)$_{4}$ (28.8 g, 24.9 mmol), Na$_{2}$CO$_{3}$ (105.5 g, 995.6 mmol), and water (500 mL) and was heated at 100° C. for 16 hours. The reaction was cooled to room temperature, extracted three times with ethyl acetate, and the combined organic phases were concentrated to dryness. The residue was purified by normal phase flash column chromatography (SiO$_{2}$) to give the title compound (60 g, 71% yield) as a white solid.

Step B: (R)-4-oxo-5-(2-phenylpyridin-4-yl)-N-(piperidin-3-yl)-4,5-dihydro-3H-1-thia-3,5,8-triazaacenaphthylene-2-carboxamide The title compound was prepared in a manner analogous to Method 1, steps C-F in Example 1, and using 2-phenylpyridin-4-amine in place of 2-methyl-4-phenoxy-aniline in step C and using (R)-tert-butyl 3-aminopiperidine-1-carboxylate in place of tert-butyl (3R,5R)-3-amino-5-fluoro-piperidine-1-carboxylate in step G.

Step C: (R,E)-N-(1-(2-Cyano-3-cyclopropylacryloyl)piperidin-3-yl)-4-oxo-5-(2-phenylpyridin-4-yl)-4,5-dihydro-3H-1-thia-3,5,8-triazaacenaphthylene-2-carboxamide The title compound was prepared in a manner analogous to Example 75 (R)-4-oxo-5-(2-phenylpyridin-4-yl)-N-(piperidin-3-yl)-4,5-dihydro-3H-1-thia-3,5,8-triazaacenaphthylene-2-carboxamide and using (E)-2-cyano-3-cyclopropylacrylic acid (Intermediate 17) in place of 3-hydroxypropanoic acid. MS (ESI): mass calcd. for C$_{32}$H$_{27}$N$_{7}$O$_{3}$S, 589.7; m/z found, 590.2 [M+H]$^{+}$. $^{1}$H NMR (400 MHz, CD$_{3}$OD): δ 8.88-8.84 (m, 1H), 8.36-8.31 (m, 1H), 8.06-8.00 (m, 3H), 7.53-7.41 (m, 4H), 6.58-6.50 (m, 1H), 6.35-6.29 (m, 1H), 4.23-3.89 (m, 3H), 3.22-2.91 (m, 2H), 2.12-1.96 (m, 2H), 1.93-1.82 (m, 1H), 1.77-1.56 (m, 2H), 1.25-1.15 (m, 2H), 1.03-0.92 (m, 1H), 0.92-0.80 (m, 1H).

Example 560: (R)—N-(1-Acryloylpiperidin-3-yl)-5-(3-(cyclohexyloxy)phenyl)-4-oxo-4,5-dihydro-3H-1-thia-3,5,8-triazaacenaphthylene-2-carboxamide

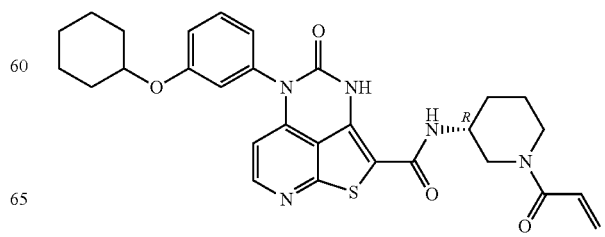

The title compound was prepared in a manner analogous to Method 1, steps A-I in Example 1, and using cyclohexyl methanesulfonate and 3-nitrophenol in place of 5-fluoro-2-nitrotoluene and phenol in step A, and using tert-butyl (3R)-3-aminopiperidine-1-carboxylate in place of tert-butyl (3R,5R)-3-amino-5-fluoro-piperidine-1-carboxylate in step G, to yield the title compound. MS (ESI): mass calcd. for $C_{29}H_{31}N_5O_4S$, 545.7; m/z found, 546.2 [M+H]$^+$. $^1$H NMR (400 MHz, CD$_3$OD): δ 8.26 (d, J=5.6 Hz, 1H), 7.50-7.38 (m, 1H), 7.11-6.99 (m, 2H), 6.99-6.92 (m, 1H), 6.84-6.71 (m, 1H), 6.25-6.15 (m, 1H), 6.11 (d, J=5.6 Hz, 1H), 5.77-5.64 (m, 1H), 4.54-4.28 (m, 2H), 4.23-3.89 (m, 2H), 3.20-3.08 (m, 1H), 2.92-2.81 (m, 1H), 2.10-1.94 (m, 3H), 1.89-1.67 (m, 4H), 1.61-1.47 (m, 4H), 1.43-1.26 (m, 3H).

Example 561: (R)—N-(1-Acryloylpiperidin-3-yl)-5-(3-(cyclopentyloxy)phenyl)-4-oxo-4,5-dihydro-3H-1-thia-3,5,8-triazaacenaphthylene-2-carboxamide

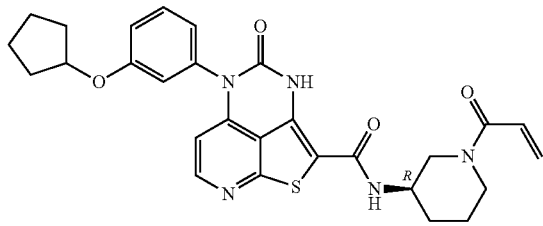

The title compound was prepared analogous to Example 33, steps A-D, and using 3-nitrophenol and 2-iodopropane in place of 3-methyl-4-nitrophenol and 5-fluoro-2-nitrotoluene in Step A. MS (ESI): mass calcd. for $C_{28}H_{29}N_5O_4S$, 531.6; m/z found, 532.2 [M+H]$^+$. $^1$H NMR (400 MHz, CD$_3$OD and DMSO-d$_6$): δ 8.44-8.33 (m, 1H), 7.58-7.48 (m, 1H), 7.16-7.08 (m, 1H), 7.07-6.97 (m, 2H), 6.90-6.78 (m, 1H), 6.27-6.15 (m, 2H), 5.84-5.72 (m, 1H), 4.94-4.84 (m, 1H), 4.38-3.93 (m, 3H), 3.26-3.06 (m, 1H), 2.97-2.78 (m, 1H), 2.14-1.91 (m, 4H), 1.90-1.75 (m, 6H), 1.71-1.64 (m, 2H).

Example 562: (R,E)-N-(1-(4-(Dimethylamino)but-2-enoyl)pyrrolidin-3-yl)-5-(4-isopropoxy-2-methylphenyl)-4-oxo-4,5-dihydro-3H-1-thia-3,5,8-triazaacenaphthylene-2-carboxamide

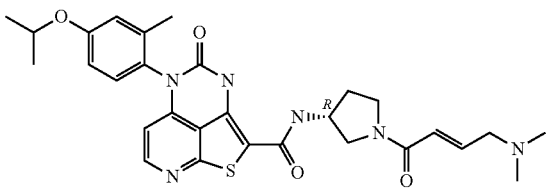

Step A: (R)-5-(4-Isopropoxy-2-methylphenyl)-4-oxo-N-(pyrrolidin-3-yl)-4,5-dihydro-3H-1-thia-3,5,8-triazaacenaphthylene-2-carboxamide The title compound was prepared analagous to Example 33, steps A-D in using (R)-tert-butyl 3-aminopyrrolidine-1-carboxylate.

Step B: (R,E)-N-(1-(4-(Dimethylamino)but-2-enoyl)pyrrolidin-3-yl)-5-(4-isopropoxy-2-methylphenyl)-4-oxo-4,5-dihydro-3H-1-thia-3,5,8-triazaacenaphthylene-2-carboxamide The title compound was prepared using a method analogous to Example 75 with (R)-5-(4-Isopropoxy-2-methylphenyl)-4-oxo-N-(pyrrolidin-3-yl)-4,5-dihydro-3H-1-thia-3,5,8-triazaacenaphthylene-2-carboxamide and (E)-4-(dimethylamino)but-2-enoic acid. MS (ESI): mass calcd. for $C_{29}H_{34}N_6O_4S$, 562.7; m/z found, 563.5 [M+H]$^+$. $^1$H NMR (400 MHz, CD3OD): δ 8.42 (s, 1H), 8.33-8.23 (m, 1H), 7.29-7.13 (m, 1H), 7.01-6.86 (m, 2H), 6.83-6.58 (m, 2H), 6.08-5.97 (m, 1H), 4.72-4.53 (m, 2H), 4.09-3.44 (m, 6H), 2.80-2.66 (m, 6H), 2.42-2.20 (m, 1H), 2.16-2.04 (m, 4H), 1.41-1.24 (m, 6H).

Example 563: (R)—N-(1-Acryloylpiperidin-3-yl)-4-oxo-5-(2'-(trifluoromethyl)-[1,1'-biphenyl]-3-yl)-4,5-dihydro-3H-1-thia-3,5,8-triazaacenaphthylene-2-carboxamide

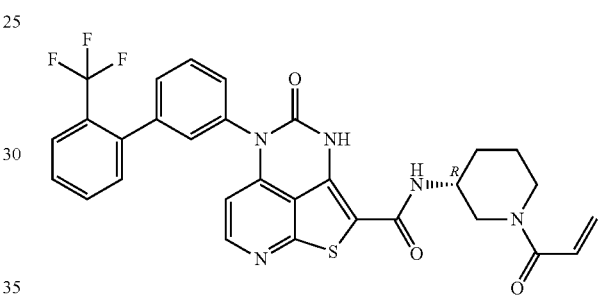

Step A: (R)-tert-Butyl 3-(5-(3-bromophenyl)-4-oxo-4,5-dihydro-3H-1-thia-3,5,8-triazaacenaphthylene-2-carboxamido)piperidine-1-carboxylate To a stirred solution of 5-(3-bromophenyl)-4-oxo-4,5-dihydro-3H-1-thia-3,5,8-triazaacenaphthylene-2-carboxylic acid (Intermediate 57) (3.5 g, 9.0 mmol) in DMF (15 mL) were added tert-butyl (3R)-3-aminopiperidine-1-carboxylate (3.6 g, 18 mmol), HATU (5.1 g, 13 mmol), and diisopropylethylamine (2.3 g, 18 mmol) and was stirred at room temperature overnight. The solvent was removed and the residue was partitioned between ethyl acetate and water. The organic layer was separated, shaken with brine and dried over anhydrous Na$_2$SO$_4$. The residue was purified by flash column chromatography to give the title compound as yellow solid (3.0 g, 58% yield).

Step B: (R)-tert-Butyl 3-(4-oxo-5-(2'-(trifluoromethyl)-[1,1'-biphenyl]-3-yl)-4,5-dihydro-3H-1-thia-3,5,8-triazaacenaphthylene-2-carboxamido)piperidine-1-carboxylate A solution of (R)-tert-butyl 3-(5-(3-bromophenyl)-4-oxo-4,5-dihydro-3H-1-thia-3,5,8-triazaacenaphthylene-2-carboxamido)piperidine-1-carboxylate (180 mg, 0.314 mmol), [2-(trifluoromethyl)phenyl]boronic acid (90.0 mg, 0.474 mmol), Pd(dppf)Cl$_2$*CH$_2$Cl$_2$ (30.0 mg, 0.0367 mmol), and Na$_2$CO$_3$ (85 mg, 0.80 mmol) in dioxane (7 mL) and H$_2$O (1 mL) was sparged with N$_2$ and stirred at 120° C. for 4 h. The reaction was cooled and purified by flash column chromatography to give the title compound as yellow solid (150 mg, 75% yield).

Step C: (R)-4-Oxo-N-(piperidin-3-yl)-5-(2'-(trifluoromethyl)-[1,1'-biphenyl]-3-yl)-4,5-dihydro-3H-1-thia-3,5,8-triazaacenaphthylene-2-carboxamide A solution of (R)-tert-butyl 3-(4-oxo-5-(2'-(trifluoromethyl)-[1,1'-biphenyl]-3-yl)-4,5-dihydro-3H-1-thia-3,5,8-triazaacenaphthylene-2-carboxamido)piperidine-1-carboxylate (150 mg, 0.235 mmol) in saturated aqueous HCl (2 mL) and MeOH (15 mL) was stirred at room temperature for about 2 hours. The reaction mixture was concentrated to dryness to give the title compound (110 mg, 87% yield), which was carrying forward to next step without purification.

Step D: (R)—N-(1-Acryloylpiperidin-3-yl)-4-oxo-5-(2'-(trifluoromethyl)-[1,1'-biphenyl]-3-yl)-4,5-dihydro-3H-1-thia-3,5,8-triazaacenaphthylene-2-carboxamide The title compound was prepared in a manner analogous to Method 1, step I in Example 1, to yield the title compound (67 mg, 55% yield). MS (ESI): mass calcd. for $C_{30}H_{24}F_3N_5O_3S$, 591.6; m/z found, 592.4 [M+H]$^+$. $^1$H NMR (400 MHz, DMSO-d$_6$): δ 10.11 (s, 1H), 8.33 (d, J=5.5 Hz, 1H), 8.13-7.99 (m, 1H), 785-7.79 (m, 1H), 7.77-7.69 (m, 1H), 7.68-7.58 (m, 2H), 7.54-7.34 (m, 4H), 6.86-6.65 (m, 1H), 6.13-6.01 (m, 1H), 5.97 (d, J=5.5 Hz, 1H), 5.70-5.58 (m, 1H), 4.51-4.10 (m, 1H), 4.06-3.88 (m, 1H), 3.84-3.69 (m, 1H), 3.15-2.89 (m, 1H), 2.81-2.56 (m, 1H), 2.00-1.85 (m, 1H), 1.82-1.71 (m, 1H), 1.68-1.54 (m, 1H), 1.48-1.31 (m, 1H).

Example 564: N—((R)-1-((R)-3-Hydroxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide

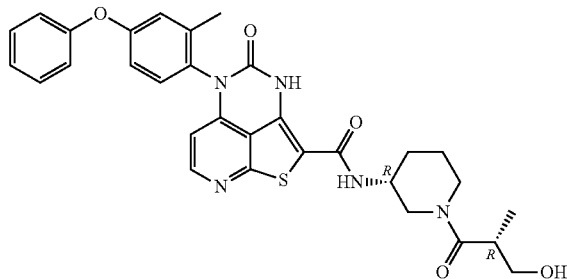

To a solution of (R)-3-hydroxy-2-methylpropanoic acid (35 mg, 0.28 mmol), HATU (106 mg, 0.279 mmol), and triethylamine (0.0521 mL, 0.347 mmol) in DMF (3 mL) was added (R)-5-(2-Methyl-4-phenoxyphenyl)-4-oxo-N-(piperidin-3-yl)-4,5-dihydro-3H-1-thia-3,5,8-triazaacenaphthylene-2-carboxamide (Example 869) (100 mg, 0.22 mmol) and was stirred at room temperature overnight. The mixture was purified by normal phase flash column chromatography (SiO$_2$) to give the title compound (20 mg, 100% yield). MS (ESI): mass calcd. for $C_{31}H_{31}N_5O_5S$, 585.7; m/z found, 586.2 [M+H]$^+$. $^1$H NMR (400 MHz, CD$_3$OD): δ 8.32 (d, J=5.1 Hz, 1H), 7.44-7.34 (m, 2H), 7.33-7.25 (m, 1H), 7.20-7.13 (m, 1H), 7.12-7.02 (m, 3H), 7.01-6.92 (m, 1H), 6.06 (d, J=5.4 Hz, 1H), 4.54-4.17 (m, 2H), 4.01-3.91 (m, 1H), 3.78-3.66 (m, 1H), 3.55-3.45 (m, 1H), 3.19-3.02 (m, 2H), 2.91-2.78 (m, 1H), 2.11 (s, 3H), 2.07-1.99 (m, 1H), 1.86-1.66 (m, 2H), 1.62-1.45 (m, 1H), 1.16-1.02 (m, 3H).

Example 565: (R)—N-(1-Acryloylpiperidin-3-yl)-5-(3-isopropoxyphenyl)-4-oxo-4,5-dihydro-3H-1-thia-3,5,8-triazaacenaphthylene-2-carboxamide

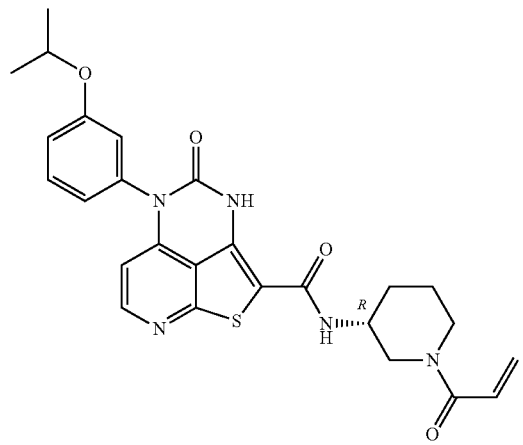

The title compound was prepared using the procedures found in Example 534, steps A-C, and using 3-isopropoxyaniline in place of 3-cyclobutylaniline in step A. MS (ESI): mass calcd. for $C_{26}H_{27}N_5O_4S$, 505.6; m/z found, 506.1 [M+H]$^+$. $^1$H NMR (600 MHz, DMSO-d$_6$): δ 10.23-10.06 (d, J=15.2 Hz, 1H), 8.39-8.27 (d, J=5.5 Hz, 1H), 8.12-8.00 (m, 1H), 7.54-7.43 (m, 1H), 7.10-7.02 (m, 2H), 7.01-6.94 (m, 1H), 6.87-6.72 (m, 1H), 6.15-6.07 (d, J=16.6 Hz, 1H), 6.06-6.00 (d, J=5.5 Hz, 1H), 5.74-5.65 (d, J=10.4 Hz, 1H), 4.67-4.56 (m, 1H), 4.53-4.16 (m, 1H), 4.11-3.93 (m, 1H), 3.85-3.73 (m, 1H), 3.16-2.94 (m, 1H), 2.80-2.63 (m, 1H), 1.99-1.90 (m, 1H), 1.82-1.75 (m, 1H), 1.74-1.60 (m, 1H), 1.49-1.36 (m, 1H), 1.31-1.26 (m, 6H).

Example 566: (R)-5-(3-Acetylphenyl)-N-(1-acryloylpiperidin-3-yl)-4-oxo-4,5-dihydro-3H-1-thia-3,5,8-triazaacenaphthylene-2-carboxamide

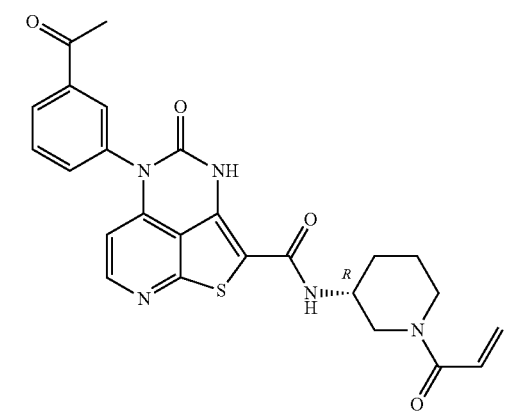

The title compound was prepared using the procedures found in Example 534, steps A-C, and using 1-(3-aminophenyl)ethanone in place of 3-cyclobutylaniline in step A, to yield the title compound. MS (ESI): mass calcd. for $C_{25}H_{23}N_5O_4S$, 489.6; m/z found, 490.0 [M+H]$^+$. $^1$H NMR (500 MHz, DMSO-d$_6$): δ 10.31-10.12 (m, 1H), 8.38-8.27 (d, J=5.5 Hz, 1H), 8.17-8.04 (m, 3H), 7.82-7.72 (m, 2H), 6.89-6.71 (m, 1H), 6.18-6.08 (d, J=16.7 Hz, 1H), 6.06-5.98 (d, J=5.5 Hz, 1H), 5.72-5.64 (d, J=10.4 Hz, 1H), 4.54-4.16 (m, 1H), 4.11-3.95 (m, 1H), 3.87-3.74 (m, 1H), 3.16-2.94 (m, 1H), 2.82-2.64 (m, 1H), 2.64-2.57 (s, 3H), 1.99-1.91 (m, 1H), 1.83-1.58 (m, 2H), 1.51-1.37 (m, 1H).

Example 567: (R)—N-(1-Acryloylpyrrolidin-3-yl)-4-oxo-5-(2-phenylpyridin-4-yl)-4,5-dihydro-3H-1-thia-3,5,8-triazaacenaphthylene-2-carboxamide

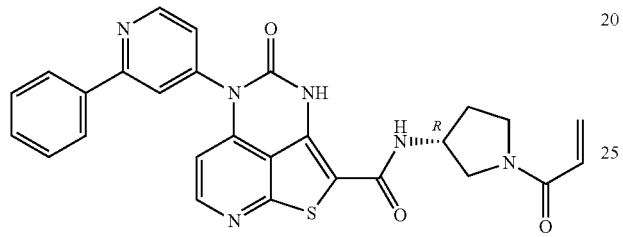

The title compound was prepared in a manner analogous to Method 1, steps C-I in Example 1, and using 2-phenylpyridin-4-amine in place of 2-methyl-4-phenoxy-aniline in step C, and using tert-butyl (3R)-3-aminopyrrolidine-1-carboxylate in place of tert-butyl (3R,5R)-3-amino-5-fluoro-piperidine-1-carboxylate in step G, to yield the title compound. MS (ESI): mass calcd. for $C_{27}H_{22}N_6O_3S$, 510.6; m/z found, 511.1 [M+H]$^+$. $^1$H NMR (400 MHz, CD$_3$OD): δ 8.87-8.80 (m, 1H), 8.28-8.22 (m, 1H), 8.05-7.98 (m, 3H), 7.51-7.41 (m, 4H), 6.66-6.52 (m, 1H), 6.30-6.22 (dd, J=16.4, 2.9 Hz, 2H), 5.76-5.70 (m, 1H), 4.67-4.56 (m, 1H), 4.02-3.48 (m, 4H), 2.38-2.21 (m, 1H), 2.20-2.03 (m, 1H).

Example 568: (R)—N-(1-Acryloylpiperidin-3-yl)-4-oxo-5-(3-(trifluoromethoxy)phenyl)-4,5-dihydro-3H-1-thia-3,5,8-triazaacenaphthylene-2-carboxamide

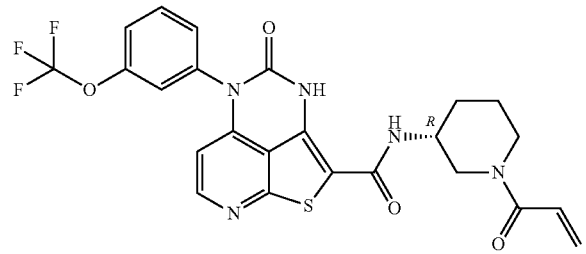

The title compound was prepared in a manner analogous to Method 1, steps B-I in Example 1, and using 1-nitro-3-(trifluoromethoxy)benzene in place of 2-methyl-1-nitro-4-phenoxy-benzene in step B, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{24}H_{20}F_3N_5O_4S$, 531.5; m/z found, 532.1 [M+H]$^+$. $^1$H NMR (400 MHz, CD$_3$OD): δ 8.30 (d, J=5.5 Hz, 1H), 7.77-7.64 (m, 1H), 7.55-7.44 (m, 3H), 6.87-6.70 (m, 1H), 6.24-6.14 (m, 1H), 6.13-6.06 (m, 1H), 5.78-5.64 (m, 1H), 4.56-4.25 (m, 1H), 4.21-3.86 (m, 2H), 3.22-3.10 (m, 1H), 2.97-2.81 (m, 1H), 2.12-1.94 (m, 1H), 1.92-1.80 (m, 1H), 1.79-1.64 (m, 1H), 1.62-1.50 (m, 1H).

Example 569: (R)—N-(1-Acryloylpiperidin-3-yl)-5-(3-cyclopropylphenyl)-4-oxo-4,5-dihydro-3H-1-thia-3,5,8-triazaacenaphthylene-2-carboxamide

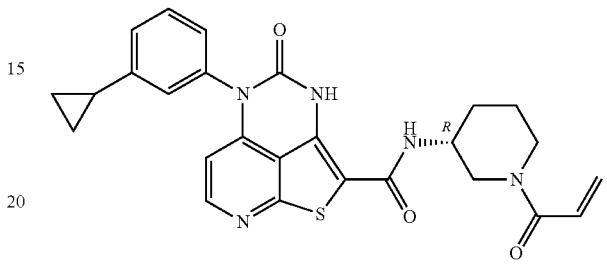

The title compound was prepared in a manner analogous to Method 1, steps C-I in Example 1, and using 3-cyclopropylaniline in place of 2-methyl-4-phenoxy-aniline in step C, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{26}H_{25}N_5O_3S$, 487.6; m/z found, 488.9 [M+H]$^+$. $^1$H NMR (400 MHz, CD$_3$OD): δ 8.31-8.22 (m, 1H), 7.51-7.41 (m, 1H), 7.28-7.22 (m, 1H), 7.20-7.11 (m, 2H), 6.84-6.72 (m, 1H), 6.25-6.13 (m, 1H), 6.11-6.03 (m, 1H), 5.78-5.67 (m, 1H), 4.56-4.26 (m, 1H), 4.21-3.90 (m, 2H), 3.21-3.10 (m, 1H), 2.97-2.81 (m, 1H), 2.10-2.03 (m, 1H), 2.02-1.93 (m, 1H), 1.91-1.82 (m, 1H), 1.79-1.65 (m, 1H), 1.63-1.52 (s, 1H), 1.05-0.97 (m, 2H), 0.79-0.70 (m, 2H)

(R,E)-5-([1,1'-Biphenyl]-3-yl)-N-(1-(4-(dimethylamino)but-2-enoyl)pyrrolidin-3-yl)-4-oxo-4,5-dihydro-3H-1-thia-3,5,8-triazaacenaphthylene-2-carboxamide

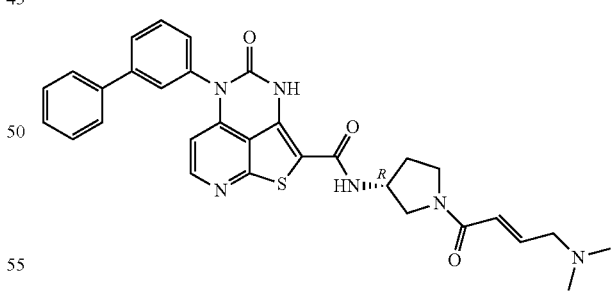

Step A: (R)-5-([11'-Biphenyl]-3-yl)-4-oxo-N-(pyrrolidin-3-yl)-4,5-dihydro-3H-1-thia-3,5,8-triazaacenaphthylene-2-carboxamide The title compound was prepared in a manner analogous to Method 1, steps C-H in Example 1, and using [1,1'-biphenyl]-3-amine (Intermediate 46) in place of 2-methyl-4-phenoxy-aniline in step C, and using (R)-tert-butyl 3-aminopyrrolidine-1-carboxylate in place of tert-butyl (3R, 5R)-3-amino-5-fluoro-piperidine-1-carboxylate in step G. MS (ESI): mass calcd. for $C_{25}H_{21}N_5O_2S$, 455.53; m/z found, 456.3 [M+H]+. $^1$H NMR (400 MHz, CD$_3$OD): δ 8.29 (d, J=5.6 Hz, 1H), 7.85-7.77 (m, 1H), 7.76-7.59 (m, 4H), 7.49-7.39 (m, 3H), 7.39-7.30 (m, 1H), 6.18 (d, J=5.6 Hz, 1H), 4.63-4.5.3 (m, 1H), 3.65-3.51 (m, 2H), 3.47-3.34 (m, 2H), 2.48-2.31 (m, 1H), 2.27-2.13 (m, 1H).

Step B: (R,E)-5-([1,1'-Biphenyl]-3-yl)-N-(1-(4-(dimethylamino)but-2-enoyl)pyrrolidin-3-yl)-4-oxo-4,5-dihydro-3H-1-thia-3,5,8-triazaacenaphthylene-2-carboxamide A solution of (E)-4-(dimethylamino)but-2-enoic acid (34 mg, 0.26 mmol), HATU (100 mg, 0.264 mmol), and triethylamine (111 mg, 1.11 mmol) in DMF (5 mL) was stirred at room temperature for 10 minutes, then (R)-5-([1,1'-biphenyl]-3-yl)-4-oxo-N-(pyrrolidin-3-yl)-4,5-dihydro-3H-1-thia-3,5,8-triazaacenaphthylene-2-carboxamide (100 mg, 0.22 mmol) was added and was stirred at room temperature for 2 h. The mixture was purified by normal phase flash column chromatography (SiO$_2$) to give the title compound (78 mg, 99% yield). MS (ESI): mass calcd. for $C_{31}H_{30}N_6O_3S$, 566.7; m/z found, 567.5 [M+H]+. $^1$H NMR (400 MHz, CD$_3$OD): δ 8.47 (s, 1H), 8.28-8.22 (m, 1H), 7.83-7.76 (m, 1H), 7.75-7.70 (m, 1H), 7.68-7.61 (m, 3H), 7.46-7.37 (m, 3H), 7.36-7.28 (m, 1H), 6.85-6.69 (m, 1H), 6.58-6.41 (m, 1H), 6.18-6.10 (m, 1H), 4.67-4.51 (m, 1H), 4.00-3.45 (m, 4H), 3.41-3.32 (m, 2H), 2.44 (s, 3H), 2.42 (s, 3H), 2.35-2.18 (m, 1H), 2.15-2.00 (m, 1H).

Example 571: N—((R)-1-((R)-3-Methoxy-2-methyl-propanoyl)piperidin-3-yl)-5-(2-methyl-4-phenoxy-phenyl)-4-oxo-4,5-dihydro-3H-1-thia-3,5,8-triazaacenaphthylene-2-carboxamide

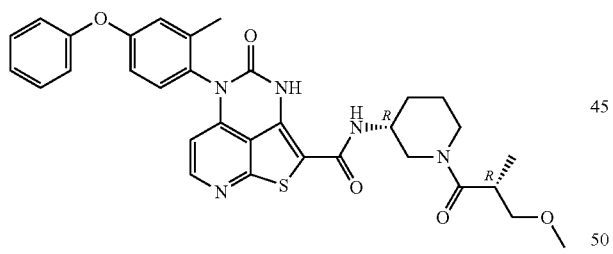

The title compound was prepared in a manner analogous to Method 1, steps G, in Example 1, and using (2R)-1-[(3R)-3-amino-1-piperidyl]-3-methoxy-2-methyl-propan-1-one (Intermediate 50) in place of tert-butyl (3R,5R)-3-amino-5-fluoro-piperidine-1-carboxylate in step G, to yield the title compound as a yellow solid (70 mg, 100% yield). MS (ESI): mass calcd. for $C_{32}H_{33}N_5O_5S$, 599.7; m/z found, 600.2 [M+H]+. $^1$H NMR (400 MHz, DMSO-d$_6$ and CD$_3$OD): δ 8.27 (d, J=5.5 Hz, 1H), 7.40-7.30 (m, 2H), 7.29-7.21 (m, 1H), 7.15-7.07 (m, 1H), 7.07-6.98 (m, 3H), 6.94-6.87 (m, 1H), 5.97 (d, J=5.5 Hz, 1H), 4.10-4.02 (m, 1H), 3.96-3.71 (m, 2H), 3.50-3.41 (m, 1H), 3.26-3.18 (m, 3H), 3.16-3.12 (m, 1H), 3.11-2.95 (m, 2H), 2.73-2.62 (m, 1H), 2.04 (s, 3H), 1.98-1.91 (m, 1H), 1.78-1.70 (m, 1H), 1.67-1.55 (m, 1H), 1.51-1.35 (m, 1H), 1.06-0.91 (m, 3H)

Example 572: (R)-5-(3-Chloro-4-phenoxyphenyl)-N-(1-(2-(dimethylamino)acetyl)piperidin-3-yl)-4-oxo-4,5-dihydro-3H-1-thia-3,5,8-triazaacenaphthylene-2-carboxamide

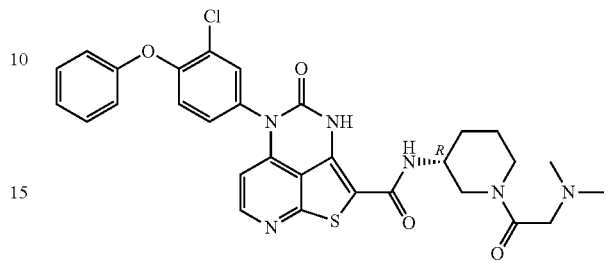

The title compound was prepared using a method analogous to Example 75 using (R)-5-(3-chloro-4-phenoxyphenyl)-4-oxo-N-(piperidin-3-yl)-4,5-dihydro-3H-1-thia-3,5,8-triazaacenaphthylene-2-carboxamide (Example 581) and using 2-(dimethylamino)acetic acid in place of 3-hydroxy-propanoic acid. MS (ESI): mass calcd. for $C_{30}H_{29}ClN_6O_4S$, 605.1; m/z found, 606.3 [M+H]+. $^1$H NMR (400 MHz, CD$_3$OD): δ 8.40 (s, 1H), 8.36-8.28 (m, 1H), 7.70-7.64 (m, 1H), 7.45-7.32 (m, 3H), 7.23-7.11 (m, 2H), 7.10-7.02 (m, 2H), 6.27-6.16 (m, 1H), 4.56-4.30 (m, 1H), 4.25-4.06 (m, 2H), 4.03-3.56 (m, 2H), 3.15-2.97 (m, 1H), 2.91-2.75 (m, 7H), 2.11-1.49 (m, 4H).

Example 573: (R,E)-5-([1,1'-Biphenyl]-3-yl)-N-(1-(4-(dimethylamino)but-2-enoyl)piperidin-3-yl)-4-oxo-4,5-dihydro-3H-1-thia-3,5,8-triazaacenaphthylene-2-carboxamide

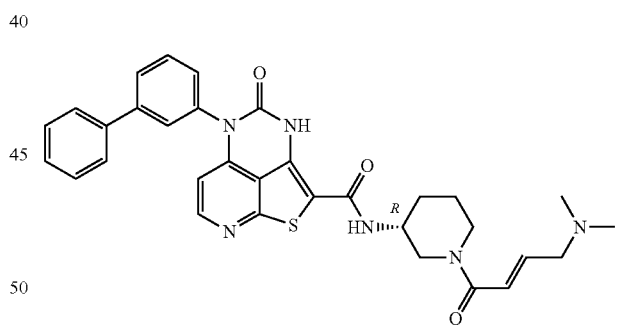

Step A: (R)-5-([1,1'-Biphenyl]-3-yl)-4-oxo-N-(piperidin-3-yl)-4,5-dihydro-3H-1-thia-3,5,8-triazaacenaphthylene-2-carboxamide The title compound was prepared in a manner analogous to Method 1, steps C-G in Example 1, and using [1,1'-biphenyl]-3-amine (Intermediate 46) in place of 2-methyl-4-phenoxy-aniline in step C, and using (R)-tert-butyl 3-aminopiperidine-1-carboxylate in place of tert-butyl (3R,5R)-3-amino-5-fluoro-piperidine-1-carboxylate in step G. MS (ESI): mass calcd. for $C_{26}H_{23}N_5O_2S$, 469.56; m/z found, 470.3 [M+H]+.

Step B: (R,E)-5-([1,1'-Biphenyl]-3-yl)-N-(1-(4-(dimethylamino)but-2-enoyl)piperidin-3-yl)-4-oxo-4,5-dihydro-3H-1-thia-3,5,8-triazaacenaphthylene-2-carboxamide To a solution of (E)-4-(dimethylamino)but-2-enoic acid (52 mg, 0.40 mmol), HATU (152 mg, 0.400 mmol), and triethylamine (81 mg, 0.80 mmol) in DMF (3 mL) was added (R)-5-([1,1'-biphenyl]-3-yl)-4-oxo-N-(piperidin-3-yl)-4,5-dihydro-3H-1-thia-3,5,8-triazaacenaphthylene-2-carboxamide (188 mg, 0.400 mmol) and was stirred at room temperature for 30 minutes. The mixture was purified by normal phase flash column chromatography (SiO$_2$) to give the title compound (101 mg, 42.0% yield). MS (ESI): mass calcd. for C$_{32}$H$_{32}$N$_6$O$_3$S, 580.7; m/z found, 581.2 [M+H]$^+$. $^1$H NMR (400 MHz, DMSO-d$_6$): δ 8.36-8.08 (m, 3H), 7.82-7.77 (m, 1H), 7.74-7.70 (m, 1H), 7.69-7.66 (m, 2H), 7.65-7.61 (m, 1H), 7.48-7.43 (m, 2H), 7.39-7.34 (m, 2H), 6.59-6.51 (m, 2H), 6.03-5.96 (m, 1H), 4.46-3.68 (m, 3H), 3.04-2.99 (m, 2H), 2.96-2.81 (m, 1H), 2.80-2.52 (m, 1H), 2.12 (s, 6H), 1.95-1.88 (m, 1H), 1.80-1.71 (m, 1H), 1.68-1.53 (m, 1H), 1.47-1.34 (m, 1H).

Example 1: N-(cis)-1-Acryloyl-3-hydroxypiperidin-4-yl)-4-oxo-5-(4-phenoxyphenyl)-4,5-dihydro-3H-1-thia-3,5,8-triazaacenaphthylene-2-carboxamide

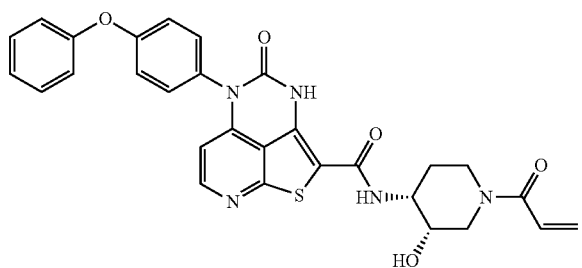 [SMILES: C=CC(=O)N1CC[C@@H](NC(=O)c2sc3nccc4c3c2NC(=O)N4c2ccc(Oc3ccccc3)cc2)[C@@H](O)C1]

The title compound was prepared using the procedures found in Method 1, step I in Example 1, and using N-(cis-3-hydroxypiperidin-4-yl)-4-oxo-5-(4-phenoxyphenyl)-4,5-dihydro-3H-1-thia-3,5,8-triazaacenaphthylene-2-carboxamide (Example 659). MS (ESI): mass calcd. for C$_{29}$H$_{25}$N$_5$O$_5$S, 555.6; m/z found, 556.9 [M+H]$^+$. $^1$H NMR (400 MHz, CD$_3$OD): δ 8.34 (d, J=5.6 Hz, 1H), 8.03 (s, 1H), 7.57 (s, 1H), 7.47-7.37 (m, 1H), 7.32 (d, J=8.5 Hz, 1H), 7.25-7.08 (m, 4H), 6.71 (dd, J=16.9, 10.6 Hz, 1H), 6.32-6.17 (m, 2H), 6.00 (s, 1H), 5.81-5.67 (m, 2H), 5.38 (s, 1H), 4.74-4.63 (m, 2H), 4.28-3.99 (m, 4H), 3.58 (s, 1H), 2.08-1.79 (m, 2H).

Example 575: (R)-5-(3-Chloro-4-phenoxyphenl)-N-(1-(2-(methylamino)acetyl)piperidin-3-yl)-4-oxo-4,5-dihydro-3H-1-thia-3,5,8-triazaacenaphthylene-2-carboxamide

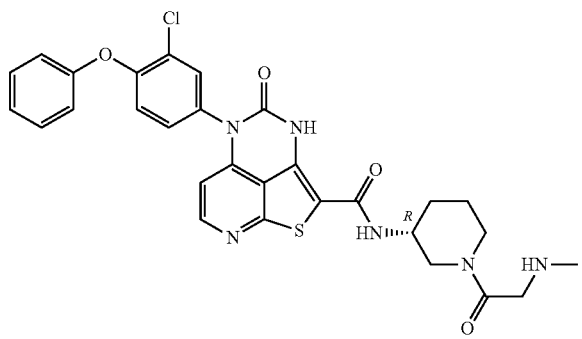

A solution of 2-((tert-butoxycarbonyl)(methyl)amino)acetic acid (61 mg, 0.32 mmol), HATU (123 mg, 0.323 mmol), and triethylamine (136 mg, 1.35 mmol) in DMF (3 mL) was stirred at room temperature for 10 minutes. Then (R)-5-(3-chloro-4-phenoxyphenyl)-4-oxo-N-(piperidin-3-yl)-4,5-dihydro-3H-1-thia-3,5,8-triazaacenaphthylene-2-carboxamide (Example 581) (150 mg, 0.27 mmol) was added and was stirred for 2 h. The mixture was purified by normal phase flash column chromatography (SiO$_2$) to give a white solid. The solid was dissolved in 6 M HCl/MeOH and then concentrated to dryness. The residue was purified by normal phase flash column chromatography (SiO$_2$) to give the title compound (101 mg, 99.4% yield) as a light yellow solid. MS (ESI): mass calcd. for C$_{29}$H$_{27}$ClN$_6$O$_4$S, 591.1; m/z found, 591.5 [M+H]$^+$. $^1$H NMR (400 MHz, CD$_3$OD): δ 8.42 (s, 1H), 8.36-8.27 (m, 1H), 7.70-7.60 (m, 1H), 7.46-7.28 (m, 3H), 7.21-7.11 (m, 2H), 7.09-7.00 (m, 2H), 6.25-6.15 (m, 1H), 4.52-4.21 (m, 1H), 4.18-4.03 (m, 2H), 4.02-3.90 (m, 1H), 3.89-3.56 (m, 1H), 3.17-3.01 (m, 1H), 2.96-2.83 (m, 1H), 2.73 (s, 3H), 2.10-1.96 (m, 1H), 1.95-1.50 (m, 3H).

Example 576: (R)—N-(1-(2-Methoxyacetyl)piperidin-3-yl)-4-oxo-5-(4-phenoxyphenyl)-4,5-dihydro-3H-1-thia-3,5,8-triazaacenaphthylene-2-carboxamide

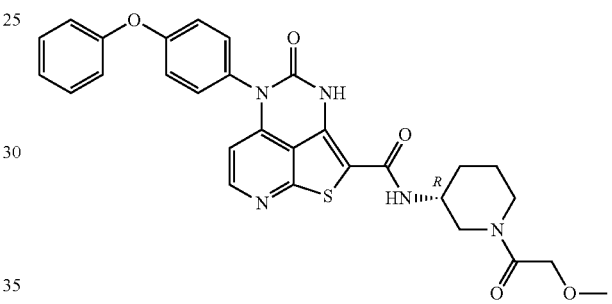

In a microwave vial were added (R)-4-oxo-5-(4-phenoxyphenyl)-N-(piperidin-3-yl)-4,5-dihydro-3H-1-thia-3,5,8-triazaacenaphthylene-2-carboxamide (Example 860) (200 mg, 0.412 mmol), methoxyacetic acid (57 mg, 0.62 mmol), THF (10 mL), and HATU (470 mg, 1.24 mmol). The reaction was heated in microwave at 100° C. for 5 minutes. The reaction was diluted with DCM and washed with water. The reaction was purified by normal phase flash column chromatography (SiO$_2$) to give the title compound (210 mg, 91% yield). MS (ESI): mass calcd. for C$_{29}$H$_{27}$N$_5$O$_5$S, 557.6; m/z found, 557.2 [M+H]$^+$. $^1$H NMR (400 MHz, CDCl$_3$): δ 9.53 (s, 1H), 8.28 (d, J=5.6 Hz, 1H), 8.21 (d, J=5.7 Hz, 1H), 7.37 (q, J=7.0, 6.4 Hz, 3H), 7.29 (s, 2H), 7.21-7.02 (m, 3H), 6.05 (dd, J=24.2, 5.5 Hz, 2H), 4.26 (s, 2H), 3.66-3.51 (m, 5H), 3.30 (s, 3H), 1.97-1.54 (m, 4H).

Example 577: (R)-5-(3-Chloro-4-phenoxyphenyl)-4-oxo-N-(pyrrolidin-3-yl)-4,5-dihydro-3H-1-thia-3,5,8-triazaacenaphthylene-2-carboxamide

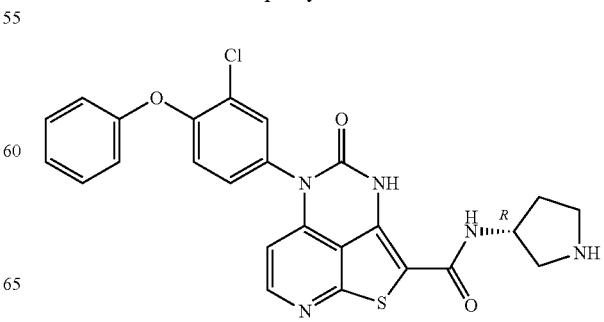

The title compound was prepared in a manner analogous to Method 1, steps A-H in Example 1, and using 2-chloro-1-fluoro-4-nitro-benzene in place of 5-fluoro-2-nitrotoluene in step A, and using tert-butyl (3R)-3-aminopyrrolidine-1-carboxylate in place of tert-butyl (3R,5R)-3-amino-5-fluoro-piperidine-1-carboxylate in step G. MS (ESI): mass calcd. for $C_{25}H_{20}ClN_5O_3S$, 506.0; m/z found, 506.1 [M+H]$^+$. $^1$H NMR (400 MHz, CD$_3$OD): δ 8.18-8.13 (m, 1H), 7.57-7.52 (m, 1H), 7.42-7.36 (m, 2H), 7.30-7.25 (m, 1H), 7.18-7.12 (m, 2H), 7.08-7.03 (m, 2H), 6.07-6.03 (m, 1H), 4.63-4.56 (m, 1H), 3.44-3.36 (m, 1H), 3.35-3.31 (m, 1H), 3.27-3.22 (m, 1H), 3.22-3.15 (m, 1H), 2.35-2.24 (m, 1H), 2.14-2.06 (m, 1H).

Example 578: 4-Oxo-N-(6-oxopiperidin-3-yl)-5-(4-phenoxyphenyl)-4,5-dihydro-3H-1-thia-3,5,8-triazaacenaphthylene-2-carboxamide

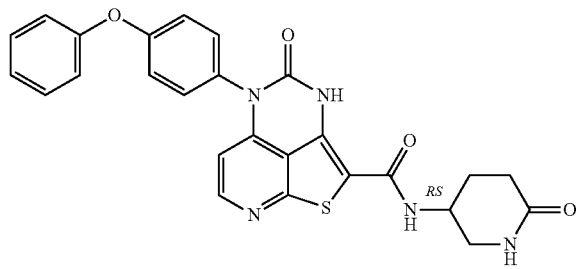

The title compound was prepared in a manner analogous to Method 1, steps A-G in Example 1, and using 4-fluoronitrobenzene in place of 5-fluoro-2-nitrotoluene in step A, and using 5-amino-piperidin-2-one hydrochloride in place of tert-butyl (3R,5R)-3-amino-5-fluoro-piperidine-1-carboxylate in step G. MS (ESI): mass calcd. for $C_{26}H_{21}N_5O_4S$, 499.5; m/z found, 500.1 [M+H]$^+$. $^1$H NMR (400 MHz, CDCl$_3$): δ 8.41-8.30 (m, 1H), 7.49-7.09 (m, 10H), 6.26-6.15 (m, 1H), 4.40 (dd, J=12.8, 7.2 Hz, 1H), 3.73-3.70 (m, 3H), 3.60 (dd, J=12.6, 5.7 Hz, 1H), 3.44-3.35 (m, 1H), 3.33-3.25 (m, 1H), 2.58-2.47 (m, 2H).

Example 579: N-((3S,4S)-4-Fluoropyrrolidin-3-yl)-4-oxo-5-(4-phenoxyphenyl)-4,5-dihydro-3H-1-thia-3,5,8-triazaacenaphthylene-2-carboxamide

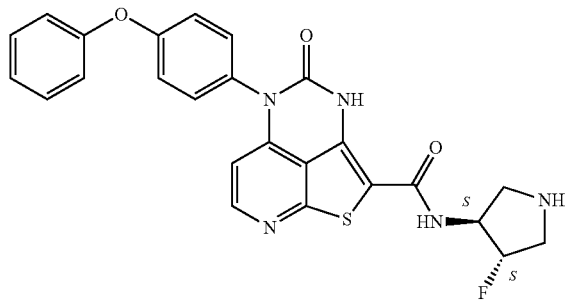

The title compound was prepared using the procedures found in Example 506, steps A-B, and using 4-phenoxyaniline and (3S,4S)-tert-butyl 3-amino-4-fluoropyrrolidine-1-carboxylate to give an off white solid. MS (ESI): mass calcd. for $C_{25}H_{20}FN_5O_3S$, 489.5; m/z found, 490.2 [M+H]$^+$. $^1$H NMR (500 MHz, CDCl$_3$): δ 8.34-8.29 (m, 1H), 7.45-7.35 (m, 2H), 7.33-7.25 (m, 2H), 7.23-7.08 (m, 5H), 6.18-6.12 (m, 1H), 4.56 (ddd, J=18.7, 6.9, 3.4 Hz, 1H), 3.48 (ddd, J=9.8, 6.8, 2.6 Hz, 1H), 3.28-3.08 (m, 6H), 2.89 (dt, J=12.0, 3.4 Hz, 1H).

Example 580: (R)-5-(4'-Methyl-[1,1'-biphenyl]-3-yl)-4-oxo-N-(piperidin-3-yl)-4,5-dihydro-3H-1-thia-3,5,8-triazaacenaphthylene-2-carboxamide

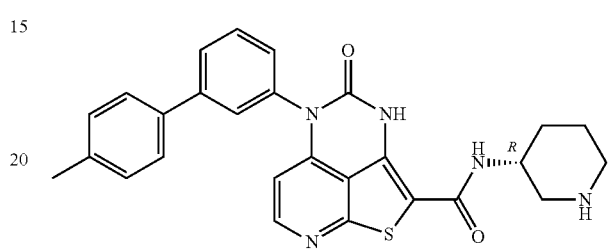

The title compound was prepared using the procedures found in Example 498, steps A-C, and using p-tolylboronic acid in place of (2,3-difluorophenyl)boronic acid in step B. MS (ESI): mass calcd. for $C_{27}H_{25}N_5O_2S$, 483.6; m/z found, 484.4 [M+H]$^+$. $^1$H NMR (400 MHz, CD$_3$OD): δ 8.52 (s, 1H), 8.26 (d, J=5.6 Hz, 1H), 7.83-7.72 (m, 1H), 7.69-7.60 (m, 2H), 7.58-7.49 (m, 2H), 7.39-7.31 (m, 1H), 7.28-7.20 (m, 2H), 6.14 (d, J=5.6 Hz, 1H), 4.28-4.15 (m, 1H), 3.53-3.40 (m, 1H), 3.27-3.16 (m, 1H), 2.97-2.83 (m, 2H), 2.34 (s, 3H), 2.12-1.95 (m, 2H), 1.90-1.65 (m, 2H).

Example 581: (R)-5-(3-Chloro-4-phenoxyphenyl)-4-oxo-N-(piperidin-3-yl)-4,5-dihydro-3H-1-thia-3,5,8-triazaacenaphthylene-2-carboxamide

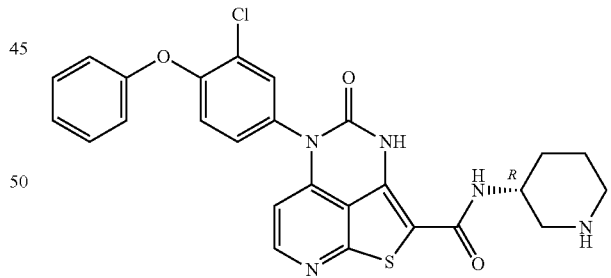

The title compound was prepared using the procedure using Method 1, steps A-H in Example 1, using 3-chloro-4-fluoronitroaniline in step A and tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{26}H_{22}ClN_5O_3S$, 520.0; m/z found, 520.9 [M+H]$^+$. $^1$H NMR (400 MHz, CD$_3$OD): δ 8.11-8.01 (m, 1H), 7.53-7.46 (m, 1H), 7.43-7.32 (m, 2H), 7.30-7.20 (m, 1H), 7.20-7.09 (m, 2H), 7.09-7.00 (m, 2H), 6.02-5.91 (m, 1H), 4.03-3.87 (m, 1H), 3.21-3.08 (m, 1H), 2.95-2.80 (m, 1H), 2.68-2.52 (m, 2H), 2.06-2.00 (m, 1H), 1.87-1.75 (m, 1H), 1.70-1.48 (m, 2H).

Example 582: (R)—N-(1-Acetylpiperidin-3-yl)-5-(3-chloro-4-phenoxyphenyl)-4-oxo-4,5-dihydro-3H-1-thia-3,5,8-triazaacenaphthylene-2-carboxamide

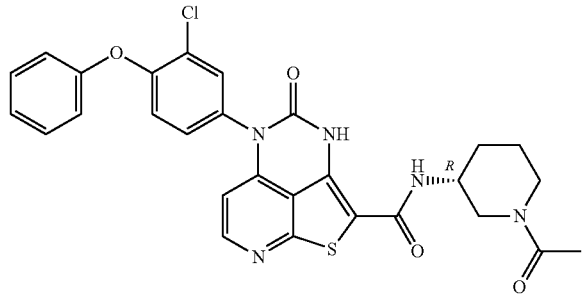

To a solution of (R)-5-(3-chloro-4-phenoxyphenyl)-4-oxo-N-(piperidin-3-yl)-4,5-dihydro-3H-1-thia-3,5,8-triazaacenaphthylene-2-carboxamide (Example 581) (150 mg, 0.288 mmol) and a catalytic amount of DMAP in DCM (25 mL) was added acetic anhydride (35 mg, 0.35 mmol) and was stirred at rt for 20 min. The reaction mixture was concentrated to dryness and the residue was purified by flash column chromatography to give the title compound as a light yellow solid (96 mg, 59% yield). MS (ESI): mass calcd. for $C_{28}H_{24}ClN_5O_4S$, 562.0; m/z found, 562.5 [M+H]$^+$. $^1$H NMR (400 MHz, CD$_3$OD): δ 8.36-8.26 (m, 1H), 7.75-7.64 (m, 1H), 7.46-7.30 (m, 3H), 7.22-7.10 (m, 2H), 7.09-7.00 (m, 2H), 6.21 (d, J=5.6 Hz, 1H), 4.55-4.20 (m, 1H), 4.08-3.68 (m, 2H), 3.14-2.98 (m, 1H), 2.82-2.65 (m, 1H), 2.12 (d, J=6.9 Hz, 3H), 2.08-1.95 (m, 1H), 1.90-1.45 (m, 3H).

Example 583: (R)-5-(3-Methyl-4-phenoxyphenyl)-4-oxo-N-(piperidin-3-yl)-4,5-dihydro-3H-1-thia-3,5,8-triazaacenaphthylene-2-carboxamide

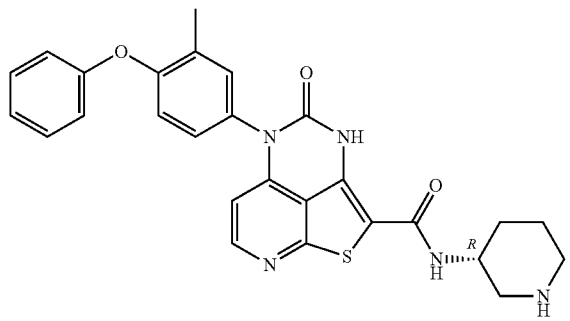

The title compound was prepared using a procedure analogous to Example 1, steps C-H, 3-methyl-4-phenoxy-aniline in place of 3-cyclobutylaniline in step C, to yield the title compound. MS (ESI): mass calcd. for $C_{27}H_{25}N_5O_3S$, 499.6; m/z found, 500.1 [M+H]$^+$. $^1$H NMR (400 MHz, CD$_3$OD): δ 8.53-8.48 (d, J=6.5 Hz, 1H), 7.42-7.35 (m, 3H), 7.28-7.23 (dd, J=8.6, 2.5 Hz, 1H), 7.18-7.12 (m, 1H), 7.06-7.01 (m, 3H), 6.51-6.46 (d, J=6.5 Hz, 1H), 4.36-4.23 (m, 1H), 3.59-3.49 (m, 1H), 3.40-3.33 (m, 1H), 3.05-2.94 (m, 2H), 2.37-2.31 (s, 3H), 2.16-2.05 (m, 2H), 1.95-1.72 (m, 2H).

Example 584: (R)—N-(1-Acryloylpiperidin-3-yl)-5-(3-chloro-4-methylphenyl)-4-oxo-4,5-dihydro-3H-1-thia-3,5,8-triazaacenaphthylene-2-carboxamide

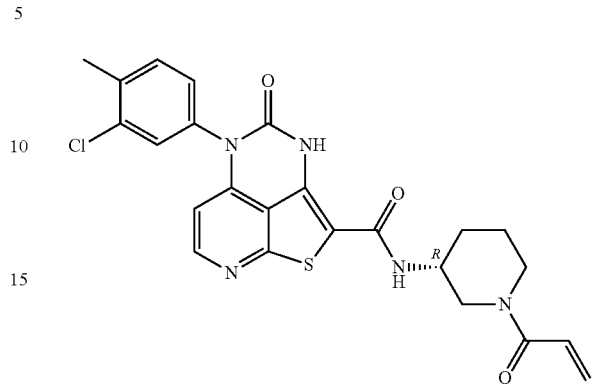

The title compound was prepared using the procedures found in Example 534, steps A-C, and using 3-chloro-4-methylaniline in place of 3-cyclobutylaniline in step A, to yield the title compound. MS (ESI): mass calcd. for $C_{24}H_{22}ClN_5O_3S$, 496.0; m/z found, 496.1 [M+H]$^+$. $^1$H NMR (400 MHz, DMSO-d$_6$): δ 10.22 (br. s., 1H), 8.33 (d, J=5.56 Hz, 1H), 8.10 (dd, J=7.83, 11.37 Hz, 1H), 7.64 (d, J=2.02 Hz, 1H), 7.59 (d, J=8.08 Hz, 1H), 7.38 (dd, J=2.02, 8.08 Hz, 1H), 6.72-6.88 (m, 1H), 6.11 (d, J=16.67 Hz, 1H), 6.07 (d, J=5.56 Hz, 1H), 5.69 (d, J=12.63 Hz, 1H), 4.43-4.53 (m, 0.5H), 4.17-4.26 (m, 0.5H), 3.94-4.10 (m, 1H), 3.72-3.86 (m, 1H), 2.91-3.16 (m, 1H), 2.60-2.84 (m, 1H), 2.43 (s, 3H), 1.90-1.99 (m, 1H), 1.73-1.84 (m, 1H), 1.57-1.73 (m, 1H), 1.33-1.51 (m, 1H).

Example 585: (R)-4-Oxo-5-(2-phenylpyridin-4-yl)-N-(piperidin-3-yl)-4,5-dihydro-3H-1-thia-3,5,8-triazaacenaphthylene-2-carboxamide

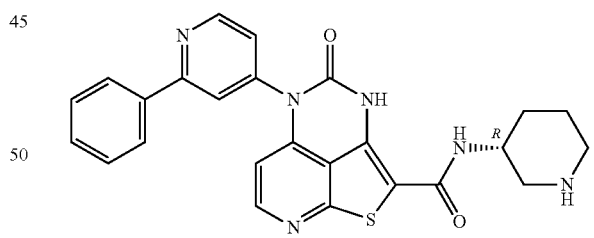

The title compound was prepared in a manner analogous to Method 1, steps C-H in Example 1, and using 2-phenylpyridin-4-amine in place of 2-methyl-4-phenoxy-aniline in step C, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{25}H_{22}N_6O_2S$, 470.5; m/z found, 471.1 [M+H]$^+$. $^1$H NMR (400 MHz, CD$_3$OD and DMSO-d$_6$): δ 8.90-8.78 (m, 1H), 8.35-8.25 (m, 1H), 8.09-8.01 (m, 3H), 7.49-7.37 (m, 4H), 6.30-6.16 (m, 1H), 4.22-4.18 (m, 1H), 3.36-3.28 (m, 1H), 3.21-3.15 (m, 1H), 2.88-2.75 (m, 2H), 1.95-1.85 (m, 2H), 1.76-1.57 (m, 2H).

Example 2: N-((3R,5R)-5-Hydroxypiperidin-3-yl)-4-oxo-5-(4-phenoxyphenyl)-4,5-dihydro-3H-1-thia-3,5,8-triazaacenaphthylene-2-carboxamide

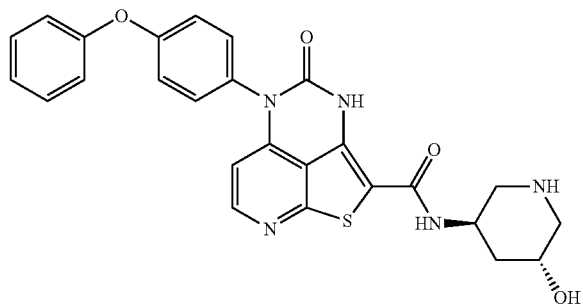 [SMILES: O=C(N[C@H]1CNC[C@H](O)C1)c1sc2nccc3c2c1NC(=O)N3c1ccc(Oc2ccccc2)cc1]

To a solution of (3R,5R)-tert-butyl 3-hydroxy-5-(4-oxo-5-(4-phenoxyphenyl)-4,5-dihydro-3H-1-thia-3,5,8-triazaacenaphthylene-2-carboxamido)piperidine-1-carboxylate (Example 611) (2700 mg, 4.49 mmol) in DCM (20 mL) at room temperature was added TFA (75 mL) dropwise. The reaction was stirred at room temperature for 30 minutes. The reaction was concentrated to dryness and the residue was purified by normal phase flash column chromatography (SiO$_2$) to give the title compound (2000 mg, 88.9% yield) as an off white solid. MS (ESI): mass calcd. for C$_{26}$H$_{23}$N$_5$O$_4$S, 501.6; m/z found, 502.2 [M+H]$^+$. $^1$H NMR (400 MHz, CD$_3$OD): δ 8.30 (d, J=5.6 Hz, 1H), 8.03 (s, 1H) 7.46-7.36 (m, 5H), 7.23-7.05 (m, 5H), 6.17 (d, J=5.6 Hz, 1H), 6.00 (s, 1H), 4.69 (tt, J=11.8, 4.3 Hz, 1H), 4.30 (p, J=2.5 Hz, 1H), 3.56-3.46 (m, 1H), 3.25 (ddt, J=13.1, 3.0, 1.6 Hz, 1H), 3.09 (dd, J=13.0, 1.8 Hz, 1H), 2.90 (t, J=11.8 Hz, 1H), 2.17 (dtd, J=12.2, 4.0, 2.0 Hz, 1H), 2.00 (bs, 1H), 1.89 (ddd, J=13.3, 12.0, 2.5 Hz, 1H).

Example 587: (R)-5-([1,1'-Biphenyl]-3-yl)-N-(1-methylpyrrolidin-3-yl)-4-oxo-4,5-dihydro-3H-1-thia-3,5,8-triazaacenaphthylene-2-carboxamide

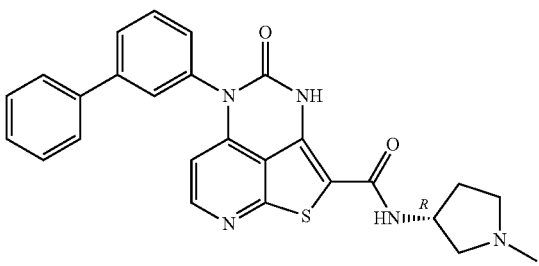

Step A: (R)-5-[1,1'-Biphenyl]-3-yl)-4-oxo-N-(pyrrolidin-3-yl)-4,5-dihydro-3H-1-thia-3,5,8-triazaacenaphthylene-2-carboxamide The title compound was prepared using analogous conditions as found in Method 1, steps C-H in Example 1, and using [1,1'-biphenyl]-3-amine (Intermediate 46) in place of 2-methyl-4-phenoxyaniline in step C, and using (R)-tert-butyl 3-aminopyrrolidine-1-carboxylate in place of tert-butyl (3R,5R)-3-amino-5-fluoropiperidine-1-carboxylate (Intermediate 1) in step G. MS (ESI): mass calcd. for C$_{25}$H$_{21}$N$_5$O$_2$S, 455.53; m/z found, 456.3 [M+H]$^+$. $^1$H NMR (400 MHz, CD$_3$OD): δ 8.29 (d, J=5.6 Hz, 1H), 7.85-7.77 (m, 1H), 7.76-7.59 (m, 4H), 7.49-7.39 (m, 3H), 7.39-7.30 (m, 1H), 6.18 (d, J=5.6 Hz, 1H), 4.63-4.5.3 (m, 1H), 3.65-3.51 (m, 2H), 3.47-3.34 (m, 2H), 2.48-2.31 (m, 1H), 2.27-2.13 (m, 1H).

Step B: (R)-5-([1,1'-Biphenyl]-3-yl)-N-(1-methylpyrrolidin-3-yl)-4-oxo-4,5-dihydro-3H-1-thia-3,5,8-triazaacenaphthylene-2-carboxamide To a solution of (R)-5-([1,1'-biphenyl]-3-yl)-4-oxo-N-(pyrrolidin-3-yl)-4,5-dihydro-3H-1-thia-3,5,8-triazaacenaphthylene-2-carboxamide (100 mg, 0.22 mmol) and formaldehyde (0.5 mL, 37 wt. % in H$_2$O) in methanol (15 mL) was added NaBH(OAc)$_3$ (140 mg, 0.66 mmol) and was stirred at room temperature for 3 h. The reaction mixture was concentrated to dryness and purified by normal phase flash column chromatography (SiO$_2$) to give the title compound as a yellow solid (73 mg, 70% yield). MS (ESI): mass calcd. for C$_{26}$H$_{23}$N$_5$O$_2$S, 469.6; m/z found, 470.3 [M+H]$^+$. $^1$H NMR (400 MHz, CD$_3$OD): δ 8.43 (s, 1H), 8.30 (d, J=5.6 Hz, 1H), 7.86-7.79 (m, 1H), 7.73-7.62 (m, 4H), 7.47-7.38 (m, 3H), 7.37-7.31 (m, 1H), 6.19 (d, J=5.6 Hz, 1H), 4.67-4.50 (m, 1H), 3.70-3.58 (m, 1H), 3.55-3.45 (m, 2H), 3.27-3.15 (m, 1H), 2.92 (s, 3H), 2.60-2.45 (m, 1H), 2.30-2.15 (m, 1H).

Example 588: N-((3S,4S)-4-Methoxypyrrolidin-3-yl)-4-oxo-5-(4-phenoxyphenyl)-4,5-dihydro-3H-1-thia-3,5,8-triazaacenaphthylene-2-carboxamide

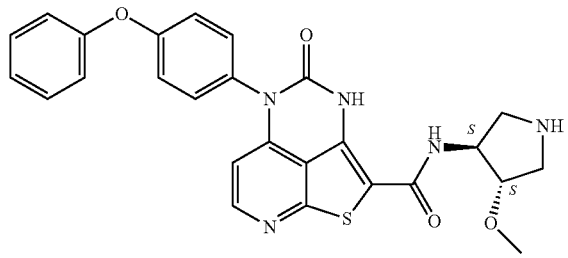

The title compound was prepared in a manner analogous to Method 1, steps A-H in Example 1, and using tert-butyl (3S,4S)-3-amino-4-methoxy-pyrrolidine-1-carboxylate in place of tert-butyl (3R,5R)-3-amino-5-fluoro-piperidine-1-carboxylate in step G, and TFA in place of HCl in step H to yield the title compound. MS (ESI): mass calcd. for C$_{26}$H$_{23}$N$_5$O$_4$S, 501.6; m/z found, 502.2 [M+H]$^+$. $^1$H NMR (500 MHz, CDCL$_3$): δ 8.25 (d, J=5.5 Hz, 4H), 7.97-7.91 (m, 1H), 7.43-7.28 (m, 4H), 7.21-7.04 (m, 5H), 6.07 (d, J=5.5 Hz, 1H), 4.66 (d, J=5.8 Hz, 1H), 4.15-4.10 (m, 1H), 3.71-3.58 (m, 2H), 3.45 (s, 3H), 3.37 (d, J=12.6 Hz, 1H).

Example 3: N-((3R,5R)-1-Acryloyl-5-hydroxypiperidin-3-yl)-4-oxo-5-(4-phenoxyphenyl)-4,5-dihydro-3H-1-thia-3,5,8-triazaacenaphthylene-2-carboxamide

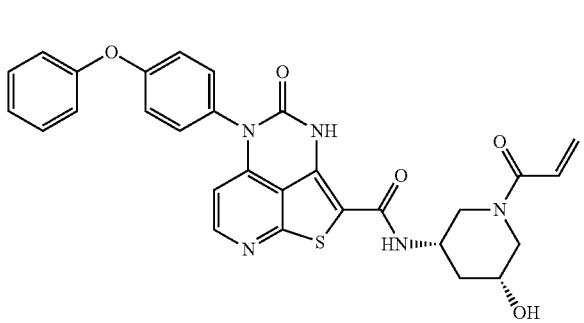 [SMILES: C=CC(=O)N1C[C@H](O)C[C@H](NC(=O)c2sc3nccc4c3c2NC(=O)N4c2ccc(Oc3ccccc3)cc2)C1]

The title compound was prepared using the procedures found in Method 1, Step I in Example 1 using N-((3R,5R)-5-hydroxypiperidin-3-yl)-4-oxo-5-(4-phenoxyphenyl)-4,5-dihydro-3H-1-thia-3,5,8-triazaacenaphthylene-2-carboxamide (Example 586). MS (ESI): mass calcd. for $C_{29}H_{25}N_5O_5S$, 555.6; m/z found, 556.2 [M+H]$^+$. $^1$H NMR (500 MHz, CDCl$_3$): δ 9.49 (s, 1H), 7.34 (dt, J=36.4, 8.2 Hz, 4H), 7.20-7.05 (m, 5H), 6.82 (s, 1H), 6.63 (dt, J=29.6, 14.1 Hz, 1H), 6.23 (d, J=16.5 Hz, 1H), 6.07-6.02 (m, 1H), 5.88 (d, J=4.9 Hz, 1H), 5.64 (d, J=10.5 Hz, 2H), 4.40 (s, 1H), 3.74 (d, J=12.7 Hz, 1H), 3.53 (s, 1H), 3.42 (s, 1H), 3.36 (d, J=12.8 Hz, 1H), 3.05 (hept, J=6.6 Hz, 2H), 2.50 (q, J=7.2 Hz, 1H).

Example 590: (R,E)-N-(1-(4-Hydroxybut-2-enoyl)piperidin-3-yl)-4-oxo-5-(4-phenoxyphenl)-4,5-dihydro-3H-1-thia-3,5,8-triazaacenaphthylene-2-carboxamide

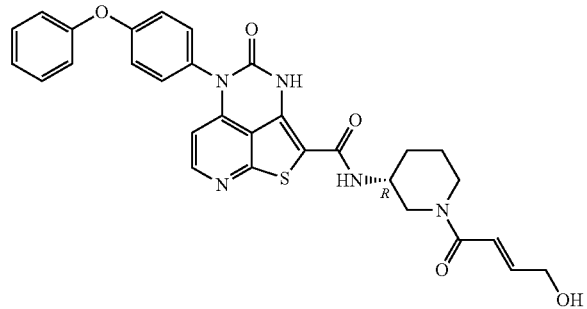

In a microwave vial were added (R)-4-oxo-5-(4-phenoxyphenyl)-N-(piperidin-3-yl)-4,5-dihydro-3H-1-thia-3,5,8-triazaacenaphthylene-2-carboxamide (Example 860) (300 mg, 0.618 mmol), 4-hydroxy-but-2-enoic acid (95 mg, 0.92 mmol), DMF (7 mL), and HATU (705 mg, 1.85 mmol) and was heated in microwave at 100° C. for 5 minutes. The reaction was diluted with DCM and washed with water. The reaction was purified by normal phase flash column chromatography (SiO$_2$) to give the title compound (70 mg, 20% yield). MS (ESI): mass calcd. for $C_{30}H_{27}N_5O_5S$, 569.6; m/z found, 570.1 [M+H]$^+$. $^1$H NMR (400 MHz, CDCl$_3$): δ 9.44 (s, 1H), 8.28 (d, J=5.5 Hz, 1H), 7.44-7.24 (m, 4H), 7.23-7.06 (m, 5H), 6.65 (d, J=16.5 Hz, 1H), 6.19 (d, J=6.3 Hz, 1H), 6.10 (d, J=5.5 Hz, 1H), 4.38-4.32 (m, 1H), 4.28 (s, 1H), 4.04-3.90 (m, 2H), 3.74 (s, 1H), 3.56 (s, 1H), 3.39 (s, 1H), 3.24 (s, 1H), 2.32 (s, 2H), 1.95 (s, 1H), 1.83-1.71 (m, 2H)

Example 591: (R)—N-(1-Acryloylpiperidin-3-yl)-5-(2-cyclobutylpyridin-4-yl)-4-oxo-4,5-dihydro-3H-1-thia-3,5,8-triazaacenaphthylene-2-carboxamide

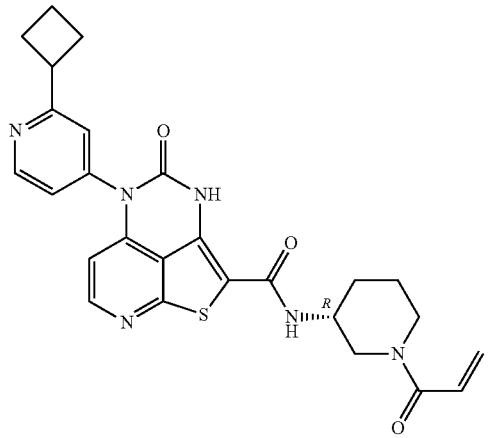

The title compound was prepared using the procedures found in Example 534, steps A-C, and using 2-cyclobutylpyridin-4-amine in place of 3-cyclobutylaniline in step A. MS (ESI): mass calcd. for $C_{26}H_{26}N_6O_3S$, 502.6; m/z found, 503.1 [M+H]$^+$. $^1$H NMR (500 MHz, CD$_3$OD): δ 8.74-8.68 (d, J=5.3 Hz, 1H), 8.34-8.29 (d, J=5.6 Hz, 1H), 7.52-7.48 (d, J=1.9 Hz, 1H), 7.42-7.37 (m, 1H), 6.85-6.74 (m, 1H), 6.24-6.16 (m, 2H), 5.78-5.67 (m, 1H), 4.59-4.29 (m, 1H), 4.23-3.90 (m, 2H), 3.85-3.73 (m, 1H), 3.23-3.09 (m, 1H), 2.95-2.82 (m, 1H), 2.47-2.33 (m, 4H), 2.18-2.02 (m, 2H), 1.99-1.82 (m, 2H), 1.80-1.67 (m, 1H), 1.63-1.50 (m, 1H).

Example 592: (R)—N-(1-Cyanopiperidin-3-yl)-4-oxo-5-(4-phenoxyphenyl)-4,5-dihydro-3H-1-thia-3,5,8-triazaacenaphthylene-2-carboxamide

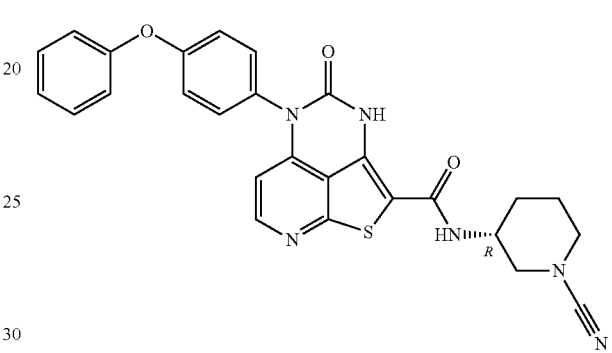

A solution of (R)-4-oxo-5-(4-phenoxyphenyl)-N-(piperidin-3-yl)-4,5-dihydro-3H-1-thia-3,5,8-triazaacenaphthylene-2-carboxamide (Example 860, 250 mg, 0.52 mmol), BrCN (65 mg, 0.62 mmol), and triethylamine (0.143 mL, 1.03 mmol) in DCM (5 mL) was stirred at room temperature for 4 hours. The reaction was concentrated to dryness and the residue was purified by normal phase flash column chromatography (SiO$_2$) to give the title compound (253 mg, 96.2% yield) as yellow solid. MS (ESI): mass calcd. for $C_{27}H_{22}N_6O_3S$, 510.6; m/z found, 511.2 [M+H]$^+$. $^1$H NMR (500 MHz, CDCl$_3$): δ 9.47 (s, 1H), 8.32 (d, J=5.5 Hz, 1H), 7.44-7.35 (m, 2H), 7.36-7.25 (m, 2H), 7.22-7.07 (m, 4H), 6.10 (dd, J=29.2, 6.5 Hz, 2H), 4.21 (ddq, J=11.9, 8.0, 3.9 Hz, 1H), 3.57 (dd, J=12.4, 3.9 Hz, 1H), 3.36-3.26 (m, 1H), 3.18-3.04 (m, 2H), 1.97 (ddt, J=10.9, 7.4, 3.9 Hz, 2H), 1.81 (dddt, J=36.2, 13.8, 9.4, 3.9 Hz, 2H), 1.62 (dtd, J=12.9, 9.0, 3.9 Hz, 1H).

Example 593: (R)—N-(1-(3-Methoxypropanoyl)piperidin-3-yl)-4-oxo-5-(4-phenoxyphenyl)-4,5-dihydro-3H-1-thia-3,5,8-triazaacenaphthylene-2-carboxamide

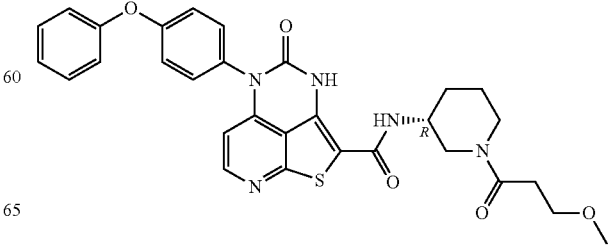

To a solution of (R)-4-oxo-5-(4-phenoxyphenyl)-N-(piperidin-3-yl)-4,5-dihydro-3H-1-thia-3,5,8-triazaacenaphthylene-2-carboxamide (Example 860) (300 mg, 0.618 mmol) in DCM (8 mL) at 0° C. was added triethylamine (0.389 mL, 2.80 mmol), followed by 3-methoxypropanoyl chloride (70 mg, 0.57 mmol) and was stirred at 0° C. for 10 minutes. The reaction was quenched with saturated aqueous NaHCO$_3$, extracted into DCM, dried over anhydrous Na$_2$SO$_4$, and concentrated to dryness. The residue was purified by normal phase flash column chromatography (SiO$_2$) to give the title compound (295 mg, 83.5% yield) as an off white solid. MS (ESI): mass calcd. for C$_{30}$H$_{29}$N$_5$O$_5$S, 571.7; m/z found, 572.2 [M+H]$^+$. $^1$H NMR (500 MHz, CDCl$_3$): δ 8.33 (dd, J=7.6, 5.4 Hz, 1H), 7.44-7.36 (m, 2H), 7.29 (dq, J=12.2, 4.4, 3.7 Hz, 2H), 7.22-7.08 (m, 5H), 6.19-6.10 (m, 2H), 5.90 (d, J=7.2 Hz, 1H), 4.13 (d, J=7.3 Hz, 1H), 3.90-3.55 (m, 3H), 3.30 (s, 3H), 3.20 (td, J=18.1, 15.8, 9.4 Hz, 1H), 3.04 (hept, J=6.5 Hz, 2H), 2.76 (dt, J=14.2, 6.8 Hz, 1H), 2.70-2.55 (m, 1H), 2.48 (q, J=7.2 Hz, 1H), 2.06 (d, J=13.3 Hz, 1H), 2.00-1.90 (m, 1H), 1.65 (tdd, J=13.4, 10.4, 6.1 Hz, 1H).

Example 594: N-(1-Cyanopiperidin-4-yl)-4-oxo-5-(4-phenoxyphenyl)-4,5-dihydro-3H-1-thia-3,5,8-triazaacenaphthylene-2-carboxamide

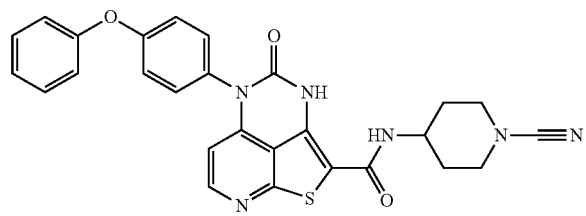 [SMILES: N#CN1CCC(NC(=O)c2sc3nccc4c3c2NC(=O)N4c2ccc(Oc3ccccc3)cc2)CC1]

A solution of 4-oxo-5-(4-phenoxyphenyl)-N-(piperidin-4-yl)-4,5-dihydro-3H-1-thia-3,5,8-triazaacenaphthylene-2-carboxamide (Example 926) (350 mg, 0.721 mmol), BrCN (92 mg, 0.87 mmol), and triethylamine (0.20 mL, 1.4 mmol) in DCM (5 mL) was stirred at room temperature for 4 hours. The reaction was concentrated to dryness and the residue was purified by normal phase flash column chromatography (SiO$_2$) to give the title compound (360.5 mg, 97.96% yield) as yellow solid. MS (ESI): mass calcd. for C$_{27}$H$_{22}$N$_6$O$_3$S, 510.6; m/z found, 511.15 [M+H]$^+$. $^1$H NMR (500 MHz, CDCl$_3$): δ 8.32 (dd, J=6.2, 2.4 Hz, 1H), 7.45-7.34 (m, 2H), 7.32-7.08 (m, 7H), 6.20-6.15 (m, 1H), 4.05 (tt, J=11.3, 3.9 Hz, 1H), 3.58 (s, 2H), 3.55-3.47 (m, 2H), 3.19 (td, J=12.8, 2.7 Hz, 2H), 2.07-1.99 (m, 2H), 1.76 (td, J=12.2, 4.2 Hz, 2H).

Example 595: (R)-5-(3-Methyl-5-phenoxypyridin-2-yl)-4-oxo-N-(piperidin-3-yl)-4,5-dihydro-3H-1-thia-3,5,8-triazaacenaphthylene-2-carboxamide

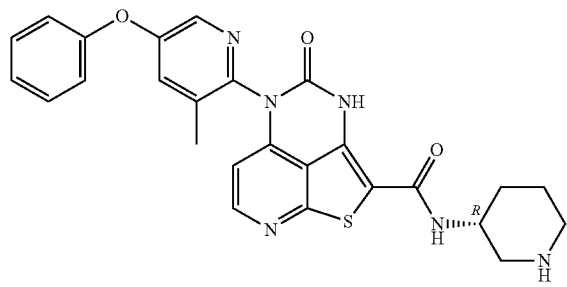

Step A: 2-Chloro-4-[(3-methyl-5-phenoxy-2-pyridyl)amino]pyridine-3-carbonitrile

To a microwave vial containing a stir bar, 2-chloro-4-iodonicotinonitrile (1243 mg, 4.700 mmol), and 3-methyl-5-phenoxy-pyridin-2-amine (890 mg, 4.44 mmol) were added DPEPhos (102 mg, 0.190 mmol), Pd(OAc)$_2$ (46 mg, 0.21 mmol), and Cs$_2$CO$_3$ (2530 mg, 7.765 mmol). The vial was treated with 1,4 dioxane (8 mL) via syringe, then the entire mixture was degassed under vacuum for 1 minute, then vented to nitrogen. The reaction mixture was heated thermally at 90° C. for 16 h. The reaction mixture was diluted with ether (100 mL) and filtered to remove the cesium carbonate. The filter cake was rinsed with EtOAc (50 mL). The combined organics were dried over anhydrous Na$_2$SO$_4$, concentrated to dryness, and treated with DCM (50 mL). The soluble material was purified by flash column chromatography to give the title compound (230 mg, 14.5% yield).

Step B: (R)-tert-butyl 3-(5-(3-methyl-5-phenoxy-pyridin-2-yl)-4-oxo-4,5-dihydro-3H-1-thia-3,5,8-triazaacenaphthylene-2-carboxamido)piperidine-1-carboxylate A microwave vial containing 2-chloro-4-[(3-methyl-5-phenoxy-2-pyridyl)amino]pyridine-3-carbonitrile (806 mg, 2.39 mmol), Cs$_2$CO$_3$ (2011 mg, 6.172 mmol), and dioxane (5 mL) was sealed, and treated with dioxane (5 mL) via syringe. To the reaction was added tert-butyl (3R)-3-[(2-sulfanylacetyl)amino]piperidine-1-carboxylate (Intermediate 22) (6.78 mmol), and was degassed under vacuum, vented to N$_2$, and heated at 122° C. for 1 h. The reaction mixture was treated with solid CDI (2000 mg, 12.33 mmol) in one portion, resealed and stirred at 70° C. for 60 min. The reaction was diluted with EtOAc (100 mL) and DCM (100 mL), washed with saturated aqueous sodium bicarbonate, and the organic layer collected. The aqueous layer was extracted again with EtOAc (100 mL), and the combined organics were dried over anhydrous MgSO$_4$, concentrated to dryness, and purified by flash column chromatography to give the title compound as an orange foam (712 mg, 49.5% yield).

Step C: (R)-5-(3-Methyl-5-phenoxypyridin-2-yl)-4-oxo-N-(piperidin-3-yl)-4,5-dihydro-3H-1-thia-3,5,8-triazaacenaphthylene-2-carboxamide To a solution of (R)-tert-butyl 3-(5-(3-methyl-5-phenoxy-pyridin-2-yl)-4-oxo-4,5-dihydro-3H-1-thia-3,5,8-triazaacenaphthylene-2-carboxamido)piperidine-1-carboxylate (710 mg, 1.18 mmol) in dioxane (5 mL) was treated with 4 M HCl-dioxane (5 mL). The reaction mixture was stirred at room temperature for 1.5 h. The reaction was then treated slowly with ether (15 mL), and the resulting suspension was stirred for 10 min at room temperature, filtered, and dried under vacuum to give the title compound as a yellow solid (672 mg, 99.1% yield). MS (ESI): mass calcd. for C$_{26}$H$_{24}$N$_6$O$_3$S, 500.6; m/z found, 501.1 [M+H]$^+$. $^1$H NMR (500 MHz, CD$_3$OD): δ 8.58-8.53 (d, J=6.5 Hz, 1H), 8.25-8.21 (d, J=3.4 Hz, 1H), 7.56-7.52 (d, J=2.7 Hz, 1H), 7.51-7.45 (m, 2H), 7.30-7.25 (m, 1H), 7.22-7.17 (m, 2H), 6.48-6.44 (dd, J=6.5, 0.9 Hz, 1H), 4.35-4.25 (m, 1H), 3.58-3.51 (m, 1H), 3.39-3.33 (m, 1H), 3.06-2.96 (m, 2H), 2.28-2.22 (s, 3H), 2.15-2.05 (m, 2H), 1.93-1.75 (m, 2H).

Example 596: (E)-N-(1-(4-Hydroxybut-2-enoyl)piperidin-4-yl)-4-oxo-5-(4-phenoxyphenyl)-4,5-dihydro-3H-1-thia-3,5,8-triazaacenaphthylene-2-carboxamide

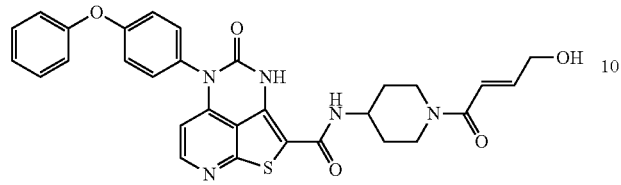

In a microwave vial were added 4-oxo-5-(4-phenoxyphenyl)-N-(piperidin-4-yl)-4,5-dihydro-3H-1-thia-3,5,8-triazaacenaphthylene-2-carboxamide (Example 926) (300 mg, 0.618 mmol), 4-hydroxy-but-2-enoic acid (95 mg, 0.93 mmol), DMF (7 mL), and HATU (705 mg, 1.85 mmol). The reaction was heated in microwave at 100° C. for 5 minutes. The reaction was diluted with DCM and washed with water. The reaction was purified by normal phase flash column chromatography (SiO$_2$) to give the title compound (61.5 mg, 17.5% yield). MS (ESI): mass calcd. for $C_{30}H_{27}N_5O_5S$, 569.6; m/z found, 570.10 [M+H]$^+$. $^1$H NMR (500 MHz, CDCl$_3$): δ 8.31 (d, J=5.5 Hz, 1H), 8.03 (s, 1H), 7.45-7.35 (m, 2H), 7.30 (dd, J=9.3, 2.6 Hz, 2H), 7.24-7.09 (m, 5H), 6.88 (dt, J=15.2, 3.8 Hz, 1H), 6.59 (dt, J=15.3, 2.1 Hz, 1H), 6.17 (dd, J=5.8, 2.2 Hz, 1H), 4.65 (d, J=13.3 Hz, 1H), 4.30 (dd, J=3.8, 2.1 Hz, 2H), 4.23-4.10 (m, 2H), 3.94 (s, 3H), 3.23 (t, J=12.8 Hz, 1H), 2.83 (t, J=12.6 Hz, 1H), 2.06 (t, J=15.7 Hz, 2H), 1.52 (d, J=12.4 Hz, 1H).

Example 597: N-(1-(3-Methoxypropanoyl)piperidin-4-yl)-4-oxo-5-(4-phenoxyphenyl)-4,5-dihydro-3H-1-thia-3,5,8-triazaacenaphthylene-2-carboxamide

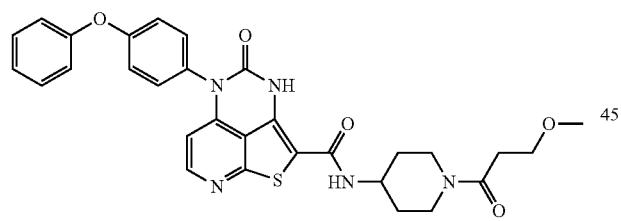

To a solution of 4-oxo-5-(4-phenoxyphenyl)-N-(piperidin-4-yl)-4,5-dihydro-3H-1-thia-3,5,8-triazaacenaphthylene-2-carboxamide (Example 926) (300 mg, 0.618 mmol) in DCM (8 mL) at 0° C. was added triethylamine (0.389 mL, 2.80 mmol), followed by 3-methoxypropanoyl chloride (70 mg, 0.57 mmol). The reaction was stirred at 0° C. for 10 minutes. The reaction was quenched with saturated aqueous NaHCO$_3$ and extracted into DCM. The organic layer was dried over anhydrous Na$_2$SO$_4$, concentrated to dryness, and the residue was purified by normal phase flash column chromatography (SiO$_2$) to give the title compound (207.3 mg, 58.7% yield) as an off white solid. MS (ESI): mass calcd. for $C_{30}H_{29}N_5O_5S$, 571.7; m/z found, 572.2 [M+H]$^+$. $^1$H NMR (500 MHz, CDCl$_3$): δ 9.48 (s, 1H), 8.35 (d, J=5.5 Hz, 1H), 7.47-7.36 (m, 2H), 7.32-7.26 (m, 2H), 7.22-7.08 (m, 5H), 6.15 (d, J=5.5 Hz, 1H), 5.97-5.91 (m, 1H), 4.70-4.62 (m, 1H), 4.18 (tdt, J=11.5, 8.0, 4.2 Hz, 1H), 3.94 (dd, J=11.2, 6.7 Hz, 1H), 3.71 (q, J=6.4 Hz, 2H), 3.35 (s, 3H), 3.23-3.13 (m, 1H), 2.76 (td, J=13.0, 2.9 Hz, 1H), 2.63 (td, J=6.5, 2.8 Hz, 2H), 2.13 (d, J=12.6 Hz, 1H), 2.04 (dd, J=13.4, 4.0 Hz, 1H), 1.46 (dd, J=12.6, 4.1 Hz, 2H).

Example 598: (R)—N-(1-Acryloylpiperidin-3-yl)-3-amino-4-((3-cyclobutoxyphenyl)amino)thieno[2,3-b]pyridine-2-carboxamide

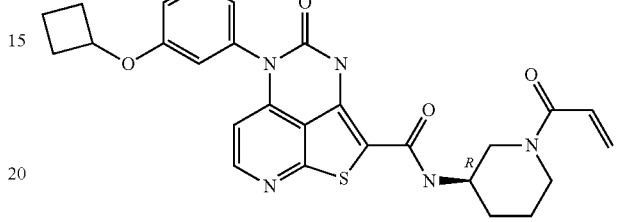

The title compound was prepared using methods analogous to Example 33 Steps A-D and using 3-nitrophenol and bromocyclobutane in place of 4-nitrophenol and 2-iodopropane in step A. MS (ESI): mass calcd. for $C_{27}H_{27}N_5O_4S$, 517.6; m/z found, 518.2 [M+H]$^+$. $^1$H NMR (400 MHz, CD$_3$OD): δ 8.31-8.24 (m, 1H), 7.51-7.41 (m, 1H), 7.09-6.89 (m, 3H), 6.85-6.73 (m, 1H), 6.23-6.14 (m, 1H), 6.13-6.08 (m, 1H), 5.78-5.63 (m, 1H), 4.78-4.67 (m, 1H), 4.57-3.86 (m, 3H), 3.24-3.09 (m, 1H), 2.94-2.80 (m, 1H), 2.51-2.39 (m, 2H), 2.18-1.99 (m, 3H), 1.92-1.79 (m, 2H), 1.78-1.62 (m, 2H), 1.61-1.50 (m, 1H).

Example 599: (R)-5-([1,1'-Biphenyl]-3-yl)-4-oxo-N-(pyrrolidin-3-yl)-4,5-dihydro-3H-1-thia-3,5,8-triazaacenaphthylene-2-carboxamide

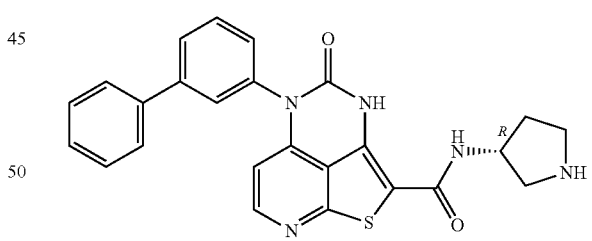

The title compound was prepared in a manner analogous to Method 1, steps C-H in Example 1, and using 3-phenylaniline in place of 2-methyl-4-phenoxy-aniline in step C, and using tert-butyl (3R)-3-aminopyrrolidine-1-carboxylate in place of tert-butyl (3R,5R)-3-amino-5-fluoro-piperidine-1-carboxylate in step G. MS (ESI): mass calcd. for $C_{25}H_{21}N_5O_2S$, 455.14; m/z found, 456.3 [M+H]$^+$. $^1$H NMR (400 MHz, CD$_3$OD): δ 8.29 (d, J=5.6 Hz, 1H), 7.85-7.77 (m, 1H), 7.76-7.59 (m, 4H), 7.49-7.39 (m, 3H), 7.39-7.30 (m, 1H), 6.18 (d, J=5.6 Hz, 1H), 4.63-4.5.3 (m, 1H), 3.65-3.51 (m, 2H), 3.47-3.34 (m, 2H), 2.48-2.31 (m, 1H), 2.27-2.13 (m, 1H).

Example 600: 2-((1-Acryloylpiperidin-3-yl)amino)-5-(2-methyl-4-phenoxyphenyl)-3H-1-thia-3,5,8-triazaacenaphthylen-4(5H)-one

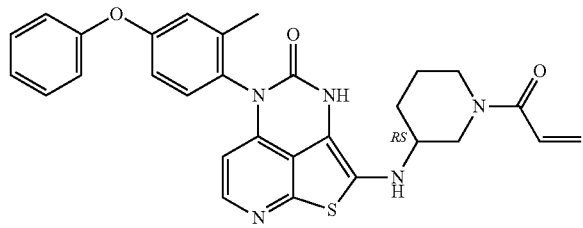

To solution of 2-amino-5-(2-methyl-4-phenoxyphenyl)-3H-1-thia-3,5,8-triazaacenaphthylen-4(5H)-one (Intermediate 56, 100 mg, 0.257 mmol) and prop-2-enoylpiperidin-3-one (Intermediate 79) (47.2 mg, 0.308 mmol) in anhydrous methanol (4 mL) was added acetic acid (0.05 mL) at room temperature under $N_2$ and was stirred for 1 h. To the reaction mixture was added $BH_3$-pyridine complex (35.8 mg, 0.386 mmol) at room temperature and was stirred overnight at room temperature under $N_2$. The reaction mixture was purified by flash column chromatography to give the title compound as a light yellow solid (51 mg, 33% yield). MS (ESI): mass calcd. for $C_{29}H_{27}N_5O_3S$, 525.6; m/z found, 526.4 [M+H]$^+$.

Example 601: (R)-5-([1,1'-Biphenyl]-3-yl)-N-(1-(2-(methylamino)acetyl)pyrrolidin-3-yl)-4-oxo-4,5-dihydro-3H-1-thia-3,5,8-triazaacenaphthylene-2-carboxamide

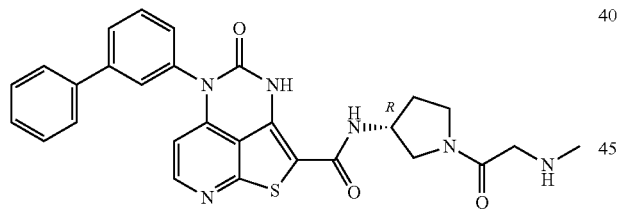

(R)-5-([1,1'-biphenyl]-3-yl)-4-oxo-N-(pyrrolidin-3-yl)-4,5-dihydro-3H-1-thia-3,5,8-triazaacenaphthylene-2-carboxamide was prepared using Method 1, steps C-G in Example 1, and using 3-phenylaniline in place of 2-methyl-4-phenoxy-aniline in step C. The title compound was prepared using a method analogous to Example 75 using and using 2-[tert-butoxycarbonyl(methyl)amino]acetic acid (Intermediate 21) followed by treatment of the purified solid with 6NHCl/MeOH and purification by column chromatography eluting with water (0.1% HCOOH)/MeOH to provide the desired compound as a light yellow solid. MS (ESI): mass calcd. for $C_{28}H_{26}N_6O_3S$, 526.6; m/z found, 527.4 [M+H]$^+$. $^1$H NMR (400 MHz, CD$_3$OD): δ 8.48 (s, 1H), 8.31-8.22 (m, 1H), 7.85-7.76 (m, 1H), 7.75-7.57 (m, 4H), 7.48-7.28 (m, 4H), 6.23-6.08 (m, 1H), 4.66-4.53 (m, 1H), 3.92-3.87 (m, 2H), 3.84-3.61 (m, 2H), 3.60-3.39 (m, 2H), 2.74-2.64 (m, 3H), 2.38-2.02 (m, 2H).

Example 602: (R)-4-Oxo-5-(2-phenylpyridin-4-yl)-N-(pyrrolidin-3-yl)-4,5-dihydro-3H-1-thia-3,5,8-triazaacenaphthylene-2-carboxamide

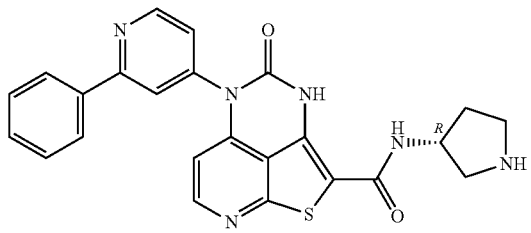

The title compound was prepared in a manner analogous to Method 1, steps C-H in Example 1, and using 2-phenylpyridin-4-amine in place of 2-methyl-4-phenoxy-aniline in step C, and using tert-butyl (3R)-3-aminopyrrolidine-1-carboxylate in place of tert-butyl (3R,5R)-3-amino-5-fluoro-piperidine-1-carboxylate in step G. MS (ESI): mass calcd. for $C_{24}H_{20}N_6O_2S$, 456.5; m/z found, 457.1 [M+H]$^+$. $^1$H NMR (400 MHz, DMSO-d$_6$ and CD$_3$OD): δ 8.77-8.74 (m, 1H), 8.09-8.06 (m, 1H), 8.05-8.01 (m, 2H), 7.90-7.87 (m, 1H), 7.45-7.37 (m, 3H), 7.31-7.28 (m, 1H), 6.03-5.98 (m, 1H), 4.52-4.42 (m, 1H), 3.35-3.27 (m, 2H), 3.19-3.16 (m, 1H), 3.15-3.13 (m, 1H), 2.24-2.14 (m, 1H), 2.03-1.94 (m, 1H).

Example 603: (R)-5-(3-Cyclobutylphenyl)-4-oxo-N-(piperidin-3-yl)-4,5-dihydro-3H-1-thia-3,5,8-triazaacenaphthylene-2-carboxamide

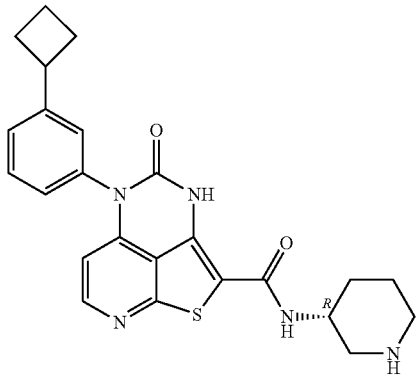

The title compound was prepared using the procedures found in Example 534, steps A-B. MS (ESI): mass calcd. for $C_{24}H_{25}N_5O_2S$, 447.6; m/z found, 448.1 [M+H]$^+$. $^1$H NMR (500 MHz, CD$_3$OD): δ 8.53-8.46 (d, J=6.6 Hz, 1H), 7.60-7.54 (t, J=7.8 Hz, 1H), 7.51-7.45 (m, 1H), 7.38-7.33 (s, 1H), 7.30-7.24 (m, 1H), 6.44-6.37 (d, J=6.6 Hz, 1H), 4.37-4.27 (m, 1H), 3.71-3.62 (m, 1H), 3.57-3.51 (dd, J=12.4, 4.0 Hz, 1H), 3.39-3.33 (m, 1H), 3.06-2.97 (m, 2H), 2.44-2.34 (m, 2H), 2.25-2.16 (m, 2H), 2.14-2.03 (m, 3H), 1.94-1.77 (m, 3H).

Example 604: (R)—N-(1-Acryloylpiperidin-3-yl)-4-oxo-5-(6-phenylpyridin-2-yl)-4,5-dihydro-3H-1-thia-3,5,8-triazaacenaphthylene-2-carboxamide

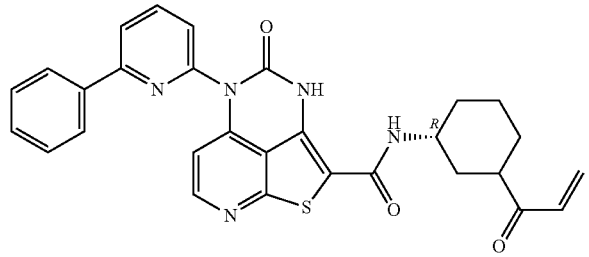

The title compound was prepared in a manner analogous to Method 1, steps C-I in Example 1, and using 6-phenylpyridin-2-amine in place of 2-methyl-4-phenoxy-aniline in step C, and using tert-butyl (3R)-3-aminopiperidine-1-carboxylate in place of tert-butyl (3R,5R)-3-amino-5-fluoropiperidine-1-carboxylate in step G. MS (ESI): mass calcd. for $C_{28}H_{24}N_6O_3S$, 524.6; m/z found, 525.1 $[M+H]^+$. $^1H$ NMR (400 MHz, DMSO-$d_6$): δ 10.24 (s, 1H), 8.34-8.27 (m, 1H), 8.20-8.07 (m, 3H), 8.06-8.02 (m, 2H), 7.58-7.52 (m, 1H), 7.50-7.41 (m, 3H), 6.82-6.69 (m, 1H), 6.23-6.16 (m, 1H), 6.11-6.03 (m, 1H), 5.68-5.62 (m, 1H), 4.50-4.09 (m, 1H), 4.09-3.88 (m, 1H), 3.86-3.68 (m, 1H), 3.11-2.93 (m, 1H), 2.80-2.62 (m, 1H), 1.96-1.89 (m, 1H), 1.79-1.72 (m, 1H), 1.71-1.57 (m, 1H), 1.46-1.35 (m, 1H).

Example 605: (R)-5-(4-Cyclobutoxy-2-methylphenyl)-4-oxo-N-(piperidin-3-yl)-4,5-dihydro-3H-1-thia-3,5,8-triazaacenaphthylene-2-carboxamide

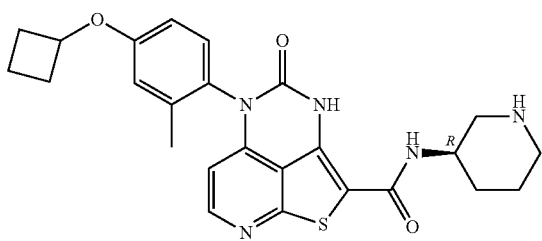

Step A: (R)-tert-Butyl 3-(3-amino-4-((4-cyclobutoxy-2-methylphenyl)amino)thieno[2,3-b]pyridine-2-carboxamido)piperidine-1-carboxylate To a sealed tube containing 2-chloro-4-((4-cyclobutoxy-2-methylphenyl)amino)nicotinonitrile (Intermediate 34, 481 mg, 1.53 mmopl) was added a 0.5 M solution of (R)-tert-butyl 3-(2-mercaptoacetamido)piperidine-1-carboxylate (Intermediate 22) (3.68 mL, 1.84 mmol) in dioxane. The suspension was heated in the sealed tube in a 150° C. aluminum block for 15 minutes. The reaction mixture was cooled in a water bath to give the title compound (845 mg), which was used directly in the next reaction without any workup.

Step B: (R)-tert-Butyl 3-(5-(4-cyclobutoxy-2-methylphenyl)-4-oxo-4,5-dihydro-3H-1-thia-3,5,8-triazaacenaphthylene-2-carboxamido)piperidine-1-carboxylate To (R)-tert-butyl 3-(3-amino-4-((4-cyclobutoxy-2-methylphenyl)amino)thieno[2,3-b]pyridine-2-carboxamido)piperidine-1-carboxylate (845 mg, 1.53 mmol) in dioxane was added CDI (0.994 g, 6.13 mmol). The tube was sealed and the vessel was evacuated and refilled with argon twice. The mixture was heated at 150° C. for 10 minutes, then the mixture was cooled to room temperature. The mixture was partitioned between EtOAc (50 mL) and water (50 mL). The aqueous phase was extracted with EtOAc (2×50 mL) and the combined organic extracts were washed with 1 M aqueous HCl (50 mL), followed by saturated aqueous NaCl (50 mL). The organic phase was dried over anhydrous $Na_2SO_4$, filtered, and concentrated to dryness. The residue was purified by flash column chromatography to give the title compound as a tan solid (524.5 mg, 59% yield).

Step C: (R)-5-(4-Cyclobutoxy-2-methylphenyl)-4-oxo-N-(piperidin-3-yl)-4,5-dihydro-3H-1-thia-3,5,8-triazaacenaphthylene-2-carboxamide To a solution of (R)-tert-butyl 3-(5-(4-cyclobutoxy-2-methylphenyl)-4-oxo-4,5-dihydro-3H-1-thia-3,5,8-triazaacenaphthylene-2-carboxamido)piperidine-1-carboxylate (521.4 mg, 0.903 mmol) in dioxane (4 mL) was added 4 M HCl in dioxane (4 mL) and the solution was stirred at room temperature for 30 minutes. The reaction mixture was concentrated to dryness and the solid was dried under vacuum to give a tan powder (556.9 mg). A 100 mg of the sample was purified by flash column chromatography to give a tan powder (70.6 mg). The material was re-purified by RP-HPLC and the pooled fractions were partially concentrated to remove $CH_3CN$, then were made basic with saturated aqueous $NaHCO_3$, and extracted twice with DCM. The organic phase was dried over anhydrous $Na_2SO_4$, filtered, and concentrated to dryness. The residue was dried under vacuum at 60° C. to give the title compound as a light yellow solid (31.3 mg). MS (ESI): mass calcd. for $C_{25}H_{27}N_5O_3S$, 477.6; m/z found, 478.2 $[M+H]^+$. 1H NMR (400 MHz, CHLOROFORM-d) δ 8.33 (d, J=5.56 Hz, 1H), 7.08-7.12 (m, 1H), 6.83 (d, J=2.53 Hz, 1H), 6.79 (dd, J=3.03, 8.59 Hz, 1H), 6.13-6.24 (m, 1H), 5.99 (d, J=5.05 Hz, 1H), 4.67 (quin, J=7.07 Hz, 1H), 4.08-4.18 (m, 1H), 3.08 (d, J=12.13 Hz, 1H), 2.72-2.91 (m, 3H), 2.42-2.52 (m, 2H), 2.14-2.26 (m, 2H), 2.12 (s, 3H), 1.66-1.95 (m, 6H), 1.50-1.63 (m, 1H).

Example 606: 2-((1-Acryloylpiperidin-4-yl)amino)-5-(2-methyl-4-phenoxyphenyl)-3H-1-thia-3,5,8-triazaacenaphthylen-4(5H)-one

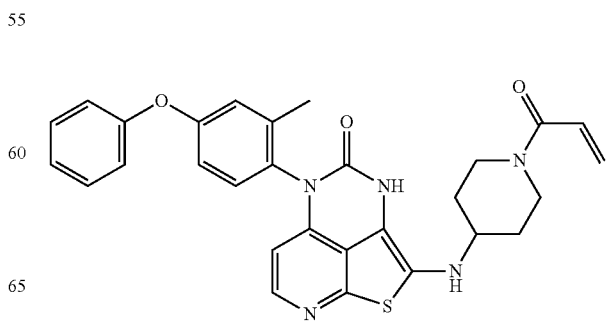

The title compound was prepared using conditions analagous to Example 600 using 1-prop-2-enoylpiperidin-4-one (Intermediate 80). MS (ESI): mass calcd. for $C_{29}H_{27}N_5O_3S$, 525.6; m/z found, 526.5 $[M+H]^+$. 1H NMR (400 MHz, DMSO-d6): δ 7.96 (d, J=5.4 Hz, 1H), 7.47-7.37 (m, 2H), 7.29 (d, J=8.5 Hz, 1H), 7.20-7.14 (m, 1H), 7.11-7.06 (m, 2H), 7.06-7.02 (m, 1H), 6.96-6.86 (m, 1H), 6.87-6.74 (m, 1H), 6.12-6.00 (m, 1H), 5.70 (d, J=5.4 Hz, 1H), 5.67-5.58 (m, 1H), 4.94-4.78 (m, 1H), 4.25-4.10 (m, 1H), 4.00-3.87 (m, 1H), 3.22-3.18 (m, 1H), 2.99-2.87 (m, 1H), 2.05 (s, 3H), 1.97-1.88 (m, 2H), 1.37-1.25 (m, 2H).

Example 607: (R)—N-(1-Acryloylpiperidin-3-yl)-5-(4-methyl-3-(trifluoromethyl)phenyl)-4-oxo-4,5-dihydro-3H-1-thia-3,5,8-triazaacenaphthylene-2-carboxamide

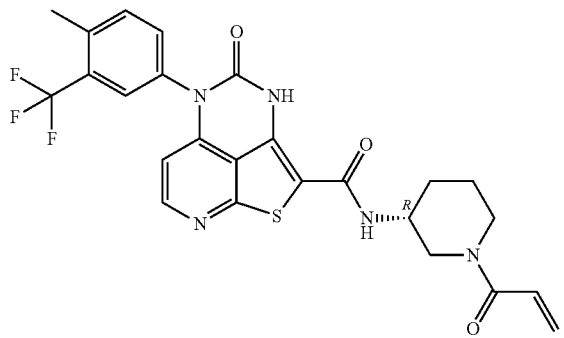

The title compound was prepared using the procedures found in Example 534, steps A-C, and using 4-methyl-3-(trifluoromethyl)aniline in place of 3-cyclobutylaniline in step A. MS (ESI): mass calcd. for $C_{25}H_{22}F_3N_5O_3S$, 529.5; m/z found, 530.1 $[M+H]^+$. $^1$H NMR (400 MHz, DMSO-d$_6$): δ 10.23 (br. s., 1H), 8.33 (d, J=5.56 Hz, 1H), 8.06-8.17 (m, 1H), 7.88 (s, 1H), 7.67-7.73 (m, 2H), 6.72-6.88 (m, 1H), 6.11 (d, J=16.67 Hz, 1H), 6.05 (d, J=5.56 Hz, 1H), 5.69 (dd, J=2.27, 10.36 Hz, 1H), 4.43-4.54 (m, 0.5H), 4.16-4.26 (m, 0.5H), 3.96-4.10 (m, 1H), 3.73-3.86 (m, 1H), 2.92-3.17 (m, 1H), 2.61-2.83 (m, 1H), 2.55 (m, 3H), 1.89-1.99 (m, 1H), 1.73-1.85 (m, 1H), 1.57-1.74 (m, 1H), 1.43 (m, 1H).

Example 608: 5-(4-Isopropoxy-2-methylphenyl)-4-oxo-N—((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide

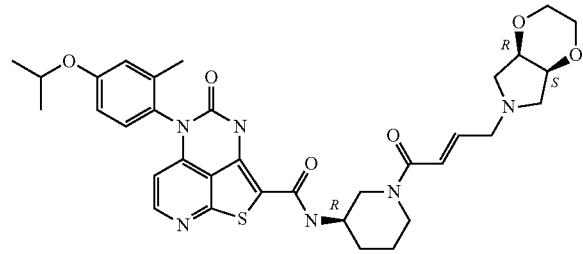

The title compound was prepared using methods analogous to Example 33, Steps A-D using (E)-4-((4aR,7aS)-tetrahydro-2H-[1,4]dioxino[2,3-c]pyrrol-6(3H)-yl)but-2-enoic acid (Intermediate 72) in Step D. MS (ESI): mass calcd. for $C_{34}H_{40}N_6O_6S$, 660.8; m/z found, 661.5 $[M+H]^+$. $^1$H NMR (400 MHz, CD$_3$OD): δ 8.31-8.24 (m, 1H), 7.24-7.17 (m, 1H), 6.98-6.87 (m, 2H), 6.80-6.56 (m, 2H), 6.04-5.96 (m, 1H), 4.70-4.58 (m, 1H), 4.20-3.84 (m, 5H), 3.80-3.63 (m, 2H), 3.58-3.32 (m, 4H), 3.24-3.05 (m, 1H), 3.04-2.72 (m, 5H), 2.13-1.97 (m, 4H), 1.92-1.65 (m, 2H), 1.65-1.51 (m, 1H), 1.38-1.28 (m, 6H).

Example 609: (R)—N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide

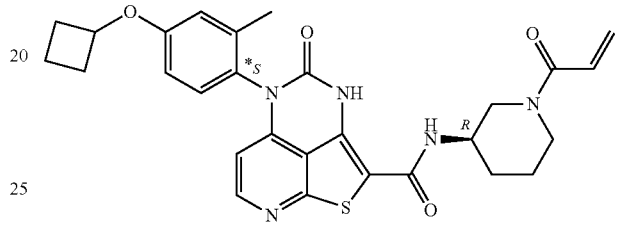

(R)-5-(4-Cyclobutoxy-2-methylphenyl)-4-oxo-N-(piperidin-3-yl)-4,5-dihydro-3H-1-thia-3,5,8-triazaacenaphthylene-2-carboxamide (Example 605) was purified by Chiral Resolution Method A to obtain the *S atropisomer, followed by Step H in Example 1, Method 1, to yield the title compound. MS (ESI): mass calcd. for $C_{28}H_{29}N_5O_4S$, 531.6; m/z found, 532.2 $[M+H]^+$. $^1$H NMR (400 MHz, CD$_3$OD): δ 8.30 (d, J=5.56 Hz, 1H), 7.20 (d, J=8.59 Hz, 1H), 6.91 (d, J=2.53 Hz, 1H), 6.74-6.88 (m, 2H), 6.21 (dd, J=3.03, 16.67 Hz, 1H), 6.02 (d, J=5.56 Hz, 1H), 5.74 (t, J=8.59 Hz, 1H), 4.75 (quin, J=7.07 Hz, 1H), 4.50-4.59 (m, 0.5H), 4.26-4.36 (m, 0.5H), 4.14-4.23 (m, 0.5H), 3.90-4.05 (m, 1.5H), 3.11-3.24 (m, 1H), 2.82-2.98 (m, 1H), 2.43-2.56 (m, 2H), 2.01-2.24 (m, 6H), 1.82-1.93 (m, 2H), 1.68-1.82 (m, 2H), 1.52-1.68 (m, 1H).

Example 610: (R)-4-Oxo-5-(4-phenylpyridin-2-yl)-N-(piperidin-3-yl)-4,5-dihydro-3H-1-thia-3,5,8-triazaacenaphthylene-2-carboxamide

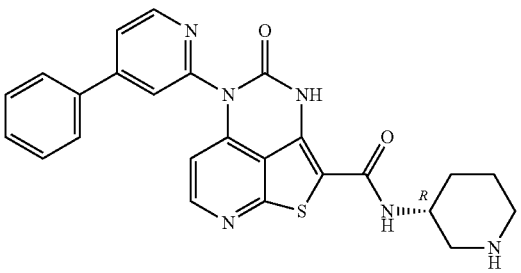

The title compound was prepared in a manner analogous to Method 1, steps C-H in Example 1, and using 4-phenylpyridin-2-amine in place of 2-methyl-4-phenoxy-aniline in step C and using tert-butyl (3R)-3-aminopiperidine-1-carboxylate in place of tert-butyl (3R,5R)-3-amino-5-fluoropiperidine-1-carboxylate in step G. MS (ESI): mass calcd.

for C$_{25}$H$_{22}$N$_6$O$_2$S, 470.5; m/z found, 471.1 [M+H]$^+$. $^1$H NMR (400 MHz, CD$_3$OD): δ 8.75-8.66 (m, 1H), 8.34-8.30 (m, 1H), 7.95-7.87 (m, 2H), 7.83-7.78 (m, 2H), 7.54-7.44 (m, 3H), 6.28-6.22 (m, 1H), 4.31-4.19 (m, 1H), 3.56-3.47 (m, 1H), 3.37-3.34 (m, 1H), 3.00-2.88 (m, 2H), 2.16-2.01 (m, 2H), 1.86-1.67 (m, 2H).

Example 4: (3R,5R)-tert-Butyl 3-hydroxy-5-(4-oxo-5-(4-phenoxyphenyl)-4,5-dihydro-3H-1-thia-3,5,8-triazaacenaphthylene-2-carboxamido)piperidine-1-carboxylate

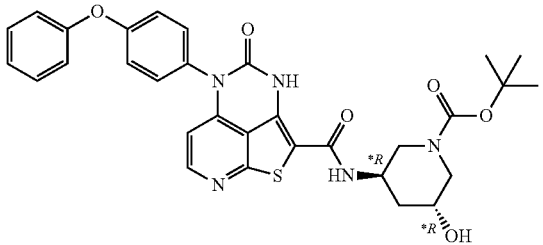

To a dry flask were added (3R,5R)-tert-butyl 3-amino-5-hydroxypiperidine-1-carboxylate (Intermediate 04) (2.00 g, 7.91 mmol), diisopropylethylamine (3.778 mL, 21.58 mmol), and THF (29 mL) and was cooled to 0° C. 4-Oxo-5-(4-phenoxyphenyl)-4,5-dihydro-3H-1-thia-3,5,8-triazaacenaphthylene-2-carbonyl chloride (Intermediate 40) (3.035 g, 7.194 mmol) was added dropwise at 0° C. The reaction was monitored by LCMS and when it had gone to completion, the reaction was quenched with saturated NaHCO$_3$, extracted with DCM, and concentrated to dryness. The residue was purified by normal phase flash column chromatography (SiO$_2$) to give the title compound (2880 mg, 66.5% yield). MS (ESI): mass calcd. for C$_{31}$H$_{31}$N$_5$O$_6$S, 601.7; m/z found, 602.2 [M+H]$^+$. $^1$H NMR (500 MHz, CDCl$_3$): δ 9.48 (s, 1H), 8.32 (d, J=5.6 Hz, 1H), 7.44-7.36 (m, 2H), 7.30 (dt, J=13.9, 5.7 Hz, 2H), 7.22-7.08 (m, 5H), 6.13 (d, J=5.5 Hz, 1H), 5.98 (s, 1H), 4.35 (d, J=5.2 Hz, 1H), 3.99 (s, 1H), 3.73 (s, 2H), 3.55 (s, 2H), 3.24 (s, 1H), 2.00-1.75 (m, 2H), 1.49 (s, 9H).

Example 612: (R)—N-(1-Acryloylpiperidin-3-yl)-5-(4-(oxetan-3-yloxy)phenyl)-4-oxo-4,5-dihydro-3H-1-thia-3,5,8-triazaacenaphthylene-2-carboxamide

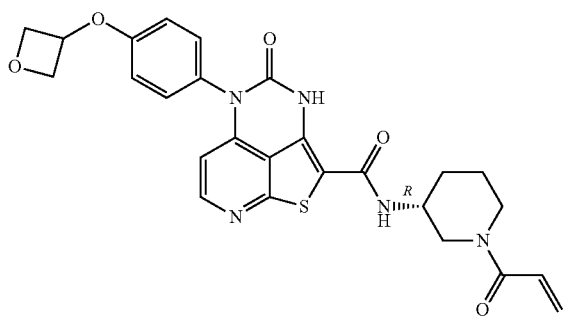

Step A: Methyl 5-(4-(oxetan-3-yloxy)phenyl)-4-oxo-4,5-dihydro-3H-1-thia-3,5,8-triazaacenaphthylene-2-carboxylate The title compound was prepared using the procedure found in Example 534, step A, and using 4-(oxetan-3-yloxy) aniline and methyl 2-sulfanylacetate in place of 3-cyclobutylaniline and tert-butyl (3R)-3-[(2-sulfanylacetyl)amino] piperidine-1-carboxylate (Intermediate 22), to yield the title compound (2.093 g, 88.07% yield).

Step B: Lithium 5-(4-(oxetan-3-yloxy)phenyl)-4-oxo-4,5-dihydro-3H-1-thia-3,5,8-triazaacenaphthylene-2-carboxylate To a round bottom flask were added methyl 5-(4-(oxetan-3-yloxy)phenyl)-4-oxo-4,5-dihydro-3H-1-thia-3,5,8-triazaacenaphthylene-2-carboxylate (2.0 g, 5.0 mmol) and THF (40 mL) and with stirring was added 2.0 equivalents of LiOH (2 M solution, 5.033 mL, 10.07 mmol). After 20 min, MeOH (10 mL) was added and was heated at 60° C. for 2 h, then water (10 mL) was added and was heated at 70° C. for 30 min, then heated at 60° C. for 4 h, and overnight at rt. The next day, it was heated at 60° C. for 6 h longer and allowed to cool to rt. The reaction mixture was concentrated to dryness and was evaporated to dryness several times with MeOH to get rid of excess solvents. The residue was dissolved in MeOH (10 mL) and the product was precipitated using ether (~800 mL). The precipitate was collected by filtration and dried to give the title compound as a brown solid (2.007 g, 102.4% yield).

Step C: (R)—N-(1-Acryloylpiperidin-3-yl)-5-(4-(oxetan-3-yloxy)phenyl)-4-oxo-4,5-dihydro-3H-1-thia-3,5,8-triazaacenaphthylene-2-carboxamide To a 40 mL vial were added lithium 5-(4-(oxetan-3-yloxy) phenyl)-4-oxo-4,5-dihydro-3H-1-thia-3,5,8-triazaacenaphthylene-2-carboxylate (250 mg, 0.64 mmol), 1-[(3R)-3-amino-1-piperidyl]prop-2-en-1-one (Intermediate 15), THF (3.0 mL), and diisopropylethylamine (1.0 mL, 6.4 mmol) and while stirring at rt was added 1-propanephosphonic anhydride (1.28 mL, 1.93 mmol) and was stirred overnight at rt. The reaction mixture was extracted with EtOAc (3×) and DCM. The combined organic phases were washed with water and brine, dried over anhydrous Na$_2$SO$_4$, filtered, and concentrated to dryness. The residue was purified by flash column chromatography, then by basic HPLC to give the title compound as a yellow solid (43 mg, 13% yield). MS (ESI): mass calcd. for C$_{26}$H$_{25}$N$_5$O$_5$S, 519.6; m/z found, 520.0 [M+H]$^+$. $^1$H NMR (400 MHz, CD$_3$OD): δ 8.18 (d, J=5.4 Hz, 1H), 7.26 (d, J=8.5 Hz, 2H), 6.89 (d, J=8.6 Hz, 2H), 6.79-6.63 (m, 1H), 6.10 (d, J=16.8 Hz, 1H), 6.01 (d, J=5.6 Hz, 1H), 5.70-5.59 (m, 1H), 5.31-5.22 (m, 1H), 5.03-4.91 (m, 2H), 4.68-4.60 (m, 2H), 4.45 (d, J=14.6 Hz, 0.5H), 4.21 (d, J=12.3 Hz, 0.5H), 4.08 (d, J=13.2 Hz, 0.5H), 3.95-3.81 (m, 1.5H), 3.15-3.03 (m, 1H), 2.87-2.74 (m, 1H), 2.02-1.95 (m, 1H), 1.87-1.74 (m, 1H), 1.71-1.59 (m, 1H), 1.55-1.43 (m, 1H).

Example 613: (R)-5-(3-(Cyclopentyloxy)phenyl)-4-oxo-N-(piperidin-3-yl)-4,5-dihydro-3H-1-thia-3,5,8-triazaacenaphthylene-2-carboxamide

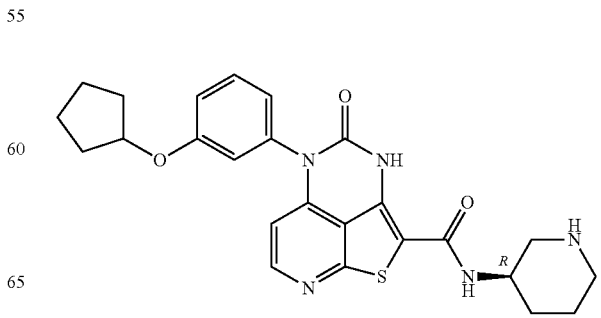

The title compound was prepared using methods analogous to Example 33 using 3-nitrophenol and bromocyclopentane in Steps A-C to yield 2-chloro-4-((3-cyclopentylphenyl)amino)nicotinonitrile. This was subjected to Method 1, steps C-H, in Example 1, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{25}H_{27}N_5O_3S$, 477.6; m/z found, 478.2 $[M+H]^+$. $^1$H NMR (400 MHz, CD3OD and DMSO-$d_6$): δ 8.50 (s, 1H), 8.39-8.35 (m, 1H), 7.57-7.48 (m, 1H), 7.16-7.08 (m, 1H), 7.04-6.97 (m, 2H), 6.20-6.15 (m, 1H), 4.93-4.86 (m, 1H), 4.35-4.24 (m, 1H), 3.48-3.40 (m, 1H), 3.34-3.30 (m, 1H), 2.99-2.86 (m, 2H), 2.08-1.95 (m, 4H), 1.90-1.78 (m, 6H), 1.72-1.63 (m, 2H).

Example 614: N-((3S,4R)-1-Acryloyl-4-hydroxy-pyrrolidin-3-yl)-5-(4-isopropoxy-2-methylphenyl)-4-oxo-4,5-dihydro-3H-1-thia-3,5,8-triazaacenaphthylene-2-carboxamide

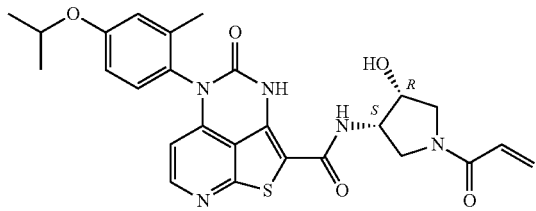

The title compound was prepared analogous to Example 33 using tert-butyl (3S,4R)-3-amino-4-hydroxy-pyrrolidine-1-carboxylate in place of tert-butyl (3R)-3-aminopiperidine-1-carboxylate in the referenced Step G, to yield the title compound. MS (ESI): mass calcd. for $C_{26}H_{27}N_5O_5S$, 521.6; m/z found, 522.5 $[M+H]^+$. $^1$H NMR (400 MHz, CD3OD): δ 8.29 (d, J=5.5 Hz, 1H), 7.31-7.15 (m, 1H), 7.01-6.85 (m, 2H), 6.70-6.50 (m, 1H), 6.38-6.20 (m, 1H), 6.02 (d, J=5.5 Hz, 1H), 5.83-5.69 (m, 1H), 4.74-4.36 (m, 3H), 4.13-3.47 (m, 4H), 2.10 (s, 3H), 1.42-1.30 (m, 6H).

Example 5: N-(trans-3-Hydroxypiperidin-4-yl)-4-oxo-5-(4-phenoxyphenyl)-4,5-dihydro-3H-1-thia-3,5,8-triazaacenaphthylene-2-carboxamide

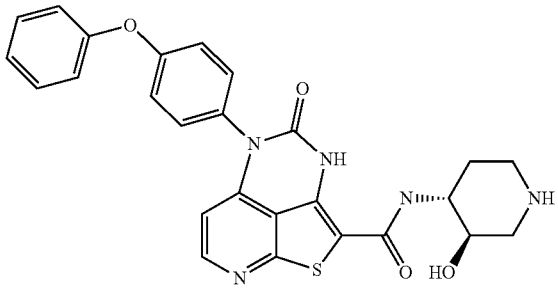 [SMILES: O=C(N[C@@H]1CCNC[C@H]1O)c1sc2nccc3c2c1NC(=O)N3c1ccc(Oc2ccccc2)cc1]

To a solution of trans-tert-butyl 3-hydroxy-4-(4-oxo-5-(4-phenoxyphenyl)-4,5-dihydro-3H-1-thia-3,5,8-triazaacenaphthylene-2-carboxamido)piperidine-1-carboxylate (Example 617) (1200 mg, 2.00 mmol) in DCM (20 mL) at room temperature was added TFA (34 mL) dropwise. The reaction was stirred at room temperature for 30 minutes. The reaction was concentrated to dryness and the residue was purified by normal phase flash column chromatography (SiO$_2$) to give the title compound (905 mg, 90.5% yield) as an off white solid. MS (ESI): mass calcd. for $C_{26}H_{23}N_5O_4S$, 501.6; m/z found, 502.2 $[M+H]^+$. $^1$H NMR (500 MHz, CDCl$_3$): δ 8.30-8.21 (m, 1H), 7.72 (s, 1H), 7.55 (s, 2H), 7.41 (tt, J=18.0, 8.9 Hz, 4H), 7.29 (d, J=11.2 Hz, 1H), 7.16 (ddt, J=27.3, 18.8, 9.9 Hz, 3H), 6.16-6.07 (m, 1H), 3.91 (s, 1H), 3.55 (d, J=12.8 Hz, 1H), 3.45-3.37 (m, 5H), 3.07 (dd, J=20.2, 10.1 Hz, 1H), 2.95 (d, J=12.0 Hz, 1H), 2.20 (d, J=15.2 Hz, 1H).

Example 616: (R)-5-(3-(Cyclohexyloxy)phenyl)-4-oxo-N-(piperidin-3-yl)-4,5-dihydro-3H-1-thia-3,5,8-triazaacenaphthylene-2-carboxamide

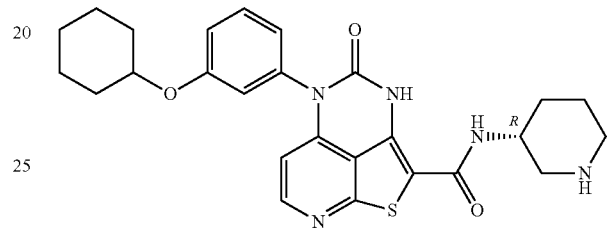

The title compound was prepared in a manner analogous to Method 1, steps A-H in Example 1, and using cyclohexyl methanesulfonate and 3-nitrophenol in place of phenol and 5-fluoro-2-nitrotoluene in step A, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{26}H_{29}N_5O_3S$, 491.6; m/z found, 492.2 $[M+H]^+$. $^1$H NMR (400 MHz, CD$_3$OD): δ 8.01 (d, J=5.7 Hz, 1H), 7.48-7.33 (m, 1H), 7.04-6.93 (m, 1H), 6.89-6.77 (m, 2H), 5.87 (d, J=5.7 Hz, 1H), 4.40-4.28 (m, 1H), 4.02-3.89 (m, 1H), 3.22-3.10 (m, 1H), 2.95-2.82 (m, 1H), 2.69-2.49 (m, 2H), 2.09-1.92 (m, 3H), 1.83-1.73 (m, 3H), 1.71-1.62 (m, 1H), 1.61-1.48 (m, 4H), 1.44-1.28 (m, 3H).

Example 6: trans-tert-Butyl 3-hydroxy-4-(4-oxo-5-(4-phenoxyphenyl)-4,5-dihydro-3H-1-thia-3,5,8-triazaacenaphthylene-2-carboxamido)piperidine-1-carboxylate

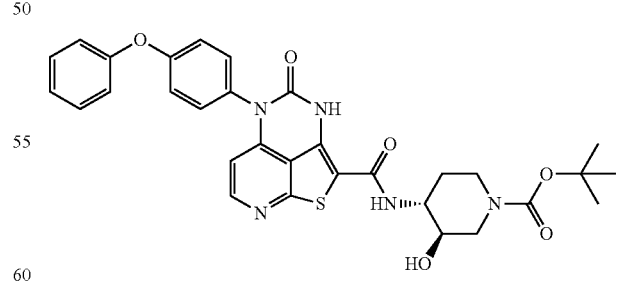

To a dry flask were added trans-4-amino-1-boc-3-hydroxypiperidine (1.00 g, 4.62 mmol), diisopropylethylamine (2.207 mL, 12.61 mmol), and THF (17 mL) and was cooled to 0° C. 4-Oxo-5-(4-phenoxyphenyl)-4,5-dihydro-3H-1-thia-3,5,8-triazaacenaphthylene-2-carbonyl chloride (Intermediate 40) (1.773 g, 4.203 mmol) was added dropwise at 0° C. The reaction was monitored by LCMS and when it had gone to completion, the reaction was quenched with saturated NaHCO₃, extracted with DCM, and concentrated to dryness. The residue was purified by normal phase flash column chromatography (SiO₂) to give the title compound. (1700 mg, 67.2% yield). MS (ESI): mass calcd. for $C_{31}H_{31}N_5O_6S$, 601.7; m/z found, 602.0 [M+H]⁺. ¹H NMR (500 MHz, CDCl₃): δ 8.17 (d, J=5.5 Hz, 1H), 7.55 (dd, J=9.0, 2.5 Hz, 1H), 7.44-7.36 (m, 2H), 7.26 (dd, J=8.6, 2.5 Hz, 1H), 7.22-7.06 (m, 6H), 6.14 (d, J=7.3 Hz, 1H), 6.03 (d, J=5.5 Hz, 1H), 4.36 (s, 2H), 4.12 (q, J=7.2 Hz, 1H), 3.93 (dd, J=14.2, 7.5 Hz, 1H), 3.60 (td, J=10.1, 5.0 Hz, 1H), 2.73 (s, 1H), 2.62 (s, 1H), 2.04 (s, 2H), 1.45 (s, 9H).

Example 618: (R)-4-Oxo-5-(5-phenylpyridin-3-yl)-N-(piperidin-3-yl)-4,5-dihydro-3H-1-thia-3,5,8-triazaacenaphthylene-2-carboxamide

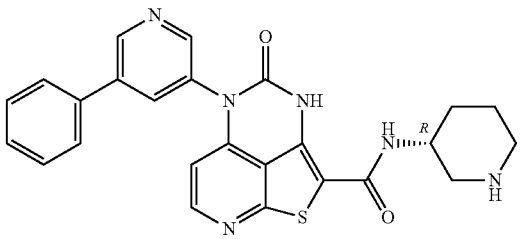

The title compound was prepared in a manner analogous to Method 1, steps C-H in Example 1, and using 5-phenylpyridin-3-amine in Step C and tert-butyl (3R)-3-aminopiperidine-1-carboxylate Step G. MS (ESI): mass calcd. for $C_{25}H_{22}N_6O_2S$, 470.5; m/z found, 471.3 [M+H]⁺. ¹H NMR (400 MHz, CD₃OD): δ 8.97-8.91 (m, 1H), 8.61-8.53 (m, 1H), 8.51 (s, 1H), 8.28-8.22 (m, 1H), 8.21-8.16 (m, 1H), 7.74-7.68 (m, 2H), 7.52-7.41 (m, 3H), 6.20-6.13 (m, 1H), 4.23-4.13 (m, 1H), 3.42-3.34 (m, 1H), 3.23-3.13 (m, 1H), 2.97-2.82 (m, 2H), 2.08-1.95 (m, 2H), 1.81-1.67 (m, 2H).

Example 619: (R)—N-(1-Acryloylpiperidin-3-yl)-5-(2-methoxypyrimidin-5-yl)-4-oxo-4,5-dihydro-3H-1-thia-3,5,8-triazaacenaphthylene-2-carboxamide

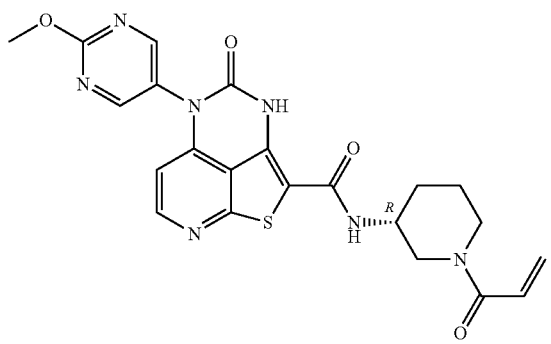

Step A: 2-Phenoxypyrimidin-5-amine

The title compound was prepared in a manner analogous to Method 1, steps A-B in Example 1, and using 2-chloro-5-nitro-pyrimidine in place of 5-fluoro-2-nitrotoluene in step A, to yield the title compound.

Step B: (R)—N-(1-Acryloylpiperidin-3-yl)-5-(2-methoxypyrimidin-5-yl)-4-oxo-4,5-dihydro-3H-1-thia-3,5,8-triazaacenaphthylene-2-carboxamide The title compound was prepared in a manner analogous to Method 1, steps C-I in Example 1 using 2-phenoxypyrimidin-5-amine in Step C, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{22}H_{21}N_7O_4S$, 479.5; m/z found, 480.4 [M+H]⁺. ¹H NMR (400 MHz, CD₃OD): δ 8.71 (s, 2H), 8.35-8.30 (m, 1H), 6.83-6.68 (m, 1H), 6.34-6.24 (m, 1H), 6.22-6.12 (m, 1H), 5.77-5.64 (m, 1H), 4.45-3.75 (m, 6H), 3.20-3.06 (m, 1H), 2.94-2.80 (m, 1H), 2.11-1.99 (m, 1H), 1.90-1.80 (m, 1H), 1.79-1.64 (m, 1H), 1.62-1.48 (m, 1H).

Example 620: (R)-4-Oxo-N-(piperidin-3-yl)-5-(3-(trifluoromethoxy)phenyl)-4,5-dihydro-3H-1-thia-3,5,8-triazaacenaphthylene-2-carboxamide

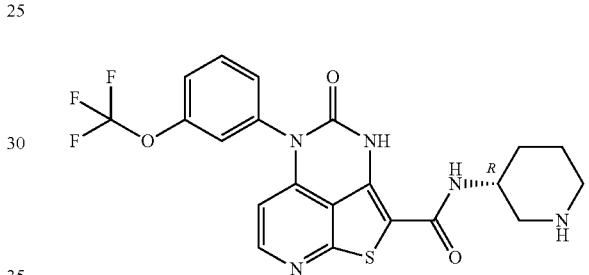

The title compound was prepared in a manner analogous to Method 1, steps B-H in Example 1, and using 1-nitro-3-(trifluoromethoxy)benzene in place of 2-methyl-1-nitro-4-phenoxy-benzene in step B, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{21}H_{18}F_3N_5O_3S$, 477.5; m/z found, 478.1 [M+H]⁺. ¹H NMR (400 MHz, CD₃OD): δ 8.04 (d, J=5.7 Hz, 1H), 7.69-7.59 (m, 1H), 7.42-7.33 (m, 2H), 7.32-7.25 (m, 1H), 5.87 (d, J=5.7 Hz, 1H), 4.01-3.91 (m, 1H), 3.22-3.11 (m, 1H), 2.92-2.83 (m, 1H), 2.65-2.54 (m, 2H), 2.08-1.99 (m, 1H), 1.83-1.75 (m, 1H), 1.71-1.52 (m, 2H).

Example 621: (R)-5-(3-Cyclobutoxyphenyl)-4-oxo-N-(piperidin-3-yl)-4,5-dihydro-3H-1-thia-3,5,8-triazaacenaphthylene-2-carboxamide

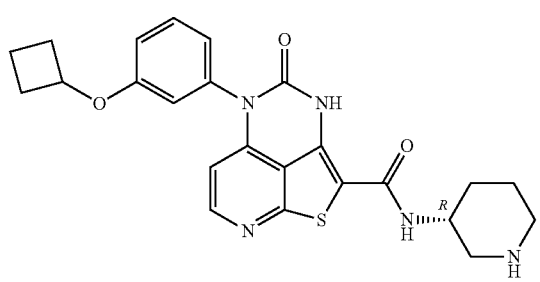

Step A: 1-cyclobutoxy-3-nitrobenzene

The title compound was prepared using a method analogous to Example 33 Step A and using 3-nitrophenol and bromocyclobutane in place of 4-nitrophenol and 2-iodopropane

Step B: (R)-5-(3-Cyclobutoxyphenyl)-4-oxo-N-(piperidin-3-yl)-4,5-dihydro-3H-1-thia-3,5,8-triazaacenaphthylene-2-carboxamide The title compound was prepared using methods analogous to Method 1, Example 1 Steps B-H. MS (ESI): mass calcd. for $C_{24}H_{25}N_5O_3S$, 463.6; m/z found, 464.2 [M+H]$^+$. $^1$H NMR (400 MHz, CD$_3$OD): δ 8.46 (s, 1H), 8.31-8.25 (m, 1H), 7.52-7.43 (m, 1H), 7.05-6.89 (m, 3H), 6.16-6.08 (m, 1H), 4.77-4.66 (m, 1H), 4.31-4.18 (m, 1H), 3.57-3.45 (m, 1H), 3.37-3.32 (m, 1H), 3.02-2.85 (m, 2H), 2.53-2.40 (m, 2H), 2.20-1.97 (m, 4H), 1.90-1.65 (m, 4H).

Example 622: (R)-4-Oxo-N-(piperidin-3-yl)-5-(3-(pyridin-2-yl)phenyl)-4,5-dihydro-3H-1-thia-3,5,8-triazaacenaphthylene-2-carboxamide

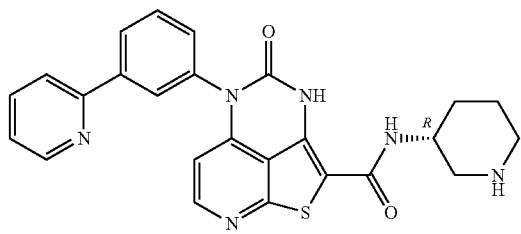

The title compound was prepared using the procedure found in Example 540, steps A-B. MS (ESI): mass calcd. for $C_{25}H_{22}N_6O_2S$, 470.5; m/z found, 471.2 [M+H]$^+$. $^1$H NMR (400 MHz, CD$_3$OD): δ 8.8.92-8.88 (m, 1H), 8.77-8.66 (m, 1H), 8.52-8.40 (m, 2H), 8.25-8.05 (m, 3H), 8.01-7.93 (m, 1H), 7.89-7.80 (m, 1H), 6.45 (d, J=6.1 Hz, 1H), 4.38-4.25 (m, 1H), 3.58-3.50 (m, 1H), 3.40-3.33 (m, 1H), 3.06-2.96 (m, 2H), 2.16-2.04 (m, 2H), 1.93-1.75 (m, 2H).

Example 623: (R)-4-Oxo-5-(6-phenylpyridin-2-yl)-N-(piperidin-3-yl)-4,5-dihydro-3H-1-thia-3,5,8-triazaacenaphthylene-2-carboxamide

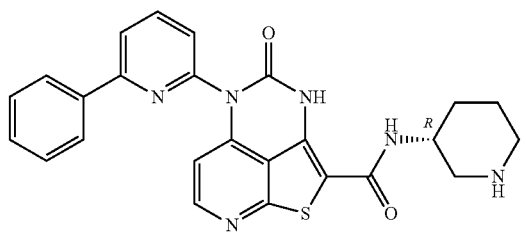

The title compound was prepared in a manner analogous to Method 1, steps C-H in Example 1, and using 3-phenylaniline in place of 2-methyl-4-phenoxy-aniline in step C, and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{25}H_{22}N_6O_2S$, 470.5; m/z found, 471.1 [M+H]$^+$. $^1$H NMR (400 MHz, CD3OD and DMSO-d$_6$): δ 8.31-8.27 (m, 1H), 8.13-8.04 (m, 2H), 8.02-7.97 (m, 2H), 7.50-7.46 (m, 1H), 7.45-7.38 (m, 3H), 6.24-6.19 (m, 1H), 4.20-4.16 (m, 1H), 3.35-3.29 (m, 1H), 3.20-3.15 (m, 1H), 2.88-2.75 (m, 2H), 1.95-1.85 (m, 2H), 1.76-1.57 (m, 2H).

Example 624: (R)—N-(1-Acryloylpiperidin-3-yl)-5-(*R)-(2-methyl-4-(trifluoromethoxy)phenyl)-4-oxo-4,5-dihydro-3H-1-thia-3,5,8-triazaacenaphthylene-2-carboxamide

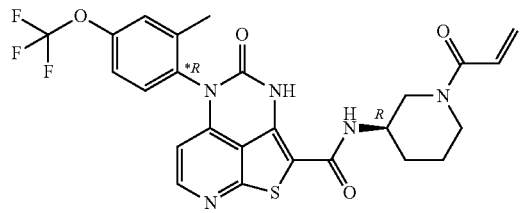

The title compound was prepared using the procedures found in Example 505, except the *R atropisomer was obtained. MS (ESI): mass calcd. for $C_{25}H_{22}F_3N_5O_4S$, 545.5; m/z found, 546.2 [M+H]$^+$. $^1$H NMR (400 MHz, CD$_3$OD): δ 8.32 (d, J=5.56 Hz, 1H), 7.48 (d, J=8.59 Hz, 1H), 7.43 (s, 1H), 7.35 (d, J=9.09 Hz, 1H), 6.73-6.87 (m, 1H), 6.21 (dd, J=3.28, 16.93 Hz, 1H), 6.02 (d, J=5.56 Hz, 1H), 5.74 (t, J=8.34 Hz, 1H), 4.53 (d, J=2.53 Hz, 0.5H), 4.31 (d, J=12.63 Hz, 0.5H), 4.14-4.23 (m, 0.5H), 3.88-4.07 (m, 1.5H), 3.15-3.26 (m, 1H), 2.81-3.02 (m, 1H), 2.22 (s, 3H), 2.02-2.14 (m, 1H), 1.83-1.95 (m, 1H), 1.66-1.84 (m, 1H), 1.50-1.66 (m, 1H).

Example 625: (3S,4S)-tert-Butyl 3-fluoro-4-(4-oxo-5-(4-phenoxyphenyl)-4,5-dihydro-3H-1-thia-3,5,8-triazaacenaphthylene-2-carboxamido)pyrrolidine-1-carboxylate

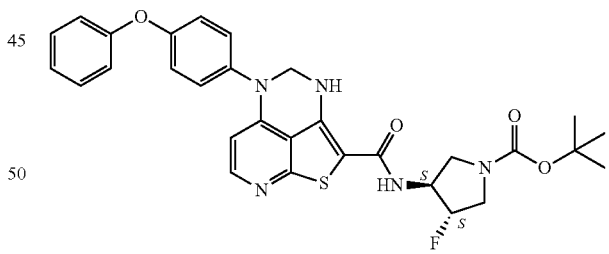

To a dry flask were added (3S,4S)-tert-butyl 3-amino-4-fluoropyrrolidine-1-carboxylate (241 mg, 1.185 mmol), diisopropylethylamine (0.622 mL, 3.56 mmol), and THF (5 mL) and was cooled to 0° C. 4-Oxo-5-(4-phenoxyphenyl)-4,5-dihydro-3H-1-thia-3,5,8-triazaacenaphthylene-2-carbonyl chloride (Intermediate 40) (0.500 g, 1.18 mmol) was added dropwise at 0° C. The reaction was monitored by LCMS and when it had gone to completion, the reaction was quenched with saturated NaHCO$_3$, extracted with DCM, and concentrated to dryness. The residue was purified by normal phase flash column chromatography (SiO$_2$) to give the title compound (480 mg, 69% yield) as an off white solid. MS (ESI): mass calcd. for $C_{30}H_{28}FN_5O_5S$, 589.6; m/z found, 590.2 [M+H]⁺. ¹H NMR (500 MHz, CDCl₃): δ 9.56 (s, 1H), 8.27 (d, J=5.5 Hz, 1H), 7.47-7.30 (m, 4H), 7.21-7.05 (m, 5H), 6.13 (d, J=5.5 Hz, 1H), 3.73 (dd, J=12.1, 5.8 Hz, 2H), 3.69-3.57 (m, 3H), 3.55-3.43 (m, 1H), 1.41 (t, J=4.6 Hz, 9H).

Example 626: (R)-5-(4-Cyclobutoxyphenyl)-4-oxo-N-(piperidin-3-yl)-4,5-dihydro-3H-1-thia-3,5,8-triazaacenaphthylene-2-carboxamide

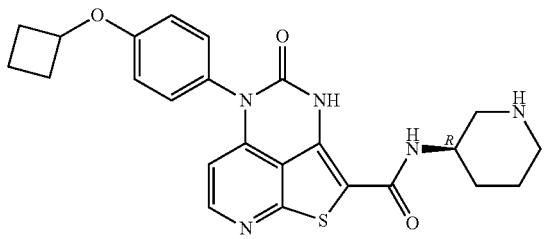

The title compound was prepared using methods analogous to Method 1, Steps C-H in Example 1, using 4-cyclobutoxyaniline in step A, and tert-butyl (3R)-3-aminopiperidine-1-carboxylate in place of tert-butyl (3R,5R)-3-amino-5-fluoro-piperidine-1-carboxylate. MS (ESI): mass calcd. for C₂₄H₂₅N₅O₃S, 463.6; m/z found, 464.1 [M+H]⁺. ¹H NMR (400 MHz, CD₃OD): δ 8.33 (d, J=5.56 Hz, 1H), 7.26-7.32 (m, 2H), 7.03 (d, J=9.09 Hz, 2H), 6.16 (d, J=5.56 Hz, 1H), 4.77 (quin, J=7.07 Hz, 1H), 4.21-4.31 (m, 1H), 3.53 (dd, J=3.79, 11.87 Hz, 1H), 3.33-3.40 (m, 1H), 2.87-3.00 (m, 2H), 2.46-2.57 (m, 2H), 2.02-2.23 (m, 4H), 1.67-1.94 (m, 4H).

Example 627: tert-Butyl 4-(4-oxo-5-(4-phenoxyphenyl)-4,5-dihydro-3H-1-thia-3,5,8-triazaacenaphthylene-2-carboxamido)piperidine-1-carboxylate

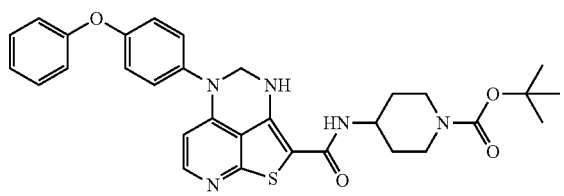 [SMILES: CC(C)(C)OC(=O)N1CCC(NC(=O)c2sc3nccc4c3c2NCN4c2ccc(Oc3ccccc3)cc2)CC1]

To a dry flask at 0° C. containing 4-amino-1-Boc-piperidine (1.62 g, 7.82 mmol), diisopropylethylamine (3.74 mL, 21.3 mmol), and THF (28 mL) was added dropwise 4-oxo-5-(4-phenoxyphenyl)-4,5-dihydro-3H-1-thia-3,5,8-triazaacenaphthylene-2-carbonyl chloride (Intermediate 40) (3.00 g, 7.11 mmol). The reaction was monitored by LCMS. When the reaction had gone to completion, the reaction was quenched saturated NaHCO₃, extracted with DCM, and concentrated to dryness. The residue was purified by normal phase flash column chromatography (SiO₂) to give the title compound (3800 mg, 91.2% yield) as an off white solid. MS (ESI): mass calcd. for C₃₁H₃₁N₅O₅S, 585.7; m/z found, 585.9 [M+H]⁺. ¹H NMR (400 MHz, CDCl₃): δ 9.46 (s, 1H), 8.35 (d, J=5.4 Hz, 1H), 7.45-7.35 (m, 2H), 7.28 (d, J=8.7 Hz, 2H), 7.23-7.07 (m, 5H), 6.15 (dd, J=5.7, 1.9 Hz, 1H), 5.55 (d, J=7.8 Hz, 1H), 4.10 (qt, J=12.0, 8.2, 7.3 Hz, 3H), 2.90 (t, J=12.7 Hz, 2H), 2.07-1.97 (m, 2H), 1.47 (s, 11H).

Example 628: (R)-tert-Butyl 3-(4-oxo-5-(4-phenoxyphenyl)-4,5-dihydro-3H-1-thia-3,5,8-triazaacenaphthylene-2-carboxamido)piperidine-1-carboxylate

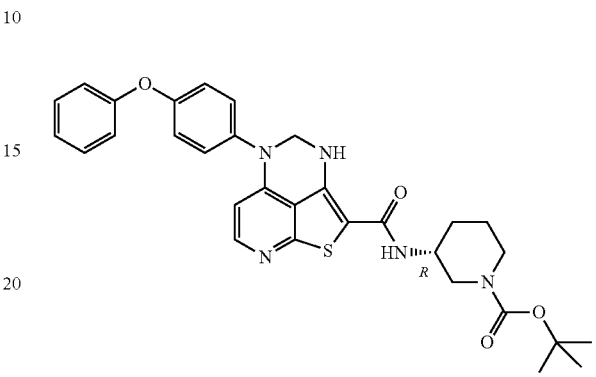

The title compound was prepared using analogous conditions as found in Example 627 using (R)-1-Boc-3-aminopiperidine step G. MS (ESI): mass calcd. for C₃₁H₃₁N₅O₅S, 585.7; m/z found, 586.0 [M+H]⁺. ¹H NMR (500 MHz, CDCl₃): δ 9.48 (s, 1H), 8.34 (d, J=5.5 Hz, 1H), 7.44-7.36 (m, 2H), 7.29 (dd, J=6.6, 2.7 Hz, 2H), 7.22-7.07 (m, 5H), 6.15 (d, J=5.5 Hz, 1H), 4.11 (p, J=6.6, 6.1 Hz, 2H), 3.63 (s, 1H), 3.46 (s, 2H), 3.39 (s, 1H), 2.04 (s, 1H), 1.73 (dq, J=12.7, 6.1 Hz, 1H), 1.59 (dt, J=13.5, 6.6 Hz, 1H), 1.50 (s, 9H), 1.26 (t, J=7.2 Hz, 1H).

Example 629: (R)-5-(3-Cyclohexylphenyl)-4-oxo-N-(piperidin-3-yl)-4,5-dihydro-3H-1-thia-3,5,8-triazaacenaphthylene-2-carboxamide

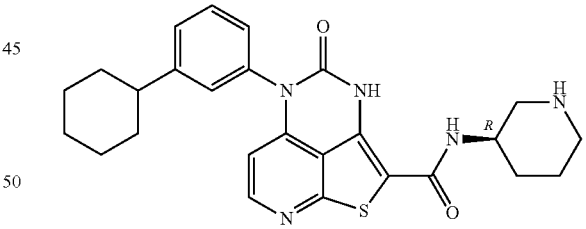

The title compound was prepared using the procedures found in Method 1, steps F-H using methyl 5-(3-cyclohexylphenyl)-4-oxo-4,5-dihydro-3H-1-thia-3,5,8-triazaacenaphthylene-2-carboxylate (synthesized as in Example 519, Step B) and using tert-butyl (3R)-3-aminopiperidine-1-carboxylate in step G. MS (ESI): mass calcd. for C₂₆H₂₉N₅O₂S, 475.6; m/z found, 476.4 [M+H]⁺. ¹H NMR (400 MHz, CD₃OD): δ 8.53 (s, 1H), 8.32 (d, J=5.5 Hz, 1H), 7.59-7.51 (m, 1H), 7.47-7.41 (m, 1H), 7.33-7.30 (m, 1H), 7.28-7.22 (m, 1H), 6.07 (d, J=5.6 Hz, 1H), 4.36-4.24 (m, 1H), 3.48-3.40 (m, 1H), 3.28-3.23 (m, 1H), 2.99-2.87 (m, 2H), 2.69-2.62 (m, 1H), 2.09-1.98 (m, 2H), 1.97-1.82 m, 5H), 1.81-1.74 (m, 2H), 1.57-1.41 (m, 4H), 1.38-1.26 (m, 1H).

Example 630: (R)-5-(3-Isopropylphenyl)-4-oxo-N-(piperidin-3-yl)-4,5-dihydro-3H-1-thia-3,5,8-triazaacenaphthylene-2-carboxamide

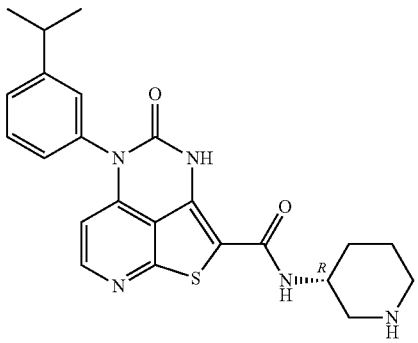

The title compound was prepared using procedures analogous to Method 1, steps E-G in Example 1 using methyl 3-amino-4-((3-isopropylphenyl)amino)thieno[2,3-b]pyridine-2-carboxylate (as prepared in Example 529, Step A) and using tert-butyl (3R)-3-aminopiperidine-1-carboxylate in step G. MS (ESI): mass calcd. for $C_{23}H_{25}N_5O_2S$, 435.5; m/z found, 436.2 [M+H]$^+$. $^1$H NMR (400 MHz, CD$_3$OD): δ 8.45 (s, 1H), 8.32-8.29 (m, 1H), 7.59-7.49 (m, 1H), 7.46-7.40 (m, 1H), 7.32-7.27 (m, 1H), 7.24-7.18 (m, 1H), 6.12-6.06 (m, 1H), 4.34-4.19 (m, 1H), 3.54-3.45 (m, 1H), 3.36-3.31 (m, 1H), 3.06-2.85 (m, 3H), 2.17-1.99 (m, 2H), 1.88-1.69 (m, 2H), 1.31-1.25 (m, 6H).

Example 631: (R)—N-(1-Acryloylpiperidin-3-yl)-4-oxo-5-(3-(pyridin-4-yl)phenyl)-4,5-dihydro-3H-1-thia-3,5,8-triazaacenaphthylene-2-carboxamide

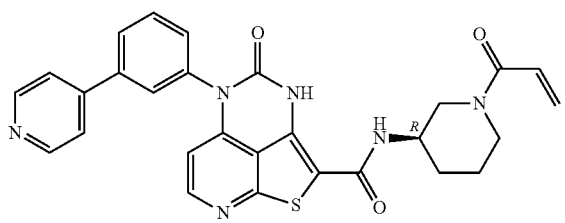

The title compound was prepared in a manner analogous to Method 1, steps C-I in Example 1, and using 3-(pyridin-4-yl)aniline in Step C and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{28}H_{24}N_6O_3S$, 524.6; m/z found, 525.5 [M+H]$^+$. $^1$H NMR (400 MHz, DMSO-d$_6$): δ 10.27-10.07 (m, 1H), 8.67-8.58 (m, 2H), 8.34-8.22 (m, 1H), 8.18-8.02 (m, 1H), 8.00-7.88 (m, 2H), 7.79-7.68 (m, 3H), 7.59-7.46 (m, 1H), 6.85-6.63 (m, 1H), 6.14-5.99 (m, 2H), 5.74-5.55 (m, 1H), 4.47-4.12 (m, 1H), 4.07-3.88 (m, 1H), 3.85-3.65 (m, 1H), 3.11-2.91 (m, 1H), 2.80-2.63 (m, 1H), 1.96-1.72 (m, 2H), 1.72-1.54 (m, 1H), 1.47-1.34 (m, 1H).

Example 632: (R)—N-(1-Acryloylpiperidin-3-yl)-5-(3-(oxetan-3-yl)phenyl)-4-oxo-4,5-dihydro-3H-1-thia-3,5,8-triazaacenaphthylene-2-carboxamide

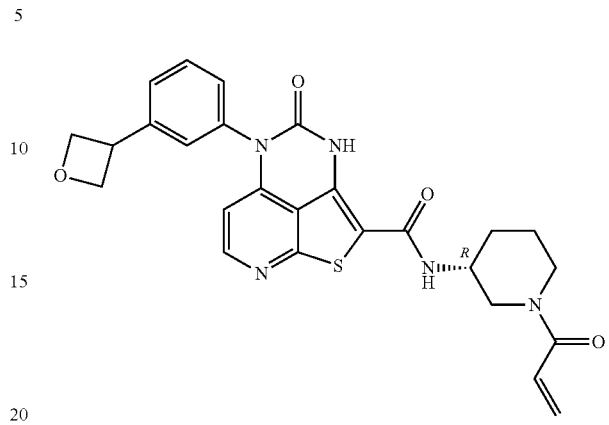

Step A: 3-(Oxetan-3-yl)aniline

To a round bottom flask were added 3-aminophenylboronic acid pinacol ester (12.28 g, 54.36 mmol), nickel(II) iodide (849 mg, 2.72 mmol), trans-2-aminocyclohexanol hydrochloride (412 mg, 2.72 mmol), sodium bis(trimethylsilyl)amide (9.967 g, 54.36 mmol), and a suspension of 3-iodooxetane (5.00 g, 27.2 mmol) in iPrOH (54 mL). The reaction was purged with N$_2$ for 30 min while stirring at rt, then purged with N$_2$ for an additional 15 min while ramping up to 120° C. The reaction was stirred at 120° C. for 3 h. The reaction was allowed to cool, quenched with water, extracted with EtOAc and brine, the organic layer collected, and the aqueous phase extracted again with EtOAc. The combined organic layers were dried over anhydrous Na$_2$SO$_4$, filtered, and concentrated to dryness. The residue was purified by flash column chromatography to give the title compound as a brown oil (3.24 g, 79.9% yield).

Step B: 5-(3-(Oxetan-3-yl)phenyl)-4-oxo-4,5-dihydro-3H-1-thia-3,5,8-triazaacenaphthylene-2-carboxylic Acid The title compound was prepared by methods analogous to Method 1, Steps C-F using 3-(oxetan-3-yl)aniline in Step C. (908 mg, 32.6% yield).

Step C: (R)—N-(1-Acryloylpiperidin-3-yl)-5-(3-(oxetan-3-yl)phenyl)-4-oxo-4,5-dihydro-3H-1-thia-3,5,8-triazaacenaphthylene-2-carboxamide To a solution of 5-(3-(oxetan-3-yl)phenyl)-4-oxo-4,5-dihydro-3H-1-thia-3,5,8-triazaacenaphthylene-2-carboxylic acid (150 mg, 0.408 mmol), 1-[(3R)-3-amino-1-piperidyl]prop-2-en-1-one (Intermediate 15) (189 mg, 1.23 mmol), THF (2 mL), and diisopropylethylamine (0.352 mL, 2.04 mmol) with stirred was added 1-propanephosphonic anhydride (0.408 mL, 0.612 mmol) and was stirred overnight at rt. To the reaction mixture was added EtOAc and H$_2$O, the organic phase collected, and the H$_2$O extracted again with EtOAc. The combined organics were washed with H$_2$O and brine, dried over anhydrous Na$_2$SO$_4$, filtered, and concentrated to dryness. The residue was purified by flash column chromatography, then by reverse phase HPLC to give the title compound as a white solid (39.9 mg, 19.4% yield). MS (ESI): mass calcd. for C$_{26}$H$_{25}$N$_5$O$_4$S, 503.6; m/z found, 504.1 [M+H]$^+$. $^1$H NMR (500 MHz, CD$_3$OD): δ 8.28 (d, J=5.6 Hz, 1H), 7.63 (d, J=5.0 Hz, 2H), 7.53 (s, 1H), 7.40-7.33 (m, 1H), 6.85-6.74 (m, 1H), 6.20 (dd, J=16.7, 7.6 Hz, 1H), 6.11 (d, J=5.6 Hz, 1H), 5.73 (dd, J=20.4, 10.8 Hz, 1H), 5.14-5.08 (m, 2H), 4.82-4.76 (m, 2H), 4.58-4.50 (m, 1H), 4.41-4.34 (m, 1H), 4.34-4.28 (m, OH), 4.20 (d, J=11.3 Hz, 1H), 4.04-3.91 (m, 1H), 3.21-3.14 (m, 1H), 2.89 (q, J=11.9 Hz, 1H), 2.11-2.04 (m, 1H), 1.91-1.83 (m, 1H), 1.80-1.67 (m, 1H), 1.65-1.53 (m, 1H).

Example 633: (R)—N-(1-Acryloylpiperidin-3-yl)-5-(4-isopropoxy-3-methylphenyl)-4-oxo-4,5-dihydro-3H-1-thia-3,5,8-triazaacenaphthylene-2-carboxamide

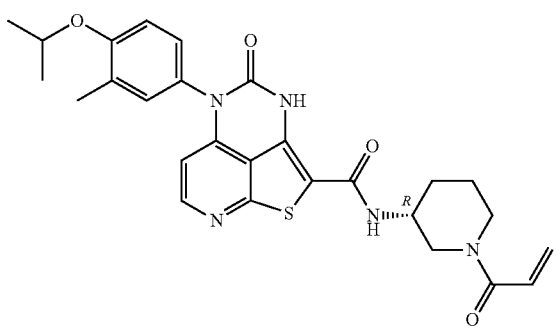

The title compound was prepared using the procedures found in Example 534, steps A-C, and using 4-isopropoxy-3-methyl-aniline in place of 3-cyclobutylaniline in step A. MS (ESI): mass calcd. for C$_{27}$H$_{29}$N$_5$O$_4$S, 519.6; m/z found, 520.2 [M+H]$^+$. $^1$H NMR (600 MHz, DMSO-d$_6$): δ 10.18-9.96 (d, J=16.7 Hz, 1H), 8.33-8.29 (d, J=5.5 Hz, 1H), 8.11-7.91 (m, 1H), 7.22-7.17 (m, 2H), 7.14-7.09 (m, 1H), 6.84-6.70 (m, 1H), 6.14-6.07 (d, J=16.6 Hz, 1H), 6.06-6.00 (d, J=5.5 Hz, 1H), 5.71-5.64 (m, 1H), 4.72-4.60 (m, 1H), 4.50-4.15 (m, 1H), 4.10-3.93 (m, 1H), 3.84-3.72 (m, 1H), 3.16-2.93 (m, 1H), 2.83-2.63 (m, 1H), 2.20-2.13 (s, 3H), 2.00-1.90 (m, 1H), 1.83-1.76 (m, 1H), 1.73-1.59 (m, 1H), 1.50-1.38 (m, 1H), 1.36-1.30 (m, 6H).

Example 634: (R)-5-(2-Cyclobutylpyridin-4-yl)-4-oxo-N-(piperidin-3-yl)-4,5-dihydro-3H-1-thia-3,5,8-triazaacenaphthylene-2-carboxamide

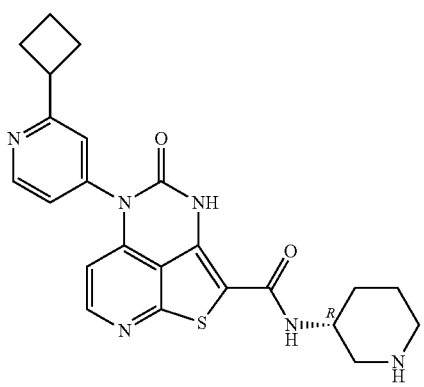

The title compound was prepared using the procedures found in Example 534, steps A-B, and using 2-cyclobutylpyridin-4-amine in place of 3-cyclobutylaniline in step A. MS (ESI): mass calcd. for C$_{23}$H$_{24}$N$_6$O$_2$S, 448.5; m/z found, 449.1 [M+H]$^+$. $^1$H NMR (500 MHz, CD$_3$OD): δ 8.72-8.66 (d, J=5.2 Hz, 1H), 8.21-8.14 (d, J=5.6 Hz, 1H), 7.45-7.38 (d, J=1.9 Hz, 1H), 7.36-7.30 (dd, J=5.3, 1.9 Hz, 1H), 6.12-6.07 (d, J=5.6 Hz, 1H), 4.22-4.13 (m, 1H), 3.85-3.74 (m, 1H), 3.40-3.33 (m, 1H), 3.20-3.09 (m, 1H), 2.97-2.82 (m, 2H), 2.47-2.32 (m, 4H), 2.18-1.89 (m, 4H), 1.82-1.68 (m, 2H).

Example 635: (R)—N-(1-Acryloylpiperidin-3-yl)-4-oxo-5-(6-phenoxypyridin-2-yl)-4,5-dihydro-3H-1-thia-3,5,8-triazaacenaphthylene-2-carboxamide

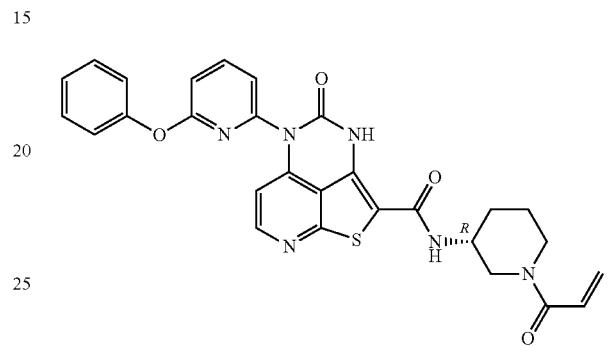

The title compound was prepared using the procedures found in Example 534, steps A-C, and using 6-phenoxy-pyridin-2-amine in place of 3-cyclobutylaniline in step A. MS (ESI): mass calcd. for C$_{28}$H$_{24}$N$_6$O$_4$S, 540.6; m/z found, 541.0 [M+H]$^+$. $^1$H NMR (600 MHz, CD$_3$OD): δ 8.34-8.24 (m, 1H), 8.11-8.04 (m, 1H), 7.40-7.34 (m, 2H), 7.32-7.27 (d, J=7.4 Hz, 1H), 7.20-7.12 (m, 4H), 6.83-6.73 (m, 1H), 6.29-6.23 (d, J=5.5 Hz, 1H), 6.23-6.16 (m, 1H), 5.77-5.69 (m, 1H), 4.55-4.24 (m, 1H), 4.20-3.91 (m, 2H), 3.23-3.12 (m, 1H), 2.97-2.85 (m, 1H), 2.12-2.01 (d, J=12.3 Hz, 1H), 1.91-1.82 (m, 1H), 1.80-1.65 (m, 1H), 1.64-1.52 (m, 1H).

Example 636: (R)-5-(2,2-Difluorobenzo[d][1,3]dioxol-5-yl)-4-oxo-N-(piperidin-3-yl)-4,5-dihydro-3H-1-thia-3,5,8-triazaacenaphthylene-2-carboxamide

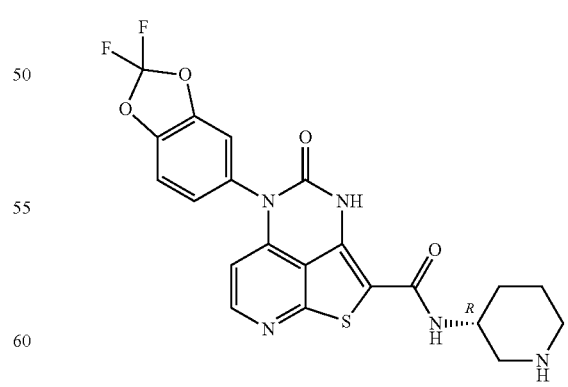

The title compound was prepared using the procedures found in Example 534, steps A-B, and using 2,2-difluoro-5-aminobenzodioxole in place of 3-cyclobutylaniline in step A, and using TFA, DCM, and DCE in place of 4 M HCl and dioxane in step B. MS (ESI): mass calcd. for C$_{21}$H$_{17}$F$_{2}$N$_{5}$O$_{4}$S, 473.5; m/z found, 474.0 [M+H]$^+$. $^1$H NMR (500 MHz, CD$_3$OD): δ 8.29 (d, J=5.6 Hz, 1H), 7.46-7.39 (m, 2H), 7.31-7.24 (m, 1H), 6.17 (d, J=5.6 Hz, 1H), 4.28-4.20 (m, 1H), 3.49-3.43 (m, 1H), 3.30-3.25 (m, 1H), 2.97-2.90 (m, 2H), 2.11-2.02 (m, 2H), 1.87-1.70 (m, 2H).

Example 637: (R)-5-(3-Isopropoxyphenyl)-4-oxo-N-(piperidin-3-yl)-4,5-dihydro-3H-1-thia-3,5,8-triazaacenaphthylene-2-carboxamide

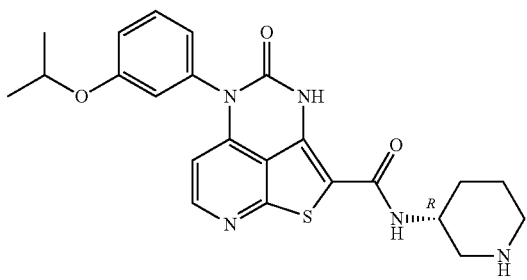

The title compound was prepared using the procedures found in Example 534, steps A-B, and using 3-isopropoxyaniline in place of 3-cyclobutylaniline in step A. MS (ESI): mass calcd. for C$_{23}$H$_{25}$N$_{5}$O$_{3}$S, 451.5; m/z found, 452.1 [M+H]$^+$. $^1$H NMR (500 MHz, DMSO-d$_6$): δ 8.62-8.50 (d, J=6.1 Hz, 1H), 8.19-8.10 (d, J=5.5 Hz, 1H), 7.46-7.39 (m, 1H), 7.03-6.98 (m, 1H), 6.90-6.82 (m, 2H), 5.89-5.83 (d, J=5.5 Hz, 1H), 4.67-4.57 (m, 1H), 4.06-3.95 (m, 1H), 3.27-3.20 (m, 2H), 3.09-3.01 (m, 1H), 2.77-2.61 (m, 2H), 1.98-1.89 (m, 1H), 1.85-1.76 (m, 1H), 1.66-1.49 (m, 2H), 1.28 (d, 6H).

Example 638: (R)—N-(1-Acryloylpiperidin-3-yl)-5-(3-(tert-buty)phenyl)-4-oxo-4,5-dihydro-3H-1-thia-3,5,8-triazaacenaphthylene-2-carboxamide

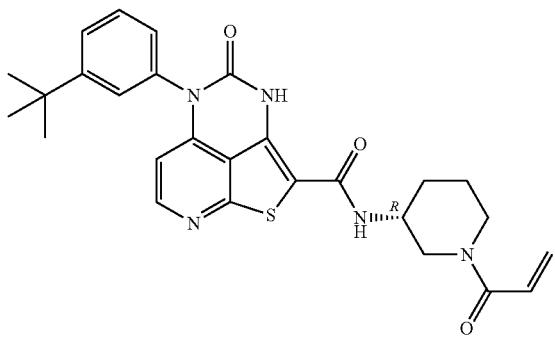

The title compound was prepared using the procedures found in Example 534, steps A-C, and using 3-(tert-butyl) aniline in place of 3-cyclobutylaniline in step A. MS (ESI): mass calcd. for C$_{27}$H$_{29}$N$_{5}$O$_{3}$S, 503.6; m/z found, 504.1 [M+H]$^+$. $^1$H NMR (500 MHz, CD$_3$OD): δ 8.27 (d, J=5.6 Hz, 1H), 7.61 (d, J=8.1 Hz, 1H), 7.54 (t, J=7.9 Hz, 1H), 7.50 (s, 1H), 7.24 (d, J=7.7 Hz, 1H), 6.86-6.74 (m, 1H), 6.20 (dd, J=16.8, 7.3 Hz, 1H), 6.06 (d, J=5.6 Hz, 1H), 5.73 (dd, J=18.1, 10.9 Hz, 1H), 4.59-4.28 (m, 1H), 4.23-3.93 (m, 2H), 3.22-3.10 (m, 1H), 2.89 (q, J=11.1 Hz, 1H), 2.12-2.03 (m, 1H), 1.90-1.83 (m, 1H), 1.80-1.66 (m, 1H), 1.66-1.52 (m, 1H), 1.37 (s, 9H).

Example 639: (3S,4S)-tert-Butyl 3-methoxy-4-(4-oxo-5-(4-phenoxyphenyl)-4,5-dihydro-3H-1-thia-3,5,8-triazaacenaphthylene-2-carboxamido)pyrrolidine-1-carboxylate

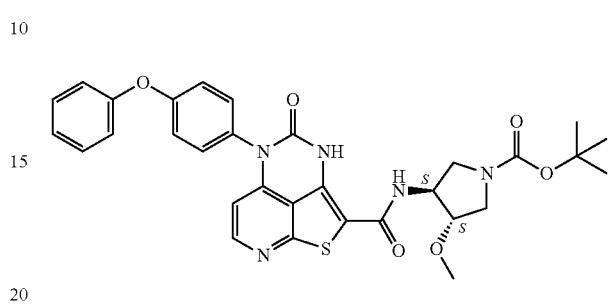

The title compound was prepared in a manner analogous to Method 1, Step G in Example 1, using 4-oxo-5-(4-phenoxyphenyl)-4,5-dihydro-3H-1-thia-3,5,8-triazaacenaphthylene-2-carboxylic acid (Intermediate 58) and using tert-butyl (3S,4S)-3-amino-4-methoxy-pyrrolidine-1-carboxylate in place of tert-butyl (3R,5R)-3-amino-5-fluoro-piperidine-1-carboxylate in step G. MS (ESI): mass calcd. for C$_{31}$H$_{31}$N$_{5}$O$_{6}$S, 601.7; m/z found, 602.2 [M+H]$^+$. $^1$H NMR (500 MHz, CDCl$_3$): δ 9.52 (s, 1H), 8.31 (d, J=5.5 Hz, 1H), 7.43-7.28 (m, 4H), 7.22-7.07 (m, 6H), 6.56 (s, 1H), 6.14 (d, J=5.5 Hz, 1H), 4.52 (tt, J=6.2, 2.6 Hz, 1H), 3.92 (dd, J=10.1, 5.1 Hz, 1H), 3.73 (dd, J=11.9, 6.0 Hz, 1H), 3.60 (dd, J=12.4, 4.9 Hz, 1H), 3.53-3.43 (m, 4H), 1.38 (m, 9H).

Example 640: (R)—N-(1-Acryloylpiperidin-3-yl)-5-(5-isopropoxy-2-methylphenyl)-4-oxo-4,5-dihydro-3H-1-thia-3,5,8-triazaacenaphthylene-2-carboxamide

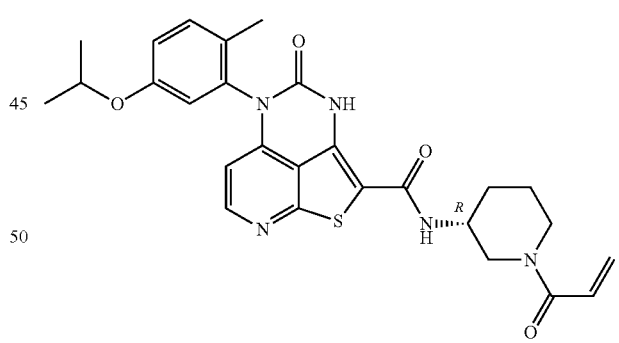

The title compound was prepared using the procedures found in Example 534, steps A-C, and using 5-isopropoxy-2-methyl-aniline in place of 3-cyclobutylaniline in step A. MS (ESI): mass calcd. for C$_{27}$H$_{29}$N$_{5}$O$_{4}$S, 519.6; m/z found, 520.1 [M+H]$^+$. $^1$H NMR (600 MHz, CD$_3$OD): δ 8.34-8.28 (d, J=5.6 Hz, 1H), 7.37-7.31 (d, J=8.5 Hz, 1H), 7.04-6.99 (m, 1H), 6.96-6.91 (d, J=2.8 Hz, 1H), 6.84-6.74 (m, 1H), 6.25-6.16 (m, 1H), 6.05-6.01 (m, 1H), 5.77-5.70 (m, 1H), 4.63-4.56 (m, 1H), 4.55-4.26 (m, 1H), 4.22-3.92 (m, 2H), 3.23-3.14 (m, 1H), 2.99-2.85 (m, 1H), 2.11-2.05 (s, 4H), 1.92-1.83 (m, 1H), 1.81-1.68 (m, 1H), 1.65-1.49 (m, 1H), 1.32-1.29 (s, 6H).

Example 641: (R)—N-(1-Acryloylpiperidin-3-yl)-5-(4-(tert-butylsulfonyl)phenyl)-4-oxo-4,5-dihydro-3H-1-thia-3,5,8-triazaacenaphthylene-2-carboxamide

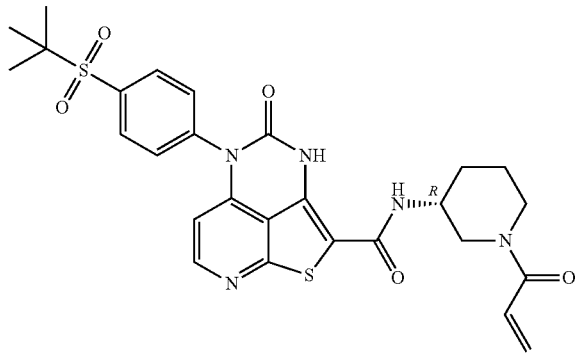

The title compound was prepared using the procedures found in Example 534, steps A-C, and using 4-(tert-butylsulfonyl)aniline in place of 3-cyclobutylaniline in step A. MS (ESI): mass calcd. for $C_{27}H_{29}N_5O_5S_2$, 567.7; m/z found, 568.0 [M+H]$^+$. $^1$H NMR (400 MHz, CDCl$_3$): δ 9.51 (s, 1H), 8.38 (d, J=5.3 Hz, 1H), 8.11 (d, J=8.6 Hz, 2H), 7.58 (d, J=8.2 Hz, 2H), 6.69-6.56 (m, 1H), 6.50-6.38 (m, 0.5H), 6.35 (s, 1H), 6.08 (d, J=4.8 Hz, 1H), 5.76 (s, 1H), 5.58 (s, 0.5H), 4.21-3.31 (m, 5H), 2.18-1.70 (m, 4H), 1.42 (s, 9H).

Example 642: (R)-5-(4-Hydroxyphenyl)-4-oxo-N-(piperidin-3-yl)-4,5-dihydro-3H-1-thia-3,5,8-triazaacenaphthylene-2-carboxamide

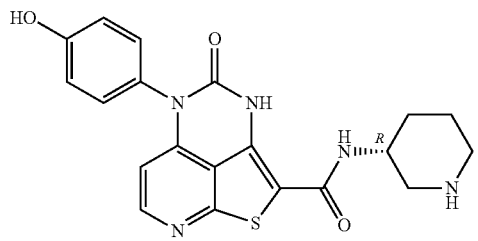

The title compound was prepared using the procedures found in Example 534, steps A-B, and using 4-(tert-butoxy)aniline in place of 3-cyclobutylaniline in step A, and using TFA and dichloroethane in place of 4 M HCl and dioxane in step B. MS (ESI): mass calcd. for $C_{20}H_{19}N_5O_3S$, 409.5; m/z found, 410.1 [M+H]$^+$. $^1$H NMR (400 MHz, CD$_3$OD): δ 8.32 (d, J=5.6 Hz, 1H), 7.22 (d, J=8.7 Hz, 2H), 6.98 (d, J=8.7 Hz, 2H), 6.17 (d, J=5.6 Hz, 1H), 4.32-4.19 (m, 1H), 3.53 (dd, J=12.1, 3.8 Hz, 1H), 3.36 (d, J=12.7 Hz, 1H), 3.01-2.90 (m, 2H), 2.16-2.02 (m, 2H), 1.94-1.67 (m, 2H).

Example 643: (R)-5-(3-Acetylphenyl)-4-oxo-N-(piperidin-3-yl)-4,5-dihydro-3H-1-thia-3,5,8-triazaacenaphthylene-2-carboxamide

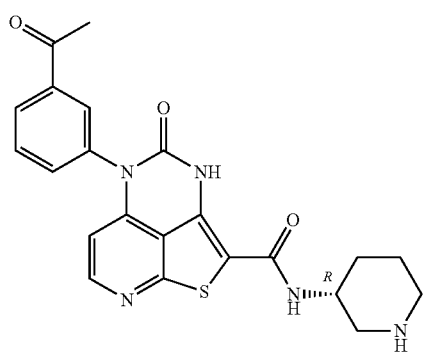

The title compound was prepared using the procedures found in Example 534, steps A-B, and using 1-(3-aminophenyl)ethanone in place of 3-cyclobutylaniline in step A. MS (ESI): mass calcd. for $C_{22}H_{21}N_5O_3S$, 435.5; m/z found, 436.0 [M+H]$^+$. $^1$H NMR (500 MHz, DMSO-d$_6$): δ 10.37-10.27 (s, 1H), 9.45-9.31 (m, 1H), 9.26-9.06 (m, 1H), 8.44-8.31 (m, 2H), 8.19-8.11 (m, 1H), 8.10-8.03 (s, 1H), 7.83-7.74 (m, 2H), 6.10-5.99 (d, J=5.6 Hz, 1H), 4.29-4.16 (m, 1H), 3.35-3.26 (d, J=11.5 Hz, 1H), 3.23-3.13 (d, J=12.2 Hz, 1H), 2.96-2.76 (m, 2H), 2.65-2.58 (s, 3H), 1.97-1.86 (m, 2H), 1.80-1.59 (m, 2H).

Example 644: (R)-5-(5-Isopropoxy-2-methylphenyl)-4-oxo-N-(piperidin-3-yl)-4,5-dihydro-3H-1-thia-3,5,8-triazaacenaphthylene-2-carboxamide

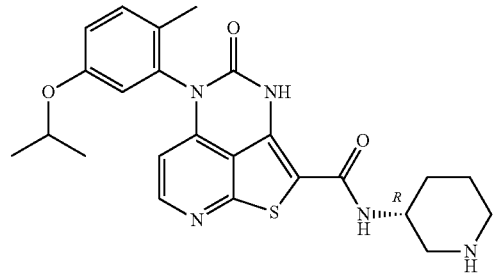

The title compound was prepared using the procedures found in Example 534, steps A-B, and using 5-isopropoxy-2-methyl-aniline in place of 3-cyclobutylaniline in step A. MS (ESI): mass calcd. for $C_{24}H_{27}N_5O_3S$, 465.6; m/z found, 466.1 [M+H]$^+$. $^1$H NMR (600 MHz, CD$_3$OD): δ 8.52-8.47 (d, J=6.4 Hz, 1H), 7.41-7.36 (d, J=8.6 Hz, 1H), 7.09-7.04 (dd, J=8.6, 2.6 Hz, 1H), 6.97-6.94 (m, 1H), 6.34-6.28 (d, J=6.4 Hz, 1H), 4.65-4.54 (dt, J=12.1, 6.0 Hz, 1H), 4.35-4.26 (m, 1H), 3.57-3.52 (m, 1H), 3.40-3.33 (m, 1H), 3.05-2.97 (m, 2H), 2.14-2.06 (m, 5H), 1.92-1.75 (m, 2H), 1.34-1.28 (dd, J=6.0, 4.5 Hz, 6H).

Example 645: (R)-4-Oxo-5-(6-phenoxypyridin-2-yl)-N-(piperidin-3-yl)-4,5-dihydro-3H-1-thia-3,5,8-triazaacenaphthylene-2-carboxamide

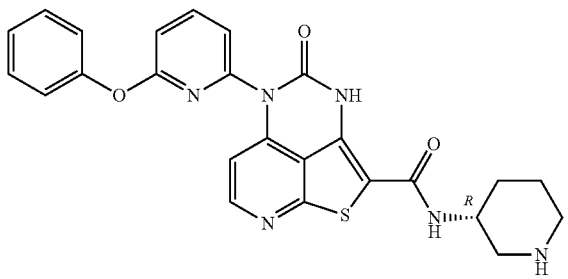

The title compound was prepared using the procedures found in Example 534, steps A-B, and using 6-phenoxypyridin-2-amine in place of 3-cyclobutylaniline in step A. MS (ESI): mass calcd. for $C_{25}H_{22}N_6O_3S$, 486.6; m/z found, 487.0 [M+H]$^+$. 1H NMR (600 MHz, MeOD) δ 8.19 (d, J=5.6 Hz, 1H), 8.09-8.04 (m, 1H), 7.42-7.37 (m, 2H), 7.28-7.23 (m, 1H), 7.22-7.16 (m, 3H), 7.09 (d, J=8.3 Hz, 1H), 6.14 (d, J=5.6 Hz, 1H), 4.21-4.11 (m, 1H), 3.31-3.28 (m, 1H), 3.15-3.09 (m, 1H), 2.93-2.82 (m, 2H), 2.08-1.93 (m, 2H), 1.79-1.70 (m, 2H).

Example 646: (R)-5-(3-(tert-Butyl)phenyl)-4-oxo-N-(piperidin-3-yl)-4,5-dihydro-3H-1-thia-3,5,8-triazaacenaphthylene-2-carboxamide

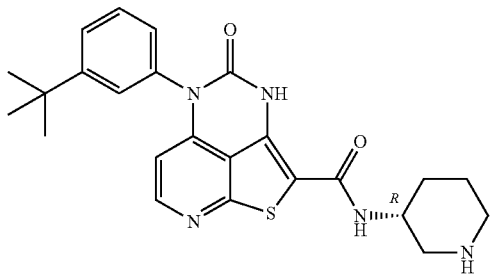

The title compound was prepared using the procedures found in Example 534, steps A-B, and using 3-tert-butylaniline in place of 3-cyclobutylaniline in step A. MS (ESI): mass calcd. for $C_{24}H_{27}N_5O_2S$, 449.6; m/z found, 450.1 [M+H]$^+$. $^1$H NMR (400 MHz, CD$_3$OD): δ 8.44 (d, J=6.3 Hz, 1H), 7.70-7.62 (m, 1H), 7.58 (t, J=7.9 Hz, 1H), 7.51 (t, J=1.9 Hz, 1H), 7.30-7.23 (m, 1H), 6.29 (d, J=6.3 Hz, 1H), 4.36-4.24 (m, 1H), 3.54 (dd, J=12.2, 4.0 Hz, 1H), 3.36 (d, J=12.7 Hz, 1H), 3.00 (t, J=11.5 Hz, 2H), 2.15-2.04 (m, 2H), 1.96-1.71 (m, 2H), 1.37 (s, 9H).

Example 647: (R)-4-Oxo-N-(piperidin-3-yl)-5-(3-(pyridin-4-yl)phenyl)-4,5-dihydro-3H-1-thia-3,5,8-triazaacenaphthylene-2-carboxamide

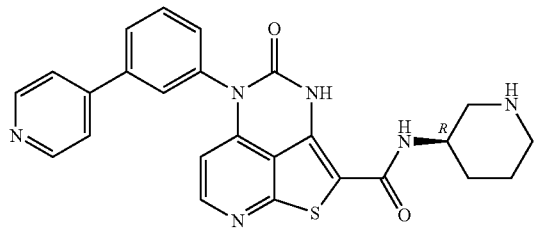

The title compound was prepared in a manner analogous to Method 1, steps C-H in Example 1, and using 3-(pyridin-4-yl)aniline in Step C and using tert-butyl (3R)-3-aminopiperidine-1-carboxylate in place of tert-butyl (3R,5R)-3-amino-5-fluoro-piperidine-1-carboxylate in step G. MS (ESI): mass calcd. for $C_{25}H_{22}N_6O_2S$, 470.5; m/z found, 471.3 [M+H]$^+$. $^1$H NMR (400 MHz, CD$_3$OD): δ 8.63-8.55 (m, 2H), 8.21 (d, J=5.6 Hz, 1H), 7.97-7.89 (m, 1H), 7.87-7.82 (m, 1H), 7.79-7.70 (m, 3H), 7.55-7.48 (m, 1H), 6.10 (d, J=5.6 Hz, 1H), 4.22-4.10 (m, 1H), 3.34-3.31 (m, 1H), 3.18-3.08 (m, 1H), 2.92-2.75 (m, 2H), 2.08-1.92 (m, 2H), 1.80-1.65 (m, 2H).

Example 648: (R)-tert-Butyl 3-(5-(3-(tert-butyl)phenyl)-4-oxo-4,5-dihydro-3H-1-thia-3,5,8-triazaacenaphthylene-2-carboxamido)piperidine-1-carboxylate

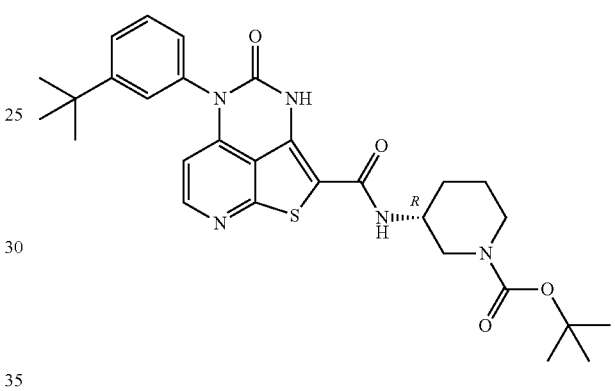

The title compound was prepared using the procedures found in Example 534, step A, and using 3-tert-butylaniline in place of 3-cyclobutylaniline. MS (ESI): mass calcd. for $C_{29}H_{35}N_5O_4S$, 549.7; m/z found, 550.2 [M+H]$^+$. $^1$H NMR (500 MHz, CD$_3$OD): δ 8.29 (d, J=5.6 Hz, 1H), 7.64-7.58 (m, 1H), 7.54 (t, J=7.9 Hz, 1H), 7.50-7.46 (m, 1H), 7.23 (d, J=7.6 Hz, 1H), 6.07 (d, J=5.6 Hz, 1H), 4.13-4.05 (m, 1H), 3.97-3.84 (m, 2H), 2.87 (t, J=12.4 Hz, 2H), 2.06-2.01 (m, 1H), 1.79 (d, J=13.0 Hz, 1H), 1.67-1.49 (m, 2H), 1.46 (s, 9H), 1.37 (s, 9H).

Example 649: (R)-tert-Butyl 3-(5-(3-acetylphenyl)-4-oxo-4,5-dihydro-3H-1-thia-3,5,8-triazaacenaphthylene-2-carboxamido)piperidine-1-carboxylate

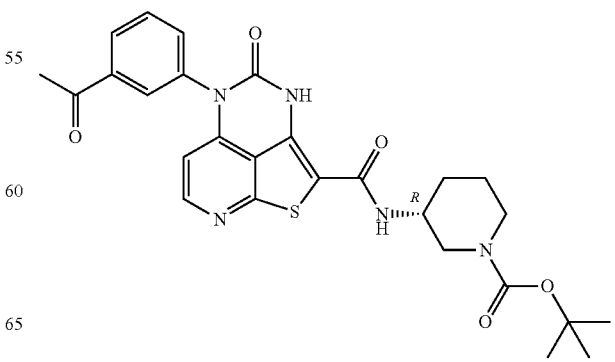

The title compound was prepared using the procedures found in Example 534, step A, and using 1-(3-aminophenyl)ethanone in place of 3-cyclobutylaniline. MS (ESI): mass calcd. for $C_{27}H_{29}N_5O_5S$, 535.6; m/z found, 536.1 [M+H]$^+$. $^1$H NMR (500 MHz, CDCl$_3$): δ 9.56-9.46 (s, 1H), 8.40-8.31 (d, J=5.5 Hz, 1H), 8.15-8.07 (m, 1H), 7.98-7.91 (s, 1H), 7.76-7.68 (m, 1H), 7.61-7.53 (s, 1H), 6.12-6.02 (d, J=5.5 Hz, 1H), 4.17-4.07 (m, 1H), 3.71-3.43 (m, 4H), 3.40-3.22 (m, 1H), 2.68-2.57 (s, 3H), 1.96-1.82 (m, 2H), 1.78-1.67 (m, 1H), 1.65-1.56 (m, 1H), 1.54-1.47 (s, 9H).

Example 650: (R)-5-(4-(tert-Butylsulfonyl)phenyl)-4-oxo-N-(piperidin-3-yl)-4,5-dihydro-3H-1-thia-3,5,8-triazaacenaphthylene-2-carboxamide

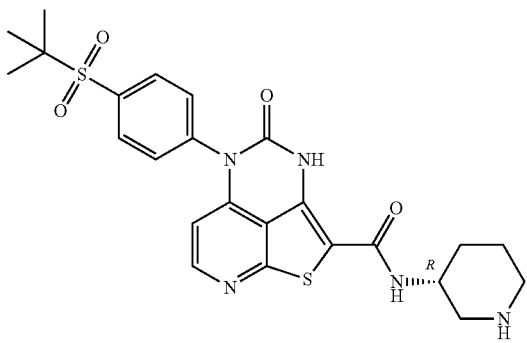

The title compound was prepared using the procedures found in Example 534, steps A-B, and using 4-(tert-butylsulfonyl)aniline in place of 3-cyclobutylaniline in step A. MS (ESI): mass calcd. for $C_{24}H_{27}N_5O_4S_2$, 513.6; m/z found, 514.0 [M+H]$^+$. $^1$H NMR (500 MHz, DMSO-d$_6$): δ 10.36 (s, 1H), 9.42-9.29 (m, 1H), 9.21-9.09 (m, 1H), 8.40 (d, J=5.5 Hz, 1H), 8.10 (d, J=8.6 Hz, 2H), 7.88-7.80 (m, 2H), 6.20 (d, J=5.6 Hz, 1H), 4.31-4.20 (m, 1H), 3.28 (dd, J=59.3, 11.4 Hz, 2H), 2.99-2.80 (m, 2H), 2.00-1.90 (m, 2H), 1.83-1.63 (m, 2H), 1.35 (s, 9H).

Example 651: (R)-tert-Butyl 3-(5-(4-(tert-butylsulfonyl)phenyl)-4-oxo-4,5-dihydro-3H-1-thia-3,5,8-triazaacenaphthylene-2-carboxamido)piperidine-1-carboxylate

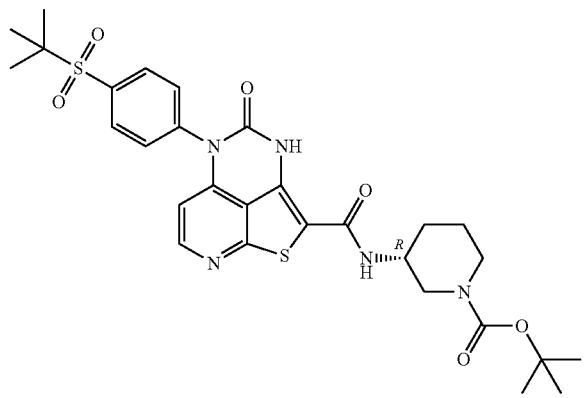

The title compound was prepared using the procedures found in Example 534, step A, and using 4-(tert-butylsul-fonyl)aniline in place of 3-cyclobutylaniline, to yield the title compound. MS (ESI): mass calcd. for $C_{29}H_{35}N_5O_6S_2$, 613.8; m/z found, 614.1 [M+H]$^+$. $^1$H NMR (400 MHz, CDCl$_3$): δ 9.55 (s, 1H), 8.38 (d, J=5.5 Hz, 1H), 8.11 (d, J=8.7 Hz, 2H), 7.58 (d, J=8.4 Hz, 2H), 6.21-5.35 (m, 2H), 4.16-4.09 (m, 1H), 3.70-3.44 (m, 3H), 3.34 (s, 1H), 1.89 (s, 2H), 1.79-1.69 (m, 1H), 1.64-1.55 (m, 1H), 1.51 (s, 9H), 1.42 (s, 9H).

Example 652: (R)-tert-Butyl 3-(5-(4-(tert-butoxy)phenyl)-4-oxo-4,5-dihydro-3H-1-thia-3,5,8-triazaacenaphthylene-2-carboxamido)piperidine-1-carboxylate

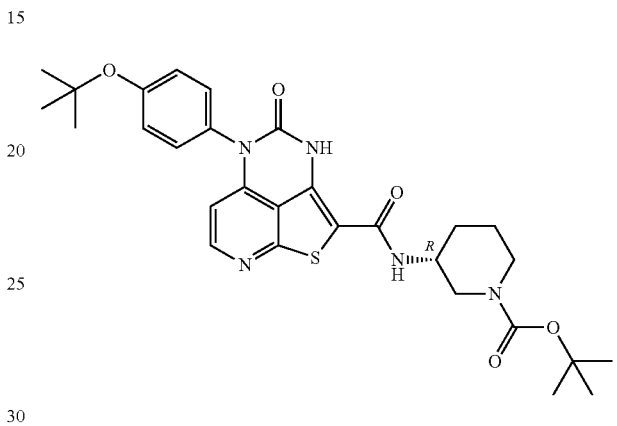

The title compound was prepared using the procedures found in Example 534, step A, and using 4-(tert-butoxy)aniline in place of 3-cyclobutylaniline, to yield the title compound. MS (ESI): mass calcd. for $C_{29}H_{35}N_5O_5S$, 565.7; m/z found, 566.2 [M+H]$^+$. $^1$H NMR (400 MHz, CD$_3$OD): δ 8.31 (d, J=5.6 Hz, 1H), 7.38-7.29 (m, 2H), 7.24-7.19 (m, 2H), 6.14 (d, J=5.6 Hz, 1H), 4.08-3.84 (m, 3H), 3.06-2.79 (m, 2H), 2.06-2.00 (m, 1H), 1.83-1.74 (m, 1H), 1.68-1.51 (m, 2H), 1.47 (s, 9H), 1.42 (s, 9H).

Example 653: (R)-tert-Butyl 3-(5-(2,2-difluorobenzo[d][1,3]dioxol-5-yl)-4-oxo-4,5-dihydro-3H-1-thia-3,5,8-triazaacenaphthylene-2-carboxamido)piperidine-1-carboxylate

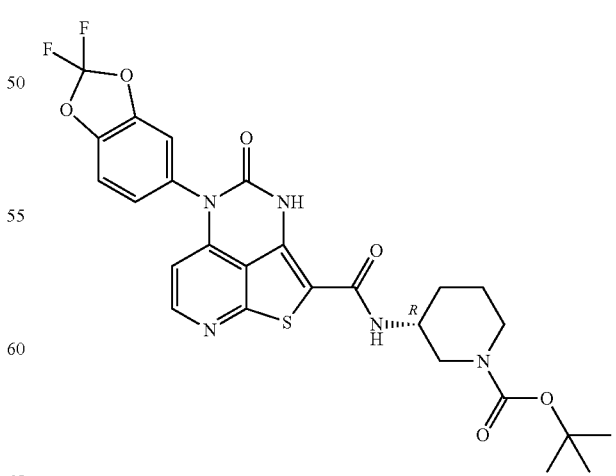

The title compound was prepared using the procedures found in Example 525, steps A-B, to yield the title compound. MS (ESI): mass calcd. for $C_{26}H_{25}F_2N_5O_6S$, 573.6; m/z found, 574.0 [M+H]⁺. ¹H NMR (500 MHz, CD₃OD): δ 8.32 (d, J=5.6 Hz, 1H), 7.47-7.40 (m, 2H), 7.30 (dd, J=8.5, 2.0 Hz, 1H), 6.20 (d, J=5.6 Hz, 1H), 4.08-4.02 (m, 1H), 3.97-3.86 (m, 2H), 3.03-2.66 (m, 2H), 2.03 (d, J=2.6 Hz, 1H), 1.82-1.74 (m, 1H), 1.66-1.50 (m, 2H), 1.46 (s, 9H).

Example 654: (R)-tert-Butyl 3-(5-(6-cyclobutoxy-pyridin-3-yl)-4-oxo-4,5-dihydro-3H-1-thia-3,5,8-triazaacenaphthylene-2-carboxamido)piperidine-1-carboxylate

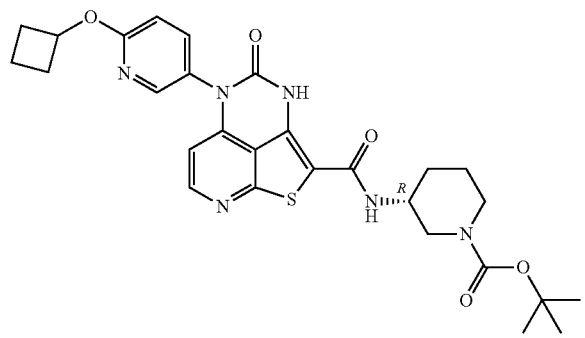

The title compound was prepared using the procedures found in Example 534, step A, and using 6-(cyclobutoxy)pyridin-3-amine in place of 3-cyclobutylaniline, to yield the title compound. MS (ESI): mass calcd. for $C_{28}H_{32}N_6O_5S$, 564.7; m/z found, 565.2 [M+H]⁺. ¹H NMR (400 MHz, CD₃OD): δ 8.32 (d, J=5.6 Hz, 1H), 8.19 (dd, J=2.7, 0.5 Hz, 1H), 7.74 (dd, J=8.8, 2.7 Hz, 1H), 6.95 (dd, J=8.8, 0.5 Hz, 1H), 6.20 (d, J=5.6 Hz, 1H), 5.28-5.17 (m, 1H), 4.08-4.02 (m, 1H), 3.97-3.86 (m, 2H), 2.99-2.74 (m, 2H), 2.56-2.45 (m, 2H), 2.24-2.11 (m, 2H), 2.07-2.01 (m, 1H), 1.94-1.83 (m, 1H), 1.82-1.69 (m, 2H), 1.68-1.51 (m, 2H), 1.46 (s, 9H).

Example 655: N-((3R,4R)-1-Acryloyl-4-hydroxypiperidin-3-yl)-4-oxo-5-(4-phenoxyphenyl)-4,5-dihydro-3H-1-thia-3,5,8-triazaacenaphthylene-2-carboxamide

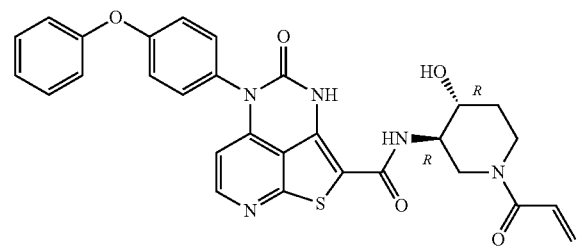

The title compound was prepared using analogous conditions found in Method 1, step I in Example 1, and using N-((3R,4R)-4-Hydroxypiperidin-3-yl)-4-oxo-5-(4-phenoxyphenyl)-4,5-dihydro-3H-1-thia-3,5,8-triazaacenaphthylene-2-carboxamide (Example 658) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide. MS (ESI): mass calcd. for $C_{29}H_{25}N_5O_5S$, 555.6; m/z found, 556.1 [M+H]⁺.

¹H NMR (400 MHz, CDCl₃): δ 9.74 (s, 1H), 8.17 (dd, J=11.1, 5.7 Hz, 1H), 7.50 (s, 1H), 7.39 (t, J=7.8 Hz, 2H), 7.28 (d, J=6.9 Hz, 2H), 7.22-7.05 (m, 5H), 6.71-6.59 (m, 1H), 6.54 (d, J=11.1 Hz, 1H), 6.26 (d, J=16.8 Hz, 1H), 6.00 (t, J=7.4 Hz, 1H), 4.60 (dd, J=27.0, 12.4 Hz, 1H), 3.86 (d, J=14.7 Hz, 3H), 3.48 (s, 1H), 2.86 (t, J=15.9 Hz, 1H), 2.68 (d, J=13.4 Hz, 1H), 2.09-2.01 (m, 1H), 1.21 (t, J=7.0 Hz, 1H).

Example 656: (R)-5-(3-Methyl-5-phenoxypyrazin-2-yl)-4-oxo-N-(piperidin-3-yl)-4,5-dihydro-3H-1-thia-3,5,8-triazaacenaphthylene-2-carboxamide

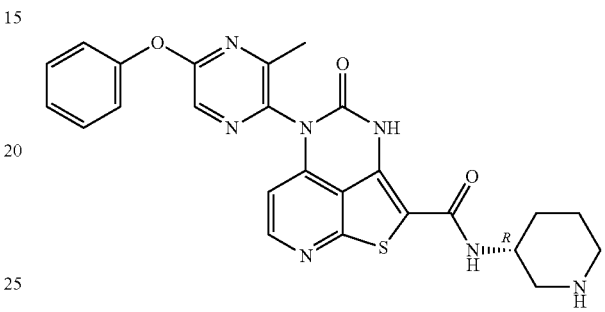

The title compound was prepared using the procedures found in Example 534, steps A-B, and using 3-methyl-5-phenoxy-pyrazin-2-amine (Intermediate 51) in place of 3-cyclobutylaniline in step A, to yield the title compound. MS (ESI): mass calcd. for $C_{25}H_{23}N_7O_3S$, 501.6; m/z found, 502.1 [M+H]⁺. ¹H NMR (400 MHz, CD₃OD): δ 8.56-8.50 (m, 1H), 8.34-8.27 (s, 1H), 7.51-7.44 (m, 2H), 7.32-7.23 (m, 3H), 6.57-6.52 (d, J=6.3 Hz, 1H), 4.36-4.23 (m, 1H), 3.59-3.50 (d, J=12.7 Hz, 1H), 3.40-3.33 (d, J=13.5 Hz, 1H), 3.05-2.93 (m, 2H), 2.36-2.29 (s, 3H), 2.18-2.04 (m, 2H), 1.94-1.72 (m, 2H).

Example 657: (R)—N-(1-Acryloylpiperidin-3-yl)-5-(3-methyl-5-phenoxypyrazin-2-yl)-4-oxo-4,5-dihydro-3H-1-thia-3,5,8-triazaacenaphthylene-2-carboxamide

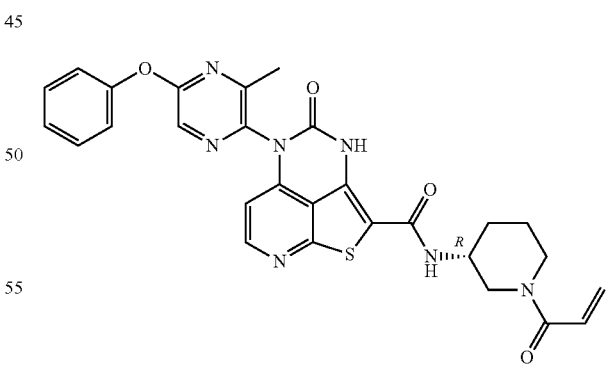

The title compound was prepared using the analogous conditions found in Method 1, step I in Example 1, and using (R)-5-(3-Methyl-5-phenoxypyrazin-2-yl)-4-oxo-N-(piperidin-3-yl)-4,5-dihydro-3H-1-thia-3,5,8-triazaacenaphthylene-2-carboxamide (Example 656) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide to yield the title compound. MS (ESI): mass calcd. for $C_{28}H_{25}N_7O_4S$, 555.6; m/z found, 556.1 [M+H]$^+$. $^1$H NMR (600 MHz, CD$_3$OD): δ 8.37-8.32 (d, J=5.5 Hz, 1H), 8.31-8.26 (s, 1H), 7.50-7.43 (m, 2H), 7.31-7.21 (m, 3H), 6.86-6.73 (m, 1H), 6.23-6.15 (m, 2H), 5.78-5.68 (m, 1H), 4.58-4.27 (m, 1H), 4.23-3.89 (m, 2H), 3.22-3.11 (m, 1H), 2.96-2.84 (m, 1H), 2.36-2.26 (d, J=2.8 Hz, 3H), 2.13-2.01 (m, 1H), 1.91-1.83 (m, 1H), 1.80-1.67 (m, 1H), 1.63-1.50 (m, 1H).

Example 658: N-((3R,4R)-4-Hydroxypiperidin-3-yl)-4-oxo-5-(4-phenoxyphenyl)-4,5-dihydro-3H-1-thia-3,5,8-triazaacenaphthylene-2-carboxamide

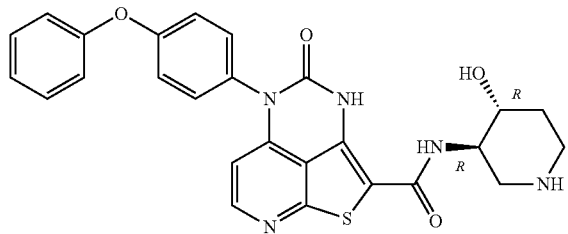

Step A: (3R,4R)-tert-Butyl 4-hydroxy-3-(4-oxo-5-(4-phenoxyphenyl)-4,5-dihydro-3H-1-thia-3,5,8-triazaacenaphthylene-2-carboxamido)piperidine-1-carboxylate To a dry flask were added tert-butyl (3R,4R)-3-amino-4-hydroxypiperidine-1-carboxylate (410 mg, 1.896 mmol), diisopropylethylamine (0.996 mL, 5.69 mmol), and THF (7.6 mL) and was cooled to 0° C. 4-Oxo-5-(4-phenoxyphenyl)-4,5-dihydro-3H-1-thia-3,5,8-triazaacenaphthylene-2-carbonyl chloride (Intermediate 40, 0.800 g, 1.90 mmol) was added dropwise at 0° C. The reaction was monitored by LCMS and when it had gone to completion, the reaction was quenched with saturated NaHCO$_3$, extracted with DCM, and concentrated to dryness. The residue was purified by normal phase flash column chromatography (SiO$_2$) to give the title compound (800 mg, 70% yield). MS (ESI): mass calcd. for $C_{31}H_{31}N_5O_6S$, 601.68; m/z found, 602.2 [M+H]$^+$.

Step B: N-((3R,4R)-4-Hydroxypiperidin-3-yl)-4-oxo-5-(4-phenoxyphenl)-4,5-dihydro-3H-1-thia-3,5,8-triazaacenaphthylene-2-carboxamide To a solution of (3R,4R)-tert-butyl 4-hydroxy-3-(4-oxo-5-(4-phenoxyphenyl)-4,5-dihydro-3H-1-thia-3,5,8-triazaacenaphthylene-2-carboxamido)piperidine-1-carboxylate (800 mg, 1.33 mmol) in DCM (20 mL) at room temperature was added TFA (22 mL) dropwise. The reaction was stirred at room temperature for 30 minutes. The reaction was concentrated to dryness and the residue was purified by normal phase flash column chromatography (SiO$_2$) to give the title compound (660 mg, 99.0% yield) as an off white solid. MS (ESI): mass calcd. for $C_{26}H_{23}N_5O_4S$, 501.6; m/z found, 502.15 [M+H]$^+$. $^1$H NMR (400 MHz, CD$_3$OD): δ 8.25 (dd, J=5.5, 1.7 Hz, 1H), 7.47-7.33 (m, 3H), 7.33-7.25 (m, 1H), 7.27-7.09 (m, 5H), 6.12 (dd, J=5.8, 1.9 Hz, 1H), 4.20 (d, J=8.2 Hz, 4H), 3.90 (td, J=8.9, 4.2 Hz, 1H), 3.71 (td, J=9.1, 4.2 Hz, 1H), 3.32 (dd, J=12.8, 4.3 Hz, 1H), 3.12 (dt, J=13.1, 4.1 Hz, 1H), 2.74-2.53 (m, 2H), 2.09 (dq, J=12.6, 3.8 Hz, 1H), 1.60 (dtd, J=13.8, 10.3, 3.9 Hz, 1H).

Example 7: N-(cis-3-Hydroxypiperidin-4-yl)-4-oxo-5-(4-phenoxyphenyl)-4,5-dihydro-3H-1-thia-3,5,8-triazaacenaphthylene-2-carboxamide

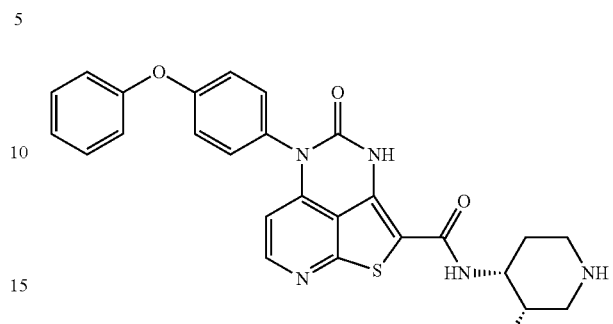

Step A: cis-tert-Butyl 3-hydroxy-4-(4-oxo-5-(4-phenoxyphenyl)-4,5-dihydro-3H-1-thia-3,5,8-triazaacenaphthylene-2-carboxamido)piperidine-1-carboxylate To a dry flask were added cis-tert-butyl 4-amino-3-hydroxypiperidine-1-carboxylate (402 mg, 1.896 mmol), diisopropylethylamine (0.996 mL, 5.69 mmol), and THF (7.5 mL) and was cooled to 0° C. 4-Oxo-5-(4-phenoxyphenyl)-4,5-dihydro-3H-1-thia-3,5,8-triazaacenaphthylene-2-carbonyl chloride (Intermediate 40) 0.800 g, 1.90 mmol) was added dropwise at 0° C. The reaction was monitored by LCMS and when it had gone to completion, the reaction was quenched with saturated NaHCO$_3$, extracted with DCM, and concentrated to dryness. The residue was purified by normal phase flash column chromatography (SiO$_2$) to give the title compound (950 mg, 83% yield). MS (ESI): mass calcd. for $C_{31}H_{31}N_5O_6S$, 601.68; m/z found, 601.8 [M+H]$^+$. $^1$H NMR (500 MHz, DMSO-d$_6$): δ 8.34 (dd, J=5.5, 1.3 Hz, 1H), 7.51-7.42 (m, 4H), 7.26-7.11 (m, 5H), 6.09 (dd, J=5.5, 1.2 Hz, 1H), 5.40 (ddd, J=25.8, 7.8, 5.4 Hz, 1H), 5.00-4.86 (m, 2H), 4.37 (d, J=14.2 Hz, 1H), 4.32-4.25 (m, 1H), 4.07-3.97 (m, 1H), 3.93-3.79 (m, 3H), 3.63 (dt, J=12.7, 6.6 Hz, 2H), 1.38 (s, 9H).

Step B: N-(Cis-3-hydroxypiperidin-4-yl)-4-oxo-5-(4-phenoxyphenyl)-4,5-dihydro-3H-1-thia-3,5,8-triazaacenaphthylene-2-carboxamide To a solution of cis-tert-butyl 3-hydroxy-4-(4-oxo-5-(4-phenoxyphenyl)-4,5-dihydro-3H-1-thia-3,5,8-triazaacenaphthylene-2-carboxamido)piperidine-1-carboxylate (950 mg, 1.58 mmol) in DCM (20 mL) at room temperature was added TFA (26 mL) dropwise. The reaction was stirred at room temperature for 30 minutes. The reaction was concentrated to dryness and the residue was purified by normal phase flash column chromatography (SiO$_2$) to give the title compound (750 mg, 94.7% yield) as an off white solid. MS (ESI): mass calcd. for $C_{26}H_{23}N_5O_4S$, 501.6; m/z found, 502.15 [M+H]$^+$. $^1$H NMR (500 MHz, CD$_3$OD): δ 8.29 (d, J=5.6 Hz, 1H), 8.03 (s, 1H), 7.45-7.26 (m, 4H), 7.23-7.07 (m, 5H), 6.15 (d, J=5.5 Hz, 1H), 4.27-4.17 (m, 2H), 3.58 (s, 1H), 3.45-3.36 (m, 3H), 3.14 (dd, J=13.4, 1.5 Hz, 1H), 3.03 (td, J=13.1, 3.2 Hz, 1H), 2.21 (qd, J=13.3, 4.4 Hz, 1H), 2.00 (bs, 1H), 1.95 (ddt, J=13.9, 6.0, 2.7 Hz, 1H).

Example 660: 4-Oxo-N-(2-oxopyrrolidin-3-yl)-5-(4-phenoxyphenyl)-4,5-dihydro-3H-1-thia-3,5,8-triazaacenaphthylene-2-carboxamide

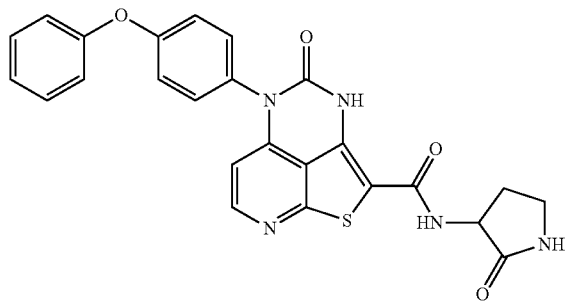 [SMILES: O=C(NC1CCNC1=O)c1sc2nccc3c2c1NC(=O)N3c1ccc(Oc2ccccc2)cc1]

The title compound was prepared using analogous conditions as found in Method 1, steps A-G in Example 1, and using 4-fluoronitrobenzene in place of 5-fluoro-2-nitrotoluene in step A, and using Pd/C and THF in place Fe, EtOH/H$_2$O, and NH$_4$Cl in step B, and using 4-phenoxyaniline in place of 2-methyl-4-phenoxyaniline in step C, and using 3-aminopyrrolidin-2-one and THF in place of tert-butyl (3R,5R)-3-amino-5-fluoropiperidine-1-carboxylate and DMF in step G. MS (ESI): mass calcd. for C$_{25}$H$_{19}$N$_5$O$_4$S, 485.5; m/z found, 486.1 [M+H]$^+$. $^1$H NMR (400 MHz, CD$_3$OD): δ 8.02 (s, 1H), 7.46-7.36 (m, 3H), 7.24-7.08 (m, 6H), 6.29-6.00 (m, 4H), 4.71-4.33 (m, 1H), 3.43-3.35 (m, 2H), 2.55-2.44 (m, 1H), 2.21-2.19 (m, 1H).

Example 661: (R)—N-(1-Acryloylpiperidin-3-yl)-5-(R)-(2-methyl-6-phenoxypyridin-3-yl)-4-oxo-4,5-dihydro-3H-1-thia-3,5,8-triazaacenaphthylene-2-carboxamide

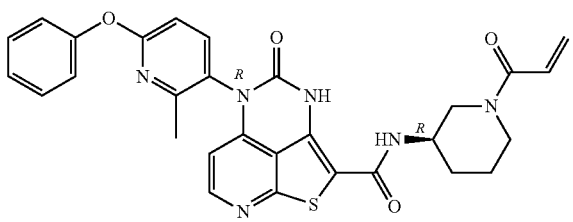

Step A: 2-Chloro-4-((2-methyl-6-phenoxypyridin-3-yl)amino)nicotinonitrile

To a round bottom flask containing 2-chloro-4-iodopyridine-3-carbonitrile (72.1 g, 273 mmol) and 2-methyl-6-phenoxypyridin-3-amine (Intermediate 49, 50.5 g, 252 mmol) were added Pd(OAc)$_2$ (1.81 g, 8.06 mmol), followed by bis(2-diphenylphosphinophenyl)ether (DPEphos, 5.66 g, 10.5 mmol), and cesium carbonate (195 g, 598 mmol). The reaction mixture was evacuated, treated with 1,4-dioxane (550 ml) via cannula, vented to N$_2$, then stirred at room temperature for 2 h. The reaction mixture was transferred to a 2 L flask and diluted with water to a total volume of 2000 mL. The mixture was stirred for 10 min, then the brown precipitate was collected by filtration. The solid was under vacuum at 60° C. to give the title compound (94.8 g, 99% yield) as a light orange solid. MS (ESI): mass calcd. for C$_{18}$H$_{13}$ClN$_4$O, 336.08; m/z found, 337.0 [M+H]$^+$.

Step B: Methyl 5-(2-methyl-6-phenoxypyridin-3-yl)-4-oxo-4,5-dihydro-3H-1-thia-3,5,8-triazaacenaphthylene-2-carboxylate To a round bottom flask containing 2-chloro-4-((2-methyl-6-phenoxypyridin-3-yl)amino)nicotinonitrile (94.8 g, 281 mmol) and dioxane (440 mL) was added cesium carbonate (129 g, 396 mmol). The reaction vessel was sealed, evacuated, and vented to N2. Methyl 2-mercaptoacetate (48.0 g, 453 mmol) was added via syringe and the reaction mixture was heated at 90° C. for 3 h. The reaction mixture was then treated with solid carbonyl diimidazole (121 g, 746) in small portions, to control a vigorous release of gas. The reaction was then diluted with water to a total volume of 2.0 L, and stirred for 10 min. The resulting precipitate was isolated by filtration. The solid was dissolved in dioxane (600 mL), then treated slowly with water (1.4 L). The resulting suspension was filtered and the solid was dried under vacuum at 80° C. to give the title compound (103 g, 85% yield) as a tan solid. MS (ESI): mass calcd. for C$_{22}$H$_{16}$N$_4$O$_4$S, 432.09; m/z found, 433.0 [M+H]$^+$.

Step C: 5-(R)-(2-Methyl-6-phenoxypyridin-3-yl)-4-oxo-4,5-dihydro-3H-1-thia-3,5,8-triazaacenaphthylene-2-carboxylic Acid To a round bottom flask were added methyl 5-(2-methyl-6-phenoxypyridin-3-yl)-4-oxo-4,5-dihydro-3H-1-thia-3,5,8-triazaacenaphthylene-2-carboxylate (52.7 g, 122 mmol), THF (300 mL), MeOH (300 mL), and water (300 mL) followed by lithium hydroxide (24.7 g, 589 mmol). The reaction mixture was stirred at 55° C. for 3 h. The mixture was transferred to a 2 L flask and 4 N HCl was added slowly until the solution was neutral. The resulting suspension was filtered, the filter cake was rinsed with water, and the solid was dried under vacuum at 60° C. to give the title compound (48.3 g, 95%) as a light orange solid. MS (ESI): mass calcd. for C$_{21}$H$_{14}$N$_4$O$_4$S, 418.07; m/z found, 419.0 [M+H]$^+$.

Chiral Separation Method: 5-(R)—(*S)-(2-Methyl-6-phenoxypyridin-3-yl)-4-oxo-4,5-dihydro-3H-1-thia-3,5,8-triazaacenaphthylene-2-carboxylic Acid The atropisomers were chromatographed to isolate the two separate atropisomers, with the respective single atropisomers arbitrarily labeled as *S or *R to indicate that the compound is a single atropisomer of unknown absolute configuration. In cases for which absolute configuration of a single atropisomeric compound was determined, the atropisomers are named as either S or R throughout (with S corresponding to the alternate designations aS, S$_a$, or P; and with R corresponding to the alternate designations aR, R$_a$, or M). The purification was performed on a chiral SFC column (Stationary phase: Stationary phase: Chiralpak AD-H 5 μm 250×30 mm. The mobile phase was: 60% CO$_2$, 40% MeOH.

Step D: tert-Butyl (R)-3-(5-(*S)-(2-methyl-6-phenoxypyridin-3-yl)-4-oxo-4,5-dihydro-3H-1-thia-3,5,8-triazaacenaphthylene-2-carboxamido)piperidine-1-carboxylate To a round bottom flask were added tert-butyl (R)-3-aminopiperidine-1-carboxylate (3.54 g, 17.7 mmol) and DMF (30 mL), followed by 5-(R)—(*S)-(2-methyl-6-phenoxypyridin-3-yl)-4-oxo-4,5-dihydro-3H-1-thia-3,5,8-triaz-aacenaphthylene-2-carboxylic acid (3.70 g, 8.83 mmol) and DIPEA (3.75 mL, 21.8 mmol). The reaction mixture was stirred until it became homogeneous, then cooled to 0° C. HATU (5.44 g, 14.3 mmol) was added, the reaction was stirred at 0° C. for 5 min then the mixture was allowed to warm to room temperature over 30 min with continuous stirring. An additional portion of HATU (590 mg, 1.55 mmol) was added, and the reaction mixture was stirred at room temperature for an additional 5 min. Water (12 mL) was added, the mixture was cooled at 0° C. for 10 minutes, the precipitate was collected by filtration and dried under vacuum. The residue was purified (FCC, 50-100% EtOAc/hexanes) to yield the title compound (4.19 g, 79%) as a yellow film. MS (ESI): mass calcd. for $C_{31}H_{32}N_6O_5S$, 600.22; m/z found, 601.1 [M+H]$^+$.

Step E: (R)-5-(*S)-(2-Methyl-6-phenoxypyridin-3-yl)-4-oxo-N-(piperidin-3-yl)-4,5-dihydro-3H-1-thia-3,5,8-triazaacenaphthylene-2-carboxamide-2 HCl A flask containing tert-butyl (R)-3-(5-(*S)-(2-methyl-6-phenoxypyridin-3-yl)-4-oxo-4,5-dihydro-3H-1-thia-3,5,8-triazaacenaphthylene-2-carboxamido)piperidine-1-carboxylate (4.18 g, 6.96 mmol) was treated with dioxane (40 mL) followed by 4 N HCl-dioxane (20 ml). The reaction was stirred at room temperature for 1 h. Et$_2$O (150 mL) was added, then the resulting solid was isolated by filtration. The solid was dried under vacuum to give the title compound (4.68 g, 97%) as a white solid. MS (ESI): mass calcd. for $C_{26}H_{24}N_6O_3S$, 500.16; m/z found, 501.1 [M+H]$^+$.

Step F: (R)—N-(1-Acryloylpiperidin-3-yl)-5-(R)-(2-methyl-6-phenoxypyridin-3-yl)-4-oxo-4,5-dihydro-3H-1-thia-3,5,8-triazaacenaphthylene-2-carboxamide To a round bottom flask were added (R)-5-(*S)-(2-methyl-6-phenoxypyridin-3-yl)-4-oxo-N-(piperidin-3-yl)-4,5-dihydro-3H-1-thia-3,5,8-triazaacenaphthylene-2-carboxamide-2 HCl (4.18 g, 7.29 mol), DIEPA (5.0 mL, 29 mmol), and DCM (70 mL). The reaction mixture was cooled at 0° C., and acrylic anhydride (0.936 mL, 8.12 mmol) was added in three portions. The reaction mixture was stirred at 0° C. for 5 min, then saturated aqueous sodium bicarbonate (100 mL) was added followed by DCM (100 mL). The mixture was stirred vigorously for 10 min, then the DCM layer was separated. The aqueous layer was extracted again with DCM (50 mL). The organic layers were dried (Na$_2$SO$_4$) and purified (FCC, SiO$_2$, isocratic EtOAc). The fractions containing product were combined and concentrated to give the title compound (2.14 g, 53%) as a white solid. Absolute stereochemical configuration of the title compound was confirmed via X-ray analysis after cocrystallization with BTK protein. MS (ESI): mass calcd. for $C_{29}H_{26}N_6O_4S$, 554.17; m/z found, 555.0 [M+H]$^+$. $^1$H NMR (600 MHz, MeOD) δ 8.34 (d, J=5.5 Hz, 1H), 7.81 (d, J=8.6 Hz, 1H), 7.47-7.41 (m, 2H), 7.28-7.23 (m, 1H), 7.21-7.16 (m, 2H), 6.90 (d, J=8.6 Hz, 1H), 6.83-6.74 (m, 1H), 6.23-6.17 (m, 1H), 6.13 (d, J=5.5 Hz, 1H), 5.77-5.69 (m, 1H), 4.58-4.27 (m, 1H), 4.22-3.97 (m, 1H), 3.95-3.86 (m, 1H), 3.20-3.12 (m, 1H), 2.96-2.80 (m, 1H), 2.24 (s, 3H), 2.10-2.02 (m, 1H), 1.92-1.84 (m, 1H), 1.80-1.66 (m, 1H), 1.63-1.52 (m, 1H).

Example 662: (R)—N-(1-Acryloylpiperidin-3-yl)-5-(*S)-(4-methyl-6-phenoxypyridin-3-yl)-4-oxo-4,5-dihydro-3H-1-thia-3,5,8-triazaacenaphthylene-2-carboxamide

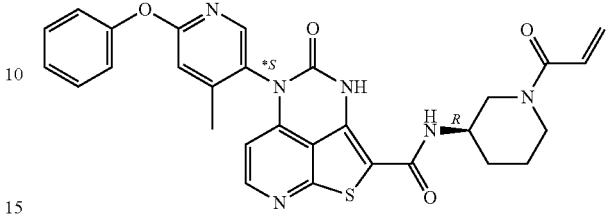

Step A: 2-Chloro-4-((4-methyl-6-phenoxypyridin-3-yl)amino)nicotinonitrile

To a round bottom flask containing a stir bar and 2-chloro-4-iodonicotinonitrile (55.6 g, 210 mmol) and 4-methyl-6-phenoxypyridin-3-amine (40.0 g, 200 mmol) were added DPEPhos (4.53 g, 8.41 mmol), Pd(OAc)$_2$ (1.42 g, 6.31 mmol), and Cs$_2$CO$_3$ (147.1 g, 451.4 mmol). The vial was evacuated, treated with dioxane (400 mL) via cannula, then vented to nitrogen. The reaction mixture was heated at 90° C. for 60 minutes. The reaction mixture was cooled on an ice bath until it was near room temperature, then it was transferred to a 2 L flask and diluted to a total volume of 2100 mL with water. The mixture was stirred for 10 min and the brown precipitate was collected by filtration. The filter cake was dried by pulling air through the frit for 10 min, then dissolved in DCM (400 mL), and dried over anhydrous MgSO$_4$, filtered, and the solid rinsed with DCM (100 mL). The DCM solution was evaporated to about 300 mL and then treated with hexanes (700 mL). The resulting suspension was stirred for 10 minutes and filtered to give the title compound (64.29 g, 90.78% yield) as a brown solid.

Step B: Methyl 5-(4-methyl-6-phenoxypyridin-3-yl)-4-oxo-4,5-dihydro-3H-1-thia-3,5,8-triazaacenaphthylene-2-carboxylate A sealed 200 mL round bottom flask containing 2-chloro-4-((4-methyl-6-phenoxypyridin-3-yl)amino)nicotinonitrile (3.70 g, 11.0 mmol), dioxane (40 mL), and Cs$_2$CO$_3$ (10.4 mg, 0.0319 mmol) was evacuated and vented to N$_2$, then treated with methyl 2-sulfanylacetate (3.30 g, 31.1 mmol) via syringe. The reaction mixture was heated at 100° C. for 3 h. The reaction mixture was treated with solid CDI (9.18 g, 56.6 mmol) in one portion under air, resealed and stirred at rt for overnight. The reaction was diluted with EtOAc (500 mL), DCM (500 mL), and saturated aqueous sodium bicarbonate (150 mL) and the organic phases collected. The aqueous layer was extracted 2 more times with EtOAc (500 mL), and the combined organics were dried over anhydrous MgSO$_4$, concentrated to dryness, and the residue purified by flash column chromatography to give the title compound (2.18 g, 45.9% yield).

Step C: (R)—N-(1-Acryloylpiperidin-3-yl)-5-(*S)-(4-methyl-6-phenoxypyridin-3-yl)-4-oxo-4,5-dihydro-3H-1-thia-3,5,8-triazaacenaphthylene-2-carboxamide The title compound was prepared using analogous conditions described in Method 1, steps F-G (including Chiral Separation Method A after step F to obtain the *S atropisomer) in Example 1, and using Methyl 5-(4-methyl-6-phenoxypyridin-3-yl)-4-oxo-4,5-dihydro-3H-1-thia-3,5,8-triazaacenaphthylene-2-carboxylate in place of Methyl 5-(2-methyl-4-phenoxyphenyl)-4-oxo-4,5-dihydro-3H-1-thia-3,5,8-triazaacenaphthylene-2-carboxylate in step F, and using 1-[(3R)-3-amino-1-piperidyl]prop-2-en-1-one (Intermediate 15) and diisopropylethylamine in place of tert-butyl (3R,5R)-3-amino-5-fluoropiperidine-1-carboxylate and triethylamine in step G, to give the title compound. MS (ESI): mass calcd. for $C_{29}H_{26}N_6O_4S$, 554.6; m/z found, 555.0 [M+H]$^+$. $^1$H NMR (400 MHz, CD$_3$OD): δ 8.40-8.30 (d, J=5.5 Hz, 1H), 8.15-8.04 (s, 1H), 7.49-7.40 (m, 2H), 7.29-7.22 (m, 1H), 7.21-7.15 (m, 2H), 7.08-7.02 (s, 1H), 6.86-6.73 (m, 1H), 6.25-6.14 (m, 2H), 5.80-5.69 (m, 1H), 4.57-4.25 (m, 1H), 4.21-3.90 (m, 2H), 3.26-3.14 (m, 1H), 3.00-2.84 (m, 1H), 2.24-2.18 (m, 3H), 2.12-2.02 (d, J=12.3 Hz, 1H), 1.93-1.83 (m, 1H), 1.81-1.68 (m, 1H), 1.65-1.53 (m, 1H).

Example 663: (R)—N-(1-Acryloylpyrrolidin-3-yl)-5-(*S)-(4-methyl-6-phenoxypyridin-3-yl)-4-oxo-4,5-dihydro-3H-1-thia-3,5,8-triazaacenaphthylene-2-carboxamide

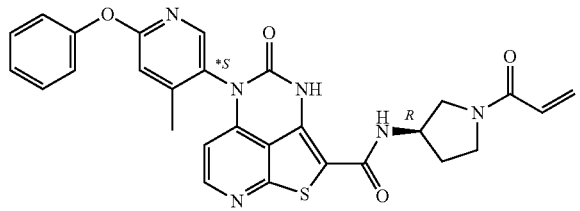

The title compound was prepared using analogous conditions described in Example 662, steps A-C, and using 1-[(3R)-3-aminopyrrolidin-1-yl]prop-2-en-1-one (Intermediate 5) in place of 1-[(3R)-3-amino-1-piperidyl]prop-2-en-1-one (Intermediate 15) in step C, to give the title compound. MS (ESI): mass calcd. for $C_{28}H_{24}N_6O_4S$, 540.6; m/z found, 541.0 [M+H]$^+$. $^1$H NMR (400 MHz, CD$_3$OD): δ 8.38-8.33 (dd, J=5.5, 1.0 Hz, 1H), 8.12-8.08 (s, 1H), 7.48-7.41 (m, 2H), 7.28-7.22 (m, 1H), 7.21-7.16 (m, 2H), 7.07-7.03 (s, 1H), 6.68-6.54 (m, 1H), 6.33-6.25 (m, 1H), 6.18-6.15 (dd, J=5.5, 1.0 Hz, 1H), 5.78-5.72 (m, 1H), 4.72-4.54 (m, 1H), 4.03-3.48 (m, 4H), 2.41-2.23 (m, 1H), 2.23-2.19 (s, 3H), 2.19-2.03 (m, 1H).

Example 664: (R)—N-(1-Acryloylpyrrolidin-3-yl)-5-(*S)-(4-methyl-2-phenoxypyrimidin-5-yl)-4-oxo-4,5-dihydro-3H-1-thia-3,5,8-triazaacenaphthylene-2-carboxamide

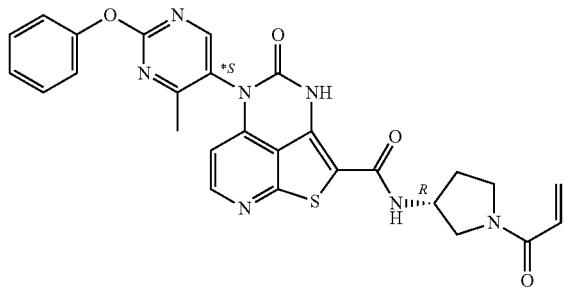

The title compound was prepared using analogous conditions described in Example 662, steps A-B, and using 4-methyl-2-phenoxypyrimidin-5-amine in place of 4-methyl-6-phenoxypyridin-3-amine in step A, and using Method 1, steps F-G (including Chiral Resolution Method A after step F to obtain the *S atropisomer) in Example 1, and using methyl 5-(4-methyl-2-phenoxypyrimidin-5-yl)-4-oxo-4,5-dihydro-3H-1-thia-3,5,8-triazaacenaphthylene-2-carboxylate in place of Methyl 5-(2-methyl-4-phenoxyphenyl)-4-oxo-4,5-dihydro-3H-1-thia-3,5,8-triazaacenaphthylene-2-carboxylate in step F, and using 1-[(3R)-3-aminopyrrolidin-1-yl]prop-2-en-1-one (Intermediate 5), 1-propanephosphonic anhydride, and diisopropylethylamine in place of tert-butyl (3R,5R)-3-amino-5-fluoropiperidine-1-carboxylate and triethylamine in step G, to give the title compound. MS (ESI): mass calcd. for $C_{27}H_{23}N_7O_4S$, 541.6; m/z found, 542.1 [M+H]$^+$. $^1$H NMR (400 MHz, CD$_3$OD): d 8.59-8.48 (d, J=1.1 Hz, 1H), 8.45-8.33 (d, J=5.5 Hz, 1H), 7.51-7.39 (m, 2H), 7.34-7.18 (m, 3H), 6.72-6.53 (m, 1H), 6.35-6.22 (m, 2H), 5.81-5.67 (m, 1H), 4.73-4.56 (m, 1H), 4.06-3.47 (m, 4H), 2.40-2.02 (m, 5H).

Example 665: (R)—N-(1-Acryloylpiperidin-3-yl)-4-oxo-5-(5-phenoxypyrimidin-2-yl)-4,5-dihydro-3H-1-thia-3,5,8-triazaacenaphthylene-2-carboxamide

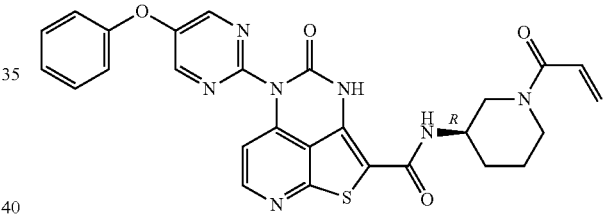

Step A: 5-phenoxypyrimidin-2-amine

The title compound was prepared using analogous conditions described in Example 528, Step A, using 5-bromopyrimidin-2-amine in place of 5-bromopyrazin-2-amine.

Step B: (R)—N-(1-Acryloylpiperidin-3-yl)-4-oxo-5-(5-phenoxypyrimidin-2-yl)-4,5-dihydro-3H-1-thia-3,5,8-triazaacenaphthylene-2-carboxamide The title compound was prepared using analogous conditions described in Method 1, and C-I in Example 1, using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{27}H_{23}N_7O_4S$, 541.6; m/z found, 542.2 [M+H]$^+$. $^1$H NMR (400 MHz, CD$_3$OD): d 8.73-8.64 (m, 2H), 8.37-8.30 (m, 1H), 7.56-7.44 (m, 2H), 7.34-7.23 (m, 3H), 6.86-6.74 (m, 1H), 6.35-6.27 (m, 1H), 6.24-6.14 (m, 1H), 5.79-5.67 (m, 1H), 4.57-4.27 (m, 1H), 4.22-3.86 (m, 2H), 3.21-3.10 (m, 1H), 2.98-2.82 (m, 1H), 2.12-2.00 (m, 1H), 1.92-1.82 (m, 1H), 1.80-1.65 (m, 1H), 1.63-1.52 (m, 1H).

Example 666: (R)—N-(1-Acryloylpyrrolidin-3-yl)-5-(*R)-(2-methyl-6-phenoxypyridin-3-yl)-4-oxo-4,5-dihydro-3H-1-thia-3,5,8-triazaacenaphthylene-2-carboxamide

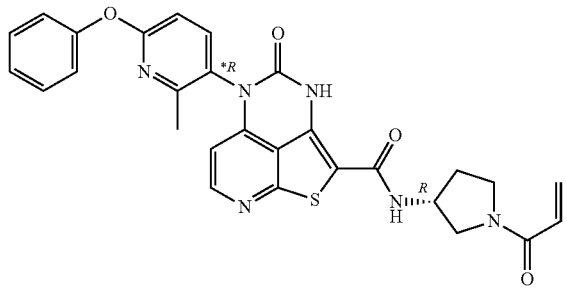

The title compound was prepared using analogous conditions described in Example 662, steps A-B, and using 2-methyl-6-phenoxypyridin-3-amine (Intermediate 49) in place of 4-methyl-6-phenoxypyridin-3-amine in step A, using analogous conditions described in Method 1, steps F-I (including Chiral Resolution Method A after step F to obtain the *R atropisomer) in Example 1, and using methyl 5-(2-methyl-6-phenoxypyridin-3-yl)-4-oxo-4,5-dihydro-3H-1-thia-3,5,8-triazaacenaphthylene-2-carboxylate in place of Methyl 5-(2-methyl-4-phenoxyphenyl)-4-oxo-4,5-dihydro-3H-1-thia-3,5,8-triazaacenaphthylene-2-carboxylate in step F, and using tert-butyl (3R)-3-aminopyrrolidine-1-carboxylate and diisopropylethylamine in place of tert-butyl (3R,5R)-3-amino-5-fluoropiperidine-1-carboxylate and triethylamine in step G, to give the title compound. MS (ESI): mass calcd. for $C_{28}H_{24}N_6O_4S$, 540.6; m/z found, 541.0 $[M+H]^+$. $^1H$ NMR (600 MHz, $CD_3OD$): d 8.39-8.35 (m, 1H), 7.80-7.76 (m, 1H), 7.47-7.42 (m, 2H), 7.27-7.23 (m, 1H), 7.21-7.17 (m, 2H), 6.92-6.89 (d, J=8.5 Hz, 1H), 6.67-6.55 (m, 1H), 6.33-6.25 (m, 1H), 6.17-6.14 (m, 1H), 5.78-5.73 (m, 1H), 4.70-4.59 (m, 1H), 4.04-3.49 (m, 4H), 2.39-2.26 (m, 1H), 2.26-2.22 (s, 3H), 2.19-2.04 (m, 1H).

Example 667: (R)—N-(1-Acryloylpiperidin-3-yl)-5-(4-methyl-6-phenoxypyridin-3-yl)-4-oxo-4,5-dihydro-3H-1-thia-3,5,8-triazaacenaphthylene-2-carboxamide

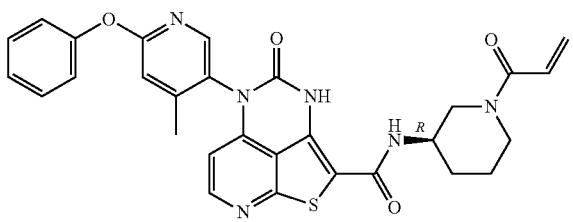

The title compound was prepared using analogous conditions described in Method 1, steps F-G in Example 1, and using methyl 5-(4-methyl-6-phenoxypyridin-3-yl)-4-oxo-4,5-dihydro-3H-1-thia-3,5,8-triazaacenaphthylene-2-carboxylate (Example 662, step B) in place of Methyl 5-(2-methyl-4-phenoxyphenyl)-4-oxo-4,5-dihydro-3H-1-thia-3,5,8-triazaacenaphthylene-2-carboxylate in step F, and using 1-[(3R)-3-amino-1-piperidyl]prop-2-en-1-one (Intermediate 15) and diisopropylethylamine in place of tert-butyl (3R,5R)-3-amino-5-fluoropiperidine-1-carboxylate and triethylamine in step G, to give the title compound. MS (ESI): mass calcd. for $C_{29}H_{26}N_6O_4S$, 554.6; m/z found, 555.0 $[M+H]^+$. 1H NMR (400 MHz, MeOD) δ 8.40-8.31 (d, J=5.5 Hz, 1H), 8.10 (s, 1H), 7.50-7.41 (m, 2H), 7.30-7.14 (m, 3H), 7.05 (s, 1H), 6.88-6.74 (m, 1H), 6.27-6.12 (m, 2H), 5.80-5.67 (m, 1H), 4.60-4.25 (m, 1H), 4.22-3.91 (m, 2H), 3.25-3.12 (m, 1H), 3.01-2.83 (m, 1H), 2.21 (s, 3H), 2.13-2.01 (m, 1H), 1.94-1.44 (m, 3H).

Example 8: N-(cis-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide

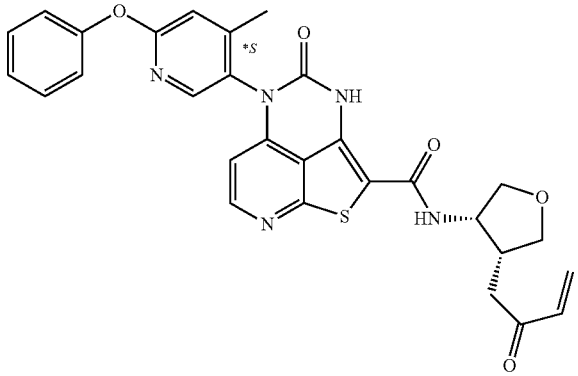 [SMILES: C=CC(=O)C[C@H]1COC[C@H]1NC(=O)c1sc2nccc3c2c1NC(=O)N3c1cnc(Oc2ccccc2)cc1C]

The title compound was prepared using analogous conditions described in Method 1, steps F-I in Example 1 (including Chiral Resolution Method A after step F to obtain the *S atropisomer), and using methyl 5-(4-methyl-6-phenoxypyridin-3-yl)-4-oxo-4,5-dihydro-3H-1-thia-3,5,8-triazaacenaphthylene-2-carboxylate (Example 662, step B) in place of Methyl 5-(2-methyl-4-phenoxyphenyl)-4-oxo-4,5-dihydro-3H-1-thia-3,5,8-triazaacenaphthylene-2-carboxylate in step F, and using cis-tetrahydrofuran-3,4-diamine, 1-propanephosphonic anhydride, and diisopropylethylamine in place of tert-butyl (3R,5R)-3-amino-5-fluoropiperidine-1-carboxylate, HATU, and triethylamine in step G, and using acrylic acid, diisopropylethylamine, and 2,4,6-tripropyl-1,3,5,2,4,6-trioxatriphosphorinane-2,4,6-trioxide in place of prop-2-enoyl chloride and triethylamine in step I, to give the title compound. MS (ESI): mass calcd. for $C_{28}H_{24}N_6O_5S$, 556.6; m/z found, 557.0 $[M+H]^+$. $^1H$ NMR (400 MHz, $CD_3OD$): δ 8.39-8.34 (d, J=5.6 Hz, 1H), 8.12-8.07 (d, J=2.0 Hz, 1H), 7.48-7.41 (m, 2H), 7.29-7.22 (m, 1H), 7.21-7.15 (m, 2H), 7.08-7.02 (s, 1H), 6.34-6.17 (m, 3H), 5.67-5.62 (m, 1H), 4.82-4.68 (m, 2H), 4.16-4.05 (m, 2H), 3.85-3.77 (m, 2H), 2.25-2.14 (s, 3H).

Example 669: (R)—N-(1-Acryloylpiperidin-3-yl)-5-(*S)-(6-isobutyl-4-methylpyridin-3-yl)-4-oxo-4,5-dihydro-3H-1-thia-3,5,8-triazaacenaphthylene-2-carboxamide

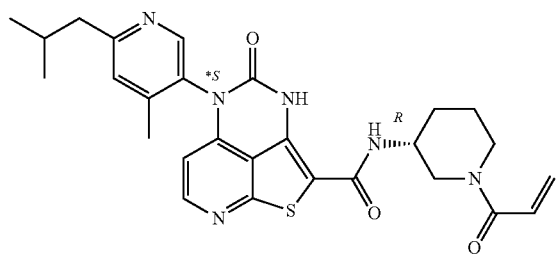

The title compound was prepared in a manner analogous to Example 1, Method 1, Step G, using 5-(*S)-(6-Isobutyl-4-methylpyridin-3-yl)-4-oxo-4,5-dihydro-3H-1-thia-3,5,8-triazaacenaphthylene-2-carboxylic acid (Intermediate 82) and 1-[(3R)-3-amino-1-piperidyl]prop-2-en-1-one (Intermediate 15). MS (ESI): mass calcd. for $C_{27}H_{30}N_6O_3S$, 518.6; m/z found, 519.1 [M+H]$^+$. 1H NMR (400 MHz, MeOD) δ 8.42 (s, 1H), 8.34 (d, J=5.5 Hz, 1H), 7.42 (s, 1H), 6.85-6.73 (m, 1H), 6.20 (d, J=15.6 Hz, 1H), 6.03 (d, J=5.5 Hz, 1H), 5.80-5.67 (m, 1H), 4.59-4.24 (m, 1H), 4.23-3.89 (m, 2H), 3.25-3.12 (m, 1H), 3.00-2.84 (m, 1H), 2.73 (d, J=7.3 Hz, 2H), 2.23 (s, 3H), 2.19-2.01 (m, 2H), 1.94-1.84 (m, 1H), 1.81-1.69 (m, 1H), 1.65-1.52 (m, 1H), 0.99 (dd, J=6.5, 1.5 Hz, 6H).

Example 670: (R)—N-(1-Acryloylpiperidin-3-yl)-5-(2-methyl-6-phenoxypyridin-3-yl)-4-oxo-4,5-dihydro-3H-1-thia-3,5,8-triazaacenaphthylene-2-carboxamide

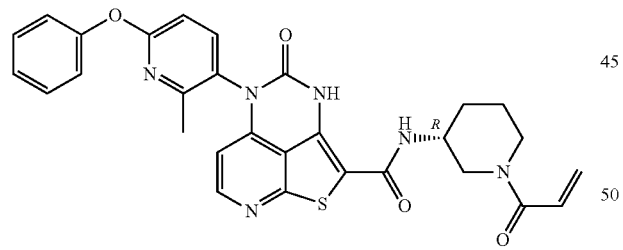

The title compound was prepared using analogous conditions described in Example 534, steps A-C, and using 2-methyl-6-phenoxypyridin-3-amine (Intermediate 49) in place of 3-cyclobutylaniline in step A, to give the title compound. MS (ESI): mass calcd. for $C_{29}H_{26}N_6O_4S$, 554.6; m/z found, 555.1 [M+H]$^+$. $^1$H NMR (400 MHz, CD3OD): d 8.36 (d, J=5.5 Hz, 1H), 7.80 (d, J=8.6 Hz, 1H), 7.48-7.40 (m, 2H), 7.28-7.22 (m, 1H), 7.22-7.16 (m, 2H), 6.91 (d, J=8.5 Hz, 1H), 6.85-6.71 (m, 1H), 6.20 (d, J=17.0 Hz, 1H), 6.15 (dd, J=5.5, 1.6 Hz, 1H), 5.78-5.68 (m, 1H), 4.58-4.25 (m, 1H), 4.21-3.91 (m, 2H), 3.18 (t, J=11.3 Hz, 1H), 2.98-2.83 (m, 1H), 2.25 (s, 3H), 2.11-2.03 (m, 1H), 1.91-1.82 (m, 1H), 1.79-1.67 (m, 1H), 1.66-1.51 (m, 1H).

Example 671: (R)—N-(1-Acryloylpiperidin-3-yl)-5-(6-isobutyl-4-methylpyridin-3-yl)-4-oxo-4,5-dihydro-3H-1-thia-3,5,8-triazaacenaphthylene-2-carboxamide

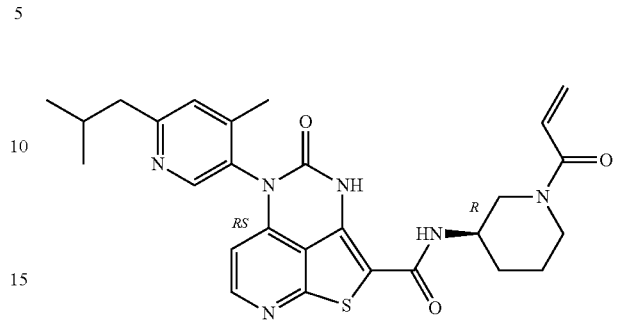

The title compound was prepared in a manner analogous to Example 1, Method 1, Step G, using 5-(6-Isobutyl-4-methylpyridin-3-yl)-4-oxo-4,5-dihydro-3H-1-thia-3,5,8-triazaacenaphthylene-2-carboxylic acid (Intermediate 81) and 1-[(3R)-3-amino-1-piperidyl]prop-2-en-1-one (Intermediate 15). MS (ESI): mass calcd. for $C_{27}H_{30}N_6O_3S$, 518.6; m/z found, 519.1 [M+H]$^+$. 1H NMR (400 MHz, MeOD) δ 8.43 (s, 1H), 8.37-8.30 (d, J=5.5 Hz, 1H), 7.41 (s, 1H), 6.86-6.74 (m, 1H), 6.24-6.16 (m, 1H), 6.04 (d, J=5.4 Hz, 1H), 5.80-5.69 (m, 1H), 4.60-4.27 (m, 1H), 4.23-3.92 (m, 2H), 3.24-3.13 (m, 1H), 3.00-2.83 (m, 1H), 2.73 (d, J=7.3 Hz, 2H), 2.25 (s, 3H), 2.19-2.02 (m, 2H), 1.93-1.84 (m, 1H), 1.81-1.50 (m, 2H), 1.05-0.95 (m, 6H).

Example 672: (R)—N-(1-Acryloylpiperidin-3-yl)-5-(6-cyclobutoxy-4-methylpyridin-3-yl)-4-oxo-4,5-dihydro-3H-1-thia-3,5,8-triazaacenaphthylene-2-carboxamide

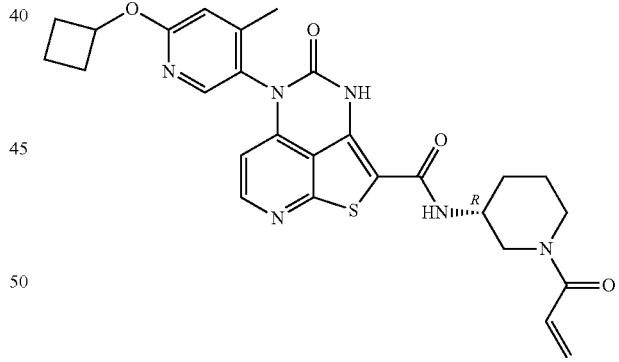

The title compound was prepared using analogous conditions as found in Method 1, steps A-G in Example 1, and using 2-fluoro-4-methyl-5-nitropyridine and cyclobutanol in place of 5-fluoro-2-nitrotoluene and phenol in step A, and using 6-cyclobutoxy-4-methylpyridin-3-amine in place of 2-methyl-4-phenoxyaniline in step C, and using (R)-1-(3-aminopiperidin-1-yl)prop-2-en-1-one (Intermediate 15), diisopropylethylamine, and 1-propanephosphonic anhydride in place of tert-butyl (3R,5R)-3-amino-5-fluoropiperidine-1-carboxylate, HATU, and triethylamine in step G (98 mg, 36% yield). MS (ESI): mass calcd. for $C_{27}H_{28}N_6O_4S$, 532.6; m/z found, 533.1 [M+H]$^+$. $^1$H NMR (500 MHz, CD$_3$OD): δ 8.34 (d, J=5.5 Hz, 1H), 8.06 (d, J=2.1 Hz, 1H), 6.87-6.73 (m, 2H), 6.20 (d, J=16.8 Hz, 1H), 6.11 (d, J=5.5 Hz, 1H), 5.74 (t, J=8.9 Hz, 1H), 5.24-5.14 (m, 1H), 4.59-4.48 (m, 0.5H), 4.33-4.14 (m, 1H), 4.04-3.91 (m, 1.5H), 3.25-3.14 (m, 1H), 3.02-2.87 (m, 1H), 2.54-2.44 (m, 2H), 2.21-2.11 (m, 5H), 2.11-2.04 (m, 1H), 1.92-1.83 (m, 2H), 1.81-1.67 (m, 2H), 1.65-1.52 (m, 1H).

Example 673: (R)—N-(1-Acryloylpyrrolidin-3-yl)-5-(2',3'-difluoro-[1,1-biphenyl]-3-yl)-4-oxo-4,5-dihydro-3H-1-thia-3,5,8-triazaacenaphthylene-2-carboxamide

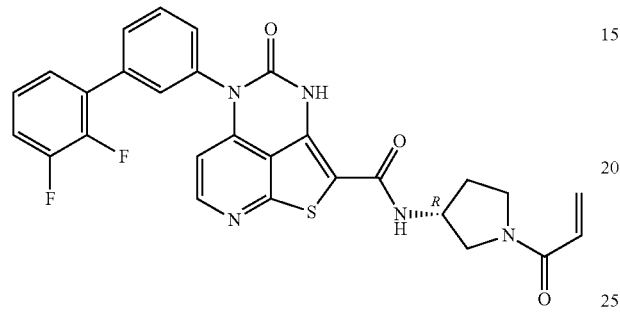

A solution of 5-(3-bromophenyl)-4-oxo-4,5-dihydro-3H-1-thia-3,5,8-triazaacenaphthylene-2-carboxylic acid (Intermediate 57, 250 mg, 0.641 mmol), 1-[(3R)-3-aminopyrrolidin-1-yl]prop-2-en-1-one (intermediate 5, 90.0 mg, 0.641 mmol), triethylamine (129 mg, 1.28 mmol), and HATU (268 mg, 0.705 mmol) in DMF (4 mL) was stirred at rt for 3 h. Water was added and the precipitate was collected by filtration to give a pale yellow solid. A mixture of the solid and (2,3-difluorophenyl)boronic acid, Pd(dppf)Cl$_2$ (52 mg, 0.064 mmol), and Na$_2$CO$_3$ (136 mg, 1.28 mmol) in dioxane (30 mL) and H$_2$O (3 mL) was stirred at 110° C. for 2 h. The reaction was concentrated to dryness and the residue was purified by flash column chromatography to give the title compound (102 mg, 28.8% yield) as a pale yellow solid. MS (ESI): mass calcd. for C$_{28}$H$_{21}$F$_2$N$_5$O$_3$S, 545.6; m/z found, 546.1 [M+H]$^+$. $^1$H NMR (400 MHz, CD$_3$OD): δ 8.30-8.24 (m, 1H), 7.77-7.66 (m, 3H), 7.54-7.47 (m, 1H), 7.36-7.28 (m, 1H), 7.29-7.17 (m, 2H), 6.66-6.49 (m, 1H), 6.31-6.19 (m, 1H), 6.19-6.13 (m, 1H), 5.76-5.68 (m, 1H), 4.65-4.53 (m, 1H), 4.00-3.46 (m, 4H), 2.36-2.00 (m, 2H).

Example 674: N-((3R,5S)-1-Acryloyl-5-hydroxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide

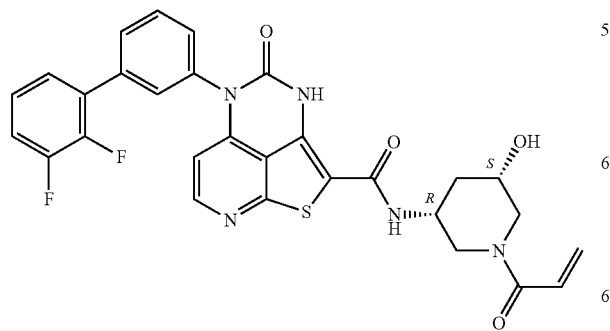

The title compound was prepared using analogues conditions as used in Example 673 and using (3R,5S)-tert-butyl 3-amino-5-hydroxypiperidine-1-carboxylate (Intermediate 2) in place of 1-[(3R)-3-aminopyrrolidin-1-yl]prop-2-en-1-one (Intermediate 5), and using Method 1, step I, to give the title compound as a yellow solid. MS (ESI): mass calcd. for C$_{29}$H$_{23}$F$_2$N$_5$O$_4$S, 575.6; m/z found, 576.2 [M+H]$^+$. $^1$H NMR (400 MHz, CD$_3$OD): δ 8.34-8.25 (m, 1H), 7.80-7.63 (m, 3H), 7.53-7.47 (m, 1H), 7.39-7.18 (m, 3H), 6.84-6.66 (m, 1H), 6.26-6.11 (m, 2H), 5.76-5.61 (m, 1H), 4.20-4.05 (m, 1H), 4.00-3.48 (m, 5H), 2.24-2.10 (m, 1H), 1.91-1.75 (m, 1H).

Example 675: (R)—N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide

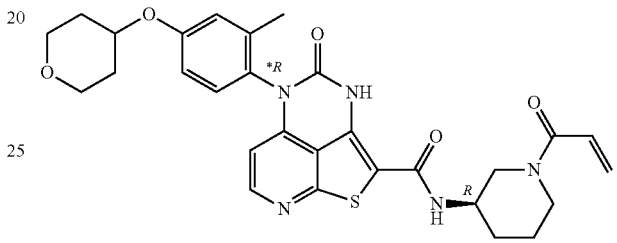

The title compound was prepared in a manner analogous to Method 1, steps A-G (including Chiral Resolution Method A after step F to obtain the *R atropisomer) in Example 1, and using tetrahydropyran-4-yl methanesulfonate and 3-methyl-4-nitrophenol in place of 4-fluoro-2-methyl-1-nitrobenzene and phenol in step A, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for C$_{29}$H$_{31}$N$_5$O$_5$S, 561.65; m/z found, 562.5 [M+H]$^+$. $^1$H NMR (400 MHz, CD$_3$OD): δ 8.31-8.24 (m, 1H), 7.27-7.19 (m, 1H), 7.06-6.92 (m, 2H), 6.83-6.70 (m, 1H), 6.25-6.12 (m, 1H), 6.04-5.97 (m, 1H), 5.76-5.65 (m, 1H), 4.67-4.56 (m, 1H), 4.33-4.12 (m, 1H), 4.05-3.82 (m, 4H), 3.66-3.53 (m, 2H), 3.23-3.07 (m, 1H), 2.95-2.80 (m, 1H), 2.14-1.99 (m, 6H), 1.90-1.79 (m, 1H), 1.79-1.65 (m, 3H), 1.63-1.51 (m, 1H)

Example 676: (R)—N-(1-Acryloylpiperidin-3-yl)-5-(*R)-(3-methyl-2-phenylpyridin-4-yl)-4-oxo-4,5-dihydro-3H-1-thia-3,5,8-triazaacenaphthylene-2-carboxamide

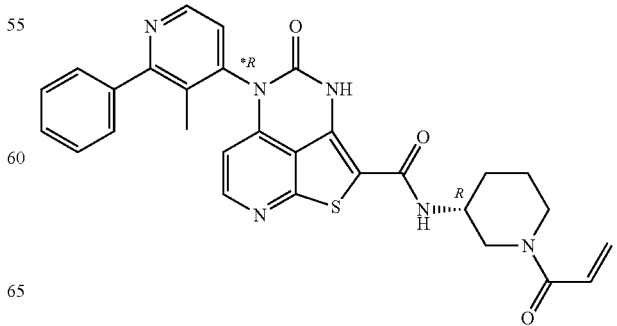

The title compound was prepared in a manner analogous to Method 1, steps C-G (including Chiral Resolution Method A after step F to obtain the *R atropisomer) in Example 1, and using 3-Methyl-2-phenylpyridin-4-amine (Intermediate 48) in place of 2-methyl-4-phenoxyaniline in step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for $C_{29}H_{26}N_6O_3S$, 538.6; m/z found, 539.4 [M+H]$^+$. $^1$H NMR (400 MHz, CD$_3$OD): δ 8.66 (d, J=5.2 Hz, 1H), 8.37 (d, J=5.5 Hz, 1H), 7.57-7.47 (m, 6H), 6.88-6.71 (m, 1H), 6.23-6.16 (m, 2H), 5.79-5.68 (m, 1H), 4.61-4.26 (m, 1H), 4.19-3.93 (m, 2H), 3.23-3.12 (m, 1H), 2.98-2.83 (m, 1H), 2.16 (s, 3H), 2.09-2.02 (m, 1H), 1.90-1.83 (m, 1H), 1.78-1.67 (m, 1H), 1.63-1.52 (m, 1H).

Example 677: (R)—N-(1-Acryloylpiperidin-3-yl)-5-(2-cyclohexylpyridin-4-yl)-4-oxo-4,5-dihydro-3H-1-thia-3,5,8-triazaacenaphthylene-2-carboxamide

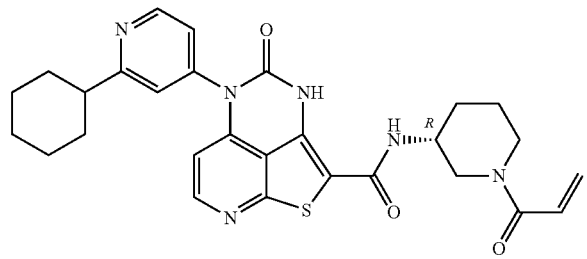

Step A: 2-Cyclohexylpyridin-4-amine

A solution of 2-chloro-4-nitropyridine (2.50 g, 15.8 mmol), cyclohexen-1-ylboronic acid (2.38 g, 18.9 mmol), Pd(dppf)Cl$_2$ (0.643 g, 0.788 mmol), and Na$_2$CO$_3$ (3.34 g, 31.5 mmol) in dioxane (50 mL) and H$_2$O (5 mL) was stirred at 110° C. overnight. The reaction was concentrated to dryness and the residue was purified by flash column chromatography to give a yellow solid. The yellow solid was dissolved in EtOH (100 mL) at rt and Pd/C (500 mg) was added. The mixture was flushed with H$_2$ (2×) and was stirred at rt for 16 h. The reaction was filtered and concentrated to dryness to give the title compound (2.0 g, 72% yield), which was used in the next step without further purification.

Step B: (R)—N-(1-Acryloylpiperidin-3-yl)-5-(2-cyclohexylpyridin-4-yl)-4-oxo-4,5-dihydro-3H-1-thia-3,5,8-triazaacenaphthylene-2-carboxamide The title compound was prepared in a manner analogous to Method 1, steps C-I in Example 1, and using 2-cyclohexylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{28}H_{30}N_6O_3S$, 530.6; m/z found, 531.5 [M+H]$^+$. $^1$H NMR (400 MHz, CD$_3$OD): δ 8.67 (d, J=5.3 Hz, 1H), 8.29 (d, J=5.6 Hz, 1H), 7.55-7.48 (m, 1H), 7.45-7.37 (m, 1H), 6.87-6.71 (m, 1H), 6.25-6.12 (m, 2H), 5.77-5.61 (m, 1H), 4.58-4.31 (m, 1H), 4.25-3.87 (m, 2H), 3.20-3.07 (m, 1H), 2.90-2.75 (m, 2H), 2.07-1.82 (m, 6H), 1.77-1.28 (m, 8H).

Example 678: (R)—N-(1-Acryloylpiperidin-3-yl)-4-oxo-5-(6-phenylpyridazin-4-yl)-4,5-dihydro-3H-1-thia-3,5,8-triazaacenaphthylene-2-carboxamide

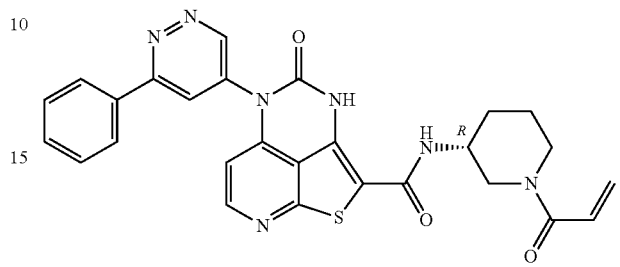

The title compound was prepared using analogous conditions described in Example 677, step A, and using 6-chloropyridazin-4-amine and phenylboronic acid in place of 2-chloro-4-nitropyridine and cyclohexen-1-ylboronic acid and no Pd/C reduction in step A, and using Method 1, steps C-I in Example 1, and using 6-phenylpyridazin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{27}H_{23}N_7O_3S$, 525.6; m/z found, 526.6 [M+H]$^+$. $^1$H NMR (400 MHz, CD$_3$OD): δ 9.33 (s, 1H), 8.53-8.42 (m, 1H), 8.33 (d, J=5.4 Hz, 1H), 8.21-8.09 (m, 2H), 7.57-7.49 (m, 3H), 6.83-6.64 (m, 1H), 6.48-6.36 (m, 1H), 6.18-6.08 (m, 1H), 5.75-5.59 (m, 1H), 4.54-4.24 (m, 1H), 4.19-3.84 (m, 2H), 3.18-3.04 (m, 1H), 2.93-2.76 (m, 1H), 2.10-1.98 (m, 1H), 1.88-1.76 (m, 1H), 1.76-1.61 (m, 1H), 1.56-1.42 (m, 1H).

Example 679: N-((3R,5S)-1-Acryloyl-5-methoxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide

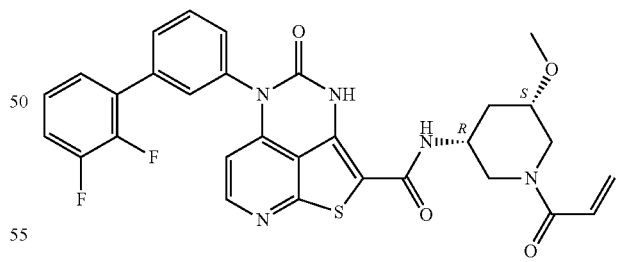

The title compound was prepared using analogues conditions described in Example 673 and using tert-butyl (3R,5S)-3-amino-5-methoxypiperidine-1-carboxylate (Intermediate 29) in place of 1-[(3R)-3-aminopyrrolidin-1-yl]prop-2-en-1-one (Intermediate 5), and using Method 1, step I, to give the title compound as a yellow solid. MS (ESI): mass calcd. for $C_{30}H_{25}F_2N_5O_4S$, 589.6; m/z found, 590.2 [M+H]$^+$. $^1$H NMR (400 MHz, CD$_3$OD): δ 8.25-8.17 (m, 1H), 7.74-7.61 (m, 3H), 7.55-7.43 (m, 1H), 7.33-7.13 (m, 3H), 6.83-6.55 (m, 1H), 6.19-5.99 (m, 2H), 5.77-5.48 (m, 1H), 4.15-3.99 (m, 2H), 3.89-3.44 (m, 4H), 3.44-3.40 (m, 3H), 2.20-2.06 (m, 1H), 1.96-1.81 (m, 1H).

Example 680: (R)—N-(1-Acryloylpyrrolidin-3-yl)-4-oxo-5-(6-phenoxypyridin-3-yl)-4,5-dihydro-3H-1-thia-3,5,8-triazaacenaphthylene-2-carboxamide

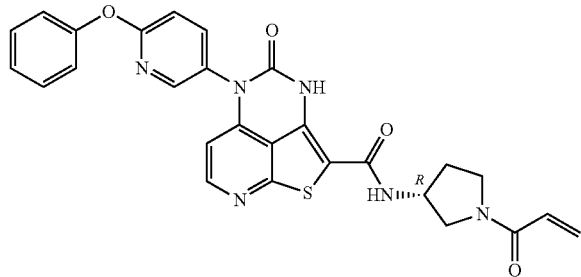

The title compound was prepared using the procedures found in Method 1, steps A-I in Example 1, and using 2-chloro-5-nitropyridine in place of 5-fluoro-2-nitrotoluene in step A, and using Pd/C and MeOH in place of Fe, EtOH/H$_2$O, and NH$_4$Cl in step B, and using 6-phenoxypyridin-3-amine in place of 2-methyl-4-phenoxyaniline in step C, and using (R)-tert-butyl 3-aminopyrrolidine-1-carboxylate in place of tert-butyl (3R,5R)-3-amino-5-fluoro-piperidine-1-carboxylate in step G. MS (ESI): mass calcd. for C$_{27}$H$_{22}$N$_6$O$_4$S, 526.6; m/z found, 526.9 [M+H]$^+$. $^1$H NMR (500 MHz, CDCl$_3$): δ 9.58 (s, 1H), 8.33-8.27 (m, 1H), 8.20 (q, J=4.3, 3.5 Hz, 1H), 7.79-7.70 (m, 1H), 7.62 (d, J=6.9 Hz, 1H), 7.43 (t, J=7.7 Hz, 2H), 7.30-7.17 (m, 3H), 7.10 (dd, J=8.7, 1.9 Hz, 1H), 6.46-6.23 (m, 2H), 6.13 (t, J=6.0 Hz, 1H), 5.67 (ddd, J=16.4, 9.2, 3.2 Hz, 1H), 4.68 (dq, J=32.2, 5.1, 4.6 Hz, 1H), 3.82-3.55 (m, 4H), 2.25 (ddt, J=38.8, 13.2, 6.1 Hz, 2H).

Example 681: N—((R)-1-((*E)-3-((S)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide

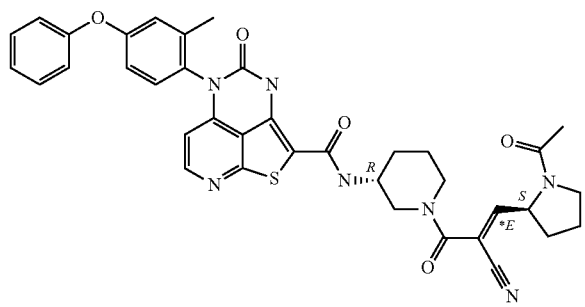

Step A: (S)-1-(2-(Hydroxymethyl)pyrrolidin-1-yl)ethanone

To a solution of (S)-pyrrolidin-2-ylmethanol (0.50 g, 4.9 mmol) in EtOAc (20 mL) was added acetic anhydride (0.555 g, 5.43 mmol) and was stirred under nitrogen for 18 h. K$_2$CO$_3$ (1.364 g, 9.886 mmol) was added and stirring was continued for few minutes. The reaction was filtered through celite and the filtrate was concentrated to dryness to give the title compound (0.57 g 80% yield) as a white solid. MS (ESI): mass calcd. for C$_7$H$_{13}$NO$_2$, 143.18; m/z found, 144.1 [M+H]$^+$.

Step B: (S)-1-Acetylpyrrolidine-2-carbaldehyde

A solution of oxalyl dichloride (0.683 g, 5.38 mmol) in dry DCM (20 mL) was cooled to −78° C. under a N$_2$ atmosphere and (methylsulfinyl)methane (0.840 g, 10.8 mmol) was added to the reaction mixture, followed by (S)-1-(2-(hydroxymethyl)pyrrolidin-1-yl)ethanone (0.700 g, 4.89 mmol) and was stirred for 30 minutes at −78° C. Triethylamine (2.473 g, 24.44 mmol) was added dropwise and the reaction was allowed to warm up to room temperature. After complete consumption of (S)-1-(2-(hydroxymethyl)pyrrolidin-1-yl)ethanone, the reaction was quenched with distilled water, stirred for 5 minutes and the reaction mixture was extracted DCM. The combined organic extracts were dried over anhydrous Na$_2$SO$_4$ and concentrated to dryness to give the title compound (0.590 g, 85.5% yield).

Step C: N—((R)-1-((*E)-3-((S)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 150 mg, 0.265 mmol), (S)-1-acetylpyrrolidine-2-carbaldehyde (112 mg, 0.795 mmol), piperidine (0.30 mL), AcOH (0.10 mL), dioxane (10.0 mL), and 4A molecular sieves (0.50 g) was stirred at 100° C. for 1 h under N2. The reaction was concentrated to dryness and purified by normal phase flash column chromatography (SiO$_2$) to give the title compound (68 mg, 99% yield) as a white solid. MS (ESI): mass calcd. for C$_{37}$H$_{35}$N$_7$O$_5$S, 689.8; m/z found, 690.5 [M+H]$^+$. $^1$H NMR (400 MHz, CD$_3$OD): δ 8.34-8.29 (m, 1H), 7.42-7.35 (m, 2H), 7.33-7.26 (m, 1H), 7.19-7.12 (m, 1H), 7.09-7.02 (m, 3H), 7.00-6.93 (m, 1H), 6.92-6.61 (m, 1H), 6.08-6.03 (m, 1H), 4.41-3.48 (m, 6H), 3.26-2.81 (m, 2H), 2.28-2.16 (m, 1H), 2.11 (s, 3H), 2.09-1.95 (m, 5H), 1.95-1.76 (m, 3H), 1.74-1.53 (m, 2H).

Example 682: (R)—N-(1-Acryloylpiperidin-3-yl)-5-(*S)-(6-cyclobutoxy-2-methylpyridin-3-yl)-4-oxo-4,5-dihydro-3H-1-thia-3,5,8-triazaacenaphthylene-2-carboxamide

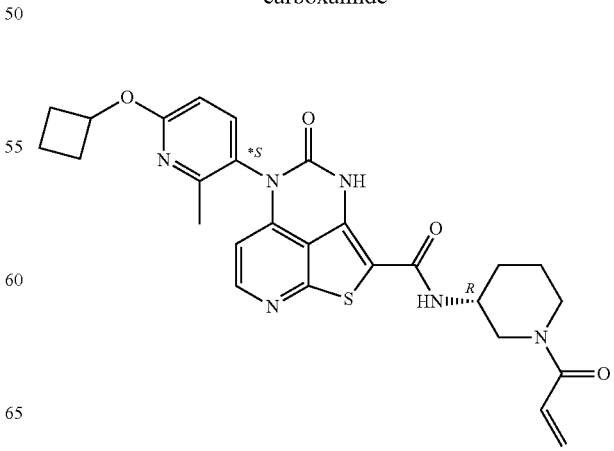

The title compound was prepared using analogous conditions described in Method 1, steps A-G, (including Chiral Resolution Method A after step F to obtain the *S atropisomer) in Example 1, and using 2-fluoro-5-nitro-6-picoline, cyclobutanol, and Cs$_2$CO$_3$ in place of 5-fluoro-2-nitrotoluene, phenol, and K$_2$CO$_3$ in step A, and using Zn in place of Fe in step B, and using 1-[(3R)-3-amino-1-piperidyl]prop-2-en-1-one (Intermediate 15), 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for C$_{27}$H$_{28}$N$_6$O$_4$S, 532.6; m/z found, 533.1 [M+H]$^+$. $^1$H NMR (400 MHz, CD$_3$OD): δ 8.33 (d, J=5.6 Hz, 1H), 7.62 (d, J=8.6 Hz, 1H), 6.86-6.72 (m, 2H), 6.20 (d, J=16.9 Hz, 1H), 6.08 (d, J=5.6 Hz, 1H), 5.80-5.69 (m, 1H), 5.26-5.17 (m, 1H), 4.59-4.25 (m, 1H), 4.21-3.91 (m, 2H), 3.19 (t, J=10.8 Hz, 1H), 3.03-2.85 (m, 1H), 2.56-2.44 (m, 2H), 2.25 (s, 3H), 2.23-2.12 (m, 2H), 2.12-2.02 (m, 1H), 1.94-1.82 (m, 2H), 1.80-1.67 (m, 2H), 1.65-1.51 (m, 1H).

Example 683: N—((R)-1-((E)-3-((R)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide

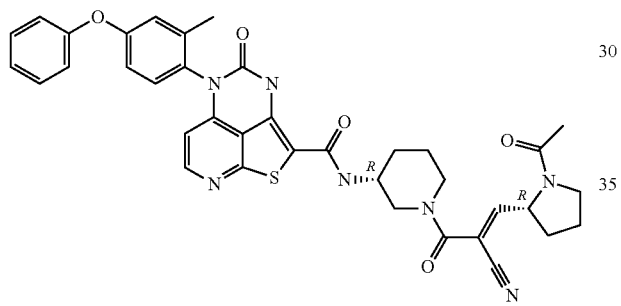

Step A: (R)-1-Acetylpyrrolidine-2-carbaldehyde

To a solution of oxalyl dichloride (439 mg, 3.46 mmol) in dry DCM (20 mL) cooled to −78° C. under a N$_2$ atmosphere was added (methylsulfinyl)methane (540 mg, 6.91 mmol), followed by (R)-1-(2-(hydroxymethyl)pyrrolidin-1-yl)ethanone (450 mg, 3.14 mmol) and was stirred for 30 minutes at −78° C. Triethylamine (1.59 g, 15.7 mmol) was added dropwise and the reaction was allowed to warm to room temperature. After the complete consumption of (R)-1-(2-(hydroxymethyl)pyrrolidin-1-yl)ethanone, the reaction was quenched with distilled water, stirred for 5 minutes, and extracted with DCM. The combined organic extracts were dried over anhydrous Na$_2$SO$_4$ and concentrated to dryness to give the title compound (330 mg, 74.4% yield).

Step B: N—((R)-1-((E)-3-((R)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide A solution of (R)—N-(1-(2-cyanoacetyl)piperidin-3-yl)-5-(2-methyl-4-phenoxyphenyl)-4-oxo-4,5-dihydro-3H-1-thia-3,5,8-triazaacenaphthylene-2-carboxamide (Example 874, 150 mg, 0.265 mmol), (R)-1-acetylpyrrolidine-2-carbaldehyde (112 mg, 0.795 mmol), piperidine (0.30 mL), AcOH (0.10 mL), dioxane (10.0 mL), and 4A molecular sieves (0.50 g) was stirred at 100° C. for 1 h under N2. The reaction was concentrated to dryness and purified by normal phase flash column chromatography (SiO$_2$) to give the title compound (48 mg, 26% yield) as a white solid. MS (ESI): mass calcd. for C$_{37}$H$_{35}$N$_7$O$_5$S, 689.8; m/z found, 690.2 [M+H]$^+$. $^1$H NMR (400 MHz, CD$_3$OD): δ 8.34-8.29 (m, 1H), 7.42-7.35 (m, 2H), 7.33-7.26 (m, 1H), 7.19-7.12 (m, 1H), 7.09-7.02 (m, 3H), 7.00-6.93 (m, 1H), 6.92-6.61 (m, 1H), 6.08-6.03 (m, 1H), 4.33-3.90 (m, 3H), 3.88-3.48 (m, 3H), 3.26-2.81 (m, 2H), 2.28-2.16 (m, 1H), 2.11 (s, 3H), 2.09-1.95 (m, 5H), 1.95-1.76 (m, 3H), 1.74-1.53 (m, 2H).

Example 9: 5-(*S)-(2-Methyl-4-phenoxyphenyl)-4-oxo-N—((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide

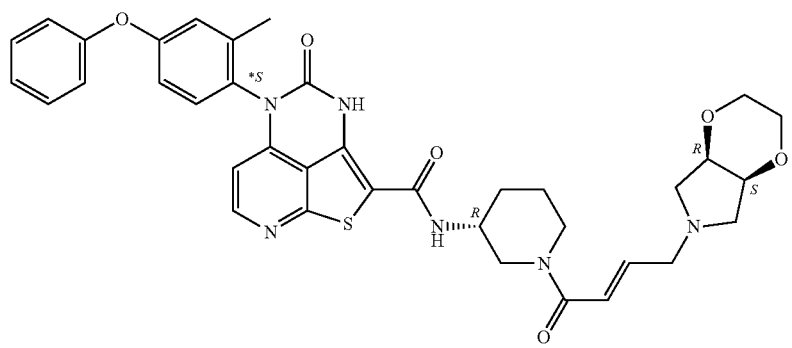

Step A: Benzyl 3,4-dihydroxypyrrolidine-1-carboxylate

To a solution of benzyl 2,5-dihydro-1H-pyrrole-1-carboxylate (5.00 g, 24.6 mmol) in THF (40 mL) and water (15 mL) were added OsO$_4$ (62 mg, 0.25 mmol) and N-methylmorpholine N-oxide (3.747 g, 31.98 mmol) and was stirred at room temperature for 15 h. The reaction mixture was concentrated to dryness and the residue was partitioned between EtOAc and water. The organic layer was collected and the aqueous layer was extracted with EtOAc. The combined organic layers were dried over anhydrous Na$_2$SO$_4$, concentrated to dryness, and purified by flash column chromatography to give the title compound (4.8 g, 82% yield).

Step B: Benzyl (4aR,7aS)-234a,5.7.7a-hexahydro-[1,4]dioxino[2,3-c]pyrrole-6-carboxylate Benzyl 3,4-dihydroxypyrrolidine-1-carboxylate (4.8 g, 20 mmol), DCM (30 mL), and tetrabutylammonium fluoride (2.645 g, 10.12 mmol) were added to a solution of NaOH (9.00 g, 225 mmol) in water (30 mL) and the mixture was stirred at 55° C. for 48 h. The reaction was extracted with DCM, concentrated to dryness, and purified by flash column chromatography to give the title compound (0.96 g, 18% yield) as a white solid.

Step C: (4aR,7aS)-3,4a,5,6,7,7a-Hexahydro-2H-[1,4]dioxino[2,3-c]pyrrole

A solution of benzyl (4aR,7aS)-2,3,4a,5,7,7a-hexahydro-[1,4]dioxino[2,3-c]pyrrole-6-carboxylate (0.96 g, 3.6 mmol) and Pd(OH)$_2$ (51 mg, 0.36 mmol) in MeOH (10 mL) was reacted at rt for 3 h under H$_2$. The mixture was filtered and concentrated to dryness to give the title compound (0.43 g, 91% yield) as a light yellow solid.

Step D: Methyl (E)-4-[(4aR,7aS)-2,3,4a,5,7,7a-hexahydro-[1,4]dioxino[2,3-c]pyrrol-6-yl]but-2-enoate (4aR,7aS)-3,4a,5,6,7,7a-Hexahydro-2H-[1,4]dioxino[2,3-c]pyrrole (30 mg, 0.23 mmol) was added to a mixture of methyl (E)-4-bromobut-2-enoate (41 mg, 0.23 mmol), diisopropylethylamine (30 mg, 0.23 mmol) in THF (10 mL) and stirred at rt for 15 h. The mixture was concentrated to dryness to give the title compound (55 mg), which was used in the next step without purification.

Step E: (E)-4-[(4aR,7aS)-2,3,4a,5.77a-Hexahydro-[1,4]dioxino[2,3-c]pyrrol-6-yl]but-2-enoic Acid Methyl (E)-4-[(4aR,7aS)-2,3,4a,5,7,7a-hexahydro-[1,4]dioxino[2,3-c]pyrrol-6-yl]but-2-enoate (55 mg, 0.24 mmol) in saturated aqueous HCl (4 M, 5 mL) was reacted at reflux for 1 h. The mixture was concentrated to dryness to give the title compound (55 mg), which was used in the next step without purification.

Step F: 5-(*S)-(2-Methyl-4-phenoxyphenyl)-4-oxo-N—((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide A solution of (R)-5-(S)-(2-methyl-4-phenoxyphenyl)-4-oxo-N-(piperidin-3-yl)-4,5-dihydro-3H-1-thia-3,5,8-triazaacenaphthylene-2-carboxamide (Example 98) (120 mg, 0.24 mmol), (E)-4-[(4aR,7aS)-2,3,4a,5,7,7a-hexahydro-[1,4]dioxino[2,3-c]pyrrol-6-yl]but-2-enoic acid (51 mg, 0.24 mmol), HATU (119 mg, 0.312 mmol), in DMF (5 mL) was stirred at rt for 5 min, then diisopropylethylamine (93 mg, 0.72 mmol) was added portion wise and stirred at rt for 1 h. The reaction mixture was purified by reverse phase HPLC and by flash column chromatography to give the title compound (29 mg, 18% yield) as a white solid. MS (ESI): mass calcd. for C$_{37}$H$_{38}$N$_6$O$_6$S, 694.8; m/z found, 695.2 [M+H]$^+$. $^1$H NMR (400 MHz, CD$_3$OD): d 8.33-8.29 (m, 1H), 7.43-7.36 (m, 2H), 7.33-7.27 (m, 1H), 7.19-7.13 (m, 1H), 7.11- 7.02 (m, 3H), 7.00-6.94 (m, 1H), 6.79-6.60 (m, 2H), 6.07-6.03 (m, 1H), 4.17-3.89 (m, 5H), 3.81-3.65 (m, 2H), 3.61-3.32 (m, 5H), 3.20-3.04 (m, 1H), 2.97-2.87 (m, 2H), 2.87-2.75 (m, 2H), 2.11 (s, 3H), 2.08-1.98 (m, 1H), 1.91-1.82 (m, 1H), 1.81-1.67 (m, 1H), 1.66-1.54 (m, 1H).

Example 685: (R)—N-(1-Acryloylpiperidin-3-yl)-4-oxo-5-(6-phenylpyrimidin-4-yl)-4,5-dihydro-3H-1-thia-3,5,8-triazaacenaphthylene-2-carboxamide

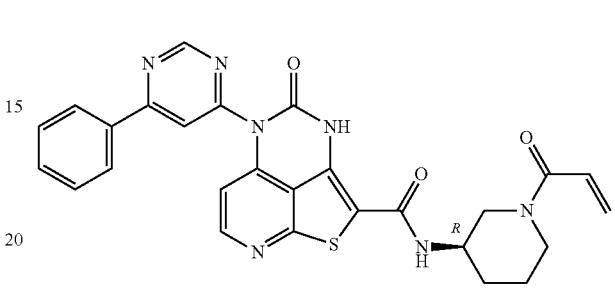

The title compound was prepared using analogous conditions described in Example 677, step A, and using 6-chloropyrimidin-4-amine and phenylboronic acid in place of 2-chloro-4-nitropyridine and cyclohexen-1-ylboronic acid and no Pd/C reduction in step A, and using Method 1, steps C-I in Example 1, and using 6-phenylpyridazin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for C$_{27}$H$_{23}$N$_7$O$_3$S, 525.6; m/z found, 526.2 [M+H]$^+$. $^1$H NMR (400 MHz, CD$_3$OD): δ 9.34-9.27 (m, 1H), 8.39-8.35 (m, 1H), 8.26-8.18 (m, 3H), 7.58-7.50 (m, 3H), 6.85-6.71 (m, 1H), 6.64-6.58 (m, 1H), 6.26-6.14 (m, 1H), 5.77-5.66 (m, 1H), 4.50-3.94 (m, 3H), 3.23-3.13 (m, 1H), 2.99-2.85 (m, 1H), 2.13-2.02 (m, 1H), 1.91-1.83 (m, 1H), 1.80-1.68 (m, 1H), 1.63-1.53 (m, 1H).

Example 686: (R)—N-(1-Acryloylpiperidin-3-yl)-5-(3-chloro-4-phenoxyphenyl)-4-oxo-4,5-dihydro-3H-1-thia-3,5,8-triazaacenaphthylene-2-carboxamide

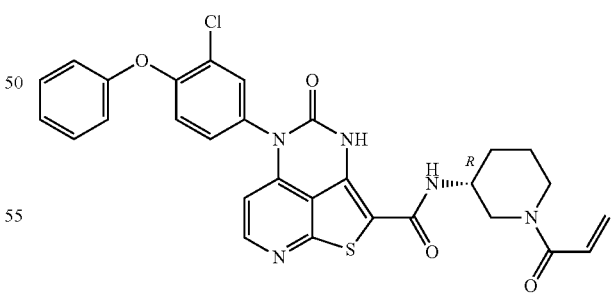

The title compound was prepared using analogous conditions described in Method 1, steps F-I in Example 1, and using methyl 5-(3-chloro-4-phenoxyphenyl)-4-oxo-4,5-dihydro-3H-1-thia-3,5,8-triazaacenaphthylene-2-carboxylate (Intermediate 68) in place of Methyl 5-(2-methyl-4-phenoxyphenyl)-4-oxo-4,5-dihydro-3H-1-thia-3,5,8-triazaacenaphthylene-2-carboxylate in step F, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{29}H_{24}ClN_5O_4S$, 574.1; m/z found, 574.1 [M+H]$^+$. $^1$H NMR (400 MHz, CD$_3$OD): δ 8.30 (d, J=5.6 Hz, 1H), 7.72-7.65 (m, 1H), 7.44-7.35 (m, 3H), 7.22-7.10 (m, 2H), 7.08-7.00 (m, 2H), 6.83-6.70 (m, 1H), 6.25-6.11 (m, 2H), 5.78-5.62 (m, 1H), 4.58-4.25 (m, 1H), 4.21-3.81 (m, 2H), 3.25-3.03 (m, 1H), 2.93-2.76 (m, 1H), 2.10-1.95 (m, 1H), 1.92-1.79 (m, 1H), 1.79-1.64 (m, 1H), 1.61-1.46 (m, 1H).

Example 687: (R)—N-(1-Acryloylpiperidin-3-yl)-5-(6-cyclobutoxypyridin-3-yl)-4-oxo-4,5-dihydro-3H-1-thia-3,5,8-triazaacenaphthylene-2-carboxamide

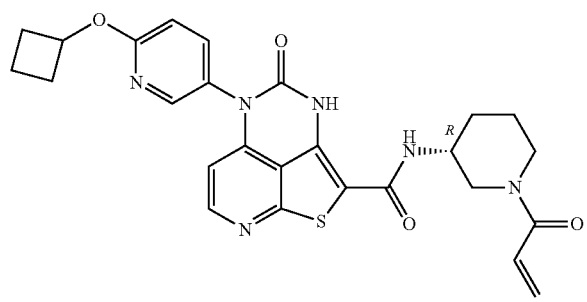

The title compound was prepared using analogous conditions described in Example 534, steps A-C, and using 6-(cyclobutoxy)pyridin-3-amine in place of 3-cyclobutylaniline in step A, to give the title compound. MS (ESI): mass calcd. for $C_{26}H_{26}N_6O_4S$, 518.6; m/z found, 519.2 [M+H]$^+$. $^1$H NMR (500 MHz, CD$_3$OD): δ 8.32 (d, J=5.6 Hz, 1H), 8.19 (d, J=2.6 Hz, 1H), 7.75 (dd, J=8.8, 2.7 Hz, 1H), 6.95 (d, J=8.8 Hz, 1H), 6.84-6.74 (m, 1H), 6.23-6.16 (m, 2H), 5.73 (t, J=11.4 Hz, 1H), 5.27-5.18 (m, 1H), 4.57-4.28 (m, 1H), 4.21-3.92 (m, 2H), 3.22-3.13 (m, 1H), 2.97-2.84 (m, 1H), 2.54-2.46 (m, 2H), 2.24-2.12 (m, 2H), 2.07 (d, J=12.6 Hz, 1H), 1.92-1.83 (m, 2H), 1.80-1.68 (m, 2H), 1.66-1.52 (m, 1H).

Example 688: (R)—N-(1-Acryloylpiperidin-3-yl)-5-(4-methyl-[1,1'-biphenyl]-3-yl)-4-oxo-4,5-dihydro-3H-1-thia-3,5,8-triazaacenaphthylene-2-carboxamide

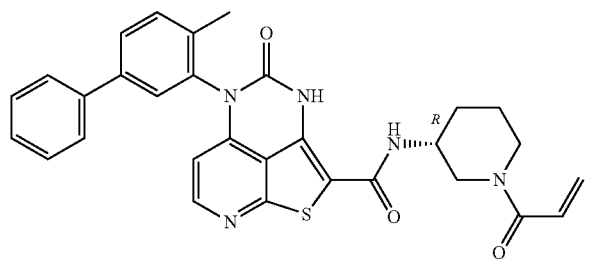

The title compound was prepared using analogous conditions described in Example 677, step A, and using 4-bromo-1-methyl-2-nitrobenzene and phenylboronic acid in place of 2-chloro-4-nitropyridine and cyclohexen-1-ylboronic acid in step A (with no Pd/C reduction step), and using Method 1, steps B-I in Example 1, and using 2-methyl-5-phenylaniline in place of 2-methyl-4-phenoxyaniline in step C, and using tert-butyl (3R)-3-aminopiperidine-1-carboxy-late in place of tert-butyl (3R,5R)-3-amino-5-fluoropiperidine-1-carboxylate (Intermediate 1) in step G, to give the title compound. MS (ESI): mass calcd. for $C_{30}H_{27}N_5O_3S$, 537.6; m/z found, 538.4 [M+H]$^+$. 1H NMR (400 MHz, CD$_3$OD): δ 8.32-8.18 (m, 1H), 7.77-7.67 (m, 1H), 7.66-7.58 (m, 3H), 7.54-7.48 (m, 1H), 7.43-7.35 (m, 2H), 7.34-7.25 (m, 1H), 6.89-6.60 (m, 1H), 6.28-6.10 (m, 1H), 6.06-5.96 (m, 1H), 5.79-5.61 (m, 1H), 4.63-4.22 (m, 1H), 4.21-3.84 (m, 2H), 3.22-3.05 (m, 1H), 2.96-2.75 (m, 1H), 2.11-2.00 (m, 1H), 1.92-1.77 (m, 1H), 1.75-1.44 (m, 2H).

Example 689: (R)—N-(1-Acryloylpiperidin-3-yl)-5-(3-isobutylphenyl)-4-oxo-4,5-dihydro-3H-1-thia-3,5,8-triazaacenaphthylene-2-carboxamide

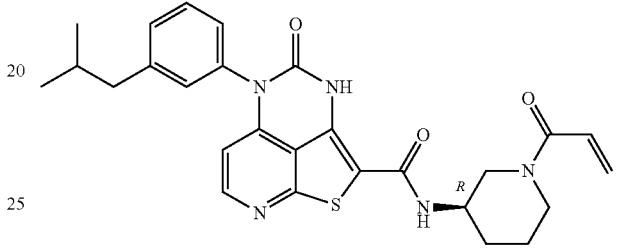

The title compound was prepared using analogous conditions described in Example 677, step A, and using 1-bromo-3-nitrobenzene and isobutylboronic acid in place of 2-chloro-4-nitropyridine and cyclohexen-1-ylboronic acid and no Pd/C reduction in step A, and using Method 1, steps B-I in Example 1, and using Pd/C in place of Fe in step B, and using 3-isobutylaniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{27}H_{29}N_5O_3S$, 503.6; m/z found, 504.2 [M+H]$^+$. $^1$H NMR (400 MHz, CD$_3$OD): δ 8.30-8.23 (m, 1H), 7.53-7.46 (m, 1H), 7.37-7.31 (m, 1H), 7.25-7.19 (m, 2H), 6.85-6.73 (m, 1H), 6.23-6.15 (m, 1H), 6.09-6.03 (m, 1H), 5.77-5.67 (m, 1H), 4.53-3.94 (m, 3H), 3.23-3.11 (m, 1H), 2.97-2.85 (m, 1H), 2.60-2.53 (m, 2H), 2.11-2.02 (m, 1H), 1.94-1.83 (m, 2H), 1.77-1.66 (m, 1H), 1.63-1.52 (m, 1H), 0.95-0.90 (m, 6H).

Example 10: (R)—N-(1-Acryloylpiperidin-3-yl)-5-(*R)-(2-methyl-6-phenoxypyridin-3-yl)-4-oxo-4,5-dihydro-3H-1-thia-3,5,8-triazaacenaphthylene-2-carboxamide

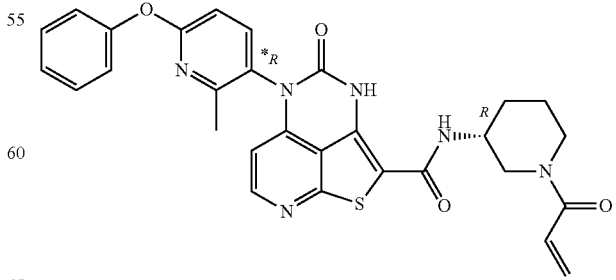

(R)—N-(1-Acryloylpiperidin-3-yl)-5-(2-methyl-6-phenoxypyridin-3-yl)-4-oxo-4,5-dihydro-3H-1-thia-3,5,8-triazaacenaphthylene-2-carboxamide (Example 670) was resolved by chiral SFC (Stationary phase: CHIRALCEL OJ-H 5 μm 250×20 mm, Mobile phase: 75% CO$_2$, 25% MeOH) give the title compound. MS (ESI): mass calcd. for C$_{29}$H$_{26}$N$_6$O$_4$S, 554.6; m/z found, 555.2 [M+H]$^+$. $^1$H NMR (400 MHz, CD$_3$OD): δ 8.36 (d, J=5.5 Hz, 1H), 7.78 (d, J=8.6 Hz, 1H), 7.50-7.39 (m, 2H), 7.30-7.16 (m, 3H), 6.91 (d, J=8.6 Hz, 1H), 6.85-6.72 (m, 1H), 6.26-6.12 (m, 2H), 5.79-5.69 (m, 1H), 4.64-4.24 (m, 1H), 4.22-3.90 (m, 2H), 3.26-3.09 (m, 1H), 3.03-2.84 (m, 1H), 2.25 (s, 3H), 2.13-2.04 (m, 1H), 1.92-1.84 (m, 1H), 1.81-1.68 (m, 1H), 1.65-1.54 (m, 1H).

Example 691: (R)—N-(1-Acryloylpiperidin-3-yl)-5-(*R)-(4-methyl-6-phenoxypyridin-3-yl)-4-oxo-4,5-dihydro-3H-1-thia-3,5,8-triazaacenaphthylene-2-carboxamide

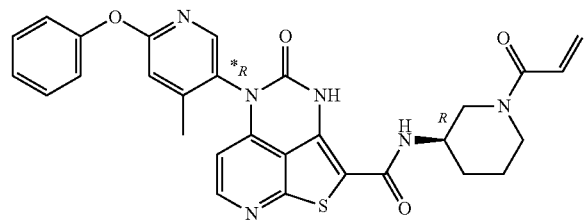

The title compound was prepared using analogous conditions described in Method 1, steps A-G, (including Chiral Resolution Step A after step F to obtain the *R atropisomer) in Example 1, and using 2-fluoro-4-methyl-5-nitropyridine in place of 5-fluoro-2-nitrotoluene in step A, and using Pd/C in place of Fe in step B, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for C$_{29}$H$_{26}$N$_6$O$_4$S, 554.6; m/z found, 555.0 [M+H]$^+$. $^1$H NMR (400 MHz, CD$_3$OD): δ 8.39-8.32 (d, J=5.5 Hz, 1H), 8.13-8.08 (s, 1H), 7.50-7.40 (m, 2H), 7.29-7.22 (m, 1H), 7.21-7.16 (m, 2H), 7.07-7.02 (s, 1H), 6.86-6.73 (m, 1H), 6.26-6.14 (m, 2H), 5.79-5.69 (m, 1H), 4.59-4.26 (m, 1H), 4.21-3.92 (m, 2H), 3.25-3.15 (m, 1H), 3.01-2.84 (m, 1H), 2.24-2.18 (s, 3H), 2.12-2.02 (m, 1H), 1.93-1.84 (m, 1H), 1.82-1.69 (m, 1H), 1.66-1.52 (m, 1H).

Example 692: (R)—N-(1-Acryloylpiperidin-3-yl)-5-(2-cyclopentylpyridin-4-yl)-4-oxo-4,5-dihydro-3H-1-thia-3,5,8-triazaacenaphthylene-2-carboxamide

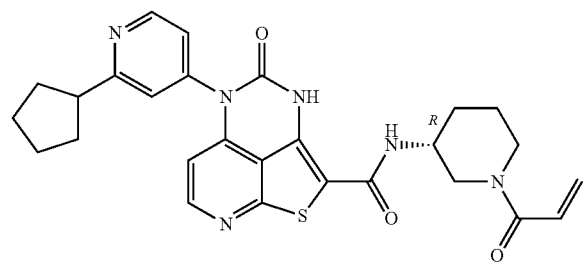

The title compound was prepared using analogous conditions described in Example 677, step A, and using cyclopenten-1-ylboronic acid in place of cyclohexen-1-ylboronic acid and no Pd/C reduction in step A, and using Method 1, steps C-I in Example 1, and using 6-cyclopentylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for C$_{27}$H$_{28}$N$_6$O$_3$S, 516.6; m/z found, 517.5 [M+H]$^+$. $^1$H NMR (400 MHz, CD$_3$OD): δ 8.68 (d, J=5.3 Hz, 1H), 8.28 (d, J=5.6 Hz, 1H), 7.54-7.51 (m, 1H), 7.42-7.36 (m, 1H), 6.86-6.69 (m, 1H), 6.25-6.09 (m, 2H), 5.77-5.62 (m, 1H), 4.56-4.29 (m, 1H), 4.24-3.86 (m, 2H), 3.29-3.23 (m, 1H), 3.19-3.05 (m, 1H), 2.89-2.76 (m, 1H), 2.16-2.00 (m, 3H), 1.91-1.65 (m, 8H), 1.60-1.48 (m, 1H).

Example 693: (R)—N-(1-Acryloylpiperidin-3-yl)-5-(4-(cyclopentyloxy)-2-methylphenyl)-4-oxo-4,5-dihydro-3H-1-thia-3,5,8-triazaacenaphthylene-2-carboxamide

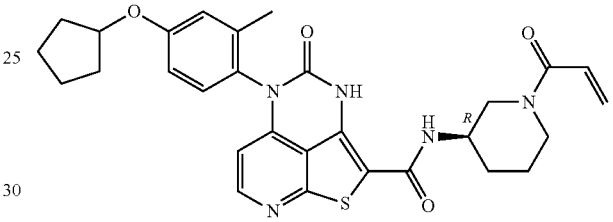

Step A: 2-Chloro-4-((4-(cyclopentyloxy)-2-methylphenyl)amino)nicotinonitrile

To a solution of 2-chloro-4-((4-hydroxy-2-methylphenyl)amino)nicotinonitrile (Intermediate 14, 500 mg, 1.93 mmol), cyclopentanol (166 mg, 1.93 mmol), and PPh$_3$ (1.0 g, 3.8 mmol) in THF (10 mL) was added DIAD (3.8 mL, 3.8 mmol) at −78° C., and warmed to 80° C. overnight. The reaction was quenched with H$_2$O (10 mL), extracted with DCM, dried over anhydrous Na$_2$SO$_4$, filtered, and concentrated to dryness. The residue was purified by flash column chromatography to give the title compound (220 mg, 35% yield) as a yellow solid. MS (ESI): mass calcd. for C$_{18}$H$_{18}$ClN$_3$O, 327.81; m/z found, 328.1 [M+H]$^+$.

Step B: (R)—N-(1-Acryloylpiperidin-3-yl)-5-(4-(cyclopentyloxy)-2-methylphenyl)-4-oxo-4,5-dihydro-3H-1-thia-3,5,8-triazaacenaphthylene-2-carboxamide The title compound was prepared using analogous conditions described in Method 1, steps D-I, in Example 1, and using 2-Chloro-4-((4-(cyclopentyloxy)-2-methylphenyl)amino)nicotinonitrile in place of 2-chloro-4-(2-methyl-4-phenoxyanilino)pyridine-3-carbonitrile in step D, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for C$_{29}$H$_{31}$N$_5$O$_4$S, 545.7; m/z found, 546.2 [M+H]$^+$. $^1$H NMR (400 MHz, DMSO-d$_6$ and CD$_3$OD): δ 8.33 (d, J=5.5 Hz, 1H), 7.26-7.21 (m, 1H), 6.99-6.96 (m, 1H), 6.93-6.90 (m, 1H), 6.84-6.75 (m, 1H), 6.21-6.12 (m, 1H), 5.99 (d, J=5.5 Hz, 1H), 5.74-5.68 (m, 1H), 4.91-4.86 (m, 1H), 4.58-4.31 (m, 1H), 4.17-3.98 (m, 1H), 3.93-3.83 (m, 1H), 3.20-3.04 (m, 1H), 2.90-2.72 (m, 1H), 2.10 (s, 3H), 2.04-1.94 (m, 3H), 1.86-1.76 (m, 5H), 1.74-1.61 (m, 3H), 1.57-1.45 (m, 1H).

Example 694: (R)—N-(1-Acryloylpiperidin-3-yl)-5-(4-methoxy-2-methylphenyl)-4-oxo-4,5-dihydro-3H-1-thia-3,5,8-triazaacenaphthylene-2-carboxamide

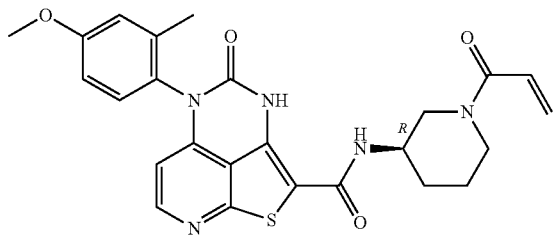

The title compound was prepared using analogous conditions described in Method 1, steps C-I, in Example 1, and using 4-methoxy-2-methylaniline in place of 2-chloro-4-iodopyridine-3-carbonitrile in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{25}H_{25}N_5O_4S$, 491.6; m/z found, 492.1 [M+H]$^+$. $^1$H NMR (400 MHz, CD$_3$OD): δ 8.34-8.24 (m, 1H), 7.29-7.19 (m, 1H), 7.05-6.99 (m, 1H), 6.98-6.91 (m, 1H), 6.85-6.72 (m, 1H), 6.27-6.13 (m, 1H), 6.06-5.96 (m, 1H), 5.79-5.68 (m, 1H), 4.61-4.26 (m, 1H), 4.20-3.89 (m, 2H), 3.84 (s, 3H), 3.22-3.10 (m, 1H), 2.96-2.81 (m, 1H), 2.16-2.00 (m, 4H), 1.92-1.80 (m, 1H), 1.79-1.66 (m, 1H), 1.62-1.51 (m, 1H).

Example 695: (R)—N-(1-Acryloylpiperidin-3-yl)-5-(5-methyl-2-phenylpyridin-4-yl)-4-oxo-4,5-dihydro-3H-1-thia-3,5,8-triazaacenaphthylene-2-carboxamide

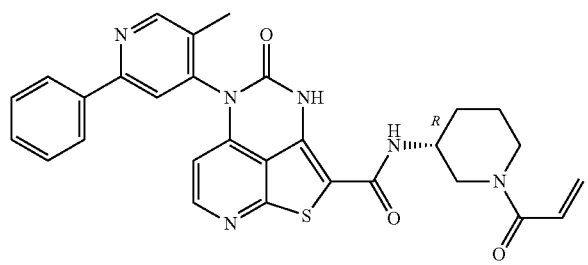

The title compound was prepared using analogous conditions described in Example 677, step A, and using 2-chloro-5-methylpyridin-4-amine, DMAP, acetic anhydride, and phenylboronic acid in place of 2-chloro-4-nitropyridine and cyclohexen-1-ylboronic acid and no Pd/C reduction in step A, and using Method 1, steps C-G in Example 1, and using 5-methyl-2-phenylpyridin-4-amine in place of 2-methyl-4-phenoxyaniline in step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for $C_{29}H_{26}N_6O_3S$, 538.6; m/z found, 539.4 [M+H]$^+$. $^1$H NMR (400 MHz, CD$_3$OD): δ 8.73 (s, 1H), 8.35-8.26 (m, 1H), 8.07-7.95 (m, 3H), 7.49-7.37 (m, 3H), 6.83-6.70 (m, 1H), 6.24-6.09 (m, 2H), 5.77-5.62 (m, 1H), 4.62-4.26 (m, 1H), 4.22-3.89 (m, 2H), 3.29-3.08 (m, 1H), 2.93-2.79 (m, 1H), 2.23 (s, 3H), 2.10-1.99 (m, 1H), 1.88-1.78 (m, 1H), 1.76-1.62 (m, 1H), 1.57-1.46 (m, 1H).

Example 696: (R)—N-(1-Acryloylpiperidin-3-yl)-5-(4-(2-isopropoxyethoxy)-2-methylphenyl)-4-oxo-4,5-dihydro-3H-1-thia-3,5,8-triazaacenaphthylene-2-carboxamide

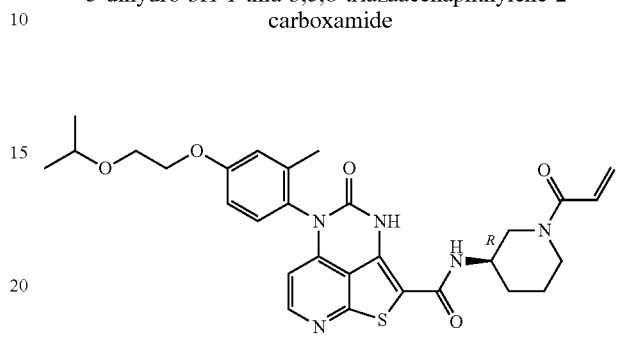

The title compound was prepared using analogous conditions described in Method 1, steps A-G, in Example 1, and using 4-fluoro-2-methyl-1-nitrobenzene and 2-isopropoxyethanol in place of 5-fluoro-2-nitrotoluene and phenol in step A, and using Pd/C in place of Fe in step B, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for $C_{29}H_{33}N_5O_5S$, 563.7; m/z found, 564.3 [M+H]$^+$. $^1$H NMR (400 MHz, CD$_3$OD): δ 8.30 (d, J=5.6 Hz, 1H), 7.27-7.20 (m, 1H), 7.06-7.00 (m, 1H), 7.00-6.93 (m, 1H), 6.84-6.73 (m, 1H), 6.28-6.12 (m, 1H), 6.02 (d, J=5.6 Hz, 1H), 5.79-5.67 (m, 1H), 4.55-4.27 (m, 1H), 4.17-4.11 (m, 2H), 4.05-3.91 (m, 2H), 3.85-3.79 (m, 2H), 3.76-3.69 (m, 1H), 3.22-3.12 (m, 1H), 2.98-2.84 (m, 1H), 2.12 (s, 3H), 2.08-2.02 (m, 1H), 1.91-1.83 (m, 1H), 1.78-1.66 (m, 1H), 1.64-1.53 (m, 1H), 1.19 (d, J=6.2, 6H).

Example 697: (R)—N-(1-Acryloylpiperidin-3-yl)-5-(2-isopropylpyridin-4-yl)-4-oxo-4,5-dihydro-3H-1-thia-3,5,8-triazaacenaphthylene-2-carboxamide

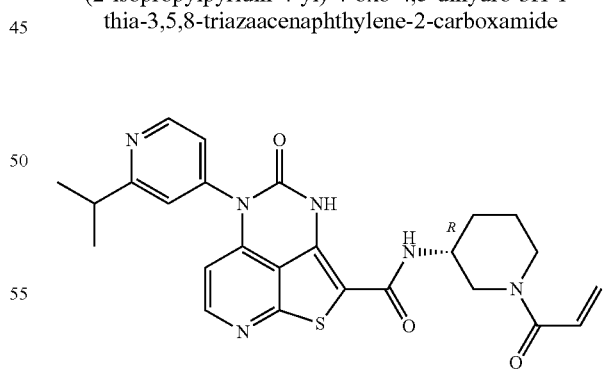

The title compound was prepared using analogous conditions described in Example 677, step A, and using 2-chloro-4-nitro-pyridine and 2-isopropenyl-4,4,5,5-tetramethyl-1,3,2-dioxaborolane in place of 2-chloro-4-nitropyridine and cyclohexen-1-ylboronic acid in step A, and using Method 1, steps C-I in Example 1, and using 2-isopropylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{25}H_{26}N_6O_3S$, 490.6; m/z found, 491.4 [M+H]$^+$. $^1$H NMR (400 MHz, CD$_3$OD): δ 8.68 (d, J=4.9 Hz, 1H), 8.26 (d, J=5.4 Hz, 1H), 7.54 (s, 1H), 7.43 (d, J=4.9 Hz, 1H), 6.86-6.70 (m, 1H), 6.24-6.06 (m, 2H), 5.76-5.59 (m, 1H), 4.59-4.30 (m, 1H), 4.27-3.84 (m, 2H), 3.22-3.04 (m, 2H), 2.88-2.74 (m, 1H), 2.11-1.97 (m, 1H), 1.89-1.78 (m, 1H), 1.76-1.64 (m, 1H), 1.59-1.47 (m, 1H), 1.34 (d, J=6.7 Hz, 6H).

Example 698: (R)—N-(1-Acryloylpyrrolidin-3-yl)-4-oxo-5-(5-phenoxypyridin-2-yl)-4,5-dihydro-3H-1-thia-3,5,8-triazaacenaphthylene-2-carboxamide

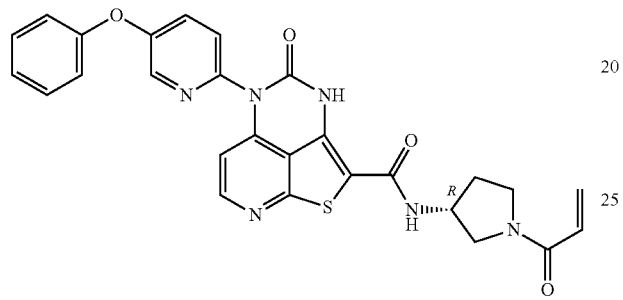

The title compound was prepared using analogous conditions described in Method 1, steps A-I, in Example 1, and using 5-bromo-2-nitropyridine in place of 5-fluoro-2-nitrotoluene in step A, and using Pd/C in place of Fe in step B, and using tert-butyl (3R)-3-aminopyrrolidine-1-carboxylate and diisopropylethylamine in place of tert-butyl (3R,5R)-3-amino-5-fluoropiperidine-1-carboxylate and triethylamine in step G, to give the title compound. MS (ESI): mass calcd. for $C_{27}H_{22}N_6O_4S$, 526.6; m/z found, 527.1 [M+H]$^+$. $^1$H NMR (400 MHz, CDCl$_3$): δ 9.55 (s, 1H), 8.55-8.21 (m, 2H), 7.57-7.36 (m, 4H), 7.30-7.19 (m, 1H), 7.17-6.71 (m, 3H), 6.49-6.31 (m, 2H), 6.26-6.17 (m, 1H), 5.77-5.65 (m, 1H), 4.80-4.61 (m, 1H), 4.01-3.38 (m, 4H), 2.41-1.94 (m, 2H).

Example 699: (R)—N-(1-Acryloylpyrrolidin-3-yl)-4-oxo-5-(5-phenoxypyrazin-2-yl)-4,5-dihydro-3H-1-thia-3,5,8-triazaacenaphthylene-2-carboxamide

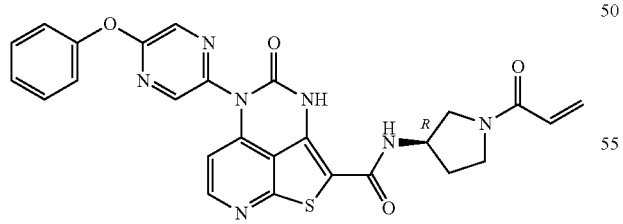

The title compound was prepared using analogous conditions described in Method 1, steps A, C-G, in Example 1, and using 5-bromopyrazin-2-amine in place of 5-fluoro-2-nitrotoluene in step A, and using 5-phenoxypyrazin-2-amine in place of 2-methyl-4-phenoxyaniline in step C, and using 1-[(3R)-3-aminopyrrolidin-1-yl]prop-2-en-1-one (Intermediate 5) and diisopropylethylamine in place of tert-butyl (3R,5R)-3-amino-5-fluoropiperidine-1-carboxylate and triethylamine in step G, to give the title compound. MS (ESI): mass calcd. for $C_{26}H_{21}N_7O_4S$, 527.6; m/z found, 528.1 [M+H]$^+$. $^1$H NMR (400 MHz, CD$_3$OD): δ 8.53-8.47 (m, 1H), 8.39-8.25 (m, 2H), 7.54-7.41 (m, 2H), 7.34-7.19 (m, 3H), 6.72-6.52 (m, 1H), 6.35 (d, J=5.6 Hz, 1H), 6.32-6.22 (m, 1H), 5.81-5.69 (m, 1H), 4.70-4.60 (m, 1H), 4.02-3.49 (m, 4H), 2.43-2.01 (m, 2H).

Example 700: (R)—N-(1-Acryloylpiperidin-3-yl)-5-(*R)-(6-cyclobutoxy-4-methylpyridin-3-yl)-4-oxo-4,5-dihydro-3H-1-thia-3,5,8-triazaacenaphthylene-2-carboxamide

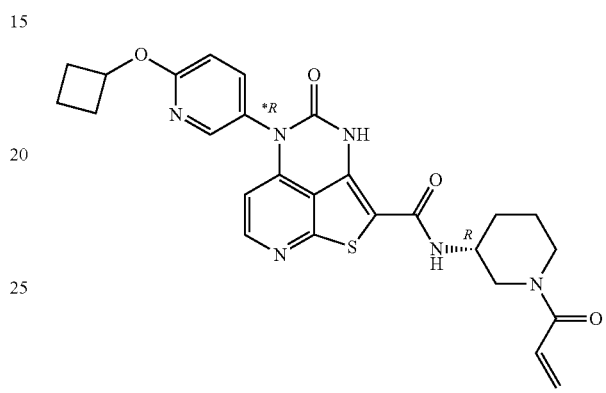

The title compound was prepared using analogous conditions described in Method 1, steps A-G, (including Chiral Resolution Method A after step F to obtain the *R atropisomer), in Example 1, and using 2-fluoro-4-methyl-5-nitropyridine, cyclobutanol, and Cs$_2$CO$_3$ in place of 5-fluoro-2-nitrotoluene, K$_2$CO$_3$, and phenol in step A, and using Zn in place of Fe in step B, and using 1-[(3R)-3-amino-1-piperidyl]prop-2-en-1-one (Intermediate 15), 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for $C_{27}H_{28}N_6O_4S$, 532.6; m/z found, 533.1 [M+H]$^+$. $^1$H NMR (500 MHz, CD$_3$OD): δ 8.34 (d, J=5.6 Hz, 1H), 8.05 (s, 1H), 6.87-6.75 (m, 2H), 6.24-6.17 (m, 1H), 6.11 (d, J=5.5 Hz, 1H), 5.74 (t, J=9.3 Hz, 1H), 5.23-5.15 (m, 1H), 4.54-4.26 (m, 1H), 4.20-3.92 (m, 2H), 3.23-3.14 (m, 1H), 2.99-2.88 (m, 1H), 2.53-2.44 (m, 2H), 2.21-2.12 (m, 5H), 2.11-2.04 (m, 1H), 1.92-1.82 (m, 2H), 1.80-1.67 (m, 2H), 1.65-1.54 (m, 1H).

Example 701: (R)-5-([2,3'-Bipyridin]-4-yl)-N-(1-acryloylpiperidin-3-yl)-4-oxo-4,5-dihydro-3H-1-thia-3,5,8-triazaacenaphthylene-2-carboxamide

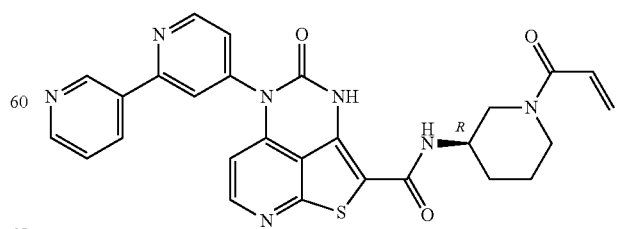

The title compound was prepared using analogous conditions described in Example 677, step A, and using 2-chloropyridin-4-amine and 3-pyridylboronic acid in place of 2-chloro-4-nitropyridine and cyclohexen-1-ylboronic acid and no Pd/C reduction in step A, and using Method 1, steps C-G in Example 1, and using 2-(3-pyridyl)pyridin-4-amine in place of 2-methyl-4-phenoxyaniline in step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for $C_{27}H_{23}N_7O_3S$, 525.6; m/z found, 526.2 [M+H]+. $^1$H NMR (400 MHz, CD$_3$OD): δ 9.27-9.23 (m, 1H), 8.95-8.90 (m, 1H), 8.62-8.57 (m, 1H), 8.53-8.49 (m, 1H), 8.35-8.30 (m, 1H), 8.23-8.18 (m, 1H), 7.60-7.57 (m, 1H), 7.57-7.53 (m, 1H), 6.84-6.70 (m, 1H), 6.35-6.30 (m, 1H), 6.21-6.12 (m, 1H), 5.76-5.63 (m, 1H), 4.58-4.25 (m, 1H), 4.22-3.89 (m, 2H), 3.20-3.07 (m, 1H), 2.93-2.77 (m, 1H), 2.09-2.02 (m, 1H), 1.88-1.80 (m, 1H), 1.77-1.62 (m, 1H), 1.58-1.47 (m, 1H).

Example 702: (R)-5-(*S)-(4-Methyl-6-phenoxypyridin-3-yl)-4-oxo-N-(pyrrolidin-3-yl)-4,5-dihydro-3H-1-thia-3,5,8-triazaacenaphthylene-2-carboxamide

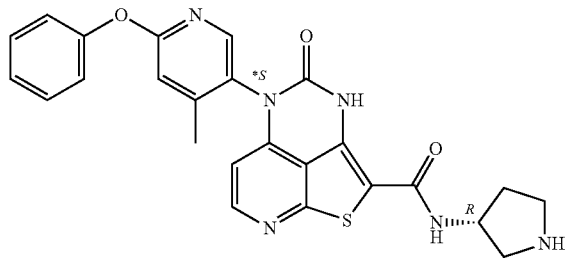

The title compound was prepared using analogous conditions described in Method 1, steps A-H, (including Chiral Resolution Method A after step F to obtain the *S atropisomer), in Example 1, and using 2-chloro-4-methyl-5-nitropyridine and Cs$_2$CO$_3$ in place of 5-fluoro-2-nitrotoluene and K$_2$CO$_3$ in step A, and using Pd/C in place of Fe in step B, and using tert-butyl (3R)-3-aminopyrrolidine-1-carboxylate and diisopropylethylamine in place of tert-butyl (3R,5R)-3-amino-5-fluoropiperidine-1-carboxylate and triethylamine in step G, to give the title compound. MS (ESI): mass calcd. for $C_{25}H_{22}N_6O_3S$, 486.6; m/z found, 487.0 [M+H]+. $^1$H NMR (600 MHz, CD$_3$OD): δ 8.60-8.56 (d, J=6.6 Hz, 1H), 8.22-8.18 (s, 1H), 7.50-7.43 (m, 2H), 7.30-7.26 (m, 1H), 7.24-7.19 (m, 2H), 7.13-7.09 (s, 1H), 6.61-6.56 (d, J=6.6 Hz, 1H), 4.68-4.60 (m, 1H), 3.64-3.58 (m, 2H), 3.51-3.44 (m, 1H), 3.43-3.35 (m, 1H), 2.49-2.38 (m, 1H), 2.30-2.20 (m, 4H).

Example 703: (R,E)-5-(3-Chloro-4-phenoxyphenyl)-N-(1-(4-(dimethylamino)but-2-enoyl)pyrrolidin-3-yl)-4-oxo-4,5-dihydro-3H-1-thia-3,5,8-triazaacenaphthylene-2-carboxamide

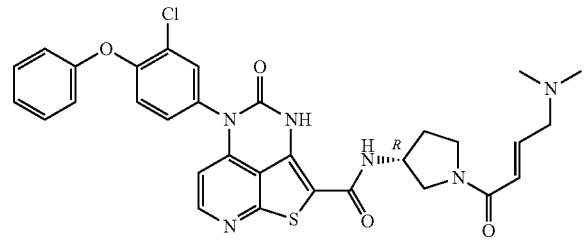

The title compound was prepared using analogous conditions described in Method 1, steps A-I, in Example 1, and using 2-chloro-1-fluoro-4-nitrobenzene in place of 5-fluoro-2-nitrotoluene in step A, and using tert-butyl (3R)-3-aminopyrrolidine-1-carboxylate in place of tert-butyl (3R,5R)-3-amino-5-fluoropiperidine-1-carboxylate (Intermediate 1) in step G, and using (E)-4-(dimethylamino)but-2-enoic acid and HATU in place of prop-2-enoyl chloride in step I, to give the title compound. MS (ESI): mass calcd. for $C_{31}H_{29}ClN_6O_4S$, 617.1; m/z found, 617.2 [M+H]+. $^1$H NMR (400 MHz, CD$_3$OD): δ 8.21-8.13 (m, 1H), 7.60-7.54 (m, 1H), 7.43-7.34 (m, 2H), 7.32-7.25 (m, 1H), 7.19-7.11 (m, 2H), 7.09-7.01 (m, 2H), 6.86-6.75 (m, 1H), 6.51-6.40 (m, 1H), 6.10-6.04 (m, 1H), 4.67-4.56 (m, 1H), 4.02-3.51 (m, 4H), 3.19-3.13 (m, 2H), 2.39-2.28 (m, 1H), 2.28-2.24 (m, 6H), 2.23-2.08 (m, 1H).

Example 704: (R)—N-(1-Acryloylpiperidin-3-yl)-5-(6-cyclobutoxy-2-methylpyridin-3-yl)-4-oxo-4,5-dihydro-3H-1-thia-3,5,8-triazaacenaphthylene-2-carboxamide

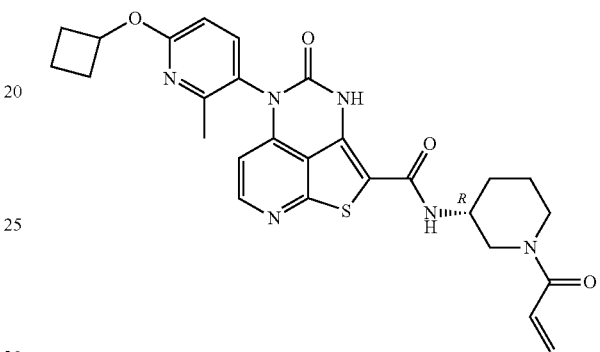

The title compound was prepared using analogous conditions described in Method 1, steps A-G, in Example 1, and using 2-fluoro-5-nitro-6-picoline and cyclobutanol in place of 5-fluoro-2-nitrotoluene and phenol in step A, and using Zn in place of Fe in step B, and using 1-[(3R)-3-amino-1-piperidyl]prop-2-en-1-one (Intermediate 15), 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for $C_{27}H_{28}N_6O_4S$, 532.6; m/z found, 533.1 [M+H]+. $^1$H NMR (500 MHz, CD$_3$OD): δ 8.34 (d, J=5.5 Hz, 1H), 7.62 (dd, J=8.6, 1.8 Hz, 1H), 6.85-6.73 (m, 2H), 6.24-6.16 (m, 1H), 6.09 (d, J=5.5 Hz, 1H), 5.78-5.69 (m, 1H), 5.26-5.16 (m, 1H), 4.58-4.25 (m, 1H), 4.21-3.92 (m, 2H), 3.24-3.14 (m, 1H), 3.01-2.86 (m, 1H), 2.55-2.45 (m, 2H), 2.25 (s, 3H), 2.21-2.12 (m, 2H), 2.11-2.04 (m, 1H), 1.92-1.83 (m, 2H), 1.81-1.68 (m, 2H), 1.66-1.54 (m, 1H).

Example 705: (R)—N-(1-Acryloylpyrrolidin-3-yl)-5-(3-isopropylphenyl)-4-oxo-4,5-dihydro-3H-1-thia-3,5,8-triazaacenaphthylene-2-carboxamide

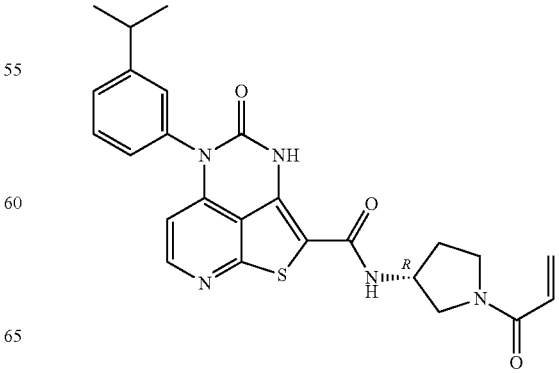

The title compound was prepared using analogous conditions described in Method 1, steps C-I in Example 1, and using 3-isopropylaniline in place of 2-methyl-4-phenoxyaniline in step C, and using tert-butyl (3R)-3-aminopyrrolidine-1-carboxylate in place of tert-butyl (3R,5R)-3-amino-5-fluoropiperidine-1-carboxylate (Intermediate 1) in step G, to give the title compound. MS (ESI): mass calcd. for $C_{25}H_{25}N_5O_3S$, 475.6; m/z found, 476.2 [M+H]$^+$. $^1$H NMR (400 MHz, CD$_3$OD): δ 8.30-8.26 (m, 1H), 7.55-7.48 (m, 1H), 7.45-7.40 (m, 1H), 7.32-7.28 (m, 1H), 7.24-7.18 (m, 1H), 6.68-6.54 (m, 1H), 6.32-6.23 (m, 1H), 6.09-6.03 (m, 1H), 5.78-5.70 (m, 1H), 4.69-4.55 (m, 1H), 4.02-3.49 (m, 4H), 3.05-2.93 (m, 1H), 2.38-2.01 (m, 2H), 1.29-1.25 (m, 6H).

Example 706: (R)-5-(2',3'-Difluoro-[1,1'-biphenyl]-3-yl)-4-oxo-N-(piperidin-3-yl)-4,5-dihydro-3H-1-thia-3,5,8-triazaacenaphthylene-2-carboxamide

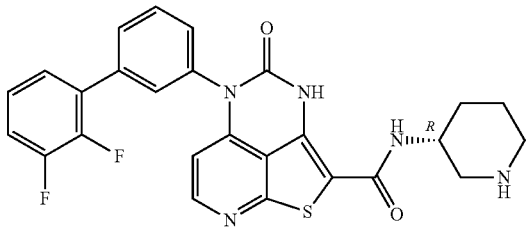

The title compound was synthesized as in Example 498, steps A-D. MS (ESI): mass calcd. for $C_{26}H_{21}F_2N_5O_2S$, 505.5; m/z found, 506.4 [M+H]$^+$. $^1$H NMR (400 MHz, CD$_3$OD): δ 8.53 (br, 1H), 8.29 (d, J=5.6 Hz, 1H), 7.82-7.69 (m, 2H), 7.65 (s, 1H), 7.54-7.45 (m, 1H), 7.41-7.17 (m, 3H), 6.18 (d, J=5.5 Hz, 1H), 4.31-4.16 (m, 1H), 3.53-3.43 (m, 1H), 3.28-3.25 (m, 1H), 2.97-2.86 (m, 2H), 2.12-1.98 (m, 2H), 1.90-1.67 (m, 2H).

Example 707: N-((1RS,2RS)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide

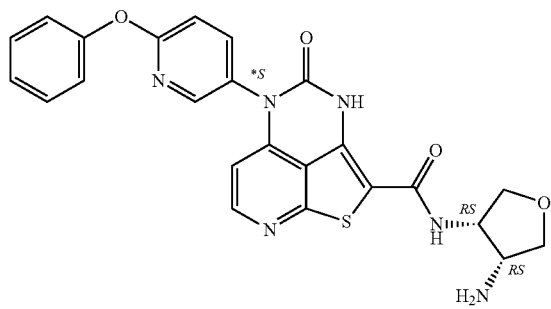

The title compound was prepared using analogous conditions described in Method 1, steps A-G (including Chiral Resolution Method A after step F to obtain the *S atropisomer) in Example 1, and using 2-chloro-4-methyl-5-nitropyridine and Cs$_2$CO$_3$ in place of 5-fluoro-2-nitrotoluene and K$_2$CO$_3$ in step A, and using Pd/C in place of Fe in step B, and using cis-diaminotetrahydrofuran, 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for $C_{25}H_{22}N_6O_4S$, 502.6; m/z found, 503.0 [M+H]$^+$. $^1$H NMR (600 MHz, CD$_3$OD): δ 8.30-8.27 (m, 1H), 8.09-8.05 (d, J=4.2 Hz, 1H), 7.46-7.41 (m, 2H), 7.27-7.22 (m, 1H), 7.21-7.16 (m, 2H), 7.05-7.02 (s, 1H), 6.11-6.04 (m, 1H), 4.71-4.63 (m, 1H), 4.15-4.09 (m, 1H), 4.08-4.03 (m, 1H), 3.85-3.80 (m, 1H), 3.78-3.73 (m, 1H), 3.72-3.66 (m, 1H), 2.23-2.15 (m, 3H).

Example 708: (R)—N-(1-Acryloylpiperidin-3-yl)-4-oxo-5-(3-(tetrahydro-2H-pyran-4-yl)phenyl)-4,5-dihydro-3H-1-thia-3,5,8-triazaacenaphthylene-2-carboxamide

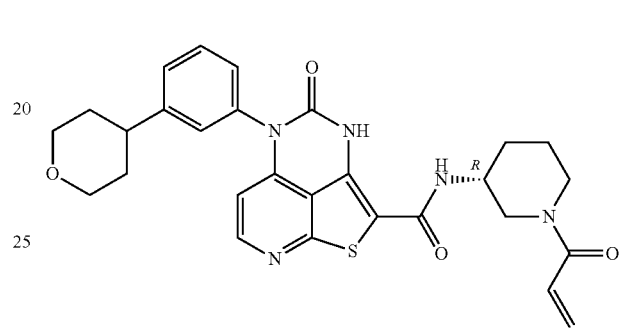

The title compound was prepared using the procedures found in Example 534, steps A-C, and using 3-tetrahydropyran-4-ylaniline (Intermediate 47) in place of 3-cyclobutylaniline in step A, to yield the title compound. MS (ESI): mass calcd. for $C_{28}H_{29}N_5O_4S$, 531.6; m/z found, 532.0 [M+H]$^+$. $^1$H NMR (500 MHz, CD$_3$OD): δ 8.29 (d, J=5.6 Hz, 1H), 7.56 (t, J=7.8 Hz, 1H), 7.46 (d, J=7.9 Hz, 1H), 7.35 (s, 1H), 7.28 (d, J=7.3 Hz, 1H), 6.85-6.75 (m, 1H), 6.20 (dd, J=16.9, 6.2 Hz, 1H), 6.08 (d, J=5.6 Hz, 1H), 5.73 (t, J=11.8 Hz, 1H), 4.58-4.27 (m, 1H), 4.22-3.92 (m, 4H), 3.61-3.52 (m, 2H), 3.22-3.14 (m, 1H), 2.97-2.86 (m, 2H), 2.12-2.04 (m, 1H), 1.91-1.66 (m, 6H), 1.65-1.52 (m, 1H).

Example 709: (R)-5-([2,2'-Bipyridin]-4-yl)-N-(1-acryloylpiperidin-3-yl)-4-oxo-4,5-dihydro-3H-1-thia-3,5,8-triazaacenaphthylene-2-carboxamide

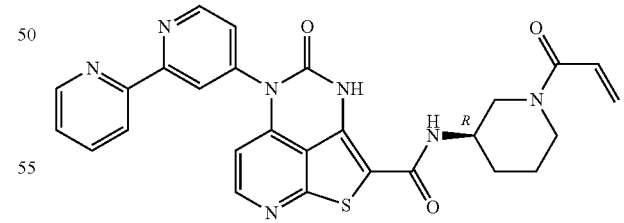

Step A: Methyl 5-(2-chloropyridin-4-yl)-4-oxo-4,5-dihydro-3H-1-thia-3,5,8-triazaacenaphthylene-2-carboxylate The title compound was prepared using analogous conditions described in Method 1, steps C-E in Example 1, and using 2-chloropyridin-4-amine in place of 2-methyl-4-phenoxyaniline in step C, to give the title compound.

Step B: Methyl 5-([2,2'-bipyridin]-4-yl)-4-oxo-4,5-dihydro-3H-1-thia-3,5,8-triazaacenaphthylene-2-carboxylate A solution of trimethyl(2-pyridyl)stannane (0.536 g, 2.22 mmol), Methyl 5-(2-chloropyridin-4-yl)-4-oxo-4,5-dihydro-3H-1-thia-3,5,8-triazaacenaphthylene-2-carboxylate (0.80 g, 1.1 mmol), and Pd(PPh$_3$)$_4$ (0.128 g, 0.111 mmol) in DMF (10 mL) was degassed under N$_2$ and was stirred at 85° C. for 4 hours. The reaction was concentrated to dryness and the residue was purified by flash column chromatography to give the title compound (0.50 g, 56% yield) as a yellow solid.

Step C: (R)-5-([2,2'-Bipyridin]-4-yl)-N-(1-acryloylpiperidin-3-yl)-4-oxo-4,5-dihydro-3H-1-thia-3,5,8-triazaacenaphthylene-2-carboxamide The title compound was prepared using analogous conditions described in Method 1, steps F-G in Example 1, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for C$_{27}$H$_{23}$N$_7$O$_3$S, 525.6; m/z found, 526.2 [M+H]$^+$. $^1$H NMR (400 MHz, CD$_3$OD): δ 8.94-8.81 (m, 1H), 8.65-8.58 (m, 1H), 8.52-8.44 (m, 1H), 8.44-8.36 (m, 1H), 8.32-8.23 (m, 1H), 7.98-7.86 (m, 1H), 7.60-7.51 (m, 1H), 7.46-7.38 (m, 1H), 6.87-6.70 (m, 1H), 6.31-6.23 (m, 1H), 6.23-6.12 (m, 1H), 5.78-5.66 (m, 1H), 4.57-4.22 (m, 1H), 4.22-3.89 (m, 2H), 3.24-3.10 (m, 1H), 2.98-2.84 (m, 1H), 2.12-2.02 (m, 1H), 1.91-1.81 (m, 1H), 1.81-1.64 (m, 1H), 1.62-1.51 (m, 1H).

Example 710: (R)-5-(2',3'-Difluoro-[1,1'-biphenyl]-3-yl)-N-(1-methylpiperidin-3-yl)-4-oxo-4,5-dihydro-3H-1-thia-3,5,8-triazaacenaphthylene-2-carboxamide

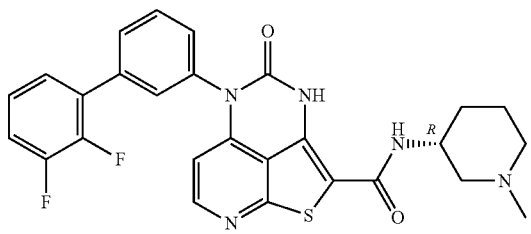

To a solution of (R)-5-(2',3'-difluoro-[1,1'-biphenyl]-3-yl)-4-oxo-N-(piperidin-3-yl)-4,5-dihydro-3H-1-thia-3,5,8-triazaacenaphthylene-2-carboxamide (Example 706, 100 mg, 0.198 mmol) and formaldehyde (0.5 mL, 37 wt. % in H$_2$O) in MeOH (5 mL) was added NaBH(AcO)$_3$ (176 mg, 0.831 mmol) and was stirred at rt overnight. The reaction was concentrated to dryness and purified by flash column chromatography to give the title compound as a pale yellow solid. MS (ESI): mass calcd. for C$_{27}$H$_{23}$F$_2$N$_5$O$_2$S, 519.6; m/z found, 520.4 [M+H]$^+$. $^1$H NMR (400 MHz, CD$_3$OD): δ 8.47 (s, 1H), 8.28 (d, J=5.6 Hz, 1H), 7.78-7.65 (m, 3H), 7.54-7.47 (m, 1H), 7.38-7.19 (m, 3H), 6.17 (d, J=5.6 Hz, 1H), 4.30-4.17 (m, 1H), 3.40-3.31 (m, 1H), 3.18-3.06 (m, 1H), 2.74-2.60 (m, 5H), 2.04-1.92 (m, 2H), 1.86-1.72 (m, 1H), 1.69-1.56 (m, 1H).

Example 711: (R)-5-(2-Methyl-6-phenoxypyridin-3-yl)-4-oxo-N-(piperidin-3-yl)-4,5-dihydro-3H-1-thia-3,5,8-triazaacenaphthylene-2-carboxamide

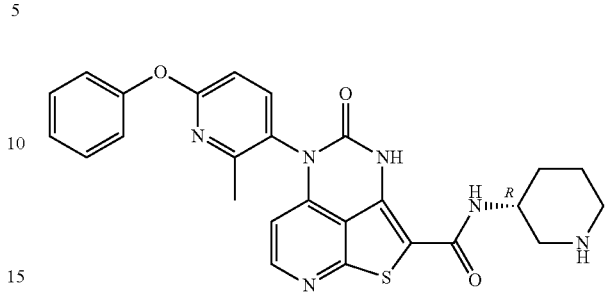

The title compound was prepared using analogous conditions described in Example 534, steps A-B, and using 2-methyl-6-phenoxypyridin-3-amine (Intermediate 49) in place of 3-cyclobutylaniline in step A, to give the title compound. MS (ESI): mass calcd. for C$_{26}$H$_{24}$N$_6$O$_3$S, 500.6; m/z found, 501.0 [M+H]$^+$. $^1$H NMR (400 MHz, CD$_3$OD): δ 8.58 (d, J=6.5 Hz, 1H), 7.88 (d, J=8.7 Hz, 1H), 7.53-7.43 (m, 2H), 7.33-7.26 (m, 1H), 7.25-7.20 (m, 2H), 6.98 (d, J=8.6 Hz, 1H), 6.54 (d, J=6.5 Hz, 1H), 4.36-4.26 (m, 1H), 3.54 (dd, J=12.1, 3.8 Hz, 1H), 3.40-3.34 (m, 1H), 3.01 (t, J=11.5 Hz, 2H), 2.30 (s, 3H), 2.15-2.06 (m, 2H), 1.94-1.73 (m, 2H).

Example 11: N-(trans-1-Acryloyl-3-hydroxypiperidin-4-yl)-4-oxo-5-(4-phenoxyphenyl)-4,5-dihydro-3H-1-thia-3,5,8-triazaacenaphthylene-2-carboxamide

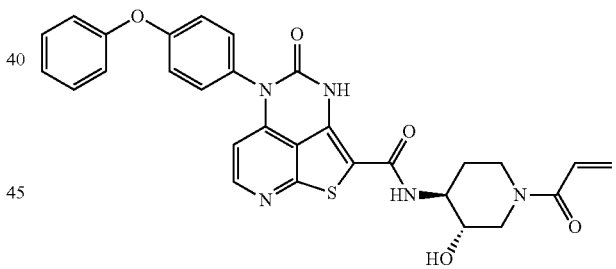

The title compound was prepared using analogous conditions described in Example 1, step I, and using N-(trans-3-Hydroxypiperidin-4-yl)-4-oxo-5-(4-phenoxyphenyl)-4,5-dihydro-3H-1-thia-3,5,8-triazaacenaphthylene-2-carboxamide (Example 615) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide. MS (ESI): mass calcd. for C$_{29}$H$_{25}$N$_5$O$_5$S, 555.6; m/z found, 556.1 [M+H]$^+$. 1H NMR (500 MHz, Chloroform-d) δ 8.29 (dq, J=5.4, 1.7 Hz, 1H), 7.46-7.38 (m, 2H), 7.38-7.25 (m, 3H), 7.25-7.09 (m, 5H), 6.63 (ddd, J=26.2, 16.2, 10.9 Hz, 1H), 6.33-6.24 (m, 1H), 6.24-6.12 (m, 1H), 5.80-5.69 (m, 1H), 4.19 (d, J=13.4 Hz, 1H), 4.06-3.98 (m, 1H), 3.50 (s, 1H), 3.44-3.35 (m, 1H), 3.20 (t, J=13.0 Hz, 1H), 3.04 (t, J=12.0 Hz, 1H), 2.77 (t, J=13.2 Hz, 1H), 2.63 (q, J=16.6, 14.2 Hz, 1H), 2.21 (d, J=13.2 Hz, 1H), 2.09 (d, J=12.9 Hz, 1H).

Example 713: (R)-5-(*S)-(2-Methyl-6-phenoxypyridin-3-yl)-4-oxo-N-(piperidin-3-yl)-4,5-dihydro-3H-1-thia-3,5,8-triazaacenaphthylene-2-carboxamide

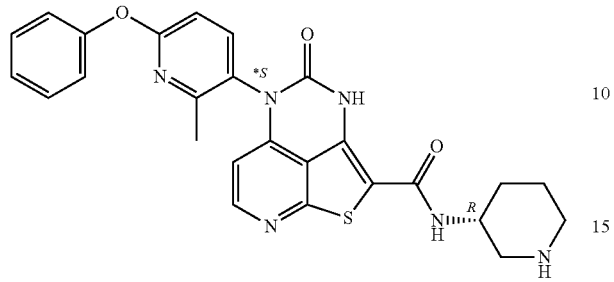

The title compound was prepared using analogous conditions described in Example 662, steps A-B, and using 2-methyl-6-phenoxypyridin-3-amine (Intermediate 49) in place of 4-methyl-6-phenoxypyridin-3-amine in step A, followed by treatment with Chiral Resolution Method A after step F to obtain the *S atropisomer in Example 1, and using methyl 5-(2-methyl-6-phenoxypyridin-3-yl)-4-oxo-4,5-dihydro-3H-1-thia-3,5,8-triazaacenaphthylene-2-carboxylate in place of methyl 4-[2-methyl-N-(methylcarbamoyl)-4-phenoxyanilino]-3a,4-dihydrothieno[2,3-b]pyridine-2-carboxylate in step F, and using tert-butyl (3R)-3-aminopiperidine-1-carboxylate and diisopropylethylamine in place of tert-butyl (3R,5R)-3-amino-5-fluoropiperidine-1-carboxylate and triethylamine in step G. MS (ESI): mass calcd. for $C_{26}H_{24}N_6O_3S$, 500.6; m/z found, 501.1 $[M+H]^+$. 1H NMR (400 MHz, MeOD) δ 8.54 (d, J=6.4 Hz, 1H), 7.84 (d, J=8.7 Hz, 1H), 7.50-7.43 (m, 2H), 7.31-7.25 (m, 1H), 7.24-7.18 (m, 2H), 6.96 (d, J=8.2 Hz, 1H), 6.47 (d, J=6.3 Hz, 1H), 4.36-4.25 (m, 1H), 3.58-3.50 (m, 1H), 3.41-3.33 (m, 1H), 3.04-2.93 (m, 2H), 2.28 (s, 3H), 2.15-2.03 (m, 2H), 1.92-1.73 (m, 2H).

Example 714: (R)—N-(1-(Methylglycyl)piperidin-3-yl)-4-oxo-5-(2-phenylpyridin-4-yl)-4,5-dihydro-3H-1-thia-3,5,8-triazaacenaphthylene-2-carboxamide

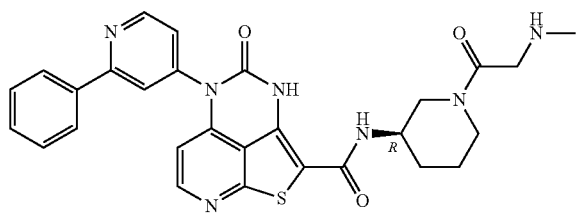

The title compound was prepared using analogous conditions described in Example 662, steps A-B, and using 2-phenylpyridin-4-amine in place of 4-methyl-6-phenoxypyridin-3-amine in step A, followed by treatment of the product with analogous conditions described in Method 1, steps F-I in Example 1, and using methyl 4-oxo-5-(2-phenylpyridin-4-yl)-4,5-dihydro-3H-1-thia-3,5,8-triazaacenaphthylene-2-carboxylate in place of methyl 4-[2-methyl-N-(methylcarbamoyl)-4-phenoxyanilino]-3a,4-dihydrothieno[2,3-b]pyridine-2-carboxylate in step F, and using tert-butyl (3R)-3-aminopiperidine-1-carboxylate in place of tert-butyl (3R,5R)-3-amino-5-fluoropiperidine-1-carboxylate (Intermediate 1) in step G, and using 2-[tert-butoxycarbonyl(methyl)amino]acetic acid (Intermediate 21) and HATU in place of prop-2-enoyl chloride in step I, followed by Boc-deprotection using saturated aqueous HCl and MeOH, to give the title compound. MS (ESI): mass calcd. for $C_{28}H_{27}N_7O_3S$, 541.6; m/z found, 542.2 $[M+H]^+$. 1H NMR (400 MHz, CD3OD): δ 8.83-8.76 (m, 1H), 8.12-8.05 (m, 1H), 8.04-7.98 (m, 2H), 7.95-7.88 (m, 1H), 7.51-7.43 (m, 3H), 7.42-7.38 (m, 1H), 6.13-5.99 (m, 1H), 4.47-3.79 (m, 4H), 3.73-3.44 (m, 2H), 3.24-3.06 (m, 1H), 2.67-2.51 (m, 3H), 2.06-1.70 (m, 3H), 1.65-1.54 (m, 1H).

Example 715: (R)-5-(*S)-(4-Methyl-2-phenoxypyrimidin-5-yl)-4-oxo-N-(pyrrolidin-3-yl)-4,5-dihydro-3H-1-thia-3,5,8-triazaacenaphthylene-2-carboxamide

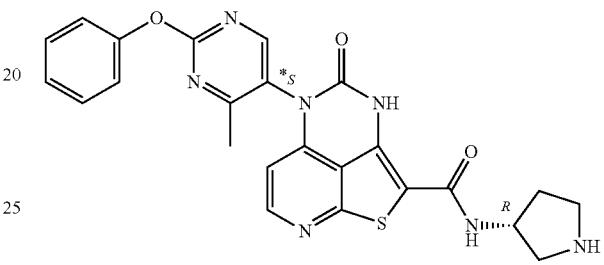

The title compound was prepared using analogous conditions described in Method 1, steps A, C-H, (including Chiral Resolution Method A after step F to obtain the *S atropisomer) in Example 1, and using 2-chloro-4-methylpyrimidin-5-amine, dimethyl glycine, and $Cs_2CO_3$ in place of 5-fluoro-2-nitrotoluene and $K_2CO_3$ in step A, and no step B, and using tert-butyl (3R)-3-aminopyrrolidine-1-carboxylate and diisopropylethylamine in place of tert-butyl (3R,5R)-3-amino-5-fluoropiperidine-1-carboxylate and triethylamine in step G, to give the title compound. MS (ESI): mass calcd. for $C_{24}H_{21}N_7O_3S$, 487.5; m/z found, 488.0 $[M+H]^+$. 1H NMR (600 MHz, CD3OD): δ 8.56-8.54 (s, 1H), 8.54-8.51 (d, J=6.1 Hz, 1H), 7.49-7.44 (m, 2H), 7.31-7.27 (m, 1H), 7.27-7.22 (m, 2H), 6.57-6.53 (d, J=6.1 Hz, 1H), 4.63-4.56 (m, 1H), 3.64-3.57 (m, 2H), 3.46-3.42 (m, 1H), 3.40-3.35 (m, 1H), 2.48-2.40 (m, 1H), 2.36-2.33 (s, 3H), 2.27-2.20 (m, 1H).

Example 716: (R)—N-(1-Acryloylpyrrolidin-3-yl)-5-(*S)-(2-methyl-6-phenoxypyridin-3-yl)-4-oxo-4,5-dihydro-3H-1-thia-3,5,8-triazaacenaphthylene-2-carboxamide

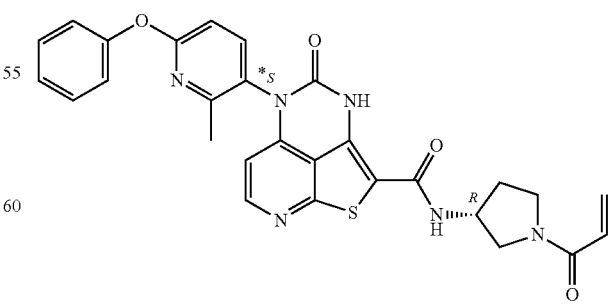

The title compound was prepared using analogous conditions described in Method 1, steps A-I, (including Chiral Resolution Method A after step F to obtain the *S atropisomer) in Example 1, and using 6-chloro-2-methyl-3-nitropyridine and Cs$_2$CO$_3$ in place of 5-fluoro-2-nitrotoluene and K$_2$CO$_3$ in step A, and using Pd/C in place of Fe in step B, and using tert-butyl (3R)-3-aminopyrrolidine-1-carboxylate and diisopropylethylamine in place of tert-butyl (3R,5R)-3-amino-5-fluoropiperidine-1-carboxylate and triethylamine in step G, and using prop-2-enoyl prop-2-enoate, acetonitrile, and diisopropylethylamine in place of prop-2-enoyl chloride, DCM, and triethylamine in step I, to give the title compound. MS (ESI): mass calcd. for C$_{28}$H$_{24}$N$_6$O$_4$S, 540.6; m/z found, 541.0 [M+H]$^+$. $^1$H NMR (600 MHz, CD$_3$OD): δ 8.38-8.35 (m, 1H), 7.80-7.76 (m, 1H), 7.48-7.42 (m, 2H), 7.27-7.18 (m, 3H), 6.93-6.89 (d, J=8.7 Hz, 1H), 6.67-6.56 (m, 1H), 6.32-6.25 (m, 1H), 6.18-6.13 (m, 1H), 5.78-5.72 (m, 1H), 4.70-4.59 (m, 1H), 4.03-3.49 (m, 4H), 2.39-2.25 (m, 1H), 2.25-2.23 (d, J=1.7 Hz, 3H), 2.19-2.04 (m, 1H).

Example 717: (R)-5-(*S)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide

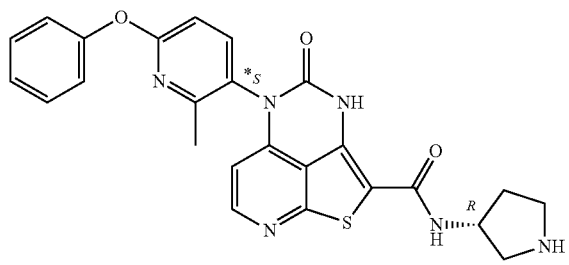

The title compound was prepared using analogous conditions described in Method 1, steps A-H, (including Chiral Resolution Method A after step F to obtain the *S atropisomer) in Example 1, and using 6-chloro-2-methyl-3-nitropyridine and Cs$_2$CO$_3$ in place of 5-fluoro-2-nitrotoluene and K$_2$CO$_3$ in step A, and using Pd/C in place of Fe in step B, and using tert-butyl (3R)-3-aminopyrrolidine-1-carboxylate and diisopropylethylamine in place of tert-butyl (3R,5R)-3-amino-5-fluoropiperidine-1-carboxylate and triethylamine in step G, to give the title compound. MS (ESI): mass calcd. for C$_{25}$H$_{22}$N$_6$O$_3$S, 486.6; m/z found, 487.0 [M+H]$^+$. $^1$H NMR (400 MHz, CD$_3$OD): δ 8.55-8.49 (d, J=6.2 Hz, 1H), 7.86-7.81 (d, J=8.7 Hz, 1H), 7.50-7.42 (m, 2H), 7.31-7.19 (m, 3H), 6.99-6.93 (d, J=8.6 Hz, 1H), 6.47-6.42 (d, J=6.3 Hz, 1H), 4.65-4.55 (m, 1H), 3.65-3.55 (m, 2H), 3.46-3.34 (m, 2H), 2.50-2.38 (m, 1H), 2.32-2.17 (m, 4H).

Example 718: N-((3S,4R)-1-Acryloyl-4-hydroxypyrrolidin-3-yl)-4-oxo-5-(2-phenylpyridin-4-yl)-4,5-dihydro-3H-1-thia-3,5,8-triazaacenaphthylene-2-carboxamide

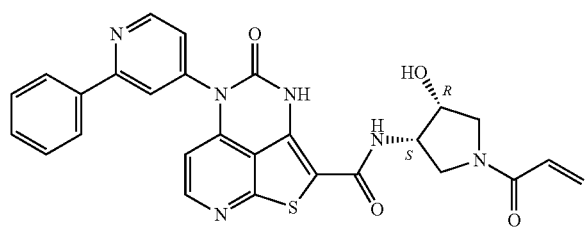

The title compound was prepared using analogous conditions described in Example 677, step A, and using 2-chloropyridin-4-amine and phenylboronic acid in place of 2-chloro-4-nitropyridine and cyclohexen-1-ylboronic acid and no Pd/C reduction in step A, and using Method 1, steps C-I in Example 1, and using 2-phenylpyridin-4-amine in place of 2-methyl-4-phenoxyaniline in step C, and using tert-butyl (3S,4R)-3-amino-4-hydroxypyrrolidine-1-carboxylate (Intermediate 24) in place of tert-butyl (3R,5R)-3-amino-5-fluoropiperidine-1-carboxylate (Intermediate 1) in step G, to give the title compound. MS (ESI): mass calcd. for C$_{27}$H$_{22}$N$_6$O$_4$S, 526.6; m/z found, 527.4 [M+H]$^+$. $^1$H NMR (400 MHz, CD$_3$OD): δ 8.86 (d, J=5.3 Hz, 1H), 8.38-8.29 (m, 1H), 8.09-8.00 (m, 3H), 7.53-7.43 (m, 4H), 6.63-6.52 (m, 1H), 6.33-6.23 (m, 2H), 5.78-5.70 (m, 1H), 4.62-4.54 (m, 1H), 4.50-4.39 (m, 1H), 4.05-3.52 (m, 4H).

Example 719: (R)-4-Oxo-5-(5-phenoxypyrimidin-2-yl)-N-(piperidin-3-yl)-4,5-dihydro-3H-1-thia-3,5,8-triazaacenaphthylene-2-carboxamide

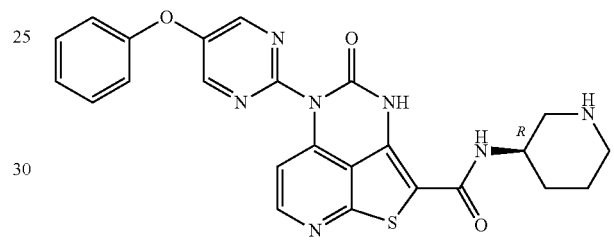

The title compound was prepared using analogous conditions described in Method 1, steps A, C-H, in Example 1, and using 5-bromopyrimidin-2-amine, N,N-dimethylglycine, and Cs$_2$CO$_3$ in place of 5-fluoro-2-nitrotoluene and K$_2$CO$_3$ in step A, and no step B, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for C$_{24}$H$_{21}$N$_7$O$_3$S, 487.5; m/z found, 488.1 [M+H]$^+$. $^1$H NMR (400 MHz, CD$_3$OD): δ 8.71-8.67 (m, 2H), 8.39-8.35 (m, 2H), 7.54-7.46 (m, 2H), 7.34-7.23 (m, 3H), 6.35-6.31 (m, 1H), 4.34-4.19 (m, 1H), 3.57-3.46 (m, 1H), 3.36-3.32 (m, 1H), 3.02-2.89 (m, 2H), 2.15-1.99 (m, 2H), 1.88-1.66 (m, 2H).

Example 720: (R)-5-(2-Cyclopentylpyridin-4-yl)-4-oxo-N-(piperidin-3-yl)-4,5-dihydro-3H-1-thia-3,5,8-triazaacenaphthylene-2-carboxamide

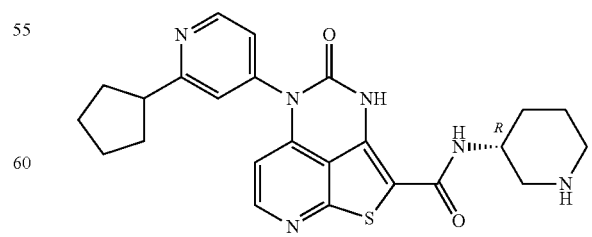

The title compound was prepared using analogous conditions described in Example 677, step A, and using cyclopenten-1-ylboronic acid in place of cyclohexen-1-ylboronic acid in step A, and using Method 1, steps C-H in Example 1, and using 2-cyclopentylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{24}H_{26}N_6O_2S$, 462.6; m/z found, 463.3 [M+H]$^+$. $^1$H NMR (400 MHz, CD$_3$OD): δ 8.73-8.66 (m, 1H), 8.39 (s, 1H), 8.34-8.29 (m, 1H), 7.53-7.48 (m, 1H), 7.44-7.33 (m, 1H), 6.26-6.15 (m, 1H), 4.32-4.22 (m, 1H), 3.58-3.47 (m, 1H), 3.38-3.31 (m, 2H), 3.01-2.90 (m, 2H), 2.18-2.02 (m, 4H), 1.90-1.69 (m, 8H).

Example 721: (R)-5-(3-Isobutylphenyl)-4-oxo-N-(piperidin-3-yl)-4,5-dihydro-3H-1-thia-3,5,8-triazaacenaphthylene-2-carboxamide

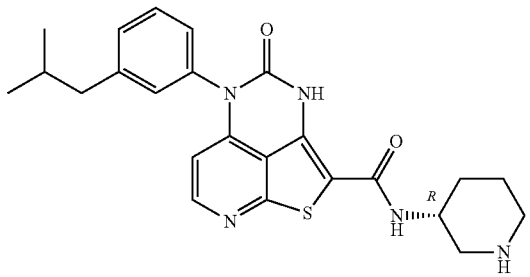

The title compound was prepared using analogous conditions described in Example 677, step A, and using 1-bromo-3-nitrobenzene and isobutylboronic acid in place of 2-chloro-4-nitropyridine and cyclohexen-1-ylboronic acid in step A to give 3-isobutylaniline. This was followed by Method 1, steps C-H in Example 1, and using 3-isobutylaniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{24}H_{27}N_5O_2S$, 449.6; m/z found, 450.2 [M+H]$^+$. $^1$H NMR (400 MHz, CD$_3$OD): δ 8.43 (s, 1H), 8.33-8.27 (m, 1H), 7.54-7.47 (m, 1H), 7.36-7.32 (m, 1H), 7.25-7.19 (m, 2H), 6.12-6.05 (m, 1H), 4.32-4.17 (m, 1H), 3.55-3.44 (m, 1H), 3.36-3.31 (m, 1H), 3.02-2.85 (m, 2H), 2.60-2.53 (m, 2H), 2.15-1.99 (m, 2H), 1.96-1.69 (m, 3H), 0.95-0.91 (m, 6H).

Example 722: (R)—N-(1-Acryloylpiperidin-3-yl)-5-(*R)-(6-isobutyl-4-methylpyridin-3-yl)-4-oxo-4,5-dihydro-3H-1-thia-3,5,8-triazaacenaphthylene-2-carboxamide The title compound was prepared in a manner analogous to Method 1, Step G, in Example 1, and using 5-(*R)-(6-Isobutyl-4-methylpyridin-3-yl)-4-oxo-4,5-dihydro-3H-1-thia-3,5,8-triazacenaphthylene-2-carboxylic acid (Intermediate 83) and 1-[(3R)-3-amino-1-piperidyl]prop-2-en-1-one (Intermediate 15) in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate. MS (ESI): mass calcd. for $C_{27}H_{30}N_6O_3S$, 518.6; m/z found, 519.1 [M+H]$^+$. $^1$H NMR (400 MHz, CD$_3$OD): δ 8.43-8.39 (s, 1H), 8.38-8.30 (d, J=5.5 Hz, 1H), 7.44-7.37 (s, 1H), 6.86-6.74 (m, 1H), 6.25-6.15 (d, J=16.5 Hz, 1H), 6.07-6.00 (d, J=5.5 Hz, 1H), 5.79-5.68 (m, 1H), 4.60-4.26 (m, 1H), 4.24-3.92 (m, 2H), 3.25-3.11 (m, 1H), 3.00-2.84 (m, 1H), 2.76-2.69 (d, J=7.2 Hz, 2H), 2.20-2.02 (m, 2H), 1.93-1.83 (m, 1H), 1.81-1.68 (m, 1H), 1.67-1.51 (m, 1H), 1.05-0.90 (dd, J=6.8, 1.5 Hz, 6H).

Example 723: (R)-4-Oxo-5-(6-phenylpyrimidin-4-yl)-N-(piperidin-3-yl)-4,5-dihydro-3H-1-thia-3,5,8-triazaacenaphthylene-2-carboxamide

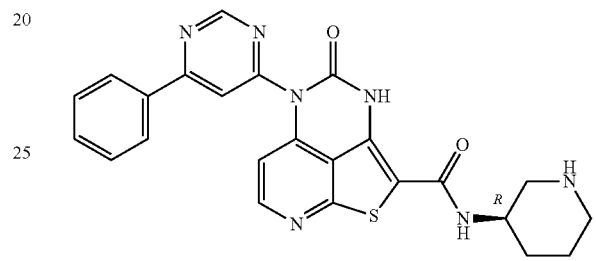

The title compound was prepared using analogous conditions described in Example 677, step A, and using 6-chloropyrimidin-4-amine and phenylboronic acid in place of 2-chloro-4-nitropyridine and cyclohexen-1-ylboronic acid and no Pd/C step in step A, and using Method 1, steps C-H in Example 1, and using 6-phenylpyrimidin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{24}H_{21}N_7O_2S$, 471.5; m/z found, 472.1 [M+H]$^+$. $^1$H NMR (400 MHz, CD$_3$OD): δ 9.35-9.28 (m, 1H), 8.42 (s, 1H), 8.37-8.32 (m, 1H), 8.25-8.17 (m, 3H), 7.58-7.50 (m, 3H), 6.61-6.55 (m, 1H), 4.30-4.20 (m, 1H), 3.54-3.44 (m, 1H), 3.36-3.31 (m, 1H), 3.01-2.89 (m, 2H), 2.15-1.99 (m, 2H), 1.88-1.71 (m, 2H).

Example 724: (R)—N-(1-Acryloylpyrrolidin-3-yl)-5-(*R)-(4-methyl-2-phenoxypyrimidin-5-yl)-4-oxo-4,5-dihydro-3H-1-thia-3,5,8-triazaacenaphthylene-2-carboxamide

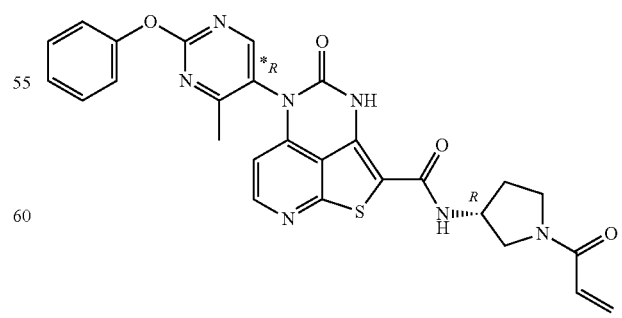

The title compound was prepared using analogous conditions described in Method 1, steps A, C-G, (including Chiral Separation Method A after step F to obtain the *R atropisomer), in Example 1, and using 2-chloro-4-methyl-pyrimidin-5-amine, 2-(dimethylamino)acetic acid, and Cs$_2$CO$_3$ in place of 5-fluoro-2-nitrotoluene and K$_2$CO$_3$ in step A, and no step B, and using 1-[(3R)-3-aminopyrrolidin-1-yl]prop-2-en-1-one (Intermediate 5), 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for C$_{27}$H$_{23}$N$_7$O$_4$S, 541.6; m/z found, 542.0 [M+H]$^+$. 1H NMR (400 MHz, MeOD) δ 8.55 (d, J=2.2 Hz, 1H), 8.38 (d, J=5.6 Hz, 1H), 7.49-7.42 (m, 2H), 7.31-7.22 (m, 3H), 6.68-6.55 (m, 1H), 6.32-6.25 (m, 2H), 5.79-5.71 (m, 1H), 4.70-4.55 (m, 1H), 4.05-3.46 (m, 4H), 2.40-2.03 (m, 5H).

Example 725: (R)-5-(4-Methyl-[1,1'-biphenyl]-3-yl)-4-oxo-N-(piperidin-3-yl)-4,5-dihydro-3H-1-thia-3,5,8-triazaacenaphthylene-2-carboxamide

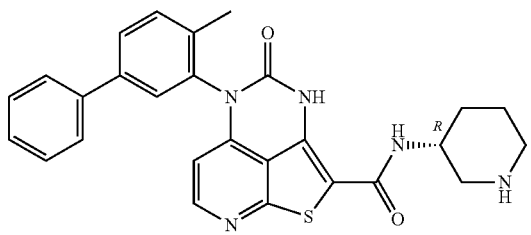

The title compound was prepared using analogous conditions described in Example 677, step A, and using 4-bromo-1-methyl-2-nitrobenzene and phenylboronic acid in place of 2-chloro-4-nitropyridine and cyclohexen-1-ylboronic acid in step A, and using Method 1, steps C-H in Example 1, and using 2-methyl-5-phenylaniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for C$_{27}$H$_{25}$N$_5$O$_2$S, 483.6; m/z found, 484.4 [M+H]$^+$. $^1$H NMR (400 MHz, CD$_3$OD): δ 8.28-8.16 (m, 1H), 7.75-7.67 (m, 1H), 7.65-7.60 (m, 2H), 7.58-7.56 (m, 1H), 7.54-7.49 (m, 1H), 7.45-7.36 (m, 2H), 7.34-7.26 (m, 1H), 6.01-5.92 (m, 1H), 4.26-4.12 (m, 1H), 3.40-3.31 (m, 1H), 3.20-3.10 (m, 1H), 2.96-2.72 (m, 2H), 2.18 (s, 3H), 2.10-1.88 (m, 2H), 1.82-1.66 (m, 2H).

Example 12: (R)—N-(1-Acryloylpiperidin-3-yl)-5-(*S)-(6-cyclobutoxy-4-methylpyridin-3-yl)-4-oxo-4,5-dihydro-3H-1-thia-3,5,8-triazaacenaphthylene-2-carboxamide

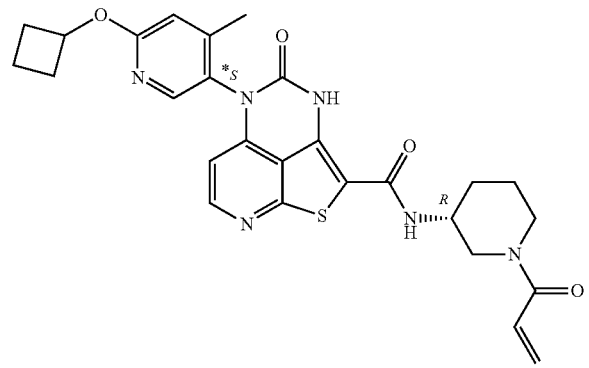

(R)—N-(1-Acryloylpiperidin-3-yl)-5-(6-cyclobutoxy-4-methylpyridin-3-yl)-4-oxo-4,5-dihydro-3H-1-thia-3,5,8-triazaacenaphthylene-2-carboxamide (Example 672) was resolved by chiral SFC (Stationary phase: Chiralpak AS-H 5 μm 250*20 mm, Mobile phase: 70% CO$_2$, 30% MeOH) to yield the title compound. MS (ESI): mass calcd. for C$_{27}$H$_{28}$N$_6$O$_4$S, 532.6; m/z found, 533.1 [M+H]$^+$. $^1$H NMR (400 MHz, CD$_3$OD): δ 8.33 (d, J=5.6 Hz, 1H), 8.06 (s, 1H), 6.87-6.73 (m, 2H), 6.20 (d, J=16.7 Hz, 1H), 6.11 (d, J=5.6 Hz, 1H), 5.79-5.69 (m, 1H), 5.24-5.12 (m, 1H), 4.58-4.26 (m, 1H), 4.21-3.91 (m, 2H), 3.26-3.12 (m, 1H), 3.01-2.84 (m, 1H), 2.54-2.44 (m, 2H), 2.23-2.12 (m, 5H), 2.11-2.03 (m, 1H), 1.92-1.83 (m, 2H), 1.79-1.67 (m, 2H), 1.66-1.52 (m, 1H).

Example 727: (R)-5-(2-Isopropylpyridin-4-yl)-4-oxo-N-(piperidin-3-yl)-4,5-dihydro-3H-1-thia-3,5,8-triazaacenaphthylene-2-carboxamide

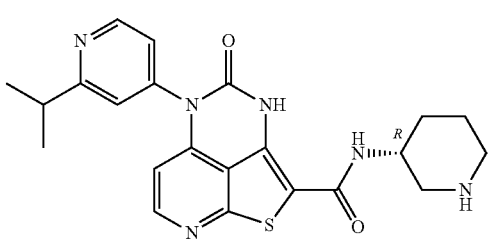

The title compound was prepared using analogous conditions described in Example 677, step A, and using 2-chloro-4-nitropyridine and 2-isopropenyl-4,4,5,5-tetramethyl-1,3,2-dioxaborolane in place of 2-chloro-4-nitropyridine and cyclohexen-1-ylboronic acid in step A, and using Method 1, steps C-H in Example 1, and using 2-isopropylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for C$_{22}$H$_{24}$N$_6$O$_2$S, 436.5; m/z found, 437.3 [M+H]$^+$. $^1$H NMR (400 MHz, CD$_3$OD): δ 8.70 (d, J=5.3 Hz, 1H), 8.44 (s, 1H), 8.32 (d, J=5.6 Hz, 1H), 7.49 (s, 1H), 7.39 (d, J=5.3 Hz, 1H), 6.20 (d, J=5.6 Hz, 1H), 4.32-4.21 (m, 1H), 3.57-3.46 (m, 1H), 3.39-3.31 (m, 1H), 3.21-3.12 (m, 1H), 3.01-2.90 (m, 2H), 2.14-2.01 (m, 2H), 1.92-1.70 (m, 2H), 1.34 (d, J=7.0 Hz, 6H).

Example 728: (R)-5-(*R)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide

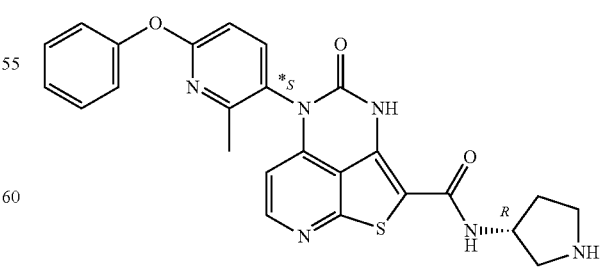

The title compound was prepared using analogous conditions described in Method 1, steps A-H, (including Chiral Resolution Method A after step F to obtain the *R atropisomer) in Example 1, and using 6-chloro-2-methyl-3-nitropyridine in place of 5-fluoro-2-nitrotoluene in step A, and using Pd/C in place of Fe in step B, and using tert-butyl (3R)-3-aminopyrrolidine-1-carboxylate and diisopropylethylamine in place of tert-butyl (3R,5R)-3-amino-5-fluoropiperidine-1-carboxylate and triethylamine in step G, to give the title compound. MS (ESI): mass calcd. for $C_{25}H_{22}N_6O_3S$, 486.6; m/z found, 487.0 [M+H]$^+$. $^1$H NMR (600 MHz, CD$_3$OD): δ 8.60-8.56 (d, J=6.5 Hz, 1H), 7.93-7.87 (d, J=8.7 Hz, 1H), 7.50-7.44 (m, 2H), 7.31-7.26 (m, 1H), 7.26-7.20 (m, 2H), 7.01-6.97 (d, J=8.6 Hz, 1H), 6.58-6.54 (d, J=6.5 Hz, 1H), 4.67-4.60 (m, 1H), 3.63-3.58 (m, 2H), 3.48-3.36 (m, 2H), 2.49-2.39 (m, 1H), 2.32-2.30 (s, 3H), 2.29-2.20 (m, 1H).

Example 729: (R)-5-(5-Methyl-2-phenylpyridin-4-yl)-4-oxo-N-(piperidin-3-yl)-4,5-dihydro-3H-1-thia-3,5,8-triazaacenaphthylene-2-carboxamide

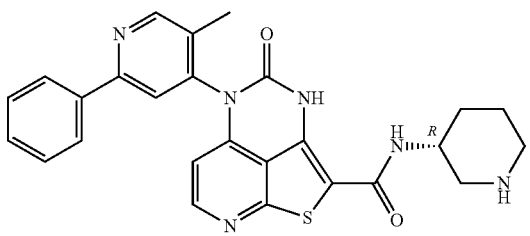

The title compound was prepared using analogous conditions described in Example 677, step A, and using 2-chloro-5-methylpyridin-4-amine, acetic anhydride, DMAP, and phenylboronic acid in place of 2-chloro-4-nitropyridine and cyclohexen-1-ylboronic acid and no Pd/C reduction in step A, and using Method 1, steps C-H in Example 1, and using 5-methyl-2-phenylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{26}H_{24}N_6O_2S$, 484.6; m/z found, 485.4 [M+H]$^+$. $^1$H NMR (400 MHz, CD$_3$OD): δ 8.76 (s, 1H), 8.44 (s, 1H), 8.37-8.32 (m, 1H), 8.02-7.98 (m, 2H), 7.94 (s, 1H), 7.53-7.41 (m, 3H), 6.20-6.12 (m, 1H), 4.32-4.22 (m, 1H), 3.55-3.48 (m, 1H), 3.37-3.31 (m, 1H), 3.00-2.92 (m, 2H), 2.24 (s, 3H), 2.12-2.03 (m, 2H), 1.88-1.71 (m, 2H).

Example 730: (R)-5-(4-(2-Isopropoxyethoxy)-2-methylphenyl)-4-oxo-N-(piperidin-3-yl)-4,5-dihydro-3H-1-thia-3,5,8-triazaacenaphthylene-2-carboxamide

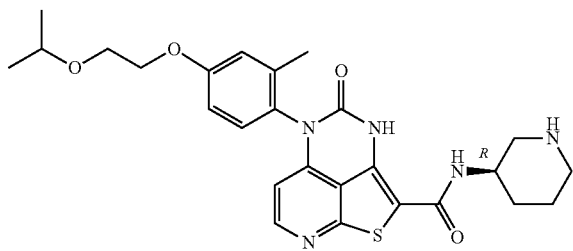

The title compound was prepared using analogous conditions described in Method 1, steps A-H, in Example 1, and using 4-fluoro-2-methyl-1-nitrobenzene and 2-isopropoxyethanol in place of 5-fluoro-2-nitrotoluene and phenol in step A, and using Pd/C in place of Fe in step B, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{26}H_{31}N_5O_4S$, 509.6; m/z found, 510.2 [M+H]$^+$. $^1$H NMR (400 MHz, CD$_3$OD): δ 8.01 (d, J=5.7 Hz, 1H), 7.12-7.07 (m, 1H), 7.02-6.97 (m, 1H), 6.95-6.88 (m, 1H), 5.72 (d, J=5.7 Hz, 1H), 4.18-4.11 (m, 2H), 4.02-3.92 (m, 1H), 3.83-3.78 (m, 2H), 3.76-3.69 (m, 1H), 3.21-3.12 (m, 1H), 2.93-2.83 (m, 1H), 2.68-2.55 (m, 2H), 2.11 (s, 3H), 2.07-2.00 (m, 1H), 1.85-1.75 (m, 1H), 1.69-1.52 (m, 2H), 1.19 (d, J=6.1, 6H).

Example 731: (R)-5-(2-Cyclohexylpyridin-4-yl)-4-oxo-N-(piperidin-3-yl)-4,5-dihydro-3H-1-thia-3,5,8-triazaacenaphthylene-2-carboxamide

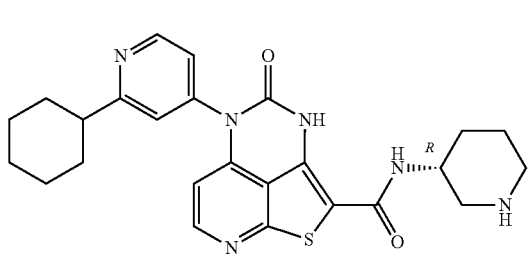

The title compound was prepared using analogous conditions described in Method 1, steps C-H in Example 1, and using 2-cyclohexylpyridin-4-amine (Example 677, step A) in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{25}H_{28}N_6O_2S$, 476.6; m/z found, 477.2 [M+H]$^+$. $^1$H NMR (400 MHz, CD3OD and DMSO-d$_6$): δ 8.62 (d, J=5.3 Hz, 1H), 8.27-8.24 (m, 2H), 7.36 (s, 1H), 7.27 (d, J=5.3 Hz, 1H), 6.10 (d, J=5.6 Hz, 1H), 4.24-4.16 (m, 1H), 3.42-3.34 (m, 1H), 3.25-3.19 (m, 1H), 2.89-2.81 (m, 2H), 2.77-2.67 (m, 1H), 1.97-1.63 (m, 9H), 1.56-1.45 (m, 2H), 1.41-1.30 (m, 2H), 1.25-1.16 (m, 1H).

Example 732: (R)—N-(1-Acryloylpiperidin-3-yl)-5-(6-isopropoxy-2-methylpyridin-3-yl)-4-oxo-4,5-dihydro-3H-1-thia-3,5,8-triazaacenaphthylene-2-carboxamide

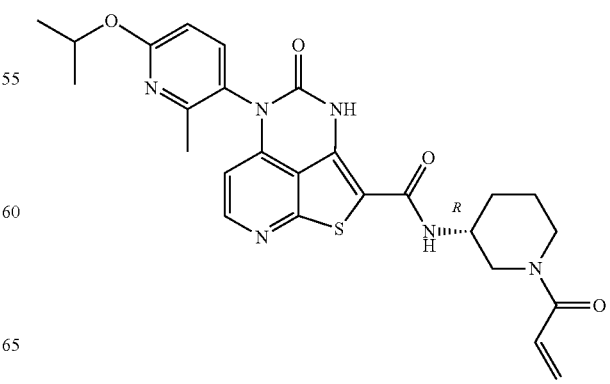

The title compound was prepared using analogous conditions described in Method 1, steps A-G, in Example 1, and using 6-fluoro-2-methyl-3-nitropyridine and 2-propanol in place of 5-fluoro-2-nitrotoluene and phenol in step A, and using Zn in place of Fe in step B, and using 1-[(3R)-3-amino-1-piperidyl]prop-2-en-1-one (Intermediate 15), 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for $C_{26}H_{28}N_6O_4S$, 520.6; m/z found, 521.1 [M+H]$^+$. $^1$H NMR (500 MHz, CD$_3$OD): δ 8.35 (d, J=5.5 Hz, 1H), 7.60 (d, J=8.6 Hz, 1H), 6.85-6.70 (m, 2H), 6.26-6.17 (m, 1H), 6.11 (d, J=5.5 Hz, 1H), 5.77-5.72 (m, 1H), 5.39-5.29 (m, 1H), 4.58-4.26 (m, 1H), 4.20-3.92 (m, 2H), 3.22-3.12 (m, 1H), 2.99-2.85 (m, 1H), 2.26 (s, 3H), 2.13-2.04 (m, 1H), 1.92-1.84 (m, 1H), 1.81-1.68 (m, 1H), 1.65-1.54 (m, 1H), 1.40-1.34 (m, 6H).

Example 733: (R)-5-(3-Methyl-2-phenylpyridin-4-yl)-4-oxo-N-(piperidin-3-yl)-4,5-dihydro-3H-1-thia-3,5,8-triazaacenaphthylene-2-carboxamide

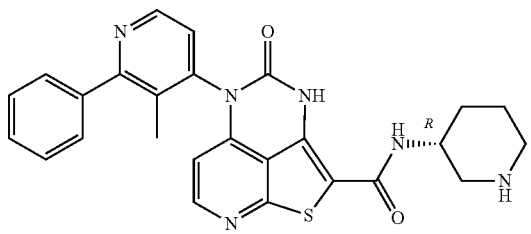

The title compound was prepared using analogous conditions described in Method 1, steps C-H in Example 1, and using 3-methyl-2-phenylpyridin-4-amine (Intermediate 48) in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{26}H_{24}N_6O_2S$, 484.6; m/z found, 485.4 [M+H]$^+$. $^1$H NMR (400 MHz, CD$_3$OD): δ 8.66 (d, J=5.2 Hz, 1H), 8.38 (d, J=5.5 Hz, 1H), 7.58-7.47 (m, 6H), 6.20 (d, J=5.5 Hz, 1H), 4.31-4.23 (m, 1H), 3.55-3.47 (m, 1H), 3.37-3.32 (m, 1H), 3.00-2.88 (m, 2H), 2.15 (s, 3H), 2.13-2.04 (m, 2H), 1.88-1.73 (m, 2H).

Example 734: (R)—N-(1-Acryloylpiperidin-3-yl)-5-(2-methyl-6-phenylpyridin-4-yl)-4-oxo-4,5-dihydro-3H-1-thia-3,5,8-triazaacenaphthylene-2-carboxamide

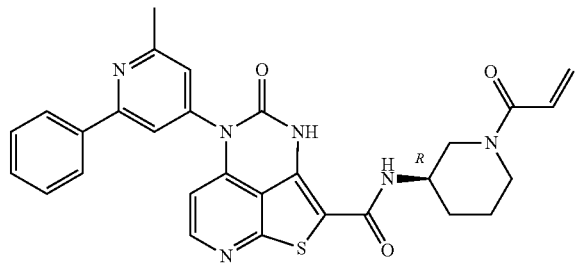

The title compound was prepared using analogous conditions described in Example 677, step A, and using 2-chloro-6-methylpyridin-4-amine, acetic anhydride, and phenylboronic acid in place of 2-chloro-4-nitropyridine and cyclohexen-1-ylboronic acid and no Pd/C reduction in step A, and using Method 1, steps C-I in Example 1, and using 2-methyl-6-phenylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{29}H_{26}N_6O_3S$, 538.6; m/z found, 539.4 [M+H]$^+$. $^1$H NMR (400 MHz, CD$_3$OD): δ 8.31 (d, J=5.6 Hz, 1H), 8.04-7.98 (m, 2H), 7.82 (s, 1H), 7.52-7.39 (m, 3H), 7.34 (s, 1H), 6.83-6.70 (m, 1H), 6.27 (d, J=5.5 Hz, 1H), 6.22-6.11 (m, 1H), 5.77-5.62 (m, 1H), 4.57-4.26 (m, 1H), 4.22-3.90 (m, 2H), 3.20-3.08 (m, 1H), 2.93-2.79 (m, 1H), 2.68 (s, 3H), 2.10-1.99 (m, 1H), 1.89-1.79 (m, 1H), 1.78-1.62 (m, 1H), 1.59-1.45 (m, 1H).

Example 735: (R)-5-(2-Methyl-6-phenylpyridin-4-yl)-4-oxo-N-(piperidin-3-yl)-4,5-dihydro-3H-1-thia-3,5,8-triazaacenaphthylene-2-carboxamide

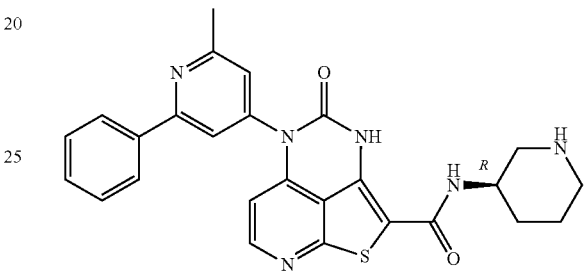

The title compound was prepared using analogous conditions described in Example 677, step A, and using 2-chloro-6-methylpyridin-4-amine, acetic anhydride, and phenylboronic acid in place of 2-chloro-4-nitropyridine and cyclohexen-1-ylboronic acid and no Pd/C reduction in step A, and using Method 1, steps C-H in Example 1, and using 2-methyl-6-phenylpyridin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{26}H_{24}N_6O_2S$, 484.6; m/z found, 485.4 [M+H]$^+$. $^1$H NMR (400 MHz, CD$_3$OD): δ 8.47-8.42 (m, 1H), 8.40-8.27 (m, 1H), 8.07-7.97 (m, 2H), 7.79 (s, 1H), 7.53-7.24 (m, 4H), 6.36-6.20 (m, 1H), 4.34-4.19 (m, 1H), 3.62-3.49 (m, 1H), 3.27-3.13 (m, 1H), 3.01-2.87 (m, 2H), 2.74-2.60 (m, 3H), 2.14-1.97 (m, 2H), 1.91-1.66 (m, 2H).

Example 13: (R)—N-(1-Acryloylpiperidin-3-yl)-5-(*R)-(6-cyclobutoxy-2-methylpyridin-3-yl)-4-oxo-4,5-dihydro-3H-1-thia-3,5,8-triazaacenaphthylene-2-carboxamide

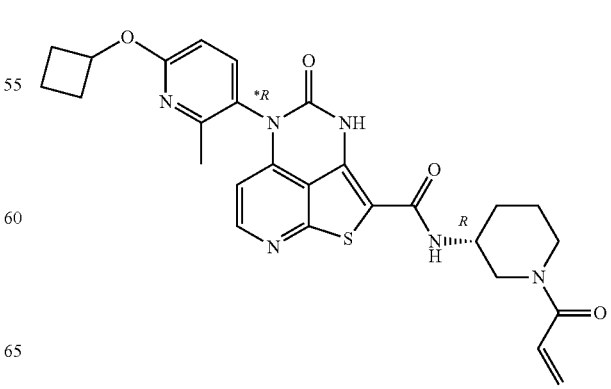

(R)—N-(1-Acryloylpiperidin-3-yl)-5-(6-cyclobutoxy-4-methylpyridin-3-yl)-4-oxo-4,5-dihydro-3H-1-thia-3,5,8-triazaacenaphthylene-2-carboxamide (Example 672) was resolved by chiral SFC (Stationary phase: Chiralpak AS-H 5 m 250*20 mm, Mobile phase: 70% $CO_2$, 30% MeOH) to yield the title compound. MS (ESI): mass calcd. for $C_{27}H_{28}N_6O_4S$, 532.6; m/z found, 533.1 [M+H]$^+$. $^1$H NMR (500 MHz, CD$_3$OD): δ 8.33 (d, J=5.5 Hz, 1H), 7.63 (d, J=8.6 Hz, 1H), 6.88-6.70 (m, 2H), 6.20 (dd, J=16.7, 4.7 Hz, 1H), 6.08 (d, J=5.5 Hz, 1H), 5.73 (t, J=11.3 Hz, 1H), 5.26-5.16 (m, 1H), 4.61-4.25 (m, 1H), 4.21-3.91 (m, 2H), 3.23-3.13 (m, 1H), 3.02-2.86 (m, 1H), 2.55-2.44 (m, 2H), 2.25 (s, 3H), 2.21-2.11 (m, 2H), 2.08 (d, J=12.3 Hz, 1H), 1.92-1.83 (m, 2H), 1.81-1.67 (m, 2H), 1.64-1.54 (m, 1H).

Example 737: (R)—N-(1-Acryloylpiperidin-3-yl)-5-(*S)-(3-methyl-2-phenylpyridin-4-yl)-4-oxo-4,5-dihydro-3H-1-thia-3,5,8-triazaacenaphthylene-2-carboxamide

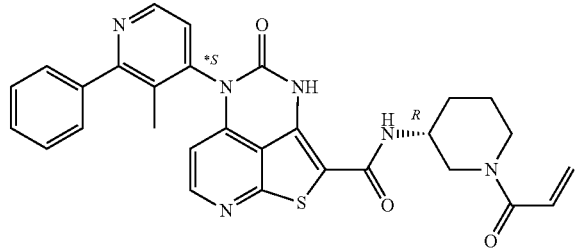

The title compound was prepared using analogous conditions described in Method 1, steps C-G, (including Chiral Resolution Method A after step F to obtain the *S atropisomer) in Example 1, and using 3-methyl-2-phenylpyridin-4-amine (Intermediate 48) in place of 2-methyl-4-phenoxyaniline in step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for $C_{29}H_{26}N_6O_3S$, 538.6; m/z found, 539.4 [M+H]$^+$. $^1$H NMR (400 MHz, CD$_3$OD): δ 8.66 (d, J=4.9 Hz, 1H), 8.35 (d, J=5.3 Hz, 1H), 7.57-7.43 (m, 6H), 6.83-6.71 (m, 1H), 6.24-6.12 (m, 2H), 5.78-5.66 (m, 1H), 4.60-4.28 (m, 1H), 4.22-3.88 (m, 2H), 3.21-3.09 (m, 1H), 2.97-2.80 (m, 1H), 2.15 (s, 3H), 2.09-2.00 (m, 1H), 1.90-1.82 (m, 1H), 1.79-1.66 (m, 1H), 1.61-1.51 (m, 1H).

Example 738: (R)-4-Oxo-N-(piperidin-3-yl)-5-(3-(tetrahydro-2H-pyran-4-yl)phenyl)-4,5-dihydro-3H-1-thia-3,5,8-triazaacenaphthylene-2-carboxamide

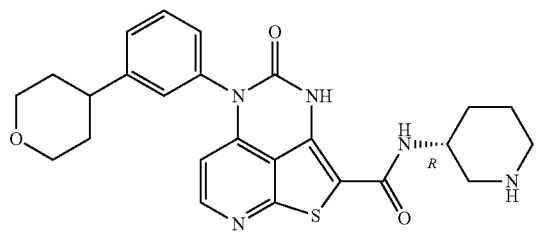

The title compound was prepared using the procedures found in Example 534, steps A-B, and using 3-tetrahydropyran-4-ylaniline (Intermediate 47) in place of 3-cyclobutylaniline in step A, to yield the title compound. MS (ESI): mass calcd. for $C_{25}H_{27}N_5O_3S$, 477.6; m/z found, 478.0 [M+H]$^+$. $^1$H NMR (500 MHz, CD$_3$OD): δ 8.49 (d, J=6.6 Hz, 1H), 7.60 (t, J=7.8 Hz, 1H), 7.52 (d, J=7.9 Hz, 1H), 7.39 (s, 1H), 7.34-7.29 (m, 1H), 6.38 (d, J=6.6 Hz, 1H), 4.35-4.26 (m, 1H), 4.08-4.00 (m, 2H), 3.61-3.52 (m, 3H), 3.36 (d, J=12.8 Hz, 1H), 3.05-2.97 (m, 2H), 2.96-2.89 (m, 1H), 2.15-2.06 (m, 2H), 1.92-1.75 (m, 6H).

Example 739: (R)-tert-Butyl 3-(4-oxo-5-(3-(tetrahydro-2H-pyran-4-yl)phenyl)-4,5-dihydro-3H-1-thia-3,5,8-triazaacenaphthylene-2-carboxamido)piperidine-1-carboxylate

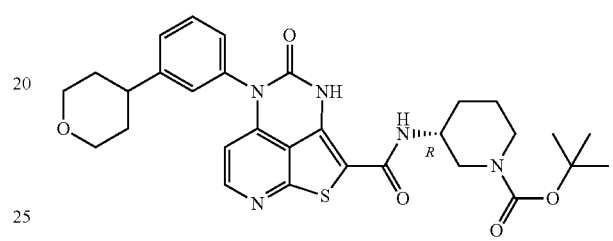

The title compound was prepared using the procedures found in Example 534, step A, and using 3-tetrahydropyran-4-ylaniline (Intermediate 47) in place of 3-cyclobutylaniline in step A, to yield the title compound. MS (ESI): mass calcd. for $C_{30}H_{35}N_5O_5S$, 577.7; m/z found, 578.1 [M+H]$^+$. $^1$H NMR (500 MHz, CD$_3$OD): δ 8.28 (d, J=5.6 Hz, 1H), 7.55 (t, J=7.8 Hz, 1H), 7.46 (d, J=7.8 Hz, 1H), 7.35 (s, 1H), 7.28 (d, J=7.9 Hz, 1H), 6.08 (d, J=5.6 Hz, 1H), 4.16-4.00 (m, 3H), 3.97-3.85 (m, 2H), 3.61-3.51 (m, 2H), 3.01-2.73 (m, 3H), 2.06-1.98 (m, 1H), 1.86-1.74 (m, 5H), 1.68-1.50 (m, 2H), 1.46 (s, 9H).

Example 740: (R)-4-Oxo-5-(6-phenylpyridazin-4-yl)-N-(piperidin-3-yl)-4,5-dihydro-3H-1-thia-3,5,8-triazaacenaphthylene-2-carboxamide

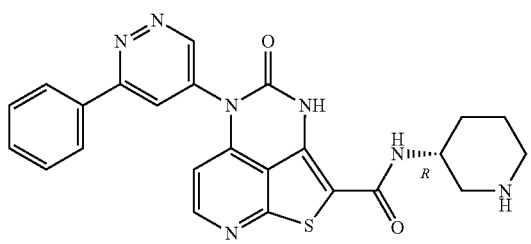

The title compound was prepared using analogous conditions described in Example 677, step A, and using 6-chloropyridazin-4-amine and phenylboronic acid in place of 2-chloro-4-nitropyridine and cyclohexen-1-ylboronic acid and no Pd/C reduction in step A, and using Method 1, steps C-H in Example 1, and using 6-phenylpyridazin-4-amine in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{24}H_{21}N_7O_2S$, 471.5; m/z found, 472.3 [M+H]$^+$. $^1$H NMR (400 MHz, CD$_3$OD): δ 9.38-9.26

(m, 1H), 8.50-8.39 (m, 2H), 8.33 (d, J=5.6 Hz, 1H), 8.19-8.10 (m, 2H), 7.62-7.51 (m, 3H), 6.40 (d, J=5.6 Hz, 1H), 4.30-4.20 (m, 1H), 3.55-3.47 (m, 1H), 3.36-3.30 (m, 1H), 3.02-2.92 (m, 2H), 2.11-2.00 (m, 2H), 1.89-1.69 (m, 2H).

Example 741: (R)-4-Oxo-5-(6-phenoxypyridin-3-yl)-N-(pyrrolidin-3-yl)-4,5-dihydro-3H-1-thia-3,5,8-triazaacenaphthylene-2-carboxamide

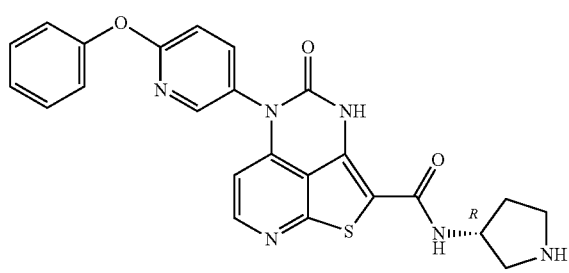

The title compound was prepared using analogous conditions described in Method 1, steps A-H, in Example 1, and using 2-chloro-5-nitropyridine in place of 5-fluoro-2-nitrotoluene in step A, and using Pd/C in place of Fe in step B, and using tert-butyl (3R)-3-aminopyrrolidine-1-carboxylate in place of tert-butyl (3R,5R)-3-amino-5-fluoropiperidine-1-carboxylate (Intermediate 1) in step G, to give the title compound. MS (ESI): mass calcd. for $C_{24}H_{20}N_6O_3S$, 472.5; m/z found, 473.0 [M+H]$^+$. $^1$H NMR (500 MHz, CDCl$_3$): δ 9.46 (s, 1H), 8.15 (s, 2H), 7.76 (s, 2H), 7.26 (s, 6H), 5.98 (s, 1H), 4.74 (d, J=71.0 Hz, 1H), 3.49 (s, 5H), 2.18 (t, J=61.7 Hz, 2H).

Example 742: (R)—N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide

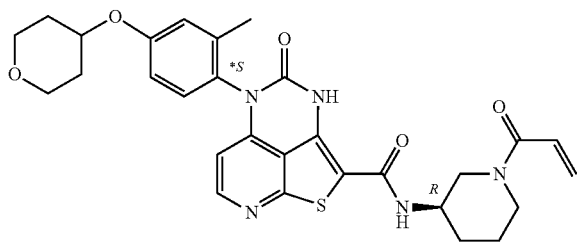

The title compound was prepared in a manner analogous to Method 1, steps D-I in Example 1, and using 2-chloro-4-(2-methyl-4-tetrahydropyran-4-yloxyanilino)pyridine-3-carbonitrile (Intermediate 31) in place of 2-chloro-4-(2-methyl-4-phenoxyanilino)pyridine-3-carbonitrile in step D, and using Chiral Resolution Method A after step F to obtain the *S atropisomer, and using tert-butyl (3R)-3-aminopiperidine-1-carboxylate in place of tert-butyl (3R,5R)-3-amino-5-fluoropiperidine-1-carboxylate (Intermediate 1) in step G. MS (ESI): mass calcd. for $C_{29}H_{31}N_5O_5S$, 561.7; m/z found, 562.1 [M+H]$^+$. $^1$H NMR (400 MHz, CD$_3$OD): δ 8.31-8.27 (m, 1H), 7.25-7.20 (m, 1H), 7.05-7.01 (m, 1H), 6.99-6.95 (m, 1H), 6.81-6.77 (m, 1H), 6.22-6.17 (m, 1H), 6.04-6.00 (m, 1H), 5.74-5.69 (m, 1H), 4.68-4.58 (m, 1H), 4.33-4.11 (m, 1H), 4.07-3.85 (m, 4H), 3.65-3.57 (m, 2H), 3.21-3.18 (m, 1H), 2.93-2.86 (m, 1H), 2.11 (s, 3H), 2.09-2.02 (m, 3H), 1.89-1.83 (m, 1H), 1.80-1.69 (m, 3H), 1.55-1.50 (m, 1H)

Example 743: (R)-tert-Butyl 3-(5-(2-methyl-6-phenoxypyridin-3-yl)-4-oxo-4,5-dihydro-3H-1-thia-3,5,8-triazaacenaphthylene-2-carboxamido)piperidine-1-carboxylate

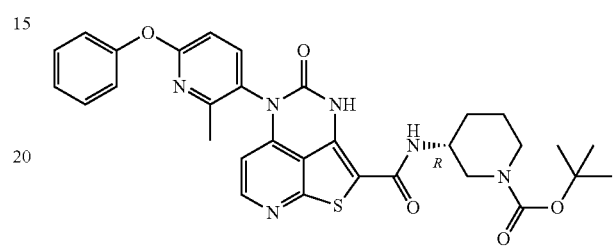

The title compound was prepared using the procedures found in Example 534, step A, and using 2-methyl-6-phenoxypyridin-3-amine (Intermediate 49) in place of 3-cyclobutylaniline in step A, to yield the title compound. MS (ESI): mass calcd. for $C_{31}H_{32}N_6O_5S$, 600.7; m/z found, 601.2 [M+H]$^+$. $^1$H NMR (500 MHz, CD$_3$OD): δ 8.36 (d, J=5.5 Hz, 1H), 7.79 (d, J=8.6 Hz, 1H), 7.47-7.42 (m, 2H), 7.28-7.23 (m, 1H), 7.21-7.18 (m, 2H), 6.91 (d, J=8.6 Hz, 1H), 6.15 (dd, J=5.5, 1.7 Hz, 1H), 4.08-4.01 (m, 1H), 3.97-3.83 (m, 2H), 3.07-2.76 (m, 2H), 2.25 (s, 3H), 2.05-2.01 (m, 1H), 1.82-1.76 (m, 1H), 1.67-1.51 (m, 2H), 1.46 (s, 9H).

Example 744: (R)-5-(6-Cyclobutoxypyridin-3-yl)-4-oxo-N-(piperidin-3-yl)-4,5-dihydro-3H-1-thia-3,5,8-triazaacenaphthylene-2-carboxamide

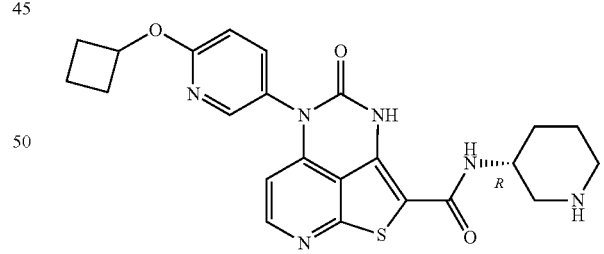

The title compound was prepared using the procedures found in Example 534, steps A-B, and using 6-(cyclobutoxy)pyridin-3-amine in place of 3-cyclobutylaniline in step A, to yield the title compound. MS (ESI): mass calcd. for $C_{23}H_{24}N_6O_3S$, 464.5; m/z found, 465.1 [M+H]$^+$. $^1$H NMR (500 MHz, CD$_3$OD): δ 8.57 (d, J=6.7 Hz, 1H), 8.32 (d, J=2.5 Hz, 1H), 7.93 (dd, J=8.9, 2.7 Hz, 1H), 7.12 (d, J=8.8 Hz, 1H), 6.63 (d, J=6.7 Hz, 1H), 5.31-5.20 (m, 1H), 4.35-4.25 (m, 1H), 3.54 (dd, J=12.3, 4.1 Hz, 1H), 3.36 (d, J=13.7 Hz, 1H), 3.01 (t, J=11.5 Hz, 2H), 2.60-2.48 (m, 2H), 2.28-2.17 (m, 2H), 2.15-2.06 (m, 2H), 1.95-1.70 (m, 4H).

Example 14: N-((3*S,4*R)-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide

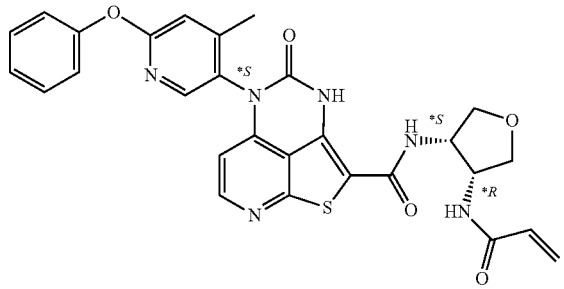

A purification was performed on Example 668 using chiral SFC (Stationary phase: CHIRALPAK IC 5 m 250×21 mm, Mobile phase: 45% CO$_2$, 55% EtOH) to give the title compound as the single enantiomer. MS (ESI): mass calcd. for C$_{28}$H$_{24}$N$_6$O$_5$S, 556.6; m/z found, 557.0 [M+H]$^+$. $^1$H NMR (400 MHz, CD$_3$OD): δ 8.40-8.31 (d, J=5.5 Hz, 1H), 8.13-8.02 (s, 1H), 7.50-7.40 (m, 2H), 7.30-7.15 (m, 3H), 7.10-7.01 (s, 1H), 6.35-6.13 (m, 3H), 5.70-5.59 (dd, J=9.7, 2.3 Hz, 1H), 4.81-4.67 (m, 2H), 4.17-4.03 (m, 2H), 3.88-3.75 (m, 2H), 2.24-2.14 (s, 3H).

Example 746: (R)—N-(1-Acryloylpiperidin-3-yl)-5-(*S)-(4-methyl-2-phenoxypyrimidin-5-yl)-4-oxo-4,5-dihydro-3H-1-thia-3,5,8-triazaacenaphthylene-2-carboxamide

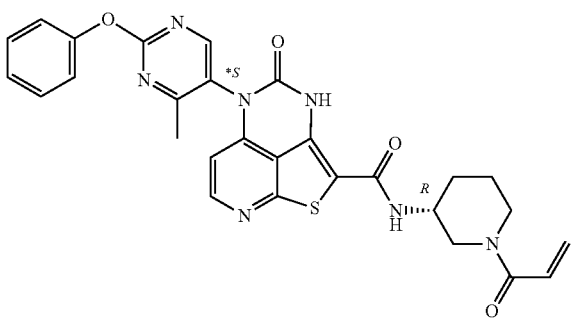

The title compound was prepared using analogous conditions described in Method 1, steps A, C-I, (including Chiral Resolution Method A after step F to obtain the *S atropisomer), in Example 1, and using 2-chloro-4-methylpyrimidin-5-amine, 2-(dimethylamino)acetic acid, and Cs$_2$CO$_3$ in place of 5-fluoro-2-nitrotoluene and K$_2$CO$_3$ in step A, and no step B, and using tert-butyl (3R)-3-aminopiperidine-1-carboxylate and diisopropylethylamine in place of tert-butyl (3R,5R)-3-amino-5-fluoropiperidine-1-carboxylate, HATU, and triethylamine in step G, and using prop-2-enoyl prop-2-enoate and diisopropylethylamine in place of prop-2-enoyl chloride and triethylamine in step I, to give the title compound. MS (ESI): mass calcd. for C$_{28}$H$_{25}$N$_7$O$_4$S, 555.6; m/z found, 556.0 [M+H]$^+$. $^1$H NMR (400 MHz, CDCl$_3$): δ 8.38 (d, J=6.2 Hz, 2H), 7.50-7.40 (m, 2H), 7.33-7.21 (m, 3H), 6.69-6.53 (m, 1H), 6.33 (dd, J=32.8, 16.8 Hz, 1H), 6.08-6.02 (m, 1H), 5.72 (s, 1H), 5.30 (s, 2H), 4.17-4.02 (m, 2H), 3.56 (s, 1H), 3.29 (s, 1H), 2.38 (d, J=6.1 Hz, 3H), 2.04 (s, 3H), 1.71-1.60 (m, 1H), 1.26 (t, J=7.1 Hz, 1H).

Example 747: (R)—N-(1-Acryloylpyrrolidin-3-yl)-5-(*S)-(6-isobutyl-4-methylpyridin-3-yl)-4-oxo-4,5-dihydro-3H-1-thia-3,5,8-triazaacenaphthylene-2-carboxamide

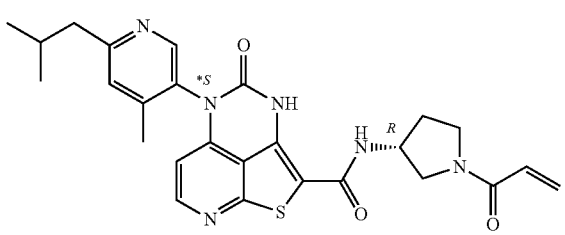

The title compound was prepared in a manner analogous to Example 1, Method 1, Steps G-I, using 5-(*S)-(6-Isobutyl-4-methylpyridin-3-yl)-4-oxo-4,5-dihydro-3H-1-thia-3,5,8-triazaacenaphthylene-2-carboxylic acid (Intermediate 82) and tert-butyl (3R)-3-aminopyrrolidine-1-carboxylate in step G. MS (ESI): mass calcd. for C$_{26}$H$_{28}$N$_6$O$_3$S, 504.6; m/z found, 505.0 [M+H]$^+$. $^1$H NMR (500 MHz, CDCl$_3$): δ 10.74 (s, 1H), 8.40 (d, J=3.1 Hz, 1H), 8.03 (s, 1H), 7.21 (s, 1H), 6.50-6.32 (m, 1H), 6.00 (s, 1H), 5.97-5.91 (m, 1H), 5.70 (ddt, J=19.1, 9.9, 1.7 Hz, 1H), 4.70 (dq, J=17.5, 5.6 Hz, 1H), 3.86-3.58 (m, 4H), 3.12 (q, J=7.4 Hz, 1H), 2.71 (d, J=7.2 Hz, 2H), 2.38 (s, 3H), 1.94-1.37 (m, 3H), 0.99 (d, J=6.6 Hz, 6H).

Example 748: (R)—N-(1-Acryloylpyrrolidin-3-yl)-4-oxo-5-(2-phenoxypyrimidin-5-yl)-4,5-dihydro-3H-1-thia-3,5,8-triazaacenaphthylene-2-carboxamide

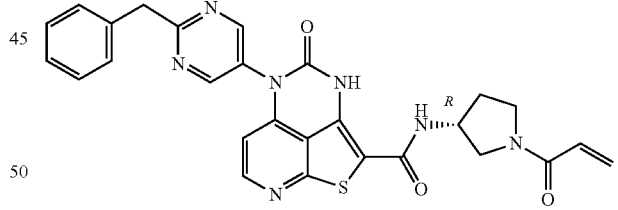

The title compound was prepared using analogous conditions described in Method 1, steps A-G, in Example 1, and using 2-chloro-5-nitropyrimidine in place of 5-fluoro-2-nitrotoluene in step A, and Pd/C in place of Fe in step B, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G, to give the title compound. MS (ESI): mass calcd. for C$_{26}$H$_{21}$N$_7$O$_4$S, 527.6; m/z found, 528.4 [M+H]$^+$. $^1$H NMR (400 MHz, DMSO-d$_6$): δ 10.36 (s, 1H), 8.78 (s, 2H), 8.50-8.32 (m, 2H), 7.54-7.43 (m, 2H), 7.35-7.24 (m, 3H), 6.68-6.50 (m, 1H), 6.45-6.36 (m, 1H), 6.19-6.06 (m, 1H), 5.72-5.61 (m, 1H), 4.58-4.38 (m, 1H), 3.92-3.37 (m, 4H), 2.27-1.84 (m, 2H).

Example 749: (R)—N-(1-Acryloylpyrrolidin-3-yl)-4-oxo-5-(5-phenoxypyrimidin-2-yl)-4,5-dihydro-3H-1-thia-3,5,8-triazaacenaphthylene-2-carboxamide

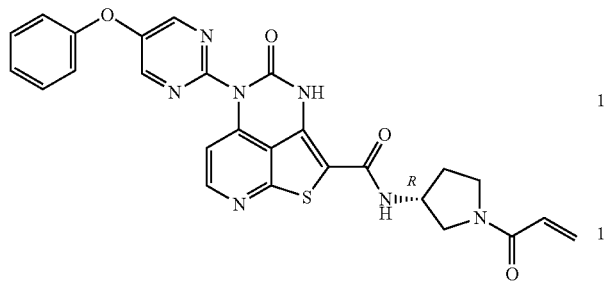

The title compound was prepared using analogous conditions described in Method 1, steps A, C-G, in Example 1, and using 5-bromopyrimidin-2-amine, N,N-dimehtylglycine, CuI, dioxane, and $Cs_2CO_3$ in place of 5-fluoro-2-nitrotoluene, $K_2CO_3$, and DMF in step A, and no step B, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G, to give the title compound. MS (ESI): mass calcd. for $C_{26}H_{21}N_7O_4S$, 527.6; m/z found, 528.1 $[M+H]^+$. $^1H$ NMR (400 MHz, $CD_3OD$): δ 8.68 (s, 2H), 8.32-8.24 (m, 1H), 7.53-7.44 (m, 2H), 7.36-7.21 (m, 3H), 6.68-6.52 (m, 1H), 6.31-6.21 (m, 2H), 5.78-5.68 (m, 1H), 4.65-4.56 (m, 1H), 4.02-3.52 (m, 4H), 2.40-2.00 (m, 2H).

Example 750: (R)-N-(1-Acryloylpiperidin-3-yl)-5-(4-isobutylphenyl)-4-oxo-4,5-dihydro-3H-1-thia-3,5,8-triazaacenaphthylene-2-carboxamide

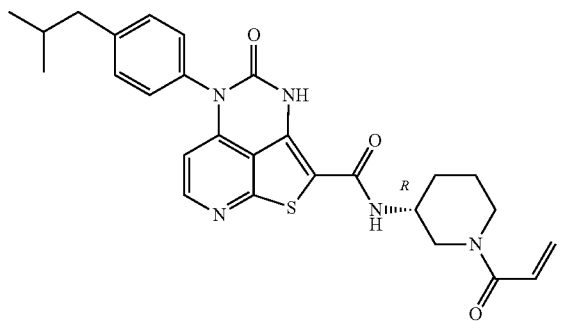

The title compound was prepared using analogous conditions described in Example 677, step A, and using isobutylboronic acid and 1-bromo-4-nitrobenzene in place of cyclohexen-1-ylboronic acid and 2-chloro-4-nitropyridine in step A, and using Method 1, steps C-G in Example 1, and using 4-isobutylaniline in place of 2-methyl-4-phenoxyaniline in step C, and using 1-[(3R)-3-amino-1-piperidyl]prop-2-en-1-one (Intermediate 15) in place of tert-butyl (3R,5R)-3-amino-5-fluoropiperidine-1-carboxylate (Intermediate 1) in step G, to give the title compound. MS (ESI): mass calcd. for $C_{27}H_{29}N_5O_3S$, 503.6; m/z found, 504.1 $[M+H]^+$. $^1H$ NMR (400 MHz, $CD_3OD$): δ 8.38-8.28 (m, 1H), 7.44-7.37 (m, 2H), 7.35-7.29 (m, 2H), 6.85-6.71 (m, 1H), 6.24-6.12 (m, 2H), 5.77-5.66 (m, 1H), 4.61-3.89 (m, 3H), 3.24-3.09 (m, 1H), 2.98-2.80 (m, 1H), 2.64-2.54 (m, 2H), 2.12-2.00 (m, 1H), 1.99-1.80 (m, 2H), 1.77-1.64 (m, 1H), 1.63-1.50 (m, 1H), 0.98-0.92 (m, 6H)

Example 751: (R)—N-(1-Acryloylpiperidin-3-yl)-4-oxo-5-(5-phenylpyridazin-3-yl)-4,5-dihydro-3H-1-thia-3,5,8-triazaacenaphthylene-2-carboxamide

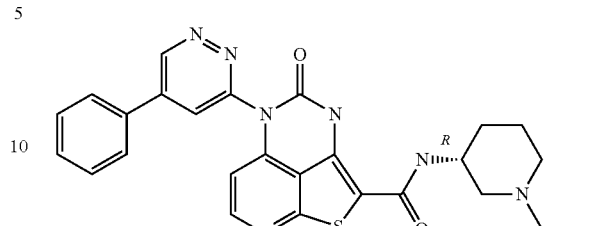

Step A: 3-chloro-5-phenylpyridazine

A solution of 3,5-dichloropyridazine (2.00 g, 13.4 mmol), phenylboronic acid (1.64 g, 13.4 mmol), $Pd(OAc)_2$ (301 mg, 1.34 mmol), 1,2,3,4,5-pentaphenyl-1'-(di-tert-butylphosphino)ferrocene (1.91 g, 33.6 mmol), KF (1.95 g, 33.6 mmol), dioxane (50 mL), and water (12 mL) was stirred at reflux for 15 h under N2. The reaction was diluted with EtOAc, washed with brine, dried over anhydrous $Na_2SO_4$, and concentrated to dryness. The residue was purified by normal phase flash column chromatography ($SiO_2$) to give the title compound (1.53 g, 59.8% yield) as a white solid. MS (ESI): mass calcd. for $C_{10}H_7ClN_2$, 190.63; m/z found, 191.0 $[M+H]^+$.

Step B: tert-Butyl (5-phenylpyridazin-3-yl)carbamate

The solution of 3-chloro-5-phenylpyridazine (1.53 g, 8.03 mmol), tert-butyl carbamate (1.88 g, 16.1 mmol), Pd(dppf)$Cl_2$ (0.592 g, 0.803 mmol)), Xphos (0.928 g, 1.61 mmol), and $Cs_2CO_3$ (6.538 g, 20.06 mmol) in dioxane (30 mL) was stirred at 100° C. for 16 hours. The reaction was diluted with EtOAc and filtered. The filtrate was partitioned between EtOAc and water, the organic layer collected and washed with water and brine, dried over anhydrous $Na_2SO_4$, and concentrated to dryness. The residue was purified by normal phase flash column chromatography ($SiO_2$) to give the title compound (0.96 g, 44% yield) as light yellow solid. MS (ESI): mass calcd. for $C_{15}H_{17}N_3O_2$, 271.31; m/z found, 272.0 $[M+H]^+$.

Step C: 5-phenylpyridazin-3-amine

A solution of tert-butyl (5-phenylpyridazin-3-yl)carbamate 0.96 g, 3.5 mmol), TFA (5 mL), and DCM (20 mL) was stirred at room temperature for 1 h. The mixture was concentrated to dryness to give the title compound (0.52 g, 86% yield) as light yellow liquid. MS (ESI): mass calcd. for $C_{10}H_9N_3$, 171.20; m/z found, 172.1 $[M+H]^+$.

Step D: (R)—N-(1-Acryloylpiperidin-3-yl)-4-oxo-5-(5-phenylpyridazin-3-yl)-4,5-dihydro-3H-1-thia-3,5,8-triazaacenaphthylene-2-carboxamide The title compound was prepared using analogous conditions described in Method 1, steps C-G in Example 1, and using 5-phenylpyridazin-3-amine in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{27}H_{23}N_7O_3S$, 525.6; m/z found, 526.6 [M+H]$^+$. $^1$H NMR (400 MHz, a mixture of CD3OD and DMSO-d$_6$): δ 9.75-9.70 (m, 1H), 8.35-8.30 (m, 1H), 8.29-8.24 (m, 1H), 7.93-7.87 (m, 2H), 7.58-7.49 (m, 3H), 6.78-6.68 (m, 1H), 6.33-6.28 (m, 1H), 6.15-6.06 (m, 1H), 5.68-5.61 (m, 1H), 4.52-4.15 (m, 1H), 4.12-3.89 (m, 1H), 3.89-3.79 (m, 1H), 3.12-2.96 (m, 1H), 2.85-2.64 (m, 1H), 2.01-1.91 (m, 1H), 1.82-1.73 (m, 1H), 1.73-1.59 (m, 1H), 1.53-1.35 (m, 1H).

Example 15: N-((*3R,*4S)-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide

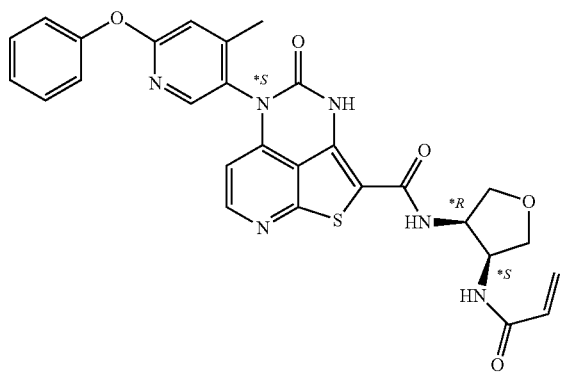

A purification was performed on Example 668 using chiral SFC (Stationary phase: CHIRALPAK IC 5 μm 250× 21 mm, Mobile phase: 45% CO$_2$, 55% EtOH) to give the title compound as the single enantiomer. MS (ESI): mass calcd. for $C_{28}H_{24}N_6O_5S$, 556.6; m/z found, 557.0 [M+H]$^+$. $^1$H NMR (400 MHz, CD$_3$OD): δ 8.40-8.30 (d, J=5.6 Hz, 1H), 8.14-8.06 (s, 1H), 7.51-7.40 (m, 2H), 7.31-7.14 (m, 3H), 7.09-7.01 (s, 1H), 6.34-6.12 (m, 3H), 5.70-5.60 (dd, J=9.5, 2.3 Hz, 1H), 4.82-4.67 (m, 2H), 4.17-4.04 (m, 2H), 3.88-3.75 (m, 2H), 2.24-2.16 (s, 3H).

Example 753: (R)—N-(1-Acryloylpiperidin-3-yl)-5-(*S)-(6-isopropoxy-2-methylpyridin-3-yl)-4-oxo-4,5-dihydro-3H-1-thia-3,5,8-triazaacenaphthylene-2-carboxamide

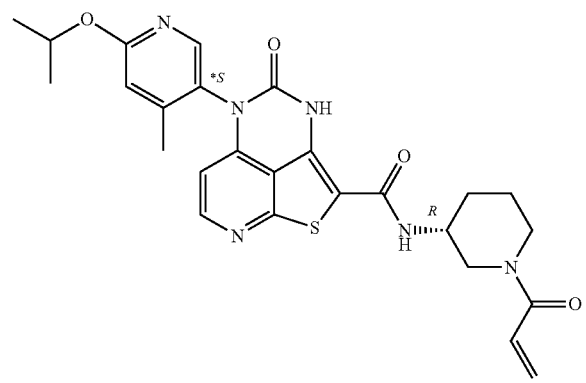

The title compound was prepared using analogous conditions described in Method 1, steps A-G, (including Chiral Resolution Method A after step F to obtain the *S atropisomer) in Example 1, and using 6-fluoro-2-methyl-3-nitropyridine, 2-propanol, acetonitrile, and Cs$_2$CO$_3$ in place of 5-fluoro-2-nitrotoluene, phenol, DMF, and K$_2$CO$_3$ in step A, and using Zn in place of Fe in step B, and using 1-[(3R)-3-amino-1-piperidyl]prop-2-en-1-one (Intermediate 15), 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for $C_{26}H_{28}N_6O_4S$, 520.6; m/z found, 521.1 [M+H]$^+$. $^1$H NMR (500 MHz, CD$_3$OD): δ 8.34 (d, J=5.5 Hz, 1H), 7.59 (d, J=8.6 Hz, 1H), 6.84-6.75 (m, 1H), 6.73 (d, J=8.6 Hz, 1H), 6.20 (d, J=17.0 Hz, 1H), 6.10 (d, J=5.5 Hz, 1H), 5.78-5.71 (m, 1H), 5.40-5.31 (m, 1H), 4.58-4.48 (m, 0.5H), 4.24 (dd, J=63.6, 12.6 Hz, 1H), 4.05-3.91 (m, 1.5H), 3.23-3.15 (m, 1H), 3.00-2.87 (m, 1H), 2.26 (s, 3H), 2.07 (d, J=10.6 Hz, 1H), 1.92-1.84 (m, 1H), 1.82-1.68 (m, 1H), 1.66-1.54 (m, 1H), 1.37 (dd, J=6.1, 2.8 Hz, 6H).

Example 754: (R)-5-(4-Isobutylphenyl)-4-oxo-N-(piperidin-3-yl)-4,5-dihydro-3H-1-thia-3,5,8-triazaacenaphthylene-2-carboxamide

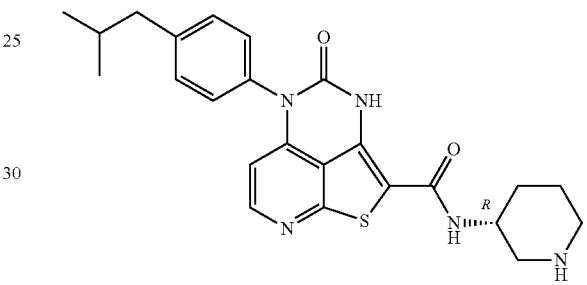

The title compound was prepared using analogous conditions described in step A of Example 677, and using isobutylboronic acid and 1-bromo-4-nitrobenzene in place of cyclohexen-1-ylboronic acid and 2-chloro-4-nitropyridine, and using Method 1, steps C-H in Example 1, using 4-isobutylaniline in place of 2-methyl-4-phenoxyaniline in step C, and using tert-butyl (3R)-3-aminopiperidine-1-carboxylate in place of tert-butyl (3R,5R)-3-amino-5-fluoropiperidine-1-carboxylate (Intermediate 1) in step G, to give the title compound. MS (ESI): mass calcd. for $C_{24}H_{27}N_5O_2S$, 449.6; m/z found, 450.2 [M+H]$^+$. $^1$H NMR (400 MHz, CD$_3$OD): δ 8.41 (s, 1H), 8.32-8.25 (m, 1H), 7.44-7.36 (m, 2H), 7.34-7.26 (m, 2H), 6.13-6.05 (m, 1H), 4.32-4.20 (m, 1H), 3.57-3.46 (m, 1H), 3.38-3.32 (m, 1H), 3.01-2.85 (m, 2H), 2.62-2.54 (m, 2H), 2.14-2.00 (m, 2H), 1.99-1.90 (m, 1H), 1.86-1.68 (m, 2H), 0.98-0.93 (m, 6H).

Example 755: (R)-4-Oxo-5-(5-phenylpyridazin-3-yl)-N-(piperidin-3-yl)-4,5-dihydro-3H-1-thia-3,5,8-triazaacenaphthylene-2-carboxamide

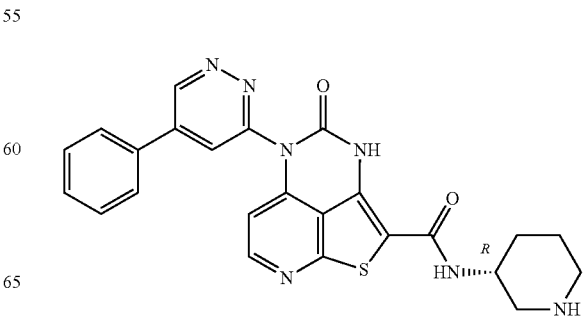

Step A: tert-Butyl (5-phenylpyridazin-3-yl)carbamate

A mixture of 3-chloro-5-phenylpyridazine (1.53 g, 8.03 mmol), tert-butyl carbamate (1.88 g, 16.05 mmol), [1,1'-Bis(diphenylphosphino)ferrocene]dichloropalladium(II) (0.59 g, 0.80 mmol), 2-Dicyclohexylphosphino-2',4',6'-triisopropylbiphenyl (0.93 g, 1.6 mmol), and cesium carbonate (6.54 g, 20 mmol) in dioxane (30 mL) was stirred at 100° C. for 16 hr. The mixture was diluted with EtOAc and filtered. The filtrate was partitioned between EtOAc and water. The organic layer was washed with water and brine, then dried over $Na_2SO_4$ and concentrated to give the crude product, which was purified by ISCO (pentane/EtOAc) to get pure product (0.96 g, 44% yield) as light yellow solid.

Step B: tert-Butyl (2-chloro-3-cyanopyridin-4-yl)(5-phenylpyridazin-3-yl)carbamate A solution of tert-butyl (5-phenylpyridazin-3-yl)carbamate (0.96 g, 3.5 mmol), 2-chloro-4-iodopyridine-3-carbonitrile (1.216 g, 4.600 mmol), Pd(OAc)$_2$ (79 mg, 0.35 mmol), DPEphos (381 mg, 0.708 mmol), Cs$_2$CO$_3$ (2.30 g, 7.08 mmol), in dioxane (20 mL) in a flask was stirred at 100° C. for 2 h under N$_2$. The reaction was concentrated to dryness and purified by normal phase flash column chromatography (SiO$_2$) to give the title compound (1.02 g, 70.7% yield) as a light yellow solid. MS (ESI): mass calcd. for $C_{21}H_{18}ClN_5O_2$, 407.85; m/z found, 352.2 (minus t-butyl group) [M+H]$^+$.

Step C: Methyl 3-amino-4-((tert-butoxycarbonyl)(5-phenylpyridazin-3-yl)amino)thieno[2,3-b]pyridine-2-carboxylate A solution of tert-butyl (2-chloro-3-cyanopyridin-4-yl)(5-phenylpyridazin-3-yl)carbamate (1.02 g, 2.50 mmol), methyl 2-mercaptoacetate (0.398 g, 3.75 mmol), and Cs$_2$CO$_3$ (1.219 g, 3.715 mmol) in dioxane (20 mL) in a flask was stirred at 100° C. for 2 h. The reaction was concentrated to dryness and purified by normal phase flash column chromatography (SiO$_2$) to give the title compound (1.05 g, 87.9% yield) as light yellow solid. MS (ESI): mass calcd. for $C_{21}H_{18}ClN_5O_2$, 477.54; m/z found, 478.3 [M+H]$^+$.

Step D: Methyl 3-amino-4-((5-phenylpyridazin-3-yl)amino)thieno[2,3-b]pyridine-2-carboxylate A solution of methyl 3-amino-4-((tert-butoxycarbonyl)(5-phenylpyridazin-3-yl)amino)thieno[2,3-b]pyridine-2-carboxylate (1.05 g, 2.20 mmol) in TFA (4 mL) and DCM (12 mL) was stirred at room temperature for 3 h. The reaction was concentrated to dryness to give the title compound (0.79 g, 95% yield) as a yellow solid, which was used in the next step directly. MS (ESI): mass calcd. for $C_{19}H_{15}N_5O_2S$, 377.42; m/z found, 378.3 [M+H]$^+$.

Step E: (R)-4-Oxo-5-(5-phenylpyridazin-3-yl)-4,5-dihydro-3H-1-thia-3,5,8-triazaacenaphthylene-2-carboxamide The title compound was prepared using analogous conditions described in Method 1, steps E-H, in Example 1, and using methyl 3-amino-4-((5-phenylpyridazin-3-yl)amino)thieno[2,3-b]pyridine-2-carboxylate in place of methyl 3-amino-4-(2-methyl-4-phenoxyanilino)thieno[2,3-b]pyridine-2-carboxylate in step E, and using tert-butyl (3R)-3-aminopiperidine-1-carboxylate in place of 5-fluoro-2-nitrotoluene in step G, to give the title compound. MS (ESI): mass calcd. for $C_{24}H_{21}N_7O_2S$, 471.5; m/z found, 472.2 [M+H]$^+$. $^1$H NMR (400 MHz, DMSO-d$_6$): δ 9.74-9.70 (m, 1H), 8.87-8.80 (m, 1H), 8.18-8.12 (m, 3H), 7.99-7.93 (m, 2H), 7.61-7.52 (m, 3H), 6.14-6.10 (m, 1H), 4.13-4.07 (m, 1H), 4.00-3.40 (br, 1H), 3.37-3.30 (m, 1H), 3.17-3.09 (m, 1H), 2.89-2.76 (m, 2H), 1.99-1.81 (m, 2H), 1.72-1.54 (m, 2H).

Example 756: (R)—N-(1-Acryloylpyrrolidin-3-yl)-5-(*R)-(6-isobutyl-4-methylpyridin-3-yl)-4-oxo-4,5-dihydro-3H-1-thia-3,5,8-triazaacenaphthylene-2-carboxamide

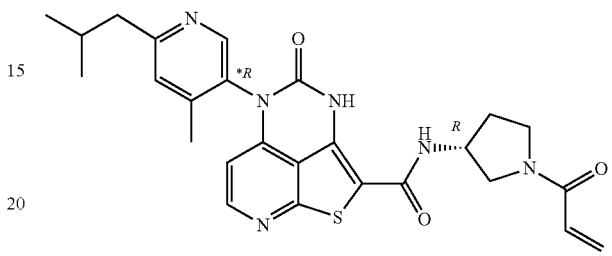

The title compound was prepared using analogous conditions described in Method 1, steps G-I, in Example 1 and using 5-(*R)-(6-Isobutyl-4-methylpyridin-3-yl)-4-oxo-4,5-dihydro-3H-1-thia-3,5,8-triazaacenaphthylene-2-carboxylic acid (Intermediate 83) and tert-butyl (3R)-3-aminopyrrolidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{26}H_{28}N_6O_3S$, 504.6; m/z found, 505.1 [M+H]$^+$. $^1$H NMR (500 MHz, CD$_3$OD): δ 8.44 (d, J=2.5 Hz, 1H), 8.33 (dd, J=5.5, 1.4 Hz, 1H), 7.41 (s, 1H), 6.68-6.54 (m, 1H), 6.32-6.24 (m, 1H), 6.03 (dd, J=5.5, 1.7 Hz, 1H), 5.79-5.71 (m, 1H), 4.70-4.57 (m, 1H), 4.01 (dd, J=10.8, 6.8 Hz, 0.5H), 3.90-3.79 (m, 1H), 3.77-3.67 (m, 1H), 3.63-3.56 (m, 1H), 3.55-3.49 (m, 0.5H), 2.73 (d, J=7.3 Hz, 2H), 2.39-2.25 (m, 1H), 2.23 (s, 3H), 2.19-2.05 (m, 2H), 0.99 (dd, J=6.6, 1.7 Hz, 6H).

Example 757: (R)—N-(1-Acryloylpiperidin-3-yl)-5-(*R)-(6-isopropoxy-2-methylpyridin-3-yl)-4-oxo-4,5-dihydro-3H-1-thia-3,5,8-triazaacenaphthylene-2-carboxamide

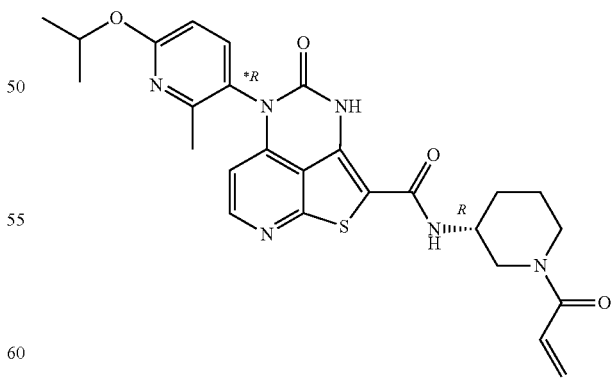

The title compound was prepared using analogous conditions described in Method 1, steps A-G, (including chiral resolution Method A after step F to obtain the *R atropisomer), in Example 1, and using 6-fluoro-2-methyl-3-nitropyridine, 2-propanol, acetonitrile, and Cs$_2$CO$_3$ in place of 5-fluoro-2-nitrotoluene, phenol, DMF, and K$_2$CO$_3$ in step A, and using Zn in place of Fe in step B, and using 1-[(3R)-3-amino-1-piperidyl]prop-2-en-1-one (Intermediate 15), 1-propanephosphonic anhydride, and diisopropylethylamine in place of tert-butyl (3R,5R)-3-amino-5-fluoropiperidine-1-carboxylate, HATU, and triethylamine in step G. MS (ESI): mass calcd. for $C_{26}H_{28}N_6O_4S$, 520.6; m/z found, 521.1 [M+H]$^+$. $^1$H NMR (500 MHz, CD$_3$OD): δ 8.34 (d, J=5.5 Hz, 1H), 7.59 (d, J=8.6 Hz, 1H), 6.85-6.75 (m, 1H), 6.74 (d, J=8.6 Hz, 1H), 6.24-6.17 (m, 1H), 6.10 (d, J=5.6 Hz, 1H), 5.74 (t, J=9.9 Hz, 1H), 5.40-5.31 (m, 1H), 4.59-4.49 (m, 0.5H), 4.24 (dd, J=61.0, 13.1 Hz, 1H), 4.04-3.93 (m, 1.5H), 3.24-3.14 (m, 1H), 2.99-2.83 (m, 1H), 2.26 (s, 3H), 2.12-2.04 (m, 1H), 1.92-1.84 (m, 1H), 1.82-1.68 (m, 1H), 1.66-1.54 (m, 1H), 1.37 (dd, J=6.1, 2.9 Hz, 6H).

Example 758: (R)-5-(*S)-(6-Isobutyl-4-methylpyridin-3-yl)-4-oxo-N-(pyrrolidin-3-yl)-4,5-dihydro-3H-1-thia-3,5,8-triazaacenaphthylene-2-carboxamide

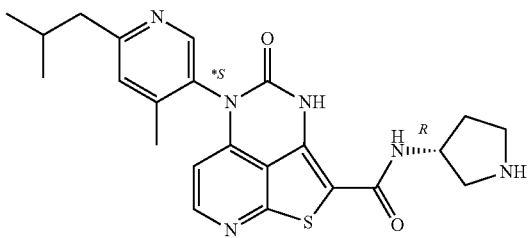

The title compound was prepared using analogous conditions described in Method 1, steps A, C-H, (including Chiral Resolution Method A after step F to obtain the *S atropisomer) in Example 1, and using 6-bromo-4-methylpyridin-3-amine, 1,1'-bis(diphenylphosphino)ferrocene-palladium(ii)dichloride dichloromethane complex, THF, and bromo(isobutyl)zinc in place of 5-fluoro-2-nitrotoluene, DMF, phenol, and K$_2$CO$_3$ in step A, and no step B, and using tert-butyl (3R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{23}H_{26}N_6O_2S$, 450.6; m/z found, 451.2 [M+H]$^+$. $^1$H NMR (500 MHz, CDCl$_3$): δ 8.73-8.10 (m, 1H), 7.83 (d, J=7.1 Hz, 1H), 7.23 (d, J=36.1 Hz, 2H), 5.94 (s, 1H), 3.69-3.50 (m, 1H), 3.10-2.70 (m, 6H), 2.71 (d, J=7.2 Hz, 1H), 2.28 (s, 3H), 2.00 (s, 1H), 1.94-1.69 (m, 3H), 0.99 (d, J=6.6 Hz, 6H).

Example 759: (R)-5-(*S)-(6-Isobutoxy-4-methylpyridin-3-yl)-4-oxo-N-(piperidin-3-yl)-4,5-dihydro-3H-1-thia-3,5,8-triazaacenaphthylene-2-carboxamide

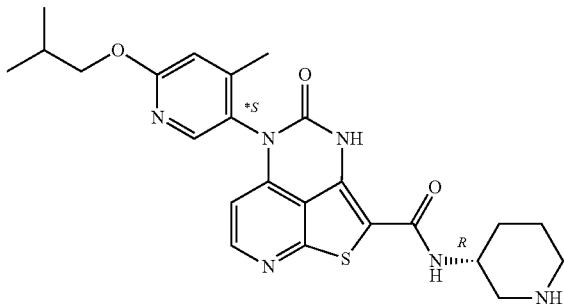

The title compound was prepared using analogous conditions described in Method 1, steps A-H, (including Chiral Resolution Method A after step F to obtain the *S atropisomer), in Example 1, and using 2-fluoro-4-methyl-5-nitropyridine, 2-methyl-1-propanol, acetonitrile, and Cs$_2$CO$_3$ in place of 5-fluoro-2-nitrotoluene, phenol, DMF, and K$_2$CO$_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G. MS (ESI): mass calcd. for $C_{24}H_{28}N_6O_3S$, 480.6; m/z found, 481.2 [M+H]$^+$. $^1$H NMR (400 MHz, CDCl$_3$): δ 8.36-8.26 (m, 1H), 8.04 (d, J=17.0 Hz, 1H), 6.79 (s, 1H), 6.24 (s, 1H), 6.01 (d, J=5.5 Hz, 1H), 4.21 (s, 1H), 4.15-4.02 (m, 2H), 3.47 (s, 2H), 3.19 (dd, J=12.2, 3.5 Hz, 1H), 3.05-2.80 (m, 3H), 2.20-2.03 (m, 4H), 1.93-1.73 (m, 2H), 1.39-1.29 (m, 2H), 1.03 (dd, J=6.8, 1.2 Hz, 6H).

Example 760: (R)-5-(*R)-(6-Isobutoxy-4-methylpyridin-3-yl)-4-oxo-N-(piperidin-3-yl)-4,5-dihydro-3H-1-thia-3,5,8-triazaacenaphthylene-2-carboxamide

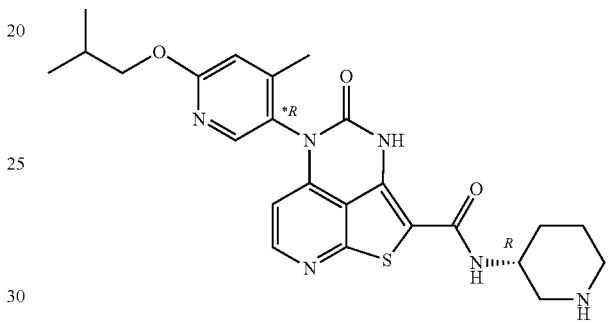

The title compound was prepared using analogous conditions described in Method 1, steps A-H, (including chiral resolution Method A after step F to obtain the *R atropisomer), in Example 1, and using 2-fluoro-4-methyl-5-nitropyridine, 2-methyl-1-propanol, acetonitrile, and Cs$_2$CO$_3$ in place of 5-fluoro-2-nitrotoluene, phenol, DMF, and K$_2$CO$_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G. MS (ESI): mass calcd. for $C_{24}H_{28}N_6O_3S$, 480.6; m/z found, 481.2 [M+H]$^+$. $^1$H NMR (500 MHz, CDCl$_3$): δ 8.36 (d, J=5.5 Hz, 1H), 8.01 (s, 1H), 6.81-6.75 (m, 1H), 6.24 (s, 1H), 6.04 (d, J=5.5 Hz, 1H), 4.18-4.04 (m, 3H), 3.47 (s, 2H), 3.19 (dd, J=12.2, 3.5 Hz, 1H), 3.07 (dd, J=11.7, 3.0 Hz, 1H), 2.89-2.76 (m, 3H), 2.17-2.05 (m, 3H), 1.77 (dtd, J=27.2, 9.1, 8.3, 3.8 Hz, 2H), 1.39-1.29 (m, 2H), 1.03 (dd, J=6.7, 1.4 Hz, 6H).

Example 761: (R)-5-(*S)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide

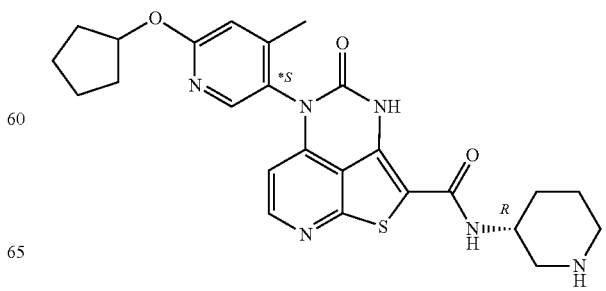

The title compound was prepared using analogous conditions described in Method 1, steps A-H, (including Chiral Resolution Method A after step F to obtain the *S atropisomer), in Example 1, and using 2-fluoro-4-methyl-5-nitropyridine, cyclopentanol, and Cs$_2$CO$_3$ in place of 5-fluoro-2-nitrotoluene, phenol, and K$_2$CO$_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for C$_{25}$H$_{28}$N$_6$O$_3$S, 492.6; m/z found, 493.1 [M+H]$^+$. $^1$H NMR (400 MHz, CDCl$_3$): δ 8.36 (d, J=5.4 Hz, 1H), 8.00 (s, 1H), 6.75-6.68 (m, 1H), 6.25 (s, 1H), 6.04 (d, J=5.5 Hz, 1H), 5.42 (tt, J=6.2, 2.9 Hz, 1H), 4.13 (ddq, J=9.3, 6.1, 3.1 Hz, 1H), 3.49 (s, 2H), 3.08 (dd, J=11.7, 3.1 Hz, 1H), 2.90-2.72 (m, 3H), 2.13 (d, J=0.8 Hz, 3H), 2.05-1.90 (m, 2H), 1.92-1.53 (m, 10H).

Example 762: (R)-5-(*R)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide

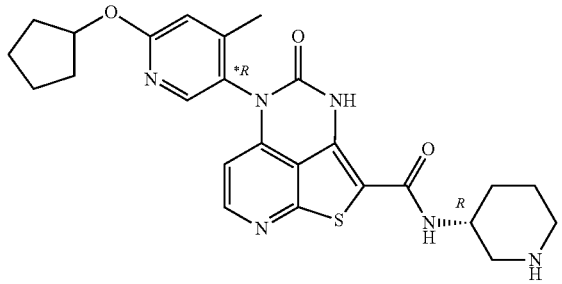

The title compound was prepared using analogous conditions described in Method 1, steps A-H, (including chiral resolution Method A after step F to obtain the *R atropisomer), in Example 1, and using 2-fluoro-4-methyl-5-nitropyridine, cyclopentanol, and Cs$_2$CO$_3$ in place of 5-fluoro-2-nitrotoluene, phenol, and K$_2$CO$_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G, to give the title compound. MS (ESI): mass calcd. for C$_{25}$H$_{28}$N$_6$O$_3$S, 492.6; m/z found, 493.2 [M+H]$^+$. $^1$H NMR (500 MHz, CDCl$_3$): δ 8.32 (d, J=5.4 Hz, 1H), 8.04 (s, 1H), 6.72 (s, 1H), 6.47-6.42 (m, 1H), 6.02 (d, J=5.4 Hz, 1H), 5.42 (tt, J=6.3, 2.7 Hz, 1H), 4.43 (s, 4H), 4.13 (tp, J=6.4, 3.1 Hz, 1H), 3.08 (dd, J=11.7, 3.2 Hz, 1H), 2.90-2.77 (m, 1H), 2.12 (s, 3H), 1.98 (qdd, J=9.1, 7.3, 6.0, 3.7 Hz, 2H), 1.90-1.70 (m, 7H), 1.69-1.51 (m, 3H).

Example 763: (R)-5-(*S)-(4-Methyl-2-phenoxypyrimidin-5-yl)-4-oxo-N-(piperidin-3-yl)-4,5-dihydro-3H-1-thia-3,5,8-triazaacenaphthylene-2-carboxamide

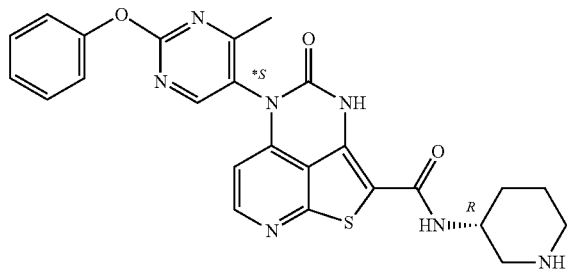

The title compound was prepared using analogous conditions described in Method 1, steps A, C-H, (including Chiral Resolution Method A after step F to obtain the *S atropisomer), in Example 1, and using 2-chloro-4-methyl-pyrimidin-5-amine, CuI, N,N-dimethylglycine, and Cs$_2$CO$_3$ in place of 5-fluoro-2-nitrotoluene, DMF, and K$_2$CO$_3$ in step A, and using no step B, and using tert-butyl (3R)-3-aminopiperidine-1-carboxylate and diisopropylethylamine in place of tert-butyl (3R,5R)-3-amino-5-fluoropiperidine-1-carboxylate and triethylamine in step G. MS (ESI): mass calcd. for C$_{25}$H$_{23}$N$_7$O$_3$S, 501.6; m/z found, 502.0 [M+H]$^+$. $^1$H NMR (400 MHz, Chloroform-d) δ 8.43-8.32 (m, 2H), 7.51-7.41 (m, 2H), 7.34-7.21 (m, 2H), 6.43 (d, J=7.4 Hz, 1H), 6.04 (d, J=5.5 Hz, 1H), 3.63 (s, 5H), 3.11 (dd, J=11.7, 3.1 Hz, 1H), 2.87 (dtd, J=21.8, 11.7, 5.3 Hz, 3H), 2.38 (s, 3H), 1.80 (ddt, J=17.5, 14.0, 5.8 Hz, 3H).

Example 764: (R)—N-(1-Acryloylpiperidin-3-yl)-5-(6-isobutyl-2-methylpyridin-3-yl)-4-oxo-4,5-dihydro-3H-1-thia-3,5,8-triazaacenaphthylene-2-carboxamide

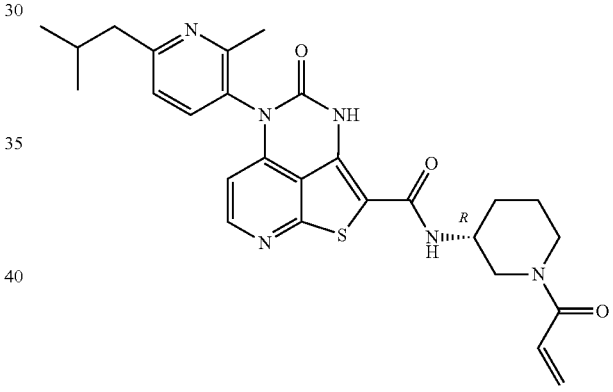

The title compound was prepared using analogous conditions described in Method 1, steps A, C-H, in Example 1, and using 6-bromo-2-methylpyridin-3-amine, 1,1'-bis(diphenylphosphino)ferrocene-palladium(ii)dichloride dichloromethane complex, THF, and bromo(isobutyl)zinc in place of 5-fluoro-2-nitrotoluene, DMF, phenol, and K$_2$CO$_3$ in step A, and no step B, and using 1-[(3R)-3-amino-1-piperidyl]prop-2-en-1-one (Intermediate 15), PYOXIM, and diisopropylethylamine in place of tert-butyl (3R,5R)-3-amino-5-fluoropiperidine-1-carboxylate, HATU, and triethylamine in step G. MS (ESI): mass calcd. for C$_{27}$H$_{30}$N$_6$O$_3$S, 518.6; m/z found, 519.2 [M+H]$^+$. $^1$H NMR (400 MHz, CD$_3$OD): δ 8.34 (d, J=5.5 Hz, 1H), 7.77 (dd, J=8.1, 1.2 Hz, 1H), 7.34 (d, J=8.1 Hz, 1H), 6.87-6.74 (m, 1H), 6.20 (d, J=16.5 Hz, 1H), 6.02 (dd, J=5.5, 1.8 Hz, 1H), 5.79-5.68 (m, 1H), 4.43 (dd, J=92.3, 12.9 Hz, 1H), 4.22-3.91 (m, 2H), 3.21-3.12 (m, 1H), 2.90 (q, J=11.7 Hz, 1H), 2.73 (d, J=7.3 Hz, 2H), 2.38 (s, 3H), 2.18-2.03 (m, 2H), 1.94-1.84 (m, 1H), 1.82-1.68 (m, 1H), 1.64-1.53 (m, 1H), 0.99 (dd, J=6.6, 1.9 Hz, 6H).

Example 765: (R)-5-(*S)-(6-Isobutyl-4-methylpyridin-3-yl)-4-oxo-N-(1-propionylpiperidin-3-yl)-4,5-dihydro-3H-1-thia-3,5,8-triazaacenaphthylene-2-carboxamide

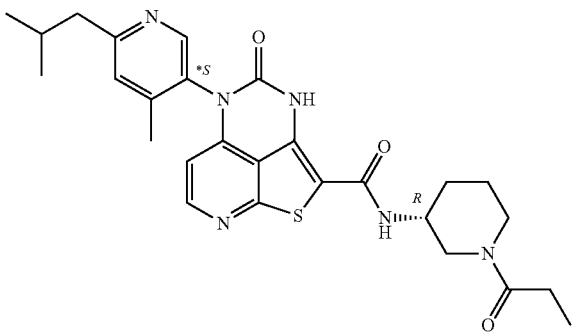

Step A: (R)-5-(6-isobutyl-4-methylpyridin-3-yl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H, (including Chiral Resolution Method A after step F to obtain the *S atropisomer), in Example 1, and using 6-bromo-4-methylpyridin-3-amine, 1,1'-bis(diphenylphosphino)ferrocene-palladium(ii)dichloride dichloromethane complex, THF, and bromo(isobutyl)zinc in place of 5-fluoro-2-nitrotoluene, DMF, phenol, and $K_2CO_3$ in step A, and no step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G.

Step B: (R)-5-(*S)-(6-Isobutyl-4-methylpyridin-3-yl)-4-oxo-N-(1-propionylpiperidin-3-yl)-4,5-dihydro-3H-1-thia-3,5,8-triazaacenaphthylene-2-carboxamide The title compound was prepared using (R)-5-(6-isobutyl-4-methylpyridin-3-yl)-4-oxo-N-(piperidin-3-yl)-4,5-dihydro-3H-1-thia-3,5,8-triazaacenaphthylene-2-carboxamide, propanoyl propanoate and diisopropylethylamine. MS (ESI): mass calcd. for $C_{27}H_{32}N_6O_3S$, 520.7; m/z found, 521.1 [M+H]$^+$. $^1$H NMR (500 MHz, CDCl$_3$): δ 9.55 (s, 1H), 8.44-8.31 (m, 2H), 7.20 (s, 1H), 5.96 (dd, J=11.0, 5.6 Hz, 1H), 3.69-3.32 (m, 5H), 2.98 (t, J=11.0 Hz, 2H), 2.25-2.12 (m, 2H), 2.05 (s, 3H), 1.82-1.75 (m, 1H), 1.32-1.14 (m, 8H), 0.99 (d, J=6.7 Hz, 6H).

Example 766: (R)—N-(1-Acryloylpiperidin-3-yl)-5-(*S)-(6-isobutoxy-4-methylpyridin-3-yl)-4-oxo-4,5-dihydro-3H-1-thia-3,5,8-triazaacenaphthylene-2-carboxamide

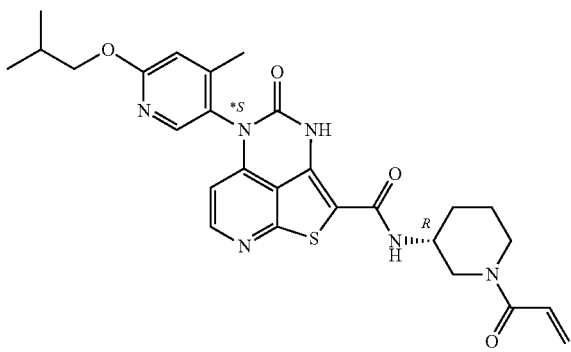

Step A: (R)-5-(6-isobutoxy-4-methylpyridin-3-yl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H, (including Chiral Resolution Method A after step F to obtain the *S atropisomer), in Example 1, and using 2-fluoro-4-methyl-5-nitropyridine, 2-methyl-1-propanol, acetonitrile, and $Cs_2CO_3$ in place of 5-fluoro-2-nitrotoluene, phenol, DMF, and $K_2CO_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G.

Step B: (R)—N-(1-Acryloylpiperidin-3-yl)-5-(*S)-(6-isobutoxy-4-methylpyridin-3-yl)-4-oxo-4,5-dihydro-3H-1-thia-3,5,8-triazaacenaphthylene-2-carboxamide The title compound was prepared using (R)-5-(6-isobutoxy-4-methylpyridin-3-yl)-4-oxo-N-(piperidin-3-yl)-4,5-dihydro-3H-1-thia-3,5,8-triazaacenaphthylene-2-carboxamide prop-2-enoyl prop-2-enoate and diisopropylethylamine. MS (ESI): mass calcd. for $C_{27}H_{30}N_6O_4S$, 534.6; m/z found, 535.2 [M+H]$^+$. $^1$H NMR (500 MHz, CDCl$_3$): δ 9.58 (s, 1H), 8.32 (d, J=5.5 Hz, 1H), 8.05 (s, 1H), 6.80 (s, 1H), 6.70-6.58 (m, 2H), 6.32 (dd, J=35.3, 16.8 Hz, 1H), 6.03 (d, J=5.6 Hz, 1H), 5.78-5.67 (m, 1H), 4.09 (tdd, J=17.6, 11.5, 5.2 Hz, 5H), 2.69 (s, 1H), 2.17-2.00 (m, 6H), 1.72-1.59 (m, 2H), 1.26 (t, J=7.1 Hz, 1H), 1.03 (d, J=6.7 Hz, 6H).

Example 767: (R)—N-(1-Acryloylpiperidin-3-yl)-5-(*R)-(6-isobutoxy-4-methylpyridin-3-yl)-4-oxo-4,5-dihydro-3H-1-thia-3,5,8-triazaacenaphthylene-2-carboxamide

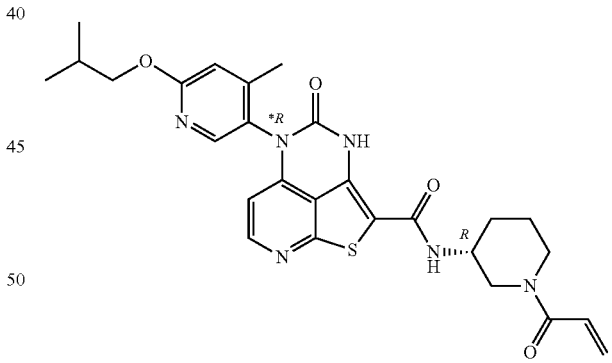

Step A: (R)-5-(6-isobutoxy-4-methylpyridin-3-yl)-4-oxo-N-(piperidin-3-yl)-4,5-dihydro-3H-1-thia-3,5,8-triazaacenaphthylene-2-carboxamide The title compound was prepared Method 1, steps A-H, (including chiral resolution Method A after step F to obtain the *R atropisomer), in Example 1, and using 2-fluoro-4-methyl-5-nitropyridine, 2-methyl-1-propanol, acetonitrile, and $Cs_2CO_3$ in place of 5-fluoro-2-nitrotoluene, phenol, DMF, and $K_2CO_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G.

Step B: (R)—N-(1-Acryloylpiperidin-3-yl)-5-(*R)-(6-isobutoxy-4-methylpyridin-3-yl)-4-oxo-4,5-dihydro-3H-1-thia-3,5,8-triazaacenaphthylene-2-carboxamide The title compound was prepared using (R)-5-(6-isobutoxy-4-methylpyridin-3-yl)-4-oxo-N-(piperidin-3-yl)-4,5-dihydro-3H-1-thia-3,5,8-triazaacenaphthylene-2-carboxamide, prop-2-enoyl prop-2-enoate and diisopropylethylamine. MS (ESI): mass calcd. for $C_{27}H_{30}N_6O_4S$, 534.6; m/z found, 535.2 $[M+H]^+$. $^1H$ NMR (500 MHz, $CDCl_3$): δ 9.49 (s, 1H), 8.35 (d, J=5.5 Hz, 1H), 8.03 (s, 1H), 6.80 (s, 1H), 6.64 (d, J=14.1 Hz, 1H), 6.04 (d, J=5.7 Hz, 2H), 5.74 (s, 1H), 4.18-4.01 (m, 4H), 3.56 (s, 1H), 3.29 (s, 1H), 2.18-1.96 (m, 7H), 1.79 (s, 1H), 1.26 (t, J=7.1 Hz, 2H), 1.03 (dd, J=6.7, 1.2 Hz, 6H).

Example 768: (R)—N-(1-Acryloylpiperidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide

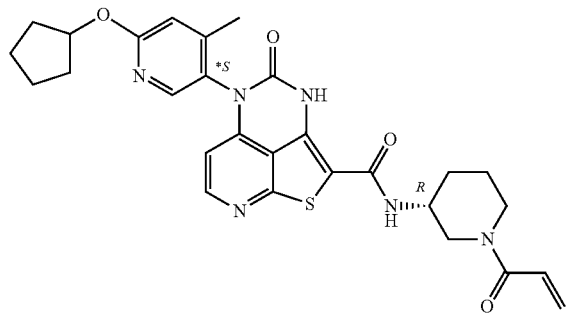

Step A: (R)-5-(6-(cyclopentyloxy)-4-methylpyridin-3-yl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H, (including Chiral Resolution Method A after step F to obtain the *S atropisomer), in Example 1, and using 2-fluoro-4-methyl-5-nitropyridine, cyclopentanol, and $Cs_2CO_3$ in place of 5-fluoro-2-nitrotoluene, phenol, and $K_2CO_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R, 5R)-3-amino-5-fluoropiperidine-1-carboxylate, HATU, and triethylamine in step G.

Step B: (R)—N-(1-Acryloylpiperidin-3-yl)-5-(*S)-(6-(cyclopentyloxy)-4-methylpyridin-3-yl)-4-oxo-4, 5-dihydro-3H-1-thia-3,5,8-triazaacenaphthylene-2-carboxamide The title compound was prepared using (R)-5-(6-(cyclopentyloxy)-4-methylpyridin-3-yl)-4-oxo-N-(piperidin-3-yl)-4,5-dihydro-3H-1-thia-3,5,8-triazaacenaphthylene-2-carboxamide, prop-2-enoyl prop-2-enoate and diisopropylethylamine. MS (ESI): mass calcd. for $C_{28}H_{30}N_6O_4S$, 546.7; m/z found, 547.2 $[M+H]^+$. $^1H$ NMR (500 MHz, $CDCl_3$): δ 9.51 (s, 1H), 8.35 (d, J=5.5 Hz, 1H), 8.03 (d, J=4.0 Hz, 1H), 6.73 (s, 1H), 6.64 (t, J=13.8 Hz, 1H), 6.39 (d, J=16.8 Hz, 1H), 6.30 (d, J=16.9 Hz, 1H), 6.05 (s, 1H), 5.73 (s, 1H), 5.41 (tt, J=6.3, 2.8 Hz, 1H), 5.30 (s, 2H), 4.16-4.04 (m, 2H), 3.56 (s, 1H), 3.26 (s, 1H), 2.16-1.91 (m, 5H), 1.82 (dtt, J=15.5, 9.0, 6.3 Hz, 5H), 1.71-1.58 (m, 3H), 1.26 (t, J=7.1 Hz, 1H).

Example 769: (R)—N-(1-Acryloylpiperidin-3-yl)-5-(*R)-(6-(cyclopentyloxy)-4-methylpyridin-3-yl)-4-oxo-4,5-dihydro-3H-1-thia-3,5,8-triazaacenaphthylene-2-carboxamide

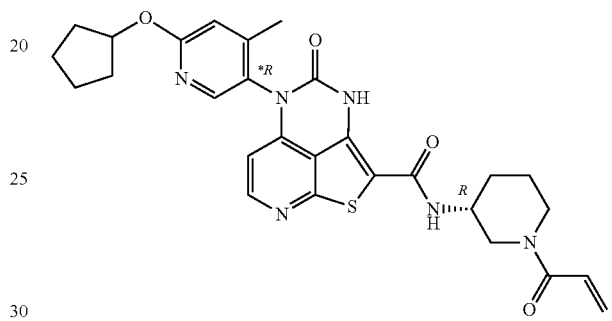

Step A: (R)-5-(6-(cyclopentyloxy)-4-methylpyridin-3-yl)-4-oxo-N-(piperidin-3-yl)-4,5-dihydro-3H-1-thia-3,5,8-triazaacenaphthylene-2-carboxamide The title compound was prepared in a manner analogous to Method 1, steps A-H, (including chiral resolution Method A after step F to obtain the *R atropisomer), in Example 1, and using 2-fluoro-4-methyl-5-nitropyridine, cyclopentanol, and $Cs_2CO_3$ in place of 5-fluoro-2-nitrotoluene, phenol, and $K_2CO_3$ in step A, and using Pd/C in place of Fe in step B, and using tert-butyl (3R)-3-aminopiperidine-1-carboxylate, 1-propanephosphonic anhydride, and diisopropylethylamine in place of tert-butyl (3R,5R)-3-amino-5-fluoropiperidine-1-carboxylate, HATU, and triethylamine in step G.

Step B: (R)—N-(1-Acryloylpiperidin-3-yl)-5-(*R)-(6-(cyclopentyloxy)-4-methylpyridin-3-yl)-4-oxo-4, 5-dihydro-3H-1-thia-3,5,8-triazaacenaphthylene-2-carboxamide The title compound was prepared using (R)-5-(6-(cyclopentyloxy)-4-methylpyridin-3-yl)-4-oxo-N-(piperidin-3-yl)-4,5-dihydro-3H-1-thia-3,5,8-triazaacenaphthylene-2-carboxamide, prop-2-enoyl prop-2-enoate and diisopropylethylamine. MS (ESI): mass calcd. for $C_{28}H_{30}N_6O_4S$, 546.7; m/z found, 547.2 $[M+H]^+$. $^1H$ NMR (400 MHz, $CDCl_3$): δ 9.51 (s, 1H), 8.35 (d, J=5.5 Hz, 1H), 8.03-7.29 (m, 2H), 6.68 (d, J=33.7 Hz, 2H), 6.39-6.05 (d, J=5.7 Hz, 3H), 5.74 (d, J=5.7 Hz, 1H), 5.52-5.19 (m, 1H), 4.40-3.95 (m, 3H), 3.48-3.26 (m, 2H), 2.16-1.91 (m, 5H), 1.82 (dtt, J=15.5, 9.0, 6.3 Hz, 5H), 1.71-1.58 (m, 3H), 1.26 (t, J=7.1 Hz, 1H).

Example 770: (R)—N-(1-Acryloylpiperidin-3-yl)-5-(2-methyl-6-((tetrahydro-2H-pyran-4-yl)oxy)pyridin-3-yl)-4-oxo-4,5-dihydro-3H-1-thia-3,5,8-triazaacenaphthylene-2-carboxamide

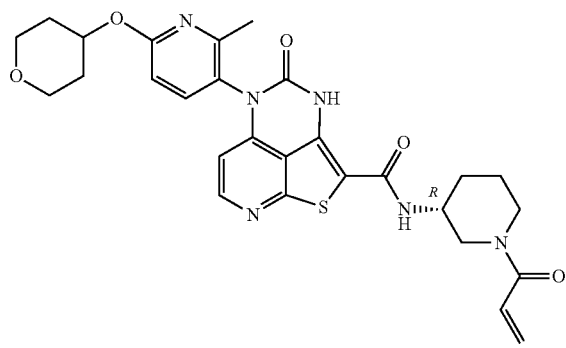

The title compound was prepared using analogous conditions described in Method 1, steps A-G, in Example 1, and using 2-fluoro-5-nitro-6-picoline, tetrahydro-4-pyranol, acetonitrile, and $Cs_2CO_3$ in place of 5-fluoro-2-nitrotoluene, phenol, DMF, and $K_2CO_3$ in step A, and using Pd/C in place of Fe in step B, and using 1-[(3R)-3-amino-1-piperidyl]prop-2-en-1-one (Intermediate 15), PYOXIM, and diisopropylethylamine in place of tert-butyl (3R,5R)-3-amino-5-fluoropiperidine-1-carboxylate, HATU, and triethylamine in step G, to give the title compound. MS (ESI): mass calcd. for $C_{28}H_{30}N_6O_5S$, 562.6; m/z found, 563.1 [M+H]$^+$. $^1$H NMR (400 MHz, $CD_3OD$): δ 8.34 (d, J=5.6 Hz, 1H), 7.63 (d, J=8.6 Hz, 1H), 6.86-6.72 (m, 2H), 6.20 (d, J=16.9 Hz, 1H), 6.11 (d, J=5.5 Hz, 1H), 5.82-5.70 (m, 1H), 5.38-5.30 (m, 1H), 4.59-4.27 (m, 1H), 4.22-3.94 (m, 4H), 3.68-3.60 (m, 2H), 3.23-3.13 (m, 1H), 3.01-2.84 (m, 1H), 2.27 (s, 3H), 2.15-2.04 (m, 3H), 1.92-1.70 (m, 4H), 1.65-1.52 (m, 1H).

Example 771: (R)—N-(1-Acryloylpiperidin-3-yl)-5-(4-((2-methylpyridin-3-yl)oxy)phenyl)-4-oxo-4,5-dihydro-3H-1-thia-3,5,8-triazaacenaphthylene-2-carboxamide

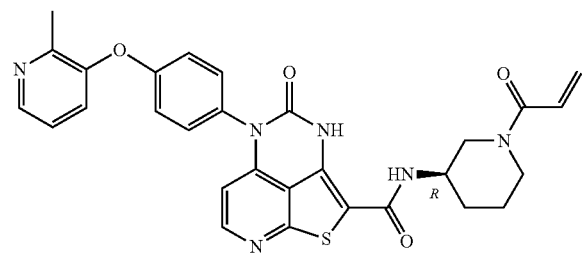

The title compound was prepared using analogous conditions as found in Method 1, steps A-G in Example 1, and using 4-fluoronitrobenzene and 2-methylpyridin-3-ol in place of 5-fluoro-2-nitrotoluene and phenol in step A, and using Pd/C in place of Fe, EtOH/H$_2$O, and NH$_4$Cl in step B, and using 4-((2-methylpyridin-3-yl)oxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{29}H_{26}N_6O_4S$, 554.6; m/z found, 555.2 [M+H]$^+$. $^1$H NMR (400 MHz, $CD_3OD$): δ 8.35-8.23 (m, 2H), 7.50-7.41 (m, 3H), 7.36-7.30 (m, 1H), 7.20-7.14 (m, 2H), 6.85-6.73 (m, 1H), 6.23-6.15 (m, 2H), 5.79-5.67 (m, 1H), 4.56-4.27 (m, 1H), 4.20-3.90 (m, 2H), 3.21-3.11 (m, 1H), 2.97-2.79 (m, 1H), 2.51 (s, 3H), 2.10-2.01 (m, 1H), 1.90-1.82 (m, 1H), 1.80-1.65 (m, 1H), 1.63-1.50 (m, 1H).

Example 772: (R)—N-(1-Acryloylpiperidin-3-yl)-5-(2-methyl-4-((6-methylpyridin-2-yl)oxy)phenyl)-4-oxo-4,5-dihydro-3H-1-thia-3,5,8-triazaacenaphthylene-2-carboxamide

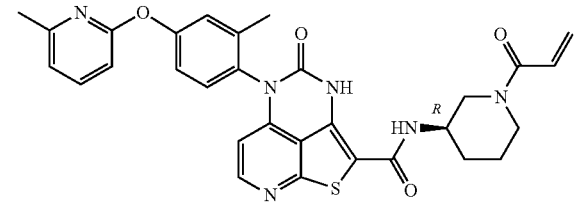

The title compound was prepared using analogous conditions as found in Method 1, steps A-G in Example 1, and using 4-amino-3-methylphenol and 2-fluoro-6-methylpyridine in place of 5-fluoro-2-nitrotoluene and phenol in step A, and using 2-methyl-4-((6-methylpyridin-2-yl)oxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{30}H_{28}N_6O_4S$, 568.6; m/z found, 569.2 [M+H]$^+$. $^1$H NMR (400 MHz, $CD_3OD$): δ 8.30 (d, J=5.5 Hz, 1H), 7.71 (t, J=7.8 Hz, 1H), 7.46-7.34 (m, 1H), 7.21-7.14 (m, 1H), 7.13-7.06 (m, 1H), 7.05-6.98 (m, 1H), 6.88-6.71 (m, 2H), 6.23-6.06 (m, 2H), 5.76-5.63 (m, 1H), 4.59-4.28 (m, 1H), 4.25-3.86 (m, 2H), 3.21-3.05 (m, 1H), 2.93-2.77 (m, 1H), 2.42 (s, 3H), 2.20-2.11 (m, 3H), 2.09-1.98 (m, 1H), 1.90-1.80 (m, 1H), 1.77-1.48 (m, 2H).

Example 773: (R)—N-(1-Acryloylpiperidin-3-yl)-5-(2-methyl-4-((2-methylpyridin-3-yl)oxy)phenyl)-4-oxo-4,5-dihydro-3H-1-thia-3,5,8-triazaacenaphthylene-2-carboxamide

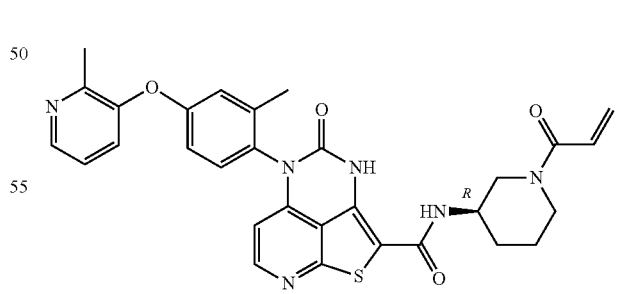

The title compound was prepared using analogous conditions as found in Method 1, steps A-G in Example 1, and using 4-fluoro-2-methyl-1-nitrobenzene and 2-methylpyridin-3-ol in place of 5-fluoro-2-nitrotoluene and phenol in step A, and using Pd/C in place Fe, EtOH/H$_2$O, and NH$_4$Cl in step B, and using 2-methyl-4-((2-methylpyridin-3-yl)oxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{30}H_{28}N_6O_4S$, 568.6; m/z found, 569.2 [M+H]$^+$. $^1$H NMR (400 MHz, CD$_3$OD): δ 8.35-8.30 (m, 1H), 8.29-8.22 (m, 1H), 7.51-7.43 (m, 1H), 7.38-7.29 (m, 2H), 7.10-7.03 (m, 1H), 7.00-6.93 (m, 1H), 6.86-6.72 (m, 1H), 6.24-6.14 (m, 1H), 6.12-6.04 (m, 1H), 5.78-5.68 (m, 1H), 4.57-4.25 (m, 1H), 4.20-3.90 (m, 2H), 3.22-3.11 (m, 1H), 3.02-2.80 (m, 1H), 2.51 (s, 3H), 2.14 (s, 3H), 2.10-2.02 (m, 1H), 1.91-1.81 (m, 1H), 1.80-1.65 (m, 1H), 1.64-1.51 (m, 1H).

Example 774: (R)—N-(1-Acryloylpiperidin-3-yl)-4-oxo-5-(4-(pyridin-3-yloxy)phenyl)-4,5-dihydro-3H-1-thia-3,5,8-triazaacenaphthylene-2-carboxamide

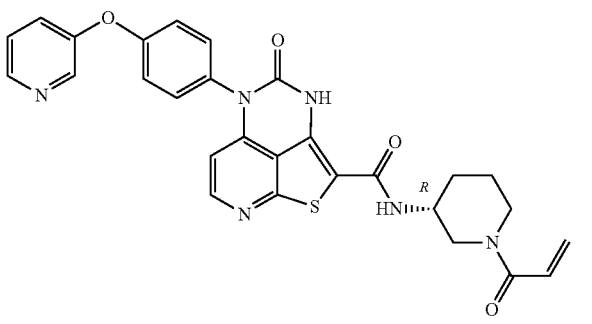

The title compound was prepared using analogous conditions as found in Method 1, steps A-G in Example 1, and using 4-fluoronitrobenzene and 3-hydroxypyridine in place of 5-fluoro-2-nitrotoluene and phenol in step A, and using Pd/C in place of Fe and NH$_4$Cl in step B, and using 1-[(3R)-3-Amino-1-piperidyl]prop-2-en-1-one (Intermediate 15), 1-propanephosphonic anhydride, DCM, and diisopropylethylamine in place of tert-butyl (3R,5R)-3-amino-5-fluoropiperidine-1-carboxylate, HATU, DMF, and triethylamine in step G. MS (ESI): mass calcd. for $C_{28}H_{24}N_6O_4S$, 540.6; m/z found, 541.0 [M+H]$^+$. $^1$H NMR (500 MHz, DMSO-d$_6$): δ 10.18 (s, 1H), 8.50 (d, J=2.7 Hz, 1H), 8.44 (dd, J=4.6, 1.3 Hz, 1H), 8.34 (d, J=5.5 Hz, 1H), 8.16-8.02 (m, 1H), 7.62-7.58 (m, 1H), 7.53-7.48 (m, 3H), 7.26 (d, J=9.0 Hz, 2H), 6.86-6.72 (m, 1H), 6.14-6.08 (m, 2H), 5.69 (d, J=10.5 Hz, 1H), 4.53-4.15 (m, 1H), 4.07-3.99 (m, 1H), 3.84-3.76 (m, 1H), 3.16-2.96 (m, 1H), 2.83-2.61 (m, 1H), 1.97-1.92 (m, 1H), 1.83-1.75 (m, 1H), 1.74-1.58 (m, 1H), 1.51-1.36 (m, 1H).

Example 775: (R)—N-(1-Acryloylpiperidin-3-yl)-5-(4-((6-methylpyridin-2-yl)oxy)phenyl)-4-oxo-4,5-dihydro-3H-1-thia-3,5,8-triazaacenaphthylene-2-carboxamide

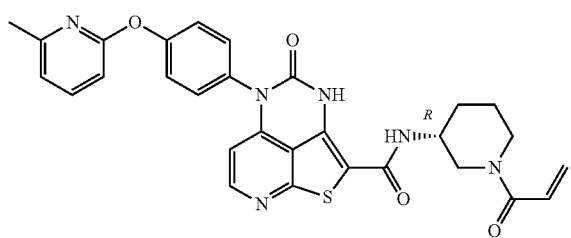

The title compound was prepared using analogous conditions as found in Method 1, steps A-G in Example 1, and using 4-aminophenol and 2-fluoro-6-methylpyridine in place of 5-fluoro-2-nitrotoluene and phenol in step A, and no step B, and using 4-((6-methylpyridin-2-yl)oxy)aniline in place of 2-methyl-4-phenoxyaniline in step C, and using 1-[(3R)-3-Amino-1-piperidyl]prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{29}H_{26}N_6O_4S$, 554.6; m/z found, 555.1 [M+H]$^+$. $^1$H NMR (400 MHz, CD$_3$OD): δ 8.35 (d, J=5.6 Hz, 1H), 7.83-7.71 (m, 1H), 7.57-7.46 (m, 2H), 7.39-7.28 (m, 2H), 7.13-7.02 (m, 1H), 6.91-6.70 (m, 2H), 6.34-6.16 (m, 2H), 5.87-5.66 (m, 1H), 4.66-3.86 (m, 3H), 3.27-3.13 (m, 1H), 3.04-2.79 (m, 1H), 2.47 (s, 3H), 2.17-2.03 (m, 1H), 1.97-1.86 (m, 1H), 1.82-1.53 (m, 2H).

Example 776: (R)—N-(1-Acryloylpyrrolidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide

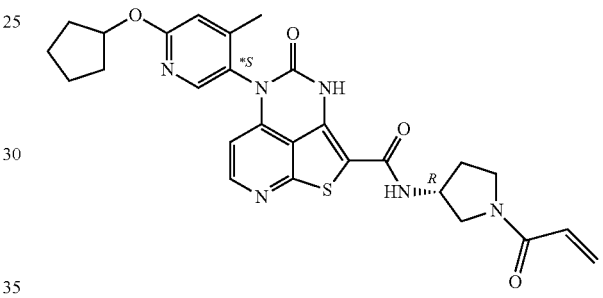

Step A: (R)-5-(6-(cyclopentyloxy)-4-methylpyridin-3-yl)-4-oxo-N-(pyrrolidin-3-yl)-4,5-dihydro-3H-1-thia-3,5,8-triazaacenaphthylene-2-carboxamide The title compound was prepared using analogous conditions as found in Method 1, steps A-H in Example 1 (including Chiral Resolution Method A after step F to obtain the *S atropisomer), and using 2-fluoro-4-methyl-5-nitropyridine and cyclopentanol in place of 5-fluoro-2-nitrotoluene and phenol in step A, and using Pd/C in place of Fe and NH$_4$Cl in step B, and using (R)-tert-butyl 3-aminopyrrolidine-1-carboxylate, diisopropylethylamine, DCM, and 1-propanephosphonic anhydride in place of tert-butyl (3R,5R)-3-amino-5-fluoropiperidine-1-carboxylate, triethylamine, HATU, and DMF in step G.

Step B: (R)—N-(1-Acryloylpyrrolidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide The title compound was prepared using (R)-5-(6-(cyclopentyloxy)-4-methylpyridin-3-yl)-4-oxo-N-(pyrrolidin-3-yl)-4,5-dihydro-3H-1-thia-3,5,8-triazaacenaphthylene-2-carboxamide, acrylic anhydride and diisopropylethylamine. MS (ESI): mass calcd. for $C_{27}H_{28}N_6O_4S$, 532.6; m/z found, 533.0 [M+H]$^+$. $^1$H NMR (500 MHz, CDCl$_3$): δ 9.69 (s, 1H), 8.32 (ddd, J=5.2, 4.0, 0.8 Hz, 1H), 8.05 (d, J=4.2 Hz, 1H), 6.73 (s, 1H), 6.49-6.29 (m, 2H), 6.03 (dd, J=6.4, 5.5 Hz, 1H), 5.69 (ddd, J=19.3, 9.7, 2.5 Hz, 1H), 5.41 (td, J=5.9, 5.4, 2.8

Hz, 1H), 5.31 (s, 2H), 4.79-4.64 (m, 1H), 3.84-3.56 (m, 4H), 3.46 (d, J=0.9 Hz, 1H), 2.19 (s, 3H), 2.03-1.90 (m, 2H), 1.90-1.73 (m, 4H), 1.64 (dtq, J=7.7, 5.4, 2.8, 2.1 Hz, 2H).

Example 777: (R)—N-(1-Acryloylpiperidin-3-yl)-5-(5-(2-fluorophenoxy)pyridin-2-yl)-4-oxo-4,5-dihydro-3H-1-thia-3,5,8-triazaacenaphthylene-2-carboxamide

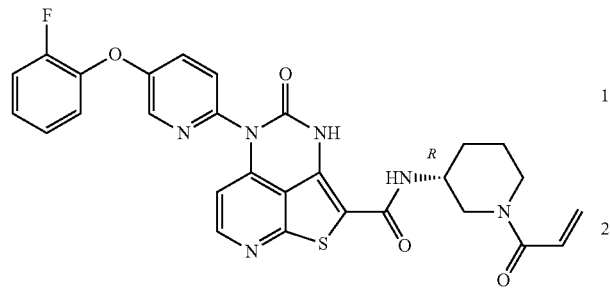

The title compound was prepared using analogous conditions as found in Method 1, steps A-G in Example 1, and using 5-bromo-2-nitropyridine and 2-fluorophenol in place of 5-fluoro-2-nitrotoluene and phenol in step A, and using Pd/C and MeOH in place of Fe, EtOH/H$_2$O, and NH$_4$Cl in step B, and using 5-(2-fluorophenoxy)pyridin-2-amine in place of 2-methyl-4-phenoxyaniline in step C, and using 1-[(3R)-3-Amino-1-piperidyl]prop-2-en-1-one (Intermediate 15) in place of tert-butyl (3R,5R)-3-amino-5-fluoropiperidine-1-carboxylate (Intermediate 1) in step G. MS (ESI): mass calcd. for C$_{28}$H$_{23}$FN$_6$O$_4$S, 558.6; m/z found, 559.1 [M+H]$^+$. $^1$H NMR (400 MHz, CD$_3$OD): δ 8.42-8.39 (m, 1H), 8.35 (d, J=5.6 Hz, 1H), 7.67-7.56 (m, 2H), 7.42-7.25 (m, 4H), 6.89-6.72 (m, 1H), 6.27-6.16 (m, 2H), 5.81-5.67 (m, 1H), 4.57-4.31 (m, 1H), 4.21-3.91 (m, 2H), 3.24-3.14 (m, 1H), 2.98-2.85 (m, 1H), 2.12-2.02 (m, 1H), 1.95-1.83 (m, 1H), 1.81-1.67 (m, 1H), 1.65-1.53 (m, 1H).

Example 778: (R)—N-(1-Acryloylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide

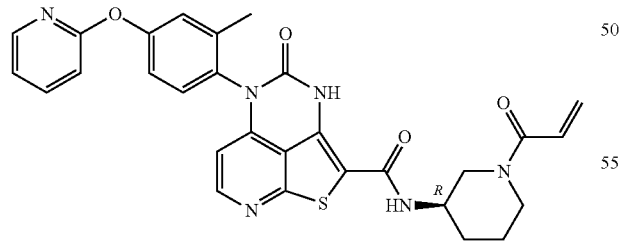

The title compound was prepared using analogous conditions as found in Method 1, steps A-G in Example 1, and using 2-fluoropyridine and 4-amino-3-methylphenol in place of 5-fluoro-2-nitrotoluene and phenol in step A, and no step B, and using 2-methyl-4-(pyridin-2-yloxy)aniline in place of 2-methyl-4-phenoxyaniline in step C, and using 1-[(3R)-3-Amino-1-piperidyl]prop-2-en-1-one (Intermediate 15) in place of tert-butyl (3R,5R)-3-amino-5-fluoropiperidine-1-carboxylate (Intermediate 1) in step G. MS (ESI): mass calcd. for C$_{29}$H$_{26}$N$_6$O$_4$S, 554.6; m/z found, 555.1 [M+H]$^+$. $^1$H NMR (400 MHz, CD$_3$OD): δ 8.34 (d, J=5.5 Hz, 1H), 8.21-8.13 (m, 1H), 7.92-7.83 (m, 1H), 7.43-7.34 (m, 1H), 7.24-7.19 (m, 1H), 7.18-7.11 (m, 2H), 7.09-7.04 (m, 1H), 6.89-6.71 (m, 1H), 6.26-6.13 m, 2H), 5.77-5.68 (m, 1H), 4.56-4.25 (m, 1H), 4.20-3.89 (m, 2H), 3.25-3.11 (m, 1H), 3.01-2.82 (m, 1H), 2.17 (s, 3H), 2.12-2.02 (m, 1H), 1.92-1.83 (m, 1H), 1.79-1.69 (m, 1H), 1.65-1.50 (m, 1H).

Example 779: (R)—N-(1-Acryloylpyrrolidin-3-yl)-5-(*S)-(6-isobutoxy-4-methylpyridin-3-yl)-4-oxo-4,5-dihydro-3H-1-thia-3,5,8-triazaacenaphthylene-2-carboxamide

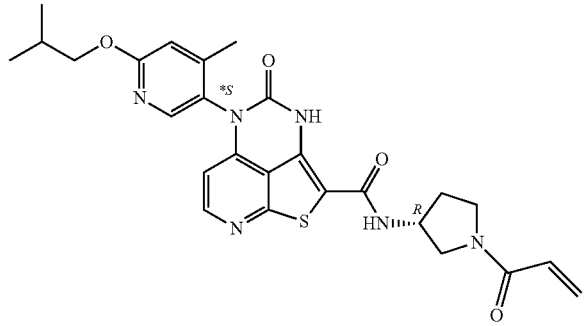

Step A: (R)-5-(6-isobutoxy-4-methylpyridin-3-yl)-4-oxo-N-(pyrrolidin-3-yl)-4,5-dihydro-3H-1-thia-3,5,8-triazaacenaphthylene-2-carboxamide The title compound was prepared in a manner analogous to Method 1, steps A-H in Example 1 (including Chiral Resolution Method A after step F to obtain the *S atropisomer), and using 2-fluoro-4-methyl-5-nitropyridine and 2-methyl-1-propanol 5-fluoro-2-nitrotoluene and phenol in step A, and using Pd/C and MeOH in place of Fe, EtOH/H$_2$O, and NH$_4$Cl in step B, and using 6-isobutoxy-4-methylpyridin-3-amine in place of 2-methyl-4-phenoxyaniline in step C, and using (R)-tert-butyl 3-aminopyrrolidine-1-carboxylate in place of tert-butyl (3R,5R)-3-amino-5-fluoropiperidine-1-carboxylate (Intermediate 1) in step G.

Step B: (R)—N-(1-Acryloylpyrrolidin-3-yl)-5-(*S)-(6-isobutoxy-4-methylpyridin-3-yl)-4-oxo-4,5-dihydro-3H-1-thia-3,5,8-triazaacenaphthylene-2-carboxamide The title compound was prepared using (R)-5-(6-isobutoxy-4-methylpyridin-3-yl)-4-oxo-N-(pyrrolidin-3-yl)-4,5-dihydro-3H-1-thia-3,5,8-triazaacenaphthylene-2-carboxamide, acrylic anhydride and diisopropylethylamine. MS (ESI): mass calcd. for C$_{26}$H$_{28}$N$_6$O$_4$S, 520.6; m/z found, 521.0 [M+H]$^+$. $^1$H NMR (400 MHz, CDCl$_3$): δ 9.69 (s, 1H), 8.33 (dd, J=5.5, 4.0 Hz, 1H), 8.03 (d, J=4.2 Hz, 1H), 7.65 (d, J=6.5 Hz, 1H), 6.80 (s, 1H), 6.50-6.33 (m, 2H), 6.03 (t, J=5.8 Hz, 1H), 5.70 (ddd, J=14.0, 8.8, 3.5 Hz, 1H), 3.81-3.63 (m, 7H), 2.18-2.01 (m, 6H), 1.03 (dd, J=6.6, 1.1 Hz, 6H).

Example 780: N¹-(15-Oxo-19-((3aR,4R,6aS)-2-oxohexahydro-1H-thieno[3,4-d]imidazol-4-yl)-4,7,10-trioxa-14-azanonadecyl)-N⁵-((E)-4-oxo-4-(3-(4-oxo-5-(5-phenoxypyridin-2-yl)-4,5-dihydro-3H-1-thia-3,5,8-triazaacenaphthylene-2-carboxamido)piperidin-1-yl)but-2-en-1-yl)glutaramide

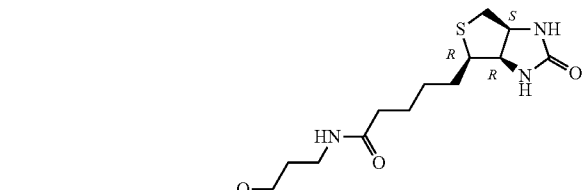
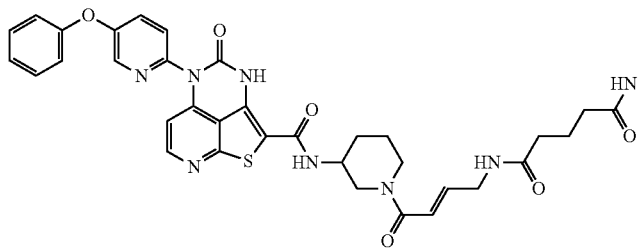

Step A: (R)-4-Oxo-5-(5-phenoxypyridin-2-yl)-N-(piperidin-3-yl)-4,5-dihydro-3H-1-thia-3,5,8-triazaacenaphthylene-2-carboxamide The title compound was prepared using analogous conditions as found in Method 1, steps A-H in Example 1, and using 5-bromo-2-nitropyridine in place of 5-fluoro-2-nitrotoluene in step A, and using Pd/C in place of Fe and NH₄Cl in step B, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (E)-4-((tert-Butoxycarbonyl)amino)but-2-enoic Acid

To a round bottom flask containing (E)-4-aminobut-2-enoic acid (612 mg, 6.05 mmol) was added (Boc)₂O (2.643 g, 12.11 mmol), Na₂CO₃ (1.674 g, 12.11 mmol), THF (30 mL), and water (15 mL) and was stirred at rt overnight. The mixture was adjusted to pH=9 with aqueous LiOH and extracted with EtOAc. The aqueous layer was adjusted to pH=3 with 1 M aqueous HCl and was extracted with EtOAc. The organic layer was collected and concentrated to dryness to give the title compound (1.10 g, 90.3% yield), which was used in the next step without further purification.

Step C: (R,E)-N-(1-(4-Aminobut-2-enoyl)piperidin-3-yl)-4-oxo-5-(5-phenoxypyridin-2-yl)-4,5-dihydro-3H-1-thia-3,5,8-triazaacenaphthylene-2-carboxamide A solution of (R)-4-oxo-5-(5-phenoxypyridin-2-yl)-N-(piperidin-3-yl)-4,5-dihydro-3H-1-thia-3,5,8-triazaacenaphthylene-2-carboxamide (187 mg, 0.358 mmol), (E)-4-((tert-butoxycarbonyl)amino)but-2-enoic acid (72.0 mg, 0.358 mmol), HATU (163 mg, 0.429 mmol) and triethylamine (109 mg, 1.07 mmol) in anhydrous DMF was stirred at rt for 20 min. The mixture was purified by flash column chromatography to give a yellow solid. The solid was diluted in 6.0 M aqueous HCl and was stirred at rt for 10 min, then concentrated to dryness to give the title compound (156 mg, 67.9% yield) as a yellow solid. MS (ESI): mass calcd. for $C_{29}H_{27}N_7O_4S$, 569.63; m/z found, 570.3 [M+H]⁺.

Step D: tert-Butyl (3-(2-(2-(3-aminopropoxy)ethoxy)ethoxy)propyl)carbamate

To a solution of 3,3'-((oxybis(ethane-2,1-diyl))bis(oxy))bis(propan-1-amine) (10 g, 45 mmol) and triethylamine (4.6 g, 45 mmol) in DCM (150 mL) was added solution of (Boc)₂O (5.0 g, 23 mmol) in DCM (100 mL) cooled in an ice-bath and was stirred at rt overnight. The solution was concentrated to dryness and purified by flash column chromatography to give the title compound (5.976 g, 82.00% yield) as a slight yellow oil. MS (ESI): mass calcd. for $C_{15}H_{32}N_2O_5$, 320.42; m/z found, 321.2 [M+H]⁺.

Step E: tert-Butyl (15-oxo-19-((3aS,4S,6aR)-2-oxohexahydro-1H-thieno[3,4-d]imidazol-4-yl)-4,7,10-trioxa-14-azanonadecyl)carbamate A solution of 5-((3aS,4S,6aR)-2-oxohexahydro-1H-thieno[3,4-d]imidazol-4-yl)pentanoic acid (4.0 g, 16 mmol), HATU (7.5 g, 20 mmol), and triethylamine (3.3 g, 33 mmol) in anhydrous DMF (50 mL) was stirred at rt for 10 min. tert-Butyl (3-(2-(2-(3-aminopropoxy)ethoxy)ethoxy)propyl)carbamate (5.976 g, 18.65 mmol) was added and the mixture was stirred for 16 h. The reaction was concentrated to dryness and purified by flash column chromatography to give the title compound (5.8 g, 65% yield). MS (ESI): mass calcd. for $C_{25}H_{46}N_4O_7S$, 546.72; m/z found, 547.4 [M+H]⁺.

Step F: N-(3-(2-(2-(3-Aminopropoxy)ethoxy)ethoxy)propyl)-5-((3aS,4S,6aR)-2-oxohexahydro-1H-thieno[3,4-d]imidazol-4-yl)pentanamide A solution of tert-butyl (15-oxo-19-((3aS,4S,6aR)-2-oxohexahydro-1H-thieno[3,4-d]imidazol-4-yl)-4,7,10-trioxa-14-azanonadecyl)carbamate (5.8 g, 11 mmol) in 5 M HCl in MeOH (30 mL) was concentrated to dryness at 50° C. to give the title compound (5.2 g, 100% yield) as a yellow oil. MS (ESI): mass calcd. for $C_{20}H_{38}N_4O_5S$, 446.61; m/z found, 447.3 [M+H]⁺.

Step G: Methyl 5,21-dioxo-25-((3aS,4S,6aR)-2-oxohexahydro-1H-thieno[3,4-d]imidazol-4-yl)-10,13,16-trioxa-6,20-diazapentacosan-1-oate A solution of 5-methoxy-5-oxopentanoic acid (1.57 g, 10.8 mmol), HATU (4.91 g, 12.9 mmol), and triethylamine (4.35 g, 43.1 mmol) in anhydrous DMF (50 mL) was stirred at rt for 10 min. N-(3-(2-(2-(3-Aminopropoxy)ethoxy)ethoxy)propyl)-5-((3aS,4S,6aR)-2-oxohexahydro-1H-thieno[3,4-d]imidazol-4-yl)pentanamide (5.2 g, 11 mmol) was added and the mixture was stirred for 16 h. The reaction was concentrated to dryness and purified by flash column chromatography to give the titled compound (3.3 g, 53% yield). MS (ESI): mass calcd. for $C_{26}H_{46}N_4O_8S$, 574.73; m/z found, 575.3 $[M+H]^+$.

Step H: 5,21-Dioxo-25-((3aS,4S,6aR)-2-oxohexahydro-1H-thieno[3,4-d]imidazol-4-yl)-10,13,16-trioxa-6,20-diazapentacosan-1-oic Acid To a solution of methyl 5,21-dioxo-25-((3aS,4S,6aR)-2-oxohexahydro-1H-thieno[3,4-d]imidazol-4-yl)-10,13,16-trioxa-6,20-diazapentacosan-1-oate (3.3 g, 5.7 mmol) and $CaCl_2$ (9.6 g, 86 mmol) in $iPrOH:H_2O$ (7:3, 108 mL) was added 0.5 M NaOH (14 mL) at rt. After 5 h, the reaction was neutralized with 5 M aqueous HCl, extracted with DCM (3×100 mL), dried over anhydrous $Na_2SO_4$, and concentrated to dryness. The residue was purified by flash column chromatography to give the titled compound (2.0 g, 42% yield) as a colorless viscous foam. MS (ESI): mass calcd. for $C_{25}H_{44}N_4O_8S$, 560.70; m/z found, 561.3 $[M+H]^+$.

Step I: $N^1$-(15-Oxo-19-((3aR,4R,6aS)-2-oxohexahydro-1H-thieno[3,4-d]imidazol-4-yl)-4,7,10-trioxa-14-azanonadecyl)-$N^5$-((E)-4-oxo-4-(3-(4-oxo-5-(5-phenoxypyridin-2-yl)-4,5-dihydro-3H-1-thia-3,5,8-triazaacenaphthylene-2-carboxamido)piperidin-1-yl)but-2-en-1-yl)glutaramide A solution of 5,21-dioxo-25-((3aS,4S,6aR)-2-oxohexahydro-1H-thieno[3,4-d]imidazol-4-yl)-10,13,16-trioxa-6,20-diazapentacosan-1-oic acid (230 mg, 0.41 mmol), HATU (156 mg, 0.411 mmol), and triethylamine (55 mg, 0.55 mmol) in anhydrous DMF (10 mL) was stirred at rt for 10 min. (R,E)-N-(1-(4-Aminobut-2-enoyl)piperidin-3-yl)-4-oxo-5-(5-phenoxypyridin-2-yl)-4,5-dihydro-3H-1-thia-3,5,8-triazaacenaphthylene-2-carboxamide (156 mg, 0.411 mmol) was added and the reaction was stirred for 2 h. The reaction was concentrated to dryness and purified by flash column chromatography to give the titled compound (102 mg, 33.2% yield) as a light yellow solid. MS (ESI): mass calcd. for $C_{54}H_{69}N_{11}O_{11}S_2$, 1112.3; m/z found, 1112.6 $[M+H]^+$. $^1$H NMR (400 MHz, $CD_3OD$): δ 8.37 (s, 1H), 8.31 (d, J=5.1 Hz, 1H), 7.60 (d, J=8.2 Hz, 2H), 7.67-7.54 (m, 2H), 7.49-7.40 (m, 1H), 7.20-7.12 (m, 2H), 6.75-6.64 (m, 1H), 6.61-6.48 (m, 1H), 6.23 (d, J=4.8 Hz, 1H), 4.51-4.40 (m, 1H), 4.32-4.10 (m, 2H), 3.99-3.85 (m, 3H), 3.63-3.42 (m, 12H), 3.27-3.10 (m, 6H), 2.96-2.82 (m, 2H), 2.72-2.62 (m, 1H), 2.32-2.12 (m, 6H), 2.10-2.00 (m, 1H), 1.94-1.80 (m, 3H), 1.79-1.46 (m, 11H), 1.46-1.34 (m, 2H).

Example 781: (R)—N-(1-Acryloylpyrrolidin-3-yl)-5-(2-methyl-4-(pyridin-2-yloxy)phenyl)-4-oxo-4,5-dihydro-3H-1-thia-3,5,8-triazaacenaphthylene-2-carboxamide

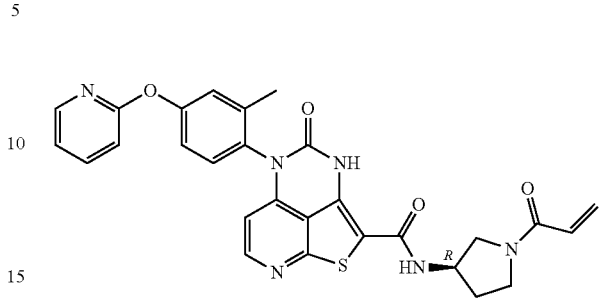

The title compound was prepared using analogous conditions as found in Method 1, steps A-G in Example 1, and using 2-fluoropyridine and 4-amino-3-methylphenol in place of 5-fluoro-2-nitrotoluene and phenol in step A, and no step B, and using 2-methyl-4-(pyridin-2-yloxy)aniline in place of 2-methyl-4-phenoxyaniline in step C, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{28}H_{24}N_6O_4S$, 540.6; m/z found, 541.1 $[M+H]^+$. $^1$H NMR (400 MHz, $CD_3OD$): δ 8.34 (d, J=5.5 Hz, 1H), 8.19-8.15 (m, 1H), 7.93-7.82 (m, 1H), 7.43-7.34 (m, 1H), 7.25-7.20 (m, 1H), 7.18-7.10 (m, 2H), 7.10-7.04 (m, 1H), 6.67-6.53 (m, 1H), 6.32-6.19 (m, 2H), 5.79-5.69 (m, 1H), 4.67-4.60 (m, 1H), 4.03-3.50 (m, 4H), 2.38-2.23 (m, 1H), 2.17 (s, 3H), 2.16-2.01 (m, 1H).

Example 782: (R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide

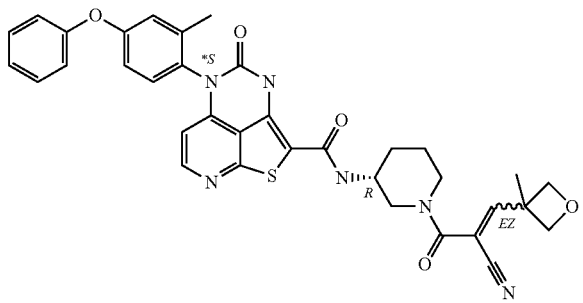

Step A: (R)—N-(1-(2-Cyanoacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide A solution of (R)-5-(*S)-(2-methyl-4-phenoxyphenyl)-4-oxo-N-(piperidin-3-yl)-4,5-dihydro-3H-1-thia-3,5,8-triazaacenaphthylene-2-carboxamide (Intermediate 98) (300 mg, 0.601 mmol), 2-cyanoacetic acid (102 mg, 1.20 mmol), HATU (297 mg, 0.780 mmol), and diisopropylethylamine (155 mg, 1.20 mmol) in DMF (5 mL) was stirred at rt for 1 h. The mixture was purified by flash column chromatography to give the title compound (225 mg, 66.2% yield) as a white solid. MS (ESI): mass calcd. for $C_{30}H_{26}N_6O_4S$, 566.63; m/z found, 567.2 $[M+H]^+$.

Step B: (R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide A solution of (R)—N-(1-(2-cyanoacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide (70.0 mg, 0.124 mmol), 3-methyloxetane-3-carbaldehyde (37 mg, 0.37 mmol), piperidine (0.30 mL), AcOH (0.10 mL), dioxane (5 mL), and 4A molecular sieves (0.3 g) was stirred at 100° C. for 0.5 h under $N_2$. The mixture was concentrated to dryness and purified by flash column chromatography to give the title compound as the E/Z mixture (55 mg, 68% yield) as white solid. MS (ESI): mass calcd. for $C_{35}H_{32}N_6O_5S$, 648.7; m/z found, 649.3 $[M+H]^+$. $^1H$ NMR (400 MHz, $CD_3OD$): δ 8.34-8.28 (m, 1H), 7.44-7.36 (m, 2H), 7.34-6.79 (m, 2H), 7.19-7.12 (m, 1H), 7.11-7.02 (m, 3H), 7.00-6.93 (m, 1H), 6.08-6.03 (m, 1H), 5.02-4.89 (m, 1H), 4.75-3.55 (m, 8H), 2.17-2.01 (m, 4H), 1.98-1.84 (m, 1H), 1.80-1.56 (m, 4H), 1.43-1.35 (m, 1H).

Example 783: (R)—N-(1-Acryloylpiperidin-3-yl)-5-(2-methyl-4-((6-methylpyridin-3-yl)oxy)phenyl)-4-oxo-4,5-dihydro-3H-1-thia-3,5,8-triazaacenaphthylene-2-carboxamide

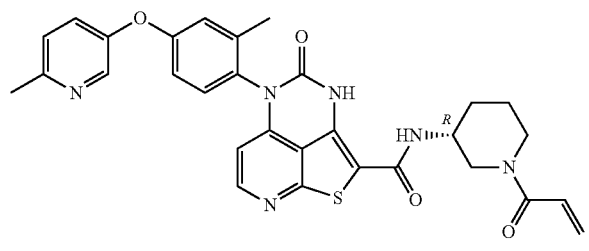

The title compound was prepared using analogous conditions as found in Method 1, steps A-G in Example 1, and using 4-fluoro-2-methyl-1-nitrobenzene and 6-methylpyridin-3-ol in place of 5-fluoro-2-nitrotoluene and phenol in step A, and using Pd/C and MeOH in place of Fe, EtOH/$H_2O$, and $NH_4Cl$ in step B, and using 2-methyl-4-((6-methylpyridin-3-yl)oxy)aniline in place of 2-methyl-4-phenoxyaniline in step C, and using 1-[(3R)-3-Amino-1-piperidyl]prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{30}H_{28}N_6O_4S$, 568.6; m/z found, 569.2 $[M+H]^+$. $^1H$ NMR (400 MHz, $CD_3OD$): δ 8.32 (d, J=5.6 Hz, 1H), 8.29-8.19 (m, 1H), 7.53-7.45 (m, 1H), 7.39-7.30 (m, 2H), 7.17-7.07 (m, 1H), 7.05-6.95 (m, 1H), 6.86-6.68 (m, 1H), 6.26-6.14 (m, 1H), 6.07 (d, J=5.7 Hz, 1H), 5.78-5.66 (m, 1H), 4.58-4.23 (m, 1H), 4.20-3.90 (m, 2H), 3.23-3.11 (m, 1H), 2.98-2.84 (m, 1H), 2.53 (s, 3H), 2.14 (s, 3H), 2.10-2.03 (m, 1H), 1.92-1.81 (m, 1H), 1.79-1.66 (m, 1H), 1.63-1.52 (m, 1H).

Example 784: (R)—N-(1-Acryloylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide

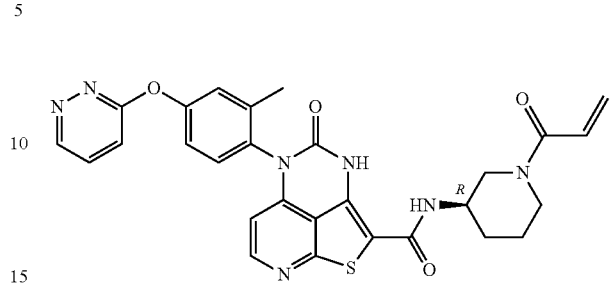

The title compound was prepared using analogous conditions as found in Method 1, steps A-G in Example 1, and using 3,6-dichloropyridazine and 3-methyl-4-nitrophenol in place of 5-fluoro-2-nitrotoluene and phenol in step A, and using Pd/C and MeOH in place of Fe, EtOH/$H_2O$, and $NH_4Cl$ in step B, and using 2-methyl-4-(pyridazin-3-yloxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{28}H_{25}N_7O_4S$, 555.6; m/z found, 556.1 $[M+H]^+$. $^1H$ NMR (400 MHz, $CD_3OD$ and DMSO-$d_6$): δ 8.97-8.93 (m, 1H), 8.33-8.28 (m, 1H), 7.74-7.68 (m, 1H), 7.46-7.38 (m, 2H), 7.31-7.27 (m, 1H), 7.23-7.17 (m, 1H), 6.78-6.68 (m, 1H), 6.15-6.01 (m, 2H), 5.69-5.61 (m, 1H), 4.51-4.01 (m, 2H), 3.88-3.78 (m, 1H), 3.12-2.97 (m, 1H), 2.85-2.66 (m, 1H), 2.11 (s, 3H), 2.01-1.90 (m, 1H), 1.83-1.72 (m, 1H), 1.71-1.56 (m, 1H), 1.55-1.41 (m, 1H).

Example 785: N—((R)-1-Acryloylpiperidin-3-yl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide

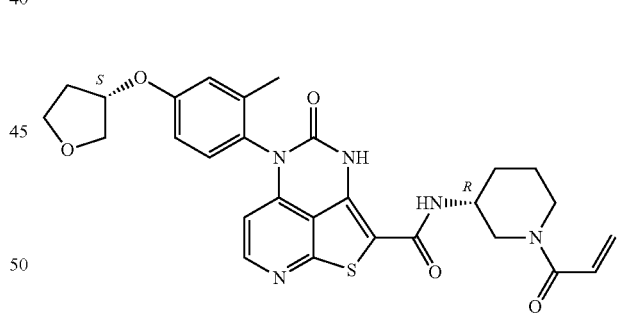

The title compound was prepared using analogous conditions as found in Method 1, steps A-G in Example 1, and using 4-fluoro-2-methyl-1-nitrobenzene and (S)-tetrahydrofuran-3-ol in place of 5-fluoro-2-nitrotoluene and phenol in step A, and using Pd/C and MeOH/THF (2:1) in place of Fe, EtOH/$H_2O$, and $NH_4Cl$ in step B, and using (S)-2-methyl-4-((tetrahydrofuran-3-yl)oxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{28}H_{29}N_5O_5S$, 547.6; m/z found, 548.2 $[M+H]^+$. $^1H$ NMR (400 MHz, $CD_3OD$): δ 8.30 (d, J=5.6 Hz, 1H), 7.30-7.19 (m, 1H), 7.01-6.96 (m, 1H), 6.96-6.88 (m, 1H), 6.85-6.73 (m, 1H), 6.24-6.11 (m, 1H), 6.02 (d, J=5.3 Hz, 1H), 5.78-5.66 (m, 1H), 5.11-5.03 (m, 1H), 4.57-4.26 (m, 1H), 4.24-3.80 (m, 6H), 3.22-3.09 (m, 1H), 2.95-2.82 (m, 1H), 2.33-2.21 (m, 1H), 2.18-2.09 (m, 4H), 2.09-2.00 (m, 1H), 1.90-1.80 (m, 1H), 1.79-1.64 (m, 1H), 1.63-1.50 (m, 1H).

Example 786: (R)—N-(1-Acryloylpiperidin-3-yl)-5-(4-((5-methylpyridin-2-yl)oxy)phenyl)-4-oxo-4,5-dihydro-3H-1-thia-3,5,8-triazaacenaphthylene-2-carboxamide

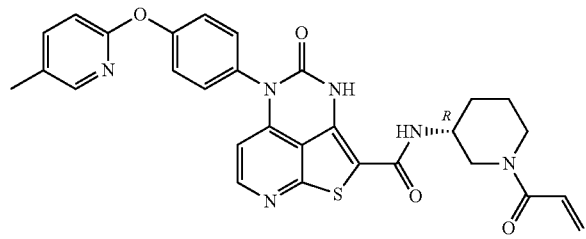

The title compound was prepared using analogous conditions as found in Method 1, steps A-G in Example 1, and using 1-fluoro-4-nitrobenzene and 6-methylpyridin-3-ol in place of 5-fluoro-2-nitrotoluene and phenol in step A, and using Pd/C and MeOH in place of Fe, EtOH/H$_2$O, and NH$_4$Cl in step B, and using 4-((6-methylpyridin-3-yl)oxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for C$_{29}$H$_{26}$N$_6$O$_4$S, 554.6; m/z found, 555.2 [M+H]$^+$. $^1$H NMR (400 MHz, CD$_3$OD): δ 8.33-8.22 (m, 2H), 7.53-7.40 (m, 3H), 7.37-7.30 (m, 1H), 7.26-7.17 (m, 2H), 6.84-6.69 (m, 1H), 6.22-6.13 (m, 2H), 5.78-5.64 (m, 1H), 4.55-4.26 (m, 1H), 4.23-3.88 (m, 2H), 3.25-3.08 (m, 1H), 2.97-2.79 (m, 1H), 2.52 (s, 3H), 2.09-1.99 (m, 1H), 1.90-1.82 (m, 1H), 1.77-1.64 (m, 1H), 1.61-1.50 (m, 1H).

Example 787: N—((R)-1-Acryloylpiperidin-3-yl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide

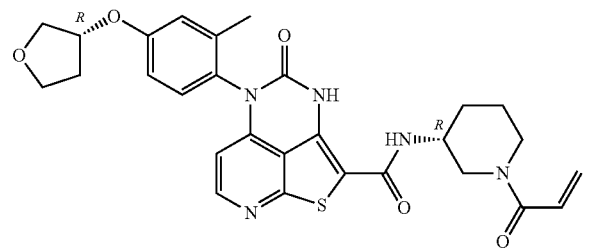

The title compound was prepared using analogous conditions as found in Method 1, steps A-G in Example 1, and using 4-fluoro-2-methyl-1-nitrobenzene and (R)-tetrahydrofuran-3-ol in place of 5-fluoro-2-nitrotoluene and phenol in step A, and using Pd/C in place Fe, EtOH/H$_2$O, and NH$_4$Cl in step B, and using (R)-2-methyl-4-((tetrahydrofuran-3-yl)oxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for C$_{28}$H$_{29}$N$_5$O$_5$S, 547.6; m/z found, 548.2 [M+H]$^+$. $^1$H NMR (400 MHz, CD$_3$OD): δ 8.30 (d, J=5.5 Hz, 1H), 7.33-7.19 (m, 1H), 7.04-6.97 (m, 1H), 6.96-6.90 (m, 1H), 6.88-6.69 (m, 1H), 6.27-6.14 (m, 1H), 6.02 (d, J=5.5 Hz, 1H), 5.80-5.65 (m, 1H), 5.15-5.04 (m, 1H), 4.63-4.24 (m, 1H), 4.21-3.80 (m, 6H), 3.24-3.11 (m, 1H), 3.00-2.81 (m, 1H), 2.37-2.23 (m, 1H), 2.20-2.01 (m, 5H), 1.93-1.83 (m, 1H), 1.82-1.67 (m, 1H), 1.65-1.52 (m, 1H).

Example 16: 1-Acryloyl-N-(5-(2-methyl-4-phenoxyphenyl)-4-oxo-4,5-dihydro-3H-1-thia-3,5,8-triazaacenaphthylen-2-yl)piperidine-3-carboxamide

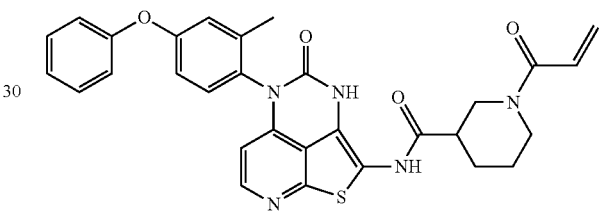

Step A: tert-Butyl (5-(2-methyl-4-phenoxyphenyl)-4-oxo-4,5-dihydro-3H-1-thia-3,5,8-triazaacenaphthylen-2-yl)carbamate 5-(2-Methyl-4-phenoxyphenyl)-4-oxo-4,5-dihydro-3H-1-thia-3,5,8-triazaacenaphthylene-2-carboxylic acid (Intermediate 27, 200 mg, 0.479 mmol) was heated under reflux in redistilled thionyl chloride (0.50 mL) for 5 h. The thionyl chloride was removed under reduced pressure and the residue was taken up in dry acetone (2 mL), cooled to 0° C., and sodium azide (500 mg, 7.69 mmol) was added dropwise with stirring and the solution was allowed to warm to 20° C. over 10 min. The reaction was diluted with water, extracted with EtOAc, and the solvent was removed under reduced pressure. The residue was taken up into t-butyl alcohol (37.5 mL) and was heated at reflux for 5 h. The reaction was concentrated to dryness to give the title compound (180 mg, 53.9% yield). MS (ESI): mass calcd. for C$_{26}$H$_{24}$N$_4$O$_4$S, 488.56; m/z found, 489.0 [M+H]$^+$.

Step B: 1-Acryloyl-N-(5-(2-methyl-4-phenoxyphenyl)-4-oxo-4,5-dihydro-3H-1-thia-3,5,8-triazaacenaphthylen-2-yl)piperidine-3-carboxamide The title compound was prepared using N-(5-(2-methyl-4-phenoxyphenyl)-4-oxo-4,5-dihydro-3H-1-thia-3,5,8-triazaacenaphthylen-2-yl)piperidine-3-carboxamide (Example 828), acrylic acid, HATU, and diisopropylethylamine. MS (ESI): mass calcd. for $C_{30}H_{27}N_5O_4S$, 553.6; m/z found, 554.2 [M+H]⁺.

Example 789: (R)—N-(1-Acryloylpiperidin-3-yl)-5-(*S)-(6-isopropoxy-4-methylpyridin-3-yl)-4-oxo-4,5-dihydro-3H-1-thia-3,5,8-triazaacenaphthylene-2-carboxamide

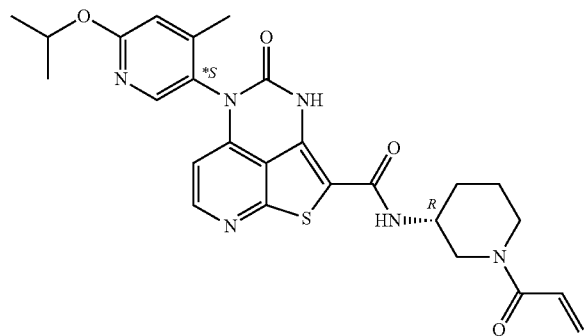

Step A: (R)-5-(6-isopropoxy-4-methylpyridin-3-yl)-4-oxo-N-(piperidin-3-yl)-4,5-dihydro-3H-1-thia-3,5,8-triazaacenaphthylene-2-carboxamide The title compound was prepared using analogous conditions as found in Method 1, steps A-H in Example 1 (including Chiral Resolution Method A after step F to obtain the *S atropisomer), and using 2-fluoro-4-methyl-5-nitropyridine and 2-propanol in place of 5-fluoro-2-nitrotoluene and phenol in step A, and using Pd/C in place of Fe and NH₄Cl in step B, and using (R)-1-Boc-3-aminopiperidine, 1-propanephosphonic anhydride, and diisopropylethylamine in place of tert-butyl (3R,5R)-3-amino-5-fluoropiperidine-1-carboxylate, HATU, and triethylamine in step G.

Step B: (R)—N-(1-Acryloylpiperidin-3-yl)-5-(*S)-(6-isopropoxy-4-methylpyridin-3-yl)-4-oxo-4,5-dihydro-3H-1-thia-3,5,8-triazaacenaphthylene-2-carboxamide The title compound was prepared using (R)-5-(6-isopropoxy-4-methylpyridin-3-yl)-4-oxo-N-(piperidin-3-yl)-4,5-dihydro-3H-1-thia-3,5,8-triazaacenaphthylene-2-carboxamide, acrylic anhydride and diisopropylethylamine. MS (ESI): mass calcd. for $C_{26}H_{28}N_6O_4S$, 520.6; m/z found, 521.2 [M+H]⁺. ¹H NMR (500 MHz, CDCl₃): δ 8.35 (d, J=5.5 Hz, 1H), 8.01 (s, 1H), 6.72 (s, 1H), 6.63 (dd, J=16.7, 10.6 Hz, 1H), 6.41 (s, 1H), 6.31 (d, J=17.5 Hz, 1H), 6.05 (d, J=5.5 Hz, 1H), 5.95 (s, 1H), 5.73 (s, 1H), 5.38-5.26 (m, 1H), 4.05 (s, 1H), 3.83-3.79 (m, 1H), 3.56 (s, 1H), 3.52-3.44 (m, 1H), 3.28 (s, 1H), 2.14 (s, 3H), 2.07 (d, J=23.7 Hz, 1H), 2.00 (s, 1H), 1.71-1.62 (m, 1H), 1.37 (dd, J=13.2, 6.2 Hz, 6H), 1.23 (dt, J=26.2, 7.1 Hz, 1H).

Example 790: (R)—N-(1-Acryloylpyrrolidin-3-yl)-5-(2-methyl-4-(pyridazin-3-yloxy)phenyl)-4-oxo-4,5-dihydro-3H-1-thia-3,5,8-triazaacenaphthylene-2-carboxamide

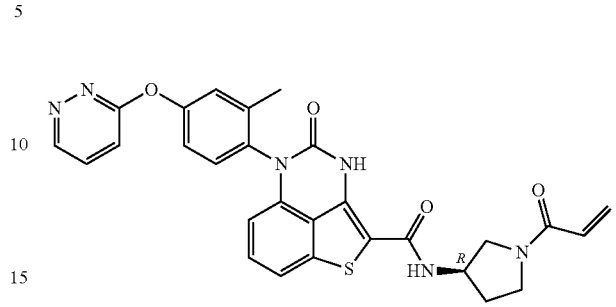

The title compound was prepared using analogous conditions as found in Method 1, steps A-G in Example 1, and using 4-amino-3-methylphenol and 3,6-dichloropyridazine in place of 5-fluoro-2-nitrotoluene and phenol in step A, and using Pd/C and MeOH in place of Fe, EtOH/H₂O, and NH₄Cl in step B, and using 2-methyl-4-(pyridazin-3-yloxy)aniline in place of 2-methyl-4-phenoxyaniline in step C, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{27}H_{23}N_7O_4S$, 541.6; m/z found, 542.2 [M+H]⁺. ¹H NMR (400 MHz, DMSO-d₆): δ 10.37 (s, 1H), 9.06-9.01 (m, 1H), 8.42-8.31 (m, 2H), 7.83-7.76 (s, 1H), 7.56-7.50 (m, 1H), 7.49-7.43 (m, 1H), 7.36-7.32 (m, 1H), 7.28-7.22 (m, 1H), 6.65-6.51 (m, 1H), 6.18-6.09 (m, 1H), 6.00-5.94 (m, 1H), 5.70-5.62 (m, 1H), 4.58-4.40 (m, 1H), 3.90-3.40 (m, 4H), 2.24-1.95 (m, 5H).

Example 791: (R)—N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide

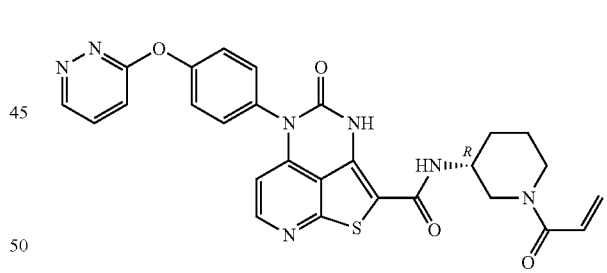

The title compound was prepared using analogous conditions as found in Method 1, steps A-G in Example 1, and using 3,6-dichloropyridazine and 4-nitrophenol in place of 5-fluoro-2-nitrotoluene and phenol in step A, and using Pd/C and MeOH in place of Fe, EtOH/H₂O, and NH₄Cl in step B, and using 4-(pyridazin-3-yloxy)aniline in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{27}H_{23}N_7O_4S$, 541.6; m/z found, 542.1 [M+H]⁺. ¹H NMR (400 MHz, CD₃OD): δ 8.98-8.94 (m, 1H), 8.35-8.31 (m, 1H), 7.81-7.75 (m, 1H), 7.55-7.48 (m, 3H), 7.47-7.42 (m, 2H), 6.85-6.73 (m, 1H), 6.34-6.19 (m, 1H), 6.24-6.16 (m, 1H), 5.77-5.69 (m, 1H), 4.55-4.27 (m, 1H), 4.21-3.90 (m, 2H), 3.24-3.10 (m, 1H), 3.00-2.82 (m, 1H), 2.17-1.99 (m, 1H), 1.94-1.83 (m, 1H), 1.79-1.66 (m, 1H), 1.65-1.53 (m, 1H).

Example 792: (R)—N-(1-Acryloylpiperidin-3-yl)-5-(*S)-(6-isobutyl-2-methylpyridin-3-yl)-4-oxo-4,5-dihydro-3H-1-thia-3,5,8-triazaacenaphthylene-2-carboxamide

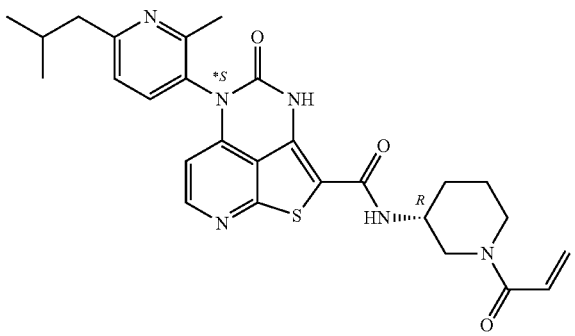

Step A: 6-Isobutyl-2-methylpyridin-3-amine

To a 500 mL round bottom flask were added 5-amino-2-bromo-6-picoline (5.0 g, 27 mmol), 1,1'-bis(diphenylphosphino)ferrocene-palladium(II)dichloride dichloromethane complex (550 mg, 0.668 mmol), and THF (27 mL) with stirring. The flask was evacuated, then refilled with $N_2$ (3×). Next was added 2-methylpropylzinc bromide (0.5 M in THF, 27 mL, 27 mmol) and was heated to 60° C. for 3 h. The reaction was cooled in an ice bath and $NaHCO_3$ was added to quench the reaction. The reaction was extracted with DCM, washed with water and brine, dried over anhydrous $Na_2SO_4$, filtered, and concentrated to dryness. The residue was purified by normal phase flash column chromatography ($SiO_2$) to give the title compound (2.46 g, 56.0% yield) as a beige solid.

Step B: (R)—N-(1-Acryloylpiperidin-3-yl)-5-(*S)-(6-isobutyl-2-methylpyridin-3-yl)-4-oxo-4,5-dihydro-3H-1-thia-3,5,8-triazaacenaphthylene-2-carboxamide The title compound was prepared using analogous conditions as found in Method 1, steps C-G in Example 1, and using 6-isobutyl-2-methylpyridin-3-amine in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. Atropisomers were resolved by chiral SFC (Stationary phase: CHIRALCEL AS-H, 5 m, 250×20 mm, Mobile phase: 65% $CO_2$, 35% MeOH), to give the title compound. MS (ESI): mass calcd. for $C_{27}H_{30}N_6O_3S$, 518.6; m/z found, 519.2 [M+H]$^+$. $^1$H NMR (500 MHz, DMSO-$d_6$): δ 10.31 (s, 1H), 8.34 (d, J=5.5 Hz, 1H), 8.21-8.07 (m, 1H), 7.75 (d, J=8.0 Hz, 1H), 7.29 (d, J=8.0 Hz, 1H), 6.86-6.72 (m, 1H), 6.11 (d, J=16.8 Hz, 1H), 5.93 (d, J=5.5 Hz, 1H), 5.69 (d, J=10.3 Hz, 1H), 4.35 (dd, J=128.2, 12.2 Hz, 1H), 4.03 (dd, J=39.6, 11.8 Hz, 1H), 3.79 (s, 1H), 3.05 (d, J=47.2, 12.1 Hz, 1H), 2.81-2.62 (m, 3H), 2.28 (s, 3H), 2.17-2.06 (m, 1H), 1.98-1.92 (m, 1H), 1.82-1.75 (m, 1H), 1.75-1.58 (m, 1H), 1.50-1.35 (m, 1H), 0.94 (d, J=6.6 Hz, 6H).

Example 793: (R)-5-(*S)-(2-Methyl-6-phenoxypyridin-3-yl)-4-oxo-N-(tetrahydrofuran-3-yl)-4,5-dihydro-3H-1-thia-3,5,8-triazaacenaphthylene-2-carboxamide

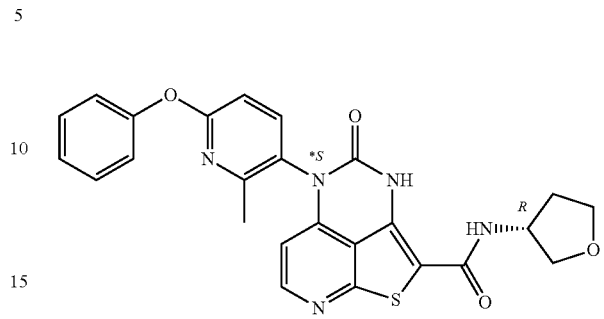

The title compound was prepared using analogous conditions as found in Method 1, steps A-G in Example 1 (including Chiral Resolution Method A after step F to obtain the *S atropisomer), and using 6-chloro-2-methyl-3-nitropyridine in place of 5-fluoro-2-nitrotoluene in step A, and using Pd/C in place of Fe and $NH_4Cl$ in step B, and using (R)-tetrahydrofuran-3-amine hydrochloride and diisopropylethylamine in place of tert-butyl (3R,5R)-3-amino-5-fluoropiperidine-1-carboxylate and triethylamine in step G. MS (ESI): mass calcd. for $C_{25}H_{21}N_5O_4S$, 487.5; m/z found, 488.0 [M+H]$^+$. $^1$H NMR (500 MHz, Methanol-$d_4$) δ 8.36 (d, J=5.5 Hz, 1H), 7.78 (d, J=8.5 Hz, 1H), 7.56-7.10 (m, 5H), 6.91 (d, J=8.6 Hz, 1H), 6.15 (d, J=5.5 Hz, 1H), 4.66-4.52 (m, 1H), 4.11-3.67 (m, 4H), 2.33-2.18 (m, 4H), 2.11-1.95 (m, 1H).

Example 794: (R)-5-(*S)-(6-Isopropoxy-4-methylpyridin-3-yl)-4-oxo-N-(piperidin-3-yl)-4,5-dihydro-3H-1-thia-3,5,8-triazaacenaphthylene-2-carboxamide

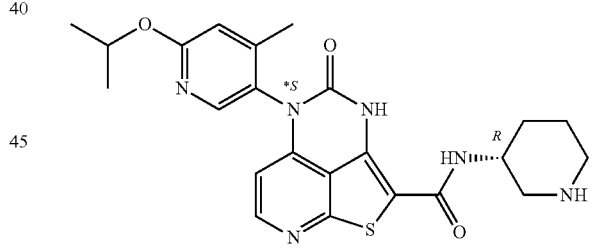

The title compound was prepared using analogous conditions as found in Method 1, steps A-H in Example 1 (including Chiral Resolution Method A after step F to obtain the *S atropisomer), and using 2-fluoro-4-methyl-5-nitropyridine and 2-propanol in place of 5-fluoro-2-nitrotoluene and phenol in step A, and using Pd/C in place of Fe and $NH_4Cl$ in step B, and using (R)-1-Boc-3-aminopiperidine, 1-propanephosphonic anhydride, and diisopropylethylamine in place of tert-butyl (3R,5R)-3-amino-5-fluoropiperidine-1-carboxylate, HATU, and triethylamine in step G. MS (ESI): mass calcd. for $C_{23}H_{26}N_6O_3S$, 466.6; m/z found, 467.2 [M+H]$^+$. $^1$H NMR (500 MHz, CDCl$_3$): δ 8.34 (d, J=5.4 Hz, 1H), 8.00 (s, 1H), 6.72 (s, 1H), 6.48 (s, 1H), 6.04 (d, J=5.5 Hz, 1H), 5.38-5.26 (m, 1H), 4.18-4.13 (m, 3H), 3.48 (s, 1H), 3.10 (dd, J=11.8, 3.2 Hz, 1H), 2.84 (dtq, J=24.2, 11.9, 6.1, 5.4 Hz, 3H), 2.13 (s, 3H), 1.79 (dtdd, J=43.5, 12.8, 8.3, 4.1 Hz, 3H), 1.37 (dd, J=13.6, 6.2 Hz, 6H).

Example 795: (S)—N-(1-Acryloylpiperidin-3-yl)-4-oxo-5-(5-phenoxypyridin-2-yl)-4,5-dihydro-3H-1-thia-3,5,8-triazaacenaphthylene-2-carboxamide

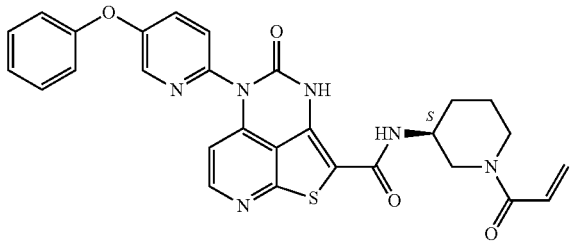

Step A: (S)-4-oxo-5-(5-phenoxypyridin-2-yl)-N-(piperidin-3-yl)-4,5-dihydro-3H-1-thia-3,5,8-triazaacenaphthylene-2-carboxamide The title compound was prepared using analogous conditions as found in Method 1, steps A-H in Example 1, and using 5-bromo-2-nitropyridine in place of 5-fluoro-2-nitrotoluene in step A, and using Pd/C in place of Fe and NH$_4$Cl in step B, and using (S)-tert-butyl 3-aminopiperidine-1-carboxylate in place of tert-butyl (3R,5R)-3-amino-5-fluoropiperidine-1-carboxylate (Intermediate 1) in step G.

Step B: (S)—N-(1-Acryloylpiperidin-3-yl)-4-oxo-5-(5-phenoxypyridin-2-yl)-4,5-dihydro-3H-1-thia-3,5,8-triazaacenaphthylene-2-carboxamide The title compound was prepared using (S)-4-oxo-5-(5-phenoxypyridin-2-yl)-N-(piperidin-3-yl)-4,5-dihydro-3H-1-thia-3,5,8-triazaacenaphthylene-2-carboxamide and acrylic anhydride. MS (ESI): mass calcd. for C$_{28}$H$_{24}$N$_6$O$_4$S, 540.6; m/z found, 541.1 [M+H]$^+$. $^1$H NMR (400 MHz, CD$_3$OD): δ 8.37 (d, J=2.8 Hz, 1H), 8.31 (d, J=5.6 Hz, 1H), 7.65-7.55 (m, 2H), 7.50-7.42 (m, 2H), 7.28-7.21 (m, 1H), 7.20-7.14 (m, 2H), 6.84-6.72 (m, 1H), 6.24-6.14 (m, 2H), 5.76-5.78 (m, 1H), 4.56-4.27 (m, 1H), 4.20-3.89 (m, 2H), 3.21-3.11 (m, 1H), 2.98-2.84 (m, 1H), 2.10-2.00 (m, 1H), 1.90-1.80 (m, 1H), 1.79-1.65 (m, 1H), 1.63-1.50 (m, 1H).

Example 796: 2-(4-Acryloylpiperazin-1-yl)-5-(2-methyl-4-phenoxyphenyl)-3H-1-thia-3,5,8-triazaacenaphthylen-4(5H)-one

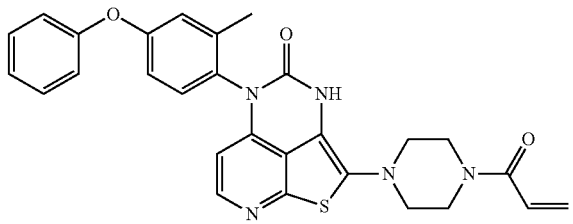 [SMILES: C=CC(=O)N1CCN(c2sc3nccc4c3c2NC(=O)N4c2ccc(Oc3ccccc3)cc2C)CC1]

Step A: 5-(2-Methyl-4-phenoxyphenyl)-3H-1-thia-3,5,8-triazaacenaphthylen-4(5H)-one To a solution of 5-(2-Methyl-4-phenoxyphenyl)-4-oxo-4,5-dihydro-3H-1-thia-3,5,8-triazaacenaphthylene-2-carboxylic acid (Intermediate 27) (7.0 g, 17 mmol) in 1-methyl-2-pyrrolidinone (70 mL) were added silver acetate (559 mg, 3.35 mmol) and potassium carbonate (695 mg, 5.03 mmol) and was stirred at 120° C. for 30 min. The reaction was filtered and concentrated to dryness. The residue was purified by FFC to give the title compound (6.0 g, 96% yield).

Step B: 2-Chloro-5-(2-methyl-4-phenoxyphenyl)-3H-1-thia-3,5,8-triazaacenaphthylen-4(5H)-one To a solution of 5-(2-methyl-4-phenoxyphenyl)-3H-1-thia-3,5,8-triazaacenaphthylen-4(5H)-one (4.5 g, 12 mmol) in CHCl$_3$ (30 mL) was added N-chlorosuccinimide (1.61 g, 12.1 mmol) and was stirred for 30 min at room temperature. The reaction was concentrated to dryness and methanol was added to the residue, the solution filtered, the precipitate washed with methanol, and dried under high vacuum to give the title compound (3.5 g, 71% yield). MS (ESI): mass calcd. for C$_{21}$H$_{14}$ClN$_3$O$_2$S, 408.87; m/z found, 407.9 [M+H]$^+$.

Step C: tert-Butyl 4-(5-(2-methyl-4-phenoxyphenl)-4-oxo-4,5-dihydro-3H-1-thia-3,5,8-triazaacenaphthylen-2-yl)piperazine-1-carboxylate To a solution of 5-(2-methyl-4-phenoxyphenyl)-4-oxo-4,5-dihydro-3H-1-thia-3,5,8-triazaacenaphthylene-2-carboxylic acid (Intermediate 27, 700 mg, 1.72 mmol) in DMSO (5 mL) were added 1-Boc-piperazine (3.20 g, 17.2 mmol), Cu (22 mg, 0.34 mmol), copper(I) iodide (65 mg, 0.34 mmol), and potassium phosphate (1.09 g, 5.15 mmol). The reaction mixture was irradiated in a microwave at 120° C. for 2.5 h. The reaction was poured into citric acid (100 mL, 4 M in water) and extracted with DCM (3×60 mL). The combined organic layers concentrated to dryness and the residue was purified by preparative reverse phase C-18 HPLC to give the title compound (600 mg, 63% yield).

Step D: 5-(2-Methyl-4-phenoxyphenyl)-2-(piperazin-1-yl)-3H-1-thia-3,5,8-triazaacenaphthylen-4(5H)-one To a solution of tert-butyl 4-(5-(2-methyl-4-phenoxyphenyl)-4-oxo-4,5-dihydro-3H-1-thia-3,5,8-triazaacenaphthylen-2-yl)piperazine-1-carboxylate (600 mg, 1.08 mmol) in EtOAc (5 mL) was added saturated aqueous HCl (5 mL) and was stirred for 3 h at room temperature. The mixture was poured into aqueous NaHCO$_3$ (50 mL) and extracted with DCM (3×30 mL). The combined organic layers were washed with saturated brine (50 mL), dried over anhydrous Na$_2$SO$_4$, filtered, and concentrated to dryness. The residue was purified by preparative reverse phase C18 HPLC to give the title compound (400 mg, 65% yield).

Step E: 2-(4-Acryloylpiperazin-1-yl)-5-(2-methyl-4-phenoxyphenyl)-3H-1-thia-3,5,8-triazaacenaphthylen-4(5H)-one To a solution of 5-(2-methyl-4-phenoxyphenyl)-2-(piperazin-1-yl)-3H-1-thia-3,5,8-triazaacenaphthylen-4(5H)-one (100 mg, 0.219 mmol), acrylic acid (19 mg, 0.26 mmol) and diisopropylethylamine (0.153 mL, 0.876 mmol) in DCM (2 mL) at 0° C. was added HATU (125 mg, 0.329 mmol) and was stirred for 2 h at 20° C. The organic layer was washed with saturated aqueous NaHCO$_3$ (50 mL), dried over anhydrous Na$_2$SO$_4$, and concentrated to dryness. The residue was purified by preparative HPLC to give the title compound (21.7 mg, 15.1% yield). MS (ESI): mass calcd. for $C_{28}H_{25}N_5O_3S$, 511.6; m/z found, 512.2 [M+H]$^+$. $^1$H NMR (400 MHz, DMSO-d$_6$): δ 10.72 (s, 1H), 8.16 (d, J=5.5 Hz, 1H), 7.48-7.42 (m, 2H), 7.35 (d, J=8.5 Hz, 1H), 7.23-7.17 (m, 1H), 7.14-7.08 (m, 3H), 6.98 (dd, J=2.6, 8.4 Hz, 1H), 6.85 (dd, J=10.5, 16.6 Hz, 1H), 6.15 (dd, J=2.4, 16.7 Hz, 1H), 5.85 (d, J=5.5 Hz, 1H), 5.72 (dd, J=2.4, 10.4 Hz, 1H), 3.78-3.69 (m, 4H), 2.91-2.85 (m, 4H), 2.07 (s, 3H).

Example 797: (R)-5-(*S)-(6-(Cyclopentyloxy)-4-methylpyridin-3-yl)-4-oxo-N-(pyrrolidin-3-yl)-4,5-dihydro-3H-1-thia-3,5,8-triazaacenaphthylene-2-carboxamide

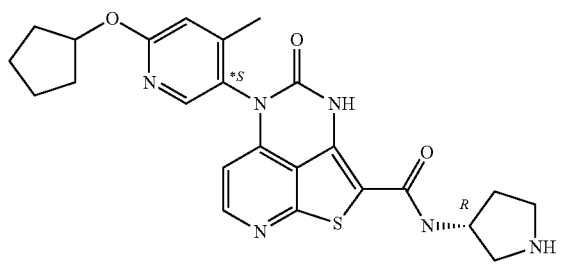

The title compound was prepared using analogous conditions as found in Method 1, steps A-H in Example 1 (including Chiral Resolution Method A after step F to obtain the *S atropisomer), and using 2-fluoro-4-methyl-5-nitropyridine and cyclopentanol in place of 5-fluoro-2-nitrotoluene and phenol in step A, and using Pd/C in place of Fe and NH$_4$Cl in step B, and using (R)-tert-butyl 3-aminopyrrolidine-1-carboxylate, diisopropylethylamine, DCM, and 1-propanephosphonic anhydride in place of tert-butyl (3R,5R)-3-amino-5-fluoropiperidine-1-carboxylate, triethylamine, HATU, and DMF in step G. MS (ESI): mass calcd. for $C_{24}H_{26}N_6O_3S$, 478.6; m/z found, 479.0 [M+H]$^+$. $^1$H NMR (500 MHz, CDCl$_3$): δ 9.57 (s, 3H), 8.27 (d, J=5.5 Hz, 1H), 8.03 (s, 1H), 7.92 (d, J=6.8 Hz, 1H), 6.69 (s, 1H), 5.98 (d, J=5.5 Hz, 1H), 5.37 (dp, J=6.2, 2.7 Hz, 1H), 5.30 (s, 1H), 4.76 (d, J=13.8 Hz, 1H), 3.64-3.45 (m, 4H), 3.34 (dt, J=11.5, 7.8 Hz, 1H), 2.42-2.33 (m, 1H), 2.22 (d, J=8.0 Hz, 1H), 2.10 (s, 3H), 1.95 (ddd, J=14.2, 11.3, 6.5 Hz, 2H), 1.83-1.73 (m, 1H), 1.63 (dtd, J=9.7, 7.6, 4.3 Hz, 2H).

Example 798: (R)-5-(*S)-(6-Isobutoxy-4-methyl-pyridin-3-yl)-4-oxo-N-(pyrrolidin-3-yl)-4,5-dihydro-3H-1-thia-3,5,8-triazaacenaphthylene-2-carboxamide

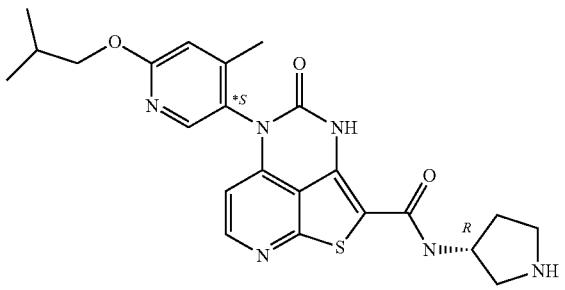

The title compound was prepared using analogous conditions as found in Method 1, steps A-H in Example 1 (including Chiral Resolution Method A after step F to obtain the *S atropisomer), and using 2-fluoro-4-methyl-5-nitropyridine and 2-methyl-1-propanol in place of 5-fluoro-2-nitrotoluene and phenol in step A, and using Pd/C in place of Fe and NH$_4$Cl in step B, and using (R)-tert-butyl 3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{23}H_{26}N_6O_3S$, 466.6; m/z found, 467.1 [M+H]$^+$. $^1$H NMR (500 MHz, CDCl$_3$): δ 8.31 (d, J=5.5 Hz, 1H), 8.02 (s, 1H), 7.71 (d, J=6.9 Hz, 1H), 6.77 (s, 1H), 6.01 (d, J=5.5 Hz, 1H), 5.30 (s, 1H), 4.78 (s, 1H), 3.62-3.43 (m, 8H), 3.31 (dtd, J=11.4, 8.5, 7.7, 3.8 Hz, 1H), 2.45-2.33 (m, 1H), 2.11 (s, 3H), 1.02 (dd, J=6.8, 1.6 Hz, 6H).

Example 799: (R)-5-(2-Methyl-4-(pyridin-2-yloxy)phenyl)-4-oxo-N-(1-propionylpiperidin-3-yl)-4,5-dihydro-3H-1-thia-3,5,8-triazaacenaphthylene-2-carboxamide

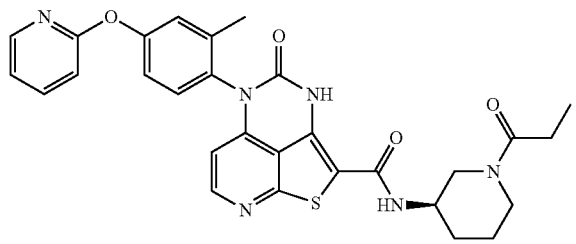 [SMILES: CCC(=O)N1CCC[C@@H](NC(=O)c2sc3nccc4c3c2NC(=O)N4c2ccc(Oc3ccccn3)cc2C)C1]

Step A: (R)-5-(2-methyl-4-(pyridin-2-yloxy)phenyl)-4-oxo-N-(piperidin-3-yl)-4,5-dihydro-3H-1-thia-3,5,8-triazaacenaphthylene-2-carboxamide The title compound was prepared using analogous conditions as found in Method 1, steps A, and C-H in Example 1, and using 2-fluoropyridine and 4-amino-3-methylphenol in place of 5-fluoro-2-nitrotoluene and phenol in step A, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (R)-5-(2-Methyl-4-(pyridin-2-yloxy)phenyl)-4-oxo-N-(1-propionylpiperidin-3-yl)-4,5-dihydro-3H-1-thia-3,5,8-triazaacenaphthylene-2-carboxamide The title compound was prepared using (R)-5-(2-methyl-4-(pyridin-2-yloxy)phenyl)-4-oxo-N-(piperidin-3-yl)-4,5-dihydro-3H-1-thia-3,5,8-triazaacenaphthylene-2-carboxamide, propionic anhydride and DIPEA. MS (ESI): mass calcd. for $C_{29}H_{28}N_6O_4S$, 556.6; m/z found, 557.2 [M+H]$^+$. $^1$H NMR (400 MHz, CD$_3$OD): δ 8.35 (d, J=5.5 Hz, 1H), 8.22-8.13 (m, 1H), 7.94-7.83 (m, 1H), 7.42-7.34 (m, 1H), 7.27-7.20 (m, 1H), 7.18-7.11 (m, 2H), 7.10-7.03 (m, 1H), 6.29-6.17 (m, 1H), 4.52-4.30 (m, 1H), 4.10-3.82 (m, 2H), 3.15-2.99 (m, 1H), 2.84-2.68 (m, 1H), 2.54-2.38 (m, 2H), 2.17 (s, 3H), 2.10-2.01 (m, 1H), 1.91-1.78 (m, 1H), 1.75-1.48 (m, 2H), 1.18-1.07 (m, 3H).

Example 800: (R)—N-(1-Acetylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide

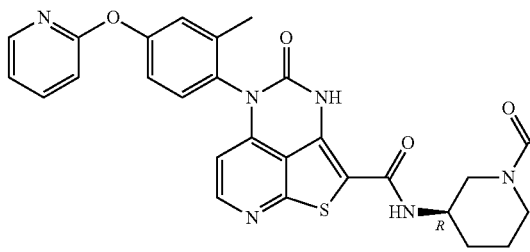

Step A: (R)-5-(2-methyl-4-(pyridin-2-yloxy)phenyl)-4-oxo-N-(piperidin-3-yl)-4,5-dihydro-3H-1-thia-3,5,8-triazaacenaphthylene-2-carboxamide The title compound was prepared using analogous conditions as found in Method 1, steps A, and C-H in Example 1, and using 2-fluoropyridine and 4-amino-3-methylphenol in place of 5-fluoro-2-nitrotoluene and phenol in step A, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (R)—N-(1-Acetylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide The title compound was prepared using (R)-5-(2-methyl-4-(pyridin-2-yloxy)phenyl)-4-oxo-N-(piperidin-3-yl)-4,5-dihydro-3H-1-thia-3,5,8-triazaacenaphthylene-2-carboxamide, acetic anhydride and DIPEA. MS (ESI): mass calcd. for $C_{28}H_{26}N_6O_4S$, 542.6; m/z found, 543.1 [M+H]$^+$. $^1$H NMR (400 MHz, CD$_3$OD): δ 8.36-8.28 (m, 1H), 8.19-8.11 (m, 1H), 7.90-7.81 (m, 1H), 7.45-7.35 (m, 1H), 7.24-7.17 (m, 1H), 7.17-7.09 (m, 2H), 7.09-7.01 (m, 1H), 6.23-6.15 (m, 1H), 4.54-4.26 (m, 1H), 4.08-3.78 (m, 2H), 3.19-3.01 (m, 1H), 2.81-2.65 (m, 1H), 2.20-2.10 (m, 6H), 2.08-2.01 (m, 1H), 1.89-1.77 (m, 1H), 1.73-1.47 (m, 2H).

Example 801: (E)-1-(2-Cyano-3-cyclopropylacryloyl)-N-(5-(2-methyl-4-phenoxyphenyl)-4-oxo-4,5-dihydro-3H-1-thia-3,5,8-triazaacenaphthylen-2-yl)piperidine-3-carboxamide

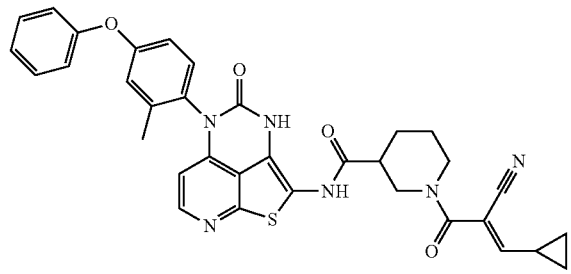 [SMILES: Cc1cc(Oc2ccccc2)ccc1N1C(=O)Nc2c(NC(=O)C3CCCN(C(=O)/C(C#N)=C/C4CC4)C3)sc3nccc1c23]

The title compound was prepared using conditions analogous to Example 877, and using N-(5-(2-methyl-4-phenoxyphenyl)-4-oxo-4,5-dihydro-3H-1-thia-3,5,8-triazaacenaphthylen-2-yl)piperidine-3-carboxamide (Example 828) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889).

Example 802: 1-Cyano-N-(5-(2-methyl-4-phenoxyphenyl)-4-oxo-4,5-dihydro-3H-1-thia-3,5,8-triazaacenaphthylen-2-yl)piperidine-3-carboxamide

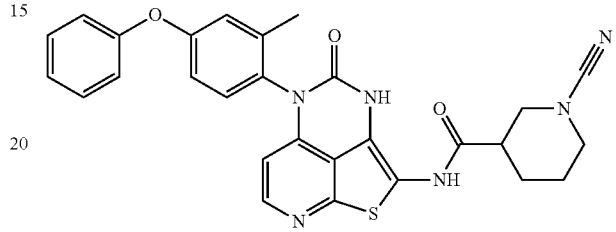

The title compound was prepared using conditions analogous Example 890, and using N-(5-(2-methyl-4-phenoxyphenyl)-4-oxo-4,5-dihydro-3H-1-thia-3,5,8-triazaacenaphthylen-2-yl)piperidine-3-carboxamide (Example 828) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{28}H_{24}N_6O_3S$, 524.6; m/z found, 525.1 [M+H]$^+$. $^1$H NMR (400 MHz, DMSO-d$_6$): δ 10.25-10.22 (m, 1H), 10.13 (s, 1H), 8.16 (d, J=5.3 Hz, 1H), 7.48-7.42 (m, 2H), 7.38-7.33 (m, 1H), 7.23-7.17 (m, 1H), 7.14-7.07 (m, 3H), 6.98 (dd, J=2.8, 8.5 Hz, 1H), 5.86 (d, J=5.5 Hz, 1H), 3.37-3.31 (m, 2H), 3.20-3.12 (m, 1H), 3.08-3.01 (m, 1H), 2.07 (s, 3H), 2.03-1.97 (m, 1H), 1.78-1.71 (m, 1H), 1.64-1.56 (m, 2H), 1.25-1.21 (m, 1H).

Example 803: (R)—N-(1-Acryloylpyrrolidin-3-yl)-4-oxo-5-(4-(pyridazin-3-yloxy)phenyl)-4,5-dihydro-3H-1-thia-3,5,8-triazaacenaphthylene-2-carboxamide

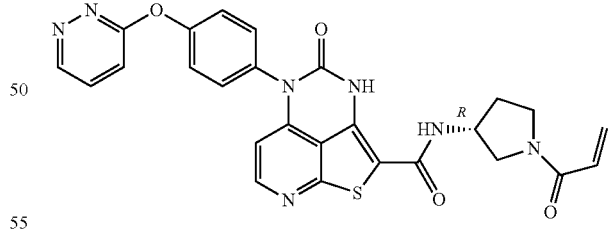

The title compound was prepared using analogous conditions as found in Method 1, steps A-G in Example 1, and using 3,6-dichloropyridazine and 4-nitrophenol in place of 5-fluoro-2-nitrotoluene and phenol in step A, and using Pd/C and MeOH in place of Fe, EtOH/H$_2$O, and NH$_4$Cl in step B, and using 4-(pyridazin-3-yloxy)aniline in place of 2-methyl-4-phenoxyaniline in step C, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{26}H_{21}N_7O_4S$, 527.6; m/z found, 528.1 [M+H]$^+$. $^1$H NMR (400 MHz, CD$_3$OD and DMSO-d$_6$ (2:1)): δ 8.96-8.91 (m, 1H), 8.28-8.23 (m, 1H), 7.73-7.66 (m, 1H), 7.50-7.42 (m, 3H), 7.40-7.34 (m, 2H), 6.61-6.47 (m, 1H), 6.20-6.13 (m, 2H), 5.69-5.61 (m, 1H), 4.63-4.43 (m, 1H), 3.91-3.73 (m, 1H), 3.65-3.40 (m, 3H), 2.25-1.96 (m, 2H).

Example 804: (R)—N-(1-Acryloylpiperidin-3-yl)-5-(*R)-(6-isopropoxy-4-methylpyridin-3-yl)-4-oxo-4,5-dihydro-3H-1-thia-3,5,8-triazaacenaphthylene-2-carboxamide

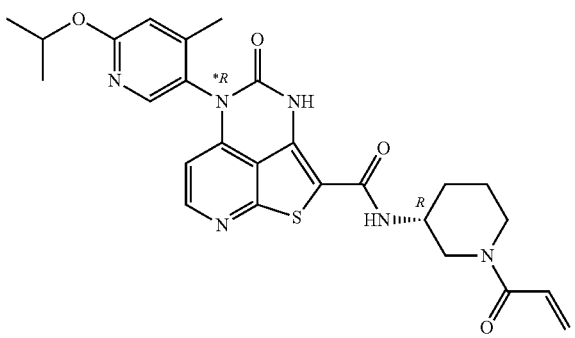

Step A: (R)-5-(6-isopropoxy-4-methylpyridin-3-yl)-4-oxo-N-(piperidin-3-yl)-4,5-dihydro-3H-1-thia-3,5,8-triazaacenaphthylene-2-carboxamide The title compound was prepared using analogous conditions as found in Method 1, steps A-H in Example 1 (including Chiral Resolution Method A after step F to obtain the *R atropisomer), and using 2-fluoro-4-methyl-5-nitropyridine and 2-propanol in place of 5-fluoro-2-nitrotoluene and phenol in step A, and using Pd/C in place of Fe and NH$_4$Cl in step B, and using (R)-tert-butyl 3-aminopiperidine-1-carboxylate, 1-propanephosphonic anhydride, diisopropylethylamine, and DCM in place of tert-butyl (3R,5R)-3-amino-5-fluoropiperidine-1-carboxylate, HATU, triethylamine, and DMF in step G.

Step B: (R)—N-(1-Acryloylpiperidin-3-yl)-5-(*R)-(6-isopropoxy-4-methylpyridin-3-yl)-4-oxo-4,5-dihydro-3H-1-thia-3,5,8-triazaacenaphthylene-2-carboxamide The title compound was prepared using (R)-5-(6-isopropoxy-4-methylpyridin-3-yl)-4-oxo-N-(piperidin-3-yl)-4,5-dihydro-3H-1-thia-3,5,8-triazaacenaphthylene-2-carboxamide, acrylic anhydride. MS (ESI): mass calcd. for C$_{26}$H$_{28}$N$_6$O$_4$S, 520.6; m/z found, 521.2 [M+H]$^+$. $^1$H NMR (500 MHz, CDCl$_3$): δ 8.35 (d, J=5.5 Hz, 1H), 8.02 (s, 1H), 6.67 (d, J=44.7 Hz, 2H), 6.39 (d, J=17.1 Hz, 1H), 6.31 (d, J=17.1 Hz, 1H), 6.14 (s, 1H), 6.08-6.03 (m, 1H), 5.72 (d, J=12.1 Hz, 1H), 5.32 (p, J=6.2 Hz, 1H), 4.17-4.04 (m, 2H), 3.56 (s, 1H), 2.13 (s, 3H), 2.05 (s, 2H), 1.65 (dd, J=12.8, 6.4 Hz, 1H), 1.37 (dd, J=13.2, 6.2 Hz, 6H), 1.26 (t, J=7.2 Hz, 2H), 1.08-1.01 (m, 1H).

Example 805: N-(5-(2-Methyl-4-phenoxyphenyl)-4-oxo-4,5-dihydro-3H-1-thia-3,5,8-triazaacenaphthylen-2-yl)-1-propionylpiperidine-4-carboxamide

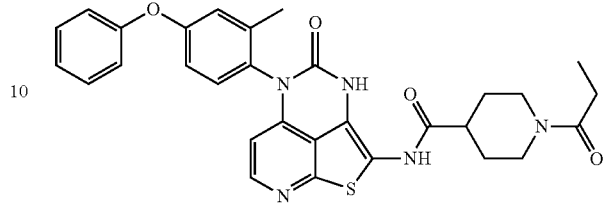

The title compound was prepared using conditions analogous to Example 75, and using N-(5-(2-methyl-4-phenoxyphenyl)-4-oxo-4,5-dihydro-3H-1-thia-3,5,8-triazaacenaphthylen-2-yl)piperidine-4-carboxamide (Example 833) and propionic acid in place of 3-hydroxypropanoic acid. MS (ESI): mass calcd. for C$_{30}$H$_{29}$N$_5$O$_4$S, 555.6; m/z found, 556.2 [M+H]$^+$. $^1$H NMR (400 MHz, DMSO-d$_6$): δ 10.24 (s, 1H), 10.12 (s, 1H), 8.16 (d, J=5.5 Hz, 1H), 7.49-7.41 (m, 2H), 7.36 (d, J=8.6 Hz, 1H), 7.22-7.18 (m, 1H), 7.15-7.06 (m, 3H), 6.98 (dd, J=8.5, 2.8 Hz, 1H), 5.87 (d, J=5.5 Hz, 1H), 4.47-4.39 (m, 1H), 3.97-3.89 (m, 1H), 3.12-3.04 (m, 1H), 2.70-2.54 (m, 2H), 2.38-2.31 (m, 2H), 2.07 (s, 3H), 1.93-1.82 (m, 2H), 1.66-1.39 (m, 2H), 1.00 (t, J=7.4 Hz, 3H).

Example 806: (R)-5-(*R)-(6-Isopropoxy-4-methylpyridin-3-yl)-4,5-dihydro-3H-1-thia-3,5,8-triazaacenaphthylene-2-carboxamide

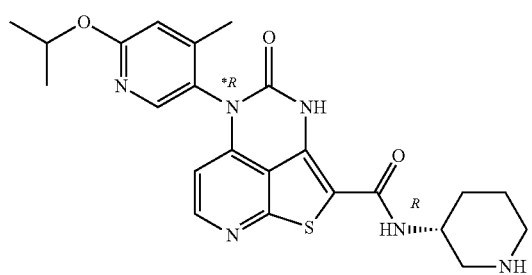

The title compound was prepared using analogous conditions as found in Method 1, steps A-H in Example 1 (including Chiral Resolution Method A after step F to obtain the *R atropisomer), and using 2-fluoro-4-methyl-5-nitropyridine and 2-propanol in place of 5-fluoro-2-nitrotoluene and phenol in step A, and using Pd/C in place of Fe and NH$_4$Cl in step B, and using (R)-tert-butyl 3-aminopiperidine-1-carboxylate, 1-propanephosphonic anhydride, diisopropylethylamine, and DCM in place of tert-butyl (3R,5R)-3-amino-5-fluoropiperidine-1-carboxylate, HATU, triethylamine, and DMF in step G. MS (ESI): mass calcd. for C$_{23}$H$_{26}$N$_6$O$_3$S, 466.6; m/z found, 467.2 [M+H]$^+$. $^1$H NMR (500 MHz, CDCl$_3$): δ 8.33 (d, J=5.5 Hz, 1H), 8.03 (s, 1H), 6.72 (t, J=0.8 Hz, 1H), 6.46-6.41 (m, 1H), 6.03 (d, J=5.5 Hz, 1H), 5.38-5.27 (m, 2H), 4.14 (ddp, J=9.3, 6.5, 3.4 Hz, 1H), 3.48 (s, 1H), 3.08 (dd, J=11.9, 3.1 Hz, 1H), 2.90-2.75 (m, 3H), 2.12 (d, J=0.9 Hz, 3H), 1.77 (dddd, J=28.7, 13.8, 11.3, 7.2 Hz, 3H), 1.57 (dtd, J=12.8, 6.3, 5.7, 2.8 Hz, 1H), 1.37 (dd, J=13.5, 6.2 Hz, 6H).

Example 807: (R)-4-Oxo-N-(1-propionylpiperidin-3-yl)-5-(4-(pyridin-2-yloxy)phenyl)-4,5-dihydro-3H-1-thia-3,5,8-triazaacenaphthylene-2-carboxamide

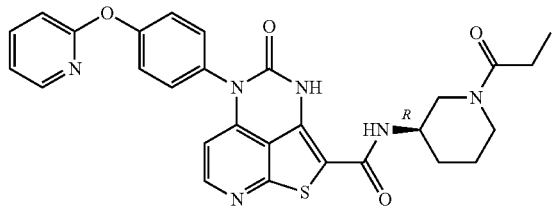

Step A: (R)-4-oxo-N-(piperidin-3-yl)-5-(4-(pyridin-2-yloxy)phenyl)-4,5-dihydro-3H-1-thia-3,5,8-triazaacenaphthylene-2-carboxamide The title compound was prepared in a manner analogous to Method 1, steps A, and C-H in Example 1, and using 2-fluoropyridine and 4-aminophenol in place of phenol and 5-fluoro-2-nitrotoluene in step A, and using 4-(pyridin-2-yloxy)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (R)-4-Oxo-N-(1-propionylpiperidin-3-yl)-5-(4-(pyridin-2-yloxy)phenyl)-4,5-dihydro-3H-1-thia-3,5,8-triazaacenaphthylene-2-carboxamide In a solution of (R)-4-oxo-N-(piperidin-3-yl)-5-(4-(pyridin-2-yloxy)phenyl)-4,5-dihydro-3H-1-thia-3,5,8-triazaacenaphthylene-2-carboxamide (200 mg) in DCM (5 mL) was added triethylamine (83 mg). The mixture was cooled in an ice bath, and propionic anhydride (80 mg) was added slowly. The solution was allowed to stir at rt for 15 min, then the mixture was poured into water, extracted with DCM, and concentrated. The crude mixture was purified by ISCO (MeOH/H$_2$O), then preparative TLC (25/1 DCM/MeOH) to yield the title compound (130 mg, 85% yield). MS (ESI): mass calcd. for C$_{28}$H$_{26}$N$_6$O$_4$S, 542.6; m/z found, 543.2 [M+H]$^+$. $^1$H NMR (400 MHz, CD$_3$OD): δ 8.31 (d, J=5.5 Hz, 1H), 8.20-8.12 (m, 1H), 7.90-7.82 (m, 1H), 7.52-7.44 (m, 2H), 7.35-7.28 (m, 2H), 7.19-7.11 (m, 1H), 7.10-7.02 (m, 1H), 6.29 (d, J=5.5 Hz, 1H), 4.54-4.29 (m, 1H), 4.12-3.81 (m, 2H), 3.14-2.96 (m, 1H), 2.79-2.65 (m, 1H), 2.55-2.34 (m, 2H), 2.09-1.96 (m, 1H), 1.90-1.76 (m, 1H), 1.75-1.47 (m, 2H), 1.16-1.08 (m, 3H).

Example 808: (R)—N-(1-Acetylpiperidin-3-yl)-4-oxo-5-(4-(pyridin-2-yloxy)phenyl)-4,5-dihydro-3H-1-thia-3,5,8-triazaacenaphthylene-2-carboxamide

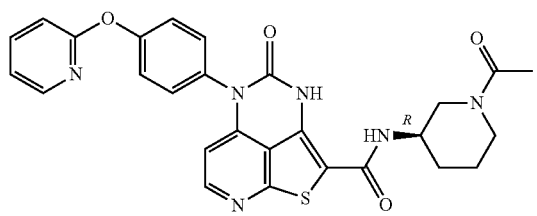

The title compound was prepared in a manner analogous to Method 1, steps A, C-I in Example 1, and using 2-fluoropyridine and 4-aminophenol in place of phenol and 5-fluoro-2-nitrotoluene in step A, and using 4-(pyridin-2-yloxy)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G, and using acetyl chloride in place of prop-2-enoyl chloride in step I. MS (ESI): mass calcd. for C$_{27}$H$_{24}$N$_6$O$_4$S, 528.6; m/z found, 529.1 [M+H]$^+$. $^1$H NMR (400 MHz, CD$_3$OD): δ 8.29 (d, J=5.6 Hz, 1H), 8.18-8.12 (m, 1H), 7.90-7.82 (m, 1H), 7.49-7.43 (m, 2H), 7.36-7.27 (m, 2H), 7.19-7.12 (m, 1H), 7.09-7.03 (m, 1H), 6.27 (d, J=5.6 Hz, 1H), 4.52-4.23 (m, 1H), 4.09-3.76 (m, 2H), 3.18-3.01 (m, 1H), 2.81-2.67 (m, 1H), 2.16-2.09 (m, 3H), 2.09-1.97 (m, 1H), 1.90-1.76 (m, 1H), 1.74-1.48 (m, 2H).

Example 809: (R)-5-(2-Methyl-4-(pyridazin-3-yloxy)phenyl)-4-oxo-N-(1-propionylpiperidin-3-yl)-4,5-dihydro-3H-1-thia-3,5,8-triazaacenaphthylene-2-carboxamide

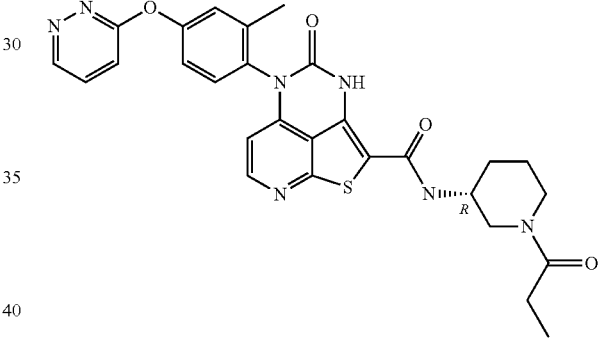

Step A: (R)-5-(2-methyl-4-(pyridazin-3-yloxy)phenyl)-4-oxo-N-(piperidin-3-yl)-4,5-dihydro-3H-1-thia-3,5,8-triazaacenaphthylene-2-carboxamide The title compound was prepared using analogous conditions as found in Method 1, steps A-H in Example 1, and using 4-amino-3-methylphenol and 3,6-dichloropyridazine in place of 5-fluoro-2-nitrotoluene and phenol in step A, and using Pd/C in place of Fe and NH$_4$Cl in step B, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (R)-5-(2-Methyl-4-(pyridazin-3-yloxy)phenyl)-4-oxo-N-(1-propionylpiperidin-3-yl)-4,5-dihydro-3H-1-thia-3,5,8-triazaacenaphthylene-2-carboxamide The title compound was prepared using analogous conditions as Example 75 and using (R)-5-(2-methyl-4-(pyridazin-3-yloxy)phenyl)-4-oxo-N-(piperidin-3-yl)-4,5-dihydro-3H-1-thia-3,5,8-triazaacenaphthylene-2- carboxamide and propionic anhydride in place of 3-hydroxypropanoic acid. MS (ESI): mass calcd. for $C_{28}H_{27}N_7O_4S$, 557.6; m/z found, 558.3 [M+H]$^+$. $^1$H NMR (400 MHz, CD$_3$OD): δ 8.96-8.90 (m, 1H), 8.32-8.26 (m, 1H), 7.79-7.71 (m, 1H), 7.52-7.42 (m, 2H), 7.32-7.27 (m, 1H), 7.27-7.20 (m, 1H), 6.19-6.14 (m, 1H), 4.58-4.30 (m, 1H), 4.13-3.78 (m, 2H), 3.12-2.92 (m, 1H), 2.77-2.60 (m, 1H), 2.51-2.32 (m, 2H), 2.20-2.12 (m, 3H), 2.07-1.95 (m, 1H), 1.86-1.74 (m, 1H), 1.72-1.60 (m, 1H), 1.60-1.43 (m, 1H), 1.13-1.05 (m, 3H).

Example 810: (R)—N-(1-Acetylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide

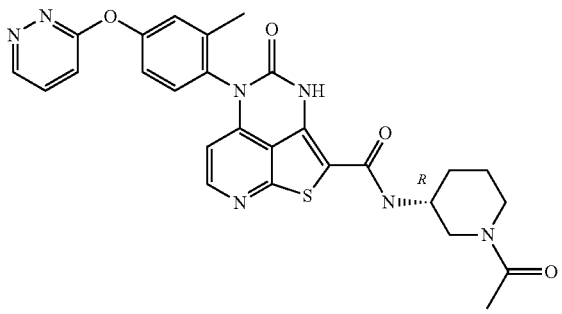

Step A: (R)-4-Oxo-N-(1-propionylpiperidin-3-yl)-5-(4-(pyridin-2-yloxy)phenyl)-4,5-dihydro-3H-1-thia-3,5,8-triazaacenaphthylene-2-carboxamide The title compound was prepared using analogous conditions as found in Method 1, steps A-H in Example 1, and using 4-amino-3-methylphenol and 3,6-dichloropyridazine in place of 5-fluoro-2-nitrotoluene and phenol in step A, and using Pd/C in place of Fe and NH$_4$Cl in step B, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (R)—N-(1-Acetylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide The title compound was prepared using conditions analogous to Example 75, and using (R)-4-Oxo-N-(1-propionylpiperidin-3-yl)-5-(4-(pyridin-2-yloxy)phenyl)-4,5-dihydro-3H-1-thia-3,5,8-triazaacenaphthylene-2-carboxamide and acetic anhydride in place of 3-hydroxypropanoic acid. MS (ESI): mass calcd. for $C_{27}H_{25}N_7O_4S$, 543.6; m/z found, 544.2 [M+H]$^+$. $^1$H NMR (400 MHz, CD$_3$OD): δ 8.96-8.90 (m, 1H), 8.32-8.26 (m, 1H), 7.79-7.71 (m, 1H), 7.52-7.42 (m, 2H), 7.32-7.27 (m, 1H), 7.27-7.20 (m, 1H), 6.20-6.16 (m, 1H), 4.56-4.27 (m, 1H), 4.10-3.76 (m, 2H), 3.12-2.99 (m, 1H), 2.79-2.66 (m, 1H), 2.21-2.14 (m, 3H), 2.15-2.09 (m, 3H), 2.07-1.95 (m, 1H), 1.91-1.74 (m, 1H), 1.71-1.61 (m, 1H), 1.61-1.43 (m, 1H).

Example 811: (R)—N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide

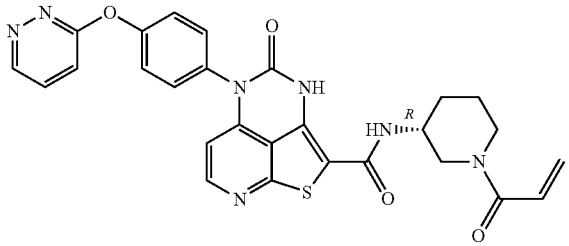

Step A: (R)-4-oxo-N-(piperidin-3-yl)-5-(4-(pyridazin-3-yloxy)phenyl)-4,5-dihydro-3H-1-thia-3,5,8-triazaacenaphthylene-2-carboxamide The title compound was prepared using analogous conditions as found in Method 1, steps A-H in Example 1, and using 3,6-dichloropyridazine and 4-nitrophenol in place of 5-fluoro-2-nitrotoluene and phenol in step A, and using Pd/C in place of Fe and NH$_4$Cl in step B, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (R)—N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide The title compound was prepared using analogous conditions as found in Example 75 and using (R)-4-oxo-N-(piperidin-3-yl)-5-(4-(pyridazin-3-yloxy)phenyl)-4,5-dihydro-3H-1-thia-3,5,8-triazaacenaphthylene-2-carboxamide and propionic anhydride in place of 3-hydroxypropanoic acid. MS (ESI): mass calcd. for $C_{27}H_{25}N_7O_4S$, 543.6; m/z found, 544.1 [M+H]$^+$. $^1$H NMR (400 MHz, CD$_3$OD): δ 8.99-8.94 (m, 1H), 8.36-8.31 (m, 1H), 7.83-7.74 (m, 1H), 7.59-7.49 (m, 3H), 7.47-7.38 (m, 2H), 6.36-6.29 (m, 1H), 4.55-4.33 (m, 1H), 4.11-3.84 (m, 2H), 3.14-2.99 (m, 1H), 2.83-2.68 (m, 1H), 2.54-2.40 (m, 2H), 2.13-2.00 (m, 1H), 1.94-1.77 (m, 1H), 1.76-1.52 (m, 2H), 1.16-1.09 (m, 3H).

Example 812: (R)—N-(1-Acetylpiperidin-3-yl)-4-oxo-5-(4-(pyridazin-3-yloxy)phenyl)-4,5-dihydro-3H-1-thia-3,5,8-triazaacenaphthylene-2-carboxamide

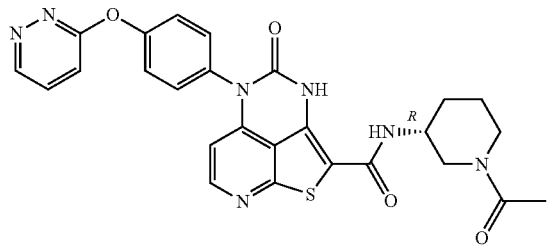

Step A: (R)-4-oxo-N-(piperidin-3-yl)-5-(4-(pyridazin-3-yloxy)phenyl)-4,5-dihydro-3H-1-thia-3,5,8-triazaacenaphthylene-2-carboxamide The title compound was prepared using analogous conditions as found in Method 1, steps A-H in Example 1, and using 3,6-dichloropyridazine and 4-nitrophenol in place of 5-fluoro-2-nitrotoluene and phenol in step A, and using Pd/C in place of Fe and NH₄Cl in step B, and using (R)-tert-butyl 3-aminopiperidine-1-carboxylate in place of tert-butyl (3R,5R)-3-amino-5-fluoropiperidine-1-carboxylate (Intermediate 1) in step G.

Step B: (R)—N-(1-Acetylpiperidin-3-yl)-4-oxo-5-(4-(pyridazin-3-yloxy)phenyl)-4,5-dihydro-3H-1-thia-3,5,8-triazaacenaphthylene-2-carboxamide The title compound was prepared using analogous conditions as found in Example 75 and using (R)-4-oxo-N-(piperidin-3-yl)-5-(4-(pyridazin-3-yloxy)phenyl)-4,5-dihydro-3H-1-thia-3,5,8-triazaacenaphthylene-2-carboxamide and acetic anhydride in place of 3-hydroxypropanoic acid. MS (ESI): mass calcd. for $C_{26}H_{23}N_7O_4S$, 529.6; m/z found, 530.1 [M+H]⁺. ¹H NMR (400 MHz, CD₃OD): δ 8.99-8.94 (m, 1H), 8.36-8.31 (m, 1H), 7.82-7.73 (m, 1H), 7.57-7.48 (m, 3H), 7.47-7.38 (m, 2H), 6.36-6.28 (m, 1H), 4.55-4.29 (m, 1H), 4.07-3.79 (m, 2H), 3.14-3.02 (m, 1H), 2.80-2.71 (m, 1H), 2.15-2.11 (m, 3H), 2.08-2.00 (m, 1H), 1.88-1.76 (m, 1H), 1.75-1.51 (m, 2H).

Example 17: (R)—N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide

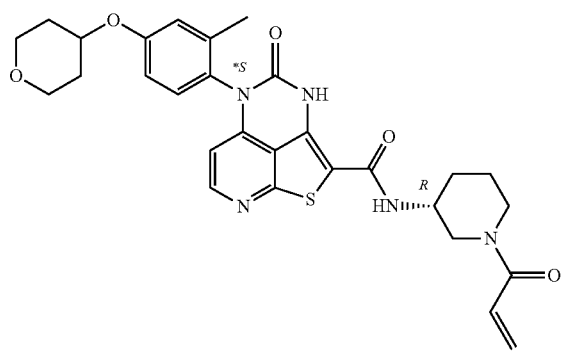

(R)—N-(1-acryloylpiperidin-3-yl)-5-(2-methyl-6-((tetrahydro-2H-pyran-4-yl)oxy)pyridin-3-yl)-4-oxo-4,5-dihydro-3H-1-thia-3,5,8-triazaacenaphthylene-2-carboxamide (Example 770) was resolved by chiral SFC (Stationary phase: Chiralpak AS-H; 5 m, 250×20 mm, Mobile phase: 65% CO₂, 35% MeOH) to yield the title compound. MS (ESI): mass calcd. for $C_{28}H_{30}N6O5S$, 562.6; m/z found, 563.0 [M+H]⁺. ¹H NMR (400 MHz, DMSO-d₆): δ 10.28 (s, 1H), 8.35 (d, J=5.5 Hz, 1H), 8.21-8.05 (m, 1H), 7.74 (d, J=8.6 Hz, 1H), 6.92-6.72 (m, 2H), 6.20-6.01 (m, 2H), 5.82-5.64 (m, 1H), 5.30-5.18 (m, 1H), 4.57-4.20 (m, 1H), 4.16-3.95 (m, 1H), 3.94-3.85 (m, 2H), 3.80 (s, 1H), 3.61-3.49 (m, 2H), 3.15-2.93 (m, 1H), 2.83-2.62 (m, 1H), 2.21 (s, 3H), 2.12-2.02 (m, 2H), 2.00-1.90 (m, 1H), 1.83-1.75 (m, 1H), 1.74-1.62 (m, 3H), 1.55-1.34 (m, 1H).

Example 18: (R)—N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide

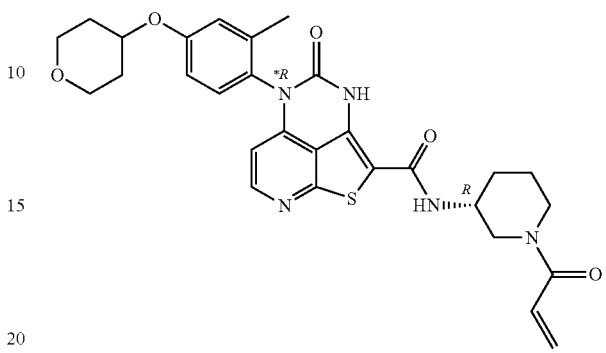

(R)—N-(1-Acryloylpiperidin-3-yl)-5-(2-methyl-6-((tetrahydro-2H-pyran-4-yl)oxy)pyridin-3-yl)-4-oxo-4,5-dihydro-3H-1-thia-3,5,8-triazaacenaphthylene-2-carboxamide (Example 770) was resolved by chiral SFC (Stationary phase: Chiralpak AS-H; 5 μm, 250×20 mm, Mobile phase: 65% CO₂, 35% MeOH) to yield the title compound. MS (ESI): mass calcd. for $C_{28}H_{30}N_6O_5S$, 562.6; m/z found, 563.0 [M+H]⁺. ¹H NMR (400 MHz, DMSO-d₆): δ 10.29 (s, 1H), 8.34 (d, J=5.5 Hz, 1H), 8.23-8.07 (m, 1H), 7.74 (d, J=8.6 Hz, 1H), 6.91-6.71 (m, 2H), 6.12 (d, J=16.7 Hz, 1H), 6.04 (d, J=5.5 Hz, 1H), 5.69 (d, J=10.4 Hz, 1H), 5.33-5.22 (m, 1H), 4.57-4.15 (m, 1H), 4.13-3.96 (m, 1H), 3.94-3.86 (m, 2H), 3.84-3.73 (m, 1H), 3.54 (t, 2H), 3.21-2.92 (m, 1H), 2.87-2.61 (m, 1H), 2.21 (s, 3H), 2.12-2.01 (m, 2H), 2.00-1.91 (m, 1H), 1.84-1.75 (m, 1H), 1.74-1.61 (m, 3H), 1.53-1.37 (m, 1H).

Example 815: (R)—N-(1-Acryloylpiperidin-3-yl)-5-(*R)-(6-isobutyl-2-methylpyridin-3-yl)-4-oxo-4,5-dihydro-3H-1-thia-3,5,8-triazaacenaphthylene-2-carboxamide

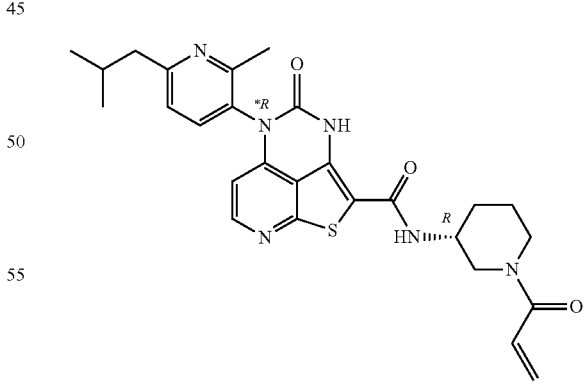

Step A: 6-Isobutyl-2-methylpyridin-3-amine

To a 500 mL round bottom flask were added 6-bromo-2-methylpyridin-3-amine (5.0 g, 27 mmol), a stir bar, and 1,1'-bis(diphenylphosphino)ferrocene-palladium(II)dichloride dichloromethane complex (520 mg, 0.631 mmol) in THF (27 mL). The vessel was evacuated then back filled with nitrogen (3×). Then isobutylzinc(II) bromide (75 mL, 37 mmol) was added via syringe and the reaction was heated to 60° C. for 3 h. The reaction was treated with saturated aqueous sodium bicarbonate, extracted with DCM, the organic phase washed with water and brine, dried over anhydrous $Na_2SO_4$, filtered, and concentrated to dryness. The residue was purified by normal phase flash column chromatography ($SiO_2$) to give the title compound (2.46 g, 56.0% yield) as a beige solid.

Step B: (R)—N-(1-Acryloylpiperidin-3-yl)-5-(*R)-(6-isobutyl-2-methylpyridin-3-yl)-4-oxo-4,5-dihydro-3H-1-thia-3,5,8-triazaacenaphthylene-2-carboxamide The title compound was prepared using analogous conditions as found in Method 1, steps C-G in Example 1, and using 6-isobutyl-2-methylpyridin-3-amine in place of 2-methyl-4-phenoxyaniline in step C, and using (R)-1-(3-aminopiperidin-1-yl)prop-2-en-1-one (Intermediate 15), PYOXIM, and diisopropylethylamine in place of tert-butyl (3R,5R)-3-amino-5-fluoropiperidine-1-carboxylate, HATU, and triethylamine in step G. Atropisomers were resolved by chiral SFC (Stationary phase: Chiralpak AS-H; 5 m, 250×20 mm, Mobile phase: 65% $CO_2$, 35% MeOH), to give the title compound. MS (ESI): mass calcd. for $C_{27}H_{30}N_6O_3S$, 518.6; m/z found, 519.1 [M+H]$^+$. $^1$H NMR (400 MHz, DMSO-d$_6$): δ 10.32 (s, 1H), 8.34 (d, J=5.5 Hz, 1H), 8.20-8.07 (m, 1H), 7.75 (d, J=8.0 Hz, 1H), 7.28 (d, J=8.0 Hz, 1H), 6.89-6.71 (m, 1H), 6.11 (d, J=16.8 Hz, 1H), 5.92 (d, J=5.4 Hz, 1H), 5.68 (d, J=10.5 Hz, 1H), 4.55-4.17 (m, 1H), 4.10-3.95 (m, 1H), 3.85-3.73 (m, 1H), 3.18-2.93 (m, 1H), 2.84-2.63 (m, 3H), 2.28 (s, 3H), 2.17-2.05 (m, 1H), 2.01-1.90 (m, 1H), 1.85-1.73 (m, 1H), 1.71-1.58 (m, 1H), 1.52-1.34 (m, 1H), 0.94 (d, J=6.6 Hz, 6H).

Example 19: (E)-1-(2-Cyano-4,4-dimethylpent-2-enoyl)-N-(5-(2-methyl-4-phenoxyphenyl)-4-oxo-4,5-dihydro-3H-1-thia-3,5,8-triazaacenaphthylen-2-yl)piperidine-3-carboxamide

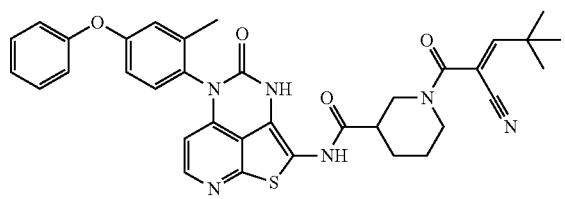 [SMILES: Cc1cc(Oc2ccccc2)ccc1N1C(=O)Nc2c(NC(=O)C3CCCN(C(=O)/C(C#N)=C/C(C)(C)C)C3)sc3nccc1c23]

The title compound was prepared using conditions analogous to Example 877, and using N-(5-(2-Methyl-4-phenoxyphenyl)-4-oxo-4,5-dihydro-3H-1-thia-3,5,8-triazaacenaphthylen-2-yl)piperidine-3-carboxamide (Example 828) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{35}H_{34}N_6O_4S$, 634.7; m/z found, 635.2 [M+H]$^+$. $^1$H NMR (400 MHz, DMSO-d$_6$): δ 11.45-11.12 (m, 1H), 10.67 (br, 1H), 8.15 (d, J=5.5 Hz, 1H), 7.49-7.41 (m, 2H), 7.36 (dd, J=3.1, 8.6 Hz, 1H), 7.23-7.18 (m, 1H), 7.15-7.10 (m, 2H), 7.10-7.07 (m, 1H), 6.97 (dd, J=2.5, 8.5 Hz, 1H), 6.84 (s, 1H), 5.85 (d, J=5.5 Hz, 1H), 4.44-3.76 (m, 2H), 3.24-3.12 (m, 1H), 3.10-2.94 (m, 1H) 2.83-2.66 (m, 1H), 2.15-2.10 (m, 1H), 2.08 (s, 3H), 1.88-1.65 (m, 2H), 1.58-1.39 (m, 1H), 1.23 (s, 9H).

Example 817: 1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-3-carboxamide

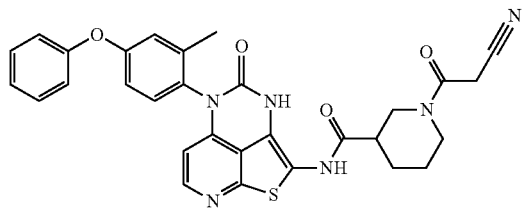 [SMILES: Cc1cc(Oc2ccccc2)ccc1N1C(=O)Nc2c(NC(=O)C3CCCN(C(=O)CC#N)C3)sc3nccc1c23]

The title compound was prepared using analogous conditions in Example 181, and using N-(5-(2-methyl-4-phenoxyphenyl)-4-oxo-4,5-dihydro-3H-1-thia-3,5,8-triazaacenaphthylen-2-yl)piperidine-3-carboxamide (Example 828) in place of (R)-4-oxo-5-(4-phenoxyphenyl)-N-(piperidin-3-yl)-4,5-dihydro-3H-1-thia-3,5,8-triazaacenaphthylene-2-carboxamide (Example 860). MS (ESI): mass calcd. for $C_{30}H_{26}N_6O_4S$, 566.6; m/z found, 567.1 [M+H]$^+$. $^1$H NMR (400 MHz, DMSO-d$_6$): δ 11.20-11.09 (m, 0.5H), 10.65 (s, 0.5H), 10.52-10.48 (m, 0.5H), 10.44 (s, 0.5H), 8.15-8.10 (m, 1H), 7.48-7.42 (m, 2H), 7.38-7.32 (m, 1H), 7.20 (t, J=7.4 Hz, 1H), 7.15-7.07 (m, 3H), 6.97 (dd, J=2.8, 8.5 Hz, 1H), 5.84-5.80 (m, 1H), 4.50-4.42 (m, 0.5H), 4.40-4.31 (m, 0.5H), 4.23-4.00 (m, 2H), 3.86-3.76 (m, 0.5H), 3.69-3.58 (m, 0.5H), 3.26-3.15 (m, 0.5H), 3.09-2.98 (m, 0.5H), 2.91-2.64 (m, 2H), 2.07 (s, 3H), 2.06-2.00 (m, 1H), 1.80-1.62 (m, 2H), 1.59-1.29 (m, 1H).

Example 20: N-(5-(2-Methyl-4-phenoxyphenyl)-4-oxo-4,5-dihydro-3H-1-thia-3,5,8-triazaacenaphthylen-2-yl)-1-propionylpiperidine-3-carboxamide

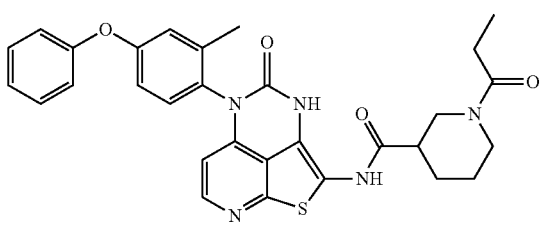 [SMILES: CCC(=O)N1CCCC(C(=O)Nc2sc3nccc4c3c2NC(=O)N4c2ccc(Oc3ccccc3)cc2C)C1]

The title compound was prepared using conditions analogous to Example 75, and using N-(5-(2-methyl-4-phenoxyphenyl)-4-oxo-4,5-dihydro-3H-1-thia-3,5,8-triazaacenaphthylen-2-yl)piperidine-3-carboxamide (Example 828) and propionic acid in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869). MS (ESI): mass calcd. for $C_{30}H_{29}N_5O_4S$, 555.6; m/z found, 556.2 [M+H]$^+$. $^1$H NMR (400 MHz, DMSO-d$_6$): δ 10.26-10.19 (m, 1H), 10.18-10.09 (m, 1H), 8.16 (d, J=5.5 Hz, 1H), 7.49-7.41 (m, 2H), 7.39-7.33 (m, 1H), 7.20 (t, J=7.3 Hz, 1H), 7.15-7.07 (m, 3H), 6.98 (dd, J=2.5, 8.5 Hz, 1H), 5.86 (d, J=5.5 Hz, 1H), 4.55-4.47 (m, 0.5H), 4.27-4.19 (m, 0.5H), 4.02-3.94 (m, 0.5H), 3.84-3.77 (m, 0.5H), 3.28-3.17 (m, 1H), 3.09-2.99 (m, 1H), 2.82-2.73 (m, 1H), 2.43-2.33 (m, 2H), 2.08 (s, 3H), 2.03-1.97 (m, 1H), 1.79-1.65 (m, 2H), 1.44-1.33 (m, 1H), 1.01 (t, J=7.4 Hz, 3H).

Example 21: 1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-4-carboxamide

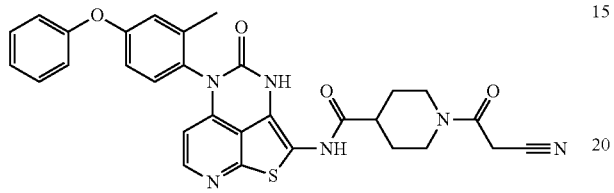

The title compound was prepared using using conditions analogous to Example 181, and using N-(5-(2-methyl-4-phenoxyphenyl)-4-oxo-4,5-dihydro-3H-1-thia-3,5,8-triazaacenaphthylen-2-yl)piperidine-4-carboxamide (Example 833). MS (ESI): mass calcd. for $C_{30}H_{26}N_6O_4S$, 566.6; m/z found, 567.1 $[M+H]^+$. $^1$H NMR (400 MHz, DMSO-$d_6$): δ 10.40 (s, 1H), 10.34 (s, 1H), 8.15 (d, J=5.5 Hz, 1H), 7.48-7.42 (m, 2H), 7.36 (d, J=8.5 Hz, 1H), 7.23-7.18 (m, 1H), 7.14-7.08 (m, 3H), 6.98 (dd, J=2.8, 8.8 Hz, 1H), 5.86 (d, J=5.5 Hz, 1H), 4.37-4.29 (m, 1H), 4.16-3.99 (m, 2H), 3.76-3.68 (m, 1H), 3.18-3.07 (m, 1H), 2.82-2.72 (m, 1H), 2.70-2.60 (m, 1H), 2.08 (s, 3H), 1.96-1.85 (m, 2H), 1.76-1.61 (m, 1H), 1.59-1.44 (m, 1H).

Example 22: 1-Acryloyl-N-(5-(2-methyl-4-phenoxyphenyl)-4-oxo-4,5-dihydro-3H-1-thia-3,5,8-triazaacenaphthylen-2-yl)piperidine-4-carboxamide

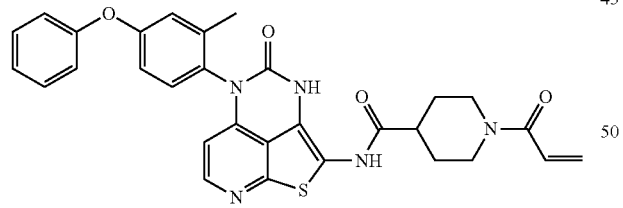

The title compound was prepared using conditions analogous to Example 75, and using N-(5-(2-methyl-4-phenoxyphenyl)-4-oxo-4,5-dihydro-3H-1-thia-3,5,8-triazaacenaphthylen-2-yl)piperidine-4-carboxamide (Example 833), acrylic acid, HATU, and diisopropylethylamine. MS (ESI): mass calcd. for $C_{30}H_{27}N_5O_4S$, 553.6; m/z found, 554.1 $[M+H]^+$. $^1$H NMR (400 MHz, DMSO-$d_6$): δ 10.51 (s, 1H), 10.38 (s, 1H), 8.14 (d, J=5.5 Hz, 1H), 7.48-7.42 (m, 2H), 7.35 (d, J=8.5 Hz, 1H), 7.23-7.18 (m, 1H), 7.15-7.07 (m, 3H), 6.98 (dd, J=2.8, 8.8 Hz, 1H), 6.84 (dd, J=10.4, 16.7 Hz, 1H), 6.11 (dd, J=2.5, 16.6 Hz, 1H), 5.85 (d, J=5.3 Hz, 1H), 5.68 (dd, J=2.5, 10.6 Hz, 1H), 4.46-4.42 (m, 1H), 4.14-4.10 (m, 1H), 3.24-3.10 (m, 1H), 2.82-2.72 (m, 1H), 2.71-2.63 (m, 1H), 2.07 (s, 3H), 1.97-1.88 (m, 2H), 1.63-1.45 (m, 2H).

Example 23: 1-Ethyl-N-(5-(2-methyl-4-phenoxyphenyl)-4-oxo-4,5-dihydro-3H-1-thia-3,5,8-triazaacenaphthylen-2-yl)piperidine-3-carboxamide

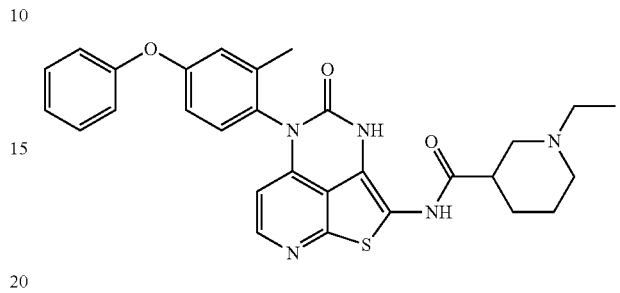

To a solution of N-(5-(2-methyl-4-phenoxyphenyl)-4-oxo-4,5-dihydro-3H-1-thia-3,5,8-triazaacenaphthylen-2-yl)piperidine-3-carboxamide (Example 828) (100 mg, 0.187 mmol) in MeOH (6 mL) was added acetaldehyde (114 mg, 0.935 mmol) and was stirred for 30 min at 20° C. Next was added sodium cyanoborohydride (59.0 mg, 0.935 mmol) and was stirred for h at 20° C. The reaction was concentrated to dryness and the residue was purified by preparative C18-reverse phase HPLC to give the title compound (45 mg, 99% yield). MS (ESI): mass calcd. for $C_{29}H_{29}N_5O_3S$, 527.6; m/z found, 528.2 $[M+H]^+$.

Example 24: 1-Cyano-N-(5-(2-methyl-4-phenoxyphenyl)-4-oxo-4,5-dihydro-3H-1-thia-3,5,8-triazaacenaphthylen-2-yl)piperidine-4-carboxamide

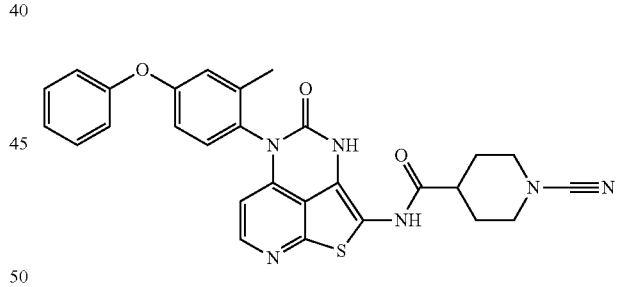

The title compound was prepared using conditions analogs to Example 890, and using N-(5-(2-methyl-4-phenoxyphenyl)-4-oxo-4,5-dihydro-3H-1-thia-3,5,8-triazaacenaphthylen-2-yl)piperidine-4-carboxamide (Example 833) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{28}H_{24}N_6O_3S$, 524.6; m/z found, 525.1 $[M+H]^+$. $^1$H NMR (400 MHz, DMSO-$d_6$): δ 10.20 (s, 1H), 10.07 (s, 1H), 8.14 (d, J=5.5 Hz, 1H), 7.48-7.42 (m, 2H), 7.35 (d, J=8.5 Hz, 1H), 7.23-7.17 (m, 1H), 7.14-7.07 (m, 3H), 6.97 (dd, J=2.6, 8.7 Hz, 1H), 5.84 (d, J=5.3 Hz, 1H), 3.49-3.42 (m, 2H), 3.18-3.09 (m, 2H), 2.07 (s, 3H), 1.94-1.86 (m, 2H), 1.78-1.64 (m, 2H), 1.25-1.21 (m, 1H).

Example 25: 1-Methyl-N-(5-(2-methyl-4-phenoxyphenyl)-4-oxo-4,5-dihydro-3H-1-thia-3,5,8-triazaacenaphthylen-2-yl)piperidine-3-carboxamide

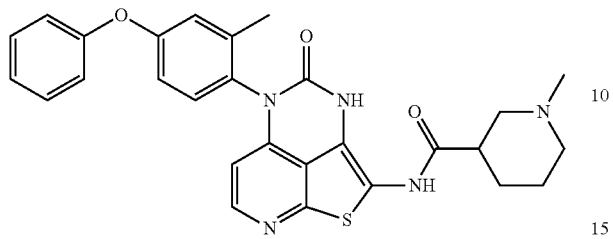 [SMILES: CCN1CCCC(C(=O)Nc2sc3nccc4c3c2NC(=O)N4c2ccc(Oc3ccccc3)cc2C)C1]

To a solution of N-(5-(2-Methyl-4-phenoxyphenyl)-4-oxo-4,5-dihydro-3H-1-thia-3,5,8-triazaacenaphthylen-2-yl)piperidine-3-carboxamide (Example 828) (100 mg, 0.202 mmol) in MeOH (5.0 mL) was added formaldehyde (84 mg, 1.0 mml, 37 wt. % in H$_2$O) and was stirred for 30 minutes at 20° C. To the reaction was added sodium cyanoborohydride (64 mg, 1.0 mmol) and was stirred for 1 h at 20° C. The reaction was concentrated to dryness and was extracted with ethyl acetate (20 mL). The organic layer was washed with water (20 mL), dried over anhydrous Na$_2$SO$_4$, filtered, and concentrated to dryness. The residue was purified by preparative reverse phase C18 HPLC to give the title compound. MS (ESI): mass calcd. for C$_{28}$H$_{27}$N$_5$O$_3$S, 513.2; m/z found, 514.2 [M+H]$^+$. 1H NMR (400 MHz, DMSO-d$_6$): δ 11.58 (s, 1H), 10.70-10.67 (m, 1H), 10.62 (br, 1H), 8.15 (d, J=5.5 Hz, 1H), 7.48-7.40 (m, 2H), 7.37-7.32 (m, 1H), 7.23-7.18 (m, 1H), 7.15-7.06 (m, 3H), 6.97 (dd, J=2.7, 8.6 Hz, 1H), 5.84 (d, J=5.4 Hz, 1H), 3.42-3.34 (m, 1.5H), 3.29-3.22 (m, 0.5H), 3.19-3.05 (m, 2H), 2.97-2.85 (m, 1H), 2.84-2.73 (m, 3H), 2.22-2.13 (m, 1H), 2.08 (s, 3H), 1.95-1.78 (m, 2H), 1.60-1.45 (m, 1H).

Example 824: 5-(2-Methyl-4-phenoxyphenyl)-2-(4-methylpiperazin-1-yl)-3H-1-thia-3,5,8-triazaacenaphthylen-4(5H)-one

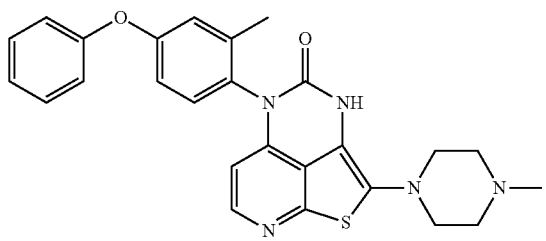 [SMILES: Cc1cc(Oc2ccccc2)ccc1N1C(=O)Nc2c(N3CCN(C)CC3)sc3nccc1c23]

To a solution of 5-(2-methyl-4-phenoxyphenyl)-2-(piperazin-1-yl)-3H-1-thia-3,5,8-triazaacenaphthylen-4(5H)-one (Example 327, 100 mg, 0.202 mmol) in MeOH (5.0 mL) was added formaldehyde (84 mg, 1.0 mml, 37 wt. % in H$_2$O) and was stirred for 30 minutes at 20° C. To the reaction was added sodium cyanoborohydride (64 mg, 1.0 mmol) and was stirred for 1 h at 20° C. The reaction was concentrated to dryness and was extracted with ethyl acetate (20 mL). The organic layer was washed with water (20 mL), dried over anhydrous Na$_2$SO$_4$, filtered, and concentrated to dryness. The residue was purified by preparative reverse phase C18 HPLC to give the title compound (5.9 mg, 5.6% yield). MS (ESI): mass calcd. for C$_{26}$H$_{25}$N$_5$O$_2$S, 471.6; m/z found, 472.0 [M+H]$^+$. 1H NMR (400 MHz, CD$_3$OD): δ 8.19 (d, J=5.5 Hz, 1H), 7.46-7.40 (m, 3H) 7.28 (d, J=8.8 Hz, 1H), 7.22-7.17 (m, 1H), 7.11 (d, J=8.0 Hz, 1H), 7.08 (d, J=2.5 Hz, 1H), 7.00 (dd, J=2.8, 8.8 Hz, 1H), 5.95 (d, J=5.5 Hz, 1H), 3.58-3.54 (m, 4H), 3.31-3.20 (m, 4H), 3.02 (s, 3H), 2.15 (s, 3H).

Example 825: (E)-4,4-Dimethyl-2-(4-(5-(2-methyl-4-phenoxyphenyl)-4-oxo-4,5-dihydro-3H-1-thia-3,5,8-triazaacenaphthylen-2-yl)piperazine-1-carbonyl)pent-2-enenitrile

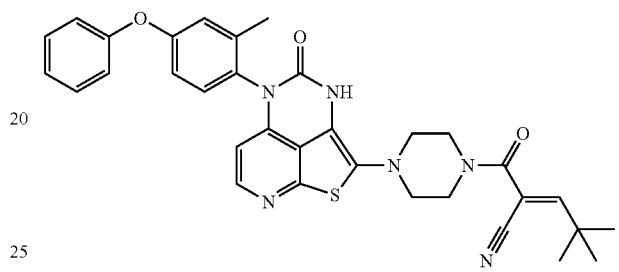

To a solution of 5-(2-methyl-4-phenoxyphenyl)-2-(piperazin-1-yl)-3H-1-thia-3,5,8-triazaacenaphthylen-4(5H)-one (Example 327, 100 mg, 0.202 mmol), (E)-2-cyano-4,4-dimethylpent-2-enoic acid (Intermediate 44) (37.1 mg, 0.242 mmol), and diisopropylethylamine (78.3 mg, 0.606 mmol) in DCM (5 mL) at 0° C. was added PyBrOP (141 mg, 0.303 mmol) and was stirred for 1 h at 20° C. The residue was purified by preparative HPLC to give the title compound (30 mg, 20% yield). MS (ESI): mass calcd. for C$_{33}$H$_{32}$N$_6$O$_3$S, 592.7; m/z found, 593.2 [M+H]$^+$. 1H NMR (400 MHz, DMSO-d$_6$): δ 10.68 (s, 1H), 8.14 (d, J=5.4 Hz, 1H), 7.48-7.42 (m, 2H), 7.34 (d, J=8.6 Hz, 1H), 7.24-7.17 (m, 1H), 7.14-7.07 (m, 3H), 6.97 (dd, J=2.7, 8.6 Hz, 1H), 6.91 (s, 1H), 5.83 (d, J=5.4 Hz, 1H), 3.73-3.64 (m, 4H), 2.97-2.88 (m, 4H), 2.07 (s, 3H), 1.25 (s, 9H).

Example 826: 4-(5-(2-Methyl-4-phenoxyphenyl)-4-oxo-4,5-dihydro-3H-1-thia-3,5,8-triazaacenaphthylen-2-yl)piperazine-1-carbonitrile

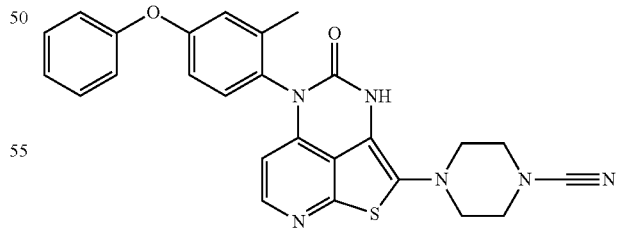

To a solution of 5-(2-methyl-4-phenoxyphenyl)-2-(piperazin-1-yl)-3H-1-thia-3,5,8-triazaacenaphthylen-4(5H)-one (Example 327, 100 mg, 0.202 mmol) and cyanogen bromide (21.4 mg, 0.202 mmol) in THF (2 mL) at 0° C. was added triethylamine (61.3 mg, 0.606 mmol) and was stirred for 12 h at 20° C. The residue was purified by preparative HPLC to give the title compound (30 mg, 24% yield). MS (ESI): mass calcd. for C$_{26}$H$_{22}$N$_6$O$_2$S, 482.6; m/z found, 483.1

[M+H]⁺. ¹H NMR (400 MHz, DMSO-d₆): δ 10.65 (s, 1H), 8.15 (d, J=5.4 Hz, 1H), 7.48-7.42 (m, 2H), 7.34 (d, J=8.6 Hz, 1H), 7.22-7.16 (m, 1H), 7.14-7.07 (m, 3H), 6.97 (dd, J=2.8, 8.4 Hz, 1H), 5.83 (d, J=5.4 Hz, 1H), 3.47-3.40 (m, 4H), 2.99-2.92 (m, 4H), 2.06 (s, 3H).

Example 827: 5-(2-Methyl-4-phenoxyphenyl)-2-(4-propionylpiperazin-1-yl)-3H-1-thia-3,5,8-triazaacenaphthylen-4(5H)-one

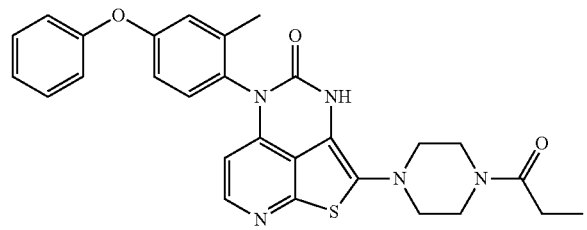 [SMILES: CCC(=O)N1CCN(c2sc3nccc4c3c2NC(=O)N4c2ccc(Oc3ccccc3)cc2C)CC1]

The title compound was prepared using analogous conditions as found in Example 75, and using 5-(2-methyl-4-phenoxyphenyl)-2-(piperazin-1-yl)-3H-1-thia-3,5,8-triazaacenaphthylen-4(5H)-one (Example 327) and propionic acid in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869). MS (ESI): mass calcd. for C₂₈H₂₇N₅O₃S, 513.6; m/z found, 514.1 [M+H]⁺. ¹H NMR (400 MHz, DMSO-d₆): δ 10.70 (s, 1H), 8.16 (d, J=5.5 Hz, 1H), 7.49-7.42 (m, 2H), 7.35 (d, J=8.6 Hz, 1H), 7.23-7.18 (m, 1H), 7.15-7.06 (m, 3H), 6.98 (dd, J=2.8, 8.6 Hz, 1H), 5.85 (d, J=5.5 Hz, 1H), 3.68-3.55 (m, 4H), 2.91-2.78 (m, 4H), 2.37 (q, J=7.4 Hz, 2H), 2.07 (s, 3H), 1.01 (t, J=7.4 Hz, 3H).

Example 828: N-(5-(2-Methyl-4-phenoxyphenyl)-4-oxo-4,5-dihydro-3H-1-thia-3,5,8-triazaacenaphthylen-2-yl)piperidine-3-carboxamide

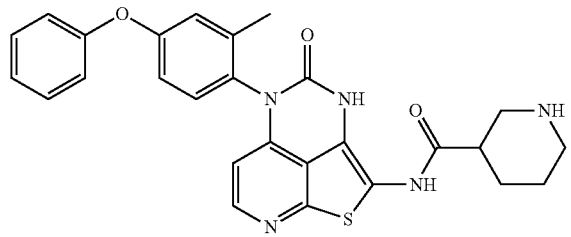 [SMILES: Cc1cc(Oc2ccccc2)ccc1N1C(=O)Nc2c(NC(=O)C3CCCNC3)sc3nccc1c23]

The title compound was prepared using analogous conditions as found in Method 1, step G-H in Example 1, and using 2-amino-5-(2-methyl-4-phenoxyphenyl)-3H-1-thia-3,5,8-triazaacenaphthylen-4(5H)-one (Intermediate 56), (±)1-Boc-piperidine-3-carboxylic acid, and diisopropylethylamine in place of 4-[2-methyl-N-(methylcarbamoyl)-4-phenoxyanilino]-3a,4-dihydrothieno[2,3-b]pyridine-2-carboxylic acid, tert-butyl (3R,5R)-3-amino-5-fluoropiperidine-1-carboxylate, and triethylamine in step G. MS (ESI): mass calcd. for C₂₇H₂₅N₅O₃S, 499.6; m/z found, 500.2 [M+H]⁺.

Example 829: (E)-1-(2-Cyano-4,4-dimethylpent-2-enoyl)-N-(5-(2-methyl-4-phenoxyphenyl)-4-oxo-4,5-dihydro-3H-1-thia-358-triazaacenaphthylen-2-yl)piperidine-4-carboxamide

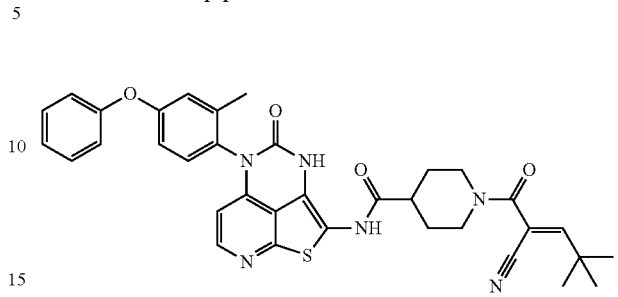

The title compound was prepared using analogous conditions as found in Method 1, steps I in Example 1, and using N-(5-(2-Methyl-4-phenoxyphenyl)-4-oxo-4,5-dihydro-3H-1-thia-3,5,8-triazaacenaphthylen-2-yl)piperidine-4-carboxamide (Example 833), (E)-2-cyano-4,4-dimethylpent-2-enoic acid (Intermediate 44), HATU, diisopropylethylamine, and DMF in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide, prop-2-enoyl chloride, DCM, and triethylamine. MS (ESI): mass calcd. for C₃₅H₃₄N₆O₄S, 634.7; m/z found, 635.2 [M+H]⁺. ¹H NMR (400 MHz, DMSO-d₆): δ 10.69 (br, 1H), 10.44 (br, 1H), 8.12 (d, J=5.4 Hz, 1H), 7.49-7.42 (m, 2H), 7.35 (d, J=8.6 Hz, 1H), 7.20 (t, J=7.4 Hz, 1H), 7.12 (d, J=7.7 Hz, 2H), 7.09 (d, J=2.6 Hz, 1H), 6.97 (dd, J=2.7, 8.6 Hz, 1H), 6.84 (s, 1H), 5.82 (d, J=5.4 Hz, 1H), 4.36-4.20 (m, 1H), 3.96-3.80 (m, 1H), 3.30-3.19 (m, 1H), 2.97-2.80 (m, 1H), 2.78-2.65 (m, 1H), 2.07 (s, 3H), 2.03-1.88 (m, 2H), 1.74-1.55 (m, 2H), 1.24 (s, 9H).

Example 26: (E)-1-(2-Cano-3-cyclopropylacryloyl)-N-(5-(2-methyl-4-phenoxyphenl)-4-oxo-4,5-dihydro-3H-1-thia-3,5,8-triazaacenaphthylen-2-yl)piperidine-4-carboxamide

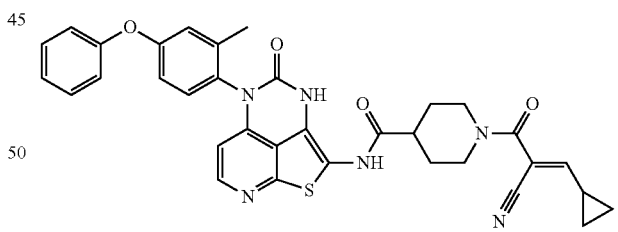

The title compound was prepared using conditions analogous to Example 877, and, using N-(5-(2-Methyl-4-phenoxyphenyl)-4-oxo-4,5-dihydro-3H-1-thia-3,5,8-triazaacenaphthylen-2-yl)piperidine-4-carboxamide (Example 833). MS (ESI): mass calcd. for C₃₄H₃₀N₆O₄S, 618.7; m/z found, 619.2 [M+H]⁺. ¹H NMR (400 MHz, DMSO-d₆): δ 10.75-10.60 (m, 1H), 10.46-10.40 (m, 1H), 8.13 (d, J=5.4 Hz, 1H), 7.48-7.42 (m, 2H), 7.35 (d, J=8.6 Hz, 1H), 7.23-7.17 (m, 1H), 7.14-7.10 (m, 2H), 7.09 (d, J=2.6 Hz, 1H), 6.97 (dd, J=2.7, 8.6 Hz, 1H), 6.62 (d, J=11.1 Hz, 1H), 5.83 (d, J=5.4 Hz, 1H), 3.21-2.85 (m, 2H), 2.77-2.65 (m, 2H), 2.07 (s, 3H), 2.00-1.85 (m, 3H), 1.70-1.55 (m, 2H), 1.26-1.20 (m, 1H), 1.20-1.15 (m, 2H), 0.96-0.90 (m, 2H).

Example 831: 1-Methyl-N-(5-(2-methyl-4-phenoxyphenl)-4-oxo-4,5-dihydro-3H-1-thia-3,5,8-triazaacenaphthylen-2-yl)piperidine-4-carboxamide

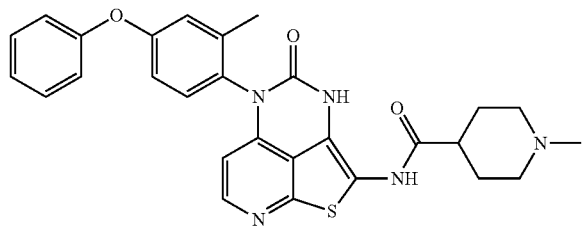 [SMILES: Cc1cc(Oc2ccccc2)ccc1N1C(=O)Nc2c(NC(=O)C3CCN(C)CC3)sc3nccc1c23]

To a solution of N-(5-(2-methyl-4-phenoxyphenyl)-4-oxo-4,5-dihydro-3H-1-thia-3,5,8-triazaacenaphthylen-2-yl)piperidine-4-carboxamide (Example 833) (150 mg, 0.28 mmol) in MeOH (10 mL) was added formaldehyde (3.0 mL, 37 wt. % in H$_2$O) and was stirred for 30 minutes at 20° C. Next was added sodium cyanoborohydride (88 mg, 1.4 mmol) and was stirred for 1 h at 20° C. The reaction was concentrated to dryness, extracted with EtOAc (20 mL), the organic phase was collected, washed with water (20 mL), dried over anhydrous Na$_2$SO$_4$, filtered, and concentrated to dryness. The residue was purified by preparative C18-reverse phase HPLC to give the title compound (25 mg, 16% yield). MS (ESI): mass calcd. for C$_{28}$H$_{27}$N$_5$O$_3$S, 513.6; m/z found, 514.1 [M+H]$^+$. $^1$H NMR (400 MHz, DMSO-d$_6$): δ 10.94 (s, 1H), 10.15 (br, 1H), 8.21 (d, J=5.8 Hz, 1H), 7.49-7.42 (m, 2H), 7.37 (d, J=8.6 Hz, 1H), 7.24-7.18 (m, 1H), 7.15-7.08 (m, 2H), 7.09 (d, J=2.6 Hz, 1H), 6.98 (dd, J=2.8, 8.6 Hz, 1H), 5.92 (d, J=5.8 Hz, 1H), 3.52-3.43 (m, 2H), 3.07-2.94 (m, 2H), 2.80-2.77 (m, 1H), 2.76-2.74 (m, 3H), 2.16-2.10 (m, 2H), 2.08 (s, 3H), 1.99-1.86 (m, 2H).

Example 832: 1-Ethyl-N-(5-(2-methyl-4-phenoxyphenyl)-4-oxo-4,5-dihydro-3H-1-thia-3,5,8-triazaacenaphthylen-2-yl)piperidine-4-carboxamide

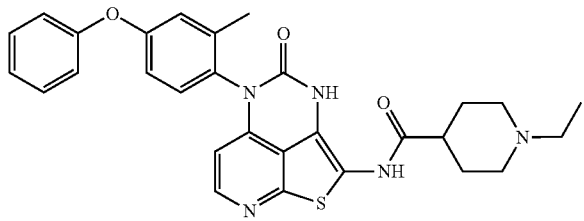 [SMILES: CCN1CCC(C(=O)Nc2sc3nccc4c3c2NC(=O)N4c2ccc(Oc3ccccc3)cc2C)CC1]

To a solution of N-(5-(2-methyl-4-phenoxyphenyl)-4-oxo-4,5-dihydro-3H-1-thia-3,5,8-triazaacenaphthylen-2-yl)piperidine-4-carboxamide (Example 833) (150 mg, 0.28 mmol) in MeOH (10 mL) was added acetaldehyde (3.0 mL) and was stirred for 30 minutes at 20° C. Next was added sodium cyanoborohydride (88 mg, 1.4 mmol) and was stirred for 1 h at 20° C. The reaction was concentrated to dryness, extracted with EtOAc (20 mL), the organic phase was collected, washed with water (20 mL), dried over anhydrous Na$_2$SO$_4$, filtered, and concentrated to dryness. The residue was purified by preparative C18-reverse phase HPLC to give the title compound (45 mg, 29% yield). MS (ESI): mass calcd. for C$_{29}$H$_{29}$N$_5$O$_3$S, 527.6; m/z found, 528.1 [M+H]$^+$. $^1$H NMR (400 MHz, DMSO-d$_6$): δ 11.00 (s, 1H), 10.08 (br, 1H), 8.22 (d, J=5.8 Hz, 1H), 7.51-7.41 (m, 2H), 7.37 (d, J=8.6 Hz, 1H), 7.24-7.17 (m, 1H), 7.15-7.11 (m, 2H), 7.09 (d, J=2.6 Hz, 1H), 6.98 (dd, J=2.7, 8.5 Hz, 1H), 5.95-5.91 (m, 1H), 3.58-3.50 (m, 2H), 3.16-3.04 (m, 2H), 3.00-2.88 (m, 2H), 2.87-2.76 (m, 1H), 2.20-2.10 (m, 2H), 2.08 (s, 3H), 2.04-1.90 (m, 2H), 1.29-1.21 (m, 3H).

Example 833: N-(5-(2-Methyl-4-phenoxyphenyl)-4-oxo-4,5-dihydro-3H-1-thia-3,5,8-triazaacenaphthylen-2-yl)piperidine-4-carboxamide

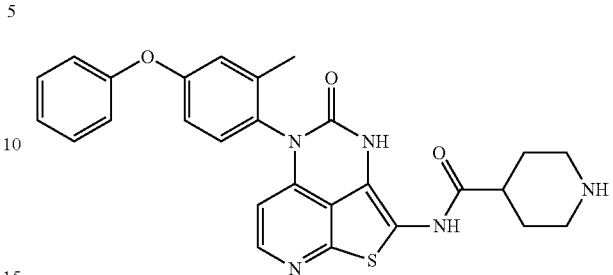

The title compound was prepared using analogous conditions as found in Method 1, step G-H in Example 1, and using 2-amino-5-(2-methyl-4-phenoxyphenyl)-3H-1-thia-3,5,8-triazaacenaphthylen-4(5H)-one (Intermediate 56), 1-(tert-butoxycarbonyl)piperidine-4-carboxylic acid, PyBOP, and diisopropylethylamine in place of 4-[2-methyl-N-(methylcarbamoyl)-4-phenoxyanilino]-3a,4-dihydrothieno[2,3-b]pyridine-2-carboxylic acid, tert-butyl (3R,5R)-3-amino-5-fluoropiperidine-1-carboxylate, HATU, and triethylamine in step G. MS (ESI): mass calcd. for C$_{27}$H$_{25}$N$_5$O$_3$S, 499.6; m/z found, 500.1 [M+H]$^+$. $^1$H NMR (400 MHz, DMSO-d$_6$): δ 11.84 (br, 1H), 10.85 (br, 1H), 8.25 (br, 1H), 8.09 (d, J=5.4 Hz, 1H), 7.48-7.42 (m, 2H), 7.33 (d, J=8.6 Hz, 1H), 7.22-7.18 (m, 1H), 7.15-7.10 (m, 2H), 7.08 (d, J=2.6 Hz, 1H), 6.96 (dd, J=8.5, 2.6 Hz, 1H), 5.78 (d, J=5.3 Hz, 1H), 3.26-3.17 (m, 2H), 2.85-2.74 (m, 3H), 2.07 (s, 3H), 2.02-1.93 (m, 2H), 1.87-1.72 (m, 2H).

Example 834: (R)-5-(*S)-(2-Methyl-4-phenoxyphenl)-4-oxo-N-(1-(vinylsulfonyl)pyrrolidin-3-yl)-4,5-dihydro-3H-1-thia-3,5,8-triazaacenaphthylene-2-carboxamide

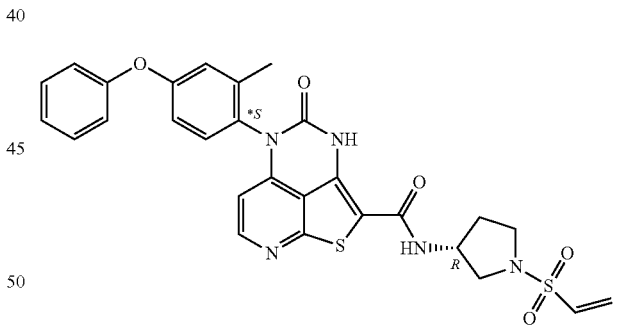

The title compound was prepared in a manner analogous to Method 1, steps A-I (including Chiral Resolution Method A after step F to obtain the *S atropisomer), and using (R)-tert-butyl 3-aminopyrrolidine-1-carboxylate in place of tert-butyl (3R,5R)-3-amino-5-fluoropiperidine-1-carboxylate (Intermediate 1) in step G, and using ethenesulfonyl chloride in place of prop-2-enoyl chloride in step I. MS (ESI): mass calcd. for C$_{28}$H$_{25}$N$_5$O$_5$S$_2$, 575.7; m/z found, 576.4 [M+H]$^+$. $^1$H NMR (400 MHz, CD$_3$OD): δ 8.33 (d, J=5.6 Hz, 1H), 7.47-7.35 (m, 2H), 7.29 (d, J=8.6 Hz, 1H), 7.20-7.13 (m, 1H), 7.12-7.03 (m, 3H), 6.99-6.93 (m, 1H), 6.77-6.65 (m, 1H), 6.20 (d, J=16.5 Hz, 1H), 6.12-6.03 (m, 2H), 4.57-4.48 (m, 1H), 3.65-3.56 (m, 1H), 3.54-3.44 (m, 1H), 3.39-3.32 (m, 1H), 3.29-3.22 (m, 1H), 2.33-2.22 (m, 1H), 2.11 (s, 3H), 2.09-2.00 (m, 1H).

Example 835: (R,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide

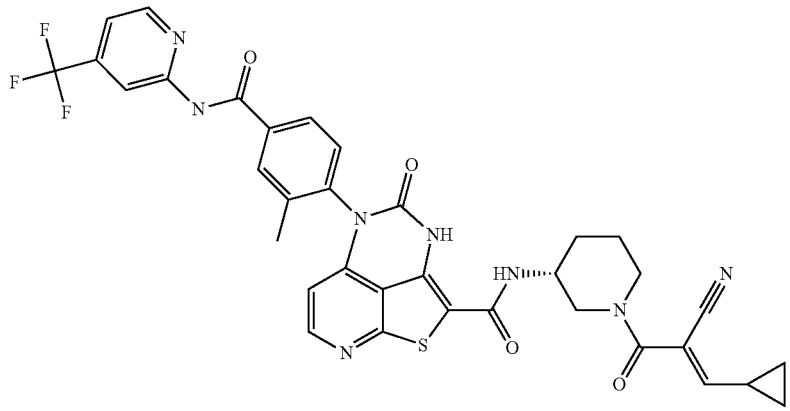 [SMILES: Cc1cc(C(=O)Nc2cc(C(F)(F)F)ccn2)ccc1N1C(=O)Nc2c(C(=O)N[C@@H]3CCCN(C(=O)/C(C#N)=C/C4CC4)C3)sc3nccc1c23]

Step A: (R)-5-(2-Methyl-4-((4-(trifluoromethyl)pyridin-2-yl)carbamoyl)phenyl)-4-oxo-N-(piperidin-3-yl)-4,5-dihydro-3H-1-thia-3,5,8-triazaacenaphthylene-2-carboxamide hydrochloride To a solution of tert-butyl (R)-3-aminopiperidine-1-carboxylate (296 mg, 1.48 mmol) in THF was added 1N AlMe₃ solution (3 mL, 3 mmol), then stirred at room temperature for 1 hour. A solution of methyl 5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxylate (Intermediate 73) (260 mg, 0.49 mmol) in THF was added and heated at reflux for 16 hours. The mixture was filtered, washed with DCM and MeOH. The filtrate was concentrated and purified by flash column chromatography eluting with DCM/MeOH to give a yellow solid, which was dissolved in MeOH and 5N HCl aq solution. The solution was concentrated at 50° C. under vacuo to yield the title compound as a yellow solid.

Step B: (R,E)-N-(1-(2-cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide The title compound was prepared using conditions analogous to in Example 877 and using (R)-5-(2-methyl-4-((4-(trifluoromethyl)pyridin-2-yl)carbamoyl)phenyl)-4-oxo-N-(piperidin-3-yl)-4,5-dihydro-3H-1-thia-3,5,8-triazaacenaphthylene-2-carboxamide hydrochloride in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a yellow solid.

Example 836: (R,E)-N-(1-(2-Cyano-3-cyclopropylacryloyl)piperidin-3-yl)-5-(2-fluoro-4-((4-(trifluoromethyl)pyridin-2-yl)carbamoyl)phen)-4-oxo-4,5-dihydro-3H-1-thia-3,5,8-triazaacenaphthylene-2-carboxamide

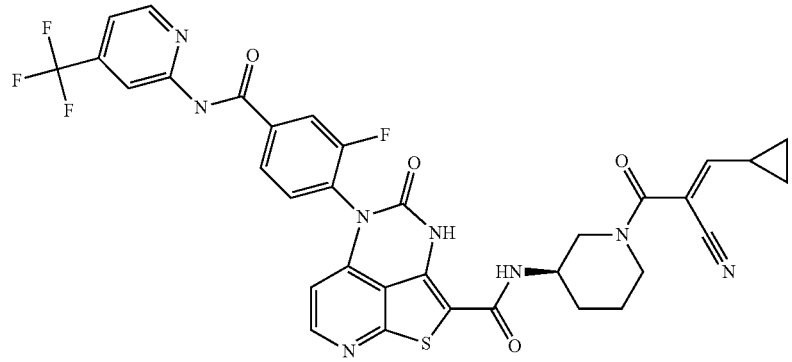 [SMILES: N#C/C(=C\C1CC1)C(=O)N1CCC[C@@H](NC(=O)c2sc3nccc4c3c2NC(=O)N4c2ccc(C(=O)Nc3cc(C(F)(F)F)ccn3)cc2F)C1]

The title compound was prepared using steps A-B in Example 835, using methyl 5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxylate (Intermediate 74) in place of methyl 5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxylate (Intermediate 73) in step A as a yellow solid.

Example 837: (R)—N-(1-Cyanopyrrolidin-3-yl)-5-(2-methyl-4-phenoxyphenyl)-4-oxo-4,5-dihydro-3H-1-thia-3,5,8-triazaacenaphthylene-2-carboxamide

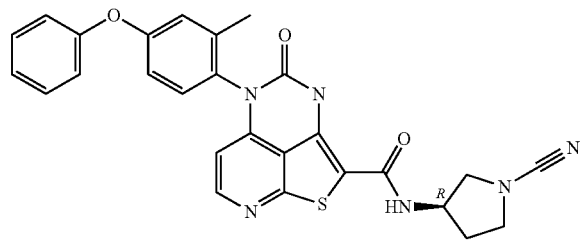

The title compound was prepared using conditions analogous to Example 890, and using (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a yellow solid. MS (ESI): mass calcd. for $C_{27}H_{22}N_6O_3S$, 510.6; m/z found, 511.2 [M+H]$^+$. $^1$H NMR (400 MHz, DMSO-d$_6$): δ 10.21 (s, 1H), 8.38-8.26 (m, 2H), 7.53-7.27 (m, 3H), 7.24-6.86 (m, 5H), 5.96 (d, J=5.3 Hz, 1H), 4.45 (d, J=5.4 Hz, 1H), 3.64-3.31 (m, 4H), 2.21-1.87 (m, 5H).

Example 838: (R)—N-(1-(2-Cyanoacetyl)pyrrolidin-3-yl)-5-(2-methyl-4-phenoxyphenyl)-4-oxo-4,5-dihydro-3H-1-thia-3,5,8-triazaacenaphthylene-2-carboxamide

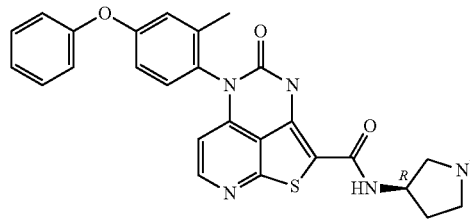

The title compound was prepared using conditions analogous to Example 181, and using (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159) in place of (R)-4-oxo-5-(4-phenoxyphenyl)-N-(piperidin-3-yl)-4,5-dihydro-3H-1-thia-3,5,8-triazaacenaphthylene-2-carboxamide (Example 860) to give a yellow solid. MS (ESI): mass calcd. for $C_{29}H_{24}N_6O_4S$, 552.6; m/z found, 553.1 [M+H]$^+$. $^1$H NMR (400 MHz, DMSO-d$_6$): δ 10.20 (s, 1H), 8.42-8.28 (m, 2H), 7.50-7.41 (m, 2H), 7.38 (d, J=8.6 Hz, 1H), 7.24-7.18 (m, 1H), 7.16-7.06 (m, 3H), 7.04-6.93 (m, 1H), 6.03-5.94 (m, 1H), 4.59-4.35 (m, 1H), 3.98-3.90 (m, 2H), 3.79-3.62 (m, 1H), 3.58-3.35 (m, 3H), 2.25-1.95 (m, 5H).

Example 839: (R)—N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide

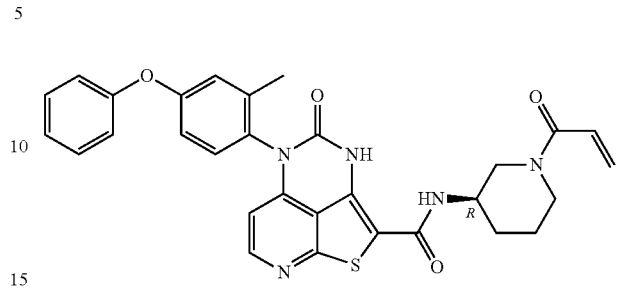

The title compound was prepared in a manner analogous to Method 1, steps A-I, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{30}H_{27}N_5O_4S$, 553.6; m/z found, 554.5 [M+H]$^+$. $^1$H NMR (400 MHz, DMSO-d$_6$): δ 10.29-10.20 (m, 1H), 8.37-8.32 (m, 1H), 8.13-8.04 (m, 1H), 7.50-7.35 (m, 3H), 7.25-7.17 (m, 1H), 7.17-7.07 (m, 3H), 7.02-6.95 (m, 1H), 6.87-6.73 (m, 1H), 6.16-6.06 (m, 1H), 6.03-5.97 (m, 1H), 5.72-5.64 (m, 1H), 4.54-4.18 (m, 1H), 4.10-3.95 (m, 1H), 3.84-3.74 (m, 1H), 3.17-2.92 (m, 1H), 2.82-2.62 (m, 1H), 2.07 (s, 3H), 2.00-1.88 (m, 1H), 1.84-1.74 (m, 1H), 1.74-1.61 (m, 1H), 1.51-1.36 (m, 1H).

Example 840: (R,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide

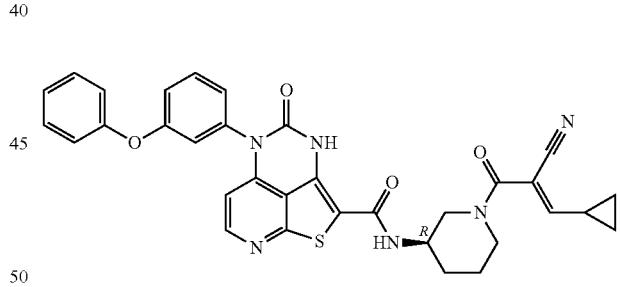

The title compound was prepared using conditions analogous to Example 877, and using (R)-4-oxo-5-(4-phenoxyphenyl)-N-(piperidin-3-yl)-4,5-dihydro-3H-1-thia-3,5,8-triazaacenaphthylene-2-carboxamide (Example 466) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{33}H_{28}N_6O_4S$, 604.7; m/z found, 605.3[M+H]$^+$. $^1$H NMR (400 MHz, CD$_3$OD): δ 8.28 (d, J=5.6 Hz, 1H), 7.58-7.52 (m, 1H), 7.40-7.30 (m, 2H), 7.18-7.09 (m, 3H), 7.09-7.03 (m, 3H), 6.52 (d, J=11.0 Hz, 1H), 6.16 (d, J=5.6 Hz, 1H), 4.26-4.10 (m, 1H), 4.08-3.92 (m, 2H), 3.25-2.95 (m, 2H), 2.09-1.93 (m, 2H), 1.90-1.82 (m, 1H), 1.78-1.57 (m, 2H), 1.23-1.15 (m, 2H), 1.01-0.92 (m, 1H), 0.87-0.78 (m, 1H).

Example 841: (R)—N-(1-(3-Methoxypropanoyl) piperidin-3-yl)-5-(2-methyl-4-phenoxyphenyl)-4-oxo-4,5-dihydro-3H-1-thia-3,5,8-triazaacenaphthylene-2-carboxamide

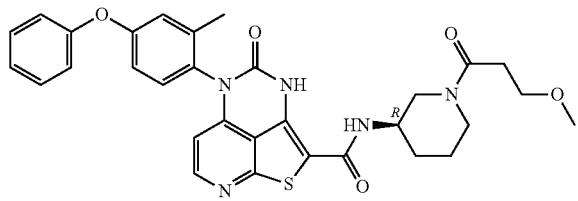

The title compound was prepared using conditions analogous to Example 75, and using 3-methoxypropanoic acid in place of 3-hydroxypropanoic acid. MS (ESI): mass calcd. for $C_{31}H_{31}N_5O_5S$, 585.9; m/z found, 586.7[M+H]$^+$. $^1$H NMR (400 MHz, CD$_3$OD): δ 8.32-8.27 (m, 1H), 7.42-7.34 (m, 2H), 7.33-7.28 (m, 1H), 7.18-7.11 (m, 1H), 7.09-7.02 (m, 3H), 6.99-6.93 (m, 1H), 6.07-6.01 (m, 1H), 4.50-4.24 (m, 1H), 4.13-3.84 (m, 2H), 3.68-3.61 (m, 2H), 3.30 (s, 3H), 3.19-2.98 (m, 1H), 2.87-2.76 (m, 1H), 2.73-2.62 (m, 2H), 2.11 (s, 3H), 2.07-1.98 (m, 1H), 1.87-1.77 (m, 1H), 1.73-1.47 (m, 2H).

Example 842: (R)—N-(1-Acryloylpiperidin-3-yl)-5-(2',3'-difluoro-4-methyl-[1,1'-biphenyl]-3-yl)-4-oxo-4,5-dihydro-3H-1-thia-3,5,8-triazaacenaphthylene-2-carboxamide

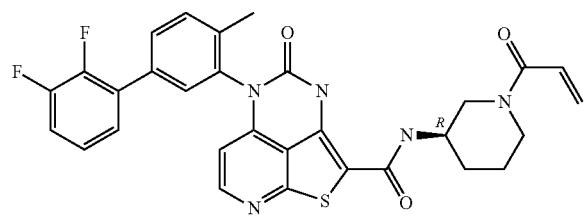

Step A: tert-butyl (R)-3-(5-(5-bromo-2-methylphenyl)-4-oxo-4,5-dihydro-3H-1-thia-3,5,8-triazaacenaphthylene-2-carboxamido)piperidine-1-carboxylate The title compound was prepared in a manner analogous to Method 1, steps B-G in Example 1, using 5-bromo-2-methylaniline in place of 2-Methyl-4-phenoxyaniline in step B, using tert-butyl (R)-3-aminopiperidine-1-carboxylate in place of tert-butyl (3R,5R)-3-amino-5-fluoropiperidine-1-carboxylate (Intermediate 1) in step G as a yellow solid.

Step B: (R)-5-(2',3'-difluoro-4-methyl-[1,1'-biphenyl]-3-yl)-4-oxo-N-(piperidin-3-yl)-4,5-dihydro-3H-1-thia-3,5,8-triazaacenaphthylene-2-carboxamide The mixture of tert-butyl (R)-3-(5-(5-bromo-2-methylphenyl)-4-oxo-4,5-dihydro-3H-1-thia-3,5,8-triazaacenaphthylene-2-carboxamido)piperidine-1-carboxylate, 2-(2,3-difluorophenyl)-4,4,5,5-tetramethyl-1,3,2-dioxaborolane, Pd(dppf)Cl$_2$, and Cs$_2$CO$_3$ in p-dioxane was stirred at 80° C. under N$_2$ for 4 hours, then was directly purified by ISCO eluting with MeOH/water. The product was dissolved in saturated aqueous HCl and MeOH, stirred at room temperature for 30 minutes, the solvent was removed under vacuo. The residue was purified by preparative TLC eluting with MeOH/DCM to yield the title compound as a brown solid.

Step C: (R)—N-(1-acryloylpiperidin-3-yl)-5-(2',3'-difluoro-4-methyl-[11'-biphenyl]-3-yl)-4-oxo-4,5-dihydro-3H-1-thia-3,5,8-triazaacenaphthylene-2-carboxamide The title compound was prepared in a manner analogous to Method 1, step I in Example 1, using (R)-5-(2',3'-difluoro-4-methyl-[1,1'-biphenyl]-3-yl)-4-oxo-N-(piperidin-3-yl)-4,5-dihydro-3H-1-thia-3,5,8-triazaacenaphthylene-2-carboxamide in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide. MS (ESI): mass calcd. for $C_{30}H_{25}F_2N_5O_3S$, 573.6; m/z found, 574.2 [M+H]$^+$. $^1$H NMR (400 MHz, CD$_3$OD): δ 8.32 (d, J=4.7 Hz, 1H), 7.71-7.63 (m, 1H), 7.62-7.54 (m, 2H), 7.35-7.17 (m, 3H), 6.85-6.72 (m, 1H), 6.26-6.14 (m, 1H), 6.08 (d, J=4.7 Hz, 1H), 5.78-5.67 (m, 1H), 4.61-4.46 (m, 1H), 4.33-4.13 (m, 1H), 3.99-3.92 (m, 1H), 3.22-3.15 (m, 1H), 3.00-2.81 (m, 1H), 2.23 (s, 3H), 2.11-2.02 (m, 1H), 1.94-1.81 (m, 1H), 1.82-1.65 (m, 1H), 1.64-1.53 (m, 1H).

Example 843: (R)-5-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide

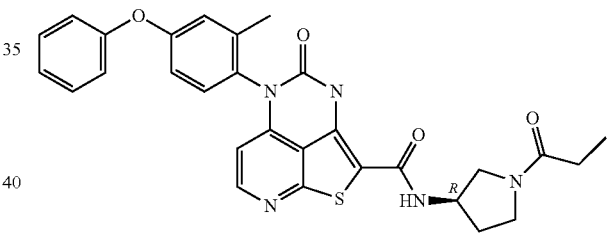

The title compound was prepared using conditions analogous to Example 104, and using propionic acid in place of 3-methylsulfonylpropanoic acid to give a yellow solid. MS (ESI): mass calcd. for $C_{29}H_{27}N_5O_4S$, 541.6; m/z found, 542.2 [M+H]$^+$. $^1$H NMR (400 MHz, DMSO-d$_6$): δ 10.24 (s, 1H), 8.45-8.21 (m, 2H), 7.57-7.32 (m, 3H), 7.29-6.84 (m, 5H), 6.04-5.94 (m, 1H), 4.62-4.29 (m, 1H), 3.79-3.35 (m, 3H), 2.29-1.91 (m, 7H), 0.99 (t, J=6.4 Hz, 3H).

Example 844: (R,E)-N-(1-(2-Cyano-3-cyclopropylacryloyl)pyrrolidin-3-yl)pyrrolidin-3-yl)-5-(2-methyl-4-phenoxyphenyl)-4-oxo-4,5-dihydro-3H-1-thia-3,5,8-triazaacenaphthylene-2-carboxamide

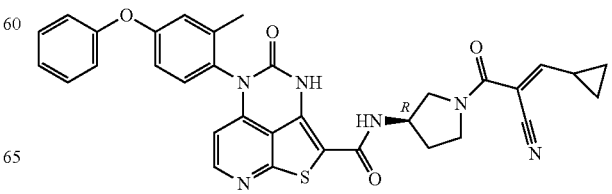

The title compound was prepared using conditions analogous to Example 877, and using (R)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Example 159) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a white solid. MS (ESI): mass calcd. for $C_{33}H_{28}N_6O_4S$, 604.7; m/z found, 605.1 [M+H]$^+$. $^1$H NMR (400 MHz, a mixture of CD$_3$OD and DMSO-d$_6$): δ 8.29 (d, J=5.4 Hz, 1H), 7.44-7.35 (m, 2H), 7.34-7.25 (m, 1H), 7.18-7.11 (m, 1H), 7.10-7.01 (m, 3H), 6.98-6.89 (m, 1H), 6.76-6.70 (m, 1H), 5.97 (d, J=5.5 Hz, 1H), 4.54-4.45 (m, 1H), 3.79-3.71 (s, 3H), 3.64-3.55 (m, 1H), 3.50-3.43 (m, 1H), 2.22-2.11 (m, 1H), 2.05 (s, 3H), 1.97-1.89 (m, 1H), 1.21-1.15 (m, 2H), 0.95-0.84 (m, 2H).

Example 845: (R,E)-5-(*S)-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide

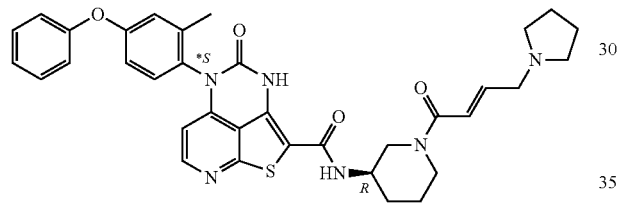

The title compound was prepared in a manner analogous to Method 1, steps A-I (including Chiral Resolution Method A after step F to obtain the *S atropisomer) in Example 1, and using tert-butyl (3R)-3-aminopiperidine-1-carboxylate in place of tert-butyl (3R,5R)-3-amino-5-fluoropiperidine-1-carboxylate (Intermediate 1) in step G, and using (E)-4-(pyrrolidin-1-yl)but-2-enoic acid, HATU, DIPEA, and DMF in place of prop-2-enoyl chloride, trimethylamine, and DCM in step I. MS (ESI): mass calcd. for $C_{35}H_{36}N_6O_4S$, 636.8; m/z found, 637.4 [M+H]$^+$. $^1$H NMR (400 MHz, CDCl$_3$): δ 8.37-8.31 (m, 1H), 7.42-7.33 (m, 2H), 7.21-7.12 (m, 2H), 7.12-7.06 (m, 2H), 7.01-6.98 (m, 1H), 6.98-6.84 (m, 2H), 6.49-6.41 (m, 1H), 6.25 (br, 1H), 6.03-5.95 (m, 1H), 5.50 (br, 1H), 4.15-3.34 (m, 5H), 3.32-3.18 (m, 2H), 2.64-2.40 (m, 4H), 2.12 (s, 3H), 2.08-1.86 (m, 2H), 1.83-1.71 (m, 6H).

Example 846: (R)—N-(1-Acryloylpiperidin-3-yl)-4-oxo-5-(4-(pyridin-2-yloxy)phenyl)-4,5-dihydro-3H-1-thia-3,5,8-triazaacenaphthylene-2-carboxamide

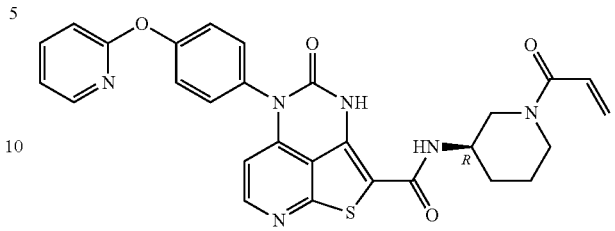

Step A: Methyl 3-amino-4-((4-(pyridin-2-yloxy)phenyl)amino)thieno[2,3-b]pyridine-2-carboxylate To a solution of 4-(pyridin-2-yloxy)aniline 3.00 g, 16.1 mmol) and 2-chloro-4-iodopyridine-3-carbonitrile (5.539 g, 20.94 mmol) in dioxane (30 mL) were added DPEphos (1.735 g, 3.221 mmol), Pd(OAc)$_2$ (0.362 g, 1.61 mmol), and Cs$_2$CO$_3$ (10.498 g, 32.222 mmol) under a N$_2$ atmosphere and was stirred at 100° C. for 4 h. After 4 h, methyl 2-mercaptoacetate (2.565 g, 24.17 mmol) was added and the reaction was stirred at 100° C. overnight. The reaction was filtered to remove the solid and was concentrated to dryness. MeOH was added to the residue with stirring and the precipitate that formed was filtered. The precipitate was added to EtOAc, stirred, filtered, and dried under a vacuum to give the title compound (2.7 g, 43% yield) as a grey solid.

Step B: (R)—N-(1-Acryloylpiperidin-3-yl)-4-oxo-5-(4-(pyridin-2-yloxy)phenyl)-4,5-dihydro-3H-1-thia-3,5,8-triazaacenaphthylene-2-carboxamide The title compound was prepared in a manner analogous to Method 1, steps E-G in Example 1, and using methyl 3-amino-4-((4-(pyridin-2-yloxy)phenyl)amino)thieno[2,3-b]pyridine-2-carboxylate in place of methyl 3-amino-4-(2-methyl-4-phenoxyanilino)thieno[2,3-b]pyridine-2-carboxylate in step E, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{28}H_{24}N_6O_4S$, 540.6; m/z found, 541.1 [M+H]$^+$. $^1$H NMR (400 MHz, DMSO-d$_6$): δ 10.24 (br, 1H), 8.39-8.27 (m, 1H), 8.26-8.12 (m, 2H), 7.98-7.84 (m, 1H), 7.52-7.42 (m, 2H), 7.38-7.29 (m, 2H), 7.23-7.16 (m, 1H), 7.17-7.09 (m, 1H), 6.89-6.70 (m, 1H), 6.16-6.07 (m, 1H), 6.06-5.98 (m, 1H), 5.74-5.61 (m, 1H), 4.57-3.87 (m, 2H), 3.86-3.68 (m, 1H), 3.18-2.96 (m, 1H), 2.88-2.61 (m, 1H), 2.03-1.89 (m, 1H), 1.83-1.73 (m, 1H), 1.72-1.58 (m, 1H), 1.50-1.37 (m, 1H).

Example 847: (R)—N-(1-Acryloylpyrrolidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide

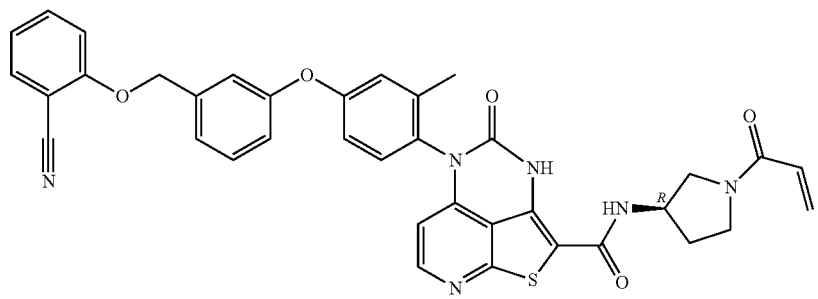

The title compound was prepared in a manner analogous to Method 1, steps G-I, in Example 1, using 5-(4-(3-((2-cyanophenoxy)methyl)phenoxy)-2-methylphenyl)-4-oxo-4,5-dihydro-3H-1-thia-3,5,8-triazaacenaphthylene-2-carboxylic acid (Intermediate 75) in place of 5-(2-methyl-4-phenoxyphenyl)-4-oxo-4,5-dihydro-3H-1-thia-3,5,8-triazaacenaphthylene-2-carboxylic acid (Intermediate 27), and using tert-butyl (R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{37}H_{30}N_6O_5S$, 670.7; m/z found, 671.1 [M+H]$^+$. $^1$H NMR (400 MHz, DMSO-d$_6$): δ 8.77 (br, 1H), 8.17-8.07 (m, 1H), 7.75-7.68 (m, 1H), 7.66-7.60 (m, 1H), 7.48-7.41 (m, 1H), 7.34-7.14 (m, 4H), 7.10-7.01 (m, 3H), 6.96-6.90 (m, 1H), 6.62-6.49 (m, 1H), 6.15-6.06 (m, 1H), 5.80-5.67 (m, 1H), 5.67-5.58 (m, 1H), 5.30 (s, 2H), 4.52-4.34 (m, 1H), 3.89-3.60 (m, 2H), 3.60-3.47 (m, 1H), 3.45-3.40 (m, 1H), 2.21-2.08 (m, 1H), 1.99 (s, 3H), 1.96-1.86 (m, 1H).

Example 848: 5-(2-Methyl-4-phenoxyphenyl)-N—((R)-1-((R)-2-(methylamino)propanoyl)piperidin-3-yl)-4-oxo-4,5-dihydro-3H-1-thia-3,5,8-triazaacenaphthylene-2-carboxamide The title compound was prepared using conditions analogous to Example 75, and using (R)-1-(tert-butoxycarbonyl)azetidine-2-carboxylic acid in place of 3-hydroxypropanoic acid to give (R)-tert-butyl 2-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)azetidine-1-carboxylate. This product was then subjected to conditions analogous to those in Method 1, step H, to give the title compound. MS (ESI): mass calcd. for $C_{31}H_{30}N_6O_4S$, 582.7; m/z found, 583.2 [M+H]$^+$. $^1$H NMR (400 MHz, CD$_3$OD): δ 8.07 (d, J=5.7 Hz, 1H), 7.45-7.31 (m, 2H), 7.23-7.04 (m, 4H), 7.04-7.00 (m, 1H), 6.98-6.90 (m, 1H), 5.80 (d, J=5.7 Hz, 1H), 4.66-4.56 (m, 1H), 4.29-3.88 (m, 2H), 3.77-3.64 (m, 1H), 3.54-3.38 (m, 2H), 3.20-3.02 (m, 2H), 2.81-2.63 (m, 1H), 2.44-2.32 (m, 1H), 2.17-2.02 (m, 4H), 1.95-1.74 (m, 2H), 1.66-1.54 (m, 1H).

Example 850: (R,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide

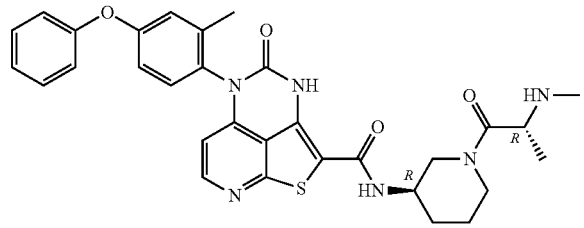

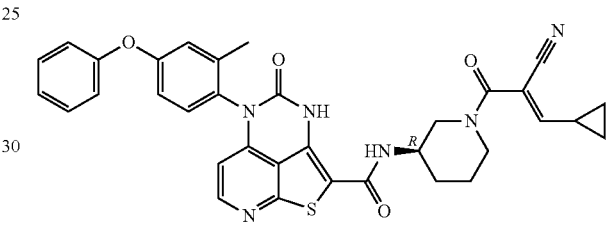

The title compound was prepared using conditions analogous to Example 75, and using (R)-2-((tert-butoxycarbonyl)(methyl)amino)propanoic acid in place of 3-hydroxypropanoic acid to give tert-butyl methyl((R)-1-((R)-3-(5-(2-methyl-4-phenoxyphenyl)-4-oxo-4,5-dihydro-3H-1-thia-3,5,8-triazaacenaphthylene-2-carboxamido)piperidin-1-yl)-1-oxopropan-2-yl)carbamate. This product was then subjected to conditions analogous to those in Method 1, step H, to give the title compound. MS (ESI): mass calcd. for $C_{31}H_{32}N_6O_4S$, 584.7; m/z found, 585.2 [M+H]$^+$. $^1$H NMR (400 MHz, CD$_3$OD): δ 8.27-8.13 (m, 1H), 7.43-7.34 (m, 2H), 7.29-7.19 (m, 1H), 7.18-7.11 (m, 1H), 7.10-7.01 (m, 3H), 7.00-6.91 (m, 1H), 6.00-5.86 (m, 1H), 4.44-3.43 (m, 5H), 3.15-2.75 (m, 1H), 2.50-2.35 (m, 3H), 2.14-1.71 (m, 6H), 1.70-1.52 (m, 1H), 1.34-1.23 (m, 3H).

Example 849: N—((R)-1-((R)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide The title compound was prepared using conditions analogous to Example 877, and using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a light yellow solid. MS (ESI): mass calcd. for $C_{34}H_{30}N_6O_4S$, 618.7; m/z found, 619.3 [M+H]$^+$. $^1$H NMR (400 MHz, a mixture of CD$_3$OD and DMSO-d$_6$): δ 8.30-8.26 (m, 1H), 7.39-7.33 (m, 2H), 7.29-7.24 (m, 1H), 7.15-7.09 (m, 1H), 7.08-7.00 (m, 3H), 6.94-6.89 (m, 1H), 6.49-6.43 (m, 1H), 6.00-5.96 (m, 1H), 4.14-4.10 (m, 1H), 3.96-3.83 (m, 2H), 3.11-2.92 (m, 2H), 2.05 (s, 3H), 1.98-1.86 (m, 2H), 1.82-1.75 (m, 1H), 1.72-1.62 (m, 1H), 1.57-1.46 (m, 1H), 1.16-1.08 (m, 2H), 0.95-0.87 (m, 1H), 0.82-0.73 (m, 1H).

Example 851: (E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide

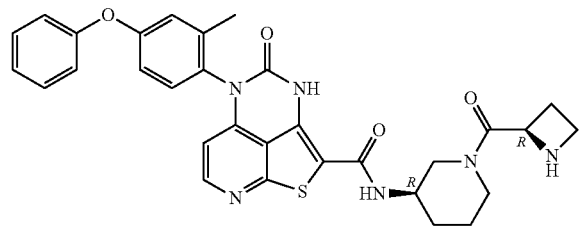

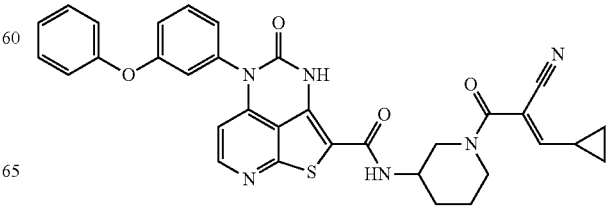

Step A: 4-Oxo-5-(3-phenoxyphenyl)-N-(piperidin-3-yl)-4,5-dihydro-3H-1-thia-3,5,8-triazaacenaphthylene-2-carboxamide The title compound was prepared in a manner analogous to Method 1, step G-H in Example 1, and using 4-oxo-5-(3-phenoxyphenyl)-4,5-dihydro-3H-1-thia-3,5,8-triazaacenaphthylene-2-carboxylic acid (Intermediate 59) in place of 5-(2-Methyl-4-phenoxyphenyl)-4-oxo-4,5-dihydro-3H-1-thia-3,5,8-triazaacenaphthylene-2-carboxylic acid in step G.

Step B: (E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide The title compound was prepared using conditions analogous to Example 877, and using 4-oxo-5-(3-phenoxyphenyl)-N-(piperidin-3-yl)-4,5-dihydro-3H-1-thia-3,5,8-triazaacenaphthylene-2-carboxamide in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a yellow solid. MS (ESI): mass calcd. for $C_{33}H_{28}N_6O_4S$, 604.7; m/z found, 605.3 [M+H]$^+$. $^1$H NMR (400 MHz, CD$_3$OD): δ 8.35 (d, J=5.6 Hz, 1H), 7.67-7.57 (m, 1H), 7.47-7.37 (m, 2H), 7.24-7.16 (m, 3H), 7.15-7.10 (m, 3H), 6.58 (d, J=11.0 Hz, 1H), 6.23 (d, J=5.6 Hz, 1H), 4.30-4.15 (m, 1H), 4.12-3.97 (m, 2H), 3.30-3.08 (m, 2H), 2.13-2.01 (m, 2H), 1.98-1.89 (m, 1H), 1.85-1.74 (m, 1H), 1.72-1.61 (m, 1H), 1.30-1.21 (m, 2H), 1.06-0.98 (m, 1H), 0.96-0.87 (m, 1H).

Example 852: (R)—N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide

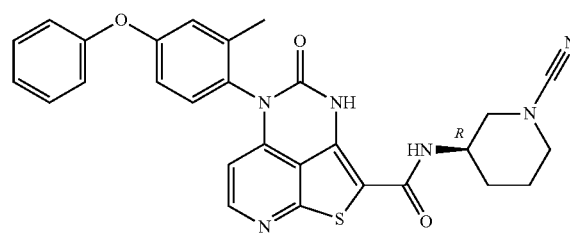

The title compound was prepared using conditions analogous to Example 890, and using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{28}H_{24}N_6O_3S$, 524.6; m/z found, 525.3[M+H]$^+$. $^1$H NMR (400 MHz, a mixture of DMSO-d$_6$ and CD$_3$OD): δ 8.34-8.30 (m, 1H), 7.44-7.37 (m, 2H), 7.35-7.30 (m, 1H), 7.20-7.13 (m, 1H), 7.12-7.03 (m, 3H), 6.99-6.92 (m, 1H), 6.01-5.96 (m, 1H), 4.02-3.94 (m, 1H), 3.47-3.40 (m, 1H), 3.33-3.24 (m, 1H), 3.01-2.91 (m, 2H), 2.06 (s, 3H), 1.95-1.84 (m, 1H), 1.83-1.74 (m, 1H), 1.70-1.50 (m, 2H).

Example 853: 5-(2-Methyl-4-phenoxyphenyl)-N—((R)-1-((S)-2-(methylamino)propanoyl)piperidin-3-yl)-4-oxo-4,5-dihydro-3H-1-thia-3,5,8-triazaacenaphthylene-2-carboxamide

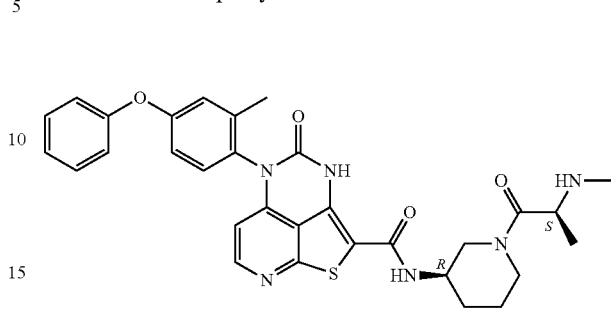

The title compound was prepared in a manner analogous to Method 1, steps A-I in Example 1, and using (R)-tert-butyl 3-aminopiperidine-1-carboxylate in place of tert-butyl (3R,5R)-3-amino-5-fluoropiperidine-1-carboxylate (Intermediate 1) in step G, and using (S)-2-((tert-butoxycarbonyl)(methyl)amino)propanoic acid, HATU, DMF, and DIPEA in place of prop-2-enoyl chloride, triethylamine, and DCM in step I, followed by a Boc-deprotection step using concentrated HCl (3 mL) in MeOH (3 mL) and stirring for 30 min. The solvent was removed under a vacuum and the residue was purified by flash column chromatography to yield the title compound as a yellow solid. MS (ESI): mass calcd. for $C_{31}H_{32}N_6O_4S$, 584.7; m/z found, 585.2 [M+H]$^+$. $^1$H NMR (400 MHz, CD$_3$OD): δ 8.36-8.30 (m, 1H), 7.45-7.36 (m, 2H), 7.32-7.25 (m, 1H), 7.21-7.14 (m, 1H), 7.12-7.04 (m, 3H), 7.01-6.94 (m, 1H), 6.10-6.04 (m, 1H), 4.53-4.28 (m, 2H), 4.04-3.72 (m, 2H), 3.22-3.05 (m, 1H), 2.96-2.83 (m, 1H), 2.70-2.56 (m, 3H), 2.14-2.09 (m, 3H), 2.09-1.99 (m, 1H), 1.94-1.70 (m, 2H), 1.69-1.45 (m, 4H).

Example 854: (R,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide

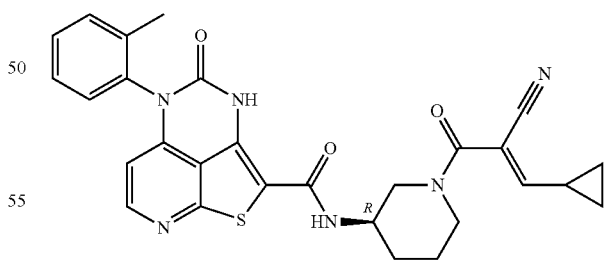

The title compound was prepared using conditions analogous to Example 866, steps A-B, and using tert-butyl (R)-3-aminopiperidine-1-carboxylate in place of tert-butyl-3-aminopiperidine-1-carboxylate in step A to give a white solid. MS (ESI): mass calcd. for $C_{28}H_{26}N_6O_3S$, 526.6; m/z found, 527.1 [M+H]$^+$. $^1$H NMR (400 MHz, DMSO-d$_6$): δ 10.18 (s, 1H), 8.33 (d, J=5.4 Hz, 1H), 8.14-8.05 (m, 1H), 7.52-7.45 (m, 2H), 7.44-7.37 (m, 2H), 6.65-6.56 (m, 1H), 5.87 (d, J=5.4 Hz, 1H), 4.28-4.02 (m, 1H), 4.00-3.82 (m, 2H), 3.12-2.78 (m, 2H), 2.11 (s, 3H), 2.02-1.92 (m, 1H), 1.92-1.86 (m, 1H), 1.84-1.79 (m, 1H), 1.75-1.63 (m, 1H), 1.58-1.46 (m, 1H), 1.20-1.13 (m, 2H), 1.07-0.95 (m, 1H), 0.91-0.84 (m, 1H).

Example 855: 5-(4-(3-((2-Cyanophenoxy)methyl)phenoxy)-2-methylphenyl)-N-(1-methylpiperidin-4-yl)-4-oxo-4,5-dihydro-3H-1-thia-3,5,8-triazaacenaphthylene-2-carboxamide

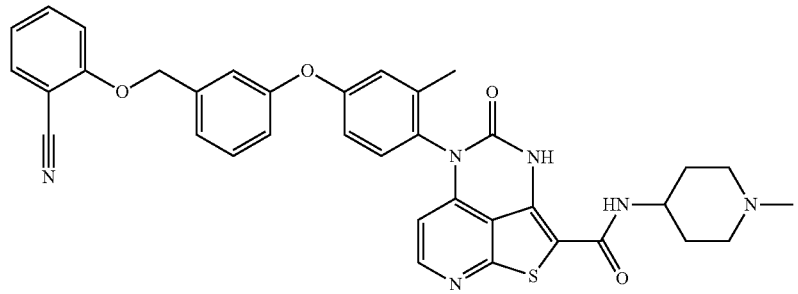

The title compound was prepared using conditions analogous to Example 835, step A, and using methyl 5-(4-(3-((2-cyanophenoxy)methyl)phenoxy)-2-methylphenyl)-4-oxo-4,5-dihydro-3H-1-thia-3,5,8-triazaacenaphthylene-2-carboxylate (Intermediate 76) (187 mg, 0.33 mmol) and 1-methylpiperidin-4-amine (76 mg, 0.67 mmol) in place of methyl 5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxylate (Intermediate 73) and tert-butyl (R)-3-aminopiperidine-1-carboxylate to give a solid (88 mg, 41% yield). MS (ESI): mass calcd. for $C_{36}H_{32}N_6O_4S$, 644.8; m/z found, 645.2 [M+H]$^+$. $^1$H NMR (400 MHz, DMSO-d$_6$): δ 8.57-8.26 (m, 1H), 8.19-8.08 (m, 1H), 7.74-7.70 (m, 1H), 7.67-7.62 (m, 1H), 7.49-7.44 (m, 1H), 7.33-7.26 (m, 2H), 7.25-7.20 (m, 2H), 7.11-7.04 (m, 3H), 6.97-6.92 (m, 1H), 5.82-5.71 (m, 1H), 5.32 (s, 2H), 3.75-3.68 (m, 1H), 2.78-2.72 (m, 2H), 2.17 (s, 3H), 2.04-1.98 (m, 5H), 1.82-1.76 (m, 2H), 1.59-1.51 (m, 2H).

Example 856: (E)-N-(1-(2-Cyano-3-cyclopropylacryloyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide

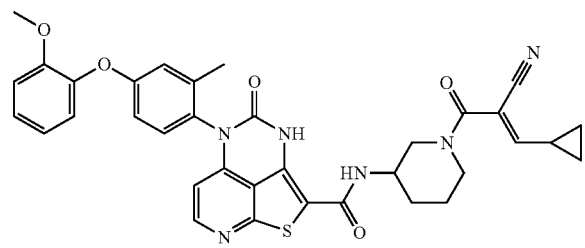 [SMILES: COc1ccccc1Oc1ccc(N2C(=O)Nc3c(C(=O)NC4CCCN(C(=O)/C(C#N)=C/C5CC5)C4)sc4nccc2c34)c(C)c1]

The title compound was prepared using conditions analogous to Example 877, and using 5-(4-(2-methoxyphenoxy)-2-methylphenyl)-4-oxo-N-(piperidin-3-yl)-4,5-dihydro-3H-1-thia-3,5,8-triazaacenaphthylene-2-carboxamide (Example 870) in place 5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{35}H_{32}N_6O_5S$, 648.7; m/z found, 649.1 [M+H]$^+$. $^1$H NMR (400 MHz, a mixture of CD$_3$OD and DMSO-d$_6$): δ 8.29 (d, J=5.4 Hz, 1H), 7.24-7.17 (m, 2H), 7.16-7.11 (m, 1H), 7.10-7.05 (m, 1H), 7.00-6.93 (m, 1H), 6.90-6.85 (m, 1H), 6.79-6.72 (m, 1H), 6.52-6.44 (m, 1H), 5.94 (d, J=5.5 Hz, 1H), 3.91-3.86 (m, 1H), 3.81 (s, 4H), 3.75 (s, 3H), 2.02 (s, 3H), 1.99-1.86 (m, 2H), 1.84-1.75 (m, 1H), 1.73-1.63 (m, 1H), 1.55-1.47 (m, 1H), 1.16-1.08 (m, 2H), 0.97-0.89 (m, 1H), 0.85-0.76 (m, 1H).

Example 857: 5-(4-(3-((2-Cyanophenoxy)methyl)phenoxy)-2-methylphenyl)-4-oxo-N-(piperidin-4-yl)-4,5-dihydro-3H-1-thia-3,5,8-triazaacenaphthylene-2-carboxamide

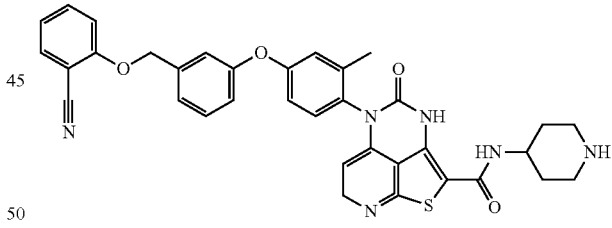

The title compound was prepared in a manner analogous to Method 1, step G in Example 1, using 5-(4-(3-((2-cyanophenoxy)methyl)phenoxy)-2-methylphenyl)-4-oxo-4,5-dihydro-3H-1-thia-3,5,8-triazaacenaphthylene-2-carboxylic acid (Intermediate 75) in place of 4-oxo-5-(4-phenoxyphenyl)-4,5-dihydro-3H-1-thia-3,5,8-triazaacenaphthylene-2-carboxylic acid (Intermediate 58). MS (ESI): mass calcd. for $C_{35}H_{30}N_6O_4S$, 630.7; m/z found, 631.3 [M+H]$^+$. $^1$H NMR (400 MHz, DMSO-d$_6$): δ 8.72-8.50 (m, 1H), 8.31-8.22 (m, 1H), 8.21-8.13 (m, 1H), 7.78-7.69 (m, 1H), 7.68-7.59 (m, 1H), 7.54-7.42 (m, 1H), 7.37-7.19 (m, 4H), 7.15-7.03 (m, 3H), 7.00-6.92 (m, 1H), 5.80 (d, J=5.4 Hz, 1H), 5.32 (s, 2H), 3.28-3.22 (m, 2H), 3.01-2.89 (m, 2H), 2.02 (s, 3H), 2.00-1.91 (m, 2H), 1.79-1.56 (m, 2H).

Example 858: 5-(2-Methyl-4-phenoxyphenyl)-N-(1-methylpiperidin-4-yl)-4-oxo-4,5-dihydro-3H-1-thia-3,5,8-triazaacenaphthylene-2-carboxamide

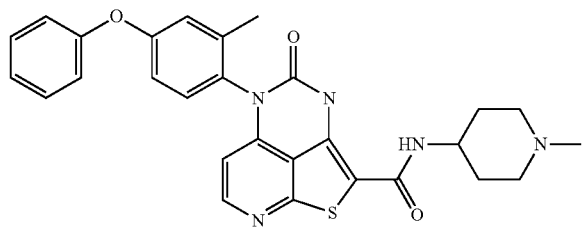 [SMILES: Cc1cc(Oc2ccccc2)ccc1N1C(=O)Nc2c(C(=O)NC3CCN(C)CC3)sc3nccc1c23]

The title compound was prepared using conditions analogous to Example 920 and using 5-(2-methyl-4-phenoxyphenyl)-4-oxo-4,5-dihydro-3H-1-thia-3,5,8-triazaacenaphthylene-2-carboxylic acid (Intermediate 27) in place of 4-oxo-5-(4-phenoxyphenyl)-4,5-dihydro-3H-1-thia-3,5,8-triazaacenaphthylene-2-carboxylic acid (Intermediate 58). MS (ESI): mass calcd. for $C_{28}H_{27}N_5O_3S$, 513.6; m/z found, 514.2 [M+H]$^+$. $^1$H NMR (400 MHz, DMSO-$d_6$): δ 8.30-8.23 (m, 1H), 8.20-8.12 (m, 2H), 7.47-7.38 (m, 2H), 7.34-7.28 (m, 1H), 7.22-7.14 (m, 1H), 7.13-7.02 (m, 3H), 6.98-6.91 (m, 1H), 5.90 (d, J=5.5 Hz, 1H), 3.79-3.74 (m, 1H), 2.91-2.84 (m, 2H), 2.25 (s, 3H), 2.19-2.09 (m, 2H), 2.03 (s, 3H), 1.84-1.73 (m, 2H), 1.68-1.57 (m, 2H).

Example 859: (R,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide

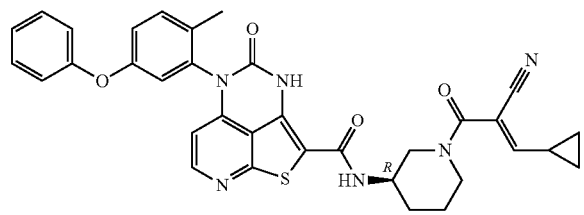

The title compound was prepared using conditions analogous to Example 877, and using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a white solid. MS (ESI): mass calcd. for $C_{34}H_{30}N_6O_4S$, 618.7; m/z found, 619.4[M+H]$^+$. $^1$H NMR (400 MHz, CD$_3$OD): δ 8.31 (d, J=5.6 Hz, 1H), 7.42 (d, J=8.5 Hz, 1H), 7.37-7.25 (m, 2H), 7.11-7.04 (m, 2H), 7.04-6.96 (m, 3H), 6.56-6.44 (m, 1H), 6.05 (d, J=5.5 Hz, 1H), 4.25-4.06 (m, 1H), 4.05-3.92 (m, 2H), 3.25-3.00 (m, 2H), 2.11 (s, 3H), 2.07-1.94 (m, 2H), 1.91-1.82 (m, 1H), 1.77-1.54 (m, 2H), 1.22-1.13 (m, 2H), 0.98-0.90 (m, 1H), 0.85-0.77 (m, 1H).

Example 860: (R)-4-Oxo-5-(4-phenoxyphenyl)-N-(piperidin-3-yl)-4,5-dihydro-3H-1-thia-3,5,8-triazaacenaphthylene-2-carboxamide

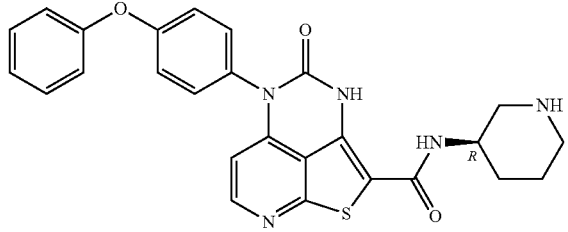

The title compound was prepared in a manner analogous to Method 1, steps A-H in Example 1, and using 4-fluoronitrobenzene in place of 5-fluoro-2-nitrotoluene in step A, and using Pt/C and THF in place of Fe, EtOH/H$_2$O, and NH$_4$Cl in step B, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{23}N_5O_3S$, 485.6; m/z found, 486.1 [M+H]$^+$. $^1$H NMR (400 MHz, CDCl$_3$): δ 9.58 (s, 1H), 9.52 (s, 1H), 9.34 (s, 1H), 8.14 (d, J=5.5 Hz, 1H), 7.42-7.33 (m, 4H), 7.27 (dd, J=8.8, 2.7 Hz, 1H), 7.21-7.04 (m, 5H), 5.96 (d, J=5.5 Hz, 1H), 4.41 (d, J=9.5 Hz, 1H), 3.60 (d, J=11.0 Hz, 1H), 3.19 (s, 4H), 2.04-1.95 (m, 2H).

Example 861: (R,E)-N-(1-(2-Cyano-3-cyclopropylacryloyl)piperidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide

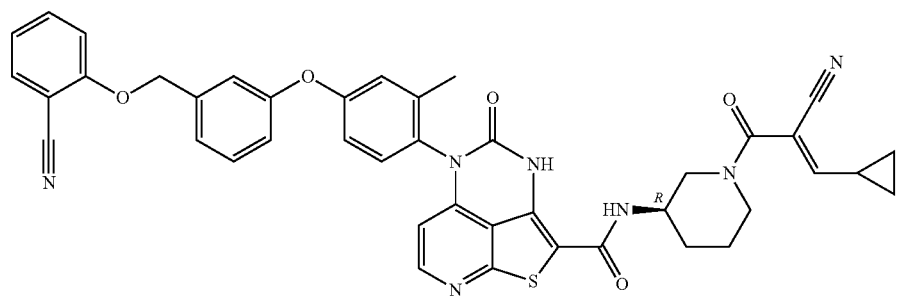

The title compound was prepared using conditions analogous to Example 877, and using (R)-5-(4-(3-((2-cyanophenoxy)methyl)phenoxy)-2-methylphenyl)-4-oxo-N-(piperidin-3-yl)-4,5-dihydro-3H-1-thia-3,5,8-triazaacenaphthylene-2-carboxamide (Intermediate 78) in place of 5-(2-methyl-4-phenoxyphenyl)-4-oxo-N-(piperidin-3-yl)-4,5-dihydro-3H-1-thia-3,5,8-triazaacenaphthylene-2-carboxamide. MS (ESI): mass calcd. for $C_{42}H_{35}N_7O_5S$, 749.9; m/z found, 750.2 [M+H]$^+$. $^1$H NMR (400 MHz, DMSO-$d_6$): δ 8.24-8.09 (br, 1H), 7.74-7.68 (m, 1H), 7.67-7.60 (m, 1H), 7.45 (t, J=7.9 Hz, 1H), 7.34-7.18 (m, 4H), 7.12-7.02 (m, 3H), 6.98-6.91 (m, 1H), 6.62-6.53 (m, 1H), 5.88-5.73 (m, 1H), 5.30 (s, 2H), 3.90-3.76 (m, 2H), 2.00 (s, 3H), 1.97-1.87 (m, 2H), 1.85-1.71 (m, 2H), 1.71-1.35 (m, 3H), 1.14-1.07 (m, 2H), 1.01-0.90 (m, 1H), 0.88-0.75 (m, 2H).

Example 862: (R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide

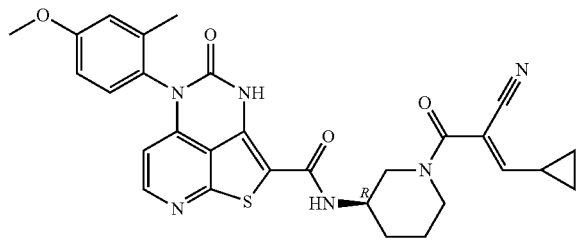

The title compound was prepared using conditions analogous to Example 878, steps A-B, using tert-butyl (R)-3-aminopiperidine-1-carboxylate in place of tert-butyl 3-aminopiperidine-1-carboxylate in Step A. MS (ESI): mass calcd. for $C_{29}H_{28}N_6O_4S$, 556.6; m/z found, 557.2 [M+H]$^+$. $^1$H NMR (400 MHz, DMSO-$d_6$): δ 10.28 (s, 1H), 8.30-8.26 (m, 1H), 8.13-8.03 (m, 1H), 7.30-7.17 (m, 1H), 7.04-6.95 (m, 1H), 6.95-6.87 (m, 1H), 6.65-6.47 (m, 1H), 5.88-5.84 (m, 1H), 4.39-4.07 (br, 1H), 3.87-3.65 (m, 5H), 3.07-2.76 (m, 2H), 2.03 (s, 3H), 1.93-1.81 (m, 2H), 1.80-1.73 (m, 1H), 1.70-1.59 (m, 1H), 1.52-1.40 (m, 2H), 1.16-1.08 (m, 2H), 1.04-0.92 (m, 1H), 0.88-0.78 (m, 1H).

Example 863: (S)—N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide

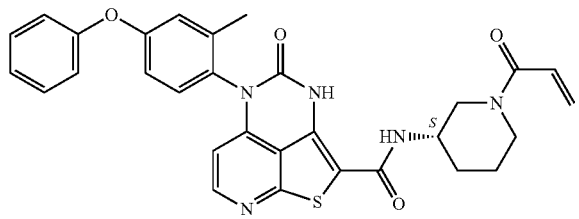

The title compound was prepared using conditions analogous to Method 1, step I, and using (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide. MS (ESI): mass calcd. for $C_{30}H_{27}N_5O_4S$, 553.6; m/z found, 554.2 [M+H]$^+$. $^1$H NMR (400 MHz, DMSO-$d_6$): δ 8.92 (d, J=7.4 Hz, 1H), 7.97 (d, J=5.5 Hz, 1H), 7.44-7.36 (m, 2H), 7.17-7.11 (m, 1H), 7.11-7.03 (m, 3H), 6.99 (d, J=2.4 Hz, 1H), 6.91-6.85 (m, 1H), 6.71 (br, 1H), 6.06-6.00 (m, 1H), 5.70 (s, 1H), 5.64-5.58 (m, 1H), 5.55 (d, J=5.5 Hz, 1H), 4.34-4.17 (m, 1H), 4.05-3.71 (m, 3H), 3.10-2.93 (m, 1H), 2.82-2.68 (m, 1H), 1.98 (s, 3H), 1.80-1.71 (m, 1H), 1.66-1.56 (m, 1H), 1.49-1.38 (m, 1H).

Example 864: (S)—N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide

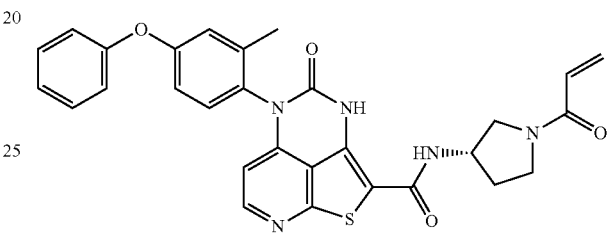

The title compound was prepared in a manner analogous to Method 1, steps A-I in Example 1, using tert-butyl (S)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{29}H_{25}N_5O_4S$, 539.6; m/z found, 540.5[M+H]$^+$. $^1$H NMR (400 MHz, a mixture of DMSO-$d_6$ and CD$_3$OD): δ 8.32-8.24 (m, 1H), 7.42-7.35 (m, 2H), 7.35-7.30 (m, 1H), 7.18-7.11 (m, 1H), 7.10-7.01 (m, 3H), 6.97-6.90 (m, 1H), 6.62-6.48 (m, 1H), 6.21-6.11 (m, 1H), 6.00-5.94 (m, 1H), 5.70-5.61 (m, 1H), 4.58-4.44 (m, 1H), 3.75-3.67 (m, 1H), 3.64-3.57 (m, 1H), 3.56-3.39 (m, 2H), 2.26-2.08 (m, 1H), 2.05 (s, 3H), 2.03-1.95 (m, 1H).

Example 865: 5-(2-Methyl-4-phenoxyphenyl)-4-oxo-N-(piperidin-4-yl)-4,5-dihydro-3H-1-thia-3,5,8-triazaacenaphthylene-2-carboxamide

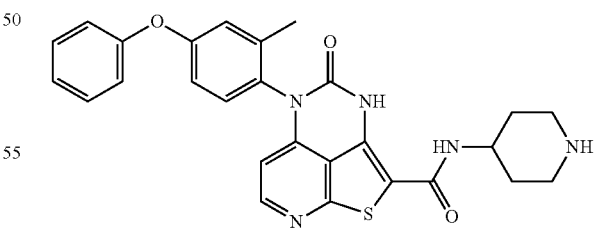

The title compound was prepared in a manner analogous to Method 1, steps A-H in Example 1, and using tert-butyl 4-aminopiperidine-1-carboxylate in place of tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 500.1 [M+H]$^+$. $^1$H NMR (400 MHz, DMSO-$d_6$): δ 8.78-8.68 (br, 1H), 8.32 (s, 1H), 8.12 (d, J=5.3 Hz, 1H), 7.46-7.37 (m, 2H), 7.24-7.00 (m, 6H), 6.96-6.88

(m, 1H), 5.72 (d, J=5.5 Hz, 1H), 4.01-3.97 (m, 1H), 3.26-3.21 (m, 2H), 2.99-2.87 (m, 2H), 2.01 (s, 3H), 1.99-1.92 (m, 2H), 1.73-1.59 (m, 2H).

Example 866: (R,E)-N-(1-(2-Cyano-4,4-dimethyl-pent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide

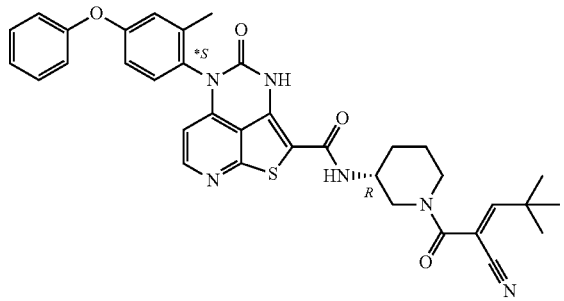

The title compound was prepared as in Example 75 using (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide (Example 98) and (E)-2-Cyano-4,4-dimethyl-pent-2-enoic acid or (E)-2-cyano-4,4-dimethylpent-2-enoic acid (Intermediate 44) in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) and 3-hydroxypropanoic acid. MS (ESI): mass calcd. for $C_{35}H_{34}N_6O_4S$, 634.7; m/z found, 635.4 [M+H]$^+$. $^1$H NMR (400 MHz, CD$_3$OD): δ 8.34-8.28 (m, 1H), 7.43-7.36 (m, 2H), 7.34-7.27 (m, 1H), 7.20-7.12 (m, 1H), 7.10-7.02 (m, 3H), 7.00-6.94 (m, 1H), 6.84 (s, 1H), 6.08-6.03 (m, 1H), 4.46-3.80 (m, 3H), 3.50-2.84 (m, 2H), 2.17-1.99 (m, 4H), 1.97-1.85 (m, 1H), 1.82-1.71 (m, 1H), 1.71-1.57 (m, 1H), 1.26 (s, 9H).

Example 867: (R,E)-5-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide

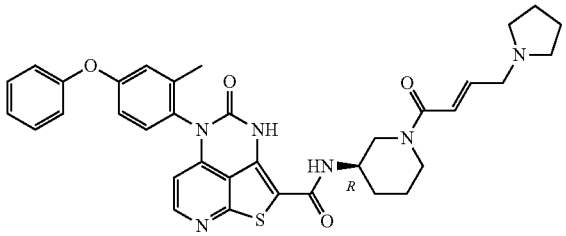

To a solution of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) (500 mg, 1.00 mmol) and (E)-4-(pyrrolidin-1-yl)but-2-enoic acid (776 mg, 2.00 mmol) in anhydrous DMF (5.0 mL) were added HATU (760 mg, 2.00 mmol) and DIPEA (390 mg, 3.00 mmol) and was stirred for 30 min at rt. The reaction was purified by flash column chromatography to give the title compound (78 mg, 12%) as a yellow solid. MS (ESI): mass calcd. for $C_{35}H_{36}N_6O_4S$, 636.8; m/z found, 637.3 [M+H]$^+$. $^1$H NMR (400 MHz, CDCl$_3$): δ 8.38-8.29 (m, 1H), 7.43-7.34 (m, 2H), 7.21-7.12 (m, 2H), 7.12-7.06 (m, 2H), 7.01-6.99 (m, 1H), 6.98-6.82 (m, 2H), 6.53-6.43 (m, 1H), 6.03-5.95 (m, 1H), 4.15-3.33 (m, 5H), 3.33-3.25 (m, 2H), 2.70-2.47 (m, 4H), 2.14-2.10 (m, 3H), 2.09-1.82 (m, 4H), 1.81-1.76 (m, 4H).

Example 868: (R,E)-N-(1-(2-Cyano-4,4-dimethyl-pent-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide

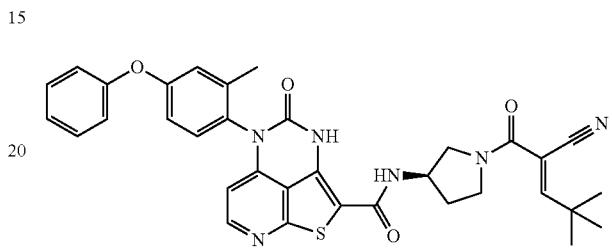

The title compound was prepared using conditions analogous to Example 104, and using (E)-2-cyano-4,4-dimethyl-pent-2-enoic acid (Intermediate 44) in place of 3-methylsulfonylpropanoic acid to give a yellow solid. MS (ESI): mass calcd. for $C_{34}H_{32}N_6O_4S$, 620.7; m/z found, 621.2 [M+H]$^+$. $^1$H NMR (400 MHz, DMSO-d$_6$): δ 10.31-10.21 (m, 1H), 8.41-8.31 (m, 2H), 7.49-7.42 (m, 2H), 7.39 (d, J=8.6 Hz, 1H), 7.24-7.18 (m, 1H), 7.16-7.08 (m, 3H), 7.04-6.96 (m, 2H), 6.00 (d, J=5.5 Hz, 1H), 4.60-4.41 (m, 1H), 3.90-3.42 (m, 4H), 2.25-2.14 (m, 1H), 2.10-1.98 (m, 4H), 1.27-1.21 (m, 9H).

Example 27: (R)-5-(2-Methyl-4-phenoxyphenyl)-4-oxo-N-(piperidin-3-yl)-4,5-dihydro-3H-1-thia-3,5,8-triazaacenaphthylene-2-carboxamide

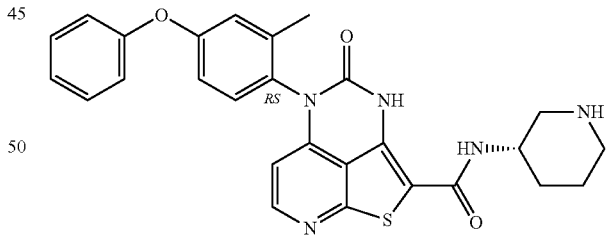

The title compound was prepared in a manner analogous to Method 1, steps A-H in Example 1, and using tert-butyl (R)-3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{27}H_{25}N_5O_3S$, 499.2; m/z found, 500.0 [M+H]$^+$. 1H NMR (400 MHz, DMSO-d6): δ 8.60 (s, 1H), 8.07 (d, J=5.2 Hz, 1H), 7.42-7.38 (m, 2H), 7.16-7.13 (m, 2H), 7.11-7.06 (m, 3H), 7.01-6.99 (m, 1H), 6.93-6.88 (m, 1H), 5.70-5.64 (m, 1H), 3.95-3.87 (br, 1H), 3.16-3.10 (m, 1H), 2.91-2.87 (m, 2H), 2.64-2.53 (m, 2H), 1.99 (s, 3H), 1.91-1.88 (m, 1H), 1.76-1.70 (m, 1H), 1.55-1.45 (m, 2H).

Example 870: 5-(4-(2-Methoxyphenoxy)-2-methylphenyl)-4-oxo-N-(piperidin-3-yl)-4,5-dihydro-3H-1-thia-3,5,8-triazaacenaphthylene-2-carboxamide

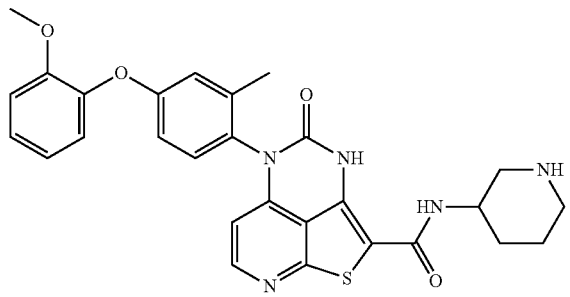 [SMILES: COc1ccccc1Oc1ccc(N2C(=O)Nc3c(C(=O)NC4CCCNC4)sc4nccc2c34)c(C)c1]

The title compound was prepared in a manner analogous to Method 1, step G-H, in Example 1, using 5-(4-(2-methoxyphenoxy)-2-methylphenyl)-4-oxo-4,5-dihydro-3H-1-thia-3,5,8-triazaacenaphthylene-2-carboxylic acid (Intermediate 67) in place of 5-(2-methyl-4-phenoxyphenyl)-4-oxo-4,5-dihydro-3H-1-thia-3,5,8-triazaacenaphthylene-2-carboxylic acid (Intermediate 27), using tert-butyl 3-aminopiperidine-1-carboxylate in place of tert-butyl (3R,5R)-3-amino-5-fluoropiperidine-1-carboxylate to yield the title product as a yellow solid. MS (ESI): mass calcd. for $C_{28}H_{27}N_5O_4S$, 529.6; m/z found, 530.1 [M+H]$^+$. $^1$H NMR (400 MHz, a mixture of CD$_3$OD and DMSO-d$_6$): δ 8.23-8.10 (m, 1H), 7.21-7.16 (m, 1H), 7.15-7.09 (m, 2H), 7.09-7.04 (m, 1H), 6.99-6.92 (m, 1H), 6.90-6.82 (m, 1H), 6.78-6.66 (m, 1H), 5.84-5.74 (m, 1H), 4.05-4.01 (m, 1H), 3.76 (s, 3H), 3.20-3.17 (m, 1H), 3.02-2.94 (m, 1H), 2.75-2.63 (m, 2H), 2.00 (s, 3H), 1.96-1.88 (m, 1H), 1.84-1.76 (m, 1H), 1.66-1.54 (m, 2H).

Example 871: (R)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide

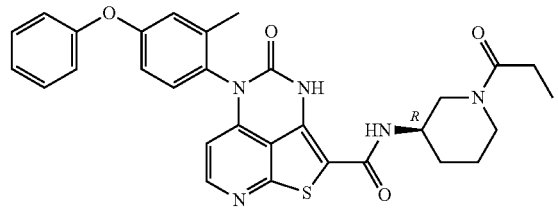

The title compound was prepared using conditions analogous to Example 75, and using propionic acid in place of 3-hydroxypropanoic acid to give a yellow solid. MS (ESI): mass calcd. for $C_{30}H_{29}N_5O_4S$, 555.7; m/z found, 556.2 [M+H]$^+$. $^1$H NMR (400 MHz, DMSO-d$_6$): δ 8.90 (s, 1H), 7.97 (d, J=5.1 Hz, 1H), 7.43-7.35 (m, 2H), 7.17-7.11 (m, 1H), 7.11-7.03 (m, 3H), 6.99 (s, 1H), 6.88 (d, J=6.9 Hz, 1H), 5.70 (s, 1H), 5.55 (d, J=5.1 Hz, 1H), 4.21-3.97 (m, 1H), 3.92-3.58 (m, 2H), 3.08-2.97 (m, 1H), 2.77-2.69 (m, 1H), 2.32-2.27 (m, 2H), 1.97 (s, 3H), 1.78-1.55 (m, 2H), 1.50-1.32 (m, 2H), 1.01-0.91 (m, 3H).

Example 872: N-(1-Cyanopiperidin-4-yl)-5-(2-methyl-4-phenoxyphenyl)-4-oxo-4,5-dihydro-3H-1-thia-3,5,8-triazaacenaphthylene-2-carboxamide

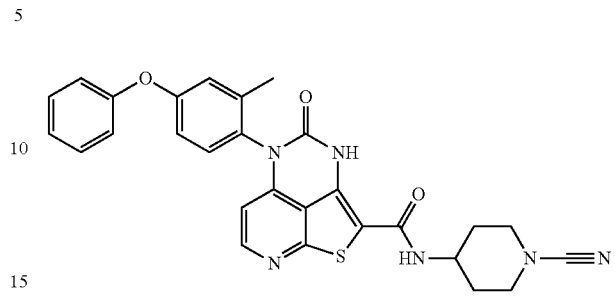

The title compound was prepared using conditions analogous to Example 890, and using 5-(2-methyl-4-phenoxyphenyl)-4-oxo-N-(piperidin-4-yl)-4,5-dihydro-3H-1-thia-3,5,8-triazaacenaphthylene-2-carboxamide (Example 865) in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{28}H_{24}N_6O_3S$, 524.6; m/z found, 525.2 [M+H]$^+$. $^1$H NMR (400 MHz, DMSO-d$_6$): δ 10.15 (s, 1H), 8.35-8.31 (m, 1H), 8.06-8.01 (m, 1H), 7.46-7.39 (m, 2H), 7.38-7.34 (m, 1H), 7.21-7.15 (m, 1H), 7.13-7.06 (m, 3H), 6.99-6.94 (m, 1H), 5.99-5.95 (m, 1H), 3.97-3.90 (m, 1H), 3.44-3.36 (m, 2H), 3.17-3.10 (m, 2H), 2.05 (s, 3H), 1.86-1.78 (m, 2H), 1.74-1.66 (m, 2H).

Example 873: (R)-5-(2-Methyl-4-phenoxyphenyl)-N-(1-methylpiperidin-3-yl)-4-oxo-4,5-dihydro-3H-1-thia-3,5,8-triazaacenaphthylene-2-carboxamide

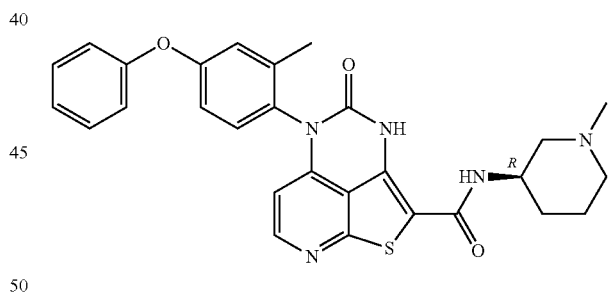

The title compound was prepared using conditions analogous to Example 930, and using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) in place of (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) to give a yellow solid. MS (ESI): mass calcd. for $C_{28}H_{27}N_5O_3S$, 513.6; m/z found, 514.4 [M+H]$^+$. $^1$H NMR (400 MHz, DMSO-d$_6$): δ 8.74 (d, J=7.0 Hz, 1H), 7.98 (d, J=5.5 Hz, 1H), 7.45-7.35 (m, 2H), 7.17-7.11 (m, 1H), 7.10-7.03 (m, 3H), 7.02-6.97 (m, 1H), 6.91-6.85 (m, 1H), 5.55 (d, J=5.5 Hz, 1H), 3.94-3.83 (m, 1H), 2.77-2.72 (m, 1H), 2.54-2.50 (m, 1H), 2.13 (s, 3H), 1.98 (s, 3H), 1.88-1.80 (m, 2H), 1.71-1.62 (m, 1H), 1.54-1.46 (m, 1H), 1.27-1.17 (m, 2H).

Example 28: (R)—N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide

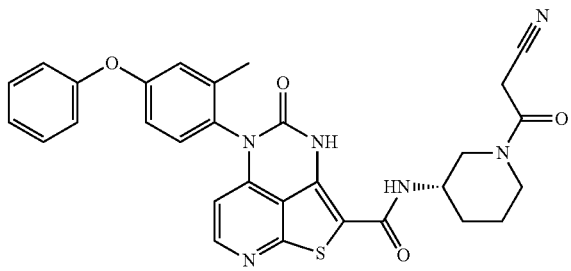 [SMILES: Cc1cc(Oc2ccccc2)ccc1N1C(=O)Nc2c(C(=O)N[C@H]3CCCN(C(=O)CC#N)C3)sc3nccc1c23]

The title compound was prepared using conditions analogous to Example 181, and using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) in place of (R)-4-oxo-5-(4-phenoxyphenyl)-N-(piperidin-3-yl)-4,5-dihydro-3H-1-thia-3,5,8-triazaacenaphthylene-2-carboxamide (Example 860). MS (ESI): mass calcd. for $C_{30}H_{26}N_6O_4S$, 566.2; m/z found, 567.2 [M+H]$^+$. 1H NMR (400 MHz, DMSO-d6): δ 9.16-9.09 (m, 1H), 8.97-8.91 (m, 1H), 7.98 (d, J=5.5 Hz, 1H), 7.44-7.36 (m, 2H), 7.16-7.12 (m, 1H), 7.12-7.04 (m, 3H), 6.99 (d, J=2.4 Hz, 1H), 6.91-6.85 (m, 1H), 5.56 (d, J=5.5 Hz, 1H), 4.29-4.13 (m, 1H), 4.11-4.00 (m, 1H), 3.97-3.59 (m, 3H), 3.14 (s, 2H), 1.98 (s, 3H), 1.86-1.82 (m, 1H), 1.70-1.63 (m, 1H), 1.53-1.50 (m, 1H), 1.45-1.39 (m, 1H).

Example 875: (E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide

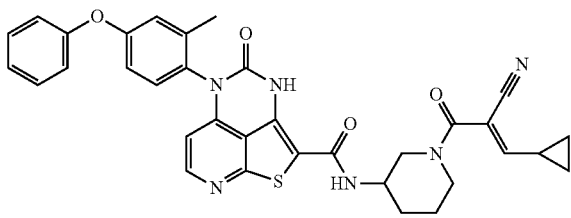 [SMILES: Cc1cc(Oc2ccccc2)ccc1N1C(=O)Nc2c(C(=O)NC3CCCN(C(=O)/C(C#N)=C/C4CC4)C3)sc3nccc1c23]

Step A: 5-(2-Methyl-5-phenoxyphenyl)-4-oxo-N-(piperidin-3-yl)-4,5-dihydro-3H-1-thia-3,5,8-triazaacenaphthylene-2-carboxamide The title compound was prepared in a manner analogous to Method 1, step G in Example 1, and using 5-(2-methyl-5-phenoxyphenyl)-4-oxo-4,5-dihydro-3H-1-thia-3,5,8-triazaacenaphthylene-2-carboxylic acid (Intermediate 64) in place of 5-(2-Methyl-4-phenoxyphenyl)-4-oxo-4,5-dihydro-3H-1-thia-3,5,8-triazaacenaphthylene-2-carboxylic acid (Intermediate 27).

Step B: 5-(2-Methyl-5-phenoxyphenyl)-4-oxo-N-(piperidin-3-yl)-4,5-dihydro-3H-1-thia-3,5,8-triazaacenaphthylene-2-carboxamide The title compound was prepared using analogous conditions to Example 877, and using 5-(2-methyl-5-phenoxyphenyl)-4-oxo-N-(piperidin-3-yl)-4,5-dihydro-3H-1-thia-3,5,8-triazaacenaphthylene-2-carboxamide in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889). MS (ESI): mass calcd. for $C_{34}H_{30}N_6O_4S$, 618.7; m/z found, 619.3[M+H]$^+$. 1H NMR (400 MHz, CD$_3$OD): δ 8.30 (d, J=5.5 Hz, 1H), 7.42 (d, J=8.5 Hz, 1H), 7.36-7.27 (m, 2H), 7.13-7.04 (m, 2H), 7.04-7.97 (m, 3H), 6.58-6.46 (m, 1H), 6.04 (d, J=5.5 Hz, 1H), 4.26-4.08 (m, 1H), 4.06-3.92 (m, 2H), 3.25-2.99 (m, 2H), 2.11 (s, 3H), 2.08-1.95 (m, 2H), 1.91-1.83 (m, 1H), 1.79-1.69 (m, 1H), 1.66-1.56 (m, 1H), 1.24-1.13 (m, 2H), 0.99-0.91 (m, 1H), 0.88-0.78 (m, 1H).

Example 876: 5-(2-Methyl-4-phenoxyphenyl)-4-oxo-N—((R)-1-((R)-pyrrolidine-2-carbonyl)piperidin-3-yl)-4,5-dihydro-3H-1-thia-3,5,8-triazaacenaphthylene-2-carboxamide

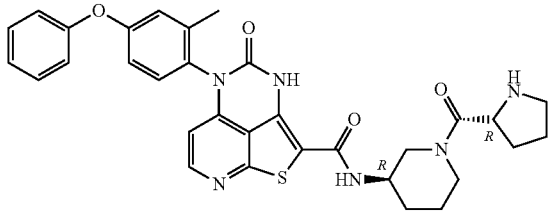

The title compound was prepared using conditions analogous to Example 75, and using (R)-1-(tert-butoxycarbonyl)pyrrolidine-2-carboxylic acid in place of 3-hydroxypropanoic acid to give (R)-tert-butyl 2-((R)-3-(5-(2-methyl-4-phenoxyphenyl)-4-oxo-4,5-dihydro-3H-1-thia-3,5,8-triazaacenaphthylene-2-carboxamido)piperidine-1-carbonyl)pyrrolidine-1-carboxylate. This product was then subjected to conditions analogous to those in Method 1, step H, to give the title compound. MS (ESI): mass calcd. for $C_{32}H_{32}N_6O_4S$, 596.7; m/z found, 597.2 [M+H]$^+$. 1H NMR (400 MHz, CD$_3$OD): δ 8.37-8.28 (m, 1H), 7.45-7.36 (m, 2H), 7.33-7.27 (m, 1H), 7.21-7.13 (m, 1H), 7.12-7.04 (m, 3H), 7.02-6.93 (m, 1H), 6.11-6.03 (m, 1H), 4.69-4.35 (m, 2H), 4.04-3.71 (m, 2H), 3.49-3.33 (m, 2H), 3.26-3.02 (m, 1H), 2.99-2.75 (m, 1H), 2.59-2.37 (m, 1H), 2.15-1.59 (m, 10H).

Example 877: (E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide

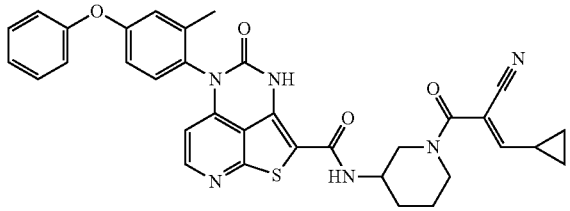 [SMILES: Cc1cc(Oc2ccccc2)ccc1N1C(=O)Nc2c(C(=O)NC3CCCN(C(=O)/C(C#N)=C/C4CC4)C3)sc3nccc1c23]

The title compound was prepared using conditions analogous to 75, and using 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) and (E)-2-cyano-3-cyclopropylprop-2-enoic acid (Intermediate 17) in place of (R)-4-Oxo-5-(4-phenoxyphenyl)-N-(piperidin-3-yl)-4,5-dihydro-3H-1-thia-3,5,8-triazaacenaphthylene-2-carboxamide (Example 860). MS (ESI): mass calcd. for $C_{34}H_{30}N_6O_4S$, 618.7; m/z found, 619.2 [M+H]$^+$. $^1$H NMR (400 MHz, a mixture of CD$_3$OD and DMSO-d$_6$): δ 8.32 (d, J=5.5 Hz, 1H), 7.43-7.35 (m, 2H), 7.34-7.28 (m, 1H), 7.19-7.12 (m, 1H), 7.10-7.02 (m, 3H), 6.97-6.92 (m, 1H), 6.54-6.46 (m, 1H), 6.00 (d, J=5.5 Hz, 1H), 4.00-3.94 (m, 1H), 3.91-3.83 (m, 2H), 3.06-2.94 (m, 2H), 2.06 (s, 3H), 1.96-1.88 (m, 2H), 1.84-1.76 (m, 1H), 1.72-1.64 (m, 1H), 1.55-1.45 (m, 1H), 1.17-1.09 (m, 2H), 1.01-0.90 (m, 1H), 0.85-0.77 (m, 1H).

Example 878: (E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide

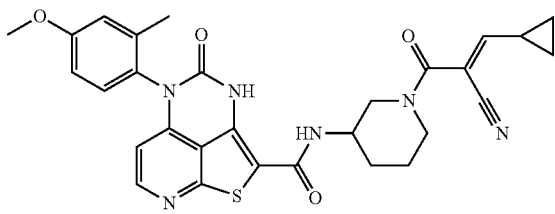 [SMILES: COc1ccc(N2C(=O)Nc3c(C(=O)NC4CCCN(C(=O)/C(C#N)=C/C5CC5)C4)sc4nccc2c34)c(C)c1]

Step A: 5-(4-Methoxy-2-methylphenyl)-4-oxo-N-(piperidin-3-yl)-4,5-dihydro-3H-1-thia-3,5,8-triazaacenaphthylene-2-carboxamide (Intermediate 66)

The title compound was prepared in a manner analogous to Method 1, step G in Example 1, and using 5-(4-methoxy-2-methylphenyl)-4-oxo-4,5-dihydro-3H-1-thia-3,5,8-triazaacenaphthylene-2-carboxylic acid (Intermediate 55) and tert-butyl-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate.

Step B: (E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide The title compound was prepared using conditions analogous to Example 877, and using 5-(4-methoxy-2-methylphenyl)-4-oxo-N-(piperidin-3-yl)-4,5-dihydro-3H-1-thia-3,5,8-triazaacenaphthylene-2-carboxamide (Intermediate 66) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a white solid. MS (ESI): mass calcd. for $C_{29}H_{28}N_6O_4S$, 556.6; m/z found, 557.1 [M+H]$^+$. $^1$H NMR (400 MHz, a mixture of CD$_3$OD and DMSO-d$_6$): δ 8.25 (d, J=5.2 Hz, 1H), 7.21-7.14 (m, 1H), 6.98-6.91 (m, 1H), 6.91-6.84 (m, 1H), 6.50-6.40 (m, 1H), 5.91 (d, J=5.4 Hz, 1H), 4.04-3.97 (m, 2H), 3.94-3.84 (m, 2H), 3.77 (s, 3H), 3.06-2.95 (m, 1H), 2.04 (s, 3H), 1.99-1.85 (m, 2H), 1.84-1.75 (m, 1H), 1.74-1.61 (m, 1H), 1.57-1.45 (m, 1H), 1.17-1.06 (m, 2H), 0.98-0.86 (m, 1H), 0.84-0.72 (m, 1H).

Example 879: (S)—N-(1-Formylpiperidin-3-yl)-5-(2-methyl-4-phenoxyphenyl)-4-oxo-4,5-dihydro-3H-1-thia-3,5,8-triazaacenaphthylene-2-carboxamide

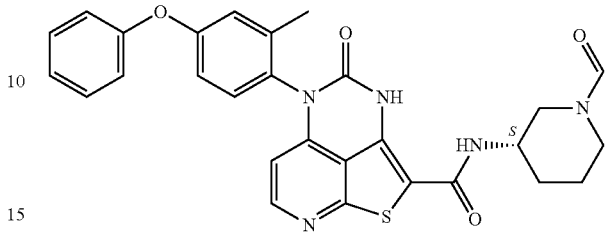

The title compound was prepared using steps A-B in Example 897, using tert-butyl (S)-3-aminopiperidine-1-carboxylate in place of tert-butyl 3-aminopiperidine-1-carboxylate in step A, using formic acid in place of (E)-2-cyano-4,4-dimethylpent-2-enoic acid in step B. MS (ESI): mass calcd. for $C_{28}H_{25}N_5O_4S$, 527.6; m/z found, 528.3[M+H]$^+$. $^1$H NMR (400 MHz, a mixture of DMSO-d$_6$ and CD$_3$OD): d 8.32-8.28 (m, 1H), 8.01-7.95 (m, 1H), 7.43-7.35 (m, 2H), 7.33-7.28 (m, 1H), 7.18-7.12 (m, 1H), 7.10-7.02 (m, 3H), 6.97-6.90 (m, 1H), 6.00-5.95 (m, 1H), 3.88-3.74 (m, 3H), 3.09-2.94 (m, 1H), 2.73-2.60 (m, 1H), 2.06 (s, 3H), 2.00-1.91 (m, 1H), 1.82-1.71 (m, 1H), 1.71-1.69 (m, 1H), 1.51-1.39 (m, 1H).

Example 880: (R,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

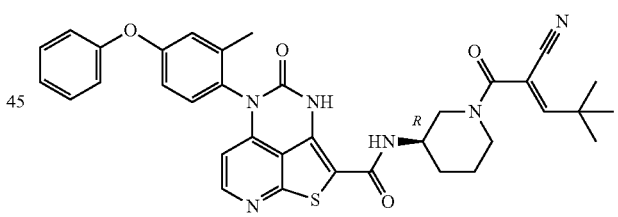

The title compound was prepared using analogous conditions to Example 921, using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) in place of 5-(2-methyl-4-phenoxyphenyl)-4-oxo-N-(piperidin-4-yl)-4,5-dihydro-3H-1-thia-3,5,8-triazaacenaphthylene-2-carboxamide (Example 865) to afford a light yellow solid. MS (ESI): mass calcd. for $C_{35}H_{34}N_6O_4S$, 634.8; m/z found, 635.3 [M+H]$^+$. $^1$HNMR (400 MHz, a mixture of DMSO-d$_6$ and CD$_3$OD): δ 8.30-8.26 (m, 1H), 7.41-7.34 (m, 2H), 7.32-7.26 (m, 1H), 7.16-7.10 (m, 1H), 7.08-7.00 (m, 3H), 6.95-6.89 (m, 1H), 6.78-6.74 (m, 1H), 5.97-5.92 (m, 1H), 3.93-3.77 (m, 3H), 3.13-3.07 (m, 2H), 2.03 (s, 3H), 1.96-1.87 (m, 1H), 1.83-1.74 (m, 1H), 1.72-1.62 (m, 1H), 1.56-1.43 (m, 1H), 1.22-1.12 (m, 9H).

Example 881: (R)—N-(1-Acryloylpyrrolidin-3-yl)-4-oxo-5-(4-(pyridin-2-yloxy)phenyl)-4,5-dihydro-3H-1-thia-3,5,8-triazaacenaphthylene-2-carboxamide

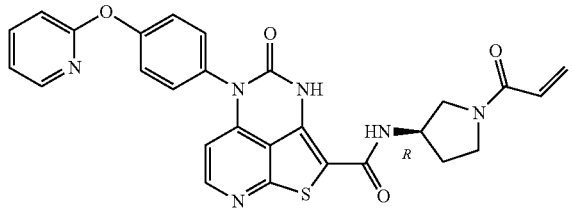

Step A: Methyl 3-amino-4-((4-(pyridin-2-yloxy)phenyl)amino)thieno[2,3-b]pyridine-2-carboxylate To a solution of 4-(pyridin-2-yloxy)aniline 3.00 g, 16.1 mmol) and 2-chloro-4-iodopyridine-3-carbonitrile (5.539 g, 20.94 mmol) in dioxane (30 mL) were added DPEphos (1.735 g, 3.221 mmol), Pd(OAc)$_2$ (0.362 g, 1.61 mmol), and Cs$_2$CO$_3$ (10.498 g, 32.222 mmol) under a N$_2$ atmosphere and was stirred at 100° C. for 4 h. After 4 h, methyl 2-mercaptoacetate (2.565 g, 24.17 mmol) was and the reaction was stirred at 100° C. overnight. The reaction was filtered to remove the solid and was concentrated to dryness. MeOH was added to the residue with stirring and the precipitate that formed was filtered. The precipitate was added to EtOAc, stirred, filtered, and dried under a vacuum to give the title compound (2.7 g, 43% yield) as a grey solid.

Step B: (R)—N-(1-Acryloylpyrrolidin-3-yl)-4-oxo-5-(4-(pyridin-2-yloxy)phenyl)-4,5-dihydro-3H-1-thia-3,5,8-triazaacenaphthylene-2-carboxamide The title compound was prepared in a manner analogous to Method 1, steps E-I in Example 1, and using methyl 3-amino-4-((4-(pyridin-2-yloxy)phenyl)amino)thieno[2,3-b]pyridine-2-carboxylate in place of methyl 3-amino-4-(2-methyl-4-phenoxyanilino)thieno[2,3-b]pyridine-2-carboxylate in step E, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for C$_{27}$H$_{22}$N$_6$O$_4$S, 526.6; m/z found, 527.1 [M+H]$^+$. $^1$H NMR (400 MHz, DMSO-d$_6$): δ 10.22 (s, 1H), 8.53-8.37 (m, 1H), 8.32 (d, J=5.5 Hz, 1H), 8.27-8.18 (m, 1H), 7.97-7.86 (m, 1H), 7.53-7.42 (m, 2H), 7.38-7.28 (m, 2H), 7.24-7.17 (m, 1H), 7.16-7.09 (m, 1H), 6.66-6.53 (m, 1H), 6.19-6.11 (m, 1H), 6.04 (d, J=5.5 Hz, 1H), 5.72-5.62 (m, 1H), 4.59-4.41 (m, 1H), 3.92-3.38 (m, 4H), 2.26-1.93 (m, 2H).

Example 882: N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide

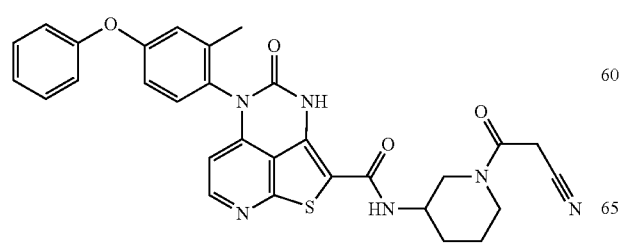

The title compound was prepared using conditions analogous to Example 181, using 5-(2-methyl-4-phenoxyphenyl)-4-oxo-N-(piperidin-3-yl)-4,5-dihydro-3H-1-thia-3,5,8-triazaacenaphthylene-2-carxamide (Example 889) in place of (R)-4-oxo-5-(4-phenoxyphenyl)-N-(piperidin-3-yl)-4,5-dihydro-3H-1-thia-3,5,8-triazaacenaphthylene-2-carboxamide (Example 860) to give a white solid. MS (ESI): mass calcd. for C$_{30}$H$_{26}$N$_6$O$_4$S, 566.6; m/z found, 567.2 [M+H]$^+$. $^1$H NMR (400 MHz, DMSO-d$_6$): δ 10.17 (s, 1H), 8.30 (d, J=5.4 Hz, 1H), 8.11-8.06 (m, 1H), 7.45-7.41 (m, 2H), 7.35 (d, J=8.5 Hz, 1H), 7.20-7.16 (m, 1H), 7.11-7.07 (m, 3H), 6.98-6.95 (m, 1H), 5.94 (d, J=5.3 Hz, 1H), 4.33-4.02 (m, 1H), 4.01-3.96 (m, 2H), 3.85-3.76 (m, 1H), 3.69-3.55 (m, 1H), 3.10-2.94 (m, 1H), 2.79-2.62 (m, 1H), 2.05 (s, 3H), 1.93-1.90 (m, 1H), 1.75-1.70 (m, 1H), 1.63-1.54 (m, 1H), 1.45-1.38 (m, 1H).

Example 883: N-(1-Cyanopiperidin-3-yl)-5-(4-(2-methoxyphenoxy)-2-methylphenyl)-4-oxo-4,5-dihydro-3H-1-thia-3,5,8-triazaacenaphthylene-2-carboxamide

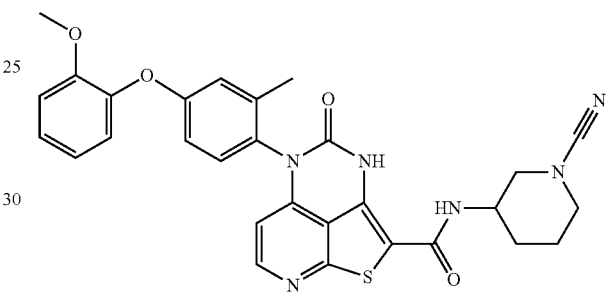

The title compound was prepared using conditions analogous to Example 890, and using 5-(4-(2-methoxyphenoxy)-2-methylphenyl)-4-oxo-N-(piperidin-3-yl)-4,5-dihydro-3H-1-thia-3,5,8-triazaacenaphthylene-2-carboxamide (Example 870) in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) to give a light yellow solid. MS (ESI): mass calcd. for C$_{29}$H$_{26}$N$_6$O$_4$S, 554.6; m/z found, 555.2 [M+H]$^+$. $^1$H NMR (400 MHz, a mixture of CD$_3$OD and DMSO-d$_6$): δ 8.28 (d, J=5.2 Hz, 1H), 7.23-7.16 (m, 2H), 7.15-7.04 (m, 2H), 7.01-6.92 (m, 1H), 6.87 (s, 1H), 6.79-6.73 (m, 1H), 5.94 (d, J=5.3 Hz, 1H), 4.01-3.88 (m, 1H), 3.75 (s, 3H), 3.48-3.40 (m, 1H), 3.30-3.23 (m, 1H), 3.00-2.88 (m, 2H), 2.02 (s, 3H), 1.94-1.86 (m, 1H), 1.82-1.74 (m, 1H), 1.70-1.61 (m, 1H), 1.60-1.50 (m, 1H).

Example 884: N-(1-Cyanopiperidin-4-yl)-5-(4-(2-methoxyphenoxy)-2-methylphenyl)-4-oxo-4,5-dihydro-3H-1-thia-3,5,8-triazaacenaphthylene-2-carboxamide

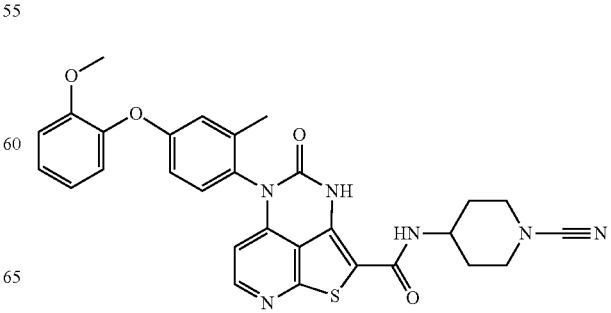

The title compound was prepared using conditions analogous to Example 890, and using 5-(4-(2-methoxyphenoxy)-2-methylphenyl)-4-oxo-N-(piperidin-4-yl)-4,5-dihydro-3H-1-thia-3,5,8-triazaacenaphthylene-2-carboxamide (Example 917) in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) to give a light yellow solid. MS (ESI): mass calcd. for $C_{29}H_{26}N_6O_4S$, 554.6; m/z found, 555.2 [M+H]$^+$. $^1$H NMR (400 MHz, DMSO-$d_6$): δ 10.12 (s, 1H), 8.31 (d, J=5.4 Hz, 1H), 8.08-7.98 (m, 1H), 7.28-7.17 (m, 3H), 7.16-7.08 (m, 1H), 7.04-6.95 (m, 1H), 6.92-6.88 (m, 1H), 6.81-6.72 (m, 1H), 5.90 (d, J=5.4 Hz, 1H), 3.98-3.88 (m, 1H), 3.76 (s, 3H), 3.43-3.35 (m, 2H), 3.16-3.06 (m, 2H), 2.01 (s, 3H), 1.85-1.75 (m, 2H), 1.74-1.61 (m, 2H).

Example 885: (R)—N-(1-Formylpiperidin-3-yl)-5-(2-methyl-4-phenoxyphenyl)-4-oxo-4,5-dihydro-3H-1-thia-3,5,8-triazaacenaphthylene-2-carboxamide

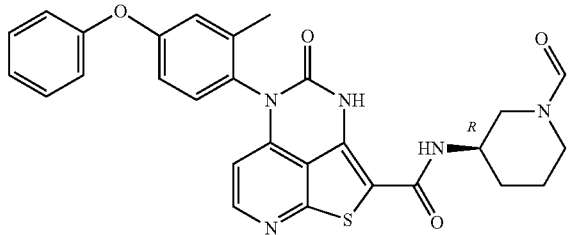

The title compound was prepared by treating (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) with formic acid and allowing the mixture to stir at room temperature for 5 hours. The mixture was purified by ISCO (MeOH/H$_2$O). MS (ESI): mass calcd. for $C_{28}H_{25}N_5O_4S$, 527.6; m/z found, 528.3[M+H]$^+$. $^1$H NMR (400 MHz, a mixture of DMSO-$d_6$ and CD$_3$OD): δ 8.27-8.21 (m, 1H), 7.98-7.90 (m, 1H), 7.39-7.31 (m, 2H), 7.28-7.21 (m, 1H), 7.14-7.07 (m, 1H), 7.05-6.97 (m, 3H), 6.93-6.86 (m, 1H), 5.94-5.88 (m, 1H), 3.82-3.68 (m, 2H), 3.14-3.08 (m, 1H), 3.05-2.92 (m, 1H), 2.72-2.60 (m, 1H), 2.02 (s, 3H), 1.96-1.87 (m, 1H), 1.78-1.67 (m, 1H), 1.67-1.65 (m, 1H), 1.47-1.35 (m, 1H).

Example 886: (E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide

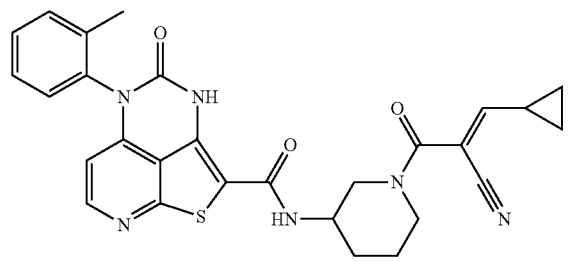 [SMILES: Cc1ccccc1N1C(=O)Nc2c(C(=O)NC3CCCN(C(=O)/C(C#N)=C/C4CC4)C3)sc3nccc1c23]

Step A: 4-Oxo-N-(piperidin-3-yl)-5-(o-tolyl)-4,5-dihydro-3H-1-thia-3,5,8-triazaacenaphthylene-2-carboxamide (Intermediate 61)

The title compound was prepared in a manner analogous to Method 1, step G-H in Example 1, using using 4-oxo-5-(o-tolyl)-4,5-dihydro-3H-1-thia-3,5,8-triazaacenaphthylene-2-carboxylic acid (Intermediate 54) and tert-butyl-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate.

Step B: (E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide The title compound was prepared using analogous conditions to Example 877, and using 4-oxo-N-(piperidin-3-yl)-5-(o-tolyl)-4,5-dihydro-3H-1-thia-3,5,8-triazaacenaphthylene-2-carboxamide (Intermediate 61) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a white solid. MS (ESI): mass calcd. for $C_{28}H_{26}N_6O_3S$, 526.6; m/z found, 527.4 [M+H]$^+$. $^1$H NMR (400 MHz, a mixture of CD$_3$OD and DMSO-$d_6$): δ 8.27 (d, J=4.7 Hz, 1H), 7.57-7.23 (m, 4H), 6.57-6.41 (m, 1H), 5.86 (d, J=4.5 Hz, 1H), 3.93-3.83 (m, 2H), 3.82-3.72 (m, 1H), 3.11-2.87 (m, 2H), 2.10 (s, 3H), 2.01-1.88 (m, 2H), 1.85-1.76 (m, 1H), 1.74-1.62 (m, 1H), 1.59-1.46 (m, 1H), 1.19-1.05 (m, 2H), 1.00-0.89 (m, 1H), 0.86-0.73 (m, 1H).

Example 887: (S)—N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide

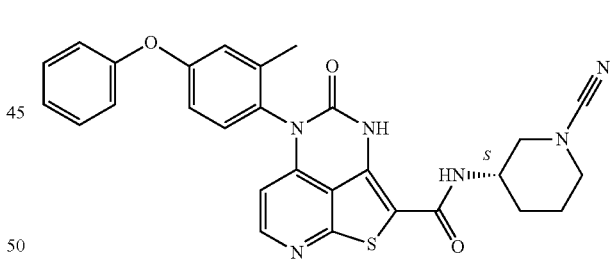

The title compound was prepared using conditions analogous to Example 890, and using (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) to give a light yellow solid. MS (ESI): mass calcd. for $C_{28}H_{24}N_6O_3S$, 524.6; m/z found, 525.3[M+H]$^+$. $^1$H NMR (400 MHz, a mixture of DMSO-$d_6$ and CD$_3$OD): δ 8.34-8.30 (m, 1H), 7.44-7.37 (m, 2H), 7.35-7.30 (m, 1H), 7.20-7.13 (m, 1H), 7.12-7.03 (m, 3H), 6.99-6.92 (m, 1H), 6.01-5.96 (m, 1H), 4.02-3.94 (m, 1H), 3.47-3.40 (m, 1H), 3.33-3.24 (m, 1H), 3.01-2.91 (m, 2H), 2.06 (s, 3H), 1.95-1.84 (m, 1H), 1.83-1.74 (m, 1H), 1.70-1.50 (m, 2H).

Example 888: (R)—N-(1-Acetylpyrrolidin-3-yl)-4-oxo-5-(4-phenoxyphenyl)-4,5-dihydro-3H-1-thia-3,5,8-triazaacenaphthylene-2-carboxamide

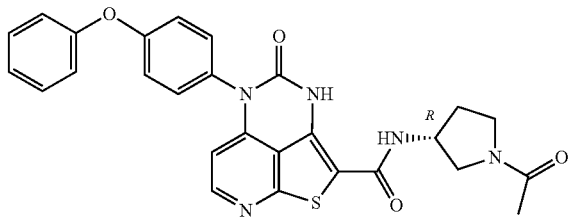

The title compound was prepared in a manner analogous to Method 1, step I in Example 1, using (R)-4-oxo-5-(4-phenoxyphenyl)-N-(pyrrolidin-3-yl)-4,5-dihydro-3H-1-thia-3,5,8-triazaacenaphthylene-2-carboxamide (Example 911) in place N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide, and using acetyl chloride in place of prop-2-enoyl chloride. MS (ESI): mass calcd. for $C_{27}H_{23}N_5O_4S$, 513.6; m/z found, 514.2 [M+H]$^+$. $^1$H NMR (400 MHz, DMSO-d$_6$): δ 10.11 (s, 1H), 8.41-8.15 (m, 2H), 7.52-7.34 (m, 4H), 7.25-7.01 (m, 5H), 6.05 (dd, J=5.4, 1.9 Hz, 1H), 4.50-4.37 (m, 1H), 3.77-3.71 (m, 1H), 3.59-3.54 (m, 1H), 3.49-3.41 (m, 2H), 2.23-1.96 (m, 2H), 1.92 (d, J=5.0 Hz, 3H).

Example 889: 5-(2-Methyl-4-phenoxyphenyl)-4-oxo-N-(piperidin-3-yl)-4,5-dihydro-3H-1-thia-3,5,8-triazaacenaphthylene-2-carboxamide

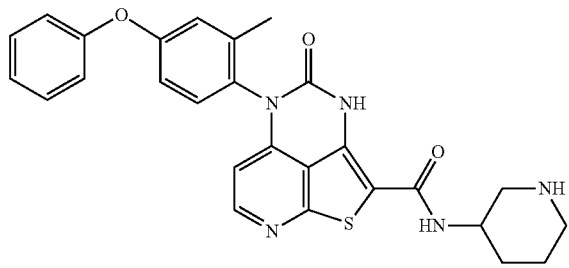 [SMILES: Cc1cc(Oc2ccccc2)ccc1N1C(=O)Nc2c(C(=O)NC3CCCNC3)sc3nccc1c23]

The title compound was prepared in a manner analogous to Method 1, step G-H, in Example 1, using tert-butyl 3-aminopiperidine-1-carboxylate in place of tert-butyl (3R,5R)-3-amino-5-fluoropiperidine-1-carboxylate (Intermediate 1) in step G, and using 2,2,2-trifluoroacetic acid in place of HCl aq solution in step H was isolated as a white solid. MS (ESI): mass calcd. for $C_{27}H_{25}N_5O_3S$, 499.6; m/z found, 500.1 [M+H]$^+$. $^1$H NMR (400 MHz, CD$_3$OD): δ 8.27-8.15 (br, 1H), 7.37-7.33 (m, 2H), 7.21-7.19 (m, 1H), 7.13-7.09 (m, 1H), 7.06-6.99 (m, 3H), 6.94-6.91 (m, 1H), 5.96-5.88 (m, 1H), 4.15-4.09 (m, 1H), 3.29-3.26 (m, 1H), 3.05-3.02 (m, 1H), 2.83-2.76 (m, 2H), 2.07 (s, 3H), 2.03-1.97 (m, 1H), 1.93-1.83 (m, 1H), 1.72-1.64 (m, 2H).

Example 890: N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide

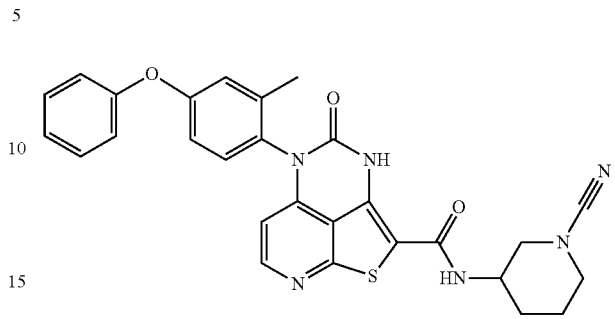

To the mixture of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889), DIEA in DCM was added cyanic bromide at 0° C., then stirred at room temperature for 2 hours. The mixture was concentrated and purified by ISCO, eluting with DCM/MeOH to yield the title product. MS (ESI): mass calcd. for $C_{28}H_{24}N_6O_3S$, 524.6; m/z found, 525.2 [M+H]$^+$. $^1$H NMR (400 MHz, a mixture of CD3OD and DMSO-d$_6$): δ 8.26 (d, J=5.5 Hz, 1H), 7.38-7.31 (m, 2H), 7.28-7.24 (m, 1H), 7.14-7.08 (m, 1H), 7.06-6.98 (m, 3H), 6.93-6.87 (m, 1H), 5.96 (d, J=5.5 Hz, 1H), 4.01-3.97 (m, 1H), 3.47-3.40 (m, 1H), 3.29-3.21 (m, 1H), 2.99-2.87 (m, 2H), 2.03 (s, 3H), 1.92-1.85 (m, 1H), 1.80-1.72 (m, 1H), 1.69-1.59 (m, 1H), 1.56-1.48 (m, 1H).

Example 891: (S)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide

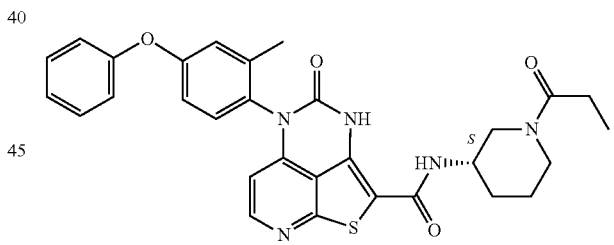

The title compound was prepared using conditions analogous to Example 75 and using (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) and propionic acid in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) and 3-hydroxypropanoic acid to give a white solid. MS (ESI): mass calcd. for $C_{30}H_{29}N_5O_4S$, 555.7; m/z found, 556.2 [M+H]$^+$. $^1$H NMR (400 MHz, DMSO-d$_6$): δ 10.18 (br, 1H), 8.43-8.33 (m, 1H), 8.21-8.15 (br, 1H), 7.42-7.38 (m, 2H), 7.26-7.24 (m, 1H), 7.17-7.03 (m, 4H), 6.93-6.91 (m, 1H), 5.82-5.76 (br, 1H), 4.36-4.04 (m, 1H), 3.88-3.67 (m, 2H), 3.05-2.91 (m, 1H), 2.77-2.55 (m, 1H), 2.37-2.22 (m, 2H), 2.01 (s, 3H), 1.91-1.85 (m, 1H), 1.79-1.53 (m, 2H), 1.47-1.30 (m, 1H), 1.04-0.90 (m, 3H).

Example 892: (S)—N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide

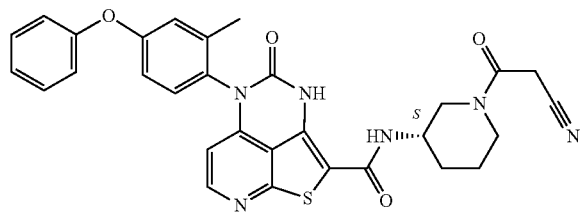

The title compound was prepared using conditions analogous to Example 75 and using (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) and 2-cyanoacetic acid in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) and 3-hydroxypropanoic acid to give a white solid. MS (ESI): mass calcd. for $C_{30}H_{26}N_6O_4S$, 566.6; m/z found, 567.2 [M+H]$^+$. $^1$H NMR (400 MHz, DMSO-d$_6$): δ 8.78-8.69 (m, 1H), 8.09 (d, J=5.4 Hz, 1H), 7.43-7.37 (m, 2H), 7.19-7.13 (m, 2H), 7.11-7.05 (m, 2H), 7.01 (d, J=2.4 Hz, 1H), 6.91 (d, J=8.5 Hz, 1H), 5.70-5.66 (m, 1H), 4.22-4.07 (m, 1H), 4.05-3.98 (m, 1H), 4.01-3.94 (m, 1H), 3.86-3.78 (m, 1H), 3.66-3.41 (m, 1H), 3.14 (s, 2H), 3.10-2.97 (m, 1H), 2.01 (s, 3H), 1.91-1.82 (m, 1H), 1.71-1.63 (m, 1H), 1.59-1.49 (m, 1H).

Example 893: 5-(2-Methyl-4-phenoxyphenyl)-4-oxo-N—((R)-1-((S)-pyrrolidine-2-carbonyl)piperidin-3-yl)-4,5-dihydro-3H-1-thia-3,5,8-triazaacenaphthylene-2-carboxamide

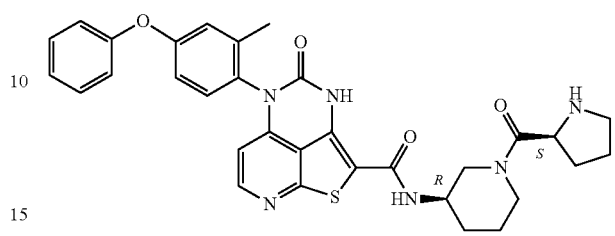

The title compound was prepared using conditions analogous to Example 75 and using (S)-1-(tert-butoxycarbonyl)pyrrolidine-2-carboxylic acid in place of 3-hydroxypropanoic acid to give a yellow solid. MS (ESI): mass calcd. for $C_{32}H_{32}N_6O_4S$, 596.7; m/z found, 597.2 [M+H]$^+$. $^1$H NMR (400 MHz, CD$_3$OD): δ 8.34-8.28 (m, 1H), 7.44-7.35 (m, 2H), 7.32-7.25 (m, 1H), 7.20-7.13 (m, 1H), 7.10-7.02 (m, 3H), 7.00-6.93 (m, 1H), 6.08-6.02 (m, 1H), 4.71-4.64 (m, 1H), 4.51-4.26 (m, 1H), 4.09-3.76 (m, 2H), 3.47-3.33 (m, 2H), 3.22-3.06 (m, 1H), 2.95-2.87 (m, 1H), 2.58-1.47 (m, 11H).

Example 894: (R)—N-(1-Acryloylpiperidin-3-5((2-cyanophenoxy)methyl)phenoxy)-2-methylphenyl)-4-oxo-4,5-dihydro-3H-1-thia-3,5,8-triazaacenaphthylene-2-carboxamide

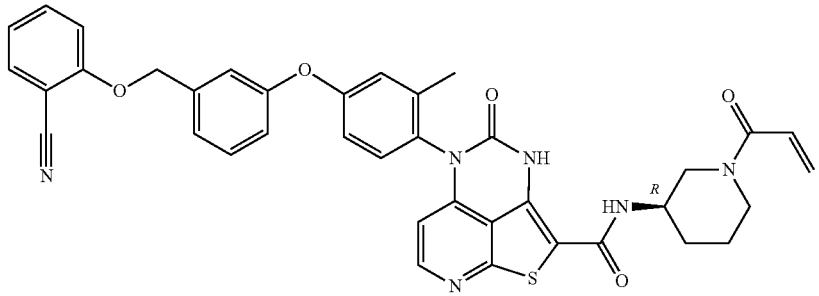

The title compound was prepared in a manner analogous to Method 1, steps G-I, in Example 1, using 5-(4-(3-((2-cyanophenoxy)methyl)phenoxy)-2-methylphenyl)-4-oxo-4,5-dihydro-3H-1-thia-3,5,8-triazaacenaphthylene-2-carboxylic acid (Intermediate 75) and tert-butyl (R)-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{38}H_{32}N_6O_5S$, 684.8; m/z found, 685.2 [M+H]$^+$. $^1$H NMR (400 MHz, DMSO-d$_6$): δ 10.30 (br, 1H), 8.49-8.13 (m, 2H), 7.74-7.67 (m, 1H), 7.66-7.61 (m, 1H), 7.49-7.42 (m, 1H), 7.35-7.23 (m, 3H), 7.23-7.19 (m, 1H), 7.10-7.03 (m, 3H), 6.99-6.92 (m, 1H), 6.82-6.67 (m, 1H), 6.10-6.01 (m, 1H), 5.95-5.86 (m, 1H), 5.68-5.60 (m, 1H), 5.31 (s, 2H), 4.45-4.11 (m, 1H), 4.05-3.87 (m, 1H), 3.82-3.68 (m, 1H), 3.11-2.91 (m, 1H), 2.82-2.61 (m, 1H), 2.01 (s, 3H), 1.94-1.88 (m, 1H), 1.78-1.58 (m, 2H), 1.43-1.35 (m, 1H).

Example 895: (S,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide

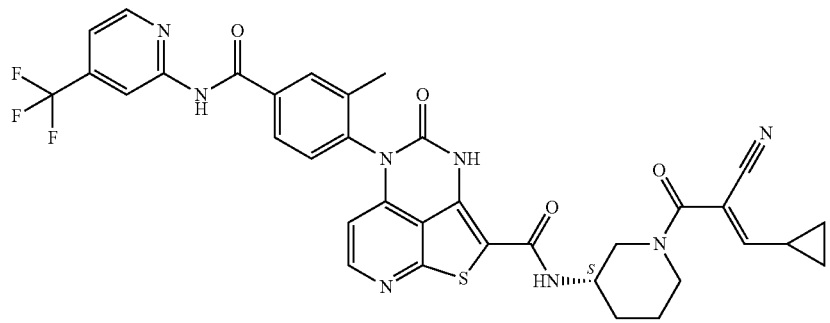

The title compound was prepared using conditions analogous to Example 835, steps A-B, using tert-butyl (S)-3-aminopiperidine-1-carboxylate in place of tert-butyl (R)-3-aminopiperidine-1-carboxylate. MS (ESI): mass calcd. for $C_{35}H_{29}F_3N_8O_4S$, 714.7; m/z found, 715.4 [M+H]$^+$. $^1$H NMR (400 MHz, DMSO-d$_6$): δ 11.35 (s, 1H), 10.98-10.02 (br, 1H), 8.66 (d, J=5.1 Hz, 1H), 8.53 (s, 1H), 8.30 (d, J=5.4 Hz, 1H), 8.25-8.07 (m, 2H), 8.02 (d, J=8.1 Hz, 1H), 7.65-7.39 (m, 2H), 6.62-6.52 (m, 1H), 5.88 (d, J=5.4 Hz, 1H), 4.40-3.97 (m, 1H), 3.95-3.70 (m, 2H), 3.17-2.72 (m, 2H), 2.17 (s, 3H), 2.04-1.73 (m, 3H), 1.72-1.56 (m, 1H), 1.55-1.32 (m, 1H), 1.22-1.09 (m, 2H), 1.01-0.70 (m, 2H).

Example 896: (E)-N-(1-(2-Cyano-4,4-dimethylpent-2-enoyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide

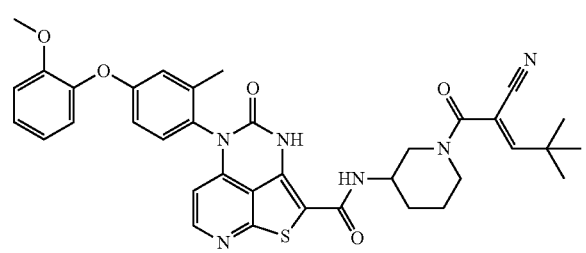 [SMILES: COc1ccccc1Oc1ccc(N2C(=O)Nc3c(C(=O)NC4CCCN(C(=O)/C(C#N)=C/C(C)(C)C)C4)sc4nccc2c34)c(C)c1]

The title compound was prepared using conditions analogous to Example 398, Step C, using 5-(4-(2-methoxyphenoxy)-2-methylphenyl)-4-oxo-N-(piperidin-3-yl)-4,5-dihydro-3H-1-thia-3,5,8-triazaacenaphthylene-2-carboxamide (Example 870) in place of (R)-tert-butyl 3-(5-(*R)-(2-methyl-4-phenoxyphenyl)-4-oxo-4,5-dihydro-3H-1-thia-3,5,8-triazaacenaphthylene-2-carboxamido)piperidine-1-carboxylate. MS (ESI): mass calcd. for $C_{36}H_{36}N_6O_5S$, 664.8; m/z found, 665.2 [M+H]$^+$. $^1$H NMR (400 MHz, a mixture of CD$_3$OD and DMSO-d$_6$): δ 8.28 (d, J=5.5 Hz, 1H), 7.24-7.16 (m, 2H), 7.15-7.11 (m, 1H), 7.09-7.05 (m, 1H), 7.00-6.93 (m, 1H), 6.90-6.85 (m, 1H), 6.80-6.71 (m, 2H), 5.93 (d, J=5.5 Hz, 1H), 3.92-3.80 (m, 5H), 3.75 (s, 3H), 2.07-1.91 (m, 4H), 1.86-1.76 (m, 1H), 1.74-1.61 (m, 1H), 1.58-1.45 (m, 1H), 1.25-1.15 (m, 9H).

Example 897: (E)-N-(1-(2-Cyano-4,4-dimethylpent-2-enol)piperidin-3-yl)-5-(2-methyl-4-phenoxyphenyl)-4-oxo-4,5-dihydro-3H-1-thia-3,5,8-triazaacenaphthylene-2-carboxamide

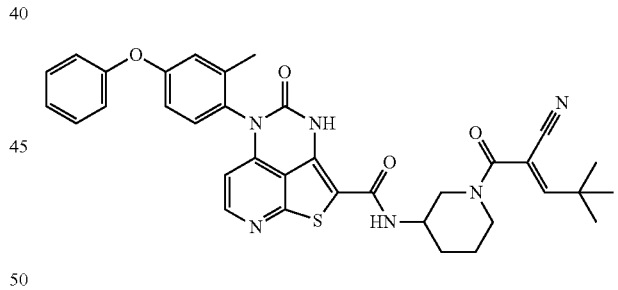

The title compound was prepared using conditions analogous to Example 398, step D, using 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) in place of (R)-5-(*R)-(2-Methyl-4-phenoxyphenyl)-4-oxo-N-(piperidin-3-yl)-4,5-dihydro-3H-1-thia-3,5,8-triazaacenaphthylene-2-carboxamide (Example 300) a dark grey solid. MS (ESI): mass calcd. for $C_{35}H_{34}N_6O_4S$, 634.8; m/z found, 635.3 [M+H]$^+$. $^1$H NMR (400 MHz, DMSO-d$_6$): δ 8.34 (d, J=5.4 Hz, 1H), 8.17-8.12 (m, 1H), 7.49-7.42 (m, 2H), 7.39-7.35 (m, 1H), 7.24-7.18 (m, 1H), 7.16-7.08 (m, 3H), 7.02-6.96 (m, 1H), 6.88-6.84 (m, 1H), 5.98 (d, J=5.4 Hz, 1H), 3.94-3.85 (m, 2H), 3.41-3.36 (m, 2H), 3.15-3.05 (m, 1H), 2.07 (s, 3H), 2.01-1.93 (m, 1H), 1.84-1.78 (m, 1H), 1.76-1.66 (m, 1H), 1.58-1.50 (m, 1H), 1.25-1.21 (m, 9H).

Example 898: 5-(2-Methyl-4-phenoxyphenyl)-N-(1-methylpiperidin-3-yl)-4-oxo-4,5-dihydro-3H-1-thia-3,5,8-triazaacenaphthylene-2-carboxamide

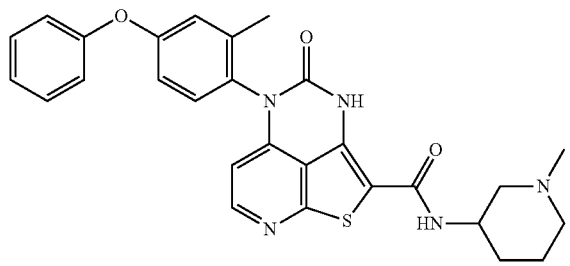 [SMILES: Cc1cc(Oc2ccccc2)ccc1N1C(=O)Nc2c(C(=O)NC3CCCN(C)C3)sc3nccc1c23]

The title compound was prepared in a manner analogous to Method 1, step G, in Example 1, using 1-methylpiperidin-3-amine in place of tert-butyl (3R,5R)-3-amino-5-fluoropiperidine-1-carboxylate as a white solid. MS (ESI): mass calcd. for $C_{28}H_{27}N_5O_3S$, 513.6; m/z found, 514.2 $[M+H]^+$. $^1H$ NMR (400 MHz, $CD_3OD$): δ 8.26 (d, J=5.6 Hz, 1H), 7.39-7.31 (m, 2H), 7.24 (d, J=8.6 Hz, 1H), 7.14-7.10 (m, 1H), 7.07-6.99 (m, 3H), 6.95-6.92 (m, 1H), 6.00 (d, J=5.6 Hz, 1H), 4.15-4.10 (m, 1H), 2.92-2.90 (m, 1H), 2.71-2.68 (m, 1H), 2.32 (s, 3H), 2.24-2.18 (m, 2H), 2.08 (s, 3H), 1.88-1.75 (m, 2H), 1.68-1.64 (m, 1H), 1.53-1.43 (m, 1H).

Example 899: (S,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide

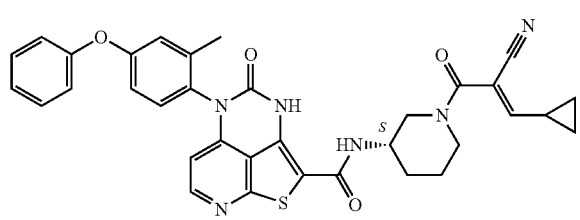

The title compound was prepared using conditions analogous to Example 877, and using (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a dark grey solid. MS (ESI): mass calcd. for $C_{34}H_{30}N_6O_4S$, 618.7; m/z found, 619.2 $[M+H]^+$. $^1H$ NMR (400 MHz, a mixture of $CD_3OD$ and DMSO-$d_6$): δ 8.30-8.26 (m, 1H), 7.39-7.33 (m, 2H), 7.29-7.24 (m, 1H), 7.15-7.09 (m, 1H), 7.08-7.00 (m, 3H), 6.94-6.89 (m, 1H), 6.49-6.43 (m, 1H), 6.00-5.96 (m, 1H), 4.14-4.10 (m, 1H), 3.96-3.83 (m, 2H), 3.11-2.92 (m, 2H), 2.05 (s, 3H), 1.98-1.86 (m, 2H), 1.82-1.75 (m, 1H), 1.72-1.62 (m, 1H), 1.57-1.46 (m, 1H), 1.16-1.08 (m, 2H), 0.95-0.87 (m, 1H), 0.82-0.73 (m, 1H).

Example 900: (R,E)-5-(2-Methyl-4-phenoxyphenyl)-4-oxo-N-(1-(4-(piperidin-1-yl)but-2-enoyl)piperidin-3-yl)-4,5-dihydro-3H-1-thia-3,5,8-triazaacenaphthylene-2-carboxamide

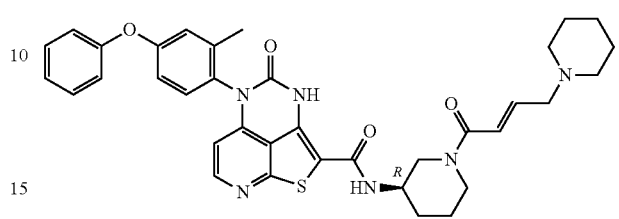

The title compound was prepared using conditions analogous to Example 75 and using (E)-4-(piperidin-1-yl)but-2-enoic acid in place of 3-hydroxypropanoic acid. MS (ESI): mass calcd. for $C_{36}H_{38}N_6O_4S$, 650.8; m/z found, 651.3 $[M+H]^+$. $^1H$ NMR (400 MHz, DMSO-$d_6$): δ 10.24 (br, 1H), 8.40-8.32 (m, 1H), 8.25-8.09 (m, 1H), 7.49-7.42 (m, 2H), 7.42-7.35 (m, 1H), 7.24-7.18 (m, 1H), 7.16-7.08 (m, 3H), 7.02-6.97 (m, 1H), 6.97-6.77 (m, 1H), 6.75-6.61 (m, 1H), 6.03-5.97 (m, 1H), 4.50-4.15 (m, 1H), 4.05-3.96 (m, 1H), 3.89-3.67 (m, 3H), 3.27-2.61 (m, 6H), 2.07 (s, 3H), 1.98-1.92 (m, 1H), 1.86-1.56 (m, 7H), 1.51-1.35 (m, 2H).

Example 901: (R,E)-N-(1-(2-Cyano-3-cyclopropylacryloyl)piperidin-3-yl)-5-(2-methyl-3-phenoxyphenyl)-4-oxo-4,5-dihydro-3H-1-thia-3,5,8-triazaacenaphthylene-2-carboxamide

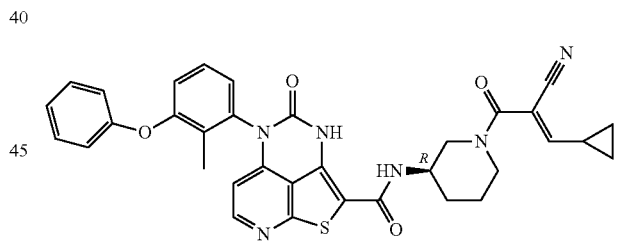

The title compound was prepared using conditions analogous to Example 877, and using (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a light yellow solid. MS (ESI): mass calcd. for $C_{34}H_{30}N_6O_4S$, 618.7; m/z found, 619.2 $[M+H]^+$. $^1H$ NMR (400 MHz, DMSO-$d_6$): δ 10.19 (s, 1H), 8.33 (d, J=5.4 Hz, 1H), 8.13 (d, J=6.9 Hz, 1H), 7.45-7.32 (m, 3H), 7.28-7.19 (m, 1H), 7.15-7.02 (m, 2H), 7.00-6.94 (m, 2H), 6.59-6.53 (m, 1H), 5.99 (d, J=5.4 Hz, 1H), 4.14-3.77 (m, 3H), 3.09-2.75 (m, 2H), 1.95 (s, 3H), 1.93-1.62 (m, 4H), 1.53-1.42 (m, 1H), 1.17-1.07 (m, 2H), 1.00-0.80 (m, 2H).

Example 902: (S,E)-N-(1-(2-Cyano-3-cyclopropylacryloyl)piperidin-3-yl)-5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxamide

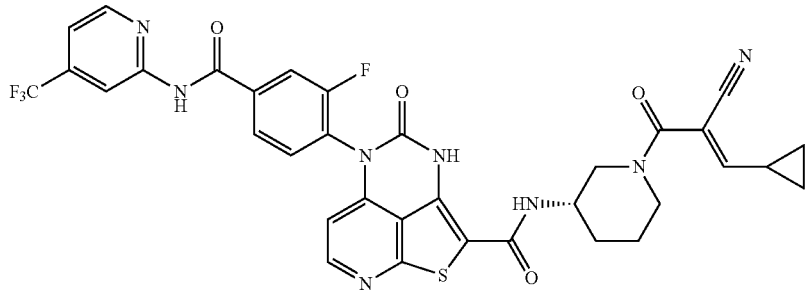 [SMILES: N#C/C(=C\C1CC1)C(=O)N1CCC[C@H](NC(=O)c2sc3nccc4c3c2NC(=O)N4c2ccc(C(=O)Nc3cc(C(F)(F)F)ccn3)cc2F)C1]

The title compound was prepared using conditions analogous to Example 836, steps A-B, using tert-butyl (S)-3-aminopiperidine-1-carboxylate in place of tert-butyl (R)-3-aminopiperidine-1-carboxylate. MS (ESI): mass calcd. for $C_{34}H_{26}F_4N_8O_4S$, 718.7; m/z found, 719.3 [M+H]$^+$. $^1$H NMR (400 MHz, DMSO-d$_6$): δ 11.50 (s, 1H), 10.39 (s, 1H), 8.68 (d, J=5.1 Hz, 1H), 8.52 (s, 1H), 8.35 (d, J=5.5 Hz, 1H), 822-8.11 (m, 2H), 8.08-8.02 (m, 1H), 7.85-7.75 (m, 1H), 7.55 (d, J=5.1 Hz, 1H), 6.62-6.52 (m, 1H), 6.18-6.11 (m, 1H), 4.19-3.74 (m, 3H), 3.10-2.77 (m, 2H), 1.98-1.75 (m, 3H), 1.71-1.58 (m, 1H), 1.54-1.38 (m, 1H), 1.19-1.10 (m, 2H), 1.03-0.91 (m, 1H), 0.87-0.71 (m, 1H).

Example 903: 5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide

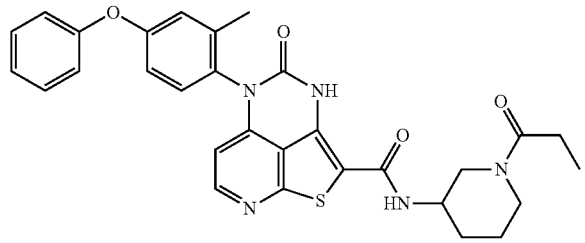 [SMILES: CCC(=O)N1CCCC(NC(=O)c2sc3nccc4c3c2NC(=O)N4c2ccc(Oc3ccccc3)cc2C)C1]

The title compound was prepared using conditions analogous to Example 75 and using 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) and propionic acid in place of (R)-5-(2-methyl-4-phenoxyphenyl)-4-oxo-N-(piperidin-3-yl)-4,5-dihydro-3H-1-thia-3,5,8-triazaacenaphthylene-2-carboxamide (Example 869) and 3-hydroxypropanoic acid. MS (ESI): mass calcd. for $C_{30}H_{29}N_5O_4S$, 555.7; m/z found, 556.2 [M+H]$^+$. $^1$H NMR (400 MHz, CD$_3$OD): δ 8.28 (d, J=5.5 Hz, 1H), 7.39-7.33 (m, 2H), 7.25 (d, J=8.6 Hz, 1H), 7.15-7.10 (m, 1H), 7.08-7.00 (m, 3H), 6.95-6.92 (m, 1H), 6.02 (d, J=5.5 Hz, 1H), 4.46-4.25 (m, 1H), 4.04-3.76 (m, 2H), 3.16-2.99 (m, 1H), 2.81-2.74 (m, 1H), 2.50-2.32 (m, 2H), 2.09 (s, 3H), 2.04-2.00 (m, 1H), 1.84-1.65 (m, 2H), 1.54-1.48 (m, 1H), 1.10 (t, J=7.3 Hz, 3H).

Example 904: (S,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide

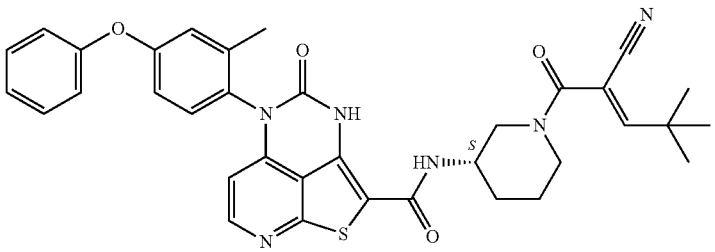

The title compound was prepared using conditions analogous to Example 921, and using (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) in place of 5-(2-methyl-4-phenoxyphenyl)-4-oxo-N-(piperidin-4-yl)-4,5-dihydro-3H-1-thia-3,5,8-triazaacenaphthylene-2-carboxamide (Example 865). MS (ESI): mass calcd. for $C_{35}H_{34}N_6O_4S$, 634.8; m/z found, 635.3[M+H]$^+$. $^1$H NMR (400 MHz, a mixture of DMSO-d$_6$ and CD$_3$OD): δ 8.30-8.26 (m, 1H), 7.41-7.34 (m, 2H), 7.32-7.26 (m, 1H), 7.16-7.10 (m, 1H), 7.08-7.00 (m, 3H), 6.95-6.89 (m, 1H), 6.78-6.74 (m, 1H), 5.97-5.92 (m, 1H), 3.93-3.77 (m, 3H), 3.13-3.07 (m, 2H), 2.05-2.03 (m, 3H), 1.96-1.87 (m, 1H), 1.83-1.74 (m, 1H), 1.72-1.62 (m, 1H), 1.56-1.43 (m, 1H), 1.22-1.12 (m, 9H).

Example 905: (S,E)-N-(1-(2-Cyano-3-cyclopropylacryloyl)pyrrolidin-3-yl)-5-(2-methyl-4-phenoxyphenyl)-4-oxo-4,5-dihydro-3H-1-thia-3,5,8-triazaacenaphthylene-2-carboxamide

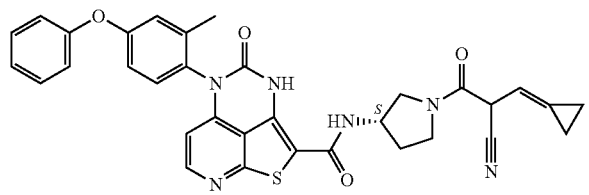

The title compound was prepared using conditions analogous to Example 877, and (S)-5-(2-methyl-4-phenoxyphenyl)-4-oxo-N-(pyrrolidin-3-yl)-4,5-dihydro-3H-1-thia-3,5,8-triazaacenaphthylene-2-carboxamide (Intermediate 71) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a light yellow solid. MS (ESI): mass calcd. for $C_{33}H_{28}N_6O_4S$, 604.7; m/z found, 605.2 [M+H]$^+$. $^1$H NMR (400 MHz, a mixture of CD3OD and DMSO-d$_6$): δ 8.29 (d, J=5.5 Hz, 1H), 7.43-7.35 (m, 2H), 7.32-7.26 (m, 1H), 7.18-7.11 (m, 1H), 7.10-7.01 (m, 3H), 6.96-6.90 (m, 1H), 6.75-6.68 (m, 1H), 5.97 (d, J=5.5 Hz, 1H), 4.55-4.45 (m, 1H), 3.99-3.86 (m, 1H), 3.85-3.77 (br, 1H), 3.76-3.66 (m, 1H), 3.64-3.55 (m, 1H), 3.52-3.42 (m, 1H), 2.24-2.11 (m, 1H), 2.05 (s, 3H), 1.97-1.86 (m, 1H), 1.22-1.16 (m, 2H), 0.93-0.87 (m, 2H).

Example 906: (R)—N-(1-(3-Chloropropanoyl)piperidin-3-yl)-4-oxo-5-(5-phenoxypyridin-2-yl)-4,5-dihydro-3H-1-thia-3,5,8-triazaacenaphthylene-2-carboxamide

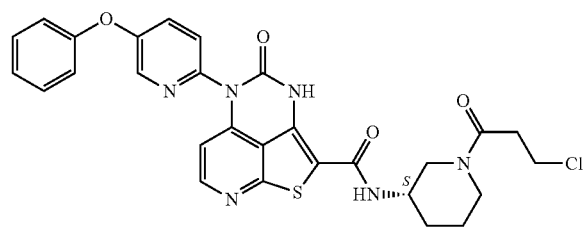

The title compound was prepared in a manner analogous to Method 1, step G in Example 1, using 4-oxo-5-(5-phenoxypyridin-2-yl)-4,5-dihydro-3H-1-thia-3,5,8-triazaacenaphthylene-2-carboxylic acid (Intermediate 60) and (S)-1-(3-aminopiperidin-1-yl)-3-chloropropan-1-one in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate. MS (ESI): mass calcd. for $C_{28}H_{25}ClN_6O_4S$, 577.1; m/z found, 577.3 [M+H]$^+$. $^1$H NMR (400 MHz, DMSO-d$_6$): δ 10.29-10.17 (m, 1H), 8.43-8.29 (m, 2H), 8.13-8.00 (m, 1H), 7.70-7.57 (m, 2H), 7.50-7.42 (m, 2H), 7.27-7.15 (m, 3H), 6.23-6.16 (m, 1H), 4.47-4.15 (m, 1H), 3.93-3.68 (m, 4H), 3.04-2.77 (m, 3H), 2.69-2.52 (m, 1H), 1.97-1.85 (m, 1H), 1.77-1.57 (m, 2H), 1.49-1.31 (m, 1H).

Example 907: 5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide

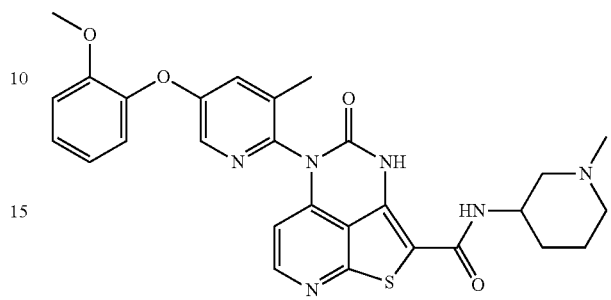

The title compound was prepared in a manner analogous to Method 1, step G, in Example 1, using 5-(4-(2-methoxyphenoxy)-2-methylphenyl)-4-oxo-4,5-dihydro-3H-1-thia-3,5,8-triazaacenaphthylene-2-carboxylic acid (Intermediate 67) and 1-methylpiperidin-3-amine in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate to yield the title product as a yellow solid. MS (ESI): mass calcd. for $C_{29}H_{29}N_5O_4S$, 543.6; m/z found, 544.2 [M+H]$^+$. $^1$H NMR (400 MHz, a mixture of CD3OD and DMSO-d$_6$): δ 8.26 (d, J=5.5 Hz, 1H), 7.23-7.16 (m, 2H), 7.16-7.10 (m, 1H), 7.09-7.02 (m, 1H), 7.01-6.91 (m, 1H), 6.91-6.84 (m, 1H), 6.80-6.71 (m, 1H), 5.91 (d, J=5.5 Hz, 1H), 4.02-3.97 (m, 1H), 3.75 (s, 3H), 2.88-2.77 (m, 1H), 2.70-2.59 (m, 1H), 2.25 (s, 3H), 2.13-1.97 (m, 5H), 1.81-1.66 (m, 2H), 1.63-1.50 (m, 1H), 1.45-1.33 (m, 1H).

Example 908: (R)—N-(1-(2-(Azetidin-1-yl)acetyl)piperidin-3-yl)-5-(2-methyl-4-phenoxyphenyl)-4-oxo-4,5-dihydro-3H-1-thia-3,5,8-triazaacenaphthylene-2-carboxamide

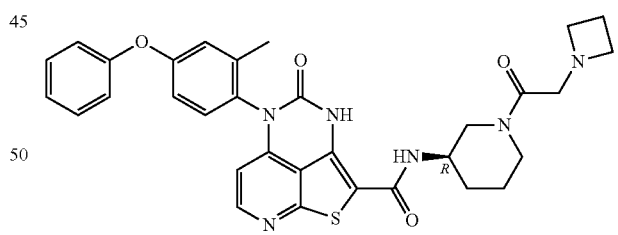

To a solution of (R)—N-(1-(2-chloroacetyl)piperidin-3-yl)-5-(2-methyl-4-phenoxyphenyl)-4-oxo-4,5-dihydro-3H-1-thia-3,5,8-triazaacenaphthylene-2-carboxamide (Example 396) (150 mg, 0.26 mmol) in DCM was added trimethylamine. Azetidine (38 mg, 0.66 mmol) in DCM was added dropwise and was stirred at rt for 2 h. The reaction was concentrated to dryness and purified by flash column chromatography, then preparative TLC (DCM/MeOH; 20/1) to give the title compound (10 mg, 6%) as a yellow solid. MS (ESI): mass calcd. for $C_{32}H_{32}N_6O_4S$, 596.7; m/z found, 597.2 [M+H]$^+$. $^1$H NMR (400 MHz, DMSO-d$_6$): δ 8.36-8.17 (m, 2H), 7.46-7.40 (m, 2H), 7.38-7.31 (m, 1H), 7.21-7.16 (m, 1H), 7.13-7.06 (m, 3H), 7.00-6.92 (m, 1H), 5.99-5.89

(m, 1H), 4.39-4.22 (m, 2H), 4.04-3.77 (m, 5H), 3.70-3.44 (m, 2H), 3.06-2.62 (m, 2H), 2.39-2.21 (m, 2H), 2.04 (s, 3H), 1.95-1.88 (m, 1H), 1.79-1.62 (m, 2H), 1.55-1.40 (m, 1H).

Example 909: 4-Oxo-5-(4-phenoxyphenyl)-N-(tetrahydro-2H-pyran-4-yl)-4,5-dihydro-3H-1-thia-3,5,8-triazaacenaphthylene-2-carboxamide

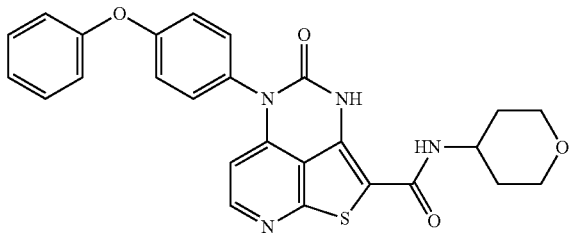 [SMILES: O=C(NC1CCOCC1)c1sc2nccc3c2c1NC(=O)N3c1ccc(Oc2ccccc2)cc1]

The title compound was prepared in a manner analogous to Method 1, step G in Example 1, using 4-oxo-5-(4-phenoxyphenyl)-4,5-dihydro-3H-1-thia-3,5,8-triazaacenaphthylene-2-carboxylic acid (Intermediate 58) and tetrahydro-2H-pyran-4-amine in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate. MS (ESI): mass calcd. for $C_{26}H_{22}N_4O_4S$, 486.6; m/z found, 487.1 [M+H]$^+$. $^1$H NMR (400 MHz, DMSO-d$_6$): δ 8.37-8.09 (m, 2H), 7.44-7.37 (m, 4H), 7.26-7.02 (m, 5H), 6.00 (d, J=5.2 Hz, 1H), 4.05-3.94 (m, 1H), 3.86-3.84 (m, 2H), 3.09-2.93 (m 2H), 1.75-1.72 (m, 2H), 1.58-1.56 (m, 2H).

Example 910: (R)—N-(1-Methylpyrrolidin-3-yl)-4-oxo-5-(4-phenoxyphenyl)-4,5-dihydro-3H-1-thia-3,5,8-triazaacenaphthylene-2-carboxamide

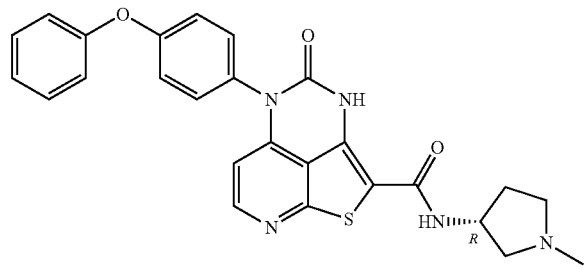

To an oven dried microwave vial containing a stir bar under Ar were added (R)-4-oxo-5-(4-phenoxyphenyl)-N-(pyrrolidin-3-yl)-4,5-dihydro-3H-1-thia-3,5,8-triazaacenaphthylene-2-carboxamide (Example 911) (117 mg, 0.249 mmol), sodium cyanoborohydride (34 mg, 0.54 mmol), and MeOH (3 mL). The flask was cooled to 0° C. in an ice bath and then aqueous HCHO (0.0174 mL, 471.45 mmol) was added via a syringe through the septum cap. The reaction was allowed to slowly warm to room temperature and was stirred for an additional 30 min. The reaction mixture was filtered through a syringe filter and purified by flash column chromatography to give the title compound (32.5 mg, 27.0% yield). MS (ESI): mass calcd. for $C_{26}H_{23}N_5O_3S$, 485.6; m/z found, 486.2 [M+H]$^+$. $^1$H NMR (500 MHz, CDCl$_3$): δ 8.43-8.23 (m, 1H), 7.48-7.35 (m, 2H), 7.33-7.27 (m, 1H), 7.27-7.02 (m, 5H), 6.23-6.09 (m, 2H), 4.72-4.56 (m, 1H), 3.06-2.94 (m, 1H), 2.85-2.74 (m, 1H), 2.66-2.52 (m, 3H), 2.47-2.36 (m, 4H), 2.33-2.22 (m, 1H), 1.87-1.72 (m, 1H).

Example 911: (R)-4-Oxo-5-(4-phenoxyphenyl)-N-(pyrrolidin-3-yl)-4,5-dihydro-3H-1-thia-3,5,8-triazaacenaphthylene-2-carboxamide

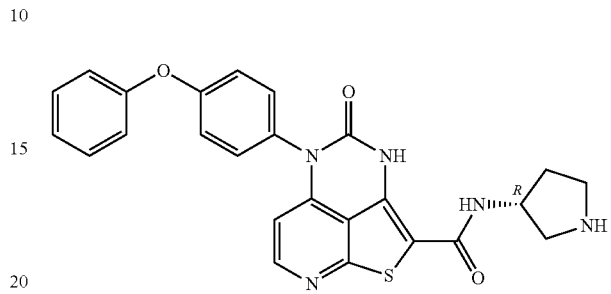

The title compound was prepared in a manner analogous to Method 1, steps A-H in Example 1, and using 4-fluoronitrobenzene in place of 5-fluoro-2-nitrotoluene in step A, and using Pt/C and THF in place of Fe, EtOH/H$_2$O, and NH$_4$Cl in step B, and using (R)-tert-butyl 3-aminopyrrolidine-1-carboxylate in place of tert-butyl (3R,5R)-3-amino-5-fluoropiperidine-1-carboxylate (Intermediate 1) in step G. MS (ESI): mass calcd. for $C_{25}H_{21}N_5O_3S$, 471.5; m/z found, 472.2 [M+H]$^+$. $^1$H NMR (400 MHz, DMSO-d$_6$): δ 8.78 (d, J=6.1 Hz, 1H), 8.33 (s, 1H), 8.21 (d, J=5.5 Hz, 1H), 7.44-7.40 (m, 2H), 7.37-7.34 (m, 2H), 7.19-7.07 (m, 5H), 5.96 (d, J=5.5 Hz, 1H), 4.54-4.48 (m, 1H), 3.40-3.22 (m, 2H), 3.21-3.06 (m, 2H), 2.21-2.12 (m, 1H), 1.97-1.88 (m, 1H).

Example 912: (S)-5-(2-Methyl-4-phenoxyphenyl)-4-oxo-N-(piperidin-3-yl)-4,5-dihydro-3H-1-thia-3,5,8-triazaacenaphthylene-2-carboxamide

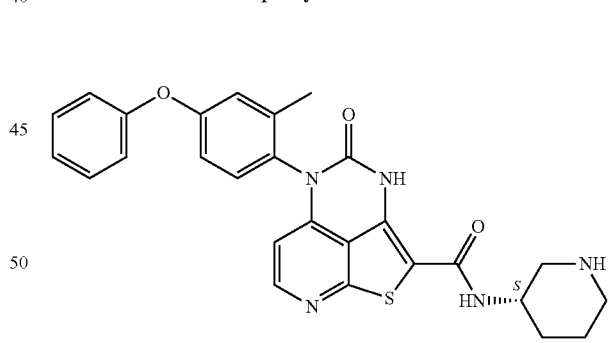

The title compound was prepared in a manner analogous to Method 1, step G-H, in Example 1, using (S)-tert-butyl 3-aminopiperidine-1-carboxylate in place of tert-butyl (3R,5R)-3-amino-5-fluoropiperidine-1-carboxylate (Intermediate 1) in step G and using 2,2,2-trifluoroacetic acid in place of HCl aq solution in step H, as a yellow solid. MS (ESI): mass calcd. for $C_{27}H_{25}N_5O_3S$, 499.6; m/z found, 500.1 [M+H]$^+$. $^1$H NMR (400 MHz, DMSO-d$_6$): δ 8.59 (s, 1H), 8.10-8.04 (m, 1H), 7.42-7.38 (m, 2H), 7.17-7.13 (m, 2H), 7.10-7.04 (m, 2H), 7.01 (d, J=2.7 Hz, 1H), 6.93-6.87 (m, 1H), 5.70-5.64 (m, 1H), 3.93-3.87 (m, 1H), 3.16-3.10 (m, 1H), 2.97-2.90 (m, 1H), 2.67-2.52 (m, 2H), 1.99 (s, 3H), 1.93-1.85 (m, 1H), 1.76-1.69 (m, 1H), 1.56-1.44 (m, 2H).

Example 913: (R,E)-N-(1-(4-(Dimethylamino)but-2-enoyl)piperidin-3-yl)-5-(4-isopropoxy-2-methylphenyl)-4-oxo-4,5-dihydro-3H-1-thia-3,5,8-triazaacenaphthylene-2-carboxamide

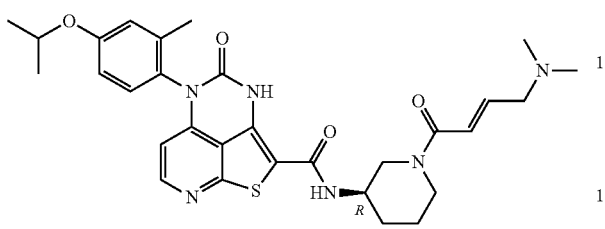

The title compounds was prepared using (R)-5-(4-isopropoxy-2-methylphenyl)-4-oxo-N-(piperidin-3-yl)-4,5-dihydro-3H-1-thia-3,5,8-triazaacenaphthylene-2-carboxamide (Intermediate 70) (200 mg, 0.43 mmol) and (E)-4-(dimethylamino)but-2-enoic acid (208 mg, 0.644 mmol) in anhydrous DMF (5 mL) were added HATU (245 mg, 0.644 mmol) and DIPEA (112 mg, 0.859 mmol) and was stirred overnight at rt. The reaction was purified by flash column chromatography to give the title compound (171 mg, 69.0% yield) as a yellow solid. MS (ESI): mass calcd. for $C_{30}H_{36}N_6O_4S$, 576.7; m/z found, 577.3 [M+H]$^+$. $^1$H NMR (400 MHz, CD$_3$OD): δ 8.34-8.28 (m, 1H), 7.22-7.17 (m, 1H), 6.98-6.95 (m, 1H), 6.93-6.83 (m, 2H), 6.75-6.62 (m, 1H), 6.06-6.00 (m, 1H), 4.69-4.62 (m, 1H), 4.54-4.26 (m, 1H), 4.22-3.87 (m, 2H), 3.74-3.65 (m, 2H), 3.24-3.13 (m, 1H), 2.97-2.86 (m, 1H), 2.73-2.66 (m, 6H), 2.12-2.01 (m, 4H), 1.92-1.83 (m, 1H), 1.82-1.65 (m, 1H), 1.65-1.52 (m, 1H), 1.35-1.32 (m, 6H).

Example 914: (R)—N-(1-Benzoylpyrrolidin-3-yl)-4-oxo-5-(4-phenoxyphenyl)-4,5-dihydro-3H-1-thia-3,5,8-triazaacenaphthylene-2-carboxamide

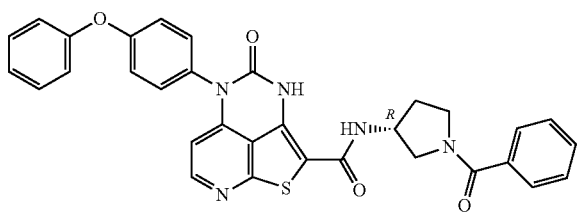

The title compound was prepared in a manner analogous to Method 1, step I in Example 1, using (R)-4-oxo-5-(4-phenoxyphenyl)-N-(pyrrolidin-3-yl)-4,5-dihydro-3H-1-thia-3,5,8-triazaacenaphthylene-2-carboxamide (Example 911) and benzoyl chloride in place of prop-2-enoyl chloride. MS (ESI): mass calcd. for $C_{32}H_{25}N_5O_4S$, 575.6; m/z found, 576.2 [M+H]$^+$. $^1$H NMR (400 MHz, DMSO-d$_6$): δ 10.19 (s, 1H), 8.35-8.25 (m, 2H), 7.52-7.38 (m, 9H), 7.29-7.00 (m, 5H), 6.05 (s, 1H), 4.57-4.34 (m, 1H), 3.88-3.63 (m, 2H), 3.53-3.46 (m, 2H), 2.26-1.93 (m, 2H).

Example 915: (R)-4-Oxo-5-(5-phenoxypyridin-2-yl)-N-(piperidin-3-yl)-4,5-dihydro-3H-1-thia-3,5,8-triazaacenaphthylene-2-carboxamide

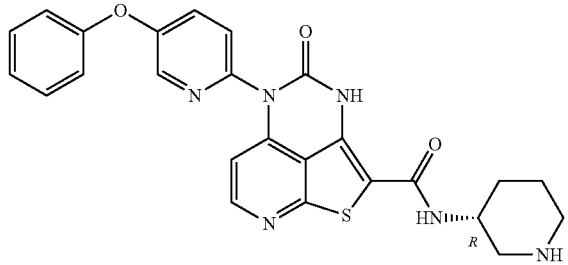

Step A: (R)-tert-Butyl 3-(4-oxo-5-(5-phenoxypyridin-2-yl)-4,5-dihydro-3H-1-thia-3,5,8-triazaacenaphthylene-2-carboxamido)piperidine-1-carboxylate To a 2-5 mL Biotage microwave vial containing a stir bar were added 5-phenoxypyridin-2-amine (137 mg, 0.736 mmol), 2-chloro-4-iodonicotinonitrile (191.9 mg, 0.726 mmol), Pd(OAc)$_2$ (3.3 mg, 0.0147 mmol), DPEPhos (12.6 mg, 0.0234 mmol), and Cs$_2$CO$_3$ (349 mg, 1.07 mmol). The vial was sealed, dioxane (1.45 mL) was added, evacuated and flushed with argon (4×), and stirred at 150° C. under argon for 30 min. The reaction was cooled to room temperature, treated with (R)-tert-butyl 3-(2-mercaptoacetamido)piperidine-1-carboxylate (Intermediate 22) (1.5 mL, 0.49 M, 0.74 mmol) via syringe, evacuated and flushed with argon (4×), and stirred at 150° C. for 15 min. The reaction was cooled to room temperature, treated with solid CDI (477 mg, 2.94 mmol) in one portion under air, resealed, evacuated and flushed with argon (4×), and stirred at 150° C. for 15 min. The reaction was diluted with EtOAc (10 mL), washed with 0.5 M citric acid in brine (2×8 mL), and 2 M K$_2$CO$_3$ (1×5 mL). The organic phase was dried over anhydrous Na$_2$SO$_4$, filtered, and concentrated to dryness. The residue was dissolved in ~5 mL DCM and purified by flash column chromatography to yield the title compound (120.7 mg, 28.35% yield). MS (ESI): mass calcd. for $C_{30}H_{30}N_6O_5S$, 586.67; m/z found, 587.3 [M+H]$^+$.

Step B: (R)-4-Oxo-5-(5-phenoxypyridin-2-yl)-N-(piperidin-3-yl)-4,5-dihydro-3H-1-thia-3,5,8-triazaacenaphthylene-2-carboxamide A solution of (R)-tert-butyl 3-(4-oxo-5-(5-phenoxypyridin-2-yl)-4,5-dihydro-3H-1-thia-3,5,8-triazaacenaphthylene-2-carboxamido)piperidine-1-carboxylate (120.7 mg, 0.206 mmol) in dioxane (1 mL) was treated with HCl (3.97 M in dioxane, 2.60 mL, 10.3 mmol) in one portion at room temperature, and was stirred at room temperature for 1 h. The reaction was then concentrated to dryness and was purified (19.1 mg of the di-HCl salt) by C18 HPLC (30×100 mm Phenomenex Kinetex column, 5 μm; mobile phase A: H$_2$O (0.1% TFA); B: acetonitrile (0.1% TFA), gradient: B in A from 10% to 90%) to give the title compound as a yellow-beige powder (19.7 mg, 13.4% yield). MS (ESI): mass calcd. for $C_{25}H_{22}N_6O_3S$, 486.6; m/z found, 487.2 [M+H]$^+$. $^1$H NMR (400 MHz, MeOH) δ 8.39 (d, J=2.53 Hz, 1H), 8.37 (d, J=5.56 Hz, 1H), 7.61-7.67 (m, 1H), 7.55-7.60 (m, 1H), 7.44-7.52 (m, 2H), 7.24-7.30 (m, 1H), 7.16-7.22

(m, 2H), 6.28 (d, J=6.06 Hz, 1H), 4.19-4.33 (m, 1H), 3.51-3.57 (m, 1H), 3.36 (br d, J=12.63 Hz, 1H), 2.89-3.02 (m, 2H), 2.02-2.15 (m, 2H), 1.67-1.91 (m, 2H).

Example 916: (E)-N-(1-(2-Cyano-3-cyclopropylacryloyl)piperidin-4-yl)-5-(2-methyl-4-phenoxyphenyl)-4-oxo-4,5-dihydro-3H-1-thia-3,5,8-triazaacenaphthylene-2-carboxamide

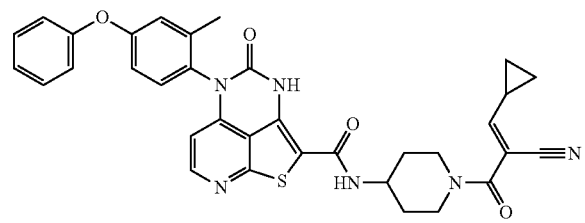 [SMILES: Cc1cc(Oc2ccccc2)ccc1N1C(=O)Nc2c(C(=O)NC3CCN(C(=O)/C(C#N)=C/C4CC4)CC3)sc3nccc1c23]

The title compound was prepared using conditions analogous to Example 877, using 5-(2-methyl-4-phenoxyphenyl)-4-oxo-N-(piperidin-4-yl)-4,5-dihydro-3H-1-thia-3,5,8-triazaacenaphthylene-2-carboxamide (Example 865) in place of 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a light yellow solid. MS (ESI): mass calcd. for $C_{34}H_{30}N_6O_4S$, 618.7; m/z found, 619.2 [M+H]$^+$. $^1$H NMR (400 MHz, a mixture of CD3OD and DMSO-d$_6$): δ 8.29 (d, J=5.5 Hz, 1H), 7.42-7.35 (m, 2H), 7.31-7.26 (m, 1H), 7.17-7.11 (m, 1H), 7.09-7.01 (m, 3H), 6.96-6.90 (m, 1H), 6.51-6.45 (m, 1H), 5.96 (d, J=5.5 Hz, 1H), 4.09-4.03 (m, 1H), 3.79-3.73 (m, 2H), 3.10-2.93 (m, 2H), 2.05 (s, 3H), 1.93-1.85 (m, 3H), 1.62-1.51 (m, 2H), 1.19-1.13 (m, 2H), 0.89-0.83 (m, 2H).

Example 917: 5-(4-(2-Methoxyphenoxy)-2-methylphenyl)-4-oxo-N-(piperidin-4-yl)-4,5-dihydro-3H-1-thia-3,5,8-triazaacenaphthylene-2-carboxamide

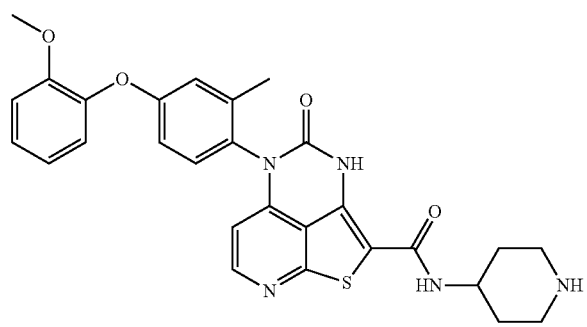 [SMILES: COc1ccccc1Oc1ccc(N2C(=O)Nc3c(C(=O)NC4CCNCC4)sc4nccc2c34)c(C)c1]

The title compound was prepared in a manner analogous to Method 1, step G-H, in Example 1, using 5-(4-(2-methoxyphenoxy)-2-methylphenyl)-4-oxo-4,5-dihydro-3H-1-thia-3,5,8-triazaacenaphthylene-2-carboxylic acid (Intermediate 67) and tert-butyl 4-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate to yield the title product as a light yellow solid. MS (ESI): mass calcd. for $C_{28}H_{27}N_5O_4S$, 529.6; m/z found, 530.2 [M+H]$^+$. $^1$H NMR (400 MHz, a mixture of CD$_3$OD and DMSO-d$_6$): δ 8.11 (d, J=5.5 Hz, 1H), 7.21-7.04 (m, 4H), 6.98-6.92 (m, 1H), 6.87-6.82 (m, 1H), 6.76-6.70 (m, 1H), 5.75 (d, J=5.5 Hz, 1H), 4.01-3.96 (m, 1H), 3.75 (s, 3H), 3.23-3.17 (m, 2H), 2.91-2.81 (m, 2H), 2.02-1.94 (m, 5H), 1.74-1.61 (m, 2H).

Example 918: 5-(4-(2-Methoxyphenoxy)-2-methylphenyl)-N-(1-methylpiperidin-4-yl)-4-oxo-4,5-dihydro-3H-1-thia-3,5,8-triazaacenaphthylene-2-carboxamide

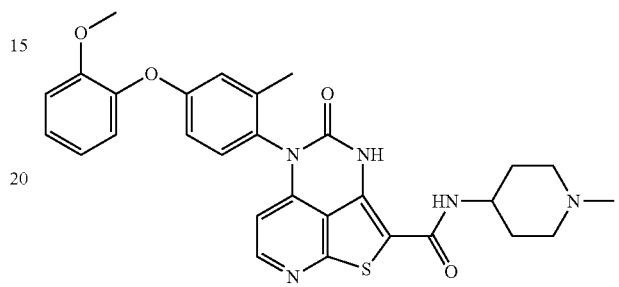

The title compound was prepared in a manner analogous to Method 1, step G, in Example 1, using 5-(4-(2-methoxyphenoxy)-2-methylphenyl)-4-oxo-4,5-dihydro-3H-1-thia-3,5,8-triazaacenaphthylene-2-carboxylic acid (Intermediate 67) and 1-methylpiperidine-4-amine in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate as a yellow solid. MS (ESI): mass calcd. for $C_{29}H_{29}N_5O_4S$, 543.6; m/z found, 544.2 [M+H]$^+$. $^1$H NMR (400 MHz, DMSO-d$_6$): δ 8.26 (d, J=5.4 Hz, 1H), 8.14-8.05 (m, 1H), 7.26-7.16 (m, 3H), 7.11-7.08 (m, 1H), 7.02-6.95 (m, 1H), 6.92-6.85 (m, 1H), 6.79-6.73 (m, 1H), 5.85 (d, J=5.4 Hz, 1H), 3.76-3.72 (m, 4H), 2.87-2.80 (m, 2H), 2.23 (s, 3H), 2.14-2.05 (m, 2H), 2.00 (s, 3H), 1.82-1.72 (m, 2H), 1.68-1.56 (m, 2H).

Example 919: (R)-5-(4-(Cyclopentyloxy)-2-methylphenyl)-4-oxo-N-(piperidin-3-yl)-4,5-dihydro-3H-1-thia-3,5,8-triazaacenaphthylene-2-carboxamide

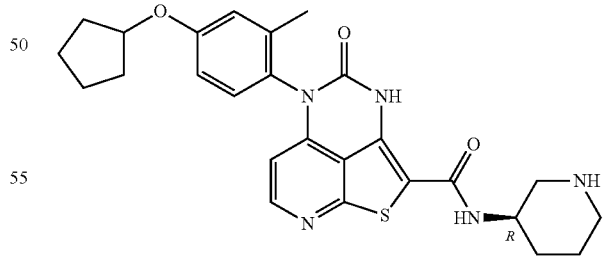

The title compound was prepared in a manner analogous to Method 1, steps C-H, and using 4-(cyclopentyloxy)-2-methylaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{26}H_{29}N_5O_3S$, 491.6; m/z found, 492.2 [M+H]$^+$. $^1$H NMR (400 MHz, CDCl$_3$): δ 8.33-8.26 (m, 1H), 7.15-7.05

(m, 1H), 6.91-6.79 (m, 2H), 6.64-6.47 (m, 1H), 5.99-5.93 (m, 1H), 4.81-4.73 (m, 1H), 4.30-4.19 (m, 1H), 3.23-3.15 (m, 1H), 3.02-2.87 (m, 3H), 2.13-2.09 (m, 3H), 1.94-1.77 (m, 9H), 1.68-1.58 (m, 3H).

Example 920: N-(1-Methylpiperidin-4-yl)-4-oxo-5-(4-phenoxyphenyl)-4,5-dihydro-3H-1-thia-3,5,8-triazaacenaphthylene-2-carboxamide

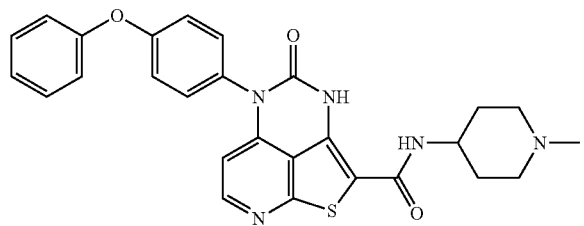 [SMILES: CN1CCC(NC(=O)c2sc3nccc4c3c2NC(=O)N4c2ccc(Oc3ccccc3)cc2)CC1]

The title compound was prepared by treating 4-oxo-5-(4-phenoxyphenyl)-4,5-dihydro-3H-1-thia-3,5,8-triazaacenaphthylene-2-carboxylic acid (Intermediate 58, 160 mg, 0.40 mmol) in DCM (10 mL) was added oxalyl chloride (100 mg, 0.80 mmol) and 1 drop of DMF, then was stirred at 40° C. for 2 hours. After concentration under vacuo to dryness, the residue was dissolved in DCM (10 mL) and was added a solution of 1-methylpiperidin-4-amine (90 mg, 0.80 mmol) in DCM (5 mL), stirred at room temperature for 5 minutes. The mixture was concentrated and purified by ISCO using MeOH/water as eluent to yield the title product as a yellow solid (129 mg, 67% yield). MS (ESI): mass calcd. for $C_{27}H_{25}N_5O_3S$, 499.6; m/z found, 500.2 $[M+H]^+$. $^1H$ NMR (400 MHz, DMSO-$d_6$): δ 8.24-8.20 (m, 3H), 7.50-7.31 (m, 4H), 7.19-7.09 (m, 5H), 5.96 (d, J=5.5 Hz, 1H), 3.75-3.73 (m, 1H), 2.82-2.79 (m, 2H), 2.20 (s, 3H), 2.09-2.04 (m, 2H), 1.81-1.73 (m, 2H), 1.63-1.55 (m, 2H).

Example 921: (E)-N-(1-(2-Cyano-4,4-dimethylpent-2-enoyl)piperidin-4-yl)-5-(2-methyl-4-phenoxyphenyl)-4-oxo-4,5-dihydro-3H-1-thia-3,5,8-triazaacenaphthylene-2-carboxamide

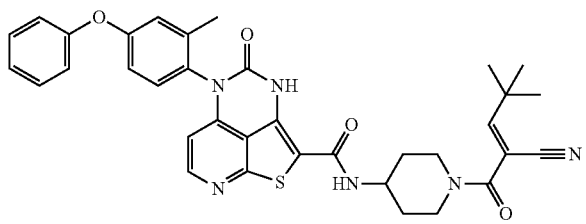 [SMILES: Cc1cc(Oc2ccccc2)ccc1N1C(=O)Nc2c(C(=O)NC3CCN(C(=O)/C(C#N)=C/C(C)(C)C)CC3)sc3nccc1c23]

To a round bottom flask were added 5-(2-methyl-4-phenoxyphenyl)-4-oxo-N-(piperidin-4-yl)-4,5-dihydro-3H-1-thia-3,5,8-triazaacenaphthylene-2-carboxamide (Example 865) (100 mg, 0.18 mmol), (E)-2-cyano-4,4-dimethylpent-2-enoic acid (Intermediate 44) (57 mg, 0.37 mmol), DIEA (40 mg, 0.27 mmol), HATU (91 mg, 0.24 mmol), and DMF (5 mL). The reaction mixture was stirred at room temperature for 5 hours. The mixture was purified by ISCO (MeOH/H$_2$O) to yield the title compound (20 mg, 18% yield) as a yellow solid. MS (ESI): mass calcd. for $C_{35}H_{34}N_6O_4S$, 634.8; m/z found, 635.2 $[M+H]^+$. $^1H$ NMR (400 MHz, a mixture of CD$_3$OD and DMSO-$d_6$): δ 8.29 (d, J=5.5 Hz, 1H), 7.42-7.34 (m, 2H), 7.31-7.27 (m, 1H), 7.17-7.11 (m, 1H), 7.09-7.01 (m, 3H), 6.96-6.91 (m, 1H), 6.76-6.73 (m, 1H), 5.98 (d, J=5.5 Hz, 1H), 4.25-4.21 (m, 1H), 4.14-4.06 (m, 2H), 3.89-3.83 (m, 2H), 2.05 (s, 3H), 1.96-1.87 (m, 2H), 1.63-1.52 (m, 2H), 1.24-1.20 (m, 9H).

Example 922: (R)-4-Oxo-5-(6-phenoxypyridin-3-yl)-N-(piperidin-3-yl)-4,5-dihydro-3H-1-thia-3,5,8-triazaacenaphthylene-2-carboxamide

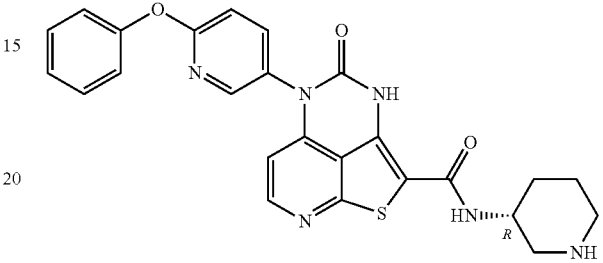

Step A: (R)-tert-Butyl 3-(4-oxo-5-(6-phenoxypyridin-3-yl)-4,5-dihydro-3H-1-thia-3,5,8-triazaacenaphthylene-2-carboxamido)piperidine-1-carboxylate To a 2-5 mL Biotage microwave vial containing a stir bar were added 6-phenoxypyridin-3-amine (182.5 mg, 0.0.9800 mmol), 2-chloro-4-iodonicotinonitrile (256.8 mg, 0.7260 mmol), Pd(OAc)$_2$ (4.7 mg, 0.021 mmol), DPEPhos (15.6 mg, 0.0290 mmol), and Cs$_2$CO$_3$ (446 mg, 1.37 mmol). The vial was sealed, dioxane (1.95 mL) was added, evacuated and flushed with argon (4×), and stirred at 150° C. under argon for 30 min. The reaction was cooled to room temperature, treated with (R)-tert-butyl 3-(2-mercaptoacetamido)piperidine-1-carboxylate (Intermediate 22) (2.0 mL, 0.49 M, 0.98 mmol) via syringe, evacuated and flushed with argon (4×), and stirred at 150° C. for 15 min. The reaction was cooled to room temperature, treated with solid CDI (628 mg, 3.87 mmol) in one portion under air, resealed, evacuated and flushed with argon (4×), and stirred at 150° C. for 15 min. The reaction was diluted with EtOAc (10 mL), washed with 0.5 M citric acid in brine (2×8 mL), and 2 M K$_2$CO$_3$ (1×5 mL). The organic phase was dried over anhydrous Na$_2$SO$_4$, filtered, and concentrated to dryness. The residue was dissolved in ~5 mL DCM and purified by flash column chromatography to yield the title compound (328.5 mg, 57.66% yield). MS (ESI): mass calcd. for $C_{30}H_{30}N_6O_5S$, 586.67; m/z found, 587.1 $[M+H]^+$.

Step B: (R)-4-Oxo-5-(6-phenoxypyridin-3-yl)-N-(piperidin-3-yl)-4,5-dihydro-3H-1-thia-3,5,8-triazaacenaphthylene-2-carboxamide A solution of (R)-tert-butyl 3-(4-oxo-5-(6-phenoxypyridin-3-yl)-4,5-dihydro-3H-1-thia-3,5,8-triazaacenaphthylene-2-carboxamido)piperidine-1-carboxylate (323.5 mg, 0.551 mmol) in dioxane (2.7 mL) was treated with HCl (3.97 M in dioxane, 6.90 mL, 27.4 mmol) in one portion at room temperature, and was stirred at room temperature for 1 h. The reaction was then concentrated to dryness and was purified (24.7 mg of the di-HCl salt) by C18 HPLC (30×100 mm Phenomenex Kinetex column, 5 μm; mobile phase A: H$_2$O (0.1% TFA); B: acetonitrile (0.1% TFA), gradient: B in A from 10% to 90%) to give the title compound as a light yellow-powder (16.1 mg, 4.09% yield). MS (ESI): mass calcd. for $C_{25}H_{22}N_6O_3S$, 486.6; m/z found, 487.2 [M+H]$^+$. $^1$H NMR (400 MHz, MeOH) δ 8.38 (d, J=5.56 Hz, 1H), 8.21 (s, 1H), 7.86-7.96 (m, 1H), 7.39-7.50 (m, 2H), 7.23-7.30 (m, 1H), 7.14-7.23 (m, 3H), 6.29 (d, J=5.56 Hz, 1H), 4.19-4.34 (m, 1H), 3.51-3.57 (m, 1H), 3.36 (br d, J=13.14 Hz, 1H), 2.94 (q, J=11.12 Hz, 2H), 2.02-2.15 (m, 2H), 1.67-1.92 (m, 2H).

Example 923: (R)-5-(4-Isopropoxy-2-methylphenyl)-N-(1-(2-(methylamino)acetyl)piperidin-3-yl)-4-oxo-4,5-dihydro-3H-1-thia-3,5,8-triazaacenaphthylene-2-carboxamide

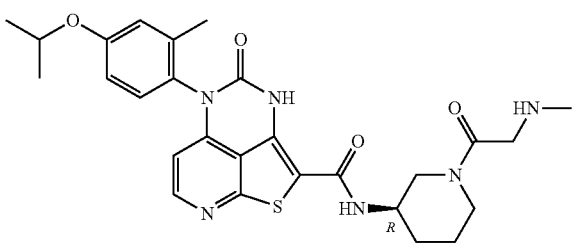

To a solution of (R)-5-(4-isopropoxy-2-methylphenyl)-4-oxo-N-(piperidin-3-yl)-4,5-dihydro-3H-1-thia-3,5,8-triazaacenaphthylene-2-carboxamide (Intermediate 70) (200 mg, 0.43 mmol) and 2-((tert-butoxycarbonyl)(methyl)amino)acetic acid (305 mg, 0.644 mmol) in anhydrous DMF (5 mL) were added HATU (245 mg, 0.644 mmol) and DIPEA (112 mg, 0.859 mmol) and was stirred overnight at rt. The reaction was purified by flash column chromatography to give the title compound (107 mg, 46.4% yield) as a yellow solid. MS (ESI): mass calcd. for $C_{27}H_{32}N_6O_4S$, 536.6; m/z found, 537.2 [M+H]$^+$. $^1$H NMR (400 MHz, CD$_3$OD): δ 8.15-8.08 (m, 1H), 7.15-7.06 (m, 1H), 6.98-6.92 (m, 1H), 6.92-6.85 (m, 1H), 5.86-5.78 (m, 1H), 4.68-4.60 (m, 1H), 4.26-3.92 (m, 2H), 3.91-3.61 (m, 3H), 3.59-3.33 (m, 2H), 2.59-2.51 (m, 3H), 2.11-2.07 (m, 3H), 2.01-1.76 (m, 3H), 1.65-1.52 (m, 1H), 1.35-1.32 (m, 6H).

Example 924: (S)—N-(1-Acetylpyrrolidin-3-yl)-4-oxo-5-(4-phenoxyphenyl)-4,5-dihydro-3H-1-thia-3,5,8-triazaacenaphthylene-2-carboxamide

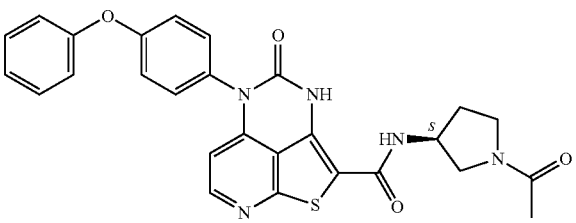

The title compound was prepared in a manner analogous to Method 1, step I in Example 1, using (S)-4-oxo-5-(4-phenoxyphenyl)-N-(pyrrolidin-3-yl)-4,5-dihydro-3H-1-thia-3,5,8-triazaacenaphthylene-2-carboxamide (Example 934) and acetyl chloride in place of prop-2-enoyl chloride. MS (ESI): mass calcd. for $C_{27}H_{23}N_5O_4S$, 513.6; m/z found, 514.2 [M+H]$^+$. $^1$H NMR (400 MHz, DMSO-d$_6$): δ 10.09 (s, 1H), 8.34-8.28 (m, 2H), 7.53-7.32 (m, 4H), 7.24-7.00 (m, 5H), 6.12-5.96 (m, 1H), 4.50-4.37 (m, 1H), 3.83-3.65 (m, 1H), 3.56-3.52 (m, 1H), 3.49-3.41 (m, 2H), 2.21-1.95 (m, 2H), 1.91 (d, J=5.1 Hz, 3H).

Example 925: (R)—N-(1-Benzylpyrrolidin-3-yl)-4-oxo-5-(4-phenoxyphenyl)-4,5-dihydro-3H-1-thia-3,5,8-triazaacenaphthylene-2-carboxamide

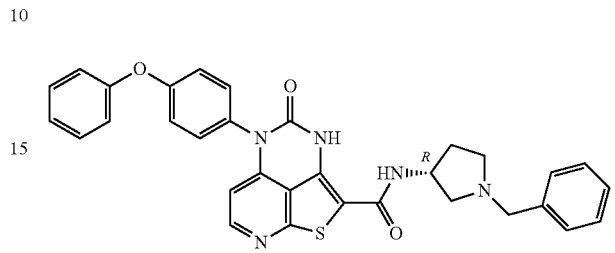

(R)-4-oxo-5-(4-phenoxyphenyl)-N-(pyrrolidin-3-yl)-4,5-dihydro-3H-1-thia-3,5,8-triazaacenaphthylene-2-carboxamide (Example 911) (150 mg, 0.318 mmol) was dissolved in DCM (30 mL), followed by the addition of NaBH(AcO)$_3$ (101 mg, 0.477 mmol) and benzaldehyde (51 mg, 0.477 mmol). The reaction mixture was stirred at room temperature under N$_2$ overnight. The mixture was washed with sat Na$_2$CO$_3$ solution and concentrated, purified by flash column chromatography eluting with water (0.5% HCOOH)/MeOH to yield the title product as a white solid (115 mg, 64% yield). MS (ESI): mass calcd. for $C_{32}H_{27}N_5O_3S$, 561.6; m/z found, 561.8 [M+H]$^+$. $^1$H NMR (400 MHz, DMSO-d$_6$): δ 8.29 (d, J=5.5 Hz, 1H), 8.21 (d, J=6.8 Hz, 1H), 8.11 (d, J=0.7 Hz, 1H), 7.4-7.402 (m, 4H), 7.30-7.27 (m, 4H), 7.26-7.06 (m, 6H), 6.04 (d, J=5.5 Hz, 1H), 4.41-4.32 (m, 1H), 3.61 (s, 2H), 2.83-2.77 (m, 1H), 2.69-2.60 (m, 1H), 2.55-2.49 m, 1H), 2.47-2.41 (m, 1H), 2.17-2.08 (m, 1H), 1.86-1.79 (m, 1H).

Example 926: 4-Oxo-5-(4-phenoxyphenyl)-N-(piperidin-4-yl)-4,5-dihydro-3H-1-thia-3,5,8-triazaacenaphthylene-2-carboxamide

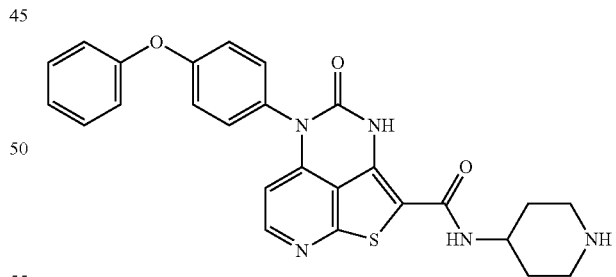

To a solution of tert-butyl 4-(4-oxo-5-(4-phenoxyphenyl)-4,5-dihydro-3H-1-thia-3,5,8-triazaacenaphthylene-2-carboxamido)piperidine-1-carboxylate (Example 627, 3.70 g, 6.32 mmol) in DCM (20 mL) was added TFA (106 mL) dropwise and was stirred at rt for 30 min. The reaction was concentrated to dryness and the residue was purified by flash column chromatography to give the title compound (2.90 g, 94.5% yield) as an off white solid. MS (ESI): mass calcd. for $C_{26}H_{23}N_5O_3S$, 485.6; m/z found, 486.1 [M+H]$^+$. $^1$H NMR (400 MHz, DMSO-d$_6$): δ 8.56 (d, J=7.5 Hz, 1H), 8.27 (s, 1H), 8.17 (d, J=5.5 Hz, 1H), 7.55-7.28 (m, 4H), 7.19-7.08

(m, 5H), 5.92 (d, J=5.5 Hz, 1H), 4.06-3.98 (m, 1H), 3.25-3.22 (m, 2H), 2.96-2.90 (m, 2H), 1.97-1.94 (m, 2H), 1.71-1.63 (m, 2H).

Example 927: 4-Oxo-5-(4-phenoxyphenyl)-N-(2-(pyrrolidin-1-yl)ethyl)-4,5-dihydro-3H-1-thia-3,5,8-triazaacenaphthylene-2-carboxamide

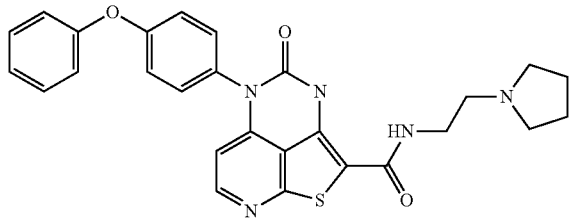 [SMILES: O=C(NCCN1CCCC1)c1sc2nccc3c2c1NC(=O)N3c1ccc(Oc2ccccc2)cc1]

The title compound was prepared in a manner analogous to Method 1, step G in Example 1, using 4-oxo-5-(4-phenoxyphenyl)-4,5-dihydro-3H-1-thia-3,5,8-triazaacenaphthylene-2-carboxylic acid (Intermediate 58) and 2-(pyrrolidin-1-yl)ethan-1-amine in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{27}H_{25}N_5O_3S$, 499.6; m/z found, 499.9 [M+H]$^+$. $^1$H NMR (400 MHz, DMSO-d$_6$): δ 8.26 (d, J=5.5 Hz, 2H), 7.45-7.37 (m, 4H), 7.20-7.08 (m, 5H), 6.01 (d, J=5.5 Hz, 1H), 2.70 (t, J=6.6 Hz, 2H), 2.67-2.61 (m, 4H), 1.74-1.68 (m, 4H).

Example 928: 4-Oxo-5-(4-phenoxyphenyl)-N-(2-(piperazin-1-yl)ethyl)-4,5-dihydro-3H-1-thia-3,5,8-triazaacenaphthylene-2-carboxamide

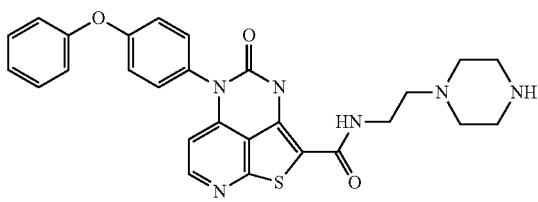 [SMILES: O=C(NCCN1CCNCC1)c1sc2nccc3c2c1NC(=O)N3c1ccc(Oc2ccccc2)cc1]

The title compound was prepared in a manner analogous to Method 1, step G-H in Example 1, using 4-oxo-5-(4-phenoxyphenyl)-4,5-dihydro-3H-1-thia-3,5,8-triazaacenaphthylene-2-carboxylic acid (Intermediate 58) and tert-butyl 4-(2-aminoethyl)piperazine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{27}H_{26}N_6O_3S$, 514.6; m/z found, 514.8 [M+H]$^+$. $^1$H NMR (400 MHz, DMSO-d$_6$): δ 8.82 (s, 1H), 8.08 (d, J=5.3 Hz, 1H), 7.41 (m, 2H), 7.28 (d, J=8.2 Hz, 2H), 7.21-7.04 (m, 5H), 5.83 (d, J=5.2 Hz, 1H), 3.39-3.33 (m, 4H), 3.03-2.96 (m, 4H), 2.58-2.49 (m, 4H).

Example 929: N-(1-Acryloylpiperidin-4-yl)-5-(2-methyl-4-phenoxyphenyl)-4-oxo-4,5-dihydro-3H-1-thia-3,5,8-triazaacenaphthylene-2-carboxamide

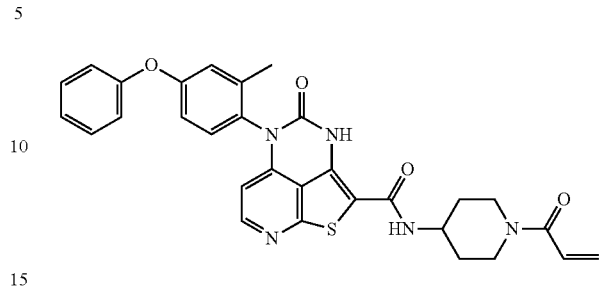

The title compound was prepared in a manner analogous to Method 1, step I in Example 1, using 5-(2-methyl-4-phenoxyphenyl)-4-oxo-N-(piperidin-4-yl)-4,5-dihydro-3H-1-thia-3,5,8-triazaacenaphthylene-2-carboxamide (Example 865) to yield a white solid. MS (ESI): mass calcd. for $C_{30}H_{27}N_5O_4S$, 553.6; m/z found, 554.2[M+H]$^+$. $^1$H NMR (400 MHz, DMSO-d$_6$): δ 8.22-8.16 (m, 1H), 8.03 (d, J=7.4 Hz, 1H), 7.44-7.38 (m, 2H), 7.32-7.26 (m, 1H), 7.20-7.14 (m, 1H), 7.12-7.06 (m, 2H), 7.07-7.02 (m, 1H), 6.96-6.90 (m, 1H), 6.22-6.15 (m, 1H), 6.08-6.03 (m, 1H), 5.86-5.82 (m, 1H), 5.56-5.53 (m, 1H), 4.15-4.04 (m, 2H), 3.91-3.86 (m, 1H), 3.17-3.12 (m, 1H), 2.03 (s, 3H), 1.99-1.93 (m, 1H), 1.84-1.79 (m, 2H), 1.43-1.35 (m, 2H).

Example 930: (S)-5-(2-methyl-4-phenoxyphenyl)-N-(1-methylpiperidin-3-yl)-4-oxo-4,5-dihydro-3H-1-thia-3,5,8-triazaacenaphthylene-2-carboxamide

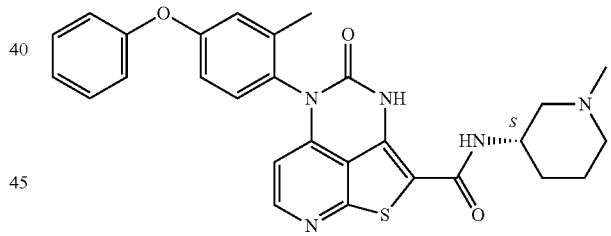

To a solution of (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) (50 mg, 0.10 mmol) in MeOH was added 37% HCHO aq solution (50 mg, 0.50 mmol), followed by addition of sodium triacetoxyborohydride (42 mg, 0.20 mmol). The reaction mixture was stirred at room temperature for 5.0 hours, concentrated and purified by flash column chromatography eluting with water (0.5% HCOOH)/MeOH to yield the title product as a white solid (42 mg, 81.71% yield). MS (ESI): mass calcd. for $C_{28}H_{27}N_5O_3S$, 513.6; m/z found, 514.1 [M+H]$^+$. $^1$H NMR (400 MHz, DMSO-d$_6$): δ 8.77 (d, J=8.1 Hz, 1H), 7.96 (d, J=5.5 Hz, 1H), 7.45-7.33 (m, 2H), 7.18-7.10 (m, 1H), 7.10-7.02 (m, 3H), 6.99 (s, 1H), 6.88 (d, J=8.4 Hz, 1H), 5.53 (d, J=5.4 Hz, 1H), 3.93-3.83 (m, 1H), 2.78-2.69 (m, 1H), 2.13 (s, 3H), 1.97 (s, 3H), 1.92-1.74 (m, 3H), 1.69-1.58 (m, 2H), 1.56-1.42 (m, 2H).

Example 931: (S)—N-(1-Methylpyrrolidin-3-yl)-4-oxo-5-(4-phenoxyphenyl)-4,5-dihydro-3H-1-thia-3,5,8-triazaacenaphthylene-2-carboxamide

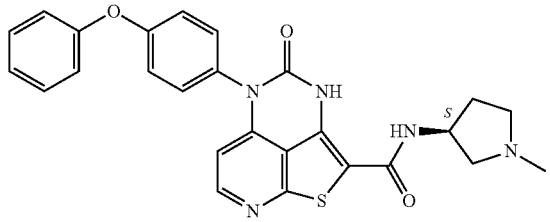

To a solution of (S)-4-oxo-5-(4-phenoxyphenyl)-N-(pyrrolidin-3-yl)-4,5-dihydro-3H-1-thia-3,5,8-triazaacenaphthylene-2-carboxamide (Example 934) (150 mg, 0.32 mmol) in MeOH was added 37% HCHO aq solution (78 mg, 0.95 mmol), followed by addition of sodium borohydride (36 mg, 0.95 mmol). The reaction mixture was stirred at room temperature for 2 hours, concentrated and purified by flash column chromatography eluting with water (0.5% HCOOH)/MeOH to yield the title product as a white solid (147 mg, 95% yield). MS (ESI): mass calcd. for $C_{26}H_{23}N_5O_3S$, 485.6; m/z found, 486.2 [M+H]$^+$. $^1$H NMR (400 MHz, DMSO-d$_6$): δ 8.37 (d, J=6.8 Hz, 1H), 8.27 (d, J=5.5 Hz, 1H), 8.17 (s, 1H), 7.49-7.31 (m, 4H), 7.20-7.09 (m, 5H), 6.02 (d, J=5.5 Hz, 1H), 4.46-4.38 (m, 1H), 2.90-2.79 (m, 2H), 2.69-2.65 (m, 1H), 2.62-2.55 (m, 1H), 2.38 (s, 3H), 2.26-2.12 (m, 1H), 1.88-1.79 (m, 1H).

Example 932: 4-Oxo-5-(4-phenoxyphenyl)-N-(2-(piperidin-1-yl)ethyl)-4,5-dihydro-3H-1-thia-3,5,8-triazaacenaphthylene-2-carboxamide

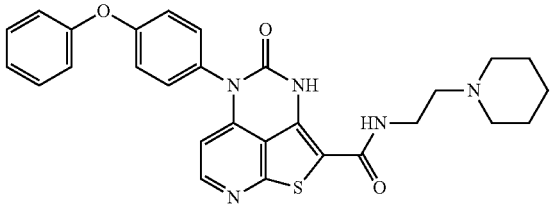 [SMILES: O=C(NCCN1CCCCC1)c1sc2nccc3c2c1NC(=O)N3c1ccc(Oc2ccccc2)cc1]

The title compound was prepared in a manner analogous to Method 1, step G in Example 1, using 4-oxo-5-(4-phenoxyphenyl)-4,5-dihydro-3H-1-thia-3,5,8-triazaacenaphthylene-2-carboxylic acid (Intermediate 58) and 2-(piperidin-1-yl)ethan-1-amine in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate. MS (ESI): mass calcd. for $C_{28}H_{27}N_5O_3S$, 513.6; m/z found, 513.8 [M+H]$^+$. $^1$H NMR (400 MHz, DMSO-d$_6$): δ 8.28 (d, J=4.8 Hz, 1H), 8.16 (s, 1H), 7.46-7.37 (m, 4H), 7.21-7.07 (m, 5H), 6.03 (d, J=4.9 Hz, 1H), 2.59-2.52 (m, 2H), 2.52-2.47 (m, 4H), 1.54-1.46 (m, 4H), 1.39-1.34 (m, 2H).

Example 933: N-(2-Morpholinoethyl)-4-oxo-5-(4-phenoxyphenyl)-4,5-dihydro-3H-1-thia-3,5,8-triazaacenaphthylene-2-carboxamide

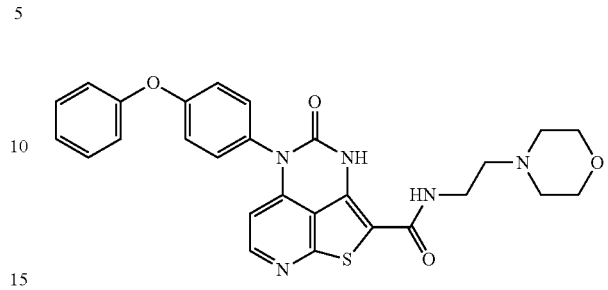

The title compound was prepared in a manner analogous to Method 1, step G in Example 1, using 4-oxo-5-(4-phenoxyphenyl)-4,5-dihydro-3H-1-thia-3,5,8-triazaacenaphthylene-2-carboxylic acid (Intermediate 58) and 2-morpholinoethan-1-amine in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate. MS (ESI): mass calcd. for $C_{27}H_{25}N_5O_4S$, 515.6; m/z found, 515.8 [M+H]$^+$. $^1$H NMR (400 MHz, DMSO-d$_6$): δ 8.29 (d, J=5.4 Hz, 1H), 8.11 (s, 1H), 7.47-7.37 (m, 4H), 7.21-7.07 (m, 5H), 6.04 (d, J=5.5 Hz, 1H), 3.56-3.53 (m, 4H), 2.45-2.42 (m, 2H), 2.42-2.36 (m, 4H).

Example 934: (S)-4-Oxo-5-(4-phenoxyphenl)-N-(pyrrolidin-3-yl)-4,5-dihydro-3H-1-thia-3,5,8-triazaacenaphthylene-2-carboxamide

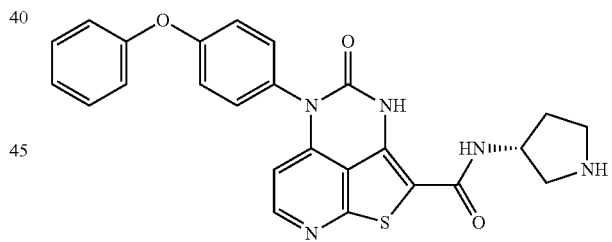

The title compound was prepared in a manner analogous to Method 1, step G-H in Example 1, using 4-oxo-5-(4-phenoxyphenyl)-4,5-dihydro-3H-1-thia-3,5,8-triazaacenaphthylene-2-carboxylic acid (Intermediate 58) and tert-butyl (S)-3-aminopyrrolidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G. MS (ESI): mass calcd. for $C_{25}H_{21}N_5O_3S$, 471.5; m/z found, 472.1 [M+H]$^+$. $^1$H NMR (400 MHz, DMSO-d$_6$): δ 8.78 (s, 1H), 8.26 (s, 1H), 8.18 (d, J=4.9 Hz, 1H), 7.50-7.27 (m, 4H), 7.19-7.09 (m, 5H), 5.93 (d, J=5.5 Hz, 1H), 4.51-4.45 (m, 1H), 3.32-3.24 (m, 2H), 3.15-3.06 (m, 2H), 2.22-2.13 (m, 1H), 1.95-1.86 (m, 1H).

Example 935: N-(2-(4-Methylpiperazin-1-yl)ethyl)-4-oxo-5-(4-phenoxyphenyl)-4,5-dihydro-3H-1-thia-3,5,8-triazaacenaphthylene-2-carboxamide

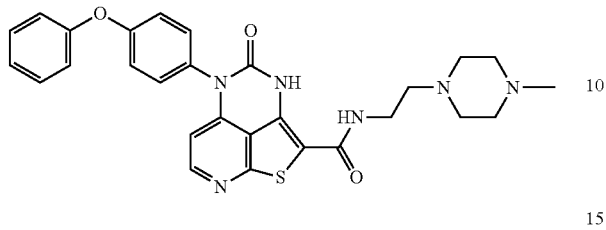

The title compound was prepared in a manner analogous to Method 1, step G in Example 1, using 4-oxo-5-(4-phenoxyphenyl)-4,5-dihydro-3H-1-thia-3,5,8-triazaacenaphthylene-2-carboxylic acid (Intermediate 58) and 2-(4-methylpiperazin-1-yl)ethan-1-amine in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G to yield a white solid. MS (ESI): mass calcd. for $C_{28}H_{28}N_6O_3S$, 528.6; m/z found, 528.8 [M+H]$^+$. $^1$H NMR (400 MHz, DMSO-$d_6$): δ 8.27 (d, J=5.2 Hz, 1H), 8.14 (s, 1H), 7.50-7.35 (m, 4H), 7.29-7.03 (m, 5H), 6.02 (d, J=5.3 Hz, 1H), 3.38-3.29 (d, J=6.0 Hz, 4H), 2.45-2.40 (d, J=6.5 Hz, 4H), 2.40-2.30 (br, 4H), 2.16 (s, 3H).

Example 936: (R)—N-(1-Acetylpiperidin-3-yl)-5-(4-isopropoxy-2-methylphenyl)-4-oxo-4,5-dihydro-3H-1-thia-3,5,8-triazaacenaphthylene-2-carboxamide

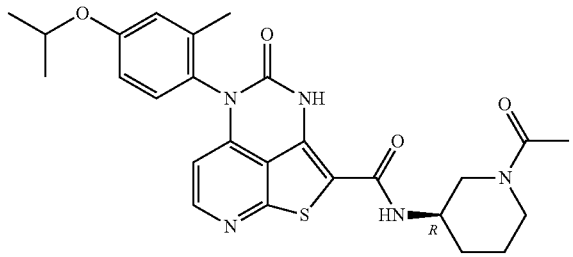

The title compound was prepared in a manner analogous to Method 1, step I in Example 1, and using (R)-5-(4-Isopropoxy-2-methylphenyl)-4-oxo-N-(piperidin-3-yl)-4,5-dihydro-3H-1-thia-3,5,8-triazaacenaphthylene-2-carboxamide (Intermediate 70), acetyl chloride and DMF in place of N-((3R,5R)-5-fluoropiperidin-3-yl)-5-(2-methyl-4-phenoxyphenyl)-4-oxo-4,5-dihydro-3H-1-thia-3,5,8-triazaacenaphthylene-2-carboxamide, prop-2-enoyl chloride and DCM. MS (ESI): mass calcd. for $C_{26}H_{29}N_5O_4S$, 507.6; m/z found, 508.2 [M+H]$^+$. $^1$H NMR (400 MHz, CD$_3$OD): δ 8.31-8.25 (m, 1H), 7.25-7.16 (m, 1H), 6.98-6.94 (m, 1H), 6.94-6.87 (m, 1H), 6.04-5.99 (m, 1H), 4.72-4.60 (m, 1H), 4.53-4.25 (m, 1H), 4.10-3.76 (m, 2H), 3.17-3.00 (m, 1H), 2.81-2.67 (m, 1H), 2.17-2.08 (m, 6H), 2.08-1.98 (m, 1H), 1.89-1.77 (m, 1H), 1.73-1.45 (m, 2H), 1.37-1.29 (m, 6H).

Example 937: (R)-4-Oxo-N-(piperidin-3-yl)-5-(3-(pyridin-3-yl)phenyl)-4,5-dihydro-3H-1-thia-3,5,8-triazaacenaphthylene-2-carboxamide

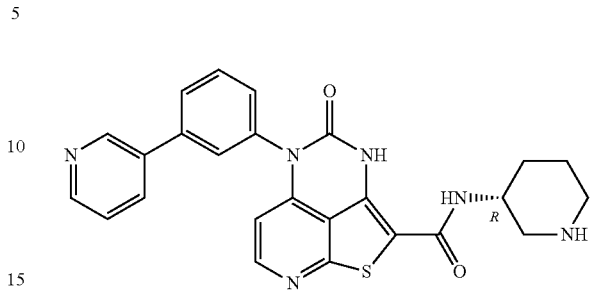

The title compound was prepared in a manner analogous to Method 1, steps C-H in Example 1, and using 3-(pyridin-3-yl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G to yield the title compound as a white solid. MS (ESI): mass calcd. for $C_{25}H_{22}N_6O_2S$, 470.5; m/z found, 471.3 [M+H]$^+$. $^1$H NMR (400 MHz, CD$_3$OD): δ 8.90-8.83 (m, 1H), 8.59-8.51 (m, 1H), 8.33 (d, J=5.6 Hz, 1H), 8.21-8.11 (m, 1H), 7.92-7.86 (m, 1H), 7.82-7.72 (m, 2H), 7.57-7.46 (m, 2H), 6.22 (d, J=5.6 Hz, 1H), 4.33-4.22 (m, 1H), 3.60-3.46 (m, 1H), 3.39-3.32 (m, 1H), 3.04-2.87 (m, 2H), 2.15-1.99 (m, 2H), 1.91-1.67 (m, 2H).

Example 938: (S,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide

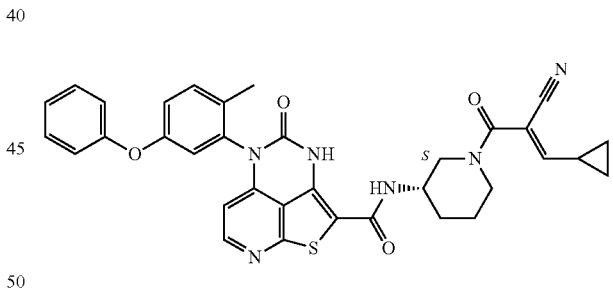

The title compound was prepared using conditions analogous to Example 877, and using (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) in place 5-(2-methyl-4-phenoxyphenyl)-4-oxo-N-(piperidin-3-yl)-4,5-dihydro-3H-1-thia-3,5,8-triazaacenaphthylene-2-carboxamide (Example 889) to give a white solid. MS (ESI): mass calcd. for $C_{34}H_{30}N_6O_4S$, 618.7; m/z found, 619.4[M+H]$^+$. $^1$H NMR (400 MHz, CD$_3$OD): δ 8.31 (d, J=5.6 Hz, 1H), 7.43 (d, J=8.5 Hz, 1H), 7.36-7.29 (m, 2H), 7.12-7.05 (m, 2H), 7.05-6.98 (m, 3H), 6.56-6.44 (m, 1H), 6.06 (d, J=5.5 Hz, 1H), 4.25-3.91 (m, 3H), 3.25-2.94 (m, 2H), 2.12 (s, 3H), 2.09-1.96 (m, 2H), 1.92-1.83 (m, 1H), 1.78-1.54 (m, 2H), 1.22-1.13 (m, 2H), 1.02-0.92 (m, 1H), 0.91-0.76 (m, 1H).

Example 939: (S,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide

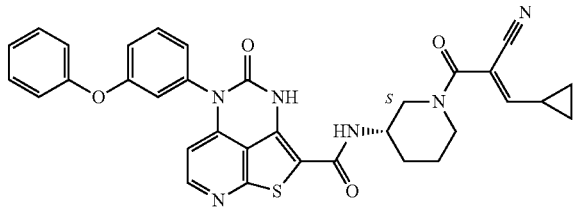

The title compound was prepared using tert-butyl (S)-3-aminopiperidine-1-carboxylate in place of tert-butyl 3-aminopiperidine-1-carboxylate in Example 851 as a white solid. MS (ESI): mass calcd. for $C_{33}H_{28}N_6O_4S$, 604.7; m/z found, 605.4[M+H]$^+$. $^1$H NMR (400 MHz, CD$_3$OD): d 8.29 (d, J=5.6 Hz, 1H), 7.59-7.53 (m, 1H), 7.40-7.31 (m, 2H), 7.18-7.09 (m, 3H), 7.09-7.03 (m, 3H), 6.53 (d, J=11.0 Hz, 1H), 6.17 (d, J=5.6 Hz, 1H), 4.30-3.92 (m, 3H), 3.25-2.92 (m, 2H), 2.07-1.94 (m, 2H), 1.91-1.82 (m, 1H), 1.79-1.55 (m, 2H), 1.24-1.15 (m, 2H), 1.02-0.92 (m, 1H), 0.90-0.79 (m, 1H).

Example 940: (S)—N-(1-benzoylpyrrolidin-3-yl)-4-oxo-5-(4-phenoxyphenyl)-4,5-dihydro-3H-1-thia-3,5,8-triazaacenaphthylene-2-carboxamide

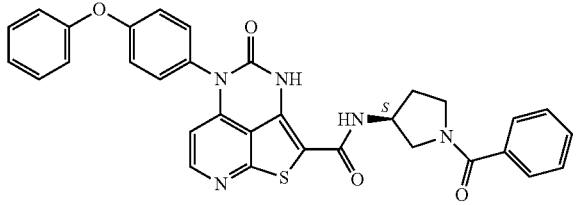

The title compound was prepared in a manner analogous to Method 1, step I in Example 1, using using (S)-4-oxo-5-(4-phenoxyphenyl)-N-(pyrrolidin-3-yl)-4,5-dihydro-3H-1-thia-3,5,8-triazaacenaphthylene-2-carboxamide (Example 934) and benzoyl chloride. MS (ESI): mass calcd. for $C_{32}H_{25}N_5O_4S$, 575.6; m/z found, 576.2 [M+H]$^+$. $^1$H NMR (400 MHz, DMSO-d$_6$): δ 8.42-8.20 (m, 2H), 7.60-7.34 (m, 9H), 7.25-7.03 (m, 5H), 6.05 (t, J=6.0 Hz, 1H), 4.56-4.34 (m, 1H), 3.83-3.63 (m, 2H), 3.57-3.47 (m, 2H), 2.25-1.87 (m, 2H).

Example 941: (R)—N-(1-Acryloylpiperidin-3-yl)-5-(3,5-dichlorophenyl)-4-oxo-4,5-dihydro-3H-1-thia-3,5,8-triazaacenaphthylene-2-carboxamide

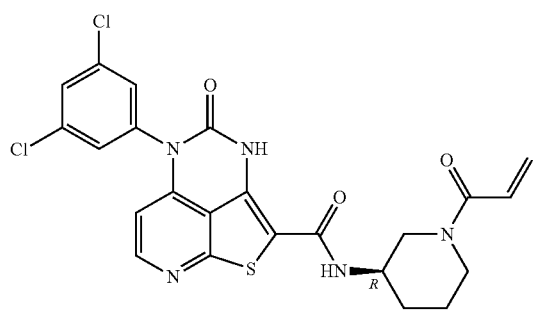

The title compound was prepared in a manner analogous to Method 1, steps C-I in Example 1, and using 3,5-dichloroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G, to yield the title compound as a white solid. MS (ESI): mass calcd. for $C_{23}H_{19}Cl_2N_5O_3S$, 516.4; m/z found, 515.8 [M+H]$^+$. $^1$H NMR (400 MHz, DMSO-d$_6$): δ 10.31 (d, J=15.7 Hz, 1H), 8.36 (d, J=5.5 Hz, 1H), 8.14-8.10 (m, 1H), 7.87-7.86 (m, 1H), 7.72 (d, J=1.8 Hz, 2H), 6.86-6.74 (m, 1H), 6.18 (d, J=5.3 Hz, 1H), 6.11 (d, J=16.5 Hz, 1H), 5.69 (d, J=11.0 Hz, 1H), 4.74-4.44 (m, 1H), 4.27-3.95 (m, 2H), 3.18-3.06 (m, 1H), 3.02-2.96 (m, 1H), 1.96-1.93 (m, 1H), 1.80-1.77 (m, 1H), 1.73-1.58 (m, 1H), 1.43 (brs, 1H).

Example 942: (S,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide

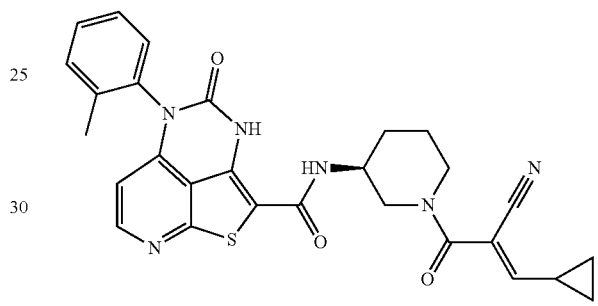

The title compound was prepared using conditions analogous to Example 886, steps A-B, using tert-butyl-3-(S)-aminopiperidine-1-carboxylate in place of tert-butyl-3-aminopiperidine-1-carboxylate in step A. MS (ESI): mass calcd. for $C_{28}H_{26}N_6O_3S$, 526.2; m/z found, 527.1 [M+H]$^+$. $^1$H NMR (400 MHz, DMSO-d$_6$): δ 10.14 (s, 1H), 8.30 (d, J=5.5 Hz, 1H), 8.04 (d, J=7.2 Hz, 1H), 7.40 (m, 4H), 6.63-6.50 (m, 1H), 5.83 (d, J=5.5 Hz, 1H), 4.17-3.99 (m, 1H), 3.98-3.78 (m, 2H), 3.07-2.73 (s, 2H), 2.08 (s, 3H), 1.95-1.89 (m, 1H), 1.89-1.81 (m, 1H), 1.81-1.73 (m, 1H), 1.73-1.59 (m, 1H), 1.55-1.40 (m, 1H), 1.18-1.09 (m, 2H), 1.03-0.92 (m, 1H), 0.87-0.78 (m, 1H).

Example 943: (R)—N-(1-Acryloylpiperidin-3-yl)-5-(3-(dimethylamino)phenyl)-4-oxo-4,5-dihydro-3H-1-thia-3,5,8-triazaacenaphthylene-2-carboxamide

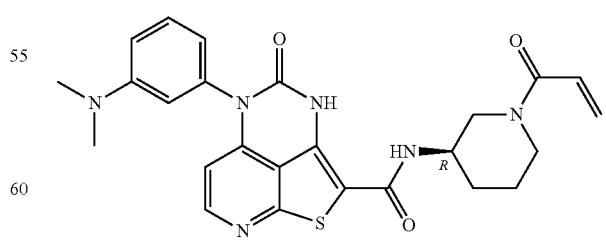

The title compound was prepared using a method analogous to Example 75, using (R)-5-(3-(Dimethylamino)phenyl)-4-oxo-N-(piperidin-3-yl)-4,5-dihydro-3H-1-thia-3,5,8-triazaacenaphthylene-2-carboxamide (Example 943) and acrylic acid. MS (ESI): mass calcd. for $C_{25}H_{26}N_6O_3S$, 490.6; m/z found, 491 [M+H]$^+$. $^1$H NMR (400 MHz, DMSO-d$_6$): δ 10.13 (d, J=14.6 Hz, 1H), 8.33 (d, J=5.5 Hz, 1H), 8.15-8.02 (m, 1H), 7.40-7.36 (m, 1H), 6.87-6.74 (m, 3H), 6.68 (d, J=7.8 Hz, 1H), 6.12 (d, J=16.6 Hz, 1H), 6.04 (d, J=5.5 Hz, 1H), 5.69 (dd, J=10.5, 2.0 Hz, 1H), 4.50-4.21 (m, 1H), 4.08-3.99 (m, 1H), 3.79 (s, 1H), 3.17-2.96 (m, 1H), 2.93 (s, 6H), 2.82-2.61 (m, 1H), 1.96-1.94 (m, 1H), 1.84-1.58 (m, 2H), 1.45 (brs, 1H).

Example 944: N-(1-(2-Cyanoacetyl)piperidin-4-yl)-5-(2-methyl-4-phenoxyphenyl)-4-oxo-4,5-dihydro-3H-1-thia-3,5,8-triazaacenaphthylene-2-carboxamide

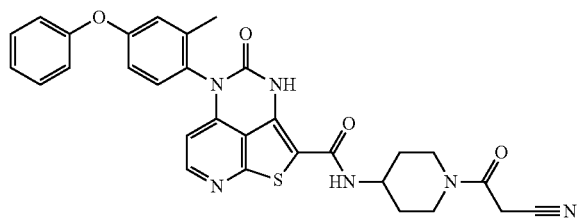 [SMILES: Cc1cc(Oc2ccccc2)ccc1N1C(=O)Nc2c(C(=O)NC3CCN(C(=O)CC#N)CC3)sc3nccc1c23]

The title compound was prepared using analogous conditions to Example 181, and using 5-(2-methyl-4-phenoxyphenyl)-4-oxo-N-(piperidin-4-yl)-4,5-dihydro-3H-1-thia-3,5,8-triazaacenaphthylene-2-carboxamide (Example 865) in place of (R)-4-oxo-5-(4-phenoxyphenyl)-N-(piperidin-3-yl)-4,5-dihydro-3H-1-thia-3,5,8-triazaacenaphthylene-2-carboxamide (Example 860) to give a white solid. MS (ESI): mass calcd. for $C_{30}H_{26}N_6O_4S$, 566.6; m/z found, 567.1 [M+H]$^+$. $^1$H NMR (400 MHz, DMSO-d$_6$): δ 8.26 (d, J=7.3 Hz, 1H), 8.14 (d, J=5.2 Hz, 1H), 7.43-7.40 (m, 2H), 7.25-7.23 (m, 1H), 7.18-7.14 (m, 1H), 7.10-7.03 (m, 3H), 6.94-6.91 (m, 1H), 5.76 (d, J=4.9 Hz, 1H), 4.13-4.08 (m, 2H), 3.85-3.79 (m, 1H), 3.58 (s, 2H), 3.18-3.08 (m, 2H), 2.02 (s, 3H), 1.83-1.76 (m, 2H), 1.47-1.34 (m, 2H).

Example 945: (S)—N-(1-Benzylpyrrolidin-3-yl)-4-oxo-5-(4-phenoxyphenyl)-4,5-dihydro-3H-1-thia-3,5,8-triazaacenaphthylene-2-carboxamide

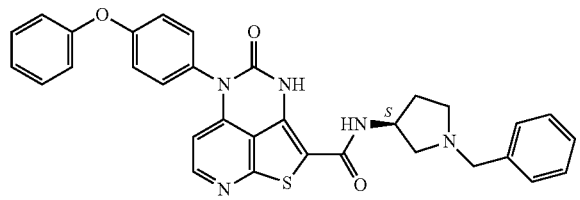

(S)-4-oxo-5-(4-phenoxyphenyl)-N-(pyrrolidin-3-yl)-4,5-dihydro-3H-1-thia-3,5,8-triazaacenaphthylene-2-carboxamide (Example 934) was dissolved in DCM (30 mL), followed by the addition of NaBH(AcO)$_3$ and benzaldehyde. The reaction mixture was stirred at room temperature under N$_2$ overnight. The mixture was washed with sat Na$_2$CO$_3$ solution and concentrated, purified by flash column chromatography eluting with water (0.5% HCOOH)/MeOH to yield the title product as a white solid. MS (ESI): mass calcd. for $C_{32}H_{27}N_5O_3S$, 561.7; m/z found, 562.2 [M+H]$^+$. $^1$H NMR (400 MHz, DMSO-d$_6$): δ 8.28 (d, J=5.1 Hz, 1H), 8.22 (d, J=6.7 Hz, 1H), 8.13 (s, 1H), 7.53-7.38 (m, 4H), 7.36-7.26 (m, 4H), 7.25-7.05 (m, 6H), 6.03 (d, J=5.3 Hz, 1H), 4.47-4.26 (m, 1H), 3.60 (s, 2H), 2.83-2.75 (m, 1H), 2.68-2.57 (m, 1H), 2.55-2.48 (m, 1H), 2.46-2.37 (m, 1H), 2.20-2.05 (m, 1H), 1.90-1.70 (m, 1H).

Example 946: (S,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide

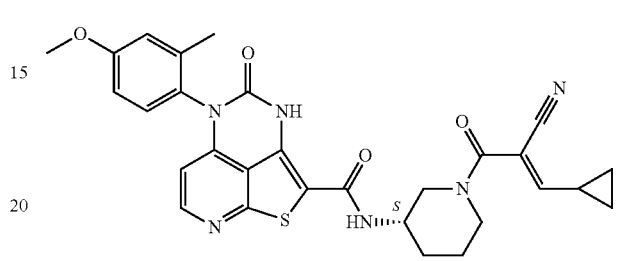

The title compound was prepared in a manner analogous to Method 1, step G-I in Example 1, using 5-(4-methoxy-2-methylphenyl)-4-oxo-4,5-dihydro-3H-1-thia-3,5,8-triazaacenaphthylene-2-carboxylic acid (Intermediate 55) and tert-butyl (3S)-3-aminopiperidine-1-carboxylate in place of 5-(2-methyl-4-phenoxyphenyl)-4-oxo-4,5-dihydro-3H-1-thia-3,5,8-triazaacenaphthylene-2-carboxylic acid (Intermediate 27) and tert-butyl (3R,5R)-3-amino-5-fluoropiperidine-1-carboxylate (Intermediate 1) in step G and using (E)-2-cyano-3-cyclopropylprop-2-enoic acid (Intermediate 17), DIEA, HATU, and DMF at room temperature instead of prop-2-enoyl chloride, triethylamine an DCM in step I to yield a white solid. MS (ESI): mass calcd. for $C_{29}H_{28}N_6O_4S$, 556.6; m/z found, 557.2 [M+H]$^+$. $^1$H NMR (400 MHz, DMSO-d$_6$): δ 10.28 (s, 1H), 8.28 (d, J=5.3 Hz, 1H), 8.16-8.04 (m, 1H), 7.29-7.20 (m, 1H), 7.04-6.95 (m, 1H), 6.95-6.86 (m, 1H), 6.68-6.46 (m, 1H), 5.88-5.84 (m, 1H), 4.11-4.00 (m, 1H), 3.88-3.69 (m, 5H), 3.18-3.09 (m, 1H), 3.02-2.86 (m, 1H), 2.03 (s, 3H), 1.94-1.83 (m, 2H), 1.82-1.73 (m, 1H), 1.70-1.59 (m, 1H), 1.53-1.41 (m, 1H), 1.17-1.08 (m, 2H), 1.03-0.90 (br, 1H), 0.88-0.78 (br, 1H).

Example 947: 5-(2-Methyl-4-phenoxyphenyl)-4-oxo-N-(1-propionylpiperidin-4-yl)-4,5-dihydro-3H-1-thia-3,5,8-triazaacenaphthylene-2-carboxamide

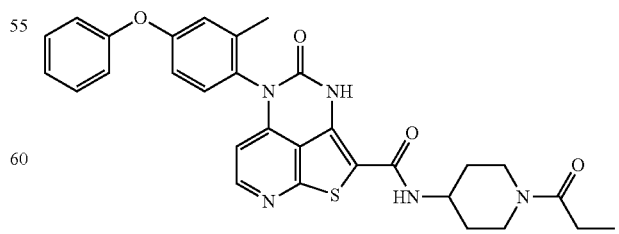

The title compound was prepared using conditions analogous to Example 921, using prop-2-ynoic acid in place of hydroxypropanoic acid to yield a white solid. MS (ESI):

mass calcd. for C₃₀H₂₉N₅O₄S, 555.7; m/z found, 556.2 [M+H]⁺. ¹H NMR (400 MHz, DMSO-d₆): δ 8.28 (d, J=5.4 Hz, 1H), 7.69 (d, J=7.4 Hz, 1H), 7.44-7.40 (m, 2H), 7.35 (d, J=8.6 Hz, 1H), 7.20-7.16 (m, 1H), 7.11-7.06 (m, 3H), 6.97-6.94 (m, 1H), 5.93 (d, J=5.4 Hz, 1H), 4.12-4.00 (m, 2H), 3.83-3.80 (m, 1H), 3.19-3.16 (m, 2H), 2.06 (s, 3H), 2.03-1.99 (m, 2H), 1.80-1.77 (m, 2H), 1.37-1.31 (m, 2H), 0.97 (t, J=7.6 Hz, 3H). Missing 1 proton signal.

Example 948: (R)—N-(1-Acryloylpiperidin-3-yl)-5-(4-aminophenyl)-4-oxo-4,5-dihydro-3H-1-thia-3,5,8-triazaacenaphthylene-2-carboxamide

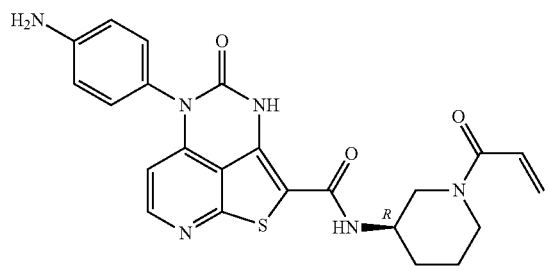

Step A: (R)—N-(1-Acryloylpiperidin-3-yl)-5-(4-nitrophenyl)-4-oxo-4,5-dihydro-3H-1-thia-3,5,8-triazaacenaphthylene-2-carboxamide The title compound was prepared in a manner analogous to Method 1, steps C-I in Example 1, and using 4-nitroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for C₂₃H₂₀N₆O₅S, 492.51; m/z found, 493.1 [M+H]⁺.

Step B: (R)—N-(1-Acryloylpiperidin-3-yl)-5-(4-aminophenyl)-4-oxo-4,5-dihydro-3H-1-thia-3,5,8-triazaacenaphthylene-2-carboxamide To a solution of (R)—N-(1-acryloylpiperidin-3-yl)-5-(4-nitrophenyl)-4-oxo-4,5-dihydro-3H-1-thia-3,5,8-triazaacenaphthylene-2-carboxamide (200 mg, 0.406 mmol) in MeOH (10 mL) in a 25 mL round bottom flask were added a saturated solution NH₄Cl (10 mL) and Zn dust (0.500 g, 7.64 mmol). The reaction mixture was stirred rt overnight, filtered, and concentrated to dryness. The residue was purified by preparative HPLC (Gemini-C18, 150×21.2 mm, 5 μm, mobile phase A: H₂O (0.1% TFA (aq.)), V/V; B: acetonitrile, B in A from 20% to 25%) to give the title compound (39.5 mg, 21.0% yield) as a yellow solid. MS (ESI): mass calcd. for C₂₃H₂₂N₆O₃S, 462.5; m/z found, 463.1 [M+H]⁺. ¹H NMR (400 MHz, DMSO-d₆): δ 10.37 (d, J=10.1 Hz, 1H), 8.39 (d, J=5.6 Hz, 1H), 8.19 (s, 1H), 7.57-7.51 (m, 4H), 6.87-6.74 (m, 1H), 6.12 (d, J=16.7 Hz, 1H), 6.07 (d, J=5.6 Hz, 1H), 5.70 (d, J=10.5 Hz, 1H), 4.50-4.20 (m, 1H), 4.12-3.96 (m, 1H), 3.79 (brs, 1H), 3.16-2.96 (m, 1H), 2.83-2.62 (m, 1H), 1.96-1.93 (m, 1H), 1.85-1.61 (m, 2H), 1.44 (brs, 1H).

Example 949: (R)-5-(4-(Dimethylamino)phenyl)-4-oxo-N-(piperidin-3-yl)-4,5-dihydro-3H-1-thia-3,5,8-triazaacenaphthylene-2-carboxamide

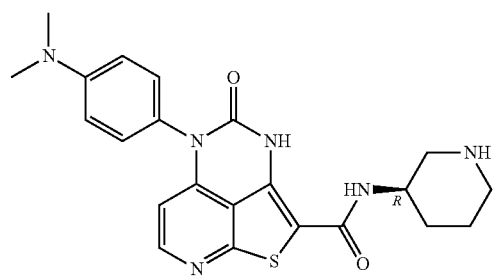

The title compound was prepared in a manner analogous to Method 1, steps C-H in Example 1, and using 4-nitroaniline and K₃PO₄ in place of 2-methyl-4-phenoxyaniline and Cs₂CO₃ in step C, and using (R)-tert-butyl 3-aminopiperidine-1-carboxylate in place of tert-butyl (3R,5R)-3-amino-5-fluoropiperidine-1-carboxylate (Intermediate 1) in step G as a white solid. MS (ESI): mass calcd. for C₂₂H₂₄N₆O₂S, 436.5; m/z found, 437.0 [M+H]⁺. ¹H NMR (400 MHz, DMSO-d₆): δ 8.31 (d, J=6.9 Hz, 1H), 8.26 (d, J=5.5 Hz, 1H), 8.18 (d, J=2.1 Hz, 1H), 7.16 (d, J=8.9 Hz, 2H), 6.85 (d, J=9.1 Hz, 2H), 5.98 (d, J=5.5 Hz, 1H), 4.09 (s, 1H), 3.28-3.25 (m, 1H), 3.14-3.11 (m, 1H), 2.98 (s, 6H), 2.80-2.70 (m, 2H), 1.96-1.81 (m, 2H), 1.68-1.55 (m, 2H).

Example 950: (R)-4-Oxo-N-(piperidin-3-yl)-5-(m-tolyl)-4,5-dihydro-3H-1-thia-3,5,8-triazaacenaphthylene-2-carboxamide

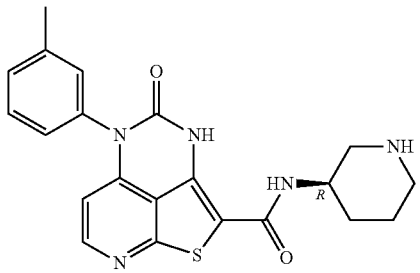

The title compound was prepared in a manner analogous to Method 1, steps C-H in Example 1, and using m-toluidine in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for C₂₁H₂₁N₅O₂S, 407.5; m/z found, 408.1 [M+H]⁺. ¹H NMR (400 MHz, DMSO-d₆): δ 8.56 (s, 1H), 8.27 (s, 1H), 8.16 (s, 1H), 7.47-7.43 (m, 1H), 7.30 (d, J=7.7 Hz, 1H), 7.15-7.12 (m, 2H), 5.84 (s, 1H), 4.04 (s, 1H), 3.25-3.22 (m, 1H), 3.09-3.05 (m, 1H), 2.73 (s, 2H), 2.38 (s, 3H), 1.95-1.92 (m, 1H), 1.85-1.82 (m, 1H), 1.67-1.50 (m, 2H).

Example 951: (R)-5-(4-Chlorophenyl)-4-oxo-N-(piperidin-3-yl)-4,5-dihydro-3H-1-thia-3,5,8-triazaacenaphthylene-2-carboxamide

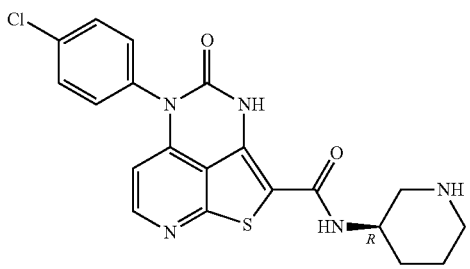

The title compound was prepared in a manner analogous to Method 1, steps C-H in Example 1, and using 4-chloroaniline in place of 2-methyl-4-phenoxyaniline in step C, and using (R)-tert-butyl 3-aminopiperidine-1-carboxylate and DIPEA in place of tert-butyl (3R,5R)-3-amino-5-fluoropiperidine-1-carboxylate and triethylamine in step G. MS (ESI): mass calcd. for $C_{20}H_{18}ClN_5O_2S$, 427.9; m/z found, 428.1 [M+H]$^+$. $^1$H NMR (400 MHz, DMSO-d$_6$): δ 10.32 (s, 1H), 9.37 (s, 1H), 9.18 (s, 1H), 8.38-8.36 (m, 2H), 7.70 (d, J=8.7 Hz, 2H), 7.53 (d, J=8.6 Hz, 2H), 6.11 (d, J=5.6 Hz, 1H), 4.28-4.15 (m, 1H), 3.31-3.29 (m, 1H), 3.20-3.17 (m, 1H), 2.94-2.81 (m, 2H), 1.92-1.89 (m, 2H), 1.82-1.57 (m, 2H).

Example 952: (R)-4-Oxo-N-(piperidin-3-yl)-5-(p-tolyl)-4,5-dihydro-3H-1-thia-3,5,8-triazaacenaphthylene-2-carboxamide

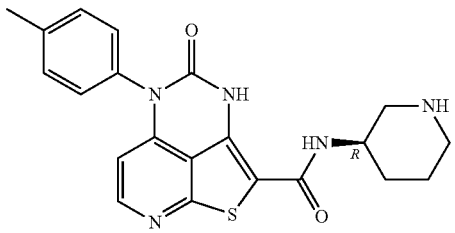

The title compound was prepared in a manner analogous to Method 1, steps C-H in Example 1, and using p-toluidine in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{21}H_{21}N_5O_2S$, 407.5; m/z found, 407.9 [M+H]$^+$. $^1$H NMR (400 MHz, DMSO-d$_6$): δ 8.56 (s, 1H), 8.27 (s, 1H), 8.19-8.15 (m, 1H), 7.59-7.56 (m, 2H), 7.51-7.47 (m, 1H), 7.36 (d, J=7.5 Hz, 2H), 5.85-5.82 (m, 1H), 4.06 (s, 1H), 3.27-3.25 (m, 1H), 3.10-3.07 (m, 1H), 2.75 (s, 2H), 1.95-1.93 (m, 1H), 1.86-1.83 (m, 1H), 1.66-1.57 (m, 2H).

Example 953: (R)-5-(4-Fluorophenyl)-4-oxo-N-(piperidin-3-yl)-4,5-dihydro-3H-1-thia-3,5,8-triazaacenaphthylene-2-carboxamide

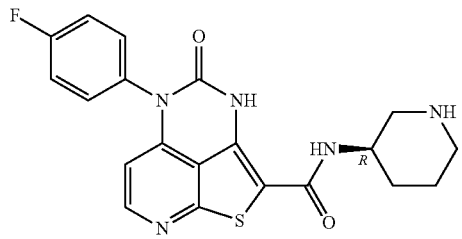

The title compound was prepared in a manner analogous to Method 1, steps C-H in Example 1, and using 4-fluoroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for $C_{20}H_{18}FN_5O_2S$, 411.5; m/z found, 411.9 [M+H]$^+$. $^1$H NMR (400 MHz, DMSO-d$_6$): δ 8.56 (s, 1H), 8.30 (s, 1H), 8.21-8.19 (m, 1H), 7.42-7.40 (m, 4H), 5.91-5.88 (m, 1H), 4.09 (s, 1H), 3.28-3.25 (m, 1H), 3.12-3.09 (m, 1H), 2.79 (s, 2H), 1.98-1.81 (m, 2H), 1.71-1.51 (m, 2H).

Example 954: (R)-5-(4-(tert-Butyl)phenyl)-4-oxo-N-(piperidin-3-yl)-4,5-dihydro-3H-1-thia-3,5,8-triazaacenaphthylene-2-carboxamide

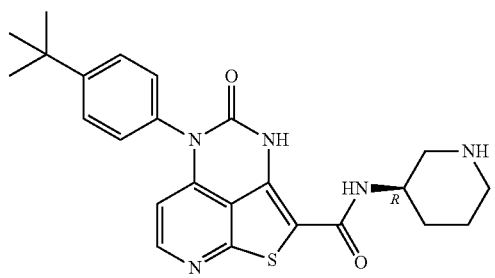

The title compound was prepared in a manner analogous to Method 1, steps C-H in Example 1, and using 4-(tert-butyl)aniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G and. MS (ESI): mass calcd. for $C_{24}H_{27}N_5O_2S$, 449.6; m/z found, 450.1 [M+H]$^+$. $^1$H NMR (400 MHz, DMSO-d$_6$): δ 10.21 (s, 1H), 9.15 (brs, 1H), 8.99 (brs, 1H), 8.35 (d, J=5.6 Hz, 1H), 8.27 (d, J=7.5 Hz, 1H), 7.62 (d, J=8.8 Hz, 2H), 7.37 (d, J=8.4 Hz, 2H), 6.01 (d, J=5.5 Hz, 1H), 4.25-4.17 (m, 1H), 3.32-3.30 (m, 1H), 3.21-3.18 (m, 1H), 2.94-2.76 (m, 2H), 1.97-1.85 (m, 2H), 1.78-1.58 (m, 2H), 1.36 (s, 9H).

Example 955: (R)-5-(4-Isopropoxy-3-methylphenyl)-4-oxo-N-(piperidin-3-yl)-4,5-dihydro-3H-1-thia-3,5,8-triazaacenaphthylene-2-carboxamide

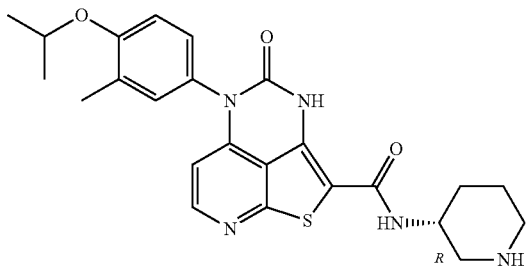

Step A: (R)-tert-Butyl 3-(3-amino-4-((4-isopropoxy-3-methylphenyl)amino)thieno[2,3-b]pyridine-2-carboxamido)piperidine-1-carboxylate To a microwave vial containing a stir bar were added 2-chloro-4-iodonicotinonitrile (1441 mg, 5.449 mmol), 4-isopropoxy-3-methylaniline (907 mg, 5.49 mmol), DPEPhos (144 mg, 0.268 mmol), Pd(OAc)$_2$ (58.0 mg, 0.258 mmol), and Cs$_2$CO$_3$ (1775 mg, 5.448 mmol). To the vial was added with dioxane (10 mL) via syringe and the mixture was degassed under a vacuum for 1 minute, then vented to nitrogen. The reaction was heated in the microwave at 150° C. for 30 minutes. The reaction was cooled to room temperature, treated with (R)-tert-butyl 3-(2-mercaptoacetamido)piperidine-1-carboxylate (Intermediate 22) (0.49 M in dioxane, 10 mL, 4.9 mmol) via syringe, evacuated and flushed with nitrogen, and stirred at 150° C. for 20 min. The reaction was then cooled to room temperature. The reaction mixture was treated with solid CDI (2230 mg, 13.75 mmol) in one portion under air, resealed, evacuated and flushed with nitrogen, and stirred at 150° C. for 20 min. The CDI reaction did not go, so the intermediate was purified. The reaction was then diluted with EtOAc (100 mL) and saturated aqueous sodium bicarbonate (100 mL) and separated. The aqueous layer was extracted again with EtOAc (100 mL), and the combined organics were dried over anhydrous MgSO$_4$, concentrated to dryness, and purified by flash column chromatography to yield the title compound (558 mg, 19.0% yield). MS (ESI): mass calcd. for C$_{28}$H$_{37}$N$_5$O$_4$S, 539.70; m/z found, 540.2 [M+H]$^+$.

Step B: (R)-tert-Butyl 3-(5-(4-isopropoxy-3-methylphenyl)-4-oxo-4,5-dihydro-3H-1-thia-3,5,8-triazaacenaphthylene-2-carboxamido)piperidine-1-carboxylate (R)-tert-Butyl 3-(3-amino-4-((4-isopropoxy-3-methylphenyl)amino)thieno[2,3-b]pyridine-2-carboxamido)piperidine-1-carboxylate (558 mg, 1.03 mmol) was added to a 25 mL microwave vessel (Biotage) and treated with Cs$_2$CO$_3$ (589 mg, 1.81 mmol) and CDI (360 mg, 2.22 mmol). The mixture was suspended in dioxane (10 mL), capped, and heated at 150° C. for 20 minutes. The reaction mixture was treated with DCM (20 mL), filtered, and concentrated to dryness. The residue was purified by flash column chromatography to yield the title compound (478.1 mg, 81.74% yield) as a yellow oil. MS (ESI): mass calcd. for C$_{29}$H$_{35}$N$_5$O$_5$S, 565.69; m/z found, 566.1 [M+H]$^+$.

Step C: (R)-5-(4-Isopropoxy-3-methylphenyl)-4-oxo-N-(piperidin-3-yl)-4,5-dihydro-3H-1-thia-3,5,8-triazaacenaphthylene-2-carboxamide A solution of (R)-tert-butyl 3-(5-(4-isopropoxy-3-methylphenyl)-4-oxo-4,5-dihydro-3H-1-thia-3,5,8-triazaacenaphthylene-2-carboxamido)piperidine-1-carboxylate (478.1 mg, 0.8450 mmol) in dioxane (4 mL) was treated with 4 M HCl in dioxane (10 mL, 40 mmol). After 30 min at room temperature, a gummy precipitate has settled on the bottom of the vial. The dioxane was poured off, and the precipitate was treated with 20 mL saturated aqueous sodium bicarbonate, extracted DCM (2×50 mL), dried over anhydrous MgSO$_4$, concentrated to dryness. The residue was purified by flash column chromatography, the pooled fractions were concentrated to dryness, taken up in DCM (2 mL), and were precipitated with 10 mL hexanes to give a white precipitate. The precipitate was collected by filtration and dried under a vacuum to give an off white solid. One fraction (63 mg) was subjected to purification by reverse phase acidic HPLC to give the title compound (38.4 mg, 9.76% yield). MS (ESI): mass calcd. for C$_{24}$H$_{27}$N$_5$O$_3$S, 465.6; m/z found, 466.2 [M+H]$^+$. $^1$H NMR (400 MHz, DMSO-d$_6$): δ 8.55-8.40 (d, J=7.6 Hz, 1H), 8.17-8.09 (d, J=5.5 Hz, 1H), 7.12-7.00 (s, 3H), 5.90-5.81 (d, J=5.5 Hz, 1H), 4.70-4.59 (m, 1H), 4.25-3.37 (m, 3H), 3.22-3.13 (m, 1H), 3.06-2.96 (d, J=12.1 Hz, 1H), 2.72-2.58 (m, 2H), 2.16 (s, 3H), 1.98-1.86 (m, 1H), 1.84-1.70 (m, 1H), 1.64-1.45 (m, 2H), 1.39-1.25 (d, J=5.9 Hz, 6H).

Example 956: (R)-5-(4-Aminophenyl)-4-oxo-N-(piperidin-3-yl)-4,5-dihydro-3H-1-thia-3,5,8-triazaacenaphthylene-2-carboxamide

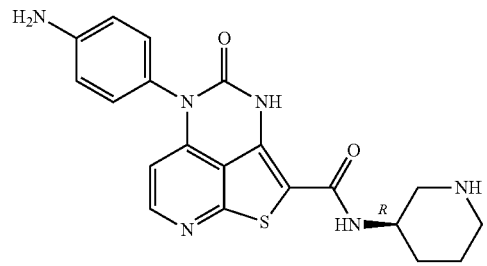

Step A: (R)-5-(4-Nitrophenyl)-4-oxo-N-(piperidin-3-yl)-4,5-dihydro-3H-1-thia-3,5,8-triazaacenaphthylene-2-carboxamide The title compound was prepared in a manner analogous to Method 1, steps C-H in Example 1, and using 4-nitroaniline in place of 2-methyl-4-phenoxyaniline in step C, and using (R)-tert-butyl 3-aminopiperidine-1-carboxylate in place of tert-butyl (3R,5R)-3-amino-5-fluoropiperidine-1-carboxylate (Intermediate 1) in step G. MS (ESI): mass calcd. for C$_{20}$H$_{18}$N$_6$O$_4$S, 438.46; m/z found, 439.1 [M+H]$^+$.

Step B: (R)-5-(4-Aminophenyl)-4-oxo-N-(piperidin-3-yl)-4,5-dihydro-3H-1-thia-3,5,8-triazaacenaphthylene-2-carboxamide To a solution of (R)-5-(4-nitrophenyl)-4-oxo-N-(piperidin-3-yl)-4,5-dihydro-3H-1-thia-3,5,8-triazaacenaphthylene-2-carboxamide (100 mg, 0.228 mmol) in MeOH (10 mL) was added 10% Pd/C (30 mg). The reaction was stirred under a H₂ atmosphere at rt overnight. The Pd/C was filtered off and the filtrate was concentrated to dryness and was purified by preparative HPLC (Gemini-C18, 150×21.2 mm, 5 μm, mobile phase A: H₂O (0.1% TFA (aq.)), V/V; B: acetonitrile, B in A from 20% to 25%) to give the title compound (11.1 mg, 12.0% yield) as yellow solid. MS (ESI): mass calcd. for C₂₀H₂₀N₆O₂S, 408.5; m/z found, 409.1 [M+H]⁺. ¹H NMR (400 MHz, DMSO-d₆): δ 10.20 (s, 1H), 9.12 (s, 1H), 8.98 (s, 1H), 8.36 (d, J=5.5 Hz, 1H), 8.29 (d, J=5.6 Hz, 1H), 7.38 (s, 2H), 7.26 (s, 2H), 6.06 (d, J=5.5 Hz, 1H), 4.20 (brs, 1H), 3.33-3.30 (m, 1H), 3.22-3.19 (m, 1H), 2.94-2.77 (m, 2H), 1.92 (brs, 2H), 1.78-1.60 (m, 2H).

Example 957: (S,E)-N-(1-(2-Cyano-3-cyclopropylacryloyl)piperidin-3-yl)-5-(2-methyl-3-phenoxyphenyl)-4-oxo-4,5-dihydro-3H-1-thia-3,5,8-triazaacenaphthylene-2-carboxamide

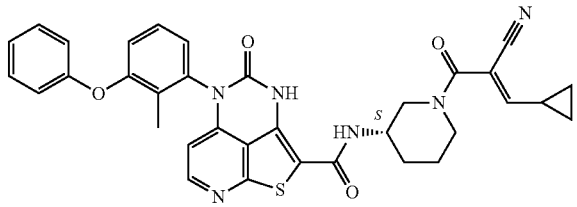

The title compound was prepared using a method analogous to Example 75, using (EZ)-2-Chloro-3-cyclopropylprop-2-enoic acid (Intermediate 39) and (S)-5-(2-methyl-4-phenoxyphenyl)-4-oxo-N-(piperidin-3-yl)-4,5-dihydro-3H-1-thia-3,5,8-triazaacenaphthylene-2-carboxamide (Example 912) to yield a white solid. MS (ESI): mass calcd. for C₃₄H₃₀N₆O₄S, 618.7; m/z found, 619.2 [M+H]⁺. ¹H NMR (400 MHz, DMSO-d₆): δ 10.22 (s, 1H), 8.37 (d, J=5.4 Hz, 1H), 8.16 (d, J=7.1 Hz, 1H), 7.48-7.37 (m, 3H), 7.30-7.23 (m, 1H), 7.16-7.06 (m, 2H), 7.03-6.97 (m, 2H), 6.63-6.57 (m, 1H), 6.03 (d, J=5.4 Hz, 1H), 4.18-3.80 (m, 3H), 3.14-2.73 (m, 2H), 1.99 (s, 3H), 1.95-1.67 (m, 4H), 1.56-1.45 (m, 1H), 1.20-1.11 (m, 2H), 1.02-0.83 (m, 2H).

Example 958: (R)-5-(*S)-(6-Isopropoxy-4-methylpyridin-3-yl)-4-oxo-N-(pyrrolidin-3-yl)-4,5-dihydro-3H-1-thia-3,5,8-triazaacenaphthylene-2-carboxamide

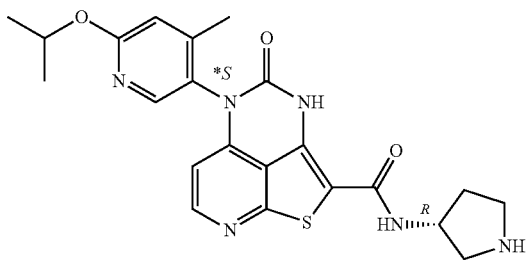

The title compound was prepared in a manner analogous to Method 1, steps A-H (including Chiral Resolution Method A after step F to obtain the *S atropisomer) in Example 1, and using 2-fluoro-4-methyl-5-nitropyridine and 2-propanol in place of 5-fluoro-2-nitrotoluene and phenol in step A, and using Pd/C and MeOH in place of Fe, EtOH/ H₂O, and NH₄Cl in step B, and using 6-isopropoxy-4-methylpyridin-3-amine in place of 2-methyl-4-phenoxyaniline in step C, and using (R)-tert-butyl 3-aminopyrrolidine-1-carboxylate in place of tert-butyl (3R,5R)-3-amino-5-fluoropiperidine-1-carboxylate (Intermediate 1) in step G and using TFA in place of HCl in step H. MS (ESI): mass calcd. for C₂₂H₂₄N₆O₃S, 452.5; m/z found, 453.2 [M+H]⁺. ¹H NMR (500 MHz, CDCl₃): δ 8.30 (d, J=5.5 Hz, 1H), 8.01 (s, 1H), 7.62 (s, 1H), 6.71 (d, J=0.8 Hz, 1H), 6.01 (d, J=5.5 Hz, 1H), 4.75 (s, 1H), 3.55-3.36 (m, 6H), 3.26 (ddd, J=11.4, 8.6, 6.4 Hz, 1H), 2.42-2.31 (m, 1H), 2.20-2.08 (m, 4H), 1.36 (dd, J=14.5, 6.1 Hz, 6H).

Example 959: (R)—N-(1-Acryloylpyrrolidin-3-yl)-5-(*S)-(6-isopropoxy-4-methylpyridin-3-yl)-4-oxo-4,5-dihydro-3H-1-thia-3,5,8-triazaacenaphthylene-2-carboxamide

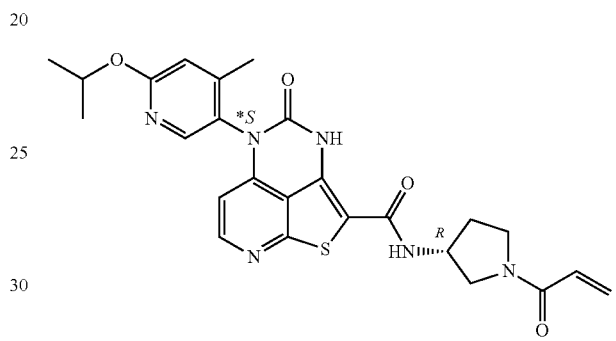

The title compound was prepared in a manner analogous to Method 1, step I in Example 1, using (R)-5-(*S)-(6-Isopropoxy-4-methylpyridin-3-yl)-4-oxo-N-(pyrrolidin-3-yl)-4,5-dihydro-3H-1-thia-3,5,8-triazaacenaphthylene-2-carboxamide (Example 958), acrylic anhydride and DIPEA in place of N-((3R,5R)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide, prop-2-enoyl chloride and triethylamine. MS (ESI): mass calcd. for C₂₅H₂₆N₆O₄S, 506.6; m/z found, 507.2 [M+H]⁺. ¹H NMR (500 MHz, CDCl₃): δ 8.34 (t, J=5.6 Hz, 1H), 8.01 (d, J=4.6 Hz, 1H), 6.72 (s, 1H), 6.49-6.31 (m, 2H), 6.04 (dd, J=8.0, 5.4 Hz, 1H), 5.70 (ddd, J=16.2, 9.1, 3.2 Hz, 1H), 5.38-5.26 (m, 1H), 4.80-4.65 (m, 1H), 4.12 (q, J=7.1 Hz, 1H), 3.85-3.61 (m, 3H), 2.39-2.19 (m, 2H), 2.16-1.99 (m, 5H), 1.45-1.28 (m, 6H).

Example 960: (R,E)-N-(1-(2-Cyano-3-(1-methylcyclobutyl)acryloyl)piperidin-3-yl)-5-(2-methyl-6-phenoxypyridin-3-yl)-4-oxo-4,5-dihydro-3H-1-thia-3,5,8-triazaacenaphthylene-2-carboxamide

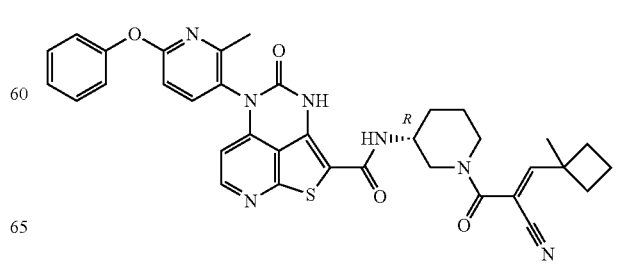

Step A: (R)-5-(2-Methyl-6-phenoxypyridin-3-yl)-4-oxo-N-(piperidin-3-yl)-4,5-dihydro-3H-1-thia-3,5,8-triazaacenaphthylene-2-carboxamide The title compound was prepared using analogous conditions described in Method 1, steps A-H in Example 1, and using 6-chloro-2-methyl-3-nitropyridine in place of 5-fluoro-2-nitrotoluene in step A and using Pd/C and MeOH in place of Fe, EtOH/H$_2$O, and NH$_4$Cl in step B, and using 2-methyl-6-phenoxypyridin-3-amine (Intermediate 49) in place of 2-methyl-4-phenoxyaniline in step C, and using (R)-tert-butyl 3-aminopiperidine-1-carboxylate in place of tert-butyl (3R,5R)-3-amino-5-fluoro-piperidine-1-carboxylate in step G to yield the title compound. MS (ESI): mass calcd. for C$_{26}$H$_{24}$N$_6$O$_3$S, 500.57; m/z found, 501.1 [M+H]$^+$.

Step B: (R,E)-N-(1-(2-Cyano-3-(1-methylcyclobutyl)acryloyl)piperidin-3-yl)-5-(2-methyl-6-phenoxypyridin-3-yl)-4-oxo-4,5-dihydro-3H-1-thia-3,5,8-triazaacenaphthylene-2-carboxamide To a round bottom flask were added (R)—N-(1-(2-cyanoacetyl)piperidin-3-yl)-5-(2-methyl-6-phenoxypyridin-3-yl)-4-oxo-4,5-dihydro-3H-1-thia-3,5,8-triazaacenaphthylene-2-carboxamide (Intermediate 77, 200 mg, 0.352 mmol), 3-methyloxetane-3-carbaldehyde (106 mg, 1.06 mmol), piperidine (0.3 mL), AcOH (0.1 mL), 4A molecular sieves (500 mg), and dioxane (5 mL) and was stirred at reflux for 1 h. The mixture was filtered and the filtrate was concentrated to dryness. The residue was purified by normal phase flash column chromatography (SiO$_2$) to give the title compound (165 mg, 72.1% yield) as light yellow solid. MS (ESI): mass calcd. for C$_{34}$H$_{31}$N$_7$O$_5$S, 649.72; m/z found, 650.2 [M+H]$^+$. $^1$H NMR (400 MHz, DMSO-d$_6$): δ 10.25 (s, 1H), 8.36-8.32 (m, 1H), 8.24-8.07 (m, 1H), 7.91-7.82 (m, 1H), 7.48-7.40 (m, 2H), 7.35-7.31 (m, 1H), 7.27-7.18 (m, 3H), 7.02-6.97 (m, 1H), 6.11-6.06 (m, 1H), 4.88-4.52 (m, 2H), 4.45-4.01 (m, 3H), 3.97-3.79 (m, 2H), 3.19-2.98 (m, 1H), 2.96-2.61 (m, 1H), 2.15-2.09 (m, 3H), 2.01-1.89 (m, 1H), 1.88-1.76 (m, 1H), 1.74-1.48 (m, 5H).

Example 961: N$^1$-((E)-4-((R)-3-(1-(2-Methyl-6-phenoxypyridin-3-yl)-2-oxo-1,2,3,5-tetrahydrocyclopenta[de]quinazoline-4-carboxamido)piperidin-1-yl)-4-oxobut-2-en-1-yl)-N$^5$-(15-oxo-19-((3aR,4R,6aS)-2-oxooctahydrocyclopenta[d]imidazol-4-yl)-4,7,10-trioxa-14-azanonadecyl)glutaramide

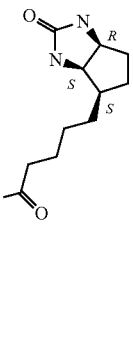

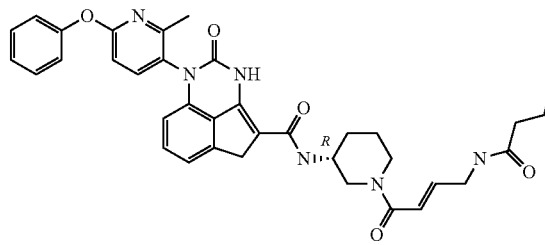

Step A: 5,21-Dioxo-25-((3aR,4R,6aS)-2-oxooctahydrocyclopenta[d]imidazol-4-yl)-10,13,16-trioxa-6,20-diazapentacosan-1-oic Acid The title compound was prepared using analogous conditions described in Example 237, steps A-E as a white solid.

Step B: (R,E)-tert-Butyl (4-(3-(5-(2-methyl-6-phenoxypyridin-3-yl)-4-oxo-4,5-dihydro-3H-1-thia-3,5,8-triazaacenaphthylene-2-carboxamido)piperidin-1-yl)-4-oxobut-2-en-1-yl)carbamate The title compound was prepared in a manner analogous to Method 1, steps A-I in Example 1, and using 6-chloro-2-methyl-3-nitropyridine in place of methyl (2R,4S)-4-hydroxypyrrolidine-2-carboxylate in step A, and using Pd/C and MeOH in place of Fe, EtOH/H$_2$O, and NH$_4$Cl in step B, and using 2-methyl-6-phenoxypyridin-3-amine (Intermediate 49) in place of 2-methyl-4-phenoxyaniline in step C, and using and using (R)-tert-butyl 3-aminopiperidine-1-carboxylate in place of tert-butyl (3R,5R)-3-amino-5-fluoropiperidine-1-carboxylate (Intermediate 1) in step G, and using (E)-4-((tert-butoxycarbonyl)amino)but-2-enoic acid, DMF, and HATU in place of prop-2-enoyl chloride and DCM in step I.

Step C: N¹-((E)-4-((R)-3-(1-(2-Methyl-6-phenoxy-pyridin-3-yl)-2-oxo-1,2,3,5-tetrahydrocyclopenta[de]quinazoline-4-carboxamido)piperidin-1-yl)-4-oxobut-2-en-1-yl)-N⁵-(15-oxo-19-((3aR,4R,6aS)-2-oxooctahydrocyclopenta[d]imidazol-4-yl)-4,7,10-trioxa-14-azanonadecyl)glutaramide A solution of (R,E)-tert-butyl (4-(3-(5-(2-methyl-6-phenoxypyridin-3-yl)-4-oxo-4,5-dihydro-3H-1-thia-3,5,8-triazaacenaphthylene-2-carboxamido)piperidin-1-yl)-4-oxobut-2-en-1-yl)carbamate (900 mg, 1.32 mmol) in 4.0 M HCl in methanol (20 mL) was stirred at room temperature for 1 hour. The reaction was concentrated to dryness to give de-Boc product. A solution of 5,21-dioxo-25-((3aR,4R,6aS)-2-oxooctahydrocyclopenta[d]imidazol-4-yl)-10,13,16-trioxa-6,20-diazapentacosan-1-oic acid (738 mg, 1.32 mmol), triethylamine (266 mg, 2.63 mmol), and HATU (600 mg, 1.58 mmol) in DMF (10 mL) was stirred at room temperature for 15 minutes to give the activated-ester solution. The de-Boc product was dissolved in DMF (10 mL) and triethylamine (266 mg, 2.63 mmol) and the activated-ester solution was added to it. The mixture was stirred at room temperature for 10 minutes and TLC showed the reaction had gone to completion. The mixture was purified by normal phase flash column chromatography (SiO₂) to give the title compound (1.1 g, 99% yield) as a light yellow solid. MS (ESI): mass calcd. for $C_{55}H_{71}D_5N_{11}O_{11}S_2$, 1126.35; m/z found, 1126.5 [M+H]⁺. ¹H NMR (400 MHz, CD₃OD): δ 8.40-8.32 (m, 1H), 7.90-7.76 (m, 1H), 7.50-7.41 (m, 2H), 7.27-7.22 (m, 1H), 7.22-7.15 (m, 2H), 6.95-6.87 (m, 1H), 6.76-6.64 (m, 1H), 6.59-6.50 (m, 1H), 6.20-6.12 (m, 1H), 4.52-4.42 (m, 1H), 4.33-4.07 (m, 2H), 4.03-3.87 (m, 3H), 3.67-3.43 (m, 12H), 3.28-3.12 (m, 6H), 3.05-2.83 (m, 2H), 2.74-2.63 (m, 1H), 2.32-2.24 (m, 5H), 2.24-2.13 (m, 4H), 2.12-1.99 (m, 1H), 1.97-1.82 (m, 3H), 1.80-1.50 (m, 10H), 1.48-1.35 (m, 2H).

Example 962: (R,E)-N-(1-(2-Cyano-4-ethoxy-4-methylpent-2-enoyl)piperidin-3-yl)-5-(2-methyl-6-phenoxypyridin-3-yl)-4-oxo-4,5-dihydro-3H-1-thia-3,5,8-triazaacenaphthylene-2-carboxamide

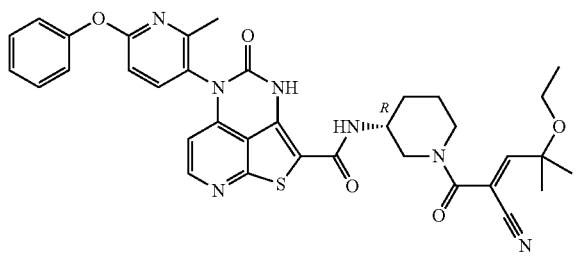

To a solution of (R)—N-(1-(2-cyanoacetyl)piperidin-3-yl)-5-(2-methyl-6-phenoxypyridin-3-yl)-4-oxo-4,5-dihydro-3H-1-thia-3,5,8-triazaacenaphthylene-2-carboxamide (Intermediate 77) (500 mg, 0.881 mmol), 2-ethoxy-2-methylpropanal (205 mg, 1.76 mmol), and acetic acid (100 μL) in dioxane (15 mL) was added piperidine (300 μL) and heated at refluxed for 1 h. The reaction was concentrated to dryness and purified by normal phase flash column chromatography (SiO₂) to give the title compound (86 mg, 14% yield) and as a pale yellow solid. MS (ESI): mass calcd. for $C_{35}H_{35}N_7O_5S$, 665.76; m/z found, 666.3 [M+H]⁺. ¹H NMR (400 MHz, CD₃OD): δ 8.36-8.26 (m, 1H), 7.85-7.74 (m, 1H), 7.48-7.38 (m, 2H), 7.28-7.14 (m, 3H), 6.93-6.83 (m, 2H), 6.15-6.06 (m, 1H), 4.52-3.81 (mz, 3H), 3.54-3.43 (m, 2H), 3.28-2.74 (m, 2H), 2.28-2.18 (m, 3H), 2.10-2.01 (m, 1H), 1.96-1.85 (m, 1H), 1.81-1.57 (m, 2H), 1.47-1.32 (m, 6H), 1.27-1.12 (m, 3H).

Example 963: (R,E)-N-(1-(2-Cyano-3-cyclopropylacryloyl)piperidin-3-yl)-5-(2-methyl-6-phenoxypyridin-3-yl)-4-oxo-4,5-dihydro-3H-1-thia-3,5,8-triazaacenaphthylene-2-carboxamide

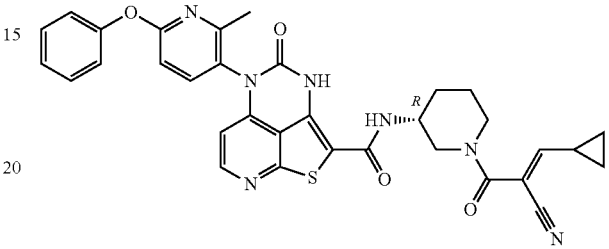

solution of (R)—N-(1-(2-cyanoacetyl)piperidin-3-yl)-5-(2-methyl-6-phenoxypyridin-3-yl)-4-oxo-4,5-dihydro-3H-1-thia-3,5,8-triazaacenaphthylene-2-carboxamide (Intermediate 77) (500 mg, 0.881 mmol), cyclopropanecarbaldehyde (617 mg, 8.81 mmol), acetic acid (0.1 mL), piperidine (0.3 mL), and 4A molecular sieves (500 mg) in dioxane (8 mL) was purged with N₂, and then was stirred at 105° C. for 1 h. The solid was filtrated off and the liquid was purified by normal phase flash column chromatography (SiO₂) to give the title compound (190 mg, 34.8% yield) as a grey solid. MS (ESI): mass calcd. for $C_{33}H_{29}N_7O_4S$, 619.69; m/z found, 620.1 [M+H]⁺. ¹H NMR (400 MHz, CDCl₃): δ 9.51 (s, 1H), 8.38 (d, J=5.5 Hz, 1H), 7.59-7.48 (m, 1H), 7.46-7.39 (m, 2H), 7.26-7.18 (m, 3H), 6.83-6.80 (m, 1H), 6.79-6.62 (m, 1H), 6.05 (d, J=5.5 Hz, 1H), 4.24-4.09 (m, 1H), 4.09-3.29 (m, 4H), 2.30-2.25 (m, 3H), 2.13-1.87 (m, 3H), 1.84-1.68 (m, 2H), 1.28-1.23 (m, 2H), 1.02-0.84 (m, 2H).

Example 29: (R)—N-(1-Acryloylpyrrolidin-3-yl)-5-(*R)-(2-meth-4-(pyridin-2-yloxy)phenyl)-4-oxo-4,5-dihydro-3H-1-thia-3,5,8-triazaacenaphthylene-2-carboxamide

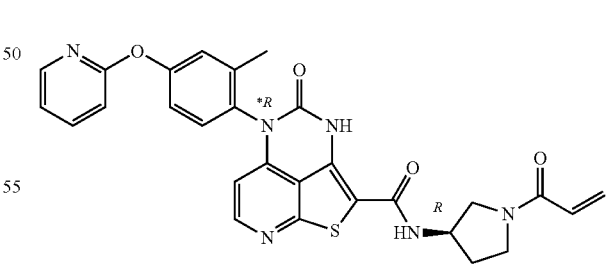

(R)—N-(1-Acryloylpyrrolidin-3-yl)-5-(2-methyl-4-(pyridin-2-yloxy)phenyl)-4-oxo-4,5-dihydro-3H-1-thia-3,5,8-triazaacenaphthylene-2-carboxamide (Example 781) was resolved by chiral SFC (Stationary phase: CHIRALCEL OJ-H, 5 μm, 250×20 mm, Mobile phase: 80% CO₂, 20% MeOH) to yield the *R atropisomer, followed by Method 1, step I in Example 1, to yield the title compound. MS (ESI): mass calcd. for $C_{28}H_{24}N_6O_4S$, 540.6; m/z found, 541.2

[M+H]+. 1H NMR (400 MHz, CDCl3): δ 9.53 (d, J=24.1 Hz, 1H), 8.37 (t, J=5.4 Hz, 1H), 8.25 (dd, J=4.9, 2.1 Hz, 1H), 7.75 (tt, J=8.3, 1.5 Hz, 1H), 7.26-6.92 (m, 5H), 6.51-6.33 (m, 2H), 6.10 (dd, J=7.1, 4.6 Hz, 1H), 5.83-5.59 (m, 1H), 5.30 (d, J=2.8 Hz, 1H), 4.73 (dd, J=14.9, 8.7 Hz, 1H), 4.06-3.51 (m, 4H), 2.45-1.72 (m, 5H).

Example 30: (R)—N-(1-Acryloylpyrrolidin-3-yl)-5-(*S)-(2-meth-4-(pyridin-2-yloxy)phenyl)-4-oxo-4,5-dihydro-3H-1-thia-3,5,8-triazaacenaphthylene-2-carboxamide

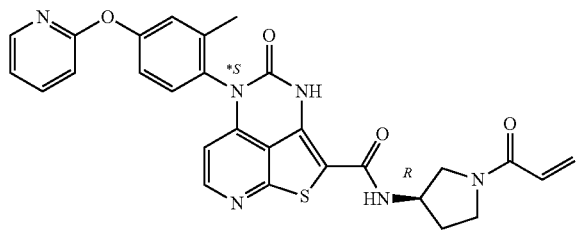

(R)—N-(1-Acryloylpyrrolidin-3-yl)-5-(2-methyl-4-(pyridin-2-yloxy)phenyl)-4-oxo-4,5-dihydro-3H-1-thia-3,5,8-triazaacenaphthylene-2-carboxamide (Example 781) was resolved by chiral SFC (Stationary phase: CHIRALCEL OJ-H, 5 μm, 250×20 mm, Mobile phase: 80% CO2, 20% MeOH) to yield the *S atropisomer, followed by Method 1, step I in Example 1, to yield the title compound. MS (ESI): mass calcd. for C28H24N6O4S, 540.6; m/z found, 541.2 [M+H]+. 1H NMR (400 MHz, Chloroform-d) δ 9.52 (d, J=24.8 Hz, 1H), 8.45-8.32 (m, 1H), 8.32-8.20 (m, 1H), 7.84-7.68 (m, 1H), 7.22-6.94 (m, 4H), 6.54-6.34 (m, 2H), 6.17-6.00 (m, 1H), 5.81-5.65 (m, 1H), 5.36-5.25 (m, 1H), 4.79-4.62 (m, 1H), 4.02-3.51 (m, 4H), 2.44-1.99 (m, 5H), 1.83-1.48 (m, 1H).

Example 31: (R)—N-(1-Acryloylpiperidin-3-yl)-5-(*R)-(2-methyl-4-(pyridin-2-yloxy)phenyl)-4-oxo-4,5-dihydro-3H-1-thia-3,5,8-triazaacenaphthylene-2-carboxamide

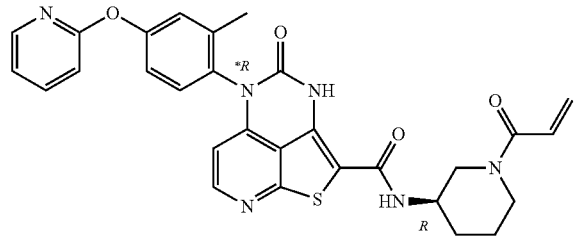

(R)—N-(1-Acryloylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide (Example 778) was resolved by chiral SFC (Stationary phase: CHIRALCEL OD-H, 5 μm, 250×30 mm, Mobile phase: 45% CO2, 55% MeOH) to yield the *R atropisomer, followed by Method 1, step I in Example 1, to yield the title compound. MS (ESI): mass calcd. for C29H26N6O4S, 554.6; m/z found, 555.2 [M+H]+. 1H NMR (400 MHz, CDCl3): δ 9.47 (s, 1H), 8.51-8.02 (m, 2H), 7.93-7.68 (m, 1H), 7.26-6.93 (m, 4H), 6.71-6.16 (m, 2H), 6.20-5.45 (m, 3H), 4.23-3.29 (m, 5H), 2.17 (s, 3H), 2.10-1.55 (m, 5H).

Example 32: (R)—N-(1-Acryloylpiperidin-3-yl)-5-(*S)-(2-methyl-4-(pyridin-2-yloxy)phenyl)-4-oxo-4,5-dihydro-3H-1-thia-3,5,8-triazaacenaphthylene-2-carboxamide

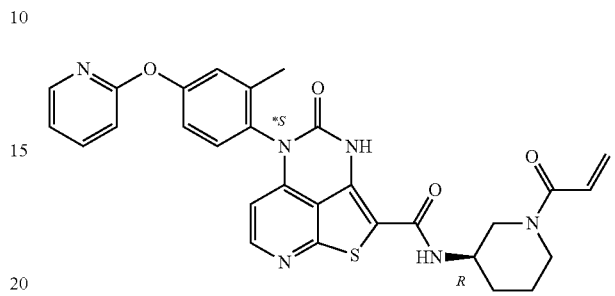

(R)—N-(1-Acryloylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide (Example 778) was resolved by chiral SFC (Stationary phase: CHIRALCEL OD-H, 5 μm, 250×30 mm, Mobile phase: 45% CO2, 55% MeOH) to yield the *S atropisomer, followed by Method 1, step I in Example 1, to yield the title compound. MS (ESI): mass calcd. for C29H26N6O4S, 554.6; m/z found, 555.2 [M+H]+. 1H NMR (400 MHz, CDCl3): δ 9.46 (s, 1H), 8.41-8.18 (m, 2H), 7.86-7.67 (m, 1H), 7.26-6.81 (m, 5H), 6.71-5.45 (m, 4H), 4.28-3.23 (m, 5H), 2.35-1.46 (m, 8H).

Example 33: (R)—N-(1-Acryloylpiperidin-3-yl)-5-(*R)-(2-methyl-4-((2-methylpyridin-3-yl)oxy)phenyl)-4-oxo-4,5-dihydro-3H-1-thia-3,5,8-triazaacenaphthylene-2-carboxamide

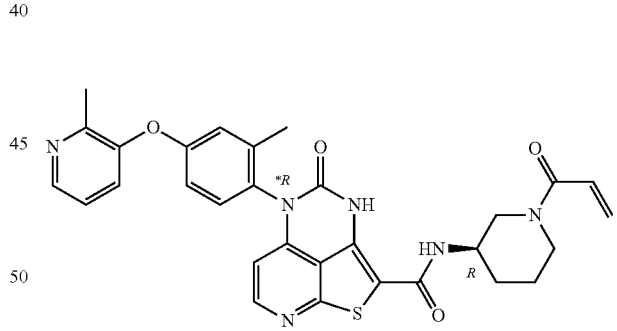

(R)—N-(1-Acryloylpiperidin-3-yl)-5-(2-methyl-4-((2-methylpyridin-3-yl)oxy)phenyl)-4-oxo-4,5-dihydro-3H-1-thia-3,5,8-triazaacenaphthylene-2-carboxamide (Example 773) was resolved by chiral SFC (Stationary phase: CHIRALCEL OD-H, 5 μm, 250×30 mm, Mobile phase: 45% CO2, 55% MeOH) to yield the *R atropisomer, followed by Method 1, step I in Example 1, to yield the title compound. MS (ESI): mass calcd. for C30H28N6O4S, 568.7; m/z found, 569.2 [M+H]+. 1H NMR (400 MHz, CDCl3): δ 9.48 (s, 1H), 8.46-8.25 (m, 2H), 7.42-7.31 (m, 1H), 7.25-7.13 (m, 2H), 7.05-6.81 (m, 2H), 6.76-6.21 (m, 3H), 6.03-5.97 (m, 1H), 5.73 (d, J=12.0 Hz, 1H), 4.26-3.21 (m, 5H), 2.54 (s, 3H), 2.16-1.64 (m, 7H).

Example 34: (R)—N-(1-Acryloylpiperidin-3-yl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide

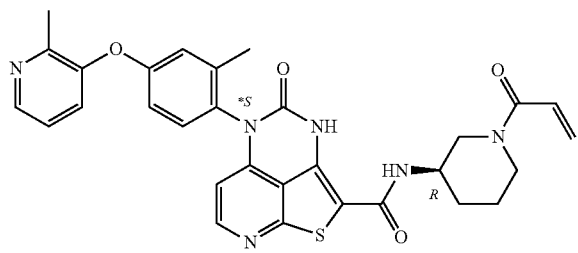

(R)—N-(1-Acryloylpiperidin-3-yl)-5-(2-methyl-4-((2-methylpyridin-3-yl)oxy)phenyl)-4-oxo-4,5-dihydro-3H-1-thia-3,5,8-triazaacenaphthylene-2-carboxamide (Example 773) was resolved by chiral SFC (Stationary phase: CHIRALCEL OD-H, 5 μm, 250×30 mm, Mobile phase: 45% $CO_2$, 55% MeOH) to yield the *S atropisomer, followed by Method 1, step I in Example 1, to yield the title compound. MS (ESI): mass calcd. for $C_{30}H_{28}N_6O_4S$, 568.7; m/z found, 569.2 [M+H]+. 1H NMR (400 MHz, $CDCl_3$): δ 9.49 (s, 1H), 8.53-8.26 (m, 2H), 7.42-7.25 (m, 1H), 7.22-7.08 (m, 2H), 7.03-6.86 (m, 2H), 6.72-6.23 (m, 3H), 6.09-5.69 (m, 2H), 4.27-3.24 (m, 5H), 2.54 (s, 3H), 2.22-1.62 (m, 7H).

Example 35: (R)—N-(1-Acryloylpiperidin-3-yl)-5-(*R)-(2-methyl-4-(pyridazin-3-yloxy)phenyl)-4-oxo-4,5-dihydro-3H-1-thia-3,5,8-triazaacenaphthylene-2-carboxamide

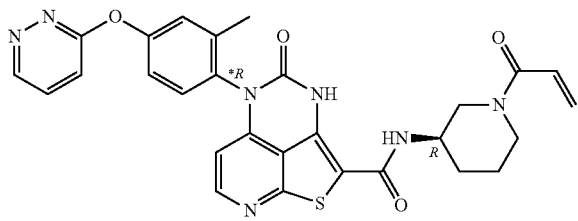

(R)—N-(1-Acryloylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide (Example 784) was resolved by chiral SFC (Stationary phase: CHIRALCEL OJ-H, 5 μm, 250×20 mm, Mobile phase: 75% $CO_2$, 25% MeOH) to yield the *R atropisomer, followed by Method 1, step I in Example 1, to yield the title compound. MS (ESI): mass calcd. for $C_{28}H_{25}N_7O_4S$, 555.6; m/z found, 556.2 [M+H]+. 1H NMR (400 MHz, $CDCl_3$): δ 9.49 (s, 1H), 9.09-8.92 (m, 1H), 8.48-8.29 (m, 1H), 7.70-7.49 (m, 1H), 7.38-7.22 (m, 5H), 6.76-5.49 (m, 3H), 4.26-3.22 (m, 5H), 2.20 (s, 3H), 2.16-1.64 (m, 5H).

Example 36: (R)—N-(1-Acryloylpiperidin-3-yl)-5-(*S)-(2-meth-4-(pyridazin-3-yloxy)phenyl)-4-oxo-4,5-dihydro-3H-1-thia-3,5,8-triazaacenaphthylene-2-carboxamide

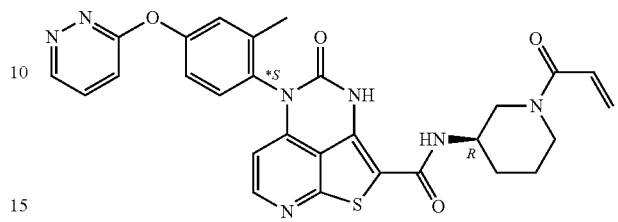

(R)—N-(1-Acryloylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide (Example 784) was resolved by chiral SFC (Stationary phase: CHIRALCEL OJ-H, 5 μm, 250×20 mm, Mobile phase: 75% $CO_2$, 25% MeOH) to yield the *S atropisomer, followed by Method 1, step I in Example 1, to yield the title compound. MS (ESI): mass calcd. for $C_{28}H_{25}N_7O_4S$, 555.6; m/z found, 556.2 [M+H]+. 1H NMR (400 MHz, $CDCl_3$): δ 9.49 (s, 1H), 9.09-8.92 (m, 1H), 8.48-8.29 (m, 1H), 7.70-7.49 (m, 1H), 7.38-7.22 (m, 5H), 6.76-5.49 (m, 3H), 4.26-3.22 (m, 5H), 2.20 (s, 3H), 2.16-1.64 (m, 5H).

Example 972: (R)—N-(1-Acryloylpiperidin-3-yl)-4-oxo-5-(5-(pyridazin-3-yloxy)pyridin-2-yl)-4,5-dihydro-3H-1-thia-3,5,8-triazaacenaphthylene-2-carboxamide

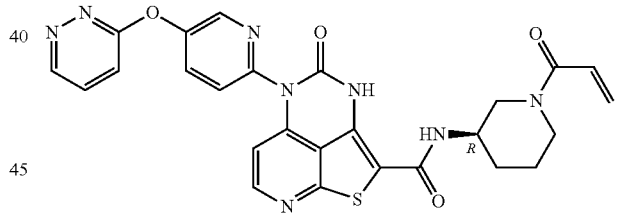

The title compound was prepared in a manner analogous to Method 1, steps A, C-G, and using 3,6-dichloropyridazine and 6-aminopyridin-3-ol in place of 5-fluoro-2-nitrotoluene and phenol in step A, and no step B, and using 5-(pyridazin-3-yloxy)pyridin-2-amine in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate (Intermediate 1) in step G. MS (ESI): mass calcd. for $C_{26}H_{22}N_8O_4S$, 542.6; m/z found, 543.2 [M+H]+. 1H NMR (400 MHz, $CD_3OD$): δ 9.02-8.94 (m, 1H), 8.62 (s, 1H), 8.27 (d, J=5.4 Hz, 1H), 8.04-7.95 (m, 1H), 7.83-7.70 (m, 2H), 7.60-7.51 (m, 1H), 6.88-6.68 (m, 1H), 6.36-6.26 (m, 1H), 6.23-6.11 (m, 1H), 5.74-5.63 (m, 1H), 4.57-4.27 (m, 1H), 4.24-3.85 (m, 2H), 3.17-3.04 (m, 1H), 2.89-2.76 (m, 1H), 2.07-1.96 (m, 1H), 1.87-1.78 (m, 1H), 1.75-1.62 (m, 1H), 1.59-1.45 (m, 1H).

Example 973: (R)—N-(1-Acryloylpyrrolidin-3-yl)-4-oxo-5-(5-(pyridazin-3-yloxy)pyridin-2-yl)-4,5-dihydro-3H-1-thia-3,5,8-triazaacenaphthylene-2-carboxamide

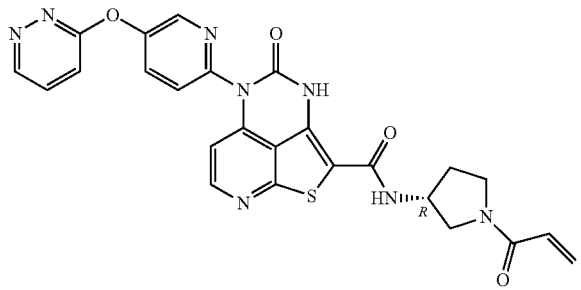

The title compound was prepared in a manner analogous to Method 1, steps A, C-G, and using 3,6-dichloropyridazine and 6-aminopyridin-3-ol in place of 5-fluoro-2-nitrotoluene and phenol in step A, and no step B, and using 5-(pyridazin-3-yloxy)pyridin-2-amine in place of 2-methyl-4-phenoxyaniline in step C, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{25}H_{20}N_8O_4S$, 528.5; m/z found, 529.1 $[M+H]^+$. $^1H$ NMR (400 MHz, DMSO-$d_6$): δ 10.31 (s, 1H), 9.07 (s, 1H), 8.64 (s, 1H), 8.42-8.30 (m, 2H), 8.10-8.02 (m, 1H), 7.90-7.80 (m, 1H), 7.80-7.70 (m, 1H), 7.68-7.60 (m, 1H), 6.66-6.47 (m, 1H), 6.24-6.06 (m, 2H), 5.70-5.60 (m, 1H), 4.57-4.38 (m, 1H), 3.93-3.48 (m, 3H), 3.48-3.36 (m, 1H), 2.26-1.90 (m, 2H).

Example 974: (R)—N-(1-Acryloylpyrrolidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide

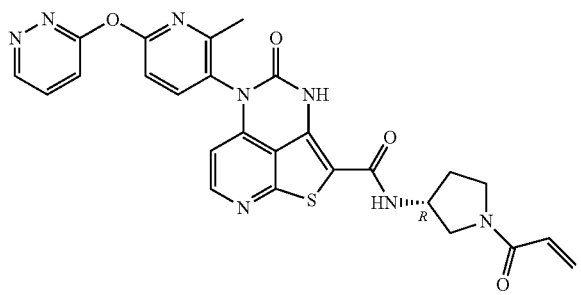

The title compound was prepared in a manner analogous to Method 1, steps A-G, and using 3,6-dichloropyridazine and 5-aminopyridin-2-ol in place of 5-fluoro-2-nitrotoluene and phenol in step A, and using Pd/C and MeOH in place of Fe, EtOH/H$_2$O, and NH$_4$Cl in step B, and using 2-methyl-6-(pyridazin-3-yloxy)pyridin-3-amine in place of 2-methyl-4-phenoxyaniline in step C, and using 1-[(3R)-3-aminopyrrolidin-1-yl]prop-2-en-1-one (Intermediate 5) in place of tert-butyl (3R,5R)-3-amino-5-fluoropiperidine-1-carboxylate (Intermediate 1) in step G. MS (ESI): mass calcd. for $C_{26}H_{22}N_8O_4S$, 542.6; m/z found, 543.1 $[M+H]^+$. $^1H$ NMR (400 MHz, CD$_3$OD): δ 9.11-9.03 (m, 1H), 8.39-8.33 (m, 1H), 8.04-7.95 (m, 1H), 7.89-7.82 (m, 1H), 7.71-7.64 (m, 1H), 7.33-7.26 (m, 1H), 6.69-6.53 (m, 1H), 6.33-6.22 (m, 2H), 5.80-5.70 (m, 1H), 4.68-4.55 (m, 1H), 4.06-3.73 (m, 2H), 3.70-3.51 (m, 2H), 2.37-2.10 (m, 5H).

Example 975: (R)—N-(1-Acryloylpiperidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide

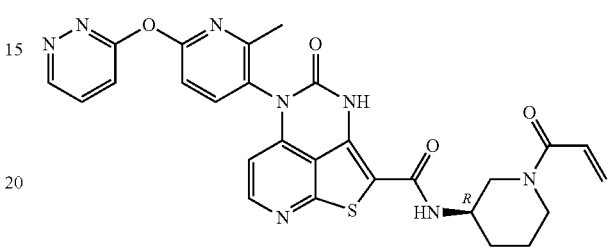

The title compound was prepared in a manner analogous to Method 1, steps A-G, and using 3,6-dichloropyridazine and 5-aminopyridin-2-ol in place of 5-fluoro-2-nitrotoluene and phenol in step A, and using Pd/C and MeOH in place of Fe, EtOH/H$_2$O, and NH$_4$Cl in step B, and using 2-methyl-6-(pyridazin-3-yloxy)pyridin-3-amine in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate. MS (ESI): mass calcd. for $C_{27}H_{24}N_8O_4S$, 556.6; m/z found, 557.1 $[M+H]^+$. $^1H$ NMR (400 MHz, CD$_3$OD): δ 9.11-9.04 (m, 1H), 8.42-8.34 (m, 1H), 8.27-8.18 (s, 1H), 8.03-7.95 (m, 1H), 7.89-7.82 (m, 1H), 7.70-7.62 (m, 1H), 7.34-7.26 (m, 1H), 6.87-6.74 (m, 1H), 6.28-6.14 (m, 2H), 5.80-5.67 (m, 1H), 4.63-4.26 (m, 1H), 4.22-3.89 (m, 2H), 3.25-3.09 (m, 1H), 2.99-2.82 (m, 1H), 2.31-2.23 (m, 3H), 2.14-2.01 (m, 1H), 1.93-1.82 (m, 1H), 1.78-1.67 (m, 1H), 1.66-1.53 (m, 1H).

Example 976: (R)—N-(1-Acryloylpiperidin-3-yl)-5-(4-methyl-6-(pyridazin-3-yloxy)pyridin-3-yl)-4-oxo-4,5-dihydro-3H-1-thia-3,5,8-triazaacenaphthylene-2-carboxamide

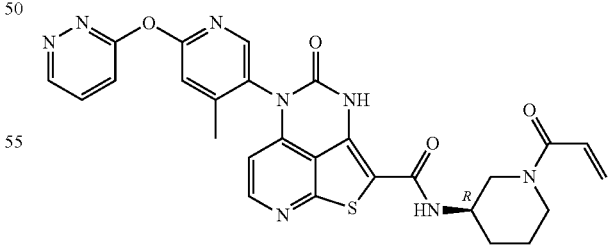

The title compound was prepared in a manner analogous to Method 1, steps A-G, and using 3,6-dichloropyridazine and 5-amino-4-methylpyridin-2-ol in place of 5-fluoro-2-nitrotoluene and phenol in step A, and using Pd/C, DIPEA, and MeOH in place of Fe, EtOH/H$_2$O, and NH$_4$Cl in step B, and using 4-methyl-6-(pyridazin-3-yloxy)pyridin-3-amine in place of 2-methyl-4-phenoxyaniline in step C, and using (R)-1-(3-aminopiperidin-1-yl)prop-2-en-1-one (Intermediate 15) in place of tert-butyl (3R,5R)-3-amino-5-fluoropiperidine-1-carboxylate. MS (ESI): mass calcd. for $C_{27}H_{24}N_8O_4S$, 556.6; m/z found, 557.2 $[M+H]^+$. $^1H$ NMR (400 MHz, $CD_3OD$): δ 8.95-8.81 (m, 1H), 8.22-8.13 (m, 1H), 8.06-7.99 (m, 1H), 7.74-7.59 (m, 1H), 7.51-7.42 (m, 1H), 7.25-7.15 (m, 1H), 6.70-6.51 (m, 1H), 6.11-5.92 (m, 2H), 5.62-5.46 (m, 1H), 4.43-4.05 (m, 1H), 4.05-3.69 (m, 2H), 3.08-2.90 (m, 1H), 2.84-2.61 (m, 1H), 2.15-2.05 (m, 3H), 1.96-1.81 (m, 1H), 1.76-1.31 (m, 3H).

Example 977: (R)—N-(1-Acryloylpyrrolidin-3-yl)-5-(4-methyl-6-(pyridazin-3-yloxy)pyridin-3-yl)-4-oxo-4,5-dihydro-3H-1-thia-3,5,8-triazaacenaphthylene-2-carboxamide

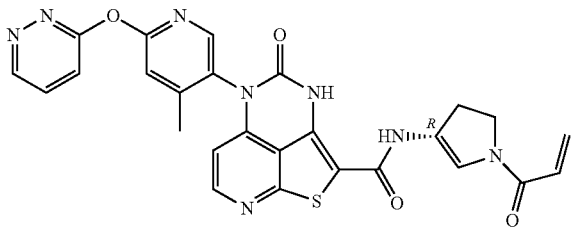

The title compound was prepared in a manner analogous to Method 1, steps A-G, and using 3,6-dichloropyridazine and 5-amino-4-methylpyridin-2-ol in place of 5-fluoro-2-nitrotoluene and phenol in step A, and using Pd/C and MeOH in place of Fe, $EtOH/H_2O$, and $NH_4Cl$ in step B, and using 4-methyl-6-(pyridazin-3-yloxy)pyridin-3-amine in place of 2-methyl-4-phenoxyaniline in step C, and using 1-[(3R)-3-aminopyrrolidin-1-yl]prop-2-en-1-one (Intermediate 5) in place of tert-butyl (3R,5R)-3-amino-5-fluoropiperidine-1-carboxylate. MS (ESI): mass calcd. for $C_{26}H_{22}N_8O_4S$, 542.6; m/z found, 543.2 $[M+H]^+$. $^1H$ NMR (400 MHz, $CD_3OD$): δ 8.89 (d, J=1.3 Hz, 1H), 8.19 (d, J=5.6 Hz, 1H), 8.04 (s, 1H), 7.72-7.61 (m, 1H), 7.48 (d, J=7.1 Hz, 1H), 7.21 (s, 1H), 6.53-6.31 (m, 1H), 6.16-6.00 (m, 2H), 5.62-5.52 (m, 1H), 4.44 (s, 1H), 3.90-3.26 (m, 4H), 2.24-2.04 (m, 4H), 2.02-1.84 (m, 1H).

BTK Kinase Lanthascreen Binding Assay:

A BTK kinase lanthascreen binding assay monitors compound binding to unphosphorylated-BTK kinase domain (UP-BTK), by competing with a fluorescent labeled tracer. UP-BTK, consisting of the kinase domain of non-phosphorylated BTK protein (389-659aa), was produced in a Baculovirus/insect cell expression system. Into a 384-well plate, 2 ng of GST-tagged human BTK (389-659aa) was incubated with compound, 50 nM of Tracer 236 and 2 nM anti-GST antibody for 60 minutes using an optimized Lanthascreen™ assay. After 60 minutes, plates were read at 340 nM and 615/665 nM in an Infinite F500 (Tecan). Data were analyzed using Xlfit™ version 5.3 from ID Business Solutions (Guildford), Microsoft Excel add-in. $pIC_{50}$ refers to the negative log of the $IC_{50}$ in molar.

TABLE 2

| Ex # | Compound Name | BTK_I_binding pIC50 |
|---|---|---|
| 1 | N-((3R,5R)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide; | 7.7 |
| 2 | N-((3R,5S)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide; | 8.2 |
| 3 | N-((3R,5S)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide; | 7.9 |
| 4 | (R)-N-(1-Acryloylpiperidin-3-yl)-5-(3-fluoro-2-methyl-4-phenoxyphenyl)-4-oxo-4,5-dihydro-3H-1-thia-3,5,8-triazaacenaphthylene-2-carboxamide; | 7.7 |
| 5 | (R)-N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 8.1 |
| 6 | N-((3R,5R)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide; | 7.9 |
| 7 | (R)-N-(1-Acryloylpyrrolidin-3-yl)-5-(3-fluoro-2-methyl-4-phenoxyphenyl)-4-oxo-4,5-dihydro-3H-1-thia-3,5,8-triazaacenaphthylene-2-carboxamide; | 7.9 |
| 8 | N-((3R,5R)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide; | 7.8 |
| 9 | (R)-N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide; | 8.1 |
| 10 | (R)-N-(1-Acryloylpiperidin-3-yl)-5-(2-fluoro-4-phenoxyphenyl)-4-oxo-4,5-dihydro-3H-1-thia-3,5,8-triazaacenaphthylene-2-carboxamide; | 8.1 |
| 11 | (R)-N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide; | 7.9 |
| 12 | (R)-N-(1-Acryloylpyrrolidin-3-yl)-5-(2-chloro-4-phenoxyphenyl)-4-oxo-4,5-dihydro-3H-1-thia-3,5,8-triazaacenaphthylene-2-carboxamide; | 7.7 |
| 13 | N-((3R,5S)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide; | 7.8 |

TABLE 2-continued

| Ex # | Compound Name | BTK_I_binding pIC50 |
|---|---|---|
| 14 | N-((3R,5S)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide; | 7.4 |
| 15 | (R)-N-(1-Acryloylpiperidin-3-yl)-5-(2-chloro-4-phenoxyphenyl)-4-oxo-4,5-dihydro-3H-1-thia-3,5,8-triazaacenaphthylene-2-carboxamide; | 7.6 |
| 16 | (R)-N-(1-Acryloylpiperidin-3-yl)-5-(4-(benzofuran-7-yloxy)-2-methylphenyl)-4-oxo-4,5-dihydro-3H-1-thia-3,5,8-triazaacenaphthylene-2-carboxamide; | 7.3 |
| 17 | (R)-N-(1-Acryloylpyrrolidin-3-yl)-5-(4-(2,6-difluorophenoxy)-2-methylphenyl)-4-oxo-4,5-dihydro-3H-1-thia-3,5,8-triazaacenaphthylene-2-carboxamide; | 7.7 |
| 18 | (R)-N-(1-Acryloylpiperidin-3-yl)-4-oxo-5-(4-phenoxyphenyl)-4,5-dihydro-3H-1-thia-3,5,8-triazaacenaphthylene-2-carboxamide; | 8.2 |
| 19 | (R)-N-(1-Acryloylpiperidin-3-yl)-5-(4-(2-ethylphenoxy)-2-methylphenyl)-4-oxo-4,5-dihydro-3H-1-thia-3,5,8-triazaacenaphthylene-2-carboxamide; | 7.2 |
| 20 | (R)-N-(1-Acryloylpiperidin-3-yl)-5-(2-fluoro-6-methyl-4-phenoxyphenyl)-4-oxo-4,5-dihydro-3H-1-thia-3,5,8-triazaacenaphthylene-2-carboxamide; | 7.4 |
| 21 | (R,E)-N-(1-(2-cyano-3-(3-methyloxetan-3-yl)acryloyl)piperidin-3-yl)-5-(2-methyl-4-phenoxyphenyl)-4-oxo-4,5-dihydro-3H-1-thia-3,5,8-triazaacenaphthylene-2-carboxamide; | 7.7 |
| 22 | (R)-N-(1-Acryloylpyrrolidin-3-yl)-5-(4-(benzofuran-7-yloxy)-2-methylphenyl)-4-oxo-4,5-dihydro-3H-1-thia-3,5,8-triazaacenaphthylene-2-carboxamide; | 7.4 |
| 23 | (R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide; | 7.5 |
| 24 | (R)-5-(4-(3-((2-Cyanophenoxy)methyl)phenoxy)-2-methylphenyl)-N-(1-methylpiperidin-3-yl)-4-oxo-4,5-dihydro-3H-1-thia-3,5,8-triazaacenaphthylene-2-carboxamide; | 7.7 |
| 25 | (S,E)-N-(1-(4-Hydroxybut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.5 |
| 26 | (R)-N-(1-(2-Chloroacryloyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 27 | (R,E)-N-(1-(4-Aminobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 28 | N-((3S,4R)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.9 |
| 29 | (R,EZ)-N-(1-(2-Cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 30 | (R,E)-N-(1-(4-Hydroxybut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.6 |
| 31 | N-(4-Cyano-1,4-oxazepan-6-yl)-5-(2-methyl-4-phenoxyphenyl)-4-oxo-4,5-dihydro-3H-1-thia-3,5,8-triazaacenaphthylene-2-carboxamide; | 7.7 |
| 32 | (R)-N-(1-Acryloylpiperidin-3-yl)-5-(4-(cyclohexyloxy)-2-methylphenyl)-4-oxo-4,5-dihydro-3H-1-thia-3,5,8-triazaacenaphthylene-2-carboxamide; | 7.3 |
| 33 | (R)-N-(1-Acryloylpiperidin-3-yl)-5-(4-isopropoxy-2-methylphenyl)-4-oxo-4,5-dihydro-3H-1-thia-3,5,8-triazaacenaphthylene-2-carboxamide; | 7.5 |
| 34 | N-((3S,4R)-1-Acryloyl-4-methoxypyrrolidin-3-yl)-5-(2-methyl-4-phenoxyphenyl)-4-oxo-4,5-dihydro-3H-1-thia-3,5,8-triazaacenaphthylene-2-carboxamide; | 7.6 |
| 35 | (R)-N-(1-Cyanopiperidin-3-yl)-5-(*S)-(2-methyl-4-phenoxyphenyl)-4-oxo-4,5-dihydro-3H-1-thia-3,5,8-triazaacenaphthylene-2-carboxamide; | 7.5 |
| 36 | N-((3S,4S)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide; | 7.7 |
| 37 | N-((3S,4R)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide; | 7.6 |
| 38 | (R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide; | 7.3 |
| 39 | (R)-N-(1-Acryloylpyrrolidin-3-yl)-5-(4-(cyclohexyloxy)-2-methylphenyl)-4-oxo-4,5-dihydro-3H-1-thia-3,5,8-triazaacenaphthylene-2-carboxamide; | 7.4 |

TABLE 2-continued

| Ex # | Compound Name | BTK_I_binding pIC50 |
|---|---|---|
| 40 | (R,E)-N-(1-(2-Cyano-4-methoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.6 |
| 41 | (R,E)-N-(1-(2-Cyano-3-13C-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 42 | (R)-N-(1-(But-2-ynoyl)piperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 43 | (R,E)-N-(1-(2-Cyano-4-methyl-4-morpholinopent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.2 |
| 44 | (S)-N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide; | 7.4 |
| 45 | (R)-N-(1-Acryloylpyrrolidin-3-yl)-5-(2-fluoro-6-methyl-4-phenoxyphenyl)-4-oxo-4,5-dihydro-3H-1-thia-3,5,8-triazaacenaphthylene-2-carboxamide; | 7.1 |
| 46 | (R)-5-(*S)-(2-methyl-4-phenoxyphenyl)-4-oxo-N-(1-propioloylpiperidin-3-yl)-4,5-dihydro-3H-1-thia-3,5,8-triazaacenaphthylene-2-carboxamide; | 7.9 |
| 47 | (R,E)-N-(1-(2-Cyano-3-cyclopropylacryloyl)piperidin-3-yl)-4-oxo-5-(4-phenoxyphenyl)-4,5-dihydro-3H-1-thia-3,5,8-triazaacenaphthylene-2-carboxamide; | 8.0 |
| 48 | (R)-N-(1-(2-Fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 49 | (R)-N-(1-(2-Fluoroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.2 |
| 50 | N-((3S,4S)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide; | 7.5 |
| 51 | (R)-N-(1-Acryloylpiperidin-3-yl)-5-(4-cyclopropoxy-2-methylphenyl)-4-oxo-4,5-dihydro-3 H-1-thia-3,5,8-triazaacenaphthylene-2-carboxamide; | 7.5 |
| 52 | (R)-5-(4-(2,6-Difluorophenoxy)-2-methylphenyl)-N-(1-methylpiperidin-3-yl)-4-oxo-4,5-dihydro-3H-1-thia-3,5,8-triazaacenaphthylene-2-carboxamide; | 7.0 |
| 54 | N-((3S,4S)-1-Acryloyl-4-methoxypyrrolidin-3-yl)-5-(2-methyl-4-phenoxyphenyl)-4-oxo-4,5-dihydro-3H-1-thia-3,5,8-triazaacenaphthylene-2-carboxamide; | 7.3 |
| 55 | (R)-N-(1-(But-2-ynoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.4 |
| 56 | (R)-N-(1-(2-(Dimethylamino)acetyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.4 |
| 57 | (R)-5-(4-(2-Fluorophenoxy)-2-methylphenyl)-N-(1-methylpiperidin-3-yl)-4-oxo-4,5-dihydro-3H-1-thia-3,5,8-triazaacenaphthylene-2-carboxamide; | 6.8 |
| 58 | N-((3S,4R)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide; | 7.6 |
| 59 | (R)-5-(3-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide; | 7.3 |
| 60 | (R)-5-(2-Methyl-4-phenoxyphenyl)-4-oxo-N-(1-propylpiperidin-3-yl)-4,5-dihydro-3H-1-thia-3,5,8-triazaacenaphthylene-2-carboxamide; | 6.8 |
| 61 | (S)-5-(3-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 7.3 |
| 62 | (R)-N-(1-Acryloylpiperidin-3-yl)-5-(4-ethyl-2-methylphenyl)-4-oxo-4,5-dihydro-3H-1-thia-3,5,8-triazaacenaphthylene-2-carboxamide; | 7.1 |
| 63 | (R,E)-N-(1-(2-Cyano-4-methyl-4-(tetrahydro-2H-pyran-4-yl)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 64 | (R)-N-(1-Acryloylpiperidin-3-yl)-5-(4-(2,6-difluorophenoxy)-2-methylphenyl)-4-oxo-4,5-dihydro-3H-1-thia-3,5,8-triazaacenaphthylene-2-carboxamide; | 7.6 |
| 65 | (R)-N-(1-Acryloylpiperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 6.6 |
| 66 | (R)-N-(1-Acryloylpiperidin-3-yl)-5-(4-ethoxy-2-methylphenyl)-4-oxo-4,5-dihydro-3H-1-thia-3,5,8-triazaacenaphthylene-2-carboxamide; | 7.4 |

TABLE 2-continued

| Ex # | Compound Name | BTK_I_binding pIC50 |
|---|---|---|
| 67 | (S)-5-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 7.5 |
| 68 | (S)-5-(*S)-(2-Methyl-4-phenoxyphenyl)-4-oxo-N-(tetrahydrofuran-3-yl)-4,5-dihydro-3H-1-thia-3,5,8-triazaacenaphthylene-2-carboxamide; | 7.7 |
| 69 | (R)-N-(1-Acryloylpiperidin-3-yl)-5-(2,6-difluoro-4-phenoxyphenyl)-4-oxo-4,5-dihydro-3H-1-thia-3,5,8-triazaacenaphthylene-2-carboxamide; | 7.7 |
| 70 | (R)-5-(4-(Benzofuran-7-yloxy)-2-methylphenyl)-N-(1-methylpiperidin-3-yl)-4-oxo-4,5-dihydro-3H-1-thia-3,5,8-triazaacenaphthylene-2-carboxamide; | 7.1 |
| 71 | (R)-5-(3-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 7.5 |
| 72 | (R)-N-(1-(3-Methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.4 |
| 73 | (R)-5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide; | 6.8 |
| 74 | (R)-N-(1-Ethylpiperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 75 | (R)-N-(1-(3-Hydroxypropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 76 | (R,E)-N-(1-(2-Cyano-3-cyclopropylacryloyl)piperidin-3-yl)-5-(4-(2-ethylphenoxy)-2-methylphenyl)-4-oxo-4,5-dihydro-3H-1-thia-3,5,8-triazaacenaphthylene-2-carboxamide; | 6.8 |
| 77 | (R)-N-(1-Acryloylpyrrolidin-3-yl)-5-(2,3-dimethyl-4-phenoxyphenyl)-4-oxo-4,5-dihydro-3H-1-thia-3,5,8-triazaacenaphthylene-2-carboxamide; | 6.9 |
| 78 | (R)-N-(1-(2-(Dimethylamino)acetyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 79 | (R,E)-N-(1-(2-Cyano-3-cyclopropylacryloyl)piperidin-3-yl)-5-(2-fluoro-4-phenoxyphenyl)-4-oxo-4,5-dihydro-3H-1-thia-3,5,8-triazaacenaphthylene-2-carboxamide; | 7.5 |
| 80 | (R)-5-(*S)-(2-Methyl-4-phenoxyphenyl)-4-oxo-N-(tetrahydrofuran-3-yl)-4,5-dihydro-3H-1-thia-3,5,8-triazaacenaphthylene-2-carboxamide; | 7.8 |
| 81 | (R)-N-(1-Acryloylpyrrolidin-3-yl)-5-(2,6-dimethyl-4-phenoxyphenyl)-4-oxo-4,5-dihydro-3H-1-thia-3,5,8-triazaacenaphthylene-2-carboxamide; | 6.6 |
| 82 | (S)-N-(1-acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide; | 7.2 |
| 83 | (R)-N-(1-Acryloylpiperidin-3-yl)-5-(2-methyl-4-(pentafluorothio)phenyl)-4-oxo-4,5-dihydro-3H-1-thia-3,5,8-triazaacenaphthylene-2-carboxamide; | 6.8 |
| 84 | (R)-5-(*S)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide; | 7.5 |
| 85 | (R)-Tetrahydro-2H-pyran-3-yl 5-(2-methyl-4-phenoxyphenyl)-4-oxo-4,5-dihydro-3H-1-thia-3,5,8-triazaacenaphthylene-2-carboxylate; | 7.6 |
| 86 | (R)-N-(1-Acryloylpiperidin-3-yl)-5-(2,4-dimethylphenyl)-4-oxo-4,5-dihydro-3H-1-thia-3,5,8-triazaacenaphthylene-2-carboxamide; | 6.7 |
| 87 | (R)-N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide; | 6.9 |
| 88 | (S)-5-(*S)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 7.6 |
| 89 | (R)-5-(3-Fluoro-2-methyl-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide; | 7.1 |
| 90 | (S)-5-(2-Methyl-4-phenoxyphenyl)-4-oxo-N-(tetrahydrofuran-3-yl)-4,5-dihydro-3H-1-thia-3,5,8-triazaacenaphthylene-2-carboxamide; | 7.5 |
| 91 | (R)-5-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide; | 7.3 |
| 92 | N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 93 | (R)-N-(1-Isopropylpyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.1 |

TABLE 2-continued

| Ex # | Compound Name | BTK_I_binding pIC50 |
|---|---|---|
| 94 | N-((3S,4R)-4-Fluoro-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.6 |
| 95 | (R)-N-(1-(2-Methoxyacetyl)piperidin-3-yl)-5-(2-methyl-4-phenoxyphenyl)-4-oxo-4,5-dihydro-3H-1-thia-3,5,8-triazaacenaphthylene-2-carboxamide; | 7.4 |
| 96 | (R)-5-(*S)-(2-Methyl-4-phenoxyphenyl)-4-oxo-N-(tetrahydro-2 H-pyran-3-yl)-4,5-dihydro-3H-1-thia-3,5,8-triazaacenaphthylene-2-carboxamide; | 7.8 |
| 97 | N-(1-Cyanoazepan-3-yl)-5-(2-methyl-4-phenoxyphenyl)-4-oxo-4,5-dihydro-3H-1-thia-3,5,8-triazaacenaphthylene-2-carboxamide; | 6.9 |
| 98 | (R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide; | 7.3 |
| 99 | (R)-N-(1-(3-Hydroxypropanoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.6 |
| 100 | (R,E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.1 |
| 101 | (R)-N-(1-Isopropylpiperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 102 | (R,E)-N-(1-(2-Cyano-3-cyclopropylacryloyl)piperidin-3-yl)-5-(4-isopropoxy-2-methylphenyl)-4-oxo-4,5-dihydro-3H-1-thia-3,5,8-triazaacenaphthylene-2-carboxamide; | 7.5 |
| 103 | N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide; | 6.7 |
| 104 | (R)-5-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide; | 7.7 |
| 105 | (R,E)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 106 | (R)-5-(2-Methyl-4-phenoxyphenyl)-N-(1-(3-(methylamino)propanoyl)piperidin-3-yl)-4-oxo-4,5-dihydro-3H-1-thia-3,5,8-triazaacenaphthylene-2-carboxamide; | 7.3 |
| 107 | (R)-5-(2-Fluoro-4-phenoxyphenyl)-4-oxo-N-(piperidin-3-yl)-4,5-dihydro-3H-1-thia-3,5,8-triazaacenaphthylene-2-carboxamide; | 7.5 |
| 108 | (R)-5-(2-Methyl-4-phenoxyphenyl)-4-oxo-N-(tetrahydrofuran-3-yl)-4,5-dihydro-3H-1-thia-3,5,8-triazaacenaphthylene-2-carboxamide; | 7.5 |
| 109 | N-(1-Acryloylazetidin-3-yl)-5-(2-methyl-4-phenoxyphenyl)-4-oxo-4,5-dihydro-3H-1-thia-3,5,8-triazaacenaphthylene-2-carboxamide; | 7.2 |
| 110 | (R)-N-(1-13C-Acryloylpiperidin-3-yl)-5-(4-methoxy-2-methylphenyl)-4-oxo-4,5-dihydro-3H-1-thia-3,5,8-triazaacenaphthylene-2-carboxamide; | 6.8 |
| 111 | N-((R)-1-((R)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 112 | (R,E)-N-(1-(2-Cyano-4-methyl-4-morpholinopent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 6.9 |
| 113 | (R)-5-(3-Fluoro-2-methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide; | 7.3 |
| 114 | (R)-5-(3-Fluoro-2-methyl-4-phenoxyphenyl)-N-(1-(2-hydroxyacetyl)piperidin-3-yl)-4-oxo-4,5-dihydro-3H-1-thia-3,5,8-triazaacenaphthylene-2-carboxamide; | 7.3 |
| 115 | (R)-5-(3-Fluoro-2-methyl-4-phenoxyphenyl)-N-(1-(2-methoxyacetyl)piperidin-3-yl)-4-oxo-4,5-dihydro-3H-1-thia-3,5,8-triazaacenaphthylene-2-carboxamide; | 7.4 |
| 116 | (R,Z)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 117 | (R)-5-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide; | 6.9 |
| 118 | (R)-N-(1-Isopropylpyrrolidin-3-yl)-5-(2-methyl-4-phenoxyphenyl)-4-oxo-4,5-dihydro-3H-1-thia-3,5,8-triazaacenaphthylene-2-carboxamide; | 6.9 |
| 119 | (R)-N-(1-Acryloylpyrrolidin-3-yl)-5-(4-ethyl-2-methylphenyl)-4-oxo-4,5-dihydro-3H-1-thia-3,5,8-triazaacenaphthylene-2-carboxamide; | 6.6 |
| 120 | N-((R)-1-((S)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |

TABLE 2-continued

| Ex # | Compound Name | BTK_I_binding pIC50 |
|---|---|---|
| 121 | (R)-N-(1-Acryloylpiperidin-3-yl)-4-oxo-5-(6-phenoxypyridazin-3-yl)-4,5-dihydro-3H-1-thia-3,5,8-triazaacenaphthylene-2-carboxamide; | 6.7 |
| 122 | N-((R)-1-((S)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.4 |
| 123 | 5-(2-Methyl-4-phenoxyphenyl)-4-oxo-N-(tetrahydro-2H-pyran-4-yl)-4,5-dihydro-3H-1-thia-3,5,8-triazaacenaphthylene-2-carboxamide; | 6.9 |
| 124 | (R)-N-(1-(2-Hydroxyacetyl)piperidin-3-yl)-5-(2-methyl-4-phenoxyphenyl)-4-oxo-4,5-dihydro-3H-1-thia-3,5,8-triazaacenaphthylene-2-carboxamide; | 7.4 |
| 125 | 5-(2-Methyl-4-phenoxyphenyl)-N-((R)-1-((S)-1-methylpyrrolidine-3-carbonyl)piperidin-3-yl)-4-oxo-4,5-dihydro-3H-1-thia-3,5,8-triazaacenaphthylene-2-carboxamide; | 7.2 |
| 126 | (R)-N-(1-Acryloylpyrrolidin-3-yl)-5-(4-isopropoxy-2-methylphenyl)-4-oxo-4,5-dihydro-3H-1-thia-3,5,8-triazaacenaphthylene-2-carboxamide; | 6.7 |
| 127 | (R)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide; | 7.3 |
| 128 | (R)-5-(3-Fluoro-2-methyl-4-phenoxyphenyl)-N-(1-(3-hydroxypropanoyl)piperidin-3-yl)-4-oxo-4,5-dihydro-3H-1-thia-3,5,8-triazaacenaphthylene-2-carboxamide; | 7.2 |
| 129 | N-(4-Methyl-1,4-oxazepan-6-yl)-5-(2-methyl-4-phenoxyphenyl)-4-oxo-4,5-dihydro-3H-1-thia-3,5,8-triazaacenaphthylene-2-carboxamide; | 6.9 |
| 130 | (R)-N-(1-(3-(Dimethylamino)propanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 131 | 5-(2-Methyl-4-phenoxyphenyl)-4-oxo-N-((R)-1-((S)-pyrrolidine-3-carbonyl)piperidin-3-yl)-4,5-dihydro-3H-1-thia-3,5,8-triazaacenaphthylene-2-carboxamide; | 7.5 |
| 132 | N-((3S,4R)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide; | 7.2 |
| 133 | (R)-5-(2-Chloro-4-phenoxyphenyl)-N-(1-methylpiperidin-3-yl)-4-oxo-4,5-dihydro-3H-1-thia-3,5,8-triazaacenaphthylene-2-carboxamide; | 7.0 |
| 134 | (R,Z)-N-(1-(2-Cyano-4-(dimethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 135 | (R)-5-(2-Fluoro-4-phenoxyphenyl)-N-(1-methylpiperidin-3-yl)-4-oxo-4,5-dihydro-3H-1-thia-3,5,8-triazaacenaphthylene-2-carboxamide; | 7.2 |
| 136 | (R)-5-(2-Methyl-4-phenoxyphenyl)-N-(1-(oxetane-3-carbonyl)piperidin-3-yl)-4-oxo-4,5-dihydro-3H-1-thia-3,5,8-triazaacenaphthylene-2-carboxamide; | 7.1 |
| 137 | (R)-N-(1-Acryloylpyrrolidin-3-yl)-N-methyl-5-(2-methyl-4-phenoxyphenyl)-4-oxo-4,5-dihydro-3H-1-thia-3,5,8-triazaacenaphthylene-2-carboxamide; | 6.6 |
| 138 | N-((3R,5R)-5-Fluoropiperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 139 | N-((3S,4S)-4-Hydroxy-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.2 |
| 140 | (R)-N-(1-(2-Cyano-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.7 |
| 141 | (R)-N-(1-Ethylpyrrolidin-3-yl)-5-(2-methyl-4-phenoxyphenyl)-4-oxo-4,5-dihydro-3H-1-thia-3,5,8-triazaacenaphthylene-2-carboxamide; | 6.8 |
| 142 | N-((R)-1-((S)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 143 | N-((R)-1-((R)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 144 | (R)-5-(2-Methyl-4-phenoxyphenyl)-4-oxo-N-(1-(2-(trifluoromethyl)acryloyl)piperidin-3-yl)-4,5-dihydro-3H-1-thia-3,5,8-triazaacenaphthylene-2-carboxamide; | 7.5 |
| 145 | 5-(2-Methyl-4-phenoxyphenyl)-N-((R)-1-((R)-1-methylpyrrolidine-3-carbonyl)piperidin-3-yl)-4-oxo-4,5-dihydro-3H-1-thia-3,5,8-triazaacenaphthylene-2-carboxamide; | 7.0 |
| 146 | (R)-5-(2-Methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide; | 7.4 |

TABLE 2-continued

| Ex # | Compound Name | BTK_I_binding pIC50 |
|---|---|---|
| 147 | (R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide; | 7.4 |
| 148 | (R)-5-(2-Methyl-4-(o-tolyloxy)phenyl)-N-(1-methylpiperidin-3-yl)-4-oxo-4,5-dihydro-3H-1-thia-3,5,8-triazaacenaphthylene-2-carboxamide; | 6.9 |
| 149 | (R)-N-(1-Cyclopropylpyrrolidin-3-yl)-5-(2-methyl-4-phenoxyphenyl)-4-oxo-4,5-dihydro-3H-1-thia-3,5,8-triazaacenaphthylene-2-carboxamide; | 6.8 |
| 150 | (R,E)-N-(1-(2-Cyano-4-methyl-4-(piperidin-1-yl)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 151 | (R)-N-(1-(2-Aminoacetyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 152 | (R,E)-N-(1-(2-Cyano-4-(cyclopropylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 153 | 5-(2-Methyl-4-phenoxyphenyl)-N-((6S)-6-methylpiperidin-3-yl)-4-oxo-4,5-dihydro-3H-1-thia-3,5,8-triazaacenaphthylene-2-carboxamide; | 6.8 |
| 154 | N-((3S,4R)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide; | 7.2 |
| 155 | N-((3R)-1-(3-Methoxybutanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 156 | N-((R)-1-((S)-3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 157 | (R)-5-(4-(2-Ethoxyphenoxy)-2-methylphenyl)-N-(1-methylpiperidin-3-yl)-4-oxo-4,5-dihydro-3H-1-thia-3,5,8-triazaacenaphthylene-2-carboxamide; | 6.6 |
| 158 | N-((3R)-1-(3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 159 | (R)-5-(2-Methyl-4-phenoxyphenyl)-4-oxo-N-(pyrrolidin-3-yl)-4,5-dihydro-3H-1-thia-3,5,8-triazaacenaphthylene-2-carboxamide; | 7.1 |
| 160 | N-((3R,5R)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide; | 6.6 |
| 161 | (R)-5-(2-Methyl-4-phenoxyphenyl)-4-oxo-N-(1-propioloylpiperidin-3-yl)-4,5-dihydro-3H-1-thia-3,5,8-triazaacenaphthylene-2-carboxamide; | 7.7 |
| 162 | 5-(2-Methyl-4-phenoxyphenyl)-N-(1-methyl-6-oxopiperidin-3-yl)-4-oxo-4,5-dihydro-3H-1-thia-3,5,8-triazaacenaphthylene-2-carboxamide; | 6.8 |
| 163 | (R)-N-(1-(3-Aminopropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 164 | N-((3R,5S)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 165 | N-(1,3-Dimethylpiperidin-4-yl)-5-(2-methyl-4-phenoxyphenyl)-4-oxo-4,5-dihydro-3H-1-thia-3,5,8-triazaacenaphthylene-2-carboxamide; | 6.6 |
| 166 | 5-(2-Methyl-4-phenoxyphenyl)-4-oxo-N-(2-oxopiperidin-4-yl)-4,5-dihydro-3H-1-thia-3,5,8-triazaacenaphthylene-2-carboxamide; | 6.9 |
| 167 | N-((3R,5S)-5-fluoropiperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 168 | N-((3R,5R)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 169 | (R)-N-(1-Acryloylpyrrolidin-3-yl)-5-(*R)-(2-methyl-4-phenoxyphenyl)-4-oxo-4,5-dihydro-3H-1-thia-3,5,8-triazaacenaphthylene-2-carboxamide; | 6.4 |
| 170 | (R)-5-(4-(2-Ethylphenoxy)-2-methylphenyl)-N-(1-methylpiperidin-3-yl)-4-oxo-4,5-dihydro-3H-1-thia-3,5,8-triazaacenaphthylene-2-carboxamide; | 7.0 |
| 171 | 5-(2-Methyl-4-phenoxyphenyl)-4-oxo-N-(quinuclidin-2-yl)-4,5-dihydro-3H-1-thia-3,5,8-triazaacenaphthylene-2-carboxamide; | 7.0 |
| 172 | 5-(2-Methyl-4-phenoxyphenyl)-N-(3-methylpiperidin-4-yl)-4-oxo-4,5-dihydro-3H-1-thia-3,5,8-triazaacenaphthylene-2-carboxamide; | 6.7 |
| 173 | 5-(2-Methyl-4-phenoxyphenyl)-N-((6R)-6-methylpiperidin-3-yl)-4-oxo-4,5-dihydro-3H-1-thia-3,5,8-triazaacenaphthylene-2-carboxamide; | 6.8 |

TABLE 2-continued

| Ex # | Compound Name | BTK_I_binding pIC50 |
|---|---|---|
| 174 | (R)-N-(5,5-Difluoropiperidin-3-yl)-5-(2-methyl-4-phenoxyphenyl)-4-oxo-4,5-dihydro-3H-1-thia-3,5,8-triazaacenaphthylene-2-carboxamide; | 6.6 |
| 175 | (R,E)-N-(1-(2-Cyano-3-cyclopropylacryloyl)piperidin-3-yl)-5-(2,6-difluoro-4-phenoxyphenyl)-4-oxo-4,5-dihydro-3H-1-thia-3,5,8-triazaacenaphthylene-2-carboxamide; | 7.6 |
| 176 | 13C-(R,Z)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide; | 7.2 |
| 177 | 13C-(R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide; | 7.4 |
| 178 | (R,E)-N-(1-(2-Cyano-3-cyclopropylacryloyl)piperidin-3-yl)-5-(4-(cyclohexyloxy)-2-methylphenyl)-4-oxo-4,5-dihydro-3H-1-thia-3,5,8-triazaacenaphthylene-2-carboxamide; | 7.0 |
| 179 | N-((3R,5R)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 180 | (R)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide; | 6.0 |
| 181 | (R)-N-(1-(2-Cyanoacetyl)piperidin-3-yl)-4-oxo-5-(4-phenoxyphenyl)-4,5-dihydro-3H-1-thia-3,5,8-triazaacenaphthylene-2-carboxamide; | 7.1 |
| 182 | (R)-N-(1-Methylpiperidin-3-yl)-4-oxo-5-(4-phenoxyphenyl)-4,5-dihydro-3H-1-thia-3,5,8-triazaacenaphthylene-2-carboxamide; | 6.7 |
| 183 | (R)-5-(*S)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide; | 7.5 |
| 184 | (R)-5-(*S)-(2-Methyl-4-phenoxyphenyl)-4-oxo-N-(1-propionylpiperidin-3-yl)-4,5-dihydro-3H-1-thia-3,5,8-triazaacenaphthylene-2-carboxamide; | 7.4 |
| 185 | (R,E)-N-(1-(2-Cyano-3-cyclopropylacryloyl)piperidin-3-yl)-5-(4-cyclopropoxy-2-methylphenyl)-4-oxo-4,5-dihydro-3H-1-thia-3,5,8-triazaacenaphthylene-2-carboxamide; | 7.5 |
| 186 | N-((3S,4S)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide; | 6.8 |
| 187 | 5-(2-Methyl-4-phenoxyphenyl)-N-(1-methylazepan-4-yl)-4-oxo-4,5-dihydro-3H-1-thia-3,5,8-triazaacenaphthylene-2-carboxamide; | 6.7 |
| 188 | (R)-N-(1-(3-Methoxy-2,2-dimethylpropanoyl)piperidin-3-yl)-5-(2-methyl-4-phenoxyphenyl)-4-oxo-4,5-dihydro-3H-1-thia-3,5,8-triazaacenaphthylene-2-carboxamide; | 6.7 |
| 189 | N-(1-Cyanoazepan-4-yl)-5-(2-methyl-4-phenoxyphenyl)-4-oxo-4,5-dihydro-3H-1-thia-3,5,8-triazaacenaphthylene-2-carboxamide; | 6.6 |
| 190 | N-((R)-1-((R)-2,3-Dimethoxypropanoyl)piperidin-3-yl)-5-(2-methyl-4-phenoxyphenyl)-4-oxo-4,5-dihydro-3 H-1-thia-3,5,8-triazaacenaphthylene-2-carboxamide; | 7.0 |
| 191 | 5-(2-Methyl-4-phenoxyphenyl)-4-oxo-N-((R)-1-((R)-pyrrolidine-3-carbonyl)piperidin-3-yl)-4,5-dihydro-3H-1-thia-3,5,8-triazaacenaphthylene-2-carboxamide; | 7.1 |
| 192 | N-(4-(Hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide; | 6.8 |
| 193 | (R,E)-N-(1-(2-Cyano-3-cyclopropylacryloyl)piperidin-3-yl)-5-(4-ethoxy-2-methylphenyl)-4-oxo-4,5-dihydro-3H-1-thia-3,5,8-triazaacenaphthylene-2-carboxamide; | 7.3 |
| 194 | (R)-N-(1-Acryloylpiperidin-3-yl)-5-(2-fluorophenyl)-4-oxo-4,5-dihydro-3H-1-thia-3,5,8-triazaacenaphthylene-2-carboxamide; | 6.9 |
| 195 | (R,Z)-N-(1-(4-Amino-2-cyano-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.4 |
| 196 | (R,E)-N-(1-(3-(1-Aminocyclopropyl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 197 | N-((3R,5S)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 198 | 5-(2-Methyl-4-phenoxyphenyl)-4-oxo-N-((R)-1-((R)-tetrahydrofuran-3-carbonyl)piperidin-3-yl)-4,5-dihydro-3H-1-thia-3,5,8-triazaacenaphthylene-2-carboxamide; | 7.0 |
| 199 | (R,E)-N-(1-(3-Cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.6 |
| 200 | N-((3S,4R)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide; | 6.6 |

TABLE 2-continued

| Ex # | Compound Name | BTK_I_binding pIC50 |
|---|---|---|
| 201 | (R)-5-(4-(2-Cyclopropylphenoxy)-2-methylphenyl)-N-(1-methylpiperidin-3-yl)-4-oxo-4,5-dihydro-3H-1-thia-3,5,8-triazaacenaphthylene-2-carboxamide; | 6.6 |
| 202 | 5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide; | 6.7 |
| 203 | N-(1,2-Dimethylpiperidin-4-yl)-5-(2-methyl-4-phenoxyphenyl)-4-oxo-4,5-dihydro-3H-1-thia-3,5,8-triazaacenaphthylene-2-carboxamide; | 6.5 |
| 204 | (R)-N-(1-Methacryloylpiperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 205 | N-(1-(Cyclopropanecarbonyl)piperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 206 | 5-(2-Methyl-4-phenoxyphenyl)-N-(1-methylazepan-3-yl)-4-oxo-4,5-dihydro-3H-1-thia-3,5,8-triazaacenaphthylene-2-carboxamide; | 7.1 |
| 207 | 5-(2-Methyl-4-phenoxyphenyl)-4-oxo-N-((R)-1-((S)-tetrahydrofuran-3-carbonyl)piperidin-3-yl)-4,5-dihydro-3H-1-thia-3,5,8-triazaacenaphthylene-2-carboxamide; | 7.1 |
| 208 | N-((3S,4R)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide; | 6.8 |
| 209 | (R)-N-(1-Acryloylpyrrolidin-3-yl)-5-(5-chlorobenzo[d][1,3]dioxol-4-yl)-4-oxo-4,5-dihydro-3H-1-thia-3,5,8-triazaacenaphthylene-2-carboxamide; | 7.1 |
| 210 | (R)-5-(2-Methyl-4-(m-tolyloxy)phenyl)-N-(1-methylpiperidin-3-yl)-4-oxo-4,5-dihydro-3H-1-thia-3,5,8-triazaacenaphthylene-2-carboxamide; | 6.7 |
| 211 | N-((3S,4R)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide; | 6.7 |
| 212 | (R,E)-N-(1-(2-Cyano-4-(ethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 213 | (R)-N-(1-Cyclopropylpiperidin-3-yl)-5-(2-methyl-4-phenoxyphenyl)-4-oxo-4,5-dihydro-3H-1-thia-3,5,8-triazaacenaphthylene-2-carboxamide; | 6.5 |
| 214 | (R)-5-(4-(3-Fluorophenoxy)-2-methylphenyl)-N-(1-methylpiperidin-3-yl)-4-oxo-4,5-dihydro-3H-1-thia-3,5,8-triazaacenaphthylene-2-carboxamide; | 6.8 |
| 215 | (R)-5-(2-Fluoro-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide; | 7.2 |
| 216 | (R)-N-(1-Acryloylpiperidin-3-yl)-4-oxo-5-(o-tolyl)-4,5-dihydro-3H-1-thia-3,5,8-triazaacenaphthylene-2-carboxamide; | 6.7 |
| 217 | 5-(2-Methyl-4-phenoxyphenyl)-4-oxo-N-(2-(2-oxoimidazolidin-1-yl)ethyl)-4,5-dihydro-3H-1-thia-3,5,8-triazaacenaphthylene-2-carboxamide; | 6.5 |
| 218 | N-((3S,4S)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide; | 6.8 |
| 219 | (R)-5-(2-Methyl-4-phenoxyphenyl)-4-oxo-N-(1-(tetrahydro-2H-pyran-4-carbonyl)piperidin-3-yl)-4,5-dihydro-3H-1-thia-3,5,8-triazaacenaphthylene-2-carboxamide; | 6.9 |
| 220 | (R)-5-(4-(2-Hydroxyphenoxy)-2-methylphenyl)-N-(1-methylpiperidin-3-yl)-4-oxo-4,5-dihydro-3H-1-thia-3,5,8-triazaacenaphthylene-2-carboxamide; | 6.5 |
| 221 | (R,E)-N-(1-(3-Ethoxyacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 222 | (R)-5-(2-Fluoro-6-methyl-4-phenoxyphenyl)-N-(1-methylpiperidin-3-yl)-4-oxo-4,5-dihydro-3H-1-thia-3,5,8-triazaacenaphthylene-2-carboxamide; | 6.7 |
| 223 | (R)-5-(4-(2-Isopropylphenoxy)-2-methylphenyl)-N-(1-methylpiperidin-3-yl)-4-oxo-4,5-dihydro-3H-1-thia-3,5,8-triazaacenaphthylene-2-carboxamide; | 6.6 |
| 224 | N-((3R,5R)-5-Methoxypiperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 225 | (R)-5-(2-Methyl-4-phenoxyphenyl)-N-(1-(3-methylbut-2-enoyl)piperidin-3-yl)-4-oxo-4,5-dihydro-3H-1-thia-3,5,8-triazaacenaphthylene-2-carboxamide; | 6.7 |
| 226 | (R)-5-(4-(3-(Methoxymethyl)phenoxy)-2-methylphenyl)-N-(1-methylpiperidin-3-yl)-4-oxo-4,5-dihydro-3H-1-thia-3,5,8-triazaacenaphthylene-2-carboxamide; | 6.5 |

TABLE 2-continued

| Ex # | Compound Name | BTK_I_binding pIC50 |
|---|---|---|
| 227 | (R)-5-(2-Methyl-4-(2-(trifluoromethoxy)phenoxy)phenyl)-N-(1-methylpiperidin-3-yl)-4-oxo-4,5-dihydro-3H-1-thia-3,5,8-triazaacenaphthylene-2-carboxamide; | 6.5 |
| 228 | (R,Z)-N-(1-(3-Cyclopropyl-2-fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.6 |
| 229 | (E)-N-(1-(2-Cyano-3-cyclopropylacryloyl)azetidin-3-yl)-5-(2-methyl-4-phenoxyphenyl)-4-oxo-4,5-dihydro-3H-1-thia-3,5,8-triazaacenaphthylene-2-carboxamide; | 6.7 |
| 230 | N-(1-Cyclopropylazetidin-3-yl)-5-(2-methyl-4-phenoxyphenyl)-4-oxo-4,5-dihydro-3H-1-thia-3,5,8-triazaacenaphthylene-2-carboxamide; | 6.4 |
| 231 | (R,EZ)-N-(1-(2-Cyano-3-methoxyacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 233 | (R,E)-N-(1-(2-Cyano-3-cyclopropylacryloyl)piperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 7.2 |
| 234 | (R,EZ)-N-(1-(2-Cyano-4-((2-methoxyethyl)amino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 235 | (R)-5-(2,6-Difluoro-4-phenoxyphenyl)-4-oxo-N-(piperidin-3-yl)-4,5-dihydro-3H-1-thia-3,5,8-triazaacenaphthylene-2-carboxamide; | 7.0 |
| 236 | N-((3S,4S)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide; | 7.0 |
| 237 | N1-((E)-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)-N5-(15-oxo-19-((3aS,4R,6aR)-2-oxohexahydro-1H-thieno[3,4-d]imidazol-4-yl)-4,7,10-trioxa-14-azanonadecyl)glutaramide; | 6.9 |
| 238 | (R,E)-N-(1-(2-Cyano-4-methyl-4-(methylamino)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 239 | (R,E)-5-(5-Chlorobenzo[d][1,3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide; | 7.4 |
| 240 | 5-(2-Methyl-4-phenoxyphenyl)-N-(1-(3-(methylsulfonyl)propanoyl)azetidin-3-yl)-4-oxo-4,5-dihydro-3H-1-thia-3,5,8-triazaacenaphthylene-2-carboxamide; | 6.7 |
| 241 | N-((3S,4R)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide; | 6.7 |
| 242 | (R)-5-(2-Methyl-4-(2-(trifluoromethyl)phenoxy)phenyl)-N-(1-methylpiperidin-3-yl)-4-oxo-4,5-dihydro-3H-1-thia-3,5,8-triazaacenaphthylene-2-carboxamide; | 6.7 |
| 243 | N-((3S,4S)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide; | 6.6 |
| 244 | N-((3S,4S)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide; | 6.6 |
| 245 | N-((3S,4S)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide; | 6.6 |
| 246 | N-(1-(3-Methoxypropanoyl)azetidin-3-yl)-5-(2-methyl-4-phenoxyphenyl)-4-oxo-4,5-dihydro-3H-1-thia-3,5,8-triazaacenaphthylene-2-carboxamide; | 6.5 |
| 247 | (R,E)-5-(2-Methyl-4-phenoxyphenyl)-N-(1-(4-methylpent-2-enoyl)piperidin-3-yl)-4-oxo-4,5-dihydro-3H-1-thia-3,5,8-triazaacenaphthylene-2-carboxamide; | 6.5 |
| 248 | 5-(2-Methyl-4-phenoxyphenyl)-N-(1-methylazetidin-3-yl)-4-oxo-4,5-dihydro-3H-1-thia-3,5,8-triazaacenaphthylene-2-carboxamide; | 6.5 |
| 249 | (S)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide; | 6.6 |
| 250 | (R)-5-(4-(Cyclohexyloxy)-2-methylphenyl)-N-(1-methylpiperidin-3-yl)-4-oxo-4,5-dihydro-3H-1-thia-3,5,8-triazaacenaphthylene-2-carboxamide; | 6.4 |
| 251 | N-(1-Ethylazetidin-3-yl)-5-(2-methyl-4-phenoxyphenyl)-4-oxo-4,5-dihydro-3H-1-thia-3,5,8-triazaacenaphthylene-2-carboxamide; | 6.4 |
| 252 | N-(Azetidin-3-yl)-5-(2-methyl-4-phenoxyphenyl)-4-oxo-4,5-dihydro-3H-1-thia-3,5,8-triazaacenaphthylene-2-carboxamide; | 6.4 |
| 253 | (R)-5-(*R)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide; | 6.2 |

TABLE 2-continued

| Ex # | Compound Name | BTK_I_binding pIC50 |
|---|---|---|
| 254 | (R)-N-(1-Acryloylpiperidin-3-yl)-5-(4-methoxy-2-methylphenyl)-4-oxo-4,5-dihydro-3H-1-thia-3,5,8-triazaacenaphthylene-2-carboxamide; | 6.6 |
| 255 | (R)-N-(1-Acryloylpiperidin-3-yl)-5-(4-fluorophenyl)-4-oxo-4,5-dihydro-3H-1-thia-3,5,8-triazaacenaphthylene-2-carboxamide; | 6.6 |
| 256 | (R)-N-(1-Acryloylpiperidin-3-yl)-5-(4-chlorophenyl)-4-oxo-4,5-dihydro-3H-1-thia-3,5,8triazaacenaphthylene-2-carboxamide; | 6.6 |
| 257 | (R)-N-(1-Acryloylpiperidin-3-yl)-4-oxo-5-phenyl-4,5-dihydro-3H-1-thia-3,5,8-triazaacenaphthylene-2-carboxamide; | 6.4 |
| 258 | 5-(2-Methyl-4-phenoxyphenyl)-N-(2-methylpiperidin-4-yl)-4-oxo-4,5-dihydro-3H-1-thia-3,5,8-triazaacenaphthylene-2-carboxamide; | 6.5 |
| 259 | N-((3R,5R)-5-Methoxy-1-methylpiperidin-3-yl)-4-oxo-5-(4-phenoxyphenyl)-4,5-dihydro-3H-1-thia-3,5,8-triazaacenaphthylene-2-carboxamide; | 6.5 |
| 260 | (R)-N-(1-(2-chloro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.5 |
| 261 | (R,Z)-N-(1-(2-Fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.5 |
| 262 | N-(1-Methyl-5-oxopyrrolidin-3-yl)-4-oxo-5-(4-phenoxyphenyl)-4,5-dihydro-3H-1-thia-3,5,8-triazaacenaphthylene-2-carboxamide; | 6.4 |
| 263 | (R)-N-(1-(2-Fluoro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.4 |
| 264 | (R)-N-(1-Acryloylpyrrolidin-3-yl)-5-(2-methyl-4-(pentafluorothio)phenyl)-4-oxo-4,5-dihydro-3H-1-thia-3,5,8-triazaacenaphthylene-2-carboxamide; | 6.4 |
| 265 | (S)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide; | 6.4 |
| 266 | N-((3R,5S)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide; | 6.3 |
| 267 | (S)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 6.3 |
| 268 | N-((3R,5S)-5-Methoxypiperidin-3-yl)-5-(2-methyl-4-phenoxyphenyl)-4-oxo-4,5-dihydro-3H-1-thia-3,5,8-triazaacenaphthylene-2-carboxamide; | 6.3 |
| 269 | (S)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide; | 6.3 |
| 270 | (R)-N-(1-Acryloylpyrrolidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 6.3 |
| 271 | (R)-N-(1-Acryloylpiperidin-3-yl)-4-oxo-5-(p-tolyl)-4,5-dihydro-3H-1-thia-3,5,8-triazaacenaphthylene-2-carboxamide; | 6.3 |
| 272 | (R)-N-(5,5-Difluoro-1-methylpiperidin-3-yl)-5-(2-methyl-4-phenoxyphenyl)-4-oxo-4,5-dihydro-3H-1-thia-3,5,8-triazaacenaphthylene-2-carboxamide; | 6.3 |
| 273 | N-(1-Isopropylazetidin-3-yl)-5-(2-methyl-4-phenoxyphenyl)-4-oxo-4,5-dihydro-3H-1-thia-3,5,8-triazaacenaphthylene-2-carboxamide; | 6.3 |
| 274 | (R,E)-N-(1-(4,4-Dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.3 |
| 275 | 5-(2-Methyl-4-phenoxyphenyl)-N-(2-morpholinoethyl)-4-oxo-4,5-dihydro-3H-1-thia-3,5,8-triazaacenaphthylene-2-carboxamide; | 6.3 |
| 276 | (R)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide; | 6.3 |
| 277 | (R,Z)-N-(1-(2-Chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.2 |
| 278 | (R)-N-(1-Acryloylpiperidin-3-yl)-4-oxo-5-(4-phenoxy-2-(trifluoromethyl)phenyl)-4,5-dihydro-3H-1-thia-3,5,8-triazaacenaphthylene-2-carboxamide; | 6.2 |
| 279 | (R)-N-(1-Acryloylpiperidin-3-yl)-4-oxo-5-(m-tolyl)-4,5-dihydro-3H-1-thia-3,5,8-triazaacenaphthylene-2-carboxamide; | 6.2 |
| 280 | (R)-5-(4-Chloro-3-(trifluoromethyl)phenyl)-4-oxo-N-(piperidin-3-yl)-4,5-dihydro-3H-1-thia-3,5,8-triazaacenaphthylene-2-carboxamide; | 5.8 |
| 281 | (R)-5-(2,3-Dimethyl-4-phenoxyphenyl)-N-(1-methylpiperidin-3-yl)-4-oxo-4,5-dihydro-3H-1-thia-3,5,8-triazaacenaphthylene-2-carboxamide; | 6.2 |
| 282 | 5-(2-Methyl-4-phenoxyphenyl)-N-((1-methylpyrrolidin-3-yl)methyl)-4-oxo-4,5-dihydro-3H-1-thia-3,5,8-triazaacenaphthylene-2-carboxamide; | 6.2 |

TABLE 2-continued

| Ex # | Compound Name | BTK_I_binding pIC50 |
|---|---|---|
| 283 | (R)-5-(4-(2-Isopropoxyphenoxy)-2-methylphenyl)-N-(1-methylpiperidin-3-yl)-4-oxo-4,5-dihydro-3H-1-thia-3,5,8-triazaacenaphthylene-2-carboxamide; | 6.2 |
| 284 | (R)-5-(4-Cyclobutoxy-2-methylphenyl)-N-(1-methylpiperidin-3-yl)-4-oxo-4,5-dihydro-3H-1-thia-3,5,8-triazaacenaphthylene-2-carboxamide; | 6.2 |
| 285 | (R)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide; | 6.2 |
| 286 | (R)-5-(4-(3,5-Difluorophenoxy)-2-methylphenyl)-N-(1-methylpiperidin-3-yl)-4-oxo-4,5-dihydro-3H-1-thia-3,5,8-triazaacenaphthylene-2-carboxamide; | 6.2 |
| 287 | (R)-N-(1-(2-(Dimethylamino)acetyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 6.2 |
| 288 | (R)-N-(1-Acryloylpiperidin-3-yl)-4-oxo-5-(3-(trifluoromethyl)phenyl)-4,5-dihydro-3H-1-thia-3,5,8-triazaacenaphthylene-2-carboxamide; | 6.2 |
| 289 | (S)-N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide; | 6.2 |
| 290 | (R)-5-(2-Methyl-4-(p-tolyloxy)phenyl)-N-(1-methylpiperidin-3-yl)-4-oxo-4,5-dihydro-3H-1-thia-3,5,8-triazaacenaphthylene-2-carboxamide; | 6.2 |
| 291 | (S)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide; | 6.1 |
| 292 | (R,E)-5-(*R)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide; | 6.1 |
| 293 | (R)-5-(2-Methyl-4-(pyridin-3-yloxy)phenyl)-N-(1-methylpiperidin-3-yl)-4-oxo-4,5-dihydro-3H-1-thia-3,5,8-triazaacenaphthylene-2-carboxamide; | 6.1 |
| 294 | (R)-N-(1-Acryloylpiperidin-3-yl)-5-(3-chlorophenyl)-4-oxo-4,5-dihydro-3H-1-thia-3,5,8-triazaacenaphthylene-2-carboxamide; | 6.1 |
| 295 | (R)-5-(4-(4-Fluorophenoxy)-2-methylphenyl)-N-(1-methylpiperidin-3-yl)-4-oxo-4,5-dihydro-3H-1-thia-3,5,8-triazaacenaphthylene-2-carboxamide; | 6.1 |
| 296 | (R)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide; | 6.1 |
| 297 | (R)-5-(4-(Cyclopentyloxy)-2-methylphenyl)-N-(1-methylpiperidin-3-yl)-4-oxo-4,5-dihydro-3H-1-thia-3,5,8-triazaacenaphthylene-2-carboxamide; | 6.1 |
| 298 | 5-(2-Methyl-4-phenoxyphenyl)-N-(2-(1-methylpyrrolidin-2-yl)ethyl)-4-oxo-4,5-dihydro-3H-1-thia-3,5,8-triazaacenaphthylene-2-carboxamide; | 6.1 |
| 299 | (R)-N-(1-Acryloylpyrrolidin-3-yl)-5-(4-methoxy-2-methylphenyl)-4-oxo-4,5-dihydro-3H-1-thia-3,5,8-triazaacenaphthylene-2-carboxamide; | 6.1 |
| 300 | (R)-5-(*R)-(2-Methyl-4-phenoxyphenyl)-4-oxo-N-(piperidin-3-yl)-4,5-dihydro-3H-1-thia-3,5,8-triazaacenaphthylene-2-carboxamide; | 6.0 |
| 301 | (R)-N-(1-Acryloylpyrrolidin-3-yl)-5-(2-fluorophenyl)-4-oxo-4,5-dihydro-3H-1-thia-3,5,8-triazaacenaphthylene-2-carboxamide; | 6.0 |
| 302 | (R)-5-(4-(2,4-Difluorophenoxy)-2-methylphenyl)-N-(1-methylpiperidin-3-yl)-4-oxo-4,5-dihydro-3H-1-thia-3,5,8-triazaacenaphthylene-2-carboxamide; | 6.0 |
| 303 | (R)-5-(5-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide; | 6.0 |
| 304 | (R)-N-(1-Acryloylpyrrolidin-3-yl)-5-(2,4-dimethylphenyl)-4-oxo-4,5-dihydro-3H-1-thia-3,5,8-triazaacenaphthylene-2-carboxamide; | 6.0 |
| 305 | (R)-5-(5-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 6.0 |
| 306 | (R)-5-(2-Methyl-4-(pyridin-2-yloxy)phenyl)-N-(1-methylpiperidin-3-yl)-4-oxo-4,5-dihydro-3H-1-thia-3,5,8-triazaacenaphthylene-2-carboxamide; | 6.0 |
| 307 | (R)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 6.0 |
| 308 | (S)-5-(5-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide; | 6.0 |
| 309 | (S)-N-(1-Benzyl-2-oxoazepan-3-yl)-5-(2-methyl-4-phenoxyphenyl)-4-oxo-4,5-dihydro-3H-1-thia-3,5,8-triazaacenaphthylene-2-carboxamide; | 6.0 |

TABLE 2-continued

| Ex # | Compound Name | BTK_I_binding pIC50 |
|---|---|---|
| 310 | (S)-5-(2-Methyl-4-phenoxyphenyl)-4-oxo-N-(piperidin-2-ylmethyl)-4,5-dihydro-3H-1-thia-3,5,8-triazaacenaphthylene-2-carboxamide; | 6.0 |
| 311 | (R)-N-(1-Acryloylpyrrolidin-3-yl)-4-oxo-5-(6-phenoxypyridazin-3-yl)-4,5-dihydro-3H-1-thia-3,5,8-triazaacenaphthylene-2-carboxamide; | 5.9 |
| 312 | N-((3R,5S)-5-Methoxy-1-methylpiperidin-3-yl)-5-(2-methyl-4-phenoxyphenyl)-4-oxo-4,5-dihydro-3H-1-thia-3,5,8-triazaacenaphthylene-2-carboxamide; | 5.9 |
| 313 | (R,EZ)-N-(1-(3-Cyclopropyl-2-(trifluoromethyl)acryloyl)piperidin-3-yl)-5-(2-methyl-4-phenoxyphenyl)-4-oxo-4,5-dihydro-3H-1-thia-3,5,8-triazaacenaphthylene-2-carboxamide; | 5.9 |
| 314 | (R)-N-(1-Acryloylpyrrolidin-3-yl)-4-oxo-5-(o-tolyl)-4,5-dihydro-3H-1-thia-3,5,8-triazaacenaphthylene-2-carboxamide; | 5.9 |
| 315 | 5-(2-Methyl-4-phenoxyphenyl)-N-(2-morpholino-2-oxoethyl)-4-oxo-4,5-dihydro-3H-1-thia-3,5,8-triazaacenaphthylene-2-carboxamide; | 6.9 |
| 317 | (R)-5-(2,6-Dimethyl-4-phenoxyphenyl)-N-(1-methylpiperidin-3-yl)-4-oxo-4,5-dihydro-3H-1-thia-3,5,8-triazaacenaphthylene-2-carboxamide; | 5.8 |
| 318 | (R)-N-(1-(3-Hydroxypropanoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 5.8 |
| 320 | (R)-N-(1-Ethylpiperidin-3-yl)-5-(4-(2-isopropylphenoxy)-2-methylphenyl)-4-oxo-4,5-dihydro-3H-1-thia-3,5,8-triazaacenaphthylene-2-carboxamide; | 6.7 |
| 321 | (R)-N-(1-Acryloylpiperidin-3-yl)-5-(*R)-(5-chlorobenzo[d][1,3]dioxol-4-yl)-4-oxo-4,5-dihydro-3H-1-thia-3,5,8-triazaacenaphthylene-2-carboxamide; | 7.1 |
| 322 | (R)-5-(4-Cyclopropoxy-2-methylphenyl)-N-(1-methylpiperidin-3-yl)-4-oxo-4,5-dihydro-3H-1-thia-3,5,8-triazaacenaphthylene-2-carboxamide; | 5.7 |
| 323 | (S)-5-(*R)-(2-Methyl-4-phenoxyphenyl)-4-oxo-N-(tetrahydrofuran-3-yl)-4,5-dihydro-3H-1-thia-3,5,8-triazaacenaphthylene-2-carboxamide; | 5.7 |
| 324 | (R)-N-(1-Acryloylpyrrolidin-3-yl)-4-oxo-5-(4-phenoxy-2-(trifluoromethyl)phenyl)-4,5-dihydro-3H-1-thia-3,5,8-triazaacenaphthylene-2-carboxamide; | 5.7 |
| 325 | (R)-5-(*R)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide; | 5.7 |
| 326 | (R)-5-(4-(2-Carbamoylphenoxy)-2-methylphenyl)-N-(1-methylpiperidin-3-yl)-4-oxo-4,5-dihydro-3H-1-thia-3,5,8-triazaacenaphthylene-2-carboxamide; | 5.7 |
| 328 | (R)-6-Methyl-4-oxo-5-(4-phenoxyphenyl)-N-(piperidin-3-yl)-4,5-dihydro-3H-1-thia-3,5,8-triazaacenaphthylene-2-carboxamide; | 5.7 |
| 329 | (R)-N-(1-Cyanopiperidin-3-yl)-5-(*R)-(2-methyl-4-phenoxyphenyl)-4-oxo-4,5-dihydro-3H-1-thia-3,5,8-triazaacenaphthylene-2-carboxamide; | 5.7 |
| 330 | (R)-5-(3,5-Dichlorophenyl)-4-oxo-N-(piperidin-3-yl)-4,5-dihydro-3H-1-thia-3,5,8-triazaacenaphthylene-2-carboxamide; | 5.6 |
| 331 | (R)-N-Methyl-5-(2-methyl-4-phenoxyphenyl)-4-oxo-N-(pyrrolidin-3-yl)-4,5-dihydro-3H-1-thia-3,5,8-triazaacenaphthylene-2-carboxamide; | 5.5 |
| 332 | (R)-5-(4-Isopropoxy-2-methylphenyl)-N-(1-methylpiperidin-3-yl)-4-oxo-4,5-dihydro-3H-1-thia-3,5,8-triazaacenaphthylene-2-carboxamide; | 5.5 |
| 333 | (R)-5-(4-Ethoxy-2-methylphenyl)-N-(1-methylpiperidin-3-yl)-4-oxo-4,5-dihydro-3H-1-thia-3,5,8-triazaacenaphthylene-2-carboxamide; | 5.5 |
| 334 | (R)-N-(1-Acryloylpiperidin-3-yl)-5-(4-(tert-butyl)phenyl)-4-oxo-4,5-dihydro-3H-1-thia-3,5,8-triazaacenaphthylene-2-carboxamide; | 5.5 |
| 336 | (R)-5-(3-Chlorophenyl)-4-oxo-N-(piperidin-3-yl)-4,5-dihydro-3H-1-thia-3,5,8-triazaacenaphthylene-2-carboxamide; | 5.4 |
| 337 | (R)-N-(1-Acryloylpyrrolidin-3-yl)-4-oxo-5-phenyl-4,5-dihydro-3H-1-thia-3,5,8-triazaacenaphthylene-2-carboxamide; | 5.4 |
| 338 | (R)-N-Methyl-5-(2-methyl-4-phenoxyphenyl)-N-(1-methylpyrrolidin-3-yl)-4-oxo-4,5-dihydro-3H-1-thia-3,5,8-triazaacenaphthylene-2-carboxamide; | 5.4 |
| 339 | (S)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide; | 5.4 |
| 340 | (R)-5-(4-Methoxy-2-methylphenyl)-N-(1-methylpiperidin-3-yl)-4-oxo-4,5-dihydro-3H-1-thia-3,5,8-triazaacenaphthylene-2-carboxamide; | 5.3 |
| 341 | (R)-4-Oxo-N-(piperidin-3-yl)-5-(4-(trifluoromethyl)phenyl)-4,5-dihydro-3H-1-thia-3,5,8-triazaacenaphthylene-2-carboxamide; | 5.2 |
| 342 | (R)-5-(4-Methoxyphenyl)-4-oxo-N-(piperidin-3-yl)-4,5-dihydro-3H-1-thia-3,5,8-triazaacenaphthylene-2-carboxamide; | 5.2 |
| 343 | (R)-5-(*R)-(2-Methyl-4-((tetrahydro-2H-pyran-4-yl)oxy)phenyl)-N-(1-methylpiperidin-3-yl)-4-oxo-4,5-dihydro-3H-1-thia-3,5,8-triazaacenaphthylene-2-carboxamide; | 5.3 |

TABLE 2-continued

| Ex # | Compound Name | BTK_I_binding pIC50 |
|---|---|---|
| 344 | (R)-5-([1,1'-Biphenyl]-4-yl)-4-oxo-N-(piperidin-3-yl)-4,5-dihydro-3H-1-thia-3,5,8-triazaacenaphthylene-2-carboxamide; | 5.0 |
| 345 | (R)-5-(*R)-(2-Methyl-4-phenoxyphenyl)-4-oxo-N-(1-propionylpiperidin-3-yl)-4,5-dihydro-3H-1-thia-3,5,8-triazaacenaphthylene-2-carboxamide; | <5 |
| 346 | (R)-5-(3,4-Dichlorophenyl)-4-oxo-N-(piperidin-3-yl)-4,5-dihydro-3H-1-thia-3,5,8-triazaacenaphthylene-2-carboxamide; | <5 |
| 347 | (R)-4-Oxo-N-(piperidin-3-yl)-5-(3-(trifluoromethyl)phenyl)-4,5-dihydro-3H-1-thia-3,5,8-triazaacenaphthylene-2-carboxamide; | <5 |
| 348 | (R)-4-Oxo-5-phenyl-N-(piperidin-3-yl)-4,5-dihydro-3H-1-thia-3,5,8-triazaacenaphthylene-2-carboxamide; | <5 |
| 349 | (R)-N-(1-Methylpiperidin-3-yl)-4-oxo-5-(4-phenoxy-2-(trifluoromethyl)phenyl)-4,5-dihydro-3H-1-thia-3,5,8-triazaacenaphthylene-2-carboxamide; | <5 |
| 350 | (R)-5-(4-Methyl-6-phenoxypyridazin-3-yl)-N-(1-methylpiperidin-3-yl)-4-oxo-4,5-dihydro-3H-1-thia-3,5,8-triazaacenaphthylene-2-carboxamide; | <5 |
| 351 | (R)-N-(1-Acryloylpyrrolidin-3-yl)-5-(4-methyl-6-phenoxypyridazin-3-yl)-4-oxo-4,5-dihydro-3H-1-thia-3,5,8-triazaacenaphthylene-2-carboxamide; | <5 |
| 352 | (R)-N-(1-Methylpiperidin-3-yl)-4-oxo-5-(o-tolyl)-4,5-dihydro-3H-1-thia-3,5,8-triazaacenaphthylene-2-carboxamide; | <5 |
| 353 | (R)-5-(*R)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide; | 5.8 |
| 354 | (R)-5-(2-Methyl-4-(pyridin-4-yloxy)phenyl)-N-(1-methylpiperidin-3-yl)-4-oxo-4,5-dihydro-3H-1-thia-3,5,8-triazaacenaphthylene-2-carboxamide; | <5 |
| 356 | (R)-5-(3-(Dimethylamino)phenyl)-4-oxo-N-(piperidin-3-yl)-4,5-dihydro-3H-1-thia-3,5,8-triazaacenaphthylene-2-carboxamide; | <5 |
| 357 | (R)-N-(1-Acryloylpiperidin-3-yl)-5-isopropyl-4-oxo-4,5-dihydro-3H-1-thia-3,5,8-triazaacenaphthylene-2-carboxamide; | 5.1 |
| 358 | (R)-N-(1-Acryloylpiperidin-3-yl)-5-(2-methylpyridin-3-yl)-4-oxo-4,5-dihydro-3H-1-thia-3,5,8-triazaacenaphthylene-2-carboxamide; | 5.2 |
| 359 | (R)-5-(2-Methylpyridin-3-yl)-4-oxo-N-(piperidin-3-yl)-4,5-dihydro-3H-1-thia-3,5,8-triazaacenaphthylene-2-carboxamide; | <5 |
| 360 | (R)-N-(1-Acryloylpiperidin-3-yl)-5-(3,4-dichlorophenyl)-4-oxo-4,5-dihydro-3H-1-thia-3,5,8-triazaacenaphthylene-2-carboxamide; | 6.7 |
| 361 | (R)-5-Isopropyl-4-oxo-N-(piperidin-3-yl)-4,5-dihydro-3H-1-thia-3,5,8-triazaacenaphthylene-2-carboxamide; | <5 |
| 362 | (R)-N-(1-Acryloylpiperidin-3-yl)-5-(4-chloro-3-(trifluoromethyl)phenyl)-4-oxo-4,5-dihydro-3H-1-thia-3,5,8-triazaacenaphthylene-2-carboxamide; | 5.4 |
| 363 | (R)-N-(1-(3-Methoxy-3-methylbutanoyl)piperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 364 | (R,Z)-N-(1-(3-Acetamidoacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 365 | (R,E)-N-(1-(2-Cyano-3-cyclopropylacryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 7.3 |
| 366 | (R)-N-(1-(2-Chloroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.1 |
| 367 | (R,E)-N-(1-(4-Aminobut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 6.2 |
| 368 | (R,E)-N-(1-(4-(Dimethylamino)but-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.6 |
| 369 | (R)-5-(2-Methyl-4-phenoxyphenyl)-4-oxo-N-(1-(vinylsulfonyl)pyrrolidin-3-yl)-4,5-dihydro-3H-1-thia-3,5,8-triazaacenaphthylene-2-carboxamide; | 7.8 |
| 370 | (R)-5-(2-Methyl-4-phenoxyphenyl)-N-(1-trideuteriomethylpiperidin-3-yl)-4-oxo-4,5-dihydro-3H-1-thia-3,5,8-triazaacenaphthylene-2-carboxamide; | 7.0 |
| 371 | (R,E)-N-(1-(4-(Dimethylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 372 | (R)-5-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide; | 7.6 |
| 373 | (R,E)-N-(1-(4-(Dimethylamino)but-2-enoyl)piperidin-3-yl)-4-oxo-5-(4-phenoxyphenyl)-4,5-dihydro-3H-1-thia-3,5,8-triazaacenaphthylene-2-carboxamide; | 7.3 |

TABLE 2-continued

| Ex # | Compound Name | BTK_I_binding pIC50 |
|---|---|---|
| 374 | (R,E)-5-(2-Methyl-4-phenoxyphenyl)-N-(1-(4-(methylsulfonyl)but-2-enoyl)piperidin-3-yl)-4-oxo-4,5-dihydro-3H-1-thia-3,5,8-triazaacenaphthylene-2-carboxamide; | 7.0 |
| 375 | (R)-N-(1-Acryloylpiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide; | 7.9 |
| 376 | (R)-N-(1-Acryloylpyrrolidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide; | 7.8 |
| 377 | (R,E)-5-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide; | 7.5 |
| 378 | (R,E)-N-(1-(2-Cyano-3-cyclopropylacryloyl)piperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide; | 7.5 |
| 379 | (R)-N-(1-Cyanopiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide; | 7.5 |
| 380 | (R)-5-(2-Methyl-4-(2,3,4,5,6-pentadeuteriophenoxy)phenyl)-N-(1-(trideuteriomethyl)piperidin-3-yl)-4-oxo-4,5-dihydro-3H-1-thia-3,5,8-triazaacenaphthylene-2-carboxamide; | 6.8 |
| 381 | (R)-5-(2-Methyl-4-(2,3,4,5,6-pentadeuteriophenoxy)phenyl)-N-(1-methylpiperidin-3-yl)-4-oxo-4,5-dihydro-3H-1-thia-3,5,8-triazaacenaphthylene-2-carboxamide; | 7.1 |
| 382 | (R,E)-N-(1-(4-Aminobut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.3 |
| 383 | (R,E)-5-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide; | 7.2 |
| 384 | (R)-N-(1-(2-(Dimethylamino)acetyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.1 |
| 385 | (R,E)-N-(1-(2-Cyanobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.9 |
| 386 | N-((R)-1-((S)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide; | 6.9 |
| 387 | (R,E)-N-(1-(2-Cyano-3-(3-methyloxetan-3-yl)acryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 7.8 |
| 388 | (R,Z)-N-(1-(2-Fluoro-4-(methylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 389 | (R)-5-(2-Methyl-4-phenoxyphenyl)-4-oxo-N-(1-(2-(pyrrolidin-1-yl)acetyl)piperidin-3-yl)-4,5-dihydro-3H-1-thia-3,5,8-triazaacenaphthylene-2-carboxamide; | 7.0 |
| 390 | (R)-2-(((1-Acryloylpiperidin-3-yl)amino)methyl)-5-(2-methyl-4-phenoxyphenyl)-3H-1-thia-3,5,8-triazaacenaphthylen-4(5H)-one; | 6.9 |
| 391 | (R)-5-(2-Methyl-4-phenoxyphenyl)-N-(1-(2-(methylamino)acetyl)pyrrolidin-3-yl)-4-oxo-4,5-dihydro-3H-1-thia-3,5,8-triazaacenaphthylene-2-carboxamide; | 7.2 |
| 392 | (R)-N-(1-(2-Aminoacetyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.4 |
| 393 | (R)-5-(2-Methyl-4-phenoxyphenyl)-4-oxo-N-(1-(2-(piperidin-1-yl)acetyl)piperidin-3-yl)-4,5-dihydro-3H-1-thia-3,5,8-triazaacenaphthylene-2-carboxamide; | 6.8 |
| 394 | (R)-5-(2-Methyl-4-phenoxyphenyl)-N-(1-(2-morpholinoacetyl)piperidin-3-yl)-4-oxo-4,5-dihydro-3H-1-thia-3,5,8-triazaacenaphthylene-2-carboxamide; | 6.8 |
| 395 | (R)-N-(1-(2-Chloroacetyl)pyrrolidin-3-yl)-5-(2-methyl-4-phenoxyphenyl)-4-oxo-4,5-dihydro-3H-1-thia-3,5,8-triazaacenaphthylene-2-carboxamide; | 8.0 |
| 396 | (R)-N-(1-(2-Chloroacetyl)piperidin-3-yl)-5-(2-methyl-4-phenoxyphenyl)-4-oxo-4,5-dihydro-3H-1-thia-3,5,8-triazaacenaphthylene-2-carboxamide; | 7.8 |
| 397 | (R)-N-(1-Acryloylpiperidin-3-yl)-4-oxo-5-(4-(thiophen-2-yl)phenyl)-4,5-dihydro-3H-1-thia-3,5,8-triazaacenaphthylene-2-carboxamide; | 6.4 |
| 398 | (R,E)-N-(1-(2-Cyano-4,4-dimethylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 6.6 |
| 399 | (R,E)-N-(1-(2-Cyano-3-cyclopropylacryloyl)piperidin-3-yl)-5-(4-isopropoxyphenyl)-4-oxo-4,5-dihydro-3H-1-thia-3,5,8-triazaacenaphthylene-2-carboxamide; | 7.5 |

TABLE 2-continued

| Ex # | Compound Name | BTK_I_binding pIC50 |
|---|---|---|
| 400 | (R)-N-(1-Acryloylpiperidin-3-yl)-5-(4-isopropoxyphenyl)-4-oxo-4,5-dihydro-3H-1-thia-3,5,8-triazaacenaphthylene-2-carboxamide; | 6.9 |
| 401 | (R,E)-N-(1-(3-Cyclopropyl-2-methylacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.5 |
| 402 | (R,EZ)-N-(1-(2-Chloro-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.5 |
| 403 | (R,E)-5-(2-Methyl-4-phenoxyphenyl)-N-(1-(4-morpholinobut-2-enoyl)piperidin-3-yl)-4-oxo-4,5-dihydro-3H-1-thia-3,5,8-triazaacenaphthylene-2-carboxamide; | 6.4 |
| 404 | (R)-N-(1-Acryloylpiperidin-3-yl)-5-(benzo[b]thiophen-5-yl)-4-oxo-4,5-dihydro-3H-1-thia-3,5,8-triazaacenaphthylene-2-carboxamide; | 6.1 |
| 405 | (R)-5-(4-Isopropoxyphenyl)-4-oxo-N-(piperidin-3-yl)-4,5-dihydro-3H-1-thia-3,5,8-triazaacenaphthylene-2-carboxamide; | 5.5 |
| 406 | (R)-5-(4-Isopropoxyphenyl)-4-oxo-N-(1-propionylpiperidin-3-yl)-4,5-dihydro-3H-1-thia-3,5,8-triazaacenaphthylene-2-carboxamide; | 5.2 |
| 407 | (R)-4-Oxo-N-(piperidin-3-yl)-5-(4-(thiophen-2-yl)phenyl)-4,5-dihydro-3H-1-thia-3,5,8-triazaacenaphthylene-2-carboxamide; | 5.1 |
| 408 | (R)-N-(1-Acryloylpiperidin-3-yl)-4-oxo-5-(4-phenoxybenzyl)-4,5-dihydro-3H-1-thia-3,5,8-triazaacenaphthylene-2-carboxamide; | 5.1 |
| 409 | (R)-N-(1-Methylpyrrolidin-3-yl)-4-oxo-5-(4-phenoxybenzyl)-4,5-dihydro-3H-1-thia-3,5,8-triazaacenaphthylene-2-carboxamide; | 5.0 |
| 410 | (R)-5-(Benzo[b]thiophen-5-yl)-4-oxo-N-(piperidin-3-yl)-4,5-dihydro-3H-1-thia-3,5,8-triazaacenaphthylene-2-carboxamide; | 5.0 |
| 411 | (R)-N-(1-Methylpiperidin-3-yl)-4-oxo-5-(4-phenoxybenzyl)-4,5-dihydro-3H-1-thia-3,5,8-triazaacenaphthylene-2-carboxamide; | <5 |
| 412 | (R)-4-Oxo-5-(4-phenoxybenzyl)-N-(piperidin-3-yl)-4,5-dihydro-3H-1-thia-3,5,8-triazaacenaphthylene-2-carboxamide; | <5 |
| 413 | (R)-5-(2-Methyl-4-(trifluoromethoxy)phenyl)-4-oxo-N-(piperidin-3-yl)-4,5-dihydro-3H-1-thia-3,5,8-triazaacenaphthylene-2-carboxamide; | 5.6 |
| 414 | (R)-N-(1-Acryloylpiperidin-3-yl)-5-(2-methyl-4-(trifluoromethoxy)phenyl)-4-oxo-4,5-dihydro-3H-1-thia-3,5,8-triazaacenaphthylene-2-carboxamide; | 7.4 |
| 415 | (R)-4-Oxo-N-(piperidin-3-yl)-5-(4-(trifluoromethoxy)phenyl)-4,5-dihydro-3H-1-thia-3,5,8-triazaacenaphthylene-2-carboxamide; | 5.2 |
| 416 | (R)-N-(1-Acryloylpiperidin-3-yl)-4-oxo-5-(4-(trifluoromethoxy)phenyl)-4,5-dihydro-3H-1-thia-3,5,8-triazaacenaphthylene-2-carboxamide; | 6.7 |
| 417 | (R)-N-(1-Acryloylpiperidin-3-yl)-5-(*S)-(4-isopropoxy-2-methylphenyl)-4-oxo-4,5-dihydro-3H-1-thia-3,5,8-triazaacenaphthylene-2-carboxamide; | 5.9 |
| 418 | (R)-N-(1-Acryloylpiperidin-3-yl)-5-(*R)-(4-isopropoxy-2-methylphenyl)-4-oxo-4,5-dihydro-3H-1-thia-3,5,8-triazaacenaphthylene-2-carboxamide; | 7.8 |
| 419 | (R)-N-(1-Acryloylpiperidin-3-yl)-5-(naphthalen-2-yl)-4-oxo-4,5-dihydro-3H-1-thia-3,5,8-triazaacenaphthylene-2-carboxamide; | 5.7 |
| 420 | (R)-N-(1-Acryloylpiperidin-3-yl)-5-(1-benzyl-1H-pyrazol-3-yl)-4-oxo-4,5-dihydro-3H-1-thia-3,5,8-triazaacenaphthylene-2-carboxamide; | 6.0 |
| 421 | (R)-5-([1,1'-Biphenyl]-3-yl)-N-(1-acryloylpiperidin-3-yl)-4-oxo-4,5-dihydro-3H-1-thia-3,5,8-triazaacenaphthylene-2-carboxamide; | 7.9 |
| 422 | (R)-N-(1-Acryloylpiperidin-3-yl)-5-(4-benzylphenyl)-4-oxo-4,5-dihydro-3H-1-thia-3,5,8-triazaacenaphthylene-2-carboxamide; | 7.5 |
| 423 | (R)-5-([1,1'-Biphenyl]-4-yl)-N-(1-acryloylpiperidin-3-yl)-4-oxo-4,5-dihydro-3H-1-thia-3,5,8-triazaacenaphthylene-2-carboxamide; | 6.3 |
| 424 | (R)-N-(1-(2-(Dimethylamino)acetyl)piperidin-3-yl)-4-oxo-5-(4-phenoxyphenyl)-4,5-dihydro-3H-1-thia-3,5,8-triazaacenaphthylene-2-carboxamide; | 7.2 |
| 425 | (R)-N-(1-(2-(Dimethylamino)acetyl)pyrrolidin-3-yl)-4-oxo-5-(4-phenoxyphenyl)-4,5-dihydro-3H-1-thia-3,5,8-triazaacenaphthylene-2-carboxamide; | 7.3 |
| 426 | (R)-5-([1,1'-Biphenyl]-3-yl)-4-oxo-N-(piperidin-3-yl)-4,5-dihydro-3H-1-thia-3,5,8-triazaacenaphthylene-2-carboxamide; | 6.9 |
| 427 | (R)-N-(1-Acryloylpiperidin-3-yl)-5-(benzo[b]thiophen-2-yl)-4-oxo-4,5-dihydro-3H-1-thia-3,5,8-triazaacenaphthylene-2-carboxamide; | 6.3 |
| 428 | (R)-5-(Benzo[b]thiophen-2-yl)-4-oxo-N-(piperidin-3-yl)-4,5-dihydro-3H-1-thia-3,5,8-triazaacenaphthylene-2-carboxamide; | <5 |
| 429 | (R)-5-(Naphthalen-2-yl)-4-oxo-N-(piperidin-3-yl)-4,5-dihydro-3H-1-thia-3,5,8-triazaacenaphthylene-2-carboxamide; | <5 |
| 430 | (R)-5-(4-Benzylphenyl)-4-oxo-N-(piperidin-3-yl)-4,5-dihydro-3H-1-thia-3,5,8-triazaacenaphthylene-2-carboxamide; | 6.3 |
| 431 | (R)-5-(1-Benzyl-1H-pyrazol-3-yl)-4-oxo-N-(piperidin-3-yl)-4,5-dihydro-3H-1-thia-3,5,8-triazaacenaphthylene-2-carboxamide; | <5 |
| 432 | 5-(*S)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide; | 7.0 |

TABLE 2-continued

| Ex # | Compound Name | BTK_I_binding pIC50 |
|---|---|---|
| 433 | 5-(*R)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide; | 5.4 |
| 434 | 5-(*S)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide; | 7.3 |
| 435 | 5-(*R)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide; | 5.9 |
| 436 | N-(4-(Hydroxymethyl)tetrahydro-2H-pyran-4-yl)-5-(*S)-(2-methyl-4-phenoxyphenyl)-4-oxo-4,5-dihydro-3H-1-thia-3,5,8-triazaacenaphthylene-2-carboxamide; | 7.3 |
| 437 | N-(4-(Hydroxymethyl)tetrahydro-2H-pyran-4-yl)-5-(*R)-(2-methyl-4-phenoxyphenyl)-4-oxo-4,5-dihydro-3H-1-thia-3,5,8-triazaacenaphthylene-2-carboxamide; | 5.8 |
| 438 | (R)-N-(1-(2-Chloro-3-methylbut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 6.7 |
| 439 | (R)-N-(1-(2-Chloro-3-methylbut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 5.7 |
| 440 | (R,E)-N-(1-(4-(Dimethylamino)but-2-enoyl)pyrrolidin-3-yl)-4-oxo-5-(4-phenoxyphenyl)-4,5-dihydro-3H-1-thia-3,5,8-triazaacenaphthylene-2-carboxamide; | 7.6 |
| 441 | (R)-N-(1-Acryloylpyrrolidin-3-yl)-N-methyl-5-(*S)-(2-methyl-4-phenoxyphenyl)-4-oxo-4,5-dihydro-3H-1-thia-3,5,8-triazaacenaphthylene-2-carboxamide; | 5.9 |
| 442 | (R)-N-(1-Acryloylpyrrolidin-3-yl)-N-methyl-5-(*R)-(2-methyl-4-phenoxyphenyl)-4-oxo-4,5-dihydro-3H-1-thia-3,5,8-triazaacenaphthylene-2-carboxamide; | 6.9 |
| 443 | (R)-N-(1-Acryloylpyrrolidin-3-yl)-4-oxo-5-(4-phenoxyphenyl)-4,5-dihydro-3H-1-thia-3,5,8-triazaacenaphthylene-2-carboxamide; | 7.7 |
| 444 | (R)-N-(1-Acryloylpiperidin-3-yl)-5-(4-isopropyl-2-methylphenyl)-4-oxo-4,5-dihydro-3H-1-thia-3,5,8-triazaacenaphthylene-2-carboxamide; | 7.2 |
| 445 | (R)-N-(1-Acryloylpyrrolidin-3-yl)-5-(4-isopropyl-2-methylphenyl)-4-oxo-4,5-dihydro-3H-1-thia-3,5,8-triazaacenaphthylene-2-carboxamide; | 6.7 |
| 446 | (R)-5-(4-Isopropyl-2-methylphenyl)-4-oxo-N-(piperidin-3-yl)-4,5-dihydro-3H-1-thia-3,5,8-triazaacenaphthylene-2-carboxamide; | 5.8 |
| 447 | (R)-5-(4-Isopropyl-2-methylphenyl)-N-(1-methylpiperidin-3-yl)-4-oxo-4,5-dihydro-3H-1-thia-3,5,8-triazaacenaphthylene-2-carboxamide; | 5.6 |
| 450 | (R,*E)-N-(1-(2-Cyano-4-methoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.6 |
| 452 | N-((1-Acryloylpyrrolidin-3-yl)methyl)-4-oxo-5-(4-phenoxyphenyl)-4,5-dihydro-3H-1-thia-3,5,8-triazaacenaphthylene-2-carboxamide; | 7.0 |
| 453 | 4-Oxo-5-(4-phenoxyphenyl)-N-(pyrrolidin-3-ylmethyl)-4,5-dihydro-3H-1-thia-3,5,8-triazaacenaphthylene-2-carboxamide; | 6.4 |
| 454 | (R)-N-(1-(1H-Imidazole-1-carbonyl)piperidin-3-yl)-5-(2,2-difluorobenzo[d][1,3]dioxol-5-yl)-4-oxo-4,5-dihydro-3H-1-thia-3,5,8-triazaacenaphthylene-2-carboxamide; | <5 |
| 455 | (R)-N-(1-Acryloylpiperidin-3-yl)-5-(4-methoxy-3-(trifluoromethyl)phenyl)-4-oxo-4,5-dihydro-3H-1-thia-3,5,8-triazaacenaphthylene-2-carboxamide; | <5 |
| 456 | (R)-N-(1-Acryloylpiperidin-3-yl)-5-(4-cyclobutoxy-2-methylphenyl)-4-oxo-4,5-dihydro-3H-1-thia-3,5,8-triazaacenaphthylene-2-carboxamide; | 7.7 |
| 457 | (R)-N-(1-Acryloylpiperidin-3-yl)-5-(4-cyclobutoxyphenyl)-4-oxo-4,5-dihydro-3H-1-thia-3,5,8-triazaacenaphthylene-2-carboxamide; | 7.6 |
| 458 | 4-Oxo-N-(2-oxopiperidin-3-yl)-5-(4-phenoxyphenyl)-4,5-dihydro-3H-1-thia-3,5,8-triazaacenaphthylene-2-carboxamide; | 6.2 |
| 459 | (R)-5-(4-Methoxy-3-(trifluoromethyl)phenyl)-4-oxo-N-(piperidin-3-yl)-4,5-dihydro-3H-1-thia-3,5,8-triazaacenaphthylene-2-carboxamide; | <5 |
| 460 | (R)-5-(3-Chloro-4-methylphenyl)-4-oxo-N-(piperidin-3-yl)-4,5-dihydro-3H-1-thia-3,5,8-triazaacenaphthylene-2-carboxamide; | 5.3 |
| 461 | (R)-5-(4-Methyl-3-(trifluoromethyl)phenyl)-4-oxo-N-(piperidin-3-yl)-4,5-dihydro-3H-1-thia-3,5,8-triazaacenaphthylene-2-carboxamide; | 5.0 |
| 462 | 4-Oxo-5-(4-phenoxyphenyl)-N-((tetrahydrofuran-2-yl)methyl)-4,5-dihydro-3H-1-thia-3,5,8-triazaacenaphthylene-2-carboxamide; | 6.4 |
| 463 | N-((3S,4S)-1-Acryloyl-4-hydroxypyrrolidin-3-yl)-4-oxo-5-(4-phenoxyphenyl)-4,5-dihydro-3H-1-thia-3,5,8-triazaacenaphthylene-2-carboxamide; | 7.9 |
| 464 | N-((3S,4S)-4-Hydroxypyrrolidin-3-yl)-4-oxo-5-(4-phenoxyphenyl)-4,5-dihydro-3H-1-thia-3,5,8-triazaacenaphthylene-2-carboxamide; | 6.8 |

TABLE 2-continued

| Ex # | Compound Name | BTK_I_binding pIC50 |
|---|---|---|
| 465 | (R)-5-(3-Benzylphenyl)-4-oxo-N-(piperidin-3-yl)-4,5-dihydro-3H-1-thia-3,5,8-triazaacenaphthylene-2-carboxamide; | 6.2 |
| 466 | (R)-4-Oxo-5-(3-phenoxyphenyl)-N-(piperidin-3-yl)-4,5-dihydro-3H-1-thia-3,5,8-triazaacenaphthylene-2-carboxamide; | 6.7 |
| 467 | N-((3R,5S)-5-Methoxypiperidin-3-yl)-5-(*S)-(2-methyl-4-phenoxyphenyl)-4-oxo-4,5-dihydro-3H-1-thia-3,5,8-triazaacenaphthylene-2-carboxamide; | 7.0 |
| 468 | N-((3R,5S)-5-Methoxypiperidin-3-yl)-5-(*R)-(2-methyl-4-phenoxyphenyl)-4-oxo-4,5-dihydro-3H-1-thia-3,5,8-triazaacenaphthylene-2-carboxamide; | 5.9 |
| 469 | (*S)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide; | 7.1 |
| 470 | (*S)-5-(*R)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide; | 5.6 |
| 471 | (*R)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide; | 5.9 |
| 472 | (*R)-5-(*R)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide; | 7.4 |
| 473 | (R,*E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 5.9 |
| 474 | (R,*E)-N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 7.6 |
| 475 | (R,*Z)-N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 6.1 |
| 476 | (R,*Z)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.4 |
| 477 | (R,*Z)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.6 |
| 478 | (R,*E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.8 |
| 479 | (R,*Z)-N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 6.7 |
| 480 | (R,*E)-N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide; | 7.2 |
| 481 | N-((3R,5R)-1-Acryloyl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide; | 8.2 |
| 482 | N-((3R,5S)-1-Acryloyl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide; | 8.0 |
| 483 | N-((3R,5R)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide; | 8.4 |
| 484 | N-((3R,5S)-1-Acryloyl-5-fluoropiperidin-3-yl)-5-(*S)-(2-methyl-4-phenoxyphenyl)-4-oxo-4,5-dihydro-3H-1-thia-3,5,8-triazaacenaphthylene-2-carboxamide; | 8.0 |
| 485 | N-(4-Cyano-1,4-oxazepan-6-yl)-5-(*S)-(2-methyl-4-phenoxyphenyl)-4-oxo-4,5-dihydro-3H-1-thia-3,5,8-triazaacenaphthylene-2-carboxamide; | 7.9 |
| 486 | N-((3S,4S)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.8 |
| 487 | (R,E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.6 |
| 488 | (R,E)-N-(1-(4-(Dimethylamino)but-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.2 |
| 489 | N-((3S,4R)-1-Acryloyl-4-hydroxypyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.6 |
| 490 | N-((3S,4S)-1-Acryloyl-4-methoxypyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.7 |

TABLE 2-continued

| Ex # | Compound Name | BTK_I_binding pIC50 |
|---|---|---|
| 491 | (R,E)-N-(1-(2-Cyano-3-cyclopropylacryloyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.6 |
| 492 | (R,E)-5-(*S)-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide; | 8.0 |
| 493 | (R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide; | 6.9 |
| 494 | (R)-5-(*S)-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide; | 8.0 |
| 495 | (R)-N-(1-(2-Methoxyacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.5 |
| 496 | N-(1-Acryloylazetidin-3-yl)-5-(*S)-(2-methyl-4-phenoxyphenyl)-4-oxo-4,5-dihydro-3H-1-thia-3,5,8-triazaacenaphthylene-2-carboxamide; | 7.4 |
| 497 | (R)-N-(1-Acryloylpiperidin-3-yl)-5-(3-methyl-5-phenoxypyridin-2-yl)-4-oxo-4,5-dihydro-3H-1-thia-3,5,8-triazaacenaphthylene-2-carboxamide; | 7.9 |
| 498 | (R)-N-(1-Acryloylpiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide; | 7.8 |
| 499 | N-((3R,5R)-1-Acryloyl-5-fluoropiperidin-3-yl)-5-(*S)-(2-methyl-4-phenoxyphenyl)-4-oxo-4,5-dihydro-3H-1-thia-3,5,8-triazaacenaphthylene-2-carboxamide; | 7.9 |
| 500 | (R)-N-(1-Acryloylpiperidin-3-yl)-5-(3'-fluoro-[1,1'-biphenyl]-3-yl)-4-oxo-4,5-dihydro-3H-1-thia-3,5,8-triazaacenaphthylene-2-carboxamide; | 8.1 |
| 501 | (R)-N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide; | 7.9 |
| 502 | (R,E)-N-(1-(4-(Dimethylamino)but-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.9 |
| 503 | (R,E)-N-(1-(4-Hydroxybut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.8 |
| 504 | (R)-N-(1-Acryloylpiperidin-3-yl)-5-(2'-methyl-[1,1'-biphenyl]-3-yl)-4-oxo-4,5-dihydro-3H-1-thia-3,5,8-triazaacenaphthylene-2-carboxamide; | 8.0 |
| 505 | (R)-N-(1-Acryloylpiperidin-3-yl)-5-(*S)-(2-methyl-4-(trifluoromethoxy)phenyl)-4-oxo-4,5-dihydro-3H-1-thia-3,5,8-triazaacenaphthylene-2-carboxamide; | 7.8 |
| 506 | (R)-N-(1-Acryloylpiperidin-3-yl)-4-oxo-5-(6-phenoxypyridin-3-yl)-4,5-dihydro-3H-1-thia-3,5,8-triazaacenaphthylene-2-carboxamide; | 7.9 |
| 507 | (R)-N-(1-Acryloylpiperidin-3-yl)-5-(3'-chloro-[1,1'-biphenyl]-3-yl)-4-oxo-4,5-dihydro-3H-1-thia-3,5,8-triazaacenaphthylene-2-carboxamide; | 7.8 |
| 508 | N-((3S,4R)-1-Acryloyl-4-methoxypyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.7 |
| 509 | (R,EZ)-N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.9 |
| 510 | (R)-N-(1-Acryloylpiperidin-3-yl)-5-(2'-chloro-[1,1'-biphenyl]-3-yl)-4-oxo-4,5-dihydro-3H-1-thia-3,5,8-triazaacenaphthylene-2-carboxamide; | 8.0 |
| 511 | (R,E)-N-(1-(4-Aminobut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.8 |
| 512 | (R)-N-(1-Acryloylpiperidin-3-yl)-4-oxo-5-(2-phenylpyridin-4-yl)-4,5-dihydro-3H-1-thia-3,5,8-triazaacenaphthylene-2-carboxamide; | 7.8 |
| 513 | (R)-N-(1-Acryloylpiperidin-3-yl)-4-oxo-5-(5-phenoxypyridin-2-yl)-4,5-dihydro-3H-1-thia-3,5,8-triazaacenaphthylene-2-carboxamide; | 8.2 |
| 514 | (R,E)-N-(1-(2-Cyano-3-cyclopropylacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.7 |
| 515 | (R)-N-(1-Acryloylpiperidin-3-yl)-5-(2',4'-difluoro-[1,1'-biphenyl]-3-yl)-4-oxo-4,5-dihydro-3H-1-thia-3,5,8-triazaacenaphthylene-2-carboxamide; | 7.7 |
| 516 | (R)-N-(1-Acryloylpiperidin-3-yl)-5-(3-benzylphenyl)-4-oxo-4,5-dihydro-3H-1-thia-3,5,8-triazaacenaphthylene-2-carboxamide; | 7.7 |
| 517 | (R)-N-(1-Acryloylpiperidin-3-yl)-5-(3'-methyl-[1,1'-biphenyl]-3-yl)-4-oxo-4,5-dihydro-3H-1-thia-3,5,8-triazaacenaphthylene-2-carboxamide; | 7.5 |

TABLE 2-continued

| Ex # | Compound Name | BTK_I_binding pIC50 |
|---|---|---|
| 518 | (S)-N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.6 |
| 519 | (R)-N-(1-Acryloylpiperidin-3-yl)-5-(3-cyclohexylphenyl)-4-oxo-4,5-dihydro-3H-1-thia-3,5,8-triazaacenaphthylene-2-carboxamide; | 7.3 |
| 520 | (R,E)-N-(1-(4-Aminobut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 8.1 |
| 521 | (R)-N-(1-Acryloylpiperidin-3-yl)-5-(4'-methyl-[1,1'-biphenyl]-3-yl)-4-oxo-4,5-dihydro-3H-1-thia-3,5,8-triazaacenaphthylene-2-carboxamide; | 7.5 |
| 522 | (R,E)-N-(1-(4-Hydroxybut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 8.0 |
| 523 | N-((3S,4S)-1-Acryloyl-4-hydroxypyrrolidin-3-yl)-5-(*S)-(2-methyl-4-phenoxyphenyl)-4-oxo-4,5-dihydro-3H-1-thia-3,5,8-triazaacenaphthylene-2-carboxamide; | 7.5 |
| 524 | 5-(*S)-(2-Methyl-4-phenoxyphenyl)-N-((R)-1-((S)-2-(methylamino)propanoyl)piperidin-3-yl)-4-oxo-4,5-dihydro-3H-1-thia-3,5,8-triazaacenaphthylene-2-carboxamide; | 7.8 |
| 525 | (R)-N-(1-Acryloylpiperidin-3-yl)-5-(2,2-difluorobenzo[d][1,3]dioxol-5-yl)-4-oxo-4,5-dihydro-3H-1-thia-3,5,8-triazaacenaphthylene-2-carboxamide; | 7.5 |
| 526 | (R)-N-(1-Acryloylpiperidin-3-yl)-4-oxo-5-(4-phenylpyridin-2-yl)-4,5-dihydro-3H-1-thia-3,5,8-triazaacenaphthylene-2-carboxamide; | 7.6 |
| 527 | (R)-N-(1-Acryloylpiperidin-3-yl)-4-oxo-5-(3-phenoxyphenyl)-4,5-dihydro-3H-1-thia-3,5,8-triazaacenaphthylene-2-carboxamide; | 8.1 |
| 528 | (R)-N-(1-Acryloylpiperidin-3-yl)-4-oxo-5-(5-phenoxypyrazin-2-yl)-4,5-dihydro-3H-1-thia-3,5,8-triazaacenaphthylene-2-carboxamide; | 7.8 |
| 529 | (R)-N-(1-Acryloylpiperidin-3-yl)-5-(3-isopropylphenyl)-4-oxo-4,5-dihydro-3H-1-thia-3,5,8-triazaacenaphthylene-2-carboxamide; | 7.6 |
| 530 | (R)-5-(*S)-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide; | 8.0 |
| 531 | (R)-5-([1,1'-Biphenyl]-3-yl)-N-(1-acryloylpyrrolidin-3-yl)-4-oxo-4,5-dihydro-3H-1-thia-3,5,8-triazaacenaphthylene-2-carboxamide; | 7.5 |
| 532 | (R,E)-5-(*S)-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide; | 7.4 |
| 533 | (R)-N-(1-Acryloylpiperidin-3-yl)-4-oxo-5-(3-propylphenyl)-4,5-dihydro-3H-1-thia-3,5,8-triazaacenaphthylene-2-carboxamide; | 7.5 |
| 534 | (R)-N-(1-Acryloylpiperidin-3-yl)-5-(3-cyclobutylphenyl)-4-oxo-4,5-dihydro-3H-1-thia-3,5,8-triazaacenaphthylene-2-carboxamide; | 7.8 |
| 535 | (R)-5-(*S)-(2-Methyl-4-phenoxyphenyl)-N-(1-trideuteriomethylpiperidin-3-yl)-4-oxo-4,5-dihydro-3H-1-thia-3,5,8-triazaacenaphthylene-2-carboxamide; | 7.5 |
| 536 | (R)-N-(1-Acryloylpiperidin-3-yl)-5-(3-methyl-4-phenoxyphenyl)-4-oxo-4,5-dihydro-3H-1-thia-3,5,8-triazaacenaphthylene-2-carboxamide; | 7.5 |
| 537 | (R)-N-(1-Acryloylpiperidin-3-yl)-4-oxo-5-(5-phenylpyridin-3-yl)-4,5-dihydro-3H-1-thia-3,5,8-triazaacenaphthylene-2-carboxamide; | 7.6 |
| 538 | (R)-N-(1-Acryloylpiperidin-3-yl)-4-oxo-5-(3-(pyridin-3-yl)phenyl)-4,5-dihydro-3H-1-thia-3,5,8-triazaacenaphthylene-2-carboxamide; | 7.0 |
| 539 | (R)-N-(1-(Ethylsulfonyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.2 |
| 540 | (R)-N-(1-Acryloylpiperidin-3-yl)-4-oxo-5-(3-(pyridin-2-yl)phenyl)-4,5-dihydro-3H-1-thia-3,5,8-triazaacenaphthylene-2-carboxamide; | 7.2 |
| 541 | (R,E)-5-(3-Chloro-4-phenoxyphenyl)-N-(1-(4-(dimethylamino)but-2-enoyl)piperidin-3-yl)-4-oxo-4,5-dihydro-3H-1-thia-3,5,8-triazaacenaphthylene-2-carboxamide; | 7.2 |
| 542 | (R)-N-(1-Isopropylpiperidin-3-yl)-5-(*S)-(2-methyl-4-phenoxyphenyl)-4-oxo-4,5-dihydro-3H-1-thia-3,5,8-triazaacenaphthylene-2-carboxamide; | 7.2 |
| 543 | N-((3S,4S)-1-Acryloyl-4-fluoropyrrolidin-3-yl)-5-(4-phenoxyphenyl)-4,5-dihydro-3H-1-thia-3,5,8-triazaacenaphthylene-2-carboxamide; | 7.5 |
| 544 | (S)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide; | 7.0 |
| 545 | (R)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide; | 6.9 |
| 546 | (R)-N-(1-(2-(Methylamino)acetyl)piperidin-3-yl)-4-oxo-5-(4-phenoxyphenyl)-4,5-dihydro-3H-1-thia-3,5,8-triazaacenaphthylene-2-carboxamide; | 7.4 |

TABLE 2-continued

| Ex # | Compound Name | BTK_I_binding pIC50 |
|---|---|---|
| 547 | N-((R)-1-((S)-3-Hydroxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.4 |
| 548 | N-((3S,4S)-1-Acryloyl-4-methoxypyrrolidin-3-yl)-4-oxo-5-(4-phenoxyphenyl)-4,5-dihydro-3H-1-thia-3,5,8-triazaacenaphthylene-2-carboxamide; | 6.9 |
| 549 | (R,Z)-N-(1-(4-Amino-2-fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 550 | (R,Z)-N-(1-(4-Amino-2-chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 551 | (R)-5-([1,1'-Biphenyl]-3-yl)-N-(1-(2-(methylamino)acetyl)piperidin-3-yl)-4-oxo-4,5-dihydro-3H-1-thia-3,5,8-triazaacenaphthylene-2-carboxamide; | 6.8 |
| 552 | (R)-5-([1,1'-Biphenyl]-3-yl)-N-(1-methylpiperidin-3-yl)-4-oxo-4,5-dihydro-3H-1-thia-3,5,8-triazaacenaphthylene-2-carboxamide; | 6.8 |
| 553 | (R)-5-(3'-Methyl-[1,1'-biphenyl]-3-yl)-4-oxo-N-(piperidin-3-yl)-4,5-dihydro-3H-1-thia-3,5,8-triazaacenaphthylene-2-carboxamide; | 6.8 |
| 554 | (R)-5-(2'-Methyl-[1,1'-biphenyl]-3-yl)-4-oxo-N-(piperidin-3-yl)-4,5-dihydro-3H-1-thia-3,5,8-triazaacenaphthylene-2-carboxamide; | 6.7 |
| 555 | 5-(*S)-(2-Methyl-4-phenoxyphenyl)-4-oxo-N-((R)-1-((E)-4-((4aR,7aS)-tetrahydro-2H-[1,4]dioxino[2,3-c]pyrrol-6(3H)-yl)but-2-enoyl)pyrrolidin-3-yl)-4,5-dihydro-3H-1-thia-3,5,8-triazaacenaphthylene-2-carboxamide; | 8.1 |
| 556 | (R)-N-(1-Acryloylpiperidin-3-yl)-4-oxo-5-(2-phenoxypyrimidin-5-yl)-4,5-dihydro-3H-1-thia-3,5,8-triazaacenaphthylene-2-carboxamide; | 7.5 |
| 557 | N-((3R,5R)-1-Acryloyl-5-hydroxypiperidin-3-yl)-5-(4-isopropoxy-2-methylphenyl)-4-oxo-4,5-dihydro-3H-1-thia-3,5,8-triazaacenaphthylene-2-carboxamide; | 7.3 |
| 558 | (R)-N-(1-Acryloylpyrrolidin-3-yl)-5-(3-chloro-4-phenoxyphenyl)-4-oxo-4,5-dihydro-3H-1-thia-3,5,8-triazaacenaphthylene-2-carboxamide; | 7.7 |
| 559 | (R,E)-N-(1-(2-Cyano-3-cyclopropylacryloyl)piperidin-3-yl)-4-oxo-5-(2-phenylpyridin-4-yl)-4,5-dihydro-3H-1-thia-3,5,8-triazaacenaphthylene-2-carboxamide; | 8.2 |
| 560 | (R)-N-(1-Acryloylpiperidin-3-yl)-5-(3-(cyclohexyloxy)phenyl)-4-oxo-4,5-dihydro-3H-1-thia-3,5,8-triazaacenaphthylene-2-carboxamide; | 7.6 |
| 561 | (R)-N-(1-Acryloylpiperidin-3-yl)-5-(3-(cyclopentyloxy)phenyl)-4-oxo-4,5-dihydro-3H-1-thia-3,5,8-triazaacenaphthylene-2-carboxamide; | 7.3 |
| 562 | (R,E)-N-(1-(4-(Dimethylamino)but-2-enoyl)pyrrolidin-3-yl)-5-(4-isopropoxy-2-methylphenyl)-4-oxo-4,5-dihydro-3H-1-thia-3,5,8-triazaacenaphthylene-2-carboxamide; | 6.7 |
| 563 | (R)-N-(1-Acryloylpiperidin-3-yl)-4-oxo-5-(2'-(trifluoromethyl)-[1,1'-biphenyl]-3-yl)-4,5-dihydro-3H-1-thia-3,5,8-triazaacenaphthylene-2-carboxamide; | 7.0 |
| 564 | N-((R)-1-((R)-3-Hydroxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 565 | (R)-N-(1-Acryloylpiperidin-3-yl)-5-(3-isopropoxyphenyl)-4-oxo-4,5-dihydro-3H-1-thia-3,5,8-triazaacenaphthylene-2-carboxamide; | 7.0 |
| 566 | (R)-5-(3-Acetylphenyl)-N-(1-acryloylpiperidin-3-yl)-4-oxo-4,5-dihydro-3H-1-thia-3,5,8-triazaacenaphthylene-2-carboxamide; | 6.6 |
| 567 | (R)-N-(1-Acryloylpyrrolidin-3-yl)-4-oxo-5-(2-phenylpyridin-4-yl)-4,5-dihydro-3H-1-thia-3,5,8-triazaacenaphthylene-2-carboxamide; | 7.4 |
| 568 | (R)-N-(1-Acryloylpiperidin-3-yl)-4-oxo-5-(3-(trifluoromethoxy)phenyl)-4,5-dihydro-3H-1-thia-3,5,8-triazaacenaphthylene-2-carboxamide; | 7.4 |
| 569 | (R)-N-(1-Acryloylpiperidin-3-yl)-5-(3-cyclopropyrphenyl)-4-oxo-4,5-dihydro-3H-1-thia-3,5,8-triazaacenaphthylene-2-carboxamide; | 7.0 |
| 570 | (R,E)-5-([1,1'-Biphenyl]-3-yl)-N-(1-(4-(dimethylamino)but-2-enoyl)pyrrolidin-3-yl)-4-oxo-4,5-dihydro-3H-1-thia-3,5,8-triazaacenaphthylene-2-carboxamide; | 7.2 |
| 571 | N-((R)-1-((R)-3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 572 | (R)-5-(3-Chloro-4-phenoxyphenyl)-N-(1-(2-(dimethylamino)acetyl)piperidin-3-yl)-4-oxo-4,5-dihydro-3H-1-thia-3,5,8-triazaacenaphthylene-2-carboxamide; | 7.1 |
| 573 | (R,E)-5-([1,1'-Biphenyl]-3-yl)-N-(1-(4-(dimethylamino)but-2-enoyl)piperidin-3-yl)-4-oxo-4,5-dihydro-3H-1-thia-3,5,8-triazaacenaphthylene-2-carboxamide; | 6.6 |
| 574 | N-(cis)-1-Acryloyl-3-hydroxypiperidin-4-yl)-4-oxo-5-(4-phenoxyphenyl)-4,5-dihydro-3H-1-thia-3,5,8-triazaacenaphthylene-2-carboxamide; | 6.8 |

TABLE 2-continued

| Ex # | Compound Name | BTK_I_binding pIC50 |
|---|---|---|
| 575 | (R)-5-(3-Chloro-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide; | 7.3 |
| 576 | (R)-N-(1-(2-Methoxyacetyl)piperidin-3-yl)-4-oxo-5-(4-phenoxyphenyl)-4,5-dihydro-3H-1-thia-3,5,8-triazaacenaphthylene-2-carboxamide; | 7.3 |
| 577 | (R)-5-(3-Chloro-4-phenoxyphenyl)-4-oxo-N-(pyrrolidin-3-yl)-4,5-dihydro-3H-1-thia-3,5,8-triazaacenaphthylene-2-carboxamide; | 7.2 |
| 578 | 4-Oxo-N-(6-oxopiperidin-3-yl)-5-(4-phenoxyphenyl)-4,5-dihydro-3H-1-thia-3,5,8-triazaacenaphthylene-2-carboxamide; | 6.9 |
| 579 | N-((3S,4S)-4-Fluoropyrrolidin-3-yl)-4-oxo-5-(4-phenoxyphenyl)-4,5-dihydro-3H-1-thia-3,5,8-triazaacenaphthylene-2-carboxamide; | 6.9 |
| 580 | (R)-5-(4'-Methyl-[1,1'-biphenyl]-3-yl)-4-oxo-N-(piperidin-3-yl)-4,5-dihydro-3H-1-thia-3,5,8-triazaacenaphthylene-2-carboxamide; | 6.9 |
| 581 | (R)-5-(3-Chloro-4-phenoxyphenyl)-4-oxo-N-(piperidin-3-yl)-4,5-dihydro-3H-1-thia-3,5,8-triazaacenaphthylene-2-carboxamide; | 6.8 |
| 582 | (R)-N-(1-Acetylpiperidin-3-yl)-5-(3-chloro-4-phenoxyphenyl)-4-oxo-4,5-dihydro-3H-1-thia-3,5,8-triazaacenaphthylene-2-carboxamide; | 6.7 |
| 583 | (R)-5-(3-Methyl-4-phenoxyphenyl)-4-oxo-N-(piperidin-3-yl)-4,5-dihydro-3H-1-thia-3,5,8-triazaacenaphthylene-2-carboxamide; | 6.7 |
| 584 | (R)-N-(1-Acryloylpiperidin-3-yl)-5-(3-chloro-4-methylphenyl)-4-oxo-4,5-dihydro-3H-1-thia-3,5,8-triazaacenaphthylene-2-carboxamide; | 6.6 |
| 585 | (R)-4-Oxo-5-(2-phenylpyridin-4-yl)-N-(piperidin-3-yl)-4,5-dihydro-3H-1-thia-3,5,8-triazaacenaphthylene-2-carboxamide; | 6.5 |
| 586 | N-((3R,5R)-5-Hydroxypiperidin-3-yl)-4-oxo-5-(4-phenoxyphenyl)-4,5-dihydro-3H-1-thia-3,5,8-triazaacenaphthylene-2-carboxamide; | 6.6 |
| 587 | (R)-5-([1,1'-Biphenyl]-3-yl)-N-(1-methylpyrrolidin-3-yl)-4-oxo-4,5-dihydro-3H-1-thia-3,5,8-triazaacenaphthylene-2-carboxamide; | 6.5 |
| 588 | N-((3S,4S)-4-Methoxypyrrolidin-3-yl)-4-oxo-5-(4-phenoxyphenyl)-4,5-dihydro-3H-1-thia-3,5,8-triazaacenaphthylene-2-carboxamide; | 6.4 |
| 589 | N-((3R,5R)-1-Acryloyl-5-hydroxypiperidin-3-yl)-4-oxo-5-(4-phenoxyphenyl)-4,5-dihydro-3H-1-thia-3,5,8-triazaacenaphthylene-2-carboxamide; | 8.1 |
| 590 | (R,E)-N-(1-(4-Hydroxybut-2-enoyl)piperidin-3-yl)-4-oxo-5-(4-phenoxyphenyl)-4,5-dihydro-3H-1-thia-3,5,8-triazaacenaphthylene-2-carboxamide; | 7.5 |
| 591 | (R)-N-(1-Acryloylpiperidin-3-yl)-5-(2-cyclobutylpyridin-4-yl)-4-oxo-4,5-dihydro-3H-1-thia-3,5,8-triazaacenaphthylene-2-carboxamide; | 7.5 |
| 592 | (R)-N-(1-Cyanopiperidin-3-yl)-4-oxo-5-(4-phenoxyphenyl)-4,5-dihydro-3H-1-thia-3,5,8-triazaacenaphthylene-2-carboxamide; | 7.4 |
| 593 | (R)-N-(1-(3-Methoxypropanoyl)piperidin-3-yl)-4-oxo-5-(4-phenoxyphenyl)-4,5-dihydro-3H-1-thia-3,5,8-triazaacenaphthylene-2-carboxamide; | 7.2 |
| 594 | N-(1-Cyanopiperidin-4-yl)-4-oxo-5-(4-phenoxyphenyl)-4,5-dihydro-3H-1-thia-3,5,8-triazaacenaphthylene-2-carboxamide; | 7.1 |
| 595 | (R)-5-(3-Methyl-5-phenoxypyridin-2-yl)-4-oxo-N-(piperidin-3-yl)-4,5-dihydro-3H-1-thia-3,5,8-triazaacenaphthylene-2-carboxamide; | 7.1 |
| 596 | (E)-N-(1-(4-Hydroxybut-2-enoyl)piperidin-4-yl)-4-oxo-5-(4-phenoxyphenyl)-4,5-dihydro-3H-1-thia-3,5,8-triazaacenaphthylene-2-carboxamide; | 6.9 |
| 597 | N-(1-(3-Methoxypropanoyl)piperidin-4-yl)-4-oxo-5-(4-phenoxyphenyl)-4,5-dihydro-3H-1-thia-3,5,8-triazaacenaphthylene-2-carboxamide; | 6.9 |
| 598 | (R)-N-(1-Acryloylpiperidin-3-yl)-3-amino-4-((3-cyclobutoxyphenyl)amino)thieno[2,3-b]pyridine-2-carboxamide; | 6.5 |
| 599 | (R)-5-([1,1'-Biphenyl]-3-yl)-4-oxo-N-(pyrrolidin-3-yl)-4,5-dihydro-3H-1-thia-3,5,8-triazaacenaphthylene-2-carboxamide; | 6.5 |
| 600 | 2-((1-Acryloylpiperidin-3-yl)amino)-5-(2-methyl-4-phenoxyphenyl)-3H-1-thia-3,5,8-triazaacenaphthylen-4(5H)-one; | 6.5 |
| 601 | (R)-5-([1,1'-Biphenyl]-3-yl)-N-(1-(2-(methylamino)acetyl)pyrrolidin-3-yl)-4-oxo-4,5-dihydro-3H-1-thia-3,5,8-triazaacenaphthylene-2-carboxamide; | 6.4 |
| 602 | (R)-4-Oxo-5-(2-phenylpyridin-4-yl)-N-(pyrrolidin-3-yl)-4,5-dihydro-3H-1-thia-3,5,8-triazaacenaphthylene-2-carboxamide; | 6.4 |
| 603 | (R)-5-(3-Cyclobutylphenyl)-4-oxo-N-(piperidin-3-yl)-4,5-dihydro-3H-1-thia-3,5,8-triazaacenaphthylene-2-carboxamide; | 6.3 |
| 604 | (R)-N-(1-Acryloylpiperidin-3-yl)-4-oxo-5-(6-phenylpyridin-2-yl)-4,5-dihydro-3H-1-thia-3,5,8-triazaacenaphthylene-2-carboxamide; | 6.3 |
| 605 | (R)-5-(4-Cyclobutoxy-2-methylphenyl)-4-oxo-N-(piperidin-3-yl)-4,5-dihydro-3H-1-thia-3,5,8-triazaacenaphthylene-2-carboxamide; | 6.3 |
| 606 | 2-((1-Acryloylpiperidin-4-yl)amino)-5-(2-methyl-4-phenoxyphenyl)-3H-1-thia-3,5,8-triazaacenaphthylen-4(5H)-one; | 6.2 |
| 607 | (R)-N-(1-Acryloylpiperidin-3-yl)-5-(4-methyl-3-(trifluoromethyl)phenyl)-4-oxo-4,5-dihydro-3H-1-thia-3,5,8-triazaacenaphthylene-2-carboxamide; | 6.2 |

TABLE 2-continued

| Ex # | Compound Name | BTK_I_binding pIC50 |
|---|---|---|
| 608 | 5-(4-Isopropoxy-2-methylphenyl)-4-oxo-N-((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide; | 6.2 |
| 609 | (R)-N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide; | 6.3 |
| 610 | (R)-4-Oxo-5-(4-phenylpyridin-2-yl)-N-(piperidin-3-yl)-4,5-dihydro-3H-1-thia-3,5,8-triazaacenaphthylene-2-carboxamide; | 6.2 |
| 611 | (3R,5R)-tert-Butyl 3-hydroxy-5-(4-oxo-5-(4-phenoxyphenyl)-4,5-dihydro-3H-1-thia-3,5,8-triazaacenaphthylene-2-carboxamido)piperidine-1-carboxylate; | 6.2 |
| 612 | (R)-N-(1-Acryloylpiperidin-3-yl)-5-(4-(oxetan-3-yloxy)phenyl)-4-oxo-4,5-dihydro-3H-1-thia-3,5,8-triazaacenaphthylene-2-carboxamide; | 6.1 |
| 613 | (R)-5-(3-(Cyclopentyloxy)phenyl)-4-oxo-N-(piperidin-3-yl)-4,5-dihydro-3H-1-thia-3,5,8-triazaacenaphthylene-2-carboxamide; | 6.1 |
| 614 | N-((3S,4R)-1-Acryloyl-4-hydroxypyrrolidin-3-yl)-5-(4-isopropoxy-2-methylphenyl)-4-oxo-4,5-dihydro-3H-1-thia-3,5,8-triazaacenaphthylene-2-carboxamide; | 6.1 |
| 615 | N-(trans-3-Hydroxypiperidin-4-yl)-4-oxo-5-(4-phenoxyphenyl)-4,5-dihydro-3H-1-thia-3,5,8-triazaacenaphthylene-2-carboxamide; | 6.1 |
| 616 | (R)-5-(3-(Cyclohexyloxy)phenyl)-4-oxo-N-(piperidin-3-yl)-4,5-dihydro-3H-1-thia-3,5,8-triazaacenaphthylene-2-carboxamide; | 6.1 |
| 617 | trans-tert-Butyl 3-hydroxy-4-(4-oxo-5-(4-phenoxyphenyl)-4,5-dihydro-3H-1-thia-3,5,8-triazaacenaphthylene-2-carboxamido)piperidine-1-carboxylate; | 6.0 |
| 618 | (R)-4-Oxo-5-(5-phenylpyridin-3-yl)-N-(piperidin-3-yl)-4,5-dihydro-3H-1-thia-3,5,8-triazaacenaphthylene-2-carboxamide; | 6.0 |
| 619 | (R)-N-(1-Acryloylpiperidin-3-yl)-5-(2-methoxypyrimidin-5-yl)-4-oxo-4,5-dihydro-3H-1-thia-3,5,8-triazaacenaphthylene-2-carboxamide; | <6 |
| 620 | (R)-4-Oxo-N-(piperidin-3-yl)-5-(3-(trifluoromethoxy)phenyl)-4,5-dihydro-3H-1-thia-3,5,8-triazaacenaphthylene-2-carboxamide; | <6 |
| 621 | (R)-5-(3-Cyclobutoxyphenyl)-4-oxo-N-(piperidin-3-yl)-4,5-dihydro-3H-1-thia-3,5,8-triazaacenaphthylene-2-carboxamide; | <6 |
| 622 | (R)-4-Oxo-N-(piperidin-3-yl)-5-(3-(pyridin-2-yl)phenyl)-4,5-dihydro-3H-1-thia-3,5,8-triazaacenaphthylene-2-carboxamide; | <6 |
| 623 | (R)-4-Oxo-5-(6-phenylpyridin-2-yl)-N-(piperidin-3-yl)-4,5-dihydro-3H-1-thia-3,5,8-triazaacenaphthylene-2-carboxamide; | <6 |
| 624 | (R)-N-(1-Acryloylpiperidin-3-yl)-5-(*R)-(2-methyl-4-(trifluoromethoxy)phenyl)-4-oxo-4,5-dihydro-3H-1-thia-3,5,8-triazaacenaphthylene-2-carboxamide; | 5.9 |
| 625 | (3S,4S)-tert-Butyl 3-fluoro-4-(4-oxo-5-(4-phenoxyphenyl)-4,5-dihydro-3H-1-thia-3,5,8-triazaacenaphthylene-2-carboxamido)pyrrolidine-1-carboxylate; | 5.9 |
| 626 | (R)-5-(4-Cyclobutoxyphenyl)-4-oxo-N-(piperidin-3-yl)-4,5-dihydro-3H-1-thia-3,5,8-triazaacenaphthylene-2-carboxamide; | 5.9 |
| 627 | tert-Butyl 4-(4-oxo-5-(4-phenoxyphenyl)-4,5-dihydro-3H-1-thia-3,5,8-triazaacenaphthylene-2-carboxamido)piperidine-1-carboxylate; | 5.9 |
| 628 | (R)-tert-Butyl 3-(4-oxo-5-(4-phenoxyphenyl)-4,5-dihydro-3H-1-thia-3,5,8-triazaacenaphthylene-2-carboxamido)piperidine-1-carboxylate; | 5.8 |
| 629 | (R)-5-(3-Cyclohexylphenyl)-4-oxo-N-(piperidin-3-yl)-4,5-dihydro-3H-1-thia-3,5,8-triazaacenaphthylene-2-carboxamide; | 5.9 |
| 630 | (R)-5-(3-Isopropylphenyl)-4-oxo-N-(piperidin-3-yl)-4,5-dihydro-3H-1-thia-3,5,8-triazaacenaphthylene-2-carboxamide; | 5.9 |
| 631 | (R)-N-(1-Acryloylpiperidin-3-yl)-4-oxo-5-(3-(pyridin-4-yl)phenyl)-4,5-dihydro-3H-1-thia-3,5,8-triazaacenaphthylene-2-carboxamide; | 5.9 |
| 632 | (R)-N-(1-Acryloylpiperidin-3-yl)-5-(3-(oxetan-3-yl)phenyl)-4-oxo-4,5-dihydro-3H-1-thia-3,5,8-triazaacenaphthylene-2-carboxamide; | 5.9 |
| 633 | (R)-N-(1-Acryloylpiperidin-3-yl)-5-(4-isopropoxy-3-methylphenyl)-4-oxo-4,5-dihydro-3H-1-thia-3,5,8-triazaacenaphthylene-2-carboxamide; | 5.8 |
| 634 | (R)-5-(2-Cyclobutylpyridin-4-yl)-4-oxo-N-(piperidin-3-yl)-4,5-dihydro-3H-1-thia-3,5,8-triazaacenaphthylene-2-carboxamide; | 5.8 |
| 635 | (R)-N-(1-Acryloylpiperidin-3-yl)-4-oxo-5-(6-phenoxypyridin-2-yl)-4,5-dihydro-3H-1-thia-3,5,8-triazaacenaphthylene-2-carboxamide; | 5.8 |
| 636 | (R)-5-(2,2-Difluorobenzo[d][1,3]dioxol-5-yl)-4-oxo-N-(piperidin-3-yl)-4,5-dihydro-3H-1-thia-3,5,8-triazaacenaphthylene-2-carboxamide; | 5.7 |
| 637 | (R)-5-(3-Isopropoxyphenyl)-4-oxo-N-(piperidin-3-yl)-4,5-dihydro-3H-1-thia-3,5,8-triazaacenaphthylene-2-carboxamide; | 5.7 |
| 638 | (R)-N-(1-Acryloylpiperidin-3-yl)-5-(3-(tert-butyl)phenyl)-4-oxo-4,5-dihydro-3H-1-thia-3,5,8-triazaacenaphthylene-2-carboxamide; | 5.7 |
| 639 | (3S,4S)-tert-Butyl 3-methoxy-4-(4-oxo-5-(4-phenoxyphenyl)-4,5-dihydro-3H-1-thia-3,5,8-triazaacenaphthylene-2-carboxamido)pyrrolidine-1-carboxylate; | 5.7 |

TABLE 2-continued

| Ex # | Compound Name | BTK_I_binding pIC50 |
|---|---|---|
| 640 | (R)-N-(1-Acryloylpiperidin-3-yl)-5-(5-isopropoxy-2-methylphenyl)-4-oxo-4,5-dihydro-3H-1-thia-3,5,8-triazaacenaphthylene-2-carboxamide; | 5.6 |
| 641 | (R)-N-(1-Acryloylpiperidin-3-yl)-5-(4-(tert-butylsulfonyl)phenyl)-4-oxo-4,5-dihydro-3H-1-thia-3,5,8-triazaacenaphthylene-2-carboxamide; | 5.6 |
| 642 | (R)-5-(4-Hydroxyphenyl)-4-oxo-N-(piperidin-3-yl)-4,5-dihydro-3H-1-thia-3,5,8-triazaacenaphthylene-2-carboxamide; | 5.3 |
| 643 | (R)-5-(3-Acetylphenyl)-4-oxo-N-(piperidin-3-yl)-4,5-dihydro-3H-1-thia-3,5,8-triazaacenaphthylene-2-carboxamide; | 5.1 |
| 644 | (R)-5-(5-Isopropoxy-2-methylphenyl)-4-oxo-N-(piperidin-3-yl)-4,5-dihydro-3H-1-thia-3,5,8-triazaacenaphthylene-2-carboxamide; | <5 |
| 645 | (R)-4-Oxo-5-(6-phenoxypyridin-2-yl)-N-(piperidin-3-yl)-4,5-dihydro-3H-1-thia-3,5,8-triazaacenaphthylene-2-carboxamide; | <5 |
| 646 | (R)-5-(3-(tert-Butyl)phenyl)-4-oxo-N-(piperidin-3-yl)-4,5-dihydro-3H-1-thia-3,5,8-triazaacenaphthylene-2-carboxamide; | <5 |
| 647 | (R)-4-Oxo-N-(piperidin-3-yl)-5-(3-(pyridin-4-yl)phenyl)-4,5-dihydro-3H-1-thia-3,5,8-triazaacenaphthylene-2-carboxamide; | <5 |
| 648 | (R)-tert-Butyl 3-(5-(3-(tert-butyl)phenyl)-4-oxo-4,5-dihydro-3H-1-thia-3,5,8-triazaacenaphthylene-2-carboxamido)piperidine-1-carboxylate; | <5 |
| 649 | (R)-tert-Butyl 3-(5-(3-acetylphenyl)-4-oxo-4,5-dihydro-3H-1-thia-3,5,8-triazaacenaphthylene-2-carboxamido)piperidine-1-carboxylate; | <5 |
| 650 | (R)-5-(4-(tert-Butylsulfonyl)phenyl)-4-oxo-N-(piperidin-3-yl)-4,5-dihydro-3H-1-thia-3,5,8-triazaacenaphthylene-2-carboxamide; | <5 |
| 651 | (R)-tert-Butyl 3-(5-(4-(tert-butylsulfonyl)phenyl)-4-oxo-4,5-dihydro-3H-1-thia-3,5,8-triazaacenaphthylene-2-carboxamido)piperidine-1-carboxylate; | <5 |
| 652 | (R)-tert-Butyl 3-(5-(4-(tert-butoxy)phenyl)-4-oxo-4,5-dihydro-3H-1-thia-3,5,8-triazaacenaphthylene-2-carboxamido)piperidine-1-carboxylate; | <5 |
| 653 | (R)-tert-Butyl 3-(5-(2,2-difluorobenzo[d][1,3]dioxol-5-yl)-4-oxo-4,5-dihydro-3H-1-thia-3,5,8-triazaacenaphthylene-2-carboxamido)piperidine-1-carboxylate; | <5 |
| 654 | (R)-tert-Butyl 3-(5-(6-cyclobutoxypyridin-3-yl)-4-oxo-4,5-dihydro-3H-1-thia-3,5,8-triazaacenaphthylene-2-carboxamido)piperidine-1-carboxylate; | <5 |
| 655 | N-((3R,4R)-1-Acryloyl-4-hydroxypiperidin-3-yl)-4-oxo-5-(4-phenoxyphenyl)-4,5-dihydro-3H-1-thia-3,5,8-triazaacenaphthylene-2-carboxamide; | 8.0 |
| 656 | (R)-5-(3-Methyl-5-phenoxypyrazin-2-yl)-4-oxo-N-(piperidin-3-yl)-4,5-dihydro-3H-1-thia-3,5,8-triazaacenaphthylene-2-carboxamide; | 6.2 |
| 657 | (R)-N-(1-Acryloylpiperidin-3-yl)-5-(3-methyl-5-phenoxypyrazin-2-yl)-4-oxo-4,5-dihydro-3H-1-thia-3,5,8-triazaacenaphthylene-2-carboxamide; | 7.7 |
| 658 | N-((3R,4R)-4-Hydroxypiperidin-3-yl)-4-oxo-5-(4-phenoxyphenyl)-4,5-dihydro-3H-1-thia-3,5,8-triazaacenaphthylene-2-carboxamide; | 6.6 |
| 659 | N-(cis-3-Hydroxypiperidin-4-yl)-4-oxo-5-(4-phenoxyphenyl)-4,5-dihydro-3H-1-thia-3,5,8-triazaacenaphthylene-2-carboxamide; | 6.6 |
| 661 | (R)-N-(1-Acryloylpiperidin-3-yl)-5-(R)-(2-methyl-6-phenoxypyridin-3-yl)-4-oxo-4,5-dihydro-3H-1-thia-3,5,8-triazaacenaphthylene-2-carboxamide; | 8.3 |
| 662 | (R)-N-(1-Acryloylpiperidin-3-yl)-5-(*S)-(4-methyl-6-phenoxypyridin-3-yl)-4-oxo-4,5-dihydro-3H-1-thia-3,5,8-triazaacenaphthylene-2-carboxamide; | 8.1 |
| 663 | (R)-N-(1-Acryloylpyrrolidin-3-yl)-5-(*S)-(4-methyl-6-phenoxypyridin-3-yl)-4-oxo-4,5-dihydro-3H-1-thia-3,5,8-triazaacenaphthylene-2-carboxamide; | 8.0 |
| 664 | (R)-N-(1-Acryloylpyrrolidin-3-yl)-5-(*S)-(4-methyl-2-phenoxypyrimidin-5-yl)-4-oxo-4,5-dihydro-3H-1-thia-3,5,8-triazaacenaphthylene-2-carboxamide; | 7.6 |
| 665 | (R)-N-(1-Acryloylpiperidin-3-yl)-4-oxo-5-(5-phenoxypyrimidin-2-yl)-4,5-dihydro-3H-1-thia-3,5,8-triazaacenaphthylene-2-carboxamide; | 7.8 |
| 666 | (R)-N-(1-Acryloylpyrrolidin-3-yl)-5-(*R)-(2-methyl-6-phenoxypyridin-3-yl)-4-oxo-4,5-dihydro-3H-1-thia-3,5,8-triazaacenaphthylene-2-carboxamide; | 6.3 |
| 667 | (R)-N-(1-Acryloylpiperidin-3-yl)-5-(4-methyl-6-phenoxypyridin-3-yl)-4-oxo-4,5-dihydro-3H-1-thia-3,5,8-triazaacenaphthylene-2-carboxamide; | 7.9 |
| 668 | N-(cis-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide; | 7.8 |
| 669 | (R)-N-(1-Acryloylpiperidin-3-yl)-5-(*S)-(6-isobutyl-4-methylpyridin-3-yl)-4-oxo-4,5-dihydro-3H-1-thia-3,5,8-triazaacenaphthylene-2-carboxamide; | 8.1 |

TABLE 2-continued

| Ex # | Compound Name | BTK_I_binding pIC50 |
|---|---|---|
| 670 | (R)-N-(1-Acryloylpiperidin-3-yl)-5-(2-methyl-6-phenoxypyridin-3-yl)-4-oxo-4,5-dihydro-3H-1-thia-3,5,8-triazaacenaphthylene-2-carboxamide; | 8.2 |
| 671 | (R)-N-(1-Acryloylpiperidin-3-yl)-5-(6-isobutyl-4-methylpyridin-3-yl)-4-oxo-4,5-dihydro-3H-1-thia-3,5,8-triazaacenaphthylene-2-carboxamide; | 7.6 |
| 672 | (R)-N-(1-Acryloylpiperidin-3-yl)-5-(6-cyclobutoxy-4-methylpyridin-3-yl)-4-oxo-4,5-dihydro-3H-1-thia-3,5,8-triazaacenaphthylene-2-carboxamide; | 7.6 |
| 673 | (R)-N-(1-Acryloylpyrrolidin-3-yl)-5-(2',3'-difluoro-[1,1'-biphenyl]-3-yl)-4-oxo-4,5-dihydro-3H-1-thia-3,5,8-triazaacenaphthylene-2-carboxamide; | 8.2 |
| 674 | N-((3R,5S)-1-Acryloyl-5-hydroxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide; | 8.2 |
| 675 | (R)-N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 7.2 |
| 676 | (R)-N-(1-Acryloylpiperidin-3-yl)-5-(*R)-(3-methyl-2-phenylpyridin-4-yl)-4-oxo-4,5-dihydro-3H-1-thia-3,5,8-triazaacenaphthylene-2-carboxamide; | 7.6 |
| 677 | (R)-N-(1-Acryloylpiperidin-3-yl)-5-(2-cyclohexylpyridin-4-yl)-4-oxo-4,5-dihydro-3H-1-thia-3,5,8-triazaacenaphthylene-2-carboxamide; | 7.3 |
| 678 | (R)-N-(1-Acryloylpiperidin-3-yl)-4-oxo-5-(6-phenylpyridazin-4-yl)-4,5-dihydro-3H-1-thia-3,5,8-triazaacenaphthylene-2-carboxamide; | 7.3 |
| 679 | N-((3R,5S)-1-Acryloyl-5-methoxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide; | 7.8 |
| 680 | (R)-N-(1-Acryloylpyrrolidin-3-yl)-4-oxo-5-(6-phenoxypyridin-3-yl)-4,5-dihydro-3H-1-thia-3,5,8-triazaacenaphthylene-2-carboxamide; | 7.3 |
| 681 | N-((R)-1-((*E)-3-((S)-1-Acetylpyrroridin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide; | 7.7 |
| 682 | (R)-N-(1-Acryloylpiperidin-3-yl)-5-(*S)-(6-cyclobutoxy-2-methylpyridin-3-yl)-4-oxo-4,5-dihydro-3H-1-thia-3,5,8-triazaacenaphthylene-2-carboxamide; | 7.3 |
| 683 | N-((R)-1-((E)-3-((R)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide; | 7.7 |
| 684 | 5-(*S)-(2-Methyl-4-phenoxyphenyl)-4-oxo-N-((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide; | 7.5 |
| 685 | (R)-N-(1-Acryloylpiperidin-3-yl)-4-oxo-5-(6-phenylpyrimidin-4-yl)-4,5-dihydro-3H-1-thia-3,5,8-triazaacenaphthylene-2-carboxamide; | 8.1 |
| 686 | (R)-N-(1-Acryloylpiperidin-3-yl)-5-(3-chloro-4-phenoxyphenyl)-4-oxo-4,5-dihydro-3H-1-thia-3,5,8-triazaacenaphthylene-2-carboxamide; | 7.6 |
| 687 | (R)-N-(1-Acryloylpiperidin-3-yl)-5-(6-cyclobutoxypyridin-3-yl)-4-oxo-4,5-dihydro-3H-1-thia-3,5,8-triazaacenaphthylene-2-carboxamide; | 7.5 |
| 688 | (R)-N-(1-Acryloylpiperidin-3-yl)-5-(4-methyl-[1,1'-biphenyl]-3-yl)-4-oxo-4,5-dihydro-3H-1-thia-3,5,8-triazaacenaphthylene-2-carboxamide; | 7.5 |
| 689 | (R)-N-(1-Acryloylpiperidin-3-yl)-5-(3-isobutylphenyl)-4-oxo-4,5-dihydro-3H-1-thia-3,5,8-triazaacenaphthylene-2-carboxamide; | 7.6 |
| 690 | (R)-N-(1-Acryloylpiperidin-3-yl)-5-(*R)-(2-methyl-6-phenoxypyridin-3-yl)-4-oxo-4,5-dihydro-3H-1-thia-3,5,8-triazaacenaphthylene-2-carboxamide; | 7.6 |
| 691 | (R)-N-(1-Acryloylpiperidin-3-yl)-5-(*R)-(4-methyl-6-phenoxypyridin-3-yl)-4-oxo-4,5-dihydro-3H-1-thia-3,5,8-triazaacenaphthylene-2-carboxamide; | 6.0 |
| 692 | (R)-N-(1-Acryloylpiperidin-3-yl)-5-(2-cyclopentylpyridin-4-yl)-4-oxo-4,5-dihydro-3H-1-thia-3,5,8-triazaacenaphthylene-2-carboxamide; | 8.0 |
| 693 | (R)-N-(1-Acryloylpiperidin-3-yl)-5-(4-(cyclopentyloxy)-2-methylphenyl)-4-oxo-4,5-dihydro-3H-1-thia-3,5,8-triazaacenaphthylene-2-carboxamide; | 7.9 |
| 694 | (R)-N-(1-Acryloylpiperidin-3-yl)-5-(4-methoxy-2-methylphenyl)-4-oxo-4,5-dihydro-3H-1-thia-3,5,8-triazaacenaphthylene-2-carboxamide; | 7.1 |
| 695 | (R)-N-(1-Acryloylpiperidin-3-yl)-5-(5-methyl-2-phenylpyridin-4-yl)-4-oxo-4,5-dihydro-3H-1-thia-3,5,8-triazaacenaphthylene-2-carboxamide; | 7.3 |

TABLE 2-continued

| Ex # | Compound Name | BTK_I_binding pIC50 |
|---|---|---|
| 696 | (R)-N-(1-Acryloylpiperidin-3-yl)-5-(4-(2-isopropoxyethoxy)-2-methylphenyl)-4-oxo-4,5-dihydro-3H-1-thia-3,5,8-triazaacenaphthylene-2-carboxamide; | 6.9 |
| 697 | (R)-N-(1-Acryloylpiperidin-3-yl)-5-(2-isopropylpyridin-4-yl)-4-oxo-4,5-dihydro-3H-1-thia-3,5,8-triazaacenaphthylene-2-carboxamide; | 6.9 |
| 698 | (R)-N-(1-Acryloylpyrrolidin-3-yl)-4-oxo-5-(5-phenoxypyridin-2-yl)-4,5-dihydro-3H-1-thia-3,5,8-triazaacenaphthylene-2-carboxamide; | 7.5 |
| 699 | (R)-N-(1-Acryloylpyrrolidin-3-yl)-4-oxo-5-(5-phenoxypyrazin-2-yl)-4,5-dihydro-3H-1-thia-3,5,8-triazaacenaphthylene-2-carboxamide; | 7.2 |
| 700 | (R)-N-(1-Acryloylpiperidin-3-yl)-5-(*R)-(6-cyclobutoxy-4-methylpyridin-3-yl)-4-oxo-4,5-dihydro-3H-1-thia-3,5,8-triazaacenaphthylene-2-carboxamide; | 8.1 |
| 701 | (R)-5-([2,3'-Bipyridin]-4-yl)-N-(1-acryloylpiperidin-3-yl)-4-oxo-4,5-dihydro-3H-1-thia-3,5,8-triazaacenaphthylene-2-carboxamide; | 7.2 |
| 702 | (R)-5-(*S)-(4-Methyl-6-phenoxypyridin-3-yl)-4-oxo-N-(pyrrolidin-3-yl)-4,5-dihydro-3H-1-thia-3,5,8-triazaacenaphthylene-2-carboxamide; | 6.8 |
| 703 | (R,E)-5-(3-Chloro-4-phenoxyphenyl)-N-(1-(4-(dimethylamino)but-2-enoyl)pyrrolidin-3-yl)-4-oxo-4,5-dihydro-3H-1-thia-3,5,8-triazaacenaphthylene-2-carboxamide; | 7.8 |
| 704 | (R)-N-(1-Acryloylpiperidin-3-yl)-5-(6-cyclobutoxy-2-methylpyridin-3-yl)-4-oxo-4,5-dihydro-3H-1-thia-3,5,8-triazaacenaphthylene-2-carboxamide; | 6.6 |
| 705 | (R)-N-(1-Acryloylpyrrolidin-3-yl)-5-(3-isopropylphenyl)-4-oxo-4,5-dihydro-3H-1-thia-3,5,8-triazaacenaphthylene-2-carboxamide; | 6.7 |
| 706 | (R)-5-(2',3'-Difluoro-[1,1'-biphenyl]-3-yl)-4-oxo-N-(piperidin-3-yl)-4,5-dihydro-3H-1-thia-3,5,8-triazaacenaphthylene-2-carboxamide; | 7.7 |
| 707 | N-((1RS,2RS)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide; | 6.7 |
| 708 | (R)-N-(1-Acryloylpiperidin-3-yl)-4-oxo-5-(3-(tetrahydro-2H-pyran-4-yl)phenyl)-4,5-dihydro-3H-1-thia-3,5,8-triazaacenaphthylene-2-carboxamide; | 6.5 |
| 709 | (R)-5-([2,2'-Bipyridin]-4-yl)-N-(1-acryloylpiperidin-3-yl)-4-oxo-4,5-dihydro-3H-1-thia-3,5,8-triazaacenaphthylene-2-carboxamide; | 6.7 |
| 710 | (R)-5 -(2',3'-Difluoro-[1,1'-biphenyl]-3-yl)-N-(1-methylpiperidin-3-yl)-4-oxo-4,5-dihydro-3H-1-thia-3,5,8-triazaacenaphthylene-2-carboxamide; | 7.4 |
| 711 | (R)-5-(2-Methyl-6-phenoxypyridin-3-yl)-4-oxo-N-(piperidin-3-yl)-4,5-dihydro-3H-1-thia-3,5,8-triazaacenaphthylene-2-carboxamide; | 6.6 |
| 713 | (R)-5-(*S)-(2-Methyl-6-phenoxypyridin-3-yl)-4-oxo-N-(piperidin-3-yl)-4,5-dihydro-3H-1-thia-3,5,8-triazaacenaphthylene-2-carboxamide; | 6.6 |
| 714 | (R)-N-(1-(Methylglycyl)piperidin-3-yl)-4-oxo-5-(2-phenylpyridin-4-yl)-4,5-dihydro-3H-1-thia-3,5,8-triazaacenaphthylene-2-carboxamide; | 6.5 |
| 715 | (R)-5-(*S)-(4-Methyl-2-phenoxypyrimidin-5-yl)-4-oxo-N-(pyrrolidin-3-yl)-4,5-dihydro-3H-1-thia-3,5,8-triazaacenaphthylene-2-carboxamide; | 6.3 |
| 716 | (R)-N-(1-Acryloylpyrrolidin-3-yl)-5-(*S)-(2-methyl-6-phenoxypyridin-3-yl)-4-oxo-4,5-dihydro-3H-1-thia-3,5,8-triazaacenaphthylene-2-carboxamide; | 8.0 |
| 717 | (R)-5-(*S)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide; | 6.4 |
| 718 | N-((3S,4R)-1-Acryloyl-4-hydroxypyrrolidin-3-yl)-4-oxo-5-(2-phenylpyridin-4-yl)-4,5-dihydro-3H-1-thia-3,5,8-triazaacenaphthylene-2-carboxamide; | 6.3 |
| 719 | (R)-4-Oxo-5-(5-phenoxypyrimidin-2-yl)-N-(piperidin-3-yl)-4,5-dihydro-3H-1-thia-3,5,8-triazaacenaphthylene-2-carboxamide; | 6.3 |
| 720 | (R)-5-(2-Cyclopentylpyridin-4-yl)-4-oxo-N-(piperidin-3-yl)-4,5-dihydro-3H-1-thia-3,5,8-triazaacenaphthylene-2-carboxamide; | 6.2 |
| 721 | (R)-5-(3-Isobutylphenyl)-4-oxo-N-(piperidin-3-yl)-4,5-dihydro-3H-1-thia-3,5,8-triazaacenaphthylene-2-carboxamide; | 6.2 |
| 722 | (R)-N-(1-Acryloylpiperidin-3-yl)-5-(*R)-(6-isobutyl-4-methylpyridin-3-yl)-4-oxo-4,5-dihydro-3H-1-thia-3,5,8-triazaacenaphthylene-2-carboxamide; | 6.4 |
| 723 | (R)-4-Oxo-5-(6-phenylpyrimidin-4-yl)-N-(piperidin-3-yl)-4,5-dihydro-3H-1-thia-3,5,8-triazaacenaphthylene-2-carboxamide; | 6.1 |
| 724 | (R)-N-(1-Acryloylpyrrolidin-3-yl)-5-(*R)-(4-methyl-2-phenoxypyrimidin-5-yl)-4-oxo-4,5-dihydro-3H-1-thia-3,5,8-triazaacenaphthylene-2-carboxamide; | 6.1 |
| 725 | (R)-5-(4-Methyl-[1,1'-biphenyl]-3-yl)-4-oxo-N-(piperidin-3-yl)-4,5-dihydro-3H-1-thia-3,5,8-triazaacenaphthylene-2-carboxamide; | 6.1 |
| 726 | (R)-N-(1-Acryloylpiperidin-3-yl)-5-(*S)-(6-cyclobutoxy-4-methylpyridin-3-yl)-4-oxo-4,5-dihydro-3H-1-thia-3,5,8-triazaacenaphthylene-2-carboxamide; | 6.0 |
| 727 | (R)-5-(2-Isopropylpyridin-4-yl)-4-oxo-N-(piperidin-3-yl)-4,5-dihydro-3H-1-thia-3,5,8-triazaacenaphthylene-2-carboxamide; | <6 |

TABLE 2-continued

| Ex # | Compound Name | BTK_I_binding pIC50 |
|---|---|---|
| 728 | (R)-5-(*R)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide; | <6 |
| 729 | (R)-5-(5-Methyl-2-phenylpyridin-4-yl)-4-oxo-N-(piperidin-3-yl)-4,5-dihydro-3H-1-thia-3,5,8-triazaacenaphthylene-2-carboxamide; | <6 |
| 730 | (R)-5-(4-(2-Isopropoxyethoxy)-2-methylphenyl)-4-oxo-N-(piperidin-3-yl)-4,5-dihydro-3H-1-thia-3,5,8-triazaacenaphthylene-2-carboxamide; | <6 |
| 731 | (R)-5-(2-Cyclohexylpyridin-4-yl)-4-oxo-N-(piperidin-3-yl)-4,5-dihydro-3H-1-thia-3,5,8-triazaacenaphthylene-2-carboxamide; | <6 |
| 732 | (R)-N-(1-Acryloylpiperidin-3-yl)-5-(6-isopropoxy-2-methylpyridin-3-yl)-4-oxo-4,5-dihydro-3H-1-thia-3,5,8-triazaacenaphthylene-2-carboxamide; | <6 |
| 733 | (R)-5-(3-Methyl-2-phenylpyridin-4-yl)-4-oxo-N-(piperidin-3-yl)-4,5-dihydro-3H-1-thia-3,5,8-triazaacenaphthylene-2-carboxamide; | <6 |
| 734 | (R)-N-(1-Acryloylpiperidin-3-yl)-5-(2-methyl-6-phenylpyridin-4-yl)-4-oxo-4,5-dihydro-3H-1-thia-3,5,8-triazaacenaphthylene-2-carboxamide; | <6 |
| 735 | (R)-5-(2-Methyl-6-phenylpyridin-4-yl)-4-oxo-N-(piperidin-3-yl)-4,5-dihydro-3H-1-thia-3,5,8-triazaacenaphthylene-2-carboxamide; | <6 |
| 736 | (R)-N-(1-Acryloylpiperidin-3-yl)-5-(*R)-(6-cyclobutoxy-2-methylpyridin-3-yl)-4-oxo-4,5-dihydro-3H-1-thia-3,5,8-triazaacenaphthylene-2-carboxamide; | <6 |
| 737 | (R)-N-(1-Acryloylpiperidin-3-yl)-5-(*S)-(3-methyl-2-phenylpyridin-4-yl)-4-oxo-4,5-dihydro-3H-1-thia-3,5,8-triazaacenaphthylene-2-carboxamide; | <6 |
| 738 | (R)-4-Oxo-N-(piperidin-3-yl)-5-(3-(tetrahydro-2H-pyran-4-yl)phenyl)-4,5-dihydro-3H-1-thia-3,5,8-triazaacenaphthylene-2-carboxamide; | <6 |
| 739 | (R)-tert-Butyl 3-(4-oxo-5-(3-(tetrahydro-2H-pyran-4-yl)phenyl)-4,5-dihydro-3H-1-thia-3,5,8-triazaacenaphthylene-2-carboxamido)piperidine-1-carboxylate; | <6 |
| 740 | (R)-4-Oxo-5-(6-phenylpyridazin-4-yl)-N-(piperidin-3-yl)-4,5-dihydro-3H-1-thia-3,5,8-triazaacenaphthylene-2-carboxamide; | <6 |
| 741 | (R)-4-Oxo-5-(6-phenoxypyridin-3-yl)-N-(pyrrolidin-3-yl)-4,5-dihydro-3H-1-thia-3,5,8-triazaacenaphthylene-2-carboxamide; | 5.9 |
| 742 | (R)-N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide; | 5.8 |
| 743 | (R)-tert-Butyl 3-(5-(2-methyl-6-phenoxypyridin-3-yl)-4-oxo-4,5-dihydro-3H-1-thia-3,5,8-triazaacenaphthylene-2-carboxamido)piperidine-1-carboxylate; | 5.8 |
| 744 | (R)-5-(6-Cyclobutoxypyridin-3-yl)-4-oxo-N-(piperidin-3-yl)-4,5-dihydro-3H-1-thia-3,5,8-triazaacenaphthylene-2-carboxamide; | 5.7 |
| 745 | N-((3*S,4*R)-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide; | 8.1 |
| 746 | (R)-N-(1-Acryloylpiperidin-3-yl)-5-(*S)-(4-methyl-2-phenoxypyrimidin-5-yl)-4-oxo-4,5-dihydro-3H-1-thia-3,5,8-triazaacenaphthylene-2-carboxamide; | 8.1 |
| 747 | (R)-N-(1-Acryloylpyrrolidin-3-yl)-5-(*S)-(6-isobutyl-4-methylpyridin-3-yl)-4-oxo-4,5-dihydro-3H-1-thia-3,5,8-triazaacenaphthylene-2-carboxamide; | 7.5 |
| 748 | (R)-N-(1-Acryloylpyrrolidin-3-yl)-4-oxo-5-(2-phenoxypyrimidin-5-yl)-4,5-dihydro-3H-1-thia-3,5,8-triazaacenaphthylene-2-carboxamide; | 6.8 |
| 749 | (R)-N-(1-Acryloylpyrrolidin-3-yl)-4-oxo-5-(5-phenoxypyrimidin-2-yl)-4,5-dihydro-3H-1-thia-3,5,8-triazaacenaphthylene-2-carboxamide; | 7.3 |
| 750 | (R)-N-(1-Acryloylpiperidin-3-yl)-5-(4-isobutylphenyl)-4-oxo-4,5-dihydro-3H-1-thia-3,5,8-triazaacenaphthylene-2-carboxamide; | 6.6 |
| 751 | (R)-N-(1-Acryloylpiperidin-3-yl)-4-oxo-5-(5-phenylpyridazin-3-yl)-4,5-dihydro-3H-1-thia-3,5,8-triazaacenaphthylene-2-carboxamide; | 6.7 |
| 752 | N-((*3R,*4S)-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide; | 6.4 |
| 753 | (R)-N-(1-Acryloylpiperidin-3-yl)-5-(*S)-(6-isopropoxy-2-methylpyridin-3-yl)-4-oxo-4,5-dihydro-3H-1-thia-3,5,8-triazaacenaphthylene-2-carboxamide; | 6.2 |
| 754 | (R)-5-(4-Isobutylphenyl)-4-oxo-N-(piperidin-3-yl)-4,5-dihydro-3H-1-thia-3,5,8-triazaacenaphthylene-2-carboxamide; | <6 |
| 755 | (R)-4-Oxo-5-(5-phenylpyridazin-3-yl)-N-(piperidin-3-yl)-4,5-dihydro-3H-1-thia-3,5,8-triazaacenaphthylene-2-carboxamide; | <6 |
| 756 | (R)-N-(1-Acryloylpyrrolidin-3-yl)-5-(*R)-(6-isobutyl-4-methylpyridin-3-yl)-4-oxo-4,5-dihydro-3H-1-thia-3,5,8-triazaacenaphthylene-2-carboxamide; | <6 |
| 757 | (R)-N-(1-Acryloylpiperidin-3-yl)-5-(*R)-(6-isopropoxy-2-methylpyridin-3-yl)-4-oxo-4,5-dihydro-3H-1-thia-3,5,8-triazaacenaphthylene-2-carboxamide; | <6 |

TABLE 2-continued

| Ex # | Compound Name | BTK_I_binding pIC50 |
|---|---|---|
| 759 | (R)-5-(*S)-(6-Isobutoxy-4-methylpyridin-3-yl)-4-oxo-N-(piperidin-3-yl)-4,5-dihydro-3H-1-thia-3,5,8-triazaacenaphthylene-2-carboxamide; | 6.7 |
| 760 | (R)-5-(*R)-(6-Isobutoxy-4-methylpyridin-3-yl)-4-oxo-N-(piperidin-3-yl)-4,5-dihydro-3H-1-thia-3,5,8-triazaacenaphthylene-2-carboxamide; | <6 |
| 761 | (R)-5-(*S)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide; | 7.1 |
| 762 | (R)-5-(*R)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide; | <6 |
| 764 | (R)-N-(1-Acryloylpiperidin-3-yl)-5-(6-isobutyl-2-methylpyridin-3-yl)-4-oxo-4,5-dihydro-3H-1-thia-3,5,8-triazaacenaphthylene-2-carboxamide; | 6.3 |
| 765 | (R)-5-(*S)-(6-Isobutyl-4-methylpyridin-3-yl)-4-oxo-N-(1-propionylpiperidin-3-yl)-4,5-dihydro-3H-1-thia-3,5,8-triazaacenaphthylene-2-carboxamide; | 6.5 |
| 766 | (R)-N-(1-Acryloylpiperidin-3-yl)-5-(*S)-(6-isobutoxy-4-methylpyridin-3-yl)-4-oxo-4,5-dihydro-3H-1-thia-3,5,8-triazaacenaphthylene-2-carboxamide; | 8.2 |
| 767 | (R)-N-(1-Acryloylpiperidin-3-yl)-5-(*R)-(6-isobutoxy-4-methylpyridin-3-yl)-4-oxo-4,5-dihydro-3H-1-thia-3,5,8-triazaacenaphthylene-2-carboxamide; | <6 |
| 768 | (R)-N-(1-Acryloylpiperidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide; | 8.2 |
| 769 | (R)-N-(1-Acryloylpiperidin-3-yl)-5-(*R)-(6-(cyclopentyloxy)-4-methylpyridin-3-yl)-4-oxo-4,5-dihydro-3H-1-thia-3,5,8-triazaacenaphthylene-2-carboxamide; | 6.2 |
| 770 | (R)-N-(1-Acryloylpiperidin-3-yl)-5-(2-methyl-6-((tetrahydro-2H-pyran-4-yl)oxy)pyridin-3-yl)-4-oxo-4,5-dihydro-3H-1-thia-3,5,8-triazaacenaphthylene-2-carboxamide; | <6 |
| 771 | (R)-N-(1-Acryloylpiperidin-3-yl)-5-(4-((2-methylpyridin-3-yl)oxy)phenyl)-4-oxo-4,5-dihydro-3H-1-thia-3,5,8-triazaacenaphthylene-2-carboxamide; | 7.4 |
| 772 | (R)-N-(1-Acryloylpiperidin-3-yl)-5-(2-methyl-4-((6-methylpyridin-2-yl)oxy)phenyl)-4-oxo-4,5-dihydro-3H-1-thia-3,5,8-triazaacenaphthylene-2-carboxamide; | 7.7 |
| 773 | (R)-N-(1-Acryloylpiperidin-3-yl)-5-(2-methyl-4-((2-methylpyridin-3-yl)oxy)phenyl)-4-oxo-4,5-dihydro-3H-1-thia-3,5,8-triazaacenaphthylene-2-carboxamide; | 7.4 |
| 774 | (R)-N-(1-Acryloylpiperidin-3-yl)-4-oxo-5-(4-(pyridin-3-yloxy)phenyl)-4,5-dihydro-3H-1-thia-3,5,8-triazaacenaphthylene-2-carboxamide; | 7.9 |
| 775 | (R)-N-(1-Acryloylpiperidin-3-yl)-5-(4-((6-methylpyridin-2-yl)oxy)phenyl)-4-oxo-4,5-dihydro-3H-1-thia-3,5,8-triazaacenaphthylene-2-carboxamide; | 7.5 |
| 776 | (R)-N-(1-Acryloylpyrrolidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide; | 8.1 |
| 777 | (R)-N-(1-Acryloylpiperidin-3-yl)-5-(5-(2-fluorophenoxy)pyridin-2-yl)-4-oxo-4,5-dihydro-3H-1-thia-3,5,8-triazaacenaphthylene-2-carboxamide; | 8.3 |
| 778 | (R)-N-(1-Acryloylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide; | 8.0 |
| 779 | (R)-N-(1-Acryloylpyrrolidin-3-yl)-5-(*S)-(6-isobutoxy-4-methylpyridin-3-yl)-4-oxo-4,5-dihydro-3H-1-thia-3,5,8-triazaacenaphthylene-2-carboxamide; | 8.0 |
| 780 | N1-(15-Oxo-19-((3aR,4R,6aS)-2-oxohexahydro-1H-thieno[3,4-d]imidazol-4-yl)-4,7,10-trioxa-14-azanonadecyl)-N5-((E)-4-oxo-4-(3-(4-oxo-5-(5-phenoxypyridin-2-yl)-4,5-dihydro-3H-1-thia-3,5,8-triazaacenaphthylene-2-carboxamido)piperidin-1-yl)but-2-en-1-yl)glutaramide; | 6.3 |
| 781 | (R)-N-(1-Acryloylpyrrolidin-3-yl)-5-(2-methyl-4-(pyridin-2-yloxy)phenyl)-4-oxo-4,5-dihydro-3H-1-thia-3,5,8-triazaacenaphthylene-2-carboxamide; | 7.4 |
| 782 | (R,EZ)-N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.7 |
| 783 | (R)-N-(1-Acryloylpiperidin-3-yl)-5-(2-methyl-4-((6-methylpyridin-2-yl)oxy)phenyl)-4-oxo-4,5-dihydro-3H-1-thia-3,5,8-triazaacenaphthylene-2-carboxamide; | 7.1 |
| 784 | (R)-N-(1-Acryloylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide; | 7.4 |

TABLE 2-continued

| Ex # | Compound Name | BTK_I_binding pIC50 |
|---|---|---|
| 785 | N-((R)-1-Acryloylpiperidin-3-yl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide; | 7.1 |
| 786 | (R)-N-(1-Acryloylpiperidin-3-yl)-5-(4-((5-methylpyridin-2-yl)oxy)phenyl)-4-oxo-4,5-dihydro-3H-1-thia-3,5,8-triazaacenaphthylene-2-carboxamide; | 6.9 |
| 787 | N-((R)-1-Acryloylpiperidin-3-yl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide; | 6.6 |
| 788 | 1-Acryloyl-N-(5-(2-methyl-4-phenoxyphenyl)-4-oxo-4,5-dihydro-3H-1-thia-3,5,8-triazaacenaphthylen-2-yl)piperidine-3-carboxamide; | 6.7 |
| 789 | (R)-N-(1-Acryloylpiperidin-3-yl)-5-(*S)-(6-isopropoxy-4-methylpyridin-3-yl)-4-oxo-4,5-dihydro-3H-1-thia-3,5,8-triazaacenaphthylene-2-carboxamide; | 8.1 |
| 790 | (R)-N-(1-Acryloylpyrrolidin-3-yl)-5-(2-methyl-4-(pyridazin-3-yloxy)phenyl)-4-oxo-4,5-dihydro-3H-1-thia-3,5,8-triazaacenaphthylene-2-carboxamide; | 6.7 |
| 791 | (R)-N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide; | 6.6 |
| 792 | (R)-N-(1-Acryloylpiperidin-3-yl)-5-(*S)-(6-isobutyl-2-methylpyridin-3-yl)-4-oxo-4,5-dihydro-3H-1-thia-3,5,8-triazaacenaphthylene-2-carboxamide; | 6.4 |
| 793 | (R)-5-(*S)-(2-Methyl-6-phenoxypyridin-3-yl)-4-oxo-N-(tetrahydrofuran-3-yl)-4,5-dihydro-3H-1-thia-3,5,8-triazaacenaphthylene-2-carboxamide; | 6.8 |
| 794 | (R)-5-(*S)-(6-Isopropoxy-4-methylpyridin-3-yl)-4-oxo-N-(piperidin-3-yl)-4,5-dihydro-3H-1-thia-3,5,8-triazaacenaphthylene-2-carboxamide; | 6.5 |
| 795 | (S)-N-(1-Acryloylpiperidin-3-yl)-4-oxo-5-(5-phenoxypyridin-2-yl)-4,5-dihydro-3H-1-thia-3,5,8-triazaacenaphthylene-2-carboxamide; | 6.4 |
| 796 | 2-(4-Acryloylpiperazin-1-yl)-5-(2-methyl-4-phenoxyphenyl)-3H-1-thia-3,5,8-triazaacenaphthylen-4(5H)-one; | 6.3 |
| 797 | (R)-5-(*S)-(6-(Cyclopentyloxy)-4-methylpyridin-3-yl)-4-oxo-N-(pyrrolidin-3-yl)-4,5-dihydro-3H-1-thia-3,5,8-triazaacenaphthylene-2-carboxamide; | 6.3 |
| 798 | (R)-5-(*S)-(6-Isobutoxy-4-methylpyridin-3-yl)-4-oxo-N-(pyrrolidin-3-yl)-4,5-dihydro-3H-1-thia-3,5,8-triazaacenaphthylene-2-carboxamide; | 6.3 |
| 799 | (R)-5-(2-Methyl-4-(pyridin-2-yloxy)phenyl)-4-oxo-N-(1-propionylpiperidin-3-yl)-4,5-dihydro-3H-1-thia-3,5,8-triazaacenaphthylene-2-carboxamide; | 6.2 |
| 800 | (R)-N-(1-Acetylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide; | 6.2 |
| 801 | (E)-1-(2-Cyano-3-cyclopropylacryloyl)-N-(5-(2-methyl-4-phenoxyphenyl)-4-oxo-4,5-dihydro-3H-1-thia-3,5,8-triazaacenaphthylen-2-yl)piperidine-3-carboxamide; | 6.2 |
| 802 | 1-Cyano-N-(5-(2-methyl-4-phenoxyphenyl)-4-oxo-4,5-dihydro-3H-1-thia-3,5,8-triazaacenaphthylen-2-yl)piperidine-3-carboxamide; | 6.1 |
| 803 | (R)-N-(1-Acryloylpyrrolidin-3-yl)-4-oxo-5-(4-(pyridazin-3-yloxy)phenyl)-4,5-dihydro-3H-1-thia-3,5,8-triazaacenaphthylene-2-carboxamide; | 6.1 |
| 804 | (R)-N-(1-Acryloylpiperidin-3-yl)-5-(*R)-(6-isopropoxy-4-methylpyridin-3-yl)-4-oxo-4,5-dihydro-3H-1-thia-3,5,8-triazaacenaphthylene-2-carboxamide; | 6.1 |
| 805 | N-(5-(2-Methyl-4-phenoxyphenyl)-4-oxo-4,5-dihydro-3H-1-thia-3,5,8-triazaacenaphthylen-2-yl)-1-propionylpiperidine-4-carboxamide; | 6.0 |
| 806 | (R)-5-(*R)-(6-Isopropoxy-4-methylpyridin-3-yl)-4-oxo-N-(piperidin-3-yl)-4,5-dihydro-3H-1-thia-3,5,8-triazaacenaphthylene-2-carboxamide; | <6 |
| 807 | (R)-4-Oxo-N-(1-propionylpiperidin-3-yl)-5-(4-(pyridin-2-yloxy)phenyl)-4,5-dihydro-3H-1-thia-3,5,8-triazaacenaphthylene-2-carboxamide; | <6 |
| 808 | (R)-N-(1-Acetylpiperidin-3-yl)-4-oxo-5-(4-(pyridin-2-yloxy)phenyl)-4,5-dihydro-3H-1-thia-3,5,8-triazaacenaphthylene-2-carboxamide; | <6 |
| 809 | (R)-5-(2-Methyl-4-(pyridazin-3-yloxy)phenyl)-4-oxo-N-(1-propionylpiperidin-3-yl)-4,5-dihydro-3H-1-thia-3,5,8-triazaacenaphthylene-2-carboxamide; | <6 |
| 810 | (R)-N-(1-Acetylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide; | <6 |
| 811 | (R)-N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide; | <6 |

TABLE 2-continued

| Ex # | Compound Name | BTK_I_binding pIC50 |
|---|---|---|
| 812 | (R)-N-(1-Acetylpiperidin-3-yl)-4-oxo-5-(4-(pyridazin-3-yloxy)phenyl)-4,5-dihydro-3H-1-thia-3,5,8-triazaacenaphthylene-2-carboxamide; | <6 |
| 813 | (R)-N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide; | <6 |
| 814 | (R)-N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide; | <6 |
| 815 | (R)-N-(1-Acryloylpiperidin-3-yl)-5-(*R)-(6-isobutyl-2-methylpyridin-3-yl)-4-oxo-4,5-dihydro-3H-1-thia-3,5,8-triazaacenaphthylene-2-carboxamide; | <6 |
| 816 | (E)-1-(2-Cyano-4,4-dimethylpent-2-enoyl)-N-(5-(2-methyl-4-phenoxyphenyl)-4-oxo-4,5-dihydro-3H-1-thia-3,5,8-triazaacenaphthylen-2-yl)piperidine-3-carboxamide; | 6.0 |
| 817 | 1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-3-carboxamide; | 6.0 |
| 818 | N-(5-(2-Methyl-4-phenoxyphenyl)-4-oxo-4,5-dihydro-3H-1-thia-3,5,8-triazaacenaphthylen-2-yl)-1-propionylpiperidine-3-carboxamide; | 5.9 |
| 819 | 1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-4-carboxamide; | 5.9 |
| 820 | 1-Acryloyl-N-(5-(2-methyl-4-phenoxyphenyl)-4-oxo-4,5-dihydro-3H-1-thia-3,5,8-triazaacenaphthylen-2-yl)piperidine-4-carboxamide; | 5.9 |
| 821 | 1-Ethyl-N-(5-(2-methyl-4-phenoxyphenyl)-4-oxo-4,5-dihydro-3H-1-thia-3,5,8-triazaacenaphthylen-2-yl)piperidine-3-carboxamide; | 5.8 |
| 822 | 1-Cyano-N-(5-(2-methyl-4-phenoxyphenyl)-4-oxo-4,5-dihydro-3H-1-thia-3,5,8-triazaacenaphthylen-2-yl)piperidine-4-carboxamide; | 5.8 |
| 823 | 1-Methyl-N-(5-(2-methyl-4-phenoxyphenyl)-4-oxo-4,5-dihydro-3H-1-thia-3,5,8-triazaacenaphthylen-2-yl)piperidine-3-carboxamide; | 5.5 |
| 834 | (R)-5-(*S)-(2-Methyl-4-phenoxyphenyl)-4-oxo-N-(1-(vinylsulfonyl)pyrrolidin-3-yl)-4,5-dihydro-3H-1-thia-3,5,8-triazaacenaphthylene-2-carboxamide; | 8.0 |
| 835 | (R,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide; | 8.0 |
| 836 | (R,E)-N-(1-(2-Cyano-3-cyclopropylacryloyl)piperidin-3-yl)-5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxamide; | 7.9 |
| 837 | (R)-N-(1-Cyanopyrrolidin-3-yl)-5-(2-methyl-4-phenoxyphenyl)-4-oxo-4,5-dihydro-3H-1-thia-3,5,8-triazaacenaphthylene-2-carboxamide; | 7.9 |
| 838 | (R)-N-(1-(2-Cyanoacetyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.9 |
| 839 | (R)-N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide; | 7.9 |
| 840 | (R,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide; | 7.8 |
| 841 | (R)-N-(1-(3-Methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide; | 7.7 |
| 842 | (R)-N-(1-Acryloylpiperidin-3-yl)-5-(2',3'-difluoro-4-methyl-[1,1'-biphenyl]-3-yl)-4-oxo-4,5-dihydro-3H-1-thia-3,5,8-triazaacenaphthylene-2-carboxamide; | 7.7 |
| 843 | (R)-5-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide; | 7.6 |
| 844 | (R,E)-N-(l-(2-Cyano-3-cyclopropylacryloyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.6 |
| 845 | (R,E)-5-(*S)-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide; | 7.6 |
| 846 | (R)-N-(1-Acryloylpiperidin-3-yl)-4-oxo-5-(4-(pyridin-2-yloxy)phenyl)-4,5-dihydro-3H-1-thia-3,5,8-triazaacenaphthylene-2-carboxamide; | 7.6 |
| 847 | (R)-N-(1-Acryloylpyrrolidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide; | 7.6 |
| 848 | 5-(2-Methyl-4-phenoxyphenyl)-N-((R)-1-((R)-2-(methylamino)propanoyl)piperidin-3-yl)-4-oxo-4,5-dihydro-3H-1-thia-3,5,8-triazaacenaphthylene-2-carboxamide; | 7.6 |

TABLE 2-continued

| Ex # | Compound Name | BTK_I_binding pIC50 |
|---|---|---|
| 849 | N-((R)-1-((R)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide; | 7.6 |
| 850 | (R,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide; | 7.6 |
| 851 | (E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide; | 7.5 |
| 852 | (R)-N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide; | 7.5 |
| 853 | 5-(2-Methyl-4-phenoxyphenyl)-N-((R)-1-((S)-2-(methylamino)propanoyl)piperidin-3-yl)-4-oxo-4,5-dihydro-3H-1-thia-3,5,8-triazaacenaphthylene-2-carboxamide; | 7.5 |
| 854 | (R,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide; | 7.5 |
| 855 | 5-(4-(3-((2-Cyanophenoxy)methyl)phenoxy)-2-methylphenyl)-N-(1-methylpiperidin-4-yl)-4-oxo-4,5-dihydro-3H-1-thia-3,5,8-triazaacenaphthylene-2-carboxamide; | 7.5 |
| 856 | (E)-N-(1-(2-Cyano-3-cyclopropylacryloyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide; | 7.5 |
| 857 | 5-(4-(3-((2-Cyanophenoxy)methyl)phenoxy)-2-methylphenyl)-4-oxo-N-(piperidin-4-yl)-4,5-dihydro-3H-1-thia-3,5,8-triazaacenaphthylene-2-carboxamide; | 7.5 |
| 858 | 5-(2-Methyl-4-phenoxyphenyl)-N-(1-methylpiperidin-4-yl)-4-oxo-4,5-dihydro-3H-1-thia-3,5,8-triazaacenaphthylene-2-carboxamide; | 7.5 |
| 859 | (R,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide; | 7.4 |
| 860 | (R)-4-Oxo-5-(4-phenoxyphenyl)-N-(piperidin-3-yl)-4,5-dihydro-3H-1-thia-3,5,8-triazaacenaphthylene-2-carboxamide; | 7.4 |
| 861 | (R,E)-N-(1-(2-Cyano-3-cyclopropylacryloyl)piperidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide; | 7.3 |
| 862 | (R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide; | 7.3 |
| 863 | (S)-N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide; | 7.3 |
| 864 | (S)-N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide; | 7.3 |
| 865 | 5-(2-Methyl-4-phenoxyphenyl)-4-oxo-N-(piperidin-4-yl)-4,5-dihydro-3H-1-thia-3,5,8-triazaacenaphthylene-2-carboxamide; | 7.3 |
| 866 | (R,E)-N-(1-(2-Cyano-4,4-dimethylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide; | 7.3 |
| 867 | (R,E)-5-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide; | 7.3 |
| 868 | (R,E)-N-(1-(2-Cyano-4,4-dimethylpent-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide; | 7.3 |
| 869 | (R)-5-(2-Methyl-4-phenoxyphenyl)-4-oxo-N-(piperidin-3-yl)-4,5-dihydro-3H-1-thia-3,5,8-triazaacenaphthylene-2-carboxamide; | 7.3 |
| 870 | 5-(4-(2-Methoxyphenoxy)-2-methylphenyl)-4-oxo-N-(piperidin-3-yl)-4,5-dihydro-3H-1-thia-3,5,8-triazaacenaphthylene-2-carboxamide; | 7.3 |
| 871 | (R)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide; | 7.3 |
| 872 | N-(1-Cyanopiperidin-4-yl)-5-(2-methyl-4-phenoxyphenyl)-4-oxo-4,5-dihydro-3H-1-thia-3,5,8-triazaacenaphthylene-2-carboxamide; | 7.2 |
| 873 | (R)-5-(2-Methyl-4-phenoxyphenyl)-N-(1-methylpiperidin-3-yl)-4-oxo-4,5-dihydro-3H-1-thia-3,5,8-triazaacenaphthylene-2-carboxamide; | 6.9 |
| 874 | (R)-N-(1-(Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide; | 7.2 |
| 875 | (E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide; | 7.2 |

TABLE 2-continued

| Ex # | Compound Name | BTK_I_binding pIC50 |
|---|---|---|
| 876 | 5-(2-Methyl-4-phenoxyphenyl)-4-oxo-N-((R)-1-((R)-pyrrolidine-2-carbonyl)piperidin-3-yl)-4,5-dihydro-3H-1-thia-3,5,8-triazaacenaphthylene-2-carboxamide; | 7.1 |
| 877 | (E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 878 | (E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide; | 7.1 |
| 879 | (S)-N-(1-Formylpiperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 880 | (R,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 7.1 |
| 881 | (R)-N-(1-Acryloylpyrrolidin-3-yl)-4-oxo-5-(4-(pyridin-2-yloxy)phenyl)-4,5-dihydro-3H-1-thia-3,5,8-triazaacenaphthylene-2-carboxamide; | 7.1 |
| 882 | N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 883 | N-(1-Cyanopiperidin-3-yl)-5-(4-(2-methoxyphenoxy)-2-methylphenyl)-4-oxo-4,5-dihydro-3H-1-thia-3,5,8-triazaacenaphthylene-2-carboxamide; | 7.0 |
| 884 | N-(1-Cyanopiperidin-4-yl)-5-(4-(2-methoxyphenoxy)-2-methylphenyl)-4-oxo-4,5-dihydro-3H-1-thia-3,5,8-triazaacenaphthylene-2-carboxamide; | 7.0 |
| 885 | (R)-N-(1-Formylpiperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 886 | (E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide; | 7.0 |
| 887 | (S)-N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 888 | (R)-N-(1-Acetylpyrrolidin-3-yl)-4-oxo-5-(4-phenoxyphenyl)-4,5-dihydro-3H-1-thia-3,5,8-triazaacenaphthylene-2-carboxamide; | 7.0 |
| 889 | 5-(2-Methyl-4-phenoxyphenyl)-4-oxo-N-(piperidin-3-yl)-4,5-dihydro-3H-1-thia-3,5,8-triazaacenaphthylene-2-carboxamide; | 7.0 |
| 890 | N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 891 | (S)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide; | 7.0 |
| 892 | (S)-N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide; | 7.0 |
| 893 | 5-(2-Methyl-4-phenoxyphenyl)-4-oxo-N-((R)-1-((S)-pyrrolidine-2-carbonyl)piperidin-3-yl)-4,5-dihydro-3H-1-thia-3,5,8-triazaacenaphthylene-2-carboxamide; | 7.0 |
| 894 | (R)-N-(1-Acryloylpiperidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide; | 7.0 |
| 895 | (S,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide; | 7.0 |
| 896 | (E)-N-(1-(2-Cyano-4,4-dimethylpent-2-enoyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide; | 6.9 |
| 897 | (E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 898 | 5-(2-Methyl-4-phenoxyphenyl)-N-(1-methylpiperidin-3-yl)-4-oxo-4,5-dihydro-3H-1-thia-3,5,8-triazaacenaphthylene-2-carboxamide; | 6.8 |
| 899 | (S,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide; | 6.8 |
| 900 | (R,E)-5-(2-Methyl-4-phenoxyphenyl)-4-oxo-N-(1-(4-(piperidin-1-yl)but-2-enoyl)piperidin-3-yl)-4,5-dihydro-3H-1-thia-3,5,8-triazaacenaphthylene-2-carboxamide; | 6.8 |
| 901 | (R,E)-N-(1-(2-Cyano-3-cyclopropylacryloyl)piperidin-3-yl)-5-(2-methyl-3-phenoxyphenyl)-4-oxo-4,5-dihydro-3H-1-thia-3,5,8-triazaacenaphthylene-2-carboxamide; | 6.8 |
| 902 | (S,E)-N-(1-(2-Cyano-3-cyclopropylacryloyl)piperidin-3-yl)-5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxamide; | 6.8 |

TABLE 2-continued

| Ex # | Compound Name | BTK_I_binding pIC50 |
|---|---|---|
| 903 | 5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide; | 6.8 |
| 904 | (S,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide; | 6.7 |
| 905 | (S,E)-N-(1-(2-Cyano-3-cyclopropylacryloyl)pyrrolidin-3-yl)-5-(2-methyl-4-phenoxyphenyl)-4-oxo-4,5-dihydro-3H-1-thia-3,5,8-triazaacenaphthylene-2-carboxamide; | 6.7 |
| 906 | (R)-N-(1-(3-Chloropropanoyl)piperidin-3-yl)-4-oxo-5-(5-phenoxypyridin-2-yl)-4,5-dihydro-3H-1-thia-3,5,8-triazaacenaphthylene-2-carboxamide; | 6.7 |
| 907 | 5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide; | 6.7 |
| 908 | (R)-N-(1-(2-(Azetidin-1-yl)acetyl)piperidin-3-yl)-5-(2-methyl-4-phenoxyphenyl)-4-oxo-4,5-dihydro-3H-1-thia-3,5,8-triazaacenaphthylene-2-carboxamide; | 6.7 |
| 909 | 4-Oxo-5-(4-phenoxyphenyl)-N-(tetrahydro-2H-pyran-4-yl)-4,5-dihydro-3H-1-thia-3,5,8-triazaacenaphthylene-2-carboxamide; | 6.7 |
| 910 | (R)-N-(1-Methylpyrrolidin-3-yl)-4-oxo-5-(4-phenoxyphenyl)-4,5-dihydro-3H-1-thia-3,5,8-triazaacenaphthylene-2-carboxamide; | 6.7 |
| 911 | (R)-4-Oxo-5-(4-phenoxyphenyl)-N-(pyrrolidin-3-yl)-4,5-dihydro-3H-1-thia-3,5,8-triazaacenaphthylene-2-carboxamide; | 6.6 |
| 912 | (S)-5-(2-Methyl-4-phenoxyphenyl)-4-oxo-N-(piperidin-3-yl)-4,5-dihydro-3H-1-thia-3,5,8-triazaacenaphthylene-2-carboxamide; | 6.5 |
| 913 | (R,E)-N-(1-(4-(Dimethylamino)but-2-enoyl)piperidin-3-yl)-5-(4-isopropoxy-2-methylphenyl)-4-oxo-4,5-dihydro-3H-1-thia-3,5,8-triazaacenaphthylene-2-carboxamide; | 6.5 |
| 914 | (R)-N-(1-Benzoylpyrrolidin-3-yl)-4-oxo-5-(4-phenoxyphenyl)-4,5-dihydro-3H-1-thia-3,5,8-triazaacenaphthylene-2-carboxamide; | 6.5 |
| 915 | (R)-4-Oxo-5-(5-phenoxypyridin-2-yl)-N-(piperidin-3-yl)-4,5-dihydro-3H-1-thia-3,5,8-triazaacenaphthylene-2-carboxamide; | 6.5 |
| 916 | (E)-N-(1-(2-Cyano-3-cyclopropylacryloyl)piperidin-4-yl)-5-(2-methyl-4-phenoxyphenyl)-4-oxo-4,5-dihydro-3H-1-thia-3,5,8-triazaacenaphthylene-2-carboxamide; | 6.4 |
| 917 | 5-(4-(2-Methoxyphenoxy)-2-methylphenyl)-4-oxo-N-(piperidin-4-yl)-4,5-dihydro-3H-1-thia-3,5,8-triazaacenaphthylene-2-carboxamide; | 6.4 |
| 918 | 5-(4-(2-Methoxyphenoxy)-2-methylphenyl)-N-(1-methylpiperidin-4-yl)-4-oxo-4,5-dihydro-3H-1-thia-3,5,8-triazaacenaphthylene-2-carboxamide; | 6.4 |
| 919 | (R)-5-(4-(Cyclopentyloxy)-2-methylphenyl)-4-oxo-N-(piperidin-3-yl)-4,5-dihydro-3H-1-thia-3,5,8-triazaacenaphthylene-2-carboxamide; | 6.4 |
| 920 | N-(1-Methylpiperidin-4-yl)-4-oxo-5-(4-phenoxyphenyl)-4,5-dihydro-3H-1-thia-3,5,8-triazaacenaphthylene-2-carboxamide; | 6.4 |
| 921 | (E)-N-(1-(2-Cyano-4,4-dimethylpent-2-enoyl)piperidin-4-yl)-5-(2-methyl-4-phenoxyphenyl)-4-oxo-4,5-dihydro-3H-1-thia-3,5,8-triazaacenaphthylene-2-carboxamide; | 6.3 |
| 922 | (R)-4-Oxo-5-(6-phenoxypyridin-3-yl)-N-(piperidin-3-yl)-4,5-dihydro-3H-1-thia-3,5,8-triazaacenaphthylene-2-carboxamide; | 6.3 |
| 923 | (R)-5-(4-Isopropoxy-2-methylphenyl)-N-(1-(2-(methylamino)acetyl)piperidin-3-yl)-4-oxo-4,5-dihydro-3H-1-thia-3,5,8-triazaacenaphthylene-2-carboxamide; | 6.3 |
| 924 | (S)-N-(1-Acetylpyrrolidin-3-yl)-4-oxo-5-(4-phenoxyphenyl)-4,5-dihydro-3H-1-thia-3,5,8-triazaacenaphthylene-2-carboxamide; | 6.3 |
| 925 | (R)-N-(1-Benzylpyrrolidin-3-yl)-4-oxo-5-(4-phenoxyphenyl)-4,5-dihydro-3H-1-thia-3,5,8-triazaacenaphthylene-2-carboxamide; | 6.3 |
| 926 | 4-Oxo-5-(4-phenoxyphenyl)-N-(piperidin-4-yl)-4,5-dihydro-3H-1-thia-3,5,8-triazaacenaphthylene-2-carboxamide; | 6.2 |
| 927 | 4-Oxo-5-(4-phenoxyphenyl)-N-(2-(pyrrolidin-1-yl)ethyl)-4,5-dihydro-3H-1-thia-3,5,8-triazaacenaphthylene-2-carboxamide; | 6.2 |
| 928 | 4-Oxo-5-(4-phenoxyphenyl)-N-(2-(piperazin-1-yl)ethyl)-4,5-dihydro-3H-1-thia-3,5,8-triazaacenaphthylene-2-carboxamide; | 6.2 |
| 929 | N-(1-Acryloylpiperidin-4-yl)-5-(2-methyl-4-phenoxyphenyl)-4-oxo-4,5-dihydro-3H-1-thia-3,5,8-triazaacenaphthylene-2-carboxamide; | 6.1 |
| 930 | (S)-5-(2-Methyl-4-phenoxyphenyl)-N-(1-methylpiperidin-3-yl)-4-oxo-4,5-dihydro-3H-1-thia-3,5,8-triazaacenaphthylene-2-carboxamide; | 6.0 |
| 931 | (S)-N-(1-Methylpyrrolidin-3-yl)-4-oxo-5-(4-phenoxyphenyl)-4,5-dihydro-3H-1-thia-3,5,8-triazaacenaphthylene-2-carboxamide; | 6.1 |
| 932 | 4-Oxo-5-(4-phenoxyphenyl)-N-(2-(piperidin-1-yl)ethyl)-4,5-dihydro-3H-1-thia-3,5,8-triazaacenaphthylene-2-carboxamide; | 6.1 |
| 933 | N-(2-Morpholinoethyl)-4-oxo-5-(4-phenoxyphenyl)-4,5-dihydro-3H-1-thia-3,5,8-triazaacenaphthylene-2-carboxamide; | 6.1 |

TABLE 2-continued

| Ex # | Compound Name | BTK_I_binding pIC50 |
|---|---|---|
| 934 | (S)-4-Oxo-5-(4-phenoxyphenyl)-N-(pyrrolidin-3-yl)-4,5-dihydro-3H-1-thia-3,5,8-triazaacenaphthylene-2-carboxamide; | 6.1 |
| 935 | N-(2-(4-Methylpiperazin-1-yl)ethyl)-4-oxo-5-(4-phenoxyphenyl)-4,5-dihydro-3H-1-thia-3,5,8-triazaacenaphthylene-2-carboxamide; | 6.0 |
| 936 | (R)-N-(1-Acetylpiperidin-3-yl)-5-(4-isopropoxy-2-methylphenyl)-4-oxo-4,5-dihydro-3H-1-thia-3,5,8-triazaacenaphthylene-2-carboxamide; | <6 |
| 937 | (R)-4-Oxo-N-(piperidin-3-yl)-5-(3-(pyridin-3-yl)phenyl)-4,5-dihydro-3H-1-thia-3,5,8-triazaacenaphthylene-2-carboxamide; | 6.0 |
| 938 | (S,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide; | 6.0 |
| 939 | (S,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide; | 6.0 |
| 940 | (S)-N-(1-Benzoylpyrrolidin-3-yl)-4-oxo-5-(4-phenoxyphenyl)-4,5-dihydro-3H-1-thia-3,5,8-triazaacenaphthylene-2-carboxamide; | 5.9 |
| 941 | (R)-N-(1-Acryloylpiperidin-3-yl)-5-(3,5-dichlorophenyl)-4-oxo-4,5-dihydro-3H-1-thia-3,5,8-triazaacenaphthylene-2-carboxamide; | 5.8 |
| 942 | (S,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide; | 5.6 |
| 943 | (R)-N-(1-Acryloylpiperidin-3-yl)-5-(3-(dimethylamino)phenyl)-4-oxo-4,5-dihydro-3H-1-thia-3,5,8-triazaacenaphthylene-2-carboxamide; | 5.6 |
| 944 | N-(1-(2-Cyanoacetyl)piperidin-4-yl)-5-(2-methyl-4-phenoxyphenyl)-4-oxo-4,5-dihydro-3H-1-thia-3,5,8-triazaacenaphthylene-2-carboxamide; | 5.6 |
| 945 | (S)-N-(1-Benzylpyrrolidin-3-yl)-4-oxo-5-(4-phenoxyphenyl)-4,5-dihydro-3H-1-thia-3,5,8-triazaacenaphthylene-2-carboxamide; | 5.5 |
| 946 | (S,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide; | 5.4 |
| 947 | 5-(2-Methyl-4-phenoxyphenyl)-4-oxo-N-(1-propionylpiperidin-4-yl)-4,5-dihydro-3H-1-thia-3,5,8-triazaacenaphthylene-2-carboxamide; | 5.4 |
| 948 | (R)-N-(1-Acryloylpiperidin-3-yl)-5-(4-aminophenyl)-4-oxo-4,5-dihydro-3H-1-thia-3,5,8-triazaacenaphthylene-2-carboxamide; | 5.2 |
| 949 | (R)-5-(4-(Dimethylamino)phenyl)-4-oxo-N-(piperidin-3-yl)-4,5-dihydro-3H-1-thia-3,5,8-triazaacenaphthylene-2-carboxamide; | 5.2 |
| 950 | (R)-4-Oxo-N-(piperidin-3-yl)-5-(m-tolyl)-4,5-dihydro-3H-1-thia-3,5,8-triazaacenaphthylene-2-carboxamide; | 5.1 |
| 951 | (R)-5-(4-Chlorophenyl)-4-oxo-N-(piperidin-3-yl)-4,5-dihydro-3H-1-thia-3,5,8-triazaacenaphthylene-2-carboxamide; | 5.1 |
| 952 | (R)-4-Oxo-N-(piperidin-3-yl)-5-(p-tolyl)-4,5-dihydro-3H-1-thia-3,5,8-triazaacenaphthylene-2-carboxamide; | 5.1 |
| 953 | (R)-5-(4-Fluorophenyl)-4-oxo-N-(piperidin-3-yl)-4,5-dihydro-3H-1-thia-3,5,8-triazaacenaphthylene-2-carboxamide; | 5.1 |
| 954 | (R)-5-(4-(tert-Butyl)phenyl)-4-oxo-N-(piperidin-3-yl)-4,5-dihydro-3H-1-thia-3,5,8-triazaacenaphthylene-2-carboxamide; | 5.0 |
| 955 | (R)-5-(4-Isopropoxy-3-methylphenyl)-4-oxo-N-(piperidin-3-yl)-4,5-dihydro-3H-1-thia-3,5,8-triazaacenaphthylene-2-carboxamide; | <5 |
| 956 | (R)-5-(4-Aminophenyl)-4-oxo-N-(piperidin-3-yl)-4,5-dihydro-3H-1-thia-3,5,8-triazaacenaphthylene-2-carboxamide; | <5 |
| 957 | (S,E)-N-(1-(2-Cyano-3-cyclopropylacryloyl)piperidin-3-yl)-5-(2-methyl-3-phenoxyphenyl)-4-oxo-4,5-dihydro-3H-1-thia-3,5,8-triazaacenaphthylene-2-carboxamide; | <5 |
| 958 | (R)-5-(*S)-(6-Isopropoxy-4-methyrpyridin-3-yl)-4-oxo-N-(pyrrolidin-3-yl)-4,5-dihydro-3H-1-thia-3,5,8-triazaacenaphthylene-2-carboxamide; | <6 |
| 959 | (R)-N-(1-Acryloylpyrrolidin-3-yl)-5-(*S)-(6-isopropoxy-4-methylpyridin-3-yl)-4-oxo-4,5-dihydro-3H-1-thia-3,5,8-triazaacenaphthylene-2-carboxamide; | 7.5 |
| 974 | (R)-N-(1-Acryloylpyrrolidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide; | 5.6 |
| 975 | (R)-N-(1-Acryloylpiperidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide; | 5.0 |

Aspects

Aspect 1. A compound of formula I':

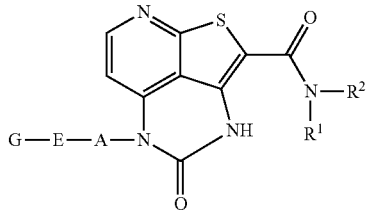

wherein
$R^1$ is H or $C_{1-6}$alkyl;
$R^2$ is —$C_{0-6}$alk-piperidinyl; —$C_{0-6}$alk-pyrrolidinyl; —$C_{0-6}$alk-oxazepanyl; —$C_{0-6}$alk-azetidinyl; —$C_{0-6}$alk-aziridinyl; —$C_{0-6}$alk-azepanyl; —$C_{0-6}$alk-quinuclidinyl; —$C_{0-6}$alk-imidazolidinyl; —$C_{0-6}$alk-piperazinyl; —$C_{0-6}$alkmorpholinyl; —$C_{0-6}$alk-tetrahydropyranyl; or —$C_{0-6}$alk-tetrahydrofuranyl wherein the $R^2$ is optionally substituted with 1, 2, or 3 substituents independently selected from the group consisting of
—$NR^8$—C(O)—C($R^3$)=C$R^4$($R^5$); —C(O)—C($R^3$)=C$R^4$($R^5$); oxo; halogen; —CN; —OH; —$NR^6R^7$; —$C_{1-6}$alkyl; —$C_{1-6}$alk-OH; —O$C_{1-6}$alkyl; —$C_{3-6}$cycloalkyl; —$C_{1-6}$haloalkyl; —$C_{1-6}$alkaryl; —SO$_2$—$C_{1-6}$alkyl; —SO$_2$—$C_{2-6}$alkenyl; —C(O)H; —C(O)—$C_{1-6}$alkyl; —C(O)—$C_{3-6}$cycloalkyl; —C(O)—$C_{1-6}$haloalkyl; —C(O)—$C_{2-6}$alkynyl; —C(O)—$C_{6-10}$aryl; —C(O)-heteroaryl; —C(O)—$C_{1-6}$alk-CN; —C(O)—$C_{1-6}$alk-OH; —C(O)—$C_{1-6}$alk-SO$_2$—$C_{1-6}$alkyl; —C(O)—O—$C_{1-6}$alkyl; —C(O)—$C_{1-6}$alk-$NR^6R^7$; —C(O)—$C_{1-6}$alk-O—$C_{1-6}$alkyl wherein the —$C_{1-6}$alk- is optionally substituted with —OH, —O$C_{1-6}$alkyl, or —$NR^6R^7$; and —C(O)—$C_{0-6}$alk-heterocycloalkyl wherein the -alk- is optionally substituted with oxo and the heterocycloalkyl is optionally substituted with —$C_{1-6}$alkyl; wherein
$R^3$ is H; —CN; halogen; —$C_{1-6}$haloalkyl; or —$C_{1-6}$alkyl;
$R^4$ and $R^5$ are each independently H; halogen; —$C_{1-6}$alkyl; —O$C_{1-6}$alkyl; —$C_{0-6}$alk-$C_{3-6}$cycloalkyl optionally substituted with $C_{1-6}$alkyl; —$C_{0-6}$alk-heterocycloalkyl optionally substituted with —C(O)$C_{1-6}$ alkyl or —$C_{1-6}$alkyl; —$C_{1-6}$alk-OH; —$C_{0-6}$alk-$NR^6R^7$; —$C_{1-6}$alk-O—$C_{1-6}$alkyl; —$C_{1-6}$alk-NH—$C_{0-6}$alk-O—$C_{1-6}$alkyl; —$C_{1-6}$alk-NHSO$_2$—$C_{1-6}$alkyl; —$C_{1-6}$alk-SO$_2$—$C_{1-6}$alkyl; —NHC(O)—$C_{1-6}$alkyl; or -linker-PEG-Biotin; and
$R^6$ and $R^7$ are each independently H; —$C_{1-6}$alkyl; —$C_{3-6}$cycloalkyl; C(O)H, or —CN; and
$R^8$ is H or $C_{1-6}$alkyl;
A is a bond, pyridyl; phenyl; napthalenyl; pyrimidinyl; pyrazinyl; pyridazinyl; benzo[d][1,3]dioxolyl optionally substituted with halogen; benzothiophenyl; or pyrazolyl; optionally substituted with 1, 2, or 3 substituents independently selected from the group consisting of —$C_{1-6}$alkyl; halogen; —SF$_5$; —O$C_{1-6}$alkyl; —C(O)—$C_{1-6}$alkyl; and —$C_{1-6}$haloalkyl;
E is —O—; a bond; —C(O)—NH—; —CH$_2$—; or —CH$_2$—O—;
G is H; —$C_{3-6}$cycloalkyl; -phenyl; -thiophenyl; —$C_{1-6}$alkyl; -pyrimidinyl; -pyridyl; -pyridazinyl; -benzofuranyl; —$C_{1-6}$haloalkyl; -heterocycloalkyl that contains an oxygen heteroatom; -phenyl-CH$_2$—O-phenyl; —$C_{1-6}$alk-O—$C_{1-6}$alkyl; —$NR^6R^7$; —SO$_2C_{1-6}$alkyl; or —OH; wherein the phenyl; thiophenyl; pyrimidinyl; pyridyl; pyridazinyl; or benzofuranyl is optionally substituted with 1, 2, or 3 substituents independently selected from the group consisting of halogen; —$C_{1-6}$alkyl; —$C_{1-6}$haloalkyl; —O$C_{1-6}$haloalkyl; —$C_{3-6}$cycloalkyl; —O$C_{1-6}$alkyl; —CN; —OH; —$C_{1-6}$alk-O—$C_{1-6}$alkyl; —C(O)—$NR^6R^7$; and —C(O)—$C_{1-6}$alkyl;
or a stereoisomer or isotopic variant thereof;
or a pharmaceutically acceptable salt thereof.

Aspect 2. The compound of aspect 1, wherein $R^1$ is H.
Aspect 3. The compound of aspect 1 or aspect 2, wherein $R^2$ is —$C_{0-6}$alk-piperidinyl, —$C_{0-6}$alk-pyrrolidinyl, —$C_{0-1}$alk-piperidinyl, —$C_{0-1}$alk-pyrrolidinyl, —$C_0$alk-piperidinyl, or —$C_0$alk-pyrrolidinyl.
Aspect 4. The compound of aspect 1 or aspect 2, wherein $R^2$ is —$C_{0-6}$alk-azetidinyl; —$C_{0-6}$alk-azepanyl; —$C_{0-6}$alk-quinuclidinyl; —$C_{0-6}$alk-imidazolidinyl; or —$C_{0-6}$alkpiperazinyl.
Aspect 5. The compound of aspect 1 or aspect 2, wherein $R^2$ is —$C_{0-6}$alk-oxazepanyl or —$C_{0-6}$alkmorpholinyl.
Aspect 6. The compound of aspect 1 or aspect 2, wherein $R^2$ is —$C_{0-6}$alk-tetrahydropyranyl or —$C_{0-6}$alk-tetrahydrofuranyl.
Aspect 7. The compound of any one of the preceding aspects, wherein $R^2$ is unsubstituted.
Aspect 8. The compound of any one of the preceding aspects, wherein $R^2$ is substituted with 1 or 2 substitutents, preferably $R^2$ is substituted with 1 substitutent.
Aspect 9. The compound of aspect 8, wherein $R^2$ is substituted with oxo.
Aspect 10. The compound of aspect 8 or aspect 9, wherein $R^2$ is substituted with halogen; —CN; —OH; —$C_{1-6}$alkyl; —$C_{1-6}$haloalkyl; —$C_{1-6}$alk-OH; —O$C_{1-6}$alkyl; —$C_{3-6}$cycloalkyl; —$NR^6R^7$; or —$C_{1-6}$alkaryl.
Aspect 11. The compound of any one of aspects 8-10, wherein $R^2$ is substituted with —C(O)H; —C(O)—$C_{1-6}$ alkyl; —C(O)—$C_{3-6}$cycloalkyl; —C(O)—$C_{1-6}$haloalkyl; —C(O)-alkynyl; —C(O)—$C_{6-10}$aryl; —C(O)—$C_{1-6}$alk-CN; —C(O)—$C_{1-6}$alk-OH; —C(O)—O—$C_{1-6}$alkyl; —C(O)—$C_{1-6}$alk-$NR^6R^7$; or —C(O)—$C_{1-6}$alk-O—$C_{1-6}$alkyl wherein the —$C_{1-6}$alk- is optionally substituted with —OH, —O$C_{1-6}$alkyl, or —$NR^6R^7$.
Aspect 12. The compound of any one of aspects 8-11, wherein $R^2$ is substituted with —C(O)-heteroaryl or —C(O)—$C_{0-6}$alk-heterocycloalkyl wherein the heterocycloalkyl is optionally substituted with —$C_{1-6}$alkyl.
Aspect 13. The compound of any one of aspects 8-12, wherein $R^2$ is substituted with —SO$_2$alkyl; —C(O)—$C_{1-6}$alk-SO$_2$—$C_{1-6}$alkyl; or —SO$_2$—$C_{2-6}$alkenyl.
Aspect 14. The compound of any one of aspects 8-13, wherein $R^2$ is substituted with —$NR^8$—C(O)—C($R^3$)=C$R^4$($R^5$).
Aspect 15. The compound of aspect 14, wherein $R^8$ is H.
Aspect 16. The compound of any one of aspects 8-15, wherein $R^2$ is substituted with —C(O)—C($R^3$)=C$R^4$($R^5$).
Aspect 17. The compound of any one of aspects 14-16, wherein $R^3$ is H.
Aspect 18. The compound of any one of aspects 14-16, wherein $R^3$ is —CN.
Aspect 19. The compound of any one of aspects 14-16, wherein $R^3$ is F or Cl.

Aspect 20. The compound of any one of aspects 14-16, wherein $R^3$ is $C^{1-6}$haloalkyl or $C_{1-6}$alkyl.

Aspect 21. The compound of any one of aspects 14-20, wherein one of $R^4$ and $R^5$ is H.

Aspect 22. The compound of any one of aspects 14-20, wherein $R^4$ is H and $R^5$ is H.

Aspect 23. The compound of any one of aspects 14-21, wherein one of $R^4$ and $R^5$ is halogen; —$C_{1-6}$alkyl; —$OC_{1-6}$alkyl; —$C_{1-6}$alk-O—$C_{1-6}$alkyl; —$C_{0-6}$alk-$C_{3-6}$ cycloalkyl optionally substituted with $C_{1-6}$alkyl; or —$C_{1-6}$alk-OH.

Aspect 24. The compound of any one of aspects 14-21, wherein one of $R^4$ and $R^5$ is —$C_{0-6}$alk-$NR^6R^7$, —$C_{1-6}$alk-$NR^6R^7$, or —$C_{1-6}$alk-NH—$C_{0-6}$alk-O—$C_{1-6}$alkyl.

Aspect 25. The compound of any one of aspects 14-21, wherein one of $R^4$ and $R^5$ is —$C_{0-6}$alk-heterocycloalkyl or —$C_{1-6}$alk-heterocycloalkyl optionally substituted with —$C(O)C_{1-6}$alkyl.

Aspect 26. The compound of any one of aspects 14-20, wherein one of $R^4$ and $R^5$ is or —NHC(O)—$C_{1-6}$alkyl.

Aspect 27. The compound of any one of aspects 14-20, wherein one of $R^4$ and $R^5$ is —$C_{1-6}$alk-$NHSO_2$—$C_{1-6}$alkyl or —$C_{1-6}$alk-$SO_2$—$C_{1-6}$alkyl.

Aspect 28. The compound of any one of the preceding aspects, wherein A is a bond, naphthalenyl, or benzo[d][1,3]dioxolyl.

Aspect 29. The compound of any one of aspects 1-27, wherein A is phenyl.

Aspect 30. The compound of any one of aspects 1-27, wherein A is pyridyl.

Aspect 31. The compound of any one of aspects 1-27, wherein A is pyrimidinyl.

Aspect 32. The compound of any one of aspects 1-27, wherein A is pyrazinyl.

Aspect 33. The compound of any one of aspects 1-27, wherein A is pyridazinyl.

Aspect 34. The compound of any one of aspects 29-33, wherein A is substituted with 1 or 2 substitutents.

Aspect 35. The compound of aspect 34, wherein A is substituted with —$C_{1-6}$alkyl, preferably —$CH_3$.

Aspect 36. The compound of any one of the preceding aspects, wherein E is O.

Aspect 37. The compound of any one of aspects 1-35, wherein E is a bond.

Aspect 38. The compound of any one of aspects 1-35, wherein E is —C(O)—NH—, —$CH_2$—, or —$CH_2$O—.

Aspect 39. The compound of any one of aspects 1-38, wherein G is H.

Aspect 40. The compound of any one of aspects 1-38, wherein G is —$C_{1-6}$alkyl; —$C_{1-6}$haloalkyl; —$C_{1-6}$alk-O—$C_{1-6}$alkyl; or —$C_{3-6}$cycloalkyl.

Aspect 41. The compound of any one of aspects 1-38, wherein G is —$C_{1-6}$alkyl or —$C_{3-6}$cycloalkyl.

Aspect 42. The compound of any one of aspects 1-38, wherein G is —$NR^6R^7$ or —OH.

Aspect 43. The compound of any one of aspects 1-38, wherein G is -heterocycloalkyl that contains an oxygen heteroatom.

Aspect 44. The compound of any one of aspects 1-38, wherein G is —$SO_2C_{1-6}$alkyl.

Aspect 45. The compound of any one of aspects 1-38, wherein G is -phenyl.

Aspect 46. The compound of any one of aspects 1-38, wherein G is -pyridyl.

Aspect 47. The compound of any one of aspects 1-38, wherein G is -pyrimidinyl or pyridazinyl.

Aspect 48. The compound of any one of aspects 1-38, wherein G is -benzofuranyl or -thiophenyl.

Aspect 49. The compound of any one of aspects 1-38, wherein G is -phenyl-$CH_2$—O-phenyl.

Aspect 50. The compound of any one of aspects 45-49, wherein G is substituted with 1 or 2 substitutents.

Aspect 51. The compound of aspect 50, wherein G is substituted with halogen.

Aspect 52. The compound of aspect 50 or aspect 51, wherein G is substituted with —$C_{1-6}$alkyl; —$C_{1-6}$haloalkyl; —$OC_{1-6}$haloalkyl; —$C_{3-6}$cycloalkyl; —$OC_{1-6}$alkyl; —$C_{1-6}$alk-O—$C_{1-6}$alkyl; or —C(O)—$C_{1-6}$alkyl.

Aspect 53. The compound of any one of aspects 50-52, wherein G is substituted with —CN.

Aspect 54. The compound of any one of aspects 50-53, wherein G is substituted with —OH.

Aspect 55. The compound of any one of aspects 50-54, wherein G is substituted with —C(O)—$NR^6R^7$.

Aspect 56. The compound of any one of aspects 1-27, wherein A-E-G is -phenyl-O-phenyl or -pyridyl-O-phenyl.

Aspect 57. The compound of aspect 56, wherein A-E-G is

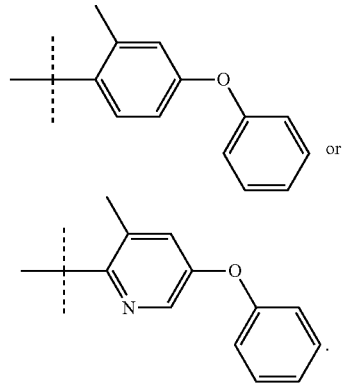

Aspect 58. The compound of aspect 1, wherein $R^1$ is H; $R^2$ is $C_0$alk-piperidinyl substituted with 1 or 2 substituents wherein one of the substituents is —C(O)—C($R^3$)=C$R^4$($R^5$), wherein $R^3$, $R^4$, and $R^5$ are each H; A is phenyl or pyridyl substituted with —$CH_3$; E is O; and G is phenyl.

Aspect 59. The compound of aspect 58, wherein $R^2$ is substituted with 1 substituent that is —C(O)—C($R^3$)=C$R^4$($R^5$).

Aspect 60. The compound of aspect 58 or aspect 59, wherein A-E-G is

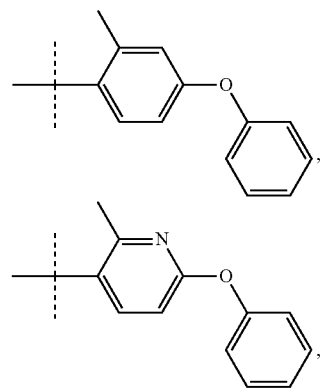

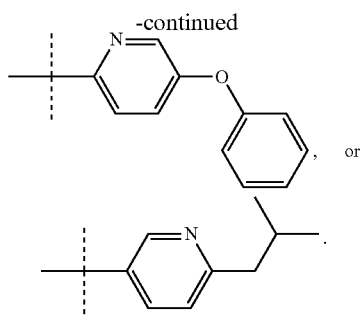

Aspect 61. The compound of any one of aspects 58, 59, or 60, wherein the compound of formula I is

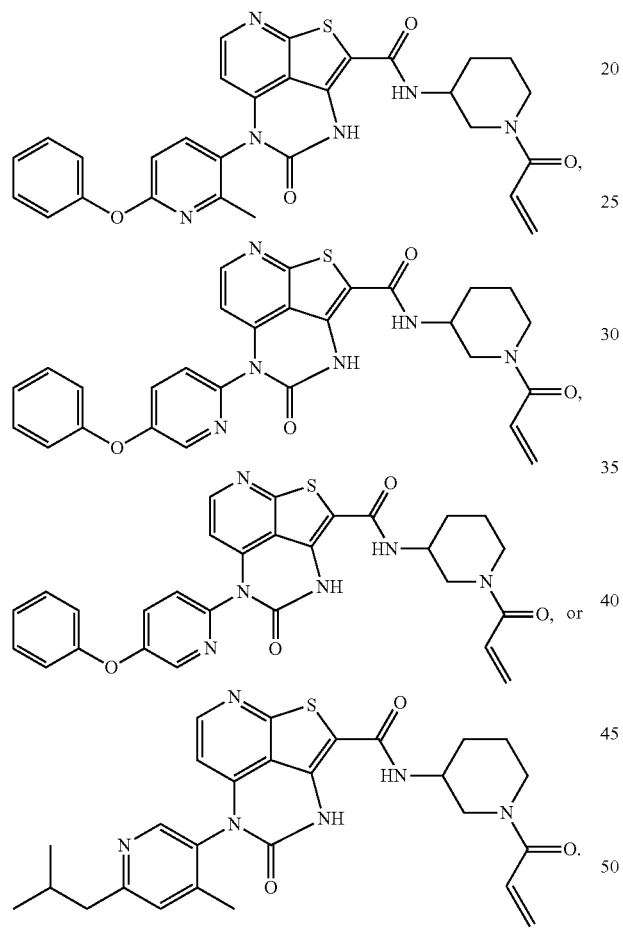

Aspect 62. The compound of any one of the preceding aspects that is a pharmaceutically acceptable salt.

Aspect 63. A pharmaceutical composition comprising a compound of any one of aspects 1-61, or a pharmaceutically acceptable salt thereof, and a pharmaceutically acceptable excipient.

Aspect 64. A method of inhibiting Bruton's tyrosine kinase comprising contacting the kinase with a compound of any one of aspects 1-61.

Aspect 65. A method of treating cancer in a patient comprising administering to the patient a compound of any one of aspects 1-61, or a pharmaceutically acceptable salt thereof.

Aspect 66. The method of aspect 65, wherein the cancer is mantle cell lymphoma, chronic lymphocytic leukemia, macroglobulinemia, or multiple myeloma.

Aspect 67. A method of treating systemic lupus erythematosus in a patient comprising administering to the patient a compound of any one of aspects 1-61, or a pharmaceutically acceptable salt thereof.

Aspect 68. A method of treating a pemphigus disorder or a pemphigoid disorder in a patient comprising administering to the patient a compound of any one of aspects 1-61, or a pharmaceutically acceptable salt thereof.

Aspect 69. A method of treating rheumatoid arthritis in a patient comprising administering to the patient a compound of any one of aspects 1-61, or a pharmaceutically acceptable salt thereof.

Aspect 70. A method of making a compound of any one of aspects 1-61, or a pharmaceutically acceptable salt thereof.

Aspect 71. A compound as recited in Table 1.

What is claimed:

1. A compound of Formula (I'), pharmaceutically acceptable salts, stereoisomers, isotopes, or N-oxides thereof,

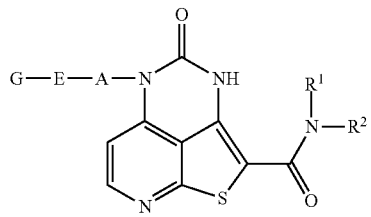

(I')

wherein $R^1$ is H or $C_{1-6}$alkyl;

$R^2$ is selected from the group consisting of: $C_{0-2}$alk-piperidinyl; $C_{0-2}$alk-pyrrolidinyl; oxazepanyl; azetidinyl; azepanyl; quinuclidinyl; $C_2$alk-imidazolidinyl; $C_2$alk-piperazinyl; $C_2$alk-morpholinyl; tetrahydropyranyl; and $C_{0-1}$alk-tetrahydrofuranyl; wherein the $R^2$ is optionally substituted with 1, 2, or 3 substituents each independently selected from the group consisting of: (C=O)—C($R^3$)=C$R^4$($R^5$); oxo; halogen; OH; $NH_2$; CN; $C_{1-6}$alkyl; $C_{1-6}$alk-OH; O$C_{1-6}$alkyl; $C_{1-6}$haloalkyl; $C_{3-6}$cycloalkyl; $SO_2C_{1-6}$alkyl; $SO_2$—$C_{2-6}$alkenyl; $C_{1-2}$alk-aryl; (C=O)H; (C=O)$C_{1-6}$alkyl; (C=O)$C_{1-6}$haloalkyl; (C=O)—$C_{2-6}$alkenyl; (C=O)—$C_{2-6}$alkynyl; (C=O)$C_{3-6}$cycloalkyl; (C=O)-phenyl; (C=O)-imidazolyl; (C=O)—$C_{1-6}$alkCN; (C=O)—$C_{1-6}$alk-OH; (C=O)—$C_{1-6}$alk-$SO_2C_{1-6}$alkyl; (C=O)—$C_{1-6}$alk-N$R^6R^7$; (C=O)—$C_{1-6}$alk-O—$C_{1-6}$alkyl wherein the —$C_{1-6}$alk- is optionally substituted with OH, O$C_{1-6}$alkyl, or N$R^6R^7$; (C=O)$C_{0-1}$alk-heterocycloalkyl wherein the -alk- is optionally substituted with oxo and the heterocycloalkyl is optionally substituted with $C_{1-6}$alkyl; and NH(C=O)—C($R^3$)=C$R^4$(R);

wherein $R^3$ is selected from the group consisting of: H, CN, halogen, $C_{1-6}$haloalkyl, and $C_{1-6}$alkyl;

$R^4$ and $R^5$ are each independently selected from the group consisting of: H; halogen; $C_{1-6}$alkyl; $CH_2$OH; $C_{1-6}$alk-O$C_{1-6}$alkyl; O$C_{1-6}$alkyl; $C_{1-4}$alk-N$R^6R^7$; $C_{3-6}$cycloalkyl substituted with $NH_2$ or $CH_3$; oxetanyl substituted with $CH_3$; 1-acetylpyrrolidin-2-yl; $CH_2$-pyrrolidinyl; $CH_2$-piperidinyl; $C(CH_3)_2$-piperidinyl;

CH$_2$-morpholinyl; C(CH$_3$)$_2$-morpholinyl; CH$_2$-(4aR, 7aS)-tetrahydro-2H-[1,4]dioxino[2,3-c]pyrrol-6(3H)-yl; C(CH$_3$)$_2$NH(CH$_2$CH$_2$OCH$_3$); CH$_2$SO$_2$CH$_3$; CH$_2$NHSO$_2$CH$_3$; NH(C=O)C$_{1-6}$alkyl; and linker-PEG-Biotin; and R$^6$ and R$^7$ are each independently selected from the group consisting of: H, C$_{1-6}$alkyl, cyclopropyl, (C=O)H, and CN;

A is selected from the group consisting of: a bond, phenyl; naphthalenyl, pyridyl; pyrimidinyl; pyrazinyl; pyridazinyl; benzothiophenyl; and pyrazolyl; wherein the A is optionally substituted with 1, 2, or 3 substituents each independently selected from the group consisting of: C$_{1-6}$alkyl, halogen, OC$_{1-6}$alkyl, (C=O)C$_{1-6}$alkyl, and C$_{1-6}$haloalkyl;

E is selected from the group consisting of: —O—, a bond, (C=O)—NH, CH$_2$, and CH$_2$—O; and G is selected from the group consisting of: H, C$_{1-6}$alkyl; C$_{1-6}$haloalkyl; C$_{1-6}$alk-OC$_{1-6}$alkyl; NR$^6$R$^7$; SO$_2$C$_{1-6}$alkyl; OH; C$_{3-6}$cycloalkyl; phenyl; thiophenyl; pyrimidinyl; pyridyl; pyridazinyl; benzofuranyl; heterocycloalkyl that contains an oxygen heteroatom; phenyl-CH$_2$—O-phenyl; wherein the phenyl, thiophenyl, pyrimidinyl, pyridyl, pyridazinyl, or benzofuranyl is optionally substituted with 1, 2, or 3 substituents each independently selected from the group consisting of: halogen, C$_{1-6}$alkyl, C$_{1-6}$haloalkyl, OC$_{1-6}$haloalkyl, OC$_{1-6}$alkyl, OC$_{1-6}$alkyl-OC$_{1-6}$alkyl, C$_{3-6}$cycloalkyl, CN, OH, NH$_2$, N(CH$_3$)$_2$, C$_{1-6}$alk-OC$_{1-6}$alkyl, SO$_2$C$_{1-6}$-alkyl, (C=O)—NR$^6$R$^7$, SF$_5$, and (C=O)C$_{1-6}$alkyl.

2. The compound of claim 1, wherein R$^1$ is H.

3. The compound of claim 1, wherein R$^2$ is piperidinyl, CH$_2$CH$_2$-piperidinyl, pyrrolidinyl, CH$_2$-pyrrolidinyl, or CH$_2$CH$_2$-pyrrolidinyl.

4. The compound of claim 1, wherein R$^2$ is substituted with (C=O)—C(R$^3$)=CR$^4$(R$^5$).

5. The compound of claim 4, wherein R$^3$ is H.

6. The compound of claim 1, wherein R$^4$ is H and R$^5$ is H.

7. The compound of claim 1, wherein A is pyridyl.

8. The compound of claim 1, wherein A is substituted with CH$_3$O.

9. The compound of claim 1, wherein E is O.

10. The compound of claim 1, wherein G is phenyl.

11. The compound of claim 1, wherein G is pyridyl.

12. The compound of claim 1, wherein R$^1$ is H; R$^2$ is piperidinyl substituted with 1 or 2 substituents wherein one of the substituents is (C=O)—C(R$^3$)=CR$^4$(R$^5$), wherein R$^3$, R$^4$, and R$^5$ are each H; A is phenyl or pyridyl substituted with CH$_3$; E is O; and G is phenyl.

13. The compound of claim 1, wherein the compound is selected from the group consisting of:

N-((3R,5R)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3-fluoro-2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5R)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(3-fluoro-2-methyl-4-phenoxyphenyl)-4-oxo-4,5-dihydro-3H-1-thia-3,5,8-triazaacenaphthylene-2-carboxamide;

N-((3R,5R)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2-fluoro-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(2-chloro-4-phenoxyphenyl)-4-oxo-4,5-dihydro-3H-1-thia-3,5,8-triazaacenaphthylene-2-carboxamide;

N-((3R,5S)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-methoxypiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2-chloro-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-(benzofuran-7-yloxy)-2-methylphenyl)-4-oxo-4,5-dihydro-3H-1-thia-3,5,8-triazaacenaphthylene-2-carboxamide;

(R)—N-(1-Acryloylpyrrolidin-3-yl)-5-(4-(2,6-difluorophenoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-5-(4-(2-ethylphenoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(2-fluoro-6-methyl-4-phenoxyphenyl)-4-oxo-4,5-dihydro-3H-1-thia-3,5,8-triazaacenaphthylene-2-carboxamide;

(R,E)-N-(1-(2-cyano-3-(3-methyloxetan-3-yl)acryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(4-(benzofuran-7-yloxy)-2-methylphenyl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylamino)but-2-enoyl)piperidin-3-yl)-4I-oxo-4,5-dihydro-3H-1-thia-3,5,8-triazaacenaphthylene-2-carboxamide;

(R)-5-(4-(3-((2-Cyanophenoxy)methyl)phenoxy)-2-methylphenyl)-N-(1-methylpiperidin-3-yl)-4I-oxo-4,5-dihydro-3H-1-thia-3,5,8-triazaacenaphthylene-2-carboxamide;

(S,E)-N-(1-(4-Hydroxybut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Chloroacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(4-Aminobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

N-((3S,4R)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,EZ)—N-(1-(2-Cyano-4-ethoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(4-Hydroxybut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;

N-(4-Cyano-1,4-oxazepan-6-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-(cyclohexyloxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-isopropoxy-2-methylphenyl)-4-oxo-4,5-dihydro-3H-1-thia-3,5,8-triazaacenaphthylene-2-carboxamide;

N-((3S,4R)-1-Acryloyl-4-methoxypyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Cyanopiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide;

N-((3S,4R)-1-Acryloyl-4-fluoropyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide;

(R)—N-(1-Acryloylpyrrolidin-3-yl)-5-(4-(cyclohexyloxy)-2-methylphenyl)-4-oxo-4,5-dihydro-3H-1-thia-3,5,8-triazaacenaphthylene-2-carboxamide;

(R,E)-N-(1-(2-Cyano-4-methoxy-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-13C-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(But-2-ynoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-methyl-4-morpholinopent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(S)—N-(1-Acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(2-fluoro-6-methyl-4-phenoxyphenyl)-4-oxo-4,5-dihydro-3H-1-thia-3,5,8-triazaacenaphthylene-2-carboxamide;

(R)-5-(*S)-(2-methyl-4-phenoxyphenyl)-4-oxo-N-(1-propioloylpiperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-4-oxo-5-(4-phenoxyphenyl)-4,5-dihydro-3H-1-thia-3,5,8-triazaacenaphthylene-2-carboxamide;

(R)—N-(1-(2-Fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Fluoroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-cyclopropoxy-2-methylphenyl)-4-oxo-4,5-dihydro-3H-1-thia-3,5,8-triazaacenaphthylene-2-carboxamide;

(R)-5-(4-(2,6-Difluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(5-chlorobenzo[d][1,3]dioxol-4-yl)-4-oxo-4,5-dihydro-3H-1-thia-3,5,8-triazaacenaphthylene-2-carboxamide;

N-((3S,4S)-1-Acryloyl-4-methoxypyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(But-2-ynoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-(2-(Dimethylamino)acetyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)-5-(4-(2-Fluorophenoxy)-2-methylphenyl)-N-(1-methylpiperidin-3-yl)-4-oxo-4,5-dihydro-3H-1-thia-3,5,8-triazaacenaphthylene-2-carboxamide;

N-((3S,4R)-1-Acryloyl-4-hydroxypyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-propylpiperidin-3-yl)-4,5-dihydro-3H-1-thia-3,5,8-triazaacenaphthylene-2-carboxamide;

(S)-5-(3-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)—N-(1-Acryloylpiperidin-3-yl)-5-(4-ethyl-2-methylphenyl)-4-oxo-4,5-dihydro-3H-1-thia-3,5,8-triazaacenaphthylene-2-carboxamide;

(R,E)-N-(1-(2-Cyano-4-methyl-4-(tetrahydro-2H-pyran-4-yl)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4-(2,6-difluorophenoxy)-2-methylphenyl)-4-oxo-4,5-dihydro-3H-1-thia-3,5,8-triazaacenaphthylene-2-carboxamide;

(R)—N-(1-Acryloylpiperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(4-ethoxy-2-methylphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(S)-5-(*S)-(2-Methyl-4-phenoxyphenyl)-4-oxo-N-(tetrahydrofuran-3-yl)-4,5-dihydro-3H-1-thia-3,5,8-triazaacenaphthylene-2-carboxamide;

(R)—N-(1-Acryloylpiperidin-3-yl)-5-(2,6-difluoro-4-phenoxyphenyl)-4-oxo-4,5-dihydro-3H-1-thia-3,5,8-triazaacenaphthylene-2-carboxamide;

(R)-5-(4-(Benzofuran-7-yloxy)-2-methylphenyl)-N-(1-methylpiperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)—N-(1-(3-Methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-Ethylpiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(3-Hydroxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-(2-ethylphenoxy)-2-methylphenyl)-4-oxo-4,5-dihydro-3H-1-thia-3,5,8-triazaacenaphthylene-2-carboxamide;

(R)—N-(1-Acryloylpyrrolidin-3-yl)-5-(2,3-dimethyl-4-phenoxyphenyl)-4-oxo-4,5-dihydro-3H-1-thia-3,5,8-triazaacenaphthylene-2-carboxamide;

(R)—N-(1-(2-(Dimethylamino)acetyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-fluoro-4-phenoxyphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(tetrahydrofuran-3-yl)-4,5-dihydro-3H-1-thia-3,5,8-triazaacenaphthylene-2-carboxamide;

(R)—N-(1-Acryloylpyrrolidin-3-yl)-5-(2,6-dimethyl-4-phenoxyphenyl)-4-oxo-4,5-dihydro-3H-1-thia-3,5,8-triazaacenaphthylene-2-carboxamide;

(S)—N-(1-acryloylpiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2-methyl-4-(pentafluorothio)phenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide;

(R)-Tetrahydro-2H-pyran-3-yl 5-(2-methyl-4-phenoxyphenyl)-4-oxo-4,5-dihydro-3H-1-thia-3,5,8-triazaacenaphthylene-2-carboxylate;

(R)—N-(1-Acryloylpiperidin-3-yl)-5-(2,4-dimethylphenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide;

(S)-5-(*S)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)-5-(3-Fluoro-2-methyl-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide;

(S)-5-(2-Methyl-4-phenoxyphenyl)-4-oxo-N-(tetrahydrofuran-3-yl)-4,5-dihydro-3H-1-thia-3,5,8-triazaacenaphthylene-2-carboxamide;

(R)-5-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;

N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Isopropylpyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4R)-4-Fluoro-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Methoxyacetyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

N-(1-Cyanoazepan-3-yl)-5-(2-methyl-4-phenoxyphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(piperidin-3-yl)-4,5-dihydro-3H-1-thia-3,5,8-triazaacenaphthylene-2-carboxamide;

(R)—N-(1-(3-Hydroxypropanoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Isopropylpiperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-isopropoxy-2-methylphenyl)-4-oxo-4,5-dihydro-3H-1-thia-3,5,8-triazaacenaphthylene-2-carboxamide;

N-(1,6-Dimethylpiperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide;

(R,E)-N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-(3-(methylamino)propanoyl)piperidin-3-yl)-4-oxo-4,5-dihydro-3H-1-thia-3,5,8-triazaacenaphthylene-2-carboxamide;

(R)-5-(2-Fluoro-4-phenoxyphenyl)-4-oxo-N-(piperidin-3-yl)-4,5-dihydro-3H-1-thia-3,5,8-triazaacenaphthylene-2-carboxamide;

(R)-5-(2-Methyl-4-phenoxyphenyl)-4-oxo-N-(tetrahydrofuran-3-yl)-4,5-dihydro-3H-1-thia-3,5,8-triazaacenaphthylene-2-carboxamide;

N-(1-Acryloylazetidin-3-yl)-5-(2-methyl-4-phenoxyphenyl)-4-oxo-4,5-dihydro-3H-1-thia-3,5,8-triazaacenaphthylene-2-carboxamide;

(R)—N-(1-13C-Acryloylpiperidin-3-yl)-5-(4-methoxy-2-methylphenyl)-4-oxo-4,5-dihydro-3H-1-thia-3,5,8-triazaacenaphthylene-2-carboxamide;

N—((R)-1-((R)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-methyl-4-morpholinopent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(2-hydroxyacetyl)piperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(2-methoxyacetyl)piperidin-3-yl)-4-oxo-4,5-dihydro-3H-1-thia-3,5,8-triazaacenaphthylene-2-carboxamide;

(R,Z)—N-(1-(But-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide;

(R)—N-(1-Isopropylpyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(4-ethyl-2-methylphenyl)-4-oxo-4,5-dihydro-3H-1-thia-3,5,8-triazaacenaphthylene-2-carboxamide;

N—((R)-1-((S)-2-Amino-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(6-phenoxypyridazin-3-yl)-4,5-dihydro-3H-1-thia-3,5,8-triazaacenaphthylene-2-carboxamide;

N—((R)-1-((S)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-(tetrahydro-2H-pyran-4-yl)-4,5-dihydro-3H-1-thia-3,5,8-triazaacenaphthylene-2-carboxamide;

(R)—N-(1-(2-Hydroxyacetyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N—((R)-1-((S)-1-methylpyrrolidine-3-carbonyl)piperidin-3-yl)-4-oxo-4,5-dihydro-3H-1-thia-3,5,8-triazaacenaphthylene-2-carboxamide;

(R)—N-(1-Acryloylpyrrolidin-3-yl)-5-(4-isopropoxy-2-methylphenyl)-4-oxo-4,5-dihydro-3H-1-thia-3,5,8-triazaacenaphthylene-2-carboxamide;

(R)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(3-Fluoro-2-methyl-4-phenoxyphenyl)-N-(1-(3-hydroxypropanoyl)piperidin-3-yl)-4-oxo-4,5-dihydro-3H-1-thia-3,5,8-triazaacenaphthylene-2-carboxamide;

N-(4-Methyl-1,4-oxazepan-6-yl)-5-(2-methyl-4-phenoxyphenyl)-4-oxo-4,5-dihydro-3H-1-thia-3,5,8-triazaacenaphthylene-2-carboxamide;

(R)—N-(1-(3-(Dimethylamino)propanoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((S)-pyrrolidine-3-carbonyl)piperidin-3-yl)-4,5-dihydro-3H-1-thia-3,5,8-triazaacenaphthylene-2-carboxamide;

N-((3S,4R)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Chloro-4-phenoxyphenyl)-N-(1-methylpiperidin-3-yl)-4-oxo-4,5-dihydro-3H-1-thia-3,5,8-triazaacenaphthylene-2-carboxamide;

(R,Z)—N-(1-(2-Cyano-4-(dimethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Fluoro-4-phenoxyphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-N-(1-(oxetane-3-carbonyl)piperidin-3-yl)-4-oxo-4,5-dihydro-3H-1-thia-3,5,8-triazaacenaphthylene-2-carboxamide;

(R)—N-(1-Acryloylpyrrolidin-3-yl)-N-methyl-5-(2-methyl-4-phenoxyphenyl)-4-oxo-4,5-dihydro-3H-1-thia-3,5,8-triazaacenaphthylene-2-carboxamide;

N-((3R,5R)-5-Fluoropiperidin-3-yl)-5-(2-methyl-4-phenoxyphenyl)-4-oxo-4,5-dihydro-3H-1-thia-3,5,8-triazaacenaphthylene-2-carboxamide;

N-((3S,4S)-4-Hydroxy-1-(3-methoxypropanoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Cyano-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Ethylpyrrolidin-3-yl)-5-(2-methyl-4-phenoxyphenyl)-4-oxo-4,5-dihydro-3H-1-thia-3,5,8-triazaacenaphthylene-2-carboxamide;

N—((R)-1-((S)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

N—((R)-1-((R)-2-Hydroxy-3-methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-(2-(trifluoromethyl)acryloyl)piperidin-3-yl)-4,5-dihydro-3H-1-thia-3,5,8-triazaacenaphthylene-2-carboxamide;

5-(2-Methyl-4-phenoxyphenyl)-N—((R)-1-((R)-1-methylpyrrolidine-3-carbonyl)piperidin-3-yl)-4-oxo-4,5-dihydro-3H-1-thia-3,5,8-triazaacenaphthylene-2-carboxamide;

(R)-5-(2-Methyl-4-phenoxyphenyl)-N-(1-(3-(methylsulfonyl)propanoyl)piperidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide;

(R)-5-(2-Methyl-4-(o-tolyloxy)phenyl)-N-(1-methylpiperidin-3-yl)-4-oxo-4,5-dihydro-3H-1-thia-3,5,8-triazaacenaphthylene-2-carboxamide;

(R)—N-(1-Cyclopropylpyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-methyl-4-(piperidin-1-yl)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Aminoacetyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-(cyclopropylamino)-4-methyl-pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((6S)-6-methylpiperidin-3-yl)-4-oxo-4,5-dihydro-3H-1-thia-3,5,8-triazaacenaphthylene-2-carboxamide;

N-((3S,4R)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide;

N-((3R)-1-(3-Methoxybutanoyl)piperidin-3-yl)-5-(2-methyl-4-phenoxyphenyl)-4-oxo-4,5-dihydro-3H-1-thia-3,5,8-triazaacenaphthylene-2-carboxamide;

N—((R)-1-((S)-3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(2-Ethoxyphenoxy)-2-methylphenyl)-N-(1-methylpiperidin-3-yl)-4-oxo-4,5-dihydro-3H-1-thia-3,5,8-triazaacenaphthylene-2-carboxamide;

N-((3R)-1-(3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(pyrrolidin-3-yl)-4,5-dihydro-3H-1-thia-3,5,8-triazaacenaphthylene-2-carboxamide;

N-((3R,5R)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-propioloylpiperidin-3-yl)-4,5-dihydro-3H-1-thia-3,5,8-triazaacenaphthylene-2-carboxamide;

5-(2-Methyl-4-phenoxyphenyl)-N-(1-methyl-6-oxopiperidin-3-yl)-4-oxo-4,5-dihydro-3H-1-thia-3,5,8-triazaacenaphthylene-2-carboxamide;

(R)—N-(1-(3-Aminopropanoyl)piperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-5-Fluoro-1-methylpiperidin-3-yl)-5-(2-methyl-4-phenoxyphenyl)-4-oxo-4,5-dihydro-3H-1-thia-3,5,8-triazaacenaphthylene-2-carboxamide;

N-(1,3-Dimethylpiperidin-4-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-(2-oxopiperidin-4-yl)-4,5-dihydro-3H-1-thia-3,5,8-triazaacenaphthylene-2-carboxamide;

N-((3R,5S)-5-fluoropiperidin-3-yl)-5-(2-methyl-4-phenoxyphenyl)-4-oxo-4,5-dihydro-3H-1-thia-3,5,8-triazaacenaphthylene-2-carboxamide;

N-((3R,5R)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(4-(2-Ethylphenoxy)-2-methylphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-4-oxo-N-(quinuclidin-2-yl)-4,5-dihydro-3H-1-thia-3,5,8-triazaacenaphthylene-2-carboxamide;

5-(2-Methyl-4-phenoxyphenyl)-N-(3-methylpiperidin-4-yl)-4-oxo-4,5-dihydro-3H-1-thia-3,5,8-triazaacenaphthylene-2-carboxamide;

5-(2-Methyl-4-phenoxyphenyl)-N-((6R)-6-methylpiperidin-3-yl)-4-oxo-4,5-dihydro-3H-1-thia-3,5,8-triazaacenaphthylene-2-carboxamide;

(R)—N-(5,5-Difluoropiperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2,6-difluoro-4-phenoxyphenyl)-4-oxo-4,5-dihydro-3H-1-thia-3,5,8-triazaacenaphthylene-2-carboxamide;

13C—(R,Z)—N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

13C—(R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-(cyclohexyloxy)-2-methylphenyl)-4-oxo-4,5-dihydro-3H-1-thia-3,5,8-triazaacenaphthylene-2-carboxamide;

N-((3R,5R)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide;

(R)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)—N-(1-(2-Cyanoacetyl)piperidin-3-yl)-4-oxo-5-(4-phenoxyphenyl)-4,5-dihydro-3H-1-thia-3,5,8-triazaacenaphthylene-2-carboxamide;

(R)—N-(1-Methylpiperidin-3-yl)-4-oxo-5-(4-phenoxyphenyl)-4,5-dihydro-3H-1-thia-3,5,8-triazaacenaphthylene-2-carboxamide;

(R)-5-(*S)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-cyclopropoxy-2-methylphenyl)-4-oxo-4,5-dihydro-3H-1-thia-3,5,8-triazaacenaphthylene-2-carboxamide;

N-((3S,4S)-4-Fluoro-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(1-methylazepan-4-yl)-4-oxo-4,5-dihydro-3H-1-thia-3,5,8-triazaacenaphthylene-2-carboxamide;

(R)—N-(1-(3-Methoxy-2,2-dimethylpropanoyl)piperidin-3-yl)-5-(2-methyl-4-phenoxyphenyl)-4-oxo-4,5-dihydro-3H-1-thia-3,5,8-triazaacenaphthylene-2-carboxamide;

N-(1-Cyanoazepan-4-yl)-5-(2-methyl-4-phenoxyphenyl)-4-oxo-4,5-dihydro-3H-1-thia-3,5,8-triazaacenaphthylene-2-carboxamide;

N—((R)-1-((R)-2,3-Dimethoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((R)-pyrrolidine-3-carbonyl)piperidin-3-yl)-4,5-dihydro-3H-1-thia-3,5,8-triazaacenaphthylene-2-carboxamide;

N-(4-(Hydroxymethyl)tetrahydro-2H-pyran-4-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-ethoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(2-fluorophenyl)-4-oxo-4,5-dihydro-3H-1-thia-3,5,8-triazaacenaphthylene-2-carboxamide;

(R,Z)—N-(1-(4-Amino-2-cyano-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(3-(1-Aminocyclopropyl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide;

N-((3R,5S)-5-Hydroxypiperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((R)-tetrahydrofuran-3-carbonyl)piperidin-3-yl)-4,5-dihydro-3H-1-thia-3,5,8-triazaacenaphthylene-2-carboxamide;

(R,E)-N-(1-(3-Cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

N-((3S,4R)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(2-Cyclopropylphenoxy)-2-methylphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

N-(1,2-Dimethylpiperidin-4-yl)-5-(2-methyl-4-phenoxyphenyl)-4-oxo-4,5-dihydro-3H-1-thia-3,5,8-triazaacenaphthylene-2-carboxamide;

(R)—N-(1-Methacryloylpiperidin-3-yl)-5-(2-methyl-4-phenoxyphenyl)-4-oxo-4,5-dihydro-3H-1-thia-3,5,8-triazaacenaphthylene-2-carboxamide;

N-(1-(Cyclopropanecarbonyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(1-methylazepan-3-yl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((S)-tetrahydrofuran-3-carbonyl)piperidin-3-yl)-4,5-dihydro-3H-1-thia-3,5,8-triazaacenaphthylene-2-carboxamide;

N-((3S,4R)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(5-chlorobenzo[d][1,3]dioxol-4-yl)-4-oxo-4,5-dihydro-3H-1-thia-3,5,8-triazaacenaphthylene-2-carboxamide;

(R)-5-(2-Methyl-4-(m-tolyloxy)phenyl)-N-(1-methylpiperidin-3-yl)-4-oxo-4,5-dihydro-3H-1-thia-3,5,8-triazaacenaphthylene-2-carboxamide;

N-((3S,4R)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-(ethylamino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Cyclopropylpiperidin-3-yl)-5-(2-methyl-4-phenoxyphenyl)-4-oxo-4,5-dihydro-3H-1-thia-3,5,8-triazaacenaphthylene-2-carboxamide;

(R)-5-(4-(3-Fluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(2-Fluoro-4-phenoxyphenyl)-N-(1-(3-methoxypropanoyl)piperidin-3-yl)-4-oxo-4,5-dihydro-3H-1-thia-3,5,8-triazaacenaphthylene-2-carboxamide;

(R)—N-(1-Acryloylpiperidin-3-yl)-4-oxo-5-(o-tolyl)-4,5-dihydro-3H-1-thia-3,5,8-triazaacenaphthylene-2-carboxamide;

5-(2-Methyl-4-phenoxyphenyl)-4-oxo-N-(2-(2-oxoimidazolidin-1-yl)ethyl)-4,5-dihydro-3H-1-thia-3,5,8-triazaacenaphthylene-2-carboxamide;

N-((3S,4S)-4-Fluoropyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-(tetrahydro-2H-pyran-4-carbonyl)piperidin-3-yl)-4,5-dihydro-3H-1-thia-3,5,8-triazaacenaphthylene-2-carboxamide;

(R)-5-(4-(2-Hydroxyphenoxy)-2-methylphenyl)-N-(1-methylpiperidin-3-yl)-4-oxo-4,5-dihydro-3H-1-thia-3,5,8-triazaacenaphthylene-2-carboxamide;

(R,E)-N-(1-(3-Ethoxyacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Fluoro-6-methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(4-(2-Isopropylphenoxy)-2-methylphenyl)-N-(1-methylpiperidin-3-yl)-4-oxo-4,5-dihydro-3H-1-thia-3,5,8-triazaacenaphthylene-2-carboxamide;

N-((3R,5R)-5-Methoxypiperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-(3-methylbut-2-enoyl)piperidin-3-yl)-4-oxo-4,5-dihydro-3H-1-thia-3,5,8-triazaacenaphthylene-2-carboxamide;

(R)-5-(4-(3-(Methoxymethyl)phenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-(2-(trifluoromethoxy)phenoxy)phenyl)-N-(1-methylpiperidin-3-yl)-4-oxo-4,5-dihydro-3H-1-thia-3,5,8-triazaacenaphthylene-2-carboxamide;

(R,Z)—N-(1-(3-Cyclopropyl-2-fluoroacryloyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)azetidin-3-yl)-5-(2-methyl-4-phenoxyphenyl)-4-oxo-4,5-dihydro-3H-1-thia-3,5,8-triazaacenaphthylene-2-carboxamide;

N-(1-Cyclopropylazetidin-3-yl)-5-(2-methyl-4-phenoxyphenyl)-4-oxo-4,5-dihydro-3H-1-thia-3,5,8-triazaacenaphthylene-2-carboxamide;

(R,EZ)—N-(1-(2-Cyano-3-methoxyacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-5-(*S)-(5-Chlorobenzo[d][1,3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R,EZ)—N-(1-(2-Cyano-4-((2-methoxyethyl)amino)-4-methylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2,6-Difluoro-4-phenoxyphenyl)-4-oxo-N-(piperidin-3-yl)-4,5-dihydro-3H-1-thia-3,5,8-triazaacenaphthylene-2-carboxamide;

N-((3S,4S)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide;

N1-((E)-4-(3-(5-(2-methyl-4-phenoxyphenyl)-4-oxo-4,5-dihydro-3H-1-thia-3,5,8-triazaacenaphthylene-2-carboxamido)piperidin-1-yl)-4-oxobut-2-en-1-yl)-N5-(15-oxo-19-((3aS,4R,6aR)-2-oxohexahydro-1H-thieno[3,4-d]imidazol-4-yl)-4,7,10-trioxa-14-azanonadecyl)glutaramide;

(R,E)-N-(1-(2-Cyano-4-methyl-4-(methylamino)pent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-5-(5-Chlorobenzo[d][1,3]dioxol-4-yl)-N-(1-(2-cyano-3-cyclopropylacryloyl)piperidin-3-yl)-4-oxo-4,5-dihydro-3H-1-thia-3,5,8-triazaacenaphthylene-2-carboxamide;

5-(2-Methyl-4-phenoxyphenyl)-N-(1-(3-(methylsulfonyl)propanoyl)azetidin-3-yl)-4-oxo-4,5-dihydro-3H-1-thia-3,5,8-triazaacenaphthylene-2-carboxamide;

N-((3S,4R)-4-Hydroxypyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-(2-(trifluoromethyl)phenoxy)phenyl)-N-(1-methylpiperidin-3-yl)-4-oxo-4,5-dihydro-3H-1-thia-3,5,8-triazaacenaphthylene-2-carboxamide;

N-((3S,4S)-4-Hydroxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

N-((3S,4S)-4-Methoxy-1-methylpyrrolidin-3-yl)-5-(2-methyl-4-phenoxyphenyl)-4-oxo-4,5-dihydro-3H-1-thia-3,5,8-triazaacenaphthylene-2-carboxamide;

N-((3S,4S)-4-Methoxypyrrolidin-3-yl)-5-(2-methyl-4-phenoxyphenyl)-4-oxo-4,5-dihydro-3H-1-thia-3,5,8-triazaacenaphthylene-2-carboxamide;

N-(1-(3-Methoxypropanoyl)azetidin-3-yl)-5-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-N-(1-(4-methylpent-2-enoyl)piperidin-3-yl)-4-oxo-4,5-dihydro-3H-1-thia-3,5,8-triazaacenaphthylene-2-carboxamide;

5-(2-Methyl-4-phenoxyphenyl)-N-(1-methylazetidin-3-yl)-4-oxo-4,5-dihydro-3H-1-thia-3,5,8-triazaacenaphthylene-2-carboxamide;

(S)-5-(*S)-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)-5-(4-(Cyclohexyloxy)-2-methylphenyl)-N-(1-methylpiperidin-3-yl)-4-oxo-4,5-dihydro-3H-1-thia-3,5,8-triazaacenaphthylene-2-carboxamide;

N-(1-Ethylazetidin-3-yl)-5-(2-methyl-4-phenoxyphenyl)-4-oxo-4,5-dihydro-3H-1-thia-3,5,8-triazaacenaphthylene-2-carboxamide;

N-(Azetidin-3-yl)-5-(2-methyl-4-phenoxyphenyl)-4-oxo-4,5-dihydro-3H-1-thia-3,5,8-triazaacenaphthylene-2-carboxamide;

(R)-5-(*R)-(2-Methyl-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;

(R)—N-(1-Acryloylpiperidin-3-yl)-5-(4-methoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-fluorophenyl)-4-oxo-4,5-dihydro-3H-1-thia-3,5,8-triazaacenaphthylene-2-carboxamide;

(R)—N-(1-Acryloylpiperidin-3-yl)-5-(4-chlorophenyl)-4-oxo-4,5-dihydro-3H-1-thia-3,5,8triazaacenaphthylene-2-carboxamide;

(R)—N-(1-Acryloylpiperidin-3-yl)-4-oxo-5-phenyl-4,5-dihydro-3H-1-thia-3,5,8-triazaacenaphthylene-2-carboxamide;

5-(2-Methyl-4-phenoxyphenyl)-N-(2-methylpiperidin-4-yl)-4-oxo-4,5-dihydro-3H-1-thia-3,5,8-triazaacenaphthylene-2-carboxamide;

N-((3R,5R)-5-Methoxy-1-methylpiperidin-3-yl)-4-oxo-5-(4-phenoxyphenyl)-4,5-dihydro-3H-1-thia-3,5,8-triazaacenaphthylene-2-carboxamide;

(R)—N-(1-(2-chloro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R,Z)—N-(1-(2-Fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

N-(1-Methyl-5-oxopyrrolidin-3-yl)-4-oxo-5-(4-phenoxyphenyl)-4,5-dihydro-3H-1-thia-3,5,8-triazaacenaphthylene-2-carboxamide;

(R)—N-(1-(2-Fluoro-3-methylbut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-5-(2-methyl-4-(pentafluorothio)phenyl)-4-oxo-4,5-dihydro-3H-1-thia-3,5,8-triazaacenaphthylene-2-carboxamide;

(S)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide;

N-((3R,5S)-5-Hydroxy-1-methylpiperidin-3-yl)-5-(2-methyl-4-phenoxyphenyl)-4-oxo-4,5-dihydro-3H-1-thia-3,5,8-triazaacenaphthylene-2-carboxamide;

(S)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

N-((3R,5S)-5-Methoxypiperidin-3-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide;

(R)—N-(1-Acryloylpyrrolidin-3-yl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-4-oxo-5-(p-tolyl)-4,5-dihydro-3H-1-thia-3,5,8-triazaacenaphthylene-2-carboxamide;

(R)—N-(5,5-Difluoro-1-methylpiperidin-3-yl)-5-(2-methyl-4-phenoxyphenyl)-4-oxo-4,5-dihydro-3H-1-thia-3,5,8-triazaacenaphthylene-2-carboxamide;

N-(1-Isopropylazetidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(4,4-Dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(2-morpholinoethyl)-4-oxo-4,5-dihydro-3H-1-thia-3,5,8-triazaacenaphthylene-2-carboxamide;

(R)-5-(2-Methyl-4-phenoxyphenyl)-4-oxo-N-(pyrrolidin-2-ylmethyl)-4,5-dihydro-3H-1-thia-3,5,8-triazaacenaphthylene-2-carboxamide;

(R,Z)—N-(1-(2-Chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(4-phenoxy-2-(trifluoromethyl)phenyl)-4,5-dihydro-3H-1-thia-3,5,8-triazaacenaphthylene-2-carboxamide;

(R)—N-(1-Acryloylpiperidin-3-yl)-4-oxo-5-(m-tolyl)-4,5-dihydro-3H-1-thia-3,5,8-triazaacenaphthylene-2-carboxamide;

(R)-5-(4-Chloro-3-(trifluoromethyl)phenyl)-4-oxo-N-(piperidin-3-yl)-4,5-dihydro-3H-1-thia-3,5,8-triazaacenaphthylene-2-carboxamide;

(R)-5-(2,3-Dimethyl-4-phenoxyphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-N-((1-methylpyrrolidin-3-yl)methyl)-4-oxo-4,5-dihydro-3H-1-thia-3,5,8-triazaacenaphthylene-2-carboxamide;

(R)-5-(4-(2-Isopropoxyphenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(4-Cyclobutoxy-2-methylphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-N-((1-methylpyrrolidin-2-yl)methyl)-4-oxo-4,5-dihydro-3H-1-thia-3,5,8-triazaacenaphthylene-2-carboxamide;

(R)-5-(4-(3,5-Difluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-(2-(Dimethylamino)acetyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(3-(trifluoromethyl)phenyl)-4,5-dihydro-3H-1-thia-3,5,8-triazaacenaphthylene-2-carboxamide;

(S)—N-(1-Acryloylpiperidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(2-Methyl-4-(p-tolyloxy)phenyl)-N-(1-methylpiperidin-3-yl)-4-oxo-4,5-dihydro-3H-1-thia-3,5,8-triazaacenaphthylene-2-carboxamide;

(S)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide;

(R,E)-5-(*R)-(2-Methyl-4-phenoxyphenyl)-N-(1-(4-(methylamino)but-2-enoyl)piperidin-3-yl)-4-oxo-4,5-dihydro-3H-1-thia-3,5,8-triazaacenaphthylene-2-carboxamide;

(R)-5-(2-Methyl-4-(pyridin-3-yloxy)phenyl)-N-(1-methylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(3-chlorophenyl)-4-oxo-4,5-dihydro-3H-1-thia-3,5,8-triazaacenaphthylene-2-carboxamide;

(R)-5-(4-(4-Fluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(2-Methyl-4-phenoxyphenyl)-N-(2-(3-methylmorpholino)ethyl)-4-oxo-4,5-dihydro-3H-1-thia-3,5,8-triazaacenaphthylene-2-carboxamide;

(R)-5-(4-(Cyclopentyloxy)-2-methylphenyl)-N-(1-methylpiperidin-3-yl)-4-oxo-4,5-dihydro-3H-1-thia-3,5,8-triazaacenaphthylene-2-carboxamide;

5-(2-Methyl-4-phenoxyphenyl)-N-(2-(1-methylpyrrolidin-2-yl)ethyl)-4-oxo-4,5-dihydro-3H-1-thia-3,5,8-triazaacenaphthylene-2-carboxamide;

(R)—N-(1-Acryloylpyrrolidin-3-yl)-5-(4-methoxy-2-methylphenyl)-4-oxo-4,5-dihydro-3H-1-thia-3,5,8-triazaacenaphthylene-2-carboxamide;

(R)-5-(*R)-(2-Methyl-4-phenoxyphenyl)-4-oxo-N-(piperidin-3-yl)-4,5-dihydro-3H-1-thia-3,5,8-triazaacenaphthylene-2-carboxamide;

(R)—N-(1-Acryloylpyrrolidin-3-yl)-5-(2-fluorophenyl)-4-oxo-4,5-dihydro-3H-1-thia-3,5,8-triazaacenaphthylene-2-carboxamide;

(R)-5-(4-(2,4-Difluorophenoxy)-2-methylphenyl)-N-(1-methylpiperidin-3-yl)-4-oxo-4,5-dihydro-3H-1-thia-3,5,8-triazaacenaphthylene-2-carboxamide;

(R)-5-(5-Fluoro-2-methyl-4-phenoxyphenyl)-N-(1-methylpiperidin-3-yl)-4-oxo-4,5-dihydro-3H-1-thia-3,5,8-triazaacenaphthylene-2-carboxamide;

(R)—N-(1-Acryloylpyrrolidin-3-yl)-5-(2,4-dimethylphenyl)-4-oxo-4,5-dihydro-3H-1-thia-3,5,8-triazaacenaphthylene-2-carboxamide;

(R)-5-(5-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(R)-5-(2-Methyl-4-(pyridin-2-yloxy)phenyl)-N-(1-methylpiperidin-3-yl)-4-oxo-4,5-dihydro-3H-1-thia-3,5,8-triazaacenaphthylene-2-carboxamide;

(R)-5-(*R)-(2-Methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(S)-5-(5-Fluoro-2-methyl-4-phenoxyphenyl)-4-oxo-N-(tetrahydro-2H-pyran-3-yl)-4,5-dihydro-3H-1-thia-3,5,8-triazaacenaphthylene-2-carboxamide;

(S)—N-(1-Benzyl-2-oxoazepan-3-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(piperidin-2-ylmethyl)-4,5-dihydro-3H-1-thia-3,5,8-triazaacenaphthylene-2-carboxamide;

(R)—N-(1-Acryloylpyrrolidin-3-yl)-4-oxo-5-(6-phenoxypyridazin-3-yl)-4,5-dihydro-3H-1-thia-3,5,8-triazaacenaphthylene-2-carboxamide;

N-((3R,5S)-5-Methoxy-1-methylpiperidin-3-yl)-5-(2-methyl-4-phenoxyphenyl)-4-oxo-4,5-dihydro-3H-1-thia-3,5,8-triazaacenaphthylene-2-carboxamide;

(R,EZ)—N-(1-(3-Cyclopropyl-2-(trifluoromethyl)acryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-4-oxo-5-(o-tolyl)-4,5-dihydro-3H-1-thia-3,5,8-triazaacenaphthylene-2-carboxamide;

5-(2-Methyl-4-phenoxyphenyl)-N-(2-morpholino-2-oxoethyl)-4-oxo-4,5-dihydro-3H-1-thia-3,5,8-triazaacenaphthylene-2-carboxamide;

(R)—N-(1-Methylpiperidin-3-yl)-4-oxo-4,5-dihydro-3H-1-thia-3,5,8-triazaacenaphthylene-2-carboxamide;

(R)-5-(2,6-Dimethyl-4-phenoxyphenyl)-N-(1-methylpiperidin-3-yl)-4-oxo-4,5-dihydro-3H-1-thia-3,5,8-triazaacenaphthylene-2-carboxamide;

(R)—N-(1-(3-Hydroxypropanoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R)-5-(*S)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide;
(R)—N-(1-Ethylpiperidin-3-yl)-5-(4-(2-isopropylphenoxy)-2-methylphenyl)-4-oxo-4,5-dihydro-3H-1-thia-3,5,8-triazaacenaphthylene-2-carboxamide;
(R)—N-(1-Acryloylpiperidin-3-yl)-5-(*R)-(5-chlorobenzo[d][1,3]dioxol-4-yl)-4-oxo-4,5-dihydro-3H-1-thia-3,5,8-triazaacenaphthylene-2-carboxamide;
(R)-5-(4-Cyclopropoxy-2-methylphenyl)-N-(1-methylpiperidin-3-yl)-4-oxo-4,5-dihydro-3H-1-thia-3,5,8-triazaacenaphthylene-2-carboxamide;
(S)-5-(*R)-(2-Methyl-4-phenoxyphenyl)-4-oxo-N-(tetrahydrofuran-3-yl)-4,5-dihydro-3H-1-thia-3,5,8-triazaacenaphthylene-2-carboxamide;
(R)—N-(1-Acryloylpyrrolidin-3-yl)-4-oxo-5-(4-phenoxy-2-(trifluoromethyl)phenyl)-4,5-dihydro-3H-1-thia-3,5,8-triazaacenaphthylene-2-carboxamide;
(R)-5-(*R)-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide;
(R)-5-(4-(2-Carbamoylphenoxy)-2-methylphenyl)-N-(1-methylpiperidin-3-yl)-4-oxo-4,5-dihydro-3H-1-thia-3,5,8-triazaacenaphthylene-2-carboxamide;
5-(2-Methyl-4-phenoxyphenyl)-2-(piperazin-1-yl)-3H-1-thia-3,5,8-triazaacenaphthylen-4(5H)-one;
(R)-6-Methyl-4-oxo-5-(4-phenoxyphenyl)-N-(piperidin-3-yl)-4,5-dihydro-3H-1-thia-3,5,8-triazaacenaphthylene-2-carboxamide;
(R)—N-(1-Cyanopiperidin-3-yl)-5-(*R)-(2-methyl-4-phenoxyphenyl)-4-oxo-4,5-dihydro-3H-1-thia-3,5,8-triazaacenaphthylene-2-carboxamide;
(R)-5-(3,5-Dichlorophenyl)-4-oxo-N-(piperidin-3-yl)-4,5-dihydro-3H-1-thia-3,5,8-triazaacenaphthylene-2-carboxamide;
(R)—N-Methyl-5-(2-methyl-4-phenoxyphenyl)-4-oxo-N-(pyrrolidin-3-yl)-4,5-dihydro-3H-1-thia-3,5,8-triazaacenaphthylene-2-carboxamide;
(R)-5-(4-Isopropoxy-2-methylphenyl)-N-(1-methylpiperidin-3-yl)-4-oxo-4,5-dihydro-3H-1-thia-3,5,8-triazaacenaphthylene-2-carboxamide;
(R)-5-(4-Ethoxy-2-methylphenyl)-N-(1-methylpiperidin-3-yl)-4-oxo-4,5-dihydro-3H-1-thia-3,5,8-triazaacenaphthylene-2-carboxamide;
(R)—N-(1-Acryloylpiperidin-3-yl)-5-(4-(tert-butyl)phenyl)-4-oxo-4,5-dihydro-3H-1-thia-3,5,8-triazaacenaphthylene-2-carboxamide;
(R)-5-(*S)-(2-Methyl-4-((tetrahydro-2H-pyran-4-yl)oxy)phenyl)-N-(1-methylpiperidin-3-yl)-4I-oxo-4,5-dihydro-3H-1-thia-3,5,8-triazaacenaphthylene-2-carboxamide;
(R)-5-(3-Chlorophenyl)-4-oxo-N-(piperidin-3-yl)-4,5-dihydro-3H-1-thia-3,5,8-triazaacenaphthylene-2-carboxamide;
(R)—N-(1-Acryloylpyrrolidin-3-yl)-4-oxo-5-phenyl-4,5-dihydro-3H-1-thia-3,5,8-triazaacenaphthylene-2-carboxamide;
(R)—N-Methyl-5-(2-methyl-4-phenoxyphenyl)-N-(1-methylpyrrolidin-3-yl)-4-oxo-4,5-dihydro-3H-1-thia-3,5,8-triazaacenaphthylene-2-carboxamide;
(S)-5-(*R)-(2-Methyl-4-phenoxyphenyl)-N-(1-methylpiperidin-3-yl)-4-oxo-4,5-dihydro-3H-1-thia-3,5,8-triazaacenaphthylene-2-carboxamide;
(R)-5-(4-Methoxy-2-methylphenyl)-N-(1-methylpiperidin-3-yl)-4-oxo-4,5-dihydro-3H-1-thia-3,5,8-triazaacenaphthylene-2-carboxamide;
(R)-4-Oxo-N-(piperidin-3-yl)-5-(4-(trifluoromethyl)phenyl)-4,5-dihydro-3H-1-thia-3,5,8-triazaacenaphthylene-2-carboxamide;
(R)-5-(4-Methoxyphenyl)-4-oxo-N-(piperidin-3-yl)-4,5-dihydro-3H-1-thia-3,5,8-triazaacenaphthylene-2-carboxamide;
(R)-5-(*R)-(2-Methyl-4-((tetrahydro-2H-pyran-4-yl)oxy)phenyl)-N-(1-methylpiperidin-3-yl)-4I-oxo-4,5-dihydro-3H-1-thia-3,5,8-triazaacenaphthylene-2-carboxamide;
(R)-5-([1,1'-Biphenyl]-4-yl)-4-oxo-N-(piperidin-3-yl)-4,5-dihydro-3H-1-thia-3,5,8-triazaacenaphthylene-2-carboxamide;
(R)-5-(*R)-(5-Chlorobenzo[d][1,3]dioxol-4-yl)-N-(1-methylpiperidin-3-yl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(trifluoromethyl)phenyl)-4,5-dihydro-3H-1-thia-3,5,8-triazaacenaphthylene-2-carboxamide;
(R)—N-(1-Acryloylpiperidin-3-yl)-5-isopropyl-4-oxo-4,5-dihydro-3H-1-thia-3,5,8-triazaacenaphthylene-2-carboxamide;
(R)—N-(1-Acryloylpiperidin-3-yl)-5-(2-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(3,4-dichlorophenyl)-4-oxo-4,5-dihydro-3H-1-thia-3,5,8-triazaacenaphthylene-2-carboxamide;
(R)—N-(1-Acryloylpiperidin-3-yl)-5-(4-chloro-3-(trifluoromethyl)phenyl)-4-oxo-4,5-dihydro-3H-1-thia-3,5,8-triazaacenaphthylene-2-carboxamide;
(R)—N-(1-(3-Methoxy-3-methylbutanoyl)piperidin-3-yl)-5-(2-methyl-4-phenoxyphenyl)-4-oxo-4,5-dihydro-3H-1-thia-3,5,8-triazaacenaphthylene-2-carboxamide;
(R,Z)—N-(1-(3-Acetamidoacryloyl)piperidin-3-yl)-5-(2-methyl-4-phenoxyphenyl)-4-oxo-4,5-dihydro-3H-1-thia-3,5,8-triazaacenaphthylene-2-carboxamide;
(R,E)-N-(1-(2-Cyano-3-cyclopropylacryloyl)piperidin-3-yl)-5 (*R)-2-methyl-4-phenoxyphenyl)-4-oxo-4,5-dihydro-3H-1-thia-3,5,8-triazaacenaphthylene-2-carboxamide;
(R)—N-(1-(2-Chloroacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;
(R,E)-N-(1-(4-Aminobut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;
(R,E)-N-(1-(4-(Dimethylamino)but-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;
(R)-5-(2-Methyl-4-phenoxyphenyl)-4-oxo-N-(1-(vinylsulfonyl)pyrrolidin-3-yl)-4,5-dihydro-3H-1-thia-3,5,8-triazaacenaphthylene-2-carboxamide;
(R)-5-(2-Methyl-4-phenoxyphenyl)-N-(1-trideuteriomethylpiperidin-3-yl)-4-oxo-4,5-dihydro-3H-1-thia-3,5,8-triazaacenaphthylene-2-carboxamide;
(R,E)-N-(1-(4-(Dimethylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide;
(R)-5-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide;
(R,E)-N-(1-(4-(Dimethylamino)but-2-enoyl)piperidin-3-yl)-4-oxo-5-(4-phenoxyphenyl)-4,5-dihydro-3H-1-thia-3,5,8-triazaacenaphthylene-2-carboxamide;

(R,E)-5-(2-Methyl-4-phenoxyphenyl)-N-(1-(4-(methylsulfonyl)but-2-enoyl)piperidin-3-yl)-4-oxo-4,5-dihydro-3H-1-thia-3,5,8-triazaacenaphthylene-2-carboxamide;

(R)—N-(1-Acryloylpiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;

(R)—N-(1-Acryloylpyrrolidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;

(R,E)-5-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;

(R)—N-(1-Cyanopiperidin-3-yl)-5-(2-methyl-4-(2,3,4,5,6-pentadeuteriophenoxy)phenyl)-4-oxo-4,5-dihydro-3H-1-thia-3,5,8-triazaacenaphthylene-2-carboxamide;

(R)-5-(2-Methyl-4-(2,3,4,5,6-pentadeuteriophenoxy)phenyl)-N-(1-(trideuteriomethyl)piperidin-3-yl)-4-oxo-4,5-dihydro-3H-1-thia-3,5,8-triazaacenaphthylene-2-carboxamide;

(R)-5-(2-Methyl-4-(2,3,4,5,6-pentadeuteriophenoxy)phenyl)-N-(1-methylpiperidin-3-yl)-4-oxo-4,5-dihydro-3H-1-thia-3,5,8-triazaacenaphthylene-2-carboxamide;

(R,E)-N-(1-(4-Aminobut-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide;

(R)—N-(1-(2-(Dimethylamino)acetyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyanobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

N—((R)-1-((S)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-(3-methyloxetan-3-yl)acryloyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,Z)—N-(1-(2-Fluoro-4-(methylamino)but-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-(2-(pyrrolidin-1-yl)acetyl)piperidin-3-yl)-4,5-dihydro-3H-1-thia-3,5,8-triazaacenaphthylene-2-carboxamide;

(R)-2-(((1-Acryloylpiperidin-3-yl)amino)methyl)-5-(2-methyl-4-phenoxyphenyl)-3H-1-thia-3,5,8-triazaacenaphthylen-4(5H)-one;

(R)-5-(2-Methyl-4-phenoxyphenyl)-N-(1-(2-(methylamino)acetyl)pyrrolidin-3-yl)-4-oxo-4,5-dihydro-3H-1-thia-3,5,8-triazaacenaphthylene-2-carboxamide;

(R)—N-(1-(2-Aminoacetyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-(2-(piperidin-1l-yl)acetyl)piperidin-3-yl)-4,5-dihydro-3H-1-thia-3,5,8-triazaacenaphthylene-2-carboxamide;

(R)-5-(2-Methyl-4-phenoxyphenyl)-N-(1-(2-morpholinoacetyl)piperidin-3-yl)-4-oxo-4,5-dihydro-3H-1-thia-3,5,8-triazaacenaphthylene-2-carboxamide;

(R)—N-(1-(2-Chloroacetyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Chloroacetyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(4-(thiophen-2-yl)phenyl)-4,5-dihydro-3H-1-thia-3,5,8-triazaacenaphthylene-2-carboxamide;

(R,E)-N-(1-(2-Cyano-4,4-dimethylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-isopropoxyphenyl)-4-oxo-4,5-dihydro-3H-1-thia-3,5,8-triazaacenaphthylene-2-carboxamide;

(R)—N-(1-Acryloylpiperidin-3-yl)-5-(4-isopropoxyphenyl)-4-oxo-4,5-dihydro-3H-1-thia-3,5,8-triazaacenaphthylene-2-carboxamide;

(R,E)-N-(1-(3-Cyclopropyl-2-methylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,EZ)—N-(1-(2-Chloro-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-N-(1-(4-morpholinobut-2-enoyl)piperidin-3-yl)-4-oxo-4,5-dihydro-3H-1-thia-3,5,8-triazaacenaphthylene-2-carboxamide;

(R)—N-(1-Acryloylpiperidin-3-yl)-5-(benzo[b]thiophen-5-yl)-4-oxo-4,5-dihydro-3H-1-thia-3,5,8-triazaacenaphthylene-2-carboxamide;

(R)-5-(4-Isopropoxyphenyl)-4-oxo-N-(piperidin-3-yl)-4,5-dihydro-3H-1-thia-3,5,8-triazaacenaphthylene-2-carboxamide;

(R)-5-(4-Isopropoxyphenyl)-4-oxo-N-(1-propionylpiperidin-3-yl)-4,5-dihydro-3H-1-thia-3,5,8-triazaacenaphthylene-2-carboxamide;

(R)-4-Oxo-N-(piperidin-3-yl)-5-(4-(thiophen-2-yl)phenyl)-4,5-dihydro-3H-1-thia-3,5,8-triazaacenaphthylene-2-carboxamide;

(R)—N-(1-Acryloylpiperidin-3-yl)-4-oxo-5-(4-phenoxybenzyl)-4,5-dihydro-3H-1-thia-3,5,8-triazaacenaphthylene-2-carboxamide;

(R)—N-(1-Methylpyrrolidin-3-yl)-4-oxo-5-(4-phenoxybenzyl)-4,5-dihydro-3H-1-thia-3,5,8-triazaacenaphthylene-2-carboxamide;

(R)-5-(Benzo[b]thiophen-5-yl)-4-oxo-N-(piperidin-3-yl)-4,5-dihydro-3H-1-thia-3,5,8-triazaacenaphthylene-2-carboxamide;

(R)-5-(2-Methyl-4-(trifluoromethoxy)phenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(2-methyl-4-(trifluoromethoxy)phenyl)-4-oxo-4,5-dihydro-3H-1-thia-3,5,8-triazaacenaphthylene-2-carboxamide;

(R)-4-Oxo-N-(piperidin-3-yl)-5-(4-(trifluoromethoxy)phenyl)-4,5-dihydro-3H-1-thia-3,5,8-triazaacenaphthylene-2-carboxamide;

(R)—N-(1-Acryloylpiperidin-3-yl)-4-oxo-5-(4-(trifluoromethoxy)phenyl)-4,5-dihydro-3H-1-thia-3,5,8-triazaacenaphthylene-2-carboxamide;

(R)—N-(1-Acryloylpiperidin-3-yl)-5-(*S)-(4-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(*R)-(4-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(naphthalen-2-yl)-4-oxo-4,5-dihydro-3H-1-thia-3,5,8-triazaacenaphthylene-2-carboxamide;

(R)—N-(1-Acryloylpiperidin-3-yl)-5-(1-benzyl-1H-pyrazol-3-yl)-4-oxo-4,5-dihydro-3H-1-thia-3,5,8-triazaacenaphthylene-2-carboxamide;

(R)-5-([1,1'-Biphenyl]-3-yl)-N-(1-acryloylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(4-benzylphenyl)-4-oxo-4,5-dihydro-3H-1-thia-3,5,8-triazaacenaphthylene-2-carboxamide;

(R)-5-([1,1'-Biphenyl]-4-yl)-N-(1-acryloylpiperidin-3-yl)-4-oxo-4,5-dihydro-3H-1-thia-3,5,8-triazaacenaphthylene-2-carboxamide;

(R)—N-(1-(2-(Dimethylamino)acetyl)piperidin-3-yl)-4-oxo-5-(4-phenoxyphenyl)-4,5-dihydro-3H-1-thia-3,5,8-triazaacenaphthylene-2-carboxamide;

(R)—N-(1-(2-(Dimethylamino)acetyl)pyrrolidin-3-yl)-4-oxo-5-(4-phenoxyphenyl)-4,5-dihydro-3H-1-thia-3,5,8-triazaacenaphthylene-2-carboxamide;

(R)-5-([1,1'-Biphenyl]-3-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(benzo[b]thiophen-2-yl)-4-oxo-4,5-dihydro-3H-1-thia-3,5,8-triazaacenaphthylene-2-carboxamide;

(R)-5-(4-Benzylphenyl)-4-oxo-N-(piperidin-3-yl)-4,5-dihydro-3H-1-thia-3,5,8-triazaacenaphthylene-2-carboxamide;

5-(*S)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide;

5-(*R)-(2-Methyl-4-phenoxyphenyl)-N-((4*S)-2-methylpiperidin-4-yl)-4-oxo-4,5-dihydro-3H-1-thia-3,5,8-triazaacenaphthylene-2-carboxamide;

5-(*S)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide;

5-(*R)-(2-Methyl-4-phenoxyphenyl)-N-((4*R)-2-methylpiperidin-4-yl)-4-oxo-4,5-dihydro-3H-1-thia-3,5,8-triazaacenaphthylene-2-carboxamide;

N-(4-(Hydroxymethyl)tetrahydro-2H-pyran-4-yl)-5-(*S)-(2-methyl-4-phenoxyphenyl)-4-oxo-4,5-dihydro-3H-1-thia-3,5,8-triazaacenaphthylene-2-carboxamide;

N-(4-(Hydroxymethyl)tetrahydro-2H-pyran-4-yl)-5-(*R)-(2-methyl-4-phenoxyphenyl)-4-oxo-4,5-dihydro-3H-1-thia-3,5,8-triazaacenaphthylene-2-carboxamide;

(R)—N-(1-(2-Chloro-3-methylbut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-(2-Chloro-3-methylbut-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,E)-N-(1-(4-(Dimethylamino)but-2-enoyl)pyrrolidin-3-yl)-4-oxo-5-(4-phenoxyphenyl)-4,5-dihydro-3H-1-thia-3,5,8-triazaacenaphthylene-2-carboxamide;

(R)—N-(1-Acryloylpyrrolidin-3-yl)-N-methyl-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-N-methyl-5-(*R)-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-5-(4-isopropyl-2-methylphenyl)-4-oxo-4,5-dihydro-3H-1-thia-3,5,8-triazaacenaphthylene-2-carboxamide;

(R)—N-(1-Acryloylpyrrolidin-3-yl)-5-(4-isopropyl-2-methylphenyl)-4-oxo-4,5-dihydro-3H-1-thia-3,5,8-triazaacenaphthylene-2-carboxamide;

(R)-5-(4-Isopropyl-2-methylphenyl)-4-oxo-N-(piperidin-3-yl)-4,5-dihydro-3H-1-thia-3,5,8-triazaacenaphthylene-2-carboxamide;

(R)-5-(4-Isopropyl-2-methylphenyl)-N-(1-methylpiperidin-3-yl)-4-oxo-4,5-dihydro-3H-1-thia-3,5,8-triazaacenaphthylene-2-carboxamide;

(R,*Z)—N-(1-(2-Cyano-4-methoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*Z)—N-(1-(2-Cyano-4-methoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-methoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-methoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

N-((1-Acryloylpyrrolidin-3-yl)methyl)-4-oxo-5-(4-phenoxyphenyl)-4,5-dihydro-3H-1-thia-3,5,8-triazaacenaphthylene-2-carboxamide;

4-Oxo-5-(4-phenoxyphenyl)-N-(pyrrolidin-3-ylmethyl)-4,5-dihydro-3H-1-thia-3,5,8-triazaacenaphthylene-2-carboxamide;

(R)—N-(1-Acryloylpiperidin-3-yl)-5-(4-cyclobutoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-cyclobutoxyphenyl)-4-oxo-4,5-dihydro-3H-1-thia-3,5,8-triazaacenaphthylene-2-carboxamide;

4-Oxo-N-(2-oxopiperidin-3-yl)-5-(4-phenoxyphenyl)-4,5-dihydro-3H-1-thia-3,5,8-triazaacenaphthylene-2-carboxamide;

(R)-5-(3-Chloro-4-methylphenyl)-4-oxo-N-(piperidin-3-yl)-4,5-dihydro-3H-1-thia-3,5,8-triazaacenaphthylene-2-carboxamide;

(R)-5-(4-Methyl-3-(trifluoromethyl)phenyl)-4-oxo-N-(piperidin-3-yl)-4,5-dihydro-3H-1-thia-3,5,8-triazaacenaphthylene-2-carboxamide;

4-Oxo-5-(4-phenoxyphenyl)-N-((tetrahydrofuran-2-yl)methyl)-4,5-dihydro-3H-1-thia-3,5,8-triazaacenaphthylene-2-carboxamide;

N-((3S,4S)-1-Acryloyl-4-hydroxypyrrolidin-3-yl)-4-oxo-5-(4-phenoxyphenyl)-4,5-dihydro-3H-1-thia-3,5,8-triazaacenaphthylene-2-carboxamide;

N-((3S,4S)-4-Hydroxypyrrolidin-3-yl)-4-oxo-5-(4-phenoxyphenyl)-4,5-dihydro-3H-1-thia-3,5,8-triazaacenaphthylene-2-carboxamide;

(R)-5-(3-Benzylphenyl)-4-oxo-N-(piperidin-3-yl)-4,5-dihydro-3H-1-thia-3,5,8-triazaacenaphthylene-2-carboxamide;

(R)-4-Oxo-5-(3-phenoxyphenyl)-N-(piperidin-3-yl)-4,5-dihydro-3H-1-thia-3,5,8-triazaacenaphthylene-2-carboxamide;

N-((3R,5S)-5-Methoxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-5-Methoxypiperidin-3-yl)-5-(*R)-(2-methyl-4-phenoxyphenyl)-4-oxo-4,5-dihydro-3H-1-thia-3,5,8-triazaacenaphthylene-2-carboxamide;

(*S)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

(*S)-5-(*R)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

(*R)-5-(*S)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

(*R)-5-(*R)-(2-Methyl-4-phenoxyphenyl)-4-oxo-N-(5-oxopyrrolidin-3-yl)-4,5-dihydro-3H-1-thia-3,5,8-triazaacenaphthylene-2-carboxamide;

(R,*E)-N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*E)-N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,*Z)—N-(1-(But-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,*Z)—N-(1-(But-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*Z)—N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,*Z)—N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

(R,*E)-N-(1-(2-Cyano-4-ethoxy-4-methylpent-2-enoyl)piperidin-3-yl)-5-(*R)-(2-methyl-4-phenoxyphenyl)-4-oxo-4,5-dihydro-3H-1-thia-3,5,8-triazaacenaphthylene-2-carboxamide;

N-((3R,5R)-1-Acryloyl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-methoxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5R)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3R,5S)-1-Acryloyl-5-fluoropiperidin-3-yl)-5-(*S)-(2-methyl-4-phenoxyphenyl)-4-oxo-4,5-dihydro-3H-1-thia-3,5,8-triazaacenaphthylene-2-carboxamide;

N-(4-Cyano-1,4-oxazepan-6-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-fluoropyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4-ethoxy-4-methylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(4-(Dimethylamino)but-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4R)-1-Acryloyl-4-hydroxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-methoxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylamino)but-2-enoyl)pyrrolidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-N-(1-methylpyrrolidin-3-yl)-4-oxo-4,5-dihydro-3H-1-thia-3,5,8-triazaacenaphthylene-2-carboxamide;

(R)-5-(*S)-(2-Methyl-4-phenoxyphenyl)-N-(1-(3-(methylsulfonyl)propanoyl)pyrrolidin-3-yl)-4-oxo-4,5-dihydro-3H-1-thia-3,5,8-triazaacenaphthylene-2-carboxamide;

(R)—N-(1-(2-Methoxyacetyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

N-(1-Acryloylazetidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3-methyl-5-phenoxypyridin-2-yl)-4-oxo-4,5-dihydro-3H-1-thia-3,5,8-triazaacenaphthylene-2-carboxamide;

(R)—N-(1-Acryloylpiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

N-((3R,5R)-1-Acryloyl-5-fluoropiperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3'-fluoro-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide;

(R,E)-N-(1-(4-(Dimethylamino)but-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-N-(1-(4-Hydroxybut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2'-methyl-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-(trifluoromethoxy)phenyl)-4-oxo-4,5-dihydro-3H-1-thia-3,5,8-triazaacenaphthylene-2-carboxamide;

(R)—N-(1-Acryloylpiperidin-3-yl)-4-oxo-5-(6-phenoxypyridin-3-yl)-4,5-dihydro-3H-1-thia-3,5,8-triazaacenaphthylene-2-carboxamide;

(R)—N-(1-Acryloylpiperidin-3-yl)-5-(3'-chloro-[1,1'-biphenyl]-3-yl)-4-oxo-4,5-dihydro-3H-1-thia-3,5,8-triazaacenaphthylene-2-carboxamide;

N-((3S,4R)-1-Acryloyl-4-methoxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2'-chloro-[1,1'-biphenyl]-3-yl)-4-oxo-4,5-dihydro-3H-1-thia-3,5,8-triazaacenaphthylene-2-carboxamide;

(R,E)-N-(1-(4-Aminobut-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(2-phenylpyridin-4-yl)-4,5-dihydro-3H-1-thia-3,5,8-triazaacenaphthylene-2-carboxamide;

(R)—N-(1-Acryloylpiperidin-3-yl)-4-oxo-5-(5-phenoxypyridin-2-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2',4'-difluoro-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(3-benzylphenyl)-4-oxo-4,5-dihydro-3H-1-thia-3,5,8-triazaacenaphthylene-2-carboxamide;

(R)—N-(1-Acryloylpiperidin-3-yl)-5-(3'-methyl-[1,1'-biphenyl]-3-yl)-4-oxo-4,5-dihydro-3H-1-thia-3,5,8-triazaacenaphthylene-2-carboxamide;

(S)—N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(3-cyclohexylphenyl)-4-oxo-4,5-dihydro-3H-1-thia-3,5,8-triazaacenaphthylene-2-carboxamide;

(R,E)-N-(1-(4-Aminobut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(4'-methyl-[1,1'-biphenyl]-3-yl)-4-oxo-4,5-dihydro-3H-1-thia-3,5,8-triazaacenaphthylene-2-carboxamide;

(R,E)-N-(1-(4-Hydroxybut-2-enoyl)pyrrolidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-hydroxypyrrolidin-3-yl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N—((R)-1-((S)-2-(methylamino)propanoyl)piperidin-3-yl)4l-oxo-4,5-dihydro-3H-1-thia-3,5,8-triazaacenaphthylene-2-carboxamide;

(R)—N-(1-Acryloylpiperidin-3-yl)-5-(2,2-difluorobenzo[d][1,3]dioxol-5-yl)-4-oxo-4,5-dihydro-3H-1-thia-3,5,8-triazaacenaphthylene-2-carboxamide;

(R)—N-(1-Acryloylpiperidin-3-yl)-4-oxo-5-(4-phenylpyridin-2-yl)-4,5-dihydro-3H-1-thia-3,5,8-triazaacenaphthylene-2-carboxamide;

(R)—N-(1-Acryloylpiperidin-3-yl)-4-oxo-5-(3-phenoxyphenyl)-4,5-dihydro-3H-1-thia-3,5,8-triazaacenaphthylene-2-carboxamide;

(R)—N-(1-Acryloylpiperidin-3-yl)-4-oxo-5-(5-phenoxypyrazin-2-yl)-4,5-dihydro-3H-1-thia-3,5,8-triazaacenaphthylene-2-carboxamide;

(R)—N-(1-Acryloylpiperidin-3-yl)-5-(3-isopropylphenyl)-4-oxo-4,5-dihydro-3H-1-thia-3,5,8-triazaacenaphthylene-2-carboxamide;

(R)-5-(*S)-(2-Methyl-4-phenoxyphenyl)-4-oxo-N-(1-(vinylsulfonyl)piperidin-3-yl)-4,5-dihydro-3H-1-thia-3,5,8-triazaacenaphthylene-2-carboxamide;

(R)-5-([1,1'-Biphenyl]-3-yl)-N-(1-acryloylpyrrolidin-3-yl)-4-oxo-4,5-dihydro-3H-1-thia-3,5,8-triazaacenaphthylene-2-carboxamide;

(R,E)-5-(*S)-(2-Methyl-4-phenoxyphenyl)-N-(1-(4-(methylsulfonamido)but-2-enoyl)piperidin-3-yl)-4-oxo-4,5-dihydro-3H-1-thia-3,5,8-triazaacenaphthylene-2-carboxamide;

(R)—N-(1-Acryloylpiperidin-3-yl)-4-oxo-5-(3-propylphenyl)-4,5-dihydro-3H-1-thia-3,5,8-triazaacenaphthylene-2-carboxamide;

(R)—N-(1-Acryloylpiperidin-3-yl)-5-(3-cyclobutylphenyl)-4-oxo-4,5-dihydro-3H-1-thia-3,5,8-triazaacenaphthylene-2-carboxamide;

(R)-5-(*S)-(2-Methyl-4-phenoxyphenyl)-N-(1-trideuteriomethylpiperidin-3-yl)-4-oxo-4,5-dihydro-3H-1-thia-3,5,8-triazaacenaphthylene-2-carboxamide;

(R)—N-(1-Acryloylpiperidin-3-yl)-5-(3-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(5-phenylpyridin-3-yl)-4,5-dihydro-3H-1-thia-3,5,8-triazaacenaphthylene-2-carboxamide;

(R)—N-(1-Acryloylpiperidin-3-yl)-4-oxo-5-(3-(pyridin-3-yl)phenyl)-4,5-dihydro-3H-1-thia-3,5,8-triazaacenaphthylene-2-carboxamide;

(R)—N-(1-(Ethylsulfonyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(3-(pyridin-2-yl)phenyl)-4,5-dihydro-3H-1-thia-3,5,8-triazaacenaphthylene-2-carboxamide;

(R,E)-5-(3-Chloro-4-phenoxyphenyl)-N-(1-(4-(dimethylamino)but-2-enoyl)piperidin-3-yl)-4-oxo-4,5-dihydro-3H-1-thia-3,5,8-triazaacenaphthylene-2-carboxamide;

(R)—N-(1-Isopropylpiperidin-3-yl)-5-(*S)-(2-methyl-4-phenoxyphenyl)-4-oxo-4,5-dihydro-3H-1-thia-3,5,8-triazaacenaphthylene-2-carboxamide;

N-((3S,4S)-1-Acryloyl-4-fluoropyrrolidin-3-yl)-4-oxo-5-(4-phenoxyphenyl)-4,5-dihydro-3H-1-thia-3,5,8-triazaacenaphthylene-2-carboxamide;

(S)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide;

(R)-1-Acryloyl-N-(5-(2-methyl-4-phenoxyphenyl)-4-oxo-4,5-dihydro-3H-1-thia-3,5,8-triazaacenaphthylen-2-yl)pyrrolidine-3-carboxamide;

(R)—N-(1-(2-(Methylamino)acetyl)piperidin-3-yl)-4-oxo-5-(4-phenoxyphenyl)-4,5-dihydro-3H-1-thia-3,5,8-triazaacenaphthylene-2-carboxamide;

N—((R)-1-((S)-3-Hydroxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;
N-((3S,4S)-1-Acryloyl-4-methoxypyrrolidin-3-yl)-4-oxo-5-(4-phenoxyphenyl)-4,5-dihydro-3H-1-thia-3,5,8-triazaacenaphthylene-2-carboxamide;
(R,Z)—N-(1-(4-Amino-2-fluorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;
(R,Z)—N-(1-(4-Amino-2-chlorobut-2-enoyl)piperidin-3-yl)-5-(2-methyl-4-phenoxyphenyl)-4-oxo-4,5-dihydro-3H-1-thia-3,5,8-triazaacenaphthylene-2-carboxamide;
(R)-5-([1,1'-Biphenyl]-3-yl)-N-(1-(2-(methylamino)acetyl)piperidin-3-yl)-4-oxo-4,5-dihydro-3H-1-thia-3,5,8-triazaacenaphthylene-2-carboxamide;
(R)-5-([1,1'-Biphenyl]-3-yl)-N-(1-methylpiperidin-3-yl)-4-oxo-4,5-dihydro-3H-1-thia-3,5,8-triazaacenaphthylene-2-carboxamide;
(R)-5-(3'-Methyl-[1,1'-biphenyl]-3-yl)-4-oxo-N-(piperidin-3-yl)-4,5-dihydro-3H-1-thia-3,5,8-triazaacenaphthylene-2-carboxamide;
(R)-5-(2'-Methyl-[1,1'-biphenyl]-3-yl)-4-oxo-N-(piperidin-3-yl)-4,5-dihydro-3H-1-thia-3,5,8-triazaacenaphthylene-2-carboxamide;
5-(*S)-(2-Methyl-4-phenoxyphenyl)-4-oxo-N—((R)-1-((E)-4-((4aR,7aS)-tetrahydro-2H-[1,4]dioxino[2,3-c]pyrrol-6(3H)-yl)but-2-enoyl)pyrrolidin-3-yl)-4,5-dihydro-3H-1-thia-3,5,8-triazaacenaphthylene-2-carboxamide;
(R)—N-(1-Acryloylpiperidin-3-yl)-4-oxo-5-(2-phenoxypyrimidin-5-yl)-4,5-dihydro-3H-1-thia-3,5,8-triazaacenaphthylene-2-carboxamide;
N-((3R,5R)-1-Acryloyl-5-hydroxypiperidin-3-yl)-5-(4-isopropoxy-2-methylphenyl)-4-oxo-4,5-dihydro-3H-1-thia-3,5,8-triazaacenaphthylene-2-carboxamide;
(R)—N-(1-Acryloylpyrrolidin-3-yl)-5-(3-chloro-4-phenoxyphenyl)-4-oxo-4,5-dihydro-3H-1-thia-3,5,8-triazaacenaphthylene-2-carboxamide;
(R,E)-N-(1-(2-Cyano-3-cyclopropylacryloyl)piperidin-3-yl)-4-oxo-5-(2-phenylpyridin-4-yl)-4,5-dihydro-3H-1-thia-3,5,8-triazaacenaphthylene-2-carboxamide;
(R)—N-(1-Acryloylpiperidin-3-yl)-5-(3-(cyclohexyloxy)phenyl)-4-oxo-4,5-dihydro-3H-1-thia-3,5,8-triazaacenaphthylene-2-carboxamide;
(R)—N-(1-Acryloylpiperidin-3-yl)-5-(3-(cyclopentyloxy)phenyl)-4-oxo-4,5-dihydro-3H-1-thia-3,5,8-triazaacenaphthylene-2-carboxamide;
(R,E)-N-(1-(4-(Dimethylamino)but-2-enoyl)pyrrolidin-3-yl)-5-(4-isopropoxy-2-methylphenyl)-4-oxo-4,5-dihydro-3H-1-thia-3,5,8-triazaacenaphthylene-2-carboxamide;
(R)—N-(1-Acryloylpiperidin-3-yl)-4-oxo-5-(2'-(trifluoromethyl)-[1,1'-biphenyl]-3-yl)-4,5-dihydro-3H-1-thia-3,5,8-triazaacenaphthylene-2-carboxamide;
N—((R)-1-((R)-3-Hydroxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;
(R)—N-(1-Acryloylpiperidin-3-yl)-5-(3-isopropoxyphenyl)-4-oxo-4,5-dihydro-3H-1-thia-3,5,8-triazaacenaphthylene-2-carboxamide;
(R)-5-(3-Acetylphenyl)-N-(1-acryloylpiperidin-3-yl)-4-oxo-4,5-dihydro-3H-1-thia-3,5,8-triazaacenaphthylene-2-carboxamide;
(R)—N-(1-Acryloylpyrrolidin-3-yl)-4-oxo-5-(2-phenylpyridin-4-yl)-4,5-dihydro-3H-1-thia-3,5,8-triazaacenaphthylene-2-carboxamide;
(R)—N-(1-Acryloylpiperidin-3-yl)-4-oxo-5-(3-(trifluoromethoxy)phenyl)-4,5-dihydro-3H-1-thia-3,5,8-triazaacenaphthylene-2-carboxamide;
(R)—N-(1-Acryloylpiperidin-3-yl)-5-(3-cyclopropylphenyl)-4-oxo-4,5-dihydro-3H-1-thia-3,5,8-triazaacenaphthylene-2-carboxamide;
(R,E)-5-([1,1'-Biphenyl]-3-yl)-N-(1-(4-(dimethylamino)but-2-enoyl)pyrrolidin-3-yl)-4-oxo-4,5-dihydro-3H-1-thia-3,5,8-triazaacenaphthylene-2-carboxamide;
N—((R)-1-((R)-3-Methoxy-2-methylpropanoyl)piperidin-3-yl)-5-(2-methyl-4-phenoxyphenyl)-4-oxo-4,5-dihydro-3H-1-thia-3,5,8-triazaacenaphthylene-2-carboxamide;
(R)-5-(3-Chloro-4-phenoxyphenyl)-N-(1-(2-(dimethylamino) acetyl)piperidin-3-yl)-4-oxo-4,5-dihydro-3H-1-thia-3,5,8-triazaacenaphthylene-2-carboxamide;
(R,E)-5-([1,1'-Biphenyl]-3-yl)-N-(1-(4-(dimethylamino)but-2-enoyl)piperidin-3-yl)-4-oxo-4,5-dihydro-3H-1-thia-3,5,8-triazaacenaphthylene-2-carboxamide;
N-(cis)-1-Acryloyl-3-hydroxypiperidin-4-yl)-4-oxo-5-(4-phenoxyphenyl)-4,5-dihydro-3H-1-thia-3,5,8-triazaacenaphthylene-2-carboxamide;
(R)-5-(3-Chloro-4-phenoxyphenyl)-N-(1-(2-(methylamino)acetyl)piperidin-3-yl)-4-oxo-4,5-dihydro-3H-1-thia-3,5,8-triazaacenaphthylene-2-carboxamide;
(R)—N-(1-(2-Methoxyacetyl)piperidin-3-yl)-4-oxo-5-(4-phenoxyphenyl)-4,5-dihydro-3H-1-thia-3,5,8-triazaacenaphthylene-2-carboxamide;
(R)-5-(3-Chloro-4-phenoxyphenyl)-4-oxo-N-(pyrrolidin-3-yl)-4,5-dihydro-3H-1-thia-3,5,8-triazaacenaphthylene-2-carboxamide;
4-Oxo-N-(6-oxopiperidin-3-yl)-5-(4-phenoxyphenyl)-4,5-dihydro-3H-1-thia-3,5,8-triazaacenaphthylene-2-carboxamide;
N-((3S,4S)-4-Fluoropyrrolidin-3-yl)-4-oxo-5-(4-phenoxyphenyl)-4,5-dihydro-3H-1-thia-3,5,8-triazaacenaphthylene-2-carboxamide;
(R)-5-(4'-Methyl-[1,1'-biphenyl]-3-yl)-4-oxo-N-(piperidin-3-yl)-4,5-dihydro-3H-1-thia-3,5,8-triazaacenaphthylene-2-carboxamide;
(R)-5-(3-Chloro-4-phenoxyphenyl)-4-oxo-N-(piperidin-3-yl)-4,5-dihydro-3H-1-thia-3,5,8-triazaacenaphthylene-2-carboxamide;
(R)—N-(1-Acetylpiperidin-3-yl)-5-(3-chloro-4-phenoxyphenyl)-4-oxo-4,5-dihydro-3H-1-thia-3,5,8-triazaacenaphthylene-2-carboxamide;
(R)-5-(3-Methyl-4-phenoxyphenyl)-4-oxo-N-(piperidin-3-yl)-4,5-dihydro-3H-1-thia-3,5,8-triazaacenaphthylene-2-carboxamide;
(R)—N-(1-Acryloylpiperidin-3-yl)-5-(3-chloro-4-methylphenyl)-4-oxo-4,5-dihydro-3H-1-thia-3,5,8-triazaacenaphthylene-2-carboxamide;
(R)-4-Oxo-5-(2-phenylpyridin-4-yl)-N-(piperidin-3-yl)-4,5-dihydro-3H-1-thia-3,5,8-triazaacenaphthylene-2-carboxamide;
N-((3R,5R)-5-Hydroxypiperidin-3-yl)-4-oxo-5-(4-phenoxyphenyl)-4,5-dihydro-3H-1-thia-3,5,8-triazaacenaphthylene-2-carboxamide;
(R)-5-([1,1'-Biphenyl]-3-yl)-N-(1-methylpyrrolidin-3-yl)-4-oxo-4,5-dihydro-3H-1-thia-3,5,8-triazaacenaphthylene-2-carboxamide;
N-((3S,4S)-4-Methoxypyrrolidin-3-yl)-4-oxo-5-(4-phenoxyphenyl)-4,5-dihydro-3H-1-thia-3,5,8-triazaacenaphthylene-2-carboxamide;

N-((3R,5R)-1-Acryloyl-5-hydroxypiperidin-3-yl)-4-oxo-5-(4-phenoxyphenyl)-4,5-dihydro-3H-1-thia-3,5,8-triazaacenaphthylene-2-carboxamide;
(R,E)-N-(1-(4-Hydroxybut-2-enoyl)piperidin-3-yl)-4-oxo-5-(4-phenoxyphenyl)-4,5-dihydro-3H-1-thia-3,5,8-triazaacenaphthylene-2-carboxamide;
(R)—N-(1-Acryloylpiperidin-3-yl)-5-(2-cyclobutylpyridin-4-yl)-4-oxo-4,5-dihydro-3H-1-thia-3,5,8-triazaacenaphthylene-2-carboxamide;
(R)—N-(1-Cyanopiperidin-3-yl)-4-oxo-5-(4-phenoxyphenyl)-4,5-dihydro-3H-1-thia-3,5,8-triazaacenaphthylene-2-carboxamide;
(R)—N-(1-(3-Methoxypropanoyl)piperidin-3-yl)-4-oxo-5-(4-phenoxyphenyl)-4,5-dihydro-3H-1-thia-3,5,8-triazaacenaphthylene-2-carboxamide;
N-(1-Cyanopiperidin-4-yl)-4-oxo-5-(4-phenoxyphenyl)-4,5-dihydro-3H-1-thia-3,5,8-triazaacenaphthylene-2-carboxamide;
(R)-5-(3-Methyl-5-phenoxypyridin-2-yl)-4-oxo-N-(piperidin-3-yl)-4,5-dihydro-3H-1-thia-3,5,8-triazaacenaphthylene-2-carboxamide;
(E)-N-(1-(4-Hydroxybut-2-enoyl)piperidin-4-yl)-4-oxo-5-(4-phenoxyphenyl)-4,5-dihydro-3H-1-thia-3,5,8-triazaacenaphthylene-2-carboxamide;
N-(1-(3-Methoxypropanoyl)piperidin-4-yl)-4-oxo-5-(4-phenoxyphenyl)-4,5-dihydro-3H-1-thia-3,5,8-triazaacenaphthylene-2-carboxamide;
(R)—N-(1-Acryloylpiperidin-3-yl)-3-amino-4-((3-cyclobutoxyphenyl)amino)thieno[2,3-b]pyridine-2-carboxamide;
(R)-5-([1,1'-Biphenyl]-3-yl)-4-oxo-N-(pyrrolidin-3-yl)-4,5-dihydro-3H-1-thia-3,5,8-triazaacenaphthylene-2-carboxamide;
2-((1-Acryloylpiperidin-3-yl)amino)-5-(2-methyl-4-phenoxyphenyl)-3H-1-thia-3,5,8-triazaacenaphthylen-4(5H)-one;
(R)-5-([1,1'-Biphenyl]-3-yl)-N-(1-(2-(methylamino)acetyl)pyrrolidin-3-yl)-4-oxo-4,5-dihydro-3H-1-thia-3,5,8-triazaacenaphthylene-2-carboxamide;
(R)-4-Oxo-5-(2-phenylpyridin-4-yl)-N-(pyrrolidin-3-yl)-4,5-dihydro-3H-1-thia-3,5,8-triazaacenaphthylene-2-carboxamide;
(R)-5-(3-Cyclobutylphenyl)-4-oxo-N-(piperidin-3-yl)-4,5-dihydro-3H-1-thia-3,5,8-triazaacenaphthylene-2-carboxamide;
(R)—N-(1-Acryloylpiperidin-3-yl)-4-oxo-5-(6-phenylpyridin-2-yl)-4,5-dihydro-3H-1-thia-3,5,8-triazaacenaphthylene-2-carboxamide;
(R)-5-(4-Cyclobutoxy-2-methylphenyl)-4-oxo-N-(piperidin-3-yl)-4,5-dihydro-3H-1-thia-3,5,8-triazaacenaphthylene-2-carboxamide;
2-((1-Acryloylpiperidin-4-yl)amino)-5-(2-methyl-4-phenoxyphenyl)-3H-1-thia-3,5,8-triazaacenaphthylen-4(5H)-one;
(R)—N-(1-Acryloylpiperidin-3-yl)-5-(4-methyl-3-(trifluoromethyl)phenyl)-4-oxo-4,5-dihydro-3H-1-thia-3,5,8-triazaacenaphthylene-2-carboxamide;
5-(4-Isopropoxy-2-methylphenyl)-4-oxo-N—((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide;
(R)—N-(1-Acryloylpiperidin-3-yl)-5-(*S)-(4-cyclobutoxy-2-methylphenyl)-4-oxo-4,5-dihydro-3H-1-thia-3,5,8-triazaacenaphthylene-2-carboxamide;
(R)-4-Oxo-5-(4-phenylpyridin-2-yl)-N-(piperidin-3-yl)-4,5-dihydro-3H-1-thia-3,5,8-triazaacenaphthylene-2-carboxamide;
(3R,5R)-tert-Butyl 3-hydroxy-5-(4-oxo-5-(4-phenoxyphenyl)-4,5-dihydro-3H-1-thia-3,5,8-triazaacenaphthylene-2-carboxamido)piperidine-1-carboxylate;
(R)—N-(1-Acryloylpiperidin-3-yl)-5-(4-(oxetan-3-yloxy)phenyl)-4-oxo-4,5-dihydro-3H-1-thia-3,5,8-triazaacenaphthylene-2-carboxamide;
(R)-5-(3-(Cyclopentyloxy)phenyl)-4-oxo-N-(piperidin-3-yl)-4,5-dihydro-3H-1-thia-3,5,8-triazaacenaphthylene-2-carboxamide;
N-((3S,4R)-1-Acryloyl-4-hydroxypyrrolidin-3-yl)-5-(4-isopropoxy-2-methylphenyl)-4-oxo-4,5-dihydro-3H-1-thia-3,5,8-triazaacenaphthylene-2-carboxamide;
N-(trans-3-Hydroxypiperidin-4-yl)-4-oxo-5-(4-phenoxyphenyl)-4,5-dihydro-3H-1-thia-3,5,8-triazaacenaphthylene-2-carboxamide;
(R)-5-(3-(Cyclohexyloxy)phenyl)-4-oxo-N-(piperidin-3-yl)-4,5-dihydro-3H-1-thia-3,5,8-triazaacenaphthylene-2-carboxamide;
trans-tert-Butyl 3-hydroxy-4-(4-oxo-5-(4-phenoxyphenyl)-4,5-dihydro-3H-1-thia-3,5,8-triazaacenaphthylene-2-carboxamido)piperidine-1-carboxylate;
(R)-4-Oxo-5-(5-phenylpyridin-3-yl)-N-(piperidin-3-yl)-4,5-dihydro-3H-1-thia-3,5,8-triazaacenaphthylene-2-carboxamide;
(R)—N-(1-Acryloylpiperidin-3-yl)-5-(2-methoxypyrimidin-5-yl)-4-oxo-4,5-dihydro-3H-1-thia-3,5,8-triazaacenaphthylene-2-carboxamide;
(R)-4-Oxo-N-(piperidin-3-yl)-5-(3-(trifluoromethoxy)phenyl)-4,5-dihydro-3H-1-thia-3,5,8-triazaacenaphthylene-2-carboxamide;
(R)-5-(3-Cyclobutoxyphenyl)-4-oxo-N-(piperidin-3-yl)-4,5-dihydro-3H-1-thia-3,5,8-triazaacenaphthylene-2-carboxamide;
(R)-4-Oxo-N-(piperidin-3-yl)-5-(3-(pyridin-2-yl)phenyl)-4,5-dihydro-3H-1-thia-3,5,8-triazaacenaphthylene-2-carboxamide;
(R)-4-Oxo-5-(6-phenylpyridin-2-yl)-N-(piperidin-3-yl)-4,5-dihydro-3H-1-thia-3,5,8-triazaacenaphthylene-2-carboxamide;
(R)—N-(1-Acryloylpiperidin-3-yl)-5-(*R)-(2-methyl-4-(trifluoromethoxy)phenyl)-4-oxo-4,5-dihydro-3H-1-thia-3,5,8-triazaacenaphthylene-2-carboxamide;
(3S,4S)-tert-Butyl 3-fluoro-4-(4-oxo-5-(4-phenoxyphenyl)-4,5-dihydro-3H-1-thia-3,5,8-triazaacenaphthylene-2-carboxamido)pyrrolidine-1-carboxylate;
(R)-5-(4-Cyclobutoxyphenyl)-4-oxo-N-(piperidin-3-yl)-4,5-dihydro-3H-1-thia-3,5,8-triazaacenaphthylene-2-carboxamide;
tert-Butyl 4-(4-oxo-5-(4-phenoxyphenyl)-4,5-dihydro-3H-1-thia-3,5,8-triazaacenaphthylene-2-carboxamido)piperidine-1-carboxylate;
(R)-tert-Butyl 3-(4-oxo-5-(4-phenoxyphenyl)-4,5-dihydro-3H-1-thia-3,5,8-triazaacenaphthylene-2-carboxamido)piperidine-1-carboxylate;
(R)-5-(3-Cyclohexylphenyl)-4-oxo-N-(piperidin-3-yl)-4,5-dihydro-3H-1-thia-3,5,8-triazaacenaphthylene-2-carboxamide;
(R)-5-(3-Isopropylphenyl)-4-oxo-N-(piperidin-3-yl)-4,5-dihydro-3H-1-thia-3,5,8-triazaacenaphthylene-2-carboxamide;
(R)—N-(1-Acryloylpiperidin-3-yl)-4-oxo-5-(3-(pyridin-4-yl)phenyl)-4,5-dihydro-3H-1-thia-3,5,8-triazaacenaphthylene-2-carboxamide;

(R)—N-(1-Acryloylpiperidin-3-yl)-5-(3-(oxetan-3-yl)phenyl)-4-oxo-4,5-dihydro-3H-1-thia-3,5,8-triazaacenaphthylene-2-carboxamide;

(R)—N-(1-Acryloylpiperidin-3-yl)-5-(4-isopropoxy-3-methylphenyl)-4-oxo-4,5-dihydro-3H-1-thia-3,5,8-triazaacenaphthylene-2-carboxamide;

(R)-5-(2-Cyclobutylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-4-oxo-5-(6-phenoxypyridin-2-yl)-4,5-dihydro-3H-1-thia-3,5,8-triazaacenaphthylene-2-carboxamide;

(R)-5-(2,2-Difluorobenzo[d][1,3]dioxol-5-yl)-4-oxo-N-(piperidin-3-yl)-4,5-dihydro-3H-1-thia-3,5,8-triazaacenaphthylene-2-carboxamide;

(R)-5-(3-Isopropoxyphenyl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(3-(tert-butyl)phenyl)-4-oxo-4,5-dihydro-3H-1-thia-3,5,8-triazaacenaphthylene-2-carboxamide;

(3S,4S)-tert-Butyl 3-methoxy-4-(4-oxo-5-(4-phenoxyphenyl)-4,5-dihydro-3H-1-thia-3,5,8-triazaacenaphthylene-2-carboxamido)pyrrolidine-1-carboxylate;

(R)—N-(1-Acryloylpiperidin-3-yl)-5-(5-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-5-(4-(tert-butylsulfonyl)phenyl)-4-oxo-4,5-dihydro-3H-1-thia-3,5,8-triazaacenaphthylene-2-carboxamide;

(R)-5-(4-Hydroxyphenyl)-4-oxo-N-(piperidin-3-yl)-4,5-dihydro-3H-1-thia-3,5,8-triazaacenaphthylene-2-carboxamide;

(R)-5-(3-Acetylphenyl)-4-oxo-N-(piperidin-3-yl)-4,5-dihydro-3H-1-thia-3,5,8-triazaacenaphthylene-2-carboxamide;

N-((3R,4R)-1-Acryloyl-4-hydroxypiperidin-3-yl)-4-oxo-5-(4-phenoxyphenyl)-4,5-dihydro-3H-1-thia-3,5,8-triazaacenaphthylene-2-carboxamide;

(R)-5-(3-Methyl-5-phenoxypyrazin-2-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(3-methyl-5-phenoxypyrazin-2-yl)-4-oxo-4,5-dihydro-3H-1-thia-3,5,8-triazaacenaphthylene-2-carboxamide;

N-((3R,4R)-4-Hydroxypiperidin-3-yl)-4-oxo-5-(4-phenoxyphenyl)-4,5-dihydro-3H-1-thia-3,5,8-triazaacenaphthylene-2-carboxamide;

N-(cis-3-Hydroxypiperidin-4-yl)-4-oxo-5-(4-phenoxyphenyl)-4,5-dihydro-3H-1-thia-3,5,8-triazaacenaphthylene-2-carboxamide;

4-Oxo-N-(2-oxopyrrolidin-3-yl)-5-(4-phenoxyphenyl)-4,5-dihydro-3H-1-thia-3,5,8-triazaacenaphthylene-2-carboxamide;

(R)—N-(1-Acryloylpiperidin-3-yl)-5-(R)-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(*S)-(4-methyl-2-phenoxypyrimidin-5-yl)-4-oxo-4,5-dihydro-3H-1-thia-3,5,8-triazaacenaphthylene-2-carboxamide;

(R)—N-(1-Acryloylpiperidin-3-yl)-4-oxo-5-(5-phenoxypyrimidin-2-yl)-4,5-dihydro-3H-1-thia-3,5,8-triazaacenaphthylene-2-carboxamide;

(R)—N-(1-Acryloylpyrrolidin-3-yl)-5-(*R)-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(4-methyl-6-phenoxypyridin-3-yl)-4-oxo-4,5-dihydro-3H-1-thia-3,5,8-triazaacenaphthylene-2-carboxamide;

N-(cis-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(6-isobutyl-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(6-isobutyl-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(6-cyclobutoxy-4-methylpyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

N-((3R,5S)-1-Acryloyl-5-hydroxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(3-methyl-2-phenylpyridin-4-yl)-4-oxo-4,5-dihydro-3H-1-thia-3,5,8-triazaacenaphthylene-2-carboxamide;

(R)—N-(1-Acryloylpiperidin-3-yl)-5-(2-cyclohexylpyridin-4-yl)-4-oxo-4,5-dihydro-3H-1-thia-3,5,8-triazaacenaphthylene-2-carboxamide;

(R)—N-(1-Acryloylpiperidin-3-yl)-4-oxo-5-(6-phenylpyridazin-4-yl)-4,5-dihydro-3H-1-thia-3,5,8-triazaacenaphthylene-2-carboxamide;

N-((3R,5S)-1-Acryloyl-5-methoxypiperidin-3-yl)-5-(2',3'-difluoro-[1,1'-biphenyl]-3-yl)-4-oxo-4,5-dihydro-3H-1-thia-3,5,8-triazaacenaphthylene-2-carboxamide;

(R)—N-(1-Acryloylpyrrolidin-3-yl)-4-oxo-5-(6-phenoxypyridin-3-yl)-4,5-dihydro-3H-1-thia-3,5,8-triazaacenaphthylene-2-carboxamide;

N—((R)-1 ((*E)-3-((S)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(*S)-(6-cyclobutoxy-2-methylpyridin-3-yl)-4-oxo-4,5-dihydro-3H-1-thia-3,5,8-triazaacenaphthylene-2-carboxamide;

N—(R)-1-((E)-3-((R)-1-Acetylpyrrolidin-2-yl)-2-cyanoacryloyl)piperidin-3-yl)-5-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-4-oxo-N—((R)-1-((E)-4-((4aR,7aS)-tetrahydro-2H-[1,4]dioxino[2,3-c]pyrrol-6(3H)-yl)but-2-enoyl)piperidin-3-yl)-4,5-dihydro-3H-1-thia-3,5,8-triazaacenaphthylene-2-carboxamide;

(R)—N-(1-Acryloylpiperidin-3-yl)-4-oxo-5-(6-phenylpyrimidin-4-yl)-4,5-dihydro-3H-1-thia-3,5,8-triazaacenaphthylene-2-carboxamide;
(R)—N-(1-Acryloylpiperidin-3-yl)-5-(3-chloro-4-phenoxyphenyl)-4-oxo-4,5-dihydro-3H-1-thia-3,5,8-triazaacenaphthylene-2-carboxamide;
(R)—N-(1-Acryloylpiperidin-3-yl)-5-(6-cyclobutoxypyridin-3-yl)-4-oxo-4,5-dihydro-3H-1-thia-3,5,8-triazaacenaphthylene-2-carboxamide;
(R)—N-(1-Acryloylpiperidin-3-yl)-5-(4-methyl-[1,1'-biphenyl]-3-yl)-4-oxo-4,5-dihydro-3H-1-thia-3,5,8-triazaacenaphthylene-2-carboxamide;
(R)—N-(1-Acryloylpiperidin-3-yl)-5-(3-isobutylphenyl)-4-oxo-4,5-dihydro-3H-1-thia-3,5,8-triazaacenaphthylene-2-carboxamide;
(R)—N-(1-Acryloylpiperidin-3-yl)-5-(*R)-(2-methyl-6-phenoxypyridin-3-yl)-4-oxo-4,5-dihydro-3H-1-thia-3,5,8-triazaacenaphthylene-2-carboxamide;
(R)—N-(1-Acryloylpiperidin-3-yl)-5-(*R)-(4-methyl-6-phenoxypyridin-3-yl)-4-oxo-4,5-dihydro-3H-1-thia-3,5,8-triazaacenaphthylene-2-carboxamide;
(R)—N-(1-Acryloylpiperidin-3-yl)-5-(2-cyclopentylpyridin-4-yl)-4-oxo-4,5-dihydro-3H-1-thia-3,5,8-triazaacenaphthylene-2-carboxamide;
(R)—N-(1-Acryloylpiperidin-3-yl)-5-(4-(cyclopentyloxy)-2-methylphenyl)-4-oxo-4,5-dihydro-3H-1-thia-3,5,8-triazaacenaphthylene-2-carboxamide;
(R)—N-(1-Acryloylpiperidin-3-yl)-5-(4-methoxy-2-methylphenyl)-4-oxo-4,5-dihydro-3H-1-thia-3,5,8-triazaacenaphthylene-2-carboxamide;
(R)—N-(1-Acryloylpiperidin-3-yl)-5-(5-methyl-2-phenylpyridin-4-yl)-4-oxo-4,5-dihydro-3H-1-thia-3,5,8-triazaacenaphthylene-2-carboxamide, (R)—N-(1-Acryloylpiperidin-3-yl)-5-(4-(2-isopropoxyethoxy)-2-methylphenyl)-4-oxo-4,5-dihydro-3H-1-thia-3,5,8-triazaacenaphthylene-2-carboxamide;
(R)—N-(1-Acryloylpiperidin-3-yl)-5-(2-isopropylpyridin-4-yl)-4-oxo-4,5-dihydro-3H-1-thia-3,5,8-triazaacenaphthylene-2-carboxamide;
(R)—N-(1-Acryloylpyrrolidin-3-yl)-4-oxo-5-(5-phenoxypyridin-2-yl)-4,5-dihydro-3H-1-thia-3,5,8-triazaacenaphthylene-2-carboxamide;
(R)—N-(1-Acryloylpyrrolidin-3-yl)-4-oxo-5-(5-phenoxypyrazin-2-yl)-4,5-dihydro-3H-1-thia-3,5,8-triazaacenaphthylene-2-carboxamide;
(R)—N-(1-Acryloylpiperidin-3-yl)-5-(*R)-(6-cyclobutoxy-4-methylpyridin-3-yl)-4-oxo-4,5-dihydro-3H-1-thia-3,5,8-triazaacenaphthylene-2-carboxamide;
(R)-5-([2,3'-Bipyridin]-4-yl)-N-(1-acryloylpiperidin-3-yl)-4-oxo-4,5-dihydro-3H-1-thia-3,5,8-triazaacenaphthylene-2-carboxamide;
(R)-5-(*S)-(4-Methyl-6-phenoxypyridin-3-yl)-4-oxo-N-(pyrrolidin-3-yl)-4,5-dihydro-3H-1-thia-3,5,8-triazaacenaphthylene-2-carboxamide;
(R,E)-5-(3-Chloro-4-phenoxyphenyl)-N-(1-(4-(dimethylamino)but-2-enoyl)pyrrolidin-3-yl)-4-oxo-4,5-dihydro-3H-1-thia-3,5,8-triazaacenaphthylene-2-carboxamide;
(R)—N-(1-Acryloylpiperidin-3-yl)-5-(6-cyclobutoxy-2-methylpyridin-3-yl)-4-oxo-4,5-dihydro-3H-1-thia-3,5,8-triazaacenaphthylene-2-carboxamide;
(R)—N-(1-Acryloylpyrrolidin-3-yl)-5-(3-isopropylphenyl)-4-oxo-4,5-dihydro-3H-1-thia-3,5,8-triazaacenaphthylene-2-carboxamide;
(R)-5-(2',3'-Difluoro-[1,1'-biphenyl]-3-yl)-4-oxo-N-(piperidin-3-yl)-4,5-dihydro-3H-1-thia-3,5,8-triazaacenaphthylene-2-carboxamide;

N-((1RS,2RS)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;
(R)—N-(1-Acryloylpiperidin-3-yl)-4-oxo-5-(3-(tetrahydro-2H-pyran-4-yl)phenyl)-4,5-dihydro-3H-1-thia-3,5,8-triazaacenaphthylene-2-carboxamide;
(R)-5-([2,2'-Bipyridin]-4-yl)-N-(1-acryloylpiperidin-3-yl)-4-oxo-4,5-dihydro-3H-1-thia-3,5,8-triazaacenaphthylene-2-carboxamide;
(R)-5-(2',3'-Difluoro-[1,1'-biphenyl]-3-yl)-N-(1-methylpiperidin-3-yl)-4-oxo-4,5-dihydro-3H-1-thia-3,5,8-triazaacenaphthylene-2-carboxamide;
(R)-5-(2-Methyl-6-phenoxypyridin-3-yl)-4-oxo-N-(piperidin-3-yl)-4,5-dihydro-3H-1-thia-3,5,8-triazaacenaphthylene-2-carboxamide;
N-(trans-1-Acryloyl-3-hydroxypiperidin-4-yl)-4-oxo-5-(4-phenoxyphenyl)-4,5-dihydro-3H-1-thia-3,5,8-triazaacenaphthylene-2-carboxamide;
(R)-5-(*S)-(2-Methyl-6-phenoxypyridin-3-yl)-4-oxo-N-(piperidin-3-yl)-4,5-dihydro-3H-1-thia-3,5,8-triazaacenaphthylene-2-carboxamide;
(R)—N-(1-(Methylglycyl)piperidin-3-yl)-4-oxo-5-(2-phenylpyridin-4-yl)-4,5-dihydro-3H-1-thia-3,5,8-triazaacenaphthylene-2-carboxamide;
(R)-5-(*S)-(4-Methyl-2-phenoxypyrimidin-5-yl)-4-oxo-N-(pyrrolidin-3-yl)-4,5-dihydro-3H-1-thia-3,5,8-triazaacenaphthylene-2-carboxamide;
(R)—N-(1-Acryloylpyrrolidin-3-yl)-5-(*S)-(2-methyl-6-phenoxypyridin-3-yl)-4-oxo-4,5-dihydro-3H-1-thia-3,5,8-triazaacenaphthylene-2-carboxamide;
(R)-5-(*S)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide;
N-((3S,4R)-1-Acryloyl-4-hydroxypyrrolidin-3-yl)-4-oxo-5-(2-phenylpyridin-4-yl)-4,5-dihydro-3H-1-thia-3,5,8-triazaacenaphthylene-2-carboxamide;
(R)-4-Oxo-5-(5-phenoxypyrimidin-2-yl)-N-(piperidin-3-yl)-4,5-dihydro-3H-1-thia-3,5,8-triazaacenaphthylene-2-carboxamide;
(R)-5-(2-Cyclopentylpyridin-4-yl)-4-oxo-N-(piperidin-3-yl)-4,5-dihydro-3H-1-thia-3,5,8-triazaacenaphthylene-2-carboxamide;
(R)-5-(3-Isobutylphenyl)-4-oxo-N-(piperidin-3-yl)-4,5-dihydro-3H-1-thia-3,5,8-triazaacenaphthylene-2-carboxamide;
(R)—N-(1-Acryloylpiperidin-3-yl)-5-(*R)-(6-isobutyl-4-methylpyridin-3-yl)-4-oxo-4,5-dihydro-3H-1-thia-3,5,8-triazaacenaphthylene-2-carboxamide;
(R)-4-Oxo-5-(6-phenylpyrimidin-4-yl)-N-(piperidin-3-yl)-4,5-dihydro-3H-1-thia-3,5,8-triazaacenaphthylene-2-carboxamide;
(R)—N-(1-Acryloylpyrrolidin-3-yl)-5-(*R)-(4-methyl-2-phenoxypyrimidin-5-yl)-4-oxo-4,5-dihydro-3H-1-thia-3,5,8-triazaacenaphthylene-2-carboxamide;
(R)-5-(4-Methyl-[1,1'-biphenyl]-3-yl)-4-oxo-N-(piperidin-3-yl)-4,5-dihydro-3H-1-thia-3,5,8-triazaacenaphthylene-2-carboxamide;
(R)—N-(1-Acryloylpiperidin-3-yl)-5-(*S)-(6-cyclobutoxy-4-methylpyridin-3-yl)-4-oxo-4,5-dihydro-3H-1-thia-3,5,8-triazaacenaphthylene-2-carboxamide;
(R)-5-(2-Isopropylpyridin-4-yl)-4-oxo-N-(piperidin-3-yl)-4,5-dihydro-3H-1-thia-3,5,8-triazaacenaphthylene-2-carboxamide;
(R)-5-(*R)-(2-Methyl-6-phenoxypyridin-3-yl)-4-oxo-N-(pyrrolidin-3-yl)-4,5-dihydro-3H-1-thia-3,5,8-triazaacenaphthylene-2-carboxamide;

(R)-5-(5-Methyl-2-phenylpyridin-4-yl)-4-oxo-N-(piperidin-3-yl)-4,5-dihydro-3H-1-thia-3,5,8-triazaacenaphthylene-2-carboxamide;

(R)-5-(4-(2-Isopropoxyethoxy)-2-methylphenyl)-4-oxo-N-(piperidin-3-yl)-4,5-dihydro-3H-1-thia-3,5,8-triazaacenaphthylene-2-carboxamide;

(R)-5-(2-Cyclohexylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(6-isopropoxy-2-methylpyridin-3-yl)-4-oxo-4,5-dihydro-3H-1-thia-3,5,8-triazaacenaphthylene-2-carboxamide;

(R)-5-(3-Methyl-2-phenylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(2-methyl-6-phenylpyridin-4-yl)-4-oxo-4,5-dihydro-3H-1-thia-3,5,8-triazaacenaphthylene-2-carboxamide;

(R)-5-(2-Methyl-6-phenylpyridin-4-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(*R)-(6-cyclobutoxy-2-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(3-methyl-2-phenylpyridin-4-yl)-4-oxo-4,5-dihydro-3H-1-thia-3,5,8-triazaacenaphthylene-2-carboxamide;

(R)-4-Oxo-N-(piperidin-3-yl)-5-(3-(tetrahydro-2H-pyran-4-yl)phenyl)-4,5-dihydro-3H-1-thia-3,5,8-triazaacenaphthylene-2-carboxamide;

(R)-tert-Butyl 3-(4-oxo-5-(3-(tetrahydro-2H-pyran-4-yl)phenyl)-4,5-dihydro-3H-1-thia-3,5,8-triazaacenaphthylene-2-carboxamido)piperidine-1-carboxylate;

(R)-4-Oxo-5-(6-phenylpyridazin-4-yl)-N-(piperidin-3-yl)-4,5-dihydro-3H-1-thia-3,5,8-triazaacenaphthylene-2-carboxamide;

(R)-4-Oxo-5-(6-phenoxypyridin-3-yl)-N-(pyrrolidin-3-yl)-4,5-dihydro-3H-1-thia-3,5,8-triazaacenaphthylene-2-carboxamide;

(R)—N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)-tert-Butyl 3-(5-(2-methyl-6-phenoxypyridin-3-yl)-4-oxo-4,5-dihydro-3H-1-thia-3,5,8-triazaacenaphthylene-2-carboxamido)piperidine-1-carboxylate, (R)-5-(6-Cyclobutoxypyridin-3-yl)-4-oxo-N-(piperidin-3-yl)-4,5-dihydro-3H-1-thia-3,5,8-triazaacenaphthylene-2-carboxamide;

N-((3*S,4*R)-4-Acrylamidotetrahydrofuran-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(4-methyl-2-phenoxypyrimidin-5-yl)-4-oxo-4,5-dihydro-3H-1-thia-3,5,8-triazaacenaphthylene-2-carboxamide;

(R)—N-(1-Acryloylpyrrolidin-3-yl)-5-(*S)-(6-isobutyl-4-methylpyridin-3-yl)-4-oxo-4,5-dihydro-3H-1-thia-3,5,8-triazaacenaphthylene-2-carboxamide;

(R)—N-(1-Acryloylpyrrolidin-3-yl)-4-oxo-5-(2-phenoxypyrimidin-5-yl)-4,5-dihydro-3H-1-thia-3,5,8-triazaacenaphthylene-2-carboxamide;

(R)—N-(1-Acryloylpyrrolidin-3-yl)-4-oxo-5-(5-phenoxypyrimidin-2-yl)-4,5-dihydro-3H-1-thia-3,5,8-triazaacenaphthylene-2-carboxamide;

(R)—N-(1-Acryloylpiperidin-3-yl)-5-(4-isobutylphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(5-phenylpyridazin-3-yl)-4,5-dihydro-3H-1-thia-3,5,8-triazaacenaphthylene-2-carboxamide;

N-((*3R,*4S)-4-Acrylamidotetrahydrofuran-3-yl)-5-(*S)-(4-methyl-6-phenoxypyridin-3-yl)-4I-oxo-4,5-dihydro-3H-1-thia-3,5,8-triazaacenaphthylene-2-carboxamide;

(R)—N-(1-Acryloylpiperidin-3-yl)-5-(*S)-(6-isopropoxy-2-methylpyridin-3-yl)-4-oxo-4,5-dihydro-3H-1-thia-3,5,8-triazaacenaphthylene-2-carboxamide;

(R)-5-(4-Isobutylphenyl)-4-oxo-N-(piperidin-3-yl)-4,5-dihydro-3H-1-thia-3,5,8-triazaacenaphthylene-2-carboxamide;

(R)-4-Oxo-5-(5-phenylpyridazin-3-yl)-N-(piperidin-3-yl)-4,5-dihydro-3H-1-thia-3,5,8-triazaacenaphthylene-2-carboxamide;

(R)—N-(1-Acryloylpyrrolidin-3-yl)-5-(*R)-(6-isobutyl-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(*R)-(6-isopropoxy-2-methylpyridin-3-yl)-4-oxo-4,5-dihydro-3H-1-thia-3,5,8-triazaacenaphthylene-2-carboxamide;

(R)-5-(*S)-(6-Isobutyl-4-methylpyridin-3-yl)-4-oxo-N-(pyrrolidin-3-yl)-4,5-dihydro-3H-1-thia-3,5,8-triazaacenaphthylene-2-carboxamide;

(R)-5-(*S)-(6-Isobutoxy-4-methylpyridin-3-yl)-4-oxo-N-(piperidin-3-yl)-4,5-dihydro-3H-1-thia-3,5,8-triazaacenaphthylene-2-carboxamide;

(R)-5-(*R)-(6-Isobutoxy-4-methylpyridin-3-yl)-4-oxo-N-(piperidin-3-yl)-4,5-dihydro-3H-1-thia-3,5,8-triazaacenaphthylene-2-carboxamide;

(R)-5-(*S)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide;

(R)-5-(*R)-(6-(Cyclopentyloxy)-4-methylpyridin-3-yl)-4-oxo-N-(piperidin-3-yl)-4,5-dihydro-3H-1-thia-3,5,8-triazaacenaphthylene-2-carboxamide;

(R)-5-(*S)-(4-Methyl-2-phenoxypyrimidin-5-yl)-4-oxo-N-(piperidin-3-yl)-4,5-dihydro-3H-1-thia-3,5,8-triazaacenaphthylene-2-carboxamide;

(R)—N-(1-Acryloylpiperidin-3-yl)-5-(6-isobutyl-2-methylpyridin-3-yl)-4-oxo-4,5-dihydro-3H-1-thia-3,5,8-triazaacenaphthylene-2-carboxamide;

(R)-5-(*S)-(6-Isobutyl-4-methylpyridin-3-yl)-4-oxo-N-(1-propionylpiperidin-3-yl)-4,5-dihydro-3H-1-thia-3,5,8-triazaacenaphthylene-2-carboxamide;

(R)—N-(1-Acryloylpiperidin-3-yl)-5-(*S)-(6-isobutoxy-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(*R)-(6-isobutoxy-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(*R)-(6-(cyclopentyloxy)-4-methylpyridin-3-yl)-4-oxo-4,5-dihydro-3H-1-thia-3,5,8-triazaacenaphthylene-2-carboxamide;

(R)—N-(1-Acryloylpiperidin-3-yl)-5-(2-methyl-6-((tetrahydro-2H-pyran-4-yl)oxy)pyridin-3-yl)-4-oxo-4,5-dihydro-3H-1-thia-3,5,8-triazaacenaphthylene-2-carboxamide;

(R)—N-(1-Acryloylpiperidin-3-yl)-5-(4-((2-methylpyridin-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-((6-methylpyridin-2-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-((2-methylpyridin-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(pyridin-3-yloxy)phenyl)-4,5-dihydro-3H-1-thia-3,5,8-triazaacenaphthylene-2-carboxamide;
(R)—N-(1-Acryloylpiperidin-3-yl)-5-(4-((6-methylpyridin-2-yl)oxy)phenyl)-4-oxo-4,5-dihydro-3H-1-thia-3,5,8-triazaacenaphthylene-2-carboxamide;
(R)—N-(1-Acryloylpyrrolidin-3-yl)-5-(*S)-(6-(cyclopentyloxy)-4-methylpyridin-3-yl)-4-oxo-4,5-dihydro-3H-1-thia-3,5,8-triazaacenaphthylene-2-carboxamide;
(R)—N-(1-Acryloylpiperidin-3-yl)-5-(5-(2-fluorophenoxy)pyridin-2-yl)-4-oxo-4,5-dihydro-3H-1-thia-3,5,8-triazaacenaphthylene-2-carboxamide;
(R)—N-(1-Acryloylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide;
(R)—N-(1-Acryloylpyrrolidin-3-yl)-5-(*S)-(6-isobutoxy-4-methylpyridin-3-yl)-4-oxo-4,5-dihydro-3H-1-thia-3,5,8-triazaacenaphthylene-2-carboxamide;
N1-(15-Oxo-19-((3aR,4R,6aS)-2-oxohexahydro-1H-thieno[3,4-d]imidazol-4-yl)-4,7,10-trioxa-14-azanonadecyl)-N5-((E)-4-oxo-4-(3-(4-oxo-5-(5-phenoxypyridin-2-yl)-4,5-dihydro-3H-1-thia-3,5,8-triazaacenaphthylene-2-carboxamido)piperidin-1-yl)but-2-en-1-yl)glutaramide;
(R)—N-(1-Acryloylpyrrolidin-3-yl)-5-(2-methyl-4-(pyridin-2-yloxy)phenyl)-4-oxo-4,5-dihydro-3H-1-thia-3,5,8-triazaacenaphthylene-2-carboxamide;
(R,EZ)—N-(1-(2-Cyano-3-(3-methyloxetan-3-yl)acryloyl)piperidin-3-yl)-5-(*S)-(2-methyl-4-phenoxyphenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-((6-methylpyridin-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide;
N—((R)-1-Acryloylpiperidin-3-yl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide;
(R)—N-(1-Acryloylpiperidin-3-yl)-5-(4-((5-methylpyridin-2-yl)oxy)phenyl)-4-oxo-4,5-dihydro-3H-1-thia-3,5,8-triazaacenaphthylene-2-carboxamide;
N—((R)-1-Acryloylpiperidin-3-yl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide;
1-Acryloyl-N-(5-(2-methyl-4-phenoxyphenyl)-4-oxo-4,5-dihydro-3H-1-thia-3,5,8-triazaacenaphthylen-2-yl)piperidine-3-carboxamide;
(R)—N-(1-Acryloylpiperidin-3-yl)-5-(*S)-(6-isopropoxy-4-methylpyridin-3-yl)-4-oxo-4,5-dihydro-3H-1-thia-3,5,8-triazaacenaphthylene-2-carboxamide;
(R)—N-(1-Acryloylpyrrolidin-3-yl)-5-(2-methyl-4-(pyridazin-3-yloxy)phenyl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide;
(R)—N-(1-Acryloylpiperidin-3-yl)-5-(*S)-(6-isobutyl-2-methylpyridin-3-yl)-4-oxo-4,5-dihydro-3H-1-thia-3,5,8-triazaacenaphthylene-2-carboxamide;
(R)-5-(*S)-(2-Methyl-6-phenoxypyridin-3-yl)-4-oxo-N-(tetrahydrofuran-3-yl)-4,5-dihydro-3H-1-thia-3,5,8-triazaacenaphthylene-2-carboxamide;
(R)-5-(*S)-(6-Isopropoxy-4-methylpyridin-3-yl)-4-oxo-N-(piperidin-3-yl)-4,5-dihydro-3H-1-thia-3,5,8-triazaacenaphthylene-2-carboxamide;
(S)—N-(1-Acryloylpiperidin-3-yl)-4-oxo-5-(5-phenoxypyridin-2-yl)-4,5-dihydro-3H-1-thia-3,5,8-triazaacenaphthylene-2-carboxamide;
2-(4-Acryloylpiperazin-1-yl)-5-(2-methyl-4-phenoxyphenyl)-3H-1-thia-3,5,8-triazaacenaphthylen-4(5H)-one;
(R)-5-(*S)-(6-(Cyclopentyloxy)-4-methylpyridin-3-yl)-4-oxo-N-(pyrrolidin-3-yl)-4,5-dihydro-3H-1-thia-3,5,8-triazaacenaphthylene-2-carboxamide;
(R)-5-(*S)-(6-Isobutoxy-4-methylpyridin-3-yl)-4-oxo-N-(pyrrolidin-3-yl)-4,5-dihydro-3H-1-thia-3,5,8-triazaacenaphthylene-2-carboxamide;
(R)-5-(2-Methyl-4-(pyridin-2-yloxy)phenyl)-4-oxo-N-(1-propionylpiperidin-3-yl)-4,5-dihydro-3H-1-thia-3,5,8-triazaacenaphthylene-2-carboxamide;
(R)—N-(1-Acetylpiperidin-3-yl)-5-(2-methyl-4-(pyridin-2-yloxy)phenyl)-4-oxo-4,5-dihydro-3H-1-thia-3,5,8-triazaacenaphthylene-2-carboxamide;
(E)-1-(2-Cyano-3-cyclopropylacryloyl)-N-(5-(2-methyl-4-phenoxyphenyl)-4-oxo-4,5-dihydro-3H-1-thia-3,5,8-triazaacenaphthylen-2-yl)piperidine-3-carboxamide;
1-Cyano-N-(5-(2-methyl-4-phenoxyphenyl)-4-oxo-4,5-dihydro-3H-1-thia-3,5,8-triazaacenaphthylen-2-yl)piperidine-3-carboxamide;
(R)—N-(1-Acryloylpyrrolidin-3-yl)-4-oxo-5-(4-(pyridazin-3-yloxy)phenyl)-4,5-dihydro-3H-1-thia-3,5,8-triazaacenaphthylene-2-carboxamide;
(R)—N-(1-Acryloylpiperidin-3-yl)-5-(*R)-(6-isopropoxy-4-methylpyridin-3-yl)-4-oxo-4,5-dihydro-3H-1-thia-3,5,8-triazaacenaphthylene-2-carboxamide;
N-(5-(2-Methyl-4-phenoxyphenyl)-4-oxo-4,5-dihydro-3H-1-thia-3,5,8-triazaacenaphthylen-2-yl)-1-propionylpiperidine-4-carboxamide;
(R)-5-(*R)-(6-Isopropoxy-4-methylpyridin-3-yl)-4-oxo-N-(piperidin-3-yl)-4,5-dihydro-3H-1-thia-3,5,8-triazaacenaphthylene-2-carboxamide;
(R)-4-Oxo-N-(1-propionylpiperidin-3-yl)-5-(4-(pyridin-2-yloxy)phenyl)-4,5-dihydro-3H-1-thia-3,5,8-triazaacenaphthylene-2-carboxamide;
(R)—N-(1-Acetylpiperidin-3-yl)-4-oxo-5-(4-(pyridin-2-yloxy)phenyl)-4,5-dihydro-3H-1-thia-3,5,8-triazaacenaphthylene-2-carboxamide;
(R)-5-(2-Methyl-4-(pyridazin-3-yloxy)phenyl)-4-oxo-N-(1-propionylpiperidin-3-yl)-4,5-dihydro-3H-1-thia-3,5,8-triazaacenaphthylene-2-carboxamide;
(R)—N-(1-Acetylpiperidin-3-yl)-5-(2-methyl-4-(pyridazin-3-yloxy)phenyl)-4-oxo-4,5-dihydro-3H-1-thia-3,5,8-triazaacenaphthylene-2-carboxamide;
(R)—N-(1-Acryloylpiperidin-3-yl)-4-oxo-5-(4-(pyridazin-3-yloxy)phenyl)-4,5-dihydro-3H-1-thia-3,5,8-triazaacenaphthylene-2-carboxamide;
(R)—N-(1-Acetylpiperidin-3-yl)-5-(4-(pyridazin-3-yloxy)phenyl)-4-oxo-4,5-dihydro-3H-1-thia-3,5,8-triazaacenaphthylene-2-carboxamide;
(R)—N-(1-Acryloylpiperidin-3-yl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(6-isobutyl-2-methylpyridin-3-yl)-4-oxo-4,5-dihydro-3H-1-thia-3,5,8-triazaacenaphthylene-2-carboxamide;

(E)-1-(2-Cyano-4,4-dimethylpent-2-enoyl)-N-(5-(2-methyl-4-phenoxyphenyl)-4-oxo-4,5-dihydro-3H-1-thia-3,5,8-triazaacenaphthylen-2-yl)piperidine-3-carboxamide;

1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-3-carboxamide;

N-(5-(2-Methyl-4-phenoxyphenyl)-4-oxo-4,5-dihydro-3H-1-thia-3,5,8-triazaacenaphthylen-2-yl)-1-propionylpiperidine-3-carboxamide;

1-(2-Cyanoacetyl)-N-(5-(2-methyl-4-phenoxyphenyl)-4-oxo-4,5-dihydro-3H-1-thia-3,5,8-triazaacenaphthylen-2-yl)piperidine-4-carboxamide;

1-Acryloyl-N-(5-(2-methyl-4-phenoxyphenyl)-4-oxo-4,5-dihydro-3H-1-thia-3,5,8-triazaacenaphthylen-2-yl)piperidine-4-carboxamide;

1-Ethyl-N-(5-(2-methyl-4-phenoxyphenyl)-4-oxo-4,5-dihydro-3H-1-thia-3,5,8-triazaacenaphthylen-2-yl)piperidine-3-carboxamide;

1-Cyano-N-(5-(2-methyl-4-phenoxyphenyl)-4-oxo-4,5-dihydro-3H-1-thia-3,5,8-triazaacenaphthylen-2-yl)piperidine-4-carboxamide;

1-Methyl-N-(5-(2-methyl-4-phenoxyphenyl)-4-oxo-4,5-dihydro-3H-1-thia-3,5,8-triazaacenaphthylen-2-yl)piperidine-3-carboxamide;

5-(2-Methyl-4-phenoxyphenyl)-2-(4-methylpiperazin-1-yl)-3H-1-thia-3,5,8-triazaacenaphthylen-4(5H)-one;

(E)-4,4-Dimethyl-2-(4-(5-(2-methyl-4-phenoxyphenyl)-4-oxo-4,5-dihydro-3H-1-thia-3,5,8-triazaacenaphthylen-2-yl)piperazine-1-carbonyl)pent-2-enenitrile;

4-(5-(2-Methyl-4-phenoxyphenyl)-4-oxo-4,5-dihydro-3H-1-thia-3,5,8-triazaacenaphthylen-2-yl)piperazine-1-carbonitrile;

5-(2-Methyl-4-phenoxyphenyl)-2-(4-propionylpiperazin-1-yl)-3H-1-thia-3,5,8-triazaacenaphthylen-4(5H)-one;

N-(5-(2-Methyl-4-phenoxyphenyl)-4-oxo-4,5-dihydro-3H-1-thia-3,5,8-triazaacenaphthylen-2-yl)piperidine-3-carboxamide;

(E)-1-(2-Cyano-4,4-dimethylpent-2-enoyl)-N-(5-(2-methyl-4-phenoxyphenyl)-4-oxo-4,5-dihydro-3H-1-thia-3,5,8-triazaacenaphthylen-2-yl)piperidine-4-carboxamide;

(E)-1-(2-Cyano-3-cyclopropylacryloyl)-N-(5-(2-methyl-4-phenoxyphenyl)-4-oxo-4,5-dihydro-3H-1-thia-3,5,8-triazaacenaphthylen-2-yl)piperidine-4-carboxamide;

1-Methyl-N-(5-(2-methyl-4-phenoxyphenyl)-4-oxo-4,5-dihydro-3H-1-thia-3,5,8-triazaacenaphthylen-2-yl)piperidine-4-carboxamide;

1-Ethyl-N-(5-(2-methyl-4-phenoxyphenyl)-4-oxo-4,5-dihydro-3H-1-thia-3,5,8-triazaacenaphthylen-2-yl)piperidine-4-carboxamide;

N-(5-(2-Methyl-4-phenoxyphenyl)-4-oxo-4,5-dihydro-3H-1-thia-3,5,8-triazaacenaphthylen-2-yl)piperidine-4-carboxamide;

(R)-5-(*S)-(2-Methyl-4-phenoxyphenyl)-4-oxo-N-(1-(vinylsulfonyl)pyrrolidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxamide;

(R)—N-(1-Cyanopyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(2-Cyanoacetyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide;

(R)—N-(1-(3-Methoxypropanoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpiperidin-3-yl)-5-(2',3'-difluoro-4-methyl-[1,1'-biphenyl]-3-yl)-4-oxo-4,5-dihydro-3H-1-thia-3,5,8-triazaacenaphthylene-2-carboxamide;

(R)-5-(2-Methyl-4-phenoxyphenyl)-4-oxo-N-(1-propionylpyrrolidin-3-yl)-4,5-dihydro-3H-1-thia-3,5,8-triazaacenaphthylene-2-carboxamide;

(R,E)-N-(1-(2-Cyano-3-cyclopropylacryloyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R,E)-5-(*S)-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide;

(R)—N-(1-Acryloylpiperidin-3-yl)-4-oxo-5-(4-(pyridin-2-yloxy)phenyl)-4,5-dihydro-3H-1-thia-3,5,8-triazaacenaphthylene-2-carboxamide;

(R)—N-(1-Acryloylpyrrolidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide;

5-(2-Methyl-4-phenoxyphenyl)-N—((R)-1-((R)-2-(methylamino)propanoyl)piperidin-3-yl)-4-oxo-4,5-dihydro-3H-1-thia-3,5,8-triazaacenaphthylene-2-carboxamide;

N—((R)-1-((R)-Azetidine-2-carbonyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide;

(R)—N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N—((R)-1-((S)-2-(methylamino)propanoyl)piperidin-3-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide;

5-(4-(3-((2-Cyanophenoxy)methyl)phenoxy)-2-methylphenyl)-N-(1-methylpiperidin-4-yl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide;

5-(4-(3-((2-Cyanophenoxy)methyl)phenoxy)-2-methylphenyl)-4-oxo-N-(piperidin-4-yl)-4,5-dihydro-3H-1-thia-3,5,8-triazaacenaphthylene-2-carboxamide;

5-(2-Methyl-4-phenoxyphenyl)-N-(1-methylpiperidin-4-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide;

(R)-4-Oxo-5-(4-phenoxyphenyl)-N-(piperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

(S)—N-(1-Acryloylpiperidin-3-yl)-5-(2-methyl-4-phenoxyphenyl)-4-oxo-4,5-dihydro-3H-1-thia-3,5,8-triazaacenaphthylene-2-carboxamide;

(S)—N-(1-Acryloylpyrrolidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-(piperidin-4-yl)-4,5-dihydro-3H-1-thia-3,5,8-triazaacenaphthylene-2-carboxamide;

(R,E)-N-(1-(2-Cyano-4,4-dimethylpent-2-enoyl)piperidin-3-yl)-5-(*S)-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-4-oxo-N-(1-(4-(pyrrolidin-1-yl)but-2-enoyl)piperidin-3-yl)-4,5-dihydro-3H-1-thia-3,5,8-triazaacenaphthylene-2-carboxamide;

(R,E)-N-(1-(2-Cyano-4,4-dimethylpent-2-enoyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-4-oxo-N-(piperidin-3-yl)-4,5-dihydro-3H-1-thia-3,5,8-triazaacenaphthylene-2-carboxamide;

5-(4-(2-Methoxyphenoxy)-2-methylphenyl)-4-oxo-N-(piperidin-3-yl)-4,5-dihydro-3H-1-thia-3,5,8-triazaacenaphthylene-2-carboxamide;

(R)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

N-(1-Cyanopiperidin-4-yl)-5-(2-methyl-4-phenoxyphenyl)-4-oxo-4,5-dihydro-3H-1-thia-3,5,8-triazaacenaphthylene-2-carboxamide;

(R)-5-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(R)—N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((R)-pyrrolidine-2-carbonyl)piperidin-3-yl)-4,5-dihydro-3H-1-thia-3,5,8-triazaacenaphthylene-2-carboxamide;

(E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

(S)—N-(1-Formylpiperidin-3-yl)-5-(2-methyl-4-phenoxyphenyl)-4-oxo-4,5-dihydro-3H-1-thia-3,5,8-triazaacenaphthylene-2-carboxamide;

(R,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acryloylpyrrolidin-3-yl)-4-oxo-5-(4-(pyridin-2-yloxy)phenyl)-4,5-dihydro-3H-1-thia-3,5,8-triazaacenaphthylene-2-carboxamide;

N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide;

N-(1-Cyanopiperidin-3-yl)-5-(4-(2-methoxyphenoxy)-2-methylphenyl)-4-oxo-4,5-dihydro-3H-1-thia-3,5,8-triazaacenaphthylene-2-carboxamide;

N-(1-Cyanopiperidin-4-yl)-5-(4-(2-methoxyphenoxy)-2-methylphenyl)-4-oxo-4,5-dihydro-3H-1-thia-3,5,8-triazaacenaphthylene-2-carboxamide;

(R)—N-(1-Formylpiperidin-3-yl)-5-(2-methyl-4-phenoxyphenyl)-4-oxo-4,5-dihydro-3H-1-thia-3,5,8-triazaacenaphthylene-2-carboxamide;

(E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide;

(S)—N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide;

(R)—N-(1-Acetylpyrrolidin-3-yl)-4-oxo-5-(4-phenoxyphenyl)-4,5-dihydro-3H-1-thia-3,5,8-triazaacenaphthylene-2-carboxamide;

5-(2-Methyl-4-phenoxyphenyl)-4-oxo-N-(piperidin-3-yl)-4,5-dihydro-3H-1-thia-3,5,8-triazaacenaphthylene-2-carboxamide;

N-(1-Cyanopiperidin-3-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

(S)—N-(1-(2-Cyanoacetyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N—((R)-1-((S)-pyrrolidine-2-carbonyl)piperidin-3-yl)-4,5-dihydro-3H-1-thia-3,5,8-triazaacenaphthylene-2-carboxamide;

(R)—N-(1-Acryloylpiperidin-3-yl)-5-(4-(3-((2-cyanophenoxy)methyl)phenoxy)-2-methylphenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-methyl-4-((4-(trifluoromethyl)pyridin-2-yl)carbamoyl)phenyl)-4-oxo-4,5-dihydro-3H-1-thia-3,5,8-triazaacenaphthylene-2-carboxamide;

(E)-N-(1-(2-Cyano-4,4-dimethylpent-2-enoyl)piperidin-3-yl)-5-(4-(2-methoxyphenoxy)-2-methylphenyl)-4-oxo-4,5-dihydro-3H-1-thia-3,5,8-triazaacenaphthylene-2-carboxamide;

(E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-methyl-4-phenoxyphenyl)-4-oxo-4,5-dihydro-3H-1-thia-3,5,8-triazaacenaphthylene-2-carboxamide;

(R,E)-5-(2-Methyl-4-phenoxyphenyl)-4-oxo-N-(1-(4-(piperidin-1-yl)but-2-enoyl)piperidin-3-yl)-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-3-phenoxyphenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-fluoro-4-((4-(trifluoromethyl)pyridin-2-yl)carbamoyl)phenyl)-4-oxo-4,5-dihydro-3H-1-thia-3,5,8-triazaacenaphthylene-2-carboxamide;

5-(2-Methyl-4-phenoxyphenyl)-4-oxo-N-(1-propionylpiperidin-3-yl)-4,5-dihydro-3H-1-thia-3,5,8-triazaacenaphthylene-2-carboxamide;

(S,E)-N-(1-(2-Cyano-4,4-dimethylpent-2-enoyl)piperidin-3-yl)-5-(2-methyl-4-phenoxyphenyl)-4-oxo-4,5-dihydro-3H-1-thia-3,5,8-triazaacenaphthylene-2-carboxamide;

(S,E)-N-(1-(2-Cyano-3-cyclopropylacryloyl)pyrrolidin-3-yl)-5-(2-methyl-4-phenoxyphenyl)-4-oxo-4,5-dihydro-3H-1-thia-3,5,8-triazaacenaphthylene-2-carboxamide;

(R)—N-(1-(3-Chloropropanoyl)piperidin-3-yl)-4-oxo-5-(5-phenoxypyridin-2-yl)-4,5-dihydro-3H-1-thia-3,5,8-triazaacenaphthylene-2-carboxamide;

5-(4-(2-Methoxyphenoxy)-2-methylphenyl)-N-(1-methylpiperidin-3-yl)-4-oxo-4,5-dihydro-3H-1-thia-3,5,8-triazaacenaphthylene-2-carboxamide;

(R)—N-(1-(2-(Azetidin-1-yl)acetyl)piperidin-3-yl)-5-(2-methyl-4-phenoxyphenyl)-4-oxo-4,5-dihydro-3H-1-thia-3,5,8-triazaacenaphthylene-2-carboxamide;

4-Oxo-5-(4-phenoxyphenyl)-N-(tetrahydro-2H-pyran-4-yl)-4,5-dihydro-3H-1-thia-3,5,8-triazaacenaphthylene-2-carboxamide;

(R)—N-(1-Methylpyrrolidin-3-yl)-4-oxo-5-(4-phenoxyphenyl)-4,5-dihydro-3H-1-thia-3,5,8-triazaacenaphthylene-2-carboxamide;

(R)-4-Oxo-5-(4-phenoxyphenyl)-N-(pyrrolidin-3-yl)-4,5-dihydro-3H-1-thia-3,5,8-triazaacenaphthylene-2-carboxamide;

(S)-5-(2-Methyl-4-phenoxyphenyl)-4-oxo-N-(piperidin-3-yl)-4,5-dihydro-3H-1-thia-3,5,8-triazaacenaphthylene-2-carboxamide;

(R,E)-N-(1-(4-(Dimethylamino)but-2-enoyl)piperidin-3-yl)-5-(4-isopropoxy-2-methylphenyl)-4-oxo-4,5-dihydro-3H-1-thia-3,5,8-triazaacenaphthylene-2-carboxamide;

(R)—N-(1-Benzoylpyrrolidin-3-yl)-4-oxo-5-(4-phenoxyphenyl)-4,5-dihydro-3H-1-thia-3,5,8-triazaacenaphthylene-2-carboxamide;

(R)-4-Oxo-5-(5-phenoxypyridin-2-yl)-N-(piperidin-3-yl)-4,5-dihydro-3H-1-thia-3,5,8-triazaacenaphthylene-2-carboxamide;

(E)-N-(1-(2-Cyano-3-cyclopropylacryloyl)piperidin-4-yl)-5-(2-methyl-4-phenoxyphenyl)-4-oxo-4,5-dihydro-3H-1-thia-3,5,8-triazaacenaphthylene-2-carboxamide;

5-(4-(2-Methoxyphenoxy)-2-methylphenyl)-4-oxo-N-(piperidin-4-yl)-4,5-dihydro-3H-1-thia-3,5,8-triazaacenaphthylene-2-carboxamide;

5-(4-(2-Methoxyphenoxy)-2-methylphenyl)-N-(1-methylpiperidin-4-yl)-4-oxo-4,5-dihydro-3H-1-thia-3,5,8-triazaacenaphthylene-2-carboxamide;

(R)-5-(4-(Cyclopentyloxy)-2-methylphenyl)-4-oxo-N-(piperidin-3-yl)-4,5-dihydro-3H-1-thia-3,5,8-triazaacenaphthylene-2-carboxamide;

N-(1-Methylpiperidin-4-yl)-4-oxo-5-(4-phenoxyphenyl)-4,5-dihydro-3H-1-thia-3,5,8-triazaacenaphthylene-2-carboxamide;

(E)-N-(1-(2-Cyano-4,4-dimethylpent-2-enoyl)piperidin-4-yl)-5-(2-methyl-4-phenoxyphenyl)-4-oxo-4,5-dihydro-3H-1-thia-3,5,8-triazaacenaphthylene-2-carboxamide;

(R)-4-Oxo-5-(6-phenoxypyridin-3-yl)-N-(piperidin-3-yl)-4,5-dihydro-3H-1-thia-3,5,8-triazaacenaphthylene-2-carboxamide;

(R)-5-(4-Isopropoxy-2-methylphenyl)-N-(1-(2-(methylamino)acetyl)piperidin-3-yl)-4-oxo-4,5-dihydro-3H-1-thia-3,5,8-triazaacenaphthylene-2-carboxamide;

(S)—N-(1-Acetylpyrrolidin-3-yl)-4-oxo-5-(4-phenoxyphenyl)-4,5-dihydro-3H-1-thia-3,5,8-triazaacenaphthylene-2-carboxamide;

(R)—N-(1-Benzylpyrrolidin-3-yl)-4-oxo-5-(4-phenoxyphenyl)-4,5-dihydro-3H-1-thia-3,5,8-triazaacenaphthylene-2-carboxamide;

4-Oxo-5-(4-phenoxyphenyl)-N-(piperidin-4-yl)-4,5-dihydro-3H-1-thia-3,5,8-triazaacenaphthylene-2-carboxamide;

4-Oxo-5-(4-phenoxyphenyl)-N-(2-(pyrrolidin-1-yl)ethyl)-4,5-dihydro-3H-1-thia-3,5,8-triazaacenaphthylene-2-carboxamide;

4-Oxo-5-(4-phenoxyphenyl)-N-(2-(piperazin-1-yl)ethyl)-4,5-dihydro-3H-1-thia-3,5,8-triazaacenaphthylene-2-carboxamide;

N-(1-Acryloylpiperidin-4-yl)-5-(2-methyl-4-phenoxyphenyl)-4-oxo-4,5-dihydro-3H-1-thia-3,5,8-triazaacenaphthylene-2-carboxamide;

(S)-5-(2-Methyl-4-phenoxyphenyl)-N-(1-methylpiperidin-3-yl)-4-oxo-4,5-dihydro-3H-1-thia-3,5,8-triazaacenaphthylene-2-carboxamide;

(S)—N-(1-Methylpyrrolidin-3-yl)-4-oxo-5-(4-phenoxyphenyl)-4,5-dihydro-3H-1-thia-3,5,8-triazaacenaphthylene-2-carboxamide;

4-Oxo-5-(4-phenoxyphenyl)-N-(2-(piperidin-1-yl)ethyl)-4,5-dihydro-3H-1-thia-3,5,8-triazaacenaphthylene-2-carboxamide;

N-(2-Morpholinoethyl)-4-oxo-5-(4-phenoxyphenyl)-4,5-dihydro-3H-1-thia-3,5,8-triazaacenaphthylene-2-carboxamide;

(S)-4-Oxo-5-(4-phenoxyphenyl)-N-(pyrrolidin-3-yl)-4,5-dihydro-3H-1-thia-3,5,8-triazaacenaphthylene-2-carboxamide;

N-(2-(4-Methylpiperazin-1-yl)ethyl)-4-oxo-5-(4-phenoxyphenyl)-4,5-dihydro-3H-1-thia-3,5,8-triazaacenaphthylene-2-carboxamide;

(R)—N-(1-Acetylpiperidin-3-yl)-5-(4-isopropoxy-2-methylphenyl)-4-oxo-4,5-dihydro-3H-1-thia-3,5,8-triazaacenaphthylene-2-carboxamide;

(R)-4-Oxo-N-(piperidin-3-yl)-5-(3-(pyridin-3-yl)phenyl)-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(2-methyl-5-phenoxyphenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-4-oxo-5-(3-phenoxyphenyl)-4,5-dihydro-3H-1-thia-3,5,8-triazaacenaphthylene-2-carboxamide;

(S)—N-(1-Benzoylpyrrolidin-3-yl)-4-oxo-5-(4-phenoxyphenyl)-4,5-dihydro-3H-1-thia-3,5,8-triazaacenaphthylene-2-carboxamide;

(R)—N-(1-Acryloylpiperidin-3-yl)-5-(3,5-dichlorophenyl)-4-oxo-4,5-dihydro-3H-1-thia-3,5,8-triazaacenaphthylene-2-carboxamide;

(S,E)-N-(1-(2-Cyano-3-cyclopropylacryloyl)piperidin-3-yl)-4-oxo-5-(o-tolyl)-4,5-dihydro-3H-1-thia-3,5,8-triazaacenaphthylene-2-carboxamide;

(R)—N-(1-Acryloylpiperidin-3-yl)-5-(3-(dimethylamino)phenyl)-4-oxo-4,5-dihydro-3H-1-thia-3,5,8-triazaacenaphthylene-2-carboxamide;

N-(1-(2-Cyanoacetyl)piperidin-4-yl)-5-(2-methyl-4-phenoxyphenyl)-4-oxo-4,5-dihydro-3H-1-thia-3,5,8-triazaacenaphthylene-2-carboxamide;

(S)—N-(1-Benzylpyrrolidin-3-yl)-4-oxo-5-(4-phenoxyphenyl)-4,5-dihydro-3H-1-thia-3,5,8-triazaacenaphthylene-2-carboxamide;

(S,E)-N-(1-(2-Cyano-3-cyclopropylacryloyl)piperidin-3-yl)-5-(4-methoxy-2-methylphenyl)-4-oxo-4,5-dihydro-3H-1-thia-3,5,8-triazaacenaphthylene-2-carboxamide;

5-(2-Methyl-4-phenoxyphenyl)-4-oxo-N-(1-propionylpiperidin-4-yl)-4,5-dihydro-3H-1-thia-3,5,8-triazaacenaphthylene-2-carboxamide;

(R)—N-(1-Acryloylpiperidin-3-yl)-5-(4-aminophenyl)-4-oxo-4,5-dihydro-3H-1-thia-3,5,8-triazaacenaphthylene-2-carboxamide;

(R)-5-(4-(Dimethylamino)phenyl)-4-oxo-N-(piperidin-3-yl)-4,5-dihydro-3H-1-thia-3,5,8-triazaacenaphthylene-2-carboxamide;

(R)-4-Oxo-N-(piperidin-3-yl)-5-(m-tolyl)-4,5-dihydro-3H-1-thia-3,5,8-triazaacenaphthylene-2-carboxamide;

(R)-5-(4-Chlorophenyl)-4-oxo-N-(piperidin-3-yl)-4,5-dihydro-3H-1-thia-3,5,8-triazaacenaphthylene-2-carboxamide;

(R)-4-Oxo-N-(piperidin-3-yl)-5-(p-tolyl)-4,5-dihydro-3H-1-thia-3,5,8-triazaacenaphthylene-2-carboxamide;

(R)-5-(4-Fluorophenyl)-4-oxo-N-(piperidin-3-yl)-4,5-dihydro-3H-1-thia-3,5,8-triazaacenaphthylene-2-carboxamide;

(R)-5-(4-(tert-Butyl)phenyl)-4-oxo-N-(piperidin-3-yl)-4,5-dihydro-3H-1-thia-3,5,8-triazaacenaphthylene-2-carboxamide;

(R)-5-(*S)-(6-Isopropoxy-4-methylpyridin-3-yl)-4-oxo-N-(pyrrolidin-3-yl)-4,5-dihydro-3H-1-thia-3,5,8-triazaacenaphthylene-2-carboxamide;

(R)—N-(1-Acryloylpyrrolidin-3-yl)-5-(*S)-(6-isopropoxy-4-methylpyridin-3-yl)-4-oxo-4,5-dihydro-3H-1-thia-3,5,8-triazaacenaphthylene-2-carboxamide;

(R,E)-N-(1-(2-Cyano-3-(1-methylcyclobutyl)acryloyl)piperidin-3-yl)-5-(2-methyl-6-phenoxypyridin-3-yl)-4-oxo-4,5-dihydro-3H-1-thia-3,5,8-triazaacenaphthylene-2-carboxamide;

N1-((E)-4-((R)-3-(1-(2-Methyl-6-phenoxypyridin-3-yl)-2-oxo-1,2,3,5-tetrahydrocyclopenta[de]quinazoline-4-carboxamido)piperidin-1-yl)-4-oxobut-2-en-1-yl)-N5-(15-oxo-19-((3aR,4R,6aS)-2-oxooctahydrocyclopenta[d]imidazol-4-yl)-4,7,10-trioxa-14-azanonadecyl)glutaramide;

(R,E)-N-(1-(2-Cyano-4-ethoxy-4-methylpent-2-enoyl)piperidin-3-yl)-5-(2-methyl-6-phenoxypyridin-3-yl)-4-oxo-4,5-dihydro-3H-1-thia-3,5,8-triazaacenaphthylene-2-carboxamide;

(R,E)-N-(1-(2-Cyano-3-cyclopropylacryloyl)piperidin-3-yl)-5-(2-methyl-6-phenoxypyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(*R)-(2-methyl-4-(pyridin-2-yloxy)phenyl)-4-oxo-4,5-dihydro-3H-1-thia-3,5,8-triazaacenaphthylene-2-carboxamide;

(R)—N-(1-Acryloylpyrrolidin-3-yl)-5-(*S)-(2-methyl-4-(pyridin-2-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-(pyridin-2-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-(pyridin-2-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-((2-methylpyridin-3-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide;

(R)—N-(1-Acryloylpiperidin-3-yl)-5-(*R)-(2-methyl-4-(pyridazin-3-yloxy)phenyl)-4-oxo-4,5-dihydro-3H-1-thia-3,5,8-triazaacenaphthylene-2-carboxamide;

(R)—N-(1-Acryloylpiperidin-3-yl)-5-(*S)-(2-methyl-4-(pyridazin-3-yloxy)phenyl)-4-oxo-4,5-dihydro-3H-1-thia-3,5,8-triazaacenaphthylene-2-carboxamide;

(R)—N-(1-Acryloylpiperidin-3-yl)-4-oxo-5-(5-(pyridazin-3-yloxy)pyridin-2-yl)-4,5-dihydro-3H-1-thia-3,5,8-triazaacenaphthylene-2-carboxamide;

(R)—N-(1-Acryloylpyrrolidin-3-yl)-4-oxo-5-(5-(pyridazin-3-yloxy)pyridin-2-yl)-4,5-dihydro-3H-1-thia-3,5,8-triazaacenaphthylene-2-carboxamide;

(R)—N-(1-Acryloylpyrrolidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide;

(R)—N-(1-Acryloylpiperidin-3-yl)-5-(2-methyl-6-(pyridazin-3-yloxy)pyridin-3-yl)-4-oxo-4,5-dihydro-3H-1-thia-3,5,8-triazaacenaphthylene-2-carboxamide;

(R)—N-(1-Acryloylpiperidin-3-yl)-5-(4-methyl-6-(pyridazin-3-yloxy)pyridin-3-yl)-4-oxo-4,5-dihydro-3H-1-thia-3,5,8-triazaacenaphthylene-2-carboxamide; and (R)—N-(1-Acryloylpyrrolidin-3-yl)-5-(4-methyl-6-(pyridazin-3-yloxy)pyridin-3-yl)-4-oxo-4,5-dihydro-3H-1-thia-3,5,8-triazaacenaphthylene-2-carboxamide;

and pharmaceutically acceptable salts thereof.

14. The compound of claim 1, wherein said compound is selected from the group consisting of:

(R)—N-(1-Acryloylpiperidin-3-yl)-5-(R)-(4-isopropoxy-2-methylphenyl)-4-oxo-4,5-dihydro-3H-1-thia-3,5,8-triazaacenaphthylene-2-carboxamide;

(R)—N-(1-Acryloylpiperidin-3-yl)-4-oxo-5-(6-phenoxypyridin-3-yl)-4,5-dihydro-3H-1-thia-3,5,8-triazaacenaphthylene-2-carboxamide;

(R)—N-(1-Acryloylpiperidin-3-yl)-4-oxo-5-(2-phenylpyridin-4-yl)-4,5-dihydro-3H-1-thia-3,5,8-triazaacenaphthylene-2-carboxamide;

(R)—N-(1-Acryloylpiperidin-3-yl)-4-oxo-5-(5-phenoxy-pyridin-2-yl)-4,5-dihydro-3H-1-thia-3,5,8-triazaacenaphthylene-2-carboxamide;

(R)—N-(1-Acryloylpiperidin-3-yl)-5-(R)-(2-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpyrrolidin-3-yl)-5-(*S)-(4-methyl-6-phenoxypyridin-3-yl)-4-oxo-4,5-dihydro-3H-1-thia-3,5,8-triazaacenaphthylene-2-carboxamide;

(R)—N-(1-Acryloylpiperidin-3-yl)-4-oxo-5-(5-phenoxypyrimidin-2-yl)-4,5-dihydro-3H-1-thia-3,5,8-triazaacenaphthylene-2-carboxamide;

(R)—N-(1-Acryloylpiperidin-3-yl)-5-(*S)-(6-isobutyl-4-methylpyridin-3-yl)-4-oxo-4,5-dihydro-3H-1-thia-3,5,8-triazaacenaphthylene-2-carboxamide; and (R)—N-(1-Acryloylpyrrolidin-3-yl)-5-(*S)-(2-methyl-6-phenoxypyridin-3-yl)-4-oxo-4,5-dihydro-3H-1-thia-3,5,8-triazaacenaphthylene-2-carboxamide, and pharmaceutically acceptable salts thereof.

15. A pharmaceutical composition comprising at least one compound of claim 1 and at least one pharmaceutically acceptable excipient.

16. A pharmaceutical composition comprising at least one compound of claim 14 and at least one pharmaceutically acceptable excipient.

17. A pharmaceutical composition comprising at least one compound of claim 14 at least one pharmaceutically acceptable excipient.

18. A method of making a compound of claim 1, or a pharmaceutically acceptable salt thereof, said method comprising reacting a compound of formula (XIX) with tert-butyl-[(2-sulfanylacetyl)amino] piperidine-1-carboxylate to form a compound of formula (XXIII)

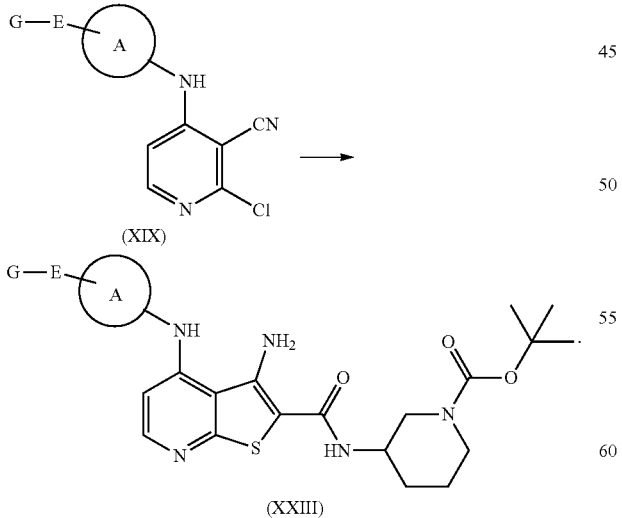

19. A compound of claim 1 having the structure of Formula (II'), stereoisomers, isotopic variants, or pharmaceutically acceptable salts thereof, wherein $R^a$ is independently selected from the group consisting of: H, Cl, F, $CH_3$, and $CF_3$;

n is 0-2;

E is O;

G is selected from the group consisting of: $C_{3-6}$cycloalkyl; oxetanyl; tetrahydrofuranyl; tetrahydropyranyl; benzofuran-7-yloxy; pyridyl; pyridyl substituted with $CH_3$; phenyl; phenyl substituted with one or two members independently selected from the group consisting of: halogen, $C_{1-6}$alkyl, $C_{1-6}$haloalkyl, OH, $OC_{1-6}$alkyl, $OC_{1-6}$haloalkyl, $CH_2OCH_3$, (C=O)$NH_2$, and $C_{3-6}$cycloalkyl; and Ring B is selected from the group consisting of:

(a)

wherein $R^b$ is selected from the group consisting of: H; $C_{1-6}$-alkyl, $C_{3-6}$cycloalkyl, (C=O)CH=$CH_2$, (C=O)$CH_2CH_2OCH_3$, (C=O)$CH_2CH_2SO_2CH_3$, and (b)

-continued

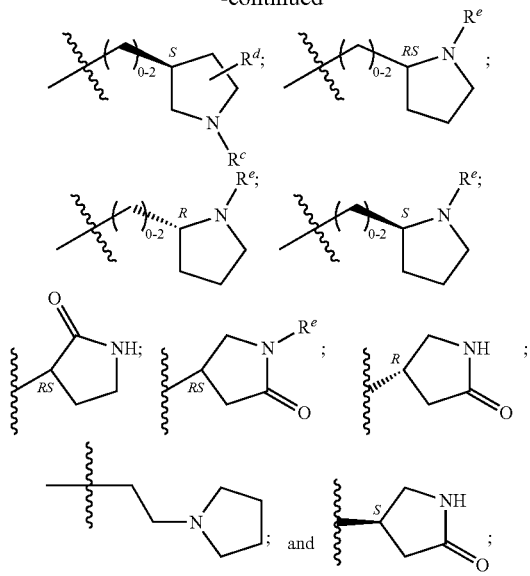

wherein R$^c$ is selected from the group consisting of: H, C$_{1-6}$alkyl, CN, (C=O)C$_{1-3}$alkyl, (C=O)CH=CH$_2$, C$_{3-6}$cycloalkyl, (C=O)CH$_2$NH$_2$, (C=O)CH$_2$NH(CH$_3$), (C=O)CH$_2$N(CH$_3$)$_2$, (C=O)CH$_2$CN, CH$_2$-phenyl, (C=O)CH$_2$C$_1$, (C=O)CH=CHCH$_2$NH$_2$, (C=O)CH$_2$CH$_2$OCH$_3$, (C=O)CH=CHCH$_2$NH(CH$_3$), (C=O)CH=CHCH$_2$N(CH$_3$)$_2$, (C=O)CH=CHCH$_2$OH, (C=O)-phenyl, SO$_2$CH=CH$_2$, (C=O)CH$_2$CH$_2$SO$_2$CH$_3$,

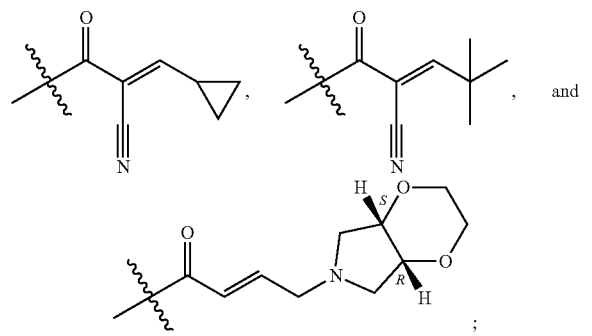

R$^d$ is selected from the group consisting of: H, F, OH, and OCH$_3$;
R$^e$ is H or C$_{1-6}$alkyl;
(c)

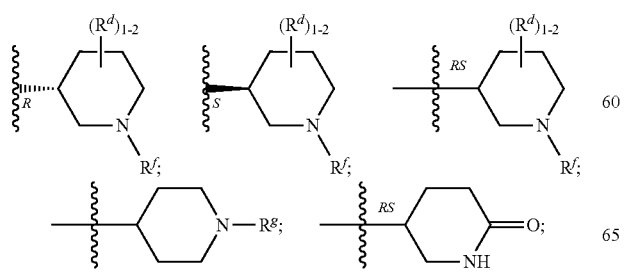

-continued

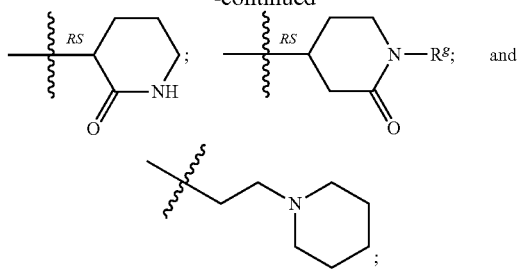

wherein
R$^d$ is selected from the group consisting of: H, F, OH, and OCH$_3$;
R$^f$ is selected from the group consisting of: (C=O)—C(R$^3$)=CR$^4$(R$^5$); H; C$_{1-6}$alkyl; CN; (C=O)C$_{1-3}$alkyl; (C=O)C$_{1-3}$haloalkyl; (C=O)C$_{2-6}$alkenyl; (C=O)C$_{2-6}$alkynyl; (C=O)(CH$_2$)$_{1-2}$OH; (C=O)(CH$_2$)$_{1-2}$OCH$_3$; (C=O)H; (C=O)(CH$_2$)$_{0-1}$CN; (C=O)CH$_2$NH$_2$; (C=O)(CH$_2$)$_{1-2}$NH(CH$_3$); (C=O)(CH$_2$)$_{1-2}$N(CH$_3$)$_2$; (C=O)CH(CH$_3$)NH(CH$_3$); (C=O)(CH$_2$)$_{1-2}$SO$_2$CH$_3$; (C=O)CH$_2$CH(CH$_3$)(OCH$_3$); (C=O)CH(CH$_3$)CH$_2$(OH); (C=O)CH(CH$_3$)CH$_2$(OCH$_3$); (C=O)C(CH$_3$)$_2$CH$_2$(OCH$_3$); (C=O)CH$_2$C(CH$_3$)$_2$(OCH$_3$); (C=O)CH(NH$_2$)CH$_2$(OCH$_3$); (C=O)CH(OCH$_3$)CH$_2$(OCH$_3$); (C=O)CH(OH)CH$_2$(OCH$_3$); C$_{3-6}$cycloalkyl; (C=O)(CH$_2$)$_{0-1}$azetidinyl; (C=O)oxetanyl; (C=O)tetrahydrofuranyl; (C=O)tetrahydropyranyl; (C=O)(CH$_2$)$_{0-1}$pyrrolidinyl, wherein said pyrrolidinyl is optionally substituted with CH$_3$; (C=O)(CH$_2$)$_{0-1}$piperidinyl; (C=O)(CH$_2$)$_{0-1}$morpholinyl; SO$_2$—C$_{2-6}$alkenyl; SO$_2$C$_{1-6}$alkyl; and linker-PEG-Biotin;
R$^3$ is selected from the group consisting of: H, CN, halogen, C$_{1-6}$haloalkyl, and C$_{1-6}$alkyl;
R$^4$ and R$^5$ are each independently selected from the group consisting of: H; halogen; C$_{1-6}$alkyl; CH$_2$OH; C$_{1-6}$alk-OC$_{1-6}$alkyl; OC$_{1-6}$alkyl; C$_{1-4}$alk-NR$^6$R$^7$; C$_{3-6}$cycloalkyl substituted with NH$_2$ or CH$_3$; oxetanyl substituted with CH$_3$; 1-acetylpyrrolidin-2-yl; CH$_2$-pyrrolidinyl; CH$_2$-piperidinyl; C(CH$_3$)$_2$-piperidinyl; CH$_2$-morpholinyl; C(CH$_3$)$_2$-morpholinyl; CH$_2$-(4aR,7aS)-tetrahydro-2H-[1,4]dioxino[2,3-c]pyrrol-6(3H)-yl; C(CH$_3$)$_2$NH(CH$_2$CH$_2$OCH$_3$); CH$_2$SO$_2$CH$_3$; CH$_2$NHSO$_2$CH$_3$; NH(C=O)C$_{1-6}$alkyl; and linker-PEG-Biotin; and
R$^6$ and R$^7$ are each independently selected from the group consisting of: H, C$_{1-6}$alkyl, C$_{3-6}$cycloalkyl, and CN;
R$^g$ is selected from the group consisting of: H, C$_{1-6}$alkyl, and CN; and
(d)

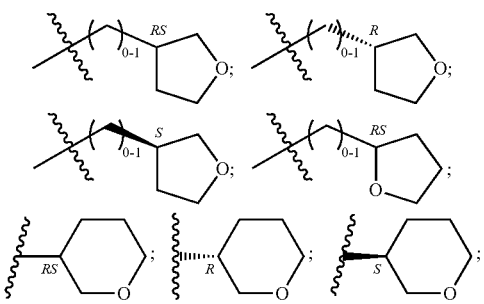

-continued

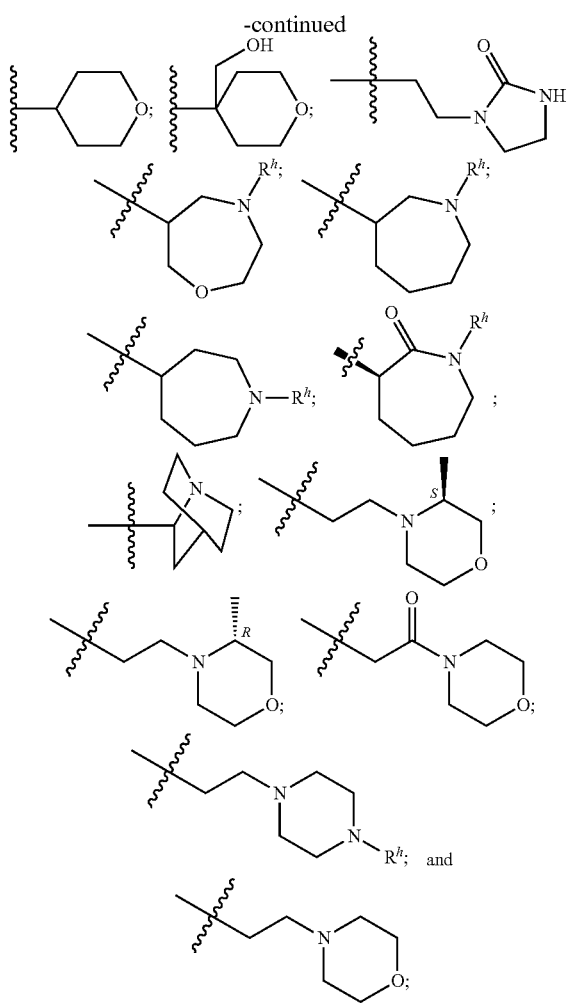

and wherein $R^h$ is selected from the group consisting of: H, CN, $CH_3$, and $CH_2$phenyl.

20. The compound of claim 1 having the structure of Formula (III'), stereoisomers, isotopic variants, or pharmaceutically acceptable salts thereof, (III')

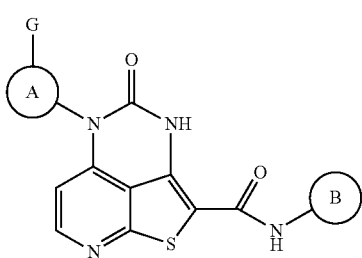

wherein
G-A is selected from the group consisting of:

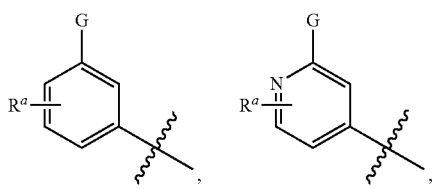

-continued

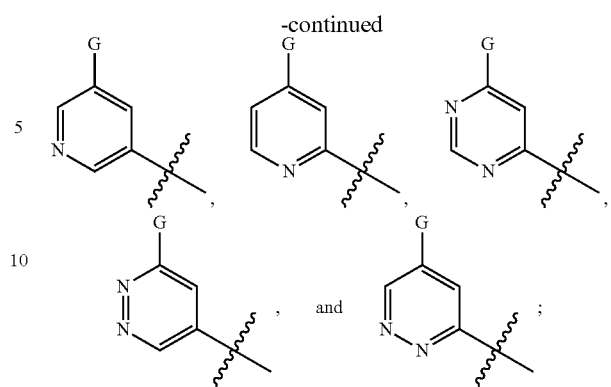

wherein G is phenyl; or phenyl substituted with one or two members independently selected from the group consisting of: halogen, $C_{1-6}$alkyl, $C_{1-6}$haloalkyl, $C_{3-6}$cycloalkyl, pyridyl, oxetan-3-yl, and tetrahydro-2H-pyran-4-yl;
$R^a$ is H or $CH_3$;
Ring B is selected from the group consisting of:

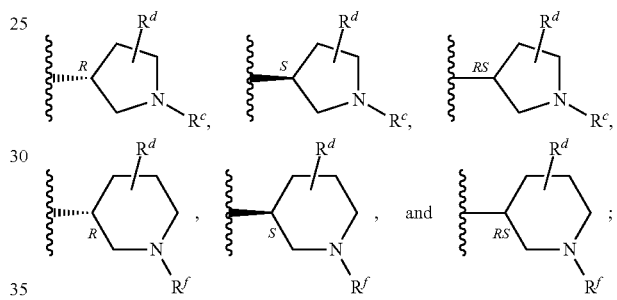

wherein $R^c$ and $R^f$ are independently selected from the group consisting of: H, $C_{1-6}$alkyl, $(C=O)CH=CH_2$, $(C=O)CH_2NH(CH_3)$, $(C=O)CH=CHCH_2N(CH_3)_2$, and

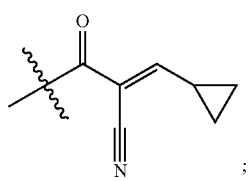 [SMILES: *C(=O)/C(C#N)=C/C1CC1]

and $R^d$ is selected from the group consisting of: H, OH and $OCH_3$.

21. The compound of claim 1 having the structure of Formula (IV'), stereoisomers, isotopic variants, or pharmaceutically acceptable salts thereof, (IV')

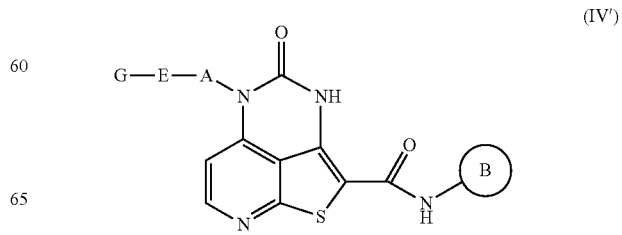

wherein
G-E-A is selected from the group consisting of:

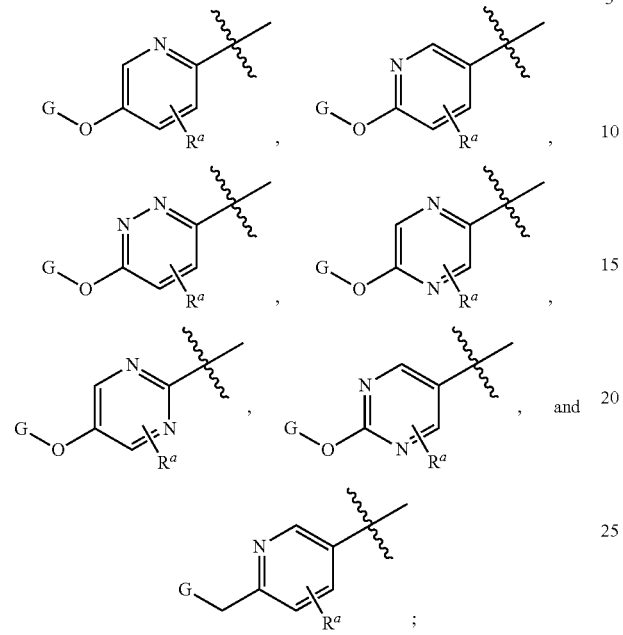

wherein G is selected from the group consisting of:
C$_{1-6}$alkyl, C$_{3-6}$cycloalkyl, tetrahydro-2H-pyran-4-yl, pyridazin-3-yl, phenyl, and phenyl substituted with F;
R$^a$ is H or CH$_3$;
Ring B is selected from the group consisting of:

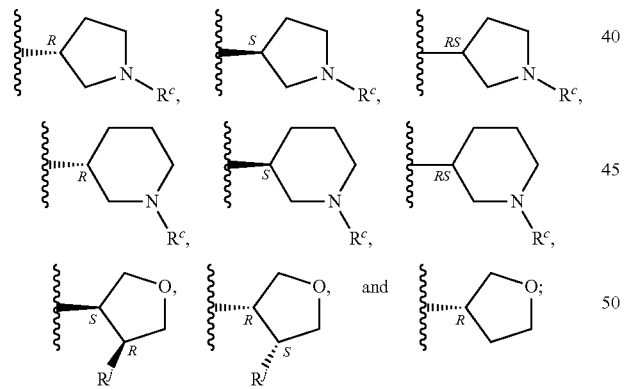

R$^c$ is selected from the group consisting of: H, C$_{1-6}$alkyl, (C=O)C$_{1-3}$alkyl, (C=O)CH=CH$_2$, (C=O)C$_{1-6}$haloalkyl,

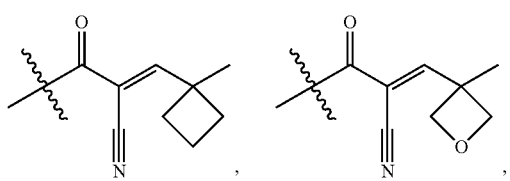

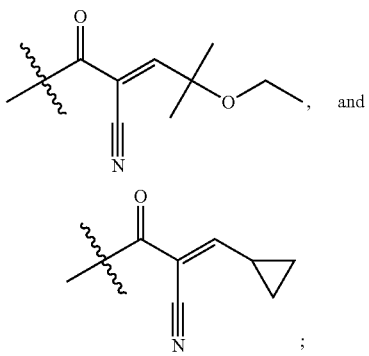

and
R$^j$ is selected from the group consisting of: H, NH$_2$, and NH(C=O)CH=CH$_2$.

22. The compound of claim 1 having the structure of Formula (V'), stereoisomers, isotopic variants, or pharmaceutically acceptable salts thereof,

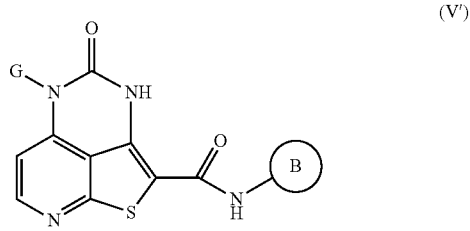

wherein
G is selected from the group consisting of: C$_{1-6}$alkyl; C$_{1-6}$haloalkyl; phenyl; phenyl substituted with one or two members independently selected from the group consisting of: halogen, C$_{1-6}$alkyl, C$_{1-6}$haloalkyl, OC$_{1-6}$alkyl, OC$_{1-6}$haloalkyl, (C=O)—C$_{1-6}$alkyl, SF$_5$, OH, NH$_2$, N(CH$_3$)$_2$, OCH$_2$CH$_2$OCH(CH$_3$)$_2$, and SO$_2$C$_{1-6}$alkyl; benzo[d][1,3]dioxolyl optionally substituted with Cl; 2-methylpyridin-3-yl; 2-isopropylpyridin-4-yl; benzothiophenyl; napthalenyl; and 2,2-difluorobenzo[d][1,3]dioxol-5-yl;

Ring B is selected from the group consisting of:

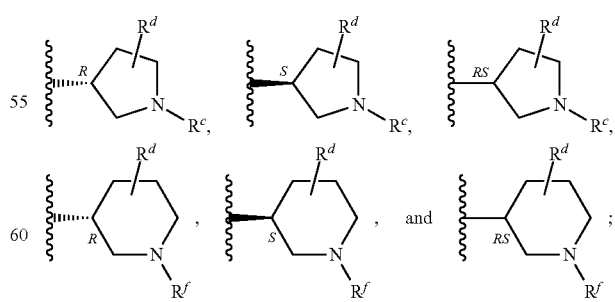

wherein R$^c$ and R$^f$ are independently selected from the group consisting of: H, C$_{1-6}$alkyl, (C=O)C$_{1-3}$alkyl, (C=O)CH=CH$_2$, (C=O)CH$_2$NHCH$_3$,

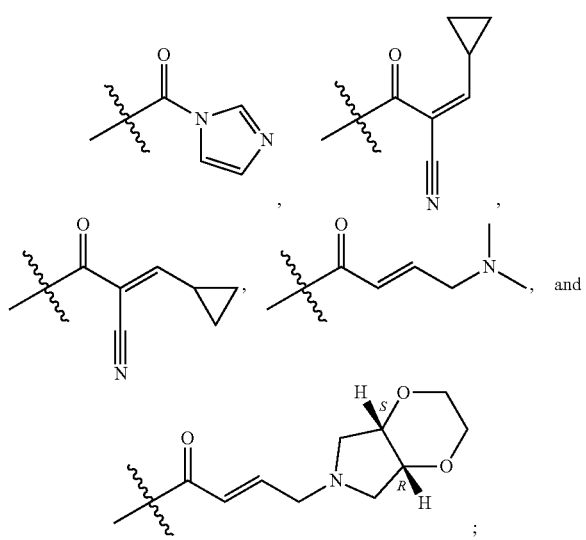

$R^d$ is H or OH.

23. A compound selected from
N-((3R,5R)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide;
N-((3R,5S)-1-Acryloyl-5-hydroxypiperidin-3-yl)-5-(*S)-(2-methyl-4-phenoxyphenyl)-4-oxo-4,5-dihydro-3H-1-thia-3,5,8-triazaacenaphthylene-2-carboxamide;
N-((3R,5S)-1-Acryloyl-5-fluoropiperidin-3-yl)-5-(2-methyl-4-phenoxyphenyl)-4-oxo-4,5-dihydro-3H-1-thia-3,5,8-triazaacenaphthylene-2-carboxamide;
(R)-N-(1-Acryloylpiperidin-3-yl)-5-(3-fluoro-2-methyl-4-phenoxyphenyl)-4-oxo-4,5-dihydro-3H-1-thia-3,5,8-triazaacenaphthylene-2-carboxamide;
(R)-N-(1-Acryloylpyrrolidin-3-yl)-5-(*S)-(2-methyl-4-phenoxyphenyl)-4-oxo-4,5-dihydro-3H-1-thia-3,5,8-triazaacenaphthylene-2-carboxamide;
N-((3R,5R)-1-Acryloyl-5-hydroxypiperidin-3-yl)-5-(2-methyl-4-phenoxyphenyl)-4-oxo-4,5-dihydro-3H-1-thia-3,5,8-triazaacenaphthylene-2-carboxamide; and
pharmaceutically acceptable salts thereof.

\* \* \* \* \*